(12) United States Patent
Kaneko et al.

(10) Patent No.: US 6,518,423 B1
(45) Date of Patent: Feb. 11, 2003

(54) BENZOPIPERIDINE DERIVATIVES

(75) Inventors: Toshihiko Kaneko; Richard Clark; Norihito Ohi; Fumihiro Ozaki; Tetsuya Kawahara; Atsushi Kamada; Kazuo Okano; Hiromitsu Yokohama; Kenzo Muramoto, all of Ibaraki; Tohru Arai, Tokyo; Masayoshi Ohkuro, Ibaraki; Osamu Takenaka, Ibaraki; Jiro Sonoda, Ibaraki, all of (JP)

(73) Assignee: Eisai Co., Ltd., Tokyo (JP)

(*) Notice: Subject to any disclaimer, the term of this patent is extended or adjusted under 35 U.S.C. 154(b) by 0 days.

(21) Appl. No.: 09/230,852

(22) PCT Filed: Aug. 8, 1997

(86) PCT No.: PCT/JP97/02787
§ 371 (c)(1),
(2), (4) Date: Apr. 5, 1999

(87) PCT Pub. No.: WO98/06720

PCT Pub. Date: Feb. 19, 1998

(30) Foreign Application Priority Data

Aug. 9, 1996 (JP) .............................................. 8-210344

(51) Int. Cl.⁷ .................... C07D 513/00; C07D 279/00; C07D 211/06
(52) U.S. Cl. ...................... 544/34; 544/58.2; 544/58.6; 544/345; 546/199; 546/236; 546/238
(58) Field of Search .................. 544/34, 58.5, 58.2, 544/345, 58.6, 58.8; 546/236, 238, 199

(56) References Cited

U.S. PATENT DOCUMENTS

| | | | |
|---|---|---|---|
| 3,506,658 A | 4/1970 | Farge et al. ................. 260/244 |
| 3,663,543 A | * 5/1972 | Gulbenk et al. ........ 260/250 R |
| 3,746,707 A | 7/1973 | Gulbank et al. ............ 260/243 |
| 3,808,208 A | 4/1974 | Gulbenil et al. ............ 260/250 |
| 3,821,213 A | 6/1974 | Tong .......................... 260/243 |
| 3,845,044 A | 10/1974 | Tong .......................... 260/243 |
| 4,223,136 A | 9/1980 | Chorvat ...................... 544/34 |
| 4,370,328 A | 1/1983 | Campbell et al. ........... 424/250 |
| 4,719,217 A | 1/1988 | King et al. .................. 514/299 |
| 4,845,222 A | 7/1989 | Morr et al. .................. 544/347 |
| 5,441,967 A | 8/1995 | Goto et al. .................. 514/326 |
| 5,552,398 A | 9/1996 | King et la. .................. 514/214 |
| 5,580,885 A | 12/1996 | King et al. .................. 514/321 |
| 5,641,786 A | 6/1997 | Lowe, III .................... 514/294 |

FOREIGN PATENT DOCUMENTS

| | | | |
|---|---|---|---|
| DE | 2702714 | | 7/1978 |
| EP | 0140709 A2 | | 5/1985 |
| EP | 0140709 | * | 5/1985 |
| EP | 140709 | * | 5/1985 |
| EP | 0671393 A1 | | 9/1995 |
| FR | 1459075 | | 9/1965 |
| FR | 1488269 | | 3/1966 |
| GB | 1168094 | | 10/1968 |
| GB | 2007654 | * | 5/1979 |
| GB | 2007654 A | | 5/1979 |
| JP | 4427974 | | 11/1969 |
| JP | 54- 98786 | | 8/1979 |
| JP | 55-130973 | | 10/1980 |
| JP | 60-115524 | | 6/1985 |
| JP | 62- 30760 | | 2/1987 |
| JP | 2225413 | | 9/1990 |
| JP | 3-173867 | | 7/1991 |
| JP | 5-507687 | | 11/1993 |
| JP | 6-510537 | | 11/1994 |
| JP | 6-510764 | | 12/1994 |
| JP | 7258561 | | 10/1995 |
| WO | 8002799 | * | 5/1985 |
| WO | 94 27965 | | 12/1994 |
| WO | 9509157 | | 4/1995 |
| WO | 95 11228 | | 4/1995 |

OTHER PUBLICATIONS

B.GE et al., Yaoxue Xuebao, 20/6,427–32(1985).*
Organic Chemistry, Morision & Boyd, Allyn and Bacon, Inc.age 206.*
R.J. Chorvat et al., Tetrahedrom Letters vol. 21, pp. 421–424 (1980).
C.O. Okafor, Journal of Herterocyclic Chemistry, 18, pp. 405–407.
C.O. Okafor, Journal of Heterocyclic Chemistry, 18, pp. 1445–1449 (1981).
W.S. Saari et al., Journal of Medicinal Chemistry, vol. 26, No. 4. 564–569 (1983).
A.P. Komin et al., Journal of Heterocyclic Chemistry, vol. 13, No. 1, pp. 13–22 (1976).
J. Armand et al., Canadian Journal of Chemistry, vol. 59, No. 23, pp. 3237–3240 (1981).

(List continued on next page.)

*Primary Examiner*—Mukund J. Shah
*Assistant Examiner*—Sudhaker B. Patel
(74) *Attorney, Agent, or Firm*—Birch, Stewart, Kolasch & Birch, LLP

(57) ABSTRACT

Benzopiperidine derivatives represented by formula (I), salts thereof or hydrates thereof, processes for producing the same and drugs comprising the same:

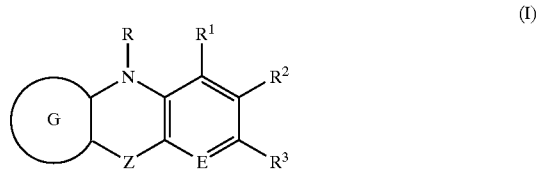

(I)

wherein the variables are as described in the specification. These compounds are useful as drugs efficacious in the prevention and treatment of these various inflammatory diseases and immunologic diseases, such as rheumatoid arthritis, atopic dermatitis, psoriasis, asthma, and rejection reaction accompanying organ transplantation.

6 Claims, No Drawings

OTHER PUBLICATIONS

S. Eguchi et al., Journal of Organic Chemistry. vol. 50, No. 11, pp. 1895–1899 (1985).

L. Yun et al., vol. 19, No. 9, pp. 671–675 (1984).

M. Langlois et al., European Journal of Medical Chemistry, vol. 28, No. 11, pp. 869–880 (1983).

B.M. Mikhailov et al., Journal of Organometallic Chemistry, vol. 220, No. 1, pp. 1–9 (1981).

B.M. Mikhailov et al., Journal of Ogranometallic Chemistry, vol. 258, No. 2, pp. 131–136 (1983).

M.S. Arias et al., Journal of Molecular Structure, 293, pp. 43–48 (1983).

Y.N. Bubnoy et al., Mendeleev Communications, 2, pp. 43–45 (1994).

B. GE et al., vol. 20, No. 6, pp. 427–432 (1985).

L. Yun et al., Yaoxue Xuebao, vol. 19, No. 9, pp. 671–675 (1984).

B. GE et al., Yaoxue Xuebao, vol. 20, No. 6, pp. 427–432 (1985).

\* cited by examiner

BENZOPIPERIDINE DERIVATIVES

This application is the national phase under 35 U.S.C. §371 of prior PCT International Application No. PCT/JP97/02787 which has an International filing date of Aug. 8, 1997 which designated the United States of America.

BACKGROUND OF THE INVENTION

1. Field of the Invention

This invention relates to benzopiperidine derivatives, salts thereof or hydrates thereof, which are useful in the prevention and treatment of immunologic diseases, etc., drugs containing the same, processes for producing the same and intermediates thereof.

2. Prior Art

In recent years, the participation adhesion molecules such as ICAM-1, VCAM-1 and E-selectin participate in the processes of extravascular infiltration of leukocytes into inflammatory tissues, metastasis of cancer cells, recognition of antigens by immunocytes and proliferation of immunocytes has come to be regarded as highly important. For example, rheumatoid arthritis is actually associated with the promoted expression of adhesion molecules in joints, the infiltration of lymphocytes into joint synovial membranes and neutrophil infiltration into the synovial fluid. It has been also reported that adhesion molecules participate in asthma, nephritis, ischemic reflow disorders, psoriasis, atopic dermatitis, the rejection reaction accompanying organ transplantation, and cancer metastasis. Therefore, it is expected that the inflammatory immunologic diseases such as asthma, nephritis, psoriasis, atopic dermatitis, inflammation, ischemic reflow disorders and the rejection reaction accompanying organ transplantation, autoimmune diseases such as rheumatism and collagen disease, and cancer metastasis can be inhibited by regulating the adhesion of leukocytes, neutrophilis, cancer cells, etc. to intravascular endothelial cells and controlling the antigen recognition process.

When treating various inflammatory diseases and immune diseases such as rheumatoid arthritis, it has been a common practice to suppress the inflammation by the use of nonsteroidal antiinflammatory drugs (NSAID) such as indomethacin and ibuprofen, and steroids, i.e., "symptomatic treatments".

Recently, attempts have been also made to use immunomodulators such as D-penicillamine which is a remedy for rheumatism and Wilson's disease, and levamisole which is an immunopotentiator activating T cells, in order to ameliorate immunopathy at the early stage, i.e., "causal treatments".

However, NSAIDs such as indomethacin have serious side effects such as gastric ulceration. Moreover, it is considered that these drugs are not efficacious against tissue disorders or the pathological progression associated with chronic inflammation. With respect to steroids too, the problem of serious side effects frequently arises.

On the other hand, hitherto no immunomodulator has been known satisfactory both in its therapeutic effects and side effects. Accordingly, the development of excellent drugs suitable for both symptomatic and causal treatments has been urgently required.

As compounds having similar structures to those of the compounds of the present invention, it was disclosed in JP-A-60-115524 that 1,4-diazaphenothiazine derivatives have 5-lipoxygenase inhibitory effects. However, this patent provides few examples, despite its broad claims. That is to say, the claims thereof are not clearly supported by the description in the specification.

Furthermore, the above-mentioned patent neither states nor suggests that these compounds are efficacious in the prevention and treatment of various diseases owing to the cell adhesion inhibitory effects thereof, as clarified in the present invention.

On the other hand, compounds analogous to the compounds of the present invention are reported as nerve relaxants in J. Med. Chem., 16 (4), 564 (1983) and as antibacterial agents, insecticides and herbicides in U.S. Pat. Nos. 3,663,543, 3,746,707, 3,808,208, 3,821,213 and 3,845,044.

SUMMARY OF THE INVENTION

The present inventors have conducted extensive studies in order to provide drugs efficacious in the prevention and treatment of these various inflammatory diseases and immunologic diseases such as rheumatoid arthritis, atopic dermatitis, psoriasis, asthma and the rejection reaction accompanying organ transplantation. As a result, they have succeeding in discovering that benzopiperidine derivatives with novel structures have excellent antiinflammatory and anti-immunologic disease effects, thus completing the present invention.

Accordingly, the present invention relates to benzopiperidine derivatives represented by the following formula (I), salts thereof or hydrates thereof, processes for producing the same and drugs comprising the same:

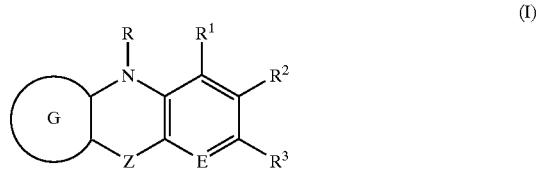

(I)

wherein $R^1$ to $R^3$ may be the same or different and each represents:

1) hydrogen,
2) optionally substituted lower alkyl;
3) optionally substituted lower alkenyl;
4) optionally substituted lower alkynyl;
5) optionally substituted lower cycloalkyl;
6) optionally substituted lower cycloalkenyl;
7) optionally substituted $C_{2-6}$ alkoxy;
8) a group represented by the following formula:

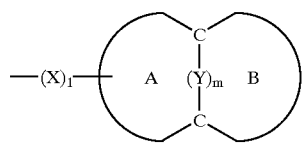

wherein X and Y represent each optionally substituted lower alkylene optionally having a heteroatom, optionally substituted lower alkenylene optionally having a heteroatom or optionally substituted lower alkynylene optionally having a heteroatom; l and m may be the same or different and each represents 0 or 1; the ring A represents an optionally substituted cycloalkyl ring optionally having one or more heteroatoms; the ring B represents a ring optionally having one or more double bonds in the ring which is selected from owing following:
a) an optionally substituted cycloalkyl ring optionally having a heteroatom;
b) an optionally substituted bicycloalkyl ring optionally having a heteroatom, wherein the different atoms (bridgehead atoms) in the ring B are bonded to each other via an optionally substituted $C_1$ or higher alkylene group optionally having a heteroatom; or
c) an optionally substituted spiro-hydrocarbon ring optionally having a heteroatom, wherein the both ends of an optionally substituted $C_1$ or higher alkylene group optionally having a heteroatom are bonded to a carbon atom (bridgehead carbon atom) in the ring B;

9) a group represented by the following formula:

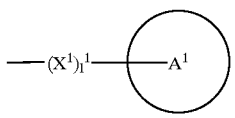

wherein
$X^1$ represents an optionally substituted lower alkylene optionally having a heteroatom, optionally substituted lower alkenylene optionally having a heteroatom or optionally substituted lower alkynylene optionally having a heteroatom;
$l^1$ is 0 or 1;
the ring $A^1$ represents:
  a) an optionally substituted cycloalkyl ring optionally having one or more heteroatoms;
  b) an optionally substituted cycloalkenyl ring optionally having one or more heteroatoms; or
  c) an optionally substituted spiro-hydrocarbon ring optionally having a heteroatom, wherein the both ends of an optionally substituted $C_1$ or higher alkylene group optionally having a heteroatom are bonded to a carbon atom (bridgehead carbon atom) in the ring $A^1$; or 10) a group represented by the following formula:

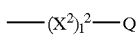

wherein
$X^2$ represents an optionally substituted lower alkylene optionally having a heteroatom, optionally substituted lower alkenylene optionally having a heteroatom or optionally substituted lower alkynylene optionally having a heteroatom;
$l^2$ is 0 or 1;
Q represents:
  a) heteroaryl consisting of one or more optionally substituted rings or aryl consisting of one or more optionally substituted rings;
  b) optionally substituted quaternary ammonio;
  c) a group represented by the following formula:

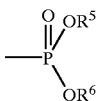

wherein $R^5$ and $R^6$ may be the same or different and each represents hydrogen or lower alkyl;
d) lower acyl;
e) lower acyloxy;
f) carbamoyl;
g) a group represented by the following formula:

wherein $R^7$ and $R^8$ may be the same or different and each represents hydrogen, lower alkyl, a group represented by the formula:

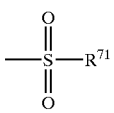

wherein $R^{71}$ represents lower alkyl, trifluoromethyl, aryl or a group represented by the formula:

wherein $R^{72}$ and $R^{73}$ may be the same or different and each represents hydrogen, lower alkyl, lower cycloalkyl or aryl;
a group represented by the following formula:

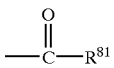

wherein $R^{81}$ represents hydrogen, lower alkyl or aryl;
a group represented by the following formula:

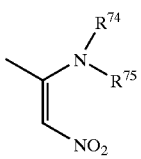

wherein $R^{74}$ and $R^{75}$ may be the same or different and each represents hydrogen or lower alkyl;
a group represented by the following formula:

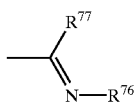

wherein $R^{76}$ represents hydrogen, lower alkyl, cyano, pyridyl or lower alkylsulfonyl; $R^{77}$ represents hydrogen or lower alkyl, or an amino protecting group;
h) protected hydroxy;
i) a group represented by the following formula:

wherein $R^{82}$ represents hydrogen, lower alkyl or a mercapto protecting group;
j) carboxy;
k) protected carboxy;
l) a group represented by the following formula:

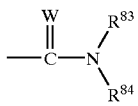

wherein W represents oxygen or sulfur; $R^{83}$ and $R^{84}$ may be the same or different and each represents hydrogen, lower alkyl, lower cycloalkyl, cyano, aryl or a group represented by the following formula:

wherein $R^{85}$ represents hydrogen, hydroxy, lower alkyl or aryl; or $R^{83}$ and $R^{84}$ may together form an optionally substituted lower cycloalkyl optionally having one or more heteroatoms;
m) sulfonyl;
n) sulfonylamido;
o) azido;
p) formyl;
q) a group represented by the following formula:

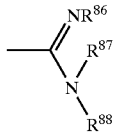

wherein $R^{86}$, $R^{87}$ and $R^{88}$ may be the same or different and each represents hydrogen, aryl, heteroaryl, optionally substituted lower alkyl, hydroxy(lower alkyl), cyano, amino, nitro, acetyl or a group represented by the following formula:

wherein $R^{89}$ represents aryl, hydroxy, optionally substituted lower alkyl, trifluoromethyl or amino; or $R^{86}$ and $R^{87}$ may together form an optionally substituted lower cycloalkyl optionally having one or more heteroatoms;
r) guanidino;
s) hydrazino;
t) isocyano;
u) cyanate;
v) isocyanate;
w) thiocyanate;
x) isothiocyanate;
y) nitroso; or
z) a group represented by the following formula:

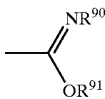

wherein $R^{90}$ and $R^{91}$ each represents hydrogen or lower alkyl, provided that the case where $R^1$ to $R^3$ each represents methyl in the case 2) of the above definition thereof is excluded;
R represents:
1) hydrogen;
2) lower alkyl;
3) optionally substituted arylalkyl;
4) optionally substituted heteroarylalkyl;
5) an amino protecting group;
6) a group represented by the following formula:

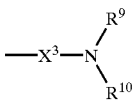

wherein $X^3$ represents an optionally substituted lower alkylene optionally having a heteroatom, optionally substituted lower alkenylene optionally having a heteroatom or optionally substituted lower alkynylene optionally having a heteroatom; $R^9$ and $R^{10}$ may be the same or different and each represents hydrogen, lower alkyl or an amino protecting group; or
7) a group represented by the following formula:

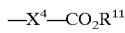

wherein $X^4$ represents optionally substituted lower alkylene optionally having a heteroatom, optionally substituted lower alkenylene optionally having a heteroatom or optionally substituted lower alkynylene optionally having a heteroatom; $R^{11}$ represents hydrogen, lower alkyl or a carboxyl protecting group;
E represents N or a group represented by the following formula:

wherein $R^4$ has the same meaning as 1 to 11) as defined above with respect to $R^1$ to $R^3$;
Z represents O, S, SO, $SO_2$ or a group represented by the following formula:

wherein $R^{12}$ represents hydrogen, lower alkyl or an amino protecting group;
the ring G represents an optionally substituted heteroaryl ring having one or more nitrogen atoms;

provided that the following cases are excluded:
a) that in which $R^1$ to $R^3$ are each hydrogen, E is CH, Z is O, S, or $SO_2$ and the ring G is an unsubstituted (i.e., all of the substituents being hydrogen atoms) heteroaryl ring having one or more nitrogen atoms;
b) that in which $R^1$ to $R^3$ are each hydrogen, E is CH, Z is O, S, $SO_2$ or NH and the substituent(s) of the ring G is optionally substituted phenyl, pyridinyl, thienyl, nitro, cyano, halogeno, acetyl, methyl, ethyl, t-butyl, ethoxy, N-methylpiperazyl, naphthyl, optionally protected carboxyalkyl or amino;
c) that in which $R^1$ to $R^3$ are each hydrogen, E is CH, Z is NH and the ring G is unsubstituted (i.e., all of the substituents are hydrogen atoms) pyridazine; and
d) that in which $R^1$ to $R^3$ are each hydrogen, E is CH, R is a group other than hydrogen, Z is $NR^{12'}$ ($R^{12'}$ being lower alkyl or an amino protecting group) and the ring G is an optionally substituted heteroaryl ring optionally having one or more nitrogen atoms.

Now, the contents of the present invention will be described in detail.

Although the contents of the present invention are as has been described above, the invention preferably relates to benzopiperidine derivatives of the above formula (I), wherein Z is S, salts thereof or hydrates thereof, processes for producing the same and drugs comprising the same, and benzopiperidine derivatives of the above formula (I), wherein the ring G is an optionally substituted pyrazine ring, salts thereof or hydrates thereof, processes for producing the same and drugs comprising the same. Still more preferably, the invention relates to benzopiperidine derivatives represented by the following formula (II), salts thereof or hydrates thereof, processes for producing the same and drugs comprising the same:

(II)

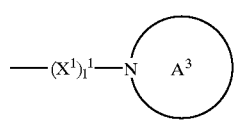

wherein
R, E, Z and the ring G are each as defined above;
U represents:
1) a group represented by the following formula:

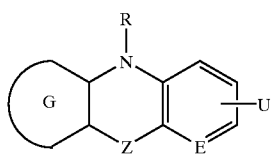

wherein X, Y, l, m and the rings A and B are each as defined above; or
2) a group represented by the following formula:

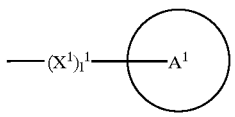

wherein $X^1$, $l^1$ and the ring $A^1$ are each as defined above.

Still more preferably, the invention relates to benzopiperidine derivatives represented by the above formula (II), salts thereof or hydrates thereof, processes for producing the same and drugs comprising the same, wherein U in the formula (II) represents:
1) a group represented by the following formula:

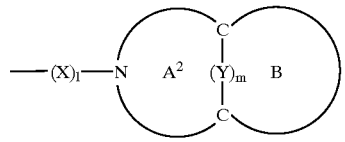

wherein
X, Y, l, m and the ring B are each as defined above; and
the ring $A^2$ represents an optionally substituted cycloalkyl ring having one or more heteroatoms; or
2) a group represented by the following formula:

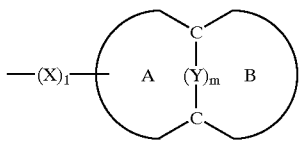

wherein
$X^1$ and $l^1$ are each as defined above; and
the ring $A^3$ represents:
a) an optionally substituted cycloalkyl ring having one or more heteroatoms;
b) an optionally substituted cycloalkenyl ring having one or more heteroatoms; or
c) an optionally substituted spiro-hydrocarbon ring having one or more heteroatoms, wherein both ends of an optionally substituted C. or higher alkylene group optionally having a heteroatom are bonded to a carbon atom (bridgehead carbon atom) in the ring $A^3$. Particularly preferably, it relates to benzopiperidine derivatives represented by the following formula (III), salts thereof or hydrates thereof, processes for producing the same and drugs comprising the same:

(III)

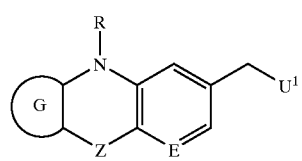

wherein
R, E, Z and the ring G are each as defined above;
$U^1$ represents:
1) a group represented by the following formula:

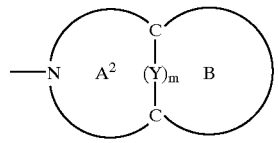

wherein Y, m and the rings $A^2$ and B are each as defined above; or
2) a group represented by the following formula:

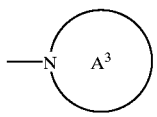

wherein the ring $A^3$ is as defined above. Still preferably, the invention relates to benzopiperidine derivatives represented by the following formula (II) or (III), wherein the ring G is an optionally substituted pyrazine ring, salts thereof or hydrates thereof, processes for producing the same and drugs comprising the same. In the most desirable case, the present invention relates to a benzopiperidine derivative selected from among those represented by the following formulae 1) to 3), its salt or hydrates thereof, a process for producing the same and drugs comprising the same:

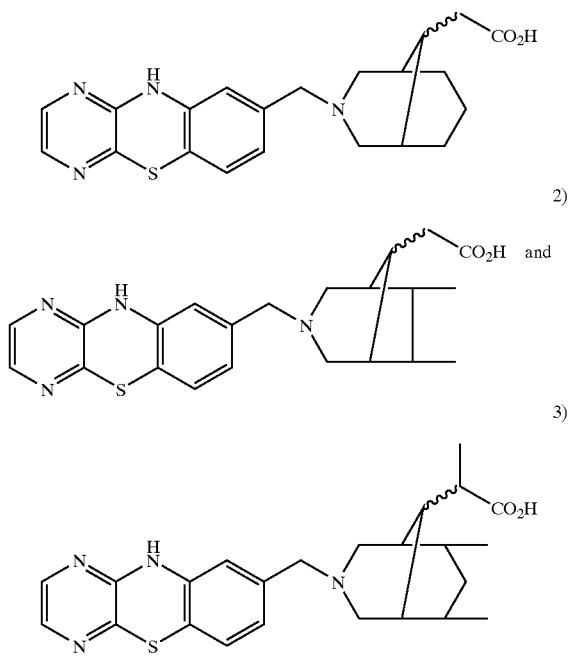

Although compounds are sometimes given as particular isomers in structural formulae herein for the sake of convenience, the compounds of the present invention are not restricted to the structural formulae given for the sake of convenience but involve all of the isomers and isomeric mixtures such as geometrical isomers occurring structurally, optical isomers depending on asymmetric carbon, stereoisomers and tautomers.

Next, the terms employed herein will be described in detail.

First, the definition of the formula (I) will be illustrated. $R^1$ to $R^4$ are each as defined above. ($R^4$, which is a group defined in E and having the same meaning as those of $R^1$ to $R^3$, is illustrated together with $R^1$ to $R^3$ herein).

The expression "optionally substituted" as used herein particularly means that the corresponding group may be substituted by substituent(s), for example, hydroxy; thiol; nitro; nitroso; morpholino; thiomorpholino; halogeno such as fluoro, bromo and iodo; nitrile; isocyano; cyanate; isocyanate; thiocyanate; isothiocyanate; azido; formyl; thioformyl; alkyl such as methyl, ethyl, propyl, isopropyl and butyl; alkenyl such as vinyl, allyl and propenyl; alkynyl such as ethynyl, butynyl and propargyl; alkoxy corresponding to lower alkyl such as methoxy, ethoxy, propoxy and butoxy; halogenoalkyl such as fluoromethyl, difluoromethyl, trifluoromethyl and fluoroethyl; hydroxyalkyl such as hydroxymethyl, hydroxyethyl and hydroxypropyl; guanidino; hydrazino; hydraozono; ureido; ureylene; amidino; formimidoyl; acetimidoyl; carbamoyl; thiocarbamoyl; carbamoylalkyl such as carbamoylmethyl and carbamoylethyl; alkylcarbamoyl such as methylcarbamoyl and dimethylcarbamoyl; carbamido; sulfoamino; sulfamoyl; sulfamoylalkyl such as sulfamoylmethyl and sulfamoylethyl; alkylsulfamoyl such as methylsulfamoyl and dimethylsulfamoyl; sulfamido; N-alkylsulfamido such as N-methylsulfamido and N-ethylsulfamido; arylsulfamido such as N-phenylsulfamido; alkanoyl such as acetyl, propionyl and butyryl; thioacetyl; amino; hydroxyamino; alkylamino such as methylamino, ethylamino and isopropylamino; dialkylamino such as dimethylamino, methylethylamino and diethylamino; acylamino such as acetylamino and benzoylamino; aminoalkyl such as aminomethyl, aminoethyl and aminopropyl; carboxy; alkoxycarbonyl such as methoxycarbonyl, ethoxycarbonyl and propoxycarbonyl; alkoxycarbonylalkyl such as methoxycarbonylmethyl, ethoxycarbonylmethyl, propoxycarbonylmethyl, methoxycarbonylethyl, ethoxycarbonylethyl and propoxycarbonylethyl; alkyloxyalkyl such as methyloxymethyl, methyloxyethyl, ethyloxymethyl and ethyloxyethyl; alkylthioalkyl such as methylthiomethyl, methylthioethyl, ethylthiomethyl and ethylthioethyl; aminoalkylaminoalkyl such as aminomethylaminomethyl and aminoethylaminomethyl; alkylcarbonyloxy such as methylcarbonyloxy, ethylcarbonyloxy and isopropylcarbonyloxy; arylalkoxyalkoxyalkyl such as oxymethyl and benzyloxyethyloxyethyl; hydroxyalkoxyalkyl such as hydroxyethyloxymethyl and hydroxyethyloxyethyl; arylalkoxyalkyl such as benzyloxymethyl, benzyloxyethyl and benzyloxypropyl; quaternary ammonio such as trimethylammonio, methylethylmethylammonio and triethylammonio; cycloalkyl such as cyclopropyl, cyclobutyl, cyclopentyl and cyclohexyl; cycloalkenyl such as cyclopropenyl, cyclobutenyl, cyclopentenyl and cyclohexenyl; aryl such as phenyl, pyridinyl, thienyl, furyl and pyrrolyl; alkylthio such as methylthio, ethylthio, propylthio and butylthio; arylthio such as phenylthio, pyridinylthio, thienylthio, furylthio and pyrrolylthio; aryl(lower alkyl) such as benzyl, trityl and dimethoxytrityl; sulfonyl and substituted sulfonyl such as mesyl and p-toluenesulfonyl; sulfinyl and substituted sulfinyl such as methylsulfinyl, ethylsulfinyl and phenylsulfinyl; sulfenyl and substituted sulfenyl such as methylsulfenyl, ethylsulfenyl and phenylsulfenyl; aryloyl such as benzoyl, toluoyl and cinnamoyl; halogenoaryl such as fluorophenyl and bromophenyl; and oxyalkoxy such as methylenedioxy.

The expression "having one or more substituents" means that the corresponding group may have an arbitrary combination of these substituents. For example, the present invention involves alkyl, alkenyl, alkynyl, alkoxy, etc. substituted by hydroxy, thiol, nitro, morpholino, thiomorpholino, halogeno, nitrile, azido, formyl, ammonio, alkylamino, dialkylamino, carbamoyl, sulfonyl, etc.

The expression "optionally substituted" as used herein below has the meaning as defined above.

The term "lower alkyl group" means a linear or branched $C_{1-6}$ alkyl group. Particular examples thereof include methyl [methyl being excluded from the definition 2) of $R^1$ to $R^4$], ethyl, n-propyl, i-propyl, n-butyl, i-butyl, sec-butyl, t-butyl, n-pentyl, i-pentyl, sec-pentyl, t-pentyl, neopentyl, 1-methylbutyl, 2-methylbutyl, 1,1-dimethylpropyl, 1,2-dimethylpropyl, n-hexyl, i-hexyl, 1-methylpentyl, 2-methylpentyl, 3-methylpentyl, 1,1-dimethylbutyl, 1,2- dimethylbutyl, 2,2,-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl groups. Preferable examples thereof include methyl, ethyl, n-propyl, i-propyl, n-butyl, i-butyl, sec-butyl, t-butyl, n-pentyl, i-pentyl, sec-pentyl, t-pentyl, neopentyl, 1-methylbutyl, 2-methylbutyl, 1,1-dimethylpropyl, 1,2-dimethylpropyl, n-hexyl and i-hexyl groups. Still more preferable ones are methyl, ethyl, n-propyl, i-propyl, n-butyl, i-butyl, sec-butyl and t-butyl groups and the most desirable ones are methyl, ethyl, n-propyl and i-propyl groups.

The term "lower alkenyl group" means a linear or branched $C_{1-6}$ alkenyl group which is the residue of a compound having a double bond in the above-mentioned alkyl group. Particular examples thereof include ethenyl, 1-propen-1-yl, 2-propen-1-yl, 3-propen-1-yl, 1-buten-1-yl, 1-buten-2-yl, 1-buten-3-yl, 1-buten-4-yl, 2-buten-1-yl, 2-buten-2-yl, 1-methyl-1-propen-1-yl, 2-methyl-1-propen-1-yl, 1-methyl-2-propen-1-yl, 2-methyl-2-propen-1-yl, 1-methyl-1-buten-1-yl, 2-methyl-1-buten-1-yl, 3-methyl-1-buten-1-yl, 1-methyl-2-buten-1-yl, 2-methyl-2-buten-1-yl, 3-methyl-2-buten-1-yl, 1-methyl-3-buten-1-yl, 2-methyl-3-buten-1-yl, 3-methyl-3-buten-1-yl, 1-ethyl-1-buten-1-yl, 2-ethyl-1-buten-1-yl, 3-ethyl-1-buten-1-yl, 1-ethyl-2-buten-1-yl, 2-ethyl-2-buten-1-yl, 3-ethyl-2-buten-1-yl, 1-ethyl-3-buten-1-yl, 2-ethyl-3-buten-1-yl, 3-ethyl-3-buten-1-yl, 1,1-dimethyl-1-buten-1-yl, 1,2-dimethyl-1-buten-1-yl, 1,3-dimethyl-1-buten-1-yl, 2,2-dimethyl-1-buten-1-yl, 3,3-dimethyl-1-buten-1-yl, 1,1-dimethyl-2-buten-1-yl, 1,2-dimethyl-2-buten-1-yl, 1,3-dimethyl-2-buten-1-yl, 2,2-dimethyl-2-buten-1-yl, 3,3-dimethyl-2-buten-1-yl, 1,1-dimethyl-3-buten-1-yl, 1,2-dimethyl-3-buten-1-yl, 1,3-dimethyl-3-buten-1-yl, 2,2-dimethyl-3-buten-1-yl, 3,3-dimethyl-3-buten-1-yl, 1-penten-1-yl, 2-penten-1-yl, 3-penten-1-yl, 4-penten-1-yl, 1-penten-2-yl, 2-penten-2-yl, 3-penten-2-yl, 4-penten-2-yl, 1-penten-3-yl, 2-penten-3-yl, 1-penten-1-yl, 2-penten-1-yl, 3-penten-1-yl, 4-penten-1-yl, 1-penten-2-yl, 2-penten-2-yl, 3-penten-2-yl, 4-penten-2-yl, 1-penten-3-yl, 2-penten-3-yl, 1-methyl-1-penten-1-yl, 2-methyl-1-penten-1-yl, 3-methyl-1-penten-1-yl, 4-methyl-1-penten-1-yl, 1-methyl-2-penten-1-yl, 2-methyl-2-penten-1-yl, 3-methyl-2-penten-1-yl, 4-methyl-2-penten-1-yl, 1-methyl-3-penten-1-yl, 2-methyl-3-penten-1-yl, 3-methyl-3-penten-1-yl, 4-methyl-3-penten-1-yl, 1-methyl-4-penten-1-yl, 2-methyl-4-penten-1-yl, 3-methyl-4-penten-1-yl, 4-methyl-4-penten-1-yl, 1-methyl-1-penten-2-yl, 2-methyl-1-penten-2-yl, 3-methyl-1-penten-2-yl, 4-methyl-1-penten-2-yl, 1-methyl-2-penten-2-yl, 2-methyl-2-penten-2-yl, 3-methyl-2-penten-2-yl, 4-methyl-2-penten-2-yl, 1-methyl-3-penten-2-yl, 2-methyl-3-penten-2-yl, 3-methyl-3-penten-2-yl, 4-methyl-3-penten-2-yl, 1-methyl-4-penten-2-yl, 2-methyl-4-penten-2-yl, 3-methyl-4-penten-2-yl, 4-methyl-4-penten-2-yl, 1-methyl-1-penten-3-yl, 2-methyl-1-penten-3-yl, 3-methyl-1-penten-3-yl, 4-methyl-1-penten-3-yl, 1-methyl-2-penten-3-yl, 2-methyl-2-penten-3-yl, 3-methyl-2-penten-3-yl, 4-methyl-2-penten-3-yl, 1-hexen-1-yl, 1-hexen-2-yl, 1-hexen-3-yl, 1-hexen-4-yl, 1-hexen-5-yl, 1-hexen-6-yl, 2-hexen-1-yl, 2-hexen-2-yl, 2-hexen-3-yl, 2-hexen-4-yl, 2-hexen-5-yl, 2-hexen-6-yl, 3-hexen-1-yl, 3-hexen-2-yl and 3-hexen-3-yl groups. Preferable examples thereof include ethenyl, 1-propen-1-yl, 2-propen-1-yl, 3-propen-1-yl, 1-buten-1-yl, 1-buten-2-yl, 1-buten-3-yl, 1-buten-4-yl, 2-buten-1-yl, 2-buten-2-yl, 1-methyl-1-propen-1-yl, 2-methyl-1-propen-1-yl, 1-methyl-2-propen-1-yl, 2-methyl-2-propen-1-yl, 1-methyl-1-buten-1-yl, 2-methyl-1-buten-1-yl, 3-methyl-1-buten-1yl, 1-methyl-2-buten-1-yl, 2-methyl-2-buten-1-yl, 3-methyl-2-buten-1-yl, 1-methyl-3-buten-1-yl, 2-methyl-3-buten-1-yl, 3-methyl-3-buten-1-yl, 1-ethyl-1-buten-1-yl, 2-ethyl-1-buten-1-yl, 3-ethyl-1-buten-1-yl, 1-ethyl-2-buten-1-yl, 2-ethyl-2-buten-1-yl, 3-ethyl-2-buten-1-yl, 1-ethyl-3-buten-1-yl, 2-ethyl-3-buten-1-yl, 3-ethyl-3-buten-1-yl, 1,1-dimethyl-1-buten-1-yl, 1,2-dimethyl-1-buten-1-yl, 1,3-dimethyl-1-buten-1-yl, 2,2-dimethyl-1-buten-1-yl, 3,3-dimethyl-1-buten-1-yl, 1,1-dimethyl-2-buten-1-yl, 1,2-dimethyl-2-buten-1-yl, 1,3-dimethyl-2-buten-1-yl, 2,2-dimethyl-2-buten-1-yl, 3,3-dimethyl-2-buten-1-yl, 1,1-dimethyl-3-buten-1-yl, 1,2-dimethyl-3-buten-1-yl, 1,3-dimethyl-3-buten-1-yl, 2,2-dimethyl-3-buten-1-yl and 3,3-dimethyl-3-buten-1-yl groups. Still more preferable ones are ethenyl, 1-propen-1-yl, 2-propen-1-yl, 3-propen-1-yl, 1-buten-1-yl, 1-buten-2-yl, 1-buten-3-yl, 1-buten-4-yl, 2-buten-1-yl, 2-buten-2-yl, 1-methyl-1-propen-1-yl, 2-methyl-1-propen-1-yl, 1-methyl-2-propen-1-yl, 2-methyl-2-propen-1-yl, 1-methyl-1-buten-1-yl, 2-methyl-1-buten-1-yl, 3-methyl-1-buten-1-yl, 1-methyl-2-buten-1-yl, 2-methyl-2-buten-1-yl, 3-methyl-2-buten-1-yl, 1-methyl-3-buten-1-yl, 2-methyl-3-buten-1-yl and 3-methyl-3-buten-1-yl groups. The most desirable ones are ethenyl, 1-propen-1-yl, 2-propen-1-yl, 3-propen-1-yl, 1-buten-1-yl, 1-buten-2-yl, 1-buten-3-yl, 1-buten-4-yl, 2-buten-1-yl and 2-buten-2-yl groups.

The term "lower alkynyl group" means a linear or branched $C_{1-6}$ alkynyl group which is the residue of a compound having a triple bond in the above-mentioned alkyl group. Particular examples thereof include ethynyl, 1-propyn-1-yl, 2-propyn-1-yl, 3-propyn-1-yl, 1-butyn-1-yl, 1-butyn-2-yl, 1-butyn-3-yl, 1-butyn-4-yl, 2-butyn-1-yl, 2-butyn-2-yl, 1-methyl-1-propyn-1-yl, 2-methyl-1-propyn-1-yl, 1-methyl-2-propyn-1-yl, 2-methyl-2-propyn-1-yl, 1-methyl-1-butyn-1-yl, 2-methyl-1-butyn-1-yl, 3-methyl-1-butyn-1-yl, 1-methyl-2-butyn-1-yl, 2-methyl-2-butyn-1-yl, 3-methyl-2-butyn-1-yl, 1-methyl-3-butyn-1-yl, 2-methyl-3-butyn-1-yl, 3-methyl-3-butyn-1-yl, 1-ethyl-1-butyn-1-yl, 2-ethyl-1-butyn-1-yl, 3-ethyl-1-butyn-1-yl, 1-ethyl-2-butyn-1-yl, 2-ethyl-2-butyn-1-yl, 3-ethyl-2-butyn-1-yl, 1ethyl-3-butyn-1-yl, 2-ethyl-3-butyn-1-yl, 3-ethyl-3-butyn-1-yl, 1,1dimethyl-1-butyn-1-yl, 1,2-dimethyl-1-butyn-1-yl, 1,3-dimethyl-1-butyn-1-yl, 2,2-dimethyl-1-butyn-1-yl, 3,3-dimethyl-1-butyn-1-yl, 1,1-dimethyl-2-butyn-1-yl, 1,2-dimethyl-2-butyn-1-yl, 1,3-dimethyl-2-butyn-1-yl, 2,2-dimethyl-2-butyn-1-yl, 3,3-dimethyl-2-butyn-1-yl, 1,1-dimethyl-3-butyn-1-yl, 1,2-dimethyl-3-butyn-1-yl, 1,3-dimethyl-3-butyn-1-yl, 2,2-dimethyl-3-butyn-1-yl, 3,3-dimethyl-3-butyn-1-yl, 1-pentyn-1-yl, 2-pentyn-1-yl, 3-pentyn-1-yl, 4-pentyn-1-yl, 1-pentyn-2-yl, 2-pentyn-2-yl, 3-pentyn-2-yl, 4-pentyn-2-yl, 1-pentyn-3-yl, 2-pentyn-3-yl, 1-pentyn-1-yl, 2-pentyn-1-yl, 3-pentyn-1-yl, 4-pentyn-1-yl, 1-pentyn-2-yl, 2-pentyn-2-yl, 3-pentyn-2-yl, 4-pentyn-2-yl, 1-pentyn-3-yl, 2-pentyn-3-yl, 1-methyl-1-pentyn-1-yl, 2-methyl-1-pentyn-1-yl, 3-methyl-1-pentyn-1-yl, 4-methyl-1-pentyn-1-yl, 1-methyl-2-pentyn-1-yl, 2-methyl-2-pentyn-1-yl, 3-methyl-2-pentyn-1-yl, 4-methyl-2-pentyn-1-yl, 1-methyl-3-pentyn-1-yl, 2-methyl-3-pentyn-1-yl, 3-methyl-3-pentyn-1-yl, 4-methyl-3-pentyn-1-yl, 1-methyl-4-pentyn-1-yl, 2-methyl-4-pentyn-1-yl, 3-methyl-4-pentyn-1-yl, 4-methyl-4-pentyn-1-yl, 1-methyl-1-pentyn-2-yl, 2-methyl-1-pentyn-2-yl, 3-methyl-1-pentyn-2-yl, 4-methyl-1-pentyn-2-yl, 1-methyl-2-pentyn-2-yl, 2-methyl-2-pentyn-2-yl, 3-methyl-2-pentyn-2-yl, 4-methyl-2-pentyn-2-yl, 1-methyl-3-pentyn-2-yl, 2-methyl-3-pentyn-2-yl, 3-methyl-3-pentyn-2-yl, 4-methyl-3-pentyn-2-yl, 1-methyl-4-pentyn-2-yl, 2-methyl-4-pentyn-2-yl, 3-methyl-4-pentyn-2-yl, 4-methyl-4-pentyn-2-yl, 1-methyl-1-pentyn-3-yl, 2-methyl-1-pentyn- 3-yl, 3-methyl-1-pentyn-3-yl, 4-methyl-1-pentyn-3-yl, 1-methyl-2-pentyn-3-yl, 2-methyl-2-pentyn-3-yl, 3-methyl-2-pentyn-3-yl, 4-methyl-2-pentyn-3-yl, 1-hexyn-1-yl, 1-hexyn-2-yl, 1-hexyn-3-yl, 1-hexyn-4-yl, 1-hexyn-5-yl, 1-hexyn-6-yl, 2-hexyn-1-yl, 2-hexyn-2-yl, 2-hexyn-3-yl, 2-hexyn-4-yl, 2-hexyn-5-yl, 2-hexyn-6-yl, 3-hexyn-1-yl, 3-hexyn-2-yl and 3-hexyn-3-yl groups. Preferable examples thereof include ethynyl, 1-propyn-1-yl, 2-propyn-1-yl, 3-propyn-1-yl, 1-butyn-1-yl, 1-butyn-2-yl, 1-butyn-3-yl, 1-butyn-4-yl, 2-butyn-1-yl, 2-butyn-2-yl, 1-methyl-1-propyn-1-yl, 2-methyl-1-propyn-1-yl, 1-methyl-2-propyn-1-yl, 2-methyl-2-propyn-1-yl, 1-methyl-1-butyn-1-yl, 2-methyl-1-butyn-1-yl, 3-methyl-1-butyn-1-yl, 1-methyl-2-butyn-1-yl, 2-methyl-2-butyn-1-yl, 3-methyl-2-butyn-1-yl, 1-methyl-3-butyn-1-yl, 2-methyl-3-butyn-1-yl, 3-methyl-3-butyn-1-yl, 1-ethyl-1-butyn-1-yl, 2-ethyl-1-butyn-1-yl, 3-ethyl-1-butyn-1-yl, 1-ethyl-2-butyn-1-yl, 2-ethyl-2-butyn-1-yl, 3-ethyl-2-butyn-1-yl, 1-ethyl-3-butyn-1-yl, 2-ethyl-3-butyn-1-yl, 3-ethyl-3-butyn-1-yl, 1,1-dimethyl-1-butyn-1-yl, 1,2-dimethyl-1-butyn-1-yl, 1,3-dimethyl-1-butyn-1-yl, 2,2-dimethyl-1-butyn-1-yl, 3,3-dimethyl-1-butyn-1-yl, 1,1-dimethyl-2-butyn-1-yl, 1,2-dimethyl-2-butyn-1-yl, 1,3-dimethyl-2-butyn-1-yl, 2,2-dimethyl-2-butyn-1-yl, 3,3-dimethyl-2-butyn-1-yl, 1,1-dimethyl-3-butyn-1-yl, 1,2-dimethyl-3-butyn-1-yl, 1,3-dimethyl-3-butyn-1-yl, 2,2-dimethyl-3-butyn-1-yl and 3,3-dimethyl-3-butyn-1-yl groups. Still preferable ones are ethynyl, 1-propyn-1-yl, 2-propyn-1-yl, 3-propyn-1-yl, 1-butyn-1-yl, 1-butyn-2-yl, 1-butyn-3-yl, 1-butyn-4-yl, 2-butyn-1-yl, 2-butyn-2-yl, 1-methyl-1-propyn-1-yl, 2-methyl-1-propyn-1-yl, 1-methyl-2-propyn-1-yl, 2-methyl-2-propyn-1-yl, -methyl-1-butyn-1-yl, 2-methyl-1-butyn-1-yl, 3-methyl-1-butyn-1-yl, 1-methyl-2-butyn-1-yl, 2-methyl-2-butyn-1-yl, 3-methyl-2-butyn-1-yl, 1-methyl-3-butyn-1-yl, 2-methyl-3-butyn-1-yl, 2-methyl-3-butyn-1-yl and 3-methyl-3-butyn-1-yl groups. The most desirable ones are ethynyl, 1-propyn-1-yl, 2-propyn-1-yl, 3-propyn-1-yl, 1-butyn-1-yl, 1-butyn-2-yl, 1-butyn-3-yl, 1-butyn-4-yl, 2-butyn-1-yl and 2-butyn-2-yl groups.

Examples of the lower cycloalkyl group include cyclopropyl, cyclobutyl, cyclopentyl and cyclohexyl groups.

Examples of the lower cycloalkenyl group include cyclopropenyl, cyclobutenyl, cyclopentenyl and cyclohexenyl groups.

The term "$C_{2-6}$ alkoxy group" means groups corresponding to $C_{2-6}$ residues of the above-mentioned lower alkyl groups. Particular examples thereof include ethoxy, n-propoxy, i-propoxy, n-butoxy, i-butoxy, sec-butoxy, t-butoxy, n-pentyloxy, i-pentyloxy, sec-pentyloxy, t-pentyloxy, neopentyloxy, 1-methylbutoxy, 2-methylbutoxy, 1,1-dimethylpropoxy, 1,2-dimethylpropoxy, n-hexyloxy, i-hexyloxy, 1-methylpentyloxy, 2-methylpentyloxy, 3-methylpentyloxy, 1,1-dimethylbutoxy, 1,2-dimethylbutoxy, 2,2-dimethylbutoxy, 1,3-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy groups. Preferable examples thereof include ethoxy, n-propoxy, i-propoxy, n-butoxy, i-butoxy, sec-butoxy, t-butoxy, n-pentyloxy, i-pentyloxy, sec-pentyloxy, t-pentyloxy, neopentyloxy, 1-methylbutoxy, 2-methylbutoxy, 1,1-dimethylpropoxy, 1,2-dimethylpropoxy, n-hexyloxy and i-hexyloxy groups. Still more preferable examples are ethoxy, n-propoxy, i-propoxy, n-butoxy, i-butoxy, sec-butoxy and t-butoxy groups.

The term "lower alkylene group" in the definition of X and Y means a divalent group formed by eliminating one hydrogen atom from each of the carbon atoms at both ends of a linear saturated $C_{1-6}$ hydrocarbon. Particular examples thereof include methylene, ethylene, propylene, butylene, pentylene and hexylene groups. Preferable examples thereof include methylene, ethylene, propylene, butylene and pentylene groups. Methylene, ethylene, propylene and butylene groups are still more preferable and methylene, ethylene and propylene groups are further preferable therefor. Among them all, a methylene group is the most desirable.

Similarly, the term "lower alkenylene group" means a divalent group formed by eliminating one hydrogen atom from each of the carbon atoms at both ends of a linear unsaturated $C_{2-6}$ hydrocarbon. Particular examples thereof include vinylene, propenylene, butenylene, pentenylene and hexenylene groups. Preferable examples thereof include vinylene, propenylene, butenylene and pentenylene groups and vinylene, propenylene and butenylene groups are still preferable. Vinylene and propenylene groups are more preferable and a vinylene group is the most desirable.

Similarly, the term "lower alkynylene group" means a divalent group formed by eliminating one hydrogen atom from each of the carbon atoms at both ends of a linear unsaturated $C_{2-6}$ hydrocarbon. Particular examples thereof include ethynyl, propynyl, butynyl, pentynyl and hexynyl groups. Preferable examples thereof include ethynyl, propynyl, butynyl and pentynyl groups. Ethynyl, propynyl and, butynyl groups are still more preferable and ethynyl and propynyl groups are further preferable therefor. An ethynyl group is the most desirable.

l and m may be the same or different and each represents 0 or 1.

The fact that l is 0 means a compound of the following formula wherein the ring A is bonded not via "optionally substituted lower alkylene optionally having a heteroatom, optionally substituted lower alkenylene optionally having a heteroatom or optionally substituted lower alkynylene optionally having a heteroatom" represented by X but directly:

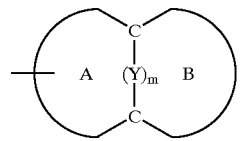

wherein Y, m and the rings A and B are each as defined above.

Similarly, the fact that m is 0 means a compound of the following formula wherein the bridgehead carbon atom of the ring A is bonded not via "optionally substituted lower alkylene optionally having a heteroatom, optionally substituted lower alkenylene optionally having a heteroatom or optionally substituted lower alkynylene optionally having a heteroatom" represented by Y but directly to the bridgehead carbon atom of the ring B:

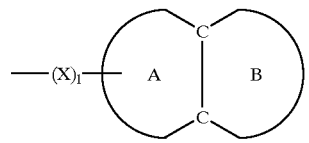

wherein X, l and the rings A and B are each as defined above.

Therefore, the fact that l and m are the same and each represents 0 means a compound of the following formula wherein the ring A is bonded not via "optionally substituted lower alkylene optionally having a heteroatom, optionally substituted lower alkenylene optionally having a heteroatom or optionally substituted lower alkynylene optionally having a heteroatom" represented by X but directly and the bridgehead carbon atom of the ring A is bonded not via "optionally substituted lower alkylene optionally having a heteroatom, optionally substituted lower alkenylene optionally having a heteroatom or optionally substituted lower alkynylene optionally having a heteroatom" represented by Y but directly to the bridgehead carbon atom of the ring B.

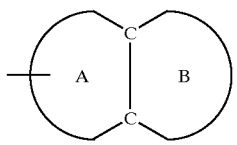

wherein the rings A and B are each as defined above.

The ring A represents an optionally substituted cycloalkyl ring optionally having one or more heteroatoms.

The term "heteroatom" as used herein means in particular oxygen, sulfur, nitrogen, phosphorus, arsenic, antimony, silicon, germanium, tin, lead, boron, mercury, etc. Preferable examples thereof include oxygen, sulfur and nitrogen atoms and a nitrogen atom is Still more preferable.

In the expression "having a heteroatom" or "optionally having a heteroatom" as used herein, the heteroatom has the meaning as defined above.

A cycloalkyl ring means a saturated monocyclic hydrocarbon. Namely, particular examples of the ring A are those represented by the following structural formulae optionally having a substituent and optionally having one or more heteroatoms:

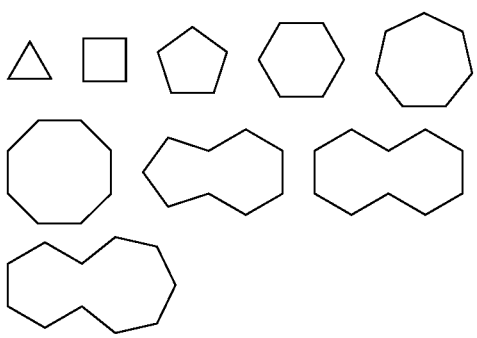

Preferable examples thereof include those represented by the following structural formulae optionally having a substituent and optionally having one or more heteroatoms:

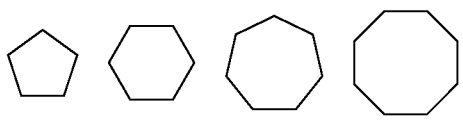

Still more preferable examples thereof include those represented by the following structural formulae optionally having a substituent and optionally having one or more heteroatoms:

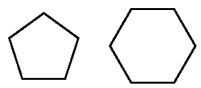

Still more preferable examples thereof include those represented by the following structural formula optionally having a substituent and optionally having one or more heteroatoms:

The most desirable one is an optionally substituted piperidine ring optionally having one or more heteroatoms.

The ring B represents a ring optionally having one or more double bonds in the ring selected from the following ones: a) an optionally substituted cycloalkyl ring optionally having a heteroatom; b) an optionally substituted bicycloalkyl ring optionally having a heteroatom wherein the different atoms (bridgehead carbon atoms) in the ring B are bonded to each other via an optionally substituted $C_1$ or higher alkylene group optionally having a heteroatom; and c) an optionally substituted spiro-hydrocarbon ring optionally having a heteroatom wherein both ends of an optionally substituted $C_1$ or higher alkylene group optionally having a heteroatom are bonded to a carbon atom (bridgehead carbon atom) in the ring B. Thus, particular examples of the ring B are those represented by the following structural formulae optionally having one or more double bond in the ring, optionally having a substituent and optionally having a heteroatom:

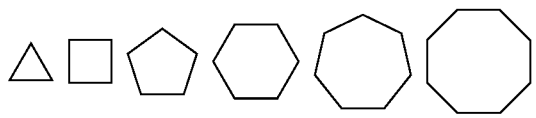
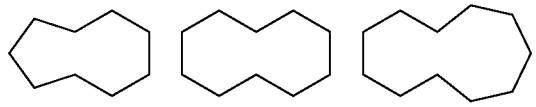
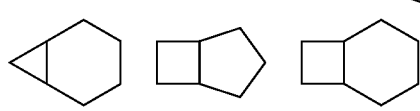
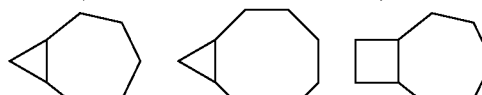
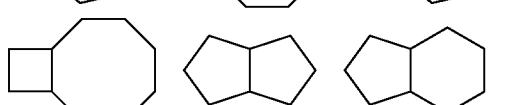
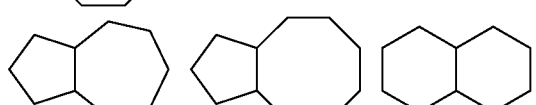
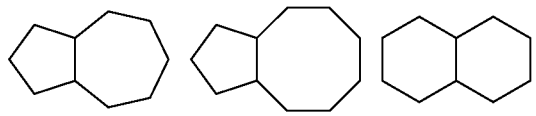

-continued
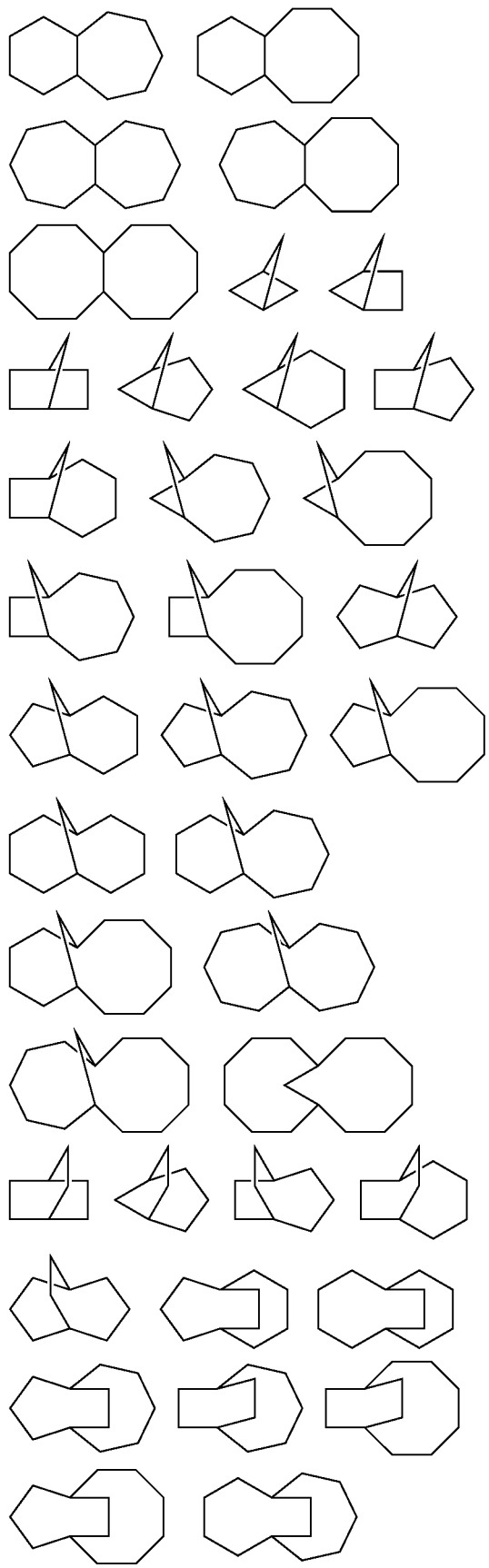
-continued
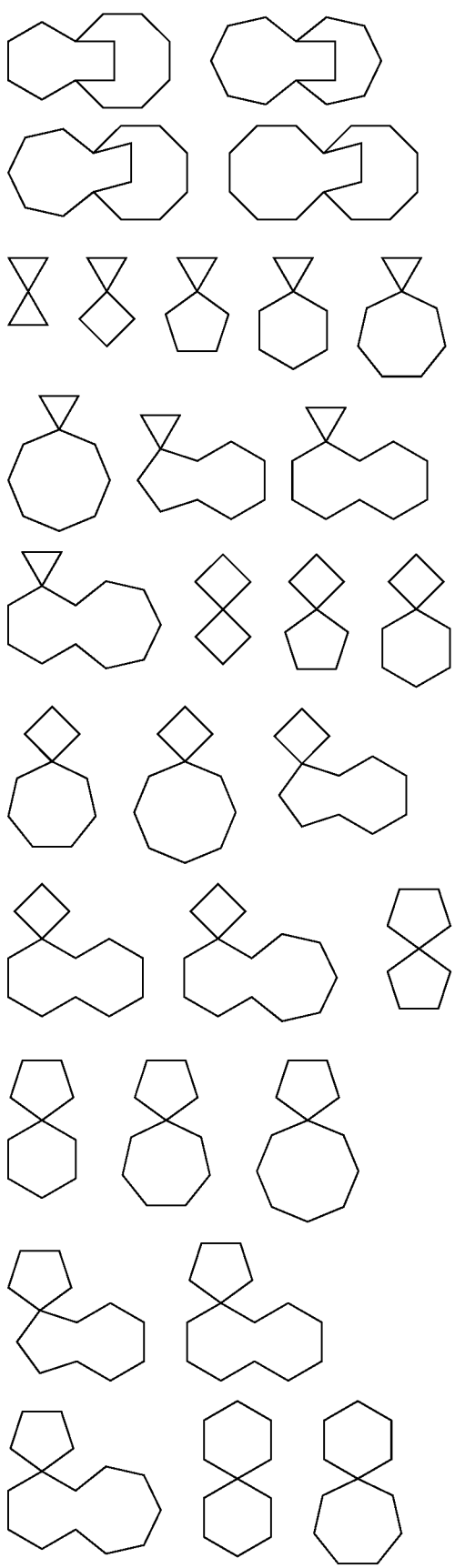

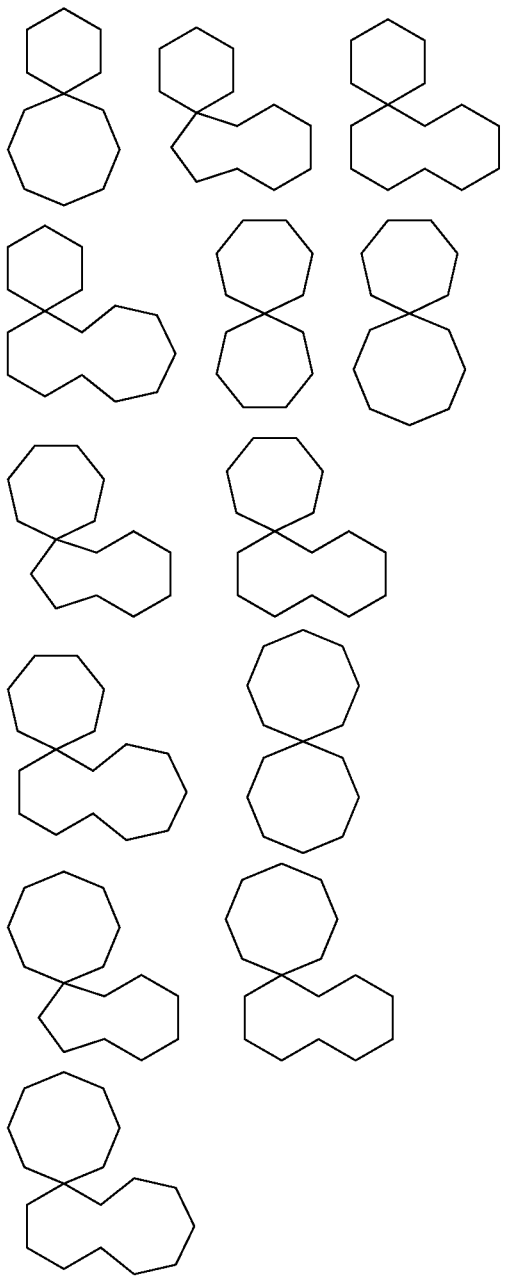
Preferable examples thereof include those represented by the following structural formulae optionally having a substituent and optionally having a heteroatom:
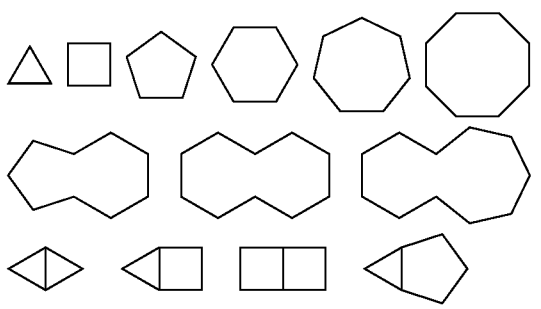
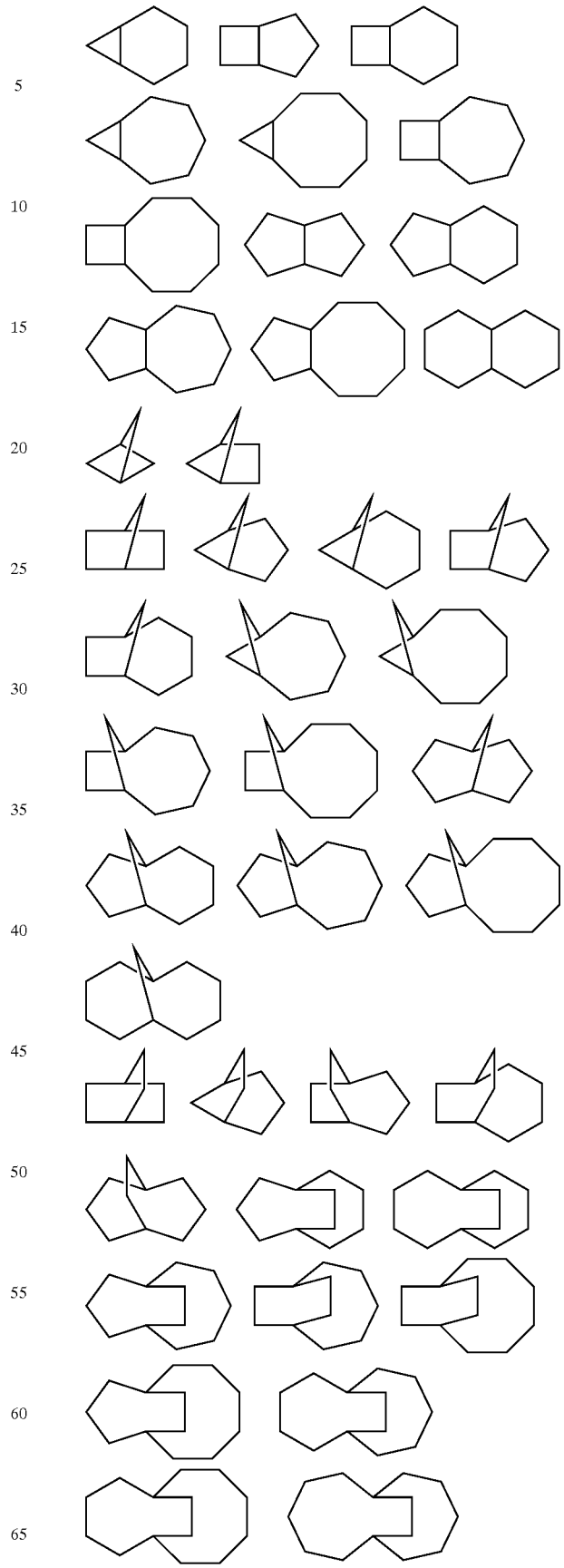

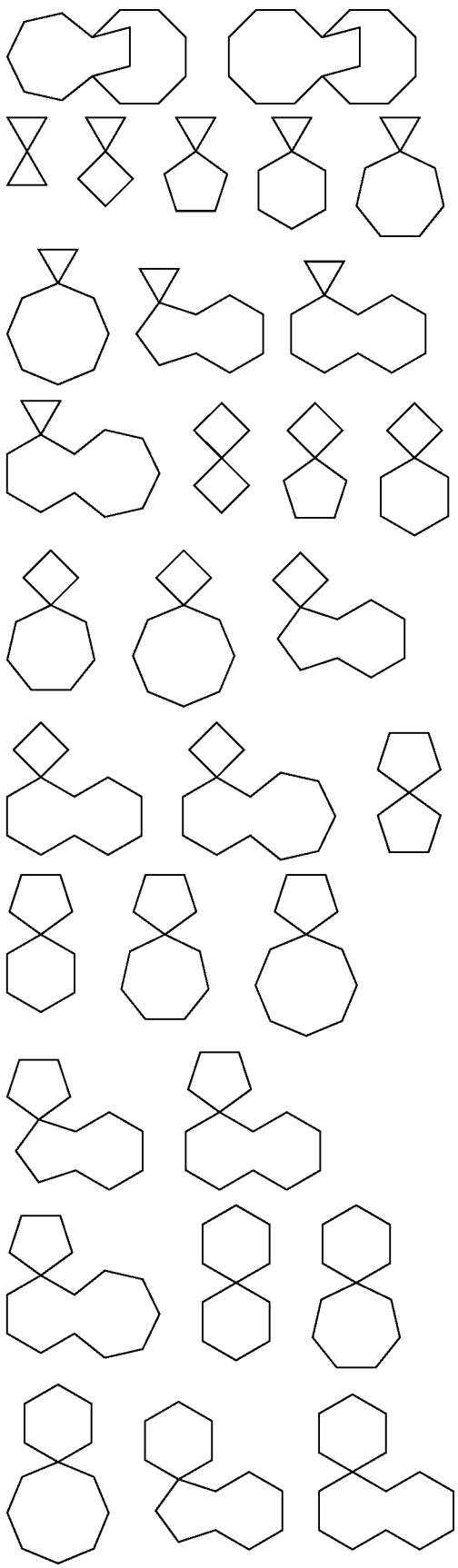
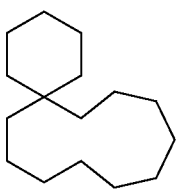
Still more preferable examples thereof include those represented by the following structural formulae optionally having a substituent and optionally having a heteroatom:
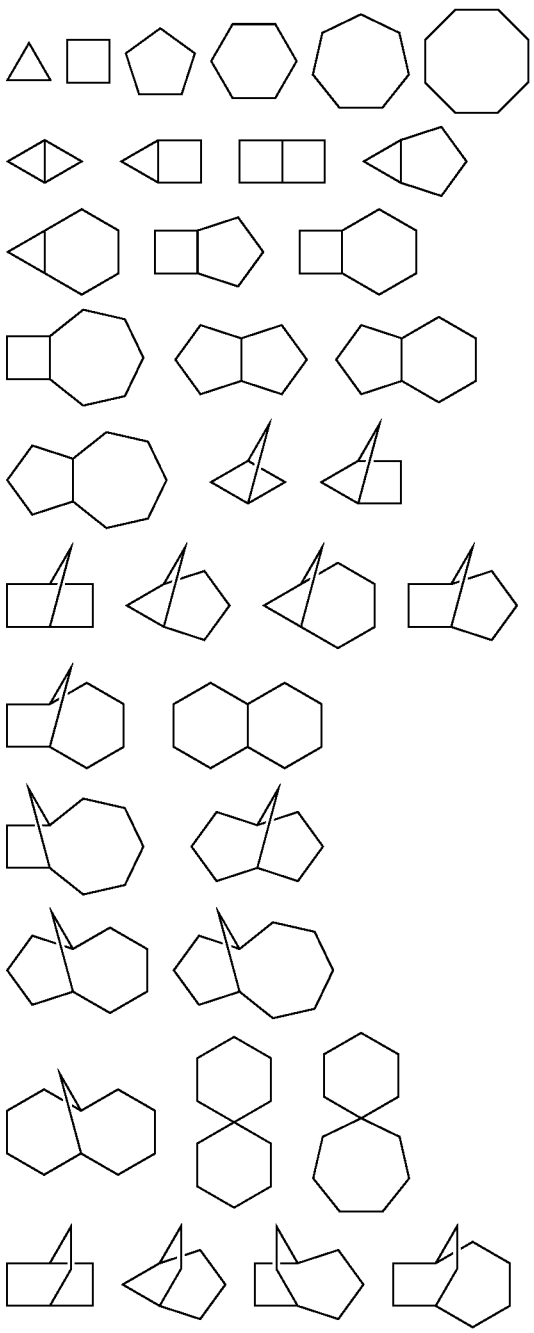

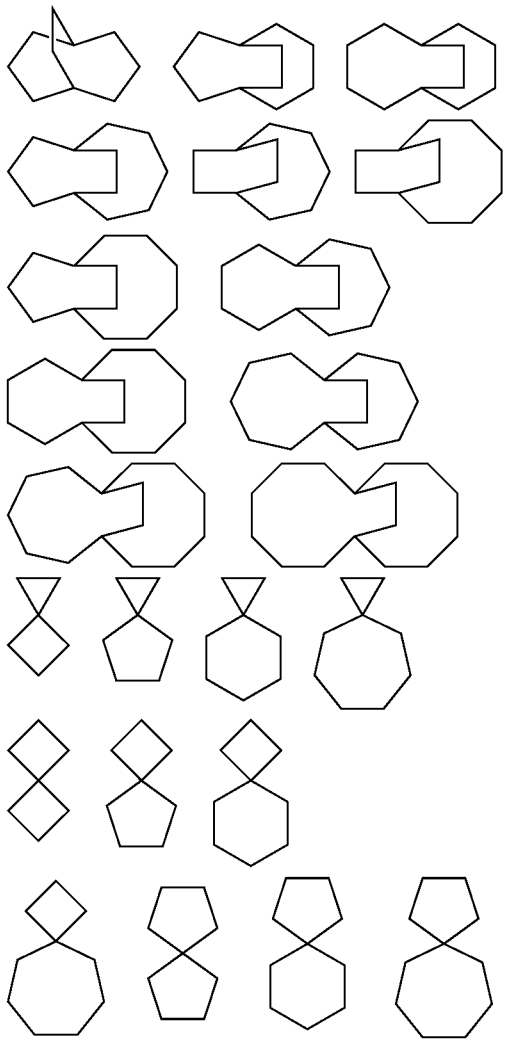

Still more preferable examples thereof include those represented by the following structural formulae optionally having a substituent and optionally having a heteroatom:

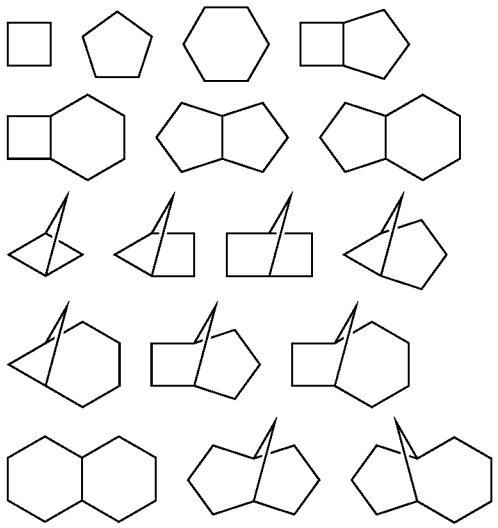

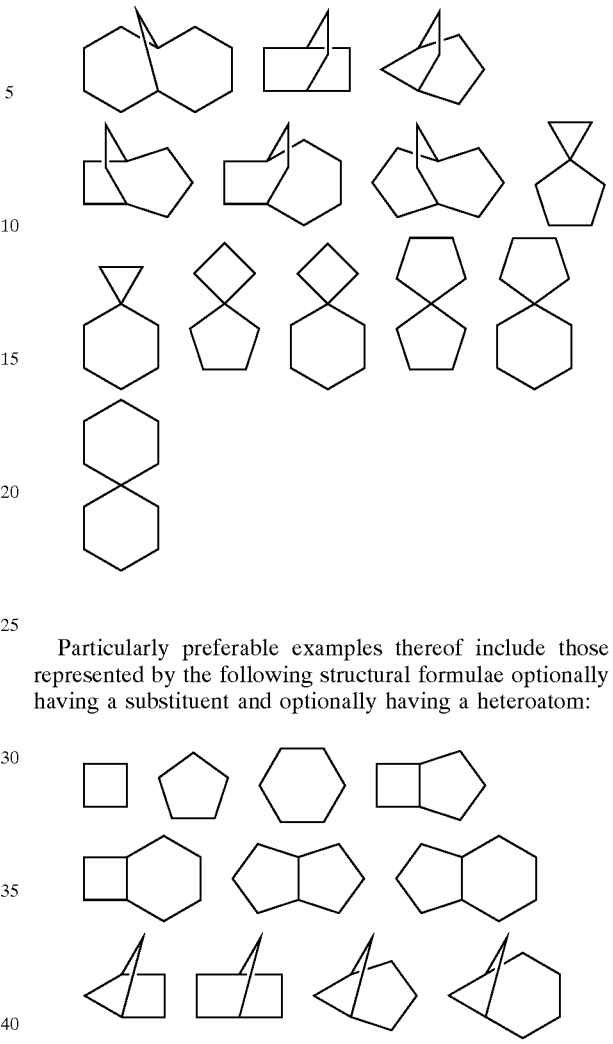

Particularly preferable examples thereof include those represented by the following structural formulae optionally having a substituent and optionally having a heteroatom:

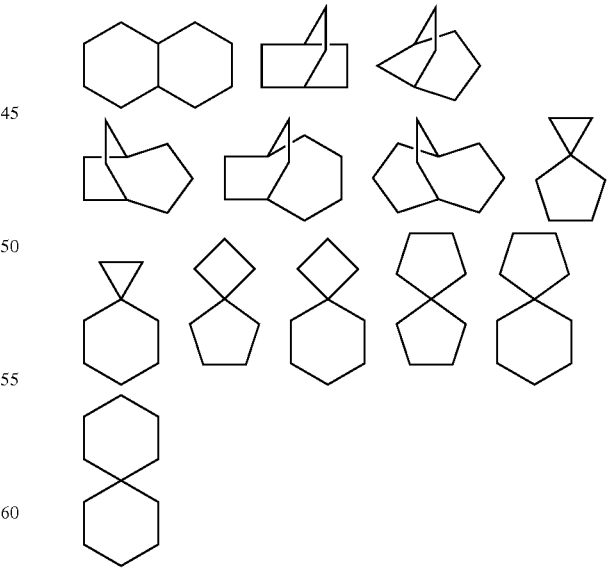

The most desirable ones are those represented by the following structural formulae optionally having a substituent and optionally having a heteroatom:

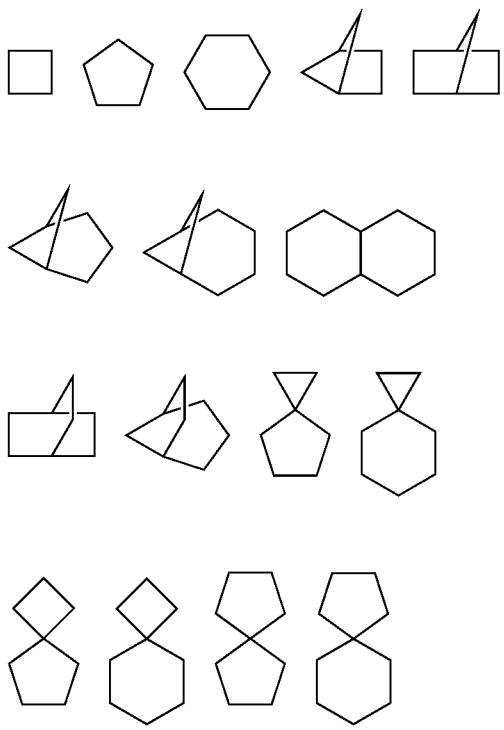

X[1] represents an optionally substituted lower alkylene optionally having a heteroatom, optionally substituted lower alkenylene optionally having a heteroatom or optionally substituted lower alkynylene optionally having a heteroatom. Thus, it has the same meaning as that of X as defined above. The heteroatom in the definition of X[1] is preferably a nitrogen atom, though it is not restricted thereto.

l[1] is 0 or 1.

When l[1] is 0, therefore, the following formula:

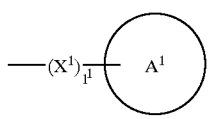

wherein X, l[1] and the ring $A^1$ are each as defined above; means the following formula:

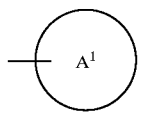

wherein the ring $A^1$ is as defined above.

The ring $A^1$ represents: a) an optionally substituted cycloalkyl ring optionally having one or more heteroatoms; b) an optionally substituted cycloalkenyl ring optionally having one or more heteroatoms; or c) an optionally substituted spiro-hydrocarbon ring optionally having a heteroatom, wherein both ends of an optionally substituted $C_1$ or higher alkylene group optionally having a heteroatom are bonded to a carbon atom (bridgehead carbon atom) in the ring $A^1$. Thus, particular examples of the ring $A^1$ include those represented by the following structural formulae optionally having a substituent, optionally having a heteroatom and optionally having a double bond in the ring:

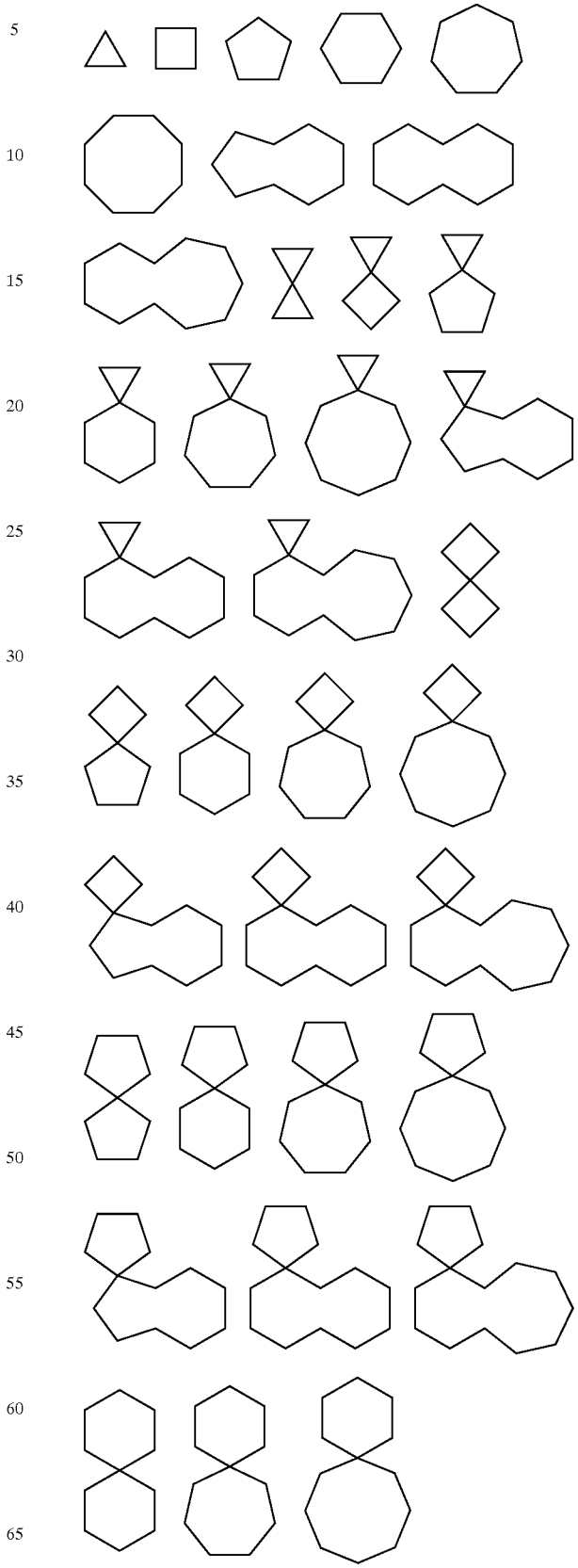

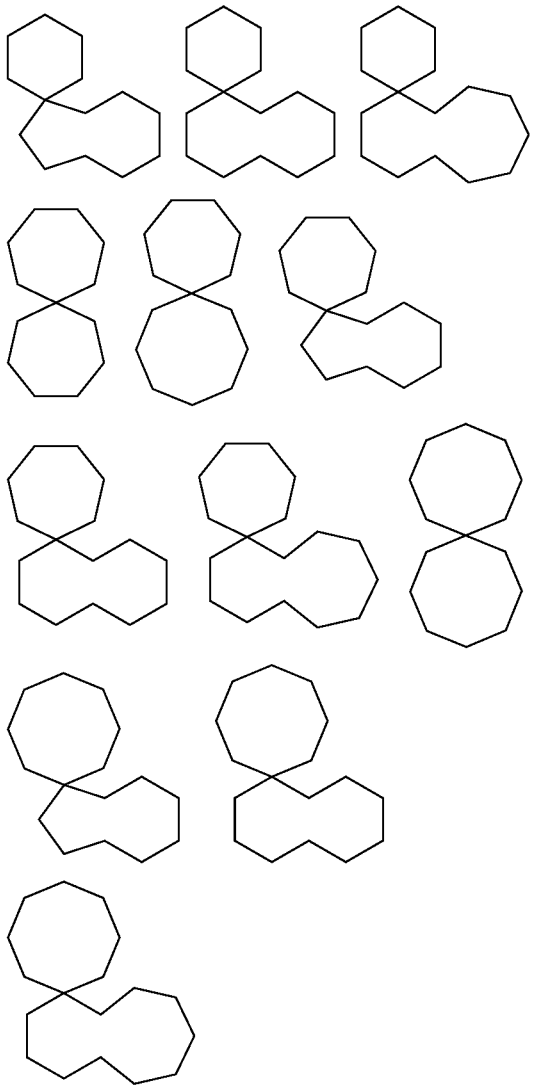

Preferable examples thereof include those represented by the following structural formulae optionally having a substituent, optionally having a heteroatom and optionally having a double bond in the ring:

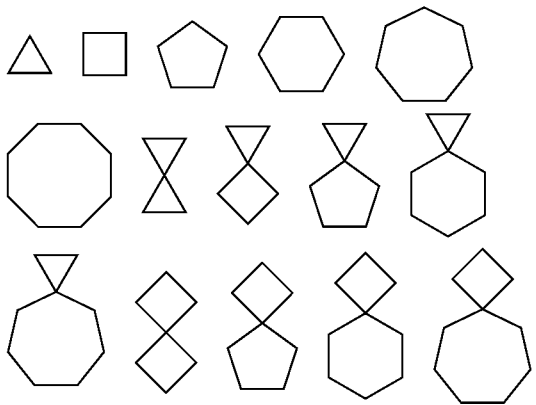

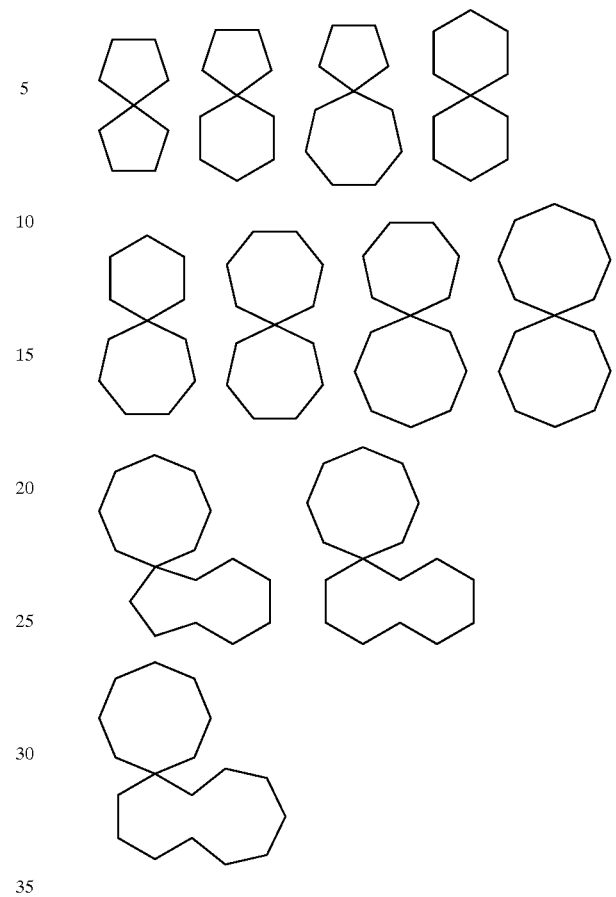

Still more preferable examples thereof include those represented by the following structural formulae optionally having a substituent, optionally having a heteroatom and optionally having a double bond in the ring:

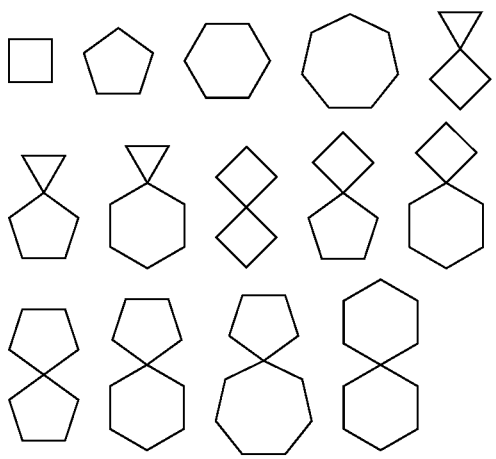

Still more preferable examples thereof include those represented by the following structural formulae optionally having a substituent, optionally having a heteroatom and optionally having a double bond in the ring:

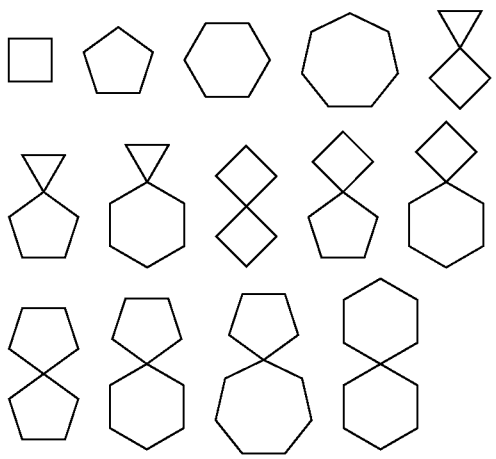

Particularly preferable examples thereof include those represented by the following structural formulae optionally having a substituent, optionally having a heteroatom and optionally having a double bond in the ring:

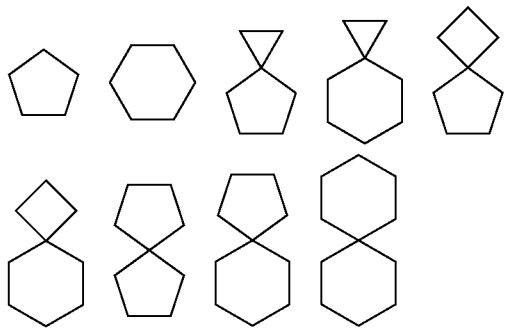

The most desirable examples thereof are those represented by the following structural formulae optionally having a substituent, optionally having a heteroatom and optionally having a double bond in the ring:

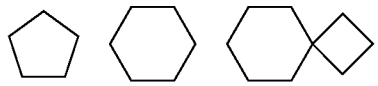

and piperidine and pyrrolidine rings optionally having a substituent, optionally having a heteroatom and optionally having a double bond in the ring.

$X^2$ represents an optionally substituted lower alkylene optionally having a heteroatom, optionally substituted lower alkenylene optionally having a heteroatom or optionally substituted lower alkynylene optionally having a heteroatom.

$l^2$ is 0 or 1.

When $l^2$ is 0, therefore, the following formula:

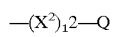

wherein $X^2$, $l^2$ and Q are each as defined above; means the following formula:

wherein Q is as defined above.

Q is as defined above. In the definition of Q, particular examples of a) heteroaryl consisting of one or more optionally substituted rings include rings represented by the following structural formulae optionally having a substituent:

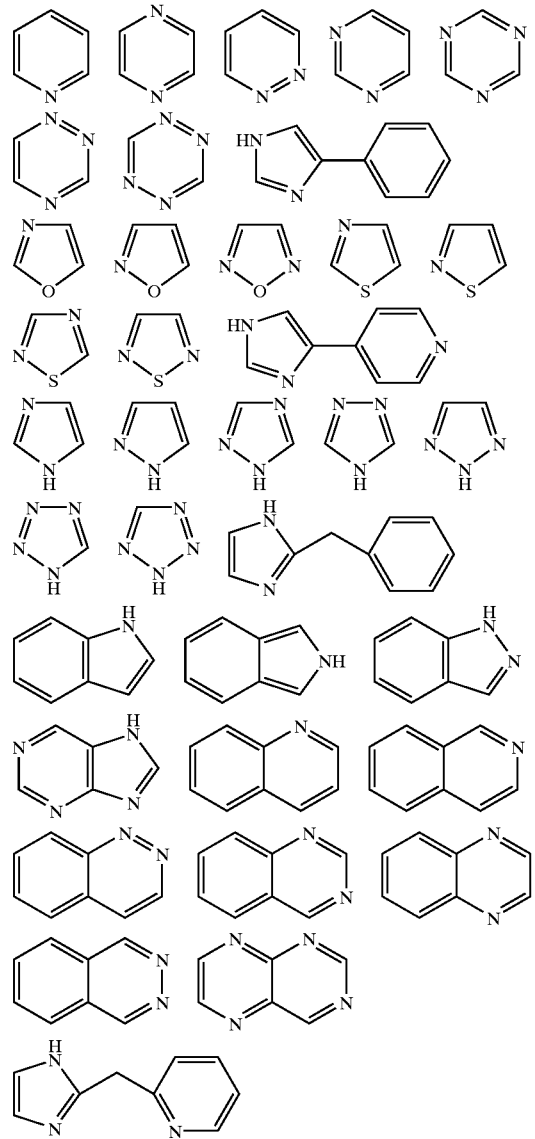

Preferable examples are those represented by the following structural formulae:

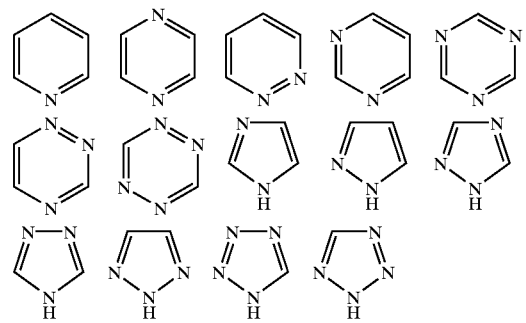

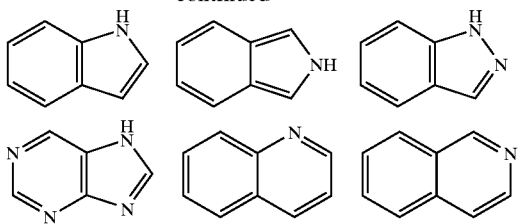

Still more preferable examples are those represented by the following structural formulae:

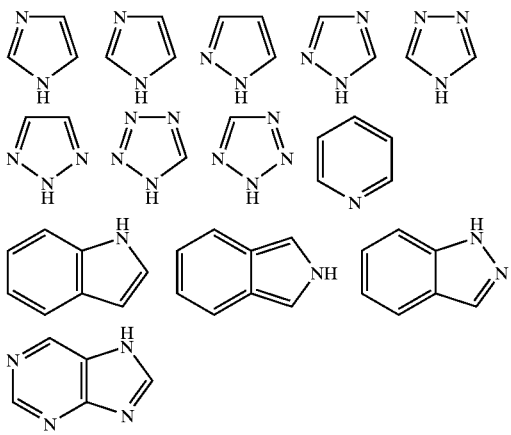

Still further preferable examples are those represented by the following structural formulae:

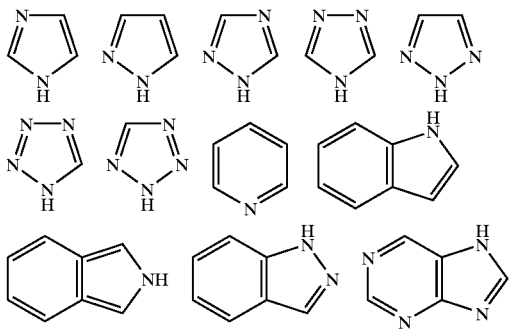

Particularly preferable examples are those represented by the following structural formulae:

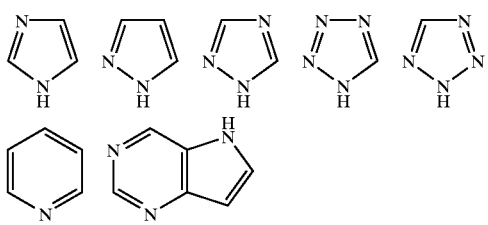

The most desirable ones are those represented by the following structural formulae:

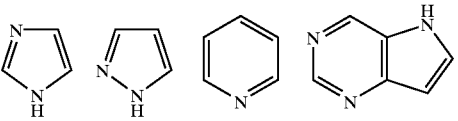

Particular examples of aryl consisting of one or more optionally substituted rings include phenyl, tolyl, xylyl, cumenyl, mesityl and naphthyl groups.

The expression "b) optionally substituted quaternary ammonio" means those having optionally substituted tetravalent nitrogen. Such a quaternary ammonio group may be an acyclic one, a cyclic one or a combination thereof. It may have one or more heteroatoms selected from among nitrogen, sulfur and oxygen. Examples of the acyclic quaternary ammonio group include those represented by the following formula:

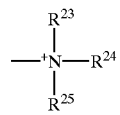

wherein $R^{23}$ to $R^{25}$ may be the same or different and each represents lower alkyl, lower alkoxy(lower alkyl), hydroxy (lower alkyl), carboxy(lower alkyl), amino(lower alkyl), carbamoyl(lower alkyl), lower alkenyl, lower alkynyl, halogeno(lower alkyl), halogeno(lower alkenyl), halogeno (lower alkynyl) or aryl. Particular examples thereof include those represented by the following formulae optionally having a substituent:

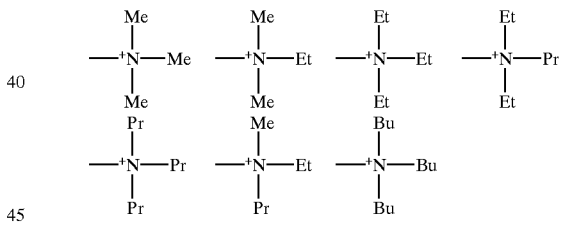

wherein Me represents methyl; Et represents ethyl; Pr represents propyl; and Bu represents butyl; the same will apply hereinafter.

Preferable examples thereof include those represented by the following formulae optionally having a substituent:

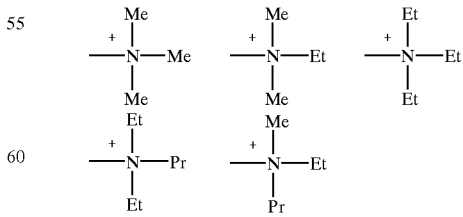

Still more preferable examples thereof include those represented by the following formulae optionally having a substituent:

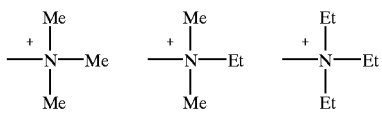

The most preferable examples thereof are those represented by the following formulae:

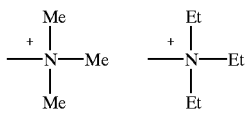

Examples of the cyclic quaternary ammonio group include those represented by the following formula:

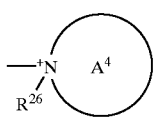

wherein $R^{26}$ represents lower alkyl, lower alkoxy(lower alkyl), hydroxy(lower alkyl), carboxy(lower alkyl), amino(lower alkyl), carbamoyl(lower alkyl), lower alkenyl, lower alkynyl, halogeno(lower alkyl), halogeno(lower alkenyl), halogeno(lower alkynyl) or aryl; and the ring $A^4$ represents an optionally substituted cycloalkyl ring optionally having a double bond in the ring;

those represented by the following formula:

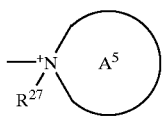

wherein $R^{27}$ represents lower alkyl, lower alkoxy(lower alkyl), hydroxy(lower alkyl), carboxy(lower alkyl), amino(lower alkyl), carbamoyl(lower alkyl), lower alkenyl, lower alkynyl, halogeno(lower alkyl), halogeno(lower alkenyl), halogeno(lower alkynyl) or aryl; and the ring $A^5$ represents an optionally substituted heteroaryl ring optionally having one or more heteroatoms;

or those represented by the following formula:

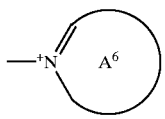

wherein the ring $A^6$ represents an optionally substituted heteroaryl ring optionally having one or more heteroatoms.

Particular examples thereof include those represented by the following structural formulae optionally having a substituent and optionally having one or more heteroatoms:

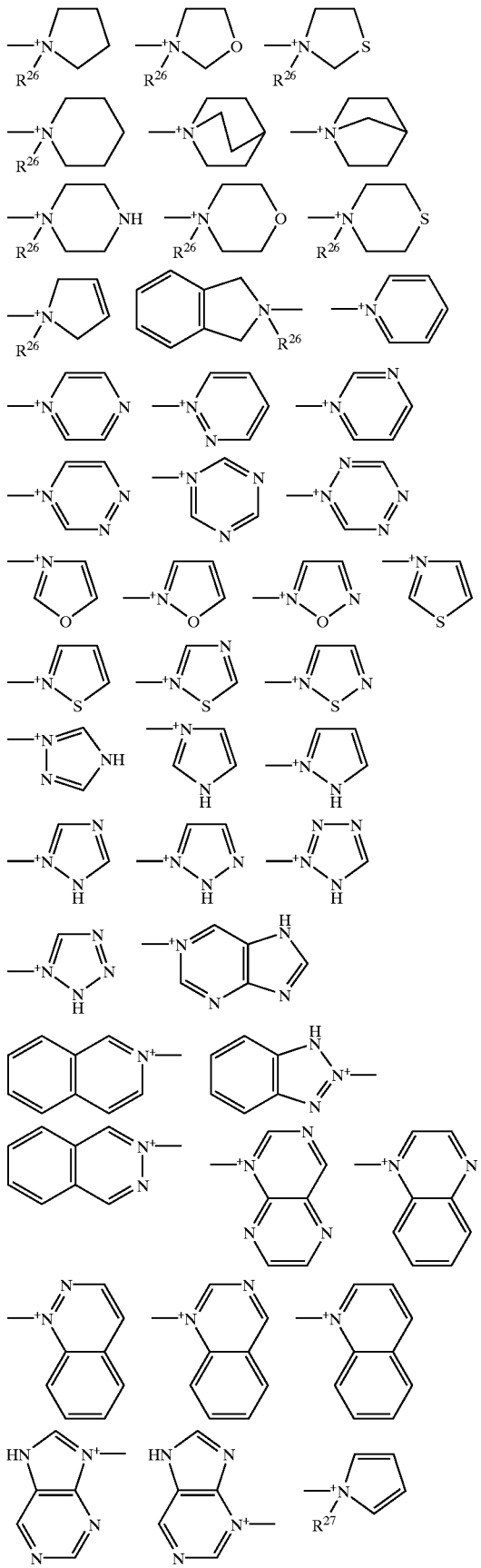

-continued

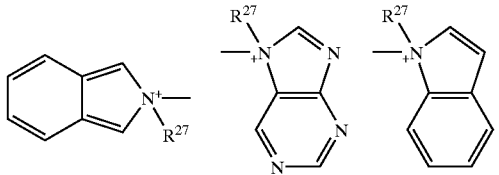

wherein $R^{26}$ and $R^{27}$ are each as defined above.

Preferable examples thereof include those represented by the following structural formulae optionally having a substituent and optionally having one or more heteroatoms:

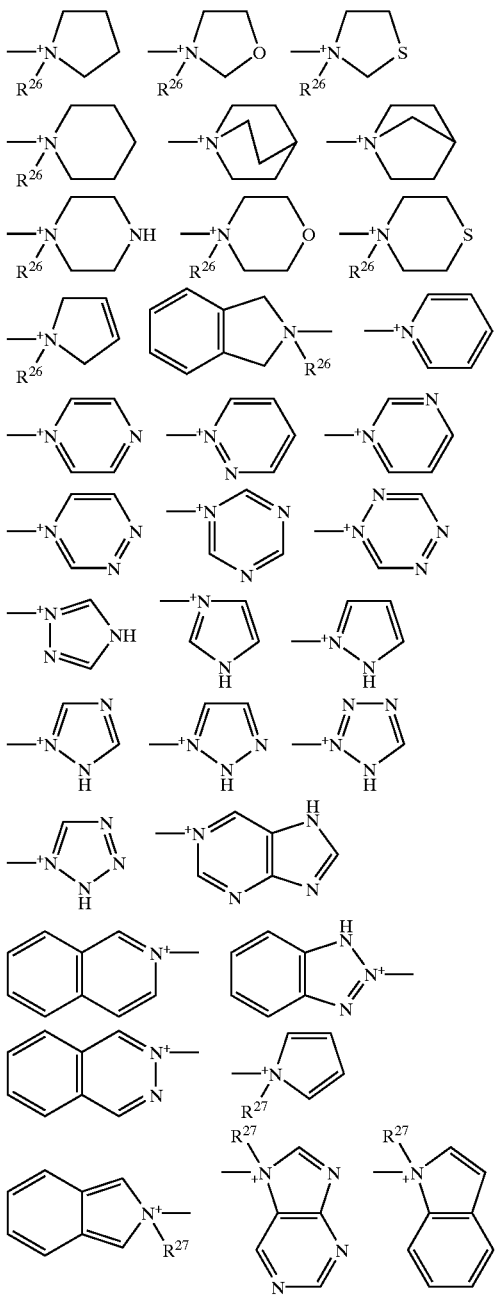

wherein $R^{26}$ and $R^{27}$ are each as defined above.

Still more preferable examples thereof include those represented by the following structural formulae optionally having a substituent and optionally having one or more heteroatoms:

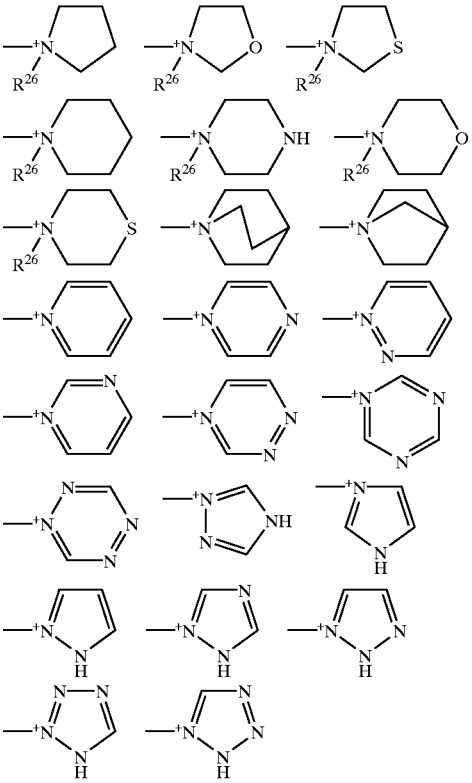

wherein $R^{26}$ is as defined above.

Still more preferable examples thereof include those represented by the following structural formulae optionally having a substituent and optionally having one or more heteroatoms:

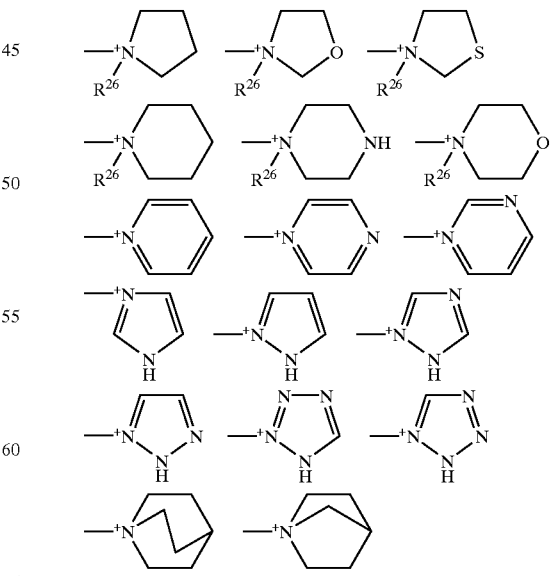

wherein $R^{26}$ is as defined above.

Particularly preferable examples thereof include those represented by the following structural formulae optionally having a substituent and optionally having one or more heteroatoms:

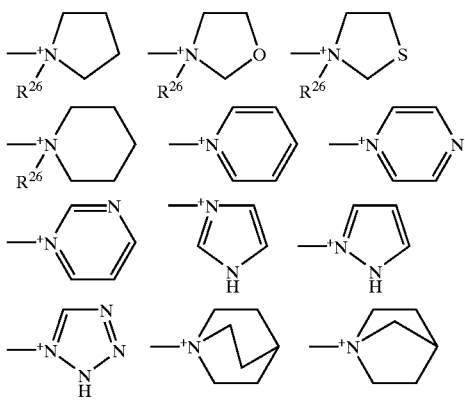

wherein $R^{26}$ is as defined above.

The most desirable ones are those represented by the following structural formulae optionally having a substituent and optionally having one or more heteroatoms:

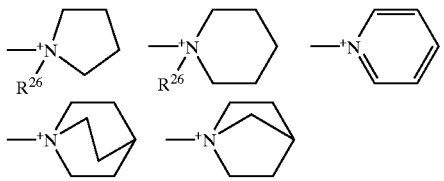

wherein $R^{26}$ is as defined above.

$R^5$ and $R^6$ may be the same or different and each represents hydrogen or lower alkyl. The term "lower alkyl" as used herein has the same meaning as the one defined above.

Thus, particular examples of c) the group represented by the following formula:

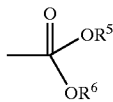

wherein $R^5$ and $R^6$ are each as defined above, include those represented by the following structural formulae:

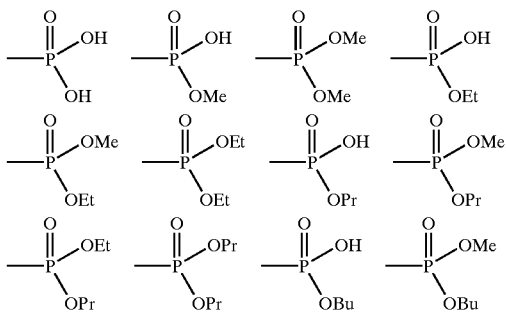

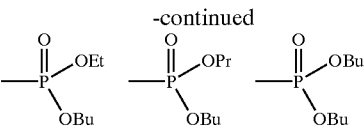

Preferable examples thereof include those represented by the following structural formulae:

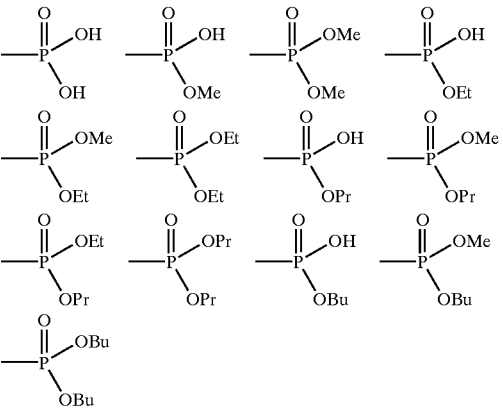

Still more preferable examples thereof include those represented by the following structural formulae:

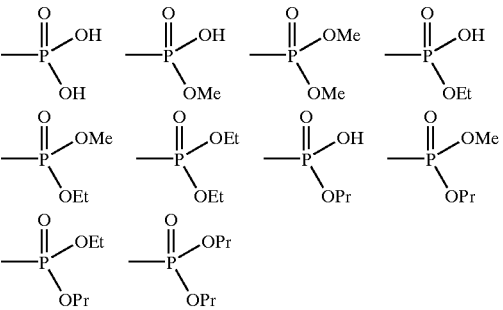

The most desirable ones are those represented by the following structural formulae:

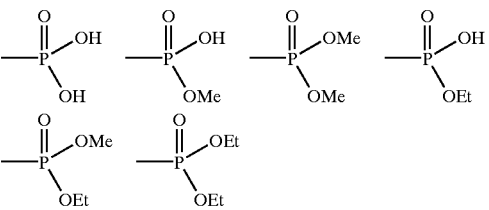

Particular examples of the lower acyl group include formyl, acetyl, propionyl, butyryl, isobutyryl, valeryl, isovaleryl, pivaloyl, hexanoyl, acryloyl, methacryloyl, crotonyl, chloroformyl, pyruvoyl, oxalo, methoxalyl, ethoxalyl and benzoyl groups.

The lower acyloxy group means those corresponding to the above-mentioned lower acyl groups. Particular examples thereof include formyloxy, acetyloxy, propionyloxy, butyryloxy, isobutyryloxy, valeryloxy, isovaleryloxy, pivaloyloxy, hexanoyloxy, acryloyloxy, methacryloyloxy, crotonyloxy, chloroformyloxy, pyruvoyloxy, oxaloxy, methoxalyloxy, ethoxalyloxy and benzoyloxy groups.

$R^7$ and $R^8$ are each as defined above. In the definition of $R^7$ and $R^8$, the lower alkyl and lower cycloalkyl groups are each as defined above.

Also, the lower alkyl groups in the definition of $R^{71}$, $R^{72}$, $R^{73}$, $R^{74}$, $R^{75}$, $R^{76}$, $R^{77}$ and $R^{81}$ and the lower cycloalkyl groups in the definition of $R^{72}$ and $R^{73}$ have each the same meaning as the one defined above.

The aryl groups in the definition of $R^{71}$, $R^{72}$, $R^{73}$, $R^{81}$, $R^{83}$, $R^{84}$ and $R^{85}$ means aromatic ring groups. Particular examples thereof include phenyl, tolyl, xylyl, cumenyl, mesityl and naphthyl groups.

The amino protecting group is not restricted but may be an arbitrary one known as an amino protecting group in organic synthesis. Examples thereof include optionally substituted lower alkanoyl groups such as formyl, acetyl, chloroacetyl, dichloroacetyl, propionyl, phenylacetyl, phenoxyacetyl and thienylacetyl groups; optionally substituted lower alkoxycarbonyl groups such as benzyloxycarbonyl, t-butoxycarbonyl and p-nitrobenzyloxycarbonyl groups; substituted lower alkyl groups such as methyl, t-butyl, 2,2,2-trichloroethyl, trityl, p-methoxybenzyl, p-nitrobenzyl, diphenylmethyl, pivaloyloxymethyl, methoxymethyl and ethoxymethyl groups; substituted silyl groups such as trimethylsilyl and t-butyldimethylsilyl groups; substituted silylalkoxyalkyl groups such as trimethylsilylmethoxymethyl, trimethylsilylethoxymethyl, t-butyldimethylsilylmethoxymethyl and t-butyldimethylsilylethoxymethyl groups; and optionally substituted benzylidene groups such as benzylidene, salicylidene, p-nitrobenzylidenei m-chlorobenzylidene, 3,5-di(t-butyl)-4-hydroxybenzylidene and 3,5-di(t-butyl)benzylidene groups.

Such a protective group can be eliminated by conventional methods such as hydrolysis or reduction selected depending on the type thereof.

The term "protected hydroxy" means a hydroxyl group protected by a hydroxyl protecting group. Examples thereof are not restricted, so long as they are protected by protecting groups commonly known as a hydroxyl protecting group in organic synthesis. Examples of the hydroxyl protecting group include lower alkylsilyl groups such as trimethylsilyl and t-butyldimethylsilyl groups; lower alkoxymethyl groups such as methoxymethyl and 2-methoxymethyl groups; a tetrahydropyranyl group; aralkyl groups such as benzyl, p-methoxybenzyl, 2,4-dimethoxybenzyl, o-nitrobenzyl, p-nitrobenzyl and trityl groups; acyl groups such as formyl and acetyl groups; lower alkoxycarbonyl groups such as t-butoxycarbonyl, 2-iodoethoxycarbonyl and 2,2,2-trichloroethoxycarbonyl groups; alkenyloxycarbonyl groups such as 2-propenyloxycarbonyl, 2-chloro-2-propenyloxycarbonyl, 3-methoxycarbonyl-2-propenyloxycarbonyl, 2-methyl-2-propenyloxycarbonyl, 2-butenyloxycarbonyl and cinnamyloxycarbonyl groups; and aralkyloxycarbonyl groups such as benzyloxycarbonyl, p-methoxybenzyloxycarbonyl, o-nitrobenzyloxycarbonyl and p-nitrobenzyloxycarbonyl groups.

$R^{82}$ represents hydrogen, lower alkyl or a mercapto protective group. The lower alkyl as used herein has the same meaning as the one defined above. The mercapto protective group may be an arbitrary one without restriction so long as it is commonly known as a mercapto protective group in organic synthesis. More particularly speaking, use can be made of the above-mentioned hydroxy protective groups or disulfide derivatives as the mercapto protective group.

The term "protected carboxy" means a carboxyl group protected by a carboxyl protecting group. The carboxyl protective group may be an arbitrary one without restriction so long as it is commonly known as a carboxyl protecting group in organic synthesis. Particular examples of the carboxyl protective group include linear and branched $C_{1-4}$ lower alkyl groups such as methyl, ethyl, isopropyl and t-butyl groups; halogeno(lower alkyl) groups such as 2-iodoethyl and 2,2,2-trichloroethyl groups; lower alkoxymethyl groups such as methoxymethyl, ethoxymethyl and isobutoxymethyl groups; lower aliphatic acyloxymethyl groups such as butyryloxymethyl and pivaloyloxymethyl groups; 1-(lower alkoxy)carbonyloxyethyl groups such as 1-methoxycarbonyloxyethyl and 1-ethoxycarbonyloxyethyl groups; aralkyl groups such as benzyl, p-methoxybenzyl, o-nitrobenzyl and p-nitrobenzyl groups; and benzhydryl and phthalidyl groups.

W represents oxygen or sulfur. When W is oxygen, therefore, the group represented by the following formula:

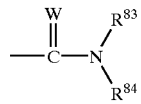

wherein W, $R^{83}$ and $R^{84}$ are each as defined above, represents a group represented by the following formula:

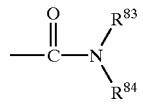

wherein W, $R^{83}$ and $R^{84}$ are each as defined above.

When W is sulfur, therefore, the group represented by the following formula:

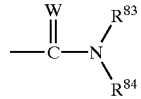

wherein W, $R^{83}$ and $R^{84}$ are each as defined above, represents a group represented by the following formula:

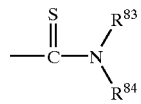

wherein W, $R^{83}$ and $R^{84}$ are each as defined above.

$R^{83}$ and $R^{84}$ may be the same or different and each represents hydrogen, lower alkyl, lower cycloalkyl, cyano or a group represented by the following formula:

wherein $R^{85}$ represents hydrogen, hydroxy or lower alkyl.

Alternatively, $R^{83}$ and $R^{84}$ together form an optionally substituted lower cycloalkyl optionally having one or more heteroatoms.

The lower alkyl groups in $R^{83}$, $R^{84}$ and $R^{85}$ and the lower cycloalkyl groups in $R^{83}$ and $R^{84}$ are each as defined above.

Particular examples of the optionally substituted lower cycloalkyl optionally having one or more heteroatoms formed by $R^{83}$ and $R^{84}$ together include optionally substituted pyrrolidyl, imidazolidyl, piperazolidyl, piperidyl, piperazyl and morpholino groups optionally having one or more heteroatoms.

$R^{86}$, $R^{87}$ and $R^{88}$ are as defined above. Also, the lower alkyl groups in $R^{86}$, $R^{87}$ and $R^{88}$ have the same meaning as the one defined above. The term "hydroxy(lower alkyl)" means a lower alkyl group substituted with hydroxy. The optionally substituted lower cycloalkyl group optionally having one or more heteroatoms formed by $R^{86}$ and $R^{87}$ together has the same meaning as the one defined above with respect to $R^{83}$ and $R^{84}$.

$R^{90}$ and $R^{91}$ each represents hydrogen or lower alkyl. The lower alkyl has the same meaning as the one defined above.

Next, the definition of R will be illustrated.

R is as defined above and the lower alkyl groups in the definition of R also have the same meaning as the one defined above.

The term "optionally substituted arylalkyl" means an optionally substituted alkyl group substituted by an optionally substituted aryl group. Particular examples of the aryl group include benzene, pentalene, indene, naphthalene, azulene, heptalene, biphenylene, indacene, acenaphthylene, fluorene, phenalene, phenanthrene and anthracene. Preferable examples thereof include benzene, pentalene, indene, naphthalene and azulene. Particular examples of the alkyl group include the optionally substituted lower alkyl groups as cited above.

The term "optionally substituted heteroarylalkyl" means an optionally substituted alkyl group substituted by an optionally substituted heteroaryl group. Particular examples of the heteroaryl group include pyridine, thiophene, furan, pyrrole, oxazole, isoxazole, thiazole, isothiazole, imidazole, triazole, pyrazole, furazan, thiadiazole, oxadiazole, pyridazine, pyrimidine, pyrazine, indole, isoindole, indazole, chromene, quinoline, isoquinoline, cinnoline, quinazoline, quinoxaline, naphthyridine, phthalazine, purine, pteridine, thienofuran, imidazothiazole, benzofuran, benzothiophene, benzoxazole, benzothiazole, benzothiadiazole, benzimidazole, imidazopyridine, pyrrolopyridine, pyrrolopyrimidine and pyridopyrimidine. Preferable examples thereof include pyridine, thiophene, thiazole, thiadiazole, imidazole, pyrimidine, benzimidazole, imidazopyridine and purine. Particular examples of the alkyl group include the optionally substituted lower alkyl groups as cited above.

The amino protecting group is as defined above.

The lower alkylene, lower alkenylene and lower alkynylene groups in $X^3$ are each as defined above.

The lower alkyl group and the amino protecting group in $R^9$ and $R^{10}$ are each as defined above.

The lower alkylene, lower alkenylene and lower alkynylene groups in $X^4$ are each as defined above.

The lower alkyl group and the carboxy protecting group in $R^{11}$ are each as defined above.

Next, the definition of E will be illustrated.

E is as defined above and $R^4$ in the definition of E also has the same meaning as the one described with respect to $R^1$ to $R^3$.

Next, the definition of Z will be illustrated.

Z is as defined above and the lower alkyl group and the amino protective group in $R^{12}$ in the definition of Z also have each the same meaning as the one defined above.

Next, the definition of the ring G will be illustrated.

The ring G represents an optionally substituted heteroaryl ring having one or more nitrogen atoms. Particular examples of the heteroaryl group having one or more nitrogen atoms include pyridine, pyrrole, oxazole, isoxazole, thiazole, isothiazole, imidazole, triazole, pyrazole, furazan, thiadiazole, oxadiazole, pyridazine, pyrimidine, pyrazine, indole, isoindole, indazole, quinoline, isoquinoline, cinnoline, quinazoline, quinoxaline, naphthyridine, phthalazine, purine, pteridine, imidazothiazole, benzoxazole, benzothiazole, benzothiadiazole, benzimidazole, imidazopyridine, pyrrolopyridine, pyrrolopyrimidine and pyridopyrimidine. Preferable examples thereof include pyridine, pyrrole, oxazole, isoxazole, thiazole, isothiazole, imidazole, triazole, pyrazole, furazan, thiadiazole, oxadiazole, pyridazine, pyrimidine and pyridine. Particularly preferable examples thereof include pyridine, pyrrole, imidazole, triazole, pyrazole, pyridazine, pyrimidine and pyrazine. Still preferable examples are imidazole, triazole, pyridazine, pyrimidine and pyrazine. Particularly preferable ones are pyridine, pyridazine, pyrimidine and pyrazine. The most desirable ones are pyrimidine and pyrazine.

Thus the compounds represented by the formula (I) have been defined, provided that the benzopiperidine derivatives as will be specified below are excluded from the present invention: a) that in which $R^1$ to $R^3$ are each hydrogen, E is CH, Z is O, S, or $SO_2$ and the ring G is an unsubstituted (i.e., all of the substituents being hydrogen atoms) heteroaryl ring having one or more nitrogen atoms; b) that in which $R^1$ to $R^3$ are each hydrogen, E is CH, Z is O, S, $SO_2$ or NH and the substituent(s) of the ring G is optionally substituted phenyl, pyridinyl, thienyl, nitro, cyano, halogeno, acetyl, methyl, ethyl, t-butyl, ethoxy, N-methylpiperazyl, naphthyl, optionally protected carboxyalkyl or amino; c) that in which $R^1$ to $R^3$ are each hydrogen, E is CH, Z is NH and the ring G is unsubstituted (i.e., all of the substituents being hydrogen atoms) pyridazine; and d) that in which $R^1$ to $R^3$ are each hydrogen, E is CH, R is a group other than hydrogen, Z is $NR^{12'}$ ($R^{12'}$ being lower alkyl or an amino protective group) and the ring G is an optionally substituted heteroaryl ring optionally having one or more nitrogen atoms. The term "optionally substituted phenyl" as used herein means a phenyl group optionally substituted by methoxy or halogeno. The term "optionally protected carboxyalkyl" means a carboxyalkyl group which may have a protecting group commonly employed as a carboxy protecting group in organic synthesis.

In particular, benzopiperidine derivatives of the formula (I) wherein Z is S, their salts or hydrates thereof are useful.

In particular, benzopiperidine derivatives of the formula (I) wherein the ring G is an optionally substituted pyrazine ring, their salts or hydrates thereof are useful.

In particular, benzopiperidine derivatives of the formula (I) wherein Z is S and the ring G is an optionally substituted pyrazine ring, their salts or hydrates thereof are useful.

In the definition of the compounds represented by the above formula (II), R, Z, E and the ring G have each the same meaning as the one defined above. Now, the definition of U will be illustrated.

U is as defined above and X, Y, l, m, the rings A and B, $X^1$, $l^1$ and the ring $A^1$ employed in the definition of U also have each the same meaning as the one defined with respect to the formula (I).

In the definition of the compounds represented by the above formula (III), R, Z, E and the ring G have each the same meaning as the one defined above. Now, the definition of $U^1$ will be illustrated.

$U^1$ is as defined above and X, Y, l, m, the rings A and B, $X^1$, $l^1$ and the ring $A^1$ employed in the definition of $U^1$ also have each the same meaning as the one defined with respect to the formula (I).

In the present invention, the type of salt is not particularly restricted. Examples thereof include inorganic acid addition salts such as hydrofluoride, hydrochloride, sulfate, nitrate, perchlorate, phosphate, carbonate, bicarbonate, hydrobromide and hydriodide; organic carboxylic acid addition salts such as acetate, maleate, fumarate, oxalate, lactate, tartrate and trifluoroacetate; organic sulfonic acid addition salts such as methanesulfonate, trifluoromethanesulfonate, ethanesulfonate, hydroxymethanesulfonate, hydroxyethanesulfonate, benzenesulfonate, toluenesulfonate and taurine salt; amine addition salts such as trimethylamine salt, triethylamine salt, pyridine salt, procaine salt, picoline salt, dicyclohexylamine salt, N,N'-dibenzylethylenediamine salt, N-methylglucamine salt, diethanolamine salt, triethanolamine salt, tris(hydroxymethylamino)methane salt and phenethylbenzylamine salt; alkali metal addition salts such as sodium salt and potassium salt; alkaline earth metal addition salts such as magnesium salt and calcium salt; and amino acid addition salts such as argininate, lysinate, serinate, glycinate, aspartate and glutamate.

The compounds of the present invention are benzopiperidine derivatives represented by the above formula (I), their salts or hydrates thereof. Preferable ones are the above compounds wherein at least one of $R^1$ to $R^3$ is a group represented by the following formula while other group(s) are hydrogen, their salts and hydrates thereof:

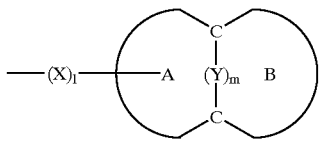

wherein X, Y, l, m and the rings A and B are each as defined above.

Still more preferable ones are benzopiperidine derivatives represented by the above formula (II), their salts or hydrates thereof. Still preferable ones are benzopiperidine derivatives represented by the above formula (III), their salts or hydrates thereof. Particularly preferable ones are those wherein Z is S and, still more preferably, the ring G is pyrazine, their salts or hydrates thereof. The most desirable ones are benzopiperidine derivatives represented by the following formula, their salts or hydrates thereof:

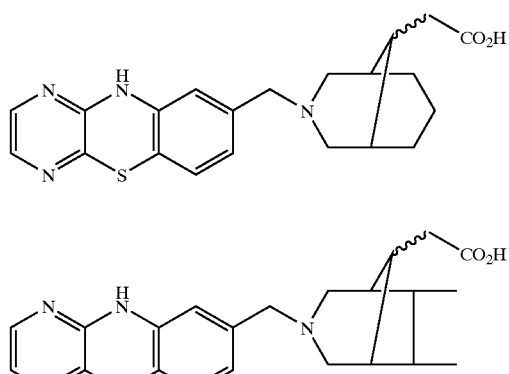

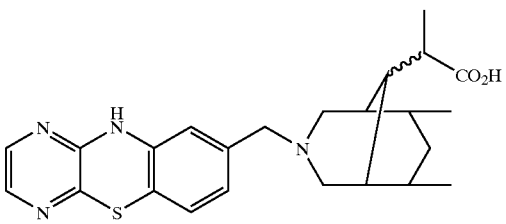

Among all, 10H-pyrazino[2,3-b][1,4]bentothiazine derivatives represented by the following formula are particularly preferable:

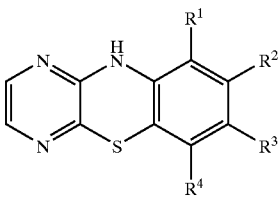

wherein $R^1$ to $R^4$ are each as defined above.

Moreover, the benzopiperidine derivatives represented by the above formula (I), i.e., the compounds of the present invention, their pharmacologically acceptable salts or hydrates thereof are useful as a drug.

Particularly preferable drugs containing these benzopiperidine derivatives represented by the above formula (I), their pharmacologically acceptable salts or hydrates thereof are preventives and remedies for inflammatory diseases or autoimmune diseases, more particularly inflammatory immune diseases, for example, asthma, nephritis, ischemic reflow disorders, psoriasis, atopic dermatitis and the rejection reaction accompanying organ transplantation and autoimmune diseases such as arthritis and collagen disease. Still more preferable drugs are preventives and remedies for arthritis which contain the benzopiperidine derivatives represented by the above formula (I), their salts or hydrates thereof.

In addition, it is highly worthwhile to use the benzopiperidine derivatives represented by the above formula (I), their salts or hydrates thereof in the production of drugs and to use the benzo-piperidine derivatives represented by the above formula (I), their salts or hydrates thereof in the treatment of immune diseases. Furthermore, the benzopiperidine derivatives represented by the above formula (I), their salts or hydrates thereof are highly useful as remedies ensuring the efficacious administration of these compounds.

The dose of the drugs according to the present invention varies depending on the severity of the symptoms, the age, sex and body weight of the patient, the administration method, the disease, etc. In usual, such a drug may be administered in a daily dose of 10 μg to 50 g to an adult one to several times per day.

The drugs according to the present invention may be administered by an arbitrary method without restriction. Namely, they can be orally or parenterally administered in a conventional manner.

To produce pharmaceutical preparations thereof, use can be made of fillers, binders, lubricants, coloring agents, corrigents, etc. commonly employed in the art optionally together with stabilizers, emulsifiers, sorbefacients, surfactants, etc. These preparations are produced by blending components commonly employed in pharmaceutical preparations in a conventional manner.

Examples of these components include animal and vegetable oils (soybean oil, beef tallow, synthetic glycerides, etc.), hydrocarbons (liquid paraffin, squalane, solid paraffin, etc.), ester oils (octyldodecyl myristate, isopropyl myristate, etc.), higher alcohols (cetostearyl alcohol, behenyl alcohol, etc.), silicone resins, silicone oils, surfactants (polyoxyethylene fatty acid esters, sorbitan fatty acid esters, glycerol fatty acid esters, polyoxyethylene sorbitan fatty acid esters, polyoxyethylene-hardened castor oil, polyoxyethylene/polyoxypropylene block copolymer, etc.), water-soluble polymers (hydroxyethylcellulose, polyacrylic acid, carboxyvinyl polymer, polyethylene glycol, polyvinylpyrrolidone, methylcellulose, etc.), alcohols (ethanol, isopropanol, etc.), polyhydric alcohols (glycerol, propylene glycol, dipropylene glycol, sorbitol, etc.), saccharides (glucose, sucrose, etc.), inorganic powders (silicic acid anhydride, aluminum magnesium silicate, aluminum silicate, etc.) and purified water. To regulate the pH value, use can be made of inorganic acids (hydrochloric acid, phosphoric acid, etc.), alkali metal salts of inorganic acids (sodium phosphate, etc.), inorganic bases (sodium hydroxide, etc.), organic acids (lower fatty acids, citric acid, lactic acid, etc.), metal salts of organic acids (sodium citrate, sodium lactate, etc.) and organic bases (arginine, ethanolamine, etc.). If needed, preservatives, antioxidants, etc. may be further added thereto.

The pharmacologically acceptable salts are not particularly restricted in type. Examples thereof include inorganic acid addition salts such as hydrochloride, sulfate, carbonate, bicarbonate, hydrobromide and hydriodide; organic carboxylic acid addition salts such as acetate, maleate, lactate, tartrate and trifluoroacetate; organic sulfonic acid addition salts such as methanesulfonate, hydroxymethanesulfonate, hydroxyethanesulfonate, benzenesulfonate, toluenesulfonate and taurine salt; amine addition salts such as trimethylamine salt, triethylamine salt, pyridine salt, procaine salt, picoline salt, dicyclohexylamine salt, N,N'-dibenzylethylenediamine salt, N-methylglucamine salt, diethanolamine salt, triethanolamine salt, tris(hydroxymethylamino)methane salt and phenethylbenzylamine salt; and amino acid addition salts such as argininate, lysinate, serinate, glycinate, aspartate and glutamate.

The compounds of the present invention can be produced by, for example, the following method. Namely, a compound represented by the formula (IV) or (IV'):

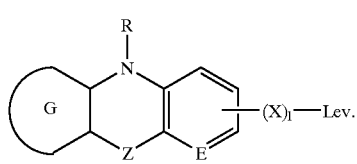
(IV)

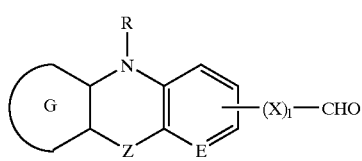
(IV')

wherein R, E, Z, the ring G, X and l are each as defined above, and Lev. represents a leaving group,
is reacted with a compound represented by the formula (V):

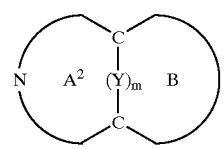
(V)

wherein Y, m and the rings $A^2$ and B are each as defined above, and the ring B is optionally protected,
followed by, if required, deblocking and thus a benzopiperidine derivative represented by the formula (VI), its salt or hydrates thereof can be produced:

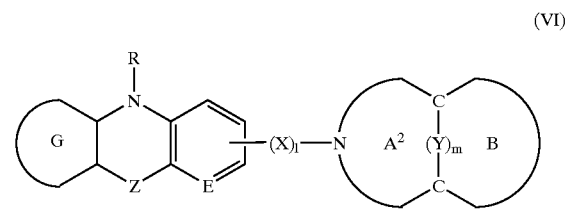
(VI)

wherein R, E, Z, the ring G, X, Y, l, m and the rings $A^2$ and B are each as defined above.

In the production of the compounds of the present invention, therefore, 10H-pyrazino[2,3-b][1,4]benzothiazine derivatives represented by the following formula (IV-1) or (IV'-1), their salts or hydrates thereof:

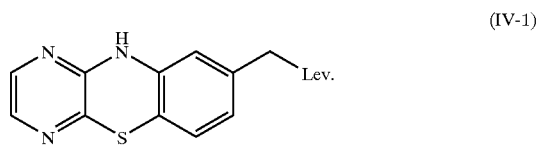
(IV-1)

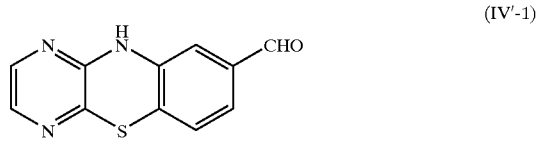
(IV'-1)

wherein Lev. is as defined above, and bicycloalkyl derivatives represented by the following formula (VII), their salts or hydrates thereof:

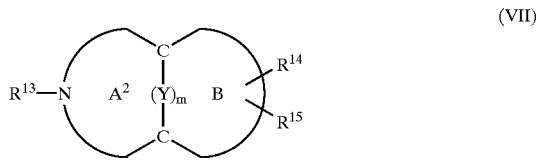
(VII)

wherein Y, m, the rings $A^2$ and B are each as defined above, $R^{13}$ represents hydrogen, lower alkyl or an amino protective group, and $R^{14}$ and $R^{15}$ may be the same or different and each represents hydrogen or lower alkyl, are useful as the production intermediates.

The term "Lev." as used herein means a leaving group which may be an arbitrary one commonly known as a leaving group in organic synthesis without restriction. Examples thereof include halogen atoms such as chlorine, bromine and iodine atoms; alkylthio groups such as methylthio, ethylthio and propylthio groups; arylthio groups such as phenylthio, toluylthio and 2-pyridylthio groups;

alkylsulfonyloxy groups such as methanesulfonyloxy, trifluoromethanesulfonyloxy, ethanesulfonyloxy and propanesulfonyloxy groups; arylsulfonyloxy groups such as benzenesulfonyloxy and p-toluenesulfonyloxy groups; alkanoyloxy groups such as acetoxy and trifluoroacetoxy groups; alkoxy groups such as methoxy, ethoxy and propoxy groups; alkylamino groups such as methylamino, ethylamino, propylamino and butylamino groups; dialkylamino groups such as dimethylamino, diethylamino, dipropylamino, methylethylamino, ethylpropylamino and methylpropylamino groups; and substituted phosphoryloxy groups such as a diphenoxyphosphoryloxy group.

In the formula (VII), the lower alkyl and the amino protective group in the definition of $R^{13}$ have each the same meaning as the one defined above. Similarly, the lower alkyl in $R^{14}$ and $R^{15}$ has the same meaning as the one defined above. Also, Y, m and the rings $A^2$ and B are each as defined above.

Among the intermediates represented by the formula (VII) in the production of the compounds of the present invention, bicycloalkyl derivatives represented by the following formula (X), their salts and hydrates thereof are useful:

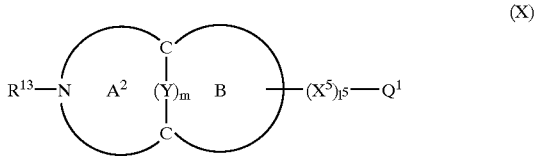

(X)

wherein Y, m, the rings $A^2$ and B and $R^{13}$ are each as defined above; $X^5$ represents an optionally substituted lower alkylene optionally having a heteroatom, optionally substituted lower alkenylene optionally having a heteroatom or optionally substituted lower alkynylene optionally having a heteroatom; $l^5$ is 0 or 1; and $Q^1$ represents carboxy, alkoxycarbonyl, sulfamoyl, amido, optionally protected hydroxy or optionally protected amino.

In particular, bicycloalkyl derivatives represented by the following formula (XI), (XII), (XIII), (XIV), (XV) or (XVI), their salts and hydrates thereof are useful:

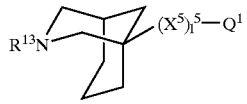

(XI)

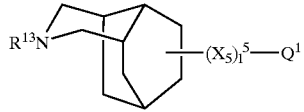

(XII)

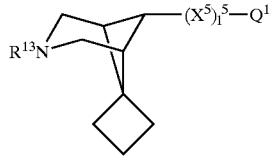

(XIII)

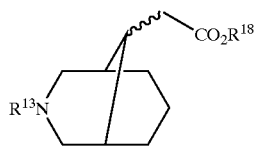

(XIV)

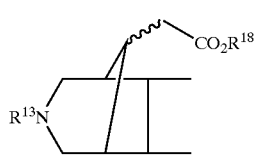

(XV)

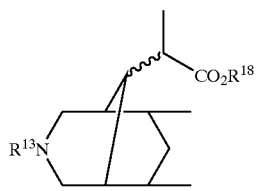

(XVI)

wherein $R^{13}$, $X^5$, $l^5$ and $Q^1$ are each as defined above; and $R^{14'}$ and $R^{15'}$ may be the same or different and each represents hydrogen or lower alkyl, provided that the following cases are excluded: that in which, in the formula (XI) or (XII), $R^{15'}$ and $R^{14'}$ are each hydrogen, $l^5$ is 0 and $Q^1$ is carboxy or ethoxycarbonyl; that in which, in the formula (XI), $R^{13}$ is methyl, $l^5$ is 1, $X^5$ has one carbon atom and forms a double bond with a carbon on the ring bonded thereto and $Q^1$ is ethoxycarbonyl, 4-methoxyphenylcarbonyl or formyl, or $R^{13}$ is methyl, $l^5$ is 1, $X^5$ is unsubstituted methylene and $Q^1$ is ethoxycarbonyl; and that in which, in the formula (XIII), $R^{13}$ is benzyl or benzoyl, $l^5$ is 0 and $Q^1$ is ethoxycarbonyl.

Further, bicycloalkyl derivatives selected from among compounds represented by the following formulae 1) to 3), their salts and hydrates thereof are still more useful:


1)

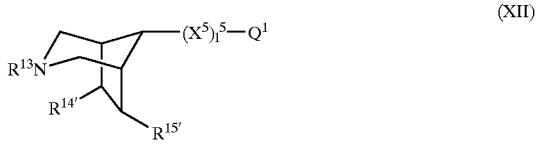

2)

3)

wherein $R^{13}$ is as defined above; and $R^{18}$ represents hydrogen, lower alkyl or a carboxy protecting group, provided that the case where, in a compound of formula 1), $R^{13}$ is methyl and $R^{18}$ is ethyl is excluded. The lower alkyl and the amino protecting group in the definition of $R^{13}$ have each the same meaning as the one defined above. Similarly, the lower alkyl and the carboxy protecting group in the definition of $R^{18}$ have each the same meaning as the one defined above.

Furthermore, piperidine derivatives represented by the formula (XVII) or (XVIII), their salts or hydrates thereof are also novel compounds. and useful as the intermediates in the synthesis of the compounds of the present invention:

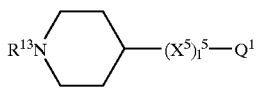
(XVII)

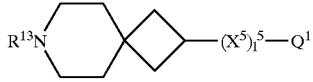
(XVIII)

wherein $R^{13}$, $X^5$, $l^5$ and $Q^1$ are each as defined above, provided that the following cases are excluded: that in which, in the formula (XVII), $X^5$ is unsubstituted $C_{1-4}$ alkylene, $l^5$ is 0 or 1 and $Q^1$ is ethoxycarbonyl, or $X^5$ is unsubstituted $C_{1-3}$ alkylene, $l^5$ is 0 or 1 and $Q^1$ is amino protected by carbonyl; and that in which, in the formula (XVIII), $l^1$ is 0 and $Q^1$ is amino optionally protected by tert-butoxycarbonyl or hydroxy optionally protected by methanesulfonyl; in particular, piperidine derivatives represented by the formula (XIX), (XX) or (XXI), their salts or hydrates thereof are useful therefor:

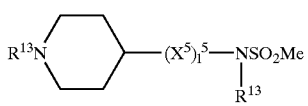
(XIX)

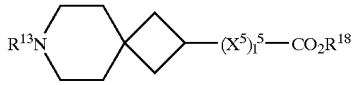
(XX)

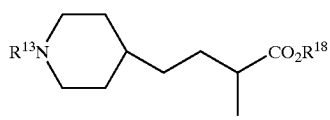
(XXI)

wherein $R^{13}$, $X^5$, $l^5$ and $R^{18}$ are each as defined above;

and, in particular, piperidine derivatives selected from among the compounds represented by the formulae 1), 2) or 3):

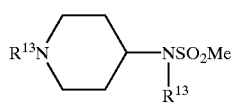
1)

2)

or

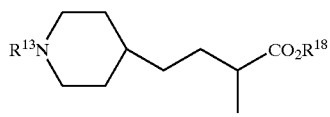
3)

wherein $R^{13}$ and $R^{18}$ are each as defined above.

Now, general processes for synthesizing the compounds of the present invention will be illustrated.

Production Process 1

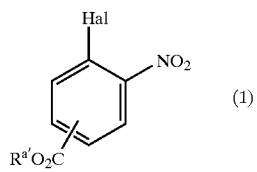
(1)

sulfurization (Step I)

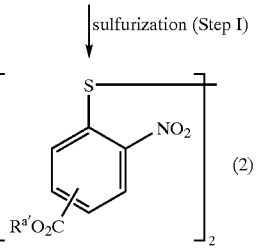
(2)

reduction reaction (Step II)

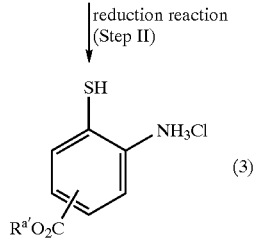
(3)

esterification (Step III)

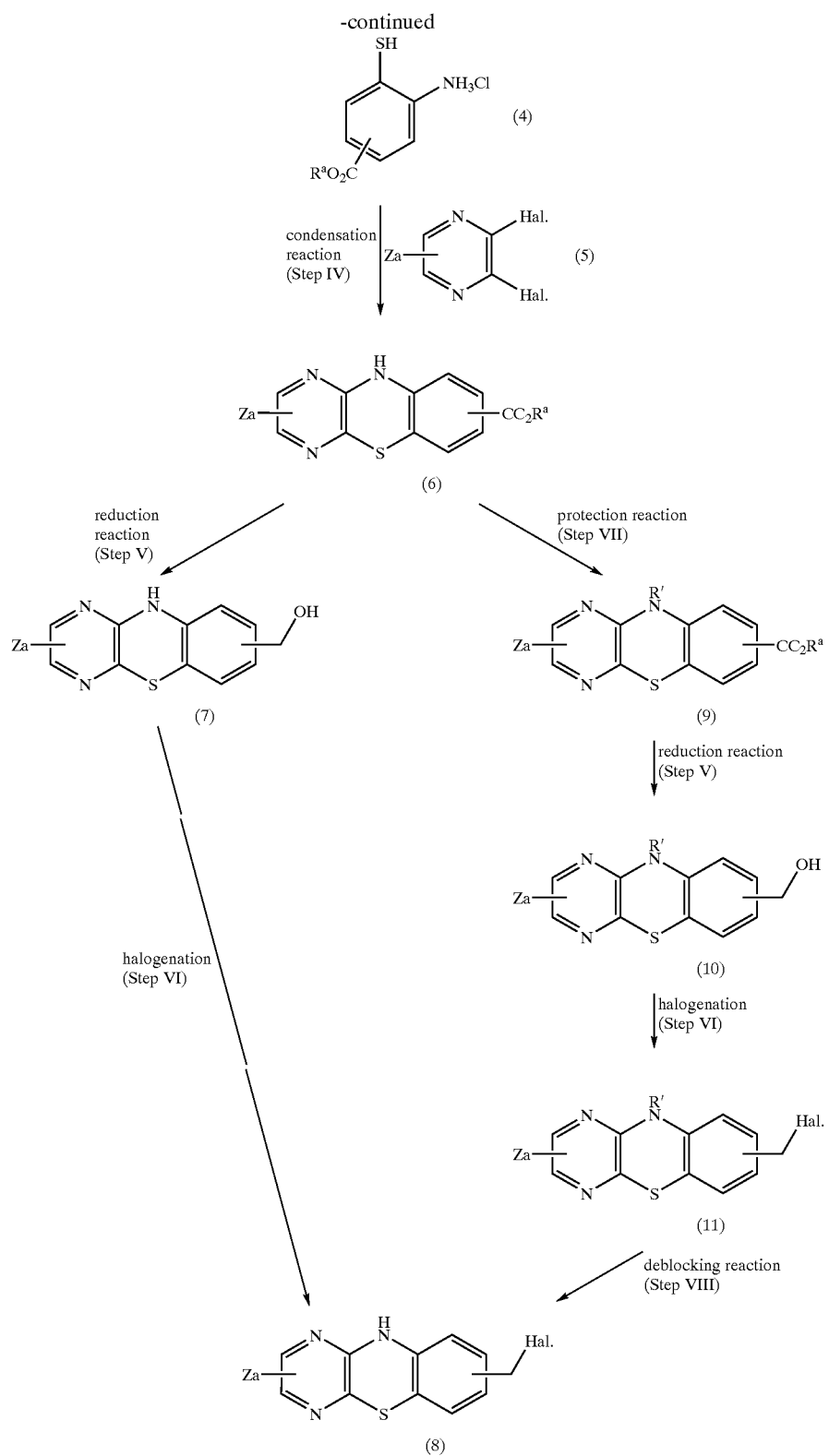
wherein Ra and Ra' represent each a carboxy protecting group; Hal. represents halogeno; Za represents a substituent of the ring G which is a pyrazine ring herein; and R' represents:
1) lower alkyl;
2) optionally substituted arylalkyl;
3) optionally substituted heteroarylalkyl;
4) an amino protecting group;
5) a group represented by the formula:

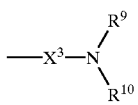

wherein $X^3$, $R^9$ and $R^{10}$ are each as defined above; or
6) a group represented by the formula:

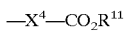

wherein $X^4$ and $R^{11}$ are each as defined above.

[Step I]

A compound represented by the formula (1) is treated with a sulfurizing agent in a solvent such as ethanol in the presence of an alkali such as sodium hydroxide to thereby give a compound of the formula (2). As the sulfurizing agent, use can be made of disodium disulfide, dilithium disulfide, etc. The reaction temperature preferably ranges from 25 to 120° C., though it is not restricted thereto.

[Step II]

Next, the intermediate represented by the formula (2) is treated with a metal such as tin in a solvent such as ethanol in the presence of an acid such as hydrochloric acid to thereby give a compound of the formula (3).

[Step III]

Subsequently, the compound of the formula (3) is reacted with an appropriate alcohol or orthoester in the presence of an acid such as hydrochloric acid or sulfuric acid to thereby give a compound represented by the formula (4).

[Step IV]

In a solvent such as dry N,N-dimethylformamide, the compound of the formula (4) is reacted with a dihalogenated pyrazine such as 2,3-dichloropyrazine [formula (5)] to thereby give a compound represented by the formula (6).

[Step VI]

The compound represented by the formula (6) or (9) is treated with a reducing agent such as diisobutylaluminum hydride or aluminum lithium hydride in a solvent to thereby give a compound represented by the formula (7) or (10). As the solvent, use can be made of dry ethers such as dry tetrahydrofuran. The reaction is preferably effected at a temperature of −50 to 50° C.

[Step VI]

The compound represented by the formula (7) or (10) is treated with a halogenating agent such as methanesulfonyl chloride in a solvent such as dry N,N-dimethylformamide in the presence of an appropriate base such as pyridine to thereby give a compound represented by the formula (8) or (11).

[Step VII]

The compound represented by the formula (6) is treated with a base such as sodium hydride and a protecting group reagent such as methoxymethyl chloride in a solvent to thereby give a compound represented by the formula (9).

[Step VIII]

The compound represented by, the formula (11) is treated with an acid such as hydrochloric acid or trifluoroacetic acid in a solvent to thereby give a compound represented by the formula (8).

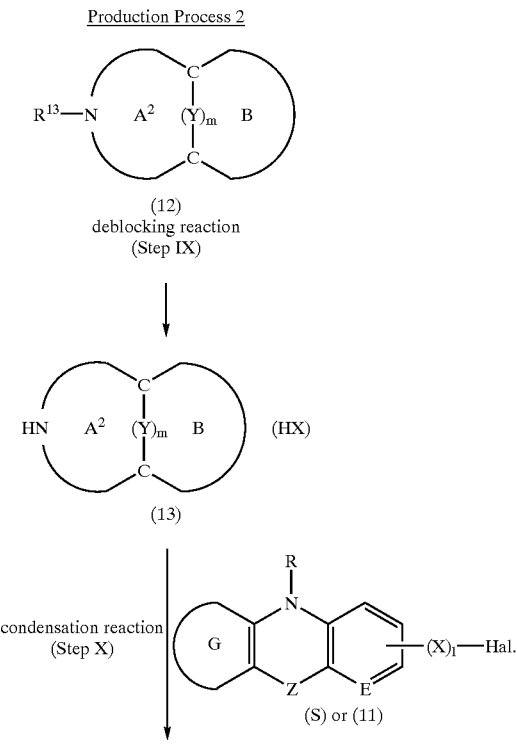

-continued

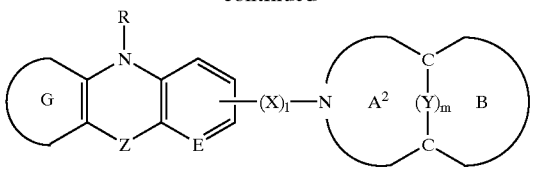

When the compound (14) has a carboxyl or ester group as a substituent, then it can be reduced to thereby give a terminal alcoholic compound, i.e., the compound (15).
(Step XXIV)

(Step XI)

When the compound (14) has an ester group as a substituent, then it can be subjected to hydrolysis to thereby give a carboxylic acid, i.e., the compound (16).

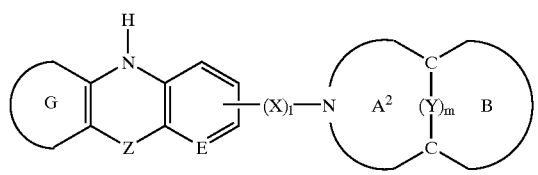

(15)

(Step VIII) When R is a substituent other than hydrogen, then it can be subjected to a deblocking reaction to thereby give the compound (15).

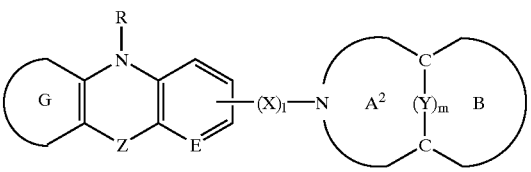

(16)

(Step VIII) When R is a substituent other than hydrogen, then it can be subjected to a deblocking reaction to thereby give the compound (16).

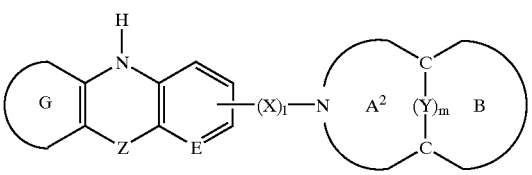

(15′)

(16′)

wherein the rings $A^2$ and B, Y, m, the ring G, R', Z, E, X, l and Hal. are each as defined above; and $R^{13a}$ represents a lower alkyl or an amino protective group.

[Step IX]

A compound represented by the formula (12) is reacted with an acid chloride such as 1-chloroethyl chloroformate or vinyl chloroformate optionally in a solvent. Next, an appropriate alcoholic solvent is added thereto and reacted therewith. Alternatively, it is treated with an appropriate solvent containing hydrochloric acid or hydrobromic acid and then heated in an alcoholic solvent. Alternatively, it is subjected to a reduction reaction in a solvent such as methanol/ethanol/tetrahydrofuran/ethyl acetate by using a metal catalyst under normal hydrogen pressure to elevated pressure. Thus, a compound represented by the formula (13) can be obtained.

[Step X]

The compound represented by the formula (13) is treated with the compound represented by the formula (8) or (11) obtained by the production process 1 in a solvent in the presence of an appropriate base such as anhydrous potassium carbonate or diisopropylamine to leave as it is give a compound represented by the formula (14). As the solvent, it is preferable to use a dry solvent such as dry N,N-dimethylformamide. The reaction is effected preferably at a temperature of 25 to 150° C. If necessary, the compound represented by the formula (14) may be subjected to optical resolution with the use of a chiral column, etc. to thereby separate enantiomers from each other.

[Step XI]

When the compound represented by the formula (14) has an ester group as a substituent, this compound is hydrolyzed by reacting with an appropriate base in an aqueous solvent to thereby give a compound of the formula (16) having a carboxyl group.

In the above reaction, it is also possible to synthesize the compound of the formula (14) by using a protecting group of the functional group commonly employed in organic synthesis, then purifying the product by an appropriate operation commonly employed in the art such as silica gel column chromatography and then deblocking the same.

[Step XXIV]

When the compound represented by the formula (14) has a carboxyl group or an ester group as a substituent, the ester of the formula (14) may be treated with a reducing agent such as aluminum lithium hydride in a dry solvent such as tetrahydrofuran, diethyl ether or dimethoxyethane at 0° C. to room temperature to thereby give a compound having a terminal alcohol group represented by the formula (15).

Production Process 3-1
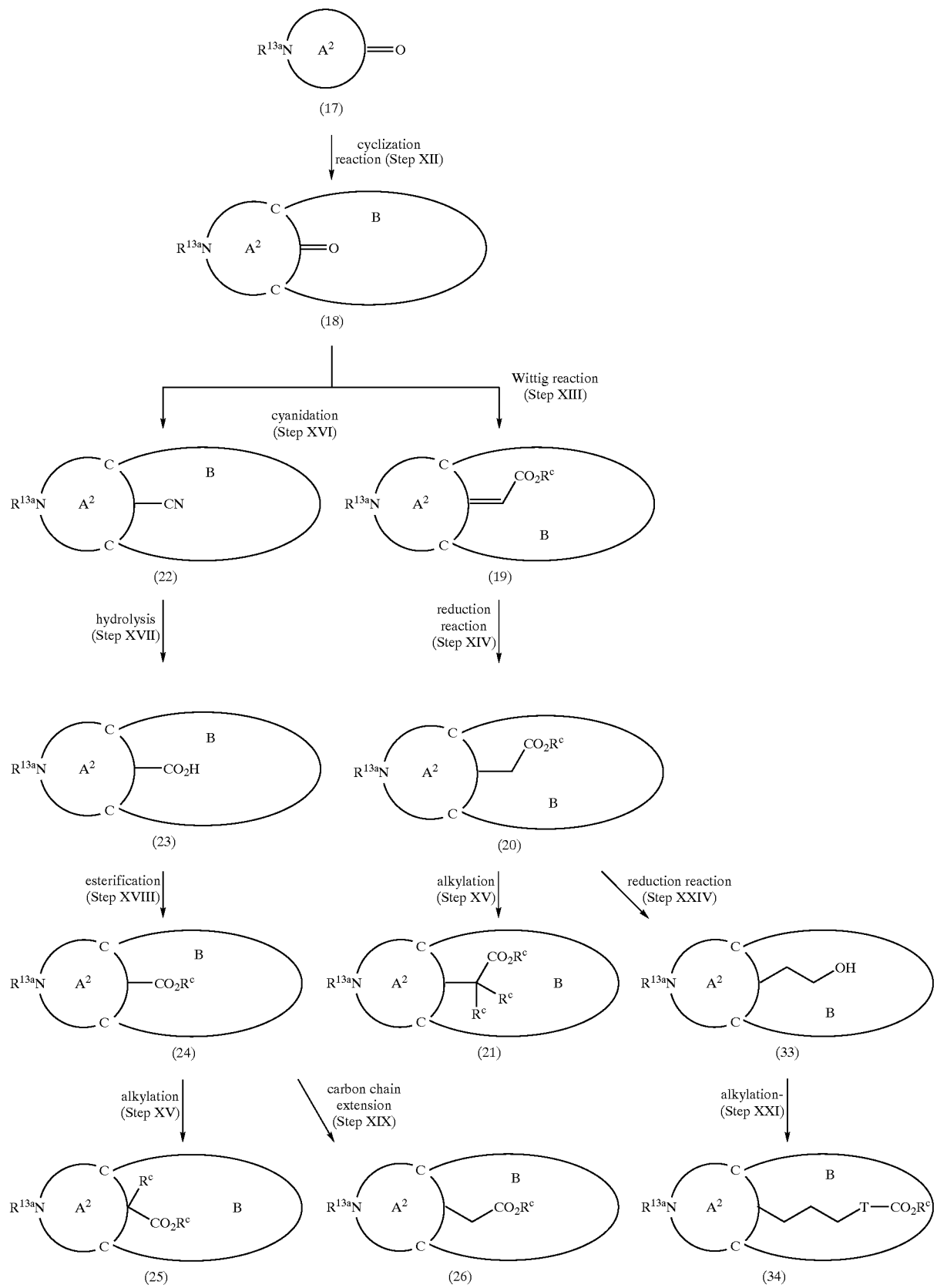

wherein $R^{13a}$ and the rings $A^2$ and B are each as defined above; $R^c$ represents lower alkyl or a carboxy protecting group; $R^d$ and $R^e$ may be the same or different and each represents lower alkyl; and T represents optionally substituted lower alkylene, optionally substituted lower alkenylene, optionally substituted lower alkynylene or optionally substituted arylene.

In the definition of T, the optionally substituted lower alkylene, optionally substituted lower alkenylene and optionally substituted lower alkynylene have each the same meaning as the one as will be defined below. On the other hand, the optionally substituted arylene means a divalent aromatic ring group optionally having substituent(s). Particular examples thereof include o-phenylene, m-phenylene, p-phenylene, methylphenylene and naphthylene groups.

[Step XII]

A compound of the formula (17), which is a commercially available product or one obtained in accordance with, for example, the method described in Bull. Soc. Chim. Fr., 2981 (1989)., is subjected to the Mannich reaction described in J.A.C.S., 84, 3139 (1962); Chem. Pharm. Bull., 11 (3), 333 (1963), etc. with an appropriate amine and an appropriate aldehyde in a solvent to thereby give a compound represented by the formula (18). As the solvent, use can be made of ethanol, methanol, acetic acid, etc. The reaction is effected preferably at from 25° C. to the reflux temperature.

[Step XIII]

The compound represented by the formula (18) is reacted with an appropriate Wittig-Horner-Emmons reagent in a solvent in the presence of an appropriate base to thereby give a compound represented by the formula (19). As the solvent, use can be made of dry solvents such as N,N-dimethylformamide, tetrahydrofuran or diethyl ether. As the base, use can be made of sodium hydride, potassium tert-butoxide, n-butyllithium, etc. The reaction can be effected at from −100° C. to the boiling point of the solvent.

[Step XIV]

The compound represented by the formula (19) is reduced with the use of an appropriate metal or an appropriate metal catalyst in a solvent to thereby give a compound represented by the formula (20). The compound of the formula (20) can be obtained by, for example, using a catalyst such as palladium in a solvent such as methanol, ethanol or ethyl acetate under normal to elevated hydrogen pressure, or treating the compound (19) with magnesium in a solvent such as methanol.

[Step XV]

Compounds represented by the formula (20), (24), etc. are reacted with a base such as lithium diisopropylamide in a dry solvent such as diethyl ether or tetrahydrofuran and then reacted with an alkyl halide to thereby give compounds represented by the formula (21), (25), etc. respectively. The reaction temperature preferably ranges from −100 to 25° C.

[Step XVI]

The compound represented by the formula (18) is treated with a cyanidation reagent such as tosylmethyl isocyanide (TosMic) in a mixture of a solvent such as dimethoxyethane, tetrahydrofuran or diethyl ether with an alcoholic solvent such as tert-butanol in the presence of a base such as potassium tert-butoxide to thereby give a cyano compound represented by the formula (22). It is preferable to effect this reaction at a temperature of 0 to 100° C.

[Step XVII]

The cyano compound of the formula (22), etc. is treated with a base such as sodium hydroxide or potassium hydroxide in an alcoholic solvent such as ethanol, propanol, ethylene glycol or diethylene glycol and heated under reflux to thereby give a carboxylic acid represented by the formula (23), etc.

[Step XVIII]

The compound of the formula (23), etc. is treated with an activator such as thionyl chloride in an alcoholic solvent such as methanol or ethanol to thereby give an ester of the formula (24), etc. The reaction temperature preferably ranges from 0° C. to room temperature.

[Step XIX]

A dihalomethane such as dibromomethane or diuodomethane is treated successively with a lithium amide such as lithium 2,2,6,6-tetramethylpiperidine and the ester of the formula (24), etc. After further treating with a base, the obtained product is hydrolyzed to thereby give an ester represented by the formula (26), etc. As a solvent, it is preferable to use tetrahydrofuran, diethyl ether, etc. The reaction temperature ranges from −90° C. to room temperature.

[Step XXI]

An alcohol represented by the formula (33) is treated with a base such as sodium hydride or sodium methoxide and then reacted with a halogenated acetate such as an alkyl iodoacetate such as ethyl iodoacetate to thereby give an ether represented by the formula (34). When a phenol derivative is employed as an alkylating agent, an ether represented by the formula (34) can be obtained by the so-called Mitsunobu reaction with the use of a condensing agent such as diethyl azadicarboxylate and triphenylphosphine.

Production Process 3-2

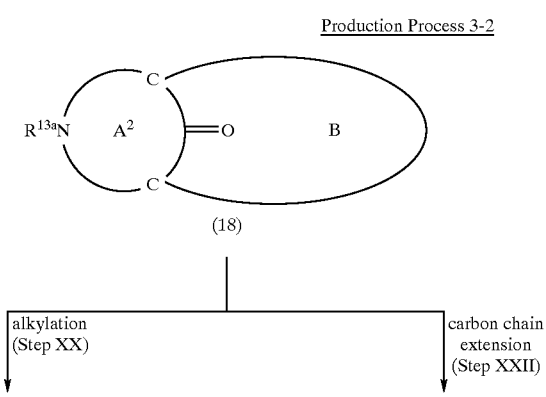

(18)

| alkylation (Step XX) | carbon chain extension (Step XXII) |

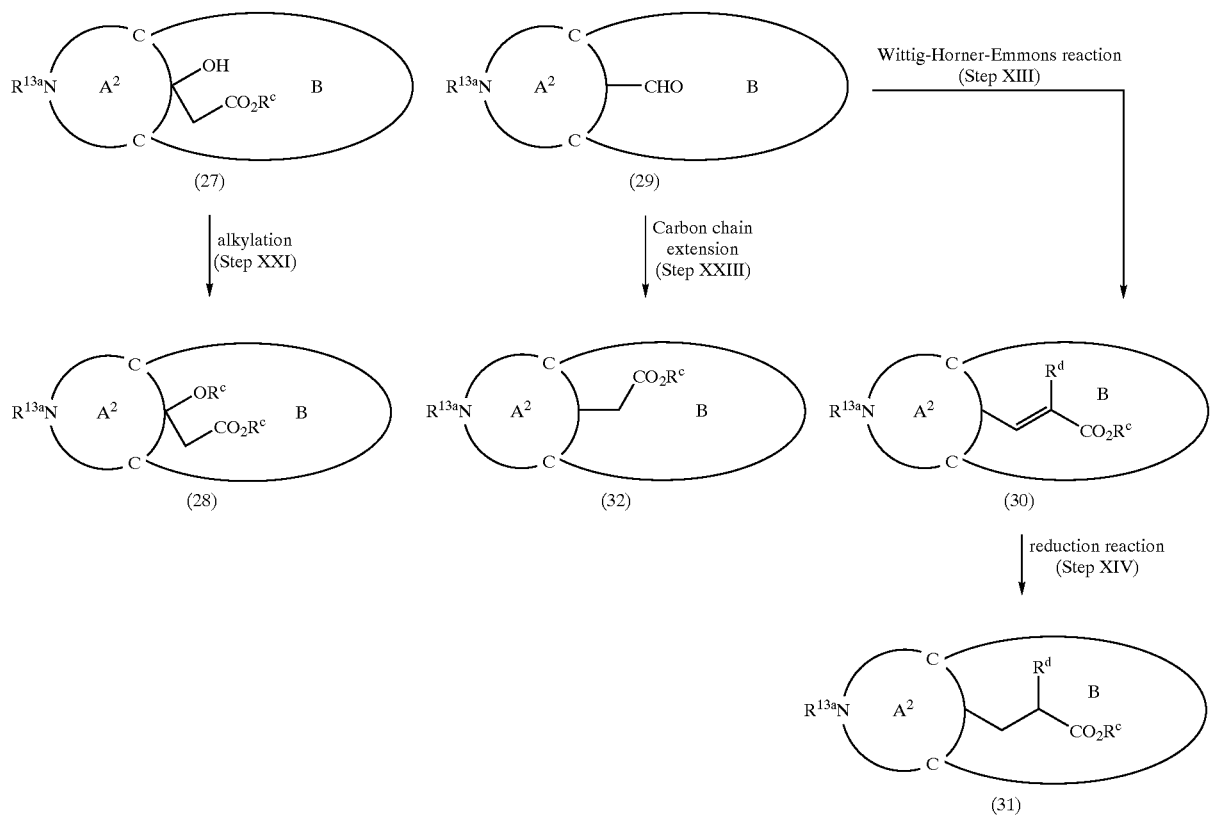

wherein the rings $A^2$ and B, $R^{13a}$, $R^c$, $R^d$ and $R^e$ are each as defined above.

[Step XX]

An ester such as methyl acetate or ethyl acetate is treated with a base such as lithium diisopropylamide and reacted with a ketone represented by the formula (18). Thus a β-hydroxyacetate represented by the formula (27) can be obtained. As the solvent, it is appropriate to use diethyl ether, tetrahydrofuran, etc. The reaction temperature ranges from −78° C. to room temperature.

[Step XXI]

The alcohol represented by the formula (27) is treated with a base such as sodium hydride or sodium methoxide and then reacted with an alkyl halide such as methyl iodide or ethyl iodide in a solvent such as dimethoxyethane, tetrahydrofuran or N,N-dimethylformamide to thereby give an ether represented by the formula (28). When a phenol derivative is employed as an alkylating agent, an ether represented by the formula (28) can be obtained by the so-called Mitsunobu reaction with the use of a condensing agent such as diethyl azadicarboxylate and triphenylphosphine.

[Step XXII]

(Methoxymethyl)trimethylsilane, methoxymethyl dimethylphosphonate, etc. is treated with a strong base such as butyllithium in a dry solvent such as tetrahydrofuran, dimethoxyethane or diethyl ether to thereby give an enol ether. Next, this product is hydrolyzed with an acid such as hydrochloric acid, sulfuric acid or acetic acid in an alcoholic solvent such as methanol or ethanol to thereby give an aldehyde having one more carbon atom as represented by the formula (29), etc.

[Step XXIII]

A dithiane such as 2-trimethyl-1,3-dithiane is reacted with a strong base such as butyllithium and the anion thus obtained is reacted with the aldehyde represented by the formula (29). The crude dithiane thus obtained is then treated with a metal salt such as mercury chloride to thereby give an ester represented by the formula (32).

[Step XIII]

The compound represented by the formula (29) is reacted with an appropriate Wittig-Horner-Emmons reagent in a solvent in the presence of an appropriate base to thereby give a compound represented by the formula (30). As the solvent, use can be made of dry solvents such as N,N-dimethylformamide, tetrahydrofuran or diethyl ether. As the base, use can be made of sodium hydride, potassium tert-butoxide, n-butyllithium, etc. The reaction can be effected at from −10° C. to the boiling point of the solvent.

[Step XIV]

The compound represented by the formula (30) is reduced with the use of an appropriate metal or an appropriate metal catalyst in a solvent to thereby give a compound represented by the formula (31). The compound of the formula (31) can be obtained by, for example, using a catalyst such as palladium in a solvent such as methanol, ethanol or ethyl acetate under normal to elevated hydrogen pressure, or treating the compound (30) with magnesium in a solvent such as methanol.

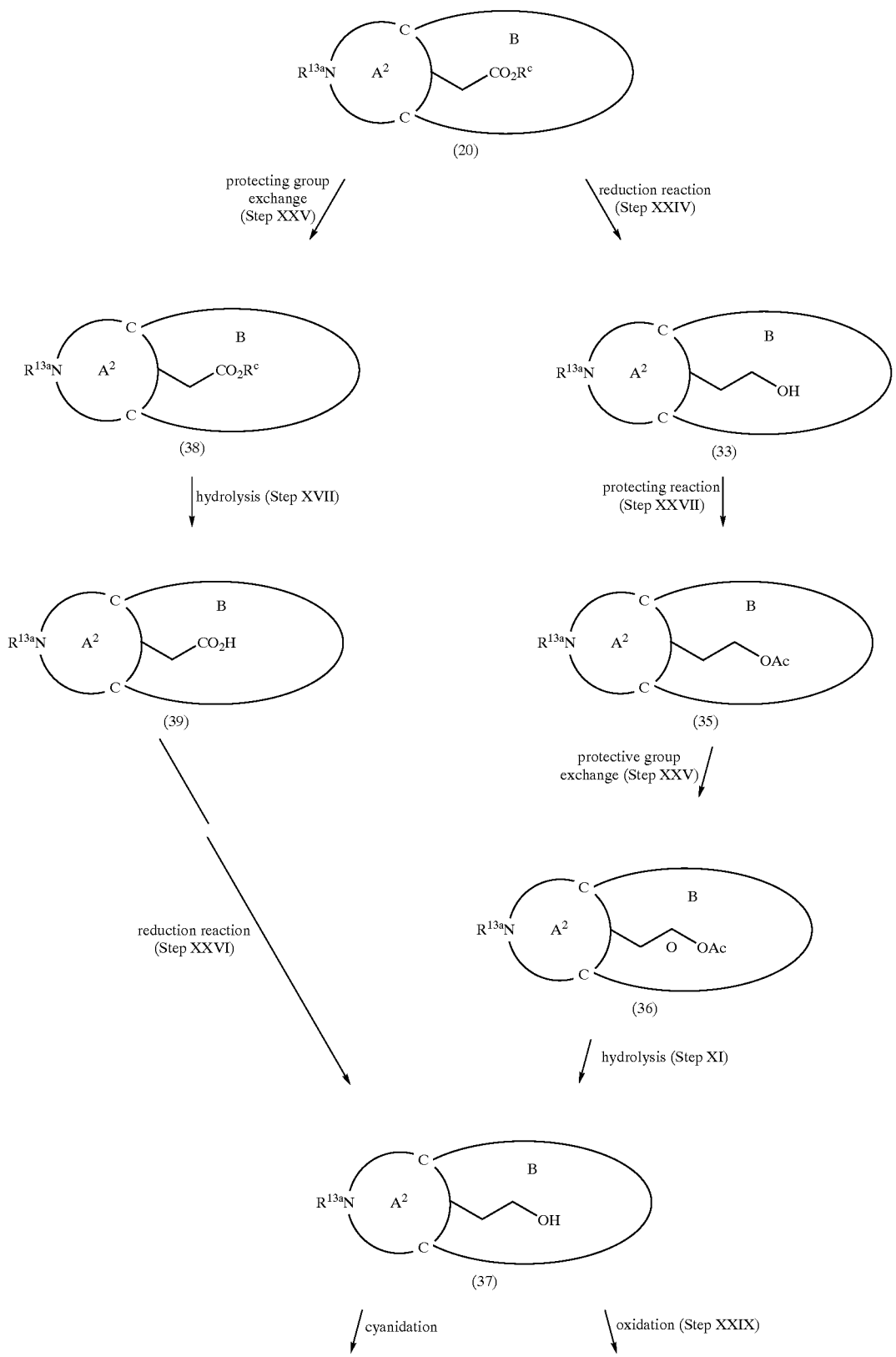

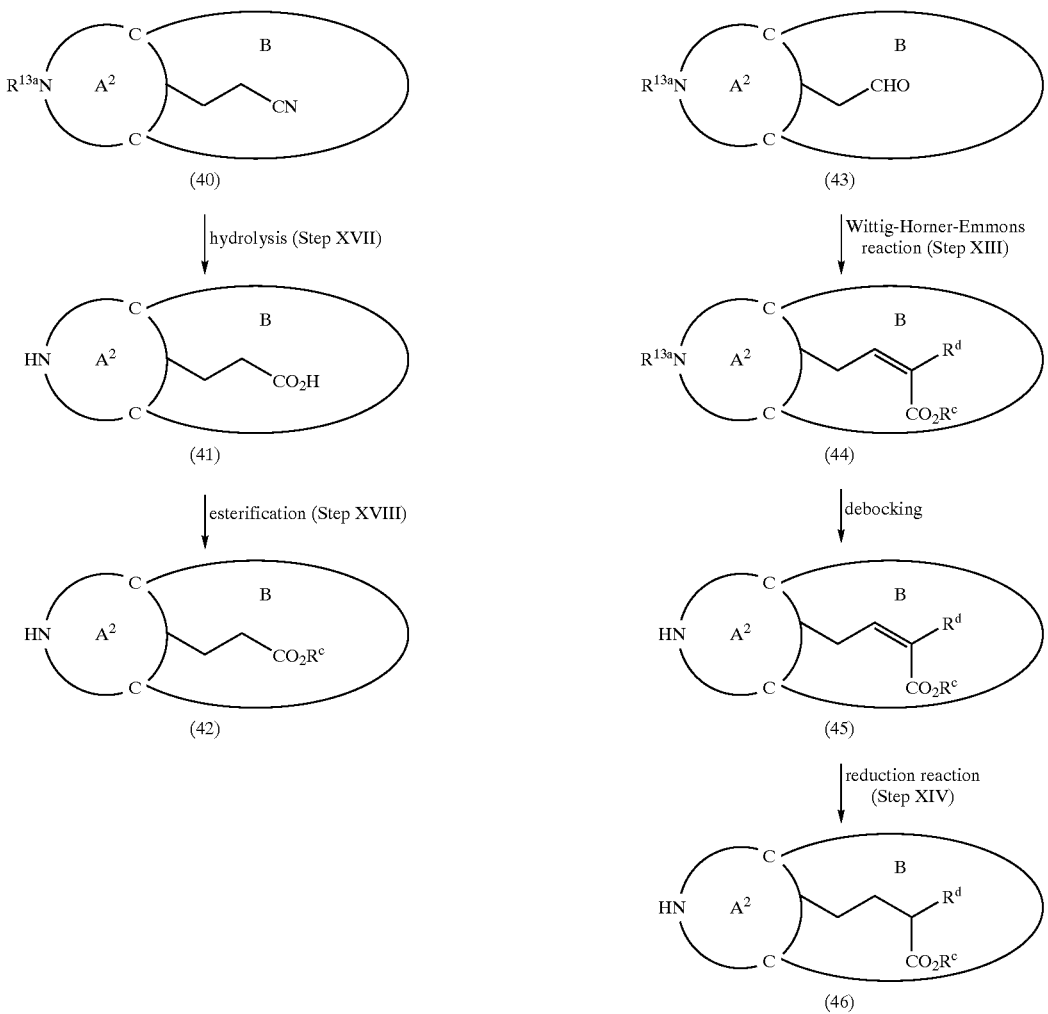

wherein the rings $A^2$ and B, $R^{13a}$, $R^c$ and $R^d$ are each as defined above; $R^{13b}$ represents lower alkyl or an amino protective group; and Ac represents acetyl.

[Step XXV]

An amine represented by the formula (20) is treated with an amino protecting group such as vinyl chloroformate optionally in an appropriate solvent such as 1,2-dichloroethane at 0° C. to the reflux temperature to thereby give an amine protected with vinylformate represented by the formula (38). It is preferable that $R^{13b}$ is a carbamate-type amino protecting group, still more preferably vinyloxycarbonyl.

[Step XI]

A compound represented by the formula (38) is reacted with an appropriate base in an aqueous solvent and then hydrolyzed to thereby give a compound of the formula (39) having a carboxyl group.

[Step XXVI]

The carboxylic acid represented by the formula (39) is reacted with active esterifying agents such as N-hydroxysuccinimide with N,N-dicyclohexylcarbodiimide or a base such as triethylamine with ethyl chloroformate to thereby give an active acid anhydride. This is then treated with an appropriate reducing agent such as sodium borohydride to thereby give an alcohol represented by the formula (37).

[Step XXIV]

Similarly to the above-mentioned procedure, the ester represented by the formula (20) is treated with a reducing agent such as aluminum lithium hydride in a dry solvent such as tetrahydrofuran, diethyl ether or dimethoxyethane to thereby give an alcohol represented by the formula (33).

[Step XXVII]

The alcohol represented by the formula (33) is treated with acetic anhydride or acetyl chloride in an appropriate solvent in the presence of pyridine as a base to thereby give an ester represented by the formula (35).

[Step XXV]

Similarly to the above-mentioned procedure, the amine compound represented by the formula (35) is treated with an amino protecting group such as vinyl chloroformate optionally in an appropriate solvent such as 1,2-dichloroethane at 0° C. to the reflux temperature to thereby give an amine protected by vinylformate represented by the formula (36). $R^{13b}$ is preferably a carbamate-type protecting group, though it is not restricted to such.

[Step XI]

Similarly to the above-mentioned procedure, the compound represented by the formula (36) is reacted with an appropriate base in an aqueous solvent and then hydrolyzed to thereby give a compound of the formula (37) having a hydroxyl group.

[Step XXVIII]

The alcohol represented by the formula (37) is reacted with an activating reagent such as methanesulfonyl chloride or p-toluenesulfonyl chloride in the presence of an appropriate base such as pyridine. Next, it is treated with a cyaniding agent such as sodium cyanide or potassium cyanide in an aprotic polar solvent such as dimethyl sulfoxide to thereby give a cyano compound represented by the formula (40). This reaction can be effected from room temperature to the boiling point of the solvent.

[Step XVII]

Similarly to the above-mentioned procedure, the cyano compound of the formula (40) is treated with a base such as sodium hydroxide or potassium hydroxide in an alcoholic solvent such as ethanol, propanol, ethylene glycol or diethylene glycol and heated under reflux to thereby give a carboxylic acid of the formula (41).

[Step XVIII]

Similarly to the above-mentioned procedure, the compound of the formula (41) is treated with an activator such as thionyl chloride in an alcoholic solvent such as methanol or ethanol to thereby give an ester of the formula (42). The reaction temperature preferably ranges from 0° C. to room temperature.

[Step XXIX]

A solution of the alcohol represented by the formula (37) in, for example, methylene chloride is added to a reaction mixture obtained from oxalyl chloride and dimethyl sulfoxide and treated with a base such as triethylamine, i.e., the so-called Swern oxidation. Thus, an aldehyde represented by the formula (43) can be obtained.

[Step XIII]

The compound represented by the formula (43) is reacted with an appropriate Wittig-Horner-Emmons reagent in a solvent in the presence of an appropriate base to thereby give a compound represented by the formula (44). As the solvent, use can be made of dry solvents such as N,N-dimethylformamide, tetrahydrofuran or diethyl ether. As the base, use can be made of sodium hydride, potassium tert-butoxide, n-butyl lithium, etc. The reaction can be effected at from 31 10° C. to the boiling point of the solvent.

[Step IX]

The compound represented by the formula (44) is treated with an appropriate solvent containing hydrobromic acid and then heated in an alcoholic solvent to thereby give a compound represented by the formula (45).

[Step XIV]

Similarly to the above-mentioned procedure, the compound represented by the formula (45) is reduced by the use of an appropriate metal or an appropriate metal catalyst in a solvent to thereby give a compound represented by the formula (46). The compound of the formula (46) can be obtained by, for example, using a catalyst such as palladium in a solvent such as methanol, ethanol or ethyl acetate under normal to elevated hydrogen pressure, or treating the compound (45) with magnesium in a solvent such as methanol.

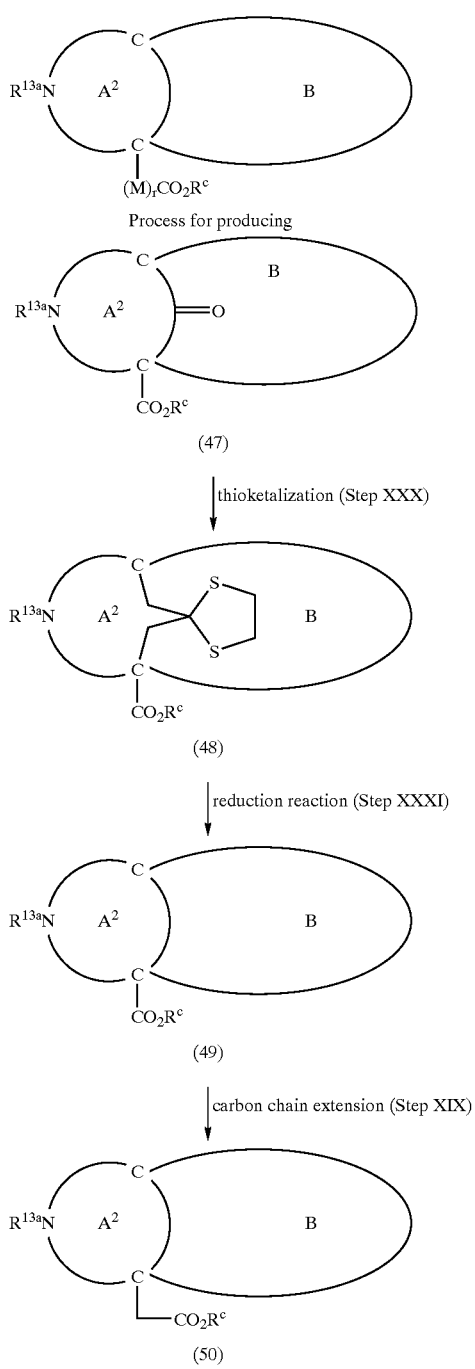

Production Process 5-1

Process for producing wherein the rings $A^2$ and B, $R^{13a}$, $R^c$, $R^d$ and l are each as defined above; and M represents an optionally substituted lower alkylene optionally having a heteroatom, optionally substituted lower alkenylene optionally having a heteroatom, optionally substituted lower alkynylene optionally having a heteroatom or optionally substituted arylene optionally having a heteroatom.

In the definition of M, the optionally substituted lower alkylene optionally having a heteroatom, the optionally substituted lower alkenylene optionally having a heteroatom and the optionally substituted lower alkynylene optionally having a heteroatom have each the same meaning as the one defined above, while the optionally substituted arylene optionally having a heteroatom means an optionally substituted divalent aromatic ring group optionally having a heteroatom. Particular examples of the divalent aromatic ring group include o-phenylene, m-phenylene, p-phenylene, methylphenylene and naphthylene groups.

[Step XXX]

A ketone represented by the formula (47) is reacted with a thioalcohol such as ethanedithiol in the presence of a boron trifluoride complex in a solvent such as dichloromethane to thereby give a thioketal represented by the formula (48).

[Step XXXI]

The thioketal represented by the formula (48) is treated with a reducing reagent such as Raney nickel to thereby give a compound represented by the formula (49). As a solvent, use can be made of ethanol, methanol etc. The reaction is preferably effected at the reflux temperature of the solvent.

[Step XIX]

Similarly to the above-mentioned procedure, a dihalomethane such as dibromomethane or diiodomethane is treated successively with a lithium amide such as lithium 2,2,6,6-tetramethylpiperidine and the ester of the formula (49). After further treating with base, the obtained product is hydrolyzed with an acid to thereby give an ester represented by the formula (50). As a solvent, it is preferable to use tetrahydrofuran, diethyl ether, etc. The reaction temperature ranges from −90° C. to room temperature.

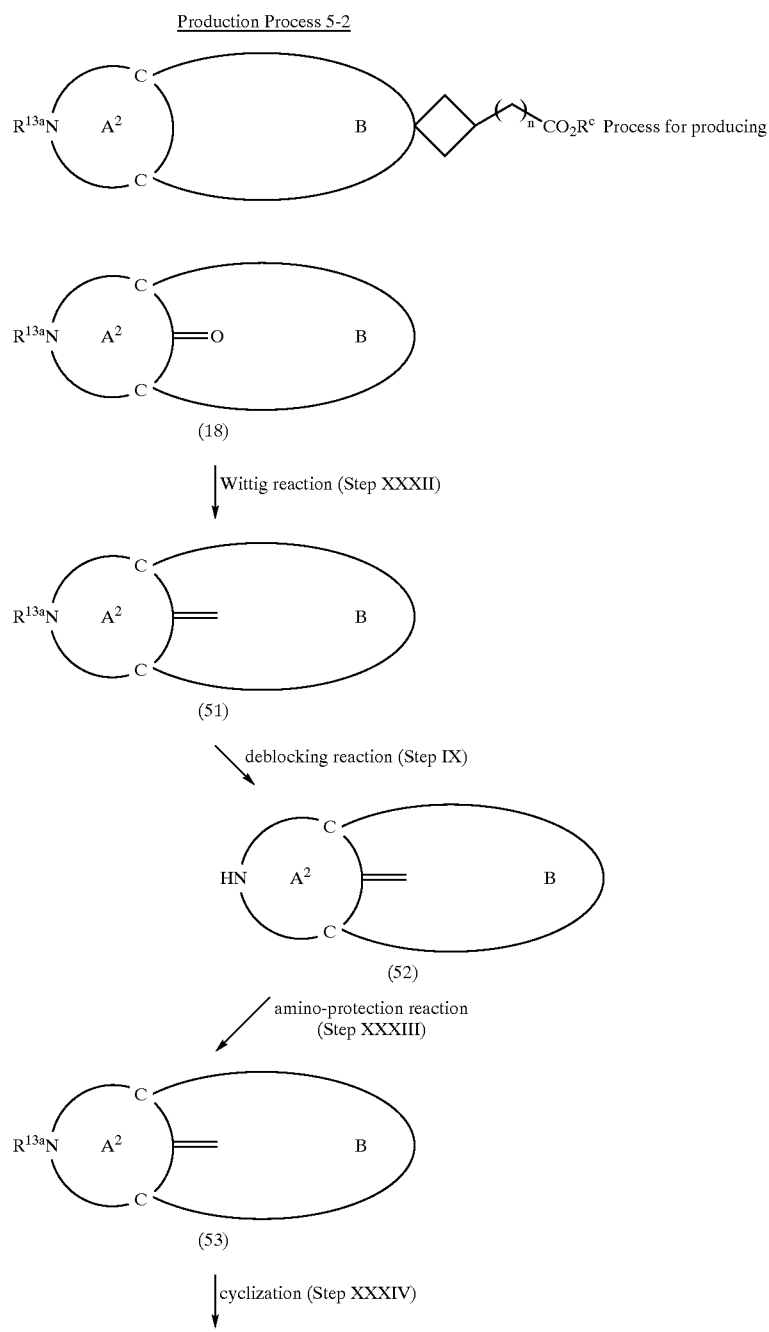

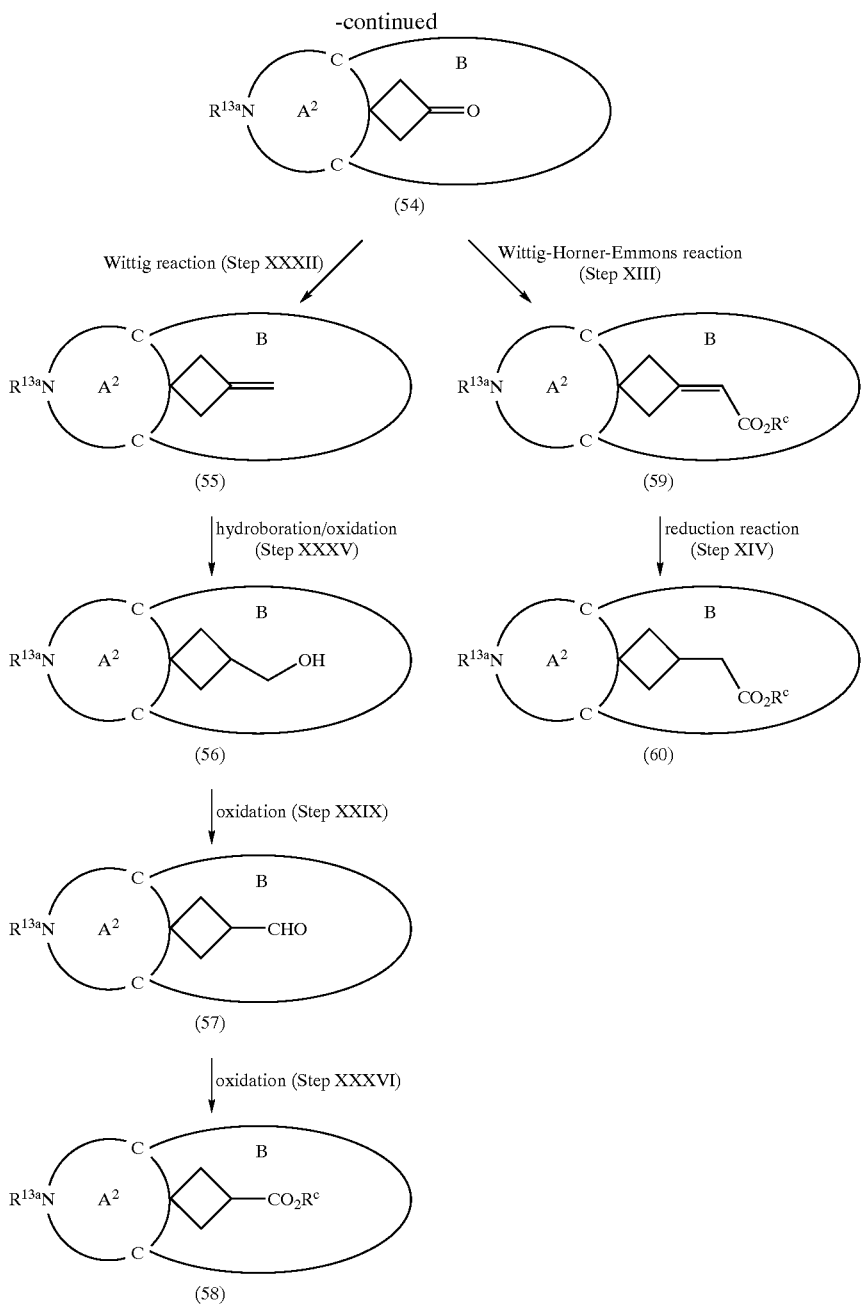

wherein the rings $A^2$ and B, $R^{13a}$, $R^{13b}$, $R^c$ and n are each as defined above.

[Step XXXII]

Methyltriphenylphosphonium bromide is treated with an appropriate base such as potassium tert-butoxide or butyllithium in a solvent such as toluene, xylene or tetrahydrofuran. Next, ketones represented by the formulae (18) and (54) are reacted therewith to thereby give compounds represented by the formulae (51) and (55). The reaction temperature preferably ranges from −78° C. to room temperature.

[Step IX]

Similarly to the above-mentioned procedure, the compound represented by the formula (51) is reacted with an acid chloride such as 1-chloroethyl chloroformate or vinyl chloroformate optionally in a solvent. Next, an appropriate alcoholic solvent is added thereto and reacted therewith. Alternatively, it is treated with an appropriate solvent containing hydrochloric acid or hydrobromic acid and then heated in an alcoholic solvent. Alternatively, it is subjected to a reduction reaction in a solvent such as methanol/ethanol/tetrahydrofuran/ethyl acetate by using a metal catalyst under normal to elevated hydrogen pressure. Thus, a compound represented by the formula (52) can be obtained.

[Step XXXIII]

The compound represented by the formula (52) is reacted with, for example, di-tert-butyl dicarbonate as an amino protecting group preferably at 0° C. to room temperature in the presence of a base such as pyridine, diisopropylethylamine or triethylamine in an appropriate solvent such as methanol to thereby give a compound represented by the formula (53). $R^{13b}$ may be arbitrary, so long as it is a lower alkyl or an amino protecting group. Preferable examples of the amino protecting group as $R^{13b}$ are those which can be converted into carbamate, amide, sulfonamide, etc. after the introduction of the protecting group. For example, butoxycarbonyl is preferable therefor.

[Step XXXIV]

The compound represented by the formula (53) is treated with zinc/copper alloy and trichloroacetyl chloride in a dry solvent such as diethyl ether, dimethoxyethane or tetrahydrofuran to thereby give a crude dichlorobutanone compound. Then the crude product thus obtained is treated with a reducing agent such as ammonium chloride/zinc in methanol to thereby give a spiroketone compound represented by the formula (54). The reaction temperature preferably ranges from 0 to 50° C.

[Step XXXV]

An exo-methylene compound represented by the formula (55) is treated with an appropriate borane compound such as a borane/tetrahydrofuran complex in an appropriate solvent such as dry tetrahydrofuran or dimethoxyethane followed by treatment with an oxidizing agent such as hydrogen peroxide in an alkaline solution. Thus, an alcohol compound represented by the formula (56) can be obtained.

[Step XXIX]

Similarly to the above-mentioned procedure, a solution of the alcohol represented by the formula (56) in, for example, methylene chloride is added to a reaction mixture obtained from oxalyl chloride and dimethyl sulfoxide and treated with a base such as triethylamine, i.e., the so-called Swern oxidation. Thus, an aldehyde represented by the formula (57) can be obtained.

[Step XXXVI]

The compound represented by the formula (57) is treated with bromine preferably at 0° C. to room temperature in an appropriate alcoholic solvent such as methanol or ethanol in the presence of an alkaline base such as sodium hydrogencarbonate or potassium carbonate to thereby give an ester compound represented by the formula (58).

[Step XIII]

Similarly to the above-mentioned procedure, the compound represented by the formula (54) is reacted with an appropriate Wittig-Horner-Emmons reagent in a solvent in the presence of an appropriate base to thereby give a compound represented by the formula (59). As the solvent, use can be made of dry solvents such as N,N-dimethylformamide, tetrahydrofuran or diethyl ether. As the base, use can be made of sodium hydride, potassium tert-butoxide, n-butyllithium, etc. The reaction can be effected at −100° C. to the boiling point of the solvent.

[Step XIV]

Similarly to the above-mentioned procedure, the compound represented by the formula (59) is reduced by the use of an appropriate metal or an appropriate metal catalyst in a solvent to thereby give a compound represented by the formula (60). The compound of the formula (60) can be obtained by, for example, using a catalyst such as palladium in a solvent such as methanol, ethanol or ethyl acetate under normal to elevated hydrogen pressure, or treating the compound (59) with magnesium in a solvent such as methanol.

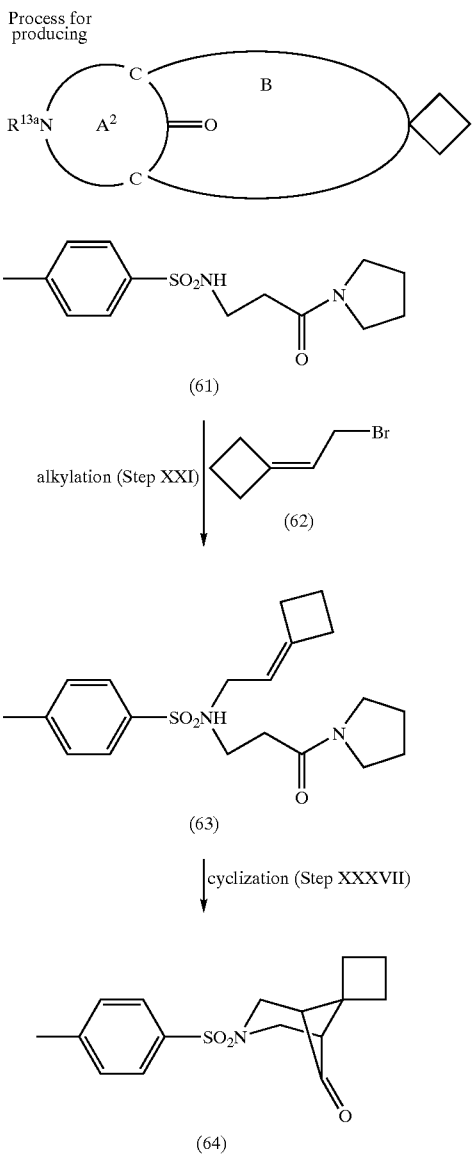

Production Process 5-3 wherein the rings $A^2$ and B and $R^{13a}$ are each as defined above.

[Step XXI]

A compound represented by the formula (61) is treated with a base such as sodium hydride or sodium methoxide and then reacted with a compound of the formula (62) in a solvent such as dimethoxyethane, tetrahydrofuran or N,N-dimethylformamide to thereby give a compound represented by the formula (63).

[Step XXXVII]

The compound represented by the formula (63) is treated in 1,2-dichloroethane employed as a solvent successively with trifluoromethanesulfonic anhydride and a base such as collidine to thereby give a cyclized product represented by the formula (64).

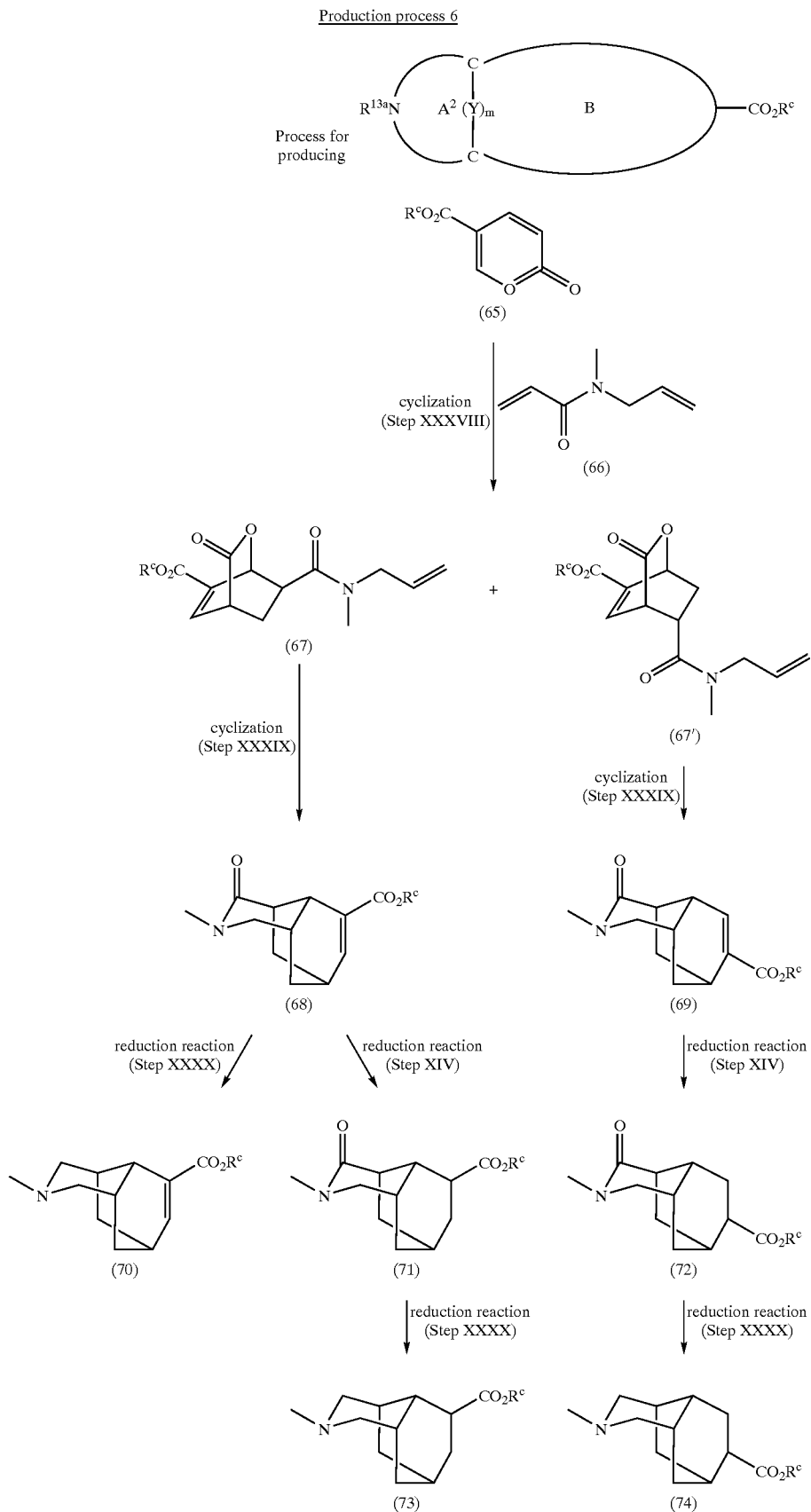

wherein the rings $A^2$ and B, $R^{13a}$, $R^c$, Y and m are each as defined above.

[Step XXXVIII]

A coumarate derivative represented by the formula (65) is reacted with a compound represented by the formula (66) under heating preferably at 80 to 150° C. to thereby give cyclized products represented by the formulae (67) and (67').

[Step XXXIX]

A compound represented by the formula (67) is cyclized by heating, optionally in an appropriate solvent, to thereby give a tricyclic compound represented by the formula (68). The compound of the formula (69) can be synthesized from the compound (67') also under the same conditions too. The reaction is preferably effected at 100 to 200° C.

[Step XXXX]

The amide compounds represented by the formulae (68), (71) and (72) are treated with a thioamidation agent such as a Lawson reagent in a solvent such as benzene, toluene or xylene to thereby give crude thioamide compounds. These crude products are treated with an alkylating agent such as methyl iodide in a solvent such as tetrahydrofuran, dimethoxyethane or diethyl ether preferably at room temperature to thereby give reduced compounds represented by the formulae (70), (73) and (74) respectively.

[Step XIV]

Similar to the above-mentioned procedure, the compounds represented by the formulae (68) and (69) are reduced by the use of an appropriate metal or an appropriate metal catalyst in a solvent to thereby give compounds represented by the formulae (71) and (72). These products can be obtained by, for example, using a catalyst such as palladium in a solvent such as methanol, ethanol or ethyl acetate under normal to elevated hydrogen pressure, or treating the starting compounds with magnesium in a solvent such as methanol.

Production process 7-1

1)

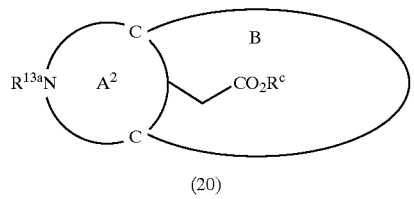

(20)

alkylation (Step XXXXI)

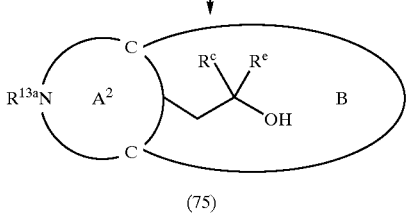

(75)

2)

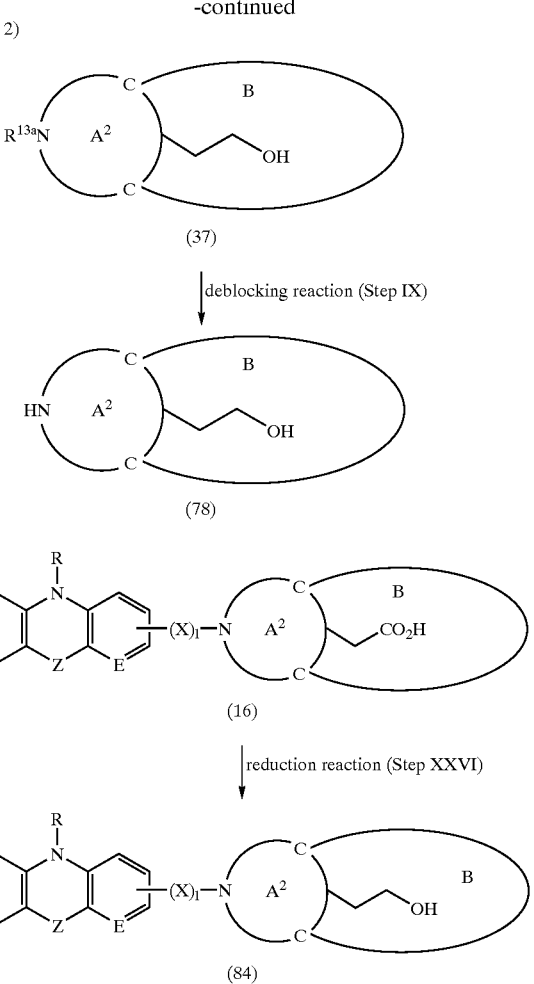

wherein the rings $A^2$, B and G, R, $R^{13a}$, $R^{13b}$, $R^c$, $R^e$, Z, E, X and l are each as defined above.

[Step XXXXI]

A compound represented by the formula (20) is treated with an alkyllithium such as methyllithium or ethyllithium or a Grignard reagent such as a methylmagnesium halide in a solvent such as dry tetrahydrofuran, diethyl ether or dimethoxyethane at −78° C. to the boiling point of the solvent to thereby give an alcohol represented by the formula (75).

[Step IX]

Similarly to the above-mentioned procedure, a compound represented by the formula (37) is reacted with an acid chloride such as 1-chloroethyl chloroformate or vinyl chloroformate optionally in a solvent. Next, an appropriate solvent is added thereto and reacted therewith. Alternatively, it is treated with an appropriate solvent containing hydrochloric acid or hydrobromic acid and then heated in an alcoholic solvent. Thus, a compound represented by the formula (78) can be obtained.

[Step XXVI]

Similarly to the above-mentioned procedure, an acid represented by the formula (16) is reacted with a reducing agent such as aluminum lithium hydride in a dry solvent such as tetrahydrofuran, diethyl ether or dimethoxyethane to thereby give an alcohol represented by the formula (84).

Production process 7-2

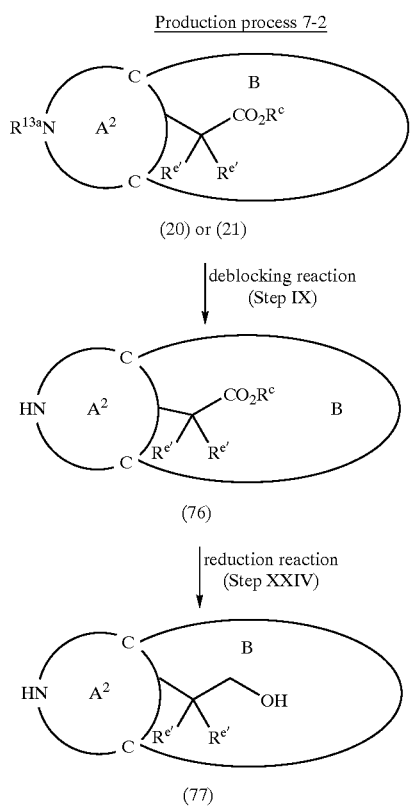

wherein the rings $A^2$ and B, $R^{13a}$ and $R^c$ are each as defined above; and $R^{e'}$ represents lower alkyl.

[Step IX]

Similarly to the above-mentioned procedure, a compound represented by the formula (20) or (21) is reacted with an acid chloride such as 1-chloroethyl chloroformate or vinyl chloroformate optionally in a solvent. Next, an appropriate alcoholic solvent is added thereto and reacted therewith. Alternatively, it is treated with an appropriate solvent containing hydrochloric acid or hydrobromic acid and then heated in an alcoholic solvent. Thus, a compound represented by the formula (76) can be obtained.

[Step XXIV]

Similarly to the above-mentioned procedure, an ester represented by the formula (76) is treated with a reducing agent such as aluminum lithium hydride in a dry solvent such as tetrahydrofuran, diethyl ether or dimethoxyethane at 0° C. to room temperature to thereby give an alcohol represented by the formula (77).

Production process 7-3

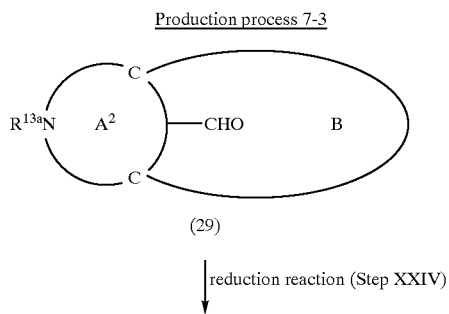

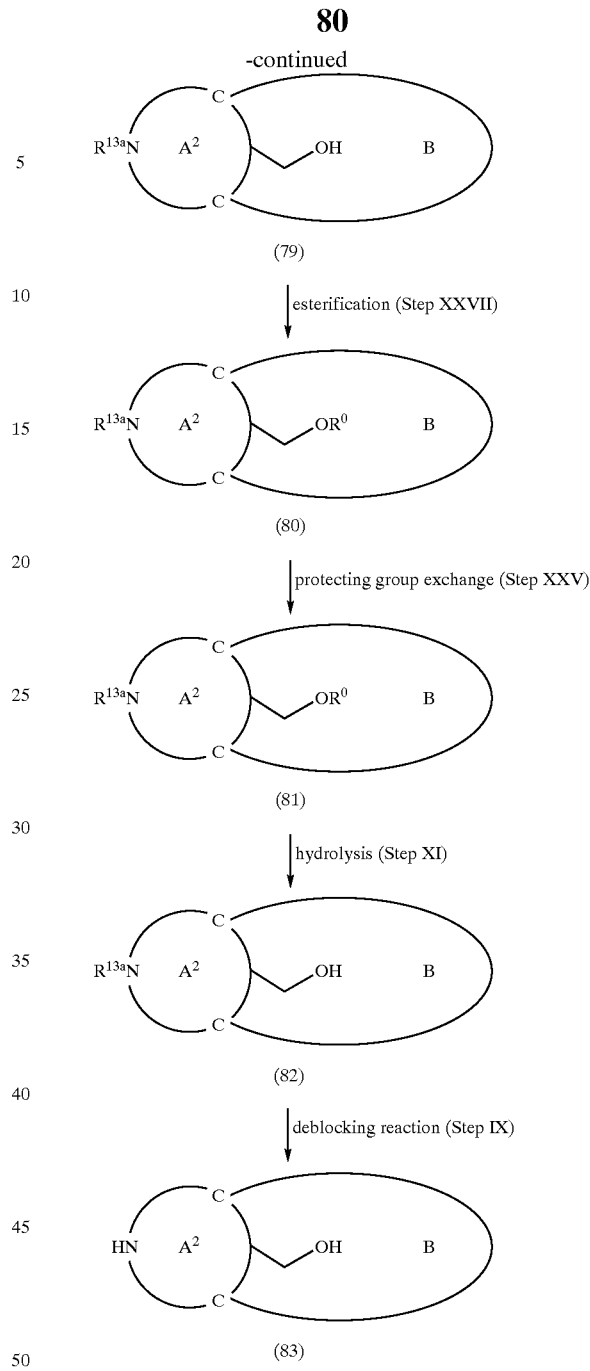

wherein the rings $A^2$ and B, $R^{13a}$ and $R^{13b}$ are each as defined above; and $R^p$ represents a hydroxy protective group.

The term "hydroxy protective group" as used in the definition of $R^p$ has the same meaning as the one defined above.

[Step XXIV]

Similarly to the above-mentioned procedure, an aldehyde represented by the formula (29) is treated with a reducing agent such as aluminum lithium hydride in a dry solvent such as tetrahydrofuran, diethyl ether or dimethoxyethane at 0° C. to room temperature to thereby give an alcohol represented by the formula (79).

[Step XXVII]

Similarly to the above-mentioned procedure, the alcohol represented by the formula (79) is treated with, for example, acetic anhydride or acetyl chloride as a hydroxy protective group in an appropriate solvent in the presence of pyridine as a base to thereby give an ester represented by the formula (80).

[Step XXV]

Similarly to the above-mentioned procedure, the amine represented by the formula (80) is treated with an amino protecting group such as vinyl chloroformate optionally in an appropriate solvent such as 1,2-dichloroethane at 0° C. to the reflux temperature to thereby give an amine protected by vinylformate represented by the formula (81). $R^{13b}$ is preferably a carbamate type amino protecting group, in particular, vinyloxycarbonyl.

[Step XI]

Similarly to the above-mentioned procedure, the compound represented by the formula (81) is reacted with an appropriate base in an aqueous solvent and then hydrolyzed to thereby give a compound of the formula (82) having a hydroxyl group.

[Step IX]

The compound represented by the formula (82) is reacted with an appropriate solvent containing hydrochloric acid or hydrobromic acid and then heated in an alcoholic solvent to thereby give a compound represented by the formula (83).

Production Process 8

The compounds of the present invention can be synthesized by using the above-mentioned methods or combining publicly known organic synthesis methods. Now, particular methods for synthesizing preferable compounds will be illustrated.

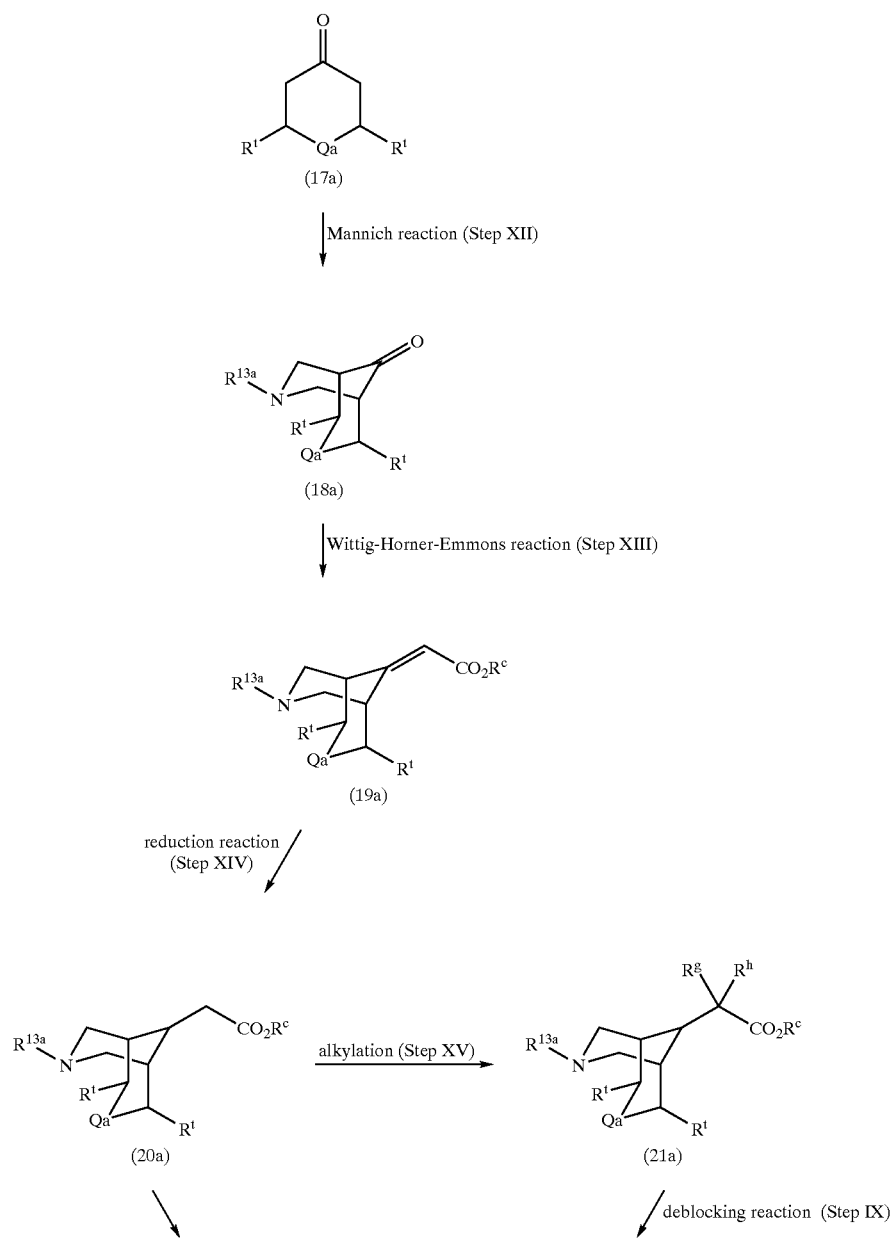

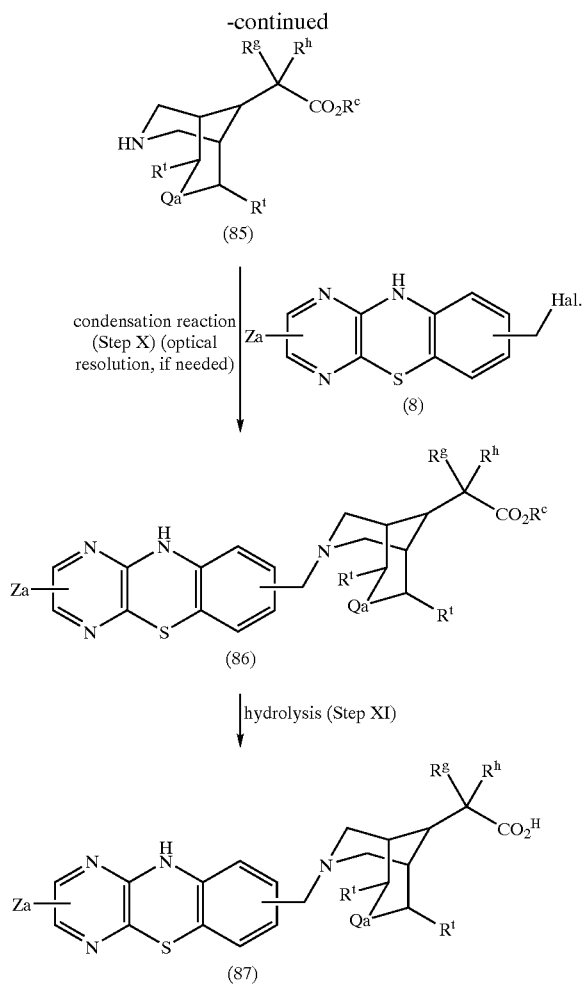

wherein $R^{13a}$ and $R^c$ and Hal. are each as defined above; $R^f$, $R^z$ and $R^h$ represent substitutents, having the same meaning as that defined above, of the rings A and B which are respectively a piperidine ring and a cyclohexyl ring having Qa; and Za represents a substituent, containing the same meaning as the one defined above, of the ring G which is a pyrazine ring.

This compound can be synthesized by combining the above-mentioned procedures.

[Step XII]

A compound of the formula (17a), which is a commercially available product or one obtained in accordance with, for example, the method described in Bull. Soc. Chim. Fr., 2981 (1989), is subjected to the Mannich reaction described in J.A.C.S., 84, 3139 (1962) and Chem. Pharm. Bull., 11 (3), 333 (1963) with an appropriate amine and an appropriate aldehyde in a solvent to thereby give a compound represented by the formula (18a). As the solvent, use can be made of ethanol, methanol, acetic acid, etc. The reaction is preferably effected at 25° C. to the reflux temperature.

[Step XIII]

The compound represented by the formula (18a) is reacted with an appropriate Wittig-Horner-Emmons reagent in a solvent in the presence of an appropriate base to thereby give a compound represented by the formula (19a). As the solvent, use can be made of dry solvents such as N,N-dimethylformamide, tetrahydrofuran or diethyl ether. As the base, use can be made of sodium hydride, potassium tert-butoxide, n-butyllithium, etc. The reaction can be effected at −100° C. to the boiling point of the solvent.

[Step XIV]

The compound represented by the formula (19a) is reduced by the use of an appropriate metal or an appropriate metal catalyst in a solvent to thereby give a compound represented by the formula (20a). The compound of the formula (20a) can be obtained by, for example, using a catalyst such as palladium in a solvent such as methanol, ethanol or ethyl acetate under normal to elevated hydrogen pressure, or treating the compound (19a) with magnesium in a solvent such as methanol.

[Step XV]

The compound represented by the formula (20a) is reacted with a base such as lithium diisopropylamide in a dry solvent such as diethyl ether or tetrahydrofuran and then reacted with an alkyl halide to thereby give a compound represented by the formula (21a). The reaction temperature preferably ranges from −100 to 25° C.

[Step IX]

The compounds represented by the formulae (20a) and (21a) are treated with an acid chloride such as 1-chloroethyl chloroformate or vinyl chloroformate optionally in a solvent. Next, an appropriate solvent such as an alcohol is added thereto and reacted therewith. Alternatively, it is treated with an appropriate solvent containing hydrochloric acid or hydrobromic acid and then heated in an alcoholic solvent. Thus, a compound represented by the formula (85) can be obtained.

[Step X]

The compound represented by the formula (85) is treated with the compound represented by the formula (8) obtained by the production process 1 in a solvent in the presence of an appropriate base such as anhydrous potassium carbonate or diisopropylamine to thereby give a compound represented by the formula (86). As the solvent, it is preferable to use a dry solvent such as dry N,N-dimethylformamide. The reaction is preferably effected at a temperature of 25 to 150° C. If necessary, the compound represented by the formula (86) may be subjected to optical resolution with the use of a chiral column, etc. to thereby separate enantiomers from each other.

[Step XI]

The compound represented by the formula (86) is reacted with an appropriate base in an aqueous solvent and then hydrolyzed to thereby give a compound of the formula (87).

In the above reaction, it is also possible to synthesize the product by using a protecting group of the functional group commonly employed in organic synthesis, then purifying the product by an appropriate operation commonly employed in the art such as silica gel column chromatography and then deblocking the same.

[Step IV]

The compound of the formula (92) is reacted with a dihalogenated heteroaryl compound as the one represented by the formula (89) in a solvent such as dry N,N-dimethylformamide to thereby give a compound represented by the formula (94).

[Step XXXXIII]

The compound represented by the formula (91) is treated with a reducing agent such as iron in a solvent mixture of an alcohol, tetrahydrofuran and water in the presence of ammonium chloride. Alternatively, it is treated with hydrosulfite sodium in a solvent mixture of tetrahydrofuran with water. Thus, an amine represented by the formula (93) can be produced. As the alcohol, use can be made of methanol, ethanol and isopropanol. In some cases, the intermediate (93) undergoes ring closure and thus a tricycloheteroaryl derivative represented by the formula (94) can be directly obtained.

[Step XXXXIV]

The amine represented by the formula (93) is heated in an appropriate solvent to thereby give a tricycloheteroaryl derivative represented by the formula (94). As the solvent, use can be made of alcohols such as methanol or ethanol, dry

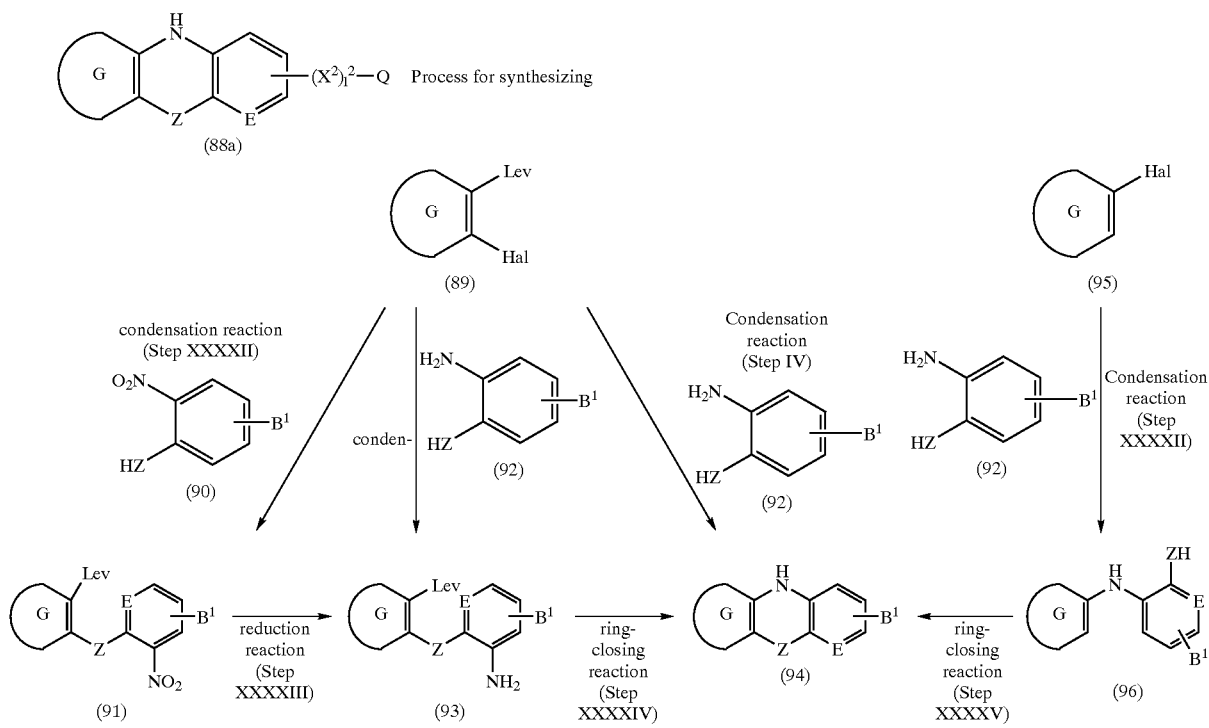

wherein G, Z, E, $X^2$, $I^2$ Q and Hal are each as defined above; and $B^1$ represents hydroxymethyl, halide, methoxy, methoxymethyl, lower alkyl or alkoxycarbonyl.

[Step XXXXII]

The compounds represented by the formulae (90) and (92) are treated with a base such as sodium hydride and then reacted with a halogen compound of the formula (89) in a solvent such as dry N,N-dimethylformamide or tetrahydrofuran to thereby give the compounds of the formulae (91) and (93) respectively. Similarly, a compound represented by the formula (96) can be obtained from the compounds (92) and (95).

N,N-dimethylformamide, etc. It is also possible to use an acid such as hydrochloric acid, acetic acid or p-toluenesulfonic acid as a catalyst. The reaction is effected preferably at 50° C. to the reflux temperature.

[Step XXXXV]

The compound represented by the formula (96) is heated in an appropriate solvent in the presence of an oxidizing agent and an acid. Alternatively, it is reacted with a base in an appropriate solvent in the presence of an oxidizing agent. Thus a tricycloheteroaryl derivative represented by the formula (94) can be obtained. As the oxidizing agent, use can be made of iodine, sulfur, etc. As the acid, use can be made of acetic acid, etc. As the base, use can be made of sodium hydride. As the solvent, use can be made of diphenyl ether, dry N,N-dimethylformamide, etc. The reaction can be carried out at 0 to 200° C.

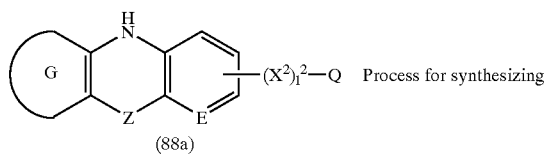

Process for synthesizing (88a)

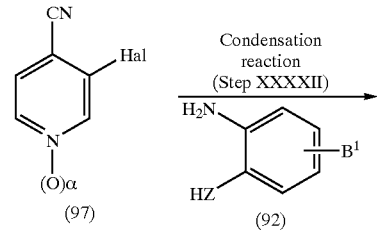

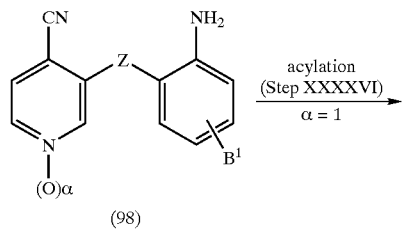

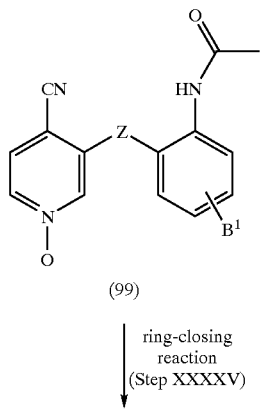

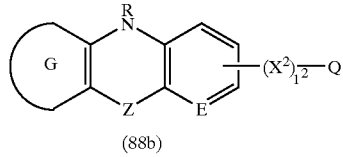

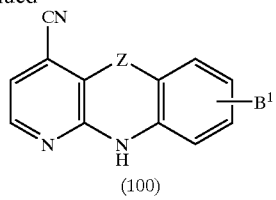

(100)

wherein G, Z, E, $X^2$, $I^2$, Q and $B^1$ are each as defined above; and $\alpha$ is 0 or 1.

[Step XXXXII]

The compound represented by the formula (92) is treated with a base such as sodium hydride and then reacted with a halogen compound (97) in a solvent such as dry N,N-dimethylformamide or tetrahydrofuran to thereby give a compound represented by the formula (98).

[Step XXXXVI]

When $\alpha$ is 1, the amine represented by the formula (98) is reacted with a carboxylic anhydride, phosphoric anhydride and an acid halide optionally in an appropriate solvent in the presence of an appropriate base such as pyridine, triethylamine or N,N-diisopropylethylamine to thereby give an amide represented by the formula (99). As the solvent, use can be made of dry dichloromethane, etc. The reaction can be carried out at 0° C. to the reflux temperature.

[Step XXXXV]

The compound represented by the formula (99) is heated in an appropriate solvent in the presence of an oxidizing agent and an acid. Alternatively, it is reacted with a base in an appropriate solvent in the presence of an oxidizing agent. Thus a tricycloheteroaryl derivative represented by the formula (100) can be obtained. As the oxidizing agent, use can be made of iodine, sulfur, etc. As the acid, use can be made of acetic acid, etc. As the base, use can be made of sodium hydride. As the solvent, use can be made of diphenyl ether, dry N,N-dimethylformamide, etc. The reaction can be carried out at 0 to 200° C.

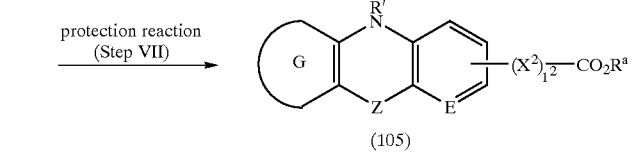

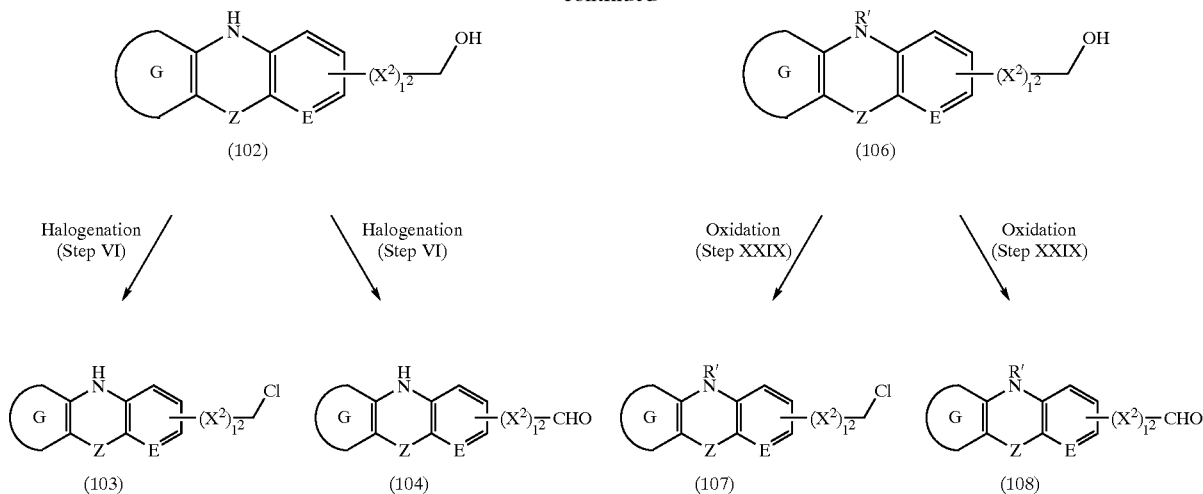

wherein G, Z, E, $X^2$, $I^2$, Q, R, R' and $R^a$ are each as defined above.

[Step VII]

An amine represented by the formula (101) is treated with a base such as sodium hydride and a protective reagent such as methoxymethyl chloride in a solvent to thereby give a compound represented by the formula (105).

[Step V]

The compound represented by the formula (101) or (105) is treated with a reducing agent such as diisobutylaluminum hydride or aluminum lithium hydride in a solvent to thereby give a compound represented by the formula (102) or (106). As the solvent, use can be made of dry tetrahydrofuran, dry diethyl ether, etc. The reaction is preferably effected at a temperature of −50° C. to the reflux temperature.

[Step VI]

The compound represented by the formula (102) or (106) is treated with a halogenating agent such as methanesulfonyl chloride in a solvent such as dry N,N-dimethylformamide in the presence of an appropriate base such as pyridine, triethylamine or N,N-diisopropylethylamine to thereby give a compound represented by the formula (103) or (107).

[Step XXIX]

Similar to the above-mentioned procedure, a solution of the compound represented by the formula (102) or (106) in, for example, methylene chloride is added to a reaction mixture obtained from oxalyl chloride and dimethyl sulfoxide and treated with a base such as triethylamine. Alternatively, it is treated with pyridinium dichromate in a solvent such as dichloromethane or N,N-dimethylformamide or treated with manganese dioxide in a solvent such as dichloromethane. Thus, an aldehyde represented by the formula (104) or (108) can be obtained.

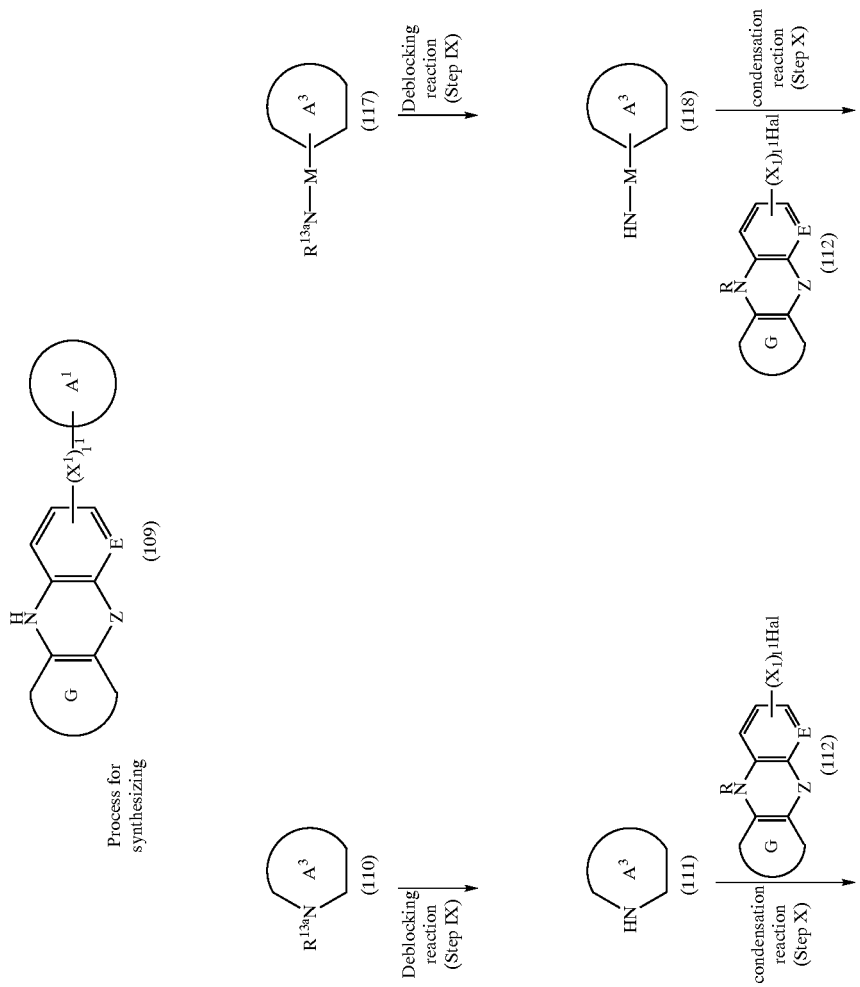

-continued
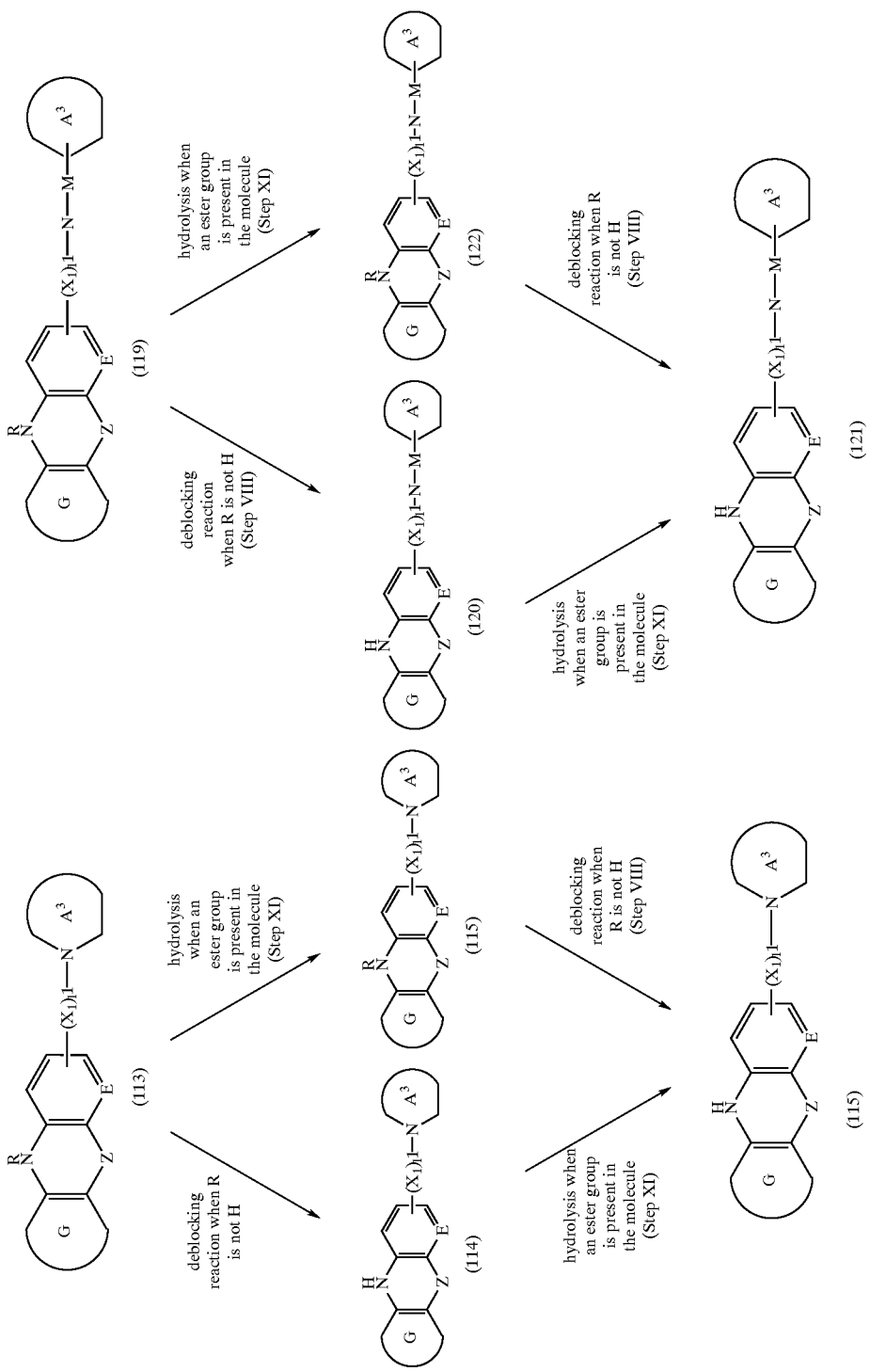

wherein the rings $A^1$ and $A^3$, G, Z, E, $X^1$, $I^1$, M, R, R', $R^{13a}$ and Hal are each as defined above.

[Step IX]

A compound represented by the (110) or (117) is treated in the following manner. 1) When $R^{13a}$ is alkyl, etc., the starting compound is reacted with an acid chloride such as 1-chloroethyl chloroformate or vinyl chloroformate optionally in a solvent. Next, an appropriate alcoholic solvent is added thereto and reacted therewith. Alternatively, it is treated with an appropriate solvent containing hydrochloric acid or hydrobromic acid and then heated in an alcoholic solvent. 2) When $R^{13a}$ is tert-butoxycarbonyl, etc., the starting compound is reacted with an appropriate acid such as acetic acid, trifluoroacetic acid or hydrochloric acid optionally in an appropriate solvent such as dichloromethane or tetrahydrofuran. 3) When $R^{13a}$ is a protective group which can be eliminated, such as benzyl, the starting compound is hydrogenated in an appropriate solvent such as methanol, ethanol, ethyl acetate or tetrahydrofuran by using a metal catalyst such as palladium or platinum (IV) oxide under normal to elevated hydrogen pressure. Thus, a compound represented by the formula (111) or (118) can be obtained.

[Step X]

The compound represented by the formula (111) or (118) is treated with a halide represented by the formula (112) in a solvent in the presence of an appropriate base such as anhydrous potassium carbonate or N,N-diisopropylethylamine to thereby give a compound represented by the formula (113) or (119). As the solvent, use can be made of N,N-dimethylformamide, etc. The reaction can be effected at a temperature of 0 to 150° C.

[Step VIII]

When R in the compounds represented by the formulae (113), (116), (119) and (122) is methoxymethyl, these compounds are treated with an appropriate acid such as acetic acid, trifluoroacetic acid or hydrochloric acid optionally in a solvent such as dichloromethane or tetrahydrofuran/water to thereby give compounds represented by the formulae (114), (115), (120) and (121). The reaction can be effected at 0° C. to the reflux temperature of the solvent.

[Step XI]

When the compounds represented by the formulae (113), (114), (119) and (120) have an ester group in the molecule, these compounds are treated with an appropriate base in an aqueous solvent to thereby give compounds represented by the formulae (116), (115), (122) and (121) respectively. As the solvent, use can be made of alcoholic solvents such as methanol or ethanol or solvent mixtures such as alcohol/tetrahydrofuran/water. As the base, use can be made of sodium hydroxide or potassium hydroxide. The reaction can be carried out at room temperature to the reflux temperature of the solvent.

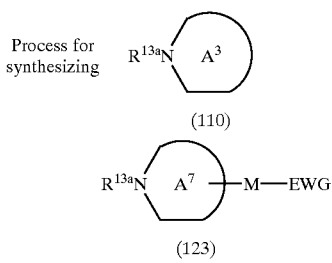

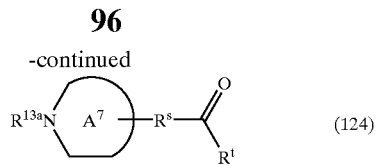

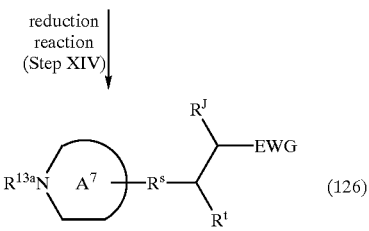

wherein the ring $A^3$, M and $R^{13a}$ are each as defined above; $R^j$ represents hydrogen, fluorine or optionally substituted lower alkyl; EWG represents ester, nitrile, optionally substituted phenyl, etc.; $A^7$ represents: 1) the same group as $A^3$; or 2) a bicyclic ring AB wherein the bridgehead carbon atoms are directly bonded to each other; $R^s$ represents optionally substituted $C_{0-6}$ alkylene; and $R^t$ represents hydrogen or lower alkyl, or, in some cases, neither $R^s$ nor $R^t$ exists and the carbon atom in the side chain to which $R^s$ and $R^t$ are bonded in the formula is one of the members of the ring $A^7$.

[Step XIII]

The compound represented by the formula (124) is reacted with an appropriate Horner-Emmons reagent in a solvent in the presence of an appropriate base to thereby give a compound represented by the formula (125). As the solvent, use can be made of dry solvents such as N,N-dimethylformamide, tetrahydrofuran or diethyl ether. As the base, use can be made of sodium hydride, potassium tert-butoxide, n-butyllithium, lithium diisopropylamide, etc. The reaction can be effected at −100° C. to the reflux temperature of the solvent.

[Step XIV]

The compound represented by the formula (125) is subjected to a reduction reaction in a solvent with the use of an appropriate metal catalyst to thereby give a compound represented by the formula (126). The reaction can be effected in a solvent such as methanol, ethanol, ethyl acetate or tetrahydrofuran with the use of palladium, platinum (IV) oxide, etc. under normal to elevated hydrogen pressure.

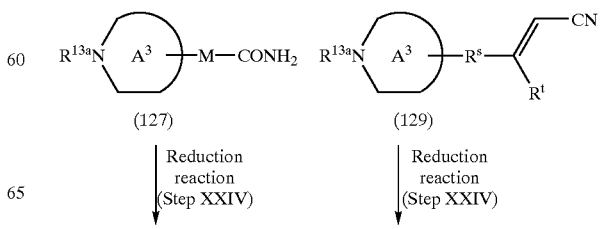

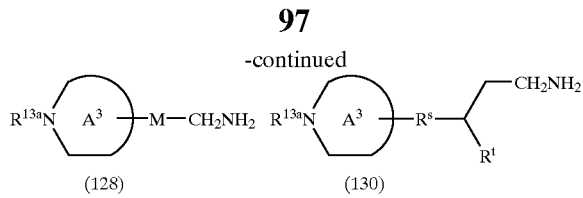

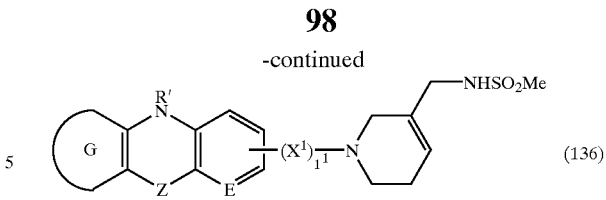

wherein M, $R^{13a}$, $A^3$, $R^5$ and $R'$ are each as defined above.

[Step XXIV]

A compound represented by the formula (127) or (129) is treated with a reducing agent such as aluminum lithium hydride in a solvent to thereby give a compound represented by the formula (128) or (130). As the solvent, use can be made of dry solvents such as tetrahydrofuran, diethyl ether or dimethoxyethane.

The reaction can be effected at −50° C. to the reflux temperature.

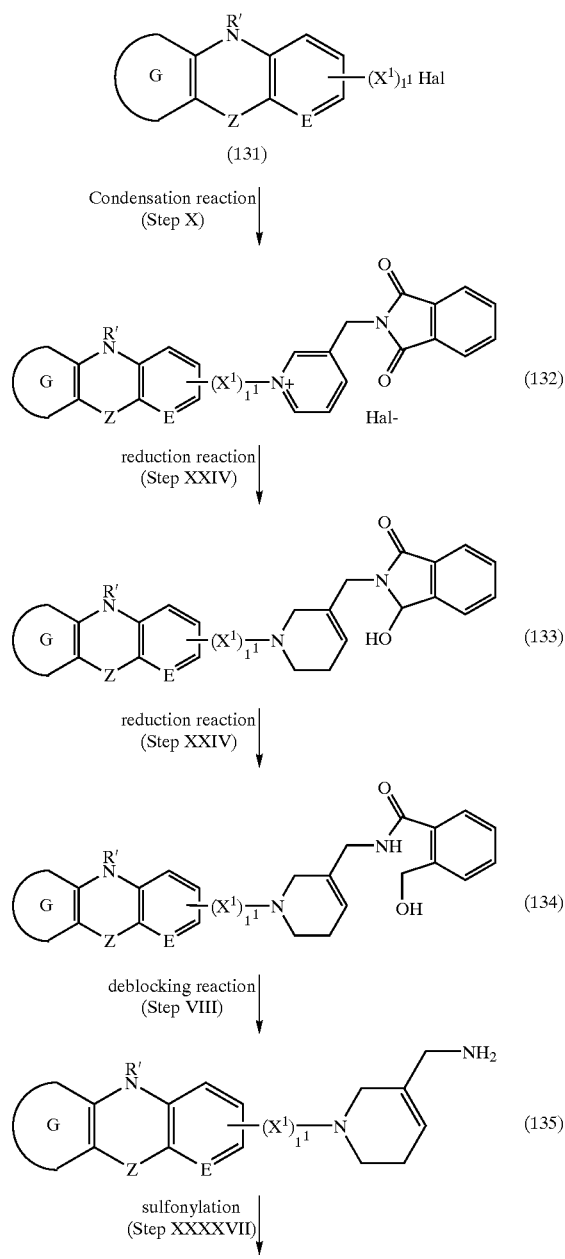

wherein G, Z, E, $X^1$, $1^1$, R' and Hal are each as defined above.

[Step X]

A compound represented by the formula (131) is treated with an appropriately protected 3-aminomethylpyridine derivative in a solvent in the presence of an appropriate base such as anhydrous potassium carbonate or N,N-diisopropylamine to thereby give a compound represented by the formula (132). As the solvent, use can be made of ethanol, dry N,N-dimethylformamide, etc. The reaction can be effected at a temperature of 0 to 150° C.

[Step XXIV]

The compound represented by the formula (132) is treated with a reducing agent such as aluminum lithium hydride in a solvent to thereby give a compound represented by the formula (133). As the solvent, use can be made of methanol, ethanol, etc. The reaction can be effected at 0° C. to the reflux temperature.

[Step XXIV]

The compound represented by the formula (133) is treated with a reducing agent such as aluminum lithium hydride in a solvent to thereby give a compound represented by the formula (134). As the solvent, it is preferable to use isopropyl alcohol. It is preferable to effect the reaction at 50° C. to the reflux temperature.

[Step VIII]

The compound represented by the formula (134) is treated with an appropriate acid such as acetic acid, trifluoroacetic acid or hydrochloric acid optionally in a solvent such as dichloromethane or tetrahydrofuran/water to thereby give a compound represented by the formula (135). Although the reaction can be effected at 0° C. to the reflux temperature of the solvent, it is carried out in acetic acid at 80° C. in the most desirable case.

[Step XXXXVII]

The amine represented by the formula (135) is reacted with methanesulfonic anhydride or the acid halide optionally in an appropriate solvent such as dichloromethane in the presence of an appropriate base such as pyridine, triethylamine or N,N-diisopropylamine to thereby give a compound represented by the formula (136).

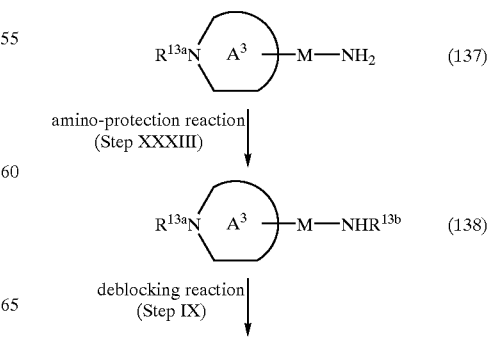

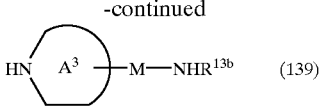

(139)

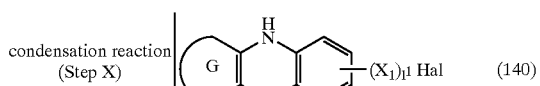

condensation reaction (Step X)

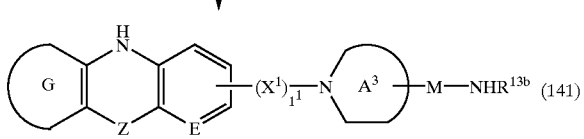

deblocking reaction (Step IX)

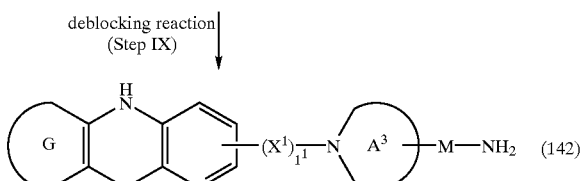

wherein G, Z, E, $X^1$, $1^1$, M, $R^{13a}$, $R^{13b}$, $A^3$ and Hal are each as defined above.

[Step XXXIII]

A compound represented by the formula (137) is reacted with, for example, di-tert-butyl dicarbonate as an amino protective group preferably at 0° C. to room temperature in the presence of a base such as pyridine, triethylamine or N,N-diisopropylethylamine in an appropriate solvent such as methanol or dichloromethane to thereby give a compound represented by the formula (138). $R^{13b}$ may be an arbitrary one, so long as it is lower alkyl or an amino protective group. The most desirable example of $R^{13b}$ is an alkyl carbamate.

[Step IX]

The compound represented by the (138) is treated in the following manner. 1) When $R^{13a}$ is alkyl, etc., the starting compound is reacted with an acid chloride such as 1-chloroethyl chloroformate or vinyl chloroformate optionally in a solvent. Next, an appropriate alcoholic solvent is added thereto and reacted therewith. Alternatively, it is treated with an appropriate solvent containing hydrochloric acid or hydrobromic acid and then heated in an alcoholic solvent. 2) When $R^{13a}$ is tert-butoxycarbonyl, etc., the starting compound is reacted with an appropriate acid such as acetic acid, trifluoroacetic acid or hydrochloric acid optionally in an appropriate solvent such as dichloromethane or tetrahydrofuran. 3) When $R^{13a}$ is a protective group which can be eliminated, such as benzyl, the starting compound is hydrogenated in an appropriate solvent such as methanol, ethanol, ethyl acetate or tetrahydrofuran by using a metal catalyst such as palladium or platinum (IV) oxide under normal to elevated hydrogen pressure. Thus, a compound represented by the formula (139) can be obtained.

[Step X]

The compound represented by the formula (139) is treated with a halide represented by the formula (140) in a solvent in the presence of an appropriate base such as anhydrous potassium carbonate or N,N-diisopropylamine to thereby give a compound represented by the formula (141). As the solvent, use can be made of dry N,N-dimethylformamide, etc. The reaction can be effected at a temperature of 50 to 150° C.

[Step IX]

The compound represented by the formula (141) is treated in the following manner. 1) When $R^{13b}$ is alkyl, etc., the starting compound is reacted with an acid chloride such as 1-chloroethyl chloroformate or vinyl chloroformate optionally in a solvent. Next, an appropriate alcoholic solvent is added thereto and reacted therewith. Alternatively, it is treated with an appropriate solvent containing hydrochloric acid or hydrobromic acid and then heated in an alcoholic solvent. 2) When $R^{13a}$ is tert-butoxycarbonyl, etc., the starting compound is reacted with an appropriate acid such as acetic acid, trifluoroacetic acid or hydrochloric acid optionally in an appropriate solvent such as dichloromethane or tetrahydrofuran. 3) When $R^{13a}$ is a protective group which can be eliminated, such as benzyl, the starting compound is hydrogenated in an appropriate solvent such as methanol, ethanol, ethyl acetate or tetrahydrofuran by using a metal catalyst such as palladium or platinum (IV) oxide under normal to elevated hydrogen pressure. Thus, a compound represented by the formula (142) can be obtained.

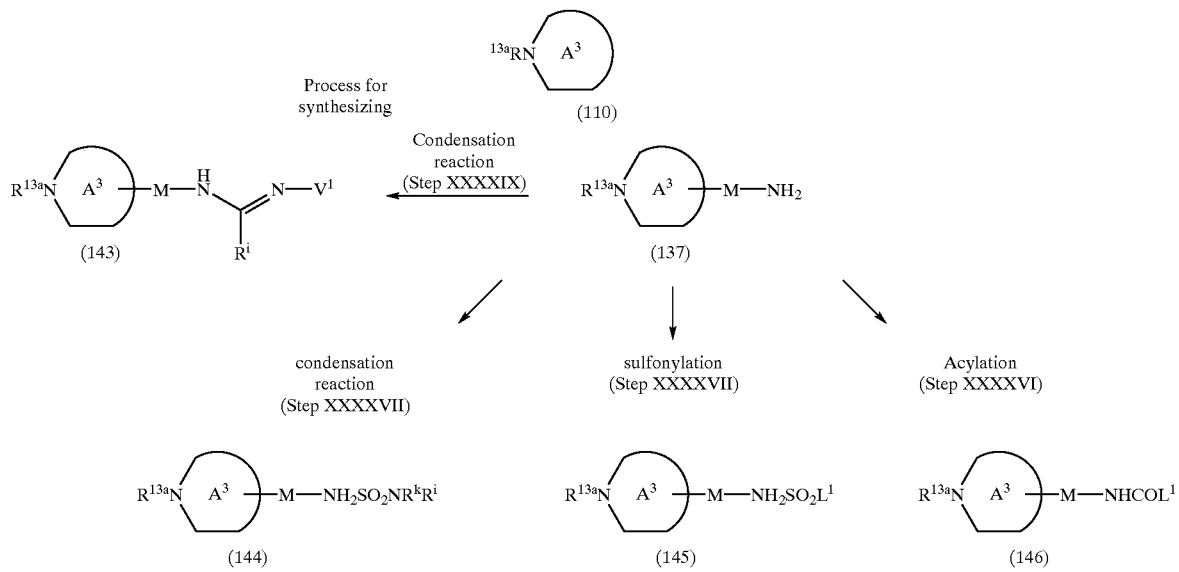

wherein $R^{13a}$, $A^3$ and M are each as defined above; $L^1$ represents optionally substituted lower alkyl, trifluoromethyl, optionally substituted aryl or optionally substituted heteroaryl; $R^k$ and $R^l$ may be the same or different and each represents hydrogen or optionally substituted lower $C_{1-10}$ alkyl optionally having a heteroatom ; $R^j$ represents hydrogen, lower alkyl, amino or protected carboxy; and $V^1$ represents nitrile or methanesulfonyl.

[Step XXXXVI]

An amine represented by the formula (137) is reacted with a carboxylic anhydride, a carboxylic phosphoric anhydride or an acid halide optionally in an appropriate solvent in the presence of an appropriate base such as pyridine, triethylamine or N,N-diisopropylethylamine to thereby give an amide represented by the formula (146). As the solvent, use can be made of dry dichloromethane, etc. The reaction can be carried out at 0° C. to the reflux temperature.

[Step XXXXVII]

The amine represented by the formula (137) is reacted with methanesulfonic anhydride or an acid halide optionally in an appropriate solvent such as dichloromethane in the presence of an appropriate base such as pyridine, triethylamine or N,N-diisopropylamine to thereby give a compound represented by the formula (145).

[Step XXXXVIII]

The amine represented by the formula (137) is treated with an appropriate sulfamic acid halide optionally in an appropriate solvent such as dichloromethane in the presence of an appropriate base such as pyridine, triethylamine or N,N-diisopropylethylamine. Alternatively, it is treated with an activated sulfamic acid ester under reflux in a solvent such as 1,4-dioxane. Alternatively, it is reacted with sulfamide in dimethoxyethane at 100° C. Thus, the compound represented by the formula (144) can be obtained.

[Step XXXXIX]

The amine represented by the formula (137) is reacted with an appropriate imidate or thioimidate in a solvent such as acetonitrile or methanol to thereby give a compound represented by the formula (143). It is preferable that the reaction is carried out at 0 to 40° C.

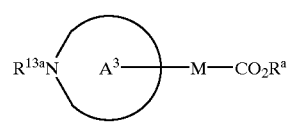

Process for synthesizing (147)

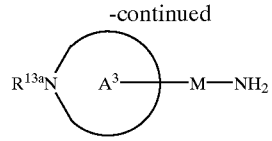

(137)

Condensation reaction (Step L)

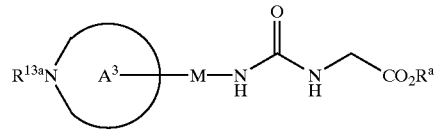

(148)

wherein M, $R^{13a}$, $A^3$ and $R^4$ are each as defined above.

[Step L]

A compound represented by the formula (137) is treated with ethyl isocyanatoacetate in an appropriate solvent to thereby give a compound represented by the formula (148). As the solvent, use can be made of tetrahydrofuran, etc. The reaction can be effected at room temperature to the reflux temperature of the solvent.

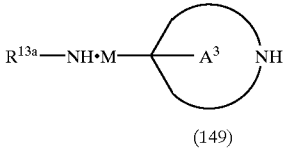

(149)

acylation (Step XXXXVI) / alkylation (Step XXI) | sulfonylation (Step XXXXVII) \

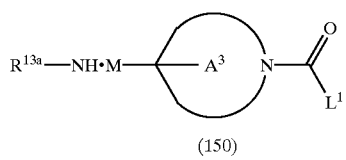

(150)

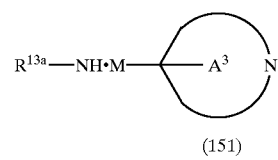

(151)

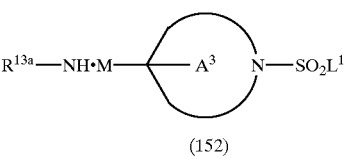

(152)

wherein M, T, $L^1$, $R^{13a}$, $A^3$ and $R^a$ are each as defined above.

[Step XXXXVI]

An amine represented by the formula (149) is reacted with an activated ester such as a carboxylic anhydride, a carboxylic phosphoric anhydride or an acid halide optionally in an appropriate solvent in the presence of an appropriate base such as pyridine, triethylamine or N,N-diisopropylethylamine to thereby give an amide represented by the formula (150). As the solvent, use can be made of dry dichloromethane, etc. The reaction can be carried out at 0° C. to the reflux temperature.

[Step XXI]

The compound represented by the formula (149) is treated with an appropriate alkyl halide having a carboxyl group or an ester group in the presence of an appropriate base such as pyridine, triethylamine or N,N-diisopropylamine in a solvent such as dichloromethane, tetrahydrofuran or N,N-dimetyl formamide to thereby give an amine compound represented by the formula (151).

[Step XXXXVII]

The amine represented by the formula (149) is reacted with an appropriate sulfonic anhydride or an acid halide optionally in an appropriate solvent such as dichloromethane in the presence of an appropriate base such as pyridine, triethylamine or N,N-diisopropylamine to thereby give a compound represented by the formula (152).

[Step XXI]

The compound represented by the formula (153) is treated with an appropriate alkyl halide having a carboxyl group or an ester group in the presence of an appropriate base such as pyridine, triethylamine or N,N-diisopropylamine in a solvent such as dichloromethane, tetrahydrofuran or N,N-dimethylformamide to thereby give an amine compound represented by the formula (155).

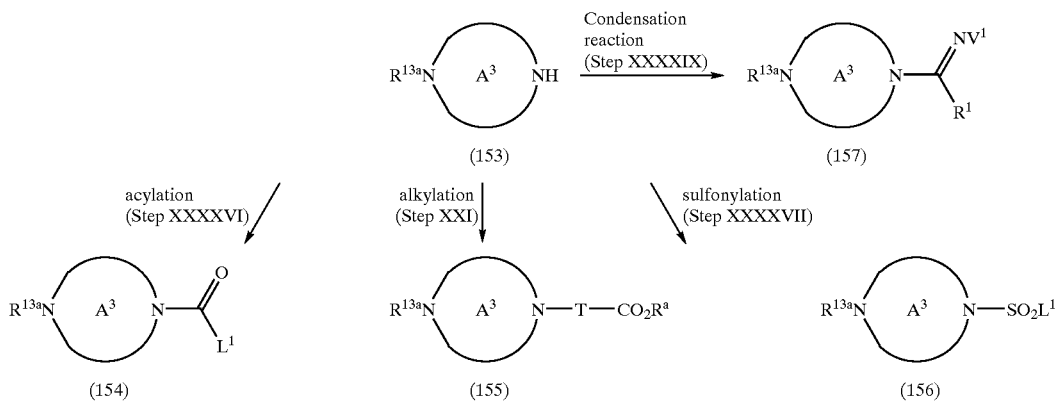

wherein T, $L^1$, $R^{13a}$, $A^3$, $V^1$, $R^j$ and $R^a$ are each as defined above.

[Step XXXXVI]

An amine represented by the formula (153) is reacted with a carboxylic anhydride, a carboxylic phosphoric anhydride or an acid halide optionally in an appropriate solvent in the presence of an appropriate base such as pyridine, triethylamine or N,N-diisopropylethylamine to thereby give an amide represented by the formula (154). As the solvent, use can be made of dry dichloromethane, etc. The reaction can be carried out at 0° C. to the reflux temperature.

[Step XXXXVII]

The amine represented by the formula (153) is reacted with an appropriate sulfonic anhydride or an acid halide optionally in an appropriate solvent such as dichloromethane in the presence of an appropriate base such as pyridine, triethylamine or N,N-diisopropylamine to thereby give a compound represented by the formula (156).

[Step XXXXIX]

The amine represented by the formula (153) is reacted with an appropriate imidate or thioimidate in a solvent such as acetonitrile or methanol to thereby give a compound represented by the formula (157). It is preferable that the reaction is carried out at 0 to 40° C.

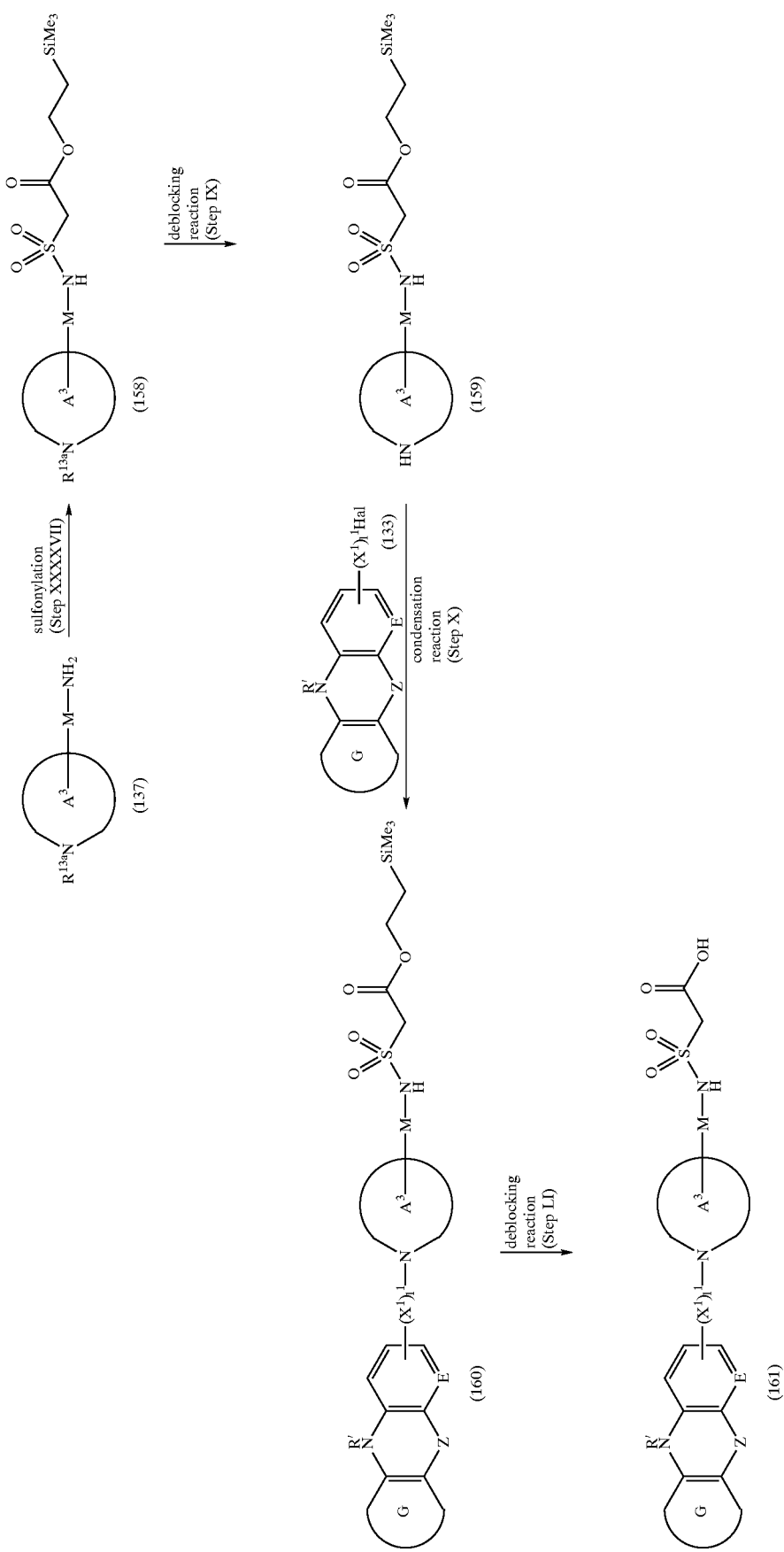

wherein G, Z, E, $X^1$, $l^1$, M, $R^{13a}$, $A^3$ and Hal are each as defined above.

[Step XXXXVII]

An amine represented by the formula (137) is reacted with an appropriate sulfonic acid halide derivative in an appropriate dry solvent such as dichloromethane or diethyl ether to thereby give a compound represented by the formula (158). The reaction is effected preferably at 0° C. to room temperature.

[Step IX]

The compound represented by the formula (158) is subjected to a reduction reaction with the use of an appropriate metal catalyst in a solvent to thereby give a compound represented by the formula (159). For example, the reaction may be effected in a solvent such as methanol, ethanol, ethyl acetate or tetrahydrofuran with the use of palladium or platinum (IV) oxide as a catalyst under normal to elevated hydrogen pressure.

[Step X]

The compound represented by the formula (159) is treated with a halide represented by the formula (133) in a solvent in the presence of an appropriate base such as anhydrous potassium carbonate or N,N-diisopropylamine to thereby give a compound represented by the formula (160). As the solvent, use can be made of dry N,N-dimethylformamide, etc. The reaction can be effected at a temperature of 50 to 150° C.

[Step LI]

The compound represented by the formula (160) is treated with a reagent such as tetra-n-butylammonium fluoride or caesium fluoride in a dry solvent such as tetrahydrofuran to thereby give a carboxylic acid represented by the formula (161). The reaction is effected preferably at 0° C. to room temperature.

wherein M, T, $R^{13a}$, $A^3$ and $R^a$ are each as defined above; and Nu represents a nucleophilic atom such as oxygen, nitrogen or sulfur.

[Step XXI]

A compound represented by the formula (162) is treated with an appropriate alkyl halide having a carboxyl group or an ester group either in a solvent such as dichloromethane, tetrahydrofuran or N,N-dimethylformamide in the presence of an appropriate base such as pyridine, triethylamine or N,N-diisopropylamine, or after being treated with a base such as sodium hydride or sodium methoxide in a solvent such as dimethoxyethane, tetrahydrofuran or N,N-dimethylformamide to thereby give a derivative represented by the formula (163). When Nu is oxygen and a phenol derivative is employed as a substitute for the alkyl halide, an ether represented by the formula (163) can be obtained by the Mitsunobu reaction with the use of a condensing agent such as diethyl azadicarboxylate or triphenylphosphine.

[Step LII]

The compound represented by the formula (162) is reacted with sodium isocyanate, potassium isocyanate, etc. in a solvent such as water or ethanol to thereby give a compound represented by the formula (164).

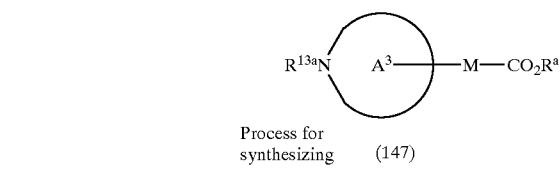

Process for synthesizing (147)

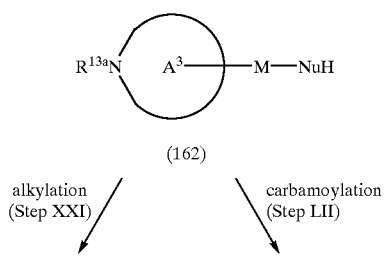

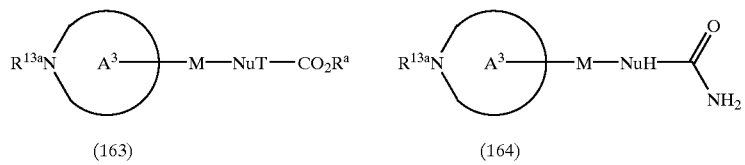

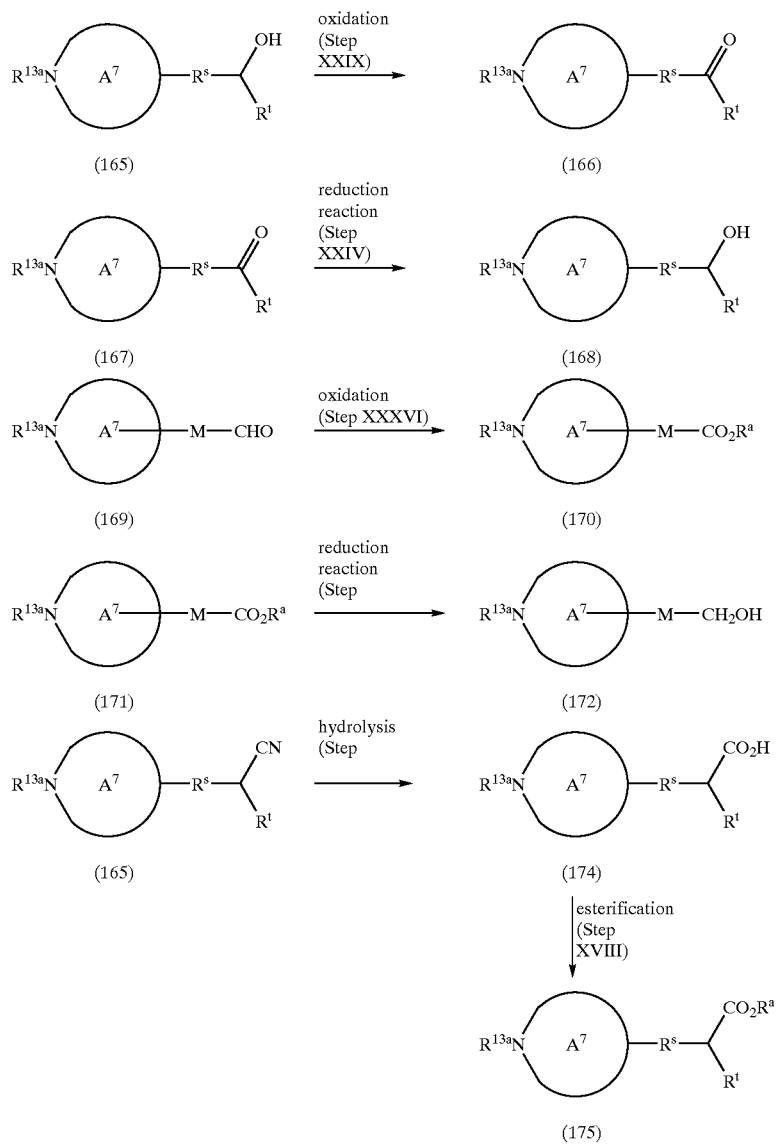

wherein M, $R^{13a}$, $A^7$, $R^s$ and $R^t$ are each as defined above.

[Step XXIX]

A solution of a compound represented by the formula (165) in, for example, methylene chloride is added to a reaction mixture obtained from oxalyl chloride and dimethyl sulfoxide and treated with a base such as triethylamine. Alternatively, it is treated with pyridinium dichromate in a solvent such as dichloromethane or treated with manganese dioxide in a solvent such as dichloromethane. Thus, a carbonyl compound represented by the formula (166) can be obtained.

[Step XXIV]

A compound represented by the formula (171) is treated with a reducing agent such as diisobutylaluminum hydride, aluminum lithium hydride or lithium borohydride in a solvent such as dry tetrahydrofuran or dry diethyl ether, or treated with a reducing agent such as sodium borohydride in an alcoholic solvent to thereby give an alcohol represented by the formula (172).

[Step XXXVI]

The compound represented by the formula (169) is treated with bromine in an appropriate alcoholic solvent such as methanol or ethanol in the presence of a base such as sodium hydrogencarbonate or potassium carbonate preferably at 0° C. to room temperature. Alternatively, the starting compound is treated with pyridinium chromate in an appropriate alcoholic solvent such as methanol or ethanol. Alternatively, it is treated with manganese dioxide in an appropriate alcoholic solvent such as methanol or ethanol in the presence of sodium cyanide and acetic acid and then treated with sulfuric acid, hydrochloric acid, thionyl chloride, etc. in an appropriate alcoholic solvent such as methanol or ethanol. Alternatively, it is treated with sodium chlorite in a solvent mixture of water and dimethyl sulfoxide in the presence of sodium dihydrogenphosphate and then reacted with trimethylsilyl-diazomethane in a solvent such as methanol. Alternatively, it is treated with an activating agent such as thionyl chloride in an appropriate alcoholic solvent such as methanol or ethanol. Thus, an ester compound represented by the formula (170) can be obtained.

[Step XXVI]

A compound represented by the formula (167) is treated with a reducing agent such as diisobutylaluminum hydride, aluminum lithium hydride or lithium borohydride in a solvent such as dry tetrahydrofuran or dry diethyl ether to thereby give an alcohol represented by the formula (168).
[Step XVII]

A cyano compound of the formula (173) is treated with a base such as sodium hydroxide or potassium hydroxide in an alcoholic solvent such as ethanol, propanol, ethylene glycol or diethylene glycol and heated under reflux to thereby give a carboxylic acid of the formula (174).
[Step XVIII]

The compound of the formula (174) is treated with an activator such as thionyl chloride in an alcoholic solvent such as methanol or ethanol to thereby give an ester of the formula (175). The reaction temperature preferably ranges from 0° C. to room temperature.

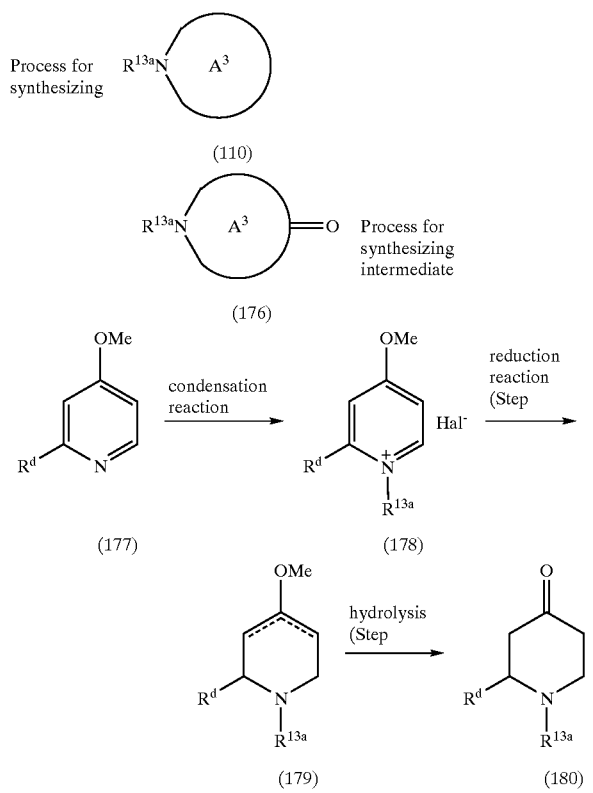

wherein Hal, $R^{13a}$, $A^3$ and $R^d$ are each as defined above.
[Step X]

A compound represented by the formula (177) is heated with a amine protecting reagent such as benzyl chloride in a solvent to thereby give a compound represented by the formula (178). As the solvent, use can be made of dry N,N-dimethylformamide, acetone, ethanol, etc. The reaction can be effected at a temperature of 50° C. to the reflux temperature.
[Step XXIV]

The compound represented by the formula (178) is treated with a reducing agent such as lithium borohydride in a solvent to thereby give a compound represented by the formula (179). As the solvent, use can be made of dry N,N-dimethylformamide, acetone, ethanol, etc. The reaction can be effected at 50° C. to the reflux temperature.
[Step VIII]

The compound represented by the formula (179) is treated optionally in an appropriate solvent such as dichloromethane or tetrahydrofuran/water in the presence of an appropriate acid such as acetic acid, trifluoroacetic acid or hydrochloric acid to thereby give a compound represented by the formula (180). The reaction can be effected at 0° C. to the reflux temperature of the solvent.

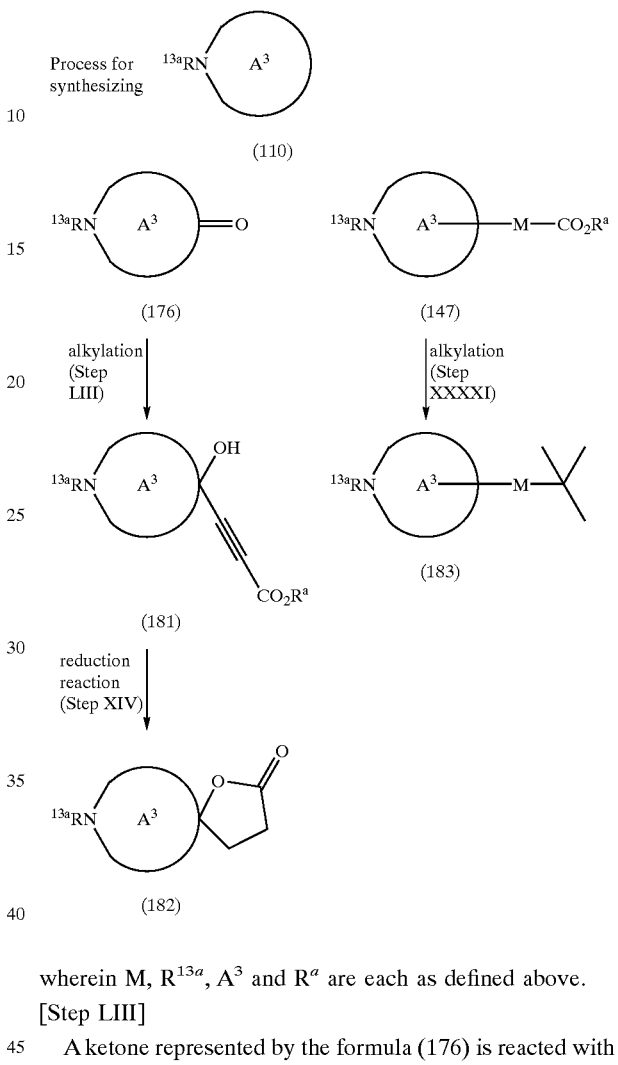

wherein M, $R^{13a}$, $A^3$ and $R^a$ are each as defined above.
[Step LIII]

A ketone represented by the formula (176) is reacted with an anion obtained by treating an alkyne with a strong base such as n-butyllithium or lithium diisopropylamine in a dry solvent such as tetrahydrofuran or diethyl ether to thereby give a compound represented by the formula (181). The reaction can be effected at −100° C. to room temperature.
[Step XIV]

The compound represented by the formula (181) is subjected to a reduction reaction in a solvent with the use of an appropriate metal catalyst to thereby give a compound represented by the formula (182). For example, use can be made of a hydrogenation reaction effected in a solvent such as methanol, ethanol, ethyl acetate or tetrahydrofuran with the use of palladium, platinum (IV) oxide, etc. under normal to elevated hydrogen pressure.
[Step XXXXI]

A compound represented by the formula (147) is treated with methyllithium or methylmagnesium halide in a solvent such as dry tetrahydrofuran, diethyl ether or dimethoxyethane at −78° C. to the boiling point of the solvent to thereby give an alcohol represented by the formula (183).

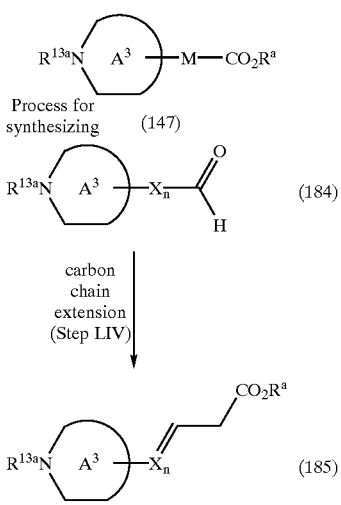

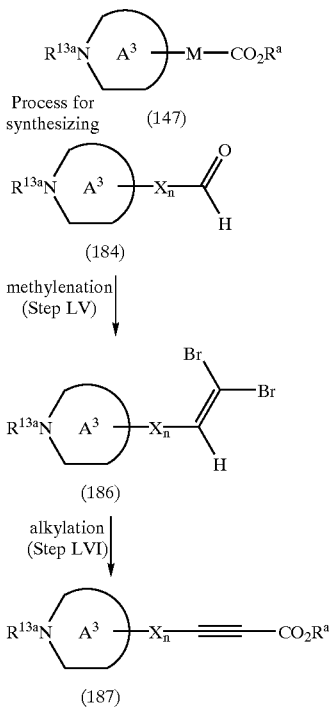

wherein M, $R^{13a}$, $A^3$ and $R^a$ are each as defined above; and $X_n$ means an alkylene side chain having n carbon atoms which is directly bonded to the ring when n is 0.

[Step LIV]

A compound of the formula (184) is reacted with dimethyl malonate in a solvent such as pyridine at room temperature to the boiling point of the solvent. Then the intermediate thus obtained is treated with diazomethane in a solvent to thereby give a compound represented by the formula (185).

wherein M, $R^{13a}$, $A^3$, $X_n$ and $R^a$ are each as defined above.

[Step LV]

An aldehyde represented by the formula (184) is treated with carbon tetrabromide and a phosphine such as triphenylphosphine in a solvent such as dry dichloromethane to thereby give a dibromoalkene derivative represented by the formula (186).

[Step LVI]

The compound represented by the formula (186) is treated with a strong base such as n-butyllithium in a dry solvent such as tetrahydrofuran or diethyl ether at −100 to 0° C. Then the intermediate thus obtained is treated with a reagent such as ethyl chloroformate or diethyl carbonate to thereby give a compound represented by the formula (187).

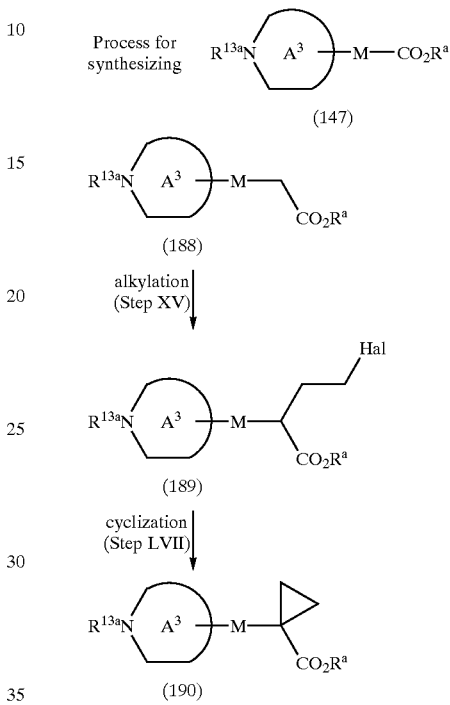

wherein M, $R^{13a}$, $A^3$, $X_n$ and $R^a$ are each as defined above.

[Step XV]

The compound represented by the formula (188) is reacted with a strong base such as lithium diisopropylamide in a dry solvent such as tetrahydrofuran, diethyl ether or hexamethylphosphorous triamide at −100 to 0° C. and then reacted with a dihalogenated ethane such as dibromoethane to thereby give a derivative represented by the formula (189).

[Step LVII]

The compound represented by the formula (189) is treated with potassium tert-butoxide in a dry solvent such as tetrahydrofuran to thereby give a cyclopropyl derivative represented by the formula (190). The reaction can be effected at 0° C. to the reflux temperature of the solvent.

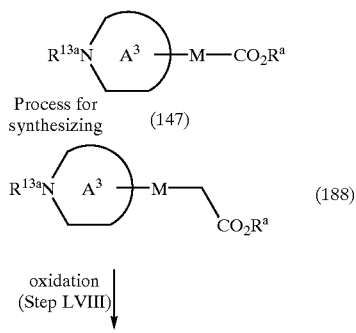

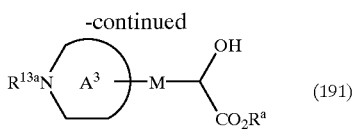

wherein M, $R^{13a}$, $A^3$, and $R^a$ are each as defined above.

[Step LVIII]

A compound represented by the formula (188) is treated with a strong base such as n-butyllithium or lithium diisopropylamide in a dry solvent such as tetrahydrofuran, diethyl ether or hexamethyl-phosphorous triamide at −100 to 0° C. and then treated with peroxymolybdeum (pyridine) hexamethylphosphorous triamide to thereby give a compound represented by the formula (191).

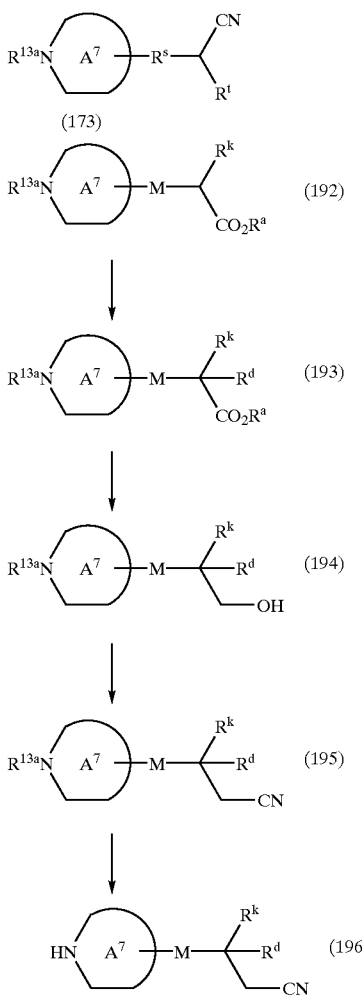

wherein M, $R^{13a}$, $A^7$, $R^d$, $R^k$ and $R^a$ are each as defined above.

[Step XV]

A compound represented by the formula (192) is treated with a strong base such as lithium diisopropylamide in a dry solvent such as tetrahydrofuran, diethyl ether or hexamethylphosphorous triamide at −100 to 0° C. and then reacted with an alkylating agent such as methyl iodide to thereby give a derivative represented by the formula (193).

[Step XXIV]

The compound represented by the formula (193) is treated with a reducing agent such as diisobutylaluminum hydride, aluminum lithium hydride or lithium borohydride in a solvent such as dry tetrahydrofuran or dry diethyl ether to thereby give an alcohol represented by the formula (194).

[Step XXVIII]

The alcohol represented by the formula (194) is reacted with methanesulfonyl chloride, p-toluenesulfonyl chloride etc. in the presence of an appropriate base such as pyridine. Next, it is treated with a cyanidation agent such as sodium cyanide or potassium cyanide in an aprotic polar solvent such as dimethyl sulfoxide or N,N-dimethylformamide to thereby give a cyano compound represented by the formula (195). This reaction can be effected at room temperature to the boiling point of the solvent.

[Step IX]

The compound represented by the formula (195) is treated in the following manner. 1) When $R^{13a}$ is alkyl, etc., the starting compound is reacted with an acid chloride such as 1-chloroethyl chloroformate or vinyl chloroformate optionally in a solvent. Next, an appropriate alcoholic solvent is added thereto and reacted therewith. Alternatively, it is treated with an appropriate solvent containing hydrochloric acid or hydrobromic acid and then heated in an alcoholic solvent. 2) When $R^{13a}$ is tert-butoxycarbonyl, etc., the starting compound is reacted with an appropriate acid such as acetic acid, trifluoroacetic acid or hydrochloric acid optionally in an appropriate solvent such as dichloromethane or tetrahydrofuran. 3) When $R^{13a}$ is a protective group which can be eliminated, such as benzyl, the starting compound is hydrogenated in an appropriate solvent such as methanol, ethanol, ethyl acetate or tetrahydrofuran by using a metal catalyst such as palladium or platinum (IV) oxide under normal to elevated hydrogen pressure. Thus, a compound represented by the formula (196) can be obtained.

[Step XXXIII]

A compound represented by the formula (196) is reacted with, for example, benzyl chloride as an amino protective group preferably at 0° C. to room temperature in the presence of a base such as pyridine, triethylamine or N,N-diisopropylethylamine in an appropriate solvent such as methanol or dichloromethane to thereby give a compound represented by the formula (197). $R^{13b}$ may be an arbitrary one, so long as it is lower alkyl or an amino protective group. The most desirable example of $R^{13b}$ is benzyl.

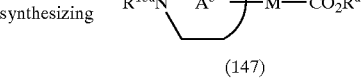

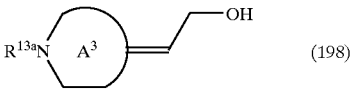

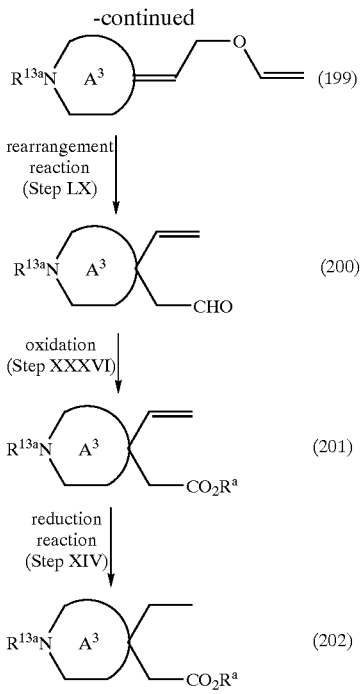

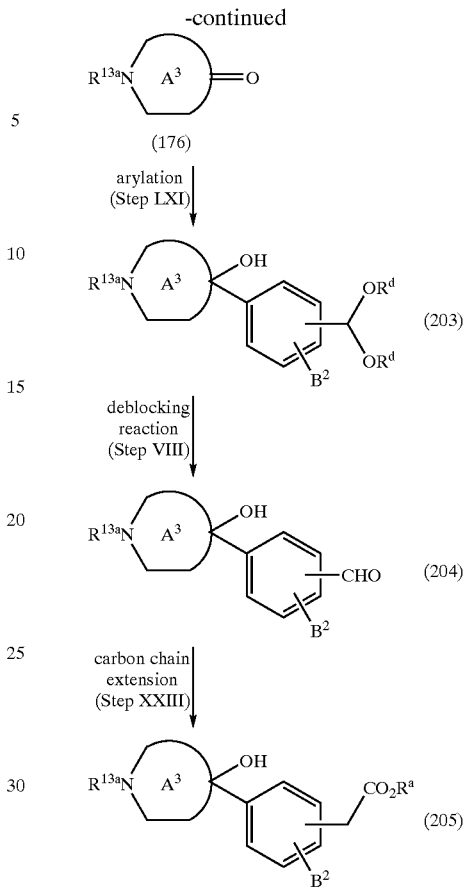

wherein M, $R^{13a}$, $A^3$ and $R^a$ are each as defined above.

[Step LIX]

The compound represented by the formula (198) is reacted with ethyl vinyl ether preferably at 0° C. to room temperature without using any solvent in the presence of a mercuric salt to thereby give an ether represented by the formula (199). Mercuric trifluoroacetate is the most desirable catalyst.

[Step LX]

The compound represented by the formula (199) is heated in an appropriate solvent to thereby give an aldehyde represented by the formula (200). As the solvent, use can be made of benzonitrile, decalin, nitrobenzene, etc. The reaction can be effected at 100° C. to the reflux temperature.

[Step XXXVI]

The compound represented by the formula (200) is treated with pyridinium dichromate in an appropriate alcoholic solvent such as methanol or ethanol to thereby give an ester represented by the formula (201).

[Step XIV]

The compound represented by the formula (201) is subjected to a reduction reaction in a solvent with the use of an appropriate metal catalyst to thereby give a compound represented by the formula (202). For example, use can be made of a hydrogenation reaction effected in a solvent such as methanol, ethanol, ethyl acetate or tetrahydrofuran with the use of palladium, platinum (IV) oxide, etc. under nor

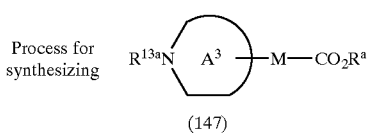

wherein M, $R^{13a}$, $A^3$, $R^d$ and $R^a$ are each as defined above; and $B^2$ represents hydrogen, lower alkyl, lower alkoxy or halide.

[Step LXI]

A compound represented by the formula (176) is subjected in an appropriate solvent to a halogen-metal exchange reaction or reacted with an aryl-Grignard or aryllithium obtained by a lithiation reaction to thereby give a compound represented by the formula (203). As the solvent, use can be made of a dry solvent such as tetrahydrofuran, diethyl ether or dimethoxyethane. The reaction can be effected at −100° C. to the reflux temperature of the solvent.

[Step VIII]

The compound represented by the formula (203) is treated optionally in an appropriate solvent such as dichloromethane or tetrahydrofuran/water with an appropriate acid such as acetic acid, trifluoroacetic acid or hydrochloric acid to thereby give a compound represented by the formula (204). The reaction can be effected at 0° C. to the reflux temperature of the solvent.

[Step XXIII]

The aldehyde represented by the formula (204) is reacted with an anion obtained by treating a dithiane such as 2-trimethyl-1,3-dithiane with a strong base such as butyllithium at −100° C. to room temperature in a dry solvent such as tetrahydrofuran. The dithiane thus obtained is then treated with a metal salt such as mercury chloride in a solvent such as methanol/water. Alternatively, it is reacted with methyl methylsulfinylmethyl sulfoxide in a solvent such as methanol at room temperature to the reflux temperature in the presence of benzyltrimethylammonium hydroxide and the intermediate thus obtained is treated under acidic conditions with the use of, for example, hydrogen chloride/methanol to thereby give an ester represented by the formula (205).

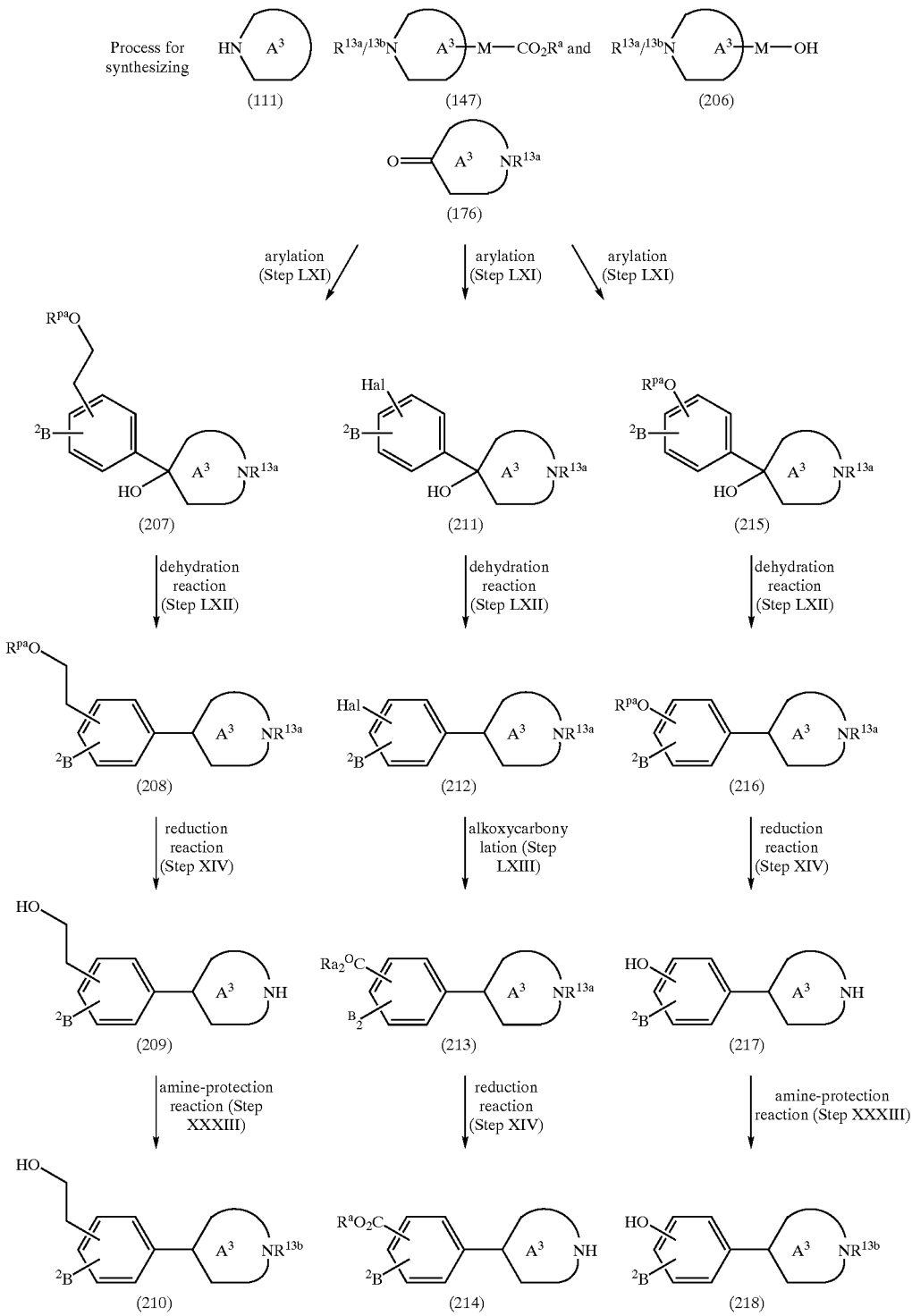

wherein M, $R^{13a}$, $R^{13b}$, $A^3$, $B^2$ and $R^a$ are each as defined above; and $R^{pa}$ represents a hydroxy protective group such as benzyl or methoxymethyl, or hydrogen.

[Step LXI]

The compound represented by the formula (176) is subjected in an appropriate solvent to a halogen-metal exchange reaction or reacted with an aryl-Grignard or aryllithium obtained by a hydrogen-metal exchange reaction to thereby give compounds represented by the formulae (207), (211) and (215). As the solvent, use can be made of a dry solvent such as tetrahydrofuran, diethyl ether or dimethoxyethane. The reaction can be effected at −100° C. to the reflux temperature of the solvent.

[Step LXVII]

The compounds represented by the formulae (207), (211) and (215) are subjected to a dehydration reaction by heating under reflux in the presence of an acid catalyst in an appropriate solvent to thereby give compounds represented by the formulae (208), (212) and (216) respectively. As the solvent, use can be made of benzene, toluene, etc.

[Step XIV]

The compounds represented by the formulae (208), (213) and (216) are subjected to a reduction reaction with the use of an appropriate metal catalyst to thereby give compounds represented by the formulae (209), (214) and (217) respectively. The reaction may be carried out in, for example, a solvent such as methanol, ethanol, ethyl acetate or tetrahydrofuran under normal to elevated hydrogen pressure with the use of palladium, platinum (IV) oxide, etc. as the catalyst.

[Step XXXIII]

The compounds represented by the formulae (209) and (217) are reacted with, for example, di-tert-butyl dicarbonate as an amino protective group preferably at 0° C. to room temperature in the presence of a base such as pyridine, triethylamine or N,N-diisopropylethylamine in an appropriate solvent such as methanol or dichloromethane to thereby give compounds represented by the formulae (210) and (218). $R^{13b}$ may be an arbitrary one, so long as it is lower alkyl or an amino protective group. The most desirable example of $R^{13b}$ is alkyl carbamate.

[Step LXIII]

The compound represented by the formula (212) is treated with n-butyllithium in a dry solvent such as tetrahydrofuran at −100 to 0° C. and the anion thus obtained is treated with a regent such as diethyl carbonate or ethyl chloroformate to thereby give a compound represented by the formula (213).

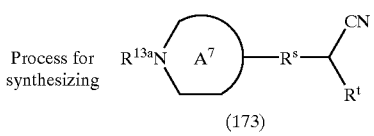

Process for synthesizing (173)

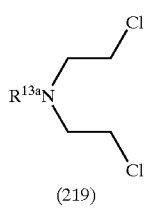

(219)

cyclization
(Step LXIV)

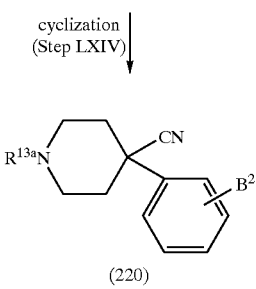

(220)

wherein $R^{13a}$, $A^7$, $B^2$, $R^s$ and $R^t$ are each as defined above.

[Step LXIV]

A compound represented by the formula (219) is reacted with an appropriate benzyl cyanide in the presence of an appropriate phase transfer catalyst in a thick aqueous solution of an alkali to thereby give a piperidine derivative represented by the formula (220). This reaction can be effected at room temperature to 100° C.

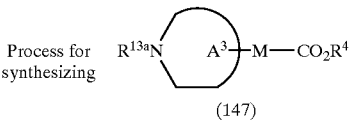

Process for synthesizing (147)

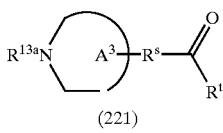

(221)

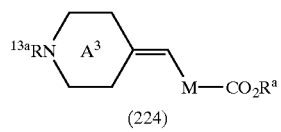

(224)

condensation reaction (Step LXV)

isomerization (Step LXVI)

(222)

(225)

alkylation (Step XXI) | $R^k$=H

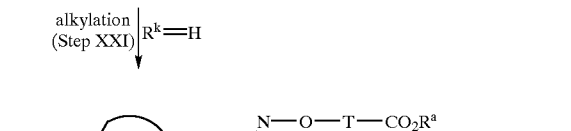

(223)

wherein $R^{13a}$, $A^3$, $R^k$, $R^s$ and $R^t$ are each as defined above.

[Step LXV]

A carbonyl derivative represented by the formula (221) is reacted with an appropriate hydroxylamine in a solvent such as ethanol in the presence of a catalyst such as sodium acetate to thereby give an oxime represented by the formula (222). This reaction can be effected at room temperature to the reflux temperature.

[Step XXI]

The oxime represented by the formula (222) is treated with a base such as sodium hydride or sodium methoxide and then reacted with an alkyl halide in a solvent such as dimethoxyethane, tetrahydrofuran or N,N-dimethylformamide to thereby give a derivative represented by the formula (223). This reaction is effected preferably at 0° C. to room temperature.

[Step LXVI]

An α,β-unsaturated ester represented by the formula (224) is treated with a base such as 1,8-diazabicyclo[5.4.0]-7-undecene at room temperature to reflux temperature in an appropriate solvent such as toluene to thereby give a β,γ-derivative represented by the formula (225). mal to elevated hydrogen pressure.

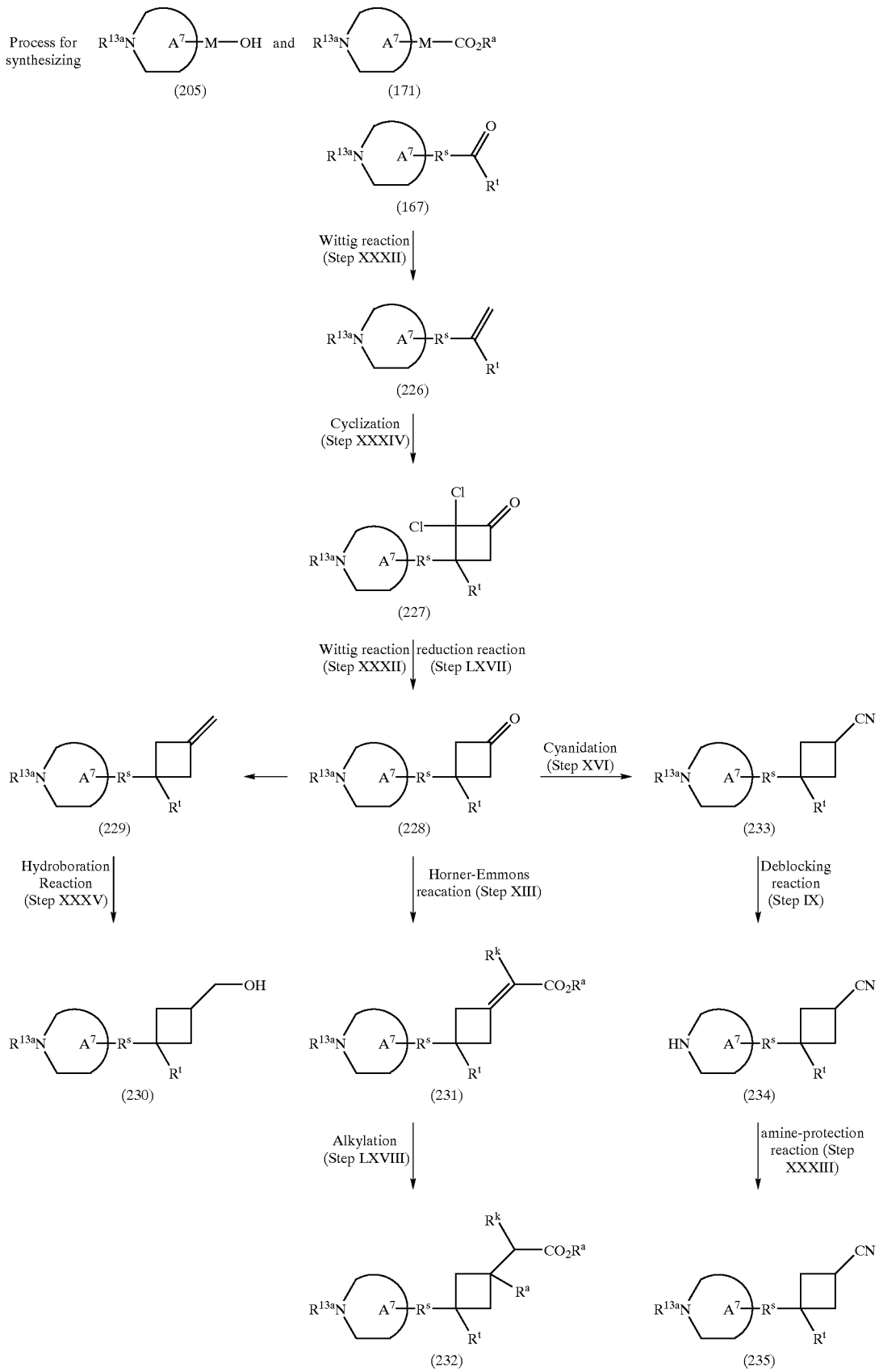

wherein M, $R^{13a}$, $A^7$, $R^a$, $R^d$, $R^k$, $R^s$ and $R^t$ are each as defined above.

[Step XXXII]

Methyltriphenylphosphonium bromide is treated with an appropriate base such as potassium tert-butoxide or butyllithium in a solvent such as toluene, xylene or tetrahydrofuran. Next, ketones represented by the formulae (167) and (228) are reacted therewith to thereby give compounds represented by the formulae (226) and (229) respectively. The reaction temperature preferably ranges from −78° C. to room temperature.

[Step XXXIV]

The compound represented by the formula (226) is treated with zinc/copper alloy and trichloroacetyl chloride in a dry solvent such as diethyl ether, dimethoxyethane or tetrahydrofuran to thereby give a crude dichlorobutyl ketone derivative represented by the formula (227). The reaction temperature preferably ranges from 0 to 50° C.

[Step LXVII]

The dichloroketone represented by the formula (227) is treated with a reducing agent such as zinc in an alcoholic solvent such as methanol in the presence of ammonium chloride to thereby give a ketone compound represented by the formula (228). The reaction temperature preferably ranges from 0 to 50° C.

[Step XXXV]

An exo-methylene compound represented by the formula (229) is treated with an appropriate borane compound such as a borane/tetrahydrofuran complex in an appropriate solvent such as dry tetrahydrofuran or dimethoxyethane followed by the treatment with an oxidizing agent such as hydrogen peroxide in an alkali solution to thereby give an alcohol compound represented by the formula (230).

[Step XIII]

The compound represented by the formula (228) is reacted with an appropriate Horner-Emmons reagent in a solvent in the presence of an appropriate base to thereby give a compound represented by the formula (231). As the solvent, use can be made of dry solvents such as N,N-dimethylformamide, tetrahydrofuran or diethyl ether. As the base, use can be made of sodium hydride, potassium tert-butoxide, n-butyllithium, lithium diisopropylamide, etc. The reaction can be effected at −100° C. to the reflux temperature of the solvent.

[Step LXVIII]

The α,β-unsaturated ester represented by the formula (231) is reacted with an alkylcopper complex in a dry solvent such as diethyl ether in the presence of an appropriate activator such as chlorotrimethylsilane to thereby give a compound represented by the formula (232). The reaction is effected preferably at −80 to 0° C.

[Step XVI]

The compound represented by the formula (228) is treated with a cyanidation reagent such as tosylmethyl isocyanide in a mixture of a solvent such as dimethoxyethane, tetrahydrofuran or diethyl ether with an alcoholic solvent such as tert-butanol in the presence of a base such as potassium tert-butoxide to thereby give a cyano compound represented by the formula (233). It is preferable to effect this reaction at a temperature of 0 to 100° C.

[Step IX]

The compound represented by the formula (233) is treated in the following manner. 1) When $R^{13a}$ is alkyl, etc., the starting compound is reacted with an acid chloride such as 1-chloroethyl chloroformate or vinyl chloroformate optionally in a solvent. Next, an appropriate alcoholic solvent is added thereto and reacted therewith. Alternatively, it is treated with an appropriate solvent containing hydrochloric acid or hydrobromic acid and then heated in an alcoholic solvent. 2) When $R^{13a}$ is tert-butoxycarbonyl, etc., the starting compound is reacted with an appropriate acid such as acetic acid, trifluoroacetic acid or hydrochloric acid optionally in an appropriate solvent such as dichloromethane or tetrahydrofuran. 3) When $R^{13a}$ is a protective group which can be eliminated, such as benzyl, the starting compound is hydrogenated in an appropriate solvent such as methanol, ethanol, ethyl acetate or tetrahydrofuran by using a metal catalyst such as palladium or platinum (IV) oxide under normal to elevated hydrogen pressure. Thus, a compound represented by the formula (234) can be obtained.

[Step XXXIII]

The compound represented by the formula (234) is reacted with, for example, benzyl chloride as an amino protective group preferably at 0° C. to room temperature in the presence of a base such as pyridine, triethylamine or N,N-diisopropylethylamine in an appropriate solvent such as methanol or dichloromethane to thereby give a compound represented by the formula (235). $R^{13b}$ may be an arbitrary one, so long as it is lower alkyl or an amino protective group. The most desirable example of $R^{13b}$ is benzyl.

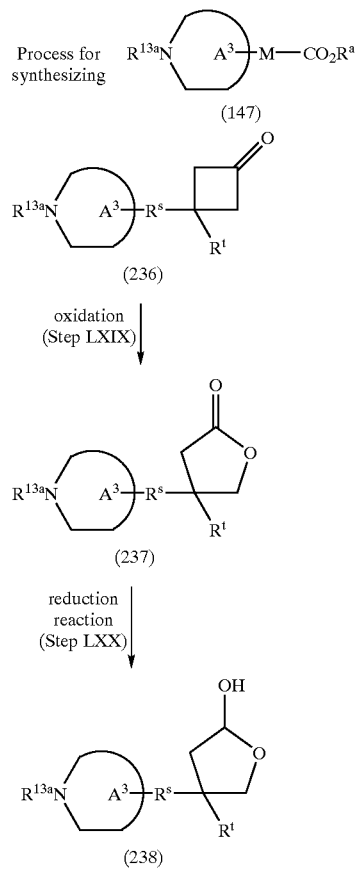

-continued

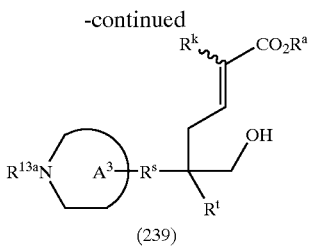

(239)

reductions reaction
(Step XIV)

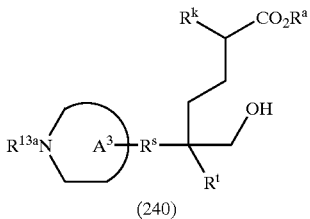

(240)

wherein M, $R^{13a}$, $A^3$, $R^a$, $R^k$, $R^s$ and $R^t$ are each as defined above.

[Step LXIX]

A ketone compound represented by the formula (236) is treated with a peroxide such as 3-chloroperbenzoic acid in an appropriate solvent such as dichloromethane in the presence of sodium carbonate, etc. to thereby give a lactone compound represented by the formula (237). The reaction temperature preferably ranges from −100 to 0° C.

[Step LXX]

The lactone compound represented by the formula (237) is treated with diisobutylaluminum hydride in an appropriate solvent such as toluene or dichloromethane to thereby give a lactol compound represented by the formula (238). The reaction temperature preferably ranges from −100 to 0° C.

[Step XIII]

The compound represented by the formula (238) is reacted with an appropriate Horner-Emmons reagent in a solvent in the presence of an appropriate base to thereby give a compound represented by the formula (239). As the solvent, use can be made of dry solvents such as N,N-dimethylformamide, tetrahydrofuran or diethyl ether. As the base, use can be made of sodium hydride, potassium tert-butoxide, n-butyllithium, lithium diisopropylamide, etc. The reaction can be effected at −100° C. to the reflux temperature of the solvent.

[Step XIV]

The compound represented by the formula (239) is subjected to a reduction reaction with the use of an appropriate metal catalyst in a solvent to thereby give a compound represented by the formula (240). The reaction may be carried out in, for example, a solvent such as methanol, ethanol, ethyl acetate or tetrahydrofuran under normal to elevated hydrogen pressure with the use of palladium, platinum (IV) oxide, etc. as the catalyst.

Process for synthesizing 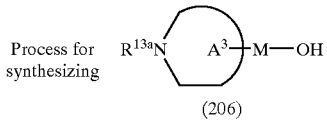

(206)

-continued

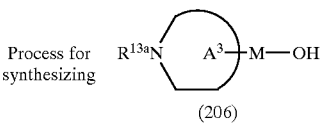

(241)

cyclopropylation
(Step LXXI)

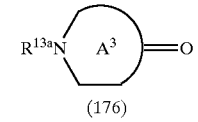

(242)

wherein M, $R^{13a}$, $A^3$ and $X_n$ are each as defined above.

[Step LXXI]

An alkene compound represented by the formula (241) is reacted with diethylzinc and iodomethane in an appropriate solvent such as dichloromethane to thereby give a cyclopropyl derivative represented by the formula (242). The reaction temperature preferably ranges from 0° C. to room temperature.

Process for synthesizing 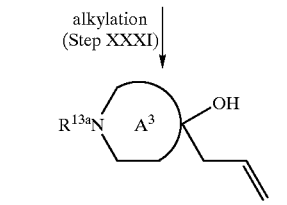

(206)

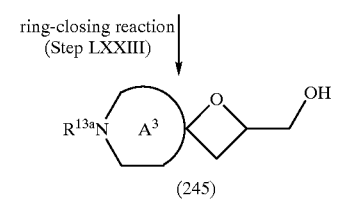

wherein M, $R^{13a}$ and $A^3$ are each as defined above.

[Step XXXXI]

A compound represented by the formula (176) is treated with allyllithium or allylmagnesium halide in a solvent such as dry tetrahydrofuran, diethyl ether or dimethoxyethane at −78° C. to the boiling point of the solvent to thereby give an alcohol represented by the formula (243).

[Step LXXII]

The alkene compound represented by the formula (243) is treated with a peroxide such as 3-chloroperbenzoic acid in an appropriate solvent such as dichloromethane in the presence of sodium carbonate, etc to thereby give an epoxide represented by the formula (244). The reaction temperature preferably ranges from room temperature to 40° C.

[Step LXXIII]

The compound represented by the formula (244) is treated with a base such as lithium hydroxide in a solvent mixture of dimethyl sulfoxide with water to thereby give a compound represented by the formula (245). The reaction temperature preferably ranges from 50 to 150° C.

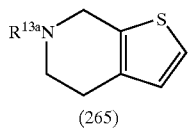

(265)

formylation
(Step LXXVI)

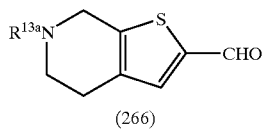

(266)

Peterson reaction
(Step LXXVII)

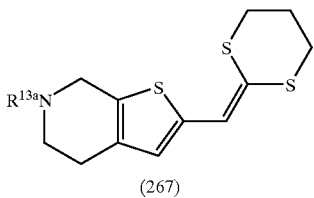

(267)

deblocking reaction
(Step IX)

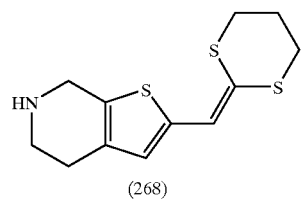

(268)

condensation reaction
(Step X)

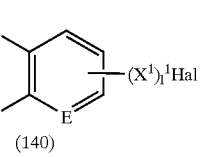

(140)

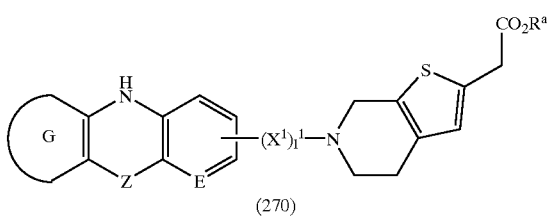

(269)

Hydrolysis
(Step LXXVIII)

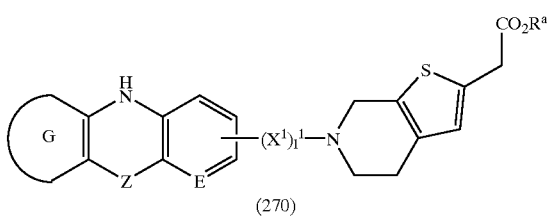

(270)

wherein G, Z, E, $X^1$, $1^1$, $R^{13a}$, Hal and $R^a$ are each as defined above.

[Step LXXVI]

A thiophene derivative represented by the formula (265) is treated with a strong base such as n-butyllithium or lithium diisopropylamide in a dry solvent such as tetrahydrofuran, diethyl ether or hexamethylphosphorous triamide at from −100 to 0° C. Then the anion thus obtained is treated with a formulation agent such as N,N-dimethylformamide to thereby give an aldehyde represented by the formula (266).

[Step LXXVII]

The aldehyde represented by the formula (266) is reacted with an anion obtained by treating a dithiane such as 2-trimethylsilyl-1,3-dithiane with a strong base such as butyllithium in a dry solvent such as tetrahydrofuran at from −100° C. to room temperature to thereby give a methylenethiazine represented by the formula (267).

[Step IX]

The compound represented by the formula (267) is treated with an appropriate acid such as hydrochloric acid, trifluoroacetic acid or acetic acid optionally in an appropriate solvent such as dichloromethane or tetrahydrofuran to thereby give an amine represented by the formula (268).

[Step X]

The compound represented by the formula (267) is treated with a halide represented by the formula (140) in a solvent in the presence of an appropriate base such as anhydrous potassium carbonate or N,N-diisopropylethylamine to thereby give a compound represented by the formula (269). As the solvent, use can be made of dry N,N-dimethylformamide, etc. The reaction can be effected at from 0 to 150° C.

[Step LXXVIII]

The methylenethiazine represented by the formula (269) is treated with a metal salt such as mercury chloride in a solvent such as methanol/water to thereby give an ester compound represented by the formula (270).

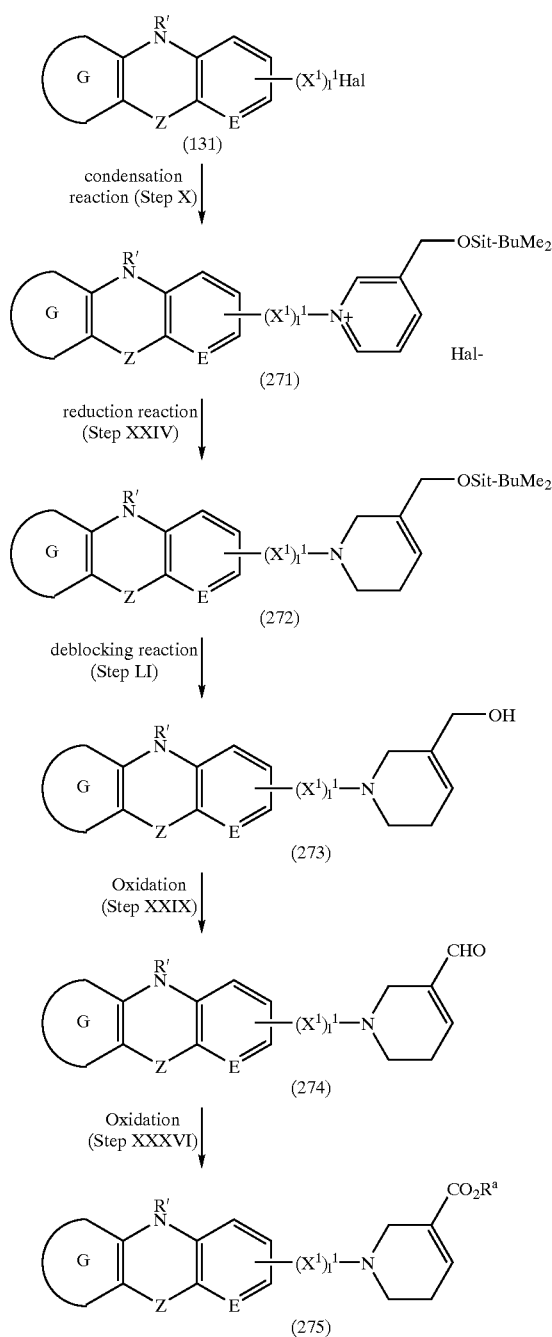

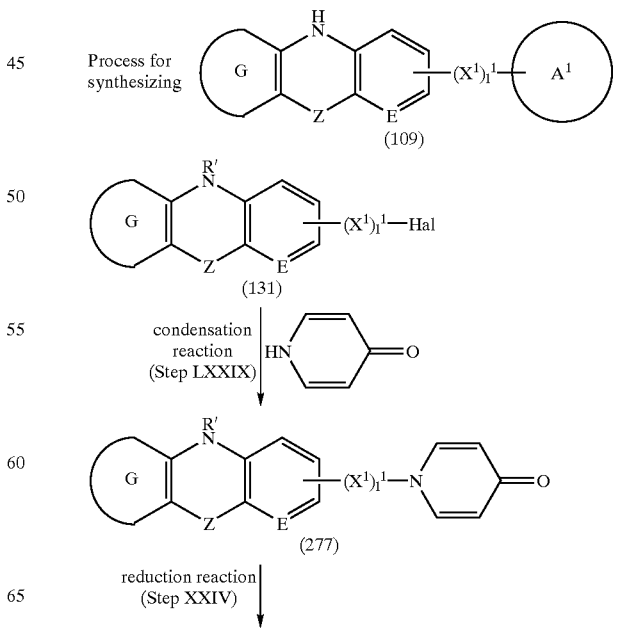

wherein G, Z, E, $X^1$, $1^1$, R', $R^a$ and Hal are each as defined above.

[Step X]

A compound represented by the formula (131) is treated with a protected 3-(hydroxymethyl)pyridine derivative in a solvent in the presence of an appropriate base such as anhydrous potassium carbonate or N,N-diisopropylethylamine to thereby give a compound represented by the formula (271). As the solvent, use can be made of dry N,N-dimethylformamide, etc. The reaction can be effected at from 0 to 150° C.

[Step XXIV]

The compound represented by the formula (271) is treated with a reducing agent such as sodium borohydride in a solvent to thereby give a compound represented by the formula (272). As the solvent, use can be made of methanol, ethanol, etc. The reaction can be effected at from 0° C. to the reflux temperature.

[Step LI]

The compound represented by the formula (272) is treated with a reagent such as tetra-n-butylammonium fluoride or caesium fluoride in a dry solvent such as tetrahydrofuran to thereby give an alcohol represented by the formula (273). The reaction is effected preferably at from 0° C. to room temperature.

[Step XXIX]

A solution of the alcohol represented by the formula (273) in, for example, methylene chloride is added to a reaction mixture obtained from oxalyl chloride and dimethyl sulfoxide and treated with a base such as triethylamine. Alternatively, it is treated with pyridinium dichromate in a solvent such as dichloromethane or N,N-dimethylformamide or treated with manganese dioxide in a solvent such as dichloromethane. Thus, an aldehyde represented by the formula (274) can be obtained.

[Step XXXVI]

The compound represented by the formula (274) is treated with bromine in an appropriate alcoholic solvent such as methanol or ethanol in the presence of a base such as sodium hydrogencarbonate or potassium carbonate preferably at from 0° C. to room temperature. Alternatively, the starting compound is treated with pyridinium chromate in an appropriate alcoholic solvent such as methanol or ethanol. Alternatively, it is treated with manganese dioxide in an appropriate alcoholic solvent such as methanol or ethanol in the presence of sodium cyanide and acetic acid and then treated with sulfuric acid, hydrochloric acid, thionyl chloride, etc. in an appropriate alcoholic solvent such as methanol or ethanol. Alternatively, it is treated with sodium chlorite in a solvent mixture of water with dimethyl sulfoxide in the presence of sodium dihydrogenphosphate and then reacted with trimethylsilyl-diazomethane in a solvent such as methanol. Alternatively, it is treated with an activating agent such as thionyl chloride in an appropriate alcoholic solvent such as methanol or ethanol. Thus, an ester compound represented by the formula (275) can be obtained.

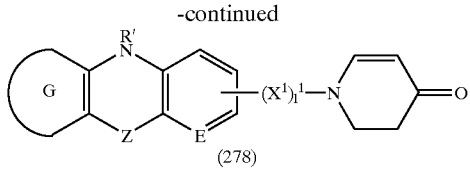
(278)

wherein G, Z, $A^1$, E, $X^1$, $1^1$, Hal and R' are each as defined above.

[Step LXXIX]

4-Hydroxypyridine is treated with a strong base such as sodium hydride or lithium diisopropylamide in a dry solvent such as tetrahydrofuran or N,N-dimethylformamide. The anion thus obtained is then treated with a halogen compound (131) at from 0 to 100° C. to thereby give a pyridone represented by the formula (277).

[Step XXIV]

The pyridone represented by the formula (277) is treated with a reducing agent such as aluminum lithium hydride in a dry solvent such as dry diethyl ether at from 0 to 50° C. to thereby give an α,β-unsaturated enone (278).

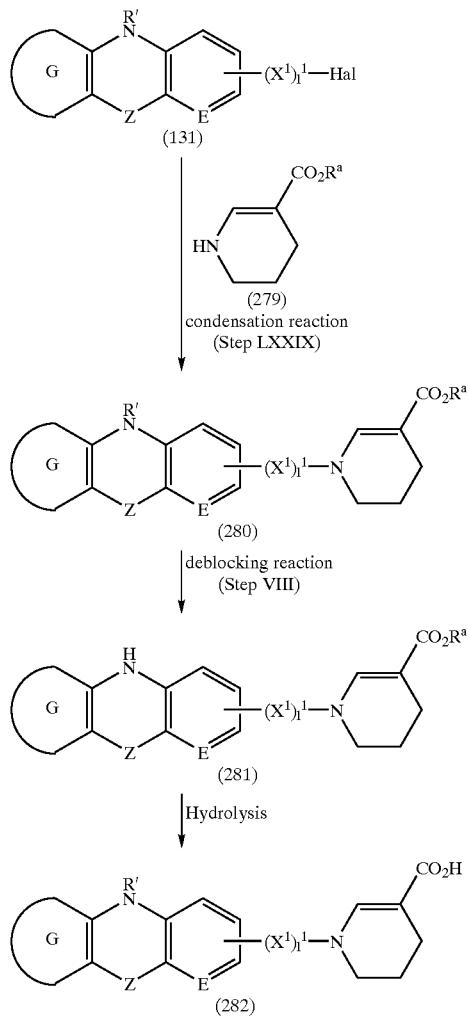

wherein G, Z, $R^a$, E, $X^1$, $1^1$, Hal and R' are each as defined above.

[Step LXXIX]

The compound represented by the formula (279) is treated with a strong base such as sodium hydride or lithium diisopropylamide in a dry solvent such as tetrahydrofuran or N,N-dimethylformamide. The anion thus obtained is then treated with a halogen compound (131) at from 0 to 100° C. to thereby give a compound represented by the formula (280).

[Step VIII]

The compound represented by the formula (280) is treated with an appropriate acid such as hydrochloric acid, trifluoroacetic acid or acetic acid optionally in an appropriate solvent such as dichloromethane or tetrahydrofuran to thereby give an amine represented by the formula (281).

[Step LXXX]

The ester compound represented by the formula (281) is treated with water and an excessive amount of a strong base such as potassium tert-butoxide in a dry solvent such as dimethyl sulfoxide to thereby give a carboxylic acid represented by the formula (282). This reaction is effected preferably at from 0 to 50° C.

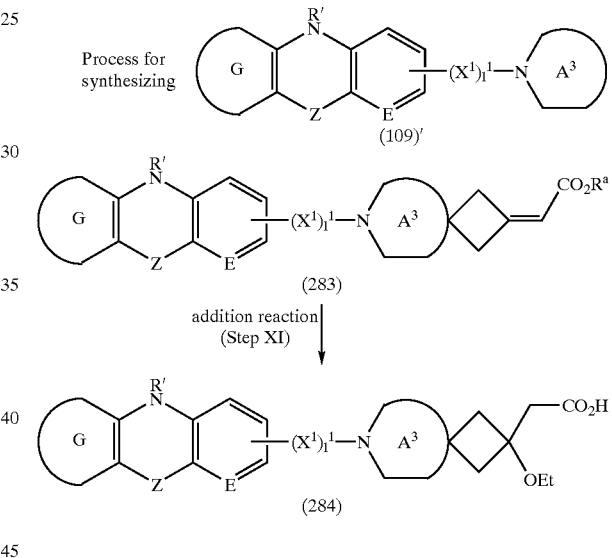

wherein $A^3$, G, Z, $R^a$, E, $X^1$, $1^1$, Hal and R' are each as defined above.

[Step XI]

A compound represented by the formula (283) is treated with an appropriate base in an aqueous ethanol solvent followed by hydrolysis to thereby give a compound having a carboxyl group represented by the formula (284). As the base, use can be made of sodium hydroxide, potassium hydroxide, etc. The reaction can be effected at from room temperature to the reflux temperature of the solvent.

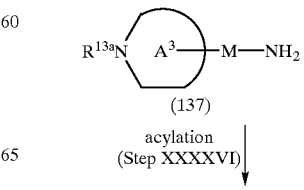

acylation
(Step XXXXVI)

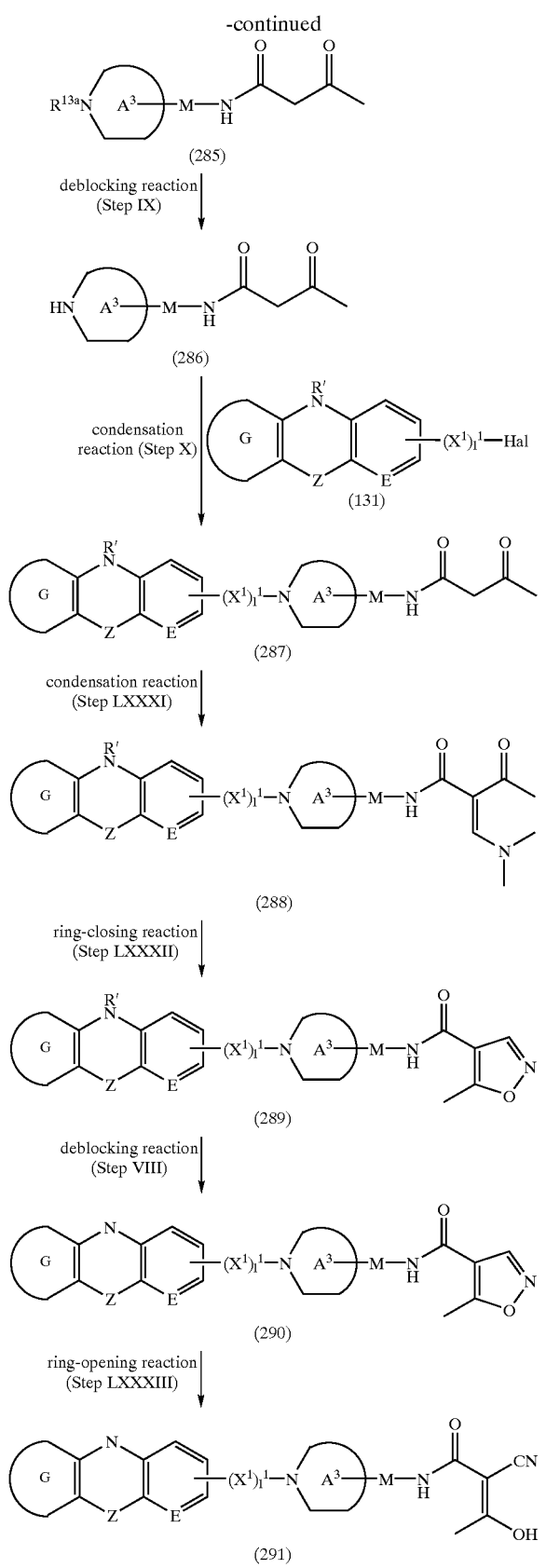

wherein G, Z, M, E, X¹, 1¹, Hal, A³ and R' are each as defined above.

[Step XXXXVI]

An amine represented by the formula (137) is reacted with diketen in an appropriate solvent to thereby give an amdie represented by the formula (285). As the solvent, use can be made of toluene, etc. The reaction can be effected at from 0° C. to the reflux temperature.

[Step IX]

The compound represented by the formula (285) is subjected to a reduction reaction in a solvent with the use of an appropriate metal catalyst to thereby give a compound represented by the formula (286). The reaction may be carried out in, for example, a solvent such as methanol, ethanol, ethyl acetate or tetrahydrofuran under normal to elevated hydrogen pressure with the use of palladium, platinum (IV) oxide, etc. as the catalyst.

[Step X]

The compound represented by the formula (286) is treated with a halide represented by the formula (131) in a solvent in the presence of an appropriate base such as anhydrous potassium carbonate or N,N-diisopropylethylamine to thereby give a compound represented by the formula (287). As the solvent, use can be made of dry N,N-dimethylformamide, etc. The reaction can be effected at from 0 to 150° C.

[Step LXXXI]

The dicarbonyl compound represented by the formula (287) is treated with N,N-dimethylformamide dimethyl acetal in an appropriate solvent at from 50 to 100° C. to thereby give a compound represented by the formula (288).

[Step LXXXII]

The compound represented by the formula (288) is reacted with hydroxylamine hydrochloride in an alcoholic solvent such as methanol at from room temperature to the reflux temperature to thereby give an oxazole represented by the formula (289).

[Step VIII]

The compound represented by the formula (289) is treated with an appropriate acid such as hydrochloric acid, trifluoroacetic acid or acetic acid optionally in an appropriate solvent such as dichloromethane or tetrahydrofuran to thereby give an amine represented by the formula (290).

[Step LXXXIII]

The isoxazole represented by the formula (290) is treated with N,N-dimethylformamide dimethyl acetal in a dry solvent such as tetrahydrofuran at from room temperature to the reflux temperature to thereby give a compound represented by the formula (291).

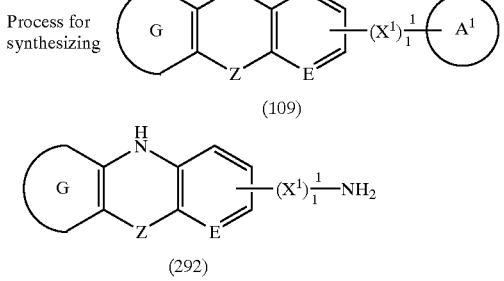

condensation reaction
(Step LXXXIV)

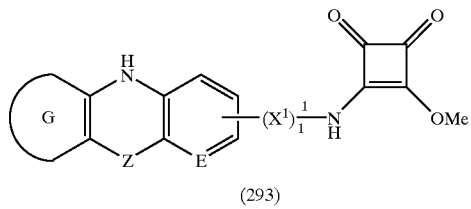

(293)

condensation reaction
(Step LXXXIV)

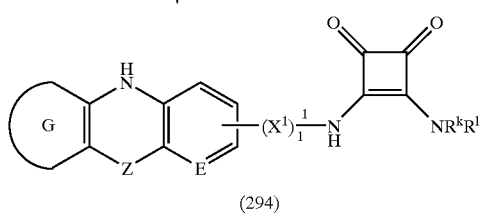

(294)

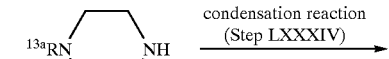

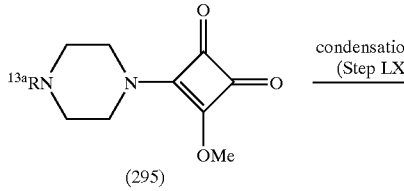

(295)

(296)

wherein G, Z, E, $X^1$, $1^1$, $A^1$, $R^k$ and $R^l$ are each as defined above.

[Step LXXXIV]

An amine represented by the formula (292) is reacted with 3,4-dimethoxy-3-cyclobutene-1,2-dione in an appropriate solvent such as N,N-dimethylformamide, ethanol, methanol or dichloromethane optionally in the presence of a base such as triethylamine at from room temperature to the reflux temperature to thereby give a compound represented by the formula (293).

[Step LXXXIV]

The compound represented by the formula (293) is treated with an appropriate amine or ammonia in an appropriate solvent such as N,N-dimethylformamide, ethanol, methanol or dichloromethane optionally in the presence of a base such as triethylamine at from room temperature to the reflux temperature to thereby give a compound represented by the formula (294).

wherein $R^{13a}$, $R^k$ and $R^l$ are each as defined above.

[Step LXXXIV]

An amine represented by the formula (153) is reacted with 3,4-dimethoxy-3-cyclobutene-1,2-dione in an appropriate solvent such as N,N-dimethylformamide, ethanol, methanol or dichloromethane optionally in the presence of a base such as triethylamine at from room temperature to the reflux temperature to thereby give a compound represented by the formula (295).

[Step LXXXIV]

The compound represented by the formula (295) is treated with an appropriate amine or ammonia in an appropriate solvent such as N,N-dimethylformamide, ethanol, methanol or dichloromethane optionally in the presence of a base such as triethylamine at from room temperature to the reflux temperature to thereby give a compound represented by the formula (296).

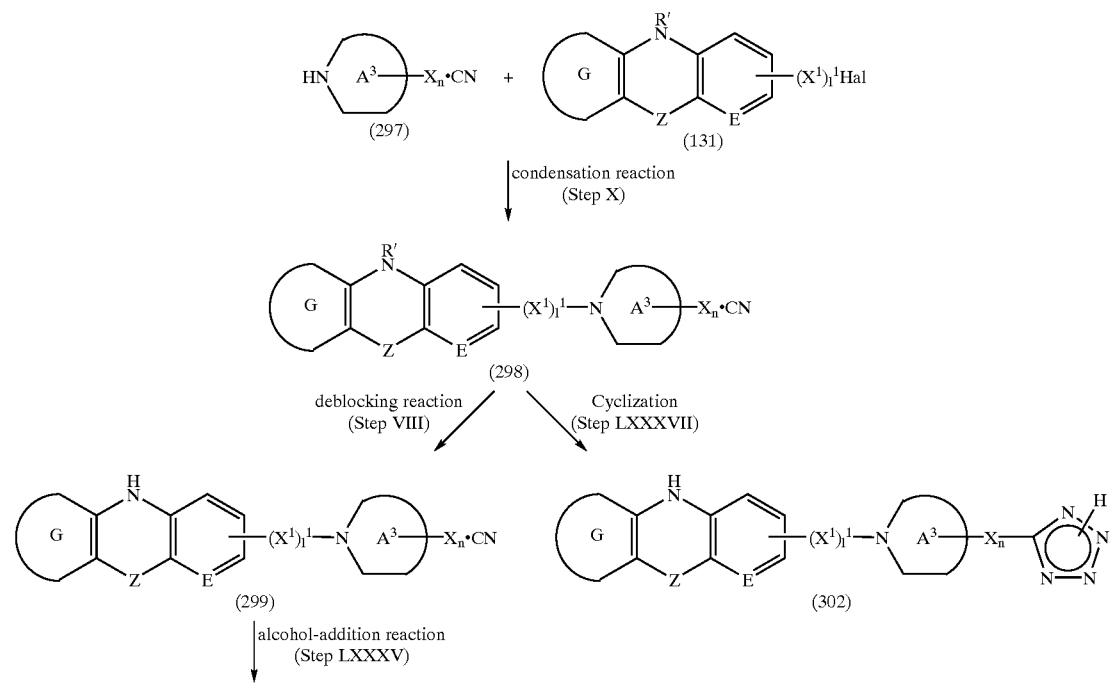

-continued

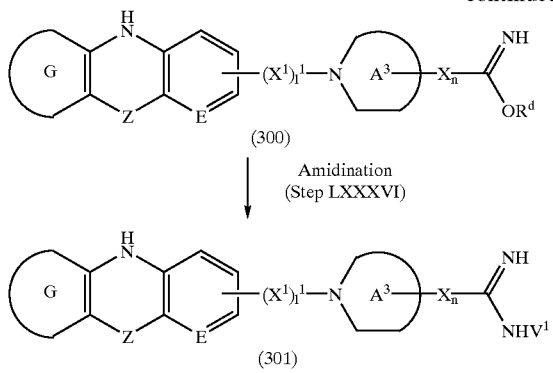

wherein G, Z, E, $X^1$, $1^1$, $A^3$, R', $R^d$, $X_n$ and $V^1$ are each as defined above.

[Step X]

A compound represented by the formula (297) is treated with a halide represented by the formula (131) in a solvent in the presence of an appropriate base such as anhydrous potassium carbonate or N,N-diisopropylethylamine to thereby give a compound represented by the formula (298). As the solvent, use can be made of dry N,N-dimethylformamide, etc. The reaction can be effected at from 0 to 150° C.

[Step VIII]

The compound represented by the formula (298) is treated with an appropriate acid such as hydrochloric acid, trifluoroacetic acid or acetic acid optionally in an appropriate solvent such as dichloromethane or tetrahydrofuran to thereby give an amine represented by the formula (299).

[Step LXXXV]

The nitrile compound represented by the formula (299) is treated with an appropriate acid in an alcoholic solvent to thereby give an imidate represented by the formula (300) (i.e., the so-called Pinner reaction). It is preferable to use hydrochloric acid as the acid. The reaction is preferably effected in methanol at from 0 to 10° C.

[Step LXXXVI]

The imidate represented by the formula (300) is reacted with an amine or an amide in an appropriate solvent to thereby give a compound represented by the formula (301). The most desirable solvent is acetonitrile. The reaction is effected preferably at from room temperature to 40° C.

[Step LXXXVII]

The nitrile represented by the formula (298) is treated with an azidation agent such as sodium azide in a dry solvent such as dimethyl sulfoxide, N,N-dimethylformamide or 1-methyl-2-pyrrolidone at from 50° C. to the reflux temperature in the presence of a catalyst such as ammonium chloride to thereby give a tetrazole derivative represented by the formula (302).

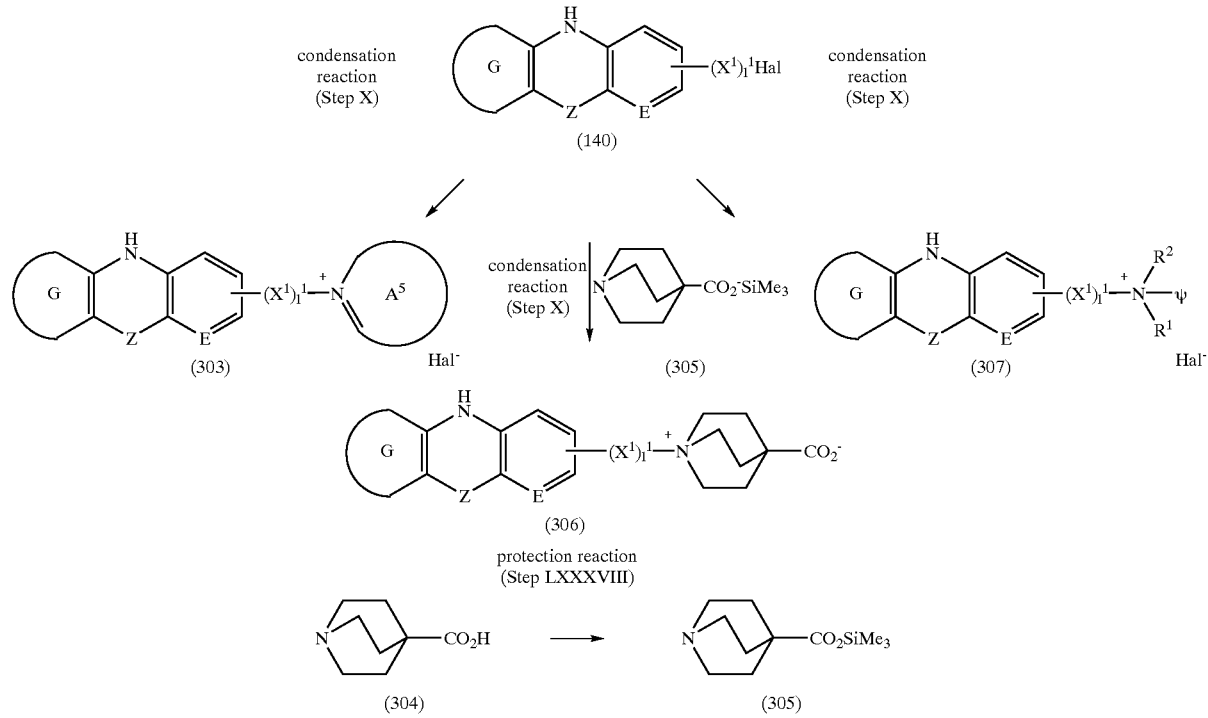

wherein G, Z, E, $X^1$, $l^1$, $R^k$, $R^l$ and Hal are each as defined above; $A^8$ represents heteroaryl having no acidic proton group such as NH; and ψ represents lower alkyl or oxygen.
[Step X]

A halogen compound represented by the formula (140) is treated with a heteroaryl compound having no acidic proton, such as pyridine, an amine compound represented by the formula (305), a tertiary amine or an N,N-dialkylhydroxylamine, to thereby give compounds represented by the formulae (303), (306) and (307) respectively. As the solvent, use can be made of ethanol, dry N,N-dimethylformamide, etc. The reaction can be effected at from 50 to 150° C.
[Step LXXXVIII]

A carboxylic acid represented by the formula (304) is reacted with a silylation agent such as chlorotrimethylsilane, trimethylsilyl trifluoroacetate or N-methyl-N-(trimethylsilyl)trifluoroacetamide in an appropriate solvent optionally in the presence of a base such as imidazole, pyridine or N,N-diisopropylethylamine to thereby give an ester compound represented by the formula (305). As the solvent, use can be made of dry solvent such as N,N-dimethylformamide, acetonitrile or dichloromethane. The reaction can be effected at from 0 to 40° C.

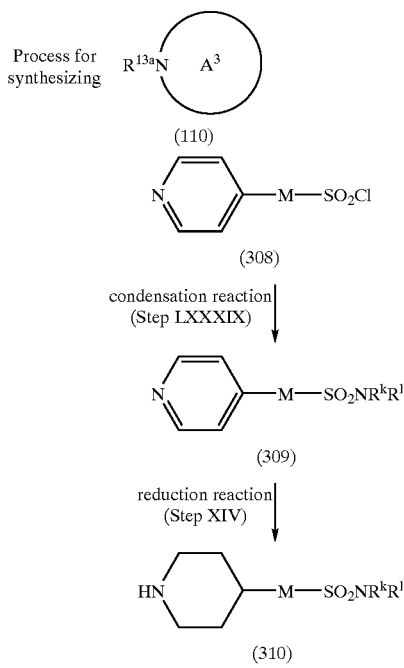

wherein $A^3$, M, $R^k$ and $R^l$ are each as defined above.
[Step LXXXIX]

An acid halide represented by the formula (308) is treated with an appropriate amine optionally in an appropriate solvent such dichloromethane or methanol in the presence of an appropriate base such as pyridine, triethylamine or N,N-diisopropylethylamine to thereby give a compound represented by the formula (309).
[Step XIV]

The compound represented by the formula (309) is subjected to a reduction reaction with the use of an appropriate metal catalyst in a solvent to thereby give a compound represented by the formula (310). The reaction may be carried out in, for example, a solvent such as methanol, ethanol, ethyl acetate or tetrahydrofuran with the use of palladium, platinum (IV) oxide, etc. as the catalyst under normal to elevated hydrogen pressure.

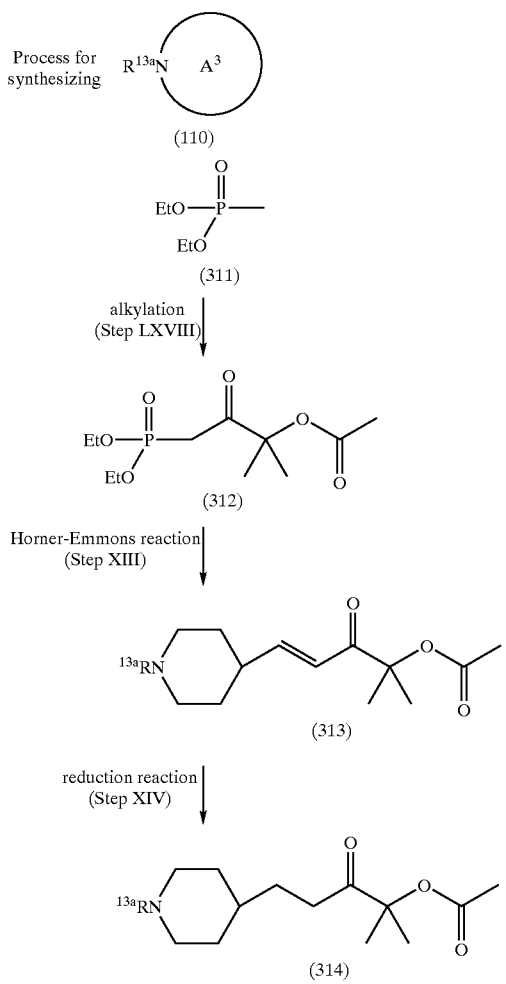

wherein M, $R^{13a}$ and $A^3$ are each as defined above.
[Step LXVIII]

A compound represented by the formula (311) is treated with a strong base such as n-butyllithium or lithium diisopropylamide in a dry solvent such as tetrahydrofuran, diethyl ether or hexamethylphosphorous triamide at from −100 to 0° C. The anion thus obtained is then treated with a metal salt such as cupric iodide to thereby effect a metal exchange reaction. The copper complex thus obtained is treated with an appropriate acid halide to thereby give a compound represented by the formula (312).
[Step XIII]

An appropriately protected 4-piperidinecarbaldehyde is reacted with a Horner-Emmons reagent represented by the formula (312) in a solvent in the presence of an appropriate base to thereby give a compound represented by the formula (313). As the solvent, use can be made of dry solvents such as N,N-dimethylformamide, tetrahydrofuran or diethyl ether. As the base, use can be made of sodium hydride, potassium tert-butoxide, n-butyllithium, lithium diisopropylamide, etc. The reaction can be effected at from −100° C. to the reflux temperature of the solvent.
[Step XIV]

The compound represented by the formula (313) is subjected to a reduction reaction with the use of an appropriate metal catalyst in a solvent to thereby give a compound represented by the formula (314). The reaction may be carried out in, for example, a solvent such as methanol, ethanol, ethyl acetate or tetrahydrofuran with the use of palladium, platinum (IV) oxide, etc. as the catalyst under normal to elevated hydrogen pressure.

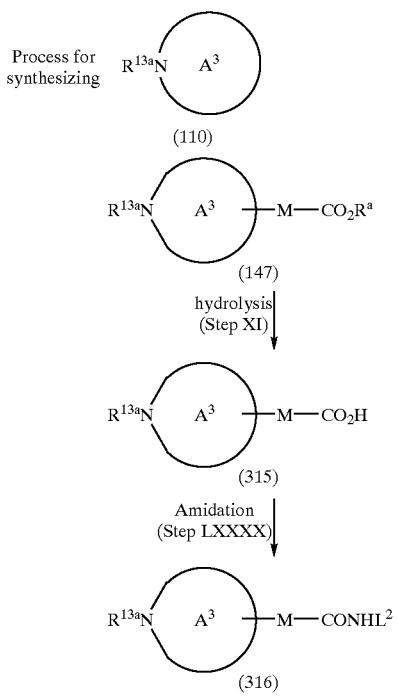

wherein M, $R^{13a}$, $R^a$ and $A^3$ are each as defined above; and $L^2$ represents a substituent such as methylsulfonyl, nitryl, tetarzol-5-yl or 8-methyl-8-azabicyclo[3.2.1]octan-3-yl.

[Step XI]

A compound represented by the formula (147) is reacted with an appropriate base in an aqueous solvent followed by hydrolysis to thereby give a compound having a carboxyl group represented by the formula (315). As the solvent, use can be made of alcoholic solvents such as methanol or ethanol or solvent mixtures such as alcohol/tetrahydrofuran/water. As the base, use can be made of sodium hydroxide, potassium hydroxide, etc. The reaction can be effected at from room temperature to the reflux temperature of the solvent.

[Step LXXXX]

The carboxylic acid represented by the formula (315) is reacted with an appropriate diimide, an appropriate chloroformate, an appropriate dichlorophosphonate or carbonyldiimidazole at from 0 to 60° C. in an appropriate dry solvent such as N,N-dimethylformamide, tetrahydrofuran, acetonitrile or dichloromethane optionally in the presence of an appropriate base such as pyridine, triethylamine or N,N-diisopropylamine. The activated ester thus obtained is then reacted with an appropriate amine or amine derivative to thereby give an amide represented by the formula (316).

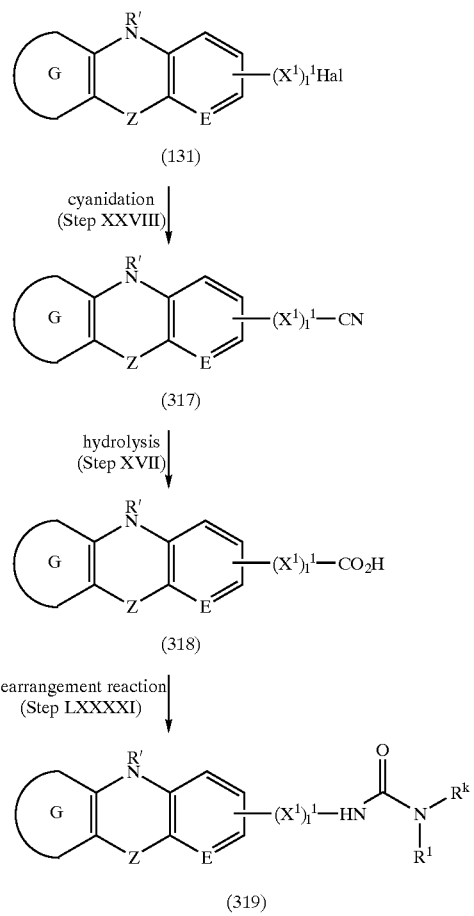

wherein G, Z, E, $X^1$, $1^1$, $R^k$, $R^l$, R' and Hal are each as defined above.

[Step XXVIII]

An alcohol represented by the formula (131) is treated with a cyanidation reagent such as sodium cyanide or potassium cyanide in an appropriate solvent such as dimethyl sulfoxide to thereby give a nitrile represented by the formula (317). The reaction can be effected at from room temperature to 100° C.

[Step XVII]

The cyano compound of the formula (317) is treated with a base such as sodium hydroxide or potassium hydroxide in an alcoholic solvent such as ethanol, propanol, ethylene glycol or diethylene glycol and heated under reflux to thereby give a carboxylic acid of the formula (318).

[Step LXXXXI]

The carboxylic acid of the formula (318) is treated with diphenyl phosphate azide in an appropriate dry solvent such as tetrahydrofuran in the presence of an appropriate tertiary amine base such as triethylamine. The intermediate thus obtained is then treated with an appropriate secondary or primary amine to thereby give a urea derivative represented by the formula (319).

Process for synthesizing

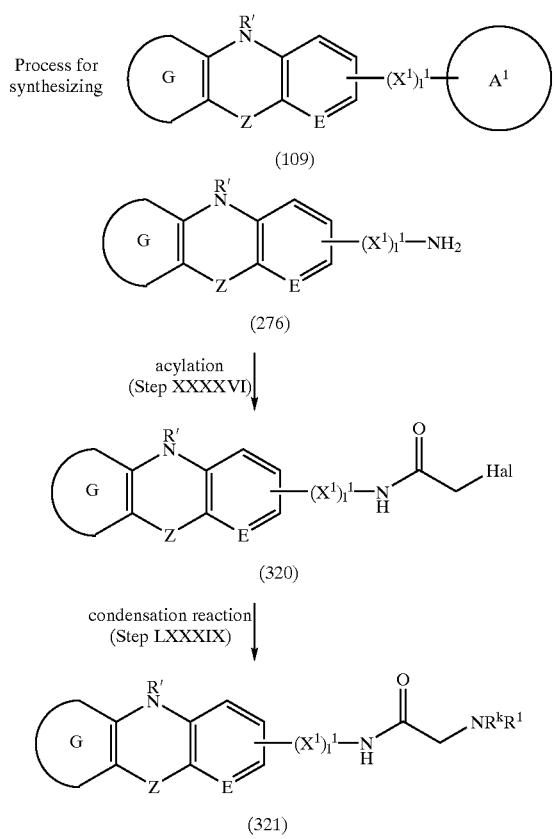

wherein G, Z, E, $X^1$, $1^1$, $A^1$, $R^k$, $R^l$, R' and Hal are each as defined above.

[Step XXXXVII]

An amine represented by the formula (276) is reacted with chloroacetyl chloride optionally in an appropriate solvent in the presence of an appropriate base such as pyridine, triethylamine or N,N-diisopropylethylamine to thereby give an amide represented by the formula (320). As the solvent, use can be made of dry N,N-dimethylformamide, dry dichloromethane, etc. The reaction can be effected at from 0° C. to room temperature.

[Step LXXXIX]

The halogen compound represented by the formula (320) is treated with an appropriate amine optionally in an appropriate solvent such as dichloromethane or dry N,N-dimethylformamide in the presence of an appropriate base such as anhydrous potassium carbonate, pyridine, triethylamine or N,N-diisopropylethylamine to thereby give a compound represented by the formula (321).

Process for synthesizing

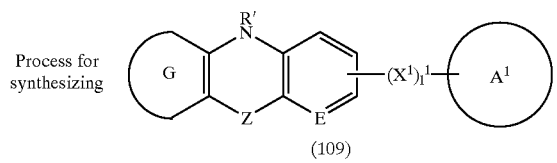

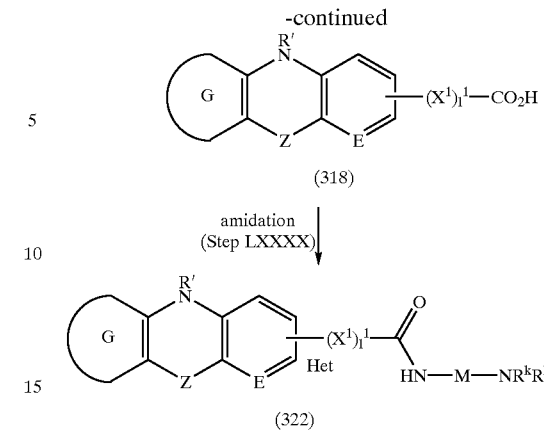

wherein G, Z, E, $X^1$, $1^1$, $A^1$, $R^k$, $R^l$, R' and Hal are each as defined above.

[Step LXXXX]

A carboxylic acid represented by the formula (318) is reacted with an appropriate diimide, an appropriate chloroformate, an appropriate dichlorophosphonate or carbonyldiimidazole at from 0 to 60° C. in an appropriate dry solvent such as N,N-dimethylformamide, tetrahydrofuran, acetonitrile or dichloromethane optionally in the presence of an appropriate base such as pyridine, triethylamine or N,N-diisopropylethylamine. The activated ester thus obtained is then reacted with an appropriate amine or amine derivative to thereby give an amide represented by the formula (322).

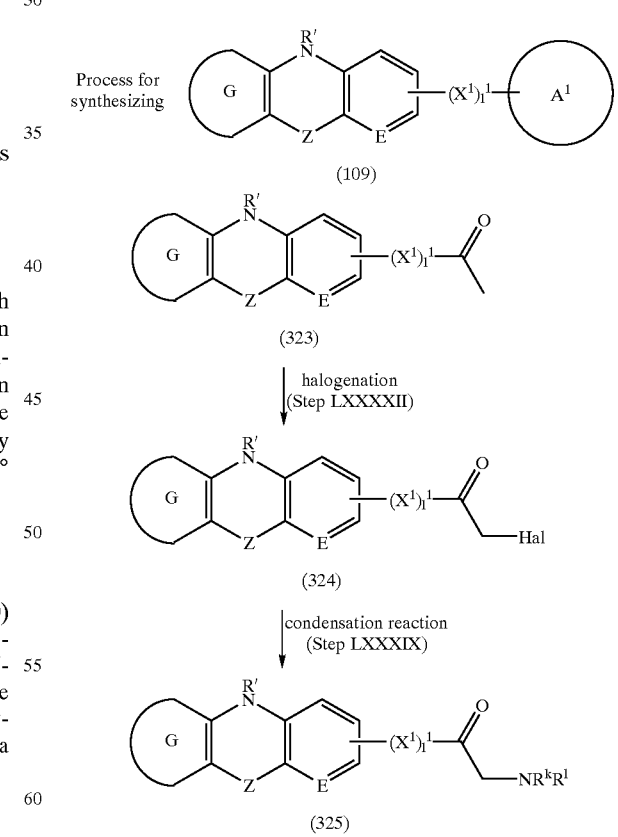

wherein G, Z, E, $X^1$, $1^1$, $A^1$, $R^k$, $R^l$, R' and Hal are each as defined above.

[Step LXXXXII]

A ketone represented by the formula (323) is treated with a bromination agent such as tetra-n-butylammonium tribromide or N-bromosuccinimide in a solvent mixture such as methanol/dichloromethane or a solvent such as tetrahydrofuran to thereby give a halogen compound represented by the formula (324).

[Step LXXXIX]

The halogen compound of the formula (324) is treated with an appropriate amine optionally in an appropriate solvent such as dichloromethane or dry N,N-dimethylformamide in the presence of an appropriate base such as anhydrous potassium carbonate, pyridine, triethylamine or N,N-diisopropylethylamine to thereby give a compound represented by the formula (325).

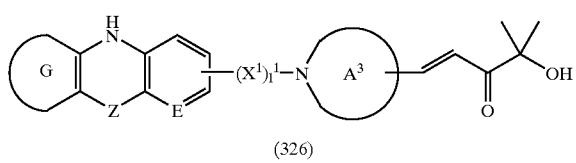

(326)

Michael reaction
(Step LXXXXIII)

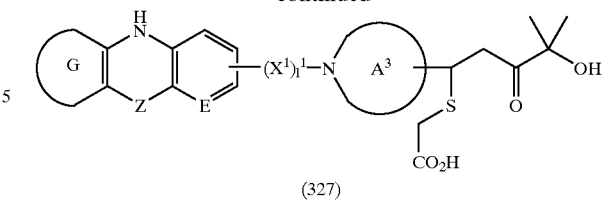

(327)

wherein G, Z, E, $X^1$, $1^1$ and $A^3$ are each as defined above.

[Step LXXXXIII]

An α,β-unsaturated ketone compound represented by the formula (326) is treated with mercaptoacetic acid in an appropriate dry solvent such as dichloromethane or tetrahydrofuran in the presence of a strong base such as sodium hydride to thereby give a compound represented by the formula (327). This reaction is effected preferably at from 0° C. to room temperature.

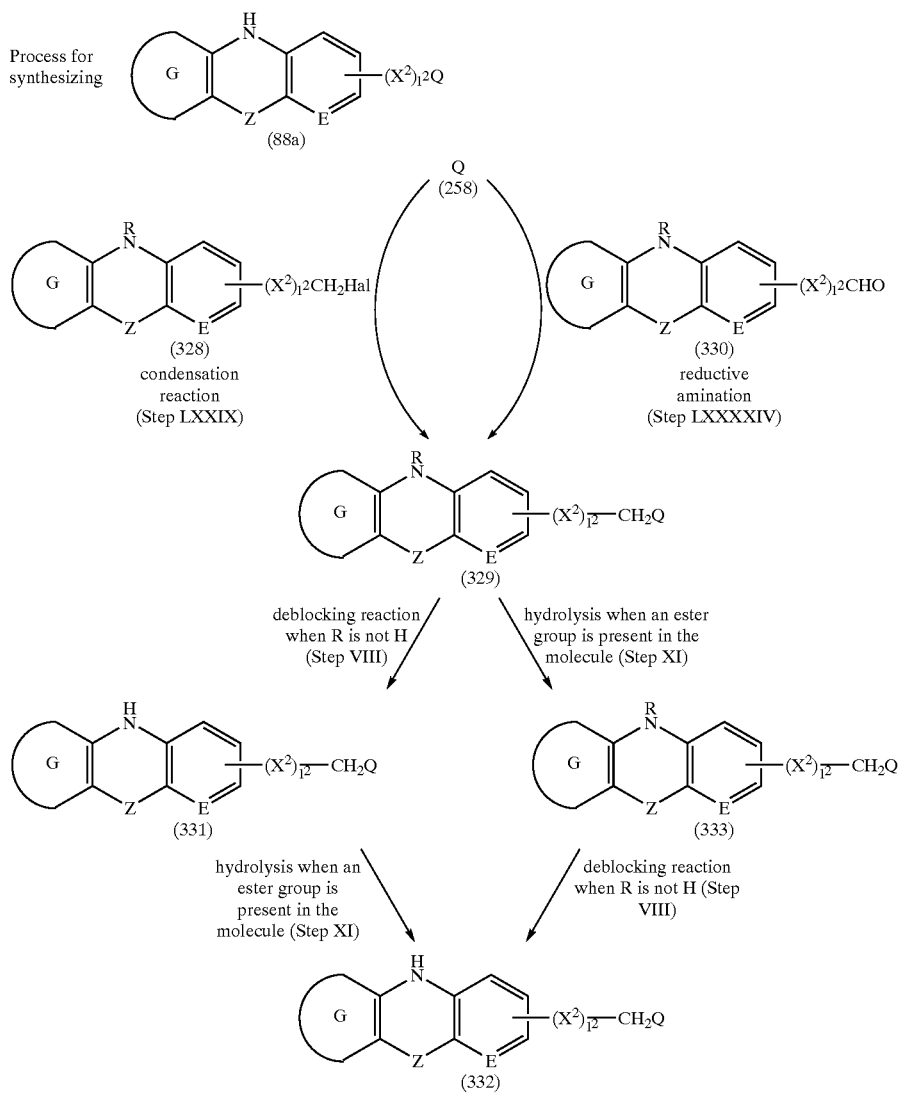

wherein G, Z, E, X², l² and R are each as defined above.
[Step LXXIX]

A compound represented by the formula (258) having a nucleophilic heteroatom is treated with a strong base such as sodium hydride or lithium diisopropylamide in a dry solvent such as tetrahydrofuran or N,N-dimethylformamide. The anion thus obtained is then treated with a halogen compound (328) at from 0 to 100° C. or reacted in an alcoholic solvent such as ethanol or methanol optionally in the presence of a base such as triethylamine at from room temperature to the reflux temperature. Thus a compound represented by the formula (329) can be obtained.

[Step LXXXXIV]

When the compound represented by the formula (258) is a primary amine, it is treated with an aldehyde represented by the formula (330) in an appropriate solvent such as toluene or benzene at from room temperature to the reflux temperature. The intermediate thus obtained is treated with an appropriate reducing agent such as sodium borohydride or sodium borocyanohydride in an appropriate alcoholic solvent such as ethanol or methanol or in an appropriate solvent mixture such as thanol/tetrahydrofuran to thereby give a compound represented by the formula (329).

[Step VIII]

The compounds represented by the formulae (329) and (333) are treated with an appropriate acid such as hydrochloric acid, trifluoroacetic acid or acetic acid optionally in an appropriate solvent such as dichloromethane or tetrahydrofuran to thereby give amines represented by the formulae (331) and (332).

[Step XI]

When the compounds represented by the formulae (329) and (331) have an ester group in the molecule, these compounds are reacted with an appropriate base in an aqueous solvent to thereby give compounds having a carboxyl group represented by the formulae (333) and (332) respectively. As the solvent, use can be made of alcoholic solvents such as methanol or ethanol or solvent mixtures such as alcohol/tetrahydrofuran/water. As the base, use can be made of sodium hydroxide or potassium hydroxide. The reaction can be carried out at from room temperature to the reflux temperature of the solvent.

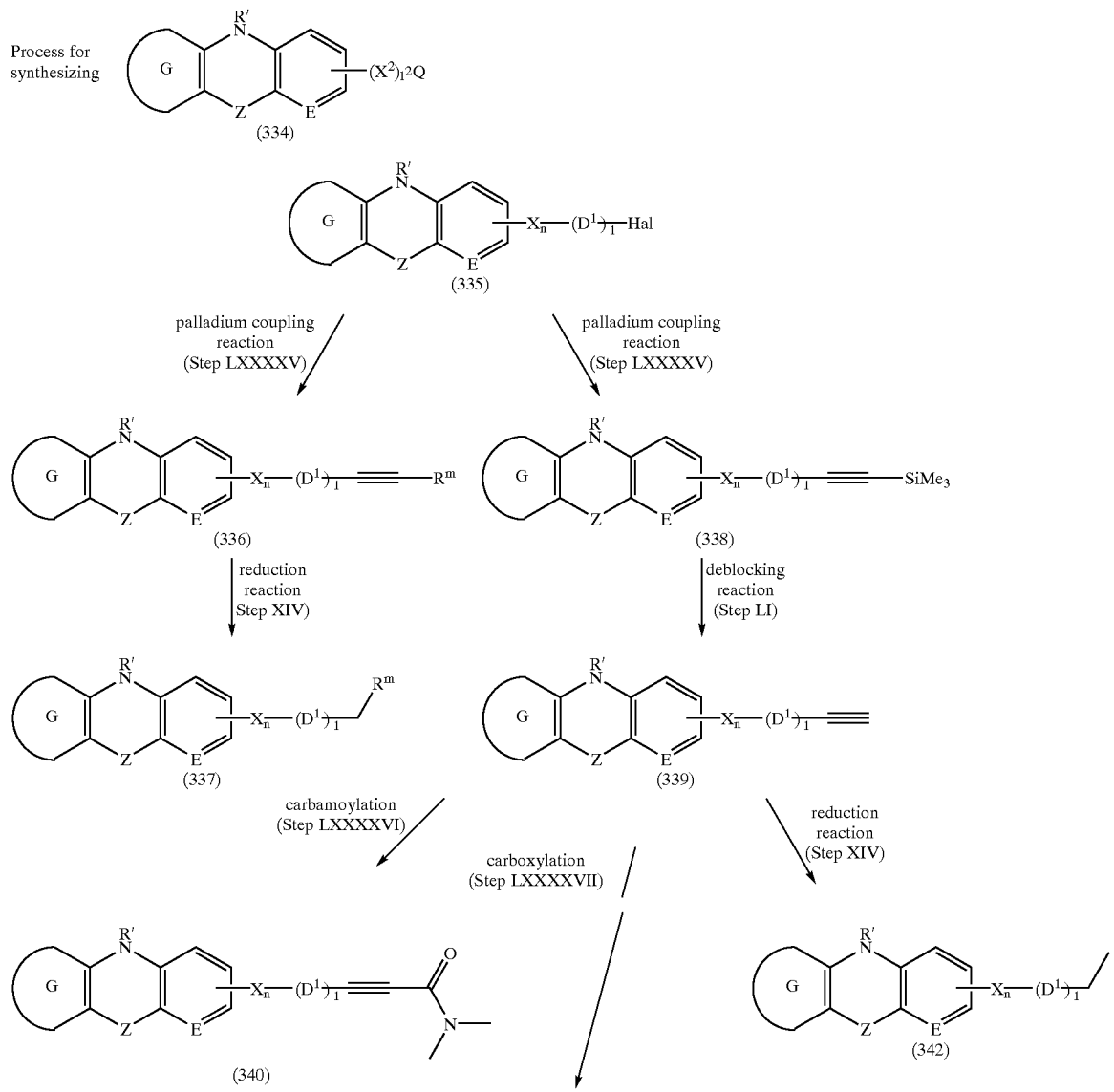

-continued

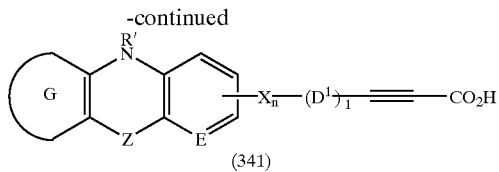

(341)

wherein G, Z, E, $X^2$, $l^2$, $X_n$, Hal and R' are each as defined above; $D^1$ represents a heteroaryl ring such as pyridine or purine; l is 0 or 1; and $R^m$ represents hydrogen, optionally substituted alkyl optionally having a heteroatom and optionally having an optionally substituted aryl, heteroaryl or heterocycloalkyl ring, optionally substituted aryl, optionally substituted heteroaryl or optionally substituted heterocycloalkyl.

[Step LXXXXV]

A halide represented by the formula (335) is reacted with an alkyne in a dry solvent such as N,N-dimethylformamide at from room temperature to 120° C. in the presence of a catalyst such as dichlorobis(triphenylphosphine)palladium with triphenylphosphine, an oxidizing agent such as cupric iodide and a base such as triethylamine to thereby give compounds represented by the formulae (336) and (338).

[Step XIV]

The compounds represented by the formulae (336) and (339) are subjected to a reduction reaction with the use of an appropriate metal catalyst in a solvent to thereby give compounds represented by the formulae (337) and (342). The reaction may be carried out in, for example, a solvent such as methanol, ethanol, ethyl acetate or tetrahydrofuran with the use of palladium, platinum (IV) oxide, etc. as the catalyst under normal to elevated hydrogen pressure.

[Step LI]

The compound represented by the formula (338) is treated with a reagent such as tetra-n-butylammonium fluoride or caesium fluoride in a dry solvent such as tetrahydrofuran to thereby give a carboxylic acid represented by the formula (339). The reaction is effected preferably at from 0° C. to room temperature.

[Step LXXXXVI]

The alkyne represented by the formula (339) is reacted with dimethylcarbamoyl chloride optionally in a dry solvent such as N,N-dimethylformamide at from room temperature to 120° C. in the presence of a catalyst such as dichlorobis (triphenylphosphine)palladium with triphenylphosphine, an oxidizing agent such as cupric iodide and a base such as triethylamine to thereby give an amide represented by the formula (340).

[Step LXXXXVII]

The alkyne represented by the formula (339) is reacted with a strong base such as n-butyllithium in a dry solvent such as tetrahydrofuran at from –100 to 0° C. and the anion thus obtained is treated with dry ice to thereby give a compound represented by the formula (341).

Process for synthesizing 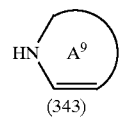 (343)

Among the compounds represented by Q, one which is a purine derivative can be synthesized in the following manner.

-continued

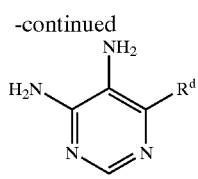

(344)

condensation reaction (Step LXXXXVIII) / condensation reaction (Step LIL)

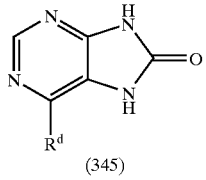 (345)  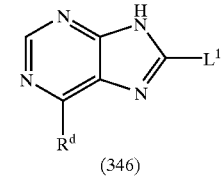 (346)

wherein $L^1$ and $R^d$ are each as defined above; and $A^9$ represents heteroaryl having an acidic proton group such as NH (for example, imidazole or purine).

[Step LXXXXVIII]

The compound represented by the formula (344) is reacted with N,N'-disuccinimidyl carbonate, carbonyldiimidazole, etc. in a dry solvent such as acetonitrile or N,N-dimethylformamide at from 0° C. to the reflux temperature to thereby give a compound represented by the formula (345).

[Step LIL]

The compound represented by the formula (344) is reacted with an acid anhydride such as trifluoroacetic anhydride at from 50 to 150° C. under elevated pressure to thereby give a purine derivative represented by the formula (346).

Process for synthesizing 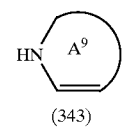 (343)

Among the compounds represented by Q, one which is a purine derivative can be synthesized in the following manner.

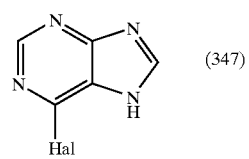 (347)

tin coupling reaction (Step C)

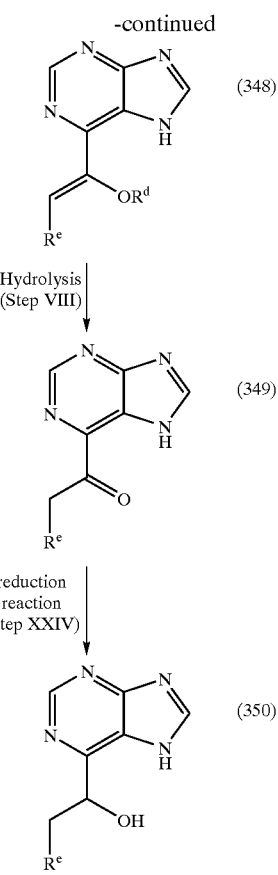

wherein $A^9$, Hal, $R^d$ and $R^e$ are each as defined above; and $R^{pb}$ represents an alcohol protective group having a silyl group.

[Step C]

A halide represented by the formula (347) is reacted with an appropriate vinyl-tri-n-butyltin (IV) derivative in a dry solvent such as N,N-dimethylformamide at from room temperature to 120° C. in the presence of a catalyst such as dichlorobis(triphenylphosphine)palladium and triphenylphosphine to thereby give an alkene represented by the formula (348).

[Step VIII]

The compound represented by the formula (348) is treated with an appropriate acid such as hydrochloric acid, trifluoroacetic acid or acetic acid optionally in an appropriate solvent such as dichloromethane or tetrahydrofuran to thereby give a ketone represented by the formula (349).

[Step XXIV]

The compound represented by the formula (349) is treated with a reducing agent such as sodium borohydride in a solvent to thereby give a compound represented by the formula (350). As the solvent, use can be made of methanol, ethanol, etc. The reaction can be effected at from 0° C. to the reflux temperature.

[Step LXXXVIII]

The alcohol represented by the formula (350) is reacted with a silylation agent such as chloro-tert-butyldimethylsilane, (tert-butyldimethylsilyl)trifluoroacetate or N-methyl-N-(tert-butyldimethylsilyl)trifluoroacetamide in an appropriate solvent optionally in the presence of a base such as imidazole, pyridine or N,N-diisopropylethylamine to thereby give an ester compound represented by the formula (351). As the solvent, use can be made of a dry solvent such as N,N-dimethylformamide, acetonitrile or dichloromethane. The reaction can be effected at from 0 to 40° C.

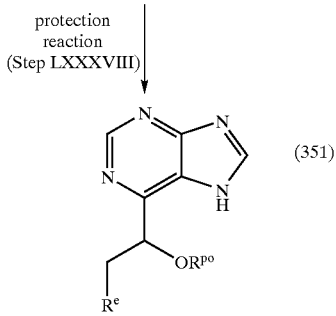

Process for synthesizing

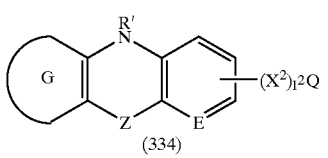

Among the compounds represented by the general formula 287, one wherein Q is an aminopurine can be synthesized in the following manner.

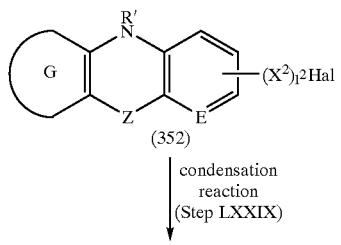

condensation reaction (Step LXXIX)

-continued

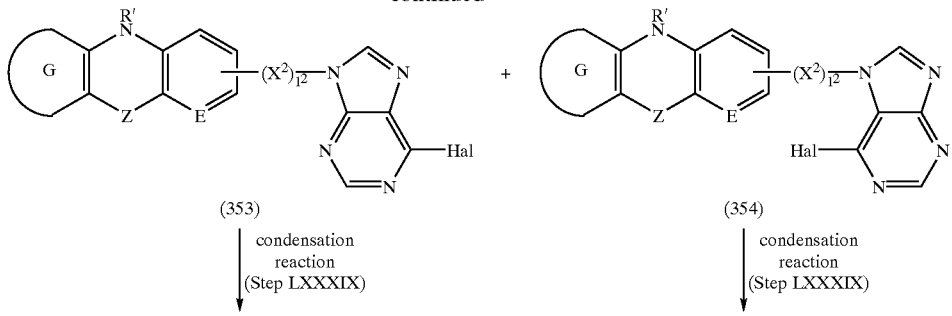

(353) (354)

condensation reaction (Step LXXXIX)

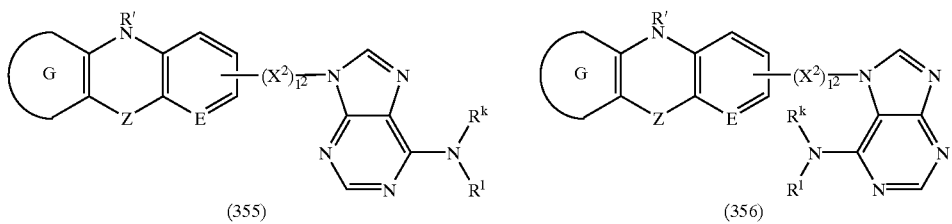

(355) (356)

wherein G, Z, E, $X^2$, $l^2$, Q, Hal, $R^k$, $R^l$ and R' are each as defined above.

[Step LXXIX]

An appropriate purine derivative is treated with a strong base such as sodium hydride or lithium diisopropylamide in a dry solvent such as tetrahydrofuran or N,N-dimethylformamide. The anion thus obtained is then treated with a halogen compound (352) at from 0 to 100° C. to thereby give compounds represented by the formulae (353) and (354).

[Step LXXXIX]

The halides represented by the formulae (353) and (354) are treated with an appropriate amine optionally in an appropriate solvent such as dichloromethane or methanol at from room temperature to the reflux temperature to thereby give compounds represented by the formulae (355) and (356) respectively.

Process for synthesizing

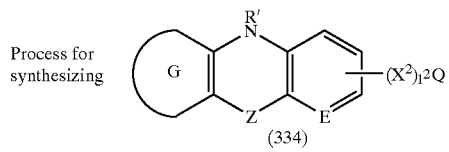

(334)

Among the compounds represented by the general formula 287, one wherein Q is a thiopurine can be synthesized in the following manner.

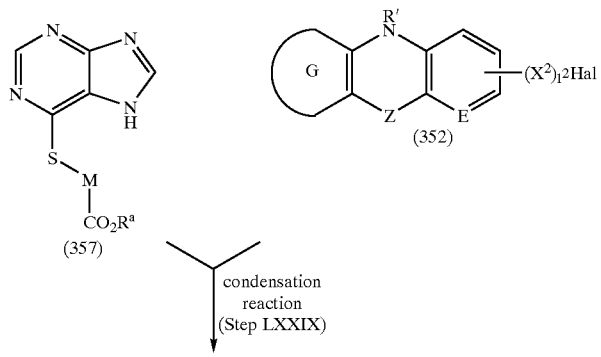

(357) (352)

condensation reaction (Step LXXIX)

-continued

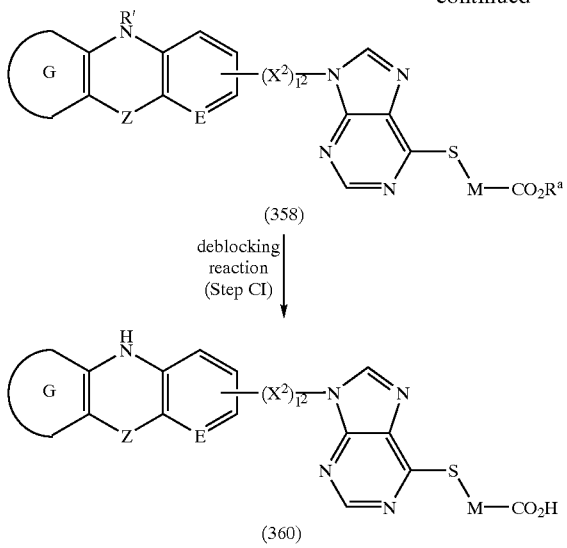

(358)

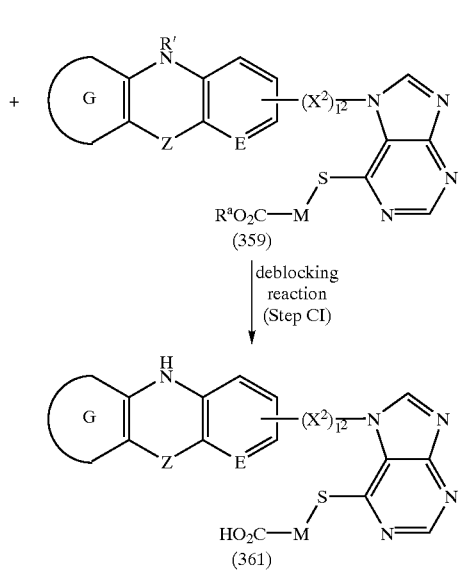

(359)

deblocking reaction (Step CI)

deblocking reaction (Step CI)

(360)

(361)

wherein G, Z, E, $X^2$, $l^2$, Q, Hal, M, $R^a$ and R' are each as defined above.

[Step LXXIX]

A purine derivative represented by the formula (357) is treated with a strong base such as sodium hydride or lithium diisopropylamide in a dry solvent such as tetrahydrofuran or N,N-dimethylformamide. The anion thus obtained is then treated with a halogen compound (352) at from 0 to 100° C. to thereby give compounds represented by the formulae (358) and (359).

[Step CI]

The compounds represented by the formulae (358) and (359) are treated with boron tribromide in an appropriate dry solvent such as dichloromethane at from 0° C. to the reflux temperature to thereby give compounds represented by the formulae (360) and (361).

Process for synthesizing

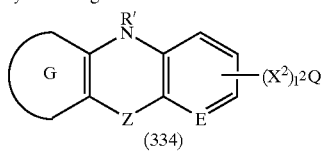

(334)

Among the compounds represented by the general formula 287, one wherein Q is an alkylpurine can be synthesized in the following manner.

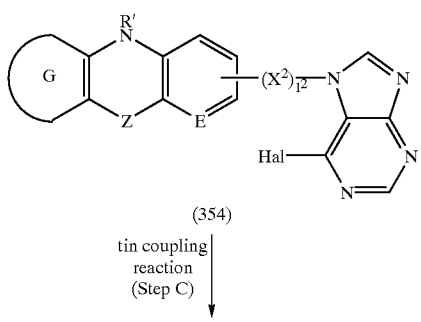

(354)

tin coupling reaction (Step C)

-continued

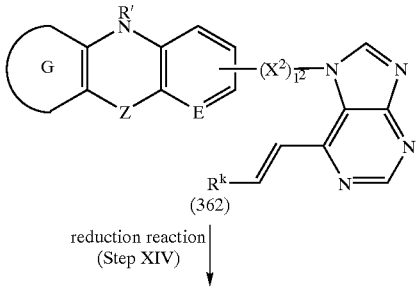

(362)

reduction reaction (Step XIV)

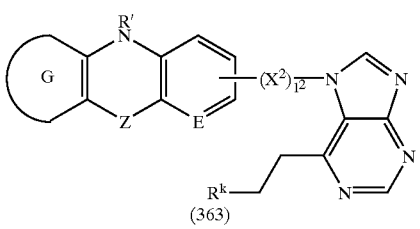

(363)

wherein G, Z, E, $X^2$, $l^2$, Q, Hal, $R^k$ and R' are each as defined above.

[Step C]

A halide represented by the formula (354) is reacted with an appropriate vinyl-tri-n-butyltin (IV) derivative in a dry solvent such as N,N-dimethylformamide at from room temperature to 120° C. in the presence of a catalyst such as dichlorobis(triphenylphosphine)palladium and triphenylphosphine to thereby give an alkene represented by the formula (362).

[Step XIV]

The compound represented by the formula (362) is subjected to a reduction reaction with the use of an appropriate metal catalyst in a solvent to thereby give a compound represented by the formula (363). The reaction may be carried out in, for example, a solvent such as methanol, ethanol, ethyl acetate or tetra-

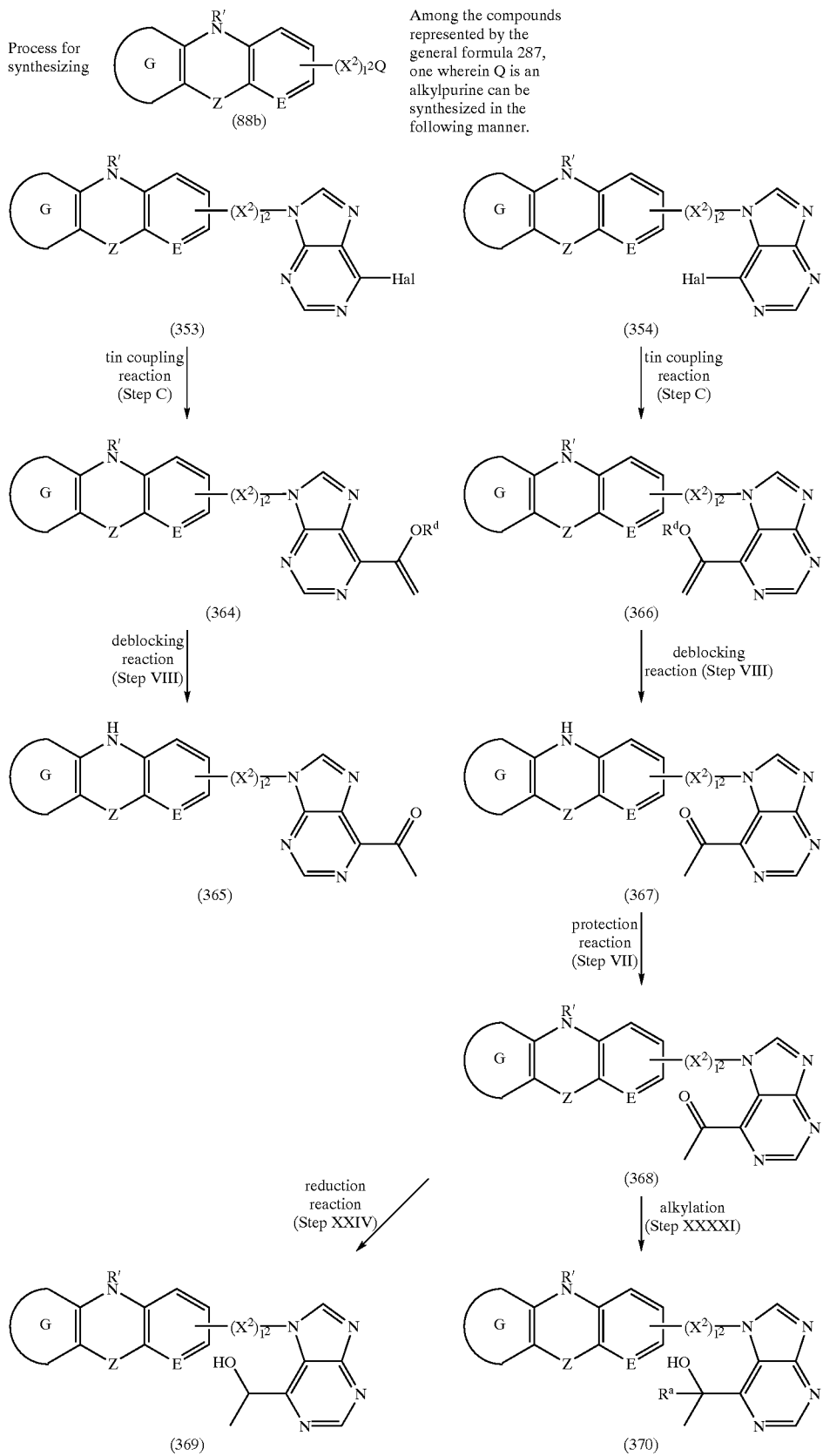

wherein G, Z, E, $X^2$, $l^2$, Q, Hal, $R^d$, $R^e$ and R' are each as defined above.

[Step C]

Halides represented by the formulae (353) and (354) are reacted with an appropriate vinyl-tri-n-butyltin (IV) derivative in a dry solvent such as N,N-dimethylformamide at from room temperature to 120° C. in the presence of a catalyst such as dichlorobis(triphenylphosphine)palladium and triphenylphosphine to thereby give alkenes represented by the formulae (364) and (366) respectively.

[Step VIII]

The compounds represented by the formulae (364) and (366) are treated with an appropriate acid such as hydrochloric acid, trifluoroacetic acid or acetic acid optionally in an appropriate solvent such as dichloromethane or tetrahydrofuran to thereby give ketones represented by the formulae (365) and (367) respectively.

[Step VII]

The amine represented by the formula (367) is treated with a base such as sodium hydride and a protecting reagent such as methoxymethyl chloride in a solvent to thereby give a compound represented by the formula (368).

[Step XXIV]

The compound represented by the formula (368) is treated with a reducing agent such as sodium borohydride in a solvent to thereby give a compound represented by the formula (369). As the solvent, use can be made of methanol, ethanol, etc. The reaction can be effected at from 0° C. to the reflux temperature.

[Step XXXXI]

A compound represented by the formula (368) is treated with methyllithium or a methylmagnesium halide in a solvent such as dry tetrahydrofuran, diethyl ether or dimethoxyethane at from −78° C. to the boiling point of the solvent to thereby give an alcohol represented by the formula (370).

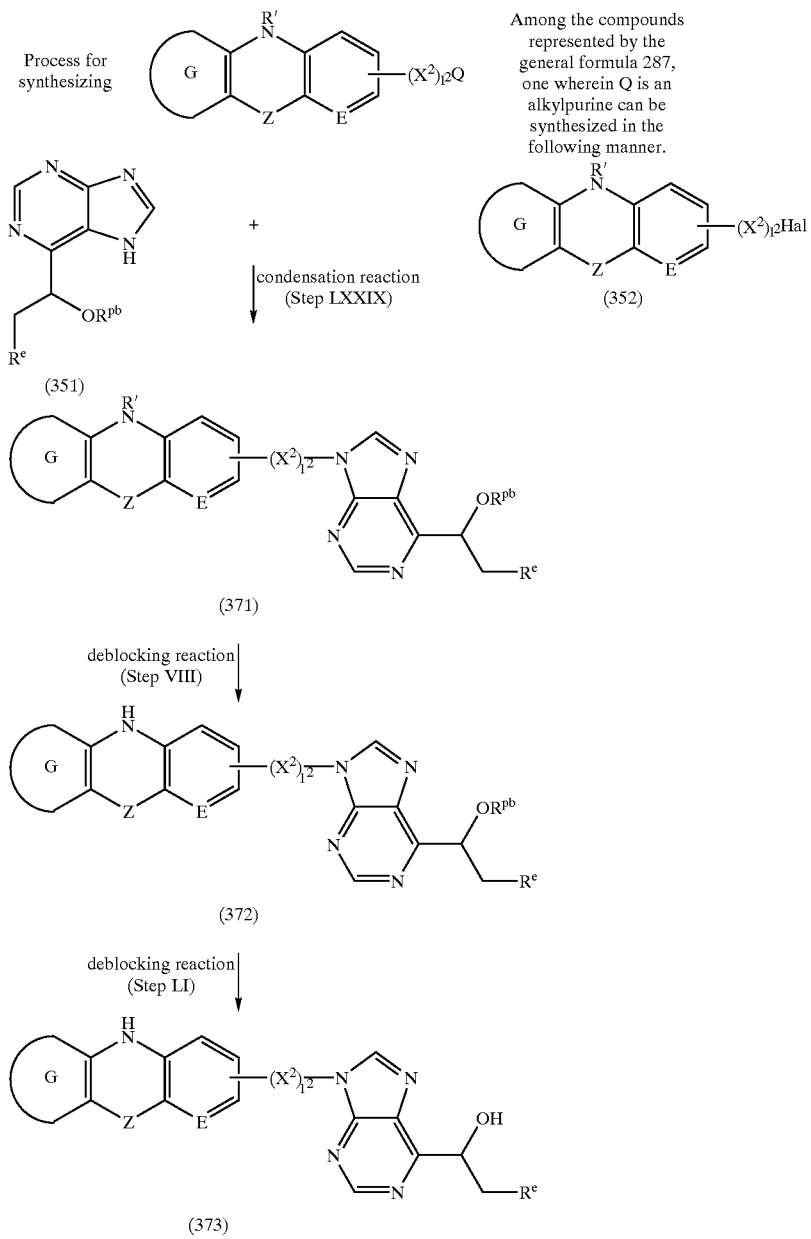

drofuran with the use of palladium, platinum (IV) oxide, etc. as the catalyst under normal to elevated hydrogen pressure.

wherein G, Z, E, $X^2$, $1^2$, Q, Hal, $R^{pb}$, $R^e$ and R' are each as defined above.

[Step LXXIX]

A purine derivative represented by the formula (351) is treated with a strong base such as sodium hydride or lithium diisopropylamide in a dry solvent such as tetrahydrofuran or N,N-dimethylformamide. The anion thus obtained is then treated with a halogen compound (352) at from 0 to 100° C. to thereby give a compound represented by the formula (371).

[Step VIII]

The compound represented by the formula (371) is treated with an appropriate acid such as hydrochloric acid, trifluoroacetic acid or acetic acid optionally in an appropriate solvent such as dichloromethane or tetrahydrofuran to thereby give a compound represented by the formula (372). Trifluoroacetic acid is the most desirable acid. The reaction is effected preferably at from 0° C. to room temperature.

[Step LI]

The compound represented by the formula (372) is treated with a reagent such as tetra-n-butylammonium fluoride or caesium fluoride in a dry solvent such as tetrahydrofuran to thereby give an alcohol represented by the formula (373). The reaction is effected preferably at from 0° C. to room temperature.

Process for synthesizing 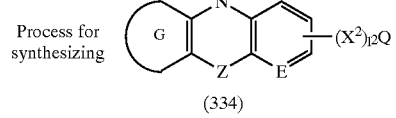 (334)

Among the compounds represented by the general formula 287, one wherein Q is an aminopurine can be synthesized in the following manner.

(374)

condensation reaction
(Step LXXXIX)

(375)

wherein G, Z, E, $X^2$, $1^2$, Q, Hal, $R^k$, $R^l$ and R' are each as defined above.

[Step LXXXIX]

A halide represented by the formula (374) is treated with an appropriate amine in an appropriate solvent such as methanol, ethanol or tetrahydrofuran or a mixture thereof at from 50 to 150° C. under elevated pressure to thereby give a compound represented by the formula (375).

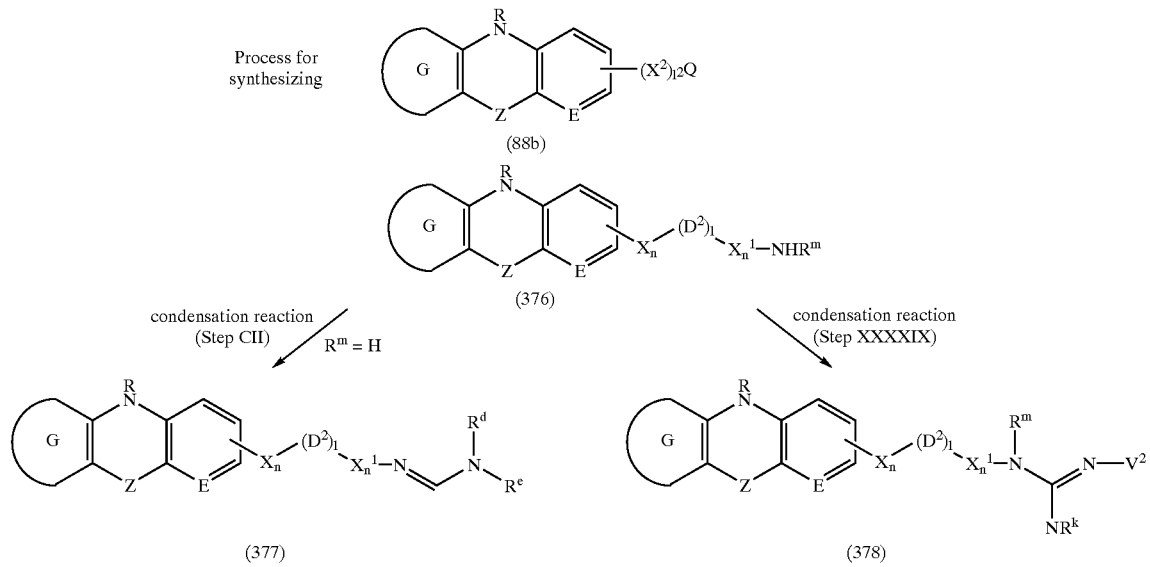

wherein G, Z, E, $X^2$, $1^2$, $X_n$, Q, $R^d$, $R^e$, $R^k$, $R^m$ and R are each as defined above; $V^2$ represents cyano, methylsulfonyl or 2-pyridyl; when $X_n^1$ is an alkylene side chain having n carbon atoms and n is 0, then the substituent is bonded directly to $D^d$ or $X_n$; $D^2$ represents a heteroaryl ring such as imidazole, purine, or 4-phenylimidazole; and 1 is 0 or 1.

[Step CII]

An amine represented by the formula (376) is treated with N,N-dimethylformamide dimethyl acetal in a solvent mixture of tetrahydrofuran with methanol at from room temperature to the reflux temperature to thereby give an amidine represented by the formula (377).

[Step XXXXIX]

The amine represented by the formula (376) is reacted with an appropriate imidate or thioimidate in a solvent such as acetonitrile or methanol to thereby give a compound represented by the formula (378). It is preferable that the reaction is carried out at from 0 to 40° C.

wherein G, Z, E, $X^2$, $I^2$, Q, $R^k$, $R^l$, $R^m$, Nu, $X_n$, $X_n^1$, $D^2$, l and R are each as defined above.

[Step CIII]

A nitrile derivative represented by the formula (379) is reacted with ammonium chloride, an appropriate primary amine hydrochloride or an appropriate secondary amine hydrochloride in a dry solvent such as toluene or benzene at from 50° C. to the reflux temperature in the presence of trimethylaluminum to thereby give an amidine represented by the formula (380).

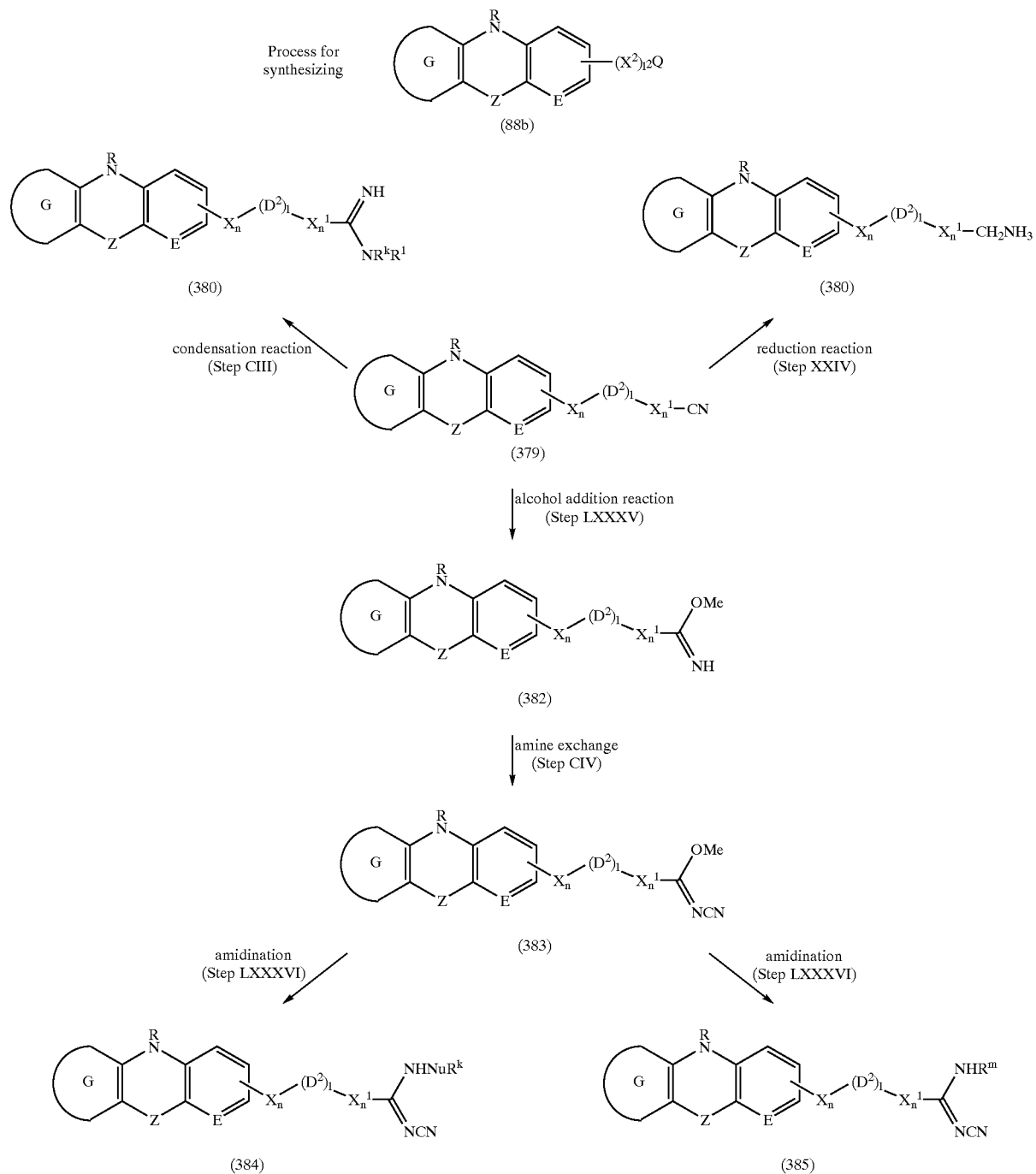

[Step XXIV]

The compound represented by the formula (379) is treated with a reducing agent such as aluminum lithium hydride or lithium borohydride in a solvent such as dry tetrahydrofuran or dry diethyl ether to thereby give an amine of the formula (381). The reaction can be effected at from 0°0 C. to the reflux temperature.

[Step LXXXV]

The nitrile compound represented by the formula (379) is treated with an appropriate acid in an alcoholic solvent to thereby give an imidate represented by the formula (382) (i.e., the so-called Pinner reaction). It is preferable to use hydrochloric acid as the acid. The reaction is preferably effected in methanol/dichloromethane at from −20 to 0° C.

[Step CIV]

The imidate represented by the formula (382) is reacted with cyanamide in an appropriate solvent in the presence of sodium monohydrogenphosphate and sodium dihydrogenphosphate to thereby give a derivative represented by the formula (383). As the solvent, it is preferable to use acetonitrile. The reaction is effected preferably at from 0° C. to room temperature.

[Step LXXXVI]

The imidate represented by the formula (383) is reacted with an amine or an amide in an appropriate solvent to thereby give compounds represented by the formulae (384) and (385). As the solvent, use can be made of acetonitrile, tetrahydrofuran, etc. The reaction is effected preferably at from 0° C. to reflux temperature.

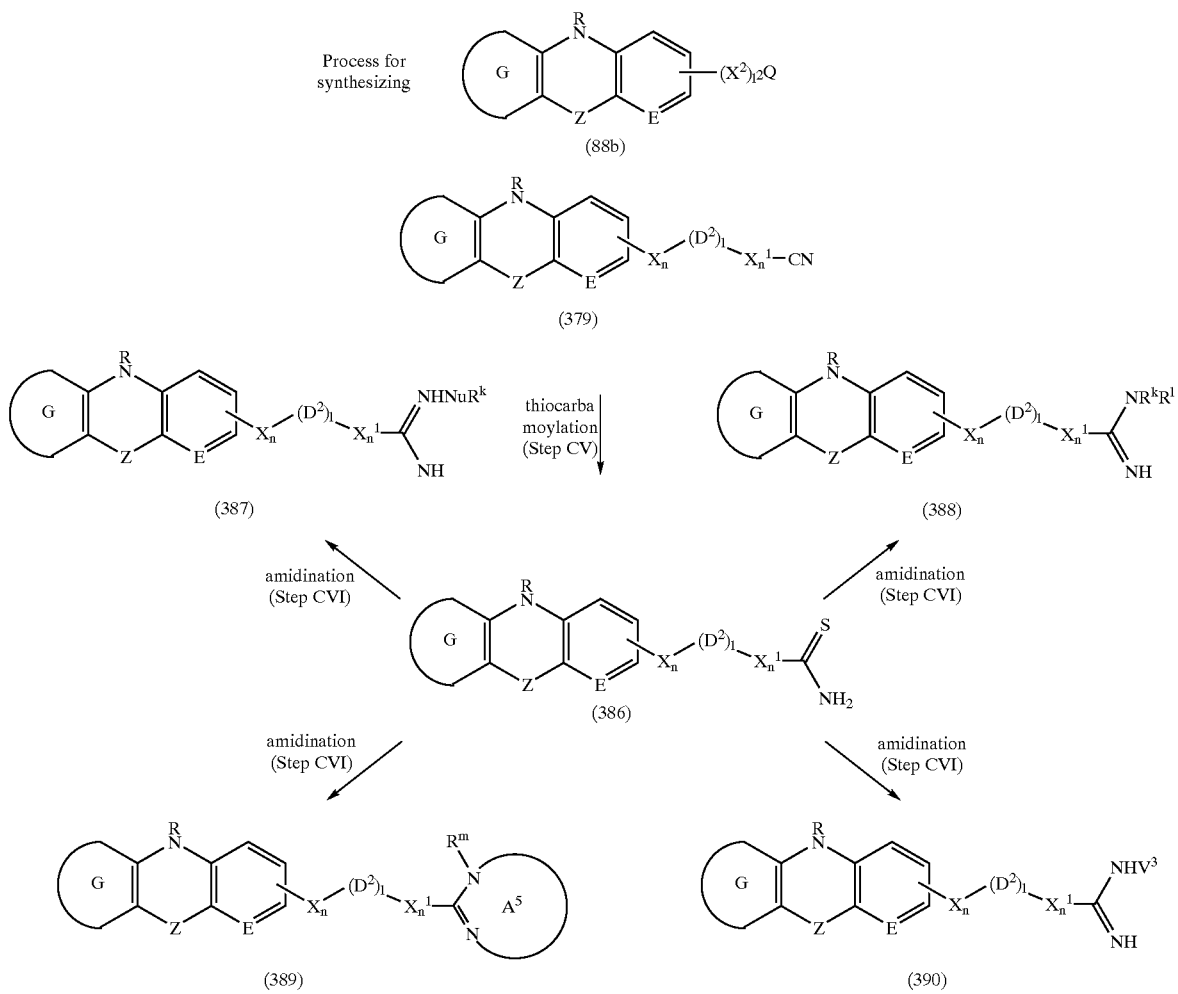

wherein G, Z, E, $X^{2'}$, $I^2$, Q, $R^k$, $R^l$, $R^m$, Nu, $X_n$, $X_n^1$, $D^2$, l and R are each as defined above; $V^3$ represents nitryl, methyl, sulfonyl, phenylsulfonyl, trifluoromethylsulfonyl, sulfamoyl or N,N-dimethylcarbamoyl; and $A^5$ represents optionally substituted tetrahydropyrimidine.

[Step CV]

A nitrile represented by the formula (379) is reacted with sodium hydrosulfide and hydrogen sulfide in an appropriate alcoholic solvent such as methanol at from −30 to 100° C. under elevated pressure to thereby give a thioamide represented by the formula (386).

[Step CVI]

The thioamide represented by the formula (386) is reacted with an alkylating agent such as methyl iodide in an appropriate solvent such as acetone. The thioimide thus obtained is then reacted with an appropriate amine or a derivative of amide or sulfonamide in an appropriate alcoholic solvent at from room temperature to 60° C. to thereby give derivatives represented by the formulae (387), (388), (389) and (390).

Process for synthesizing

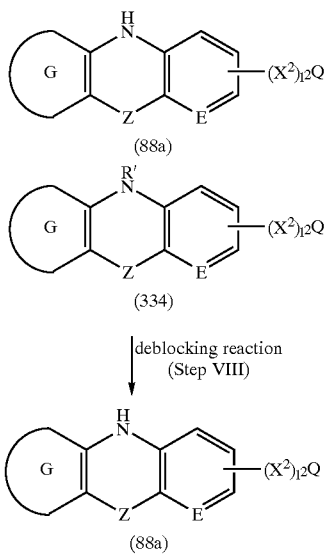

wherein G, Z, E, $X^2$, $l^2$, Q and R' are each as defined above.

[Step VIII]

A compound represented by the formula (334) is treated with an appropriate acid such as hydrochloric acid, trifluoroacetic acid or acetic acid optionally in an appropriate solvent such as dichloromethane or tetrahydrofuran to thereby give an amine represented by the formula (88a).

wherein G, Z, E, $X^2$, $l^2$, Q, $R^d$, $R^m$ and R' are each as defined above; and Ar represents aryl having no acidic proton or heteroaryl having no acidic proton.

[Step XXXXI]

A compound represented by the formula (108) is treated with methyllithium or a methylmagnesium halide in a solvent such as dry tetrahydrofuran, diethyl ether or dimethoxyethane at from −78° C. to the boiling point of the solvent to thereby give an alcohol represented by the formula (391).

[Step LXI]

The compound represented by the formula (108) is reacted in an appropriate solvent with an aryl-Grignard or aryllithium obtained by a halogen-metal exchange reaction or a hydrogen-metal exchange reaction or an aryl cerium complex obtained by treating the former compound with cerium (III) chloride to thereby give a compound represented by the formula (392). As the solvent, use can be made of a dry solvent such as tetrahydrofuran, diethyl ether or dimethoxyethane. The reaction can be effected at from −100° C. to the reflux temperature of the solvent.

[Step LIII]

A ketone represented by the formula (108) is reacted with an anion obtained by treating an alkyne with a strong base such as n-butyllithium or lithium diisopropylamine in a dry solvent such as tetrahydrofuran or diethyl ether to thereby give a compound represented by the formula (393). The reaction can be effected at from −100° C. to room temperature.

[Step XIV]

The compound represented by the formula (393) is subjected to a reduction reaction in a solvent with the use of an

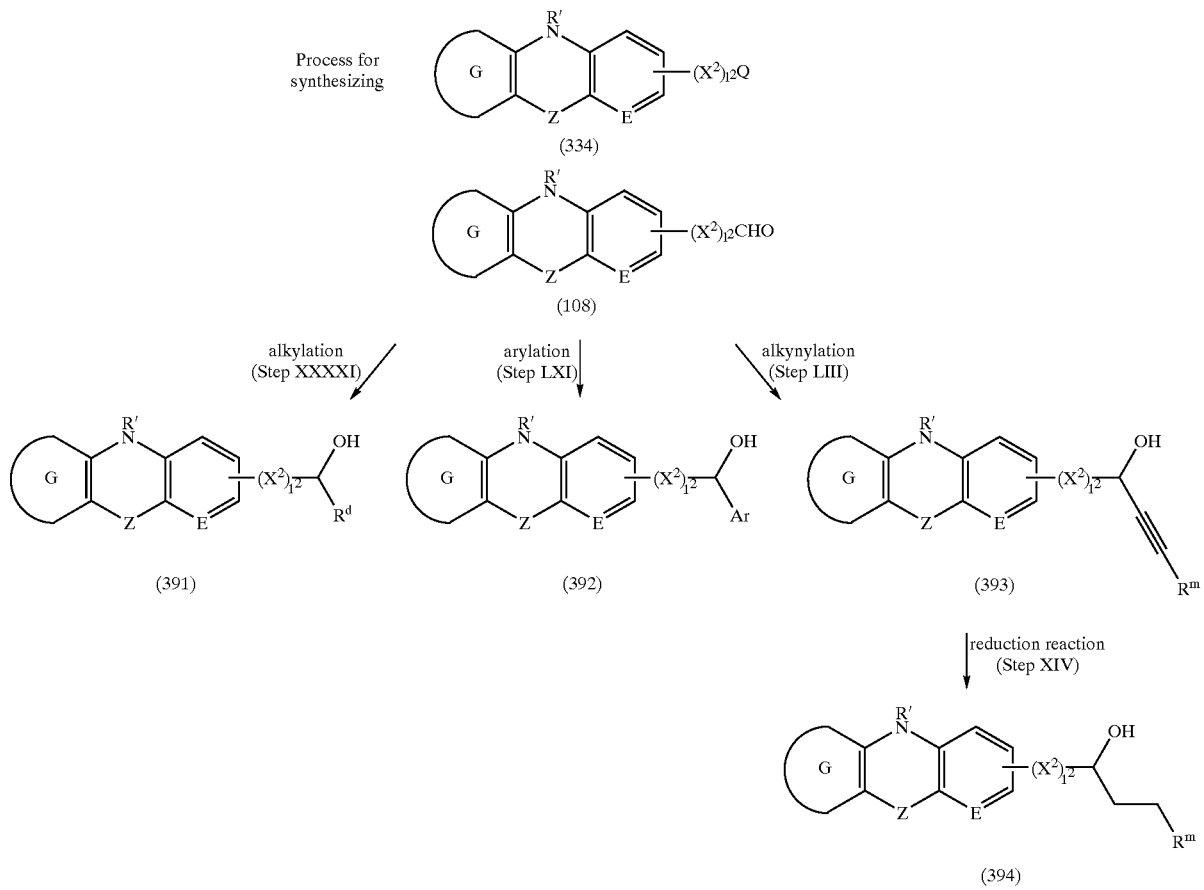

appropriate metal catalyst to thereby give a compound represented by the formula (394). For example, use can be made of a hydrogenation reaction effected in a solvent such as methanol, ethanol, ethyl acetate or tetrahydrofuran with the use of palladium, platinum (IV) oxide, etc. under normal to elevated hydrogen pressure.

a solvent such as dimethoxyethane, tetrahydrofuran or N,N-dimethylformamide and then reacted with an alkyl halide to thereby give a derivative represented by the formula (396). This reaction is effected preferably at from 100° C. to room temperature.
[Step XXIX]

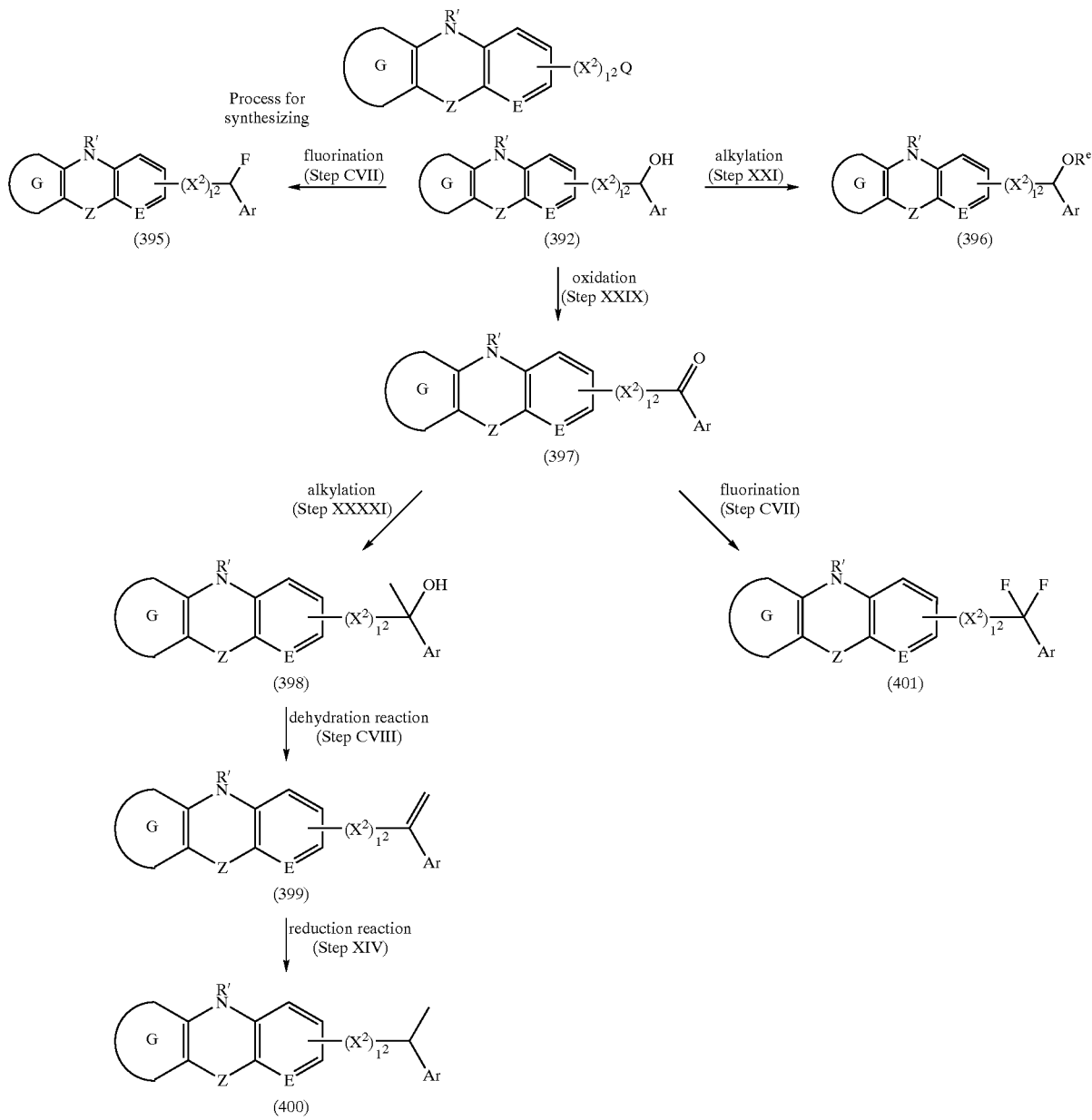

wherein G, Z, E, $X^2$, $1^2$, Q, Ar, $R^e$ and R' are each as defined above.
[Step CVII]
Compounds represented by the formulae (392) and (397) are reacted with dimethylaminosulfur trifluoride optionally in a dry solvent such as dichloromethane at from room temperature to 50° C. to thereby give compounds represented by the formulae (395) and (401) respectively.
[Step XXI]
The compound represented by the formula (392) is treated with a base such as sodium hydride or sodium methoxide in A solution of the alcohol represented by the formula (392) in, for example, methylene chloride is added to a reaction mixture obtained from oxalyl chloride and dimethyl sulfoxide and treated with a base such as triethylamine. Alternatively, it is treated with pyridinium dichromate in a solvent such as dichloromethane or treated with manganese dioxide in a solvent such as dichloromethane. Thus, a ketone represented by the formula (397) can be obtained.
[Step XXXXI]
The compound represented by the formula (397) is treated with methyllithium or a methylmagnesium halide in a solvent such as dry tetrahydrofuran, diethyl ether or dimethoxyethane at from −78° C. to the boiling point of the solvent to thereby give an alcohol represented by the formula (398).

[Step CVIII]

The compound represented by the formula (398) is reacted with chloromethanesulfonyl chloride in an appropriate dry solvent such as dichloromethane in the presence of an appropriate base such as pyridine to thereby give a compound represented by the formula (399). The reaction can be effected at from 0° C. to the reflux temperature.

[Step XIV]

The compound represented by the formula (399) is subjected to a reduction reaction in a solvent with the use of an appropriate metal catalyst to thereby give a compound represented by the formula (400). For example, use can be made of a hydrogenation reaction effected in a solvent such as methanol, ethanol, ethyl acetate or tetrahydrofuran with the use of palladium, platinum (IV) oxide, etc. under normal to elevated hydrogen pressure.

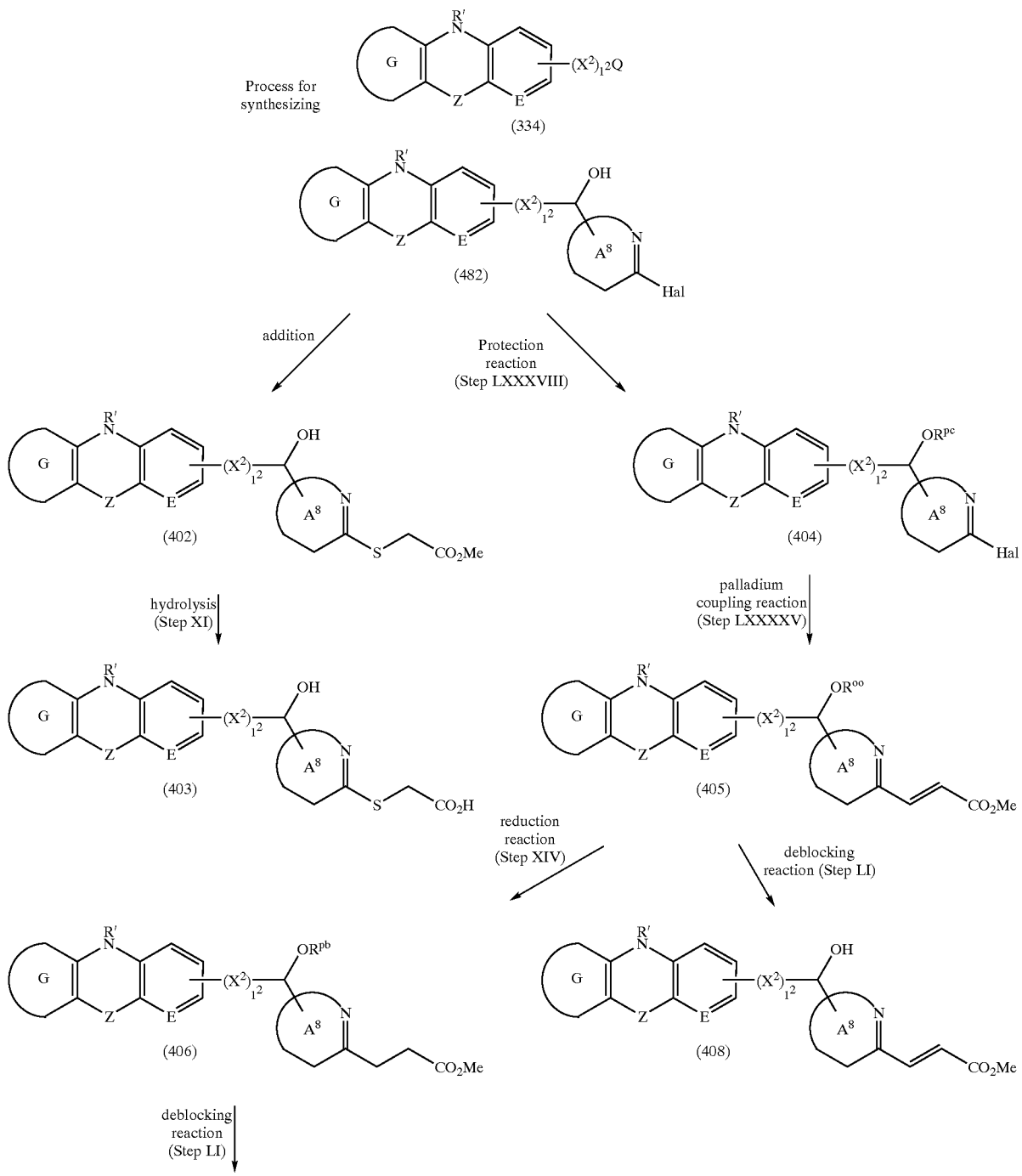

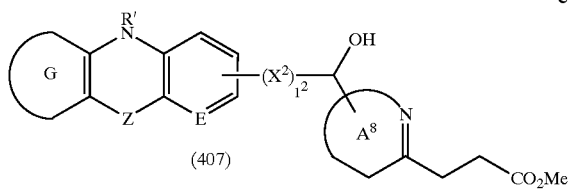

(407)

wherein G, Z, E, $X^2$, $l^2$, Q, $A^8$, $R^{pb}$ and R' are each as defined above.

[Step LXXXXIII]

A compound represented by the formula (482) is treated with mercaptoacetic acid in an appropriate dry solvent such as dichloromethane or tetrahydrofuran in the presence of a strong base such as sodium hydride to thereby give a compound represented by the formula (402). The reaction can be effected at from 0 to 100° C.

[Step XI]

The compound represented by the formula (402) is reacted with an appropriate base in an aqueous solvent to thereby give a compound having a carboxyl group (403). As the solvent, use can be made of alcoholic solvents such as methanol or ethanol or solvent mixtures such as alcohol/tetrahydrofuran/water. As the base, use can be made of sodium hydroxide, potassium hydroxide, etc. The reaction can be effected at from room temperature to the reflux temperature of the solvent.

[Step LXXXVIII]

The alcohol represented by the formula (482) is reacted with a silylation agent such as chloro-tert-butyldimethylsilane, (tert-butyldimethylsilyl) trifluoroacetate or N-methyl-N-(tert-butyldimethyl-silyl) trifluoroacetamide in an appropriate solvent optionally in the presence of a base such as imidazole, pyridine or N,N-diisopropylethylamine to thereby give an ester compound represented by the formula (404). As the solvent, use can be made of a dry solvent such as N,N-dimethylformamide, acetonitrile or dichloromethane. The reaction can be effected at from 0 to 40° C.

[Step LXXXXV]

A halide represented by the formula (404) is reacted with an appropriate alkyne in a dry solvent such as N,N-dimethylformamide at from room temperature to 120° C. in the presence of a catalyst such as palladium (II) acetate with triphenylphosphine and a base such as triethylamine to thereby give a compound represented by the formula (405).

[Step XIV]

The compound represented by the formula (405) is subjected to a reduction reaction with the use of an appropriate metal catalyst in a solvent to thereby give compound represented by the formula (406). The reaction may be carried out in, for example, a solvent such as methanol, ethanol, ethyl acetate or tetrahydrofuran with the use of palladium, platinum (IV) oxide, etc. as the catalyst under normal to elevated hydrogen pressure.

[Step LI]

The compounds represented by the formulae (405) and (406) are treated with a reagent such as tetra-n-butylammonium fluoride or caesium fluoride in a dry solvent such as tetrahydrofuran to thereby give compounds represented by the formulae (408) and (407) respectively. The reaction is effected preferably at from 0° C. to room temperature.

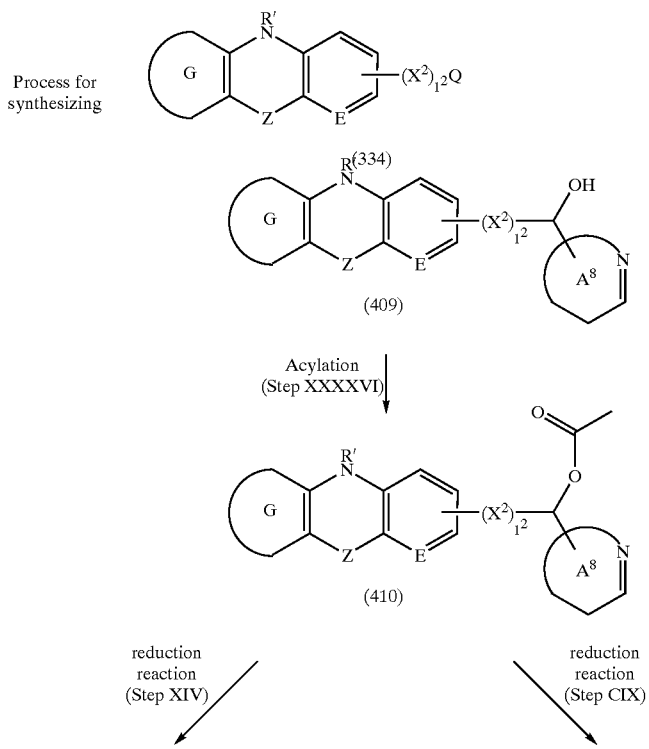

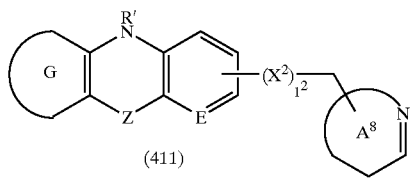

(411)

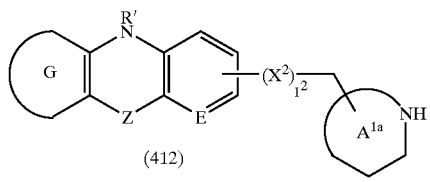

(412)

wherein G, Z, E, $X^2$, $l^2$, Q, $A^8$ and R' are each as defined above; and $A^{1a}$ represents saturated heterocycloalkyl.

[Step XXXXVI]

An alcohol represented by the formula (409) is reacted with a carboxylic anhydride and an acid halide optionally in an appropriate solvent in the presence of an appropriate base such as pyridine, triethylamine or N,N-diisopropylethylamine to thereby give an ester represented by the formula (410). As the solvent, use can be made of dry dichloromethane, etc. The reaction can be effected at from 0° C. to reflux temperature.

[Step XIV]

The compound represented by the formula (410) is subjected to a reduction reaction with the use of an appropriate metal catalyst in a solvent to thereby give a compound represented by the formula (411). The reaction may be carried out in, for example, a solvent such as methanol, ethanol, ethyl acetate or tetrahydrofuran with the use of palladium, platinum (IV) oxide, etc. as the catalyst under normal to elevated hydrogen pressure.

[Step CIX]

The compound represented by the formula (410) is subjected to a reduction reaction with the use of an appropriate metal catalyst in a solvent to thereby give a compound represented by the formula (412). The reaction may be carried out in, for example, a solvent such as methanol, ethanol, ethyl acetate or tetrahydrofuran with the use of palladium, platinum (IV) oxide, etc. as the catalyst under normal to elevated hydrogen pressure.

Process for synthesizing

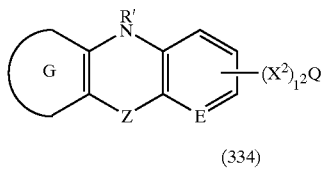

(334)

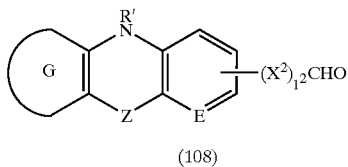

(108)

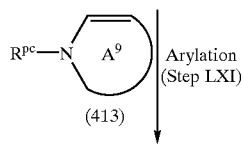

(413)

Arylation
(Step LXI)

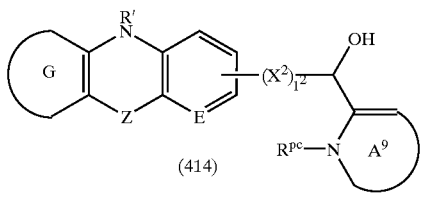

(414)

deblocking reaction
(Step VIII or XI)

Acylation
(Step XXXXVI)

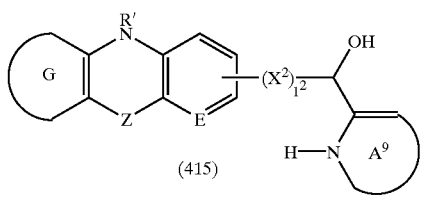

(415)

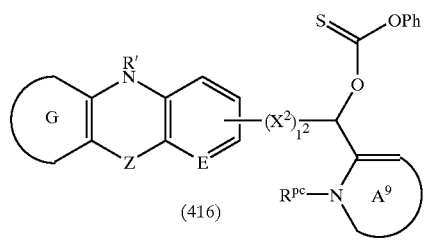

(416)

radical reduction reaction (Step CX)

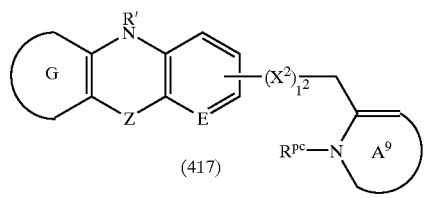

(417)

deblocking reaction (Step XI)

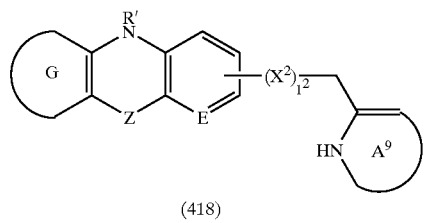

(418)

wherein G, Z, E, $X^2$, $l^2$, Q, $A^9$ and R' are each as defined above; and RPC represents a protective group such as trityl or dimethylsulfamoyl.

[Step LXI]

A compound represented by the formula (108) is reacted in an appropriate solvent with an aryl-Grignard or aryl-lithium obtained from the compound represented by the formula (413) by a halogen-metal exchange reaction or a hydrogen-metal exchange reaction or an arylcerium complex obtained by treating the former compound with cerium (III) chloride to thereby give a compound represented by the formula (414). As the solvent, use can be made of a dry solvent such as tetrahydrofuran, diethyl ether or dimethoxyethane. The reaction can be effected at from −100° C. to the reflux temperature of the solvent.

[Step VIII]

When $R^{pc}$ is a protective group which can be eliminated by treating with an acid, such as trityl, a compound represented by the formula (414) is treated with an appropriate acid such as hydrochloric acid, trifluoroacetic acid or acetic acid optionally in an appropriate solvent such as dichloromethane or tetrahydrofuran to thereby give an amine represented by the formula (415).

[Step XXXXVI]

An alcohol represented by the formula (414) is reacted with phenyl chlorothioformate optionally in an appropriate solvent in the presence of an appropriate base such as pyridine, triethylamine or N,N-diisopropylethylamine to thereby give an ester represented by the formula (416). As the solvent, use can be made of dry acetonitrile, dry dichloromethane, etc. The reaction can be effected at from 0° C. to reflux temperature.

[Step CX]

The compound represented by the formula (416) is treated with a reducing agent such as tri-n-butyltin (IV) hydride in an appropriate solvent such as toluene or benzene at from room temperature to the reflux temperature to thereby give a compound represented by the formula (417).

[Step XI]

When $R^{pc}$ is a protective group which can be eliminated by treating with an alkali, such as dimethylsulfamoyl, the compounds represented by the formulae (414) and (417) are reacted with an appropriate base in an aqueous solvent to thereby give compounds represented by formulae (415) and (418) respectively. As the solvent, use can be made of alcoholic solvents such as methanol or ethanol or solvent mixtures such as alcohol/tetrahydrofuran/water. As the base, use can be made of sodium hydroxide, potassium hydroxide, etc. The reaction can be effected at from room temperature to the reflux temperature of the solvent.

Process for synthesizing

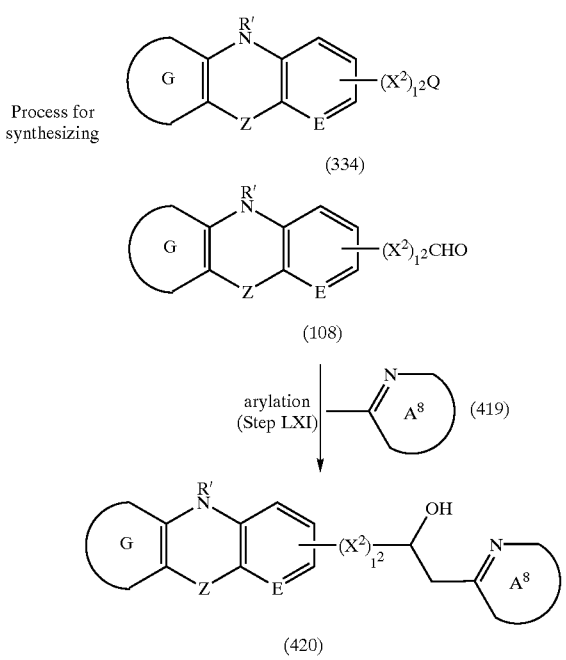

wherein G, Z, E, $X^2$, $1^2$, Q, $A^8$ and R' are each as defined above.

[Step LXI]

A compound represented by the formula (108) is reacted in an appropriate solvent with a lithium anion obtained from the compound represented by the formula (419) by a hydrogen-metal exchange reaction to thereby give a compound represented by the formula (420). As the solvent, use can be made of a dry solvent such as tetrahydrofuran, diethyl ether or dimethoxyethane. The reaction can be effected at from −100° C. to the reflux temperature of the solvent.

Process for synthesizing

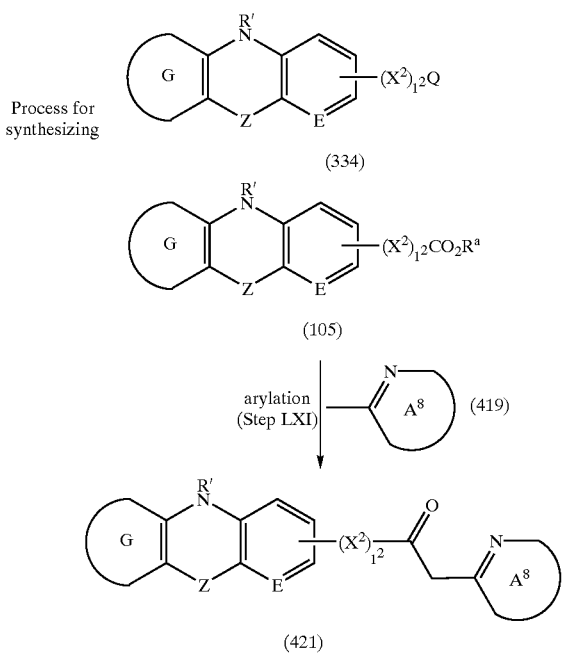

wherein G, Z, E, $X^2$, $1^2$, Q, $R^a$, $A^8$ and R' are each as defined above.

[Step LXI]

A compound represented by the formula (105) is reacted in an appropriate solvent with a lithium anion obtained from the compound represented by the formula (419) by a hydrogen-metal exchange reaction to thereby give a compound represented by the formula (421). As the solvent, use can be made of a dry solvent such as tetrahydrofuran, diethyl ether or dimethoxyethane. The reaction can be effected at from −100° C. to the reflux temperature of the solvent.

Process for synthesizing

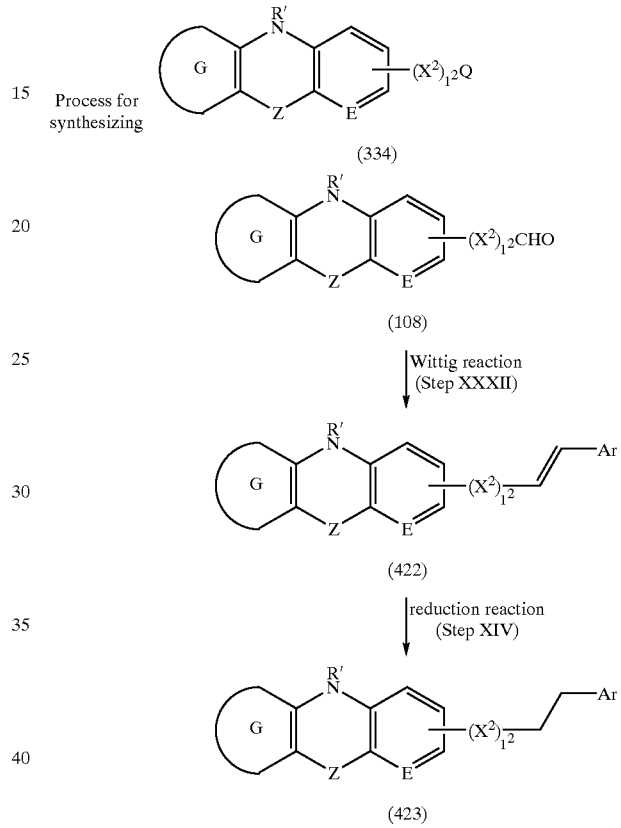

wherein G, Z, E, $X^2$, $1^2$, Q, Ar and R' are each as defined above.

[Step XXXII]

An appropriate arylmethyltriphenylphosphonium bromide or heteroarylmethyltriphenylphosphonium bromide is treated with an appropriate base such as potassium tert-butoxide or butyllithium in a solvent such as toluene, xylene or tetrahydrofuran followed by a reaction with an aldehyde represented by the formula (108). Thus a compound represented by the formula (422) can be obtained. The reaction temperature preferably ranges from −78° C. to the reflux temperature of the solvent.

[Step XIV]

The compound represented by the formula (422) is subjected to a reduction reaction with the use of an appropriate metal catalyst in a solvent to thereby give a compound represented by the formula (423). The reaction may be carried out in, for example, a solvent such as methanol, ethanol, ethyl acetate or tetrahydrofuran with the use of palladium, platinum (IV) oxide, etc. as the catalyst under normal to elevated hydrogen pressure.

Process for synthesizing

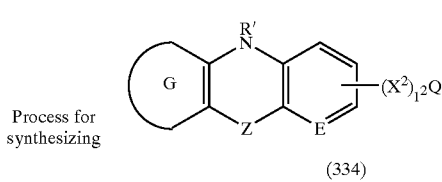
(334)

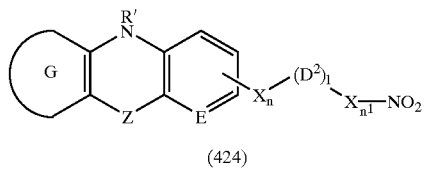
(424)

reduction reaction
(Step XIV)

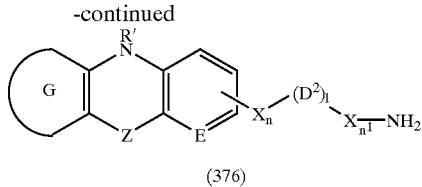
(376)

wherein G, Z, E, $X^2$, $l^2$, Q, $X_n$, $X_n^1$, $D^2$, l and R' are each as defined above.

[Step XIV]

A compound represented by the formula (424) is subjected to a reduction reaction with the use of an appropriate metal catalyst in a solvent to thereby give a compound represented by the formula (376). The reaction may be carried out in, for example, a solvent such as methanol, ethanol, ethyl acetate or tetrahydrofuran with the use of palladium, platinum (IV) oxide, etc. as the catalyst under normal to elevated hydrogen pressure.

Process for synthesizing

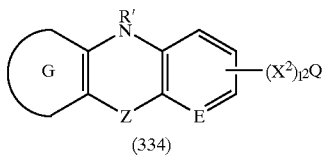
(334)

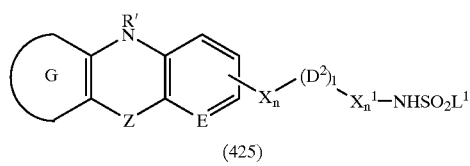
(425)

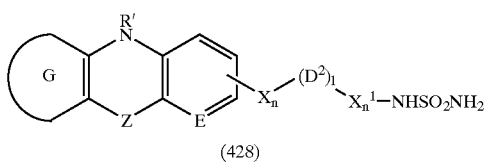
(428)

sulfonylation
(Step XXXXVII)

condensation reaction
(Step XXXXVIII)

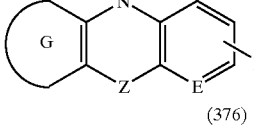
(376)

Acylation
(Step XXXXVI)

Acylation
(Step XXXXVI)

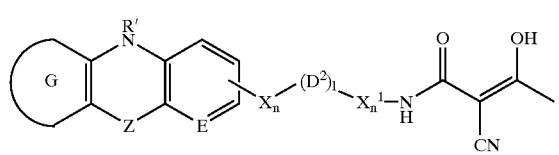
(426)

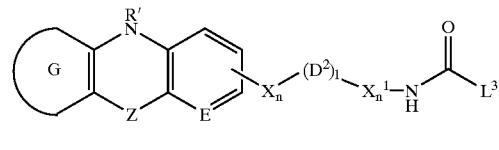
(429)

ring-opening reaction
(Step LXXXIII)

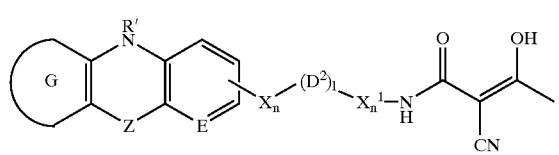
(427)

wherein G, Z, E, $X^2$, $l^2$, $L^1$, Q, $X_n$, $X_n^1$, $D^2$, l and R' are each as defined above.

[Step XXXXVI]

An amine represented by the formula (376) is reacted with a carboxylic anhydride and an acid halide optionally in an appropriate solvent in the presence of an appropriate base such as pyridine, triethylamine or N,N-diisopropylethylamine to thereby give amides represented by the formulae (426) and (429). As the solvent, use can be made of dry dichloromethane, etc. The reaction can be effected at from 0° C. to reflux temperature.

[Step XXXXVII]

The compound represented by the formula (376) is reacted with an appropriate sulfonic anhydride or acid halide optionally in an appropriate solvent such as dichloromethane in the presence of an appropriate base such as pyridine, triethylamine or N,N-diisopropylethylamine to thereby give a compound represented by the formula (425).

[Step XXXXVIII]

The amine represented by the formula (376) is treated with an acid halide of an appropriate sulfamic acid optionally in an appropriate solvent such as dichloromethane in the presence of an appropriate base such as pyridine, triethylamine or N,N-diisopropylethylamine. Alternatively, it is treated with chlorosulfonyl isocyanate in a dry solvent such as tetrahydrofuran and the intermediate is treated with an appropriate acid such as formic acid. Alternatively, it is reacted with sulfamide in dimethoxyethane at 100° C. Thus, a compound represented by the formula (428) can be obtained.

[Step LXXXIII]

The isoxazole represented by the formula (426) is treated with N,N-dimethylformamide dimethyl acetal in a dry solvent such as tetrahydrofuran at from room temperature to the reflux temperature to thereby give a compound represented by the formula (427).

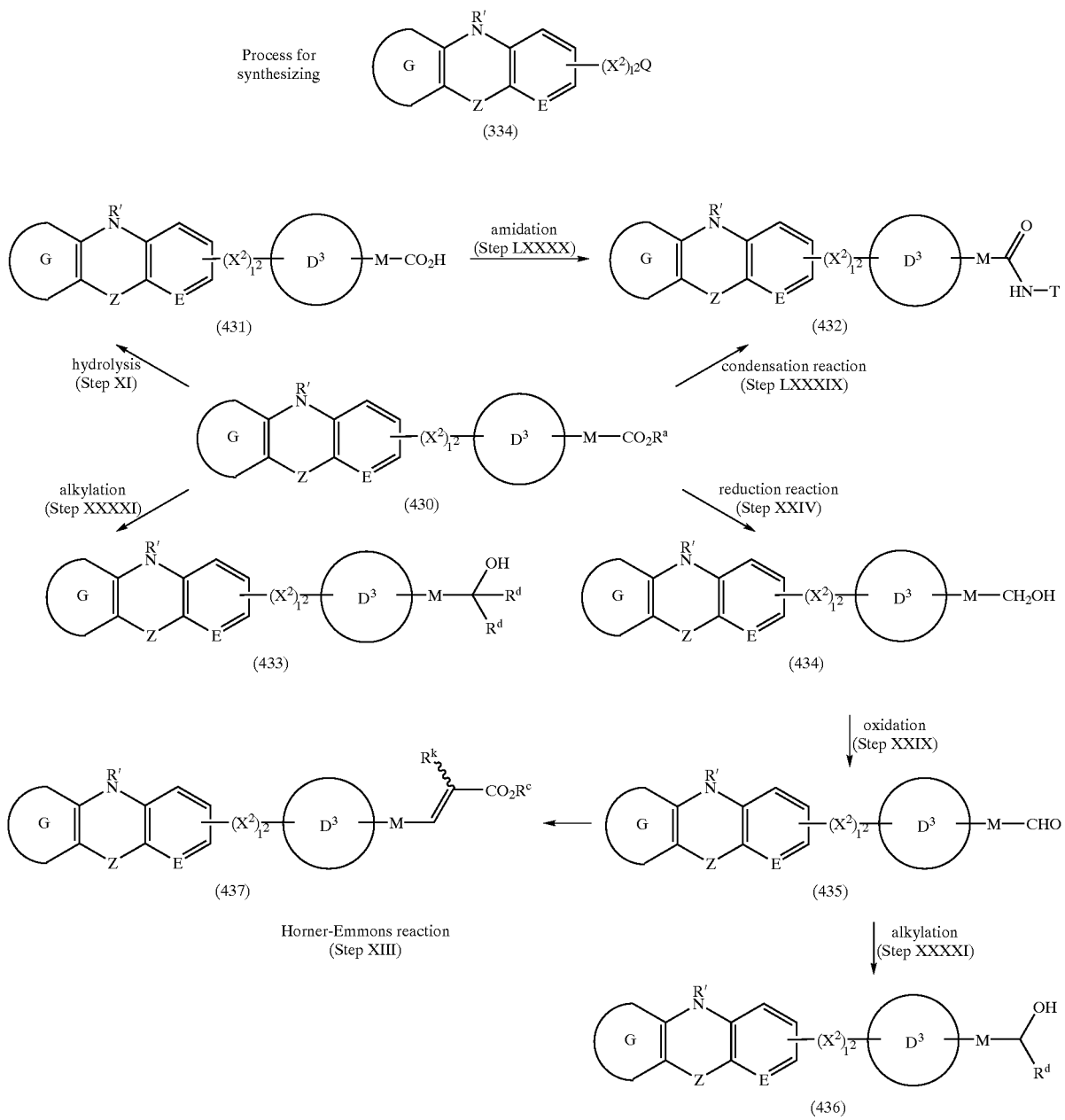

wherein G, Z, E, $X^2$, $l^2$, M, Q, $R^a$, $R^c$, $R^d$, $R^k$ and R' are each as defined above; and $D^3$ represents an imidazole or pyridine ring.

[Step LXXXX]

A carboxylic acid represented by the formula (431) is reacted with an appropriate diimide, an appropriate chloroformate, an appropriate dichlorophosphonate or carbonyldiimidazole at from 0 to 60° C. in an appropriate dry solvent such as N,N-dimethylformamide, tetrahydrofuran, acetonitrile or dichloromethane optionally in the presence of an appropriate base such as pyridine, triethylamine or N,N-diisopropylethylamine. The activated ester thus obtained is then reacted with ammonia to thereby give an amide represented by the formula (432).

[Step XI]

The compound represented by the formula (430) is reacted with an appropriate base in an aqueous solvent to thereby give a compound having a carboxyl group (431). As the solvent, use can be made of alcoholic solvents such as methanol or ethanol or solvent mixtures such as alcohol/tetrahydrofuran/water. As the base, use can be made of sodium hydroxide, potassium hydroxide, etc. The reaction can be effected at from room temperature to the reflux temperature of the solvent.

[Step LXXXIX]

The ester represented by the formula (430) is treated with an appropriate amine optionally in an appropriate solvent such as methanol, ethanol or tetrahydrofuran at from room temperature to 150° C. under atmospheric or elevated pressure to thereby give a compound represented by the formula (432).

[Step XXXXI]

The compounds represented by the formulae (430) and (435) are treated with methyllithium or a methylmagnesium halide in a solvent such as dry tetrahydrofuran, diethyl ether or dimethoxyethane at from −78° C. to the boiling point of the solvent to thereby give alcohols represented by the formulae (433) and (436) respectively.

[Step XXIV]

The compound represented by the formula (430) is treated with a reducing agent such as aluminum lithium hydride or lithium borohydride in a solvent such as dry tetrahydrofuran or dry diethyl ether to thereby give an amine of the formula (434). The reaction can be effected at from 0° C. to the reflux temperature.

[Step XXIX]

A solution of the alcohol represented by the formula (434) in, for example, methylene chloride is added to a reaction mixture obtained from oxalyl chloride and dimethyl sulfoxide and treated with a base such as triethylamine.

Alternatively, it is treated with pyridinium dichromate in a solvent such as dichloromethane or treated with manganese dioxide in a solvent such as dichloromethane or N,N-dimethylformamide. Thus, a carbonyl compound represented by the formula (435) can be obtained.

[Step XIII]

The compound represented by the formula (435) is reacted with an appropriate Horner-Emmons reagent in a solvent in the presence of an appropriate base to thereby give a compound represented by the formula (437). As the solvent, use can be made of dry solvents such as N,N-dimethylformamide, tetrahydrofuran or diethyl ether. As the base, use can be made of sodium hydride, potassium tert-butoxide, n-butyllithium, lithium diisopropylamide, etc. The reaction can be effected at from −100° C. to the reflux temperature of the solvent.

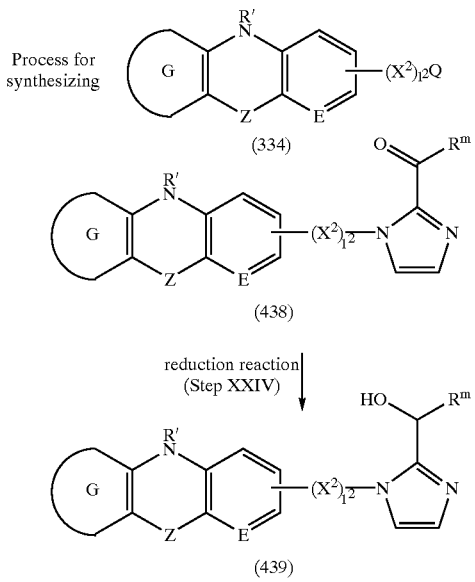

wherein G, Z, E, $X^2$, $l^2$, R', Q and $R^m$ are each as defined above.

[Step XXIV]

A compound represented by the formula (438) is treated with a reducing agent such as aluminum lithium hydride or lithium borohydride in a solvent such as dry tetrahydrofuran or dry diethyl ether, or with a reducing agent such as sodium borohydride in an alcoholic solvent such as methanol or ethanol to thereby give an amine of the formula (439). The reaction can be effected at from 0° C. to the reflux temperature.

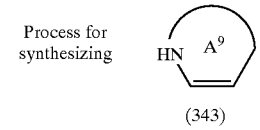

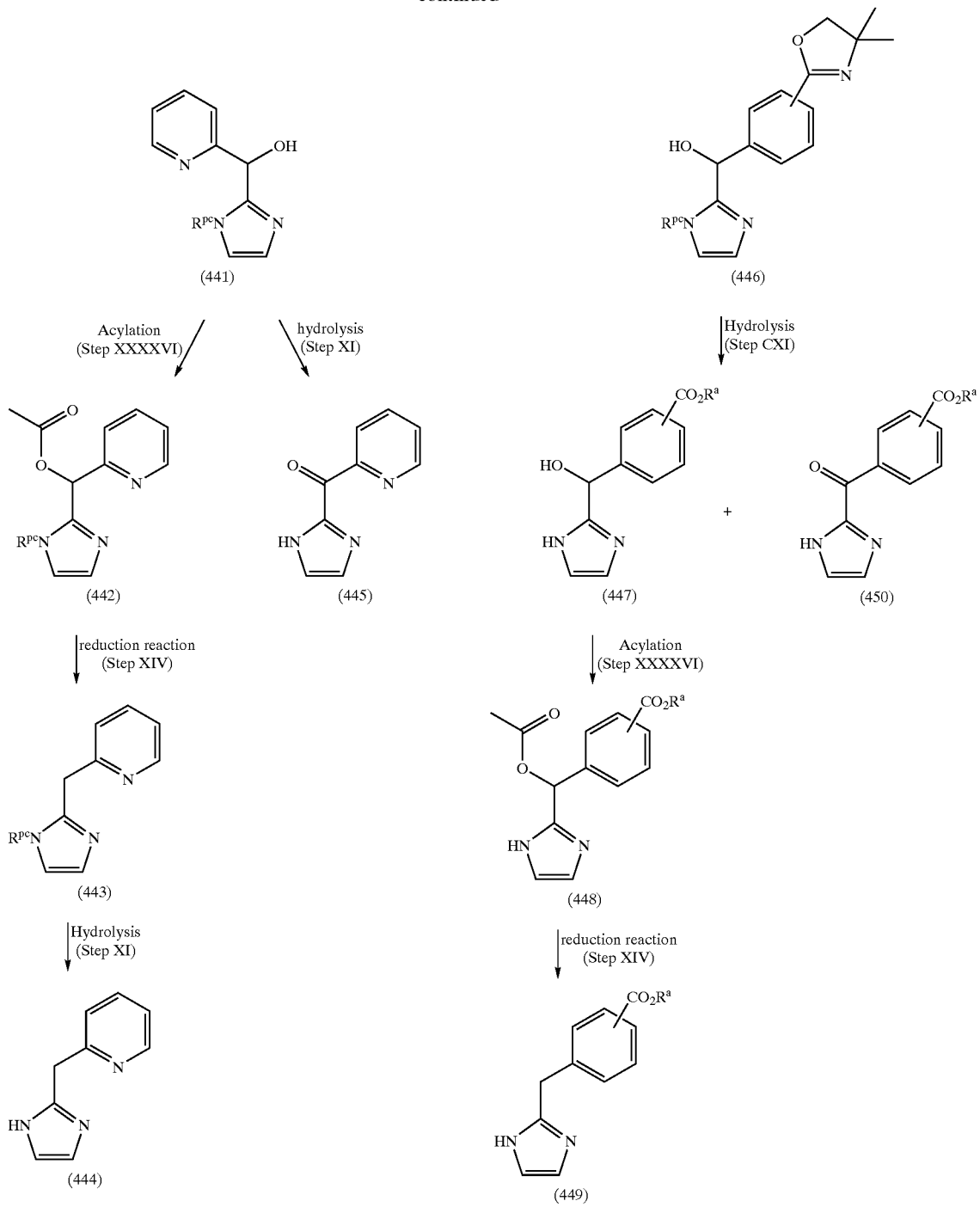

wherein $R^a$, $A^9$ and $R^{pc}$ are each as defined above.

[Step LXI]

An appropriate aldehyde is reacted in an appropriate solvent with an aryl-Grignard obtained from the compound represented by the formula (440) by a halogen-metal exchange reaction or a hydrogen-metal exchange reaction or an arylcerium complex obtained by treating the former compound with cerium (III) chloride to thereby give compounds represented by the formulae (441) and (446). As the solvent, use can be made of a dry solvent such as tetrahydrofuran, diethyl ether or dimethoxyethane. The reaction can be effected at from −100° C. to the reflux temperature of the solvent.

[Step XXXXVI]

Alcohols represented by the formulae (441) and (447) are reacted with a carboxylic anhydride, a carboxylic phosphoric anhydride and an acid halide optionally in an appropriate solvent in the presence of an appropriate base such as pyridine, triethylamine or N,N-diisopropylethylamine to thereby give esters represented by the formulae (442) and (448) respectively. As the solvent, use can be made of dry dichloromethane, etc. The reaction can be effected at from 0° C. to reflux temperature.

[Step XIV]

The compounds represented by the formulae (442) and (448) are subjected to a reduction reaction with the use of an appropriate metal catalyst in a solvent to thereby give compounds represented by the formulae (443) and (449) respectively. The reaction may be carried out in, for example, a solvent such as methanol, ethanol, ethyl acetate or tetrahydrofuran with the use of palladium, platinum (IV) oxide, etc. as the catalyst under normal to elevated hydrogen pressure.

[Step XI]

The compounds represented by the formulae (441) and (443) are reacted with an appropriate base in an aqueous solvent to thereby give compounds represented by the formulae (445) and (444). As the solvent, use can be made of alcoholic solvents such as methanol or ethanol or solvent mixtures such as alcohol/tetrahydrofuran/water. As the base, use can be made of sodium hydroxide, potassium hydroxide, etc. The reaction can be effected at from room temperature to the reflux temperature of the solvent.

[Step CXI]

The compound represented by the formula (446) is reacted with an appropriate base such as potassium hydroxide in an appropriate solvent such as ethanol at from room temperature to the reflux temperature. The intermediate thus obtained is then treated with an acid such as sulfuric acid in an appropriate solvent such as methanol or ethanol at from room temperature to the reflux temperature to thereby give compounds represented by the formulae (447) and (450).

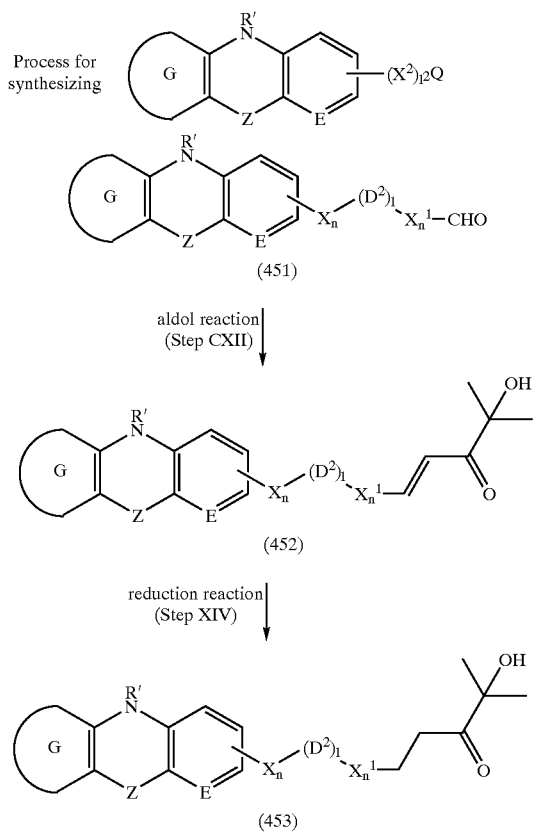

wherein G, Z, E, $X^2$, $l^2$, R', Q, $X_n$, $X_n^1$, $D^2$ and l are each as defined above.

[Step CXII]

An aldehyde represented by the formula (451) is treated with 3-hydroxy-3-methyl-2-butanone in a solvent such as methanol or tetrahydrofuran or a mixture thereof in the presence of an appropriate base such as lithium hydroxide to thereby give a compound represented by the formula (452).

[Step XIV]

The compound represented by the formula (452) is subjected to a reduction reaction with the use of an appropriate metal catalyst in a solvent to thereby give a compound represented by the formula (453). The reaction may be carried out in, for example, a solvent such as methanol, ethanol, ethyl acetate or tetrahydrofuran with the use of palladium, platinum (IV) oxide, etc. as the catalyst under normal to elevated hydrogen pressure.

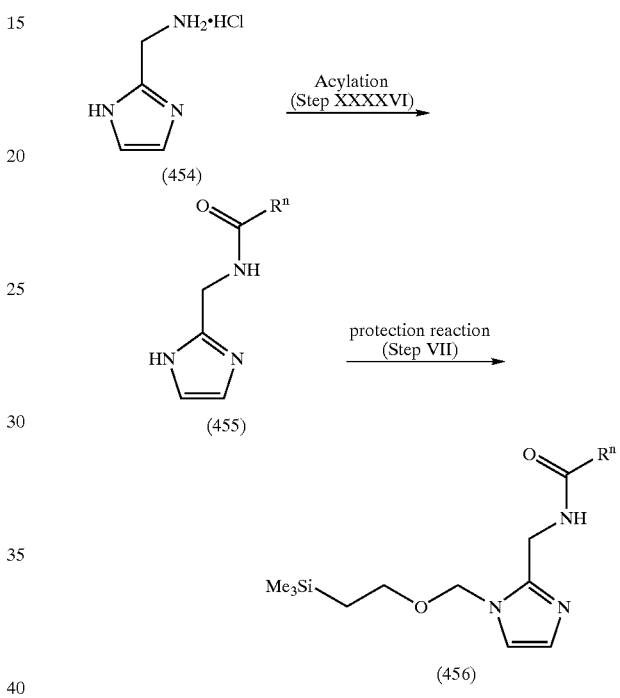

wherein $R^n$ represents methyl or tert-butyloxy.

[Step XXXXVI]

An amine represented by the formula (454) is reacted with sodium hydride optionally in an appropriate solvent in the presence of an appropriate base such as pyridine, triethylamine or N,N-diisopropylethylamine and the free compound thus obtained is then reacted with a carboxylic anhydride and an acid halide to thereby give an amide represented by the formula (455). As the solvent, it is preferable to use dry N,N-dimethylformamide. The reaction can be effected at from 0° C. to the reflux temperature.

[Step VII]

The amine represented by the formula (455) is treated with a base such as sodium hydride and a protecting reagent such as (2-trimethylsilyl)ethoxymethyl chloride in a solvent such as dry N,N-dimethylformamide at from 0° C. to room temperature to thereby give a compound represented by the formula (456).

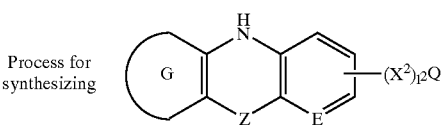

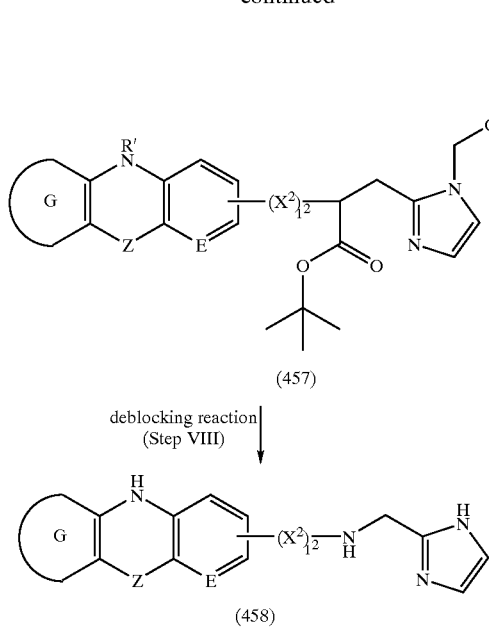

(457)

deblocking reaction
(Step VIII)

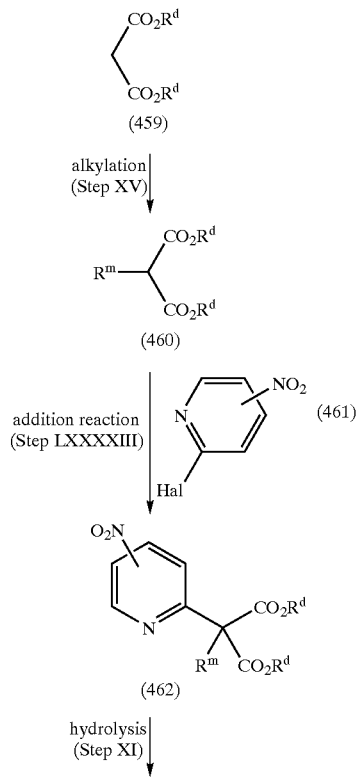

wherein G, Z, E, $X^2$, $l^2$ and R' are each as defined above.

[Step VIII]

A compound represented by the formula (457) is treated with an appropriate acid such as hydrochloric acid, trifluoroacetic acid or acetic acid optionally in an appropriate solvent such as dichloromethane or tetrahydrofuran to thereby give an amine represented by the formula (458).

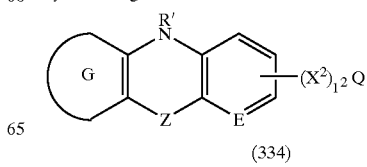

wherein Hal, $R^d$ and $R^m$ are each as defined above.

[Step XV]

A compound represented by the formula (459) is reacted with a base such as sodium hydride in a solvent such as dry N,N-dimethylformamide. Then the anion thus obtained is reacted with an appropriate halide at from room temperature to 100° C. to thereby give a compound represented by the formula (460).

[Step LXXXXIII]

The diester represented by the formula (460) is treated with a base such as sodium hydride in a solvent such as dry N,N-dimethylformamide at from 0° C. to room temperature. Then the anion thus obtained is reacted with a halide represented by the formula (461) at from room temperature to 100° C. to thereby give a compound represented by the formula (462).

[Step XI]

The compound represented by the formula (462) is reacted with an appropriate base such as sodium hydroxide or potassium hydroxide in an alcoholic solvent such as methanol or ethanol or an aqueous solvent such as a solvent mixture of alcohol, tetrahydrofuran and water at from room temperature to the reflux temperature the solvent. Alternatively, it is reacted with lithium chloride in a solvent such as dry N,N-dimethylformamide. Thus compounds represented by the formulae (463) and (465) can be obtained.

[Step XIV]

The compounds represented by the formulae (463) and (465) are subjected to a reduction reaction with the use of an appropriate metal catalyst in a solvent to thereby give compounds represented by the formulae (464) and (466). The reaction may be carried out in, for example, a solvent such as methanol, ethanol, ethyl acetate or tetrahydrofuran with the use of palladium, platinum (IV) oxide, etc. as the catalyst under normal to elevated hydrogen pressure.

Process for synthesizing

-continued

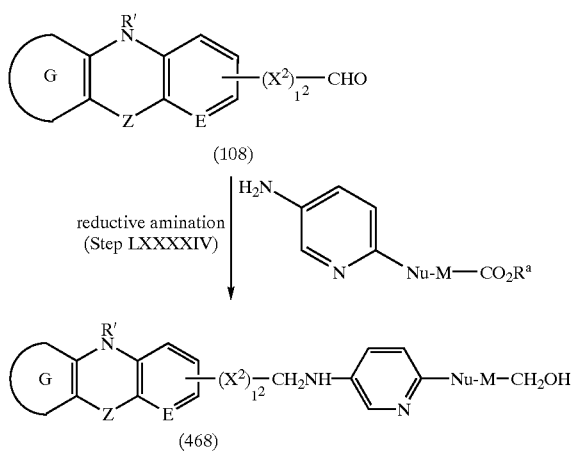

wherein G, Z, E, $X^2$, $l^2$, Nu, M, R' and $R^a$ are each as defined above.

[Step LXXXXIV]

A compound represented by the formula (460) is reacted with an aldehyde represented by the formula (108) in an appropriate solvent such as toluene or benzene at from room temperature to the reflux temperature. The intermediate thus obtained is then treated with an appropriate reducing agent such as sodium borohydride or sodium borocyanohydride in an appropriate alcoholic solvent such as ethanol or methanol or an appropriate solvent mixture such as ethanol/tetrahydrofuran at from 50° C. to the reflux temperature to thereby give a compound represented by the formula (468).

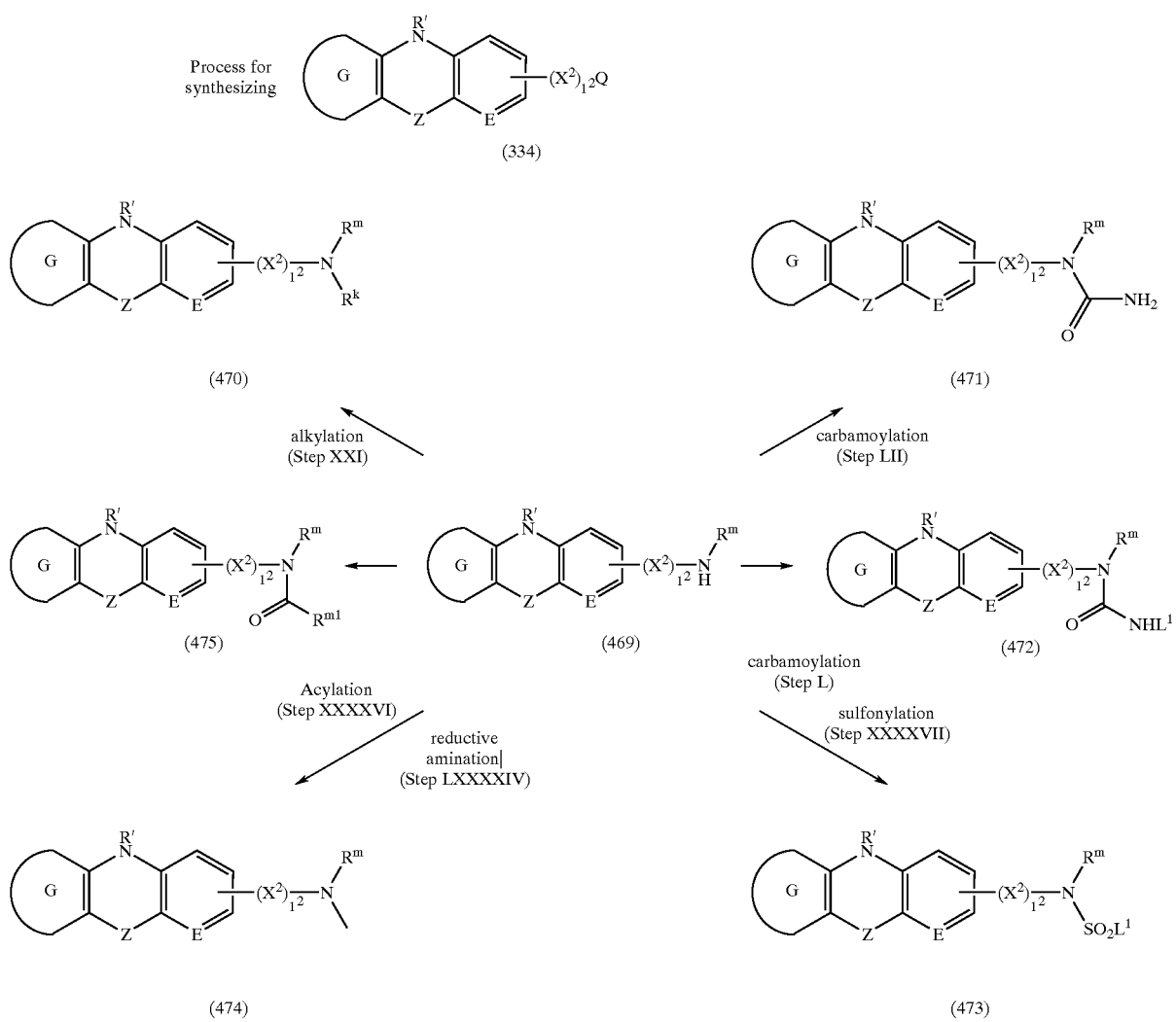

wherein G, Z, Q, E, $X^2$, $l^2$, R', $L^1$, $R^k$ and $R^m$ are each as defined above; and $R^{ml}$ has the same meaning as that of $R^m$, provided that when $R^m$ and $R^{ml}$ both exist in the molecule, then they may be the same or different.

[Step XXI]

An amine represented by the formula (469) is reacted with an appropriate alkyl halide in the presence of an appropriate amine such as pyridine, triethylamine or N,N-diisopropylethylamine in a solvent such as dichloromethane, tetrahydrofuran or N,N-dimethylformamide to thereby give an amine represented by the formula (470).

[Step XXXXVI]

An amine represented by the formula (469) is reacted with a carboxylic anhydride and an acid halide optionally in an appropriate solvent in the presence of an appropriate base such as pyridine, triethylamine or N,N-diisopropylethylamine to thereby give an amide represented by the formula (475). As the solvent, use can be made of dry dichloromethane, etc. The reaction can be effected at from 0° C. to reflux temperature.

[Step LXXXXIV]

The compound represented by the formula (469) is reacted with formalin in an appropriate solvent such as acetonitrile at from room temperature to the reflux temperature in the presence of an appropriate reducing agent such as sodium borohydride or sodium borocyanohydride to thereby give a compound represented by the formula (474).

[Step XXXXVII]

The amine represented by the formula (469) is reacted with an appropriate sulfonic anhydride or acid halide optionally in an appropriate solvent such as dichloromethane in the presence of an appropriate base such as pyridine, triethylamine or N,N-diisopropylethylamine to thereby give a compound represented by the formula (473).

[Step LII]

The compound represented by the formula (469) is reacted with sodium isocyanate, potassium isocyanate, etc. in a solvent such as water or ethanol optionally in the presence of an appropriate acid such as acetic acid. Alternatively, it is reacted with trimethylsilyl isocyanate in a dry solvent such as tetrahydrofuran in the presence of a base such as triethylamine at from room temperature to the reflux temperature to thereby give a compound represented by the formula (471).

[Step L]

The compound represented by the formula (469) is reacted with an appropriate isocyanate in an appropriate solvent to thereby give a compound represented by the formula (472). As the solvent, use can be made of tetrahydrofuran, toluene, etc. The reaction can be effected at from room temperature to the reflux temperature of the solvent.

Process for synthesizing

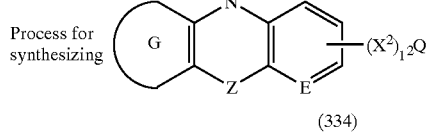

(334)

Process for synthesizing

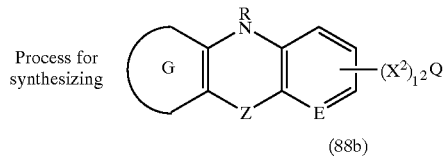

(88b)

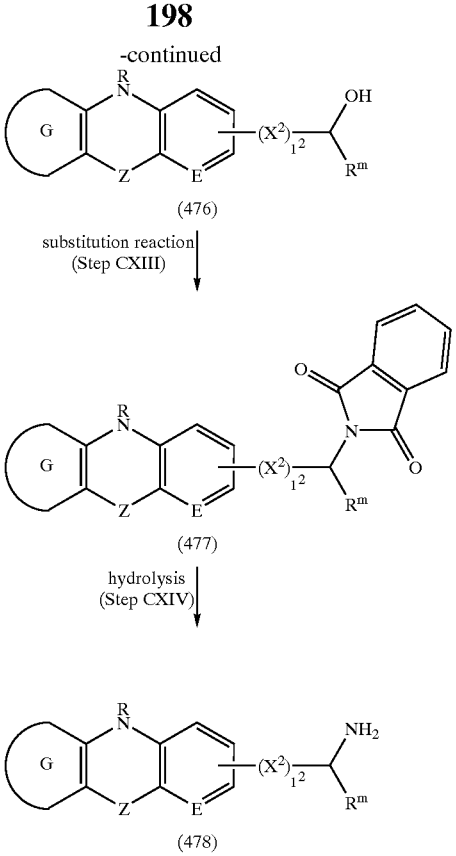

wherein G, Z, Q, E, $X^2$, $1^2$, R and $R'''$ are each as defined above.

[Step CXIII]

A compound represented by the formula (476) is reacted with phthalimide in an appropriate dry solvent such as tetrahydrofuran or dichloromethane in the presence of triphenylphosphine and diethyl diazodicarboxylate to thereby give a compound represented by the formula (477). The reaction can be effected at from 0° C. to the reflux temperature.

[Step CXIV]

The compound represented by the formula (477) is reacted with hydrazine in an alcoholic solvent such as ethanol to thereby give an amine derivative represented by the formula (478). The reaction is effected preferably at from 50° C. to the reflux temperature.

-continued

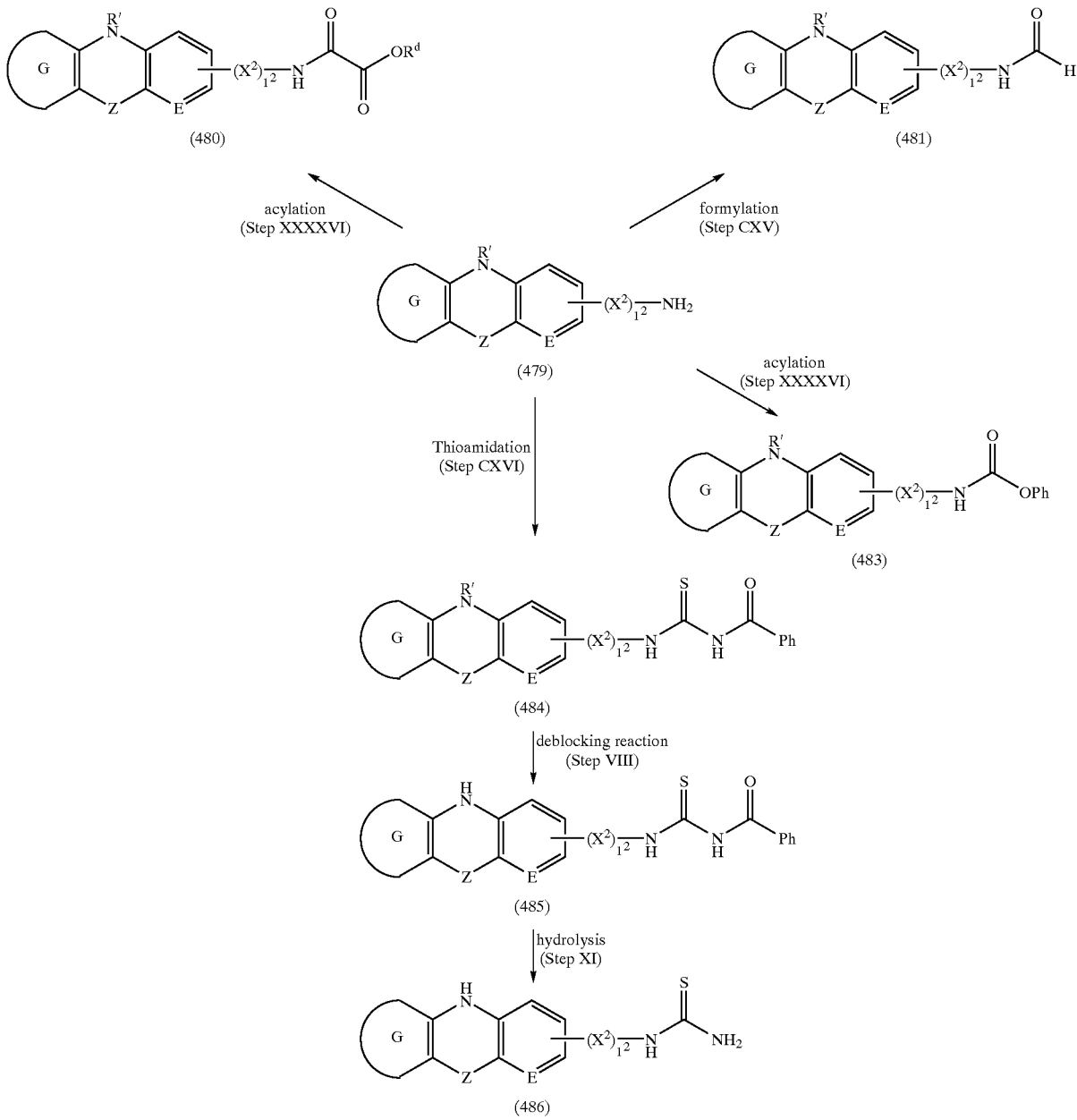

wherein G, Q, Z, E, $X^2$, $l^2$, R, R' and $R^d$ are each as defined above.

[Step XXXXVI]

An amine represented by the formula (479) is reacted with a carboxylic anhydride and an acid halide optionally in an appropriate solvent in the presence of an appropriate base such as pyridine, triethylamine or N,N-diisopropylethylamine to thereby give amides represented by the formulae (480) and (483). As the solvent, use can be made of dry dichloromethane, dry tetrahydrofuran, etc. The reaction can be effected at from 0° C. to the reflux temperature.

[Step CXV]

The amine represented by the formula (479) is heated under reflux in ethyl formate to thereby give an amdie derivative represented by the formula (481).

[Step CXVI]

Benzoyl chloride is treated with ammonium thiocyanate in acetone. The reagent thus obtained is then reacted with the amine represented by the formula (479) to thereby give a thiourea derivative represented by the formula (484).

[Step VIII]

A compound represented by the formula (484) is treated with an appropriate acid such as hydrochloric acid, trifluoroacetic acid or acetic acid optionally in an appropriate solvent such as dichloromethane or tetrahydrofuran to thereby give an amine represented by the formula (485).

[Step XI]

The compound represented by the formula (485) is reacted with an appropriate base such as sodium hydroxide or potassium hydroxide in an alcoholic solvent such as methanol or ethanol or an aqueous solvent such as a solvent mixture of alcohol, tetrahydrofuran and water at from room temperature to the reflux temperature of the solvent to thereby give a compound represented by the formula (486).

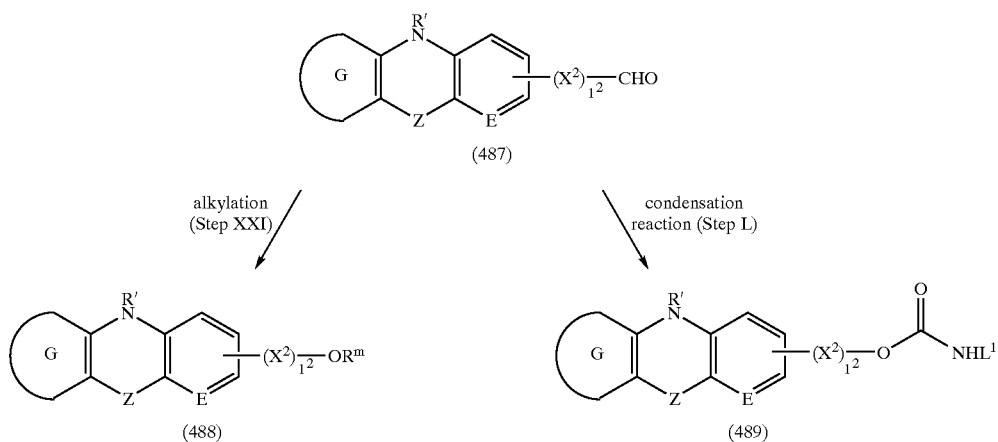

wherein G, Q, Z, E, $X^2$, $l^2$, R', $R^m$ and $L^1$ are each as defined above.

[Step XXI]

A compound represented by the formula (487) is treated with an appropriate base such as sodium hydride or sodium methoxide in a solvent such as dimethoxyethane, tetrahydrofuran or N,N-dimethylformamide and then reacted with an appropriate alkyl halide to thereby give a derivative represented by the formula (488). The reaction can be effected at from −100° C. to room temperature.

[Step L]

The compound represented by the formula (487) is reacted with an isocyanate in an appropriate solvent to thereby give a compound represented by the formula (489). As the solvent, use can be made of tetrahydrofuran or toluene. The reaction can be effected at from room temperature to the reflux temperature of the solvent. It is sometimes preferable to effect the reaction in the presence of a base such as pyridine or triethylamine.

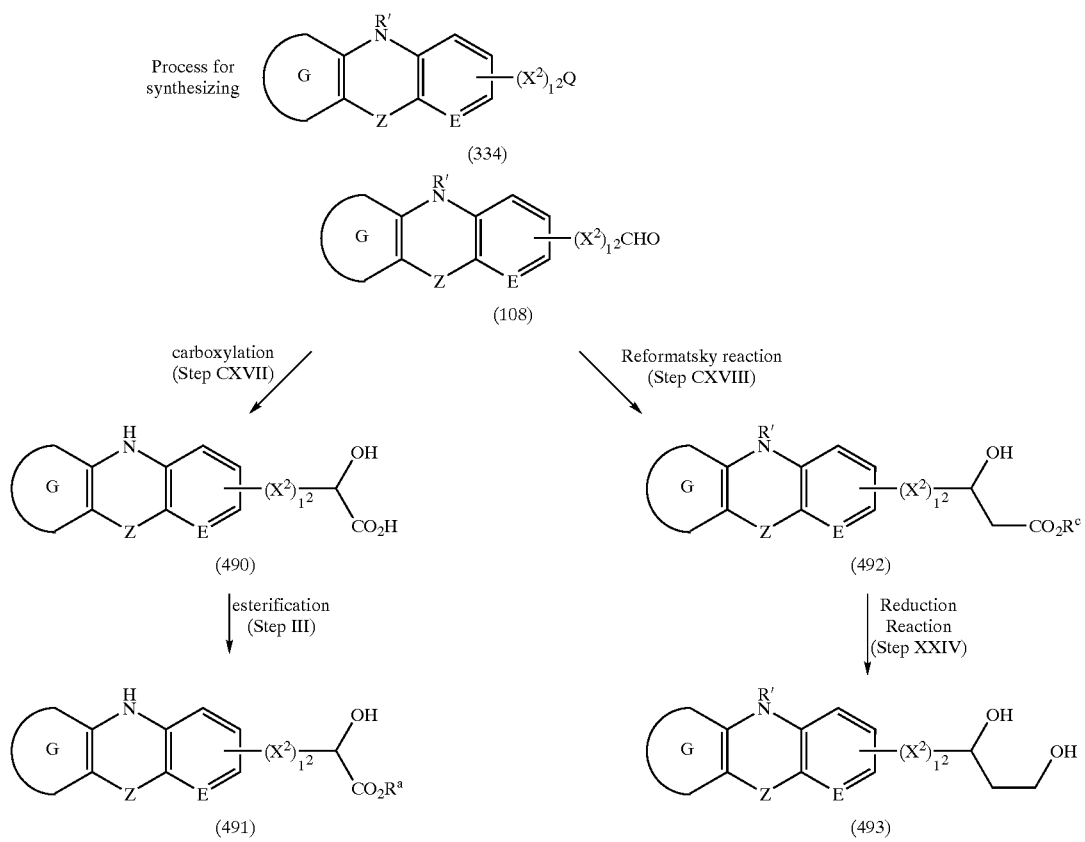

wherein G, Z, Q, E, $X^2$, $l^2$, R', $R^a$ and $R^c$ are each as defined above.

[Step CXVII]

an aldehyde represented by the formula (108) is reacted with a trihalomethane such as tribromoethane in an aqueous solvent mixture such as water/1,4-dioxane at from 0° C. to room temperature in the presence of a base such as potassium hydroxide or sodium hydroxide and lithium chloride to thereby give a compound represented by the formula (490).

[Step III]

The compound represented by the formula (490) is reacted with an alkylating agent such as methyl iodide in a dry solvent such as N,N-dimethylformamide or tetrahydrofuran at from 0 to 40° C. in the presence of a base such as potassium carbonate to thereby give an ester represented by the formula (491).

[Step CXVIII]

The aldehyde represented by the formula (108) is reacted with a haloacetic acid derivative such as methyl bromoacetate in an appropriate dry solvent such as dry tetrahydrofuran in the presence of trimethyl borate and zinc dust to thereby give a compound represented by the formula (492).

[Step XXIV]

The compound represented by the formula (492) is treated with a reducing agent such as aluminum lithium hydride or lithium borohydride in a solvent such as dry tetrahydrofuran or dry diethyl ether to thereby give an amine of the formula (493). The reaction can be effected at from 0° C. to the reflux temperature.

Process for synthesizing

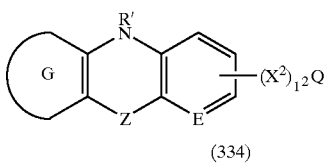

(334)

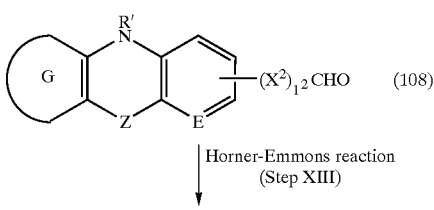

(108)

Horner-Emmons reaction
(Step XIII)

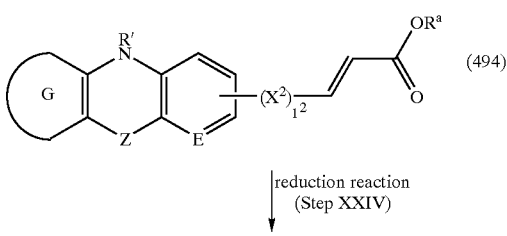

(494)

reduction reaction
(Step XXIV)

Process for synthesizing

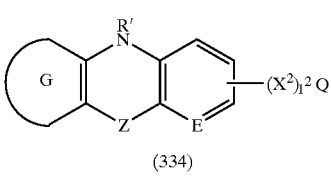

(334)

-continued

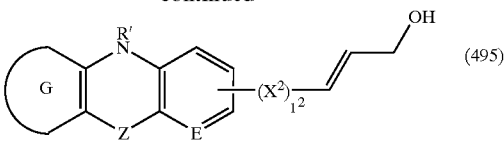

(495)

reduction reaction
(Step XIV)

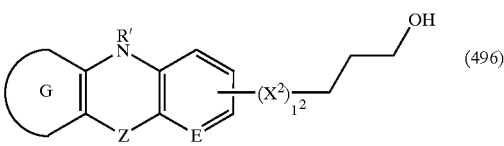

(496)

wherein G, Q, Z, E, $X^2$, $l^2$, R' and $R^a$ are each as defined above.

[Step XIII]

The compound represented by the formula (108) is reacted with an appropriate Horner-Emmons reagent in a solvent in the presence of an appropriate base to thereby give a compound represented by the formula (494). As the solvent, use can be made of dry solvents such as N,N-dimethylformamide, tetrahydrofuran or diethyl ether. As the base, use can be made of sodium hydride, potassium tert-butoxide, n-butyllithium, lithium diisopropylamide, etc. The reaction can be effected at from −100° C. to the reflux temperature of the solvent.

[Step XXIV]

The compound represented by the formula (494) is treated with a reducing agent such as aluminum lithium hydride or lithium borohydride in a solvent such as dry tetrahydrofuran or dry diethyl ether to thereby give an alcohol of the formula (495). The reaction can be-effected at from 0° C. to the reflux temperature.

[Step XIV]

The compound represented by the formula (495) is subjected to a reduction reaction with the use of an appropriate metal catalyst in a solvent to thereby give a compound represented by the formula (496). The reaction may be carried out in, for example, a solvent such as methanol, ethanol, ethyl acetate or tetrahydrofuran with the use of palladium, platinum (IV) oxide, etc. as the catalyst under normal to elevated hydrogen pressure.

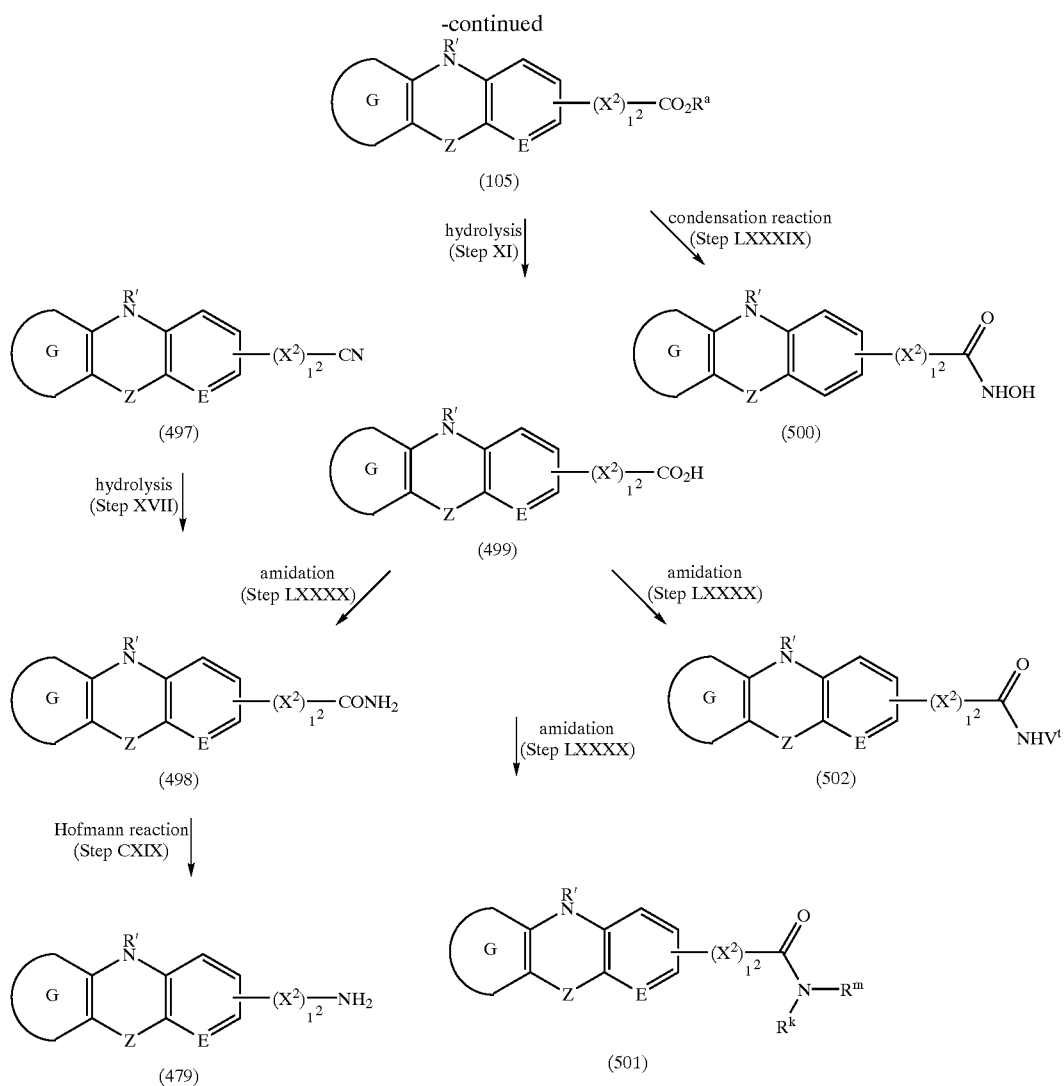

wherein G, Q, Z, E, $X^2$, $l^2$, $R^m$, $V^1$, R' and $R^a$ are each as defined above.

[Step XI]

A compound represented by the formula (105) is reacted with an appropriate base such as sodium hydroxide or potassium hydroxide in an alcoholic solvent such as methanol or ethanol or an aqueous solvent such as a solvent mixture of alcohol, tetrahydrofuran and water at from room temperature to the reflux temperature of the solvent to thereby give a compound represented by the formula (499).

[Step XVII]

The compound represented by the formula (497) is treated with hydrogen peroxide in a solvent such as ethanol or dimethyl sulfoxide or a mixture thereof in the presence of a base such as sodium hydroxide or potassium hydroxide at from 0° C. to room temperature. Alternatively, it is reacted with an alkali such as sodium hydroxide or potassium hydroxide in a solvent such as dimethyl sulfoxide at from 50 to 100° C. to thereby give a compound represented by the formula (498).

[Step CXIX]

The amide represented by the formula (498) is treated with bromine in water in the presence of a base such as sodium hydroxide or potassium hydroxide to thereby give an amine represented by the formula (479).

[Step LXXXIX]

The ester represented by the formula (105) is treated with hydroxylamine hydrochloride in a solvent mixture such as tetrahydrofuran/water in the presence of a base such as sodium hydroxide or potassium hydroxide to thereby give a compound represented by the formula (500).

[Step LXXXX]

The carboxylic acid represented by the formula (499) is reacted with an appropriate diimide, an appropriate chloroformate, an appropriate dichlorophosphonate or carbonyldiimidazole at from 0 to 60° C. in an appropriate dry solvent such as N,N-dimethylformamide, tetrahydrofuran, acetonitrile or dichloromethane optionally in the presence of an appropriate base such as pyridine, triethylamine or N,N-diisopropylethylamine. The activated ester thus obtained is then reacted with ammonia or an appropriate amine or amine derivative to thereby give amides represented by the formulae (498), (501) and (502).

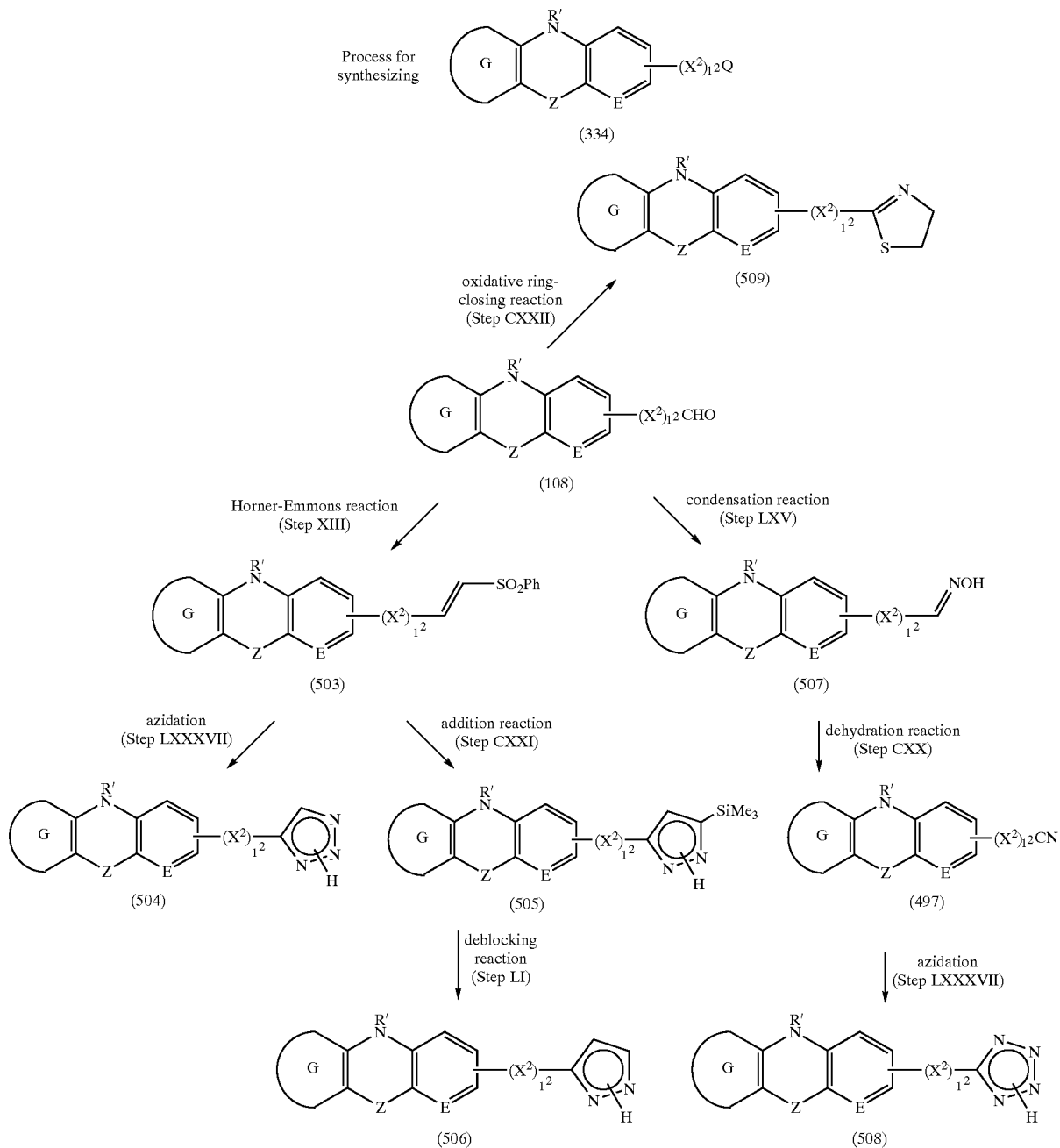

wherein G, Z, Q, E, $X^2$, $l^2$ and R' are each as defined above.

[Step XIII]

The compound represented by the formula (108) is reacted with an appropriate Horner-Emmons reagent in a solvent in the presence of an appropriate base to thereby give a compound represented by the formula (503). As the solvent, use can be made of dry solvents such as N,N-dimethylformamide, tetrahydrofuran or diethyl ether. As the base, use can be made of sodium hydride, potassium tert-butoxide, n-butyllithium, lithium diisopropylamide, etc. The reaction can be effected at from −100° C. to the reflux temperature of the solvent.

[Step LXXXVII]

The nitrile represented by the formula (503) is treated with an azidation agent such as sodium azide in a dry solvent such as dimethyl sulfoxide, N,N-dimethylformamide or 1-methyl-2-pyrrolidone at from 50° C. to the reflux temperature to thereby give a tetrazole derivative represented by the formula (504)

[Step CXXI]

In a dry solvent such as tetrahydrofuran, (tirmethylsilyl) dizaomethane is treated with a strong base such as n-butyllithium at from −100° C. to room temperature. The anion thus obtained is reacted with the compound of the formula (503) to thereby give a pyrazole derivative represented by the formula (505).

[Step LI]

The compound represented by the formula (505) is treated with a reagent such as tetra-n-butylammonium fluoride or caesium fluoride in a dry solvent such as tetrahydrofuran to thereby give a compound represented by the formula (506).

[Step LXV]

An aldehyde derivative represented by the formula (108) is reacted with hydroxylamine in a solvent such as ethanol or tetrahydrofuran in the presence of a catalyst such as sodium acetate or ammonium acetate to thereby give an oxime represented by the formula (507). This reaction can be effected at from room temperature to the reflux temperature.

[Step CXX]

The oxime represented by the formula (507) is heated under reflux in trifluoroacetonitrile to thereby give a nitrile represented by the formula (497).

[Step LXXXVII]

The nitrile represented by the formula (497) is treated with an azidation agent such as sodium azide in a dry solvent such as dimethyl sulfoxide, N,N-dimethylformamide or 1-methyl-2-pyrrolidone at from 50° C. to the reflux temperature in the presence of a catalyst such as ammonium chloride to thereby give a tetrazole derivative represented by the formula (508).

[Step CXXII]

The aldehyde represented by the formula (108) is reacted with 2-aminoethanethiol in an alcoholic solvent such as methanol in the presence of a base such as sodium methoxide at from room temperature to the reflux temperature to thereby give a compound represented by the formula (509).

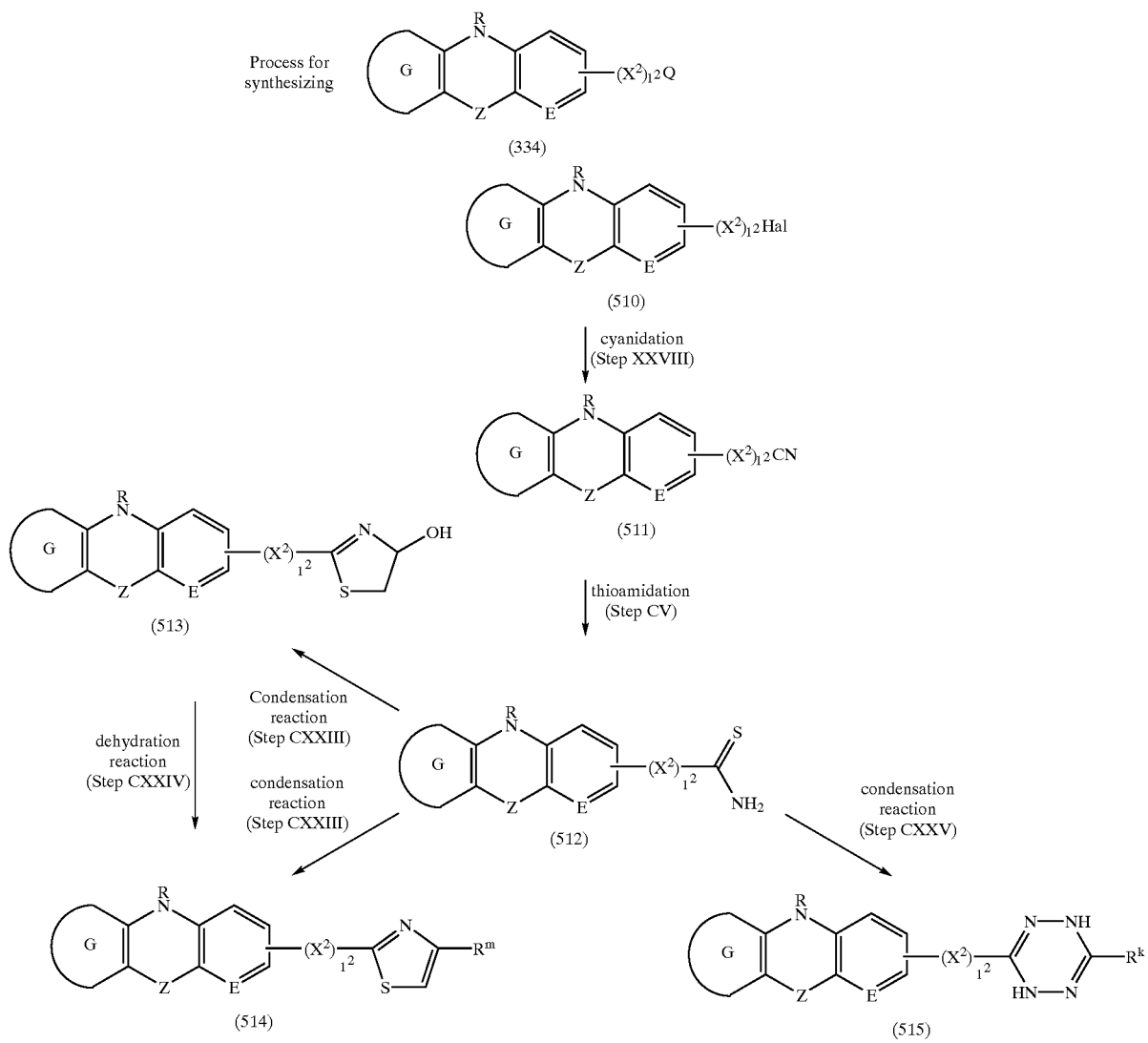

wherein G, Z, Q, E, $X^2$, $1^2$, Hal, $R^m$, $R^k$ and R are each as defined above.

[Step XXVIII]

A halide represented by the formula (510) is treated with a cyanidation reagent such as sodium cyanide or potassium cyanide in an appropriate solvent such as dimethyl sulfoxide to thereby give a nitrile compound represented by the formula (511). The reaction can be effected at from room temperature to 100° C.

[Step CV]

The nitrile represented by the formula (511) is reacted with sodium hydrosulfide and hydrogen sulfide in an appropriate solvent such as methanol at from −30 to 100° C. under elevated pressure to thereby give a thioamide represented by the formula (512).

[Step CXXIII]

The thioamide represented by the formula (512) is reacted with an appropriate α-halocarbonyl derivative in an appropriate solvent mixture such as tetrahydrofuran/dimethoxyethane or ethanol/N,N-dimethylformamide at from room temperature to 100° C. optionally in the presence of an appropriate base such as potassium hydrogencarboante or sodium hydrogencarbonate to thereby give compounds represented by the formulae (513) and (514).

[Step CXXIV]

The compound represented by the formula (513) is reacted with an appropriate acid anhydride such as trifluoroacetic anhydride, an acid halide, etc. in an appropriate solvent such as dimethoxyethane in the presence of an appropriate base such as pyridine to thereby give a thiazole represented by the formula (514).

[Step CXXV]

The thioamide represented by the formula (512) is reacted with hydrazine in an appropriate solvent such as tetrahydrofuran or ethanol or a mixture thereof at from room temperature to the reflux temperature. The intermediate thus obtained is treated with an appropriate orthoester in an appropriate solvent such as tetrahydrofuran or ethanol or a mixture thereof at from room temperature to the reflux temperature to thereby give a compound represented by the formula (515).

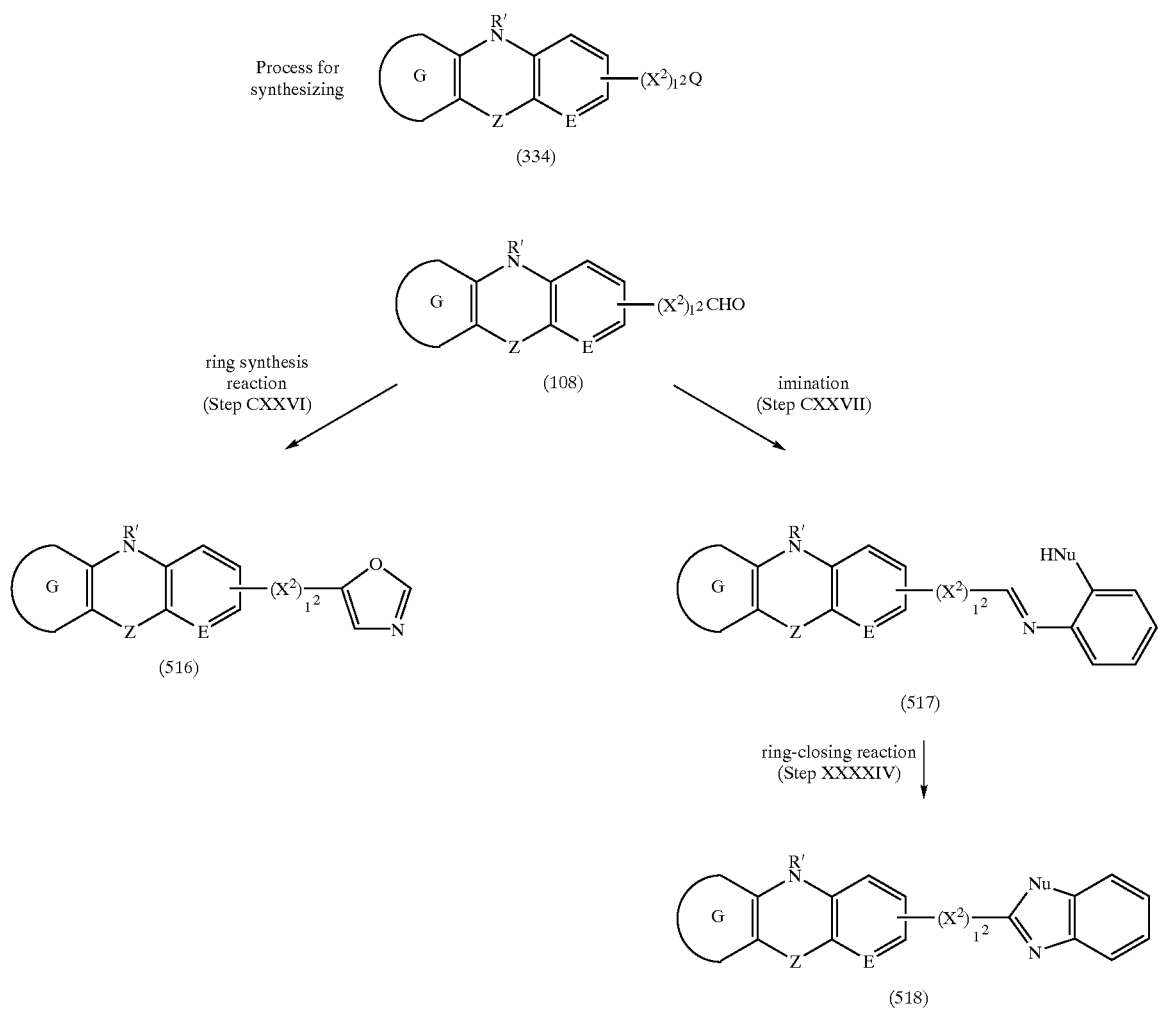

wherein G, Z, Q, E, $X^2$, $l^2$, Nu and R' are each as defined above.

[Step CXXVI]

An aldehyde represented by the formula (108) is treated with a tosylmethylisocyanide in an appropriate alcoholic solvent such as methanol or ethanol in the presence of an appropriate base such as potassium carbonate or sodium carbonate to thereby give an oxazole represented by the formula (516). The reaction can be effected at from room temperature to the reflux temperature of the solvent.

[Step CXXVII]

The aldehyde represented by the formula (108) is reacted with an appropriate secondary amine in pyridine to thereby give a compound represented by the formula (517). The reaction is effected preferably at from 50° C. to the reflux temperature.

[Step XXXXIV]

The imine represented by the formula (517) is heated under reflux in pyridine in the presence of oxygen to thereby give a cyclized product represented by the formula (518).

Process for synthesizing

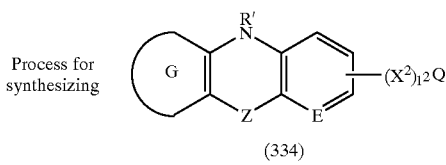

(334)

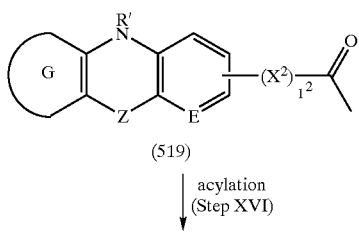

(519)

acylation
(Step XVI)

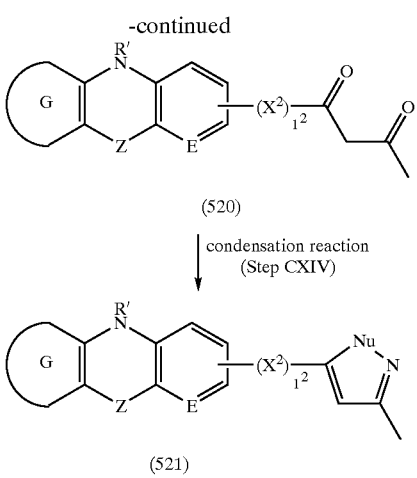

wherein G, Z, Q, E, $X^2$, $l^2$, Nu and R' are each as defined above.

[Step XVI]

The ketone compound represented by the formula (519) is treated with a strong base such as lithium diisopropylamide in a dry solvent such as tetrahydrofuran or diethyl ether. Then the anion thus obtained is treated with an acetylation agent such as acetic anhydride or acetyl chloride to thereby give a diketone compound represented by the formula (520).

[Step CXIV]

The compound represented by the formula (520,) is reacted with hydrazine or hydroxylamine in an alcoholic solvent such as methanol or ethanol to thereby give a compound represented by the formula (521). The reaction can be effected preferably at from 50° C. to the reflux temperature.

Process for synthesizing

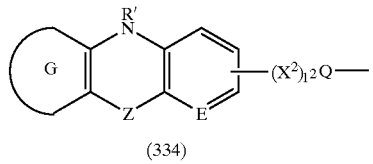

(334)

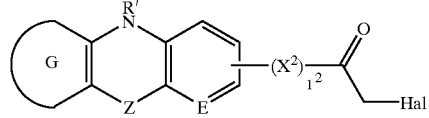

(522)

condensation reaction (Step LXXXIX)

Condensation reaction (Step CXXIII)

Condensation reaction (Step CXXIII)

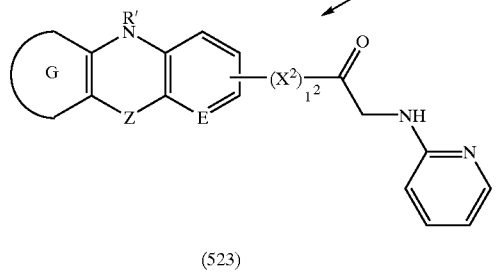

(523)

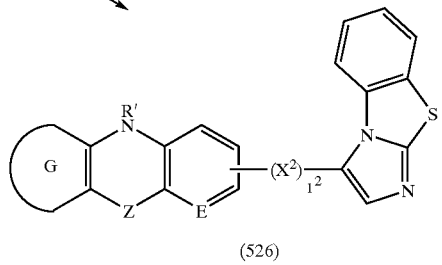

(526)

dehydration reaction (Step CXXVIII)

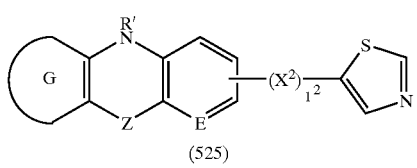

(525)

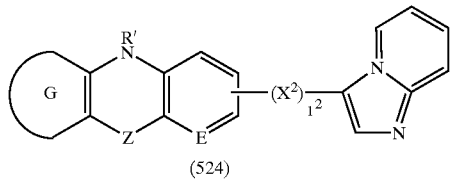

(524)

wherein G, Z, Q, E, $X^2$, $l^2$, Hal and R' are each as defined above.

[Step LXXXIX]

An acid halide represented by the formula (522) is treated with 2-aminopyridine optionally in an appropriate solvent such as dichloromethane, methanol or tetrahydrofuran or a solvent mixture such as ethanol/tetrahydrofuran in the presence of an appropriate base such as sodium hydrogencarbonate, pyridine, triethylamine or N,N-diisopropylethylamine to thereby give a compound represented by the formula (523). The reaction can be effected at from 0° C. to the reflux temperature.

[Step CXXVIII]

The ketone compound represented by the formula (523) is treated with thionyl chloride in an appropriate dry solvent such as carbon tetrachloride at from room temperature to the reflux temperature to thereby give a compound represented by the formula (524).

[Step CXXIII]

The haloketone represented by the formula (522) is reacted with an appropriate thioamide derivative or thioimidate in an appropriate solvent mixture such as tetrahydrofuran/dimethoxyethane or ethanol/N,N-dimethylformamide at from room temperature to 100° C. optionally in the presence of an appropriate base such as potassium hydrogencarbonate or sodium hydrogencarbonate to thereby give compounds represented by the formulae (525) and (526).

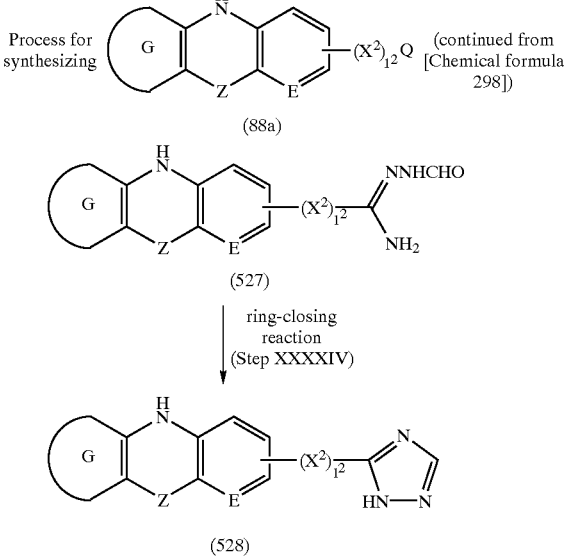

wherein G, Z, Q, E, $X^2$ and $l^2$ are each as defined above.

[Step XXXXIV]

An amine represented by the formula (527) is heated in an appropriate solvent to thereby give a triazole derivative represented by the formula (528). As the solvent, use can be made of dry N,N-dimethylformamide, etc. The reaction is effected preferably at from 50 to 150° C.

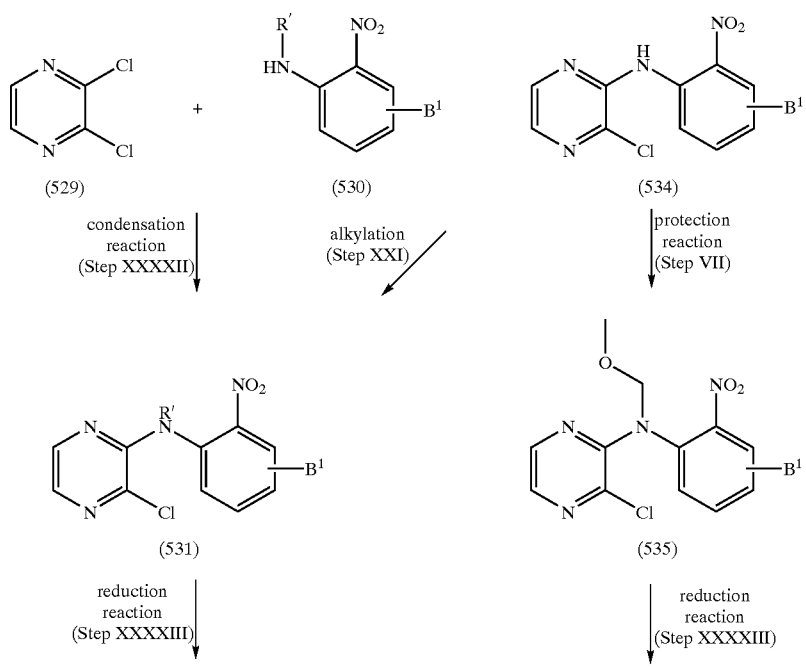

-continued

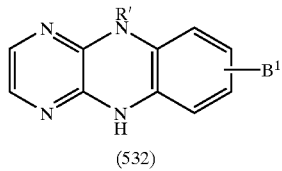

(532)

protection reaction (Step VII) ↓

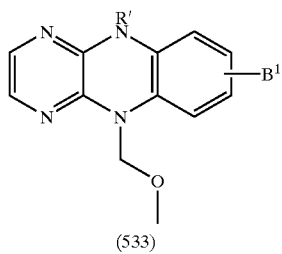

(533)

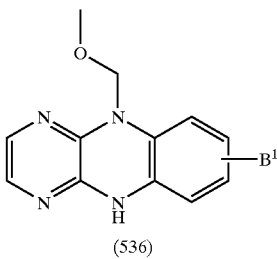

(536)

alkylation (Step XXI) ↓

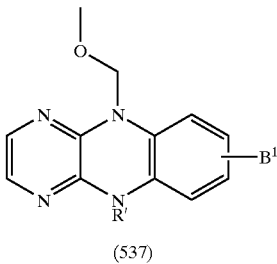

(537)

wherein $B^1$ and $R'$ are each as defined above.

[Step XXXXII]

A compound represented by the formula (530) is treated with a base such as sodium hydride and then reacted with a halogen compound (529) in a solvent such as dry N,N-dimethylformamide or tetrahydrofuran to thereby give a compound represented by the formula (531).

[Step XXXXIII]

The nitro compounds represented by the formulae (531) and (535) are treated with a reducing agent such as iron in a solvent mixture of an alcohol, tetrahydrofuran and water in the presence of ammonium chloride. Alternatively, it is treated with sodium hydrosulfite in a solvent mixture of tetrahydrofuran with water. Thus, compounds represented by the formulae (532) and (536) can be produced respectively. As the alcohol, use can be made of methanol, ethanol, isopropanol etc.

[Step VII]

The amines represented by the formulae (532) and (534) are treated with a base such as sodium hydride and a protecting reagent such as methoxymethyl chloride in a solvent such as N,N-dimethylformamide to thereby give compounds represented by the formulae (533) and (535) respectively.

[Step XXI]

The compounds represented by the formulae (534) and (536) are treated with a base such as sodium hydride and an appropriate alkylating agent in a dry solvent such as N,N-dimethylformamide to thereby give compounds represented by the formulae (531) and (537) respectively.

Process for synthesizing

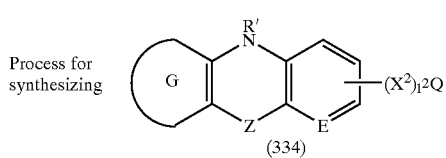

(334)

-continued

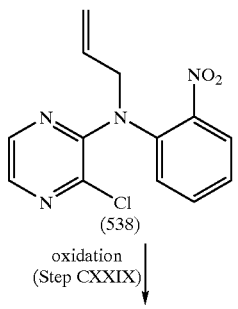

(538)

oxidation (Step CXXIX) ↓

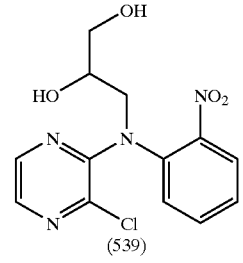

(539)

reduction reaction (Step XXXXIII) ↓

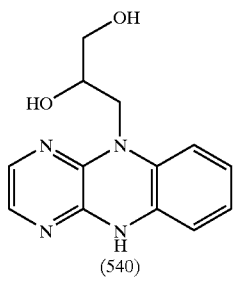

(540)

wherein G, Z, Q, E, $X^2$, $I^2$ and $R'$ are each as defined above.

[Step CXXIX]

An alkene represented by the formula (538) is treated with osmium tetraoxide in a solvent such as acetone or tert-butanol or a mixture thereof in the presence of an oxidizing agent such as N-methyl-morpholine to thereby give a diol represented by the formula (539).

[Step XXXXIII]

The nitro compound represented by the formula (539) is treated with a reducing agent such as iron in a solvent mixture of an alcohol, tetrahydrofuran and water in the presence of ammonium chloride. Alternatively, it is treated with sodium hydrosulfite in a solvent mixture of tetrahydrofuran with water. Thus, a compound represented by the formula (540) can be produced. As the alcohol, use can be made of methanol, ethanol, isopropanol, etc.

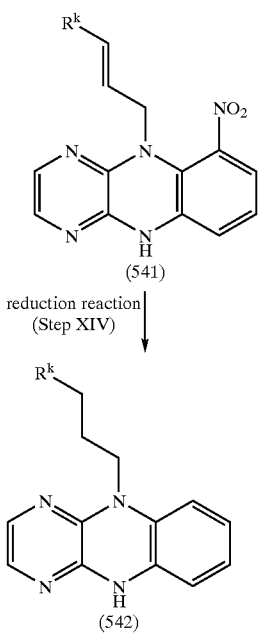

wherein $R^k$ is as defined above.

[Step XIV]

The compound represented by the formula (541) is subjected to a reduction reaction with the use of an appropriate metal catalyst in a solvent to thereby give a compound represented by the formula (542). The reaction may be carried out in, for example, a solvent such as methanol, ethanol, ethyl acetate or tetrahydrofuran with the use of palladium, platinum (IV) oxide, etc. as the catalyst under normal to elevated hydrogen pressure.

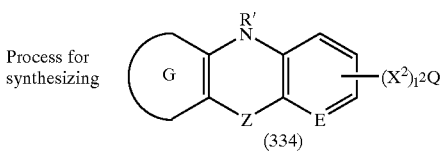

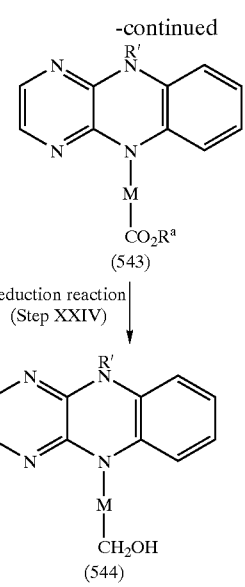

wherein G, Z, Q, E, $X^2$, $l^2$, M, $R^a$ and R' are each as defined above.

[Step XXIV]

A compound represented by the formula (543) is treated with a reducing agent such as aluminum lithium hydride or lithium borohydride in a solvent such as dry tetrahydrofuran or dry diethyl ether to thereby give an alcohol of the formula (544). The reaction can be effected at from 0° C. to the reflux temperature.

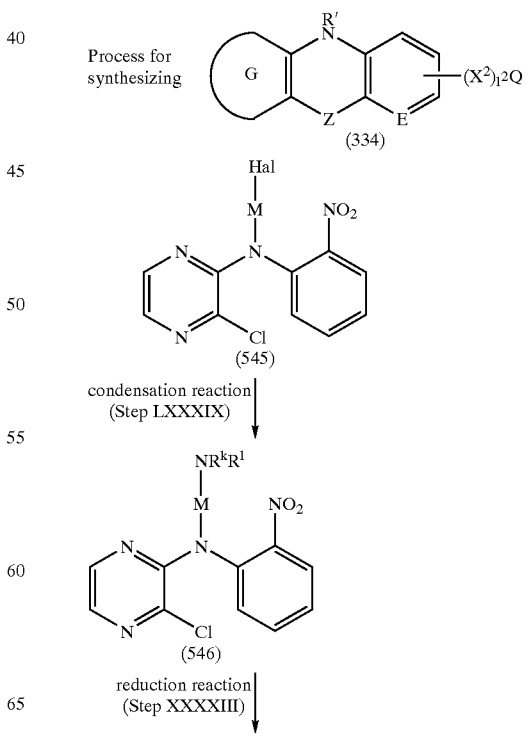

-continued

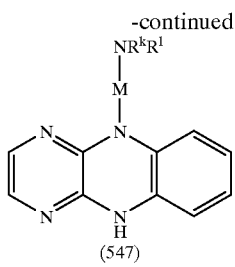
(547)

wherein G, Z, Q, E, X², 1², M, R^k, R¹ and R' are each as defined above.

[Step LXXXIX]

A halide represented by the formula (545) is treated with an appropriate amine in an appropriate alcoholic solvent such as methanol or ethanol to thereby give an amine derivative represented by the formula (546). The reaction can be effected at from room temperature to the reflux temperature.

[Step XXXXIII]

The nitro compound represented by the formula (546) is treated with a reducing agent such as iron in a solvent mixture of an alcohol, tetrahydrofuran and water in the presence of ammonium chloride. Alternatively, it is treated with sodium hydrosulfite in a solvent mixture of tetrahydrofuran with water. Thus, a compound represented by the formula (547) can be produced. As the alcohol, use can be made of methanol, ethanol, isopropanol, etc.

Process for synthesizing
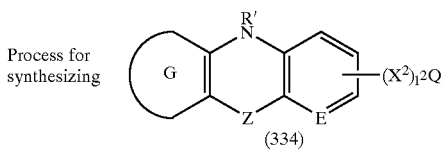
(334)

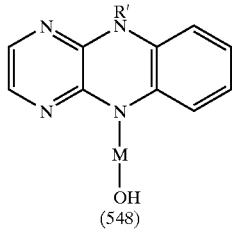
(548)

sulfonylation
(Step XXXXVII)

-continued

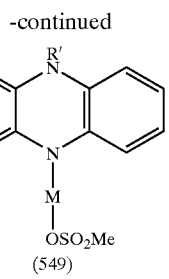
(549)

condensation reaction
(Step LXXIX)

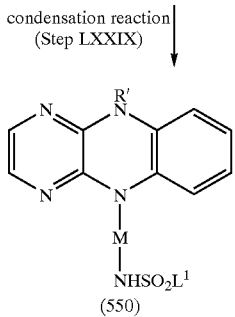
(550)

wherein G, Z, Q, E, X², 1², M, L¹ and R' are each as defined above.

[Step XXXXVII]

An amine represented by the formula (548) is reacted with an appropriate sulfonic anhydride or acid halide optionally in an appropriate solvent such as dichloromethane in the presence of an appropriate base such as pyridine, triethylamine or N,N-diisopropylethylamine to thereby give a compound represented by the formula (549).

[Step LXXIX]

The sulfonic acid derivative represented by the formula (549) is treated with an appropriate sulfonamide in a dry solvent such as tetrahydrofuran or N,N-dimethylformamide in the presence of a strong base such as sodium hydride or lithium diisopropylamide at from 0 to 100° C. to thereby give a compound represented by the formula (550).

Process for synthesizing
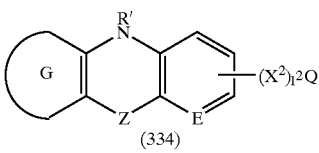
(334)

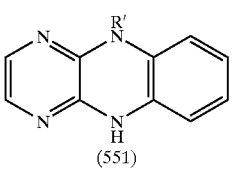
(551)

alkylation
(Step XXI)

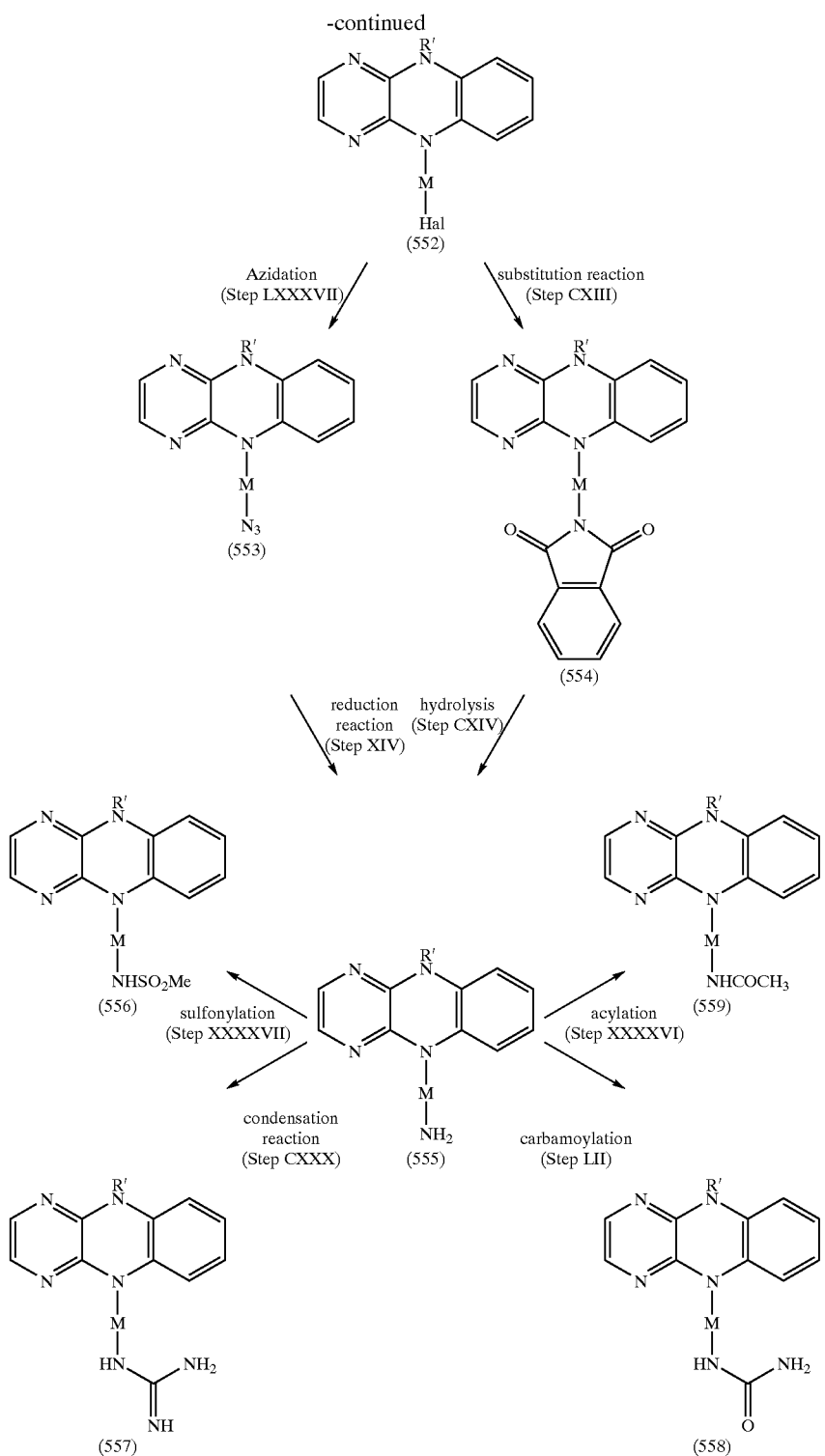

wherein G, Z, Q, E, $X^2$, $I^2$, M, Hal and R' are each as defined above.

[Step XXI]

A compound represented by the formula (551) is treated with a base such as sodium hydride and an appropriate alkylating agent in a dry solvent such as N,N-dimethylformamide to thereby give a compound represented by the formula (552).

[Step LXXXVII]

The nitrile represented by the formula (552) is treated with an azidation agent such as sodium azide in a dry solvent such as dimethyl sulfoxide, N,N-dimethylformamide or 1-methyl-2-pyrrolidone at from 50° C. to the reflux temperature to thereby give an azide represented by the formula (553).

[Step XIV]

The compound represented by the formula (553) is subjected to a reduction reaction with the use of an appropriate metal catalyst in a solvent to thereby give a compound represented by the formula (555). The reaction may be carried out in, for example, a solvent such as methanol, ethanol, ethyl acetate or tetrahydrofuran with the use of palladium, platinum (IV) oxide, etc. as the catalyst under normal to elevated hydrogen pressure.

[Step CXIII]

The compound represented by the formula (552) is reacted with phthalimide in an appropriate dry solvent such as tetrahydrofuran or dichloromethane in the presence of triphenylphosphine and diethyl diazodicarboxylate to thereby give a compound represented by the formula (554). The reaction can be effected at from 0° C. to the reflux temperature.

[Step CXIV]

The compound represented by the formula (554) is reacted with hydrazine in an alcoholic solvent such as ethanol to thereby give an amine derivative represented by the formula (555). The reaction is effected preferably at from 50° C. to the reflux temperature.

[Step XXXXVII]

The amine represented by the formula (555) is reacted with an appropriate sulfonic anhydride or acid halide optionally in an appropriate solvent such as dichloromethane or N,N-dimethylformamide in the presence of an appropriate base such as pyridine, triethylamine or N,N-diisopropylethylamine to thereby give a compound represented by the formula (556).

[Step CXXX]

The amine represented by the formula (555) is reacted with formamidinesulfonic acid or an appropriate methyl-isothiourea derivative in an appropriate alcoholic solvent such as methanol at from 0° C. to the ref lux temperature to thereby give a compound represented by the formula (557).

[Step LII]

The compound represented by the formula (555) is reacted with sodium isocyanate, potassium isocyanate, etc. in a solvent such as water or ethanol optionally in the presence of an appropriate acid such as acetic acid. Alternatively, it is reacted with trimethylsilyl isocyanate in a dry solvent such as tetrahydrofuran in the presence of a base such as triethylamine at from room temperature to the reflux temperature to thereby give a compound represented by the formula (558).

[Step XXXXVI]

An amine represented by the formula (555) is reacted with a carboxylic anhydride, a carboxylic phosphoric anhydride or an acid halide optionally in an appropriate solvent in the presence of an appropriate base such as pyridine, triethylamine or N,N-diisopropylethylamine to thereby give an amide represented by the formula (559). As the solvent, use can be made of dry N,N-dimethylformamide, dry dichloromethane, etc. The reaction can be effected at from 0° C. to the reflux temperature.

Process for synthesizing

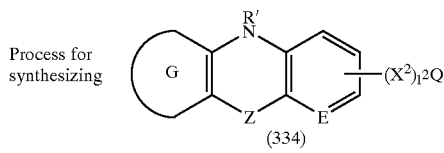

(334)

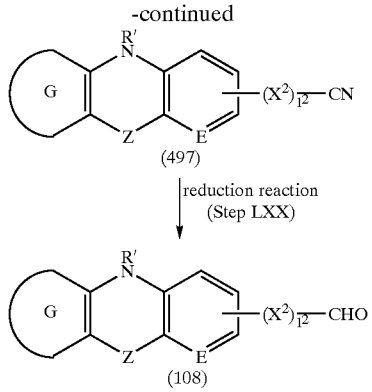

(497)

reduction reaction
(Step LXX)

(108)

wherein G, Z, Q, E, $X^2$, $l^2$ and R' are each as defined above.

[Step LXX]

The nitrile compound represented by the formula (497) is treated with diisobutylaluminum hydride in an appropriate solvent such as toluene or dichloromethane to thereby give an aldehyde compound represented by the formula (108). The reaction temperature preferably ranges from −100° C. to room temperature.

Process for synthesizing

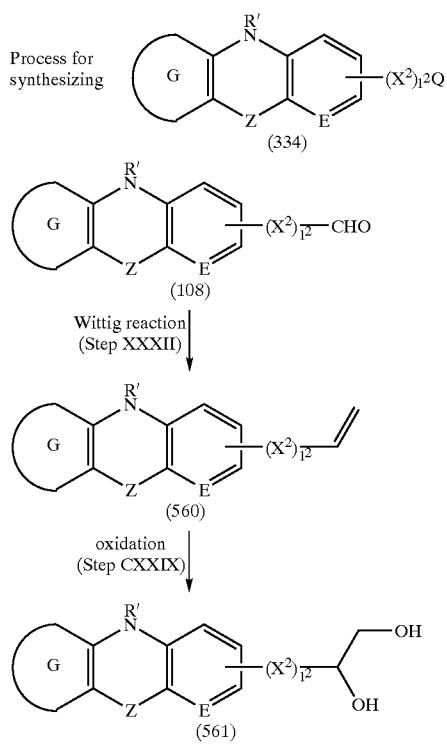

(334)

(108)

Wittig reaction
(Step XXXII)

(560)

oxidation
(Step CXXIX)

(561)

wherein G, Z, Q, E, $X^2$, $l^2$ and R' are each as defined above.

[Step XXXII]

Methyltriphenylphosphonium bromide is reacted with an appropriate base such as potassium tert-butoxide or butyl-lithium in a solvent such as N,N-dimethylformamide, toluene, xylene or tetrahydrofuran followed by a reaction with an aldehyde represented by the formula (108). Thus a compound represented by the formula (560) can be obtained. The reaction temperature preferably ranges from room temperature to 100° C.

[Step CXXIX]

The alkene represented by the formula (560) is treated with osmium tetraoxide in a solvent such as acetone or tert-butanol or a mixture thereof in the presence of an oxidizing agent such as N-methylmorpholine oxide to thereby give a diol represented by the formula (561).

Process for synthesizing

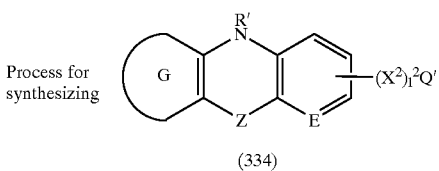

(334)

wherein G, Z, Q, E, $X^2$, $l^2$, Hal, Ar and R' are each as defined above.

[Step CXXXI]

A halide represented by the formula (562) is reacted with an appropriate arylcopper complex or heteroarylcopper complex in a dry solvent such as toluene or N,N-dimethylformamide in the presence of triphenylphosphine to thereby give a compound represented by the formula (563).

Process for synthesizing

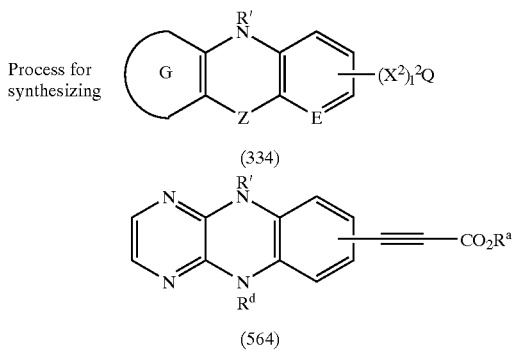

(334)

(564)

addition reaction (Step LXXXIX) / \ addition reaction (Step LXXXXIII)

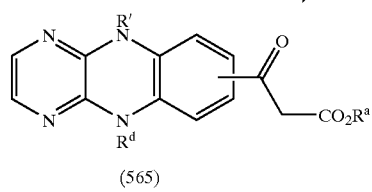

(565)

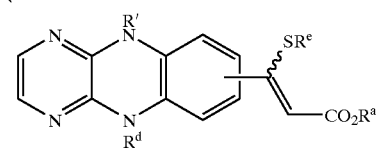

(566)

oxidation (Step LXIX)

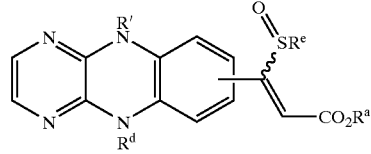

(567)

wherein G, Z, Q, E, $X^2$, $l^2$, $R^a$, $R^d$ and R' are each as defined above.

[Step LXXXIX]

An alkyne compound represented by the formula (564) is treated with an appropriate amine such as dimethylamine in an appropriate alcoholic solvent such as methanol or ethanol to thereby give a ketone compound represented by the formula (565). The reaction can be effected at from room temperature to the reflux temperature.

[Step LXXXXIII]

The α,β-alkynyl ester compound represented by the formula (564) is treated with sodium thiomethoxide in a solvent mixture of N,N-dimethylformamide with methanol to thereby give a compound represented by the formula (566). The reaction is effected preferably at from 0° C. to room temperature.

[Step LXIX]

A sulfide compound represented by the formula (566) is treated with a peroxide such as 3-chloroperbenzoic acid in -continued

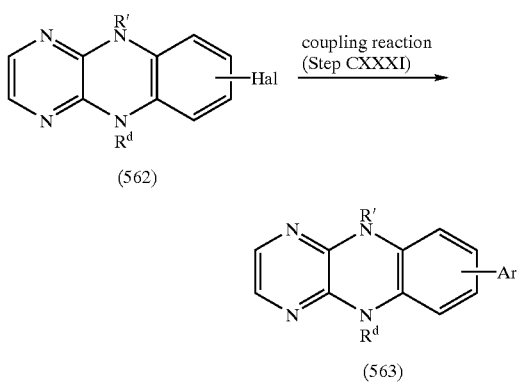

an appropriate solvent such as dichloromethane in the presence of sodium carbonate, etc. to thereby give a sulfoxide compound represented by the formula (567). The reaction temperature preferably ranges from room temperature to 40° C.

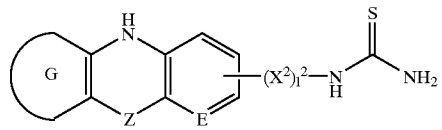

(486)

alkylation
(Step XXI)

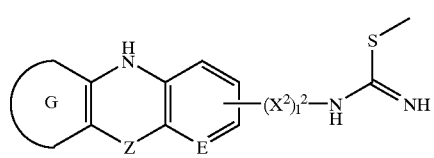

(586)

condensation reaction
(Step LXXXIX)

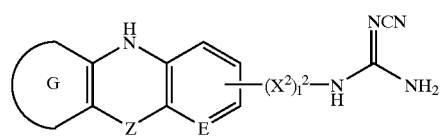

(569)

wherein G, Z, Q, E, $X^2$ and $l^2$ are each as defined above.
[Step XXI]

A thiourea compound represented by the formula (486) is treated with an appropriate methylating agent such as methyl iodide in a solvent such as acetone to thereby give a methyliosthiourea derivative represented by the formula (568).
[Step LXXXIX]

The thiourea compound represented by the formula (568) is treated with cyanamide in a dry solvent such as tetrahydrofuran or N,N-dimethylformamide to thereby give a compound represented by the formula (569). The reaction is effected preferably at from 50 to 100° C.

wherein G, Z, Q, E, $X^2$ and $l^2$ are each as defined above; and $V^4$ represents nitro or methylsulfonyl.
[Step CXXX]

An amine represented by the formula (570) is reacted with formamidinesulfonic acid or an appropriate methylisothiourea derivative in an appropriate alcoholic solvent such as methanol at from 0° C. to the reflux temperature to thereby give compounds represented by the formulae (571) and (572).

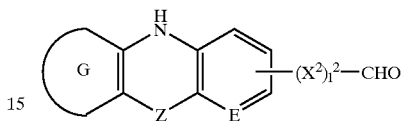

(104)

ring synthesis reaction
(Step CXXXII)

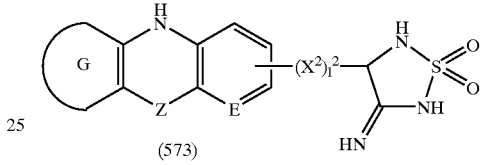

(573)

wherein G, Z, Q, E, $X^2$ and $l^2$ are each as defined above.
[Step CXXXII]

An aldehyde represented by the formula (104) is reacted with an appropriate cyanidation agent such as sodium cyanide or potassium cyanide in a solvent mixture of ethanol with water at from room temperature to the reflux temperature to thereby give an amidine compound represented by the formula (573).

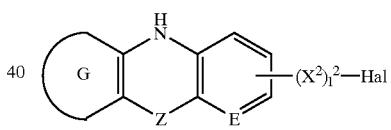

(574)

Arbuzov reaction
(Step CXXXIII)

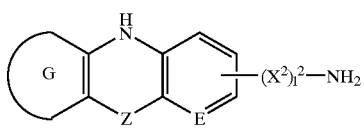

(570)

condensation reaction          condensation reaction
(Step CXXX)                    (Step CXXX)

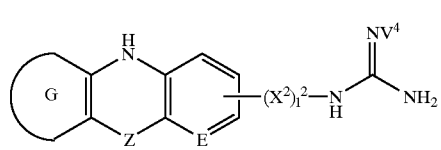          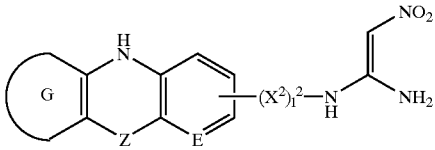

(571)                         (572)

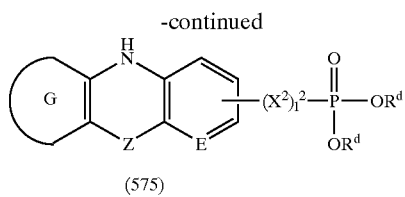

(575)

wherein G, Z, Q, E, $R^d$, Hal, $X^2$ and $l^2$ are each as defined above.

[Step CXXXIII]

A halide represented by the formula (574) is heated in an appropriate trialkyl phosphite to thereby give a dialkyl phosphonate represented by the formula (575). The reaction is effected preferably at from 100 to 200° C.

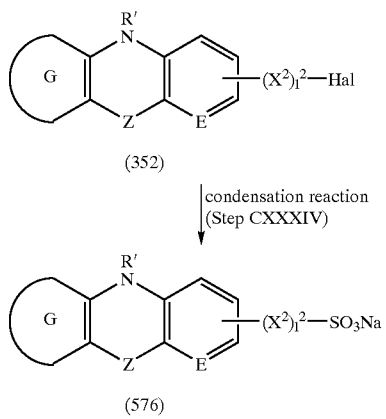

(352)

condensation reaction
(Step CXXXIV)

(576)

wherein G, Z, Q, E, R', Hal, $X^2$ and $l^2$ are each as defined above.

[Step CXXXIV]

A halide represented by the formula (352) is reacted with sodium sulfite in a solvent mixture of an appropriate alcohol such as methanol with water at from room temperature to the reflux temperature to thereby give a sulfonic acid derivative represented by the formula (576).

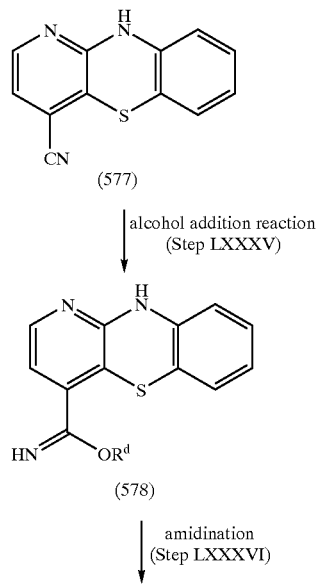

(577)

alcohol addition reaction
(Step LXXXV)

(578)

amidination
(Step LXXXVI)

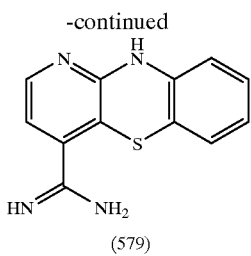

(579)

wherein $R^d$ is as defined above.

[Step LXXXV]

A nitrile compound represented by the formula (577) is treated with an appropriate acid in an alcoholic solvent to thereby give an imidate represented by the formula (578) (i.e., the so-called Pinner reaction). It is preferable to use hydrochloric acid as the acid. The reaction is preferably effected in methanol/dichloromethane at from 0 to 10° C.

[Step LXXXVI]

The imidate represented by the formula (578) is reacted with an amine or an amide in an appropriate solvent to thereby give a compound represented by the formula (579). Acetonitrile or a mixture of acetonitrile with methanol may be cited as the most desirable solvent. The reaction is effected preferably at from room temperature to 40° C.

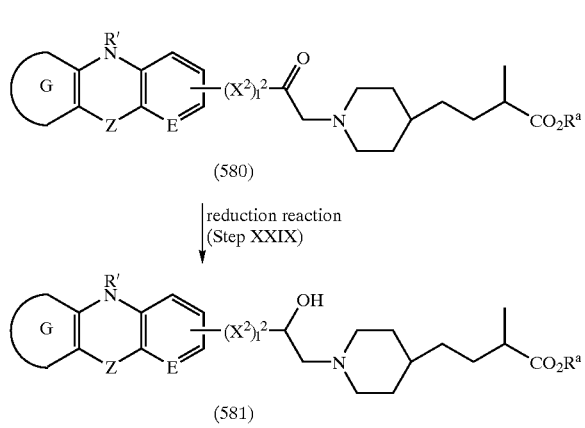

(580)

reduction reaction
(Step XXIX)

(581)

wherein G, Z, E, R', $R^a$, $X^2$, and $l^2$ are each as defined above.

[Step XXIX]

A compound represented by the formula (580) is reacted with a reducing agent such as sodium borohydride in a solvent to thereby give a compound represented by the formula (581). As the solvent, use can be made of methanol, ethanol, etc. The reaction can be effected at from 0° C. to the reflux temperature.

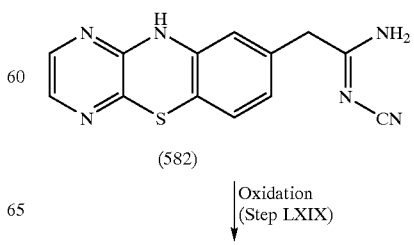

(582)

Oxidation
(Step LXIX)

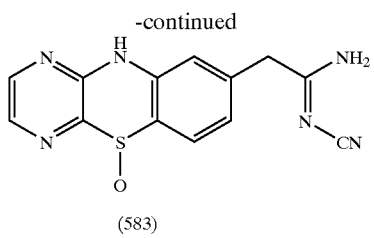

(583)

[Step LXIX]

A sulfide compound represented by the formula (582) is treated with a peroxide such as 3-chloroperbenzoic acid in an appropriate solvent such as dichloromethane in the presence of sodium carbonate, etc. Alternatively, it is treated with hydrogen peroxide in acetic acid. Thus, a sulfoxide compound represented by the formula (583) can be obtained. The reaction temperature preferably ranges from room temperature to 40° C.

Production Process 8

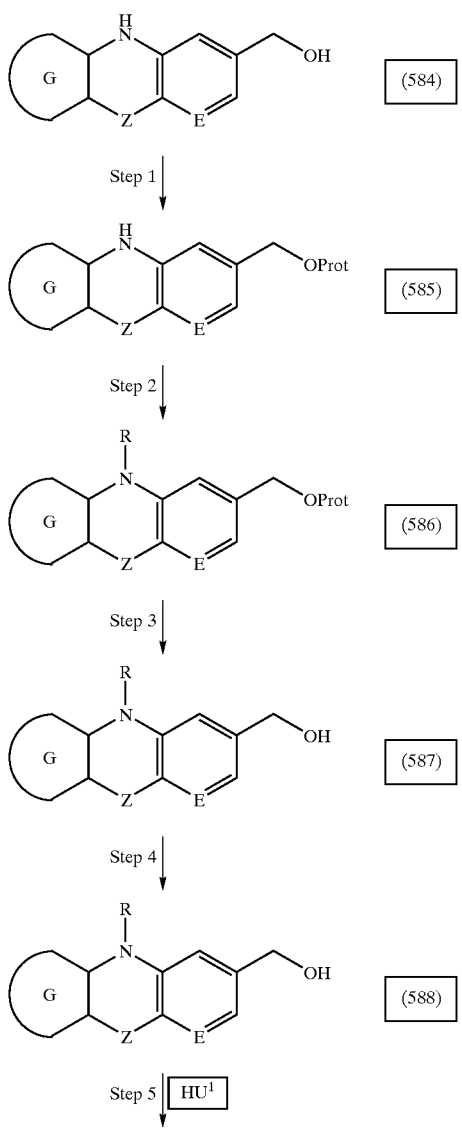

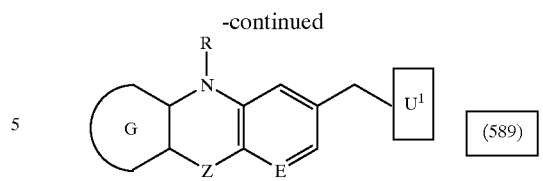

wherein the ring G, E, Z, R' and $U^1$ are as defined above.

(Step 1)

This step comprises protecting the hydroxyl group of a compound represented by the general formula (584) to thereby give a compound represented by the general formula (585). Although the protective group is nonlimitative and any arbitrary group may be used so long as it is known as a hydroxyl protective group in organic synthesis, preferable examples thereof are alkylsilyl groups such as trimethylsilyl, isopropyldimethylsilyl, tert-butyldimethylsilyl and tert-butyldiphenylsilyl. When the protective group is an alkyl-silyl group, the reaction is conducted by treating a compound (584) with an alkylsilyl chloride such as tert-butyldimethylsilyl chloride at a temperature of −50 to 50° C. in a solvent such as N,N-dimethylformamide, N,N-dimethylacetamide, tetrahydrofuran or dioxane in the presence of a base such as imidazole, pyridine or dimethylpyridine.

(Step 2)

This step comprises introducing a lower alkyl group, optionally substaituted arylalkyl gorup, optionally substituted heteroaryl group, amino protective group, group represented by $—X^3—NR^9R^{10}$; wherein $X^3$, $R^9$ and $R^{10}$ are as defined above, group represented by $—X^4—CO_2R^{11}$; wherein $X^4$ and $R^{11}$ are as defined above, into the NH group of the compound represented by the general formula (585). The reaction is conducted in the conventional method.

(Step 3)

This step comprises eliminating the hydroxyl protective group of the compound represented by the general formula (586). When the protective group is an alkylsilyl group, this reaction is conducted by using potassium carbonate/methanol, acetic acid/water, boron trifluoride etherate/chloroform, tetra-n-butylammonium chloride/potassium fluoride/acetonitrile, or tetra-n-butylammonium fluoride/dioxane or tetrahydrofuran, among which preferred is tetra-n-butylammonium fluoride/tetrahydrofuran. The reaction temperature ranges from 0 to 50° C.

(Step 4)

This step comprises oxidizing the hydroxymethyl group of the compound represented by the general formula (587) to thereby give an aldehyde represented by the general formula (588). The aldehyde is obtained by adding a solution of the alcohol represented by the formula (587) in a solvent such as methylene chloride to a liquid reaction mixture prepared from oxalyl chloride and dimethyl sulfoxide and treating the resultant mixture with a base such as triethylamine, by treating the above solution of the alcohol with pyridinium dichromate in a solvent such as dichloromethane or N,N-dimethylformamide, or by treating the above solution with manganese dioxide in a solvent such as dichloromethane.

(Step 5)

This step comprises conducting a reductive amination by treating the compound represented by the formula (588) with a secondary amine in the presence of a reducing agent.

The reaction of the aldehyde reprsented by the formula (588) with the secondary amine is conducted in an appropriate solvent such as toluene or benzene at room temperature to the solvent reflux temperature and treating the intermediate thus obtained with an appropriate reducing agent such as sodium borohydride or sodium boron cyanohydride in an appropriate alcoholic solvent such as ethanol or methanol or an appropriate solvent mixture such as ethanol/tetrahydrofuran at a temperature of 50° C. to the solvent reflux temperature to thereby obtain the compound represented by the formula (589).

The compounds of the present invention can be easily produced by the above-mentioned production processes or publicly known processes.

The solvent usable in the present invention described above may be an arbitrary one without restriction so long as it doesn't inhibit the reaction and has been employed commonly in organic synthesis. Examples thereof include lower alcohols such as methanol, ethanol, propanol and butanol; polyalcohols such as ethylene glycol and glycerol; ketones such as acetone, methyl ethyl ketone, diethyl ketone and cyclohexanone; ethers such as diethyl ether, isopropyl ether, tetrahydrofuran, dioxane, 2-methoxyethanol and 1,2-dimethoxyethane; nitriles such as acetonitrile and propionitrile; esters such as methyl acetate, ethyl acetate, isopropyl acetate, butyl acetate and diethyl phthalate; halogenated hydrocarbons such as dichloromethane, chloroform, carbon tetrachloride, 1,2-dichloroethane, trichloroethylene and tetrachloroethylene; aromatic solvents such as benzene, toluene, xylene, monochlorobenzene, nitrobenzene, indene, pyridine, quinoline, collidine and phenol; hydrocarbons such as pentane, cyclohexane, hexane, heptane, octane, isooctane, petroleum benzene and petroleum ether; amines such as ethanolamine, diethylamine, triethylamine, pyrrolidine, piperidine, piperazine, morpholine, aniline, dimethylaniline, benzylamine and toluidine; amides such as formamide, N-methylpyrrolidone, N,N-dimethylimidazolone, N,N-dimethylacetamide and N,N-dimethylformamide; phosphoramides such as hexamethylphosphoric triamide and hexamethylphosphorous triamide; water, other solvents commonly employed in the art and mixtures thereof. The mixing ratio is not particularly restricted.

The base to be used in the present invention, partially above described, may be an arbitrary one without restriction so long as it has been well known as a base for organic synthesis and as it doesn't inhibit the reaction. Examples thereof include sodium carbonate, sodium hydrogencarbonate, potassium carbonate, sodium hydride, potassium hydride, t-butoxypotassium, pyridine, dimethylaminopyridine, trimethylamine, triethylamine, N,N-diisopropylethylamine, N-methylmorpholine, N-methylpyrrolidine, N-methylpiperidine, N,N-dimethylaniline, 1,8-diazabicyclo[5.4.0]undec-7-ene (DBU), pyridine, 4-dimethylaminopyridine, picoline, lutidine, quinoline, isoquinoline, sodium hydroxide, potassium hydroxide, lithium hydroxide, butyllithium and, sodium and potassium alcoholates such as sodium methylate and potassium methylate.

As the halogenation agent, use can be made of an arbitrary one commonly employed in the synthesis of acid halides. Examples thereof include phosgene, diphosgene (phosgene dimer), triphosgene (phosgene trimer), thionyl chloride, thionyl bromide, phosphorus trichloride, phosphorus tribromide, phosphorus oxychloride, phosphorus pentachloride, trichloromethyl chloroformate, oxalyl chloride and Vilsmeier reagents obtained by treating acid amides or phosphoramide with these halogenation agents.

The reducing agent is not particularly restricted but may be an arbitrary one commonly employed in organic synthesis. Examples thereof include $NaBH_4$, $LIBH_4$, $Zn(BH_4)_2$, $Me_4NBH$ $(OAc)_3$, $NaBH_3CN$, Selctride, Super Hydride $(LiBHEt_3)$, $LiAlH_4$, DIBAL, $LiAlH(t-BuO)_3$, Red-al, binap, and catalytic hydrogenation catalysts of platinum, palladium, rhodium, ruthenium, nickel, etc.

After the completion of these reactions, the products may be purified by conventional procedures, for example, column chromatography with the use of silica gel, adsorbent resins, etc. or recrystallization from appropriate solvents, if desired.

To illustrate the usefulness of the present invention, the following pharmacological experimental examples will be given.

EXPERIMENTAL EXAMPLE 1

Effect on the Expression of ICAM-1 in Human Cultured Umbilical Cord Endothelial Cells Examination was made on the effect on the expression of ICAM-1 which is one of adhesion molecules expressed on the surfaces of cultured endothelia cells. The endotheliall cells were suspended in an MCDB131 medium containing 10% of fetal calf serum and pipetted into a 96-well culture plate (10,000 cells/well). After culturing at 37° C. in the presence of 5% of carbon dioxide for 2 days, 1 ng/ml of a tumor necrosis factor (TNF) and a test compound were added to the 96-well culture plate. After culturing at 37° C. in the presence of 5% of carbon dioxide for 4 hours and then washing with a phosphate buffer once, 0.05% of glutaraldehyde was added thereto. Six minutes thereafter, the plate was washed twice and 1 $\mu$g/ml of a mouse antihuman ICAM-1 antibody was added thereto. After allowing to stand for 1 hour, it was washed twice and a peroxidase-labeled sheep antimouse immunoglobulin antibody was added thereto. After allowing to stand for 1 hour, it was washed twice and a color developing substrate for peroxidase (o-phenylenediamine) was added thereto. After allowing to stand at room temperature for 10 minutes, a 1 N solution of sulfuric acid was added thereto. Then the absorbance at 490 nm was measured with the use of an absorptiometer for 96-well plate. The value thus obtained was employed as an indication of the ICAM-1 expression.

The following Table 1 shows the 50% inhibitory concentrations ($IC_{50}$; $\mu$M) calculated by taking the expression dose under the addition of TNF as 100% and that under the addition of no TNF as 0%.

TABLE 1

| Compd. (Ex. No.) | $IC_{50}$ ($\mu$M) |
| --- | --- |
| 15 | 2.3 |
| 18 | 3.5 |
| 23 | 1.6 |
| 24 | 4.1 |
| 30 | 0.5 |
| 31 | 1.1 |
| 70 | 2.8 |
| 71 | 0.8 |
| 73 | 0.6 |
| 74 | 1.9 |
| 75 | 2.4 |
| 77 | 2.8 |
| 78 | 1.4 |
| 78 | 0.5 |
| 80 | 4.1 |
| 82 | 3.4 |
| 83 | 2.8 |
| 85 | 6.4 |
| 87 | 2.9 |

TABLE 1-continued

| Compd. (Ex. No.) | IC$_{50}$ ($\mu$M) |
|---|---|
| 88 | 2.6 |
| 89 | 2.8 |
| 90 | 2.8 |
| 91 | 2.9 |
| 98 | 2.4 |
| 100 | 3.8 |
| 101 | 2.6 |
| 102 | 2.6 |
| 103 | 6.6 |
| 104 | 2.8 |
| 105 | 5.8 |
| 106 | 2.8 |
| 107 | 3.3 |
| 113 | 2.5 |
| 118 | 1.6 |
| 121 | 7.4 |
| 402 | 0.32 |
| 403 | 0.34 |
| 460 | 0.32 |
| 659 | 0.71 |
| 677 | 0.90 |
| 686 | 0.90 |
| 698 | 0.49 |
| 717 | 1.15 |
| 729 | 1.30 |
| 901 | 1.8 |
| 1145 | 0.77 |
| 1241 | 3.6 |
| 1409 | 0.67 |
| 1439 | 0.49 |
| 1487 | 0.67 |
| 1568 | 0.5 |

EXPERIMENTAL EXAMPLE 2

Effect on Carrageenin-induced Rat Pleurisy

200 μl of a carrageenin solution (10 mg/ml in physiological saline) was intrathoracically injected into rats. Five hours thereafter, blood of the animals was collected from the abdominal aorta under etherization so as to induce death from blood loss. The exudate was taken up from the thoracic cavity and weighed with a single-pan balance. Further, the exudate was diluted with Turk's solution and the cells were counted by using a counting chamber. Next the total cell count was calculated by multiplying the cell count by the exudate volume. Thus the inhibitory ratio was calculated by taking the total cell count with the administration of carrageenin as 100% and that with the administration of physiological saline as 0%. Each test compound was suspended in a 0.5% solution of methylcellulose and orally administered at a dose of 5 ml/kg 30 minutes before the injection of carrageenin. Table 2 shows the results.

TABLE 2

| Compd. (Ex. No.) | Dose (mg/kg) | Inhibitory ratio (%) | Compd. (Ex. No.) | Dose (mg/kg) | Inhibitory ratio (%) |
|---|---|---|---|---|---|
| 15 | 10 | 64 | 121 | 10 | 70 |
| 18 | 10 | 67 | 402 | 10 | 57 |
| 23 | 10 | 52 | 403 | 10 | 35 |
| 24 | 10 | 54 | 460 | 10 | 57 |
| 30 | 10 | 85 | 659 | 10 | 20 |

TABLE 2-continued

| Compd. (Ex. No.) | Dose (mg/kg) | Inhibitory ratio (%) | Compd. (Ex. No.) | Dose (mg/kg) | Inhibitory ratio (%) |
|---|---|---|---|---|---|
| 31 | 10 | 38 | 677 | 10 | 76 |
| 71 | 10 | 94 | 686 | 10 | 71 |
| 73 | 10 | 74 | 698 | 10 | 26 |
| 79 | 10 | 44 | 717 | 10 | 32 |
| 83 | 10 | 34 | 729 | 10 | 64 |
| 88 | 10 | 65 | 901 | 30 | 38 |
| 89 | 10 | 83 | 1145 | 10 | 29 |
| 91 | 10 | 76 | 1241 | 100 | 28 |
| 98 | 10 | 30 | 1439 | 30 | 77 |
| 101 | 10 | 48 | 1487 | 30 | 32 |
| 106 | 10 | 46 | 1568 | 30 | 50 |

As described above, the compounds of the present invention have excellent anti-immune effect and, therefore, are highly useful as preventives and remedies for inflammatory immune diseases or autoimmune diseases, in particular, as preventives and remedies for rheumatism, atopic dermatitis, psoriasis, asthma and the rejection reaction accompanying organ transplantation.

As the above experimental examples show, the compounds of the present invention inhibit the functions of adhesion molecules and thus exhibit anti-immune and anti-inflammatory effects. Accordingly, they are useful as preventives and remedies for inflammatory immune diseases such as inflammation, ischemic reflow disorders and the rejection reaction accompanying organ transplantation, autoimmune diseases such as rheumatism and collagen disease and cancer metastasis. More particularly, these compounds are useful as preventives and remedies for asthma, nephritis, ischemic reflow disorders, psoriasis, atopic dermatitis, rheumatism, collagen disease, the rejection reaction accompanying organ transplantation and cancer metastasis.

Of them, particularly useful compounds are as follows:

1) (endo, syn)-[3-(10H-pyrazino[2,3-b][1,4]benzothiazin-8-ylmethyl)-3-azabicyclo[3.3.1]non-9-yl]acetic acid;
2) (endo, anti)-[3-(10H-pyrazino[2,3-b][1,4]benzothiazin-8-ylmethyl)-3-azabicyclo[3.3.1]non-9-yl]acetic acid;
3) (+)-(anti)-(6R*,7R*)-[3-(10H-pyrazino[2,3-b][1,4]benzothiazin-8-ylmethyl)-6,7-dimethyl-3-azabicyclo[3.2.1]oct-8-yl]acetic acid;
4) (−)-(anti)-(6R*,7R*)-[3-(10H-pyrazino[2,3-b][1,4]benzothiazin-8-ylmethyl)-6,7-dimethyl-3-azabicyclo[3.2.1]oct-8-yl]acetic acid;
5) (+)-(anti)-(6R*,8R*)-2-[3-(10H-pyrazino[2,3-b][1,4]benzothiazin-8-ylmethyl)-6,8-dimethyl-3-azabicyclo[3.3.1]non-9-yl]propanoic acid; and
6) (−)-(anti)-(6R*,8R*)-2-[3-(10H-pyrazino[2,3-b][1,4]benzothiazin-8-ylmethyl)-6,8-dimethyl-3-azabicyclo[3.3.1]non-9-yl]propanoic acid.

EXAMPLES

To further illustrate the present invention in greater detail, and not by way of limitation, the following Examples will be given.

Example 1

Methyl 10H-pyrazino[2,3-b][1,4]benzothiazine-8-carboxylate

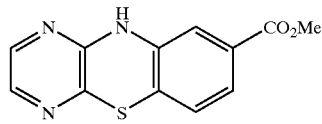

600 g of sodium sulfide nonahydrate and 80 g of flower of sulfur was heated to prepare a homogeneous solution of disodium disulfide. To a suspension of 4-chloro-3-nitrobenzoic acid in ethanol (2,250 ml) was added a solution of 67 g of sodium hydroxide in water (125 ml). To the mixture obtained was added the solution prepared above under stirring and the resulting mixture was heated under reflux for 30 minutes. Next, the reaction mixture was brought back to room temperature and the crystals formed were taken up by filtration and air-dried to thereby give 450 g of dark green powdery crystals. By repeating the same procedure, 4.67 kg of dark green crystals were obtained from 5.20 kg of 4-chloro-3-nitrobenzoic acid.

500 g of the crystals thus obtained and 1220 g of tin dust were suspended in 2,800 ml of ethanol and conc. hydrochloric acid was added dropwise thereinto until the reaction was completed. After completion of the reaction, the tin residue was eliminated and the solvent was reduced to a small volume through distillation under reduced pressure. After adding conc. hydrochloric acid and ethanol to the residue, the crystals thus precipitated were taken up by filtration and air-dried to thereby give 300 g of a pale yellow powder. By repeating the same procedure, 2.79 kg of the product was obtained from 4.67 kg of the starting material. 2,400 ml of methanol was saturated with hydrogen chloride gas and 800 g of the above-mentioned pale yellow powder was added thereto. After heating under reflux for 7 hours, the solvent was completely distilled off to dryness to thereby give 950 g of pale yellow crystals. By repeating the same procedure, 3.70 kg of the product was obtained from 2.79 kg of the starting material.

1.0 kg of the crystals obtained were suspended in 1000 ml of N,N-dimethylformamide and 800 g of 2,3-dichloropyrazine was added dropwise thereinto with stirring. After the completion of the addition, the mixture was further reacted at 100° C. for 30 minutes and then brought back to room temperature. After adding 2 l of water to the reaction system, the crystals thus precipitated were taken up by filtration and washed successively with water and diethyl ether to thereby give 400 g of the title compound as a yellow powder.

$^1$H-NMR(DMSO-$d_6$) δ ppm; 3.78(s, 3H), 7.02(d, J=8.2 Hz, 1H), 7.29(dd, J=1.9, 8.2 Hz, 1H), 7.31(d, J=1.9 Hz, 1H), 7.64(d, J=2.9 Hz, 1H), 7.65(d, J=2.9 Hz, 1H), 9.63(s, 1H)

m.p.: 265–268° C.

MS: FAB(+)259(M$^+$)

Example 2

10H-Pyrazino[2,3-b][1,4]benzothiazine-8-methanol

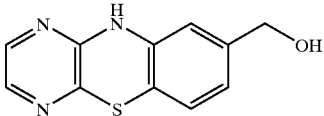

259 g of methyl 10H-pyrazino[2,3-b][1,4]benzothiazine-8-carboxylate was dissolved in a solvent mixture of 3 l of methylene chloride with 0.5 l of tetrahydrofuran under a nitrogen atmosphere. Next, 2.5 l of a 1.01 M solution of diisobutylaluminum hydride in toluene was added dropwise thereinto while cooling the mixture so as to maintain the temperature in the system at 15° C. or below. After the completion of the reaction, the reaction mixture was poured into a mixture of 5 kg of ice with 3 l of methylene chloride. After adding 5 l of tetrahydrofuran, the resulting mixture was stirred for 1 hour. Then it was filtered and the filtrate was washed with water. After distilling off the solvent under reduced pressure, the obtained crystals were washed with diisopropyl ether to thereby give 125 g of the title compound as yellow crystals.

$^1$H-NMR(DMSO-$d_6$δ ppm; 4.30(d, J=6.0 Hz, 2H), 5.17(t, J=6.0 Hz, 1H), 6.70(d, J=7.9 Hz, 1H), 6.75(s, 1H), 6.83(d, J=7.9 Hz, 1H), 7.61(d, J=2.6 Hz, 1H), 7.63(d, J=2.6 Hz, 1H), 9.50(s, 1H)

m.p.: 187–189° C.

Example 3

10H-Pyrazino[2,3-b][1,4]benzothiazine-8-methanol

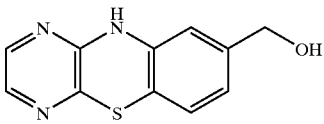

Into a solution of 40 g of lithium aluminum lithium hydride in tetrahydrofuran (1 l) was dropped a solution of 200 g of methyl 10H-pyrazino[2,3-b][1,4]benzothiazine-8-carboxylate in tetrahydrofuran (2.5 l) while maintaining the mixture at a temperature not exceeding 15° C. After continuing the reaction at 15° C. or below for 1 hour, 40 ml of water, 40 ml of a 15% aqueous solution of sodium hydroxide and 120 ml of water were successively added and the resulting mixture was stirred for an additional 1 hour. After filtering off the insoluble matter, the solvent was distilled off under reduced pressure to thereby give 125 g of the title compound as yellow crystals.

$^1$H-NMR(DMSO-$d_6$) δ ppm; 4.30(d, J=6.0 Hz, 2H), 5.17 (t, J=6.0 Hz, 1H), 6.70(d, J=7.9 Hz, 1H), 6.75(s, 1H), 6.83(d, J=7.9 Hz, 1H), 7.61(d, J=2.6 Hz, 1H), 7.63(d, J=2.6 Hz, 1H), 9.50(s, 1H)

m.p.: 187–189° C.

MS: FAB(+)231(M$^+$)

Example 4

8-Chloromethyl-10H-pyrazino[2,3-b][1,4] benzothiazine

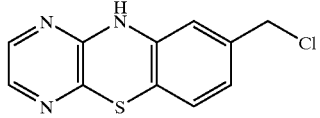

Into a solution of 7 g of 10H-pyrazino[2,3-b][1,4]benzothiazine-8-methanol and 6.1 ml of pyridine in N,N-dimethylformamide (50 ml) was added dropwise 5.9 ml of methanesulfonyl chloride at 0° C. After stirring at room temperature for 1 hour, the reaction mixture was poured into a pre-cooled aqueous solution of methylene chloride/sodium hydrogencarbonate, extracted with ethyl acetate, washed with water and dried over anhydrous sodium sulfate. After distilling off the solvent under reduced pressure, the crystals thus precipitated were diluted with a small amount of ethyl acetate, taken up by filtration and washed with diethyl ether. Thus 4.7 g of the title compound was obtained as a yellow powder.

$^1$H-NMR(DMSO-$d_6$) δ ppm; 4.58(s, 2H), 6.78–6.80(m, 1H), 6.80–6.84(m, H), 6.90(dd, J=1.7, 7.9 Hz, 1H), 7.63–7.66(m, 2H), 9.58(s, 1H)

m.p.: 161–162° C.

MS: FAB(+)249(M$^+$)

Example 5

Methyl 10-methoxymethyl-10H-pyrazino[2,3-b][1,4]benzothiazine-8-carboxylate

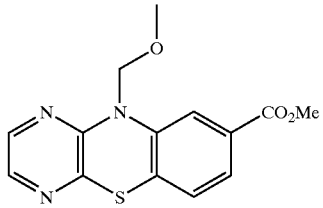

415 g of methyl 10H-pyrazino[2,3-b][1,4]benzothiazine-8-carboxylate was suspended in 2.5 l of N,N-dimethylformamide in a nitrogen atmosphere. Then 66 g of sodium hydride (oily: 60% or more) was added in portions thereto while maintaining the mixture at −10 to 0° C. Then the resulting mixture was stirred for 1 hour. Next, 110 g of chloromethyl methyl ether was dropped thereinto while maintaining the mixture at a temperature not exceeding 5° C. After the completion of the reaction, the reaction mixture was poured into ice, extracted with methylene chloride twice, washed with water and dried over anhydrous sodium sulfate. After distilling off the solvent under reduced pressure, diisopropyl ether was added to the residues and the crystals thus precipitated were taken up by filtration to thereby give 335 g of the title compound as yellow crystals.

$^1$H-NMR(CDCl$_3$) δ ppm; 3.55(s, 3H), 3.91(s, 3H), 5.30(s, 2H), 7.55(d, J=8.5 Hz, 1H), 7.61(d, J=8.5 Hz, 1H), 7.74(s, 1H), 7.85(s, 2H)

m.p.: 151–152° C.

MS: FAB(+)303(M$^+$)

Example 6

10-Methoxymethyl-10H-pyrazino[2,3-b][1,4]benzothiazine-8-methanol

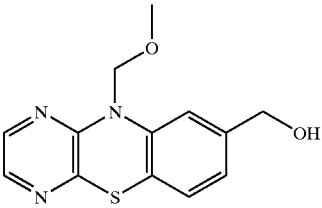

Into a solution of 350 g of methyl 10-methoxymethyl-10H-pyrazino[2,3-b][1,4]benzothiazine-8-carboxylate in methylene chloride (2.5 l) was added dropwise under a nitrogen atmosphere 3.2 l of a 1.01 M solution of diisobutylaluminum hydride in toluene while maintaining the system at a temperature not exceeding 15° C. Then the reaction mixture was poured into ice and stirred for 1 hour. After filtering off the insoluble matter, the filtrate was washed with water. After distilling off the solvent under reduced pressure, the crude crystals thus obtained were washed with diisopropyl ether to thereby give 250 g of the title compound as pale yellow crystals.

$^1$H-NMR(CDCl$_3$) δ ppm; 3.53(s, 3H), 4.63(s, 2H), 5.29(s, 2H), 6.97(dd, J=1.3, 7.9 Hz, 1H), 7.01(d, J=7.9 Hz, 1H), 7.15(d, J=1.3 Hz, 1H), 7.84(d, J=2.9 Hz, 1H), 7.85(d, J=2.9 Hz, 1H)

Example 7

8-Chloromethyl-10-methoxymethyl-10H-pyrazino[2,3-b][1,4]benzothiazine

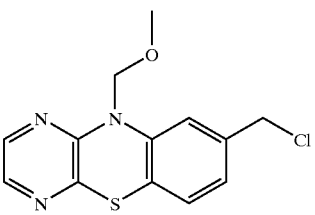

Into a solution of 19 g of 10-methoxymethyl-10H-pyrazino[2,3-b][1,4]benzothiazine-8-methanol and 13.9 ml of pyridine in N,N-dimethylformamide (150 ml) was added dropwise under a nitrogen atmosphere 13.3 ml of methanesulfonyl chloride at 0° C. Then the reaction mixture was stirred at room temperature for 1 hour and then poured into a pre-cooled aqueous solution of methylene chloride/sodium hydrogen carbonate. Then it was extracted with ethyl acetate, washed with water and dried over anhydrous sodium sulfate. After distilling off the solvent under reduced pressure, the residue was purified by silica gel column chromatography (eluted with methylene chloride) to thereby give 13.6 g of the title compound as pale yellow crystals.

$^1$H-NMR(CDCl$_3$) δ ppm; 3.55(s, 3H), 4.52(s, 2H), 5.29(s, 2H), 6.99(d, J=7.6 Hz, 1H), 7.00(d, J=7.6 Hz, 1H), 7.16(s, 1H), 7.84(d, J=2.9 Hz, 1H), 7.85(d, J=2.9 Hz, 1H)

m.p. 125–126° C.

MS: FAB(+)293(M$^+$)

Example 8

8-Chloromethyl-10H-pyrazino[2,3-b][1,4] benzothiazine

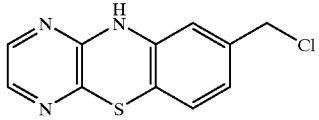

6 g of 8-chloromethyl-10-methoxymethyl-10H-pyrazino [2,3-b][1,4]benzothiazine was dissolved in 50 ml of tetrahydrofuran and 20 ml of 6 N hydrochloric acid was added thereto at 0° C. After stirring at room temperature for 30 minutes, the reaction mixture was poured into ice-water and extracted with ethyl acetate. The extract was washed with water, dried over anhydrous magnesium sulfate, filtered and concentrated under reduced pressure. The crystals precipitating in the course of the concentration were taken up by filtration and washed with diethyl ether to thereby give 4.8 g of the title compound as yellow crystals.

$^1$H-NMR(DMSO-d$_6$) δ ppm; 4.58(s, 2H), 6.78–6.80(m, 1H), 6.80–6.84(m, 1H), 6.90(dd, J=1.7, 7.9 Hz, 1H), 7.63–7.66(m, 2H), 9.58(s, 1H)

m.p.: 161–162° C.

MS: FAB(+)249(M$^+$)

Example 9

8-Chloromethyl-10H-pyrazino[2,3-b][1,4] benzothiazine

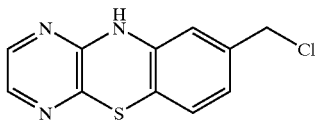

Into 250 ml of a solution of 26.9 g of 8-chloromethyl-10-methoxymethyl-10H-pyrazino[2,3-b][1,4]benzothiazine in methylene chloride was dropped 50 ml of trifluoroacetic acid at 0° C. After reacting at room temperature for 12 hours, the reaction mixture was cooled to 0° C. and neutralized by adding an aqueous solution of sodium hydrogencarbonate. The crystals thus precipitated were taken up by filtration and washed successively with water and diethyl ether to thereby give 19.1 g of the title compound as yellow crystals.

$^1$H-NMR(DMSO-d$_6$) δ ppm; 4.58(s, 2H), 6.78–6.80(m, 1H), 6.80–6.84(m, 1H), 6.90(dd, J=1.7, 7.9 Hz, 1H), 7.63–7.66(m, 2H), 9.58(s, 1H)

m.p.: 161–162° C.

MS: FAB(+)249(M$^+$)

Example 10

Methyl (syn)-(3-methyl-3-azabicyclo[3.3.1]non-9-yl)acetate oxalate

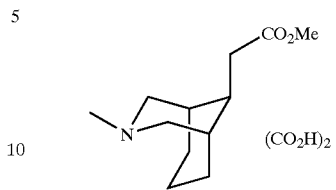

37.13 g of ethyl (3-methyl-3-azabicyclo[3.3.1]non-9-ylidene)acetate was dissolved in 815 ml of methanol. After adding 20.24 g of magnesium, the resulting mixture was stirred at room temperature for 18 hours. Then a saturated aqueous solution of ammonium chloride was added to the reaction mixture followed by extraction with ethyl acetate. The ethyl acetate layer was washed successively with water and a saturated aqueous solution of sodium chloride and dried over anhydrous magnesium sulfate. After concentrating the solvent under reduced pressure, 34.32 g of crude methyl (3-methyl-3-azabicyclo[3.3.1]non-9-yl)acetate was obtained.

34.32 g of this oily substance was dissolved in 343 ml of ethanol. After adding 19.58 g of oxalic acid dehydrate, the resulting mixture was allowed to stand at room temperature. The crystals thus precipitated were recrystallized from 550 ml of ethanol to thereby give 17.76 g of the title compound as white needles.

$^1$H-NMR(DMSO-d$_6$) δ ppm; 1.51(m, 1H), 1.64–1.75(m, 2H), 1.78–1.86(m, 4H), 1.96(m, 1H), 2.07(m, 1H), 2.60(d, J=8.6 Hz, 2H), 2.61(s, 3H), 2.88–2.96(m, 2H), 3.16–3.24(m, 2H), 3.61(s, 3H)

m.p.: 181–185° C. (decomp.)

Example 11

Ethyl (syn)-(3-methyl-3-azabicyclo[3.3.1]non-9-yl) acetate

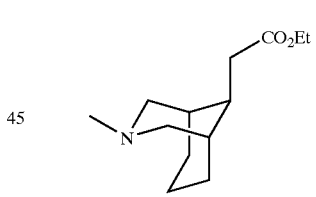

67.36 g of methyl (syn)-(3-methyl-3-azabicyclo[3.3.1] non-9-yl)acetate oxalate was dissolved in water and the solution made basic by adding aqueous ammonia. Then it was extracted with ethyl acetate. The ethyl acetate layer was washed successively with water and a saturated aqueous solution of sodium chloride and dried over anhydrous magnesium sulfate. After concentrating the solvent under reduced pressure, 46.64 g of crude methyl (syn)-(3-methyl-3-azabicyclo[3.3.1]non-9-yl)acetate was obtained.

46.64 g of this oily substance was dissolved in 500 ml of ethanol. After adding 100 ml of 4 N hydrogen chloride/dioxane, the resulting mixture was heated under reflux for 8 hours. Then the reaction mixture was concentrated under reduced pressure. After adding water, the residue was made basic by adding aqueous ammonia and then extracted with ethyl acetate. The ethyl acetate layer was washed with water and a saturated aqueous solution of sodium chloride and dried over anhydrous magnesium sulfate. After concentrating the solvent under reduced pressure, 45.50 g of the title compound was obtained as a slightly yellow oily substance.

$^1$H-NMR(CDCl$_3$) δ ppm; 1.26(t, J=7.1 Hz, 3H), 1.46(m, 1H), 1.55–1.76(m, 4H), 1.78–1.88(m, 2H), 2.00(m, 1H), 2.13(s, 3H), 2.32–2.38(m, 2H), 2.41(d, J=7.9 Hz, 2H), 2.46(m, 1H), 2.57–2.65(m, 2H), 4.12(q, J=7.1 Hz, 2H)

Example 12

Ethyl (syn)-[3-(vinyloxycarbonyl)-3-azabicyclo [3.3.1]non-9-yl]acetate

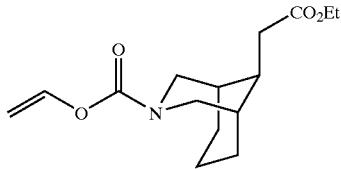

45.50 g of ethyl (syn)-(3-methyl-3-azabicyclo[3.3.1]non-9-yl)acetate was dissolved in 155 ml of 1,2-dichloroethane. After adding 51.6 ml of vinyl chloroformate, the resulting mixture was stirred at room temperature for 45 minutes and then heated under reflux for 4 hours. Next, the reaction mixture was concentrated under reduced pressure and the residue was purified by silica gel column chromatography (eluted with toluene/ethyl acetate) to thereby give 37.63 g of the title compound as a slightly yellow oily substance.

$^1$H-NMR(CDCl$_3$) δ ppm; 1.26(t, J=7.1 Hz, 3H), 1.52(m, 1H), 1.66–1.82(m, 5H), 1.84–1.93(m, 2H), 2.16(m, 1H), 2.46(d, J=7.9 Hz, 2H), 3.23(m, 1H), 3.33(m, 1H), 3.88–3.96 (m, 2H), 4.15(q, J=7.1 Hz, 2H), 4.45(dd, J=1.6, 6.3 Hz, 1H), 4.79(dd, J=1.6, 13.9 Hz, 1H), 7.25(dd, J=6.3, 13.9 Hz, 1H)

Example 13

Ethyl (syn)-(3-azabicyclo[3.3.1]non-9-yl)acetate

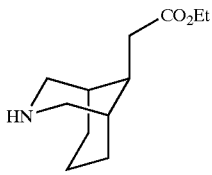

To 37.63 g of ethyl (syn)-[3-(vinyloxycarbonyl)-3-azabicyclo[3.3.1]non-9-yl]acetate was added 150 ml of 4 N-hydrogen chloride/dioxane and the resulting mixture was stirred at room temperature for 1 hour. After adding 300 ml of ethanol, the reaction mixture was heated under reflux for 30 minutes. Then the reaction mixture was concentrated under reduced pressure and the residue was made basic by adding ice-water and aqueous ammonia followed by extraction with methylene chloride. After drying over anhydrous sodium sulfate, the residue was concentrated under reduced pressure to thereby give 27.34 g of the title compound as a pale yellow oily substance.

$^1$H-NMR(CDCl$_3$) δ ppm; 1.26(t, J=7.1 Hz, 3H), 1.54(br.s, 2H), 1.67(m, 1H), 1.76–1.94(m, 4H), 2.10–2.34(m, 3H), 2.55(d, J=7.9 Hz, 2H), 2.81–2.89(m, 2H), 3.14–3.24(m, 2H), 4.13(q, J=7.1 Hz, 2H)

Example 14

Ethyl (syn)-[3-(10H-pyrazino[2,3-b][1,4] benzothiazin-8-ylmethyl)-3-azabicyclo-[3.3.1]non-9-yl]acetate

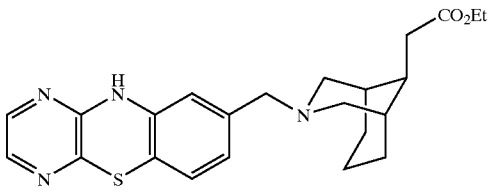

To 300 ml of N,N-dimethylformamide were added 30.79 g of 8-chloromethyl-10H-pyrazino[2,3-b][1,4]-benzothiazine, 27.34 g of ethyl (syn)-(3-azabicyclo[3.3.1]non-9-yl)acetate and 23.65 ml of diisopropylethylamine and the resulting mixture was stirred at 80° C. for 3 hours. Then the reaction mixture was poured into ice/water and extracted with ethyl acetate. The ethyl acetate layer was washed with water and a saturated aqueous solution of sodium chloride, dried over anhydrous magnesium sulfate and concentrated under reduced pressure. The residue was purified by silica gel column chromatography (eluted with toluene/ethyl acetate). Next, it was dissolved in 1 l of ethyl acetate and extracted with 1 N hydrochloric acid. The aqueous layer was made basic with aqueous ammonia and extracted with ethyl acetate. The ethyl acetate layer was washed with water and a saturated aqueous solution of sodium chloride, dried over anhydrous magnesium sulfate and concentrated under reduced pressure. After adding n-hexane, the crystals thus precipitated were taken up by filtration and washed with diisopropyl ether to thereby give 36.99 g of the title compound as a yellow powder.

$^1$H-NMR(CDCl$_3$) δ ppm; 1.25(t, J=7.1 Hz, 3H), 1.55(m, 1H), 1.60–1.86(m, 6H), 2.00–2.08(m, 1H), 2.36–2.47(m, 4H), 2.53–2.68(m, 3H), 3.23(s, 2H), 4.12(q, J=7.1 Hz, 2H), 6.41(br.s, 1H), 6.49(d, J=1.3 Hz, 1H), 6.76(dd, J=1.3, 8.1 Hz, 1H), 6.83(d, J=8.1 Hz, 1H), 7.57(d, J=2.9 Hz, 1H), 7.69(d, J=2.9 Hz, 1H)

m.p.: 114–116° C.

Example 15

(syn)-[3-(10H-Pyrazino[2,3-b][1,4]benzothiazin-8-ylmethyl)-3-azabicyclo[3.3.1]non-9-yl]acetic acid

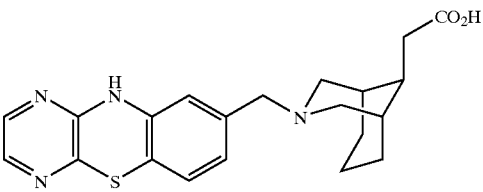

36.00 g of ethyl (syn)-[3-(10H-pyrazino[2,3-b][1,4] benzothiazin-8-ylmethyl)-3-azabicyclo[3.3.1]non-9-yl] acetate was dissolved in tetrahydrofuran (380 ml) and ethanol (380 ml). After adding 187 ml of 1 N sodium hydroxide, the resulting mixture was stirred at room temperature for 15 hours. Then the reaction mixture was concentrated under reduced pressure. After adding 200 ml of water, the residue was concentrated under reduced pressure to thereby reduce the volume by half. After adding 500 ml of water, it was acidified (about pH 5) by adding a solution of sodium dihydrogenphosphate. After adding 800 ml of ethyl acetate and stirring, the crystals thus precipitated were taken up by filtration, washed with water and dried at 50° C. to thereby give 31.2 g of the title compound as a yellow powder.

$^1$H-NMR(DMSO-d$_6$) δ ppm; 1.46(m, 1H), 1.56–1.69(m, 4H), 1.73–1.82(m, 2H), 1.89(m, 1H), 2.30–2.37(m, 4H), 2.53–2.70(m, 3H), 3.18(s, 2H), 6.69(dd, J=1.5, 7.9 Hz, 1H), 6.73(d, J=1.5 Hz, 1H), 6.84(d, J=7.9 Hz, 1H), 7.63(d, J=2.7 Hz, 1H), 7.64(d, J=2.7 Hz, 1H), 9.57(s, 1H)

m.p.: 235–239° C.

MS: FAB(+)397(MH$^+$)

Example 16

Ethyl (anti)-(3-methyl-3-azabicyclo[3.3.1]non-9-yl) acetate

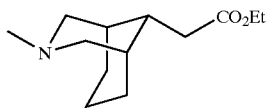

70 g of ethyl (3-methyl-3-azabicyclo[3.3.1]non-9-ylidene)acetate was dissolved in 700 ml of ethanol. After adding 42 ml of conc. Hydrochloric acid and 21 g of 10% palladium-carbon (moisture content: 50%), the mixture was hydrogenated for 12 hours under atmospheric pressure at ordinary temperature. After filtering off the palladium-carbon, the filtrate was concentrated under reduced pressure. Next the residue was made basic by adding an aqueous solution of sodium hydroxide and was extracted with ethyl acetate. The extract was washed with a saturated aqueous solution of sodium chloride and dried over anhydrous magnesium sulfate. After filtering, the solvent was distilled off under reduced pressure to thereby give 65 g of the title compound as a colorless oily substance.

$^1$H-NMR(CDCl$_3$) δ ppm; 1.25(t, J=7 Hz, 3H), 1.30–1.50 (m, 1H), 1.40–1.70(m, 2H), 1.63(br.s, 2H), 1.60–1.93(m, 2H), 1.90–2.05(m, 1H), 2.13(s, 3H) 2.23(br.d, J=10 Hz, 2H), 2.30–2.58(m, 1H), 2.48(d, J=8 Hz, 2H), 2.88(br.d, J=10 Hz, 2H), 4.13(q, J=7 Hz, 2H)

Example 17

Ethyl (anti)-[3-(10H-pyrazino[2,3-b][1,4] benzothiazin-8-ylmethyl)-3-azabicyclo[3.3.1]non-9-yl]acetate

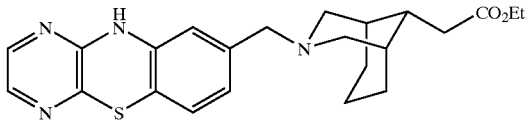

61 g of ethyl (anti)-(3-methyl-3-azabicyclo[3.3.1]non-9-yl)acetate was cooled to 0° C. and 85.2 g of 1-chloroethyl chloroformate was added dropwise thereinto. After stirring at the same temperature for 15 minutes, the reaction mixture was reacted at 100° C. for 1 hour. Then it was brought back to room temperature and the 1-chloroethyl chloroformate was distilled off under reduced pressure. After adding 500 ml of ethanol, the residue was heated under reflux for 1 hour. After distilling off the solvent under reduced pressure, 71 g of crude ethyl (anti)-(3-azabicyclo[3.3.1]non-9-yl)acetate hydrochloride was obtained.

To 500 ml of a solution of this crude product in N,N-dimethylformamide were added 52 g of 8-chloromethyl-10H-pyrazino[2,3-b][1,4]benzothiazine and 115 g of anhydrous potassium carbonate and the resulting mixture was reacted at 100° C. for 4 hours and 30 minutes. Then the reaction mixture was cooled to 0° C., added to a mixture of ice/water with ethyl acetate and extracted with ethyl acetate. The extract was washed with a saturated aqueous solution of sodium chloride and dried over anhydrous magnesium sulfate. After distilling off the solvent under reduced pressure, the obtained residue was purified by silica gel column chromatography (eluted with methylene chloride/ethyl acetate) to thereby give 51 g of the title compound as a yellow powder.

$^1$H-NMR(DMSO-d$_6$) δ ppm; 1.14(t, J=7 Hz, 3H), 1.34–1.48(m, 3H), 1.56(br.s, 2H), 1.60–1.75(m, 2H), 1.82–1.92(m, 1H), 2.15(br.d, J=11 Hz, 2H), 2.43(d, J=8 Hz, 2H), 2.4–2.6(m, 1H), 2.85(br.d, J=9 Hz, 2H), 3.15(s, 2H), 4.02(q, J=7 Hz, 2H), 6.67(dd, J=2, 8 Hz, 1H), 6.71(d, J=2 Hz, 1H), 6.82(d, J=8 Hz, 1H), 7.61(d, J=3 Hz, 1H), 7.62(d, J=3 Hz, 1H), 9.55(s, 1H)

m.p.: 142–143° C.

MS: FAB(+)425(MH$^+$)

Example 18

(anti)-[3-(10H-Pyrazino[2,3-b][1,4]benzothiazin-8-ylmethyl)-3-azabicyclo[3.3.1]non-9-yl]acetic acid

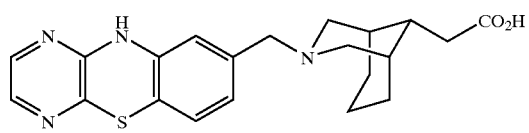

31 g of ethyl (anti)-[3-(10H-pyrazino[2,3-b][1,4) benzothiazin-8-ylmethyl)-3-azabicyclo[3.3.1]non-9-yl] acetate was dissolved in ethanol (150 ml) and tetrahydrofuran (150 ml). After adding 75 ml of an aqueous solution of 8.8 g of sodium hydroxide, the resulting mixture was heated under reflux in a nitrogen atmosphere for 1 hour. Then the reaction mixture was washed with a saturated aqueous solution of sodium chloride, dried over anhydrous magnesium sulfate and filtered. After distilling off the solvent under reduced pressure, the crystals precipitated in the course of the distillation were taken up by filtration to thereby give 18.6 g of the title compound as a yellow powder.

$^1$H-NMR(DMSO-d$_6$) δ ppm; 1.34–1.48(m, 3H), 1.58(br.s, 2H), 1.60–1.76(m, 2H), 1.80–1.90(m, 1H), 2.14(br.d, J=10 Hz, 2H), 2.33(d, J=8 Hz, 2H), 2.44–2.60(m, 1H), 2.85(br.d, J=10 Hz, 2H), 3.15(s, 2H), 6.67(d, J=8 Hz, 1H), 6.72(s, 1H), 6.82(d, J=8 Hz, 1H), 7.60(d, J=3 Hz, 1H), 7.62(d, J=3 Hz, 1H), 9.54(s, 1H)

m.p.: 215–217° C.

MS: FAB(+)397(MH$^+$)

Example 19

Ethyl (±)-(6R*,7R*)-(3,6,7-trimethyl-3-azabicyclo [3.2.1]oct-8-ylidene)acetate

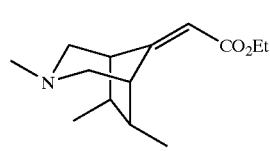

To a solution of 8 g of paraformaldehyde in methanol (100 ml) were added 10 ml of a 40% solution of methylamine in methanol, 7.7 ml of acetic acid and 10 g of 3,4-dimethylcyclopentanone and the resulting mixture was heated under reflux for 1.5 hours. After distilling off the solvent under reduced pressure, the residue was acidified by adding a dilute aqueous solution of hydrochloric acid and then was extracted with ethyl acetate. The aqueous layer was made basic with a dilute aqueous solution of sodium hydroxide and then extracted with ethyl acetate. The organic layer was dried over anhydrous magnesium sulfate and the solvent was distilled off under reduced pressure. Then the obtained residue was distilled under reduced pressure (70–75° C./1 mmHg) to thereby give 2.7 g of crude (6R*,7R*)-3,6,7-trimethyl-3-azabicyclo[3.2.1]octan-8-one as a pale yellow oily substance.

To a solution of 4.35 g of triethyl phosphonoacetate in tetrahydrofuran (50 ml) was added 0.85 g of sodium hydride (oily: 60–72%) under ice-cooling and the resulting mixture was stirred at 0° C. for 10 minutes. Then a solution of 2.7 g of the crude (6R*,7R*)-3,6,7-trimethyl-3-azabicyclo [3.2.1]octan-8-one in tetrahydrofuran (20 ml) was added thereto and the reaction mixture was heated under reflux for 1 hour. After adding ethyl acetate, the reaction mixture was washed with a saturated aqueous solution of sodium chloride and the organic layer was dried over anhydrous magnesium sulfate. After distilling off the solvent under reduced pressure, the residue was purified by silica gel column chromatography (eluted with n-hexane/ethyl acetate) to thereby give 1.6 g of the title compound as a pale yellow oily substance.

$^1$H-NMR(CDCl$_3$) δ ppm; 0.90(d, J=7.2 Hz, 3H), 1.17(d, J=7.2 Hz, 3H), 1.29(t, J=7.2 Hz, 3H), 1.40–1.50(m, 1H), 1.74–1.93(m, 1H), 2.08–2.30(m, 3H), 2.20(s, 3H), 2.80–2.90(m, 1H), 2.90–3.00(m, 1H), 3.35–3.44, 3.50–3.58 (m, total 1H), 4.15(q, J=7.2 Hz, 2H), 5.58, 5.66(s, total 1H)

Example 20

Ethyl (±)-(anti)-(6R*,7R*)-(3,6,7-trimethyl-3-azabicyclo[3.2.1]oct-8-yl)acetate

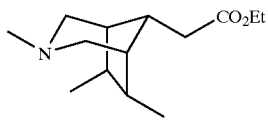

To a solution of 1.6 g of ethyl (6R*,7R*)-(3,6,7-trimethyl-3-azabicyclo[3.2.1]oct-8-ylidene)acetate in methanol (100 ml) was added 0.4 g of 10% palladium-carbon (moisture content: 50%) and the resulting mixture was stirred under a hydrogen gas stream at room temperature overnight. Then the reaction mixture was filtered through celite. After distilling off the solvent under reduced pressure, 1.6 g of the title compound was obtained as a pale yellow oily substance.

$^1$H-NMR(CDCl$_3$) δ ppm; 1.06(d, J=7.2 Hz, 3H), 1.08(d, J=7.2 Hz, 3H), 1.26(t, J=6.4 Hz, 3H), 1.63–1.84(m, 4H), 1.92(t, J=8.0 Hz, 1H), 2.02(d, J=9.6 Hz, 1H), 2.08(d, J=9.6 Hz, 1H), 2.21(s, 3H), 2.37(d, J=8.0 Hz, 2H), 2.67(d, J=9.6 Hz, 1H), 2.85(d, J=9.6 Hz, 1H), 4.13(q, J=6.4 Hz, 2H)

Example 21

Ethyl (±)-(anti)-(6R*,7R*)-[3-(10H-pyrazino[2,3-b] [1,4]benzothiazin-8-ylmethyl)-6,7-dimethyl-3-azabicyclo[3.2.1]oct-8-yl]acetate

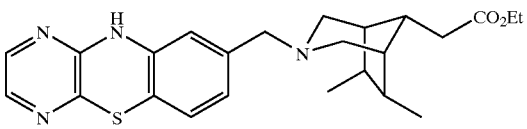

To a solution of 1.6 g of ethyl (anti)-(6R*,7R*)-(3,6,7-trimethyl-3-azabicyclo[3.2.1]oct-8-yl)acetate in 1,2-dichloroethane (70 ml) was added 2.2 ml of 1-chloroethyl chloroformate and the resulting mixture was heated under reflux for 1.5 hours. After distilling off the solvent under reduced pressure, 500 ml of methanol was added to the residue and the mixture was heated under reflux for 1 hour. After distilling off the solvent under reduced pressure, a dilute aqueous solution of sodium hydroxide was added to the residue followed by the extraction with ethyl acetate. The organic layer was dried over anhydrous magnesium sulfate and then the solvent was distilled off under reduced pressure. To a solution of the residue in N,N-dimethylformamide (50 ml) were added 1.1 g of 8-chloromethyl-10H-pyrazino[2,3-b][1,4]benzothiazine and 1.9 g of potassium carbonate and the resulting mixture was stirred for 2 hours at 100° C. After adding ethyl acetate, the reaction mixture was washed with a saturated aqueous solution of sodium chloride thrice and then the organic layer was dried over anhydrous magnesium sulfate. After distilling off the solvent under reduced pressure, the residue was purified by silica gel column chromatography (eluted with methylene chloride/methanol) to thereby give 2.0 g of the title compound as a yellow oily substance.

$^1$H-NMR(CDCl$_3$) δ ppm; 1.06(d, J=7.2 Hz, 3H), 1.09(d, J=7.2 Hz, 3H), 1.25(t, J=7.2 Hz, 3H), 1.60–1.82(m, 4H), 1.96(t, J=8.0 Hz, 1H), 2.05(d, J=9.2 Hz, 1H), 2.13(d, J=9.2 Hz, 1H), 2.37(d, J=7.2 Hz, 2H), 2.64(dd, J=3.6, 9.2 Hz, 1H), 2.84(dd, J=3.6, 9.2 Hz, 1H), 3.24(d, J=13.2 Hz, 1H), 3.36(d, J=13.2 Hz, 1H), 4.13(q, J=7.2 Hz, 2H), 6.49(d, J=1.6 Hz, 1H), 6.52(s, 1H), 6.76(dd, J=1.6, 8.0 Hz, 1H), 6.81(d, J=8.0 Hz, 1H), 7.57(d, J=2.8 Hz, 1H), 7.69(d, J=2.8 Hz, 1H)

Example 22

Ethyl (+)-(anti)-(6R*,7R*)-[3-(10H-pyrazino[2,3-b] [1,4]benzothiazin-8-ylmethyl)-6,7-dimethyl-3-azabicyclo[3.2.1]oct-8-yl]acetate and ethyl (−)-(anti)-(6R*,7R*)-[3-(10H-pyrazino[2,3-b][1,4] benzothiazin-8-ylmethyl)-6,7-dimethyl-3-azabicyclo [3.2.1]oct-8-yl]acetate 0.2 g of ethyl (±)-(anti)-(6R*,7R*)-[3-(10H-pyrazino[2,3-b][1,4]benzothiazin-8-ylmethyl)-6,7-dimethyl-3-azabicyclo-[3.2.1]oct-8-yl]acetate was dissolved in ethanol (5 ml) and n-hexane (5 ml) and the enantiomers were resolved by using CHIRALPAK AD [20 (diameter)×250 mm; mfd. by Daicel Chemical Industries, Ltd.; eluted with ethanol at 10 ml/min]. Thus the (+)-compound was eluted first followed by the (−)-compound. From 1.4 g of the racemic modification, 0.59 g (99% e.e. or above) and 0.52 g (98.7% e.e.) of the (+)- and (−)-compounds were obtained respectively each as a yellow oily substance.

(+)-compound: $\alpha^{25}_D$+20.6° (c=1.02 THF)

(−)-compound: $\alpha^{25}_D$−19.7° (c=1.01 THF)

Example 23

(+)-(anti)-(6R*,7R*)-[3-(10H-Pyrazino[2,3-b][1,4]
benzothiazin-8-ylmethyl)-6,7-dimethyl-3-azabicyclo
[3.2.1]oct-8-yl]acetic acid

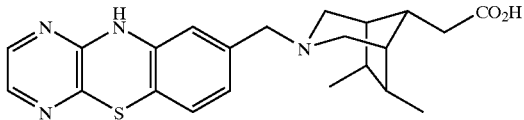

To a solution of 0.575 g of ethyl (+)-(anti)-(6R*,7R*)-
[3-(10H-pyrazino[2,3-b][1,4]benzothiazin-8-ylmethyl)-6,7-
dimethyl-3-azabicyclo[3.2.1]oct-8-yl]acetate in a solvent.
mixture of tetrahydrofuran (10 ml) with methanol (10 ml)
was added 2 ml of a 4 N aqueous solution of sodium
hydroxide and the resulting mixture was stirred at 60° C. for
50 minutes. After further adding 1 ml of a 4 N aqueous
solution of sodium hydroxide, the resulting mixture was
reacted at the same temperature for 30 minutes. After the
completion of the reaction, the solvent was distilled off
under reduced pressure and the residue was suspended in
water. The pH value thereof was regulated to 5 with a 1 N
aqueous solution of hydrochloric acid then the mixture was
extracted with ethyl acetate. The extract was dried over
anhydrous magnesium sulfate and concentrated under
reduced pressure. Then the residue was purified by silica gel
column chromatography (eluted with methylene chloride/
methanol) to thereby give 0.49 g of the title compound as
yellow crystals.

$^1$H-NMR(DMSO-$d_6$) δ ppm; 1.01(d, J=7.2 Hz, 3H), 1.05
(d, J=7.2 Hz, 3H), 1.60–1.80(m, 4H), 1.83(t, J=7.2 Hz, 1H),
1.97(d, J=10 Hz, 1H), 2.04(d, J=10 Hz, 1H), 2.27(d, J=7.6
Hz, 2H), 2.59(dd, J=4.0, 10 Hz, 1H), 2.78(dd, J=2.8, 10 Hz,
1H), 3.21(d, J=13.2 Hz, 1H), 3.30(d, J=13.2 Hz, 1H), 6.70(d,
J=8.0 Hz, 1H), 6.74(br.s, 1H), 6.84(d, J=8.0 Hz, 1H), 7.63(d,
J=2.8 Hz, 1H), 7.65(d, J=2.8 Hz, 1H), 9.55(s, 1H)
$\alpha^{25}_D$+21.2° (c=1.03 THF)
m.p.: 179–180° C.
MS: FAB(+)411(MH$^+$)

Example 24

(−)-(anti)-(6R*,7R*)-[3-(10H-Pyrazino[2,3-b][1,4]
benzothiazin-8-ylmethyl)-6,7-dimethyl-3-azabicyclo
[3.2.1]oct-8-yl]acetic acid

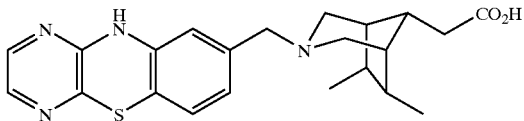

0.277 g of the title compound was obtained as yellow
crystals by treating 0.509 g of ethyl (−)-(anti)-(6R*,7R*)-
[3-(10H-pyrazino[2,3-b][1,4]benzothiazin-8-ylmethyl)-6,7-
dimethyl-3-azabicyclo[3.2.1]oct-8-yl]acetate in the same
manner as described in Example 23.

$^1$H-NMR(DMSO-$d_6$) δ ppm; 1.01(d, J=7.2 Hz, 3H), 1.05
(d, J=7.2 Hz, 3H), 1.60–1.80(m, 4H), 1.83(t, J=7.2 Hz, 1H),
1.97(d, J=10 Hz, 1H), 2.04(d, J=10 Hz, 1H), 2.27(d, J=7.6
Hz, 2H), 2.59(dd, J=4.0, 10 Hz, 1H), 2.78(dd, J=2.8, 10 Hz,
1H), 3.21(d, J=13.2 Hz, 1H), 3.30(d, J=13.2 Hz, 1H), 6.70(d,
J=8.0 Hz, 1H), 6.74(br.s, 1H), 6.84(d, J=8.0 Hz, 1H), 7.63(d,
J=2.8 Hz, 1H), 7.65(d, J=2.8 Hz, 1H), 9.55(s, 1H)
$\alpha^{25}_D$−21.3° (c=1.01 THF)
m.p.: 179–180° C.
MS: FAB(+)411(MH$^+$)

Example 25

Ethyl (±)-(6R*,8R*)-(3,6,8-trimethyl-3-azabicyclo
[3.3.1]non-9-ylidene)acetate

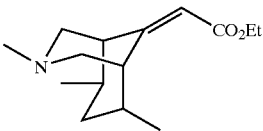

To a solution of 180 g of paraformaldehyde in methanol
(500 ml) were slowly added under ice-cooling 230 ml of a
40% solution of methylamine in methanol and 17 ml of
acetic acid. After adding dropwise a solution of 250 ml of
3,5-dimethylcyclohexanone in methanol (1 l) thereinto, the
resulting mixture was heated under reflux for 5 hours. Then
the reaction mixture was cooled to room temperature and the
solvent was distilled off under reduced pressure. The residue
was acidified by adding dilute hydrochloric acid and then
extracted with ethyl acetate. The aqueous layer was made
basic by adding sodium hydroxide and then extracted with
ethyl acetate. The organic layer was dried over anhydrous
magnesium sulfate and the solvent was distilled off under
reduced pressure. Then the residue was distilled under
reduced pressure (100–110° C./1 mmHg) to thereby give 79
g of crude (6R*,8R*)-3,6,8-trimethyl-3-azabicyclo[3.3.1]
nonan-9-one as a pale yellow oily substance.

To a solution of 130 g of triethyl phosphono acetate in
tetrahydrofuran (600 ml) was added 25 g of sodium hydride
(oily: 60% or above) under ice-cooling and the resulting
mixture was stirred at room temperature for 10 minutes.
Then a solution of 70 g of the crude (6R*,8R*)-3,6,8-
trimethyl-3-azabicyclo[3.3.1]nonan-9-one in tetrahydrofu-
ran (300 ml) was added thereto and the reaction mixture was
heated under reflux for 2 hours. After adding ethyl acetate,
the reaction mixture was washed twice with a saturated
aqueous solution of sodium chloride and the organic layer
was dried over anhydrous magnesium sulfate. After distill-
ing off the solvent under reduced pressure, the residue was
purified by silica gel column chromatography (eluted with
n-hexane/ethyl acetate) to thereby give 31.5 g of the title
compound as a pale yellow oily substance.

$^1$H-NMR(CDCl$_3$) δ ppm; 0.80–1.00(m, 1H), 0.96(d,
J=6.8 Hz, 3H), 1.02(d, J=6.8 Hz, 3H), 1.28(t, J=6.8 Hz, 3H),
1.70–1.77(m, 1H), 1.81–1.86(m, 1H), 2.00–2.12(m, 4H),
2.20(s, 3H), 2.75(m, 2H), 3.58–3.62(m, 1H), 4.16(q, J=6.8
Hz, 2H), 5.66(s, 1H)

Example 26

Ethyl (±)-(anti)-(6R*,8R*)-(3,6,8-trimethyl-3-
azabicyclo[3.3.1]non-9-yl)acetate

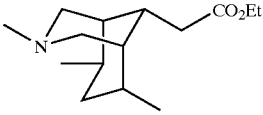

To a solution of 31.5 g of ethyl (±)-(6R*,8R*)-(3,6,8-
trimethyl-3-azabicyclo[3.3.1]non-9-ylidene)acetate in
methanol (300 ml) was added 6 g of 10% palladium-carbon
(moisture content: 50%) and the resulting mixture was
stirred at room temperature for 12 hours under a hydrogen gas stream. Then the reaction mixture was filtered through celite and the solvent was distilled off under reduced pressure. Thus 30.7 g of the title compound was obtained as a pale yellow oily substance.

$^1$H-NMR(CDCl$_3$) δ ppm; 0.80–1.00(m, 1H), 1.02(d, J=6.8 Hz, 6H), 1.28(t, J=6.8 Hz, 3H), 1.38–1.48(m, 2H), 1.70–1.90(m, 2H), 1.92–2.08(m, 2H), 2.10–2.15(m, 2H), 2.22(s, 3H), 2.45(d, J=6.8 Hz, 2H), 2.56–2.70(m, 2H), 4.41(q, J=6.8 Hz, 2H)

Example 27

Ethyl (±)-(anti)-(6R*,8R*)-2-(3,6,8-trimethyl-3-azabicyclo[3.3.1]non-9-yl)propanoate

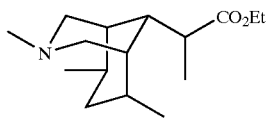

To a solution of 6 g of diisopropylamine in tetrahydrofuran (60 ml) was added 33 ml of a 1.6 M solution of n-butyllithium in hexane at −70° C. and the resulting mixture was stirred at 0° C. for 30 minutes. After recooling to −70° C., a solution of 10.1 g of ethyl (anti)-(6R*,8R*)-2-(3,6,8-trimethyl-3-azabicyclo[3.3.1]non-9-yl)acetate in tetrahydrofuran (40 ml) was added dropwise thereinto and the resulting mixture was stirred at −70° C. for 2 hours. Then 3 ml of methyl iodide was added dropwise into the reaction mixture and the mixture was stirred at −70° C. for 2 hours. After adding a saturated aqueous solution of ammonium chloride, the mixture was extracted with ethyl acetate twice. The organic layer was dried over anhydrous magnesium sulfate and the solvent was distilled off under reduced pressure. Thus 11.2 g of the title compound was obtained as a pale yellow oily substance.

$^1$H-NMR(CDCl$_3$) δ ppm; 0.80–1.00(m, 1H), 1.00(d, J=6.8 Hz, 3H), 1.02(d, J=6.8 Hz, 3H), 1.18(d, J=6.8 Hz, 3H), 1.30(t, J=6.8 Hz, 3H), 1.30–1.40(m, 2H), 1.70–1.85(m, 2H), 1.90–2.00(m, 2H), 2.05–2.16(m, 2H), 2.20(s, 3H), 2.52–2.78(m, 3H), 4.14(q, J=6.8 Hz, 2H)

Example 28

Ethyl (±)-(anti)-(6R*,8R*)-2-[3-10H-pyrazino[2,3-b][1,4]benzothiazin-8-ylmethyl)-6,8-dimethy-3-azabicyclo[3.3.1]non-9-yl)propanoate

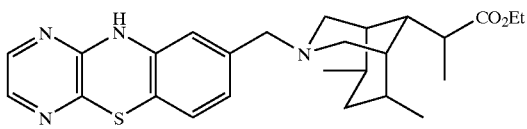

To a solution of 18.2 g of ethyl (anti)-(6R*,8R*)-2-(3,6,8-trimethyl-3-azabicyclo[3.3.1]non-9-yl)propanoate in 1,2-dichloroethane (180 ml) was added 9 ml of 1-chloroethyl chloroformate and the resulting mixture was heated under reflux for 2 hours. After distilling off the solvent under reduced pressure, 200 ml of methanol was added to the residue and the mixture was heated under reflux for 1 hour. After distilling off the solvent under reduced pressure, the residue was made basic by adding a dilute aqueous solution of sodium hydroxide and was then extracted with ethyl acetate. The organic layer was dried over anhydrous magnesium sulfate and then the solvent was distilled off under reduced pressure. To a solution of the residue in N,N-dimethylformamide (100 ml) were added 2 g of 8-chloromethyl-10H-pyrazino[2,3-b][1,4]benzothiazine and 3.3 g of potassium carbonate and the resulting mixture was stirred at 80° C. for 2 hours. After adding ethyl acetate, the reaction mixture was washed with a saturated aqueous solution of sodium chloride thrice and then the organic layer was dried over anhydrous magnesium sulfate. After distilling off the solvent under reduced pressure, the residue was purified by silica gel column chromatography (eluting with n-hexane/ethyl acetate) to thereby give 3 g of the title compound as a yellow oily substance.

$^1$H-NMR(CDCl$_3$) δ ppm; 0.80–1.00(m, 1H), 0.98(d, J=6.8 Hz, 3H), 1.00(d, J=6.8 Hz, 3H), 1.15(d, J=6.8 Hz, 3H), 1.26(t, J=6.8 Hz, 3H), 1.30–1.37(m, 1H), 1.42–1.50(m, 1H), 1.55–1.85(m, 4H), 1.98(d, J=7.2 Hz, 2H), 2.58(d, J=7.2 Hz, 1H), 2.64(d, J=7.2 Hz, 1H), 2.65–2.80(m, 1H), 3.26(s, 2H), 4.14(q, J=6.8 Hz, 2H), 6.40(br.s, 1H), 6.51(s, 1H), 6.76(d, J=8.0 Hz, 1H), 6.82(d, J=8.0 Hz, 1H), 7.56(d, J=2.8 Hz, 1H), 7.68(d, J=2.8 Hz, 1H)

Example 29

Ethyl (+)-(anti)-(6R*,8R*)-2-[3-(10H-pyrazino[2,3-b][1,4]benzothiazin-8-ylmethyl)-6,8-dimethyl-3-azabicyclo[3.3.1]non-9-yl)propanoate and ethyl (−)-(anti)-(6R*,8R*)-2-[3-(10H-pyrazino[2,3-b][1,4]benzothiazin-8-ylmethyl)-6,8-dimethyl-3-azabicyclo[3.3.1]non-9-yl]propanoate 0.53 g of ethyl (+)-(anti)-(6R*,8R*)-2-[3-(10H-pyrazino[2,3-b][1,4]benzothiazin-8-ylmethyl)-6,8-dimethyl-3-azabicyclo[3.3.1]non-9-yl]propanoate was dissolved in a solvent mixture of n-hexane with ethanol (97:3) and the enantiomers were resolved by using CHIRALPAK AD [5 (diameter)×50 cm; mfd. by Daicel Chemical Industries, Ltd.; eluting with n-hexane/ethanol (97.5:2.5) at 150 ml/min]. Thus the (+)-compound was eluted first followed by the (−)-compound. From 120 g of the racemic mixture, 41 g (100% e.e.) and 37 g (99% e.e. or above) of the (+)- and (−)-compounds were obtained respectively each as yellow crystals.

---

(+)-compound: α$^{25}$$_D$ +15.0° (c = 1.00 EtOH)
m.p. : 135 – 136° C.
MS : FAB(+)467(MH$^+$)
(−)-compound: α$^{25}$$_D$ − 14.7° (c = 1.02 EtOH)
m.p. : 135 – 136° C.
MS : FAB(+)467(MH$^+$)

---

Example 30

(+)-(anti)-(6R*,8R*)-2-[3-(10H-pyrazino[2,3-b][1,4]benzothiazin-8-ylmethyl)-6,8-dimethyl-3-azabicyclo[3.3.1]non-9-yl]propanoic acid

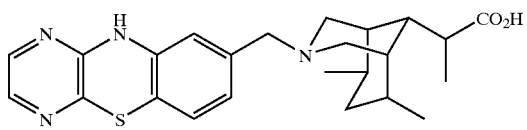

22.2 g of ethyl (+)-(anti)-(6R*,8R*)-2-[3-(10H-pyrazino[2,3-b][1,4]benzothiazin-8-ylmethyl)-6,8-dimethyl-3-azabicyclo[3.3.1]non-9-yl]propanoate was dissolved in ethanol (530 ml) and water (130 ml). After adding 6.0 g of lithium hydroxide, the resulting mixture was heated under reflux under a nitrogen gas stream for 24 hours. After distilling off the solvent under reduced pressure, the residue was neutralized by adding a dilute aqueous solution of hydrochloric acid and then acidified by adding an aqueous solution of sodium dihydrogenphosphate then the mixture was extracted with ethyl acetate. The organic layer was dried over anhydrous magnesium sulfate and the solvent was concentrated under reduced pressure to thereby give yellow crystals. After recrystallizing from ethyl acetate/diisopropyl ether, 18 g of the title compound was obtained as yellow crystals.

$^1$H-NMR(DMSO-$d_6$) δ ppm; 0.84–1.00(m, 1H), 0.95(d, J=6.8 Hz, 3H), 0.98(d, J=6.8 Hz, 3H), 1.06(d, J=6.8 Hz, 3H), 1.28–1.38(m, 2H), 1.54–1.82(m, 4H), 1.87(d, J=7.2 Hz, 1H), 1.89(d, J=7.2 Hz, 1H), 2.48–2.55(m, 1H), 2.55(d, J=7.2 Hz, 1H), 2.60(d, J=7.2 Hz, 1H), 3.24(s, 2H), 6.68(d, J=8.0 Hz, 1H), 6.75(s, 1H), 6.84(d, J=8.0 Hz, 1H), 7.61(d, J=2.8 Hz, 1H), 7.63(d, J=2.8 Hz, 1H), 9.52(br.s, 1H), 12.0(br.s, 1H)

$α^{25}_D$+6.31° (c=1.03, THF)

m.p.: 205–210° C.

MS: FAB(+)439(MH$^+$)

Example 31

(−)-(anti)-(6R*,8R*)-2-[3-(10H-pyrazino[2,3-b][1,4]benzothiazin-8-ylmethyl)-6,8-dimethyl-3-azabicyclo[3.3.1]non-9-yl]propanoic acid

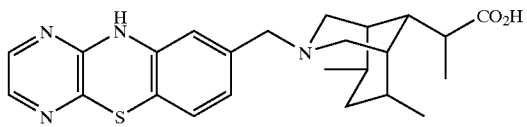

0.3 g of the title compound was obtained as yellow crystals by treating 0.5 g of ethyl (−)-(anti)-(6R*,8R*)-2-[3-(10H-pyrazino[2,3-b][1,4]benzothiazin-8-ylmethyl)-6,8-dimethyl-3-azabicyclo[3.3.1]non-9-yl]propanoate in the same manner as described in Example 30.

$^1$H-NMR(DMSO-$d_6$) δ ppm; 0.84–1.00(m, 1H), 0.95(d, J=6.8 Hz, 3H), 0.98(d, J=6.8 Hz, 3H), 1.06(d, J=6.8 Hz, 3H), 1.28–1.38(m, 2H), 1.54–1.82(m, 4H), 1.87(d, J=7.2 Hz, 1H), 1.89(d, J=7.2 Hz, 1H), 2.48–2.55(m, 1H), 2.55(d, J=7.2 Hz, 1H), 2.60(d, J=7.2 Hz, 1H), 3.24(s, 2H), 6.68(d, J=8.0 Hz, 1H), 6.75(s, 1H), 6.84(d, J=8.0 Hz, 1H), 7.61(d, J=2.8 Hz, 1H), 7.63(d, J=2.8 Hz, 1H), 9.52(br.s, 1H), 12.0(br.s, 1H)

$α^{25}_D$−5.72° (c=1.03, THF)

m.p.: 205–210° C.

MS: FAB(+)439(MH$^+$)

Production Example 1

[(anti)-2-(6R*,8R*)-3,6,8-Trimethyl-3-azabicyclo[3.3.1]non-9-yl]ethyl acetate

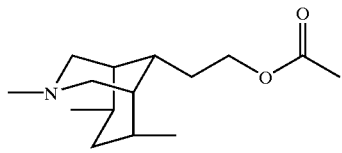

To a solution of 8.5 g of ethyl (anti)-(6R*,8R*)-[3,6,8-trimethyl-3-azabicyclo[3.3.1]non-9-yl]acetate in tetrahydrofuran (100 ml) was slowly added 0.9 g of aluminum hydride under ice-cooling and the resulting mixture was stirred at 0 OC for 30 minutes. Next, a mixture of methanol with water was slowly added to the reaction mixture. After being diluted with ethyl acetate, the reaction mixture was filtered through celite. After distilling off the solvent under reduced pressure, 7.6 g of a pale yellow oily substance was obtained.

To a solution of 7.6 g of this pale yellow oily substance in methylene chloride (100 ml) were added 5.5 g of acetic anhydride, 7.5 ml of triethylamine and 0.44 g of 4-dimethylaminopyridine and the resulting mixture was stirred at room temperature for 2.5 days. Then the reaction mixture was washed with water and the organic layer was dried over anhydrous magnesium sulfate. After distilling off the solvent under reduced pressure, the residue was purified by silica gel column chromatography (eluting with methylene chloride/methanol) to thereby give 7.6 g of the title compound as a pale yellow oily substance.

$^1$H-NMR(CDCl$_3$) δ ppm; 0.70–1.08(m, 6H), 0.98(d, J=6.8 Hz, 3H), 1.02(d, J=6.8 Hz, 3H), 1.60–2.00(m, 5H), 2.05(s, 3H), 2.06(s, 3H), 2.60–2.70(m, 2H), 4.07(t, J=6.8 Hz, 2H)

Production Example 2

[(anti)-2-[(6R*,8R*)-3-(Vinyloxycarbonyl)-6,8-dimethyl-3-azabicyclo[3.3.1]non-9-yl]ethyl]acetate

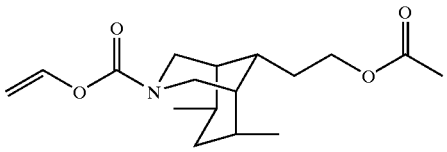

To a solution of 7.6 g of [(anti)-2-[(6R*,8R*)-3,6,8-trimethyl-3-azabicyclo[3.3.1]nonan-9-yl]ethyl]acetate in 1,2-dichloroethane (100 ml) was added 3.8 ml of vinyl chloroformate and the resulting mixture was heated under reflux for 1 hour. After distilling off the solvent under reduced pressure, the residue was purified by silica gel column chromatography (eluting with n-hexane/ethyl acetate) to thereby give 5.1 g of the title compound as a pale yellow oily substance.

$^1$H-NMR(CDCl$_3$) δ ppm; 0.90–1.0(m, 1H), 0.98(d, J=6.8 Hz, 3H), 1.02(d, J=6.8 Hz, 3H), 1.40–1.60(m, 4H), 1.74–1.90(m, 3H), 2.05(s, 3H), 2.70–2.90(m, 2H), 3.92–4.26(m, 4H), 4.43(m, 2H), 4.78(d, J=16 Hz, 1H), 7.12–7.25(m, 1H)

Production Example 3

(anti)-(6R*,8R*)-[3-(Vinyloxycarbonyl)-6,8-dimethyl-3-azabicyclo[3.3.1]non-9-yl]acetaldehyde

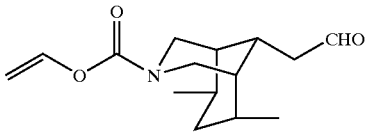

To a solution of 5.1 g of [(anti)-2-azabicyclo[3.3.1]non-9-yl]ethyl]acetate in methanol (50 ml) was added 7 ml of a 5 N aqueous solution of sodium hydroxide and the resulting mixture was stirred at room temperature for 1 hour. After distilling off the solvent under reduced pressure, the residue was neutralized by adding dilute hydrochloric acid and then extracted with ethyl acetate. The organic layer was dried over anhydrous magnesium sulfate and the solvent was distilled off under reduced pressure to thereby give 4.3 g of (anti)-(6R*,8R*)-2-[3-(vinyloxycarbonyl)-6,8-dimethyl-3-azabicyclo[3.3.1]non-9-yl]ethanol as a yellow oily substance.

Into a solution of 3.6 g of oxalyl chloride in methylene chloride (50 ml) was added dropwise 2.6 ml of dimethyl sulfoxide at −70° C. After stirring for 10 minutes, a solution of 2.5 g of (anti)-(6R*,8R*)-2-[3-(vinyloxycarbonyl)-6,8-dimethyl-3-azabicyclo[3.3.1]non-9-yl]ethanol in methylene chloride (30 ml) was added dropwise thereinto. After stirring at −70° C. for 3 hours, 7.8 ml of triethylamine was added thereto. Then the reaction mixture was brought back to room temperature and washed with water. The organic layer was dried over anhydrous magnesium sulfate and the solvent was distilled off under reduced pressure. The residue was purified by silica gel column chromatography (eluting with n-hexane/ethyl acetate) to thereby give 2.1 g of the title compound as a pale yellow oily substance.

$^1$H-NMR(CDCl$_3$) δ ppm; 0.98(d, J=6.8 Hz, 3H), 1.02(d, J=6.8 Hz, 3H), 1.42–1.70(m, 5H), 1.85–1.95(m, 1H), 2.17–2.23(m, 1H), 2.64(d, J=6.8 Hz, 2H), 2.80–2.95(m, 2H), 3.94–4.08(m, 2H), 4.46(d, J=6.8 Hz, 1H), 4.78(d, J=16 Hz, 1H), 7.20(dd, J=6.8, 16 Hz, 1H), 9.72(t, J=6.8 Hz, 1H)

Production Example 4

Ethyl (anti)-[3-(vinyloxycarbonyl)-3-azabicyclo[3.3.1]non-9-yl]acetate

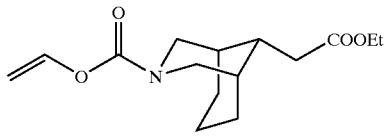

0.78 g of ethyl (anti)-(3-methyl-3-azabicyclo[3.3.1]non-9-yl]acetate was dissolved in 10 ml of 1,2-dichloroethane. After adding 0.6 ml of vinyl chloroformate, the resulting mixture was stirred at room temperature for 1 hour and then heated under reflux for 2 hours. The reaction mixture was concentrated and, after adding water, extracted with ethyl acetate. The ethyl acetate layer was washed with 1 N hydrochloric acid, a saturated aqueous solution of sodium hydrogencarbonate and a saturated aqueous solution of sodium chloride and dried over anhydrous sodium sulfate. After concentrating the solvent under reduced pressure, 0.52 g of the title compound was obtained as a pale brown oily substance.

$^1$H-NMR(CDCl$_3$) δ ppm; 1.27(t, J=7.1 Hz, 3H), 1.48(m, 1H), 1.59–1.83(m, 7H), 2.21(m, 1H), 2.53(d, J=7.5 Hz, 2H), 3.15(m, 1H), 3.23(m, 1H), 4.15(q, J=7.1 Hz, 2H), 4.17–4.26 (m, 2H), 4.45(dd, J=1.5, 6.3 Hz, 1H), 4.79(dd, J=1.5, 13.9 Hz, 1H), 7.25(dd, J=6.3, 13.9 Hz, 1H)

Production Example 5

(anti)-[3-(Vinyloxycarbonyl)-3-azabicyclo[3.3.1]non-9-yl]acetic acid

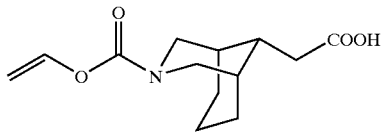

3.01 g of ethyl (anti)-[3-(vinyloxycarbonyl)-3-azabicyclo[3.3.1]non-9-yl]acetate was dissolved in 30 ml of ethanol. After adding 16.1 ml of 1 N sodium hydroxide, the resulting mixture was stirred at room temperature for 4 hours. Then the reaction mixture was concentrated and water was added thereto. The aqueous layer was washed with ether and acidified with 1 N hydrochloric acid and then extracted with ethyl acetate. After drying the extracts over anhydrous sodium sulfate and concentrating the solvent under reduced pressure, 2.9 g of the title compound was obtained as a pale yellow oily substance.

$^1$H-NMR(CDCl$_3$) δ ppm; 1.50(m, 1H), 1.60–1.86(m, 7H), 2.22(m, 1H), 2.60(d, J=7.5 Hz, 2H), 3.15(m, 1H), 3.23(m, 1H), 4.17–4.28(m, 2H), 4.45(dd, J=1.6, 6.4 Hz, 1H), 4.79(dd, J=1.6, 14.1 Hz, 1H), 7.24(dd, J=6.4, 14.1 Hz, 1H)

Production Example 6

(anti)-2-[3-(Vinyloxycarbonyl)-3-azabicyclo[3.3.1]non-9-yl]ethanol

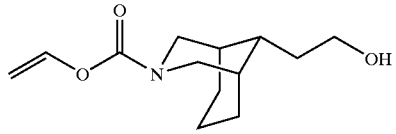

To a solution of 500 mg of (anti)-[3-(vinyloxycarbonyl)-3-azabicyclo[3.3.1]non-9-yl]acetic acid in tetrahydrofuran (10 ml) were added 294 mg of N-hydroxysuccinimide and 449 mg of N,N'-dicyclohexyl carbodiimide and the resulting mixture was stirred at room temperature for 8 hours. Next, the reaction mixture was ice-cooled and 187 mg of sodium borohydride was added thereto. After stirring for 20 minutes, the reaction mixture was stirred at room temperature for an additional 15 hours and then was extracted with ethyl acetate containing ice/water. The ethyl acetate layer was washed with water, 1 N sodium hydroxide and a saturated aqueous solution of sodium chloride and dried over anhydrous magnesium sulfate. After concentrating under reduced pressure, the matters insoluble in methylene chloride were filtered off. Then the residue was purified by silica gel column chromatography (eluting with methylene chloride/methanol) to thereby give 348 mg of the title compound as a colorless oily substance.

$^1$H-NMR(CDCl$_3$) δ ppm; 1.41–1.90(m, 12H), 3.12(m, 1H), 3.19(m, 1H), 3.73(t, J=6.4 Hz, 2H), 4.17–4.25(m, 2H), 4.44(dd, J=1.5, 6.2 Hz, 1H), 4.78(dd, J=1.5, 14.1 Hz, 1H), 7.25(dd, J=6.2, 14.1 Hz, 1H)

Production Example 7

(anti)-[3-(Vinyloxycarbonyl)-3-azabicyclo[3.3.1]non-9-yl]acetaldehyde

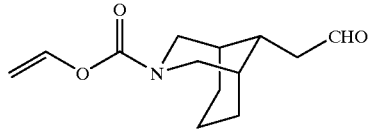

0.32 ml of oxalyl chloride was dissolved in 8 ml of methylene chloride, cooled to −60° C. and stirred. 0.28 ml of dimethyl sulfoxide was dissolved in 1 ml of methylene chloride and then was added dropwise to the above solution while maintaining the bulk temperature at −50° C. or below. 5 minutes thereafter, 580 mg of (anti)-2-[3-(vinyloxycarbonyl)-3-azabicyclo[3.3.1]non-9-yl]ethanol was dissolved in 2 ml of methylene chloride and added dropwise to the above mixture while maintaining the bulk temperature at −50° C. or below. After 15 minutes, 1.7 ml of triethylamine was added dropwise to while maintaining the bulk temperature at −50° C. or below. After 20 minutes, the reaction mixture was heated to room temperature and stirred for 1 hour. After adding water, the reaction mixture was extracted with ethyl acetate. The ethyl acetate layer was washed with 1 N hydrochloric acid, a saturated aqueous solution of sodium hydrogencarbonate and a saturated aqueous solution of sodium chloride, dried over anhydrous sodium sulfate and concentrated under reduced pressure. Then the residue was purified by silica gel column chromatography (eluting with n-hexane/ethyl acetate) to thereby give 451 mg of the title compound as a colorless oily substance.

$^1$H-NMR(CDCl$_3$) δ ppm; 1.48(m, 1H), 1.60–1.82(m, 7H), 2.33(m, 1H), 2.66–2.72(m, 2H), 3.18(m, 1H), 3.25(m, 1H), 4.08–4.13(m, 2H), 4.45(dd, J=1.6, 6.2 Hz, 1H), 4.79(dd, J=1.6, 14.0 Hz, 1H), 7.25(dd, J=6.2, 14.0 Hz, 1H), 9.83(t, J=1.6 Hz, 1H)

Production Example 8

1-[3-[N-(2-Cyclobutylidene)ethyl)-N-(P-tolylsulfonyl)amino]-1-oxypropyl]pyrrolidine

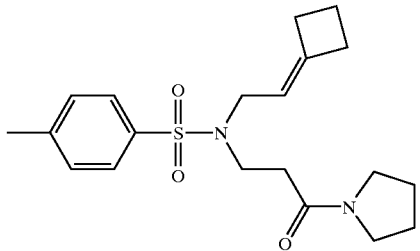

5.84 g of 1-[3-(p-tolylsulfonylamino)-1-oxopropyl]pyrrolidine was dissolved in 300 ml of dry N,N-dimethylformamide under a nitrogen atmosphere. After adding 0.83 g of sodium hydride, the resulting mixture was stirred for 30 minutes. Then 4.76 g of 2-bromoethylidenecyclobutane was added thereto and the resulting mixture was stirred at 90° C. for 3 hours. After adding 500 ml of water and 500 ml of ethyl acetate, the organic layer was washed with water, dried over anhydrous magnesium sulfate and filtered. After distilling off the solvent under reduced pressure, the residue was purified by silica gel column chromatography (eluting with methanol/methylene chloride) to thereby give 6.78 g of the title compound as a yellow oily substance.

$^1$H-NMR(CDCl$_3$) δ ppm; 1.63(d, J=1 Hz, 3H), 1.65(d, J=1 Hz, 3H), 1.86(m, 2H), 1.96(m, 2H), 2.42(s, 3H), 2.68(t, J=8 Hz, 2H), 3.38(t, J=8 Hz, 2H), 3.44(t, J=7 Hz, 4H), 3.80(d, J=7 Hz, 2H), 4.98(t, sept, J=1, 7 Hz, 1H), 7.29(d, J=8 Hz, 2H), 7.69(d, J=8 Hz, 2H)

Production Example 9

3-(p-Tolylsulfonyl)-6-oxo-3-azabicyclo [3.3.1]heptane-7-spiro-cyclobutane

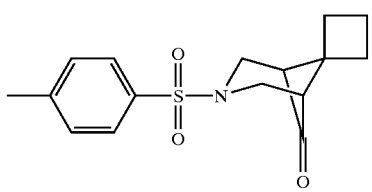

7.56 g of trifluoromethanesulfonic acid was dissolved in 180 ml of dry 1,2-dichloroethane in a nitrogen atmosphere. Into the solution thus obtained was added dropwise 6.77 g of 1-[3-[N-(2-cyclobutylidene)ethyl)-N-(p-tolylsulfonyl)amino]-1-oxopropyl]pyrrolidine in 180 ml of 1,2-dichloroethane. Further, 2.37 g of collidine in 180 ml of 1,2-dichloroethane was added dropwise thereinto and the resulting mixture was heated under reflux at 90° C. for 2 hours. After distilling off the solvent under reduced pressure, the residue was dissolved in 300 ml of water and 300 ml of carbon tetrachloride and then heated to 100° C. under a nitrogen atmosphere for 3 hours. The solvent was decanted and the organic layer was dried over anhydrous magnesium sulfate and filtered. After distilling off the solvent under reduced pressure, the residue was purified by silica gel column chromatography (eluting with n-hexane/ethyl acetate) to thereby give 3.41 g of the title compound as an orange oily substance.

$^1$H-NMR(CDCl$_3$) δ ppm; 1.89(m, 4H), 2.01(m, 2H), 2.44(s, 3H), 2.85(s, 2H), 3.77(dd, J=2, 10 Hz, 2H), 3.89(dd, J=2, 10 Hz, 2H), 7.31(d, J=8 Hz, 2H), 7.69(d, J=8 Hz, 2H)

Production Example 10

1,3,5-Trimethyl-3-azabicyclo[3.3.1]nonan-9-one

To 1 l of a solution of 25 g of 2,6-dimethylcyclohexanone in acetic acid were added 13.5 g of methylamine hydrochloride and 32.4 g of formalin (37% aqueous solution) and the resulting mixture was heated to 100° C. for 2 hours. After removing the solvent under reduced pressure, the obtained residue was distributed between ethyl acetate and an aqueous solution of potassium carbonate. The organic layer was extracted and dried over anhydrous sodium sulfate. Then the residue was purified by silica gel column chromatography (eluting with ethyl acetate/n-hexane) to thereby give 19 g of the title compound as a colorless oily substance.

$^1$H-NMR(CDCl$_3$) δ ppm; 0.92(s, 6H), 1.36–1.45(m, 1H), 1.66–1.76(m, 2H), 2.02–2.09(m, 2H), 2.16(s, 3H), 2.17–2.22(m, 2H), 2.92–2.98(m, 2H), 3.02–3.17(m, 1H)

Production Example 11

1,3,5-Trimethyl-9-methoxymethylene-3-azabicyclo[3.3.1]nonane

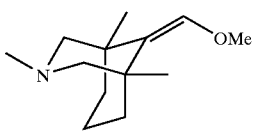

100 ml of a solution of 20.5 ml of (methoxymethyl)trimethylsilane in dry tetrahydrofuran was cooled under a nitrogen atmosphere. Then 92 ml of a 1.3 M solution of s-butyllithium in cyclohexane was added dropwise thereinto at −78° C. After the completion of the addition, the mixture was stirred at −35° C. for 30 minutes. After adding 10.9 g of 1,3,5-trimethyl-3-azabicyclo[3.3.1]nonan-9-one, the resulting mixture was stirred at room temperature for 2 hours and then poured into a cooled aqueous solution of ammonium chloride. Then it was made alkaline by adding potassium carbonate and extracted with ethyl acetate. The organic layer was washed with water and dried over anhydrous sodium sulfate. After distilling off the solvent under reduced pressure, 9.2 g of the title compound was obtained as a pale-brown oily substance.

¹H-NMR(CDCl₃) δ ppm; 0.83(s, 3H), 1.15(s, 3H), 1.20–1.37(m, 2H), 1.42–1.59(m, 2H), 1.62–1.68(m, 1H), 1.69(dd, J=3.3, 10.7 Hz, 1H), 1.86(dd, J=3.3, 10.7 Hz, 1H), 1.99(s, 3H), 2.50(d, J=10.7 Hz, 1H), 2.61(d, J=10.7 Hz, 1H), 2.67–2.83(m, 1H), 3.41(s, 3H), 5.59(s, 1H)

Production Example 12

(1,3,5-Trimethyl-3-azabicyclo[3.3.1]non-9-yl)carbaldehyde

9.2 g of 1,3,5-trimethyl-9-methoxymethylene-3-azabicyclo-[3.3.1]nonane was slowly added dropwise to 30 ml of formic acid at room temperature. After completion of the addition, the formic acid was distilled off under reduced pressure. Then the residue was distributed between ethyl acetate and an aqueous solution of potassium carbonate. The organic layer was extracted and dried over anhydrous sodium sulfate. After distilling off the solvent under reduced pressure, the residue was purified by silica gel column chromatography (eluting with n-hexane/ethyl acetate) to thereby give 7.3 g of the title compound as a colorless oily substance.

¹H-NMR(CDCl₃) δ ppm; 0.83(s, 6H), 1.55–1.64(m, 4H), 1.65–1.80(m, 3H), 1.73(d, J=7.0 Hz, 1H), 2.08(s, 3H), 2.60(d, J=12.0 Hz, 2H), 2.74–2.91(m, 1H), 10.06(d, J=7.0 Hz, 1H)

Production Example 13

(6R*,8R*)-(3,6,8-Trimethyl-3-azabicyclo[3.3.1]non-9-yl)carbaldehyde

Into a solution of 19.2 g of (methoxymethyl)triphenylphosphonium chloride in dry tetrahydrofuran (200 ml) was added dropwise 32 ml of a 1.6 M solution of n-butyllithium at −70° C. and the resulting mixture was stirred at 0° C. for 30 minutes. Then a solution of 6 g of (6R*,8R*)-3,6,8-trimethyl-3-azabicyclo[3.3.1]nonan-9-one in dry tetrahydrofuran (30 ml) was dropped into the reaction mixture and the mixture was stirred at room temperature overnight. After adding ethyl acetate, the reaction mixture was washed with water and the organic layer was dried over anhydrous magnesium sulfate. After distilling off the solvent under reduced pressure, a yellow oily substance was obtained.

To a solution of this oily substance in acetone (50 ml) was added 15 ml of a 6 N aqueous solution of hydrochloric acid and the resulting mixture was stirred at room temperature for 4 hours. Then the reaction mixture was made alkaline by adding a 1 N aqueous solution of sodium hydroxide and extracted with ethyl acetate. The organic layer was dried over anhydrous magnesium sulfate and the solvent was distilled off under reduced pressure. Then the residue was purified by silica gel column chromatography (eluted with n-hexane/ethyl acetate) to thereby give 2.0 g of the title compound as a pale yellow oily substance.

¹H-NMR(CDCl₃) δ ppm; 1.02(d, J=6.8 Hz, 6H), 1.50–2.00(m, 7H), 2.08–2.15(m, 2H), 2.24(br.s, 3H), 2.68–2.80(m, 2H), 9.85(s, 1H)

Production Example 14

3-Methyl-9-methylene-3-azabicyclo[3.3.1]nonane

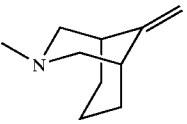

To a solution of 6.9 g of methyltriphenyl phosphonium bromide in toluene (30 ml) was added 2.2 g of potassium tert-butoxide at 0° C. and the resulting mixture was stirred for 30 minutes. Next, 3.0 g of 3-methyl-3-azabicyclo[3.3.1]nonan-9-one was added thereto and the mixture was reacted for 1 hour. After adding ether, the reaction mixture was washed with a saturated aqueous solution of sodium chloride and dried over anhydrous magnesium sulfate. After filtering and concentrating, the residue was purified by silica gel column chromatography (eluted with ether/n-hexane) to thereby give 3.1 g of the title compound as a yellow oily substance.

¹H-NMR(CDCl₃) δ ppm; 1.40–1.50(m, 1H), 1.65–1.80 (m, 2H), 1.80–2.00(m, 2H), 2.13(s, 3H), 2.1–2.4(m, 4H), 2.45–2.65(m, 1H), 2.83–2.98(m, 2H), 4.58(s, 2H)

Production Example 15

3-(tert-Butoxycarbonyl)-9-methylene-3-azabicyclo[3.3.1]nonane

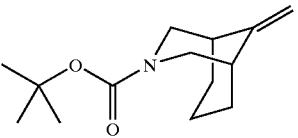

1.0 g of 3-methyl-9-methylene-3-azabicyclo[3.3.1]nonane was dissolved in 1,2-dichloroethane (5 ml). After adding 1.37 g of 1-chloroethyl chloroformate, the resulting mixture was heated under reflux at 110° C. for 2 hours. After distilling off the solvent under reduced pressure, methanol was added to the residue and the mixture was heated under reflux for 1 hour. After distilling off the solvent under reduced pressure, 1.0 g of brown crude crystals were obtained. These crystals were dissolved in 30 ml of methanol and 1.8 ml of triethylamine and 1.7 g of di-tert-butyl dicarbonate were added thereto. After reacting at room temperature for 1 hour, water was added to the reaction mixture. Then the mixture was extracted with ethyl acetate, washed with dilute hydrochloric acid and a saturated aqueous solution of potassium hydrogencarbonate and dried over anhydrous magnesium sulfate. After concentrating under reduced pressure, the residue was purified by silica gel column chromatography (eluted with ethyl acetate/n-hexane) to thereby give 0.8 g of the title compound as a yellow oily substance.

$^1$H-NMR(CDCl$_3$) δ ppm; 1.47(s, 9H), 1.6–2.0(m, 6H), 2.33(br.s, 1H), 2.39(br.s, 1H), 2.95(br.d, J=13 Hz, 1H), 3.04(br.d, J=13 Hz, 1H), 4.13(d, J=12 Hz, 1H), 4.27(d, J=12 Hz, 1H), 4.67(s, 2H)

Production Example 16

3-(tert-Butoxycarbonyl)-3-azabicyclo[3.3.1]nonane-9-spirocyclobutan-3'-one

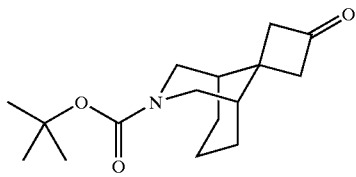

To 3.7 g of zinc/copper alloy was added a solution of 1.4 g of 3-(tert-butoxycarbonyl)-9-methylene-3-azabicyclo[3.3.1]-nonane in dry ether (30 ml). Subsequently, a solution of 2.6 ml of trichloroacetyl chloride in dry dimethoxyethane (50 ml) was dropped thereinto and the resulting mixture was reacted at room temperature for 3 hours. Then a saturated aqueous solution of sodium hydrogencarbonate was added to the reaction mixture while maintaining the mixture at 0° C. or below. After filtering off the zinc/copper alloy, the filtrate was extracted with ethyl acetate, washed with a saturated aqueous solution of sodium chloride and dried over anhydrous magnesium sulfate. After concentrating under reduced pressure, the residue was purified by silica gel column chromatography (eluted with ethyl acetate/n-hexane) to thereby give 1.5 g of a yellow oily substance. This product was dissolved in 40 ml of a saturated solution of ammonium chloride in methanol. After adding 1.7 g of zinc, the resulting mixture was reacted at room temperature for 24 hours. After filtering off the zinc, water was added to the residue. Next, it was extracted with ethyl acetate, washed with a saturated aqueous solution of sodium chloride and dried over anhydrous magnesium sulfate. After concentrating, the residue was purified by silica gel column chromatography (eluted with ethyl acetate/n-hexane) to thereby give 0.8 g of the title compound as a colorless oily substance.

$^1$H-NMR(CDCl$_3$) δ ppm; 1.47(s, 9H), 1.55–1.90(m, 8H), 2.8–2.95(m, 4H), 3.06(d, J=14 Hz, 1H), 3.15(d, J=14 Hz, 1H), 4.02(d, J=13 Hz, 1H), 4.15(d, J=13 Hz, 1H)

Production Example 16'

(6R*,8R*)-3-(tert-Butoxycarbonyl)-6,8-dimethyl-3-azabicyclo[3.3.1]-nonane-9-spirocyclobutan-3'-one

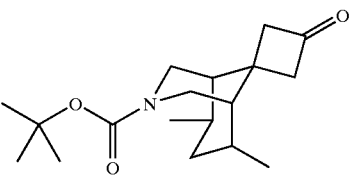

The title compound was obtained by treating (±)-(6R*, 8R*)-3,6,8-trimethyl-3-azabicyclo[3.3.1]nonan-9-one by the same methods as those of Production Examples 14, 15 and 16.

$^1$H-NMR(CDCl$_3$) δ ppm; 1.01–1.13(m, 6H), 1.3–1.95(m, 5H), 1.45(s, 9H), 2.65–3.0(m, 3H), 2.89(s, 4H), 3.7–3.85(m, 1H), 3.9–4.0(m, 1H)

Production Examples 17 to 24

The following unsaturated esters were obtained by the same method as the one of Example 19.

TABLE 3

| Prodn. Ex. | Structural formula | NMR |
|---|---|---|
| 17 | ethyl (3,6-dimethyl-3-azabicyclo[3.3.1]non-9-ylidene)acetate | $^1$H-NMR(CDCl$_3$) δ ppm: 0.9, 0.95(d, J=7Hz, total 3H), 1.0–1.2(m, 1H), 1.26(t, J=7Hz 3H), 1.5–2.0(m, 2H), 2.14(s, 3H), 2.0–2.3(m, 4H), 2.6–2.8(m, 1H), 2.85–3.0(m, 2H), 3.70–3.90(s, total 1H), 4.15(q, J=7Hz, 2H), 5.59, 5.74(s, total 1H) |

TABLE 3-continued

| Prodn. Ex. | Structural formula | NMR |
|---|---|---|
| 18 | ethyl (3-methyl-3-azabicyclo[3.2.1]oct-8-ylidene)acetate | $^1$H-NMR(CDCl$_3$) δ ppm: 1.29(t, J=7Hz, 3H), 1.69(m, 3H), 1.7–2.0(m, 2H), 2.15–2.30(m, 1H), 2.25(s, 3H), 2.48(m, 1H), 2.8–2.9(m, 2H), 3.75(m, 1H), 4.17(q, J=7Hz, 2H), 5.64(s, 1H) |
| 19 | ethyl (3-methyl-7-oxa-3-azabicyclo[3.3.1]non-9-ylidene)acetate | $^1$H-NMR(CDCl$_3$) δ ppm: 1.2–1.4(m, 3H), 1.83(s, 1H), 2.26(s, 4H), 2.45(d, J=8Hz, 2H), 3.14–3.23(m, 2H), 3.78(d, J=8Hz, 2H), 3.98(s, 1H), 4.1–4.25(m, 3H), 5.74(s, 1H) |
| 20 | ethyl (3-benzyl-7-methyl-3,7-diazabicyclo[3.3.1]non-9-ylidene)acetate | $^1$H-NMR(CDCl$_3$) δ ppm: 1.26(t, J=6.8Hz, 3H), 2.25(s, 3H), 2.34–2.41(m, 2H), 2.49–2.54(m, 1H), 2.74–2.81(m, 2H), 2.78(d, J=4.2Hz, 2H), 2.83–2.89(m, 2H), 3.49(d, J=14.2Hz, 1H), 3.53(d, J=14.2Hz, 1H), 4.13(q, J=6.8Hz, 2H), 4.18–4.25(m, 1H), 5.71(s, 1H), 7.20–7.36(m, 5H) |
| 21 | ethyl (8-methyl-8-azabicyclo[4.3.1]dec-10-ylidene)acetate | $^1$H-NMR(CDCl$_3$) δ ppm: 1.28(t, J=7.2Hz, 3H), 1.32–1.43(m, 2H), 1.60–1.72(m, 3H), 1.78–1.94(m, 3H), 1.99–2.05(m, 1H), 2.05–2.10(m, 1H), 2.17(s, 3H), 2.51–2.58(m, 1H), 2.60–2.66(m, 2H), 3.93–4.00(m, 1H), 4.14(q, J=7.2Hz, 2H), 5.65(s, 1H) |

TABLE 4

| Prodn. Ex. | Structural formula | NMR |
|---|---|---|
| 22 | ethyl (3,7-dimethyl-3-azabicyclo[3.3.1]non-9-ylidene)acetate | $^1$H-NMR(CDCl$_3$) δ ppm: 0.78(d, J=4.6Hz, 3H), 1.28(t, J=6.4Hz, 3H), 1.30–1.43(m, 2H), 1.90–2.10(m, 2H), 2.14(s, 3H), 2.18–2.32(m, 4H), 2.93–3.10(m, 3H), 4.15(q, J=6.4Hz, 2H), 5.62(s, 1H) |
| 23 | ethyl (3,7,7-trimethyl-3-azabicyclo[3.3.1]non-9-ylidene)acetate | $^1$H-NMR(CDCl$_3$) δ ppm: 0.89(s, 3H), 0.95(s, 3H), 1.28(t, J=7.0Hz, 3H), 1.69–1.81(m, 2H), 1.84–1.91(m, 2H), 2.00–2.09(m, 2H), 2.21(s, 3H), 2.35–2.43(m, 1H), 2.71–2.81(m, 2H), 4.00–4.07(m, 1H), 4.16(q, J=7.0Hz, 2H), 5.73(s, 1H) |

TABLE 4-continued

| Prodn. Ex. | Structural formula | NMR |
|---|---|---|
| 24 | ethyl (3-methyl-7-tert-butyl-3-azabicyclo[3.3.1]non-9-ylidene)acetate | ¹H-NMR(CDCl₃) δ ppm: 0.8 & 0.84(s, 9H(1:1)), 1.29(t, J=7.2Hz, 3H), 1.45–1.58(m, 1H), 1.60–1.72(m, 1H), 1.94–2.07(m, 3H), 2.13 & 2.20(s, 3H(1:1)), 2.18–2.40(m, 2H), 2.70–2.97(m, 3H), 3.92–4.04(m, 1H), 4.15(q, J=7.2Hz, 2H), 5.61 & 5.64(s, 1H(1:1)) |

Production Example 25

Ethyl[[3-(p-tolylsulfonyl)-3-azabicyclo[3.3.1]heptane-7-spiro-cyclobutan]-6-ylidene]acetate To a solution of 1.61 g of triethyl phosphonoacetate in dry tetrahydrofuran (40 ml) was added 0.288 g of sodium hydride (oily: 60% or above) and the resulting mixture was stirred at room temperature for 20 minutes. Then a solution of 1.83 g of 3-(p-tolylsulfonyl)-6-oxo-3-azabicyclo[3.3.1]heptane-7-spiro-cyclobutane in tetrahydrofuran (10 ml) was added thereto and the resulting mixture was reacted for 2 hours. After distilling off the solvent under reduced pressure, the residue was poured into a 0.1 N aqueous solution of sodium hydroxide and extracted with ethyl acetate. The extract was dried over anhydrous magnesium sulfate and distilled off under reduced pressure. The residue was purified by silica gel column chromatography (eluted with ethyl acetate/n-hexane) to thereby give 2.1 g of the title compound as a colorless oily substance.

¹H-NMR(CDCl₃) δ ppm; 1.26(t, J=7 Hz, 3H), 1.66(m, 2H), 1.77(m, 2H), 1.94(m, 2H), 2.42(s, 3H), 2.73(td, J=3, 6 Hz, 1H), 3.35(m, 1H), 3.62(dd, J=3, 10 Hz, 1H), 3.69(d, J=2 Hz, 1H), 3.71(t, J=2 Hz, 1H), 3.81(dd, J=3, 10 Hz, 1H), 4.12(q, J=7 Hz, 2H), 5.58(s, 1H), 7.26(d, J=8 Hz, 2H), 7.67(d, J=8 Hz, 2H)

Production Examples 26 to 32

The following saturated esters were obtained by the same method as the one of Example 20.

TABLE 5

| Prodn. Ex. | Structural formula | NMR |
|---|---|---|
| 26 | 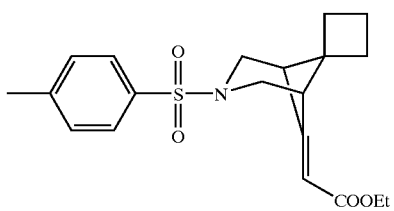 ethyl (3-methyl-3-azabicyclo[3.2.1]oct-9-yl)acetate (syn : anti ≈ 1 : 2) | ¹H-NMR(CDCl₃) δ ppm: 1.26(t, J=7Hz, 3H, anti), 1.26(t, J=7Hz, 3H, syn), 1.65–1.80(m, 4H, anti and syn), 1.90–2.06(m, 3H, anti and syn), 2.09(d, J=10Hz, 2H, anti), 2.17(d, J=8Hz, 2H, anti), 2.22(s, 3H, anti), 2.25(s, 3H, syn), 2.34(d, J=11Hz, 2H, syn), 2.48(dd, J=4, 11Hz, 2H, syn), 2.57(d, J=8Hz, 2H, syn), 2.72(dd, J=4, 11Hz, 2H, anti), 4.14(q, J=7Hz, 2H, syn and anti) |

TABLE 6

| Prodn. Ex. | Structural formula | NMR |
|---|---|---|
| 27 | ethyl (3,7-dimethyl-3-azabicyclo[3.3.1]non-9-yl)acetate | $^1$H-NMR(CDCl$_3$) δ ppm: 0.81(d, J=6.8Hz, 3H), 1.25–1.36(m, 2H), 1.26(t, J=7.2Hz, 3H), 1.62–1.70(m, 2H), 1.90–2.04(m, 2H), 2.14(s, 3H), 2.12–2.24(m, 2H), 2.41(d, J=7.2Hz, 2H), 2.54–2.74(m, 2H), 2.83–2.92(m, 2H), 4.13(q, J=7.2Hz, 2H) |
| 28 | ethyl [[3-(p-tolylsulfonyl)-3-azabicyclo[3.1.1]heptane-7-spiro-cyclobutan]-6-yl]acetate | $^1$H-NMR(CDCl$_3$) δ ppm: 1.21(t, J=7Hz, 3H), 1.40(m, 1H), 1.52(m, 1H), 1.66–1.80(m, 2H), 2.04–2.06(m, 4H), 2.22(m, 2H), 2.42–2.52(m, 4H), 3.42–3.55(m, 4H), 4.26(q, J=7Hz, 2H), 7.30(m, 2H), 7.71(m, 2H) |
| 29 | ethyl (3-methyl-7-tert-butyl-3-azabicyclo[3.3.1]non-9-yl)acetate | $^1$H-NMR(CDCl$_3$) δ ppm: 0.83 & 0.84(s, 9H)(1:1)), 1.26(t, J=7.2Hz, 3H), 1.30–1.62(m, 4H), 1.68–2.00(m, 6H), 2.12 & 2.14(s, 3H(1:1)), 2.36(d, J=7.2Hz, 1H), 2.47(d, 7.2Hz, 1H), 2.52–2.57(m, 1H), 2.81–2.86(m, 1H), 4.13(q, J=7.2Hz, 2H) |

TABLE 7

| Prodn. Ex. | Structural formula | NMR |
|---|---|---|
| 30 | ethyl (3,7,7-trimethyl-3-azabicyclo[3.3.1]non-9-yl)acetate | $^1$H-NMR(CDCl$_3$) δ ppm: 0.98(s, 3H), 1.25(t, J=7.0Hz, 3H), 1.32(s, 3H), 1.32–1.40(m, 2H), 1.64–1.72(m, 4H), 1.81–1.88(m, 1H), 2.12(s, 3H), 2.12–2.18(m, 2H), 2.35(d, J=7.6Hz, 2H), 2.68–2.73(m, 2H), 4.12(q, J=7.0Hz, 2H) |
| 31 | ethyl (3,6-dimethyl-3-azabicyclo[3.3.1]non-9-yl)acetate | $^1$H-NMR(CDCl$_3$) δ ppm: 1.03(d, J=8Hz, 3H), 1.25(t, J=5Hz, 3H), 1.1–1.3(m, 1H), 1.4–1.7(m, 3H), 1.8–2.0(m, 3H), 2.0–2.30(m, 5H), 2.35–2.43(m, 3H), 2.6–2.9(m, 2H), 4.0–4.1(m, 2H) |

TABLE 7-continued

| Prodn. Ex. | Structural formula | NMR |
|---|---|---|
| 32 | 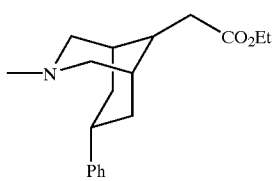<br>ethyl (3-methyl-7-oxa-3-azabicyclo[3.3.1]non-9-yl)acetate | $^1$H-NMR(CDCl$_3$) δ ppm: 1.2–1.3(m, 3H), 1.56(br.s, 1H), 2.06–2.16(m, 1H), 2.24–2.30(m, 3H), 2.30–2.38(m, 2H), 2.42–2.52(m, 1H), 2.6–2.68(m, 2H), 3.12(br.d, J=11Hz, 2H), 3.81(d, J=12Hz, 2H), 3.9–3.98(m, 2H), 4.1–4.2(m, 2H) |

Production Example 33

Ethyl(3-methyl-7-phenyl-3-azabicyclo[3.3.1]non-9-yl)acetate

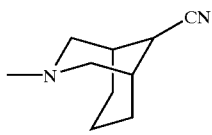

The title compound was obtained by treating 4-phenylcyclohexanone by the same methods as those of Examples 19 and 20.

$^1$H-NMR(CDCl$_3$) δ ppm; 1.28(t, J=7.2 Hz, 3H), 1,70–2.34(m, 10H), 2.22(s, 3H), 2.59(d, J=7.2 Hz, 2H), 2.5–2.70(m, 1H), 2.92–3.04(m, 1H), 4.16(q, J=7.2 Hz, 2H), 7.12–7.38(m, 5H)

Production Example 34

(3-Methyl-3-azabicyclo[3.3.1]nonan-9-yl)carbonitrile

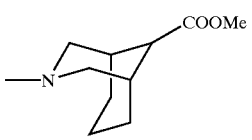

6.2 g of 3-methyl-3-azabicyclo[3.3.1]nonan-9-one was dissolved in 150 ml of dry dimethoxyethane and 40 ml of tert-butanol. Then 46 g of potassium tert-butoxide and 15.8 g of tosylmethyl isocyanide were added thereto at 0° C. After stirring for 30 minutes, the resulting mixture was heated under reflux for 3 hours. Then the reaction mixture was brought back to room temperature and water was added thereto. The resulting mixture was extracted with ethyl acetate, washed with a saturated aqueous solution of sodium chloride and dried over anhydrous magnesium sulfate. After concentrating under reduced pressure, the obtained residue was purified by silica gel column chromatography (eluted with ethyl acetate/n-hexane) to thereby give 5.5 g of the title compound as a yellow oily substance.

$^1$H-NMR(CDCl$_3$) δ ppm;
One Isomer
1.45–1.60(m, 1H), 1.55–1.70(m, 2H), 1.7–1.8(m, 2H), 1.95–2.1(m, 2H), 2.14(s, 3H), 2.18(d, J=10 Hz, 2H), 2.4–2.6(m, 1H), 2.64(s, 1H), 2.93(d, J=10 Hz, 2H)

Other Isomer
1.4–1.5(m, 1H), 1.54–1.70(m, 2H), 1.84–1.94(m, 2H), 2.04–2.12(m, 2H), 2.18(s, 3H), 2.44–2.6(m, 1H), 2.58(d, J=12 Hz, 2H), 2.64–2.68(m, 1H), 2.80(d, J=12 Hz, 2H)

Production Example 35

Methyl(3-methyl-3-azabicyclo[3.3.1]non-9-yl)carboxylate

To a solution of 5.5 g of (3-methyl-3-azabicyclo[3.3.1] nonan-9-yl)carbonitrile in 20 ml of ethylene glycol was added a solution of 48 g of potassium hydroxide in 50 ml of water and the resulting mixture was reacted at 200° C. for 6 hours. Then the reaction mixture was brought back to room temperature and made weakly acidic by adding an aqueous solution of sodium dihydrogenphosphate. After concentrating under reduced pressure, the residue was washed with tetrahydrofuran and ethanol and the washing liquor was concentrated. Next, 500 ml of methanol was added thereto. After further adding 10 ml of thionyl chloride, the resulting mixture was reacted at 70° C. for 3 hours. The reaction mixture was cooled to 0° C. and made alkaline by adding an aqueous solution of sodium hydroxide. Then it was extracted with ethyl acetate, washed with a saturated aqueous solution of sodium chloride and dried over anhydrous magnesium sulfate. After concentrating under reduced pressure, the residue was purified by silica gel column chromatography (eluted with n-hexane/ethyl acetate) to thereby give 3.4 g of the title compound as a pale brown oily substance.

$^1$H-NMR(CDCl$_3$) δ ppm; 1.3–1.5(m, total 1H), 1.55–1.92 (m, total 4H), 2.08 and 2.15(s, total 3H), 2.16–2.38(m, total 5H), 2.38–2.58(m, total 1H), 2.93 and 2.67(d, J=10 Hz, total 2H), 3.72 and 3.70(s, total 3H)

Production Example 36

The following compound was obtained by the same method as the one of Production Example 35.

TABLE 8

| Prodn. Ex. | Structural formula | NMR |
|---|---|---|
| 36 | methyl (3-methyl-3-azabicyclo[3.2.1]oct-8-yl)carboxylate | $^1$H-NMR(CDCl$_3$) δ ppm: 1.64–1.76(m, 4H), 2.05(s, 1H), 2.08(s, 1H), 2.24(s, 3H), 2.30(s, 1H), 2.50(br.s, 2H), 2.75(dd, J=4, 11Hz, 2H), 3.66(s, 3H) |

Production Examples 37 to 39

The following compounds were obtained by the same method as the one of Production Example 25.

TABLE 9

| Prodn. Ex. | Structural formula | NMR |
|---|---|---|
| 37 | ethyl (anti)-(6R*, 8R*)-4-[3-(vinyloxycarbonyl)-6,8-dimethyl-3-azabicyclo[3.3.1]non-9-yl]-2-methyl-2-butenoate | $^1$H-NMR(CDCl$_3$) δ ppm: 1.03(d, J=6.8Hz, 3H), 1.05(d, J=6.8Hz, 3H), 1.31(t, J=7.2Hz, 3H), 1.44–1.63(m, 7H), 1.85(s, 3H), 2.35(t, J=6.8Hz, 2H), 2.75(d, J=12.8Hz, 1H), 2.83(d, J=12.8Hz, 1H), 3.98(d, J=12.8Hz, 1H), 4.03(d, J=12.8Hz, 1H), 4.21(q, J=7.2Hz, 2H), 4.43(d, J=6.4Hz, 1H), 4.78(d, J=14.4Hz, 1H), 6.73(t, J=6.8Hz, 1H), 7.21(dd, J=6.4, 14.4Hz, 1H) |
| 38 | ethyl (anti)-(6R*, 8R*)-(E)-4-[3-(vinyloxycarbonyl)-6,8-dimethyl-3-azabicyclo[3.3.1]non-9-yl]-2-butenoate | $^1$H-NMR(CDCl$_3$) δ ppm: 1.00(d, J=6.8Hz, 3H), 1.04(d, J=6.8Hz, 3H), 1.30(t, J=7.2Hz, 3H), 1.22–1.33(m, 2H), 1.42–1.64(m, 4H), 1.88–2.40(m, 1H), 2.38(t, J=6.8Hz, 2H), 2.72–2.86(m, 2H), 3.95–4.07(m, 2H), 4.22(q, J=7.2Hz, 2H), 4.40–4.50(m, 1H), 4.78(d, J=14Hz, 1H), 5.82(d, J=15.6Hz, 1H), 6.89(td, J=6.8, 15.6Hz, 1H), 7.21(dd, J=6.4, 14Hz, 1H) |
| 39 | ethyl (anti)-(E)-4-[3-(vinyloxycarbonyl)-3-azabicyclo[3.3.1]nonan-9-yl]-2-methyl-2-butenoate | $^1$H-NMR(CDCl$_3$) δ ppm: 1.31(t, J=7.1Hz, 3H), 1.49(m, 1H), 1.58–1.85(m, 8H), 1.89(d, J=1.3Hz, 3H), 2.40(t, J=7.1Hz, 2H), 3.10(m, 1H), 3.18(m, 1H), 4.16–4.26(m, 4H), 4.45(dd, J=1.6, 6.2Hz, 1H), 4.79(dd, J=1.6, 13.9Hz, 1H), 6.74(m, 1H), 7.25(dd, J=6.2, 13.9Hz, 1H) |

Production Examples 40 to 43

The following compounds were obtained by the same methods as those of Production Example 25 and Example 20.

TABLE 10

| Prodn. Ex. | Structural formula | NMR |
|---|---|---|
| 40 | ethyl (6R*, 8R*)-3-(3,6,8-trimethyl-3-azabicyclo[3.3.1]nonan-9-yl)propanoate | $^1$H-NMR(CDCl$_3$) δ ppm: 0.80–1.00(m, 4H), 1.01(d, J=7.2Hz, 6H), 1.26(t, J=7.2Hz, 3H), 1.40–1.48(m, 2H), 1.78(q, J=7.6Hz, 2H), 1.78–1.95(m, 2H), 2.04–2.12(m, 1H), 2.19(br.s, 3H), 2.31(t J=7.6Hz, 2H), 2.55–2.67(m, 2H), 4.13(q, J=7.2Hz, 2H) |

TABLE 10-continued

| Prodn. Ex. | Structural formula | NMR |
|---|---|---|
| 41 | ethyl (6R*, 8R*)-3-(3,6,8-trimethyl-3-azabicyclo[3.3.1]non-9-yl)-2-methyl-propanoate | ¹H-NMR(CDCl₃) δ ppm: 0.80–1.05(m, 4H), 1.00(d, J=7.2Hz, 3H), 1.02(d, J=7.2Hz, 3H), 1.13(d, J=6.8Hz, 3H), 1.26(t, J=6.8Hz, 3H), 1.20–1.95(m, 7H), 2.19(br.s, 3H), 2.40–2.68(m, 3H), 4.13(q, J=6.8Hz, 2H) |
| 42 | ethyl [3-(tert-butoxycarbonyl)-3-azabicyclo[3.3.1]nonane-9-spiro-cyclobut-3′-yl]acetate | ¹H-NMR(CDCl₃) δ ppm: 1.2–1.9(m, 10H), 1.24(t, J=7Hz, 3H), 1.45(s, 9H), 2.17–2.33(m, 2H), 2.39(d, J=7Hz, 2H), 2.4–2.6(m, 1H), 2.9–3.25(m, 2H), 3.82(t, J=14Hz, 1H), 3.95(t, 13Hz, 1H), 4.11(q, J=7Hz, 2H) |
| 43 | ethyl (6R*,8R*)-[3-(tert-butoxycarbonyl)-6,8-dimethyl-3-azabicyclo[3.3.1]nonane-9-spiro-cyclobut-3′-yl]acetate | ¹H-NMR(CDCl₃) δ ppm: 0.95–1.15(m, 6H), 1.24(t, J=5Hz, 3H), 1.43(s, 9H), 1.2–1.6(m, 8H), 2.1–2.25(m, 2H), 2.38(d, J=8Hz, 2H), 2.5–2.65(m, 1H), 2.6–2.9(m, 2H), 3.5–3.65(m, 2H), 4.09(q, J=5Hz, 2H) |

Production Example 44

The following compound was obtained by the same methods as those of Examples 19 and 12.

TABLE 11

| Prodn. Ex. | Structural formula | NMR |
|---|---|---|
| 44 | ethyl [3-(-vinyloxycarbonyl)-3-azabicyclo[3.3.1]non-9-ylidene]fluoroacetate | ¹H-NMR(CDCl₃) δ ppm: 1.35(t, J=7.7Hz, 3H), 1.50–1.58(m, 1H), 1.74–1.98(m, 3H), 2.00–2.09(m, 2H), 3.07–3.23(m, 3H), 3.81–3.88(m, 1H), 4.30(q, J=7.7Hz, 2H), 4.31–4.38(m, 2H), 4.48(dd, J=1.7, 5.9Hz, 1H), 4.82(dd, J=1.7, 14.7Hz, 1H), 7.25(dd, J=5.9, 14.7Hz, 1H) |

Production Example 45

Ethyl 3-[3-(vinyloxycarbonyl)-1,5-dimethyl-3-azabicyclo[3.3.1]non-9-yl]-2-methylpropenoate

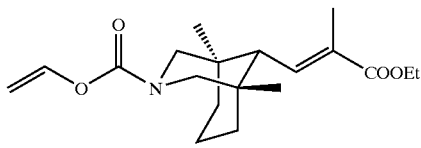

The title compound was obtained by treating (1,3,5-trimethyl-3-azabicyclo [3.3.1]-non-9-yl)carbaldehyde by the same methods as those of Production Example 25 and Example 12.

$^1$H-NMR(CDCl$_3$) δ ppm;
0.73(s, 6H), 1.32(t, J=7.0 Hz, 3H), 1.42–1.51(m, 2H), 1.54–1.70(m, 3H), 1.72–1.88(m, 1H), 1.90(d, J=1.9 Hz, 3H), 2.18(d, J=11.4 Hz, 1H), 2.70(d, J=11.3 Hz, 1H), 2.78(d, J=11.3 Hz, 1H), 4.00(d, J=13.1 Hz, 1H), 4.07(d, J=13.1 Hz, 1H), 4.21(q, J=7.0 Hz, 2H), 4.46(dd, J=1.7, 5.9 Hz, 1H), 4.80(dd, J=1.7, 14.7 Hz, 1H), 6.93(qd, J=1.9, 11.4 Hz, 1H), 7.25(dd, J=5.9, 14.7 Hz, 1H)

Production Example 46

Ethyl[3-(vinyloxycarbonyl)-3-azabicyclo[3.3.1non-9-yl]fluoroacetate

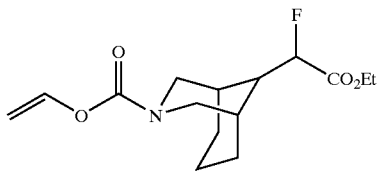

The title compound was obtained by treating 3-methyl-3-azabicyclo[3.3.1]nonan-9-one by the same methods as those of Production Example 25 and Examples 20 and 12 with the use of an appropriate Horner-Emmons reagent.

$^1$H-NMR(CDCl$_3$) δ ppm; 1.32(t, J=7.4 Hz, 3H), 1.51–1.59(m, 1H), 1.64–1.94(m, 6H), 2.06–2.18(m, 2H), 3.05–3.12(m, 1H), 3.14–3.21(m, 1H), 4.16–4.33(m, 2H), 4.28(q, J=7.4 Hz, 2H), 4.46(dd, J=1.8, 6.3 Hz, 1H), 4.79(dd, J=1.8, 14.0 Hz, 1H), 5.17(dd, J=10.4, 49.2 Hz, 1H), 7.25(dd, J=6.3, 14.0 Hz, 1H)

Production Example 47

Ethyl (syn)-(6R*,7R*)-[6,7-dimethyl-3-(vinyloxycarbonyl)-3-azabicyclo[3.2.1]oct-8-yl] acetate

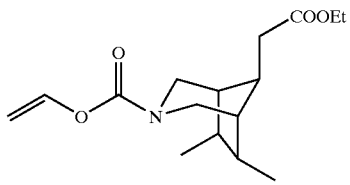

The title compound was obtained by treating ethyl(6R*, 7R*)-[3,6,7trimethyl3-azabicyclo[3.2.1]oct-8-ylidene] acetate by the same methods as those of Examples 10, 11 and 12.

$^1$H-NMR(CDCl$_3$) δ ppm; 0.98, 1.05(d, J=7.0 Hz, total 3H), 0.99, 1.06(d, J=7.1 Hz, total 3H), 1.26(t, J=7.1 Hz, 3H), 1.37–1.45(m, 1H), 1.53–1.63(m, 1H), 1.67–1.74(m, 1H), 1.84–1.94(m, 1H), 2.29–2.37(m, 1H), 2.48–2.62(m, 2H), 3.06, 3.14(dd, J=2.4, 13.7 Hz, total 1H), 3.13, 3.22(dd, J=2.0, 13.0 Hz, total 1H), 3.60, 3.63(t, J=2.7 Hz, total 1H), 3.82, 3.86(br.m, total 1H), 4.15(q, J=7.1 Hz, 2H), 4.44, 4.45(dd, J=1.5, 6.2 Hz, total 1H), 4.76, 4.79(dd, J=1.5, 13.9 Hz, total 1H), 7.23, 7.24(dd, J=6.2, 13.9 Hz, total 1H)

Production Example 48

Ethyl(3-methyl-9-oxo-3-azabicyclo[3.3.1]non-1-yl) carboxylate ethylenedithioketal

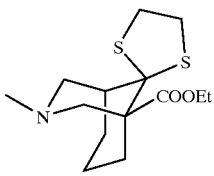

5.0 g of ethyl(3-methyl-9-oxo-3-azabicyclo[3.3.1]non-1-yl)carboxylate and 2.8 ml of 1,2-ethanedithiol were dissolved in methylene chloride (45 ml) and ice-cooled. Then 4.1 ml of a boron trifluoride/diethyl ether complex was dropped thereinto and the resulting mixture was stirred at room temperature for 5 days. The reaction mixture was concentrated and 1 N sodium hydroxide was added thereto. After extracting with ethyl acetate, the ethyl acetate layer was washed with 1 N sodium hydroxide, water and a saturated aqueous solution of sodium chloride, dried over anhydrous sodium sulfate and concentrated under reduced pressure. The obtained residue was purified by silica gel column chromatography (eluted with n-hexane/ethyl acetate) to thereby give 2.42 g of the title compound as a colorless oily substance.

$^1$H-NMR(CDCl$_3$) δ ppm; 1.26(t, J=7.1 Hz, 3H), 1.46(m, 1H), 1.82(m, 1H), 1.91–2.02(m, 2H), 2.18(s, 3H), 2.20(m, 1H), 2.48(m, 1H), 2.59–2.86(m, 4H), 3.05(dd, J=0.9, 12.1 Hz, 1H), 3.15–3.25(m, 4H), 4.13(m, 2H)

Production Example 49

Ethyl(3-methyl-3-azabicyclo[3.3.1]non-1-yl) carboxylate

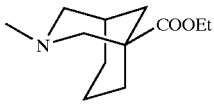

2.42 g of ethyl(3-methyl-9-oxo-3-azabicyclo[3.3.1]non-1-yl)carboxylate ethylenedithioketal was dissolved in ethanol (200 ml). After adding 40 g of Raney nickel, the resulting mixture was heated under reflux for 2 hours. Then the reaction mixture was filtered and concentrated under reduced pressure. The obtained residue was purified by silica gel column chromatography (eluted with toluene/ethyl acetate) to thereby give 0.95 g of the title compound as a slightly yellow oily substance.

$^1$H-NMR(CDCl$_3$) δ ppm; 1.24(t, J=7.1 Hz, 3H), 1.46–1.63(m, 3H), 1.64–1.78(m, 3H), 1.90–1.99(m, 2H), 2.06–2.18(m, 5H), 2.59(m, 1H), 2.78(m, 1H), 3.02(m, 1H), 4.10(q, J=7.1 Hz, 2H)

Production Example 50

Ethyl(3-methyl-3-azabicyclo[3.3.1]non-1-yl)acetate

1.1 ml of dibromomethane was dissolved in tetrahydrofuran (20 ml) and cooled to −90° C. Into the solution thus obtained were dropped 9.77 ml of a 1.6 M solution of n-butyllithium in hexane and 20 ml of a solution of lithium 2,2,6,6-tetramethylpiperidide, which had been prepared from 2.88 ml of 2,2,6,6-tetramethylpiperidine, in tetrahydrofuran while maintaining the bulk temperature at 10° C. or below. 5 minutes thereafter, 10 ml of a solution of 1.0 g of ethyl (3-methyl-3-azabicyclo[3.3.1]non-1-yl)carboxylate in tetrahydrofuran was dropped thereinto. After 20 minutes, 0.8 ml of 2,2,6,6-tetramethylpiperidine was added thereto. 5 minutes thereafter, 23.7 ml of a 1.6 M solution of n-butyllithium in hexane was dropped thereinto and the resulting mixture was stirred. After 10 minutes, the reaction mixture was heated to 30° C. and stirred for 1 hour. Then the reaction mixture was quickly dropped into a solution of hydrogen chloride prepared from 25 ml of acetyl chloride and 250 ml of ethanol and stirred at room temperature for 14 hours. The reaction mixture was concentrated and an aqueous solution of potassium carbonate was added thereto followed by the extraction with ethyl acetate. The ethyl acetate layer was washed with water and a saturated aqueous solution of sodium chloride and dried over anhydrous sodium sulfate. After concentrating under reduced pressure, the residue was purified by silica gel column chromatography (eluted with n-hexane/ethyl acetate) to thereby give 0.63 g of the title compound as a slightly yellow oily substance.

$^1$H-NMR(CDCl$_3$) δ ppm; 1.26(t, J=7.1 Hz, 3H), 1.34(m, 1H), 1.40–1.60(m, 4H), 1.68–1.78(m, 2H), 1.83–1.93(m, 2H), 2.06(m, 1H), 2.07(s, 2H), 2.11(s, 3H), 2.56(m, 1H), 2.76–2.86(m, 2H), 4.11(q, J=7.1 Hz, 2H)

Production Example 51

Ethyl (syn)-(3-benzyl-3-azabicyclo[3.3.1]non-7-yl) acetate

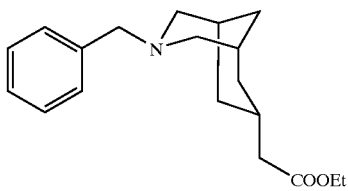

The title compound was obtained from ethyl(3-benzyl-3-azabicyclo[3.3.1]non-7-yl)carboxylate by the same method as the one of Production Example 50.

$^1$H-NMR(CDCl$_3$) δ ppm; 1.03(m, 1H), 1.23(m, 2H), 1.25(t, J=7.1 Hz, 3H), 1.77(m, 1H), 1.85–2.09(m, 7H), 2.24(d, J=7.0 Hz, 2H), 2.50–2.58(m, 2H), 3.43(s, 2H), 4.13(q, J=7.1 Hz, 2H), 7.20–7.35(m, 5H)

Production Example 52

[(anti)-2-[3-(Vinyloxycarbonyl)-3-azabicyclo[3.3.1]-non-9-yl]ethyl]methanesulfonate]

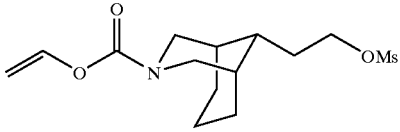

290 mg of (anti)-2-[3-(vinyloxycarbonyl)-3-azabicyclo-[3.3.1]non-9-yl]ethanol was dissolved in 4 ml of methylene chloride and 0.23 ml of pyridine was added thereto followed by ice-cooling. After adding 0.2 ml of methanesulfonyl chloride, the resulting mixture was stirred at room temperature for 14 hours. Then the reaction mixture was concentrated and the residue was purified by silica gel column chromatography (eluted with n-hexane/ethyl acetate) to thereby give 370 mg of the title compound as a colorless oily substance.

$^1$H-NMR(CDCl$_3$) δ ppm; 1.48(m, 1H), 1.60–1.87(m, 8H), 1.95–2.03(m, 2H), 3.03(s, 3H), 3.12(m, 1H), 3.19(m, 1H), 4.18–4.27(m, 2H), 4.30(t, J=6.4 Hz, 2H), 4.45(dd, J=1.6, 6.2 Hz, 1H), 4.79(dd, J=1.6, 14.1 Hz, 1H), 7.25(dd, J=6.2, 14.1H, 1H)

Production Example 53

(anti)-3-[3-(Vinyloxycarbonyl)-3-azabicyclo[3.3.1] non-9-yl]propanenitrile

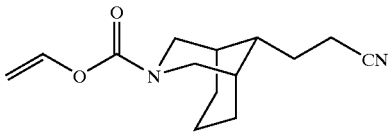

370 mg of [(anti)-2-[3-(vinyloxycarbonyl)-3-azabicyclo [3.3.1]non-9-yl]ethyl] methanesulfonate was dissolved in dimethyl sulfoxide (3 ml). After adding 108 mg of sodium cyanide, the resulting mixture was stirred at 80° C. for 2 hours. After adding water, the reaction mixture was extracted with ethyl acetate. Then the ethyl acetate layer was washed with water and a saturated aqueous solution of sodium chloride, dried over anhydrous magnesium sulfate and concentrated under reduced pressure. Then the residue was purified by silica gel column chromatography (eluted with n-hexane/ethyl acetate) to thereby give 167 mg of the title compound as a colorless oily substance.

$^1$H-NMR(CDCl$_3$) δ ppm; 1.48(m, 1H), 1.61–1.84(m, 8H), 1.87–1.95(m, 2H), 2.39(t, J=7.3 Hz, 2H), 3.12(m, 1H), 3.20(m, 1H), 4.20–4.30(m, 2H), 4.46(dd, J=1.6, 6.2 Hz, 1H), 4.79(dd, J=1.6, 14.1 Hz, 1H), 7.25(dd, J=6.2, 14.1 Hz, 1H)

Production Example 54

Methyl (anti)-3-(3-azabicyclo[3.3.1]non-9-yl) propanoate

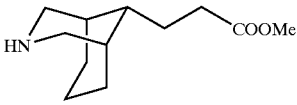

167 mg of (anti)-3-[3-(vinyloxycarbonyl)-3-azabicyclo-[3.3.1]non-9-yl]propanenitrile was dissolved in ethanol (2 ml). After adding 2 ml of water and 107 mg of potassium hydroxide, the resulting mixture was heated under reflux for 12 hours. After further adding 2 ml of ethanol and 107 mg of potassium hydroxide, the resulting mixture was heated under reflux for additional 10 hours. Then the reaction mixture was concentrated under reduced pressure. After adding 10 ml of 10% hydrogen chloride/methanol, the reaction mixture was heated under reflux for 3 hours and then concentrated under reduced pressure. An aqueous solution of potassium carbonate was added to the residue followed by the extraction with methylene chloride. After drying over anhydrous potassium carbonate, it was concentrated under reduced pressure. Then the residue was purified by silica gel column chromatography (eluted with methylene chloride/methanol/conc. aqueous ammonia) to thereby give 97 mg of the title compound as a pale brown oily substance.

$^1$H-NMR(CDCl$_3$) δ ppm; 1.49–1.67(m, 6H), 1.71–2.03 (m, 5H), 2.12(m, 1H), 2.31(t, J=7.7 Hz, 2H), 2.96–3.04(m, 2H), 3.12–3.18(m, 2H), 3.68(s, 3H)

Production Examples 55 and 56

The following compounds were obtained by the same method as the one of Example 27.

TABLE 12

| Prodn. Ex. | Structural formula | | NMR |
|---|---|---|---|
| 55 | ethyl 2-(3-methyl-3-azabicyclo[3.3.1]non-9-yl)propanoate | | $^1$H-NMR(CDCl$_3$) δ ppm: 1.11(d, J=7.0Hz, 3H), 1.25(t, J=7.1Hz, 3H), 1.38–1.68(m, 6H), 1.77(br.s, 1H), 1.87(m, 1H), 2.09–2.21(m, 5H), 2.42(m, 1H), 2.77–2.89 (m, 2H), 2.94(m, 1H), 4.13(q, J=7.1Hz, 2H) |
| 56 | methyl (3,9-dimethyl-3-azabicyclo[3.3.1]non-9-yl)carboxylate | | $^1$H-NMR(CDCl$_3$) δ ppm: 1.24 and 1.25(s, 3H), 1.30–1.38, 1.64–1.70, 1.76–1.92, 1.96–1.98, 2.08–2.12(m, 8H), 2.07 and 2.18(s, 3H), 2.30–2.35, 2.38–2.46, 2.58–2.70(m, 4H), 3.67 and 3.72(s, 3H) |

Production Examples 57 to 60

The following compounds were obtained by the same method as the one of Example 12.

TABLE 13

| Prodn. Ex. | Structural formula | NMR |
|---|---|---|
| 57 | ethyl (anti)-2-[3-(vinyloxycarbonyl)-3-azabicyclo[3.3.1]non-9-yl]propanoate | $^1$H-NMR(CDCl$_3$) δ ppm: 1.15(d, J=7Hz, 3H), 1.26(t, J=7Hz, 3H), 1.45–1.52(m, 1H), 1.58–1.72(m, 5H), 1.78(br.d, J=11Hz, 1H), 1.84–1.91(m, 2H), 2.84(qd, J=7, 11Hz, 1H), 3.05–3.20(m, 2H), 4.15–4.18(q, J=7Hz, 2H), 4.18–4.29(s, 2H), 4.44(dd, J=2, 6Hz, 0.5H), 4.44(dd, J=2, 6Hz, 0.5H), 4.77(dd, J=2, 14Hz, 0.5H), 4.78(dd, J=2, 14Hz, 0.5H), 7.22(dd, J=6, 14Hz, 1H) |
| 58 | ethyl (syn)-2-[3-(vinyloxycarbonyl)-3-azabicyclo[3.3.1]non-9-yl]propanoate | $^1$H-NMR(CDCl$_3$) δ ppm: 1.15(d, J=7Hz, 1.5H), 1.17(d, J=7Hz, 1.5H), 1.25(t, J=7Hz, 1.5H), 1.26(t, J=7Hz, 1.5H), 1.43–1.54(m, 2H), 1.64–1.78(m, 4H), 1.82–1.88(m, 1H), 1.89–2.01(m, 2H), 2.74(dq, J=7, 9Hz, 1H), 3.16(ddd, J=15, 3, 1Hz), 0.5H), 3.23(ddd, J=1, 3, 14Hz, 0.5H), 3.36(ddd, J=2, 5, 14Hz, 0.5H), 3.43(ddd, J=2, 4, 15Hz, 0.5H), 3.88(m, 2H), 4.14(q, J=7Hz, 2H), 4.44(dd, J=1, 6Hz, 1H), 4.78(dd, J=1, 14Hz, 1H), 7.25(dd, J=6, 14Hz, 1H) |

TABLE 13-continued

| Prodn. Ex. | Structural formula | NMR |
|---|---|---|
| 59 | methyl (syn)-[3-(vinyloxycarbonyl)-(anti)-9-methyl-3-azabicyclo[3.3.1]non-9-yl]carboxylate | $^1$H-NMR(CDCl$_3$) δ ppm: 1.36–1.42(m, 1H), 1.55(s, 3H), 1.64–1.82(m, 5H), 2.12(br.s, 1H), 2.17(br.s, 1H), 3.43(ddd, J=2, 5, 14Hz, 1H), 3.51(ddd, , J=2, 5, 14Hz, 1H), 3.74(s, 3H), 3.92(dd, J=2, 5Hz, 1H), 3.95(dd, J=2, 5Hz, 1H), 4.46(dd, J=2, 6Hz, 1H), 4.80(dd, J=2, 14Hz, 1H), 7.25(dd, J=6, 14Hz, 1H) |
| 60 | methyl (anti)-[3-(vinyloxycarbonyl)-(syn)-9-methyl-3-azabicyclo[3.3.1]non-9-yl]carboxylate | $^1$H-NMR(CDCl$_3$) δ ppm: 1.45–1.52(m, 1H), 1.55(s, 3H), 1.64–1.76(m, 3H), 1.95(br.s, 2H), 2.12(br.s, 1H), 2.16(br.s, 1H), 3.33(ddd, J=2, 4, 13Hz, 1H), 3.35(ddd, J=3, 4, 13Hz, 1H), 3.72(s, 3H), 3.99(br.t, J=13Hz, 2H), 4.43(dd, J=2, 6Hz, 1H), 4.77(dd, J=2, 14Hz, 1H), 7.22(dd, J=6, 14Hz, 1H) |

Production Example 61

Ethyl(11-hydroxy-9-methyl-9-azabicyclo[5.3.1]undec-11-yl)acetate

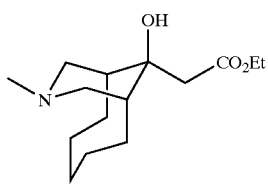

A solution of 2.1 g of ethyl ethynyl ether (a 50% hexane solution) in dry diethyl ether (25 ml) was cooled in a nitrogen atmosphere to −78° C. After dropping 6 ml of a 2.5 M solution of n-butyllithium in hexane, the resulting mixture was stirred for 10 minutes. Next, 10 ml of a solution of 78 g of 3-methyl-3-azabicyclo[5.3.1]undecan-11-one in dry diethyl ether (10 ml) was dropped into the reaction mixture. After stirring for 15 minutes, the mixture was brought back to room temperature and then distributed into an aqueous solution of ammonium chloride and ethyl acetate. The organic layer was extracted and dried over anhydrous sodium sulfate. After distilling off the solvent, an oily component was obtained. Then 100 ml of tetrahydrofuran was added thereto and the resulting mixture was stirred. After dropping 10 mmol of conc. sulfuric acid thereinto, the reaction mixture was distributed into an aqueous solution of sodium bicarbonate and ethyl acetate and the organic layer was extracted. After distilling off the solvent under reduced pressure, the residue was purified by silica gel column chromatography (eluted with ethyl acetate/n-hexane) to thereby give 1.29 g of the title compound as a colorless oily substance.

$^1$H-NMR(CDCl$_3$) δ ppm; 1.14–1.26(m, 2H), 1.26(t, J=7.2 Hz, 3H), 1.50–1.65(m, 3H), 1.68–1.73(m, 2H), 1.77–1.90 (m, 3H), 2.02–2.12(m, 2H), 2.15(s, 3H), 2.15–2.22(m, 2H), 2.64(d, J=12.6 Hz, 2H), 2.67(s, 2H), 3.92(s, 1H), 4.15(q, J=7.2 Hz, 2H)

Production Example 62

9-(1,3-Dithian-2-ylidenemethyl)-1,3,5-trimethyl-3-azabicyclo[3.3.1]nonane

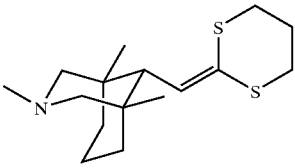

Into 50 ml of a solution of 2.85 ml of 2-trimethylsilyl-1,3-dithiane in dry tetrahydrofuran was dropped 5.2 ml of a 2.5 M solution of n-butyllithium in hexane at −30° C. After stirring for 30 minutes, 1.93 g of (1,3,5-trimethyl-3-azabicyclo[3.3.1]non-9-yl)carbaldehdye was added thereto and the resulting mixture was stirred at room temperature over day and night. Then the reaction mixture was poured into an aqueous solution of ammonium chloride, made alkaline with potassium carbonate and extracted with ethyl acetate. The organic layer was washed with water and dried over anhydrous sodium sulfate. After distilling off the solvent under reduced pressure, the residue was recrystallized from n-hexane to thereby give 1.78 g of the title compound as colorless needles.

$^1$H-NMR(CDCl$_3$) δ ppm; 0.55(s, 6H), 1.14–1.24(m, 2H), 1.24–1.34(m, 3H), 1.65(dd,J=2.2, 11.8H, 2H), 1.91(s, 3H), 1.98–2.05(m, 2H), 2.10(d, J=11.0 Hz, 1H), 2.42–2.55(m, 1H), 2.49(d, J=11.8 Hz, 2H), 2.65–2.74(m, 4H), 6.03(d, J=11.0 Hz, 1H)

Production Example 63

Methyl(1.3.5-trimethyl-3-azabicyclo[3.3.1]non-9-yl)acetate

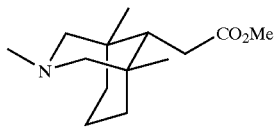

To a solution of 1.78 g of 9-(1,3-dithian-2-ylidenemethyl)-1,3,5-trimethyl-3-azabicyclo[3.3.1]nonane in a solvent mixture of methanol (27 ml) with water (3 ml) was added 3.53 g of mercuric chloride under stirring and the resulting mixture was then refluxed for 20 hours. Next, the reaction mixture was poured into ethyl acetate/an aqueous solution of potassium carbonate and filtered through celite. After. distilling off the solvent under reduced pressure, the residue was purified by silica gel column chromatography (eluted with n-hexane/ethyl acetate) to thereby give 0.23 g of the title compound as a colorless oily substance.

$^1$H-NMR(CDCl$_3$) δ ppm; 0.57(s, 6H), 1.09–1.24(m, 5H), 1.51(t, J=6.0 Hz, 1H), 1.70(dd, J=2.5, 11.6 Hz, 2H), 1.90(s, 3H), 2.17(d, J=6.0 Hz, 2H), 2.45(d, J=11.6 Hz, 2H), 2.42–2.49(m, 1H), 3.51(s, 3H)

Production Example 64

(anti)-2-(3-Methyl-3-azabicyclo[3.3.1]non-9-yl)ethanol

To a solution of 2.8 g of ethyl (anti)-(3-methyl-3-azabicyclo[3.3.1]non-9-yl)acetate in dry tetrahydrofuran (50 ml) was added 0.47 g of lithium aluminum hydride at 0° C. and the resulting mixture was reacted for 20 minutes. After adding a 10% aqueous solution of sodium hydroxide to the reaction mixture, the insoluble matters were filtered off and the filtrate was concentrated under reduced pressure to thereby give 2.5 g of the title compound as a colorless oily substance.

$^1$H-NMR(CDCl$_3$) δ ppm; 1.3–1.45(m, 1H), 1.45–1.65(m, 6H), 1.75(q, J=5 Hz, 4H), 2.14(s, 3H), 2.0–2.25(m, 2H), 2.3–2.50(m, 1H), 2.83–2.98(m, 2H), 3.68(q, J=5 Hz, 2H)

Production Example 65

Methyl 4-[2-((anti)-3-methyl-3-azabicyclo[3.3.1]non-9-yl)ethyloxylphenylacetate

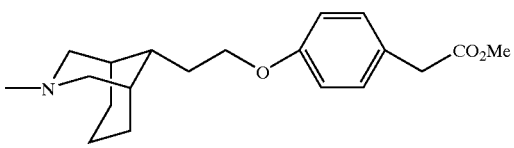

To a solution of 0.9 g of (anti)-2-(3-methyl-3-azabicyclo[3.3.1]non-9-yl)ethanol, 1.2 g of methyl 4-hydroxyphenylacetate and 1.95 g of triphenylphosphine in dry tetrahydrofuran (30 ml) was added 1.2 ml of diethyl azodicarboxylate at 0° C. The obtained mixture was reacted for 10 minutes and then stirred at room temperature for 72 hours. After adding water and dilute hydrochloric acid, the reaction mixture was washed with ethyl acetate. Then aqueous ammonia was added to the aqueous layer followed by the extraction with ethyl acetate. The extract was washed with a saturated aqueous solution of sodium chloride, dried over anhydrous magnesium sulfate and concentrated under reduced pressure. The residue was purified by silica gel column chromatography (eluted with ethyl acetate/n-hexane) to thereby give 1.0 g of the title compound as a colorless oily substance.

$^1$H-NMR(CDCl$_3$) δ ppm; 1.4–1.7(m, 7H), 1.7–1.9(m, 2H), 1.96(q, J=7 Hz, 2H), 2.1–2.25(m, 4H), 2.35–2.50(m, 1H), 2.85–2.95(m, 2H), 3.56(s, 2H), 3.68(s, 3H), 3.97(t, J=7 Hz, 2H), 6.85(d, J=8 Hz, 2H), 7.18(d, J=8 Hz, 2H)

Production Examples 66 and 67

The following compounds were obtained by the same method as the one of Production Example 65.

TABLE 14

| Prodn. Ex. | Structural formula | NMR |
|---|---|---|
| 66 | 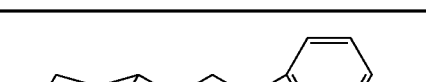<br>methyl 3-[2-[(anti)-3-methyl-3-azabicyclo[3.3.1]-non-9-yl]-ethyloxy]benzoate | $^1$H-NMR(CDCl$_3$) δ ppm: 1.3–1.45(m, 1H), 1.4–1.6(m, 3H), 1.5–1.65(m, 3H), 1.67–1.8(m, 2H), 1.92(q, J=8Hz, 2H), 2.0–2.2(m, 4H), 2.3–2.5(m, 1H), 2.8–2.95(m, 2H), 3.85(s, 3H), 3.97(t, J=7Hz, 2H), 7.03(ddd, J=1, 3, 8Hz, 1H), 7.27(t, J=8Hz, 1H), 7.48(dd, J=1, 3Hz, 1H), 7.55(ddd, J=1, 3, 8Hz, 1H) |

TABLE 14-continued

| Prodn. Ex. | Structural formula | NMR |
|---|---|---|
| 67 | ![structure] | ¹H-NMR(CDCl₃) δ ppm: 1.36(t, J=5Hz, 3H), 1.3–1.5(m, 1H), 1.5–1.6(m, 3H), 1.6–1.7(m, 2H), 1.7–1.9(m, 2H), 1.95–2.05(m, 2H), 2.13(s, 3H), 2.19(d, J=10Hz, 2H), 2.35–2.50(m, 1H), 2.93(d, J=10Hz, 2H), 4.04(t, J=5Hz, 2H), 4.33(q, J=5Hz, 2H), 6.90(d, J=8Hz, 2H), 8.00(d, J=8Hz, 2H) |
| | ethyl 4-[2-[(anti)-3-methyl-3-azabicyclo[3.3.1]-non-9-yl]-ethyloxy]benzoate | |

Production Example 68 tert-Butyl [2-((anti)-3-methyl-3-azabicyclo[3.3.1]non-9-yl)ethyloxy]acetate

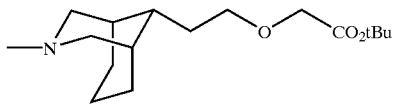

To 17 ml of a 50% aqueous solution of sodium hydroxide and 5 ml of methylene chloride were added 0.7 g of (anti)-2-[3-methyl-3-azabicyclo[3.3.1]non-9-yl]ethanol, 5.6 ml of tert-butyl bromoacetate and 1.3 g of tetrabutylammonium hydrogensulfate and the resulting mixture was vigorously stirred at room temperature for 2 hours. After adding dilute hydrochloric acid, the reaction mixture was washed with ether. Then aqueous ammonia was added thereto and the mixture was extracted with ethyl acetate. The extract was washed with a saturated aqueous solution of sodium chloride, dried over anhydrous magnesium sulfate and concentrated under reduced pressure. Thus, 1.3 g of the title compound was obtained as a yellow oily substance.

¹H-NMR(CDCl₃) δ ppm; 1.46(s, 9H), 1.40–1.90(m, 10H), 2.11(s, 3H), 2.1–2.2(m, 2H), 2.3–2.5(m, 1H), 2.83–2.95(m, 2H), 3.53(t, J=5 Hz, 2H), 3.94(s, 2H)

Production Example 69

Ethyl[2-((anti)-3-methyl-3-azabicyclo[3.3.1]non-9-yl)ethyloxy]acetate

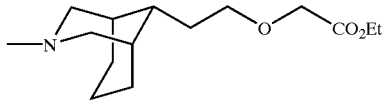

To a solution of 1.3 g of tert-butyl [2-((anti)-3-methyl-3-azabicyclo[3.3.1]non-9-yl)ethyloxy]acetate in methylene chloride (10 ml) was added 3.92 ml of trifluoroacetic acid and the resulting mixture was reacted at 50° C. for 30 minutes. Then the reaction mixture was concentrated under reduced pressure to thereby give 1.0 g of a crude carboxylic acid as a yellow oily substance. To 1.0 g of this crude carboxylic acid was added 100 ml of ethanol. Next, 3 ml of thionyl chloride was dropped thereinto and the resulting mixture was heated under reflux for 1 hour. The reaction mixture was concentrated and aqueous ammonia was added thereto. Then it was extracted with ethyl acetate, washed with a saturated aqueous solution of sodium chloride and dried over anhydrous magnesium sulfate. After concentrating under reduced pressure, 0.7 g of the title compound was obtained as a pale brown oily substance.

¹H-NMR(CDCl₃) δ ppm; 1.28(t, J=5 Hz, 3H), 1.25–1.70 (m, 6H), 1.70–1.85(m, 4H), 2.13(s, 3H), 2.05–2.25(m, 2H), 2.25–2.50(m, 1H), 2.80–3.00(m, 2H), 3.55(t, J=5 Hz, 2H), 4.05(s, 2H), 4.21(q, J=5 Hz, 2H)

Production Example 70

Ethyl (anti)-(3-methyl-(syn)-9-methoxy-3-azabicyclo[3.3.1]non-9-yl)acetate and ethyl (syn)-(3-methyl-(anti)-9-methoxy-3-azabicyclo[3.3.1]non-9-yl)acetate

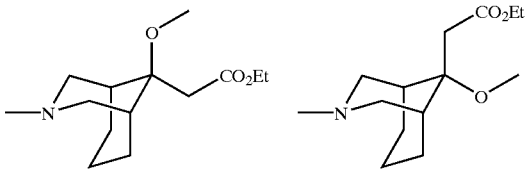

To a solution of 2.5 ml of ethyl acetate in dry tetrahydrofuran (100 ml) was added at −78° C. 27.5 ml of a 1.0 M solution of lithium bis(trimethylsilyl)amide in hexane and the resulting mixture was stirred for 1 hour. Next, 3.0 g of 3-methyl-3-azabicyclo[3.3.1]nonan-9-one was dropped thereinto and the mixture was slowly heated from −78° C. to room temperature and reacted for 3 hours. After adding a cold saturated aqueous solution of ammonium chloride, the reaction mixture was extracted with ethyl acetate. The extract was washed with a saturated aqueous solution of sodium chloride, dried over anhydrous magnesium sulfate and concentrated under reduced pressure to thereby give 5.3 g of a yellow oily substance.

To a solution of 1.0 g of this oily substance and 0.34 ml of methyl iodide in dry N,N-dimethylformamide (20 ml) was added sodium hydride (oily: 60% or above) at room temperature and the mixture was reacted for 12 hours. After adding ice/water, the reaction mixture was extracted with ethyl acetate, washed with a saturated aqueous solution of sodium chloride and dried over anhydrous magnesium sulfate. After concentrating under reduced pressure, the residue was purified by silica gel column chromatography (eluted with n-hexane/ethyl acetate) to thereby give 0.3 g (anti) and 0.1 g (syn) of the title compounds each as a yellow oily substance.

$^1$H-NMR(CDCl$_3$) δ ppm;
Anti
  1.24(t, J=5 Hz, 3H), 1.30–1.45(m, 1H), 1.45–1.55(m, 2H), 1.55–1.65(m, 1H), 1.9–2.11(m, 3H), 2.19(s, 3H), 2.3–2.5(m, 1H), 2.50(br.d, J=13 Hz, 2H), 2.76(s, 2H), 2.84(br.d, J=13 Hz, 2H), 3.28(s, 3H), 4.13(q, J=5 Hz, 2H)
Syn
  1.25(t, J=5 Hz, 3H), 1.35–1.50(m, 1H), 1.55(br.s, 2H), 1.74–1.90(m, 4H), 1.98(br.s, 2H), 2.13(br.s, 2H), 2.58(br.s, 3H), 2.4–2.6(m-1H), 2.76(s, 2H), 3.25(s, 3H), 4.14(q, J=5 Hz, 2H)

Production Example 71

3-(tert-Butoxycarbonyl)-3-azabicyclo[3.3.1]nonane-9-spiro-(3'-methylene)cyclobutane

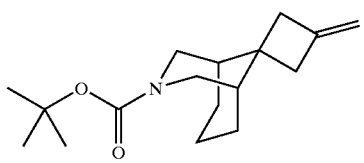

7 g of the title compound was obtained as a colorless oily substance from 9.7 g of 3-(tert-butoxycarbonyl)-3-azabicyclo[3.3.1]nonane-9-spiro-cyclobutan-3'-one by the same method as the one of Production Example 14.

$^1$H-NMR(CDCl$_3$) δ ppm; 1.46(s, 9H), 1.3–1.8(m, 8H), 2.52(s, 2H), 2.56(s, 2H), 3.03(d, J=12 Hz, 1H), 3.11(d, J=12 Hz, 1H), 3.88(d, J=13 Hz, 1H), 4.01(d, J=13 Hz, 1H), 4.81(m, 2H)

Production Example 72

[3-(tert-Butoxycarbonyl)-3-azabicyclo[3.3.1]nonane-9-spiro-cyclobut-3'-yl]methanol

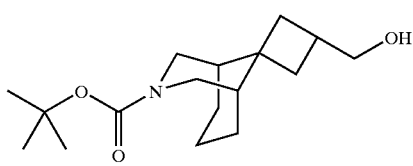

To a solution of 5 g of 3-(tert-butoxycarbonyl)-3-azabicyclo[3.3.1]nonane-9-spiro-(3'-methylene)cyclobutane in dry tetrahydrofuran (100 ml) was added 106 ml of a 1 M solution of a borane/tetrahydrofuran complex in tetrahydrofuran at 0° C. and the resulting mixture was reacted for 12 hours. After adding 33 ml of 4 N sodium hydroxide at 0° C., 49 ml of a 30% aqueous solution of hydrogen peroxide was further added thereto and the resulting mixture was stirred at room temperature for 3 hours. After adding an aqueous solution of sodium thiosulfate, the reaction mixture was extracted with ethyl acetate, washed with a saturated aqueous solution of sodium chloride and dried over anhydrous magnesium sulfate. After concentrating, the residue was purified by silica gel column chromatography (eluted with ethyl acetate/n-hexane) to thereby give 4.7 g of the title compound as a colorless oil.

$^1$H-NMR(CDCl$_3$) δ ppm; 1.3–1.9(m, 10H), 1.45(s, 9H), 2.0–2.18(m, 2H), 2.28–2.44(m, 1H), 2.94–3.2(m, 2H), 3.58 (d, J=6 Hz, 2H), 3.64(t, J=6 Hz, 1H), 3.83(br.t, J=15 Hz, 1H), 3.96(br.t, J=13 Hz, 1H)

Production Example 73

[3-(tert-Butoxycarbonyl)-3-azabicyclo[3.3.1]nonane-9-spiro-cyclobut-3'-yl]carbaldehyde

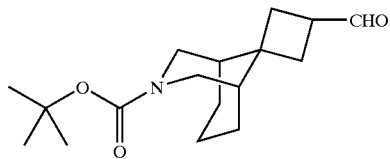

Into a solution of 1.6 ml of oxalyl chloride in methylene chloride (50 ml) was dropped 1.4 ml of dry dimethyl sulfoxide at −78° C. Next, a solution of 4.6 g of [3-(tert-butoxy-carbonyl)-3-azabicyclo[3.3.1]nonane-9-spiro-cyclobut-3'-yl]-methanol in methylene chloride (20 ml) was added thereto. After reacting at −78° C. for 40 minutes, 8.7 ml of triethylamine was dropped thereinto. Then the reaction mixture was stirred from −78° C. to room temperature over 30 minutes. After adding water, the reaction mixture was extracted with ethyl acetate, washed with a saturated aqueous solution of sodium chloride and dried over anhydrous magnesium sulfate. After concentrating under reduced pressure, the residue was purified by silica gel column chromatography (eluted with ethyl acetate/n-hexane) to thereby give 3.4 g of the title compound as a pale yellow oily substance.

$^1$H-NMR(CDCl$_3$) δ ppm; 1.37((br.s, 1H), 1.4–1.85(m, 7H), 1.45(s, 9H), 2.0–2.25(m, 4H), 2.95–3.20(m, 2H), 3.83 (d, J=13 Hz, 1H), 3.88(d, J=13 Hz, 1H), 3.99(t, J=14 Hz, 1H), 9.75(s, 1H)

Production Example 74

Methyl[3-(tert-butoxycarbonyl)-3-azabicyclo [3.3.1] nonane-9-spiro-cyclobut-3'-yl]carboxylate

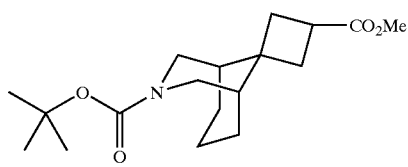

To a solution of 3.4 g of [3-(tert-butoxycarbonyl)-3-azabicyclo[3.3.1]nonane-9-spiro-cyclobut-3'-yl] carbaldehyde in methanol (17 ml) was added 15.4 g of sodium hydrogencarbonate. Then 2 ml of bromine was dropped thereinto. After reacting at room temperature for 1 hour, ice/water and an aqueous solution of sodium thiosulfate were added thereto followed by the extraction with ethyl acetate. The extract was washed with a saturated aqueous solution of sodium chloride, dried over anhydrous magnesium sulfate and concentrated under reduced pressure. The obtained residue was purified by silica gel column chromatography (eluted with ethyl acetate/n-hexane) to thereby give 1.4 g of the title compound as a colorless oily substance.

$^1$H-NMR(CDCl$_3$) δ ppm;
1.1–1.2(m, 1H), 1.45(s, 9H), 1.5–1.8(m, 8H), 2.00–2.15 (m, 2H), 2.15–2.33(m, 2H), 2.93–3.05(m, 1H), 3.08(br.d, J=13 Hz, 1H), 3.68(s, 3H), 3.85(br.t, J=11 Hz, 1H), 3.99(br.t, J=11 Hz, 1H)

Production Example 75

N-Allyl-N-methyl-6-methoxycarbonyl-2-oxa-3-oxobicyclo[2.2.2]oct-5-ene-7-carboxamide and N-allyl-N-methyl-6-methoxycarbonyl-2-oxa-3-oxobicyclo[2.2.2]oct-5-ene-8-carboxamide A mixture of 10.42 g of methyl coumalate with 10.56 g of N-allyl-N-methylacrylamide was stirred at 100° C. for 17 hours. Then the reaction mixture was purified by silica gel column chromatography (eluted with n-hexane/ethyl acetate) to thereby give two isomers. From the less polar fraction, 7.90 g of N-allyl-N-methyl-6-methoxycarbonyl-2-oxa-3-oxobicyclo[2.2.2]oct-5-ene-8-carboxamide was obtained as a slightly yellow powder. From the more polar fraction, on the other hand, 4.19 g of N-allyl-N-methyl-6-methoxycarbonyl-2-oxa-3-oxobicyclo[2.2.2]oct-5-ene-7-carboxamide was obtained as a pale yellow oily substance.

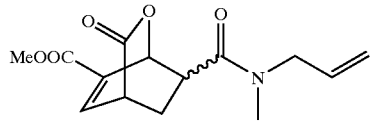

$^1$H-NMR(CDCl$_3$) δ ppm; 1.81, 1.90(m, total 1H), 2.28, 2.34(m, total 1H), 2.88, 3.05(s, total 3H), 3.49, 3.57(m, total 1H), 3.65–3.72(m, 1H), 3.82, 3.84(s, total 3H), 3.96–4.07 (m, 2H), 5.12–5.32(m, 2H), 5.56–5.86(m, 2H), 7.32–7.38 (m, 1H)

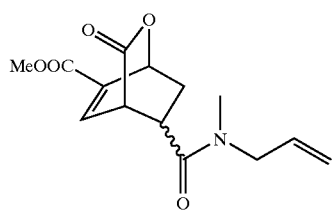

$^1$H-NMR(CDCl$_3$) δ ppm; 1.74, 1.77(d, J=5.1 Hz, total 1H), 2.66, 2.75(ddd, J=4.2, 6.4, 10.4 Hz, total 1H), 2.89, 2.97(s, total 3H), 3.23, 3.31(m, total 1H), 3,79(s, 3H), 3.82–4.00(m, 3H), 5.10–5.30(m, 2H), 5.64–5.81(m, 2H), 7.51, 7.53(d, J=2.2 Hz, total 1H)

Production Example 76

Methyl 3-methyl-2-oxo-3-azatricyclo[5.3.1.0$^{5,10}$] undec-8-ene-9-carboxylate

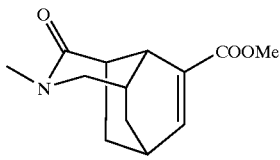

4.75 g of N-allyl-N-methyl-6-methoxycarbonyl-2-oxa-3-oxobicyclo[2.2.2]oct-5-ene-7-carboxamide was stirred at 180° C. for 6 hours. Then the reaction mixture was purified by silica gel column chromatography (eluted with n-hexane/ethyl acetate) to thereby give 0.93 g of the title compound as a pale yellow oily substance.

$^1$H-NMR(CDCl$_3$) δ ppm; 1.33(ddd, J=2.0, 5.3, 12.6 Hz, 1H), 1.57(dt, J=3.1, 13.2 Hz, 1H), 1.69–1.84(m, 2H), 1.90 (m, 1H), 2.38(m, 1H), 2.79(m, 1H), 2.98(br.s, 3H), 3.17(dd, J=1.5, 12.3 Hz, 1H), 3.32(m, 1H), 3.53(dd, J=4.4, 12.3 Hz, 1H), 3.77(s, 3H), 7.44(dd, J=1.5, 7.0 Hz, 1H)

Production Example 77

Methyl 3-methyl-2-oxo-3-azatricyclo[5.3.1.0$^{5,10}$] undec-8-ene-8-carboxylate

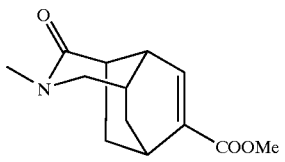

The title compound was obtained as a pale yellow oily substance from N-allyl-N-methyl-6-methoxycarbonyl-2-oxa-3-oxobicyclo[2.2.2]oct-5-ene-8-carboxamide by the same method as the one of Production Example 76.

$^1$H-NMR(CDCl$_3$) δ ppm; 1.34(ddd, J=2.0, 5.1, 12.8 Hz, 1H), 1.59(dt, J=3.1, 13.2 Hz, 1H), 1.71–1.94(m, 3H), 2.38 (m, 1H), 2.86(m, 1H), 2.98(s, 3H), 3.18–3.25(m, 2H), 3.49 (dd, J=4.2, 12.3 Hz, 1H), 3.77(s, 3H), 7.29(dd, J=1.6, 7.0 Hz, 1H)

Production Example 78

Methyl 3-methyl-2-oxo-3-azatricyclo[5.3.1.0$^{5,10}$] undecane-9-carboxylate

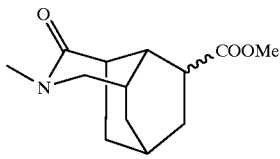

0.7 g of methyl 3-methyl-2-oxo-3-azatricyclo-[5.3.1 0$^{5,10}$]undec-8-ene-9-carboxylate was dissolved in methanol (15 ml). After adding 0.3 g of 10% palladium-carbon, the resulting mixture was hydrogenated at ordinary temperature under atmospheric pressure for 19 hours. After filtering off the catalyst, the residue was concentrated under reduced pressure. After adding ethyl acetate to the residue, it was filtered and the filtrate was concentrated under reduced pressure to thereby give 0.78 g of the title compound as a slightly yellow oily substance.

¹H-NMR(CDCl₃) δ ppm; 1.30(m, 1H), 1.46(m, 1H), 1.59(m, 1H), 1.76–2.14(m, 5H), 2.17(m, 1H), 2.54(m, 1H), 2.71(m, 1H), 2.94(br.s, 3H), 3.03(dd, J=1.6, 12.1 Hz, 1H), 3.47(dd, J=1.6, 12.1 Hz, 1H), 3.68(s, 3H)

Production Example 79

Methyl 3-methyl-2-oxo-3-azatricyclo[5.3.1.0$^{5,10}$]undecane-8-carboxylate

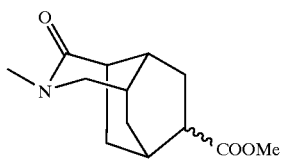

The title compound was obtained as a slightly yellow oily substance from methyl 3-methyl-2-oxo-3-azatricyclo-[5.3.1.0$^{5,10}$]undec-8-ene-8-carboxylate by the same method as the one of Production Example 78.

¹H-NMR(CDCl₃) δ ppm; 1.36(m, 1H), 1.44(m, 1H), 1.78–1.91(m, 3H), 1.93–2.13(m, 4H), 2.49–2.62(m, 2H), 2.94(s, 3H), 3.02(dd, J=1.3, 11.9 Hz, 1H), 3.44(dd, J=3.7, 11.9 Hz, 1H), 3.70(s, 3H)

Production Example 80

Methyl 3-methyl-2-thioxo-3-azatricyclo[5.3.1.0$^{5,10}$]undec-8-ene-9-carboxylate

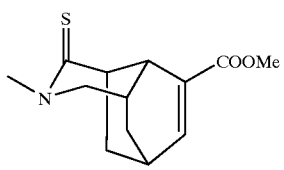

2.24 g of methyl 3-methyl-2-oxo-3-azatricyclo[5.3.1.0$^{5,10}$]undec-8-ene-9-carboxylate was dissolved in toluene (30 ml). After adding 2.31 g of Lawson's reagent, the resulting mixture was heated to 100° C. for 1 hour. Then the reaction mixture was purified as such by silica gel column chromatography (eluted with n-hexane/ethyl acetate) to thereby give 1.91 g of the title compound as colorless needles.

¹H-NMR(CDCl₃) δ ppm; 1.31(ddd, J=2.2, 5.1, 13.0 Hz, 1H), 1.59(dt, J=3.3, 13.4 Hz, 1H), 1.80(ddt, J=3.5, 11.7, 13.0 Hz, 1H), 1.98–2.08(m, 2H), 2.78(m, 1H), 3.14(ddd, J=3.3, 6.0, 12.7 Hz, 1H), 3.28(m, 1H), 3.46(dd, J=1.3, 13.7 Hz, 1H), 3.49(s, 3H), 3.76(s, 3H), 3.80(ddd, J=0.4, 4.8, 13.7 Hz, 1H), 7.45(dd, J=1.5, 7.0 Hz, 1H)

Production Example 81 ethyl 3-methyl-3-azatricyclo5.3.1.0$^{5,10}$]undec-8-ene-9-carboxylate

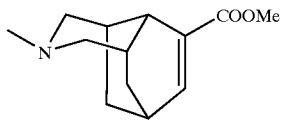

1.0 g of methyl 3-methyl-2-oxo-3-azatricyclo5.3.1.0$^{5,10}$]undec8-ene-9-carboxylate was dissolved in tetrahydrofuran (32 ml). After adding 2.5 ml of methyl iodide, the resulting mixture was stirred at room temperature for 19 hours. After distilling off the solvent under reduced pressure, a yellow amorphous product was obtained. Then it was dissolved in methanol (26 ml). After adding 0.18 g of sodium borohydrie, the resulting mixture was stirred under ice-cooling. After 30 minutes, 0.18 g of sodium borohydride was added thereto and the resulting mixture was stirred at room temperature for additional 1 hour. After adding ice/water, the reaction mixture was extracted with ethyl acetate. The organic layer was washed with water and a saturated aqueous solution of sodium chloride and extracted with 1 N hydrochloric acid. Then aqueous ammonia was added to the aqueous layer followed by the extraction with ethyl acetate. The organic layer was washed successively with water and a saturated aqueous solution of sodium chloride and dried over anhydrous magnesium sulfate. After distilling off the solvent under reduced pressure, 0.88 g of the title compound was obtained as a colorless oily substance.

¹H-NMR(CDCl₃) δ ppm;
1.35–1.48(m, 2H), 1.50–1.72(m, 4H), 1.92–2.07(m, 2H), 2.28(br.s, 3H), 2.61–2.80(m, 4H), 3.75(s, 3H), 7.42(dd, J=1.3, 6.8 Hz, 1H)

Production Example 82 ethyl 3-methyl-3-azatricyclo[5.3.1.0$^{5,10}$]undecane-9-carboxylate

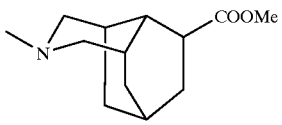

632 g of the title compound was obtained as a slightly yellow oily substance from 778 mg of 3-methyl-2-oxo-3-azatricyclo[5.3.1.0$^{5,10}$]undecane-9-carboxylate by the same methods as those of Production Examples 80 and 81.

¹H-NMR(CDCl₃) δ ppm; 1.46–2.06(m, 12H), 2.28(br.s, 3H), 2.50–2.70(m, 3H), 3.69(s, 3H)

Production Example 83

Methyl 3-methyl-3-azatricyclo[5.3.1.0$^{5,10}$]undecane-8-carboxylate

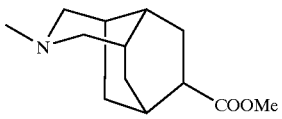

The title compound was obtained from 3-methyl-2-oxo-3-azatricyclo[5.3.1.0$^{5,10}$]undecane-8-carboxylate by the same methods as those of Production Examples 80 and 81.

¹H-NMR(CDCl₃) δ ppm; 1.21(br.s, 1H), 1.57–1.80(m, 7H), 1.84–2.14(m, 4H), 2.26(br.s, 3H), 2.44–2.74(m, 3H), 3.68(s, 3H)

Examples 32 to 43

The following compounds were obtained by the same methods as those of Examples 12, 13 and 14 optionally using potassium carbonate as a base.

TABLE 15

| Ex. | Structural formula | NMR |
|---|---|---|
| 32 | ethyl [3-(10H-pyrazino[2,3-b][1,4]-benzothiazin-8-ylmethyl)-3-azabicyclo[3.3.1]non-9-ylidene]acetate | $^1$H-NMR(CDCl$_3$) δ ppm: 1.28(t, J=7Hz, 3H), 1.47–1.65(m, 2H), 1.75–1.90(m, 2H), 1.95–2.05(m, 2H), 2.07(m, 1H), 2.25–2.35(m, 3H), 2.70–2.87(m, 1H), 2.98–3.05(m, 2H), 3.95(m, 1H), 4.15(q, J=7Hz, 2H), 5.63(s, 1H), 6.44(s, 1H), 6.52(d, J=1Hz, 1H), 6.79(dd, J=1, 8Hz, 1H), 6.85(d, J=8Hz, 1H), 7.58(d, J=2Hz, 1H), 7.70(d, J=2Hz, 1H) |
| 33 | methyl [3-[10H-pyrazino[2,3-b][1,4]benzothiazin-8-ylmethyl)-3-azabicyclo[3.3.1]non-9-yl]carboxylate (syn:anti ≈ 1:1) | $^1$H-NMR(CDCl$_3$) δ ppm: 1.4–1.9(m, total 7H), 2.20–2.28, 2.28–2.38(m, total 2H), 2.37(m, total 1H), 2.5–2.76(m, total 1H), 2.66–2.70, 2.94–3.00(m, total 2H), 3.17, 3.24(s, total 2H), 3.71, 3.72(s, total 3H), 6.40(br.s, total 1H), 6.48, 6.52(m, total 1H), 6.76–6.80(m, total 1H), 6.82, 6.84(d, J=8Hz, total 1H), 7.55–7.58(m, total 1H), 7.68–7.72(m, total 1H) |
| 34 | ethyl [3-(10H-pyrazino[2,3-b][1,4]-benzothiazin-8-ylmethyl)-3-aza-7-oxabicyclo[3.3.1]non-9-yl]acetate | $^1$H-NMR(CDCl$_3$) δ ppm: 1.26(t, J=7Hz, 3H), 1.58(br.s, 2H), 2.10–2.18(m, 1H), 2.41(d, J=11Hz, 2H), 2.65(d, J=8Hz, 2H), 3.0–3.15(m, 2H), 3.35(s, 2H), 3.77(d, J=12Hz, 2H), 3.97(d, J=12Hz, 2H), 4.14(q, J=7Hz, 2H), 6.75(d, J=8Hz, 1H), 6.78(s, 1H), 6.79(d, J=8Hz, 1H), 7.14–7.18(m, 1H), 7.55(d, J=3Hz, 1H), 7.65(d, J=3Hz, 1H) |

TABLE 16

| Ex. | Structural formula | NMR |
|---|---|---|
| 35 | methyl [3-(10H-pyrazino[2,3-b][1,4]-benzothiazin-8-ylmethyl)-7-methyl-3-azabicyclo[3.3.1]non-9-yl]acetate | $^1$H-NMR(CDCl$_3$) δ ppm: 0.86(d, J=6.4Hz, 3H), 1.24–1.37(m, 2H), 1.60–1.70(m, 2H), 1.90–2.05(m, 2H), 2.15–2.27(m, 2H), 2.40–2.48(m, 1H), 2.43(d, J=7.2Hz, 2H), 2.73–2.92(m, 3H), 3.23(s, 2H), 3.67(s, 3H), 6.37(br.s, 1H), 6.46(s, 1H), 6.76(d, J=8.0Hz, 1H), 6.84(d, J=8.0Hz, 1H), 7.57(d, J=7.2Hz, 1H), 7.69(d, J=7.2Hz, 1H) |

TABLE 16-continued

| Ex. | Structural formula | NMR |
|---|---|---|
| 36 | 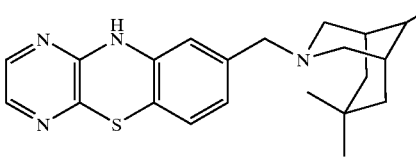<br>ethyl [3-(10H-pyrazino[2,3-b][1,4]benzothiazin-8-ylmethyl)-7,7-dimethyl-3-azabicyclo[3.3.1]non-9-yl]acetate | $^1$H-NMR(CDCl$_3$) δ ppm: 0.99(s, 3H), 1.24(t, J=7.0Hz, 3H), 1.31–1.39(m, 2H), 1.42(s, 3H), 1.64–1.74(m, 4H), 1.85–1.93(m, 1H), 2.12–2.19(m, 2H), 2.35(d, J=7.9Hz, 2H), 2.74–2.81(m, 2H), 3.25(s, 2H), 4.12(q, J=7.0Hz, 2H), 6.38–6.43(br.s, 1H), 6.45(d, J=1.6Hz, 1H), 6.74(dd, J=1.6, 7.9Hz, 1H), 6.81(d, J=7.9Hz, 1H), 7.56(d, J=3.0Hz, 1H), 7.68(d, J=3.0Hz, 1H) |
| 37 | 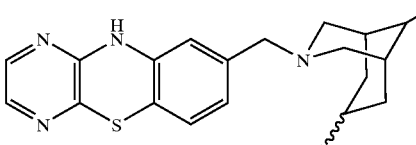<br>methyl [3-(10H-pyrazino[2,3-b][1,4]benzothiazin-8-ylmethyl)-7-phenyl-3-azabicyclo[3.3.1]non-9-yl]acetate | $^1$H-NMR(CDCl$_3$) δ ppm: 1.73–1.94(m, 7H), 2.07–2.14(m, 1H), 2.30–2.38(m, 2H), 2.59(d, J=7.2Hz, 2H), 2.96–3.05(m, 2H), 3.31(s, 2H), 3.69(s, 3H), 6.37(br.s, 1H), 6.49(s, 1H), 6.84–6.90(m, 2H), 7.16–7.39(m, 5H), 7.57(d, J=7.2Hz, 1H), 7.69(d, J=7.2Hz, 1H) |

TABLE 17

| Ex. | Structural formula | NMR |
|---|---|---|
| 38 | 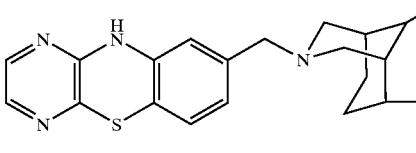<br>ethyl [3-(10H-pyrazino[2,3-b][1,4]benzothiazin-8-ylmethyl)-6-methyl-3-azabicyclo[3.3.1]non-9-yl]acetate | $^1$H-NMR(CDCl$_3$) δ ppm: 1.06(d, J=8Hz, 3H), 1.2–1.3(m, 3H), 1.4–2.1(m, 7H), 2.19(dd, J=2, 10Hz, 1H), 2.22–2.30(m, 1H), 2.40–2.70(m, 3H), 2.75–2.90(m, 2H), 3.19(d, J=14Hz, 1H), 3.26(d, J=14Hz, 1H), 4.05–4.20(m, 2H), 6.36–6.40(m, 1H), 6.50(d, J=1Hz, 1H), 6.76(dd, J=1, 8Hz, 1H), 6.82(d, J=8Hz, 1H), 7.56(d, J=3Hz, 1H), 7.69(d, J=3Hz, 1H) |
| 39 | 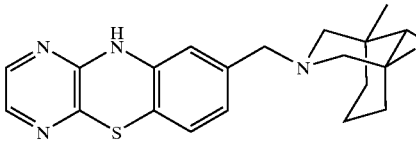<br>methyl [3-(10H-pyrazino[2,3-b][1,4]-benzothiazin-8-ylmethyl)-1,5-dimethyl-3-azabicyclo[3.3.1]non-9-yl]acetate | $^1$H-NMR(CDCl$_3$) δ ppm: 0.71(s, 6H), 1.29–1.46(m, 5H), 1.73(t, J=5.9Hz, 1H), 1.90(d, J=11.8Hz, 2H), 2.33(d, J=5.9Hz, 2H), 2.63(d, J=11.8Hz, 2H), 2.66–2.83(m, 1H), 3.14(s, 2H), 3.66(s, 3H), 6.48(s, 1H), 6.75(d, J=7.7Hz, 1H), 6.80(s, 1H), 6.81(d, J=7.7Hz, 1H), 7.55(d, J=2.6Hz, 1H), 7.68(d, m J=2.6Hz, 1H) |

TABLE 17-continued

| Ex. | Structural formula | NMR |
|---|---|---|
| 40 | methyl 3-(10H-pyrazino[2,3-b][1,4]benzothiazin-8-ylmethyl)-3-azatricyclo[5.3.1.0^{5,10}]undecane-9-carboxylate | $^1$H-NMR(CDCl$_3$) δ ppm: 1.51–1.66(m, 6Hz), 1.70–1.79(m, 3H), 1.84–2.00(m, 3H), 2.51–2.63(m, 3H), 3.27(d, J=13.6Hz, 1H), 3.32(d, J=13.6Hz, 1H), 3.68(s, 3H), 5.57(br.s, 1H), 6.60(br.s, 1H), 6.79(dd, J=1.5, 7.9Hz, 1H), 6.82(d, J=7.9Hz, 1H), 7.57(d, J=2.9Hz, 1H), 7.69(d, J=2.9Hz, 1H) |

TABLE 18

| Ex. | Structural formula | NMR |
|---|---|---|
| 41 | ethyl (anti)-(6R*,8R*)-3-[3-(10H-pyrazino[2,3-b][1,4]-benzothiazin-8-ylmethyl)-6,8-dimethyl-3-azabicyclo[3.3.1]non-9-yl]propanoate | $^1$H-NMR(CDCl$_3$) δ ppm: 0.75–0.90(m, 2H), 0.99(d, J=7.2Hz, 6H), 1.15–1.24(m, 1H), 1.26(t, J=7.2Hz, 3H), 1.35–1.44(m, 2H), 1.72–1.84(m, 3H), 1.93(d, J=10.4Hz, 2H), 2.25–2.36(m, 1H), 2.32(t, J=7.2Hz, 2H), 2.59(d, J=10.4Hz, 2H), 3.25(s, 2H), 4.12(q, J=7.2Hz, 2H), 6.38(br.s, 1H), 6.51(s, 1H), 6.76(d, J=8.0Hz, 1H), 6.82(d, J=8.0Hz, 1H), 7.57(d, J=2.8Hz, 1H), 7.69(d, J=2.8Hz, 1H) |
| 42 | methyl 3-(10H-pyrazino[2,3-b][1,4]benzothiazin-8-ylmethyl)-3-azatricyclo[5.3.1.0^{5,10}]-undecane-8-carboxylate | $^1$H-NMR(CDCl$_3$) δ ppm: 1.23(m, 1H), 1.45(m, 1H), 1.55–1.76(m, 6H), 1.89–1.96(m, 2H), 2.00–2.08(m, 2H), 2.44–2.60(m, 2H), 3.30(s, 2H), 3.69(s, 3H), 6.49(br.s, 1H), 6.56(br.s, 1H), 6.80(dd, J=1.3, 8.2Hz, 1H), 6.83(d, J=8.2Hz, 1H), 7.57(d, J=2.7Hz, 1H), 7.69(d, J=2.7Hz, 1H) |
| 43 | methyl 3-(10H-pyrazino[2,3-b][1,4]benzothiazin-8-ylmethyl)-3-azatricyclo[5.3.1.0^{5,10}]-undecane-8-ene-9-carboxylate | $^1$H-NMR(CDCl$_3$) δ ppm: 1.34–1.44(m, 2H), 1.56–1.65(m, 4H), 2.01–2.08(m, 2H), 2.66–2.76(m, 4H), 3.35(s, 2H), 3.75(s, 3H), 6.58(br.s, 2H), 6.83(br.s, 2H), 7.41(dd, J=1.3, 7.0Hz, 1H), 7.57(d, J=2.9Hz, 1H), 7.69(d, J=2.9Hz, 1H) |

Example 44

Ethyl[8-(10H-pyrazino[2,3-b][1,4]benzothiazin-8-ylmethyl)-8-azabicyclo[4.3.1]dec-10-yl]acetate

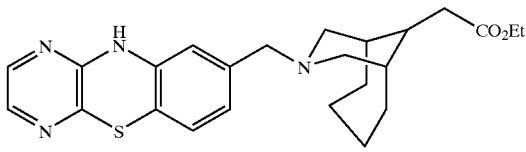

The title compound was obtained as a yellow oily substance by treating ethyl(8-methyl-8-azabicyclo[4.3.1]dec-10-ylidene)acetate by the same methods as those of Examples 20, 12, 13 and 14 by using potassium carbonate as a base.

$^1$H-NMR(CDCl$_3$) δ ppm; 1.25(t, J=7.0 Hz, 3H), 1.50–1.62(m, 4H), 1.75–1.87(m, 2H), 1.87–1.95(m, 2H), 1.97–2.10(m, 4H), 2.17–2.26(m, 1H), 2.50(d, J=7.3 Hz, 2H), 2.62–2.68(m, 2H), 3.20(s, 2H), 4.12(q, J=7.0 Hz, 2H), 6.42–6.47(br.s, 1H), 6.51(d, J=1.5 Hz, 1H), 6.78(dd, J=1.5, 7.8 Hz, 1H), 6.82(d, J=7.8 Hz, 1H), 7.56(d, J=3.1 Hz, 1H), 7.68(d, J=3.1 Hz, 1H)

Examples 45 to 47

The following compounds were obtained by the same methods as those of Examples 13 and 14 by using potassium carbonate as a base.

TABLE 19

| Ex. | Structural formula | NMR |
|---|---|---|
| 45 | ethyl (syn)-2-[3-(10H-pyrazino[2,3-b][1,4]benzothiazin-8-ylmethyl)-3-azabicyclo[3.3.1]non-9-yl]propanoate | $^1$H-NMR(CDCl$_3$) δ ppm: 1.10(d, J=7Hz, 3H), 1.24(t, J=7Hz, 3H), 1.52–1.90(m, 9H), 2.29(br.d, J=12Hz, 1H), 2.49(br.d, J=12Hz, 2H), 2.63(br.d, J=12Hz, 1H), 2.80(dd, J=8, 12Hz, 1H), 3.23(s, 2H), 4.13(q, J=7Hz, 2H), 6.38(br.s, 1H), 6.50(d, J=2Hz, 1H), 6.76(dd, J=2, 8Hz, 1H), 6.82(d, J=8Hz, 1H), 7.56(d, J=3Hz, 1H), 7.69(d, J=3Hz, 1H) |
| 46 | ethyl (anti)-2-[3-(10H-pyrazino[2,3-b][1,4]benzothiazin-8-ylmethyl)-3-azabicyclo[3.3.1]non-9-yl]propanoate | $^1$H-NMR(CDCl$_3$) δ ppm: 1.11(d, J=7Hz, 3H), 1.24(t, J=7Hz, 3H), 1.46–1.55(m, 4H), 1.56–1.64(s, 2H), 1.77(br.s, 1H), 1.82–1.95(m, 1H), 2.20(m, 2H), 2.55(m, 1H), 2.82(dd, J=7, 11Hz, 1H), 2.88(br.d, J=11Hz, 1H), 2.96(br.d, J=11Hz, 1H), 3.21(s, 2H), 4.12(q, J=7Hz, 2H), 6.43(br.s, 1H), 6.50(d, J=2Hz, 1H), 6.77(dd, J=2, 8Hz, 1H), 6.82(d, J=8Hz, 1H), 7.56(d, J=3Hz, 1H), 7.68(d, J=3Hz, 1H) |
| 47 | ethyl (syn)-(6R*,7R*)-[3-(10H-pyrazino[2,3-b][1,4]benzothiazin-8-ylmethyl)-6,7-dimethyl-3-azabicyclo[3.2.1]oct-8-yl]acetate | $^1$H-NMR(CDCl$_3$) δ ppm: 1.01(d, J=7.1Hz, 3H), 1.09(d, J=7.0Hz, 3H), 1.25(t, J=7.1Hz, 3H), 1.49–1.59(m, 2H), 1.64(m, 1H), 1.74(m, 1H), 2.22(m, 1H), 2.27(d, J=10.0Hz, 1H), 2.36(d, J=12.5Hz, 1H), 2.39(dd, J=3.9, 11.2Hz, 1H), 2.48(dd, J=7.1, 15.0Hz, 1H), 2.53–2.60(m, 2H), 3.28(d, J=13.2Hz, 1H), 3.38(d, J=13.2Hz, 1H), 4.13(q, J=7.1Hz, 2H), 6.49(d, J=1.3Hz, 1H), 6.50(br.s, 1H), 6.76(dd, J=1.3, 7.9Hz, 1H), 6.81(d, J=7.9Hz, 1H), 7.57(d, J=2.9Hz, 1H), 7.69(d, J=2.9Hz, 1H) |

Examples 48 to 59

The following compounds were obtained by the same method as the one of Example 17.

TABLE 20

| Ex. | Structural formula | NMR |
| --- | --- | --- |
| 48 | ethyl [3-(10H-pyrazino[2,3-b][1,4]benzothiazin-8-ylmethyl)-3-azabicyclo[3.2.1]oct-8-yl]acetate (syn:anti ≈ 1:2) | ¹H-NMR(CDCl₃) δ ppm: 1.25(t, J=7Hz, 3H, anti), 1.26(t, J=7Hz, 3H, syn), 1.5–2.1(m, 7H), 2.08–2.15(m, 2H, anti), 2.16(d, J=8Hz, 2H, anti), 2.35–2.45(m, 4H, syn), 2.58(d, J=7Hz, 2H, syn), 2.62–2.70(m, 2H, anti), 3.31(s, 2H, anti), 3.34(s, 2H, syn), 4.13(q, J=7Hz, 2H, anti), 4.14(q, J=7Hz, 2H, syn), 6.42(br.s, 1H), 6.53(br.s, 1H), 6.77(d, J=8Hz, 1H), 6.82(d, J=8Hz, 1H), 7.57(d, J=3Hz, 1H), 7.69(d, J=3Hz, 1H) |
| 49 | ethyl [3-(10H-pyrazino[2,3-b][1,4]benzothiazin-8-ylmethyl)-3-azabicyclo[3.2.1]oct-8-ylidene]acetate | ¹H-NMR(CDCl₃) δ ppm: 1.28(t, J=7Hz, 3H), 1.50–1.75(m, 2H), 1.8–2.0(m, 2H), 2.21(d, J=10Hz, 1H), 2.29(d, J=10Hz, 1H), 2.47(m, 1H), 2.83(dd, J=4, 10Hz, 2H), 3.31(d, J=16Hz, 1H), 3.37(d, J=16Hz, 1H), 3.75(m, 1H), 4.16(q, J=7Hz, 2H), 5.63(s, H), 6.46–6.56(m, 1H), 6.54(s, 1H), 6.78(d, J=8Hz, 1H), 6.83(d, J=8Hz, 7.58(d, J=3Hz, 1H), 7.70(d, J=3Hz, 1H) |
| 50 | methyl [3-(10H-pyrazino[2,3-b][1,4]benzothiazin-8-ylmethyl)-3-azabicyclo[3.2.1]oct-8-yl]carboxylate | ¹H-NMR(CDCl₃) δ ppm: 1.70(m, 4H), 2.10(d, J=10Hz, 2H), 2.34(s, 1H), 2.50(br.s, 2H), 2.71(dd, J=4, 10Hz, 2H), 3.33(s, 2H), 3.66(s, 3H), 6.44(br.s, 1H), 6.53(d, J=1Hz, 1H), 6.77(dd, J=1, 8Hz, 1H), 6.83(d, J=8Hz, 1H), 7.57(d, J=3Hz, 1H), 7.69(d, J=3Hz, 1H) |

TABLE 21

| Ex. | Structural formula | NMR |
| --- | --- | --- |
| 51 | methyl [3-(10H-pyrazino[2,3-b][1,4]benzothiazin-8-ylmethyl)-7-tert-butyl-3-azabicyclo[3.2.1]non-9-yl]acetate | ¹H-NMR(CDCl₃) δ ppm: 0.89(s, 9H), 1.24–1.36(m, 3H), 1.76–1.92(m, 5H), 2.01–2.06(m, 2H), 2.50(d, J=7.2Hz, 2H), 2.56–2.63(m, 2H), 3.23(s, 2H), 3.68(s, 3H), 6.22(br.s, 1H), 6.52(s, 1H), 6.78(d, J=8.0Hz, 1H), 6.82(d, J=8.0Hz, 1H), 7.57(d, J=2.8Hz, 1H), 7.69(d, J=2.8Hz, 1H) |

TABLE 21-continued

| Ex. | Structural formula | NMR |
|---|---|---|
| 52 | methyl (anti)-(6R*,8R*)-[4-(10H-pyrazino[2,3-b][1,4]benzothiazin-9-ylmethyl)-6,8-dimethyl-3-azabicyclo[3.3.1]non-9-yl]acetate | $^1$H-NMR(CDCl$_3$) δ ppm: 0.80–1.00(m, 1H), 0.99(d, J=6.8Hz, 6H), 1.40–1.45(m, 2H), 1.68–1.90(m, 4H), 2.03(d, J=10Hz, 2H), 2.46(d, J=7.6Hz, 2H), 2.58(d, J=10Hz, 2H), 3.26(s, 2H), 3.67(s, 3H), 6.38(br.s, 1H), 6.51(s, 1H), 6.76(d, J=8.0Hz, 1H), 6.82(d, J=8.0Hz, 1H), 7.56(d, J=2.8Hz, 1H), 7.69(d, J=2.8Hz, 1H) |
| 53 | ethyl 3-(10H-pyrazino[2,3-b][1,4]benzothiazin-8-ylmethyl)-3-azabicyclo[3.3.1]non-9-yl]carboxylate | $^1$H-NMR(CDCl$_3$) δ ppm: 1.23(t, J=7.1Hz, 3H), 1.54–1.82(m, 6H), 1.88–1.98(m, 2H), 2.13(m, 1H), 2.13(m, 1H), 2.20(dd, J=2.0, 10.8Hz, 1H), 2.70(m, 1H), 2.81(m, 1H), 3.06(m, 1H), 3.21(d, J=13.4Hz, 1H), 3.27(d, J=13.4Hz, 1H), 4.09(q, J=7.1Hz, 2H), 6.43(br.s, 1H), 6.49(d, J=1.3Hz, 1H), 6.77(dd, J=1.3, 7.9Hz, 1H), 6.84(d, J=7.9Hz, 1H), 7.57(d, J=2.9Hz, 1H), 7.69(d, J=2.9Hz, 1H) |

TABLE 22

| Ex. | Structural formula | NMR |
|---|---|---|
| 54 | ethyl (anti)-2-[3-(10H-pyrazino[2,3-b][1,4]benzothiazin-8-ylmethyl)-6-methyl-3-azabicyclo[3.3.1]non-9-yl]ethoxyacetate | $^1$H-NMR(CDCl$_3$) δ ppm: 1.28(t, J=7Hz, 3H), 1.4–1.55(m, 2H), 1.56–1.65(m, 3H), 1.7–1.85(m, 5H), 2.22(br.d, J=11Hz, 2H), 2.45–2.6(m, 1H), 2.91(d, J=11Hz, 2H), 3.21(s, 2H), 3.55(t, J=7Hz, 2H), 4.06(s, 2H), 4.21(q, J=7Hz, 2H), 6.40(br.s, 1H), 6.51(s, 1H), 6.77(d, J=8Hz, 1H), 6.82(d, J=8Hz, 1H), 7.56(d, J=3Hz, 1H), 7.68(d, J=3Hz, 1H) |
| 55 | methyl (anti)-4-[2-[3-(10H-pyrazino[2,3-b][1,4]benzothiazin-8-ylmethyl)-3-azabicyclo[3.3.1]non-9-yl]ethoxy]phenylacetic acid | $^1$H-NMR(CDCl$_3$) δ ppm: 1.45–1.55(m, 2H), 1.62–1.75(m, 4H), 1.75–1.90(m, 2H), 1.96(q, J=7Hz, 2H), 2.20–2.25(m, 2H), 2.50–2.63(m, 1H), 2.90–2.95(m, 2H), 3.22(s, 2H), 3.56(s, 2H), 3.68(s, 3H), 3.97(t, J=6Hz, 2H), 6.46–6.50(m, 1H), 6.51(d, J=1Hz, 1H), 6.78(dd, J=1, 8Hz, 1H), 6.83(d, J=8Hz, 1H), 6.85(d, J=8Hz, 2H), 7.18(d, J=8Hz, 2H), 7.56(d, J=3Hz, 1H), 7.68(d, J=3Hz, 1H) |

TABLE 22-continued

| Ex. | Structural formula | NMR |
|---|---|---|
| 56 | ethyl (anti)-[3-(10H-pyrazino[2,3-b][1,4]benzothiazin-8-ylmethyl)-(syn)-9-methoxy-3-azabicyclo[3.3.1]non-9-yl]acetate | $^1$H-NMR(CDCl$_3$) δ ppm: 1.24(t, J=7Hz, 3H), 1.44–1.54(m, 2H), 1.59(d, J=5Hz, 1H), 1.9–2.3(m, 4H), 2.53(br.d, J=12Hz, 3H), 2.77(s, 2H), 2.85(br.d, J=12Hz, 2H), 3.28(s, 3H), 3.29(s, 2H), 4.13(q, J=7Hz, 2H), 6.42(m, 1H), 6.49(d, J=1Hz, 1H), 6.76(dd, J=1, 8Hz, 1H), 6.83(d, J=8Hz, 1H), 7.57(d, J=3Hz, 1H), 7.67(d, J=3Hz, 1H) |

TABLE 23

| Ex. | Structural formula | NMR |
|---|---|---|
| 57 | ethyl 3-[(10H-pyrazino[2,3-b][1,4]benzothiazin-8-ylmethyl)-3-azabicyclo[3.3.1]non-1-yl]acetate | $^1$H-NMR(CDCl$_3$) δ ppm: 1.22(t, J=7.1Hz, 3H), 1.36–1.61(m, 5H), 1.66–1.78(m, 2H), 1.88–1.97(m, 2H), 2.06(s, 2H), 2.10(m, 1H), 2.69(m, 1H), 2.78–2.88(m, 2H), 3.17(d, J=13.6Hz, 1H), 3.23(d, J=13.6Hz, 1H), 4.10(q, J=7.1Hz, 2H), 6.42(br.s, 1H), 6.49(d, J=1.6Hz, 1H), 6.76(dd, J=1.6, 7.9Hz, 1H), 6.83(d, J=7.9Hz, 1H), 7.57(d, J=2.9Hz, 1H), 7.69(d, J=2.9Hz, 1H) |
| 58 | ethyl (syn)-[3-[10H-pyrazino[2,3-b][1,4]benzothiazin-8-ylmethyl)-(anti)-9-methoxy-3-azabicyclo[3.3.1]non-9-yl]acetate | $^1$H-NMR(CDCl$_3$) δ ppm: 1.25(t, J=7Hz, 3H), 1.45–1.55(m, 1H), 1.72–1.80(m, 2H), 1.80–1.95(m, 2H), 1.99(br.s, 2H), 2.3–2.35(m, 1H), 2.5–2.65(m, 4H), 2.77(s, 2H), 3.22(s, 2H), 3.20(s, 3H), 4.14(q, J=7Hz, 2H), 6.40(s, 1H), 6.49(d, J=1Hz, 1H), 6.77(dd, J=1, 8Hz, 1H), 6.82(d, J=8Hz, 1H), 7.56(d, J=3Hz, 1H), 7.68(d, J=3Hz, 1H) |
| 59 | methyl (anti)-3-[2-[3-(10H-pyrazino[2,3-b][1,4]benzothiazin-8-ylmethyl)-3-azabicyclo[3.3.1]non-9-yl]-ethyloxy]benzoate | $^1$H-NMR(CDCl$_3$) δ ppm: 1.2–2.2(m, 10H), 2.23(br.d, J=10Hz, 2H), 2.4–2.6(m, 1H), 2.94(br.d, J=10Hz, 2H), 3.21(s, 2H), 3.90(s, 3H), 4.03(t, J=5Hz, 2H), 6.35(s, 1H), 6.51(s, 1H), 6.78(d, J=7Hz, 1H), 6.84(d, J=7Hz, 1H), 7.0–7.1(m, 1H), 7.3–7.4(m, 1H), 7.5–7.8(m, 4H) |

Example 60

Ethyl (anti)-(6R*,8R*)-4-[3-(10H-pyrazino[2,3-b][1,4]benzothiazin-8-ylmethyl)-6,8-dimethyl-3-azabicyclo[3.3.1]non-9-yl]butanoate

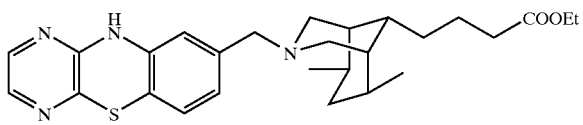

To a solution of 1.0 g of ethyl(6R*,8R*)-4-[3-(vinyloxycarbonyl)-6,8-dimethyl-3-azabicyclo[3.3.1]non-9-yl]-2-butenoate in dioxane (10 ml) was added 30 ml of a 4 N solution of hydrochloric acid in dioxane and the resulting mixture was stirred at room temperature. After distilling off the solvent under reduced pressure, 10 ml of methanol was added to the residue and the resulting mixture was heated under reflux for 1 hour. After distilling off the solvent under reduced pressure, the residue was made alkaline by adding a dilute aqueous solution of sodium hydroxide and extracted with ethyl acetate. The organic layer was dried over anhydrous magnesium sulfate. After distilling off the solvent under reduced pressure, 0.25 g of 10% palladium-carbon (moisture content: 50%) was added to the residual methanolic solution and the resulting mixture was stirred under a hydrogen gas stream at room temperature overnight. Then the reaction mixture was filtered through celite. After distilling off the solvent under reduced pressure, 0.9 g of a pale yellow oily substance was obtained.

To a solution of 0.9 g of this yellow oily substance and 0.75 g of 8-chloromethyl-10H-pyrazino[2,3-b][1,4]benzothiazine in N,N-dimethylformamide was added 1.24 g of potassium carbonate and the resulting mixture was stirred at 100° C. for 3 hours. After adding ethyl acetate, the reaction mixture was washed with a saturated aqueous solution of sodium chloride. Then the organic layer was dried over anhydrous magnesium sulfate. After distilling off the solvent under reduced pressure, the residue was purified by silica gel column chromatography (eluted with n-hexane/ethyl acetate) to thereby give 1.0 g of the title compound as a yellow oily substance.

H-NMR(CDCl$_3$) δ ppm; 0.98(d, J=7.2 Hz, 6H), 1.18–1.80 (m, 13H), 1.93(d, J=9.2 Hz, 2H), 2.28(t, J=7.2 Hz, 2H), 2.58(d, J=9.2 Hz, 2H), 3.02(d, J=9.2 Hz, 1H), 3.25(s, 2H), 4.13(q, J=7.2 Hz, 2H), 6.43(br.s, 1H), 6.52(s, 1H), 6.76(d, J=8.0 Hz, 1H), 6.82(d, J=8.0 Hz, 1H), 7.56(d, J=2.8 Hz, 1H), 7.68(d, J=2.8 Hz, 1H)

Examples 61 and 62

The following compounds were obtained by the same method as the one of Example 60.

TABLE 24

| Ex. | Structural formula | NMR |
|---|---|---|
| 61 | 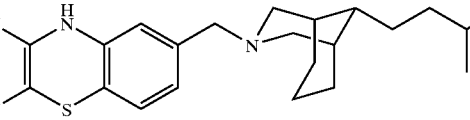<br>ethyl (anti)-4-[3-(10H-pyrazino[2,3-b][1,4]benzothiazin-8-ylmethyl)-3-azabicyclo[3.3.1.]non-9-yl]-2-methylbutanoate | $^1$H-NMR(CDCl$_3$) δppm: 1.16(d, J=7.0Hz, 3H), 1.26(d, J=7.1Hz, 3H), 1.32–1.68(m, 10H), 1.68–1.83(m, 2H), 2.15–2.22(m, 2H), 2.41(m, 1H), 2.52(m, 1H), 2.88–2.95(m, 2H), 3.21(s, 2H), 4.14(q, J=7.1Hz, 2H), 6.38(br.s, 1H), 6.52(d, J=1.5Hz, 1H), 6.78(dd, J=1.5, 7.9Hz, 1H), 6.83(d, J=7.9Hz, 1H), 7.57(d, J=2.9Hz, 1H), 7.69(d, J=2.9Hz, 1H) |
| 62 | 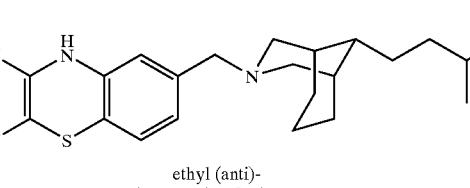<br>ethyl (anti)-(6R*,8R*)-4-[3-(10H-pyrazino[2,3-b][1,4]benzothiazin-8-ylmethyl)-6,8-dimethyl-3-azabicyclo[3.3.1]non-9-yl]-2-methylbutanoate | $^1$H-NMR(CDCl$_3$) δppm: 0.97(d, J=6.8Hz, 6H), 1.14(d, J=6.8Hz, 3H), 1.26(t, J=7.2Hz, 3H), 1.30–1.80(m, 11H), 1.93(d, J=12.4Hz, 2H), 2.34–2.45(m, 1H), 2.58(d, J=12.4Hz, 2H), 3.24(s, 2H), 4.12(d, J=7.2Hz, 2H), 6.36(br.s, 1H), 6.52(s, 1H), 6.76(d, J=8.0Hz, 1H), 6.81(d, J=8.0Hz, 1H), 7.57(d, J=2.8Hz, 1H), 7.68.(d, J=2.8Hz, 1H) |

Example 63

Methyl (anti)-3-[3-(10H-pyrazino[2,3-b][1,4]benzothiazin-8-ylmethyl)-3-azabicyclo[3.3.1]non-9-yl]propanoate

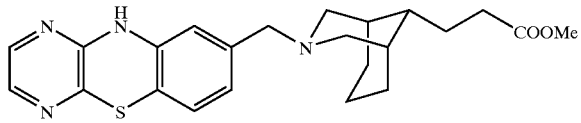

The title compound was obtained by treating methyl (anti)-3-(3-azabicyclo[3.3.1]non-9-yl)propanoate by the same method as the one of Example 14 by using potassium carbonate as a base.

$^1$H-NMR(CDCl$_3$) δ ppm; 1.37–1.55(m, 4H), 1.58–1.90 (m, 6H), 2.16–2.23(m, 2H), 2.30(t, J=7.2 Hz, 2H), 2.53(m, 1H), 2.88–2.96(m, 2H), 3.22(s, 2H), 3.68(s, 3H), 6.37(br.s, 1H), 6.51(d, J=1.3 Hz, 1H), 6.77(dd, J=1.3, 7.9 Hz, 1H), 6.83(d, J=7.9 Hz, 1H), 7.57(d, J=2.9 Hz, 1H), 7.69(d, J=2.9 Hz, 1H)

Example 64

Methyl (syn)-[3-(10H-pyrazino[2,3-b][1,4]benzothiazin-8-ylmethyl)-3-azabicyclo[3.3.1]non-7-yl]carboxylate

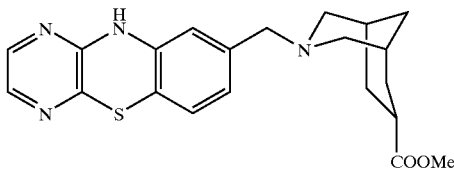

360 mg of methyl (syn)-[3-benzyl-3-azabicyclo[3.3.1]non-7-yl]carboxylate was dissolved in methanol (15 ml). After adding 0.5 g of 10% palladium-carbon and 0.3 ml of conc. hydrochloric acid, the resulting mixture was hydrogenated at 60° C. under atmospheric pressure for 2 hours. After filtering off the catalyst, the residue was concentrated under reduced pressure to thereby give a slightly yellow oily substance.

This oily substance was dissolved in 5 ml of N,N-dimethylformamide. After adding 320 mg of 8-chloromethyl-10H-pyrazino[2,3-b][1,4]benzothiazine and 0.68 ml of N,N-diisopropylethylamine, the resulting mixture was stirred at 80° C. for 3 hours. After adding water, the reaction mixture was extracted with ethyl acetate. The ethyl acetate layer was washed with water and a saturated aqueous solution of sodium chloride, dried over anhydrous sodium sulfate and concentrated under reduced pressure. Next, the residue was purified by silica gel column chromatography (eluted with n-hexane/ethyl acetate) to thereby give 111 mg of the title compound as a yellow solid.

$^1$H-NMR(CDCl$_3$) δ ppm; 1.31(m, 1H), 1.51(m, 1H), 1.74–1.88(m, 4H), 2.16–2.26(m, 2H), 2.37–2.47(m, 2H), 2.53(m, 1H), 2.65–2.74(m, 2H), 3.30(s, 2H), 3.72(s, 3H), 6.48(br.s, 1H), 6.62(d, J=7.9 Hz, 1H), 6.63(br.s, 1H), 6.81(d, J=7.9 Hz, 1H), 7.53(d, J=2.9 Hz, 1H), 7.68(d, J=2.9 Hz, 1H)

Example 65

The following compound was obtained by the same method as the one of Example 64.

TABLE 25

| Ex. | Structural formula | NMR |
|---|---|---|
| 65 | ethyl (syn)-[3-(10H-pyrazino[2,3-b][1,4]benzothiazin-8-ylmethyl)-3-azabicyclo[3.3.1]non-7-yl]acetate | $^1$H-NMR(CDCl$_3$) δppm: 1.05(m, 1H), 1.28(t, J=7.1Hz, 3H), 1.35–1.46(m, 2H), 1.72–1.80(m, 2H), 1.85–2.08(m, 6H), 2.33(d, J=6.0Hz, 2H), 2.50–2.57(m, 2H), 3.28(s, 2H), 4.18(q, J=7.1Hz, 2H), 6.70(d, J=7.9Hz, 1H), 6.79(d, J=7.9Hz, 1H), 6.81(s, 1H), 7.19(br.s, 1H), 7.56(d, J=2.9Hz, 1H), 7.65(d, J=2.9Hz, 1H) |

Example 66

Ethyl[3-(10H-pyrazino[2,3-b][1,4]benzothiazin-8-ylmethyl)-3-azabicyclo[3.3.1]nonane-9-spiro-cyclobut-3'-yl]acetate To a solution of 4.7 g of ethyl[3-(tert-butoxycarbonyl)-3-azabicyclo[3.3.1]nonane-9-spiro-cyclobut-3'-yl]acetate in tetrahydrofuran (50 ml) was added 20 ml of conc. hydrochloric acid and the resulting mixture was stirred at room temperature for 1 hour. After concentrating the reaction mixture under reduced pressure, 3.7 g of crude ethyl(3-azabicyclo[3.3.1]nonane-9-spiro-cyclobut-3'-yl)acetate was obtained. To a solution of 2.0 g of this crude product in N,N-dimethylformamide (30 ml) were added 1.3 g of 8-chloromethyl-10H-pyrazino[2,3-b][1,4]benzothiazine and 3 g of anhydrous potassium carbonate and the resulting mixture was stirred at 100° C. for 3 hours. Then the reaction mixture was brought back to room temperature and ice/water was added thereto followed by the extraction with ethyl acetate. Next, it was washed with a saturated aqueous solution of sodium chloride and dried over anhydrous magnesium sulfate. After distilling off the solvent under reduced pressure, the residue was purified by silica gel column chromatography (eluted with ethyl acetate/toluene) to thereby give 1.0 g of the title compound as a yellow oily substance.

$^1$H-NMR(CDCl$_3$) δ ppm; 1.18(t, J=7 Hz, 3H), 1.2–1.90 (m, 10H), 2.1–2.6(m, 7H), 2.29(d, J=12 Hz), 3.08(s, 2H), 4.04(q, J=2 Hz, 2H), 6.3–6.45(m, 1H), 6.43(d, J=2 Hz, 1H), 6.69(dd, J=2, 8 Hz, 1H), 6.75(d, J=8 Hz, 1H), 7.49(d, J=3 Hz, 1H), 7.62(d, J=3 Hz, 1H)

Examples 67 and 68

The following compounds were obtained by the same method as the one of Example 66.

to −70° C. Into the above sulfonamide solution was dropped in a nitrogen atmosphere a green solution of sodium naphthalenide obtained by reacting 6.8 g of naphthalene with 0.97 g of sodium in 100 ml of dimethoxyethane. After adding 5 ml of an aqueous solution of sodium hydrogencarbonate, 6 g of anhydrous sodium carbonate and 150 ml of ethyl acetate, the organic layer was dried over potassium carbonate and distilled off under reduced pressure. To a solution of the crude product thus obtained in 35 ml of N,N-dimethylformamide were added 1.99 g 8-chloromethyl-10H-pyrazino[2,3-b][1,4]benzothiazine and 0.89 g of anhydrous potassium hydrogencarbonate and the resulting mixture was reacted at 90° C. in a nitrogen atmosphere for 2 hours. Then the reaction mixture was cooled to room temperature and added to 350 ml of water

TABLE 26

| Ex. | Structural formula | NMR |
|---|---|---|
| 67 | 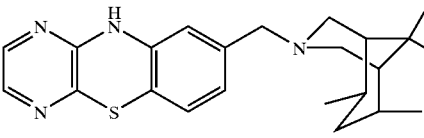<br>ethyl (6R*,8R*)-[3-(10H-pyrazino[2,3-b][1,4]benzothiazin-8-ylmethyl)-6,8-dimethyl-3-azabicyclo[3.3.1]nonane-9-spiro-cyclobut-3'-yl]acetate | $^1$H-NMR(CDCl$_3$) δppm: 0.70(q, J=10Hz, 1H), 0.99(d, J=7Hz, 3H), 1.04(d, J=7Hz, 3H), 1.24(t, J=7Hz, 3H), 1.4–1.55(m, 3H), 1.6–1.7(m, 2H), 1.7–1.9(m, 2H), 1.98(d, J=10Hz, 1H), 2.10(d, J=10Hz, 1H), 2.15–2.25(m, 2H), 2.25–2.4(m, 2H), 2.36(d, J=8Hz, 2H), 2.45–2.6(m, 1H), 3.18(s, 2H), 4.10(q, J=7Hz, 2H), 6.49(s, 1H), 6.6–6.7(br.s, 1H), 6.74(d, J=8Hz, 1H), 6.80(d, J=8Hz, 1H), 7.56(d, J=3Hz, 1H), 7.66–7.69(m, 1H) |
| 68 | 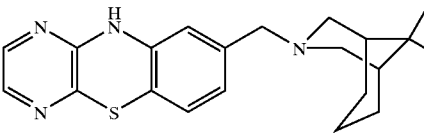<br>methyl [3-(10H-pyrazino[2,3-b][1,4]benzothiazin-8-ylmethyl)-3-azabicyclo[3.3.1]nonane-9-spiro-cyclobut-3'-yl]carboxylate | $^1$H-NMR(CDCl$_3$) δppm: 1.3–1.4(m, 1H), 1.5–1.64(m, 5H), 1.7–1.86(m, 1H), 1.96–2.14(m, 2H), 2.12–2.38(m, 3H), 2.29(br.d, J=12Hz, 1H), 2.44–2.60(m, 1H), 2.66(t, J=13Hz, 2H), 2.92(quint, J=9Hz, 1H), 3.13(d, J=14Hz, 1H), 3.17(d, J=14Hz, 1H), 3.67(s, 3H), 6.49(s, 1H), 6.53(s, 1H), 6.75(d, J=8Hz, 1H), 6.81(d, J=8Hz, 1H), 7.56(d, J=3Hz, 1H), 7.68(d, J=3Hz, 1H) |

Example 69

Ethyl (anti)-[[3-(10H-pyrazino[2,3-b][1,4benzothiazin-8-ylmethyl)-3-azabicyclo[3.1.1] heptane-7-spiro-cyclobutan]-6-yl]acetate and ethyl (syn)-[[3-(10H-pyrazino[2,3-b][1,4]benzothiazin-8-ylmethyl)-3-azabicyclo[3.1.1]heptane-7-spiro-cyclobutan]-6-yl]acetate In a nitrogen atmosphere, 2.00 g of ethyl [[3-(p-tolylsulfonyl)-3-azabicyclo[3.3.1]heptane-7-spiro-cyclobutan]-6-yl]acetate was dissolved in 90 ml of dry 1,2-dimethoxyethane and the obtained solution was cooled and 350 ml of ethyl acetate. The organic layer was washed with water, dried over anhydrous magnesium sulfate, filtered and distilled under reduced pressure. The residue was purified by silica gel column chromatography (eluted with methylene chloride/methanol) to thereby give 0.62 g of ethyl (anti)-[[3-(10H-pyrazino[2,3-b][1,4]benzothiazin-8-ylmethyl)-3-azabicyclo[3.1.1]heptane-7-spiro-cyclobutan]-6-yl]acetate and 0.49 g of ethyl (syn)-[[3-(10H-pyrazino[2,3-b][1,4]benzothiazin-8-ylmethyl)-3-azabicyclo[3.1.1]heptane-7-spiro-cyclobutan]-6-yl]acetate each as a yellow powder.

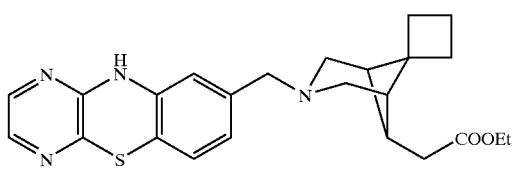

¹H-NMR(CDCl₃) δ ppm; 1.25(t, J=7 Hz, 3H), 1.80(m, 2H), 1.86(m, 2H), 2.14(m, 4H), 2.25(m, 1H), 2.62(d, J=7 Hz, 2H), 2.81(d, J=11 Hz, 2H), 2.87(d, J=11 Hz, 2H), 3.45(s, 2H), 4.13(q, J=7 Hz, 2H), 6.44(s, 1H), 6.51(s, 1H), 6.74(d, J=(d, J=8 Hz, 1H), 6.82(d, J=8 Hz, 1H), 7.58(d, J=3 Hz, 1H), 7.68(d, J=3 Hz, 1H)

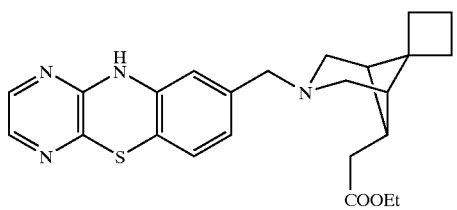

¹H-NMR(CDCl₃) δ ppm; 1.25(t, J=7 Hz, 3H), 1.85(m, 3H), 1.93(br.s, 2H), 2.10(br.s, 2H), 2.30(t, J=8 Hz, 2H), 2.60(d, J=8 Hz, 2H), 2.98(br.s, 4H), 3.58(br.s, 2H), 4.12(q, J=7 Hz, 2H), 6.55(s, 1H), 6.75(d, J=8 Hz, 1H), 6.82(d, J=8 Hz, 1H), 7.57(d, J=3 Hz, 1H), 7.68(d, J=3 Hz, 1H)

Examples 70 to 111

The compounds listed in the following tables were obtained by the same method as the one of Example 18.

TABLE 27

| Ex. | Structural formula | MS | M.p. | NMR |
|---|---|---|---|---|
| 70 | [3-(10H-pyrazino[2,3-b][1,4]benzothiazin-8-ylmethyl)-3-azabicyclo[3.2.1]oct-8-ylidene]acetic acid | FAB(+) 381(MH⁺) | 268–271° C. | ¹H-NMR(DMSO-d₆) δppm: 1.46–1.62(m, 2H), 1.74–1.90(m, 2H), 2.02–2.14(m, 2H), 2.68–2.80(m, 2H), 3.28(s, 2H), 3.20–3.40(m, 1H), 3.52–3.66(m, 1H), 5.53(s, 1H), 6.68(dd, J=1, 8Hz, 1H), 6.80(s, 1H), 6.82(d, J=8Hz, 1H), 7.55–7.65(m, 1H), 7.62(d, J=3Hz, 1H), 9.53(s, 1H) |
| 71 | [3-(10H-pyrazino[2,3-b][1,4]benzothiazin-8-ylmethyl)-3-azabicyclo[3.2.1]oct-8-yl]acetic acid | FAB(+) 383(MH⁺) | 244–245° C. | ¹H-NMR(DMSO-d₆) δppm: 1.50–2.10(m, 10H), 2.2–2.3(m, 1H), 2.4–2.65(m, 2H), 3.25 and 3.28(s, 2H), 6.68(d, J=8Hz, 1H), 6.78(s, 1H), 6.81(d, J=8Hz, 1H), 7.55–7.65(m, 2H), 9.53(s, 1H) |
| 72 | [3-(10H-pyrazino[2,3-b][1,4]benzothiazin-8-ylmethyl)-3-azabicyclo[3.3.1]non-9-ylidene]acetic acid | FAB(+) 395(MH⁺) | 253–255° C. | ¹H-NMR(DMSO-d₆) δppm: 1.36–1.48(m, 1H), 1.60–1.76(m, 2H), 1.86–1.98(m, 2H), 2.08–2.20(m, 2H), 2.26–2.34(m, 1H), 2.68–2.86(m, 1H), 2.90–3.00(m, 2H), 3.14(d, J=13Hz, 1H), 3.18(d, J=13Hz, 1H), 3.80–3.86(m, 1H), 5.55(s, 1H), 6.70(dd, J=1, 8Hz, 1H), 6.74(s, 1H), 6.85(d, J=8Hz, 1H), 7.61(d, J=3Hz, 1H), 7.63(d, J=3Hz, 1H), 9.57(s, 1H), 11.9–12.1(m, 1H) |

TABLE 28

| Ex. | Structural formula | MS | M.p. | NMR |
|---|---|---|---|---|
| 73 | 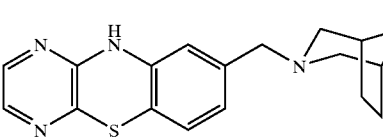<br>[3-(10H-pyrazino[2,3-b][1,4]benzothiazin-8-ylmethyl)-3-azabicyclo[3.2.1]oct-8-yl]carboxylic acid | FAB(+) 369(MH⁺) | 261–264° C. | $^1$H-NMR(DMSO-$d_6$) δppm: 1.52–1.68(m, 4H), 1.98–2.08(m, 2H), 2.25(s, 1H), 2.32–2.40(m, 2H), 2.54–2.66(m, 2H), 3.26(s, 2H), 6.68(d, J=8Hz, 1H), 6.79(s, 1H), 6.81(d, J=8Hz, 1H), 7.61(d, J=3Hz, 1H), 7.63(d, J=3Hz, 1H), 9.54(s, 1H), 12.0–12.2(m, 1H) |
| 74 | 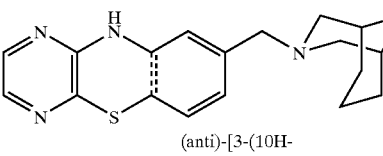<br>(anti)-[3-(10H-pyrazino[2,3-b][1,4]benzothiazin-8-ylmethyl)-3-azabicyclo[3.3.1]non-9-yl]carboxylic acid | FAB(+) 383(MH⁺) | 272–275° C. | $^1$H-NMR(DMSO-$d_6$) δppm: 1.38–1.40(m, 1H), 1.48–1.56(m, 2H), 1.64–1.76(m, 2H), 2.08(br.s, 2H), 2.16(br.d, J=10Hz, 2H), 2.28(br.s, 1H), 2.46–2.64(m, 1H), 2.82–2.90(m, 2H), 3.16(s, 2H), 6.69(dd, J=1, 8Hz, 1H), 6.73(d, J=1Hz, 1H), 6.84(d, J=8Hz, 1H), 7.61(d, J=3Hz, 1H), 7.63(d, J=3Hz, 1H), 9.56(s, 1H) |
| 75 | 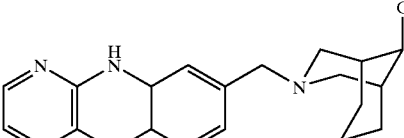<br>(syn)-[3-(10H-pyrazino[2,3-b][1,4]benzothiazin-8-ylmethyl)-3-azabicyclo[3.3.1]non-9-yl]carboxylic acid | FAB(+) 383(MH⁺) | 278–281° C. | $^1$H-NMR(DMSO-$d_6$) δppm: 1.36–1.46(m, 1H), 1.56–1.68(m, 2H), 1.70–1.80(m, 2H), 2.15(br.s, 2H), 2.22(br.d, J=11Hz, 2H), 2.28(br.s, 1H), 2.50–2.70(m, 1H), 2.62(br.d, J=10Hz, 2H), 3.08(s, 2H), 6.67(dd, J=1, 8Hz, 1H), 6.70(d, J=1Hz, 1H), 6.82(d, J=8Hz, 1H), 7.61(d, J=3Hz, 1H), 7.63(d, J=3Hz, 1H), 9.54(s, 1H) |

TABLE 29

| Ex. | Structural formula | MS | M.p. | NMR |
|---|---|---|---|---|
| 76 | 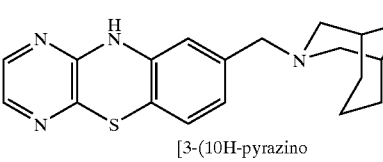<br>[3-(10H-pyrazino[2,3-b][1,4]benzothiazin-8-ylmethyl)-3-aza-7-oxabicyclo[3.3.1]non-9-yl]acetic acid | FAB(+) 399(MH⁺) | oily substance | $^1$H-NMR(DMSO-$d_6$) δppm: 1.54(br.s, 2H), 1.86–1.96(m, 1H), 2.18–2.28(m, 2H), 2.53(br.d, J=8Hz, 2H), 2.84–2.94(m, 2H), 3.23(s, 2H), 3.57(br.d, J=8Hz, 2H), 3.72–3.84(m, 2H), 6.74(s, 1H), 6.70–6.80(m, 1H), 6.83(d, J=8Hz, 1H), 7.61(d, J=2Hz, 1H), 7.62(d, J=2Hz, 1H), 9.52(s, 1H) |

TABLE 29-continued

| Ex. | Structural formula | | MS | M.p. | NMR |
|---|---|---|---|---|---|
| 77 | 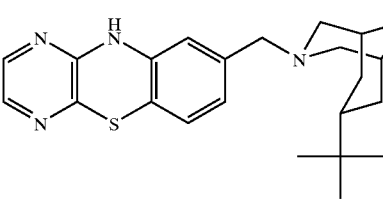 [3-(10H-pyrazino [2,3-b][1,4] benzothiazin-8- ylmethyl)-7-tert- butyl-3-azabicyclo [3.3.1]non-9-yl] acetic acid | | FAB(+) 453(MH$^+$) | 138– 140° C. | $^1$H-NMR(DMSO-d$_6$) δppm: 0.80(s, 9H), 1.10– 1.25(m, 3H), 1.60– 2.00(m, 7H), 2.34(d, J=6.8Hz, 2H), 2.54(d, J=10.4Hz, 2H), 3.17(s, 2H), 6.58(s, 1H), 6.78(d, J=8.0Hz, 1H), 6.82(d, J=8.0Hz, 1H), 7.61(d, J=2.8Hz, 1H), 7.62(d, J=2.8Hz, 1H), 9.42(s, 1H) |
| 78 | 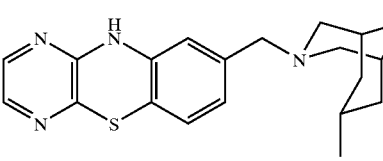 [3-(10H-pyrazino [2,3-b][1,4] benzothiazin-8- ylmethyl)-7-methyl- 3-azabicyclo[3.3.1] non-9-yl]acetic acid | | FAB(+) 411(MH$^+$) | 142– 146° C. | $^1$H-NMR(DMSO-d$_6$) δppm: 0.86(d, J=6.8Hz, 3H), 1.32–1.43(m, 2H), 1.53–1.62(m, 2H), 1.64–1.76(m, 2H), 1.93–2.02(m, 2H), 2.27(d, J=9.6Hz, 2H), 2.38(d, J=7.2Hz, 2H), 2.94(d, J=9.6Hz, 2H), 3.26(s, 2H), 6.63(s, 1H), 6.76(d, J=8.0Hz, 1H), 6.79(d, J=8.0Hz, 1H), 7.55(d, J=2.8Hz, 1H), 7.56(d, J=2.8Hz, 1H) |

TABLE 30

| Ex. | Structural formula | MS | M.p. | NMR |
|---|---|---|---|---|
| 79 | 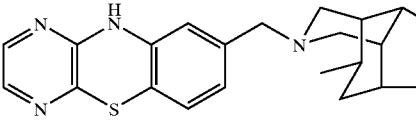 (anti)-(6R*,8R*)-[3- (10H-pyrazino[2,3- b][1,4]benzothiazin- 8-ylmethyl)-6,8- dimethyl-3- azabicyclo[3.3.1]non- 9-yl]acetic acid | FAB(+) 425(MH$^+$) | 200– 212° C. | $^1$H-NMR(DMSO-d$_6$) δppm: 0.77–0.90(m, 1H), 0.92(d, J=6.8Hz, 6H), 1.35(br.s, 2H), 1.60–1.80(m, 4H), 1.91(d, J=10.4Hz, 2H), 2.32(d, J=6.8Hz, 2H), 2.53(d, J=10.4Hz, 2H), 3.20(s, 2H), 6.67(d, J=8.0Hz, 1H), 6.74(s, 1H), 6.81(d, J=8.0Hz, 1H), 7.61(d, J=2.8Hz, 1H), 7.62(d, J=2.8Hz, 1H), 9.52(s, 1H) |
| 80 | 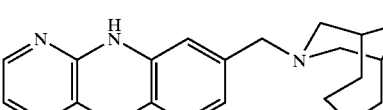 [8-(10H- pyrazino[2,3- b][1,4]benzothiazin- 8-ylmethyl)-8- azabicyclo[4.3.1]dec- 10-yl]acetic acid | FAB(+) 411(MH$^+$) | 217– 218° C. | $^1$H-NMR(DMSO-d$_6$) δppm: 1.41–1.54(m, 4H), 1.67– 1.77(m, 2H), 1.82–1.89(m, 2H), 1.92–2.09(m, 5H), 2.37(d, J=7.4Hz, 2H), 2.56–2.62(m, 2H), 3.14(s, 2H), 6.68–6.72(m, 2H), 6.83(dd, J=1.8, 7.7Hz, 1H), 7.61(d, J=2.8Hz, 1H), 7.63(d, J=2.8Hz, 1H), 9.55(s, 1H) |

TABLE 30-continued

| Ex. | Structural formula | MS | M.p. | NMR |
|---|---|---|---|---|
| 81 | 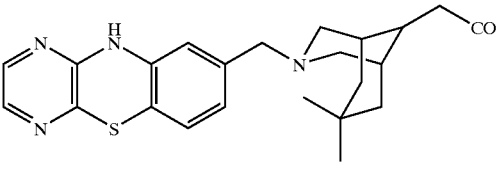[3-(10H-pyrazino[2,3-b][1,4]benzothiazin-8-ylmethyl)-7,7-dimethyl-3-azabicyclo[3.3.1]non-9-yl]acetic acid | FAB(+) 381(MH$^+$) | 211–214° C. | $^1$H-NMR(DMSO-d$_6$) δppm: 0.93(s, 3H), 1.23–1.29(m, 2H), 1.38(s, 3H), 1.56–1.68(m, 4H), 1.68–1.77(m, 1H), 2.03–2.10(m, 2H), 2.22(d, J=8.0Hz, 2H), 2.68–2.74(m, 2H), 3.20(s, 2H), 6.64(d, J=1.5Hz, 1H), 6.67(dd, J=1.5, 7.7Hz, 1H), 6.83(d, J=7.7Hz, 1H), 7.61(d, J=2.8Hz, 1H), 7.63(d, J=2.8Hz, 1H), 9.50(s, 1H) |

TABLE 31

| Ex. | Structural formula | MS | M.p. | NMR |
|---|---|---|---|---|
| 82 | (syn)-2-[3-(10H-pyrazino[2,3-b][1,4]benzothiazin-8-ylmethyl)-3-azabicyclo[3.3.1]non-9-yl]propanoic acid | FAB(+) 411(MH$^+$) | 126–128° C. | $^1$H-NMR(CD$_3$OD) δppm: 1.11(d, J=7Hz, 3H), 1.49–1.56(m, 1H), 1.58–1.62(d, J=11Hz, 1H), 1.63–1.74(m, 3H), 1.81–1.83(dd, J=4, 9Hz, 1H), 1.86–1.94(m, 2H), 2.38–2.42(br.d, J=11Hz, 1H), 2.57–2.62(br.d, J=11Hz, 1H), 2.64–2.80(m, 4H), 3.27(s, 2H), 6.67(s, 1H), 6.79(s, 2H), 7.55(d, J=3Hz, 1H), 7.57(d, J=3Hz, 1H) |
| 83 | (anti)-2-[3-(10H-pyrazino[2,3-b][1,4]benzothiazin-8-ylmethyl)-3-azabicyclo[3.3.1]non-9-yl]propanoic acid | FAB(+) 411(MH$^+$) | 233–234° C. | $^1$H-NMR(CD$_3$OD) δppm: 1.11(d, J=7Hz, 3H), 1.46–1.58(m, 4H), 1.65(br.s, 1H), 1.64–1.74(m, 1H), 1.83(br.s, 1H), 1.89–2.00(m, 1H), 2.27(t, J=10Hz, 2H), 2.56–2.66(m, 1H), 2.76–2.83(dt, J=7, 11Hz, 1H), 2.96(d, J=11Hz, 1H), 3.04(d, J=11Hz, 1H), 3.26(s, 2H), 6.67(s, 1H), 6.79(s, 2H), 7.55(d, J=3Hz, 1H), 7.57(d, J=3Hz, 1H) |
| 84 | (anti)-4-[3-(10H-pyrazino[2,3-b][1,4]benzothiazin-8-ylmethyl)-3-azabicyclo[3.3.1]non-9-yl]-2-methylbutanoic | FAB(+) 439(MH$^+$) | 104–108° C. | $^1$H-NMR(DMSO-d$_6$) δppm: 1.24(d, J=7.0Hz, 3H), 1.34–1.83(m, 12H), 2.13–2.23(m, 2H), 2.46(m, 1H), 2.59(m, 1H), 2.88–2.98(br.s, 2H), 3.22(br.s, 2H), 6.65(br.s, 1H), 6.69–6.83(m, 2H), 7.35(d, J=2.7Hz, 1H), 7.60(d, J=2.7Hz, 1H), 8.97(br.s, 1H) |

TABLE 32

| Ex. | Structural formula | MS | M.p. | NMR |
|---|---|---|---|---|
| 85 | 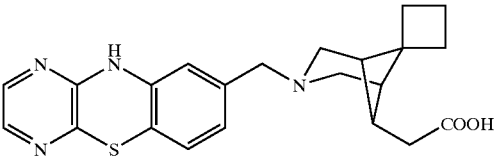 (anti)-[[3-(10H-pyrazino[2,3-b][1,4]benzothiazin-8-ylmethyl)-3-azabicyclo[3.1.1]heptane-7-spiro-cyclobutan-6-yl]acetic acid | FAB(+) 409(MH$^+$) | 175–180° C. | $^1$H-NMR(CD$_3$OD) δppm: 1.88(m, 2H), 1.99(m, 2H), 2.26(s, 2H), 2.38(t, J=8Hz, 2H), 2.54–2.60(m, 1H), 2.68(d, J=8Hz, 2H), 3.46(d, J=12Hz, 2H), 3.63(d, J=12Hz, 2H), 4.08(s, 2H), 6.84(s, 1H), 6.95(d, J=8Hz, 1H), 6.99(d, J=8Hz, 1H), 7.61(s, 2H) |
| 86 | 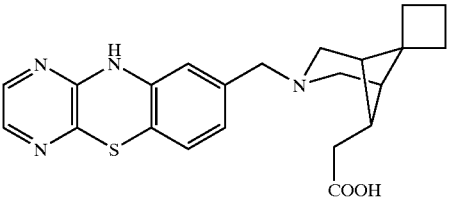 (syn)-[[3-(10H-pyrazino[2,3-b][1,4]benzothiazin-8-ylmethyl-3-azabicyclo[3.1.1]heptane-7-spiro-cyclobutan-6-yl]acetic acid | FAB(+) 409(MH$^+$) | 90–92° C. | $^1$H-NMR(CD$_3$OD) δppm: 1.78–1.85(m, 2H), 1.90–1.94(m, 2H), 2.14–2.18(m, 4H), 2.46–2.52(m, 1H), 2.59(d, J=7Hz, 2H), 2.89(d, J=11Hz, 2H), 2.97(d, J=11Hz, 2H), 3.49(s, 2H), 6.67(d, J=2Hz, 1H), 6.76(dd, J=2, 8Hz, 1H), 6.79(d, J=8Hz, 1H), 7.55(d, J=3Hz, 1H), 7.57(d, J=3Hz, 1H) |
| 87 | 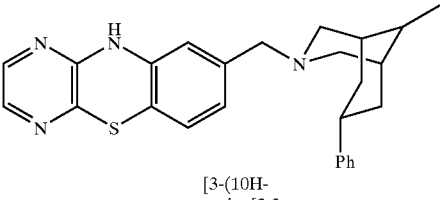 [3-(10H-pyrazino[2,3-b][1,4]benzothiazin-8-ylmethyl)-7-phenyl-3-azabicyclo[3.3.1]non-9-yl]acetic acid | FAB(+) 473(MH$^+$) | 128–131° C. | $^1$H-NMR(DMSO-d$_6$) δppm: 1.59–1.96(m, 10H), 2.21(d, J=10Hz, 2H), 2.93(d, J=10Hz, 2H), 3.23(s, 2H), 6.73(s, 1H), 6.77(d, J=8.0Hz, 1H), 6.89(d, J=8.0Hz, 1H), 7.10–7.20(m, 2H), 7.25–7.35(m, 3H), 7.61(d, J=2.8Hz, 1H), 7.63(d, J=2.8Hz, 1H), 9.56(s, 1H) |

TABLE 33

| Ex. | Structural formula | MS | M.p. | NMR |
|---|---|---|---|---|
| 88 | 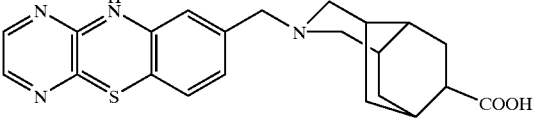 3-(10H-pyrazino[2,3-b][1,4]benzothiazin-8-ylmethyl)-3-azatricyclo[5.3.1.0$^{5,10}$]undecane-8-carboxylic acid | FAB(+) 409(MH$^+$) | 254–259° C. | $^1$H-NMR(DMSO-d$_6$) δppm: 1.16(m, 1H), 1.41–1.70(m, 7H), 1.84–1.98(m, 4H), 2.37(m, 1H), 2.43–2.56(m, 2H), 3.26(s, 2H), 6.72(dd, J=1.5, 7.9Hz, 1H), 6.83(d, J=7.9Hz, 1H), 6.84(d, J=1.5Hz, 1H), 7.63(d, J=2.9Hz, 1H), 7.64(d, J=2.9Hz, 1H), 9.55(s, 1H), 12.02(br.s, 1H) |

TABLE 33-continued

| Ex. | Structural formula | MS | M.p. | NMR |
|---|---|---|---|---|
| 89 | 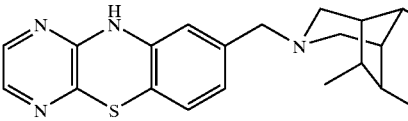<br>(anti)-(6R*,7R*)-[3-(10H-pyrazino[2,3-b][1,4]benzothiazin-8-ylmethyl)-6,7-dimethyl-3-azabicyclo[3.2.1]oct-8-yl]acetic acid | FAB(+) 411(MH⁺) | | $^1$H-NMR(DMSO-d$_6$) δppm: 0.99(d, J=7.2Hz, 3H), 1.03(d, J=7.2Hz, 3H), 1.57–1.74(m, 5H), 1.80(t, J=8.0Hz, 1H), 1.95(d, J=8.0Hz, 1H), 2.02(d, J=8.0Hz, 1H), 2.24(d, J=7.6Hz, 1H), 2.57(d, J=10Hz, 1H), 2.75(d, J=10Hz, 1H), 3.18(d, J=12.8Hz, 1H), 3.29(d, J=12.8Hz, 1H), 6.67(d, J=8.0Hz, 1H), 6.72(s, 1H), 6.81(d, J=8.0Hz, 1H), 7.60(d, J=2.8Hz, 1H), 7.62(d, J=2.8Hz, 1H), 9.53(s, 1H), 12.0(br.s, 1H) |
| 90 | 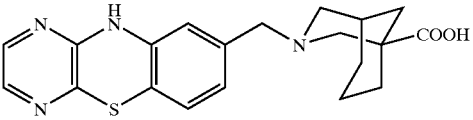<br>[3-(10H-pyrazino[2,3-b][1,4]benzothiazin-8-ylmethyl)-3-azabicyclo[3.3.1]non-1-yl]carboxylic acid | FAB(+) 383(MH⁺) | 186–188° C. | $^1$H-NMR(DMSO-d$_6$) δppm: 1.46–1.72(m, 6H), 1.82(m, 1H), 1.91(m, 1H), 2.02–2.13(m, 2H), 2.71(m, 1H), 2.79(m, 1H), 2.93(m, 1H), 3.12(d, J=13.4Hz, 1H), 3.25(d, J=13.4Hz, 1H), 6.70(dd, J=1.2, 7.9Hz, 1H), 6.74(d, J=1.2Hz, 1H), 6.86(d, J=7.9Hz, 1H), 7.63(d, J=2.9Hz, 1H), 7.64(d, J=2.9Hz, 1H), 9.58(s, 1H), 12.20(br.s, 1H) |

TABLE 34

| Ex. | Structural formula | MS | M.p. | NMR |
|---|---|---|---|---|
| 91 | 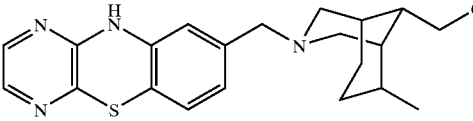<br>[3-(10H-pyrazino[2,3-b][1,4]benzothiazin-8-ylmethyl)-6-methyl-3-azabicyclo[3.3.1]non-9-yl]acetic acid | FAB(+) 411(MH⁺) | 125–130° C. | $^1$H-NMR(DMSO-d$_6$) δppm: 1.00(d, J=7Hz, 3H), 1.10–1.20(m, 1H), 1.30–1.45(m, 1H), 1.50(br.s, 1H), 1.60(br.s, 1H), 1.70–1.90(m, 3H), 2.08(d, J=8Hz, 1H), 2.14(d, J=8Hz, 1H), 2.3–2.5(m, 2H), 2.68(m, 1H), 2.73(d, J=10Hz, 1H), 2.82(d, J=10Hz, 1H), 3.13(d, J=13Hz, 1H), 3.20(d, J=13Hz, 1H), 6.67(d, J=8Hz, 1H), 6.72(s, 1H), 6.82(d, J=8Hz, 1H), 7.06(d, J=3Hz, 1H), 7.62(d, J=3Hz, 1H), 9.54(s, 1H), 12.3(br.s, 1H) |
| 92 | 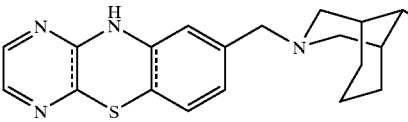<br>(anti)-3-[3-(10H-pyrazino[2,3-b][1,4]benzothiazin-8-ylmethyl)-3-azabicyclo[3.3.1]non-9-yl]propanoic acid | FAB(+) 411(MH⁺) | 223–225° C. | $^1$H-NMR(DMSO-d$_6$) δppm: 1.33–1.48(m, 4H), 1.54–1.78(m, 6H), 2.08–2.21(m, 4H), 2.54(m, 1H), 2.84–2.91(m, 2H), 3.17(s, 2H), 6.70(dd, J=1.5, 7.9Hz, 1H), 6.73(d, J=1.5Hz, 1H), 6.84(d, J=7.9Hz, 1H), 7.63(d, J=2.7Hz, 1H), 7.64(d, J=2.7Hz, 1H), 9.56(s, 1H) |

TABLE 34-continued

| Ex. | Structural formula | MS | M.p. | NMR |
|---|---|---|---|---|
| 93 | 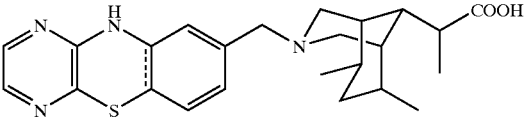<br>(anti)-(6R*,8R*)-2-[3-(10H-pyrazino[2,3-b][1,4]benzothiazin-8-ylmethyl)-6,8-dimethyl-3-azabicyclo[3.3.1]non-9-yl]propanoic acid | FAB(+)<br>439(MH$^+$) | | $^1$H-NMR(DMSO-d$_6$) δppm:<br>0.84–1.00(m, 1H), 0.95(d, J=6.8Hz, 3H), 0.98(d, J=6.8Hz, 3H), 1.06(d, J=6.8Hz, 3H), 1.28–1.38(m, 2H), 1.54–1.82(m, 4H), 1.87(d, J=7.2Hz, 1H), 1.89(d, J=7.2Hz, 1H), 2.48–2.55(m, 1H), 2.55(d, J=7.2Hz, 1H), 2.60(d, J=7.2Hz, 1H), 3.24(s, 2H), 6.68(d, J=8.0Hz, 1H), 6.75(s, 1H), 6.84(d, J=8.0Hz, 1H), 7.61(d, J=2.8Hz, 1H), 7.63(d, J=2.8Hz, 1H), 9.52(br.s, 1H), 12.0(br.s, 1H) |

TABLE 35

| Ex. | Structural formula | MS | M.p. | NMR |
|---|---|---|---|---|
| 94 | (anti)-3-[2-[3-(10H-pyrazino[2,3-b][1,4]benzothiazin-8-ylmethyl)-3-azabicyclo[3.3.1]non-9-yl]ethyloxy]benzoic acid | FAB(+)<br>503<br>(MH$^+$) | 234–236° C. | $^1$H-NMR(DMSO-d$_6$) δppm:<br>1.30–1.50(m, 3H), 1.55–1.60(br.s, 3H), 1.70–1.85(m, 2H),1.80–1.95(m, 2H), 2.15(br.d, J=10Hz, 2H), 2.50–2.60(m, 1H), 2.87(br.d, J=11Hz, 2H), 3.15(s, 2H), 3.95–4.05(m, 2H), 6.68(d, J=8Hz, 1H), 6.72(s, 1H), 6.83(d, J=8Hz, 1H), 7.16(dd, J=2.8Hz, 1H), 7.37(t, J=8Hz, 1H), 7.40(s, 1H), 7.49(d, J=8Hz, 1H), 7.60(d, J=3Hz, 1H), 7.62(d, J=3Hz, 1H), 9.56(s, 1H), 12.97(br.s, 1H) |
| 95 | (anti)-[2-[3-(10H-pyrazino[2,3-b][1,4]benzothiazin-8-ylmethyl)-3-azabicyclo[3.3.1]non-9-yl]ethyloxy]acetic acid | FAB(+)<br>441<br>(MH$^+$) | 108–113° C. | $^1$H-NMR(DMSO-d$_6$) δppm:<br>1.30–1.45(m, 3H), 1.45–1.60(m, 3H), 1.60–1.80(m, 4H), 2.06–2.20(m, 2H), 2.50(m, 1H), 2.80–2.90(m, 2H), 3.15(s, 2H), 3.43(t, J=6Hz, 2H), 3.93(s, 2H), 6.68(d, J=8Hz, 1H), 6.72(s, 1H), 6.83(d, J=8Hz, 1H), 7.61(d, J=3Hz, 1H), 7.62(d, J=3Hz, 1H), 9.55(s, 1H) |
| 96 | (anti)-4-[2-[3-(10H-pyrazino[2,3-b][1,4]benzonthiazin-8-ylmethyl)-3-azabicyclo[3.3.1]non-9-yl]ethyloxy]phenylacetic acid | FAB(+)<br>517<br>(MH$^+$) | 208–210° C. | $^1$H-NMR(DMSO-d$_6$) δppm:<br>1.36–1.50(m, 3H), 1.63(br.s, 3H), 1.7–1.86(m, 2H), 1.80–1.92(m, 2H), 2.15(br.d, J=11Hz, 2H), 2.46–2.64(m, 1H), 2.87(br.d, J=10Hz, 2H), 3.16(s, 2H), 3.45(s, 2H), 3.95(t, J=7Hz, 2H), 6.69(d, J=7Hz, 1H), 6.73(s, 1H), 6.83(d, J=7Hz, 1H), 6.84(d, J=8Hz, 2H), 7.12(d, J=8Hz, 2H), 7.61(d, J=3Hz, 1H), 7.62(d, J=3Hz, 1H), 9.55(s, 1H), 12.21(s, 1H) |

TABLE 36

| Ex. | Structural formula | MS | M.p. | NMR |
|---|---|---|---|---|
| 97 | (syn)-(6R*, 7R*)-[3-(10H-pyrazino[2,3-b][1,4]benzothiazin-8-ylmethyl)-6,7-dimethyl-3-azabicyclo[3.2.1]oct | | | δ ppm: 0.97(d, J=7.1Hz, 3H), 1.06(d, J=7.1Hz, 3H), 1.44(m, 1H), 1.52(m, 1H), 1.63(m, 1H), 1.69(m, 1H), 2.09(m, 1H), 2.23(d, J=10.6Hz, 1H), 2.26–2.34(m, 2H), 2.38(dd, J=7.5, 15.6Hz, 1H), 2.42–2.52(m, 2H), 3.23(d, J=13.0Hz, 1H), 3.32(d, J=13.0Hz, 1H), 6.69(dd, J=1.5, 7.7Hz, 1H), 6.73(d, J=1.5Hz, 1H), 6.83(d, J=7.7Hz, 1H), 7.62(d, J=2.9Hz, 1H), 7.63(d, J=2.9Hz, 1H), 9.54(s, 1H), 12.02(s, 1H) |
| 98 | (syn)-[3-(10H-pyrazino[2,3-b][1,4]benzothiazin-8-ylmethyl)-3-azabicyclo[3.3.1]non-7-yl]carboxylic acid | FAB(+) 383(MH+) | | ¹H-NMR(DMSO-d₆) δ ppm: 1.28(m, 1H), 1.46(m, 1H), 1.68–1.78(m, 4H), 2.11–2.18(m, 2H), 2.24–2.33(m, 2H), 2.41(m, 1H), 2.59–2.66(m, 2H), 3.18(s, 2H), 6.58(d, J=1.6Hz, 1H), 6.65(d, J=7.9Hz, 1H), 6.83(dd, J=1.6, 7.9Hz, 1H), 7.63(d, J=2.9Hz, 1H), 7.64(d, J=2.9Hz, 1H), 9.37(s, 1H), 11.54(br.s, 1H) |
| 99 | [3-(10H-pyrazino[2,3-b][1,4]benzothiazin-8-ylmethyl)-1,5-dimethyl-3-azabicyclo[3.3.1]non-9-yl]acetic acid | FAB(+) 425(MH+) | 226–229° C. | ¹H-NMR(DMSO-d₆) δ ppm: 0.66(s, 6H), 1.21–1.39(m, 6H), 1.57(t, J=5.9Hz, 1H), 1.78(d, J=11.8Hz, 2H), 2.20(d, J=5.9Hz, 2H), 2.40(d, J=11.8Hz, 2H), 3.08(s, 2H), 6.67(dd, J=1.0, 7.7Hz, 1H), 6.70(d, J=1.0Hz, 1H), 6.83(d, J=7.7Hz, 1H), 7.61(d, J=2.6Hz, 1H), 7.62(d, J=2.6Hz, 1H), 9.54(s, 1H), 12.00(s, 1H) |

TABLE 37

| Ex. | Structural formula | MS | M.p. | NMR |
|---|---|---|---|---|
| 100 | (anti)-(6R*, 8R*)-4-[3-(10H-pyrazino[2,3-b][1,4]benzothiazin-8-ylmethyl)-6,8-dimethyl-3-azabicyclo[3.3.1]non-9-yl]-2-methylbutanoic acid | | 110–115° C. | ¹H-NMR(CDCl₃) δ ppm: 0.97(d, J=7.6Hz, 3H), 0.99(d, J=7.6Hz, 3H), 1.21(d, J=6.8Hz, 3H), 1.30–2.00(m, 12H), 2.38–2.64(m, 4H), 3.25(s, 2H), 6.56(s, 1H), 6.66–6.82(m, 2H), 7.42(d, J=2.8Hz, 1H), 7.63(d, J=2.8Hz, 1H), 8.03(s, 1H) |

TABLE 37-continued

| Ex. | Structural formula | MS | M.p. | NMR |
|---|---|---|---|---|
| 101 | 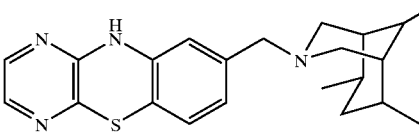<br>(6R*, 8R*)-3-[3-(10H-pyrazino[2,3-b][1,4]benzothiazin-8-ylmethyl)-6,8-dimethyl-3-azabicyclo[3.3.1]non-9-yl]propanoic acid | FAB(+) 439(MH+) | 110–115° C. | $^1$H-NMR(DMSO-d$_6$) δ ppm: 0.76–0.87(m, 1H), 0.93(d, J=6.4Hz, 6H), 1.50–1.90(m, 1H), 1.32–1.39(m, 2H), 1.56–1.78(m, 5H), 1.84(d, J=9.6Hz, 2H), 2.17(t, J=7.2Hz, 2H), 2.52(d, J=10Hz, 2H), 3.19(s, 2H), 6.67(d, J=8Hz, 1H), 6.74(s, 1H), 6.81(d, J=8Hz, 1H), 7.61(d, J=2.8Hz, 1H), 7.62(d, J=2.8Hz, 1H), 9.52(s, 1H) |
| 102 | 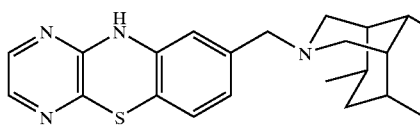<br>(anti)-(6R*, 8R*)-4-[3-(10H-pyrazino[2,3-b][1,4]benzothiazin-8-ylmethyl)-6,8-dimethyl-3-azabicyclo[3.3.1]non-9-yl]butanoic acid | | 98–105° C. | $^1$H-NMR(DMSO-d$_6$) δ ppm: 0.92(d, J=6.8Hz, 6H), 1.38–1.92(m, 13H), 2.01(t, J=6.4Hz, 2H), 2.52(d, J=10.8Hz, 2H), 3.18(s, 2H), 6.67(d, J=8.4Hz, 1H), 6.74(s, 1H), 6.82(d, J=8.4Hz, 1H), 7.60(d, J=2.4Hz, 1H), 7.62(d, J=2.4Hz, 1H), 9.53(s, 1H) |

TABLE 38

| Ex. | Structural formula | MS | M.p. | NMR |
|---|---|---|---|---|
| 103 | 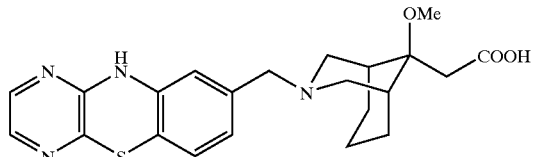<br>(anti)-[3-(10H-pyrazino[2,3-b][1,4]-benzothiazin-8-ylmethyl)-(syn)-9-methoxy-3-azabicyclo[3.3.1]non-9-yl]acetic acid | FAB(+) 427(MH+) | 217–219° C. | $^1$H-NMR(DMSO-d$_6$) δ ppm: 1.30–1.46(m, 3H), 1.84–2.00(m, 4H), 2.40–2.60(m, 3H), 2.66(s, 2H), 2.68–2.78(m, 2H), 3.15(s, 3H), 3.22(s, 2H), 6.68(dd, J=1, 8Hz, 1H), 6.71(s, 1H), 6.83(d, J=8Hz, 1H), 7.61(d, J=3Hz, 1H), 7.63(d, J=3Hz, 1H), 9.56(s, 1H) |
| 104 | 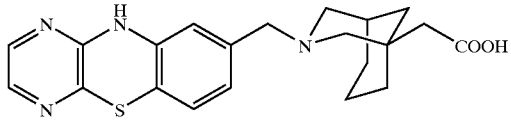<br>[3-(10H-pyrazino[2,3-b][1,4]benzothiazin-8-ylmethyl)-3-azabicyclo[3.3.1]non-1-yl]acetic acid | FAB(+) 397(MH+) | 215–217° C. | $^1$H-NMR(DMSO-d$_6$) δ ppm: 1.32–1.54(m, 5H), 1.62–1.74(m, 2H), 1.83–1.90(m, 2H), 1.96(s, 2H), 2.06(m, 1H), 2.64–2.85(m, 3H), 3.12(d, J=13.7Hz, 1H), 3.16(d, J=13.7Hz, 1H), 6.69(dd, J=1.5, 7.9Hz, 1H), 6.73(d, J=1.5Hz, 1H), 6.85(d, J=7.9Hz, 1H), 7.63(d, J=2.9Hz, 1H), 7.64(d, J=2.9Hz, 1H), 9.57(s, 1H) |

TABLE 38-continued

| Ex. | Structural formula | MS | M.p. | NMR |
|---|---|---|---|---|
| 105 | (syn)-[3-(10H-pyrazino[2,3-b][1,4]ben-zothiazin-8-ylmethyl)-(anti)-9-methoxy-3-azabicyclo[3.3.1]non-9-yl]acetic acid | FAB(+) 427(MH+) | 225–228° C. | $^1$H-NMR(DMSO-d$_6$) δ ppm: 1.30–1.45(m, 1H), 1.56–1.68(m, 2H), 1.70–1.90(m, 3H), 1.99(br.s, 1H), 2.16(s, 2H), 2.34–2.70(m, 5H), 3.13(s, 2H), 3.15(s, 3H), 6.70(d, J=8Hz, 1H), 6.72(s, 1H), 6.83(d, J=8Hz, 1H), 7.61(d, J=3Hz, 1H), 7.63(d, J=3Hz, 1H), 9.56(s, 1H) |

TABLE 39

| Ex. | Structural formula | MS | M.p. | NMR |
|---|---|---|---|---|
| 106 | 3-(10H-pyrazino[2,3-b][1,4]benzothiazin-8-ylmethyl)-3-azatricyclo[5.3.1.0$^{5,10}$]-undecane-9-carboxylic acid | FAB(+) 409(MH+) | 263–266° C. | $^1$H-NMR(DMSO-d$_6$) δ ppm: 1.44–1.60(m, 6H), 1.64–1.79(m, 4H), 1.84(m, 1H), 1.93(m, 1H), 2.45–2.57(m, 3H), 3.26(s, 2H), 6.46(dd, J=1.6, 7.9Hz, 1H), 6.83(d, J=1.6Hz, 1H), 6.84(d, J=7.9Hz, 1H), 7.63(d, J=2.7Hz, 1H), 7.64(d, J=2.7Hz, 1H), 9.56(s, 1H), 12.06(br.s, 1H) |
| 107 | (syn)-[3-(10H-pyrazino[2,3-b][1,4]-benzothiazin-8-ylmethyl)-3-azabicyclo[3.3.1]non-7-yl]acetic acid | ESI397.1 (MH+) | 206–209° C. | $^1$H-NMR(DMSO-d$_6$) δ ppm: 0.96(m, 1H), 1.07–1.18(m, 2H), 1.70(m, 1H), 1.79–1.94(m, 7H), 2.15(d, J=6.0Hz, 2H), 2.42–2.50(m, 2H), 3.23(s, 2H), 6.73(dd, J=1.5, 7.9Hz, 1H), 6.77(d, J=1.5Hz, 1H), 6.84(d, J=7.9Hz, 1H), 7.63(d, J=2.9Hz, 1H), 7.64(d, J=2.9Hz, 1H), 9.58(s, 1H), 11.97(br.s, 1H) |
| 108 | [3-(10H-pyrazino[2,3-b][1,4]benzothiazin-8-ylmethyl)-3-azabicyclo[3.3.1]nonane-9-spiro-cyclobut-3'-yl]acetic acid | FAB(+) 437(MH+) | 199–201° C. | $^1$H-NMR(DMSO-d$_6$) δ ppm: 1.22–1.82(m, 9H), 2.02–2.38(m, 3H), 2.26(d, J=8Hz, 2H), 2.22–2.38(m, 2H), 2.44–2.66(m, 3H), 3.08(s, 2H), 6.67(d, J=8Hz, 1H), 6.70(d, J=8Hz, 1H), 6.82(d, J=8Hz, 1H), 7.61(d, J=3Hz, 1H), 7.62(d, J=3Hz, 1H), 9.54(s, 1H), 11.93(s, 1H) |

TABLE 40

| Ex. | Structural formula | MS | M.p. | NMR |
|---|---|---|---|---|
| 109 | (anti)-(6R*, 8R*)-[3-(10H-pyrazino[2,3-b][1,4]benzothiazin-8-ylmethyl)-6,8-dimethyl-3-azabicyclo[3.3.1]nonane-9-spiro-cyclobut-3'-yl]acetic acid | FAB(+) 465(MH+) | 205–206° C. | $^1$H-NMR(DMSO-d$_6$) δ ppm: 0.68(q, J=12Hz, 1H), 0.95(d, J=7Hz, 3H), 0.99(d, J=7Hz, 3H), 1.21(m, 1H), 1.34–1.50(m, 3H), 1.58(m, 1H), 1.80(m, 2H), 1.90(d, J=9Hz, 1H), 2.00–2.16(m, 3H), 2.16–2.30(m, 2H), 2.26(d, J=8Hz, 2H), 2.39(m, J=8Hz, 1H), 3.13(s, 2H), 6.66(d, J=8Hz, 1H), 6.72(s, 1H), 6.80(d, J=8Hz, 1H), 7.60(d, J=3Hz, 1H), 7.62(d, J=3Hz, 1H), 9.51(s, 1H), 11.9(s, 1H) |
| 110 | 3-(10H-pyrazino[2,3-b][1,4]benzothiazin-8-ylmethyl)-3-azatricyclo[5.3.1.0$^{5,10}$]-undec-8-ene-9-carboxylic acid | FAB(+) 409(MH$^{3o}$) | 263–266° C. | $^1$H-NMR(DMSO-d$_6$) δ ppm: 1.26–1.36(m, 2H), 1.46–1.55(m, 2H), 1.56–1.65(m, 2H), 1.93–2.01(m, 2H), 2.58(s, 1H), 2.62–2.74(m, 3H), 3.13(s, 2H), 6.77(d, J=7.9Hz, 1H), 6.84(d, J=7.9Hz, 1H), 6.87(s, 1H), 7.29(dd, J=1.1, 6.8Hz, 1H), 7.63(d, J=2.9Hz, 1H), 7.64(d, J=2.9Hz, 1H), 9.56(s, 1H), 12.11(s, 1H) |
| 111 | [3-(10H-pyrazino[2,3-b][1,4]benzothiazin-8-ylmethyl)-3-azabicyclo[3.3.1]nonane-9-spiro-cyclobut-3'-yl]carboxylic acid | FAB(+) 423(MH+) | 98–101° C. | $^1$H-NMR(DMSO-d$_6$) δ ppm: 1.22–1.32(m, 1H), 1.42–1.80(m, 6H), 1.86(dd, J=8, 12Hz, 1H), 1.93(dd, J=8, 12Hz, 1H), 2.04–2.18(m, 3H), 2.23(br.d, J=11Hz, 1H), 2.42–2.66(m, 1H), 2.59(br.t, J=12Hz, 2H), 2.83(m, 1H), 3.09(s, 2H), 6.66(dd, J=2, 8Hz, 1H), 6.70(s, 1H), 6.82(d, J=8Hz, 1H), 7.61(d, J=2Hz, 1H), 7.62(d, J=2Hz, 1H), 9.55(s, 1H), 12.0(s, 1H) |

Examples 112 to 116

The following compounds were obtained by the same methods as those of Examples 13 and 14 (optionally using anhydrous potassium carbonate as a substitute for diisopropylamine) and that of Example 18.

TABLE 41

| Ex. | Structural formula | MS | M.p. | NMR |
|---|---|---|---|---|
| 112 | 3-[3-(10H-pyrazino[2,3-b][1,4]benzothiazin-8-ylmethyl)-1,5-dimethyl-3-azabicyclo[3.3.1]non-9-yl]-2-methyl-2-propenoic acid | FAB(+) 449(MH+), 451(MH+) | 249–251° C. | $^1$H-NMR(DMSO-$d_6$) δ ppm: 0.58(s, 6H), 1.28–1.38(m, 2H), 1.38–1.55(m, 3H), 1.76(d, J=1.7Hz, 3H), 1.82(br.d, J=11.5Hz, 2H), 2.00(br.d, J=11.9Hz, 1H), 2.67(br.d, J=11.5Hz, 2H), 2.74–2.89(m, 1H), 3.13(s, 2H), 6.68(d, J=8.1Hz, 1H), 6.73(d, J=1.1Hz, 1H), 6.84(dd, J=1.1, 8.1Hz, 1H), 6.85(dd, J=1.7, 11.9Hz, 1H), 7.60–7.64(m, 2H), 9.56(s, 1H), 12.18–12.25(br.s, 1H) |
| 113 | (syn)-[3-(10H-pyrazino[2,3-b][1,4]-benzothiazin-8-ylmethyl)-(anti)-9-methyl-3-azabicyclo[3.3.1]non-9-yl]carboxylic acid | FAB(+) 397(MH+) | 264–265° C. | $^1$H-NMR(DMSO-$d_6$) δ ppm: 1.18(s, 3H), 1.27–1.35.(m, 1H), 1.53–1.61(m, 2H), 1.75–1.88(m, 5H), 2.53–2.64(m, 4H), 3.23(s, 2H), 6.68(dd, J=1.8Hz, 1H), 6.72(d, J=1Hz, 1H), 6.83(d, J=8Hz, 1H), 7.61(d, J=3Hz, 1H), 7.62(d, J=3Hz, 1H), 9.44(br.s, 1H) |
| 114 | [3-(10H-pyrazino[2,3-b][1,4]-benzothiazin-8-ylmethyl)-3-azabicyclo[3.3.1]non-9-ylidene]fluoroacetic acid | FAB(+) 413(MH+) | 223–225° C. (dec) | $^1$H-NMR(DMSO-$d_6$) δ ppm: 1.39–1.49(m, 1H), 1.60–1.72(m, 2H), 1.88–1.96(m, 2H), 2.10–2.19(m, 2H), 2.69–2.84(m, 1H), 2.88–2.99(m, 3H), 3.14(d, J=12.3Hz, 1H), 3.20(d, J=12.3Hz, 1H), 3.61–3.67(m, 1H), 6.70(d, J=7.6Hz, 1H), 6.74(d, J=1.0Hz, 1H), 6.85(dd, J=1.0, 7.6Hz, 1H), 7.61(d, J=2.8Hz, 1H), 7.63(d, J=2.8Hz, 1H), 9.57(s, 1H) |

TABLE 42

| Ex. | Structural formula | MS | M.p. | NMR |
|---|---|---|---|---|
| 115 | [3-(10H-pyrazino[2,3-b][1,4]benzothiazin-8-ylmethyl)-3-azabicyclo[3.3.1]non-9-yl]fluoroacetic acid | FAB(+) 415(MH+) | 185–187° C. | $^1$H-NMR(DMSO-$d_6$) δ ppm: 1.40–1.55(m, 3H), 1.58–1.90(m, 4H), 2.08–2.18(m, 2H), 2.50–2.68(m, 1H), 2.83–2.95(m, 2H), 3.13–3.18(m, 1H), 3.17(s, 2H), 5.18(dd, J=10.6, 49.6Hz, 1H), 6.68(d, J=8.2Hz, 1H), 6.73(s, 1H), 6.84(d, J=8.2Hz, 1H), 7.60–7.64(m, 2H), 9.57(s, 1H) |

TABLE 42-continued

| Ex. | Structural formula | MS | M.p. | NMR |
|---|---|---|---|---|
| 116 | (anti)-[3-(10H-pyrazino[2,3-b][1,4]benzothiazin-8-ylmethyl)-(syn)-9-methyl-3-azabicyclo[3.3.1]non-9-yl]carboxylic acid | FAB(+) 397(MH+) | 183–185° C. | ¹H-NMR(CD₃OD) δ ppm: 1.28(s, 3H), 1.41–1.52(m, 1H), 1.56(dd, J=6, 12Hz, 2H), 1.98(m, 3H), 2.08(s, 2H), 2.57(m, 2H), 2.73(m, 2H), 3.24(s, 2H), 6.64(d, J=2Hz, 1H), 6.77(dd, J=2, 8Hz, 1H), 6.79(d, J=8Hz, 1H), 7.55(d, J=3Hz, 1H), 7.57(d, J=3Hz, 1H) |

Examples 117 to 119

The following compounds were obtained from known compounds by the same methods as those of Examples 12, 13 and 14 (using anhydrous potassium carbonate as a substitute for diisopropylamine) and that of Example 18.

TABLE 43

| Ex. | Structural formula | MS | M.p. | NMR |
|---|---|---|---|---|
| 117 | [8-(10H-pyrazino[2,3-b][1,4]benzothiazin-8-ylmethyl)-8-azabicyclo[3.2.1]oct-8-yl]acetic acid | FAB(+) 383(MH+) | 155–158° C. | ¹H-NMR(DMSO-d₆) δ ppm: 1.15–1.23(m, 2H), 1.51–1.60(m, 2H), 1.88–1.96(m, 2H), 1.97–2.05(m, 2H), 2.07–2.19(m, 1H), 2.30(d, J=8.4Hz, 2H), 2.97–3.06(m, 2H), 3.26(s, 2H), 6.72(dd, J=1.6, 8.2Hz, 1H), 6.80(d, J=8.2Hz, 1H), 6.84(d, J=1.6Hz, 1H), 7.61(d, J=2.6Hz, 1H), 7.62(d, J=2.6Hz, 1H), 9.45(s, 1H) |
| 118 | [8-(10H-pyrazino[2,3-b][1,4]benzothiazin-8-ylmethyl)-8-azabicyclo[3.2.1]oct-3-ylidene]acetic acid | FAB(+) 381(MH+) | 206–208° C. | ¹H-NMR(DMSO-d₆) δ ppm: 1.27(m, 2H), 1.77–1.88(m, 2H), 1.88–1.98(m, 1H), 2.12–2.23(m, 1H), 2.49–2.57(m, 1H), 3.12–3.22(m, 2H), 3.34–3.51(m, 3H), 5.60(s, 1H), 6.75(d, J=8.6Hz, 1H), 6.82(d, J=8.6Hz, 1H), 6.87(s, 1H), 7.60(d, J=2.7Hz, 1H), 7.61(d, J=2.7Hz, 1H), 9.46(s, 1H) |
| 119 | [8-(10H-pyrazino[2,3-b][1,4]benzothiazin-8-ylmethyl)-8-azabicyclo[3.2.1]oct-3-yl]carboxylic acid | FAB(+) 369(MH+) | 158° C. (dec) | ¹H-NMR(DMSO-d₆) δ ppm: 1.49–1.58(m, 4H), 1.65–1.74(m, 2H), 1.86–1.94(m, 2H), 2.44–2.55(m, 1H), 3.05–3.11(m, 2H), 3.29(s, 2H), 6.71(dd, J=1.3, 8.0Hz, 1H), 6.81(d, J=8.0Hz, 1H), 6.87(d, J=1.3Hz, 1H), 7.61(d, J=2.9Hz, 1H), 7.62(d, J=2.9Hz, 1H), 9.48(s, 1H) |

Example 120

The following compound was obtained by treating (6R*, 8R*)-3-(3,6,8-trimethyl-3-azabicyclo[3.3.1]non-9-yl)-2-methylpropanoic acid by the same methods as those of Examples 12, 13 and 14 (using anhydrous potassium carbonate as a substitute for diisopropylamine) and that of Example 18.

TABLE 44

| Ex. | Structural formula | MS | M.p. | NMR |
|---|---|---|---|---|
| 120 | 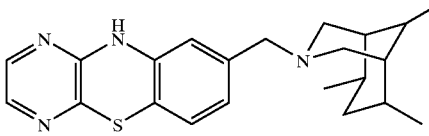<br>(6R*, 8R*)-3-[3-(10H-pyrazino[2,3-b][1,4]-benzothiazin-8-ylmethyl)-6,8-dimethyl-3-azabicyclo[3.3.1]non-9-yl]-2-methylpropanoic acid | FAB(+)<br>453(MH+) | 110–115° C. | $^1$H-NMR(DMSO-$d_6$) δ ppm:<br>0.75–0.90(m, 1H), 0.94(d, J=6.8Hz, 6H), 1.00(d, J=6.8Hz, 3H), 1.14–1.43(m, 4H), 1.55–1.78(m, 5H), 1.85(d, J=10.8Hz, 2H), 2.52(d, J=10.8Hz, 2H), 2H), 3.19(s, 2H), 6.67(d, J=7.6Hz, 1H), 6.73(s, 1H), 6.81(d, J=7.6Hz, 1H), 7.61(d, J=2.8Hz, 1H), 7.62(d, J=2.8Hz, 1H), 9.51(s, 1H) |

Example 121

The following compound was obtained by treating ethyl 4-[2-[(anti)-3-methyl-3-azabicyclo[3.3.1]non-9-yl]ethyloxy]benzoate by the same methods as those of Examples 17 and 18.

TABLE 45

| Ex. | Structural formula | MS | M.p. | NMR |
|---|---|---|---|---|
| 121 | 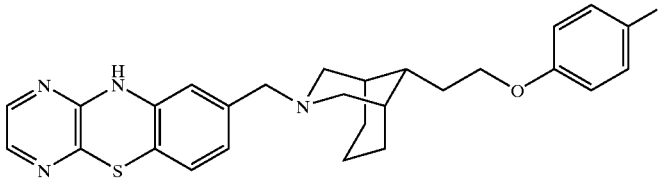<br>(anti)-4-[2-[3-[10H-pyrazino[2,3-b][1,4]benzothiazin-8-ylmethyl)-3-azabicyclo[3.3.1]non-9-yl]ethyloxy]benzoic acid | FAB(+)<br>503<br>(MH+) | 239–242° C. | $^1$H-NMR(DMSO-$d_6$) δ ppm:<br>1.35–1.50(m, 3H), 1.62(br.s, 3H), 1.65–1.75(m, 2H), 1.80–1.95(m, 2H), 2.14(br.d, J=10Hz, 2H), 2.45–2.65(m, 1H), 2.87(br.d, J=10Hz, 2H), 3.15(s, 2H), 4.05(t, J=6Hz, 2H), 6.68(d, J=8Hz, 1H), 6.72(s, 1H), 6.83(d, J=8Hz, 1H), 6.98(d, J=8Hz, 1H), 7.61(s, 2H), 7.85(d, J=8Hz, 2H), 9.55(s, 1H), 12.58(br.s, 1H) |

Example 122

The following compound was obtained by treating ethyl (11-hydroxy-9-methyl-9-azabicyclo[5.3.1]undec-11-yl)acetate by the same methods as those of Examples 12, 13, 14 and 18.

TABLE 46

| Ex. | Structural formula | MS | M.p. | NMR |
|---|---|---|---|---|
| 122 | [9-(10H-pyrazino[2,3-b][1,4]benzothiazin-8-ylmethyl)-11-hydroxy-9-azabicyclo[5.3.1]undec-11-yl]acetic acid | FAB(+) 441(MH⁺) | 217–218° C. (dec) | $^1$H-NMR(CDCl$_3$) δ ppm: 1.10–1.25(m, 2H), 1.50–1.65(m, 4H), 1.77–1.93(m, 4H), 1.97–2.09(m, 2H), 2.23–2.32(m, 2H), 2.70–2.77(m, 2H), 2.79(s, 2H), 3.23(s, 2H), 6.45(d, J=1.6Hz, 1H), 6.74(s, 1H), 6.79(d, J=7.8Hz, 1H), 6.85(dd, J=1.6, 7.8Hz, 1H), 7.27(d, J=3.1Hz, 1H), 7.59(d, J=3.1Hz, 1H), 8.85–9.04(br.s. 1H) |

Example 123

The following compound was obtained by treating ethyl (3-benzyl-7-methyl-3,7-diazabicyclo[3.3.1]non-9-ylidene) acetate by the same methods as those of Examples 64 and 18.

mixture followed by the extraction with chloroform. Then it was dried over anhydrous sodium sulfate and concentrated under reduced pressure. The obtained residue was purified by silica gel column chromatography (eluted with methylene chloride/methanol/conc. aqueous ammonia) to thereby give 342 mg of the title compound as a colorless oily substance.

TABLE 47

| Ex. | Structural formula | MS | M.p. | NMR |
|---|---|---|---|---|
| 123 | [3-(10H-pyrazino[2,3-b][1,4]benzothiazin-8-ylmethyl)-7-methyl-3,7-diazabicyclo[3.3.1]non-9-yl]acetic acid | FAB(+) 412(MH⁺) | 220° C. (dec) | $^1$H-NMR(CDCl$_3$) δ ppm: 2.00–2.04(m, 2H), 2.13–2.20 and 2.24–2.30(m, 1H)(3:7)), 2.35 and 2.37(d, J=8.5Hz, 2H(7:3)), 2.80 and 2.82(s, 3H(7:3)), 2.50–2.56 and 2.73–2.79(m, 2H(3:7)), 2.89–2.95 and 3.18–3.23(m, 2H(7:3)), 3.16–3.21 and 3.28–3.48(m, 2H(7:3)), 3.35–3.41 and 3.55–3.60(m, 2H(3:7)), 3.47 and 3.49(s, 2H(3:7)), 6.59–6.62(m, 1H), 6.78–6.82(m, 1H), 6.87(d, J=7.9Hz, 1H), 7.58(d, J=3.0Hz, 1H), 7.59(d, J=3.0Hz, 1H) |

Production Example 84

(anti)-3-(Vinyloxycarbonyl)-9-aminomethyl-3-azabicyclo[3.3.1]nonane

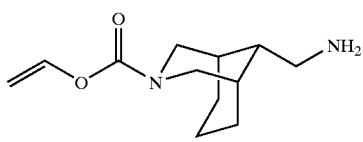

To 10 ml of benzene were added 500 mg of (anti)-[3-(vinyloxycarbonyl)-3-azabicyclo[3.3.1]non-9-yl]acetic acid, 0.31 ml of triethylamine and 0.45 ml of diphenylphosphoryl azide and the resulting mixture was stirred at 80° C. for 3 hours. After concentrating the reaction mixture, a colorless oily substance was obtained. This oily substance was dissolved in 10 ml of tetrahydrofuran and 5.0 ml of 1 N sodium hydroxide was added thereto. After stirring at room temperature for 30 minutes, water was added to the reaction $^1$H-NMR(CDCl$_3$) δ ppm; 1.46(m, 1H), 1.57–1.95(m, 10H), 2.91(d, J=7.5 Hz, 2H), 3.11(m, 1H), 3.18(m, H), 4.18–4.28(m, 2H), 4.45(dd, J=1.5, 6.2 Hz, 1H), 4.79(dd, J=1.5, 13.9 Hz, 1H), 7.25(dd, J=6.2, 13.9 Hz, 1H)

Production Example 85

N-[(anti)-3-(Vinyloxycarbonyl)-3-azabicyclo[3.3.1]non-9-yl]methyl-N',N'-dimethylsulfamide

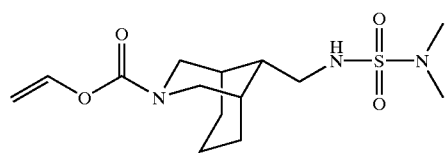

342 mg of (anti)-3-(vinyloxycarbonyl)-9-aminomethyl-3-azabicyclo[3.3.1]nonane was dissolved in 10 ml of methylene chloride. After adding 0.25 ml of triethylamine, the resulting mixture was ice-cooled. Then 0.2 ml of dimethylsulfamoyl chloride was dropped thereinto and the mixture was stirred at room temperature for 14 hours. After further adding 0.25 ml of triethylamine and 0.2 ml of dimethylsulfamoyl chloride, the reaction mixture was stirred at room temperature for additional 4 hours. Then the reaction mixture was concentrated and the residue was purified by silica gel column chromatography (eluted with n-hexane/ethyl acetate) to thereby give 406 mg of the title compound as a colorless oily substance.

$^1$H-NMR(CDCl$_3$) δ ppm; 1.46–1.89(m, 9H), 2.83(s, 6H), 3.10(m, 1H), 3.18(m, 1H), 3.23–3.30(m, 2H), 4.05(br.s, 1H), 4.20–4.29(m, 2H), 4.46(dd, J=1.6, 6.2 Hz, 1H), 4.79(dd, J=1.6, 14.1 Hz, 1H), 7.24(dd, J=6.2, 14.1 Hz, 1H)

Production Example 86

(anti)-1-(3-Methyl-3-azabicyclo[3.3.1]non-9-yl)-2-methyl-2-propanol

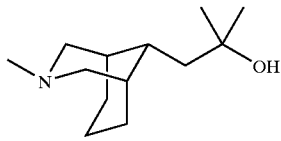

To 5 ml of ether was added 13 ml of a solution of methylmagnesium iodide in ether (ca 2M). Next, 10 ml of a solution of 2.25 g of ethyl (anti)-(3-methyl-3-azabicyclo-[3.3.1]non-9-yl)acetate in ether was dropped at room temperature thereinto and the resulting mixture was heated under reflux for 2 hours. After adding a saturated aqueous solution of ammonium chloride, the reaction mixture was extracted with ether. The ether layer was washed with water and saturated aqueous solution of sodium chloride, dried over anhydrous sodium sulfate and concentrated under reduced pressure. The obtained residue was purified by alumina chromatography (eluted with n-hexane/ethyl acetate) to thereby give 1.01 g of the title compound as a colorless oily substance.

$^1$H-NMR(CDCl$_3$) δ ppm; 1.18(s, 1H), 1.24(s, 6H), 1.39 (m, 1H), 1.48–1.66(m, 7H), 1.72–1.84(m, 2H), 2.13(s, 3H), 2.18–2.27(m, 2H) 2.42(m, 1H), 2.85–2.94(m, 2H)

Production Example 87

(anti)-1-(3-Azabicyclo[3.3.1]non-9-yl)-2-methyl-2-propanol hydrochloride

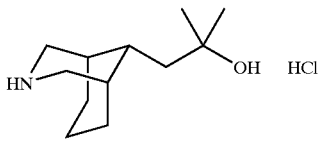

To 0.91 g of (anti)-1-[3-methyl-3-azabicyclo[3.3.1]-non-9-yl]-2-methyl-2-propanol was added 0.7 ml of 1-chloroethyl chloroformate and the resulting mixture was stirred at room temperature for 30 minutes and then heated to 60° C. for 1 hour. After concentrating the reaction mixture under reduced pressure, 10 ml of ethanol was added to the residue and the mixture was heated at 60° C. for 1 hour. The reaction mixture was concentrated under reduced pressure and the crystals thus obtained were washed with ethyl acetate to thereby give 740 mg of the title compound as a slightly yellow powder.

$^1$H-NMR(DMSO-d$_6$) δ ppm; 1.17(s, 6H), 1.45–1.60(m, 6H), 1.70–1.92(m, 6H), 3.08–3.19(m, 2H), 3.21–3.28(m, 2H), 4.18(br.s, 1H)

Production Example 88

Ethyl (anti)-2-[3-(vinyloxycarbonyl)-3-azabicyclo [3.3.1]non-9-yl)-2-methylpropionate

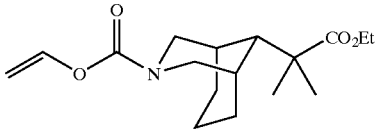

To 40 ml of dry tetrahydrofuran was added 9.04 ml of diisopropylamine and the resulting mixture was cooled to −60° C. Then 40.3 ml of a 1.6 M solution of n-butyllithium in hexane was added thereto and the resulting mixture was stirred for 50 minutes. After dropping 10 ml of a solution of 3.08 g of ethyl (anti)-2-(3-methyl-azabicyclo[3.3.1]non-9-yl)propionate in tetrahydrofuran, the resulting mixture was stirred at 0° C. for 30 minutes. After cooling the mixture to −60° C. again, 4.02 ml of methyl iodide was dropped thereinto and the reaction mixture was stirred at room temperature for 3 days. After adding ice/water, the reaction mixture was extracted with ethyl acetate. Then the ethyl acetate layer was washed with water and a saturated aqueous solution of sodium chloride, dried over anhydrous sodium sulfate and concentrated under reduced pressure. The residue was purified by silica gel column chromatography (eluted with n-hexane/ethyl acetate) to thereby give 2.82 g of a pale yellow oily substance.

This oily substance was dissolved in 10 ml of 1,2-dichloroethane and 1.5 ml of vinyl chloroformate was added thereto. The obtained mixture was stirred at room temperature for 35 minutes and then heated under reflux for 9.5 hours. The reaction mixture was concentrated under reduced pressure and ice/water was added thereto followed by the extraction with ethyl acetate. The ethyl acetate layer was washed with 1 N hydrochloric acid, water, a saturated aqueous solution of sodium hydrogencarbonate and a saturated aqueous solution of sodium chloride, dried over anhydrous sodium sulfate and concentrated under reduced pressure. The residue was purified by silica gel column chromatography (eluted with n-hexane/ethyl acetate) to thereby give 1.03 g of the title compound as a slightly yellow oily substance.

$^1$H-NMR(CDCl$_3$) δ ppm; 1.26(t, J=7.1 Hz, 3H), 1.31(s, 6H), 1.45(m, 1H), 1.56–2.06(m, 8H), 3.12(m, 1H), 3.20(m, 1H), 4.10–4.20(m, 4H), 4.44(dd, J=1.6, 6.2 Hz, 1H), 4.78 (dd, J=1.6, 14.1 Hz, 1H), 7.24(dd, J=6.2, 14.1 Hz, 1H)

Production Example 89

Ethyl (anti)-2-(3-Azabicyclo[3.3.1]non-9-yl)-2-methylpropionate

To 1.03 g of ethyl (anti)-2-[3-(vinyloxycarbonyl)-3-azabicyclo[3.3.1]non-9-yl]-2-methylpropionate was added 5 ml of 4 N hydrogenchloride in dioxane and the resulting mixture was stirred at room temperature for 30 minutes. The reaction mixture was concentrated under reduced pressure and 20 ml of ethanol was added to the residue. Then the resulting mixture was heated under reflux for 25 minutes. After concentrating the reaction mixture under reduced pressure, water and potassium carbonate were added to the residue followed by the extraction with methylene chloride. Next, it was dried over anhydrous sodium sulfate and concentrated under reduced pressure to thereby give 802 mg of the title compound as a slightly yellow oily substance.

$^1$H-NMR(CDCl$_3$) δ ppm; 1.26(t, J=7.1 Hz, 3H), 1.28(s, 6H), 1.54–1.65(m, 3H), 1.76–2.22(m, 7H), 2.98–3.16(m, 4H), 4.11(q, J=7.1 Hz, 2H)

Production Example 90

(anti)-2-(3-Azabicyclo[3.3.1]non-9-yl)-2-methyl-1-propanol

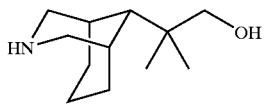

250 mg of lithium aluminum hydride was suspended in tetrahydrofuran (30 ml) and ice-cooled. Into this suspension was dropped a solution of 802 mg of ethyl (anti)-2-(3-azabicyclo[3.3.1]non-9-yl)-2-methylpropionate in tetrahydrofuran (10 ml) and the resulting mixture was stirred for 30 minutes. By successively adding 0.25 ml of water, 0.25 ml of 15% sodium hydroxide and 0.75 ml of water, the excessive reagent was decomposed. After further adding anhydrous sodium sulfate and celite, the reaction mixture was stirred at room temperature. Then the reaction mixture was filtered and concentrated to thereby give 757 mg of the title compound as a slightly yellow oily substance.

$^1$H-NMR(CDCl$_3$) δ ppm; 1.01(s, 6H), 1.59–1.71(m, 4H), 1.82–2.06(m, 6H), 2.14(m, 1H), 3.01–3.07(m, 2H), 3.09–3.14(m, 2H), 3.42(s, 2H)

Production Example 91

(anti)-2-(3-Azabicyclo[3.3.1]non-9-yl)-1-propanol

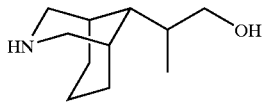

The title compound was obtained as a colorless oily substance from ethyl (anti)-2-(3-azabicyclo[3.3.1]non-9-yl)propionate by the same methods as those of Example 12 and Production Examples 89 and 90.

$^1$H-NMR(CDCl$_3$) δ ppm; 0.97(d, J=6.8 Hz, 3H), 1.36(m, 1H), 1.54–2.26(m, 11H), 2.95–3.03(m, 2H), 3.16(m, 2H), 3.46(dd, J=6.4, 10.6 Hz, 1H), 3.71(dd, J=3.3, 10.6 Hz, 1H)

Production Example 92

(syn)-2-(3-Azabicyclo[3.3.1]non-9-yl)ethanol

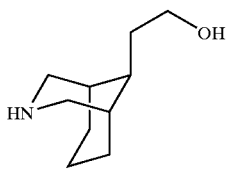

The title compound was obtained as a colorless oily substance from ethyl (syn)-(3-azabicyclo[3.3.1]non-9-yl) acetate by the same method as the one of Production Example 90.

$^1$H-NMR(CDCl$_3$) δ ppm; 01.50(br.s, 2H), 1.62–1.94(m, 9H), 2.19(m, 1H), 2.78–2.86(m, 2H), 3.18–3.25(m, 2H), 3.70(t, J=6.8 Hz, 2H), 3.75(m, 1H)

Production Example 93

3-Methyl-9-methoxymethylene-3-azabicyclo[3.3.1]nonane

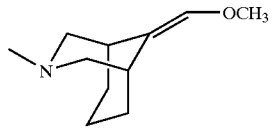

3.67 ml of methoxytrimethylsilane was dissolved in 30 ml of tetrahydrofuran and cooled to −60° C. Next, 18.1 ml of a 1.3 M solution of sec-butyllithium in cyclohexane was dropped thereinto while maintaining the bulk temperature at −50° C. or below. After the completion of the dropping, the resulting mixture was stirred at −25 to −30° C. for 30 minutes. Then it was cooled to −35° C. and a solution of 3.0 g of 3-methyl-3-azabicyclo[3.3.1]nonan-9-one in tetrahydrofuran (10 ml) was dropped thereinto while maintaining the bulk temperature at −25° C. or below. Subsequently, the reaction mixture was slowly heated to room temperature. After stirring for 6 hours, a saturated aqueous solution of ammonium chloride was added to the reaction mixture followed by the extraction with ethyl acetate. The ethyl acetate layer was washed with water and a saturated aqueous solution of sodium chloride, dried over anhydrous magnesium sulfate and concentrated under reduced pressure. Thus 4.96 g of a pale yellow oily substance was obtained.

3.91 g of this oily substance was dissolved in tetrahydrofuran (50 ml). After adding 3.01 g of 35% potassium hydride, the resulting mixture was stirred at 60° C. for 30 minutes. Then a saturated aqueous solution of ammonium chloride was added to the reaction mixture followed by the extraction with ethyl acetate. The ethyl acetate layer was washed with water and a saturated aqueous solution of sodium chloride, dried over anhydrous sodium sulfate and concentrated under reduced pressure. Then the residue was purified by silica gel column chromatography (eluted with n-hexane/ethyl acetate) to thereby give 1.14 g of the title compound as a colorless oily substance.

$^1$H-NMR(CDCl$_3$) δ ppm; 1.46(m, 1H), 1.54–1.74(m, 3H), 1.79–1.91(m, 2H), 2.06–2.21(br.m, 5H), 2.58(m, 1H), 2.82–2.95(m, 3H), 3.54(s, 3H), 5.80(s, 1H)

Production Example 94

[(anti)-(3-Methyl-3-azabicyclo[3.3.1]non-9-yl)methyl]acetate

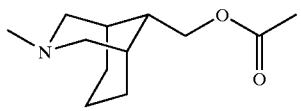

To 1.14 g of 3-methyl-9-methoxymethylene-3-azabicyclo[3.3.1]nonane were added 10 ml of 1 N hydrochloric acid and 20 ml of methanol and the resulting mixture was stirred at room temperature for 2 hours. After adding 5 ml of conc. hydrochloric acid, the resulting mixture was stirred for additional 16 hours. After adding an aqueous solution of potassium carbonate, the reaction mixture was extracted with ethyl acetate. The ethyl acetate layer was washed with water and a saturated aqueous solution of sodium chloride, dried over anhydrous sodium sulfate and concentrated under reduced pressure. The residue was purified by silica gel column chromatography (eluted with n-hexane/ethyl acetate) to thereby give 450 mg of a colorless oily substance.

150 mg of lithium aluminum hydride was suspended in tetrahydrofuran (10 ml) and ice-cooled. Then 450 mg of the above-mentioned oily substance dissolved in tetrahydrofuran (5 ml) was dropped thereinto and the resulting mixture was stirred for 2 hours. Next, 0.15 ml of water, 0.15 ml of 15% sodium hydroxide and 0.45 ml of water were successively added thereto to thereby decompose the excessive reagent. After further adding anhydrous sodium sulfate and celite, the reaction mixture was stirred at room temperature. Then the reaction mixture was filtered and concentrated to thereby give 500 mg of a colorless oily substance.

500 mg of this oily substance was dissolved in methylene chloride (10 ml) and 0.5 ml of triethylamine, 0.34 ml of acetic anhydride and a catalytic amount of 4-dimethylaminopyridine were added thereto. The obtained mixture was stirred at room temperature for 2 hours. Then the reaction mixture was concentrated and a saturated aqueous solution of sodium hydrogencarbonate was added thereto followed by the extraction with ethyl acetate. The ethyl acetate layer was washed with water and a saturated aqueous solution of sodium chloride, dried over anhydrous sodium sulfate and concentrated under reduced pressure. The residue was purified by silica gel column chromatography (eluted with n-hexane/ethyl acetate) to thereby give 149 mg of the title.compound as a colorless oily substance.

$^1$H-NMR(CDCl$_3$) δ ppm; 1.42(m, 1H), 1.51–1.61(m, 2H), 1.65–1.79(m, 5H), 2.06(s, 3H), 2.10–2.21(m, 5H), 2.44(m, 1H), 2.88–2.95(m, 2H), 4.23(d, J=7.3 Hz, 2H)

Production Example 95

[(anti)-[3-(Vinyloxycarbonyl)-3-azabicyclo[3.3.1]non-9-yl]methyl]acetate

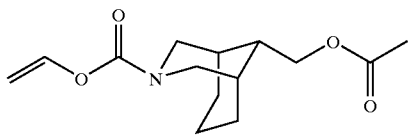

168 mg of [(anti)-(3-methyl-3-azabicyclo[3.3.1]non-9-yl)methyl]acetate was dissolved in 1,2-dichloroethane (5 ml). After adding 1 ml of vinyl chloroformate, the resulting mixture was stirred at room temperature for 35 minutes and then heated under reflux for 5 hours. Then the reaction mixture was concentrated under reduced pressure and the residue was purified by silica gel column chromatography (eluted with n-hexane/ethyl acetate) to thereby give 101 mg of the title compound as a white solid.

$^1$H-NMR(CDCl$_3$) δ ppm; 1.49(m, 1H), 1.60–1.90(m, 7H), 2.00(m, 1H), 2.08(s, 3H), 3.11(m, 1H), 3.19(m, 1H), 4.18–4.30(m, 4H), 4.46(dd, J=1.5, 6.2 Hz, 1H), 4.79(dd, J=1.5, 14.1 Hz, 1H), 7.25(dd, J=6.2, 14.1 Hz, 1H)

Production Example 96

(anti)-[3-[Vinyloxycarbonyl)-3-azabicyclo[3.3.1]non-9-yl]methanol

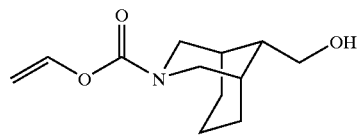

101 mg of [(anti)-[3-(vinyloxycarbonyl)-3-azabicyclo[3.3.1]non-9-yl]methyl]acetate was dissolved in methanol (3 ml). After adding 1 ml of 1 N sodium hydroxide, the resulting mixture was stirred at room temperature for 1 hour. Then the reaction mixture was concentrated under reduced pressure and, after adding water, extracted with ethyl acetate. The ethyl acetate layer was washed with a saturated aqueous solution of sodium chloride, dried over anhydrous sodium sulfate and concentrated under reduced pressure to thereby give 91 mg of the title compound as a colorless oily substance.

$^1$H-NMR(CDCl$_3$) δ ppm; 1.36–1.96(m, 10H), 3.12(m, 1H), 3.19(m, 1H), 3.83(d, J=7.5 Hz, 2H), 4.19–4.27(m, 2H), 4.45(dd, J=1.5, 6.2 Hz, 1H), 4.79(dd, J=1.5, 13.9 Hz, 1H), 7.25(dd, J=6.2, 13.9 Hz, 1H)

Production Example 97

(anti)-3-(Vinyloxycarbonyl)-3-azabicyclo[3.3.1]nonan-9-ol and (syn)-3-(vinyloxycarbonyl)-3-azabicyclo[3.3.1]nonan-9-ol The title compounds were obtained from (3-methyl-3-azabicyclo[3.3.1]non-9-yl)acetate by the same methods as those of Production Examples 95 and 96.

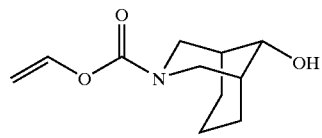

$^1$H-NMR(CDCl$_3$) δ ppm; 1.46(m, 1H), 1.57–1.77(m, 4H), 1.84–1.92(m, 2H), 1.97–2.12(m, 2H), 3.14(m, 1H), 3.22(m, 1H), 3.93(t, J=3.5 Hz, 1H), 4.20–4.30(m, 2H), 4.46(dd, J=2.1, 6.2 Hz, 1H), 4.79(dd, J=2.1, 13.9 Hz, 1H), 7.23(dd, J=6.2, 13.9 Hz, 1H)

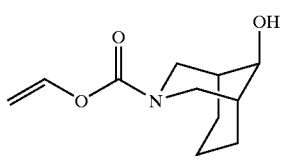

¹H-NMR(CDCl₃) δ ppm; 1.42(m, 1H), 1.56–1.75(m, 4H), 1.80–1.99(m, 4H), 3.44(m, 1H), 3.53(m, 1H), 3.83(t, J=3.5 Hz, 1H), 3.88–3.98(m, 2H), 4.44(dd, J-1.5, 6.3 Hz, 1H), 4.78(dd, J=1.5, 13.9 Hz, 1H), 7.25(dd, J=6.3, 13.9 Hz, 1H)

Example 124

(anti)-2-[3-(10H-Pyrazino[2,3-b][1,4]benzothiazin-8-ylmethyl)-3-azabicyclo[3.3.1]non-9-yl]ethanol

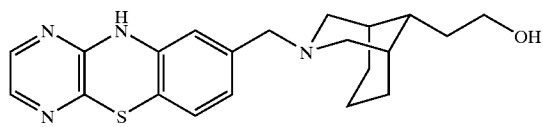

To 348 mg of (anti)-2-[3-(vinyloxycarbonyl)-3-azabicyclo-[3.3.1]non-9-yl]ethanol was added 5 ml of 4 N hydrogen chloride in dioxane and the resulting mixture was stirred at room temperature for 1 hour. Then it was concentrated under reduced pressure and 20 ml of methanol was added to the residue. After heating under reflux for 1 hour, the reaction mixture was concentrated under reduced pressure to thereby give crude (anti)-2-(3-azabicyclo[3.3.1]non-9-yl)ethanol hydrochloride as a white solid. Next, 5 ml of N,N-dimethylformamide was added thereto. After further adding 374 mg of 8-chloromethyl-10H-pyrazino[2,3-b][1,4] benzothiazine and 622 mg of anhydrous potassium carbonate, the resulting mixture was stirred at 80° C. for 4 hours. Then ice/water was added to the reaction mixture followed by the extraction with ethyl acetate. The ethyl acetate layer was washed with water and a saturated aqueous solution of sodium chloride, dried over anhydrous magnesium sulfate and concentrated under reduced pressure. The residue was purified by silica gel column chromatography (eluted with methylene chloride/methanol) to thereby give 341 mg of the title compound as a dark yellow powder.

¹H-NMR(CDCl₃) δ ppm; 1.33(m, 1H), 1.44–1.85(m, 10H), 2.18–2.26(m, 2H), 2.55(m, 1H), 2.89–2.95(m, 2H), 3.22(s, 2H), 3.69(q, J=6.8 Hz, 2H), 6.52(br.s 2H), 6.78(dd, J=1.5, 7.9 Hz, 1H), 6.83(d, J=7.9 Hz, 1H), 7.57(d, J=2.9 Hz, 1H), 7.69(d, J=2.9 Hz, 1H)

MS: FAB(+)383(MH⁺)

m.p. 123–127° C.

Examples 125 to 128

The following compounds were obtained by the same method as the one of Example 124.

TABLE 48

| Ex. | Structural formula | MS | M.p. | NMR |
|---|---|---|---|---|
| 125 | (anti)-[3-(10H-pyrazino[2,3-b][1,4]-benzothiazin-8-ylmethyl)-3-azabicyclo[3.3.1]non-9-yl]methyl-N',N'-dimethylsulfamide | FAB(+) 475(MH⁺) | 215–219° C. | ¹H-NMR(CDCl₃) δ ppm: 1.45–1.79(m, 8H), 2.16–2.23(m, 2H), 2.56(m, 1H), 2.82(s, 6H), 2.92–2.99(m, 2H), 3.19–3.26(m, 4H), 4.16(m, 1H), 6.51(d, J=1.5Hz, 1H), 6.57(br.s, 1H), 6.77(dd, J=1.5, 8.1Hz, 1H), 6.83(d, J=8.1Hz, 1H), 7.56(d, J=2.9Hz, 1H), 7.69(d, J=2.9Hz, 1H) |
| 126 | (anti)-3-(10H-pyrazino[2,3-b][1,4]benzothiazin-8-ylmethyl)-3-azabicyclo[3.3.1]nonan-9-ol | FAB(+) 355(MH⁺) | 215–219° C. | ¹H-NMR(DMSO-d₆) δ ppm: 1.30–1.41(m, 3H), 1.60–1.66(m, 2H), 1.90–2.03(m, 2H), 2.13–2.20(m, 2H), 2.52(m, 1H), 2.79–2.88(m, 2H), 3.15(s, 2H), 3.53(m, 1H), 4.62(d, J=2.9Hz, 1H), 6.70(dd, J=1.3, 7.9Hz, 1H), 6.73(d, J=1.3Hz, 1H), 6.84(d, J=7.9Hz, 1H), 7.63(d, J=2.9Hz, 1H), 7.64(d, J=2.9Hz, 1H), 9.56(s, 1H) |

TABLE 48-continued

| Ex. | Structural formula | MS | M.p. | NMR |
|---|---|---|---|---|
| 127 | (syn)-3-(10H-pyrazino[2,3-b][1,4]benzothiazin-8-ylmethyl)-3-azabicyclo[3.3.1]nonan-9-ol | FAB(+) 355(MH$^+$) | 189–192° C. | $^1$H-NMR(DMSO-d$_6$) δ ppm: 1.34(m, 1H), 1.52–1.68(m, 4H), 1.72–1.80(m, 2H), 2.43–2.62(m, 5H), 3.14(s, 2H), 3.49(m, 1H), 4.57(d, J=2.6Hz, 1H), 6.69(dd, J=1.3, 7.9Hz, 1H), 6.73(d, J=1.3Hz, 1H), 6.83(d, J=7.9Hz, 1H), 7.63(d, J=2.9Hz, 1H), 7.64(d, J=2.9Hz, 1H), 9.55(s, 1H) |
| 128 | (anti)-2-[3-(10H-pyrazino[2,3-b][1,4]-benzothiazin-8-ylmethyl)-3-azabicyclo[3.3.1]non-9-yl]methanol | FAB(+) 368(MH$^+$) | 233–236° C. | $^1$H-NMR(DMSO-d$_6$) δ ppm: 1.36–1.58(m, 4H), 1.60–1.75(m, 4H), 2.08–2.16(m, 2H), 2.56(m, 1H), 2.35-2.42(m, 2H), 3.18(s, 2H), 3.52(dd, J=5.7, 7.3Hz, 2H), 4.37(t, J=5.7Hz, 1H), 6.71(dd, J=1.5, 7.9Hz, 1H), 6.74(d, J=1.5Hz, 1H), 6.85(d, J=7.9Hz, 1H), 7.63(d, J=2.9Hz, 1H), 7.64(d, J=2.9Hz, 1H), 9.57(s, 1H) |

Example 129

(anti)-(6R*,8R*)-[3-(10H-Pyrazino[2,3-b][1,4]benzothiazin-8-ylmethyl)-6,8-dimethyl-3-azabicyclo[3.3.1]non-9-yl]ethanol

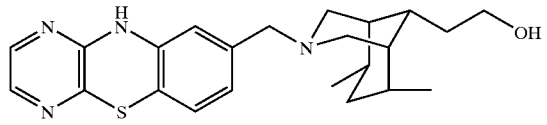

To a solution of 2.0 g of (anti)-(6R*,8R*)-[3-(10H-pyrazino[2,3-b][1,4]benzothiazin-8-ylmethyl)-6,8-dimethyl-3-azabicyclo[3.3.1]non-9-yl]acetate in tetrahydrofuran were added 0.08 ml of triethylamine and 0.05 ml of ethyl chloroformate and the resulting mixture was stirred at room temperature for 30 minutes. After adding an aqueous solution of 0.05 g of sodium borohydride, the reaction mixture was stirred at room temperature for 30 minutes. Then the reaction mixture was washed with water and the organic layer was dried over anhydrous magnesium sulfate. After distilling off the solvent under reduced pressure, the residue was purified by silica gel column chromatography (eluted with methylene chloride/methanol) to thereby give 0.16 g of the title compound as a yellow amorphous substance.

$^1$H-NMR(CDCl$_3$) δ ppm; 100(d, J=7.2 Hz, 6H), 1.37–1.80(m, 10H), 1.97(d, J=8.0 Hz, 2H), 2.59(d, J=8.0 Hz, 2H), 3.26(s, 2H), 3.60–3.70(m, 2H), 6.38(br.s, 1H), 6.52(s, 1H), 6.77(d, J=8.0 Hz, 1H), 6.82(d, J=8.0 Hz, 1H), 7.5,6(d, J=2.8 Hz, 1H), 7.68(d, J=2.8 Hz, 1H)

MS: FAB(+)411(MH$^+$)

Example 130

(anti)-1-[3-(10H-pyrazino[2,3-b][1,4]benzothiazin-8-ylmethyl)-3-azabicyclo[3.3.1]non-9-yl]-2-methyl-2-propanol

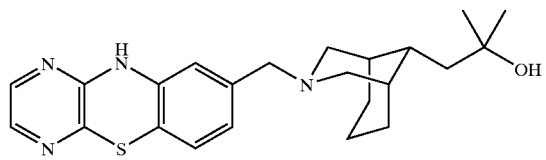

To 10 ml of N,N-dimethylformamide were added 790 mg of 8-chloromethyl-10H-pyrazino[2,3-b][1,4]benzothiazine, 740 mg of (anti)-1-(3-azabicyclo[3.3.1]non-9-yl)-2-methyl-2-propanol hydrochloride and 1.31 g of anhydrous potassium carbonate and the resulting mixture was stirred at 80° C. for 3.5 hours. After adding ice/water, the reaction mixture was extracted with ethyl acetate. The ethyl acetate layer was washed with water and a saturated aqueous solution of sodium chloride, dried over anhydrous sodium sulfate and concentrated under reduced pressure. Then the residue was purified by silica gel column chromatography (eluted with toluene/ethyl acetate) to thereby give 568 mg of the title compound as a yellow powder.

$^1$H-NMR(CDCl$_3$) δ ppm; 1.24(s, 6H), 1.38–1.56(m, 3H), 1.58–1.70(m, 6H), 1.74–1.86(m, 2H), 2.24–2.30(m, 2H), 2.55(m, 1H), 2.87–2.94(m, 2H), 3.22(s, 2H), 6.52(d, J=1.5 Hz, 1H), 6.59(br.s, 1H), 6.78(dd, J=1.5, 7.9 Hz, 1H), 6.83(d, J=7.9 Hz, 1H), 7.56(d, J=2.9 Hz, 1H), 7.69(d, J=2.9 Hz, 1H)

MS: FAB(+)411(MH$^+$)

m.p.: 182–185° C.

Examples 131 to 133

The following compounds were obtained by the same method as the one of Example 130.

TABLE 49

| Ex. | Structural formula | MS | M.p. | NMR |
|---|---|---|---|---|
| 131 | (anti)-2-[3-(10H-pyrazino[2,3-b][1,4]benzothiazin-8-ylmethyl)-3-azabicyclo[3.3.1]non-9-yl]-2-methyl-1-propanol | FAB (+) 411 (MH+) | 181–183° C. | $^1$H-NMR (DMSO-$d_6$) δ ppm: 0.91(s, 6H), 1.34–1.54(m, 4H), 1.80–1.94(m, 4H), 2.12–2.20(m, 2H), 2.60(m, 1H), 2.79–2.86 (m, 2H), 3.16(m, 4H), 4.49(t, J=5.1Hz, 1H), 6.70(dd, J=1.5, 7.9Hz, 1H), 6.73(d, J=1.5Hz, 1H), 6.84(d, J=7.9Hz, 1H), 7.63(d, J=2.7Hz, 1H), 7.64(d, J=2.7Hz, 1H), 9.56(s, 1H) |
| 132 | (anti)-2-[3-(10H-pyrazino[2,3-b][1,4]benzothiazin-8-ylmethyl)-3-azabicyclo[3.3.1]non-9-yl]-1-propanol | FAB (+) 397 (MH+) | 88–92° C. | $^1$H-NMR (CDCl$_3$) δ ppm: 0.97(d, J=6.8Hz, 3H), 1.19(m, 1H), 1.35(t, J=5.4Hz, 1H), 1.43–1.55(m, 3H), 1.66–1.84(m, 4H), 1.97(m, 1H), 2.13–2.22(m, 2H), 2.56(m, 1H), 2.88–2.98(m, 2H), 3.21(s, 2H), 3.48(m, 1H), 3.52(m, 1H), 6.52(br.s, 1H), 6.60(br.s, 1H), 6.78(dd, J=1.5, 7.9Hz, 1H), 6.83(d, J=7.9Hz, 1H), 7.56(d, J=2.7Hz, 1H), 7.69(d, J=2.7Hz, 1H) |
| 133 | (syn)-2-[3-(10H-pyrazino[2,3-b][1,4]benzothiazin-8-ylmethyl)-3-azabicyclo[3.3.1]non-9-yl]ethanol | FAB (+) 368 (MH+) | 171–173° C. | $^1$H-NMR (CDCl$_3$) δ ppm: 1.40(br.t, J=4.9Hz, 1H), 1.49–1.75(m, 8H), 1.76–1.86(m, 2H), 2.38–2.46(m, 2H), 2.55–2.69(m, 3H), 3.21(s, 2H), 3.68(q, J=6.8Hz, 2H), 6.50(br.s, 1H), 6.59(br.s, 1H), 6.77(br.d, J= 7.7Hz, 1H), 7.82(d, J=7.7Hz, 1H), 7.57(d, J= 2.9Hz, 1H), 7.69(d, J=2.9Hz, 1H) |

Production Example 98

4-[(3-Chloropyrazin-2-yl)thio]-3-nitrobenzyl alcohol 1.876 g of 4-chloro-3-nitrobenzyl alcohol was dissolved in 20 ml of dimethyl sulfoxide. After adding 820 mg of anhydrous sodium sulfide, the resulting mixture was stirred at room temperature for 15 hours. After adding 1.19 g of 2,3-dichloropyrazine thereto, the reaction mixture was stirred at 100° C. for 1 hour. After adding ice/water, the reaction mixture was extracted with ethyl acetate, washed successively with water, 1 N hydrochloric acid, water, 1 N sodium hydroxide, and a saturated aqueous solution of sodium chloride and dried over anhydrous magnesium sulfate. After distilling off the solvent under reduced pressure, the residue was purified by silica gel column chromatography (eluted with ethyl acetate/n-hexane) to thereby give 1.60 g of the title compound as yellow crystals.

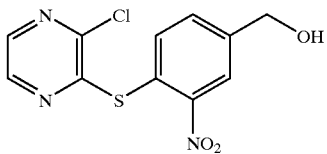

$^1$H-NMR(DMSO-$d_6$) δ ppm: 4.46(d, J=5.9 Hz, 2H), 5.61 (t, J=5.9 Hz, 1H), 7.70(dd, J=1.8, 8.1 Hz, 1H), 7.76(d, J=8.1 Hz, 1H), 8.09(d, J=1.8 Hz, 1H), 8.33(d, J=2.6 Hz, 1H), 8.41(d, J=2.6 Hz, 1H)
m.p.: 110–113° C.

Production Example 99

3-Amino-4-[(3-chloropyrazin-2-yl)thio]benzyl alcohol 1.60 g of 4-[(3-chloropyrazin-2-yl)thio]-3-nitrobenzyl alcohol was dissolved in a solvent mixture of tetrahydrofuran (20 ml)/2-propanol (20 ml)/water (7 ml). After adding 0.16 g of ammonium chloride and 1.50 g of iron powder, the resulting mixture was heated under reflux for 30 minutes. Then the reaction mixture was filtered through celite and concentrated under reduced pressure. After adding ethanol, the reaction mixture was concentrated under reduced pressure. Then tetrahydrofuran was added to the residue and the insoluble matters were separated by filtration. After distilling off the solvent under reduced pressure, 1.47 g of the title compound was obtained as yellow crystals.

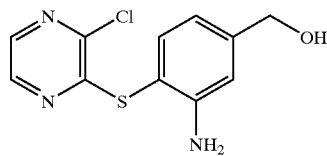

$^1$H-NMR(DMSO-$d_6$) δ ppm: 4.41(d, J=5.9 Hz, 2H), 5.16 (t, J=5.9 Hz, 1H), 5.38(br.s, 2H), 6.51(dd, J=1.8, 7.9 Hz, 1H), 6.77(d, J=1.8 Hz, 1H), 7.18(d, J=7.9 Hz, 1H), 8.17(d, J=2.6 Hz, 1H), 8.34(d, J=2.6 Hz, 1H)
m.p.: 148–150° C. (decompose)

Production Example 100

Methyl 3-amino-4-(4-cyanopyridin-3-yl) thiobenzoate

To a solution of 34.8 g of methyl 3-amino-4-mercaptobenzoate in degassed dimethylformamide (150 ml) was added 11.7 g of sodium hydride at 10° C. or below in a nitrogen atmosphere. After stirring for 20 minutes, 16.86 g of 3-chloro-4-cyanopyridine was added thereto and the resulting mixture was stirred for additional 20 minutes. After adding ethyl acetate, the mixture was washed with water and the aqueous layer was extracted with ethyl acetate. The organic layers were combined, washed with water and a saturated aqueous solution of sodium chloride, dried over anhydrous magnesium sulfate, filtered and concentrated under reduced pressure. The solid matter precipitated during the above procedure was taken up by filtration and washed with ether. Thus, 23.1 g of the title compound was obtained as a yellow solid.

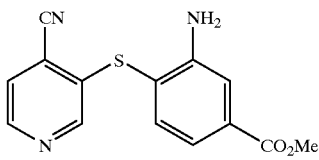

$^1$H-NMR(CDCl$_3$) δ ppm: 3.92(s, 3H), 4.46(br.s, 2H), 7.41(dd, J=2,8 Hz, 1H), 7.46(dd, J=1,5 Hz, 1H), 7.49(d, J=2 Hz, 1H), 7.53(d, J=8 Hz, 1H), 8.20(d, J=1 Hz, 1H), 8.51(d, J=5 Hz, 1H)

Production Example 101

Methyl 3-amino-4-(1-oxo-4-cyano-3-pyridylthio) benzoate

To a solution of 9.33 g of methyl 3-amino-4-mercaptobenzoate in dimethylformamide (50 ml) was added 2.04 g of sodium hydride at 0° C. in a nitrogen atmosphere. After stirring for 30 minutes, a solution of 5.25 g of 3-chloro-4-cyanopyridine oxide in N,N-dimethylformamide (20 ml) was added thereto and the resulting mixture was stirred for additional 2 hours. After diluting with ethyl acetate, the mixture was washed with water, dried over anhydrous magnesium sulfate, filtered and concentrated under reduced pressure. The residue was purified by silica gel column chromatography (eluted with dichloromethane/methanol) to thereby give 0.85 g of the title compound as a pale yellow solid.

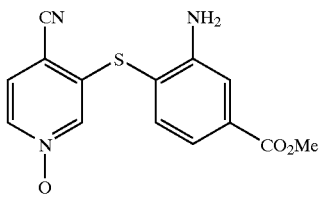

$^1$H-NMR(DMSO-d$_6$) δ ppm: 3.83(s, 3H), 6.07(br.s, 2H), 7.14(dd, J=2,8 Hz, 1H), 7.20(d, J=2 Hz, 1H), 7.48(d, J=2 Hz, 1H), 7.49(d, J=8 Hz, 1H), 7.94(d, J=7 Hz, 1H), 8.16(d, J=2,7 Hz, 1H)

Production Example 102

4-Chloro-5-nitro-o-anisic acid

To a solution of 33 g of 4-chloro-o-anisic acid in sulfuric acid (100 ml) was added 20 g of potassium nitrate under ice-cooling and the resulting mixture was stirred for 2 hours. The reaction mixture was added to ice/water and extracted with ethyl acetate and the organic layer was dried over anhydrous magnesium sulfate. After distilling off the solvent under reduced pressure, 41 g of the title compound was obtained as pale yellow crystals.

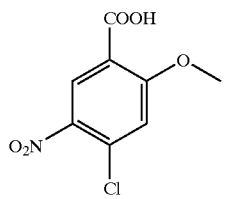

$^1$H-NMR(DMSO-d$_6$) δ ppm: 3.96(s, 3H), 7.49(s, 1H), 8.38(s, 1H)

Production Example 103

Methyl 4-mercapto-5-nitro-o-anisate

To a solution of 3.1 g of 4-chloro-5-nitro-o-anisic acid in methanol (100 ml) was added a catalytic amount of sulfuric acid and the resulting mixture was heated under reflux for 3 hours. Then the reaction mixture was poured into ice/water and extracted with ethyl acetate. The organic layer was washed with a saturated aqueous solution of sodium chloride and dried over anhydrous magnesium sulfate. After distilling off the solvent under reduced pressure, 3.3 g of methyl 4-chloro-5-nitro-o-anisate was obtained as pale yellow crystals.

To a solution of 3.3 g of the crystals obtained above in methanol (50 ml) was added 3.2 g of sodium hydrogensulfide and the resulting mixture was heated under reflux for 30 minutes. After distilling off the solvent under reduced pressure, dilute hydrochloric acid was added to the residue followed by extraction with ethyl acetate and the organic layer was then dried over anhydrous magnesium sulfate. After distilling off the solvent under reduced pressure, diethyl ether was added to the residue and the crystals thus precipitated were taken up by filtration. Thus 2.1 g of the title compound was obtained as yellow crystals.

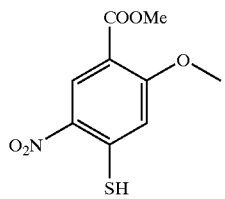

$^1$H-NMR(CDCl$_3$) δ ppm: 3.91(s, 3H), 4.00(s, 3H), 4.28(s, 1H), 6.89(s, 1H), 8.81(s, 1H)

Production Example 104

Methyl 2-methoxy-4-(2-chloropyrazin-3-yl)thio-5-nitrobenzoate

To a solution of 6.45 g of methyl 4-mercapto-5-nitro-o-anisate in N,N-dimethylformamide (100 ml) were added 4.4 g of potassium carbonate and 4.75 g of 2,3-dichloropyrazine. Then the mixture was allowed to react at 80° C. for 2 hours. After adding ethyl acetate, the reaction mixture was washed with a saturated aqueous solution of sodium chloride and the organic layer was dried over anhydrous magnesium sulfate. After distilling off the solvent under reduced pressure, the residue was purified by silica gel column chromatography (eluted with n-hexane/ethyl acetate) to thereby give 3.14 g of the title compound as a brown solid.

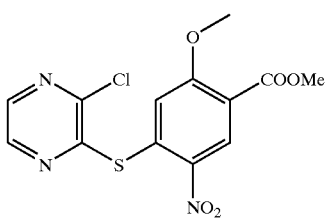

¹H-NMR(CDCl₃) δ ppm: 3.93(s, 3H), 3.94(s, 3H), 7.16(s, 1H), 8.19(d, J=2.4 Hz, 1H), 8.23(d, J=2.4 Hz, 1H), 8.71(s, 1H)

Production Example 105

Methyl 5-amino-6-mercaptonicotinate

To a solution of 6 g of methyl 6-chloro-5-nitronicotinate in methanol (100 ml) was added 6.7 g of sodium hydrogensulfide and the resulting mixture was heated under reflux for 2 hours. After distilling off the solvent under reduced pressure, dilute hydrochloric acid was added to the residue followed by extraction with ethyl acetate. The organic layer was dried over anhydrous magnesium sulfate and the solvent was distilled off under reduced pressure. Diisopropyl ether was added to the residue and the crystals thus precipitated were taken up by filtration to thereby give 24.7 g of the title compound as yellow crystals.

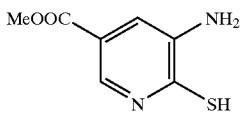

¹H-NMR(DMSO-d₆) δ ppm: 3.78(s, 3H),5.91–6.00(br.s, 2H), 7.12(d, J=2.0 Hz, 1H), 7.53(dd, J=2.0, 6.4 Hz, 1H)

Production Example 106

Diethyl 4-(methoxymethoxy)cyclohexane-1,1-dicarboxylate 12.3 g of diethyl 4-hydroxycyclohexane-1,1-dicarboxylate was dissolved in 160 ml of dichloromethane and 26.3 ml of diisopropylethylamine was added thereto followed by ice-cooling. Next, 9.6 ml of chloromethyl methyl ether was added thereto and the reaction mixture was stirred at room temperature for 15 hours. Then the reaction mixture was concentrated and the residue was purified by silica gel column chromatography (eluted with n-hexane/ethyl acetate) to thereby give 11.10 g of the title compound as a colorless oily substance.

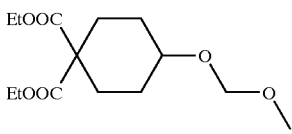

¹H-NMR(CDCl₃) δ ppm: 1.24(t, J=7.1 Hz, 3H), 1.26(t, J=7.1 Hz, 3H), 1.51–1.62(m, 2H), 1.81–1.90(m, 4H), 2.25–2.34(m, 2H), 3.36(s, 3H), 3.61(m, 1H), 4.17(q, J=7.1 Hz, 2H), 4.20(q, J=7.1 Hz, 2H), 4.66(s, 2H)

Production Example 107

4-(Methoxymethoxy)cyclohexane-1,1-dimethanol 1.76 g of lithium aluminum hydride was suspended in 90 ml of tetrahydrofuran and ice-cooled. Then 11.1 g of diethyl 4-(methoxymethoxy)cyclohexane-1,1-dicarboxylate dissolved in 30 ml of tetrahydrofuran was dropped thereinto. After stirring for 40 minutes, 1.8 ml of water, 1.8 ml of 15% sodium hydroxide and 5.4 ml of water were successively added thereto so as to decompose the excessive reagent. After further adding anhydrous sodium sulfate and celite, the reaction mixture was stirred at room temperature, filtered and concentrated under reduced pressure. The residue was purified by silica gel column chromatography (eluted with dichlorometheane/methanol) to thereby give 6.84 g of the title compound as a white solid.

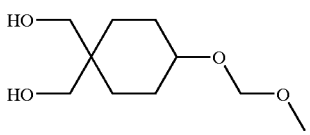

¹H-NMR(CDCl₃) δ ppm: 1.17–1.26(m, 2H), 1.44–1.54 (m, 2H), 1.66–1.74(m, 2H), 1.75–1.84(m, 2H), 2.12(br.s, 2H), 3.37(s, 3H), 3.56(s, 2H), 3.59(m, 1H), 3.71(s, 2H), 4.68(s, 2H)

Production Example 108

4-(Methoxymethoxy)cyclohexane-1,1-dimethyl dimethanesulfonate 6.84 g of 4-(methoxymethoxy)cyclohexane-1,1-dimethanol was dissolved in 110 ml of dichloromethane and 13.56 g of pyridine was added thereto and ice-cooled. 7.79 ml of methanesulfonyl chloride was added thereto and the resulting mixture was stirred at room temperature for 17 hours. Then the reaction mixture was concentrated and the residue was purified by silica gel column chromatography (eluted with n-hexane/ethyl acetate) to thereby give 11.91 g of the title compound as a colorless oily substance.

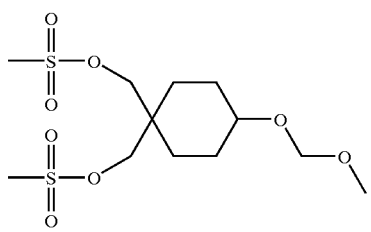

¹H-NMR(CDCl₃) δ ppm: 1.37–1.46(m, 2H), 1.52–1.63 (m, 2H), 1.71–1.84(m, 4H), 3.05(s, 6H), 3.37(s, 3H), 3.65 (m, 1H), 4.10(s, 2H), 4.17(s, 2H), 4.66(s, 2H)

Production Example 109

N-Benzyl-cis-1,2,3,6-tetrahydrophthalimide 30.2 g of cis-1,2,3,6-tetrahydrophthalimide was dissolved in 200 ml of N,N-dimethylformamide. After adding 38.7 g of potassium carbonate and 30.4 g of benzyl chloride, the resulting mixture was stirred at 50° C. for 3 hours and further at room temperature overnight. Then the reaction mixture was diluted with ethyl acetate and washed with water. The aqueous layer was extracted with ethyl acetate. The organic layer was washed successively with water and a saturated aqueous solution of sodium chloride and dried over anhydrous magnesium sulfate. After filtering, the solvent was distilled off under reduced pressure. The crude crystals thus obtained were ground and washed with diisopropyl ether and n-hexane followed by filtration. Thus 39.1 g of the title compound was obtained as pale yellow crystals.

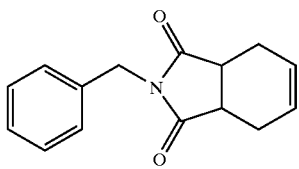

¹H-NMR(CDCl₃) δ ppm: 2.16–2.29(m, 2H), 2.55–2.68 (m, 2H), 3.04–3.15(m, 2H), 4.63(s, 2H), 5.83–5.92(m, 2H), 7.22–7.33(m, 5H)

Production Example 110

3-Benzyl-3-azabicyclo[4.3.0]-7-nonene 11.6 g of N-benzyl-cis-1,2,3,6-tetrahydrophthalimide was dissolved in 280 ml of tetrahydrofuran. Then 5.47 g of lithium aluminum hydride was gradually added thereto under ice-cooling. After the completion of the addition, the resulting mixture was stirred at room temperature overnight. Into the reaction mixture were successively dropped 6 ml of water, 6 ml of a 15% solution of sodium hydroxide and 13 ml of water under ice-cooling. The suspended matters thus formed were taken up by filtration and the mother liquor was dried over anhydrous magnesium sulfate. After filtration, the solvent was concentrated under reduced pressure and the residue thus obtained was purified by silica gel column chromatography (eluted with n-hexane/ethyl acetate) to thereby give 8.33 g of the title compound as a pale yellow oily substance.

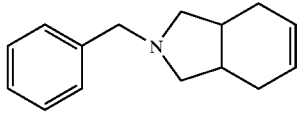

¹H-NMR(CDCl₃) δ ppm: 1.84–1.90(m, 2H), 2.10–2.30 (m, 4H), 2.40(br.s, 2H), 2.92–2.98(m, 2H), 3.62(s, 2H), 5.81(m, 2H),7.22–7.40(m, 5H)

Production Example 111

N-Methyl-2-(pyridin-4-yl)ethanesulfonamide

To 50 ml of a 40% solution of methylamine in methanol was added 3.0 g of 2-(pyridin-4-yl)ethanesulfonyl chloride hydrochloride as such (i.e., as a solid). After stirring for a while at room temperature, a solution of 2.1 g of sodium hydrogencarbonate in 15 ml of water was carefully added thereto. The reaction mixture was concentrated under reduced pressure and the residue was purified by silica gel column chromatography (eluted with dichloromethane/methanol) to thereby give 1.3 g of the title compound as brownish white scaly crystals.

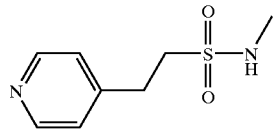

¹H-NMR(CDCl₃) δ ppm: 2.80(d, J=6 Hz, 3H), 3.12(m, 2H), 3.31(m, 2H), 4.49(q, J=6 Hz, 1H), 7.18(d, J=6 Hz, 2H), 8.47(d, J=6 Hz, 2H)

Production Examples

The following compounds were obtained by the same procedure as the one of Production Example 111.

| Prodn. Ex. | Structural formula | NMR |
|---|---|---|
| 112 | ![structure] N,N-dimethyl-2-(pyridin-4-yl)ethanesulfonamide | ¹H-NMR (CDCl₃) δ ppm: 2.87(s, 6H), 3.09–3.19(m, 4H), 7.16(d, J=6Hz, 2H), 8.55(d, J=6Hz, 2H) |
| 113 | ![structure] N,N-(3-oxapentamethylene)-2-(pyridin-4-yl)ethane-sulfonamide | ¹H-NMR (CDCl₃) δ ppm: 3.08–3.21(m, 4H), 3.27(t, J=5Hz, 4H), 3.75(t, J=5Hz, 4H), 7.16(d, J=6Hz, 2H), 8.55(d, J=6Hz, 2H) |

Production Example 114

3-[4-(tert-Butoxycarbonyl)piperazino]-3-methoxy-3-cyclobutene-1,2-dione 10.05 g of 1-(tert-butoxycarbonyl)piperazine and 7.67 g of 3,4-dimethoxy-3-cyclobutene-1,2-dione were dissolved in 180 ml of ethanol and stirred at room temperature for 18 hours. The precipitate thus formed was taken up by filtration to thereby give 6.92 g of the title compound as white needles.

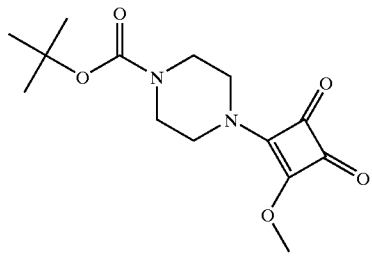

¹H-NMR(CDCl₃) δ ppm: 1.48(s, 9H), 3.51–3.57(m, 6H), 3.87(m, 2H), 4.40(s, 3H)

Production Example 115

4-Amino-3-[4-(tert-butoxycarbonyl)piperazino]-3-cyclobutene-1,2-dione 2.00 g of 3-[4-(tert-butoxycarbonyl)piperazino]-3-methoxy-3-cyclobutene-1,2-dione was dissolved in 25 ml of methanol. After adding 0.43 g of ammonium chloride, the resulting mixture was stirred at room temperature for 65 hours. The precipitate thus formed was taken up by filtration and washed with ethanol to thereby give 1.83 g of the title compound as a slightly yellow powder.

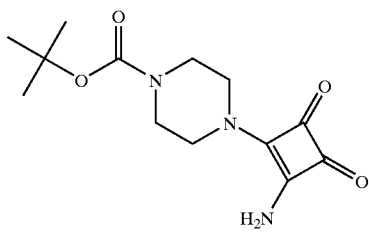

$^1$H-NMR(DMSO-$d_6$) δ ppm: 1.42(s, 9H), 3.42(m, 4H), 3.63(m, 4H), 7.73(br.s, 2H)

Production Examples

The following compounds were obtained by the same procedure as the one of Production Example 115.

ml) of n-buthyllithium in hexane at −70° C. in a nitrogen atmosphere. After adding 4.00 g of anhydrous cuprous iodide, the reaction mixture was heated to −35° C. and stirred for 30 minutes. After cooling to −70° C. again, the solution was added to a solution of 4.93 g of 2-acetoxy-2-methylpropanoyl chloride in tetrahydrofuran (30 ml) which had been cooled to −70° C. in a nitrogen atmosphere. Then the internal temperature was elevated to room temperature and the mixture was stirred for 15 hours. After adding ethyl acetate, the pH value of the mixture was regulated to 6 with sodium dihydrogenphosphate. The insoluble matters were separated by filtration and the organic layer was dried over anhydrous magnesium sulfate, filtered and concentrated under reduced pressure. The residue was purified by silica gel column chromatography (eluted with dichloromethane/ethyl acetate) to thereby give 2.61 g of the title compound as a pale yellow oily substance.

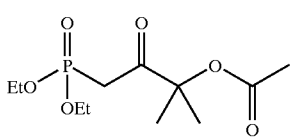

$^1$H-NMR(CDCl$_3$) δ ppm:
1.33(t, J=7 Hz, 6H), 1.52(s, 6H), 2.08(s, 3H), 3.14(d, J=21 Hz, 2H), 4.16(m, 4H)

| Prodn. Ex. | Structural formula | NMR |
|---|---|---|
| 116 | ![structure] 3-[4-(tert-butoxycarbonyl)piperazino]-4-methylamino-3-cyclobutene-1,2-dione | $^1$H-NMR (DMSO-$d_6$) δ ppm: 1.41(s, 9H), 3.17(s, 3H), 3.39–3.44(m, 4H), 3.57–3.64(m, 4H), 7.65(m, 1H) |
| 117 | ![structure] 3-[4-(tert-butoxycarbonyl)piperazino]-4-dimethylamino-3-cyclobutene-1,2-dione | $^1$H-NMR (DMSO-$d_6$) δ ppm: 1.39(s, 9H), 3.14(s, 6H), 3.39–3.44(m, 4H), 3.52–3.57(m, 4H) |

Production Example 118

(4-Diethylphosphono-3-oxo-2-methylbutan-2-yl)acetate

Into a solution of 3.04 g of diethyl methylphosphonate in tetrahydrofuran (20 ml) was dropped a 1.6 M solution (12.5

Production Example 119

Ethyl [4-(ethoxycabronyl)-1-(nitromethyl)cyclohex-1-yl]acetate 1.28 g of anhydrous potassium carbonate was suspended in 9 ml of dimethyl sulfoxide and heated to 90° C. Then 4.43 g of ethyl [4-(ethoxycarbonyl)cyclohexylidene]acetate and 1.5 ml of nitromethane dissolved in 5 ml of dimethyl sulfoxide were dropped thereinto over 2 hours. After heating for 2 hours and 15 minutes, the reaction mixture was ice-cooled and 3 ml of conc. hydrochloric acid was dropped thereinto. After adding water, it was extracted with ethyl acetate. The organic layer was washed successively with water and a saturated aqueous solution of sodium chloride and dried over anhydrous sodium sulfate. Then it was concentrated under reduced pressure and the residue was purified by silica gel column chromatography (eluted with n-hexane/ethyl acetate). Thus 4.72 g of the title compound was obtained as a slightly yellow oily substance.

$^1$H-NMR(CDCl$_3$) δ ppm: 1.23–1.30(m, 6H), 1.35–1.45 (m, 2H), 1.61–1.76(m, 2H), 1.80–1.93(m, 4H), 2.25–2.38 (m, 1H), 2.47 and 2.60(s, total 2H), 4.10–4.19(m, 4H), 4.64 and 4.80(s, total 2H)

Example 134

(anti)-[3-(10H-Pyrazino[2,3-b][1,4]benzothiazin-8-ylmethyl)-3-azabicyclo[3.3.1]non-9-yl]acetic acid methanesulfonate 30.00 g of (anti)-[3-(10H-pyrazino[2,3-b][1,4]benzothiazin-8-ylmethyl)-3-azabicyclo[3.3.1]non-9-yl]acetic acid was dissolved in 900 ml of tetrahydrofuran. After adding dropwise 5.16 ml of methanesulfonic acid thereinto, the resulting mixture was stirred at room temperature for 2 hours. The precipitate was cillected by filtration, washed with tetrahydrofuran and hot-air dried at 80° C. for 6 hours to thereby give 37.7 g of a yellow powder.

This powder was dissolved in a mixture of 200 ml of water with 0.49 ml of methanesulfonic acid and the insoluble matter was separated by filtration. After concentrating under reduced pressure, seed crystals were added and the mixture was allowed to stand at room temperature for 4 days. After adding 50 ml of cold water, the mixture was well ground and collected by filtration. Then it was washed with 30 ml of cold water, hot-air dried at 80° C. for 10 hours and ground in an agate mortar to thereby give 32.30 g of the title compound as a yellow powder.

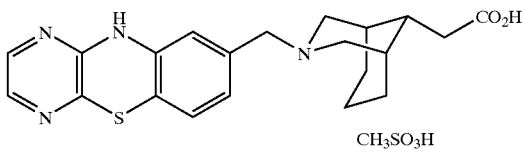

$^1$H-NMR(CD$_3$OD) δ ppm: 1.65–1.82(m, 4H), 1.87–2.00 (m, 2H), 2.07(br.m, 2H), 2.28(m, 1H), 2.57(d, J=7.5 Hz, 2H), 2.73(s, 3H), 3.29–3.37(m, 2H), 3.52–3.60(m, 2H), 4.17(s, 2H), 6.83(br.s, 1H), 6.95(d, J=8.0 Hz, 1H), 6.97(dd, J=1.5, 8.0 Hz, 1H), 7.60(d, J=2.9 Hz, 1H), 7.61(d, J=2.9 Hz, 1H)

m.p.: 263–265° C.

Example 135

(anti)-[3-(10H-Pyrazino[2,3-b][1,4]benzothiazin-8-ylmethyl)-3-azabicyclo[3.3.1]non-9-yl]acetic acid hydrochloride 10.00 g of (anti)-[3-(10H-pyrazino[2,3-b][1,4]benzothiazin-8-ylmethyl)-3-azabicyclo[3.3.1]non-9-yl] acetic acid was dissolved in 300 ml of tetrahydrofuran and the insoluble matter was separated by filtration. After adding 27.8 ml of 1 N hydrochloric acid, the resulting mixture was allowed to stand at room temperature for 2 hours. The precipitate thus formed was collected by filtration, washed with tetrahydrofuran and hot-air dried at 80° C. for 3 hours to thereby give 11.19 g of a yellow powder.

These crystals were added to a mixture of 1.7 l of water with 25.8 ml of 1 N hydrochloric acid and dissolved therein by heating. The insoluble matter was separated by filtration. After adding seed crystals, the mixture was allowed to stand at 4° C. for 20 hours. The precipitate thus formed was collected by filtration, washed with cold water and hot-air dried at 80° C. for 8 hours to thereby give 8.98 g of the title compound as yellow needles.

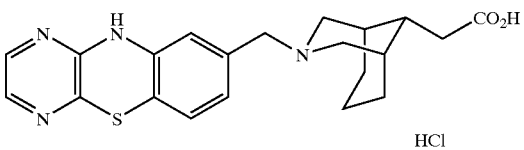

$^1$H-NMR(CD$_3$OD) δ ppm: 1.63–2.00(m, 6H), 2.06(br.m, 2H), 2.26(m, 1H), 2.57(d, J=7.7 Hz, 2H), 3.25–3.36(m, 2H), 3.48–3.58(m, 2H), 4.15(s, 2H), 6.83(s, 1H), 6.97(s, 2H), 7.61(s, 2H)

m.p.: 271–276° C. (decomposes)

Example 136

(anti)-[3-(10H-Pyrazino[2,3-b][1,4]benzothiazin-8-ylmethyl)-3-azabicyclo[3.3.1]non-9-yl]acetic acid p-toluenesulfonate 1.50 g of (anti)-[3-(10H-pyrazino[2,3-b][1,4]benzothiazin-8-ylmethyl)-3-azabicyclo[3.3.1]non-9-yl] acetic acid was dissolved in 45 ml of tetrahydrofuran and 0.721 g of p-toluenesulfonic acid monohydrate was added thereto. After stirring the resulting mixture at room temperature for 1.5 hours, the precipitate thus formed was collected by filtration, washed with tetrahydrofuran and hot-air dried at 80° C. for 6 hours to thereby give a yellow powder.

These crystals were suspended in a solvent mixture of 60 ml of water with 6 ml of ethanol and allowed to stand at room temperature overnight. The precipitate thus formed was collected by filtration, washed with water and hot-air dried at 80° C. for 10 hours to thereby give 1.70 g of the title compound as yellow needles.

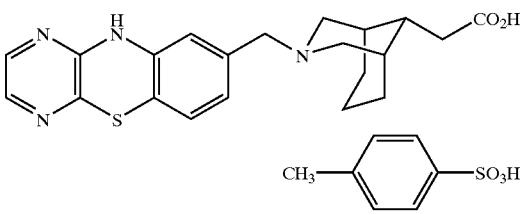

$^1$H-NMR(CD$_3$OD) δ ppm: 1.42–1.78(m, 4H), 1.85–1.96 (m, 2H), 2.05 (br.m, 2H), 2.25(m, 1H), 2.36(s, 3H), 2.56(d, J=7.5 Hz, 2H), 3.27–3.35(m, 2H), 3.50–3.58(m, 2H), 4.16(s, 2H), 6.82(s, 1H), 6.95(s, 2H), 7.21–7.25(m, 2H), 7.60(d, J=2.9 Hz, 1H), 7.61(d, J=2.9 Hz, 1H), 7.69–7.73(m, 2H)

m.p.: 265–268° C.

Example 137

(anti)-[3-(10H-Pyrazino[2,3-b][1,4]benzothiazin-8-ylmethyl)-3-azabicyclo[3.3.1]nonan-9-yl]acetic acid hemi1,2-ethanedisulfonate 1.00 g of (anti)-[3-(10H-pyrazino[2,3-b][1,4]benzothiazin-8-ylmethyl)-3-azabicyclo[3.3.1]non-9-yl]

acetic acid was dissolved in 30 ml of tetrahydrofuran and 0.571 g of 1,2-ethanedisulfonic acid dehydrate and 60 ml of ethanol were added thereto. After stirring the resulting mixture at room temperature for 4 hours, the precipitate thus formed was collected by filtration, washed with ethanol, and hot-air dried at 80° C. for 6 hours to thereby give 1.419 g of a yellow powder.

2.815 g of these crystals were suspended in 90 ml of water and allowed to stand at room temperature overnight. The precipitate thus formed was collected by filtration, washed with water and hot-air dried at 80° C. for 10 hours to thereby give 2.202 g of the title compound as yellow needles.

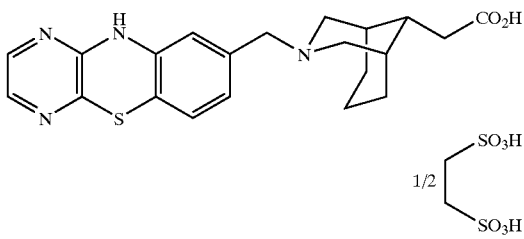

$^1$H-NMR(DMSO-$d_6$) δ ppm: 1.50–1.64(m, 3H), 1.66–1.80(m, 3H), 1.95(br.m, 2H), 2.21(m, 1H), 2.45(d, J=7.5 Hz, 2H), 2.65(s, 2H), 3.22–3.31(m, 2H), 3.35–3.45(m, 2H), 4.13(s, 2H), 6.87(s, 1H), 7.01(s, 2H), 7.67(d, J=2.7 Hz, 1H), 7.68(d, J=2.7 Hz, 1H)

m.p.: 272–279° C. (decomposes)

Example 138

Sodium (anti)-[3-(10H-pyrazino[2,3-b][1,4]benzothiazin-8-ylmethyl)-3-azabicyclo[3.3.1]non-9-yl]acetate 1.50 g of (anti)-[3-(10H-pyrazino[2,3-b][1,4]benzothiazin-8-ylmethyl)-3-azabicyclo[3.3.1]non-9-yl]acetic acid was dissolved in a solvent mixture of 45 ml of tetrahydrofuran with 45 ml of ethanol. After adding 3.79 ml of 1 N sodium hydroxide, the resulting mixture was filtered. After almost completely distilling off the solvent under reduced pressure, ethyl acetate was added to the residue. Then the precipitate thus formed was collected by filtration, washed with ethyl acetate, hot-air dried at 80° C. for 6 hours and air-dried at room temperature to thereby give 1.516 g of the title compound as a yellow powder.

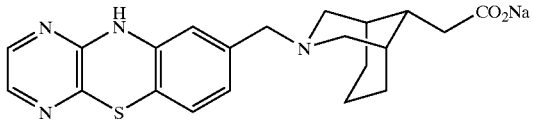

$^1$H-NMR(CD$_3$OD) δ ppm: 1.42–1.53(m, 3H), 1.66(br.m, 2H), 1.83–1.95(m, 2H), 2.02(m, 1H), 2.25–2.31(m, 2H), 2.36(d, J=7.7 Hz, 2H), 2.66(m, 1H), 2.90–2.96(m, 2H), 3.21(s, 2H), 6.67(s, 1H), 6.78(s, 2H), 7.54(d, J=2.9 Hz, 1H), 7.56(d, J=2.9 Hz, 1H)

m.p.: 270° C. (decomposes)

Example 139

Potassium (anti)-[3-(10H-pyrazino[2,3-b][1,4]benzothiazin-8-ylmethyl)-3-azabicyclo[3.3.1]non-9-yl]acetate 3.00 g of (anti)-[3-(10H-pyrazino[2,3-b][1,4]benzothiazin-8-ylmethyl)-3-azabicyclo[3.3.1]non-9-yl] acetic acid was dissolved in a solvent mixture of 45 ml of tetrahydrofuran with 45 ml of ethanol. After adding 7.58 ml of 1 N potassium hydroxide, the resulting mixture was filtered. After distilling off the solvent under reduced pressure, ethanol was added to the residue followed by concentration again. After adding ethyl acetate, the precipitate thus formed was collected by filtration and dried at room temperature under reduced pressure to thereby give 3.26 g of a yellow powder.

3.60 g of these crystals were hot-recrystallized from 36 ml of ethanol. The precipitate thus formed was collected by filtration, washed with ethanol, hot-air dried at 50° C. for 5 hours, ground in mortar and hot-air dried at 100° C. for 10 hours. After allowing to stand at room temperature, 1.92 g of the title compound was obtained as a yellow powder.

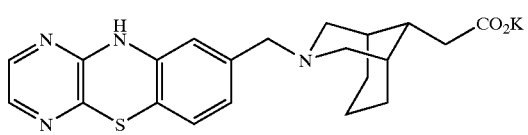

$^1$H-NMR(CD$_3$OD) δ ppm: 1.42–1.54(m, 3H), 1.66(br.m, 2H), 1.83–1.95(m, 2H), 2.02(m, 1H), 2.24–2.32(m, 2H), 2.37(d, J=7.7 Hz, 2H), 2.66(m, 1H), 2.90–2.96(m, 2H), 3.21(s, 2H), 6.67(s, 1H), 6.78(s, 2H), 7.54(d, J=2.7 Hz, 1H), 7.56(d, J=2.7 Hz, 1H)

m.p.: 280° C. (decomposes)

Example 140

(syn)-[3-(10H-Pyrazino[2,3-b][1,4]benzothiazin-8-ylmethyl)-3-azabicyclo[3.3.1]non-9-yl]acetic acid hydrochloride 1.5 g of (syn)-[3-(10H-pyrazino[2,3-b][1,4]benzothiazin-8-ylmethyl)-3-azabicyclo[3.3.1]non-9-yl]acetic acid was dissolved in 80 ml of tetrahydrofuran. After adding 0.35 ml of conc. hydrochloric acid and 160 ml of acetone, the resulting mixture was stirred at room temperature for 1 hour. Then about 200 ml of water was added and to dissolve the precipitate. After concentrating the solution under reduced pressure to about 30 ml, the precipitate was collected by filtration and dried under reduced pressure at room temperature to thereby give 1.5 g of the title compound as yellow crystals.

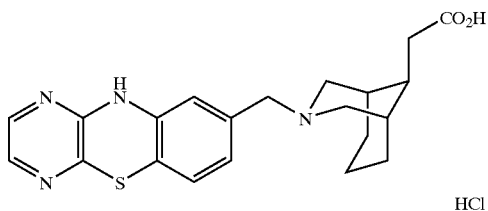

$^1$H-NMR(CD$_3$OD) δ ppm: 1.76–2.02(m, 6H), 2.08(br.m, 2H), 2.18(m, 1H), 2.51(d, J=7.7 Hz, 2H), 3.25–3.40(m, 4H), 4.18(s, 2H), 6.86(d, J=1.3 Hz, 1H), 6.97(d, J=8.1 Hz, 1H), 6.99(dd, J=1.3, 8.1 Hz, 1H), 7.61(d, J=2.7 Hz, 1H), 7.62(d, J=2.7 Hz, 1H)

m.p.: 238–248° C.

Example 141

(syn)-[3-(10H-Pyrazino[2,3-b][1,4]benzothiazin-8-ylmethyl)-3-azabicyclo[3.3.1]non-9-yl]acetic acid methanesulfonate 10.00 g of (syn)-[3-(10H-pyrazino[2,3-b][1,4]benzothiazin-8-ylmethyl)-3-azabicyclo[3.3.1]non-9-yl]

acetic acid was dissolved in 400 ml of tetrahydrofuran and the insoluble matter was filtered off. Then 1.64 ml of methanesulfonic acid was dropped thereinto and the resulting mixture was stirred at room temperature. 30 minutes thereafter, 800 ml of acetone was added and the resulting mixture was stirred for additional 1 hour. The precipitate was collected by filtration and washed with acetone to thereby give a yellow powder.

This powder was dissolved in 1.3 l of water and the insoluble matter was filtered off. The residue was concentrated under reduced pressure to about 100 ml and the precipitate was collected by filtration, washed with a small amount of water and hot-air dried at 50° C. for 2 hours. Then it was dried under reduced pressure in a desiccator for 64 hours to thereby give 9.70 g of the title compound as a yellow powder.

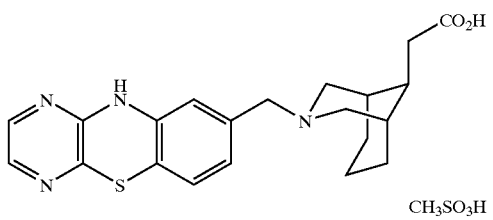

CH$_3$SO$_3$H $^1$H-NMR(CD$_3$OD) δ ppm: 1.74–2.02(m, 6H), 2.07(br.m, 2H), 2.17(m, 1H), 2.51(d, J=7.7 Hz, 2H), 2.72(s, 3H), 3.25–3.39(m, 4H), 4.18(s, 2H), 6.84(br.s, 1H), 6.96(d, J=8.1 Hz, 1H), 6.98(dd, J=8.1 Hz, 1H), 7.61(s, 2H)

m.p.: 267–271° C. (decompose)

Example 142

(syn)-[3-(10H-Pyrazino[2,3-b][1,4]benzothiazin-8-ylmethyl)-3-azabicyclo[3.3.1]non-9-yl]acetic acid p-toluenesulfonate 1.3 g of (syn)-[3-(10H-pyrazino[2,3-b][1,4]benzothiazin-8-ylmethyl)-3-azabicyclo[3.3.1]non-9-yl]acetic acid was dissolved in 80 ml of tetrahydrofuran. After adding 0.62 g of p-toluenesulfonic acid monohydrate, the mixture was stirred at room temperature for 30 minutes. The precipitate was collected by filtration and dried under reduced pressure.

The crystals were suspended in 5 ml of ethanol and stirred at room temperature for 3 hours. After collected by filtration, the product was hot-air dried at 50° C. for 8 hours and then air-dried at room temperature for 11 hours. Thus 1.4 g of the title compound was obtained as yellow needles.

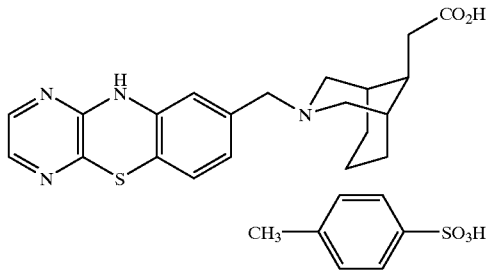

$^1$H-NMR(CD$_3$OD) δ ppm: 1.72–1.99(m, 6H), 2.06(br.m, 2H), 2.17(m, 1H), 2.37(s, 3H), 2.50(d, J=7.7 Hz, 2H), 3.24–3.38(m, 4H), 4.16(s, 2H), 6.82(br.s, 1H), 6.97(s, 2H), 7.21–7.25(m, 2H), 7.61(d, J=3.1 Hz, 1H), 7.62(d, J=3.1 Hz, 1H), 7.69–7.73(m, 2H)

m.p.: 157° C. (decomposes)

Example 143

(syn)-[3-(10H-Pyrazino[2,3-b][1,4]benzothiazin-8-ylmethyl)-3-azabicyclo[3.3.1]non-9-yl]acetic acid sulfate 1.3 g of (syn)-[3-(10H-pyrazino[2,3-b][1,4]benzothiazin-8-ylmethyl)-3-azabicyclo[3.3.1]non-9-yl]acetic acid was dissolved in 60 ml of tetrahydrofuran. After adding 0.18 ml of conc. sulfuric acid and 120 ml of acetone, the resulting mixture was stirred at room temperature for 1 hour. Then water (about 200 ml) was added thereto to thereby dissolve the precipitate and the mixture was concentrated to about 20 ml under reduced pressure. After adding seed crystals, the precipitate was collected by filtration to thereby give 1.1 g of the title compound as yellow crystals.

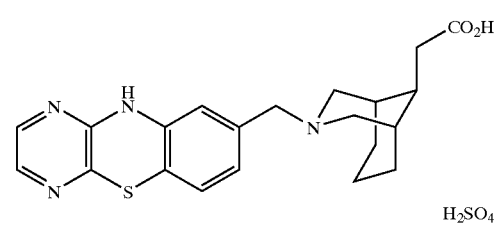

H$_2$SO$_4$ $^1$H-NMR(CD$_3$OD) δ ppm: 1.73–2.04(m, 6H), 2.08(br.m, 2H), 2.18(m, 1H), 2.51(d, J=7.7 Hz, 2H), 3.25–3.40(m, 4H), 4.18(s, 2H), 6.85(d, J=1.3 Hz, 1H), 6.97(br.s, 2H), 7.61(s, 2H)

m.p.: 2256° C. (decomposes)

Example 144

Sodium (syn)-[3-(10H-pyrazino[2,3-b][1,4]benzothiazin-8-ylmethyl)-3-azabicyclo[3.3.1]non-9-yl]acetate 1.310 g of (syn)-[3-(10H-pyrazino[2,3-b][1,4]benzothiazin-8-ylmethyl)-3-azabicyclo[3.3.1]non-9-yl]acetic acid was suspended in a solvent mixture of 50 ml of tetrahydrofuran with 50 ml of ethanol. After adding 3.31 ml of 1 N sodium hydroxide, the resulting mixture was filtered. After distilling off the solvent under reduced pressure, ethanol was added and the solvent was almost completely distilled off under reduced pressure. Then the precipitate was collected by filtration, washed with a small portion of ethanol and hot-air dried at 90° C. for 10 hours. Then it was allowed to stand at room temperature to thereby give 1.408 g of the title compound as a yellow powder.

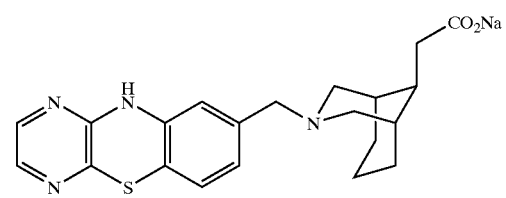

$^1$H-NMR(CD$_3$OD) δ ppm: 1.50(m, 1H), 1.65–1.86(m, 6H), 2.03(m, 1H), 2.31(d, J=7.7 Hz, 2H), 2.47–2.53(m, 2H), 2.59–2.64(m, 2H), 2.73(m, 1H), 3.22(s, 2H), 6.65(s, 1H), 6.77(s, 2H), 7.54(d, J=2.9 Hz, 1H), 7.56(d, J=2.9 Hz, 1H)

m.p.: 260° C. (decomposes)

Example 145

Potassium (syn)-[3-(10H-pyrazino[2,3-b][1,4]benzothiazin-8-ylmethyl)-3-azabicyclo[3.3.1]non-9-yl]acetate 1.310 g of (syn)-[3-(10H-pyrazino[2,3-b][1,4]benzothiazin-8-ylmethyl)-3-azabicyclo[3.3.1]non-9-yl]

acetic acid was suspended in a solvent mixture of 50 ml of tetrahydrofuran with 50 ml of ethanol. After adding 3.31 ml of 1 N potassium hydroxide, the resulting mixture was filtered. After distilling off the solvent under reduced pressure, ethanol was added and the mixture was concentrated again. After adding ethyl acetate, the precipitate was collected by filtration and hot-air dried at 90° C. for 10 hours. Then it was allowed to stand at room temperature to thereby give 1.566 g of the title compound as a yellow powder.

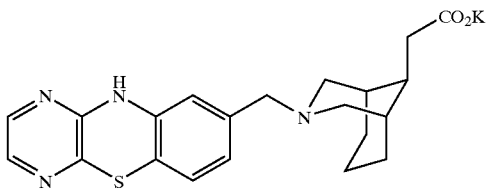

$^1$H-NMR(CD$_3$OD) δ ppm: 1.50(m, 1H), 1.65–1.86(m, 6H), 2.03(m, 1H), 2.31(d, J=7.9 Hz, 2H), 2.46–2.54(m, 2H), 2.58–2.65(m, 2H), 2.73(m, 1H), 3.22(s, 2H), 6.66(s, 1H), 6.77(s, 2H), 7.54(d, J=2.8 Hz, 1H), 7.56(d, J=2.8 Hz, 1H)

m.p.: 272° C. (decomposes)

Example 146

(10H-Pyrazino[2,3-b][1,4]benzothiazin-8-yl) methanol

To 1.47 g of 3-amino-4-[(3-chloropyrazin-2-yl)thio] benzyl alcohol were added 20 ml of methanol and 0.45 ml of conc. hydrochloric acid and the resulting mixture was heated under reflux for 30 minutes. Then the reaction mixture was made alkaline by adding ice-water and aqueous ammonia. The precipitate was collected by filtration and dried to thereby give 1.23 g of the title compound as yellow crystals.

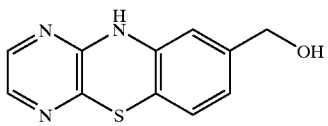

$^1$H-NMR(DMSO-d$_6$) δ ppm: 4.30(d, J=6.0 Hz, 2H), 5.17 (t, J=6.0 Hz, 1H), 6.70(d, J=7.9 Hz, 1H), 6.75(s, 1H), 6.83(d, J=7.9 Hz, 1H), 7.61(d, J=2.6 Hz, 1H), 7.63(d, J=2.6 Hz, 1H), 9.50(s, 1H)

Example 147

Methyl 10H-pyrazino[2,3-b][1,4]benzoxazine-8-carboxylate 21.3 g of methyl 3-amino-4-hydroxybenzoate and 23 g of 2,3-dichloropyrazine were added to 40 ml of dry N,N-dimethylformamide and the resulting mixture was stirred under heating to 160° C. for 6 hours. Then the reaction mixture was brought back to room temperature and the crystals thus precipitated were taken up by filtration and washed with ethyl acetate. Thus 23 g of the title compound was obtained as brown crystals.

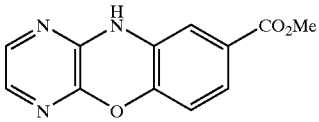

$^1$H-NMR(DMSO-d$_6$) δ ppm: 3.80(s, 3H), 6.86(d, J=8 Hz, 1H), 7.20(d, J=2 Hz, 1H), 7.30(dd, J=2, 8 Hz, 1H), 7.30(d, J=3 Hz, 1H), 7.51(d, J=3 Hz, 1H), 9.81(s, 1H)

Example 148

Methyl 10H-pyrido[3,2-b][1,4]benzothiazine-8-carboxylate 150 g of methyl 3-amino-4-mercaptobenzoate hydrochloride was suspended in 200 ml of diphenyl ether and heated to 100° C. After dropping 2-chloropyridine thereinto, 10.3 g of iodine was further added and the resulting mixture was reacted at 200° C. for 3 hours. After adding 20 ml of sulfuric acid and 300 ml of methanol at room temperature, the resulting mixture was heated under reflux for 3 hours. Then the reaction mixture was brought back to room temperature and poured into a cold saturated aqueous solution of sodium bicarbonate. Next, it was extracted with ethyl acetate, washed with a saturated aqueous solution of sodium chloride and then dried over anhydrous magnesium sulfate. The extract was distilled off under reduced pressure and the residue was purified by silica gel column chromatography (eluted with ethyl acetate/n-hexane) to thereby give 1.3 g of the title compound as yellow crystals.

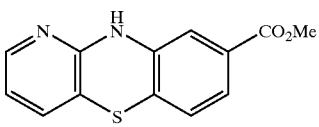

$^1$H-NMR(CDCl$_3$) δ ppm: 3.88(s, 3H), 6.72(dd, J=5, 7 Hz, 1H), 6.84(br.s, 1H), 6.95(d, J=8 Hz, 1H), 7.15(dd, J=2, 8 Hz, 1H), 7.17(d, J=2 Hz, 1H), 7.47(dd, J=2, 8 Hz, 1H), 7.84(dd, J=2, 5 Hz, 1H)

Example 149

Methyl 5H-pyrido[3,4-b][1,4]benzothiazine-7-carboxylate

To a solution of 18.43 g of methyl 3-amino-4-(4-cyanopyridin-3-yl)thiobenzoate in dimethylformamide (70 ml) was added 22.2 g of p-toluenesulfonic acid in a nitrogen atmosphere. Then the resulting mixture was stirred at 120° C. for 2 hours. Then the reaction mixture was cooled to room temperature and the crystals thus precipitated in the course of cooling were taken up by filtration and washed with ethyl acetate. Thus 13.5 g of p-toluenesulfonate of the title compound was obtained as yellow crystals. A 10.3 g portion of this salt was suspended in a solution mixture of 50 ml of a saturated aqueous solution of sodium hydrogencarbonate with 5 ml of tetrahydrofuran and the suspension was stirred for 20 minutes. The suspended matters were taken up by filtration, washed successively with water and ether and dried under reduced pressure overnight. Thus, 6.48 g of the title compound was obtained as yellow crystals.

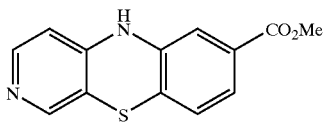

¹H-NMR(CDCl₃) δ ppm: 3.79(s, 3H), 6.48(d, J=6 Hz, 1H), 7.04(d, J=8 Hz, 1H), 7.21(d, J=1 Hz, 1H), 7.33(dd, J=1, 8 Hz, 1H), 7.87(s, 1H), 7.98(d, J=6 Hz, 1H), 9.26(s, 1H)

Example 150

Methyl 4-cyano-10-(methoxyethyl)-10H-pyrido[3,2-b][1,4]-benzothiazine-8-carboxylate To a solution of methyl 3-amino-4-(1-oxo-4-cyano-3-pyridylthio)benzoate in pyridine (20 ml) was added 5 ml of acetic anhydride and the resulting mixture was stirred for 16 hours. Then the reaction mixture was concentrated under reduced pressure and the residue was purified by silica gel column chromatography (eluted with dichloromethane/ethyl acetate) to thereby give 0.45 g of methyl 3-acetamido-4-(1-oxo-4-cyano-3-pyridylthio)benzoate as a colorless solid. 0.079 g of sodium hydride was added in a nitrogen atmosphere to a solution of 0.45 g of methyl 3-acetamido-4-(1-oxo-4-cyano-3-pyridylthio)benzoate in N,N-dimethylformamide (15 ml) and the resulting mixture was stirred for 10 minutes. After adding 0.503 g of sulfur, the resulting mixture was stirred at 130° C. for 15 minutes. The reaction mixture was diluted with water and the crystals thus precipitated were taken up by filtration and washed with water. Thus 0.267 g of methyl 4-cyano-10H-pyrido[3,2-b][1,4]-benzothiazine-8-carboxylate was obtained as yellow crystals. To a solution of 0. 267 g of methyl 4-cyano-10H-pyrido[3,2-b][1,4]-benzothiazine-8-carboxylate in N,N-dimethylformamide (20 ml) were successively added in a nitrogen atmosphere 0.045 g of sodium hydride and a solution of 0.12 ml of chloromethyl methyl ether in N,N-dimethylformamide (9 ml) and the resulting mixture was stirred for 1 hour. Then the reaction mixture was diluted with water and eluted with ethyl acetate. The organic layer was washed with water and a saturated aqueous solution of sodium chloride, dried over anhydrous magnesium sulfate, filtered and concentrated under reduced pressure. The residue was purified by silica gel column chromatography (eluted with n-hexane/dichloromethane) to thereby give 0.152 g of the title compound as pale yellow crystals.

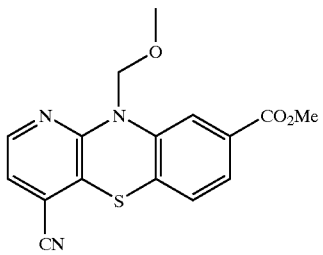

¹H-NMR(CDCl₃) δ ppm: 3.40(s, 3H), 3.95(s, 3H), 5.37(s, 2H), 7.22(d, J=8 Hz, 1H), 7.26(d, J=5 Hz, 1H), 7.76(dd, J=2, 8 Hz, 1H), 7.77(d, J=2 Hz, 1H), 8.19(d, J=5 Hz, 1H)

Example 151

Methyl 10H-pyrazino[2,3-b][1,4]-benzothiazine-7-carboxylate 40 g of methyl 3-(N,N-dimethylcarbamoylthio)-4-nitrobenzoate was added to a solvent mixture of a 30% aqueous solution of potassium hydroxide (50 ml) with methanol (20 ml) and the resulting mixture was stirred under heating to 80° C. for 1.5 hours. Then the reaction mixture was brought back to room temperature and acidified with dilute hydrochloric acid. The brown crystals thus precipitated were taken up by filtration and dried. Into a solution of 20 g of the crystals thus obtained and 40 g of a tin powder (200-mesh) in ethanol (200 ml) was dropped 10 ml of conc. hydrochloric acid in such a manner that the temperature in the reaction system did not exceed 70° C. After diluting with methanol, the mixture was filtered through celite to thereby eliminate the residual tin. After distilling off the solvent under reduced pressure, ethyl acetate saturated with hydrogen chloride gas was added to the oily substance thus obtained and the pale yellow crystals thus precipitated were filtered. To 15 g of the crystals thus obtained was added 200 ml of a 10% solution of hydrochloric acid in methanol and the resulting mixture was heated under reflux for 6 hours. After distilling off the solvent under reduced pressure completely, 30 ml of N,N-dimethylformamide was added thereto. Next, 15 g of dichloropyrazine was further added and the resulting mixture was heated to 110° C. for 1 hour. After diluting with water, the crystals thus precipitated were filtered and washed well with water and diethyl ether. Thus 13.5 g of the title compound was obtained as yellow crystals.

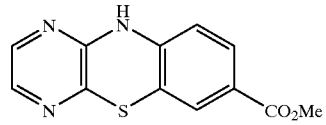

¹H-NMR(DMSO-d₆) δ ppm: 3.75(s, 3H), 6.77(d, J=8.4 Hz, 1H), 7.40(d, J=1.8 Hz, 1H), 7.53(dd, J=1.8, 8.4 Hz, 1H), 7.68(d, J=2.9 Hz, 1H), 7.69(d, J=2.9 Hz, 1H), 9.93(s, 1H)

Example 152

Methyl 10H-pyrimido[5,4-b][1,4]-benzothiazine-8-carboxylate 100 ml of a solution of 16.3 g of crude methyl 3-mercapto-4-aminobenzoate hydrochloride and 20 ml of triethylamine in methanol was stirred under ice-cooling and 7.2 g of 4-chloro-5-bromopyrimidine was dropped thereinto. The colorless precipitate thus formed was filtered to thereby give 9.0 g of crude methyl 4-[5-bromopyrimidin-4-yl)thio]-3-aminobenzoate. 9.0 g of methyl 4-[5-bromopyrimidin-4-yl)thio]-3-aminobenzoate, 200 mg of a copper powder and 1.3 g of potassium carbonate were heated in 5 ml of N,N-dimethylformamide to 110° C. for 1 hour. Then the mixture was hot-filtered to thereby eliminate the copper powder. After recrystallization, the crystals thus precipitated were taken up by filtration and washed with water to thereby give 6.2 g of the title compound as a pale yellow crude product.

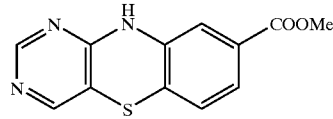

¹H-NMR(DMSO-d₆) δ ppm: 3.79(s, 3H), 7.06(d, J=8.5 Hz, 1H), 7.36(d, J=1.1 Hz, 1H), 7.37(dd, J=1.1, 8.5 Hz, 1H), 7.89–8.02(br.s, 1H), 8.18–8.28(br.s, 1H), 9.43(s, 1H)

Example 153

Methyl 7-methoxy-10H-pyrazino[2,3-b][1,4]-benzothiazine-8-carboxylate

To a solution of 2.7 g of methyl 2-methoxy-4-(2-chloropyrazin-3-yl)thio-5-nitrobenzoate in tetrahydrofuran (100 ml) were added 50 ml of a saturated aqueous solution of sodium hydrosufide and 30 ml of 27% aqueous ammonia and the resulting mixture was vigorously stirred at room temperature for 1 hour. Then the reaction mixture was extracted with ethyl acetate and the organic layer was dried over anhydrous magnesium sulfate. After distilling off the solvent under reduced pressure, a solution of the residue in tetrahydrofuran was stirred at 70° C. for 1 hour. After distilling off the solvent under reduced pressure, dichloroemthane was added to the residue. The crystals thus precipitated were filtered to thereby give 1.9 g of the title compound as red crystals.

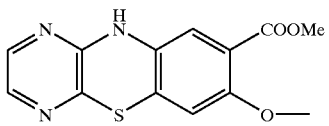

$^1$H-NMR(CDCl$_3$) δ ppm: 3.83(s, 3H), 3.86(s, 3H), 6.36–6.43(br.s, 1H), 6.53(s, 1H), 7.00(s, 1H), 7.59(d, J=2.8 Hz, 1H), 7.69(d, J=2.8 Hz, 1H)

Example 154

Methyl 10-(methoxymethyl)-10H-pyrazino[2,3-b]pyrido[3,2-e][1,4]thiazine-8-carboxylate To a solution of 1.0 g of methyl 5-amino-6-mercaptonicotinate in N,N-dimethylformamide (30 ml) were added 0.52 g of sodium hydride (oily: 60% or more) and 0.97 g of 2,3-dichloropyrazine and the resulting mixture was reacted at 100° C. for 2 hours. Then ethyl acetate was added to the reaction mixture, which was then washed with a saturated aqueous solution of sodium chloride and dried over anhydrous magnesium sulfate. After distilling off the solvent under reduced pressure, diethyl ether was added to the residue and the crystals thus precipitated were taken up by filtration to thereby give 0.43 g of crude methyl 10H-pyrazino[2,3-b]pyrido[3,2-e][1,4]thiazin-8-carboxylate as a brown solid. To a solution of 1.43 g of these crude crystals in N,N-dimethylformamide (50 ml) were added 0.26 g of sodium hydride (60% oily) and 0.5 g of chloromethyl methyl ether and the resulting mixture was reacted under ice-cooling for 1 hour. After adding ethyl acetate, the mixture was washed with a saturated aqueous solution of sodium chloride. The organic layer was dried over anhydrous magnesium sulfate. After distilling off the solvent under reduced pressure, diethyl ether was added to the residue and the crystals thus precipitated were taken up by filtration to thereby give 1.5 g of the title compound as red crystals.

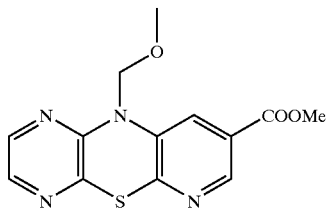

$^1$H-NMR(CDCl$_3$) δ ppm: 3.52(s, 3H), 3.93(s, 3H), 5.27(s, 2H), 7.78(d, J=1.6 Hz, 1H), 7.82(d, J=2.8 Hz, 1H), 7.85(d, J=2.8 Hz, 1H), 8.58(d, J=1.6 Hz, 1H)

Examples 155 to 157

The following compounds were obtained by the same procedure as the one of Example 5.

| Ex. | Structural formula | NMR |
|---|---|---|
| 155 | methyl 10-(methoxymethyl)-10H-pyrazino-[2,3-b][1,4]-benzoxazine-8-carboxylate | $^1$H-NMR (DMSO-d$_6$) δ ppm: 3.33(s, 3H), 3.81(s, 3H), 5.27(s, 2H), 6.97(d, J=8Hz, 1H), 7.41(d, J=2Hz, 1H), 7.46(dd, J=2, 8Hz, 1H), 7.48(d, J=4Hz, 1H), 7.69(d, J=4Hz, 1H) |
| 156 | methyl 5-(methoxymethyl)-5H-pyrido-[3,4-b][1,4]-benzothiazine-7-carboxylate | $^1$H-NMR (CDCl$_3$) δ ppm: 3.56(s, 3H), 3.92(s, 3H), 5.03(s, 2H), 6.88 (d, J=6Hz, 1H), 7.15(d, J=8Hz, 1H), 7.67(m, 2H), 8.18(s, 1H), 8.30(d, J=6Hz, 1H) |

| Ex. | Structural formula | NMR |
|---|---|---|
| 157 | methyl 7-methoxy-10-(methoxymethyl)-10H-pyrazino[2,3-b][1,4]-benzothiazine-7-carboxylate | $^1$H-NMR (CDCl$_3$) δ ppm: 3.53(s, 3H), 3.87(s, 3H), 3.89(s, 3H), 5.28(s, 2H), 6.34(s, 1H), 7.60(s, 1H), 7.84(d, J=2.8Hz, 1H), 7.85(d, J=2.8Hz, 1H) |

Example 158

10-(Methoxymethyl)-10H-pyrazino[2,3-b][1,4]-benzothiazine-7-methanol 100 ml of a solution of 7.0 g of ethyl 10H-pyrazino[2,3-b][1,4]benzothiazine-7-carboxylate in N,N-dimethylformamide was ice-cooled in a nitrogen atmosphere and 1.3 g of sodium hydride (60% oily) was added thereto. Then the resulting mixture was brought back to room temperature and stirred for 1 hour. Next, it was ice-cooled again and 2.5 ml of chloromethyl ether was dropped thereinto. After the completion of the reaction, the reaction mixture was distributed into water and ethyl acetate. The organic layer was extracted, washed with water and dried over anhydrous sodium sulfate. After distilling off the solvent under reduced pressure, the residue was purified by silica gel column chromatography (eluted with ethyl acetate/hexane) to thereby give 5.0 g of ethyl 10-(methoxymethyl)-10H-pyrazino[2,3-b][1,4]benzothiazine-7-carboxylate as pale yellow crystals.

200 ml of a solution of 9.8 g of ethyl 10-(methoxymethyl)-10H-pyrazino[2,3-b][1,4]benzothiazine-7-carboxylate in dichloromethane was ice-cooled in a nitrogen atmosphere and 81 ml of diisobutylaluminum hydride (1.01 M toluene solution) was dropped thereinto. After the completion of the reaction, ice and celite were added to the reaction mixture and stirred at room temperature for 1 hour. Then the mixture was diluted with ethyl acetate and filtered through celite to thereby separate the organic layer. After distilling off the solvent under reduced pressure, 8.0 g of the title compound was obtained as pale yellow crystals.

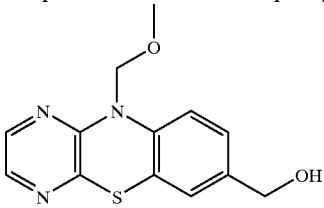

$^1$H-NMR(CDCl$_3$) δ ppm: 1.78(t, J=6.0 Hz, 1H), 3.52(s, 3H), 4.57(d, J=6.0 Hz, 2H), 5.25(s, 2H), 7.03(s, 1H), 7.10(d, J=8.2 Hz, 1H), 7.12(d, J=8.2 Hz, 1H), 7.82(d, J=2.8 Hz, 1H), 7.83(d, J=2.8 Hz, 1H)

Examples 159 and 160

Starting with methyl 10H-pyrimido[5,4-b][1,4]-benzothiazine-8-carboxylate and methyl 5-(methoxymethyl)-5H-pyrido[3,4-b][1,4]benzothiazine-7-carboxylate, the following compounds were obtained by the same procedure as the one of Example 6.

| Ex. | Structural formula | NMR |
|---|---|---|
| 159 | 10H-pyrimido[5,4-b][1,4]-benzothiazine-8-methanol | $^1$H-NMR (DMSO-d$_6$) δ ppm: 4.30(d, J=6.5Hz, 2H), 5.17(t, J=6.5Hz, 1H), 6.76(d, J=7.4Hz, 1H), 6.80(s, 1H), 6.87(d, J=7.4Hz, 1H), 7.84–8.00(br.s, 1H), 8.22(s, 1H), 9.83(s, 1H) |
| 160 | 5-(methoxymethyl)-5H-pyrido[3,4-b][1,4]benzothiazine-7-methanol | $^1$H-NMR (CDCl$_3$) δ ppm: 3.54(s, 3H), 4.65(s, 2H), 5.03(s, 2H), 6.87(d, J=6Hz, 1H), 7.00(d, J=8Hz, 1H), 7.08(s, 1H), 7.09(d, J=8Hz, 1H), 8.18(s, 1H), 8.27(d, J=6Hz, 1H) |

Example 161

4-Cyano-10-(methoxymethyl)-10H-pyrido[3,2-b][1,4]-benzothiazine-8-methanol

To a solution of 0.19 g of methyl 4-cyano-10-(methoxymethyl)-10H-pyrido[3,2-b][1,4]-benzothiazine-8-carboxylate in dry tetrahydrofuran (5 ml) was added in a nitrogen atmosphere a solution of 0.026 g of lithium borohydride in tetrahydrofuran (10 ml) and the resulting mixture was heated under reflux for 20 minutes. After bringing back to room temperature, the mixture was extracted with 15 ml of water and 15 ml of acetic acid and dried over anhydrous magnesium sulfate. After distilling off the solvent under reduced pressure, the residue was purified by silica gel column chromatography (eluted with dichloromethane/methanol) to thereby give 0.12 g of the title compound as a pale yellow solid.

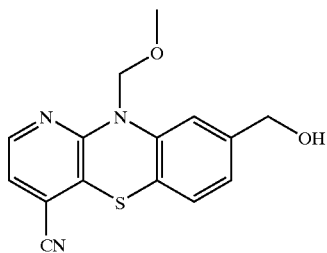

$^1$H-NMR(CDCl$_3$) δ ppm: 1.92(br.s, 1H), 3.39(s, 3H), 4.68(s, 2H), 5.34(s, 2H), 7.09(dd, J=2, 8 Hz, 1H), 7.14(d, J=8 Hz, 1H), 7.18(d, J=2 Hz, 1H), 7.22(d, J=5 Hz, 1H), 8.16(d, J=5 Hz, 1H)

Examples 162 to 165

The following compounds were obtained by the same procedure as the one of Example 3.

| Ex. | Structural formula | NMR |
|---|---|---|
| 162 | 10-(methoxymethyl)-10H-pyrazino[2,3-b][1,4]-benzoxazine-8-methanol | $^1$H-NMR (CDCl$_3$) δ ppm: 1.74(br.s, 1H), 3.46(s, 3H), 4.58(s, 2H), 5.31(s, 2H), 6.82–6.86(m, 2H), 6.92–6.94(m, 1H), 7.43(d, J=3Hz, 1H), 7.78(d, J=3Hz, 1H) |
| 163 | 10H-pyrazino[2,3-b][1,4]-benzoxazine-8-methanol | $^1$H-NMR (DMSO-d$_6$) δ ppm: 4.28(d, J=6Hz, 2H), 5.12(t, J=6Hz, 1H), 6.60(d, J=8Hz, 1H), 6.61(s, 1H), 6.69(d, J=8Hz, 1H), 7.24(d, J=3Hz, 1H), 7.44(d, J=3Hz, 1H), 9.63(s, 1H) |
| 164 | 10H-pyrido[2,3-b][1,4]-benzothiazine-8-methanol | $^1$H-NMR (CDCl$_3$) δ ppm: 4.56(s, 2H), 6.58–6.60(m, 1H), 6.64–6.70(m, 1H), 6.71(dd, J=5, 7Hz, 1H), 6.80–6.84(m, 1H), 6.98(m, 1H), 7.17(dd, J=1, 7Hz, 1H), 7.81(dd, J=1, 5Hz, 1H) |
| 165 | 7-methoxy-10-(methoxymethyl)-10H-pyrazino[2,3-b][1,4]-benzoxyazine-8-methanol | $^1$H-NMR (CDCl$_3$) δ ppm: 2.23(t, J=6Hz, 1H), 3.52(s, 3H), 3.82(s, 3H), 4.62(d, J=6Hz, 2H), 5.26(s, 2H), 6.54(s, 1H), 7.13(s, 1H), 7.82(s, 2H) |

Examples 166 to 171

The following compounds were obtained by the same procedure as the one of Example 4.

| Ex. | Structural formula | NMR |
|---|---|---|
| 166 | 8-(chloromethyl)-10-(methoxymethyl)-10H-pyrazino[2,3-b][1,4]benzoxazine | $^1$H-NMR (CDCl$_3$) δ ppm: 3.25(s, 3H), 4.48(s, 2H), 5.3(s, 2H), 6.81(d, J=8Hz, 1H), 6.88(d, J=8Hz, 1H), 6.93(s, 1H), 7.43(s, 1H), 7.58(s, 1H) |
| 167 | 8-(chloromethyl)-10H-pyrazino[2,3-b][1,4]benzoxazine | $^1$H-NMR (DMSO-d$_6$) δ ppm: 4.58(s, 2H), 6.65(s, 1H), 6.75(s, 2H), 7.26(s, 1H), 7.46(s, 1H), 9.73(s, 1H) |
| 168 | 8-(chloromethyl)-10H-pyrido[2,3-b][1,4]benzothiazine | $^1$H-NMR (CDCl$_3$) δ ppm: 4.41(s, 2H), 6.70(dd, J=2, 8Hz, 1H), 6.76(d, J=2Hz, 1H), 6.85(d, J=8Hz, 1H), 6.91(dd, J=2, 8Hz, 1H), 7.22(dd, J=2, 7Hz, 1H), 7.56(dd, J=1, 6Hz, 1H), 9.3–9.4(m, 1H) |
| 169 | 5-(methoxymethyl)-7-(chloromethyl)-5H-pyrido[3,4-b]-[1,4]benzothiazine | $^1$H-NMR (CDCl$_3$) δ ppm: 3.60(s, 3H), 4.55(s, 2H), 5.09(s, 2H), 7.09–7.13(m, 3H), 7.18(dd, J=2, 8Hz, 1H), 8.21(s, 1H), 8.33(d, J=6Hz, 1H) |
| 170 | 4-cyano-10-(methoxymethyl)-8-(chloromethyl)-10H-pyrido[3,2-b][1,4]benzothiazine | $^1$H-NMR (CDCl$_3$) δ ppm: 3.40(s, 3H), 4.65(s, 2H), 5.33(s, 2H), 7.12(dd, J=2, 8Hz, 1H), 7.15(d, J=8Hz, 1H), 7.18(d, J=2Hz, 1H), 7.25(d, J=5Hz, 1H), 8.18(d, J=5Hz, 1H) |
| 171 | 7-(chloromethyl)-10-(methoxymethyl)-10H-pyrazino[2,3-b][1,4]benzothiazine | $^1$H-NMR (CDCl$_3$) δ ppm: 3.51(s, 3H), 4.47(s, 2H), 5.26(s, 2H), 7.04(d, J=1.8Hz, 1H), 7.12(d, J=7.9Hz, 1H), 7.14(dd, J=1.8, 7.9Hz, 1H), 7.83(d, J=2.7Hz, 1H), 7.85(d, J=2.7Hz, 1H) |

Example 172

8-(Chloromethyl)-10-(methoxymethyl)-10H-pyrazino[2,3-b]pyrido[3,2-e][1,4]thiazine Methyl 10-(methoxymethyl)-10H-pyrazino[2,3-b]pyrido[3,2-e][1,4]thiazine-8-carboxylate was treated in the same manner as those of Examples 6 and 4 to thereby give the title compound as yellow crystals.

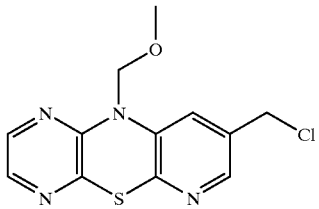

$^1$H-NMR(CDCl$_3$) δ ppm: 3.52(s, 3H), 4.49(s, 2H), 5.26(s, 2H), 7.32(d, J=2.0 Hz, 1H), 7.81(d, J=2.6 Hz, 1H), 7.86(d, J=2.6 Hz, 1H), 8.02(d, J=2.0 Hz, 1H)

Example 173

7-Methoxy-10-(methoxymethyl)-10H-pyrazino[2,3-b][1,4]-benzoxazine-8-carboxaldehyde To a solution of 1.17 g of 7-methoxy-10-(methoxymethyl)-10H-pyrazino[2,3-b][1,4]-benzoxazine-8-methanol in 50 ml of 1,2-dichloroethane was added 3.2 g of manganese dioxide and the resulting mixture was heated under reflux for 2 hours. The reaction mixture was filtered through celite. After distilling off the solvent under reduced pressure, 0.75 g of the title compound was obtained as a brown solid.

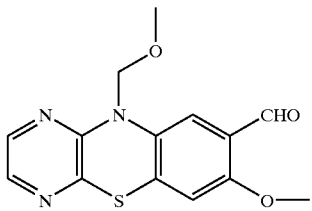

$^1$H-NMR(CDCl$_3$) δ ppm: 3.53(s, 3H), 3.89(s, 3H), 5.26, (s, 2H), 6.66(s, 1H), 7.53(s, 1H), 7.84(d, J=3 Hz, 1H), 7.87(d, J=3 Hz, 1H)10.34(s, 1H)

Example 174

10-(Methoxymethyl)-10H-pyrazino[2,3-b][1,4]-benzothiazine-8-carboxaldehyde

To a solution of 20 g of 10-(methoxymethyl)-10H-pyrazino[2,3-b][1,4]-benzoxazine-8-methanol in 200 ml of dichloromethane was added 132 g of manganese dioxide and the resulting mixture was reacted at room temperature for 18 hours. After filtering off the manganese dioxide, the filtrate was concentrated to thereby give 16 g of the title compound as yellow crystals.

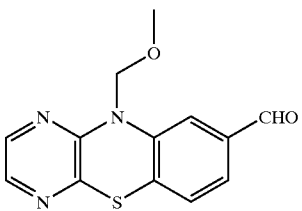

$^1$H-NMR(CDCl$_3$) δ ppm: 3.56(s, 3H), 5.32(s, 2H), 7.15(d, J=8.0 Hz, 1H), 7.45(dd, J=1.6, 8.0 Hz, 1H), 7.58(d, J=1.6 Hz, 1H), 7.87(s, 2H), 9.90(s, 1H)

Example 175

Ethyl 3-[10-(methoxymethyl)-10H-pyrazino[2,3-b][1,4]-benzothiazin-8-yl]propanoate 1.5 g of 10-(methoxymethyl)-10H-pyrazino[2,3-b][1,4]-benzothiazine-8-carboxaldehyde was successively treated in the same manners as those of Production Example 25 and Example 20 to thereby give 1.3 g of the title compound as a yellow oily substance.

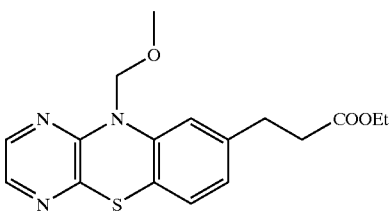

$^1$H-NMR(CDCl$_3$) δ ppm: 1.15–1.20(m, 3H), 2.53(t, J=8 Hz, 2H), 2.83(t, J=8 Hz, 2H), 3.46(s, 3H), 4.0–4.1(m, 2H), 5.20(s, 2H), 6.75(d, J=8 Hz, 1H), 6.86(d, J=8 Hz, 1H), 6.94(s, 1H), 7.95(s, 2H)

Example 176

3-[10-(Methoxymethyl)-10H-pyrazino[2,3-b][1,4]-benzothiazin-8-yl]propionaldehyde 1.3 g of ethyl 3-[10-(methoxymethyl)-10H-pyrazino[2,3-b][1,4]-benzothiazin-8-yl]propanoate was successively treated in the same manners as those of Production Example 64 and Example 7 to thereby give 0.5 g of the title compound as a yellow oily substance.

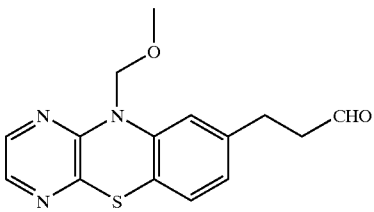

$^1$H-NMR(CDCl$_3$) δ ppm: 2.79(t, J=8 Hz, 2H), 2.90(t, J=8 Hz, 2H), 3.54(s, 3H), 5.27(s, 2H), 6.80(d, J=8 Hz, 1H), 6.94(d, J=8 Hz, 1H), 7.00(s, 1H), 7.9–7.95(m, 2H), 9.83(s, 1H)

Example 177

3-(10-(Methoxymethyl)-10H-pyrazino[2,3-b][1,4]benzothiazin-8-yl)propyl methanesulfonate 3.0 g of ethyl 3-[10-(methoxymethyl)-10H-pyrazino[2,3-b][1,4]benzothiazin-8-yl)propanoate was treated successively by the methods described in Example 3 and Production Example 52 to thereby give 2.7 g of the title compound as a yellow oily substance.

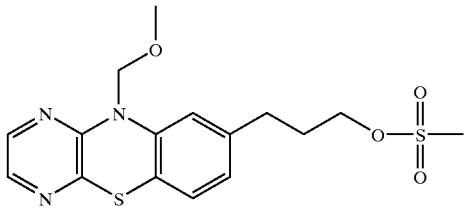

$^1$H-NMR(CDCl$_3$) δ ppm: 2.06(quint., J=7.2 Hz, 2H), 2.70(t, J=7.2 Hz, 2H), 2.88(s, 3H), 3.54(s, 3H), 4.23(t, J=7.2 Hz, 2H), 5.27(s, 2H), 6.82(d, J=8.6 Hz, 1H), 6.96(d, J=8.6 Hz, 1H), 6.99(s, 1H), 7.84(s, 2H)

Example 178

10H-Pyrazino[2,3-b][1,4]benzothiazine-8-ethanol

Starting with 2.3 g of methyl 10H-pyrazino[2,3-b][1,4]benzothiazine-8-acetate, the procedure of Example 3 was repeated to thereby give 2.5 g of the. title compound as a brown oily substance.

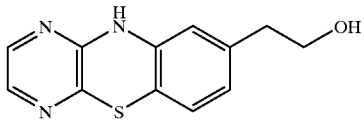

$^1$H-NMR(CDCl$_3$) δ ppm: 2.51(t, J=7 Hz, 2H), 3.33(br.s, 1H), 3.50(t, J=7 Hz, 2H), 6.62(s, 1H), 6.63(d, J=8 Hz, 1H), 6.78(d, J=8 Hz, 1H), 7.58–7.65(m, 2H), 9.44(m, 1H)

Example 179

8-[(2-(tert-Butyldimethylsiloxy)ethyl]-10H-pyrazin[2,3-b][1,4]benzothiazine 500 mg of 2-(10H-pyrazino[2,3-b][1,4]benzothiazin-8-yl)ethanol was dissolved in 7 ml of N,N-dimethylformamide. After adding 369 mg of tert-butyldimethylsilyl chloride, 0.34 ml of triethylamine and a catalytic amount of 4-dimethylaminopyridine, the resulting mixture was stirred at room temperature for 14 hours. After adding water, the reaction mixture was extracted with ethyl acetate. The ethyl acetate layer was washed with water and a saturated aqueous solution of sodium chloride, dried over anhydrous sodium sulfate and concentrated under reduced pressure. Then the residue was purified by silica gel column chromatography (eluted with n-hexane/ethyl acetate) to thereby give 671 mg of the title compound as a yellow solid.

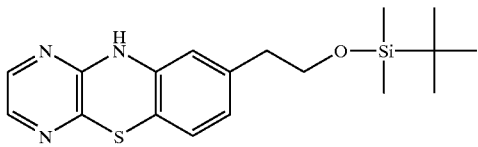

$^1$H-NMR(CDCl$_3$) δ ppm: 0.00(s, 6H), 0.87(s, 9H), 2.66(t, J=6.8 Hz, 2H), 3.75(t, J=6.8 Hz, 2H), 6.37(d, J=1.6 Hz, 1H), 6.57(br.s, 1H), 6.69(dd, J=1.6, 7.9 Hz, 1H), 6.80(d, J=7.9 Hz, 1H), 7.56(d, J=2.9 Hz, 1H), 7.69(d, J=2.9 Hz, 1H)

Example 180

8-[(2(tert-Butyldimethylsiloxy)ethyl]-10-(methoxymethyl)-10H-pyrazino[2,3-b][1,4]benzothiazine 603 mg of 8-[(2-(tert-butyldimethylsilyloxy)ethyl]-10H-pyrazino[2,3-b][1,4]benzothiazine was dissolved in 6 ml of tetrahydrofuran. After adding 63 mg of 70% sodium hydride, the resulting mixture was stirred under ice-cooling for 15 minutes. Then 0.14 ml of chloromethyl methyl ether was added thereto and the resulting mixture was stirred for 1 hour and for additional 18 hours at room temperature. The reaction mixture was concentrated under reduced pressure and the residue was purified by silica gel column chromatography (eluted with n-hexane/ethyl acetate) to thereby give 463 mg of the title compound as a brown oily substance.

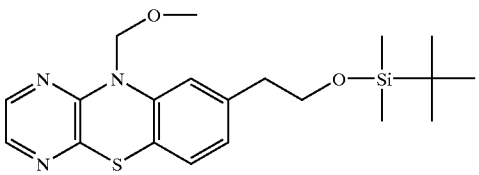

$^1$H-NMR(CDCl$_3$) δ ppm: 0.01(s, 6H), 0.88(s, 9H), 2.76(t, J=7.0 Hz, 2H), 3.53(s, 3H), 3.79(t, J=7.0 Hz, 2H), 5.27(s, 2H), 6.83(dd, J=1.6, 7.9 Hz, 1H), 6.93(d, J=7.9 Hz, 1H), 7.00(d, J=1.6 Hz, 1H), 7.82(d, J=2.7 Hz, 1H), 7.83(d, J=2.7 Hz, 1H)

Example 181

10-(Methoxymethyl)-10H-pyrazino[2,3-b][1,4]benzothiazine-8-ethanol 463 mg of 8-[(2-(tert-butyldimethylsilyloxy)ethyl]-10-(methoxymethyl)-10H-pyrazino[2,3-b][1,4]benzothiazine was dissolved in 5 ml of tetrahydrofuran. After adding 1.3 ml of n-tetrabutylammonium fluoride (1.0 M solution in tetrahydrofuran), the resulting mixture was stirred at room temperature for 1 hour and then at 4° C. for additional 13 hours. The reaction mixture was concentrated under reduced pressure and the residue was purified by silica gel column chromatography (eluted with n-hexane/ethyl acetate) to thereby give 281 mg of the title compound as a pale orange solid.

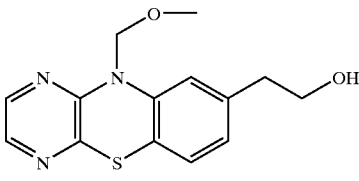

$^1$H-NMR(CDCl$_3$) δ ppm: 1.51(t, J=5.5 Hz, 1H), 2.82(t, J=6.6 Hz, 2H), 3.54(s, 3H), 3.85(dt, J=5.5, 6.6 Hz, 2H), 5.28(s, 2H), 6.86(dd, J=1.6, 7.9 Hz, 1H), 6.96(d, J=7.9 Hz, 1H), 7.03(d, J=1.6 Hz, 1H), 7.83(d, J=2.7 Hz, 1H), 7.84(d, J=2.7 Hz, 1H)

Example 182

8-[2-(Methanesulfonyloxy)ethyl]-10-(methoxymethyl)-10H-pyrazino[2,3-b][1,4]benzothiazine Starting with 10-(methoxymethyl)-10H-pyrazino[2,3-b][1,4]benzothiazine-8-ethanol, the title compound was obtained by the same method as the one of Production Example 52.

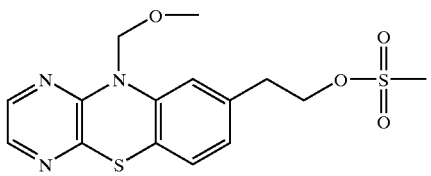

¹H-NMR(CDCl₃) δ ppm: 2.94(s, 3H), 3.00(t, J=6.8 Hz, 2H), 3.54(s, 3H), 4.40(t, J=6.8 Hz, 2H), 5.28(s, 2H), 6.85 (dd, J=1.6, 7.9 Hz, 1H), 6.97(d, J=7.9 Hz, 1H), 7.04(d, J=1.6 Hz, 1H), 7.83(d, J=2.7 Hz, 1H), 7.85(d, J=2.7 Hz, 1H)

Example 183

2-Benzyl-7-(methoxymethoxy)-2-azaspiro[3,5]nonane 11.91 g of 4-(methoxymethoxy)cyclohexane-1,1-dimethyl dimethanesulfonate was dissolved in 30 ml of diphenyl ether. After adding 5.94 g of anhydrous potassium carbonate and 7.23 ml of benzylamine, the resulting mixture was stirred at 180° C. for 21 hours. Then water was added to the reaction mixture followed by extraction with ethyl acetate. The organic layer was washed with water and a saturated aqueous solution of sodium chloride, dried over anhydrous sodium sulfate and concentrated under reduced pressure. The residue was purified by silica gel column chromatography (eluted with dichloromethane/methanol) to thereby give 5.15 g of the title compound as a pale yellow oily substance.

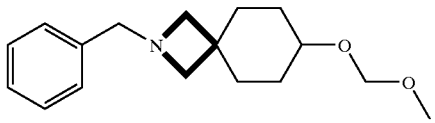

¹H-NMR(CDCl₃) δ ppm: 1.32–1.43(m, 2H), 1.44–1.53 (m, 2H), 1.74–1.82(m, 2H), 1.86–1.96(m, 2H), 3.00(s, 2H), 3.04(s, 2H), 3.36(s, 3H), 3.51(m, 1H), 3.65(s, 2H), 4.66(s, 2H), 7.21–7.34(m, 5H)

Example 184

2-Benzyl-2-azaspiro[3,5]nonan-7-one 900 mg of 2-benzyl-7-(methoxymethyloxy)-2-azaspiro-[3,5]nonane was dissolved in 40 ml of acetone. After adding 10 ml of 6 N hydrochloric acid, the resulting mixture was stirred at room temperature for 1.5 hours. Then the reaction mixture was concentrated under reduced pressure and an aqueous solution of potassium hydrogencarbonate was added thereto followed by extraction with ether. The organic layer was washed with water and a saturated aqueous solution of sodium chloride, dried over anhydrous sodium sulfate and concentrated under reduced pressure. Thus, 794 mg of a pale yellow oily substance was obtained.

0.43 ml of oxalyl chloride was dissolved in 8 ml of dichloromethane and stirred under cooling to −70° C. 0.37 ml of dimethyl sulfoxide was dissolved in 1 ml of dichloromethane and dropped into the above solution while maintaining the inner temperature at −50° C. or below. 10 minutes thereafter, 794 mg of the oily substrate obtained above was dissolved in 2 ml of dichloromethane and dropped into the mixture while maintaining the bulk temperature at −50° C. or below. 25 minutes thereafter, 2.3 ml of triethylamine was dropped thereinto. After 15 minutes, the mixture was heated to room temperature and stirred for 1 hour. After adding water, the reaction mixture was extracted with ethyl acetate. The organic layer was washed with water and a saturated aqueous solution of sodium chloride, dried over anhydrous sodium sulfate and concentrated under reduced pressure. The residue was purified by silica gel column chromatography (eluted with dichloromethane/methanol) to thereby give 655 mg of the title compound as a pale yellow oily substance.

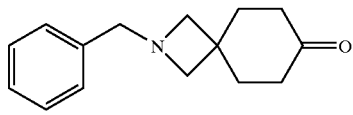

¹H-NMR(CDCl₃) δ ppm: 2.06(t, J=7.0 Hz, 4H), 2.31(t, J=7.0 Hz, 4H), 3.17(s, 4H), 3.69(s, 2H), 7.23–7.35(m, 5H)

Example 185

8-Benzyl-8-azabicyclo[4.3.0]nonan-3-ol 8.33 g of 8-benzyl-8-azabicyclo[4.3.0]-3-nonene was dissolved in 100 ml of tetrahydrofuran and 167 ml of a 1 M solution of borane in tetrahydrofuran was dropped thereinto in a nitrogen atmosphere under ice-cooling. Then the resulting mixture was brought back to room temperature and stirred for 1 hour and 15 minutes. To the reaction mixture were added 50 ml of a 4 N aqueous solution of sodium hydroxide and 23 ml of a 30% aqueous solution of hydrogen peroxide under ice-cooling and the resulting mixture was stirred at the same temperature for 1 hour. The reaction mixture was then concentrated under reduced pressure, extracted with ethyl acetate and concentrated under reduced pressure. 6 N hydrochloric acid was added to the residue and the resulting mixture was stirred at 90° C. for 20 minutes. The reaction mixture was ice-cooled and made basic by adding sodium hydroxide pellets. Then it was extracted with ethyl acetate and the organic layer was dried over anhydrous potassium carbonate. After filtration, the solvent was distilled off under reduced pressure to thereby give 8.29 g of the title compound as a pale yellow oily substance.

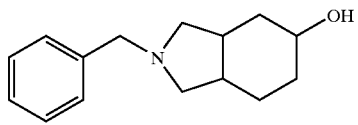

¹H-NMR(CDCl₃) δ ppm: 1.24–1.91(m, 7H), 2.02–2.36 (m, 2H), 2.42–2.89(m, 4H), 3.63–3.91(m, 3H), 7.20–7.4(m, 5H)

Example 186

8-(tert-Butoxycarbonyl)-8-azabicyclo[4.3.0]nonan-3-ol 6.87 g of 8-benzyl-8-azabicyclo[4.3.0]nonan-3-ol was dissolved in 100 ml of methanol and 500 mg of palladium-carbon and 4 ml of formic acid were added thereto. The resulting mixture was stirred at 50° C. for 20 minutes and then at 65° C. for 4 hours and 20 minutes. After further adding 500 mg of palladium-carbon and 3 ml of formic acid, the resulting mixture was heated under reflux for 3 hours. After filtering off the palladium-carbon, the solvent was distilled off under reduced pressure. The residue was then dissolved in 150 ml of methanol. After adding 7 ml of triethylamine and 6.5 g of t-butyl dicarbonate, the resulting mixture was stirred at room temperature for 20 minutes. The reaction mixture was concentrated under reduced pressure, diluted with ethyl acetate, washed successively with 1 N hydrochloric acid, a saturated solution of sodium hydrogencarbonate and a saturated aqueous solution of sodium chloride and dried over anhydrous magnesium sulfate. After filtration, the solvent was concentrated under reduced pressure. The residue thus obtained was purified by silica gel column chromatography (eluted with n-hexane/ethyl acetate) to thereby give 3.73 g of the title compound as a colorless oily substance.

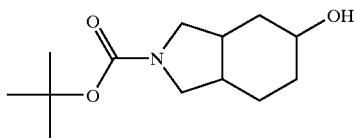

$^1$H-NMR(CDCl$_3$) δ ppm: 1.30–1.43(m, 2H), 1.45(s, 9H), 1.50–1.59(m, 1H), 1.75–1.90(m, 3H), 2.07–2.21(m, 1H), 2.42–2.52(m, 1H), 3.11–3.22(m, 2H), 3.30–3.43(m, 3H), 3.85–3.93(m, 1H)

Example 187

8-(tert-Butoxycarbonyl)-8-azabicyclo[4.3.0]nonan-3-one 4.9 g of oxalyl chloride was dissolved in 250 ml of dichloromethane and cooled to −78° C. in a nitrogen atmosphere. Then a solution of 4.83 g of dimethyl sulfoxide in dichloromethane (20 ml) was dropped thereinto over 17 minutes. Subsequently, a solution of 3.73 g of 8-(tert-butoxycarbonyl)-8-azabicyclo[4.3.0]nonan-3-ol in dichloromethane (40 ml) was dropped thereinto over 10 minutes. After stirring for 10 minutes, 7.82 g of triethylamine was dropped thereinto over 10 minutes and stirring was continued for additional 1 hour. The reaction mixture was brought back to room temperature, diluted with dichloromethane, washed with water and a saturated aqueous solution of sodium chloride and then dried over anhydrous magnesium sulfate. After filtration, the solvent was distilled off under reduced pressure. The residue thus obtained was purified by silica gel column chromatography (eluted with n-hexane/ethyl acetate) to thereby give 3.21 g of the title compound as a colorless oily substance.

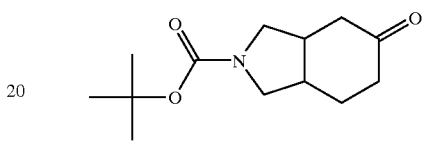

$^1$H-NMR(CDCl$_3$) δ ppm: 1.45(s, 9H), 1.81–1.93(m, 1H), 2.00–2.10(m, 1H), 2.30–2.55(m, 5H), 2.65–2.75(m, 1H), 3.05–3.14(m, 1H), 3.30–3.38(m, 1H), 3.48–3.55(m, 2H)

Examples 188 to 191

Appropriate known compounds were treated in the same manner as those described in Production Example 14 and Example 16 to thereby give the following compounds.

| Ex. | Structural Formula | NMR |
|---|---|---|
| 188 | ![structure] 7-(tert-butoxycarbonyl)-7-azaspiro[3.5]nonan-2-one | $^1$H-NMR (CDCl$_3$) δ ppm: 1.46(s, 9H), 1.69(t, J=6Hz, 4H), 2.81(s, 4H), 3.41(t, J=6Hz, 4H) |
| 189 | ![structure] 3-(tert-butoxycarbonyl)-3-azabicyclo[3.3.0]octane-7-spiro-(3'-cyclobutanone) | $^1$H-NMR (CDCl$_3$) δ ppm: 1.45(s, 9H), 1.75(dd, J=6.4, 13.2Hz, 2H), 2.11(dd, J=7.6, 13.2Hz, 2H), 2.67–2.99(m, 2H), 2.88(d, J=2.4Hz, 2H), 3.04(dd, J=3.2, 4.0Hz, 2H), 3.23–3.36(m, 2H), 3.41–3.52(m, 2H) |
| 190 | ![structure] 6-(tert-butoxycarbonyl)-6-azaspiro[3.4]octan-2-one | $^1$H-NMR (CDCl$_3$) δ ppm: 1.46(s, 9H), 2.01–2.08(m, 2H), 2.90–3.14(m, 4H), 3.36–3.53(m, 4H), |

| Ex. | Structural Formula | NMR |
|---|---|---|
| 191 | 3-[1-(tert-butoxycarbonyl)piperidin-4-yl]cyclobuta-1-one | ¹H-NMR (CDCl₃) δ ppm: 1.08–1.21(m, 2H), 1.34–1.50(m, 1H), 1.46(s, 9H), 1.67–1.77(m, 2H), 2.04–2.17(m, 1H), 2.60–2.80(m, 2H), 2.72–2.83(m, 2H), 3.03–3.14(m, 2H), 4.01–4.27(m, 2H) |

Example 192

1-Benzyl-2-methyl-4-piperidone 6.97 g of 4-methoxy-2-methylpyridine was dissolved in 200 ml of acetone and 13.5 g of benzyl bromide was added thereto. Then the resulting mixture was heated under reflux for 2 hours and 30 minutes. The reaction mixture was cooled to room temperature and diluted with diethyl ether. The precipitate was taken up by filtration and the solid matter was dissolved in 60 ml of water. Next, 5.35 g of sodium borohydride was added thereto in portions. After stirring for 15 minutes, the reaction mixture was concentrated under reduced pressure, diluted with ethyl acetate, washed successively with water and a saturated aqueous solution of sodium chloride and dried over anhydrous magnesium sulfate. After filtration, the solvent was distilled off under reduced pressure. To the obtained residue was added 5 N hydrochloric acid and the resulting mixture was stirred at room temperature overnight. The reaction mixture was made basic by adding potassium carbonate, extracted with ethyl acetate, washed with a saturated aqueous solution of sodium chloride and dried over anhydrous magnesium sulfate. After filtration, the solvent was distilled off under reduced pressure and the residue was purified by silica gel column chromatography (eluted with n-hexane/ethyl acetate) to thereby give 6.84 g of the title compound as a colorless oily substance.

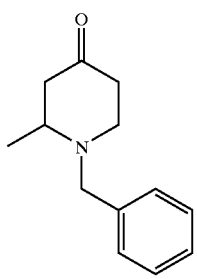

¹H-NMR(CDCl₃) δ ppm: 1.18(d, J=6.4 Hz, 3H), 2.29(dd, J=7.6, 14.4 Hz, 1H), 2.34–2.42(m, 2H), 2.50–2.60(m, 2H), 2.94–3.06(m, 2H), 3.45(d, J=12.8 Hz, 1H), 3.97(d, J=12.8 Hz, 1H), 7.25–7.40(m, 5H)

Example 193

1-Benzyl-2-methyl-4-methylenepiperidine 6.84 g of 1-benzyl-2-methyl-4-piperidone was treated in the same manner as the one of Production Example 14 to thereby give 6.41 g of the title compound as a pale yellow oily substance.

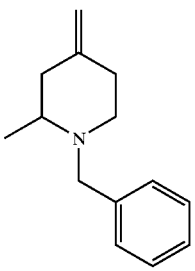

¹H-NMR(CDCl₃) δ ppm: 1.14(d, J=6.0 Hz, 3H), 2.00–2.38(m, 5H), 2.46–2.62(m, 1H), 2.70–2.82(m, 1H), 3.26–3.38(m, 1H), 3.87–4.00(m, 1H), 4.65(d, J=10.4 Hz, 2H), 7.14–7.42(m, 5H)

Example 194

1-(tert-Butoxycarbonyl)-2-methyl-4-methylenepiperidine 6.41 g of 1-benzyl-2-methyl-4-methylenepiperidone was dissolved in 70 ml of dichloroethane and 5.92 g of 1-chloroethyl chloroformate was added thereto under ice-cooling. After heating the mixture under reflux for 50 minutes, 100 ml of methanol was added thereto and the resulting mixture was allowed to stand at room temperature overnight. Then triethylamine was added to the reaction mixture under ice-cooling until the pH value reached 9. Further, 7.64 g of tert-butyl dicarbonate was added thereto and the resulting mixture was stirred at room temperature for 1 hour. The reaction mixture was concentrated under reduced pressure, diluted with ethyl acetate, washed successively with water, 1 N hydrochloric acid, a saturated aqueous solution of sodium chloride and a saturated aqueous solution of sodium bicarbonate and dried over anhydrous magnesium sulfate. After filtration, the solvent was distilled off under reduced pressure and the obtained residue was purified by silica gel column chromatography (eluted with n-hexane/ethyl acetate) to thereby give 7.2 g of the title compound as a colorless oily substance.

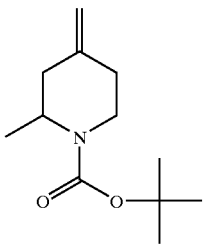

¹H-NMR(CDCl₃) δ ppm: 1.06(d, J=6.8 Hz, 3H), 1.47(s, 9H), 1.99–2.05(m, 1H), 2.08–2.23(m, 2H), 2.35–2.43(m, 1H), 2.81–2.90(m, 1H), 3.98–4.06(m, 1H), 4.45–4.55(m, 1H), 4.72–4.75(m, 1H), 4.83–4.86(m, 1H)

Example 195

7-(tert-Butoxycarbonyl)-6-methyl-7-azaspiro[3.5]nonan-2-one 7.2 g of 1-(tert-butoxycarbonyl)-2-methyl-4-methylenepiperidine was treated in the same manner as the one described in Production Example 16 to thereby give 2.98 g of the title compound as a yellow oily substance.

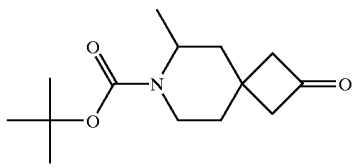

¹H-NMR(CDCl₃) δ ppm: 1.10–1.18(m, 3H), 1.47(s, 9H), 1.61–1.75(m, 3H), 2.00(dd, J=6.4, 13.6 Hz, 1H), 2.72–3.04 (m, 5H), 4.01–4.09(m, 1H), 4.42–4.52(m, 1H)

Example 196

1-Benzyl-4-[4-[2-(methoxymethoxy)ethyl]phenyl]piperidin-4-ol

Into a solution of 10 g of 4-bromophenethyl methoxymethyl ether in 200 ml of tetrahydrofuran was dropped 28 ml of a 1.6 M solution of n-butyllithium in hexane at −78° C. and the resulting mixture was stirred at the same temperature for 30 minutes. After heating to −20° C., a solution of 7.0 g of 1-benzyl-4-piperidone in tetrahydrofuran (10 ml) was added thereto. The mixture was reacted at the same temperature for 2 hours. After adding water, the resulting mixture was extracted with ethyl acetate, washed with a saturated aqueous solution of sodium chloride and dried over anhydrous magnesium sulfate. After distilling off the solvent under reduced pressure, 7.6 g of the title compound was obtained as a yellow oily substance.

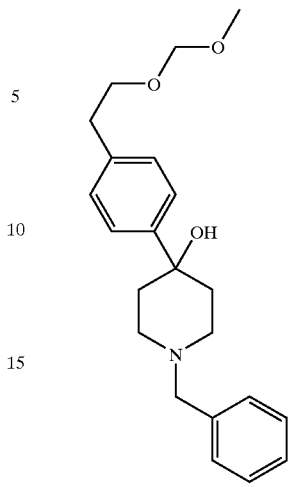

¹H-NMR(CDCl₃) δ ppm: 1.65(br.t, J=13 Hz, 2H), 2.0–2.18(m, 2H), 2.40(br.t, J=10 Hz, 2H), 2.6–2.75(m, 2H), 2.83(t, J=7 Hz, 2H), 3.23(s, 3H), 3.51(s, 2H), 3.69(t, J=7 Hz, 2H), 4,54(s, 2H), 7.1–7.35(m, 7H), 7.35(d, J=8 Hz, 2H)

Example 197

4-(1-Benzyl-1,2,5,6-tetrahydropyrid-4-yl)phenethyl alcohol

To a solution of 1.0 g of 1-benzyl-4-[4-[2-(methoxymethoxy)ethyl]phenyl]piperidin-4-ol in 30 ml of toluene was added 2.0 g of p-toluenesulfonic acid. Then the resulting mixture was heated under reflux for 1 hour while eliminating the water thus formed with a Dean Stark trap. Then the reaction mixture was brought back to room temperature and a saturated aqueous solution of sodium bicarbonate was added thereto. Then it was extracted with ethyl acetate, washed with a saturated aqueous solution of sodium chloride and dried over anhydrous magnesium sulfate. After distilling off the solvent under reduced pressure, the residue was purified by silica gel column chromatography (eluted with n-hexane/ethyl acetate) to thereby give 0.2 g of the title compound as a brown oily substance.

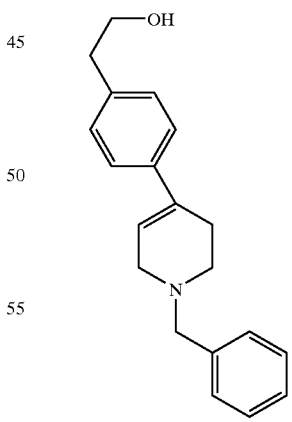

¹H-NMR(CDCl₃) δ ppm: 2.55(m, 2H), 2.71(t, J=6 Hz, 2H), 2.85(t, J=6 Hz, 2H), 3.17(dd, J=2, 6 Hz, 2H), 3.64(s, 2H), 3.84(t, J=6 Hz, 2H), 6.04(m, 1H), 7.14–7.40(m, 9H)

Examples 198 to 202

The following compounds were obtained by the same methods as those described in Examples 196 and 197.

| Ex. | Structural formula | NMR |
|---|---|---|
| 198 | 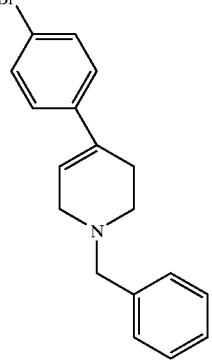<br>4-(4-bromophenyl)-1-benzyl-1,2,3,6-tetrahydropyridine | $^1$H-NMR (CDCl$_3$) δ ppm: 2.43(br.s, 2H), 2.55–2.65(m, 2H), 3.03(br.s, 2H), 3.55(s, 2H), 6.18(s, 1H), 7.2–7.5(m, 9H) |
| 199 | 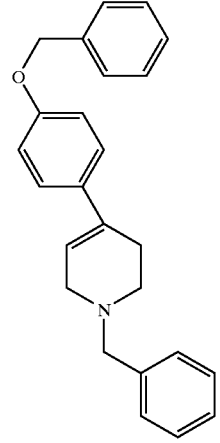<br>4-(4-benzyloxyphenyl)-1-benzyl-1,2,3,6-tetrahydropyridine | $^1$H-NMR (CDCl$_3$) δ ppm: 2.5–2.57(m, 2H), 2.70(t, J=6Hz, 2H), 3.15(d, J=3Hz, 2H), 3.63(s, 2H), 5.05(s, 2H), 5.97(s, 1H), 6.92(d, J=9Hz, 2H), 7.23–7.45(m, 12H) |
| 200 | 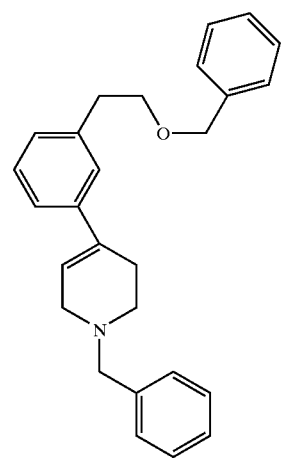<br>4-[3-[2-(benzyloxy)ethyl]phenyl]-1-benzyl-1,2,3,6-tetrahydropyridine | $^1$H-NMR (CDCl$_3$) δ ppm: 2.54(s, 2H), 2.71(t, J=5Hz, 2H), 2.93(t, J=5Hz, 2H), 3.16(s, 2H), 3.65(s, 2H), 3.69(t, J=5Hz, 2H), 4.52(s, 2H), 6.04(s, 1H), 7.10(s, 1H), 7.2–7.4(m, 13H) |

-continued

| Ex. | Structural formula | NMR |
|---|---|---|
| 201 | 4-[4-methoxy-3-[2-(benzyloxy)ethyl]phenyl]-1-benzyl-1,2,3,6-tetrahydropyridine | ¹H-NMR (CDCl₃) δ ppm: 2.53(s, 2H), 2.70(t, J=6Hz, 2H), 2.95(t, J=6Hz, 2H), 3.15(s, 2H), 3.63(s, 2H), 3.6–3.7(m, 2H), 3.78(s, 3H), 4.53(s, 2H), 5.94(s, 1H), 7.2–7.4(m, 13H) |
| 202 | 4-[4,5-dimethoxy-3-[2-(benzyloxy)ethyl]-phenyl]-1-benzyl-1,2,3,6-tetrahydropyridine | ¹H-NMR (CDCl₃) δ ppm: 2.52(br.s, 2H), 2.70(t, J=6Hz, 2H), 2.95(t, J=8Hz, 2H), 3.16(dd, J=3, 6Hz, 2H), 3.64(s, 2H), 3.66(t, J=8Hz, 2H), 3.79(s, 3H), 3.85(s, 3H), 4.52(s, 2H), 5.94–5.98(m, 1H), 6.81(d, J=2Hz, 1H), 6.84(d, J=2Hz, 1H), 7.22–7.40(m, 10H) |

Example 203

4-[1-(Benzyloxycarbonyl)piperidin-4-yl]phenethyl alcohol

To a solution of 8.0 g of 4-(1-benzyl-1,2,5,6-tetrahydropyrid-4-yl)phenethyl alcohol in ethanol (200 ml) was added 15 g of 10% palladium-carbon (moisture content: 50%) and hydrogenation was effected at ordinary temperature under atmospheric pressure for 12 hours. After the completion of the reaction, the palladium-carbon was filtered off and the filtrate was distilled under reduced pressure to thereby give 4.0 g of crude 4-(piperidin-4-yl)phenethyl alcohol as a colorless oily substance. To 4.0 g of this crude product and 3.3 ml of triethylamine dissolved in dichloromethane (30 ml) was added 3.1 ml of benzyl chloroformate at 0° C. and the mixture was reacted at room temperature for 1 hour. After adding water, the reaction mixture was extracted with ethyl acetate, washed with a saturated aqueous solution of sodium chloride and dried over anhydrous magnesium sulfate. After distilling off the solvent under reduced pressure, the residue was purified by silica gel column chromatography (eluted with n-hexane/ethyl acetate) to thereby give 4.0 g of the title compound as a yellow oily substance.

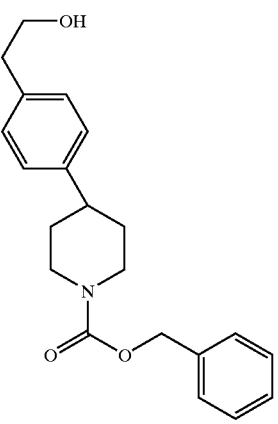

¹H-NMR(CDCl₃) δ ppm: 1.55–1.70(m, 2H), 1.77–1.90 (m, 2H), 2.6–2.7(m, 1H), 2.84(t, J=7 Hz, 2H), 2.8–3.0(m, 2H), 3.8–3.9(m, 2H), 4.2–4.4(m, 2H), 5.15(s, 2H), 7.14(d, J=8 Hz, 2H), 7.18(d, J=8 Hz, 2H), 7.30–7.40(m, 5H)

Examples 204 and 205

The following compounds were obtained by the same method as that of Example 203.

| Ex. | Structural formula | NMR |
|---|---|---|
| 204 | 4-[1-(benzyloxycarbonyl)piperidin-4-yl]phenol | $^1$H-NMR (CDCl$_3$) δ ppm: 1.50–1.70(m, 2H), 1.77–1.85(m, 2H), 2.55–2.65(m, 1H), 2.8–3.0(m, 2H), 4.2–4.4(m, 2H), 5.15(s, 2H), 6.78(d, J=7Hz, 2H), 7.04(d, J=7Hz, 2H), 7.3–7.4(m, 5H) |
| 205 | 3-[1-(benzyloxycarbonyl)piperidin-4-yl]phenethyl alcohol | $^1$H-NMR (CDCl$_3$) δ ppm: 1.55–1.73(m, 2H), 1.8–1.9(m, 2H), 2.6–2.7(m, 1H), 2.85(t, J=6Hz, 2H), 2.8–3.0(m, 2H), 3.86(t, J=6Hz, 2H), 4.2–4.4(m, 2H), 5.16(s, 2H), 7.04–7.12(m, 3H), 7.23–7.41(m, 6H) |

Example 206
2-[1-(Benzyloxycarbonyl)piperidin-4-yl]phenethyl alcohol

The title compound was obtained by the same operations as those described in Examples 196, 197 and 203.

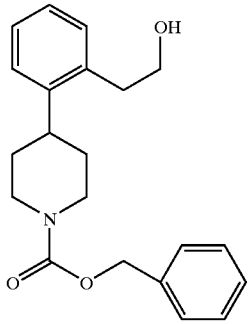

$^1$H-NMR(CDCl$_3$) δ ppm: 1.5–1.8(m, 4H), 2.8–3.0(m, 2H), 2.95(t, J=7 Hz, 2H), 3.83(t, J=7 Hz, 2H), 4.11(q, J=7 Hz, 2H), 4.2–4.4(m, 2H), 5.15(s, 2H), 7.1–7.3(m, 4H), 7.3–7.4(m, 5H)

Example 207
4-[1-(Benzyloxycarbonyl)piperidin-4-yl]phenylacetaldehyde 4.0 g of 4-[1-(benzyloxycarbonyl)piperidin-4-yl]phenethyl alcohol was treated in the same manner as the one of Production Example 7 to thereby give 1.7 g of the title compound as a yellow oily substance.

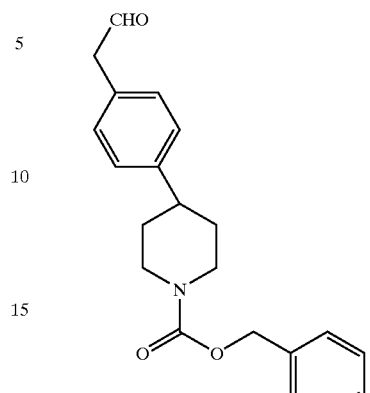

$^1$H-NMR(CDCl$_3$) δ ppm: 1.55–1.70(m, 2H), 1.77–1.90(m, 2H), 2.6–2.73(m, 1H), 2.7–3.0(m, 2H), 3.67(d, J=1 Hz, 2H), 4.2–4.43(m, 2H), 5.16(s, 2H), 7.16(d, J=8 Hz, 2H), 7.20(d, J=8 Hz, 2H), 7.3–7.4(m, 5H), 9.74(t, J=2 Hz, 1H)

Examples 208 to 210

The following compounds were obtained by the same procedure as the one of Production Example 7.

| Ex. | Structural formula | NMR |
|---|---|---|
| 208 | 3-[1-(benzyloxycarbonyl)piperidin-4-yl]phenylacetaldehyde | $^1$H-NMR (CDCl$_3$) δ ppm: 1.5–1.75(m, 2H), 1.75–1.9(m, 2H), 2.6–2.75(m, 1H), 2.8–3.0(m, 2H), 3.67(d, J=2Hz, 2H), 4.3–4.45(m, 2H), 5.16(s, 2H), 7.0–7.4(m, 9H), 9.74(t, J=2Hz, 1H) |
| 209 | 2-[1-(benzyloxycarbonyl)piperidin-4-yl]phenylacetaldehyde | $^1$H-NMR (CDCl$_3$) δ ppm: 1.57–1.8(m, 4H), 2.65–2.8(m, 1H), 2.75–3.0(m, 2H), 3.77(s, 2H), 4.2–4.45(m, 2H), 5.16(s, 2H), 7.1–7.4(m, 9H), 9.75(s, 1H) |

-continued

| Ex. | Structural formula | NMR |
|---|---|---|
| 210 | 2-methoxy-5-[1-(benzyloxycarbonyl)piperidin-4-yl]phenylacetaldehyde | $^1$H-NMR (CDCl$_3$) δ ppm: 1.5–1.7(m, 2H), 1.7–1.9(m, 2H), 2.8–3.0(m, 2H), 3.0–3.2(m, 1H), 3.60(s, 2H), 3.83(s, 3H), 4.2–4.4(m, 2H), 5.15(s, 2H), 6.85(d, J=8Hz, 1H), 6.95(s, 1H), 7.04(d, J=8Hz, 1H), 7.2–7.4(m, 5H), 9.7(s, 1H) |

Example 211

4-[1-(Benzyloxycarbonyl)piperidin-4-yl]phenylacetic acid

To a solution of 0.7 g of 4-[1-(benzyloxycarbonyl)-piperidin-4-yl]phenylacetaldehyde and 0.5 g of sodium dihydrogenphosphate in 5 ml of water and 30 ml of dimethyl sulfoxide was added a solution of 0.35 g of sodium chlorite in water (5 ml) and the resulting mixture was reacted at room temperature for 20 minutes. After adding water, the reaction mixture was extracted with ethyl acetate, washed with a saturated aqueous solution of sodium chloride and dried over anhydrous magnesium sulfate. After distilling off the solvent under reduced pressure, 0.7 g of the title compound was obtained as a colorless oily substance.

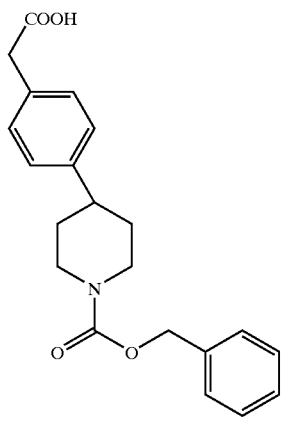

$^1$H-NMR(CDCl$_3$) δ ppm: 1.5–1.7(m, 2H), 1.7–1.9(m, 2H), 2.6–2.7(m, 1H), 2.8–3.0(m, 2H), 3.62(s, 2H), 4.2–4.45(m, 2H), 5.15(s, 2H), 7.15(d, J=8 Hz, 2H), 7.23(d, J=8 Hz, 2H), 7.28–7.40(m, 5H)

Example 212

Methyl 4-[1-(benzyloxycarbonyl)piperidin-4-yl]phenylacetate

To a solution of 1.55 g of 4-[1-(benzyloxycarbonyl)-piperidin-4-yl]phenylacetic acid in methanol (20 ml) was added 13.2 ml of trimethylsilyldiazomethane (2 M solution in hexane) and the resulting mixture was reacted at room temperature for 1 hour. After distilling off the reaction mixture under reduced pressure, the residue was purified by silica gel column chromatography (eluted with n-hexane/ethyl acetate) to thereby give 1.0 of the title compound as a colorless oily substance.

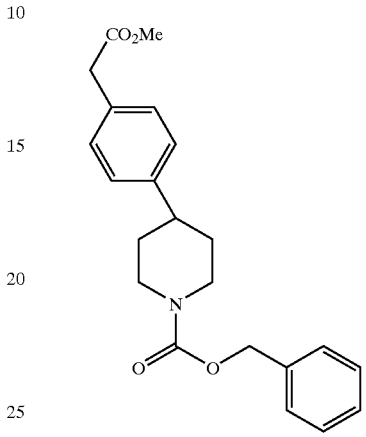

$^1$H-NMR(CDCl$_3$) δ ppm: 1.5–1.7(m, 2H), 1.75–1.88(m, 2H), 2.6–2.7(m, 1H), 2.8–2.95(m, 2H), 3.60(s, 2H), 3.69(s, 3H), 4.2–4.4(m, 2H), 5.15(s, 2H), 7.15(d, J=8 Hz, 2H), 7.22(d, J=8 Hz, 2H), 7.3–7.4(m, 5H)

Example 213

Methyl 3-[1-(benzyloxycarbonyl)piperidin-4-yl]phenylacetate

To a solution of 2.0 g of 3-[1-(benzyloxycarbonyl)-piperidin-4-yl]phenylacetaldehyde and 1.0 g of sodium dihydrogenphosphate in 10 ml of water and 50 ml of dimethyl sulfoxide was added a solution of 2.0 g of sodium chlorite in water (10 ml) and the resulting mixture was reacted at room temperature for 20 minutes. After adding water, the reaction mixture was extracted with ethyl acetate, washed with a saturated aqueous solution of sodium chloride and dried over anhydrous magnesium sulfate. After distilling off the solvent under reduced pressure, 2.0 g of crude 3-[1-(benzyloxycarbonyl)piperidin-4-yl]phenylacetic acid was obtained as a colorless oily substance. To a solution of 2.0 g of this oily substance in 50 ml of methanol was added 0.47 ml of thionyl chloride at 0° C. and the resulting mixture was reacted at room temperature for 2 hours. The reaction mixture was distilled off under reduced pressure and the residue was purified by silica gel column chromatography (eluted with n-hexane/ethyl acetate) to thereby give 1.2 g of the title compound as a yellow oily substance.

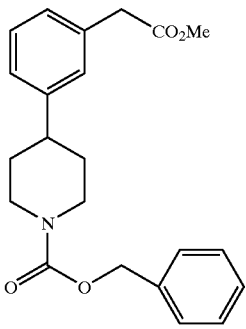

¹H-NMR(CDCl₃) δ ppm: 1.5–1.7(m, 2H), 1.8–1.9(m, 2H), 2.6–2.7(m, 1H), 2.8–2.95(m, 2H), 3.61(s, 2H), 3.69(s, 3H), 4.25–4.40(m, 2H), 5.16(s, 2H), 7.13–7.16(m, 3H), 7.24–7.40(m, 6H)

Examples 214 to 216

The following compounds were obtained by the same procedure as that of Example 213.

| Ex. | Structural formula | NMR |
|---|---|---|
| 214 | 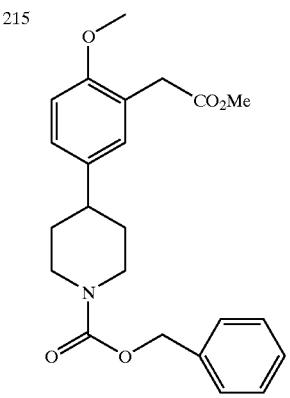<br>methyl 2-[1-(benzyloxycarbonyl)piperidin-4-yl]phenylacetate | ¹H-NMR (CDCl₃) δ ppm: 1.55–1.8(m, 4H), 2.8–2.95(m, 3H), 3.68(s, 3H), 3.70(s, 2H), 4.2–4.4(m, 2H), 5.16(s, 2H), 7.14–7.40(m, 9H) |
| 215 | methyl 2-methoxy-5-[1-(benzyloxycarbonyl)piperidin-4-yl]phenylacetate | ¹H-NMR (CDCl₃) δ ppm: 1.5–1.7(m, 2H), 1.75–1.85(m, 2H), 2.8–3.0(m, 2H), 3.0–3.2(m, 1H), 3.55(s, 2H), 3.69(s, 3H), 3.81(s, 3H), 4.2–4.4(m, 2H), 5.16(s, 2H), 6.81(d, J=8Hz, 1H), 7.03(d, J=2Hz, 1H), 7.10(dd, J=2, 8Hz, 1H), 7.3–7.4(m, 5H) |
| 215 | methyl 2,3-dimethoxy-5-[1-(benzyloxycarbonyl)piperidin-4-yl]phenylacetate | ¹H-NMR (CDCl₃) δ ppm: 1.5–1.7(m, 2H), 1.8–1.9(m, 2H), 2.55–2.65(m, 1H), 2.75–2.95(m, 2H), 3.63(s, 2H), 3.70(s, 3H), 3.80(s, 3H), 3.95(s, 3H), 4.2–4.4(m, 2H), 5.15(s, 2H), 6.64(s, 1H), 6.66(s, 1H), 7.3–7.40(m, 5H) |

Example 217

Ethyl 4-[1-benzyl-1,2,3,6-tetrahydropyrid-4-yl]benzoate

To a solution of 11 g of 4-(4-bromophenyl)-1-benzyl-1,2,3,6-tetrahydropyridine in 200 ml of tetrahydrofuran was added 27 ml of a 2.5 M solution of n-butyllithium in hexane at −78° C. and the resulting mixture was stirred at the same temperature for 15 minutes. Into the reaction mixture was dropped 42 ml of diethyl carbonate and the mixture was heated to room temperature over 15 minutes. After adding water, the reaction mixture was extracted with ethyl acetate, washed with a saturated aqueous solution of sodium chloride and dried over anhydrous magnesium sulfate. After distilling off the solvent under reduced pressure, the residue was purified by silica gel column chromatography (eluted with n-hexane/ethyl acetate) to thereby give 2.8 g of the title compound as a yellow oily substance.

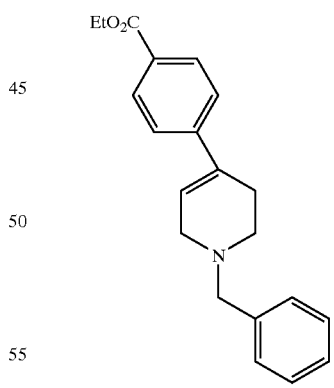

¹H-NMR(CDCl₃) δ ppm: 1.39(t, J=7 Hz, 3H), 2.5–2.62(m, 2H), 2.73(t, J=6 Hz, 2H), 3.07–3.11(m, 2H), 3.65(s, 2H), 4.37(q, J=7 Hz, 2H), 6.20(s, 1H), 7.24–7.42(m, 5H), 7.44(d, J=8 Hz, 2H), 7.98(d, J=8 Hz, 2H)

Example 218

Ethyl 4-[1-(benzyloxycarbonyl)piperidin-4-yl]phenoxyacetate

To a solution of 0.5 g of [1-(benzyloxycarbonyl)piperidin-4-yl]phenol in 20 ml of N,N-dimethylformamide was added 0.083 g of sodium hydride (60% or more oily) and the resulting mixture was stirred at room temperature for 10 minutes. Next, ethyl iodoacetate was added thereto and the resulting mixture was reacted at 60° C. for 1.5 hours. The reaction mixture was poured into water, extracted with ethyl acetate, washed with a saturated aqueous solution of sodium chloride and dried over anhydrous magnesium sulfate. After distilling off the solvent under reduced pressure, the residue was purified by silica gel column chromatography (eluted with n-hexane/ethyl acetate) to thereby give 0.4 g of the title compound as a colorless oily substance.

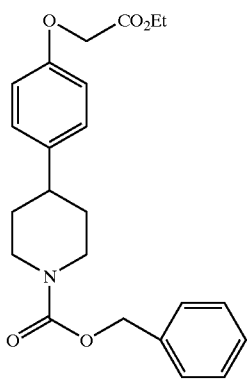

$^1$H-NMR(CDCl$_3$) δ ppm: 1.30(t, J=7 Hz, 3H), 1.5–1.70(m, 2H), 1.75–1.90(m, 2H), 2.55–2.70(m, 1H), 2.8–2.95(m, 2H), 4.27(q, J=7 Hz, 2H), 4.2–4.4(m, 2H), 4.60(s, 2H), 5.15(s, 2H), 6.85(d, J=9 Hz, 2H), 7.11(d, J=9 Hz, 2H), 7.28–7.40(m, 5H)

Example 219

Ethyl 4-(1-benzylpiperidin-4-yl)-2-methylpropanoate

To a solution of 40 g of ethyl 4-(1-benzylpiperidin-4-yl)-2-methylpropanoate in ethanol (500 ml) were added 25 ml of formic acid and 15 g of 10% palladium-carbon (moisture content: 50%) and hydrogenation was effected at ordinary temperature under atmospheric pressure for 12 hours. Then the palladium-carbon was filtered off and the solvent was distilled off. The residue was poured into an aqueous solution of sodium bicarbonate and extracted with ethyl acetate. The extract was washed with a saturated aqueous solution of sodium chloride and dried over anhydrous magnesium sulfate. After distilling off the solvent under reduced pressure, 37.8 g of the title compound was obtained as a colorless oily substance.

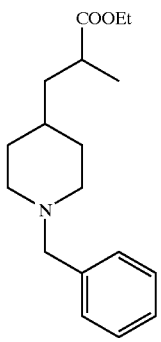

$^1$H-NMR(CDCl$_3$) δ ppm: 1.10(t, J=7 Hz, 3H), 1.00–1.25(m, 6H), 1.50–1.80(m, 4H), 1.80–1.97(m, 2H), 2.43–2.62(m, 1H), 2.80–2.90(m, 2H), 3.46(s, 2H), 4.05–4.18(m, 2H), 7.20–7.30(m, 5H)

Example 220

Ethyl 3-(1-benzylpiperidin-4-yl)-2,2-dimethylpropanoate

To a solution of 68 ml of diisopropylamine in tetrahydrofuran (500 ml) was added 325 ml of a 1.6 M solution of n-butyllithium in hexane and the resulting mixture was stirred at 0° C. for 30 minutes. Then the reaction mixture was cooled to −78° C. and reacted with a solution of 30 g of ethyl 4-(1-benzylpiperidin-4-yl)-2-methylpropanoate in tetrahydrofuran (50 ml) at 0° C. for 30 minutes. After cooling to −78° C. again, 45.3 ml of methyl iodide was dropped thereinto and the resulting mixture was brought back to room temperature over 30 minutes. The reaction mixture was poured into water, extracted with dichloromethane and dried over anhydrous magnesium sulfate. After distilling off the solvent under reduced pressure, the residue was purified by silica gel column chromatography (eluted with n-hexane/ethyl acetate) to thereby give 21.5 g of the title compound as a yellow oily substance.

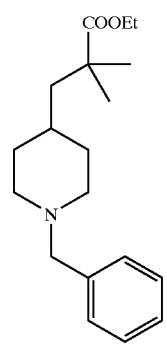

$^1$H-NMR(CDCl$_3$) δ ppm: 1.15(s, 6H), 1.23(t, J=7 Hz, 3H), 1.1–1.4(m, 3H), 1.53(d, J=7 Hz, 2H), 1.5–1.60(m, 2H), 1.90(br.t, J=10 Hz, 2H), 2.80(br.d, J=10 Hz, 2H), 3.45(s, 2H), 4.08(q, J=7 Hz, 2H), 7.2–7.34(m, 5H)

Example 221

Ethyl 2-(1-benzylpiperidin-4-yl)-2-methylpropanoate

Ethyl 2-(1-benzylpiperidin-4-yl)propanoate was treated in the same manner as the one of Example 27 to thereby give the title compound as an oily substance.

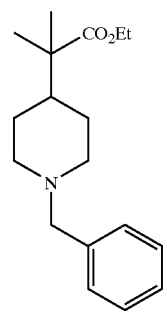

$^1$H-NMR(CDCl$_3$) δ ppm: 1.10(s, 6H), 1.23(t, J=7 Hz, 3H), 1.39(dt, J=4, 12 Hz, 2H), 1.44–1.52(m, 2H), 1.52–1.62

(m, 1H), 1.92(dt, J=2, 12 Hz, 2H), 2.93(br.d, J=12 Hz, 2H), 3.48(s, 2H), 4.11(q, J=7 Hz, 2H), 7.2–7.35(m, 5H)

Example 222

3-[1-(tert-Butoxycarbonyl)piperidin-4-yl]-2,2-dimethylpropanol

Into a solution of 2.7 g of lithium aluminum hydride in tetrahydrofuran (200 ml) was slowly dropped at 0° C. a solution of 21.5 g of ethyl 3-(1-benzylpiperidin-4-yl)-2,2-dimethylpropanoate in tetrahydrofuran (20 ml) and the resulting mixture was stirred at room temperature for 30 minutes. After adding water and a 10% aqueous solution of sodium hydroxide to the reaction mixture, the insoluble matters were filtered off. After distilling off the solvent under reduced pressure, 19 g of crude 3-(1-benzylpiperidin-4-yl)-2,2-dimethylpropanol was obtained as a yellow oily substance. This oily substance was dissolved in 300 ml of ethanol. After adding 20 ml of acetic acid, the mixture was subjected to hydrogenation at ordinary temperature under atmospheric pressure for 12 hours. After filtering off palladium-carbon, the solvent was concentrated under reduced pressure to thereby give 23 g of crude 3-(piperidin-4-yl)-2,2-dimethylpropanol as a yellow oily substance. This crude product was further dissolved in 200 ml of dichloromethane and 23 ml of pyridine was added thereto. Then 15.5 g of di-tert-butyl dicarbonate was dropped thereinto at 0° C. and the resulting mixture was reacted at room temperature for 2 hours. After adding water, the reaction mixture was extracted with ethyl acetate, washed with a saturated aqueous solution of sodium chloride and dried over anhydrous magnesium sulfate. After distilling off the solvent under reduced pressure, the residue was purified by silica gel column chromatography (eluted with n-hexane/ethyl acetate) to thereby give 14.9 g of the title compound as colorless crystals.

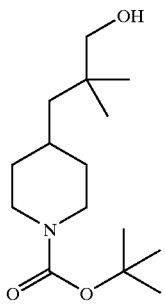

$^1$H-NMR(CDCl$_3$) δ ppm: 0.9(s, 6H), 1.1–1.2(m, 2H), 1.2(d, J=5 Hz, 2H), 1.3–1.4(m, 1H), 1.45(s, 9H), 1.6–1.7(m, 2H), 2.6–2.8(m, 2H), 3.31(s, 2H), 3.9–4.1(m, 2H)

Example 223

4-[1-(tert-Butoxycarbonyl)piperidin-4-yl]-3,3-dimethyl-butyronitrile

To a solution of 14.9 g of 3-[1-(tert-butoxycarbonyl)-piperidin-4-yl]-2,2-dimethylpropanol in 100 ml of carbon tetrachloride was added 64 g of triphenylphosphine and the resulting mixture was heated under reflux for 8 hours. The reaction mixture was concentrated under reduced pressure and the residue was purified by silica gel column chromatography (eluted with n-hexane/ethyl acetate) to thereby give 14.7 g of colorless crystals. These crystals were dissolved in 200 ml of dimethyl sulfoxide and 9.2 g of sodium iodide and 8.8 g of sodium cyanide were added thereto. After stirring at 180° C. for 6 hours, water was added to the mixture at room temperature. Then the reaction mixture was extracted with ethyl acetate, washed with a saturated aqueous solution of sodium chloride and dried over anhydrous magnesium sulfate. After distilling off the solvent under reduced pressure, the residue was purified by silica gel column chromatography (eluted with n-hexane/ethyl acetate) to thereby give 6.7 g of the title compound as a colorless oily substance.

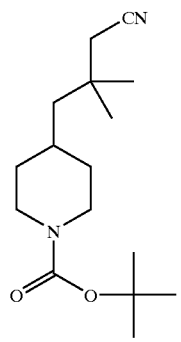

$^1$H-NMR(CDCl$_3$) δ ppm: 1.09(s, 6H), 1.1–1.3(m, 2H), 1.33(d, J=5 Hz, 2H), 1.45(s, 9H), 1.45(m, 1H), 1.6–1.7(m, 2H), 2.24(s, 2H), 2.6–2.8(m, 2H), 3.9–4.1(m, 2H)

Example 224

4-(1-Benzylpiperidin-4-yl)-3,3-dimethylbutyronitrile

To a solution of 6.7 g of 4-[1-(tert-butoxycarbonyl)-piperidin-4-yl]-3,3-dimethylbutyronitrile in 50 ml of tetrahydrofuran was added at room temperature 20 ml of conc. hydrochloric acid and the resulting mixture was stirred for 2 hours. Then the reaction mixture was concentrated under reduced pressure to thereby give crude 4-(piperidin-4-yl)-3,3-dimethylbutyronitrile hydrochloride. This crude product was dissolved in 100 ml of dichloromethane. After adding 10.5 g of anhydrous potassium carbonate and 3.3 ml of benzyl bromide, the reaction mixture was reacted at room temperature for 12 hours. After adding water, the reaction mixture was extracted with ethyl acetate, washed with a saturated aqueous solution of sodium chloride and dried over anhydrous magnesium sulfate. After distilling off the solvent under reduced pressure, the residue was purified by silica gel column chromatography (eluted with n-hexane/ethyl acetate) to thereby give 4.7 g of the title compound as a colorless oily substance.

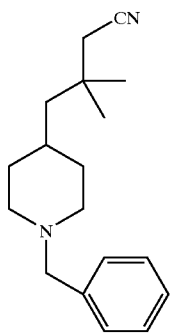

$^1$H-NMR(CDCl$_3$) δ ppm: 1.07(s, 6H), 1.3–1.4(m, 5H), 1.6–1.7(m, 2H), 1.96(br.t, J=12 Hz, 2H), 2.23(s, 2H), 2.83 (br.d, J=12 Hz, 2H), 3.48(s, 2H), 7.2–7.4(m, 5H)

Example 225

Methyl 4-(1-benzylpiperidin-4-yl)-3,3-dimethylbutanoate

To a solution of 4.7 g of 4-(1-benzylpiperidin-4-yl)-3,3-dimethylbutyronitrile in ethylene glycol (20 ml) was added 30 ml of an aqueous solution of 23 g of potassium hydroxide and the resulting mixture was reacted at 200° C. for 10 hours. After bringing back to room temperature, water was added to the reaction mixture. Then the reaction mixture was made weakly acidic with hydrochloric acid. After adding ethanol, the solvent was distilled off under reduced pressure. The crude product thus obtained was suspended in 500 ml of methanol and 6.3 ml of thionyl chloride was dropped thereinto at 0° C. After stirring at room temperature for 72 hours, the solvent was distilled off under reduced pressure. Then an aqueous solution of sodium hydroxide was added to the residue followed by extraction with ethyl acetate. The extract was washed with a saturated aqueous solution of sodium chloride and dried over anhydrous magnesium sulfate. After distilling off the solvent under reduced pressure, the residue was purified by silica gel column chromatography (eluted with n-hexane/ethyl acetate) to thereby give 3.5 g of the title compound as a colorless oily substance.

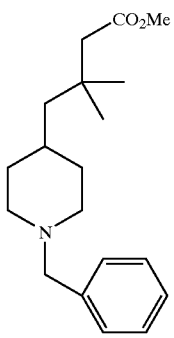

$^1$H-NMR(CDCl$_3$) δ ppm: 1.0(s, 6H), 1.2–1.4(m, 5H), 1.55–1.8(m, 2H), 1.9–2.0(m, 2H), 2.21(s, 2H), 2.82(br.d, J=12 Hz, 2H), 3.47(s, 2H), 3.64(s, 3H), 7.2–7.35(m, 5H)

Example 226

Methyl 3-[1-benzylpiperidin-4-yl]-3-methylbutanoate

Ethyl 2-(1-benzylpiperidin-4-yl)-2-methylpropanoate was treated in the same manner as those of Examples 222, 223, 224 and 225 to thereby give the title compound as a yellow oily substance.

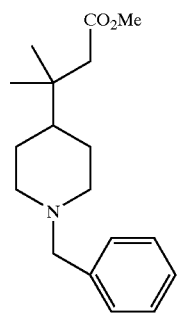

$^1$H-NMR(CDCl$_3$) δ ppm: 0.96(s, 6H), 1.1–1.26(m, 1H), 1.25–1.44(m, 2H), 1.56–1.68(m, 2H), 1.84–1.96(m, 2H), 2.23(s, 2H), 2.96(br.d, J=12 Hz, 2H), 3.48(s, 2H), 3.64(s, 3H), 7.4–7.65(m, 5H)

Examples 227 to 236

The following compounds were obtained by treating known compounds in the same manner as the one of Production Example 25.

| Ex. | Structural formula | NMR |
|---|---|---|
| 227 | ethyl (E)-4-[1-(benzyloxycarbonyl)piperidin-4-yl]-2-methyl-2-butenoate | $^1$H-NMR (CDCl$_3$) δ ppm: 1.26(t, J=6Hz, 3H), 1.10–1.30(m, 2H), 1.50–1.60(m, 1H), 1.62–1.76(m, 2H), 1.82(s, 3H), 2.14(t, J=7Hz, 2H), 2.70–2.82(m, 2H), 4.10–4.23(m, 2H), 4.18(q, J=6Hz, 2H), 5.12(s, 2H), 6.76(t, J=7Hz, 1H), 7.20–7.40(m, 5H) |
| 228 | ethyl (E)-4-[1-(tert-butoxycarbonyl)-piperidin-4-yl]-2-butenoate | $^1$H-NMR (CDCl$_3$) δ ppm: 1.04–2.20(m, 2H), 1.27(t, J=6Hz, 3H), 1.43(s, 9H), 1.58–1.70(m, 3H), 2.16(t, J=6Hz, 2H), 2.60–2.75(m, 2H), 4.00–4.18(m, 2H), 4.18(q, J=6Hz, 2H), 5.80(d, J=16Hz, 1H), 6.92(dt, J=6, 16Hz, 1H) |

| Ex. | Structural formula | NMR |
|---|---|---|
| 229 | ethyl 2-(1-benzylpiperidin-4-ylidene)propanoate | ¹H-NMR (CDCl₃) δ ppm: 1.29(t, J=7Hz, 3H), 1.86(s, 3H), 2.36(t, J=6Hz, 2H), 2.42–2.52(m, 4H), 2.63(t, J=6Hz, 2H), 3.51(s, 2H), 4.18(q, J=7Hz, 2H), 7.2–7.4(m, 5H) |
| 230 | ethyl (E)-(1-benzylpyrrolidin-3-ylidene)acetate | ¹H-NMR (CDCl₃) δ ppm: 1.26(t, J=7Hz, 3H), 2.73(t, J=7Hz, 2H), 2.92–3.00(m, 2H), 3.26(d, J=1Hz, 2H), 3.65(s, 2H), 4.15(q, J=7Hz, 2H), 5.74(t, J=2Hz, 1H), 7.2–7.4(m, 5H), |
| 231 | ethyl (Z)-(1-benzylpiperidin-3-ylidene)acetate | ¹H-NMR (CDCl₃) δ ppm: 1.21(t, J=7Hz, 3H), 1.65–1.80(m, 2H), 2.23(t, J=6Hz, 2H), 2.50(t, J=6Hz, 2H), 3.61(s, 2H), 3.69(s, 2H), 4.10(q, J=7Hz, 2H), 5.67(s, 1H), 7.35(m, 5H) |
| 232 | (E)-(1-benzylpiperidin-3-ylidene)acetic acid | ¹H-NMR (CDCl₃) δ ppm: 1.26(t, J=7Hz, 3H), 1.68–1.76(m, 2H), 2.56(t, J=5Hz, 2H), 2.82–2.88(m, 2H), 2.95(s, 2H), 3.54(s, 2H), 4.14(q, J=7Hz, 2H), 5.63(s, 1H), 7.2–7.35(m, 5H) |

| Ex. | Structural formula | NMR |
|---|---|---|
| 233 | ethyl (E)-4-(1-benzylpiperidin-4-yl)-3-methyl-2-butenoate | ¹H-NMR (CDCl₃) δ ppm: 1.27(t, J=7Hz, 3H), 1.2–1.34(m, 2H), 1.4–1.7(m, 3H), 1.88–1.98(m, 2H), 2.05(d, J=7Hz, 2H), 2.13(d, J=1Hz, 3H), 2.87(br.d, J=12Hz, 2H), 3.49(s, 2H), 4.14(q, J=7Hz, 2H), 5.61–5.63(m, 1H), 7.2–7.35(m, 5H) |
| 234 | ethyl (1,3,5-trimethylpiperidin-4-ylidene)acetate | ¹H-NMR (CDCl₃) δ ppm: 1.21(t, J=7Hz, 3H), 1.28(br.s, 6H), 1.9–2.4(m, 2H), 2.21(br.s, 3H), 2.3–2.5(m, 1H), 2.5–2.7(m, 2H), 3.65–3.8(m, 1H), 4.08(q, J=7Hz, 2H), 5.58(s, 1H) |
| 235 | ethyl 4-[(1-benzylpiperidin-4-ylidene)methyl]benzoate | ¹H-NMR (CDCl₃) δ ppm: 1.37(t, J=6Hz, 3H), 2.35–2.50(m, 4H), 2.50–2.60(m, 4H), 3.52(s, 2H), 4.35(q, J=6Hz, 2H), 6.30(br.s, 1H), 7.18–7.28(m, 3H), 7.28–7.40(m, 4H), 7.86(d, J=7Hz, 2H) |
| 236 | ethyl 4-[1-(tert-butoxycarbonyl)-piperidin-4-yl]-2-methyl-2-butenoate | ¹H-NMR (CDCl₃) δ ppm: 1.00–1.20(m, 2H), 1.29(d, J=7Hz, 3H), 1.20–1.4(m, 1H), 1.45(s, 9H), 1.6–1.7(m, 2H), 1.82(s, 3H), 2.13(t, J=8Hz, 2H), 2.60–2.75(m, 2H), 4.00–4.20(m, 2H), 4.19(q, J=7Hz, 2H), 6.76(t, J=8Hz, 1H) |

Example 237

Methyl 4-[1-(tert-butoxycarbonyl)piperidin-4-yl]-3-butenoate 3.12 g of maleic acid and one drop of piperidine were added to 50 ml of xylene and the resulting mixture was heated under reflux for 30 minutes. After adding 2.27 g of [1-(tert-butoxycarbonyl)piperidin-4-yl]acetaldehyde, the resulting mixture was heated under reflux for 2 hours and 20 minutes while eliminating water with a Dean Stark trap. Then the reaction mixture was distributed into diethyl ether and water, washed with a saturated aqueous solution of sodium chloride and dried over anhydrous magnesium sulfate. After filtration, the solvent was distilled off under reduced pressure. The obtained residue was dissolved in 150 ml of diethyl ether and treated with a solution of diazomethane in diethyl ether. After distilling off the solvent under reduced pressure, the residue was purified by silica gel column chromatography (eluted with n-hexane/ethyl acetate) to thereby give 0.71 g of the title compound as an oily substance.

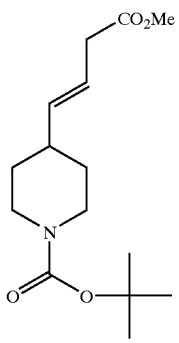

¹H-NMR(CDCl₃) δ ppm: 1.03–1.25(m, 2H), 1.43(s, 9H), 1.60–1.70(m, 2H), 2.03–2.20(m, 2H), 2.55–2.80(m, 2H), 3.00–3.04(m, 1H), 3.67and3.73(s, 3H), 4.06(br.s, 2H), 5.43–5.58(m, 2H)

Example 238

1-(tert-Butoxycarbonyl)piperidine-4-spiro-3'-(4'-butanolide)

To a solution of 0.856 g of 7-(tert-butoxycarbonyl)-7-azaspiro[3.5]nonan-2-one in dichloromethane (30 ml) was added an aqueous solution of 1.86 g of 3-chloroperbenzoic acid (purity: 50–60%) and 1.20 g of sodium hydrogencarbonate and the resulting mixture was stirred for 18 hours. After adding 50 ml of water and 50 ml of dichloromethane, the organic layer was dried over magnesium sulfate, filtered and concentrated under reduced pressure. Then the residue was purified by silica gel column chromatography (eluted with dichloromethane/ethyl acetate) to thereby give 0.542 g of the title compound as white crystals.

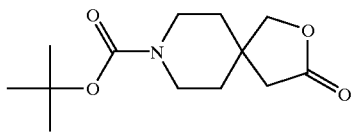

¹H-NMR(CDCl₃) δ ppm: 1.45(s, 9H), 1.58(m, 2H), 1.62 (t, J=6 Hz, 2H), 2.44(s, 2H), 3.26(dt, J=6, 14 Hz, 2H), 3.57(dt, J=6, 14 Hz, 2H), 4.09(s, 2H)

Example 239

8-(tert-Butoxycarbonyl)-2-oxa-8-azaspiro[4.5]decan-3-ol

Into a solution of 0.54 g of 1-(tert-butoxycarbonyl)-piperidine-4-spiro-3'-(4'-butanolide) in dichloromethane (30 ml) was dropped in a nitrogen atmosphere 3.6 ml of a 0.93 M solution of diisobutylaluminum hydride in hexane and the reaction mixture was stirred at –70° C. for 3 hours. After adding 1 ml of methanol, water and dichloromethane were further added thereto and the insoluble matters were filtered off. The aqueous layer was extracted with dichloromethane. The organic layers were combined, dried over magnesium sulfate, filtered and concentrated under reduced pressure. The residue was purified by silica gel column chromatography (eluted with n-hexane/ethyl acetate) to thereby give 0.43 g of the title compound as a colorless oily substance.

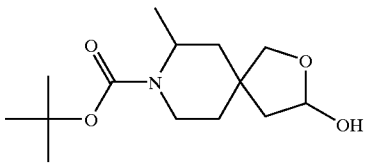

¹H-NMR(CDCl₃) δ ppm: 1.45(s, 9H), 1.52(m, 2H), 1.66(m, 2H), 1.76(dd, J=2, 13 Hz, 1H), 1.99(dd, J=5, 13 Hz, 1H), 2.49(d, J=3 Hz, 1H), 3.29–3.48(m, 4H), 3.72(d, J=9 Hz, 1H), 3.84(d, J=9 Hz, 1H), 5.58(m, 1H)

Example 240

Ethyl (E)-4-[1-(tert-butoxycarbonyl)-4-(hydroxymethyl)-piperidin-4-yl]-2-methyl-2-butenoate By using the same method as the one of Production Example 25, the title compound was obtained as an oily substance.

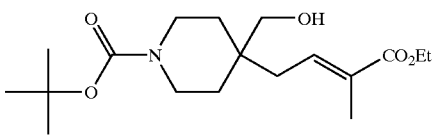

¹H-NMR(CDCl₃) δ ppm: 1.29(t, J=7 Hz, 3H), 1.45(s, 9H), 1.44–1.51(m, 4H), 1.87(s, 3H), 2.30(d, J=7 Hz, 2H), 3.25(ddd, J=4, 7, 12 Hz, 2H), 3.46(ddd, J=4, 7, 12 Hz, 2H), 3.49(d, J=6 Hz, 2H), 4.19(q, J=7 Hz, 2H), 6.81(tq, J=1, 7 Hz, 1H)

Examples 241 to 249

Appropriate ketones synthesized in Examples 188, 190, 189, 187, 184 and 195 and appropriate Wittig-Horner-Emons reagents were treated in the same manner as the one of Production Example 25 to thereby give the following compounds.

| Ex. | Structural formula | NMR |
|---|---|---|
| 241 | ethyl [7-(tert-butoxycarbonyl)-7-azaspiro[3.5]non-2-ylidene]acetate | ¹H-NMR (CDCl₃) δ ppm: 1.27(t, J=7Hz, 3H), 1.46(s, 9H), 1.56–1.62(m, 4H), 2.55(br.s, 2H), 2.87(br.s, 2H), 3.27–3.41(m, 4H), 4.15(q, J=7Hz, 2H), 5.69(quint, J=2Hz, 1H) |

-continued

| Ex. | Structural formula | NMR |
|---|---|---|
| 242 | ethyl 2-[7-(tert-butoxycarbonyl)-7-azaspiro[3.5]non-2-ylidene]propanoate | $^1$H-NMR (CDCl$_3$) δ ppm: 1.27(t, J=7Hz, 3H), 1.45(s, 9H), 1.50–1.60(m, 4H), 1.71(t, J=1Hz, 3H), 2.50(br.s, 2H), 2.80(br.s, 2H), 3.35(m, 4H), 4.16(q, J=7Hz, 2H) |
| 243 | ethyl [3-(tert-butoxycarbonyl)-3-azabicyclo[3.3.0]oct-7-ylidene]acetate | $^1$H-NMR (CDCl$_3$) δ ppm: 1.27(t, J=7Hz, 3H), 1.44(s, 9H), 2.36–2.48(m, 1H), 2.64–2.83(m, 4H), 2.98–3.22(m, 3H), 3.48–3.60(m, 2H), 4.14(q, J=7.2Hz, 2H), 5.79–5.83(m, 1H) |
| 244 | ethyl [6-(tert-butoxycarbonyl)-6-azaspiro[3.4]oct-2-ylidene]acetate | $^1$H-NMR (CDCl$_3$) δ ppm: 1.27(t, J=7.2Hz, 3H), 1.45(s, 9H), 1.90(dt, J=2.4, 6.8Hz, 2H), 2.68–2.86(m, 2H), 2.99–3.19(m, 2H), 3.31–3.43(br.s, 4H), 4.08–4.22(m, 2H), 5.67–5.71(m, 1H) |
| 245 | ethyl [3-(tert-butoxycarbonyl)-3-azabicyclo[3.3.0]-octane-7-spirocyclobut-3′-ylidene]acetate | $^1$H-NMR (CDCl$_3$) δ ppm: 1.22–1.28(m, 3H), 1.45(s, 9H), 1.53–1.65(m, 2H), 1.96–2.06(m, 2H), 2.58–2.72(m, 3H), 2.78(d, J=1.6Hz, 1H), 2.93(dd, J=2.4, 4.8Hz, 1H), 3.07(d, J=1.6Hz, 1H), 3.17–3.27(m, 2H), 3.38–3.50(m, 2H), 4.08–4.20(m, 2H), 5.61–5.67(m, 1H) |
| 246 | ethyl (E)-[8-(tert-butoxycarbonyl)-8-azabicyclo[4.3.0]-non-3-ylidene]acetate | $^1$H-NMR (CDCl$_3$) δ ppm: 1.24–1.32(m, 3H), 1.49(s, 9H), 1.74–1.86(m, 1H), 2.10–2.58(m, 5H), 2.70–2.78(m, 1H), 3.02–3.46(m, 5H), 4.10–4.18(m, 2H), 5.66(s, ½H), 5.73(s, ½H) |
| 247 | ethyl (2-benzyl-2-azaspiro[3.5]non-7-ylidene)acetate | $^1$H-NMR (CDCl$_3$) δ ppm: 1.27(t, J=7.1Hz, 3H), 1.78–1.87(m, 4H), 2.13–2.19(m, 2H), 2.77–2.82(m, 2H), 3.09(s, 4H), 3.68(s, 2H), 4.13(q, J=7.1Hz, 2H), 5.62(s, 1H), 7.23–7.27(m, 1H), 7.28–7.35(m, 4H) |

-continued

| Ex. | Structural formula | NMR |
|---|---|---|
| 248 | 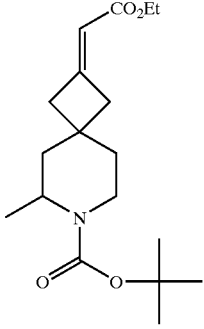<br>ethyl [7-(tert-butoxycarbonyl)-6-methyl-7-azaspiro[3.5]-non-2-ylidene]acetate | $^1$H-NMR (CDCl$_3$) δ ppm: 1.08–1.18(m, 3H), 1.23–1.33(m, 3H), 1.45(s, 9H), 1.40–1.80(m, 3H), 2.43–3.26(m, 5H), 3.91–4.08(m, 1H), 4.10–4.24(m, 3H), 4.33–4.50(m, 1H), 5.65–5.69(m, 1H) |
| 249 | 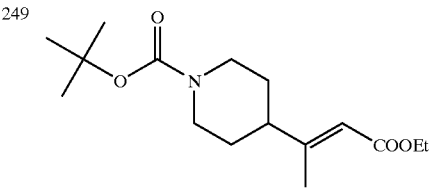<br>ethyl (E)-3-[1-(tert-butoxycarbonylpiperidin-4-yl]-2-butenoate | $^1$H-NMR (CDCl$_3$) δ ppm: 1.28(t, J=6.8Hz, 3H), 1.35–1.48(m, 2H), 1.46(s, 9H), 1.64–1.73(m, 2H), 2.03–2.17(m, 1H), 2.15(s, 3H), 2.62–2.76(m, 2H), 4.04–4.25(m, 2H), 4.15(q, J=6.8Hz, 2H), 5.66(s, 1H) |

Examples 250 to 257

The compounds obtained in Examples 241, 243, 244, 245, 246, 234, 248 and 236 were treated in the same manner as the one of Example 20 to thereby give the following compounds.

| Ex. | Structural formula | NMR |
|---|---|---|
| 250 | 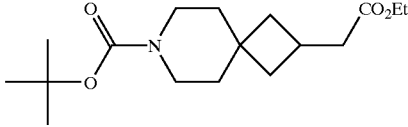<br>ethyl [7-(tert-butoxycarbonyl)-7-azaspiro[3.5]non-2-yl]acetate | $^1$H-NMR (CDCl$_3$) δ ppm: 1.25(t, J=7Hz, 3H), 1.45(s, 9H), 1.44–1.55(m, 6H), 2.04(m, 2H), 2.41(d, J=7Hz, 2H), 2.64(sept, J=7Hz, 1H), 3.25(t, J=6Hz, 2H), 3.34(t, J=6Hz, 2H), 4.11(q, J=7Hz, 2H) |
| 251 | 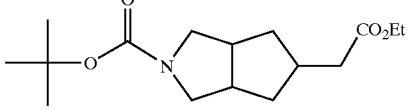<br>ethyl [3-(tert-butoxycarbonyl)-3-azabicyclo[3.3.0]oct-7-yl]acetate | $^1$H-NMR (CDCl$_3$) δ ppm: 1.00–1.13(m, 2H), 1.25(t, J=7Hz, 3H), 1.45(s, 9H), 2.08–2.16(m, 2H), 2.24–2.40(m, 3H), 2.55–2.75(m, 2H), 3.00–3.62(m, 4H), 4.13(q, J=7.2Hz, 2H) |

-continued

| Ex. | Structural formula | NMR |
|---|---|---|
| 252 | ethyl [6-(tert-butoxycarbonyl)-6-azaspiro[3.5]non-2-yl]acetate | $^1$H-NMR (CDCl$_3$) δ ppm: 1.21–1.28(m, 3H), 1.44 and 1.45(s, total 9H, 5:4), 1.64–1.79(m, 2H), 1.84–1.93(m, 1H), 2.05–2.21(m, 2H), 2.38–2.44(m, 2H), 2.58–2.69(m, 1H), 3.14–3.40(m, 5H), 4.07–4.15(m, 2H) |
| 253 | ethyl [3-(tert-butoxycarbonyl)-3-azabicyclo[3.3.0]octane-7-spirocyclobut-3'-yl]acetate | $^1$H-NMR (CDCl$_3$) δ ppm: 1.23(t, J=7.2Hz, 3H), 1.40–1.62(m, 3H), 1.44(s, 9H), 1.74(dd, J=9.2, 11.2Hz, 1H), 1.81(dd, J=7.6, 12.8Hz, 1H), 1.99–2.14(m, 3H), 2.36 and 2.37(s, total 2H, 2:3), 2.50–2.67(m, 3H), 3.06–3.26(m, 2H), 3.36–3.48(m, 2H), 4.09(q, J=7.2Hz, 2H) |
| 254 | ethyl [8-(tert-butoxycarbonyl)-8-azabicyclo[4.3.0]non-3-yl]acetate | $^1$H-NMR (CDCl$_3$) δ ppm: 0.88–1.16(m, 2H), 1.24(t, J=6.8Hz, 3H), 1.45(s, 9H), 1.50–1.84(m, 4H), 1.90–2.42(m, 5H), 3.08–3.38(m, 4H), 4.12(q, J=6.8Hz, 2H) |
| 255 | ethyl (1,3,5-trimethylpiperidin-4-yl)acetate | $^1$H-NMR (CDCl$_3$) δ ppm: 0.86(d, J=7Hz, 6H), 1.25(d, J=7Hz, 3H), 1.69(br.t, J=12Hz, 2H), 1.95–2.05(m, 2H), 2.15(d, J=6Hz, 2H), 2.25(s, 3H), 2.2–2.3(m, 1H), 2.51(br.d, J=12Hz, 2H), 4.12(q, J=7Hz, 2H) |
| 256 | ethyl [7-(tert-butoxycarbonyl)-6-methyl-7-azaspiro[3.5]-non-2-yl]acetate | $^1$H-NMR (CDCl$_3$) δ ppm: 1.07 and 1.15(d, J=7.2Hz, total 3H, 1:1), 1.25(t, J=7.2Hz, 3H), 1.45(s, 9H), 1.34–2.00(m, 7H), 2.16–2.94(m, 5H), 3.78–3.94(m, 1H), 4.10(q, J=7.2Hz, 2H), 4.22–4.37(m, 1H) |

-continued

| Ex. | Structural formula | NMR |
|---|---|---|
| 257 | ethyl 4-[1-(tert-butoxycarbonyl)-piperidin-4-yl]-2-methyl-butanoate | $^1$H-NMR (CDCl$_3$) δ ppm: 1.0–1.7(m, 7H), 1.15(d, J=7Hz, 3H), 1.25(t, J=7Hz, 3H), 1.44(s, 9H), 2.36(m, 3H), 2.0–2.7(m, 2H), 4.0–4.2(m, 2H), 4.12(q, J=7Hz, 2H) |

Example 258

Ethyl 3-[1-(tert-butoxycarbonyl)piperidin-4-yl] cyclobutylacetate

3-[1-(Tert-butoxycarbonyl)piperidin-4-yl]cyclobutan-1-one was treated in the same manner as those of Production Example 25 and Example 20 to thereby give the title compound.

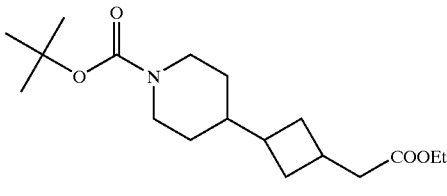

$^1$H-NMR(CDCl$_3$) δ ppm: 0.87–1.00(m, 2H), 1.24(t, J=7.0 Hz, 3H), 1.30–1.39(m, 1H), 1.45(s, 9H), 1.53–1.67(m, 4H), 1.73–1.84(m, 1H), 1.86–1.97(m, 1H), 2.17–2.26(m, 1H), 2.35(t, J=7.5 Hz, 1H), 2.48(t, J=7.5 Hz, 1H), 2.54–2.72(m, 3H), 4.00–4.19(m, 2H), 4.11(q, J=7.0 Hz, 2H)

Example 259

Ethyl 3-[1-(tert-butoxycarbonyl)piperidin-4-yl] butanoate 1-(tert-Butoxycarbonyl)piperidin-4-yl methyl ketone was treated in the same manner as those of Production Example 25 and Example 20 to thereby give the title compound.

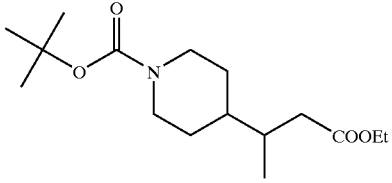

$^1$H-NMR(CDCl$_3$) δ ppm: 0.91(d, J=6.8 Hz, 3H), 1.13–1.27(m, 2H), 1.26(t, J=7.0 Hz, 3H), 1.27–1.48(m, 1H), 1.45(s, 9H), 1.53–1.62(m, 2H), 1.87–1.95(m, 1H), 2.10(dd, J=8.6, 14.9 Hz, 1H), 2.36(dd, J=4.7, 14.9 Hz, 1H), 2.57–2.69 (m, 2H), 4.04–4.22(m, 2H), 4.13(q, J=7.0 Hz, 2H)

Example 260

2-Trimethylsilylethyl N-(1-benzylpiperidin-4-yl) sulfamoylacetate

Into a solution of 1.586 g of chlorosulfonylacetyl chloride in diethyl ether (12 ml) was dropped in a nitrogen atmosphere at −10° C. a solution of 1.060 g of 2-trimethylsilylethanol in diethyl ether (10 ml). After stirring at 0° C. for 1 hour, the reaction mixture was concentrated under reduced pressure and the residue was dissolved in diethyl ether (15 ml) again. Into this solution was dropped a solution of 3.41 g of 1-benzyl-4-aminopiperidine in diethyl ether (15 ml) and the resulting mixture was stirred for 20 hours. After adding 50 ml of water and 50 ml of ethyl acetate, the organic layer was dried over magnesium sulfate, filtered and concentrated under reduced pressure. The residue was purified by silica gel column chromatography (eluted with dichloromethane/methanol) to thereby give 2.21 g of the title compound as a colorless oily substance.

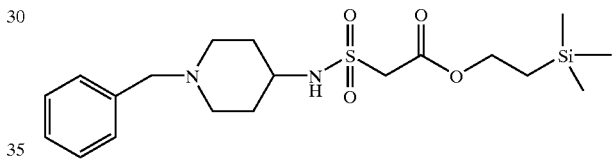

$^1$H-NMR(CDCl$_3$) δ ppm: 0.00(s, 9H), 0.95(m, 2H), 1.59 (qd, J=3, 12 Hz, 2H), 1.94(br.d, J=12 Hz, 2H), 2.09(br.t, J=12 Hz, 2H), 2.77(br.d, J=12 Hz, 2H), 3.31(br.s, 1H), 3.46(s, 2H), 3.92(s, 2H), 4.22(m, 2H), 4.70(br.s, 1H), 7.25–7.30(m, 5H)

Example 261

Ethyl 4-[1-(tert-butoxycarbonyl)piperidin-4-yl]-2,2-dimethylbutanoate 4.792 g of ethyl 4-[1-(tert-butoxycarbonyl)piperidin-4-yl]-2-methylbutanoate was treated in the same manner as the one of Example 220 to thereby give 4.21 g of the title compound as a colorless oily substance.

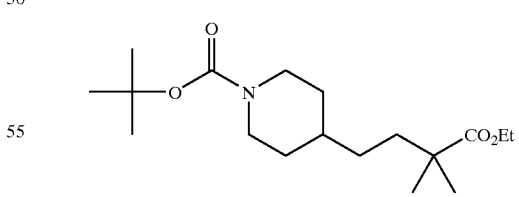

$^1$H-NMR(CDCl$_3$) δ ppm: 1.0–1.20(m, 4H), 1.13(s, 6H), 1.20–1.38(m, 1H), 1.22(t, J=6 Hz, 3H), 1.42(s, 9H), 1.48–1.70(m, 4H), 2.58–2.70(m, 2H), 4.00–4.10(m, 2H), 4.12(q, J=6 Hz, 2H)

Examples 262 to 265

The ketones obtained in Examples 189, 190, 187 and 195 were treated by the same method as the one of Production Example 14 to thereby give the following compounds.

| Ex. | Structural formula | NMR |
|---|---|---|
| 262 | 3-(tert-butoxycarbonyl)-3-azabicyclo-[3.3.0]octane-7-spiro-(3'-methylenecyclobutane) | ¹H-NMR (CDCl₃) δ ppm: 1.45(s, 9H), 1.53(dd, J=6.4, 13.2Hz, 2H), 1.99(dd, J=8.0, 13.2Hz, 2H), 2.48–2.52(m, 2H), 2.57–2.69(m, 4H), 3.22(dd, J=3.2, 11.6Hz, 2H), 3.44(dd, J=8.0, 11.6Hz, 2H), 4.74–4.78(m, 2H) |
| 263 | 6-(tert-butoxycarbonyl)-2-methylene-6-azaspiro[3.4]octane | ¹H-NMR (CDCl₃) δ ppm: 1.46(s, 9H), 1.88(t, J=6.8Hz, 2H), 2.54–2.61(m, 2H), 2.64–2.71(m, 2H), 3.32(s, 2H), 3.36(t, J=6.8Hz, 2H), 4.82–4.86(m, 2H) |
| 264 | 8-(tert-butoxycarbonyl)-3-methylene-8-azabicyclo[4.3.0]nonane | ¹H-NMR (CDCl₃) δ ppm: 1.46(s, 9H), 1.42–1.55(m, 1H), 1.67–1.76(m, 1H), 1.99–2.08(m, 1H), 2.10–2.38(m, 5H), 3.06–3.17(m, 1H), 3.18–3.27(m, 1H), 3.29–3.40(m, 2H), 4.67(s, 1H), 4.73(s, 1H) |
| 265 | 7-(tert-butoxycarbonyl)-6-methyl-2-methylene-7-azaspiro[3.5]nonane | ¹H-NMR (CDCl₃) δ ppm: 1.11(d, J=7.2Hz, 3H), 1.45(s, 9H), 1.39–1.49(m, 1H), 1.57–1.74(m, 3H), 2.28–2.36(m, 1H), 2.44–2.56(m, 2H), 2.60–2.67(m, 1H), 2.82–2.91(m, 1H), 3.89–3.96(m, 1H), 4.30–4.40(m, 1H), 4.77–4.82(m, 2H) |

Examples 266 to 269

The compounds obtained in Examples 262, 263, 264 and 265 were treated in the same manner as the one of Production Example 72 to thereby give the following compounds.

| Ex. | Structural formula | NMR |
|---|---|---|
| 266 | [3-(tert-butoxycarbonyl)-3-azabicyclo[3.3.0]octane-7-spiro-cyclobut-3'-yl]methanol | ¹H-NMR (CDCl₃) δ ppm: 1.44(s, 9H), 1.45–1.62(m, 2H), 1.74–2.09(m, 6H), 2.34–2.47(m, 1H), 2.52–2.68(m, 2H), 3.14(dd, J=4.0, 11.2Hz, 1H), 3.22(dd, J=3.2, 11.2Hz, 1H), 3.43(dd, J=8.0, 11.2Hz, 2H), 3.58(d, J=9.2Hz, 2H) |

| Ex. | Structural formula | NMR |
|---|---|---|
| 267 | [6-(tert-butoxycarbonyl)-6-azaspiro[3.4]oct-2-yl]-methanol | ¹H-NMR (CDCl₃) δ ppm: 1.45 and 1.46(s, total 9H, 1:1), 1.70–1.83(m, 3H), 1.89(t, J=6.8Hz, 1H), 1.96–2.10(m, 2H), 2.43–2.63(m, 1H), 3.21(s, 1H), 3.28–3.38(m, 2H), 3.34(s, 1H), 3.62 and 3.63(d, J=4.0Hz, total 2H, 1:1) |
| 268 | [8-(tert-butoxycarbonyl)-8-azabicyclo[4.3.0]non-3-yl]methanol | ¹H-NMR (CDCl₃) δ ppm: 0.87–1.34(m, 2H), 1.44–1.83(m, 5H), 1.46(s, 9H), 1.97–2.13(m, 1H), 2.31–2.47(m, 1H), 3.15–3.23(m, 2H), 3.29–3.39(m, 2H), 3.47(d, J=3.2Hz, 1H), 3.48(d, J=2.8Hz, 1H) |
| 269 | [7-(tert-butoxycarbonyl)-6-methyl-7-azaspiro[3.5]non-2-yl]methanol | ¹H-NMR (CDCl₃) δ ppm: 1.09(d, J=7.2Hz, 1H), 1.16(d, J=7.2Hz, 2H), 1.36–1.90(m, 7H), 1.45(s, 9H), 2.03–2.23(m, 1H), 2.42–2.54(m, 1H), 2.81–2.97(m, 1H), 3.58–3.64(m, 2H), 3.80–3.95(m, 1H), 4.24–4.38(m, 1H) |

Example 270

4-Allyl-1-(tert-butoxycarbonyl)piperidin-4-ol

Into a solution of 4.98 g of 1-(tert-butoxycarbonyl)-4-piperidone in diethyl ether (150 ml) was dropped at 0° C. in a nitrogen atmosphere 30 ml of a 1.0 M solution of allyl-magnesium bromide in diethyl ether and the resulting mixture was stirred for 3 hours. Then the reaction mixture was poured into an aqueous solution of sodium dihydrogenphosphate and extracted with ethyl acetate. The organic layer was dried over anhydrous magnesium sulfate, filtered and concentrated under reduced pressure. The residue was purified by silica gel column chromatography (eluted with n-hexane/ethyl acetate) to thereby give 4.12 g of the title compound as a white solid.

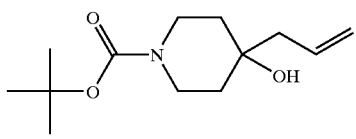

¹H-NMR(CDCl₃) δ ppm: 1.45(s, 9H), 1.54(m, 4H), 2.23 (br.d, J=7 Hz, 2H), 3.15(br.s, 2H), 3.80(br.s, 2H), 5.15(ddt, J=1, 2, 16 Hz, 1H), 5.21(ddt, J=1, 2, 10 Hz, 1H), 5.86(ddt, J=7, 10, 16 Hz, 1H)

Example 271

4-(2,3-Epoxypropan-1-yl)-1-(tert-butoxycarbonyl)piperidin-4-ol

To a solution of 4.115 g of 4-allyl-1-(tert-butoxycarbonyl)piperidin-4-ol in dichloromethane (100 ml) were added 7.07 g of 3-chloroperbenzoic acid and 2.87 g of sodium hydrogencarbonate and the resulting mixture was heated under reflux for 24 hours. To the reaction mixture were added ethyl acetate and an aqueous solution of sodium metabisulfite and the resulting mixture was stirred for 1 hour. The organic layer was dried over anhydrous magnesium sulfate, filtered and concentrated under reduced pressure. The residue was purified by silica gel column chromatography (eluted with dichloromethane/ethyl acetate) to thereby give 1.43 g of the title compound as a colorless solid.

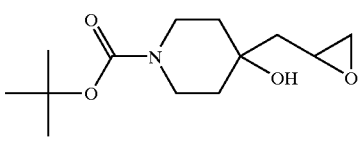

¹H-NMR(CDCl₃) δ ppm: 1.45(s, 9H), 1.40–1.56(m, 5H), 1.88(dd, J=3, 14 Hz, 1H), 2.00(br.s, 1H), 2.50(dd, J=3, 6 Hz, 1H), 2.82(t, J=3 Hz, 1H), 3.14–3.27(m, 3H), 3.91(br.s, 2H)

Example 272

[7-(tert-Butoxycarbonyl)-1-oxa-7-azaspiro[3.5]non-2-yl]methanol

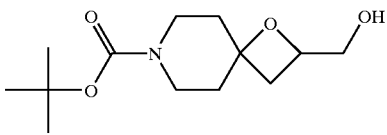

To a solution of 1.42 g of 4-(2,3-epoxypropan-1-yl)-1-(tert-butoxycarbonyl)piperidin-4-ol in dimethyl sulfoxide (20 ml) were added in a nitrogen atmosphere 5 ml of water and 2.32 g of lithium hydroxide and the resulting mixture was heated to 140° C. for 30 minutes. After adding ethyl acetate, the reaction mixture was washed with water thrice. The organic layer was dried over anhydrous magnesium sulfate, filtered and concentrated under reduced pressure. The residue was purified by silica gel column chromatography (eluted with dichloromethane/ethyl acetate) to thereby give 0.336 g of the title compound as colorless crystals.

$^1$H-NMR(CDCl$_3$) δ ppm:1.46(s, 9H), 1.72–1.85(m, 3H), 1.91(m, 1H), 1.97(dd, J=5, 8 Hz, 1H)2.26(dd, J=7, 10 Hz, 1H), 2.37(dd, J=8, 10 Hz, 1H), 3.32–3.52(m, 3H), 3.57(ddd, J=4, 8, 11 Hz, 1H), 3.78(ddd, J=3, 4, 11 Hz, 1H), 4.75(m, 1H)

Examples 273 to 276

The compounds obtained in Examples 266, 267, 269 and 272 were treated in the same manner as the one of Production Example 73 to thereby give the following compounds.

| Ex. | Structural formula | NMR |
| --- | --- | --- |
| 273 | [3-(tert-butoxycarbonyl)-3-azabicyclo[3.3.0]octane-7-spiro-cyclobut-3′-yl]carbaldehyde | $^1$H-NMR (CDCl$_3$) δ ppm: 1.45(s, 9H), 1.44–1.50(m, 1H), 1.52–1.59(m, 1H), 1.84–1.92(m, 1H), 1.98–2.08(m, 4H), 2.25–2.31(m, 1H), 2.55–2.70(m, 2H), 3.04–3.28(m, 3H), 3.39–3.47(m, 2H), 9.71 and 9.72(s, total 1H, 1:1) |
| 274 | [6-(tert-butoxycarbonyl)-6-azaspiro[3.5]non-2-yl]carbaldehyde | $^1$H-NMR (CDCl$_3$) δ ppm: 1.45 and 1.46(s, total 9H, 1:1), 1.78 and 1.92(t, J=6.8Hz, total 2H, 1:1), 2.06–2.35(m, 4H), 3.06–3.43(m, 5H), 9.74 and 9.77(d, J=2.0Hz, total 1H, 1:1) |
| 275 | [7-(tert-butoxycarbonyl)-6-methyl-7-azaspiro[3.5]non-2-yl]carbaldehyde | $^1$H-NMR (CDCl$_3$) δ ppm: 1.10 and 1.14(d, J=7.2Hz, total 3H, 1:2), 1.32–1.42(m, 1H), 1.45(s, 9H), 1.45–2.27(m, 7H), 2.80–2.96(m, 1H), 3.08–3.24(m, 1H), 3.81–4.00(m, 1H), 4.25–4.40(m, 1H), 9.73 and 9.78(d J=1.6Hz, total 1H, 1:2) |
| 276 | [7-(tert-butoxycarbonyl)-1-oxa-7-azaspiro[3.5]non-2-yl]carbaldehyde | $^1$H-NMR (CDCl$_3$) δ ppm: 1.45(s, 9H), 1.66–2.01(m, 4H), 2.24–2.36(m, 2H), 3.47–3.51(m, 4H), 4.65(t, J=7Hz, 1H), 9.80(s, 1H) |

Example 277

[3-(tert-Butoxycarbonyl)-3-azabicyclo[3.3.0]oct-7-yl]-carbaldehyde 3-(tert-Butoxycarbonyl)-3-azabicyclo [3.3.0]octan-7-one was successively treated by the procedures of Production Examples 71, 72 and 73 to thereby give the title compound.

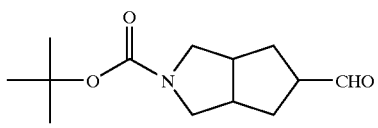

$^1$H-NMR(CDCl$_3$) δ ppm: 1.44(s, 9H), 1.65–1.77(m, 2H), 2.06–2.18(m, 2H), 2.63–2.75(m, 2H), 2.81–2.91 and 2.95–3.04(m, total 1H, 2:1), 3.12–3.23(m, 2H), 3.43–3.56 (m, 2H), 9.62–9.64(m, 1H)

Examples 278 to 282

The aldehydes obtained in Examples 277, 273, 274, 276 and 275 were treated in the same manner as that of Production Example 74 to thereby give the following compounds.

| Ex. | Structural formula | NMR |
|---|---|---|
| 278 | methyl [3-(tert-butoxycarbonyl)-3-azabicyclo[3.3.0]oct-7-yl]carboxylate | $^1$H-NMR(CDCl$_3$) δ ppm: 1.44(s, 9H), 1.65–1.84(m, 2H), 2.03–2.23(m, 2H), 2.56–3.02(m, 3H), 3.02–3.59(m, 4H), 3.67(s, 3H) |
| 279 | methyl [3-(tert-butoxycarbonyl)-3-azabicyclo[3.3.0]-octane-7-spiro-cyclobut-3'-yl]carboxylate | $^1$H-NMR(CDCl$_3$) δ ppm: 1.45(s, 9H), 1.46–1.56(m, 2H), 1.88–1.96(m, 1H), 2.01–2.19(m, 4H), 2.28–2.35(m, 1H), 2.53–2.69(m, 2H), 3.03(quint, J=8.8Hz, 1H), 3.11–3.18(m, 1H), 3.20–3.28(m, 1H), 3.40–3.47(m, 2H), 3.67(s, 3H) |
| 280 | methyl [6-(tert-butoxycarbonyl)-6-azaspiro[3.4]-oct-2-yl]carboxylate | $^1$H-NMR(CDCl$_3$) δ ppm: 1.42–1.52(m, 9H), 1.81–1.93(m, 2H), 2.10–2.38(m, 4H), 3.04–3.14(m, 1H), 3.22–3.46(m, 4H), 3.69(s, 3H) |
| 281 | methyl [7-(tert-butoxycarbonyl)-1-oxa-7-azaspiro[3.5]-non-2-yl]carboxylate | $^1$H-NMR(CDCl$_3$) δ ppm: 1.46(s, 9H), 1.76(m, 2H), 1.95(m, 2H), 2.46(dd, J=7, 11Hz, 1H, 2.66(dd, J=9, 11Hz, 1H), 3.36–3.54(m, 4H), 3.80(s, 3H), 5.00(dd, J=7, 9Hz, 1H) |

| Ex. | Structural formula | NMR |
|---|---|---|
| 282 | 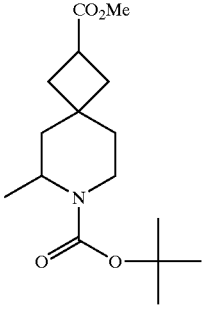<br>methly [7-(tert-butoxycarbonyl)-6-methyl-7-azaspiro[3.5]-non-2-yl]carboxylate | $^1$H-NMR(CDCl$_3$) δ ppm: 1.08 and 1.14(d, J=7.2Hz, total 3H), 1.45(s, 9H), 1.56–1.83(m, 4H), 1.87–2.11(m, 2H), 2.17–2.37(m, 2H), 2.81–2.94(m, 1H), 3.04–3.16(m, 1H), 3.68 and 3.69(s, total 3H), 3.81–3.98(m, 1H), 4.24–4.38(m, 1H) |

Example 283

Methyl [8-(tert-butoxycarbonyl)-8-azabicyclo[4.3.0]non-3-yl-carboxylate

[8-(tert-Butoxycarbonyl)-8-azabicyclo [4.3.0]non-3-yl]methanol was successively treated by the same methods as those of Production Examples 73 and 74 to thereby give the title compound.

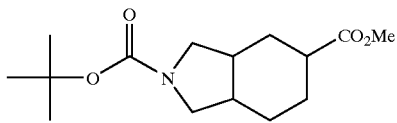

$^1$H-NMR(CDCl$_3$) δ ppm: 1.46(s, 9H), 1.24–1.95(m, 6H), 2.03–2.14(m, 1H), 2.24–2.52(m, 2H), 3.14–3.25(m, 2H), 3.31–3.42(m, 2H), 3.67(s, 3H)

Example 284

Methyl (3-benzyloxycarbonyl-3-azabicyclo [4.1.0]hept-6-yl)acetate 1.41 g of oxalyl chloride was dissolved in 70 ml of dichloromethane and cooled to −78° C. in a nitrogen atmosphere. Then a solution of 1.38 g of dimethyl sulfoxide in dichloromethane (3 ml) was dropped thereinto over 5 minutes. Further, a solution of 1.22 g of (3-benzyloxycarbonyl-3-azabicyclo[4.1.0]hept-6-yl)ethanol in dichloromethane (10 ml) was dropped thereinto over 5 minutes. After stirring the mixture for 15 minutes, 2.24 g of triethylamine was dropped thereinto over 5 minutes and stirring was continued for additional 30 minutes. Then the reaction mixture was diluted with dichloromethane, washed with 1 N hydrochloric acid and a saturated aqueous solution of sodium chloride and dried over anhydrous magnesium sulfate. After filtration, the solvent was distilled off under reduced pressure and the residue was purified by silica gel column chromatography (eluted with n-hexane/ethyl acetate) to thereby give 450 mg of a product. This product was dissolved in 6 ml of dimethyl sulfoxide and 5 ml of an aqueous solution of 257 mg of sodium dihydrogenphosphate was added thereto. Further, 5 ml of an aqueous solution of 496 mg of sodium chlorite was added thereto over 5 minutes and the resulting mixture was stirred at room temperature for 10 minutes. Next, the reaction mixture was diluted with ethyl acetate, washed successively with water and a saturated aqueous solution of sodium chloride, dried over anhydrous magnesium sulfate and filtered. After distilling off the solvent under reduced pressure, the obtained residue was dissolved in 40 ml of toluene. After adding 6 ml of a 2 M solution of trimethylsilyldiazomethane in hexane and 10 ml of methanol, the resulting mixture was stirred at room temperature for 50 minutes. Then the reaction mixture was concentrated under reduced pressure and the obtained residue was purified by silica gel column chromatography (eluted with ethyl acetate/methanol) to thereby give 180 mg of the title compound as a colorless oily substance.

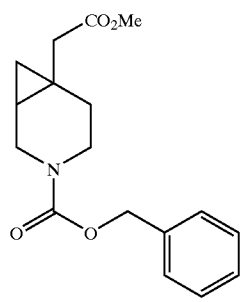

$^1$H-NMR(CDCl$_3$) δ ppm: 0.41–0.48(m, 1H), 0.54–0.66 (m, 1H), 0.88–1.04(m, 1H), 1.76–1.92(m, 2H), 2.16–2.42 (m, 2H), 3.15–3.24(m, 1H), 3.32–3.44(m, 1H), 3.60–3.68 (m, 1H), 3.68(s, 3H), 3.80–3.88(m, 1H), 5.10(s, 2H), 7.28–7.40(m, 5H)

Example 285

[7-(tert-Butoxycarbonyl)-7-azaspiro[3.5]non-2-yl]carbonitrile 2.39 g of [7-(tert-butoxycarbonyl)-7-azaspiro[3.5]nonan-2-one was treated in the same manner as the one of Production Example 34 to thereby give 0.99 g of the title compound as colorless crystals.

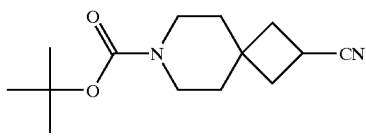

¹H-NMR(CDCl₃) δ ppm: 1.45(s, 9H), 1.55(dd, J=5, 6 Hz, 2H), 1.62(dd, J=5, 6 Hz, 2H), 2.18(m, 2H), 2.25(m, 2H), 3.17(m, 1H), 3.32(m, 4H)

Example 286

(7-Benzyl-7-azaspiro[3.5]non-2-yl)carbonitrile

To a solution of 1.44 g of [7-(tert-butoxycarbonyl)-7-azaspiro[3.5]non-2-yl]carbonitrile in dichloromethane (40 ml) was added 10 ml of trifluoroacetic acid and the resulting mixture was stirred at room temperature for 2.5 hours. Then an aqueous solution of disodium hydrogenphosphate was added to the reaction mixture followed by extraction with ethyl acetate and dichloromethane. The extract was dried over anhydrous magnesium sulfate and then the solvent was concentrated under reduced pressure. Thus 0.935 g of crude (7-azaspiro[3.5]non-2-yl)carbonitrile was obtained. This crude product was dissolved in 40 ml of dichloromethane. After adding at 0° C. 0.94 g of triethylamine and 1.27 g of benzyl bromide, the resulting mixture was stirred at room temperature for 12 hours. To the reaction mixture was added an aqueous solution of disodium hydrogenphosphate. Then the resulting mixture was extracted with ethyl acetate and dried over anhydrous magnesium sulfate. After distilling off the solvent under reduced pressure, the residue was purified by silica gel column chromatography (eluted with methanol/dichloromethane) to thereby give 1.12 g of the title compound as a colorless oily substance.

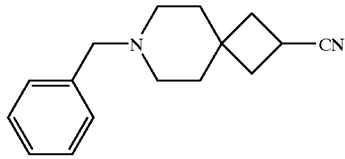

¹H-NMR(CDCl₃) δ ppm: 1.60(t, J=5 Hz, 2H), 1.69(t, J=5 Hz, 2H), 2.13(dd, J=8, 12 Hz, 2H), 2.21(J=10, 12 Hz, 2H), 2.31(br.s, 4H), 3.02(m, 1H), 3.44(s, 2H), 7.22–7.33(m, 5H)

Example 287

Methyl(7-benzyl-7-azaspiro[3.5]non-2-yl)carboxylate (7-Benzyl-7-azaspiro[3.5]non-2-yl)carbonitrile was treated in the same manner as the one of Production Example 35 to thereby give the title compound.

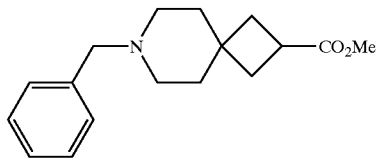

¹H-NMR(CDCl₃) δ ppm: 1.58(t, J=5 Hz, 2H), 1.64(t, J=5 Hz, 2H), 2.00(s, 2H), 2.02(s, 2H), 2.28(br.s, 2H), 2.34(br.s, 2H), 3.04(quint, J=9 Hz, 1H), 3.43(s, 2H), 3.67(s, 3H), 7.22–7.33(m, 5H)

Example 288

Methyl 4-[1-(benzyloxycarbonyl)piperidin-4-yloxy]phenylacetate 1-(Benzyloxycarbonyl)piperidin-4-ol and methyl 4-hydroxyphenylacetate were treated in the same manner as the one of Production Example 65 to thereby give the title compound as a pale green powder.

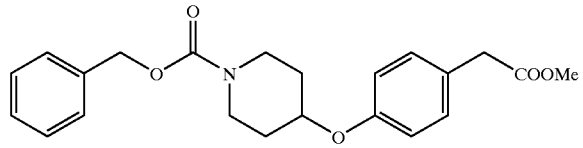

¹H-NMR(CDCl₃) δ ppm: 1.73–1.83(m, 2H), 1.86–1.96 (m, 2H), 3.42–3.50(m, 2H), 3.56(s, 2H), 3.69(s, 3H), 3.70–3.78(m, 2H), 4.47(m, 1H), 5.14(s, 2H), 6.83–6.88(m, 2H), 7.17–7.21(m, 2H), 7.29–7.38(m, 5H)

Example 289

Methyl 4-[1-(benzyloxycarbonyl)piperidin-4-yl]methyloxy]-phenylacetate

[1-(Benzyloxycarbonyl)piperidin-4-yl]methanol and methyl p-hydroxyphenylacetate were treated in the same manner as the one of Production Example 65 to thereby give the title compound as a pale green powder.

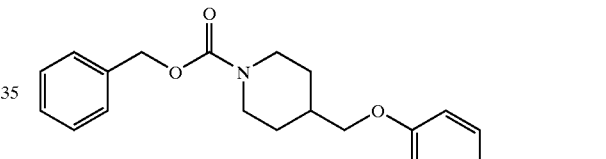

¹H-NMR(CDCl₃) δ ppm: 1.22–1.35(m, 2H), 1.80–1.88 (m, 2H), 1.98(m, 1H), 2.76–2.89(m, 2H), 3.56(s, 2H), 3.68 (s, 3H), 3.78(d, J=6.4 Hz, 2H), 4.15–4.32(m, 2H), 5.14(s, 2H), 6.81–6.86(m, 2H), 7.16–7.21(m, 2H), 7.29–7.38(m, 5H)

Example 290

Ethyl 1-(1-benzylpiperidin-4-yl)cyclopropane carboxylate 13 ml of diisopropylamine was dissolved in a solvent mixture of tetrahydrofuran (140 ml) with HMPA (15 ml) in a nitrogen atmosphere and cooled to −78° C. Into the obtained solution was dropped 42 ml of a 2.5 M solution of n-butyllithium in hexane and the resulting mixture was stirred at 0° C. for 30 minutes. After cooling to −78° C. again, 15 ml of a solution of 5.8 g of ethyl (1-benzylpiperidin-4-yl)acetate in tetrahydrofuran was dropped thereinto. The reaction mixture was stirred at 0° C. for 1 hour. Then 1,2-dibromoethane was dropped thereinto at −78° C. again. The reaction mixture was stirred at 0° C. for 30 minutes and then brought back to room temperature. Next, it was distributed into water and ethyl acetate. The organic layer was extracted, washed with water and dried over magnesium sulfate. After distilling off the solvent under reduced pressure, the residue was purified by silica gel column chromatography (eluted with n-hexane/ethyl acetate) to thereby give 1.40 g of ethyl 2-(1-benzyl-4-piperidyl)-4-bromobutanoate as a colorless oily substance. A solution of 1.40 g of ethyl 2-(1-benzyl-4-piperidyl)-4-bromobutanoate in tetrahydrofuran (20 ml) was stirred at room temperature and 1.0 g of t-butoxypotassium was added thereto. The reaction mixture was distributed into water and ethyl acetate. The organic layer was extracted and washed with water. After distilling off the solvent under reduced pressure, the obtained residue was purified by silica gel column chromatography (eluted with n-hexane/ethyl acetate) to thereby give 800 mg of the title compound as a colorless oily substance.

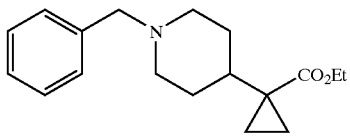

$^1$H-NMR(CDCl$_3$) δ ppm: 0.74(dd, J=3.9, 6.7 Hz, 2H), 1.08(dd, J=3.9, 6.7 Hz, 2H), 1.22(t, J=7.0 Hz, 3H), 1.32–1.44(m, 2H), 1.52–1.59(m, 2H), 1.70–1.79(m, 1H), 1.90–1.99(m, 2H), 2.87–2.93(m, 2H), 3.48(s, 2H), 4.19(q, J=7.0 Hz, 2H), 7.20–7.33(m, 5H)

Example 291

Ethyl [2-methyl-7-(tert-butoxycarbonyl)-7-azaspiro[3.5]non-2-yl]acetate

To a suspension of 2.85 g of cuprous iodide in diethyl ether was added in a nitrogen atmosphere at 23° C. 22 ml of a 1.4 M solution of methyllithium in diethyl ether. After stirring at −23° C. for 30 minutes, the mixture was cooled to −75° C. Into this solution was dropped 20 ml of a solution of 0.927 g of ethyl 7-(tert-butoxycarbonyl)-7-azaspiro[3.5]non-2-ylidene]acetate and trimethylsilyl chloride in diethyl ether. The bulk temperature was elevated to room temperature and the reaction mixture was stirred for 15 hours. After adding 100 ml of ethyl acetate and sodium hydrogencarbonate thereto, the insoluble matters were filtered off, dried over anhydrous magnesium sulfate, filtered and concentrated under reduced pressure. The residue was purified by silica gel column chromatography (eluted with dichloromethane/methanol) to thereby give 0.609 g of the title compound as white crystals.

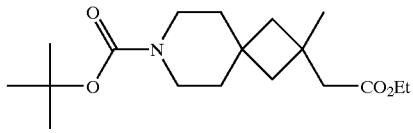

$^1$H-NMR(CDCl$_3$) δ ppm: 1.22(s, 3H), 1.25(t, J=7 Hz, 3H), 1.44(s, 9H), 1.49(m, 2H), 1.56(m, 2H), 1.71(d, J=13 Hz, 2H), 1.88(d, J=13 Hz, 2H), 2.39(s, 2H), 3.29(m, 4H), 4.14(q, J=7 Hz, 2H)

Example 292

1-Benzylpiperidin-4-ylideneethyl vinyl ether

To a solution of 1.08 g of (1-benzylpiperidin-4-ylidene) ethanol in vinyl ethyl ether (30 ml) was added in a nitrogen atmosphere 0.107 g of mercurous trifluoroacetate. After stirring at room temperature for 18 hours, 10 ml of a 10% aqueous solution of sodium hydroxide was added thereto and the resulting mixture was extracted with n-hexane (50 ml). The organic layer was washed with an aqueous solution of sodium chloride (3×10 ml), dried over anhydrous magnesium sulfate and concentrated under reduced pressure to thereby give 1.153 g of the title compound as a colorless oily substance.

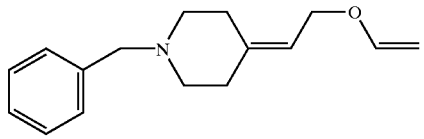

$^1$H-NMR(CDCl$_3$) δ ppm: 2.24(t, J=5 Hz, 2H), 2.32(t, J=6 Hz, 2H), 2.45(tt, J=5, 6 Hz, 4H), 3.51(s, 2H), 4.01(d, J=5 Hz, 2H), 4.18–4.23(m, 2H), 5.38(t, J=5 Hz, 1H), 6.47(dd, J=9, 15 Hz, 1H), 7.34–7.36(m, 5H)

Example 293

(1-Benzyl-4-vinylpiperidin-4-yl)acetaldehyde

A solution of 0.82 g of (1-benzylpiperidin-4-ylidene)-ethyl vinyl ether in benzonitrile (30 ml) was degassed in a nitrogen atmosphere and heated to 190° C. for 1 hour. Then the reaction mixture was concentrated under reduced pressure and the residue was purified by silica gel column chromatography (eluted with dichloromethane/methanol) to thereby give 0.67 g of the title compound as a colorless oily substance.

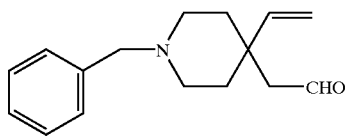

$^1$H-NMR(CDCl$_3$) δ ppm: 1.66–1.72(m, 2H), 1.78–1.83 (m, 2H), 2.37–2.41(m, 2H), 2.40(s, 2H), 2.47–2.54(m, 2H), 3.48(s, 2H), 5.07(d, J=16 Hz, 1H), 5.24(d, J=10 Hz, 1H), 5.84(dd, J=10, 16 Hz, 1H), 7.31–7.35(m, 5H), 9.71(s, 1H)

Example 294

Methyl (1-benzyl-4-vinylpiperidin-4-yl)acetate

To a solution of 0.486 g of (1-benzyl-4-vinylpiperidin-4-yl)acetaldehyde in N,N-dimethylformamide (10 ml) were added 0.48 g of methanol and 4.50 g of pyridinium dichromate and the resulting mixture was stirred at room temperature for 20 hours. After adding 100 ml of diethyl ether, the reaction mixture was filtered through celite. After concentrating under reduced pressure, the residue was purified by silica gel column chromatography (eluted with dichloromethane/methanol) to thereby give 0.321 g of the title compound as a colorless oily substance.

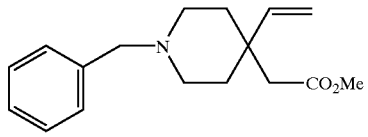

$^1$H-NMR(CDCl$_3$) δ ppm: 1.66(m, 2H), 1.78–1.84(m, 2H), 2.30–2.35(m, 2H), 2.37(s, 2H), 2.49–2.55(m, 2H), 3.48(s, 2H), 3.61(s, 3H), 5.01(d, J=17 Hz, 1H), 5.15(d, J=11 Hz, 1H), 5.76(dd, J=11, 17 Hz, 1H), 7.30–7.32(m, 5H)

Example 295

4-(1-Benzyl-4-hydroxypiperidin-4-yl)benzaldehyde

Starting with 0.74 g of magnesium, 6.42 g of 4-bromobenzaldehyde dimethyl acetal and 50 ml of tetrahydrofuran, a Grignard reagent was prepared in a conventional manner. Then it was ice-cooled and 10 ml of a solution of 5.67 ml of 1-benzyl-4-piperidone in tetrahydrofuran was dropped thereinto in such a manner that the bulk temperature did not exceed 20° C. After stirring at room temperature for 1 hour, 50 ml of a saturated aqueous solution of ammonium chloride was added thereto and then 1 N-hydrochloric acid was added until the pH value reached about 2. After stirring for 1 hour, the reaction mixture was concentrated under reduced pressure and the tetrahydrofuran was distilled off. To the residue were added anhydrous potassium carbonate and ethyl acetate and the resulting mixture was stirred for 15 minutes. The organic layer was separated, washed with water and a saturated aqueous solution of sodium chloride and dried over anhydrous sodium sulfate. After distilling off the solvent under reduced pressure, the residue was purified by silica gel column chromatography (eluted with n-hexane/ethyl acetate) to thereby give 4.27 g of the title compound as a slightly yellow solid.

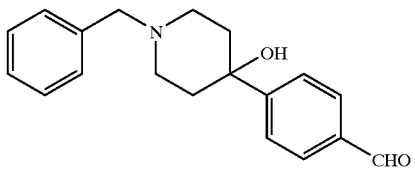

$^1$H-NMR(CDCl$_3$) δ ppm: 1.69–1.78(m, 3H), 2.18(dt, J=4.6, 13.3 Hz, 2H), 2.47(dt, J=2.6, 13.3 Hz, 2H), 2.79–2.86 (m, 2H), 3.59(s, 2H), 7.25–7.29(m, 1H), 7.31–7.38(m, 4H), 7.68–7.72(m, 2H), 7.85–7.89(m, 2H), 10.00(s, 1H)

Example 296

4-(1-Benzyl-4-hydroxypiperidin-4-yl)-2-methoxybenzaldehyde dimethyl acetal 15.0 g of 4-bromo-2-methoxybenzaldehyde dimethyl acetal was dissolved in 150 ml of ether and the obtained solution was cooled to −50° C. Then 25.3 ml of a 1.6 M solution of n-butyllithium in hexane was dropped thereinto. 1 hour thereafter, 30 ml of a solution of 11.7 ml of 1-benzyl-4-piperidone in diethyl ether was dropped thereinto in such a manner that the bulk temperature did not exceed −35° C. After stirring at room temperature for 50 minutes, water was added thereto followed by extraction with ethyl acetate. The organic layer was washed with water and a saturated aqueous solution of sodium chloride and dried over anhydrous sodium sulfate. After distilling off the solvent under reduced pressure, 23.82 g of a pale yellow oily substance was obtained. 13.82 g of this oily substance was purified by silica gel column chromatography (eluted with dichloromethane/methanol) to thereby give 6.31 g of the title compound as a pale yellow solid.

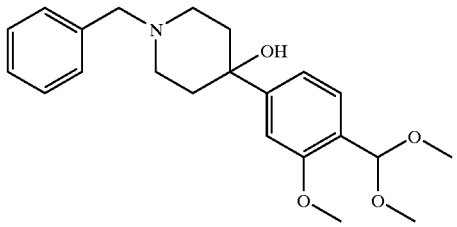

$^1$H-NMR(CDCl$_3$) δ ppm: 1.59(s, 1H), 1.68–1.76(m, 2H), 2.11–2.22(m, 2H), 2.42–2.52(m, 2H), 2.77–2.84(m, 2H), 3.36(s, 6H), 3.59(s, 2H), 3.86(s, 3H), 5.64(s, 1H), 7.01–7.11 (m, 2H), 7.24–7.29(m, 2H) 7.31–7.38(m, 3H), 7.48(dd, J=0.5, 7.7 Hz, 1H)

Example 297

4-(1-Benzyl-4-hydroxypiperidin-4-yl)-2-methoxybenzaldehyde

To 10.0 g of 4-(1-benzyl-4-hydroxypiperidin-4-yl)-2-methoxybenzaldehyde dimethyl acetal were added 100 ml of toluene and 6.15 g of p-toluenesulfonic acid monohydrate and the resulting mixture was heated under reflux for 1 hour. To the reaction mixture were added water and triethylamine followed by extraction with ethyl acetate. The organic layer was washed with water and a saturated aqueous solution of sodium chloride and dried over anhydrous sodium sulfate. After distilling off the solvent under reduced pressure, the residue was purified by silica gel column chromatography (eluted with dichloromethane/methanol) to thereby give 3.43 g of the title compound as a pale brown oily substance.

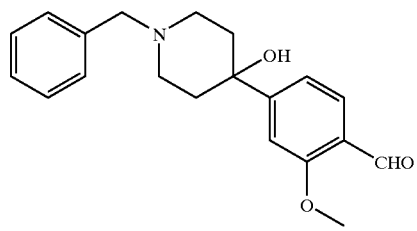

$^1$H-NMR(CDCl$_3$) δ ppm: 1.67–1.78(m, 3H), 2.13–2.22 (m, 2H), 2.41–2.50(m, 2H), 2.79–2.87(m, 2H), 3.60(s, 2H), 3.94(s, 3H), 7.14(ddd, J=0.7, 1.6, 8.1 Hz, 1H), 7.22(d, J=1.6 Hz, 1H), 7.24–7.38(m, 5H), 7.80(d, J=8.1 Hz, 1H), 10.4(s, 1H)

Example 298

4-[1-Benzyl-4-(3-methoxy-4-[2-methylthio-2-(methylsulfinyl)-vinyl]phenyl]piperidin-4-ol 3.43 g of 4-(1-benzyl-4-hydroxypiperidin-4-yl)-2-methoxybenzaldehyde was dissolved in 30 ml of tetrahydrofuran. To the resulting solution were added 2.42 ml of methyl methylsulfinylmethyl sulfoxide and 2 ml of a 40% solution of benzyltrimethylammonium hydroxide in methanol and the resulting mixture was heated under reflux for 3 hours. After concentrating the reaction mixture, water was added thereto followed by extraction with ethyl acetate. The organic layer was washed with water and a saturated aqueous solution of sodium chloride and dried over anhydrous sodium sulfate. After distilling off the solvent under reduced pressure, the residue was purified by silica gel column chromatography (eluted with dichloromethane/methanol) to thereby give 4.58 g of the title compound as a pale yellow oily substance.

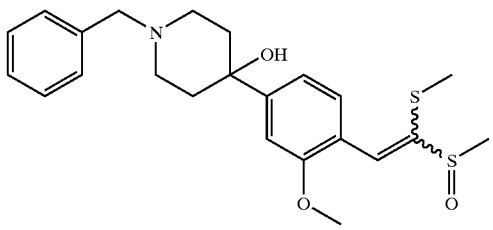

¹H-NMR(CDCl₃) δ ppm: 1.71–1.78(m, 2H), 1.94(br.s, 1H), 2.13–2.23(m, 2H), 2.29(s, 3H), 2.44–2.53(m, 2H), 2.75(s, 3H), 2.79–2.85(m, 2H), 3.60(s, 2H), 3.85(s, 3H), 7.10–7.14(m, 2H), 7.24–7.39(m, 5H), 7.95(s, 1H), 8.12(d, J=8.6 Hz, 1H)

Example 299

4-[1-Benzyl-4-[4-[2-methylthio-2-(methylsulfinyl) vinyl]phenyl-piperidin-4-ol

The title compound was obtained as a pale yellow oily substance by the same method as the one of Example 298.

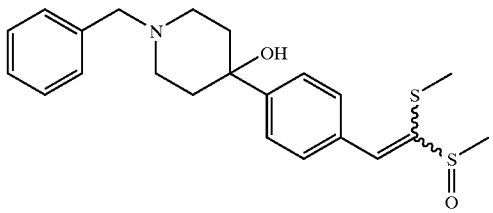

¹H-NMR(CDCl₃) δ ppm: 1.70–1.78(m, 3H), 2.13–2.23 (m, 2H), 2.32(s, 3H), 2.44–2.52(m, 2H), 2.76(s, 3H), 2.78–2.84(m, 2H), 3.59(s, 2H), 7.30–7.38(m, 4H), 7.56–7.60(m, 2H), 7.60(s, 1H), 7.58–7.91(m, 2H)

Example 300

Methyl 4-(1-benzyl-4-hydroxypiperidin-4-yl)-2-methoxyphenyl-acetate 4.58 g of 4-[1-benzyl-4-[3-methoxy-4-[2-methylthio-2-(methylsulfinyl)vinyl]phenyl]piperidin-4-ol was dissolved in 100 ml of a 10% solution of hydrogen chloride in methanol and the solution was heated under reflux for 1 hour and 40 minutes. Then the reaction mixture was concentrated under reduced pressure. After adding an aqueous solution of sodium carbonate, the mixture was extracted with ethyl acetate. The organic layer was washed with water and a saturated aqueous solution of sodium chloride and dried over anhydrous sodium sulfate. After distilling off the solvent under reduced pressure, 3.41 g of the title compound was obtained as a slightly brown oily substance.

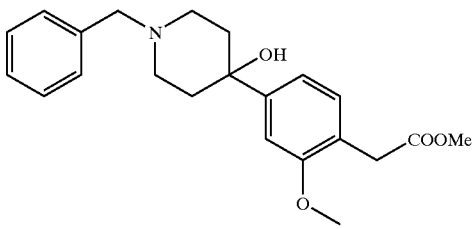

¹H-NMR(CDCl₃) δ ppm: 1.58(br.s, 1H), 1.69–1.76(m, 2H), 2.11–2.21(m, 2H), 2.43–2.51(m, 2H), 2.77–2.83(m, 2H), 3.59(s, 2H), 3.61(s, 2H), 3.69(s, 3H), 3.82(s, 3H), 7.03(dd, J=1.8, 7.7 Hz, 1H), 7.07(d, J=1.8 Hz, 1H), 7.15(d, J=7.7 Hz 1H), 7.24–7.38(m, 5H)

Example 301

Methyl 4-(1-benzyl-4-hydroxypiperidin-4-yl) phenylacetate

The title compound was obtained as a pale yellow oily substance by the same method as the one of Example 300.

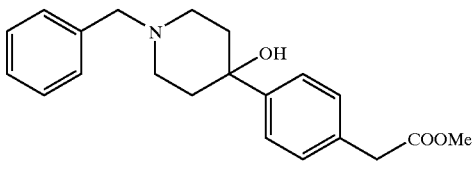

¹H-NMR(CDCl₃) δ ppm: 1.54(br.s, 1H), 1.69–1.76(m, 2H), 2.15(dt, J=4.6, 13.2 Hz, 2H), 2.47(dt, J=2.6, 13.2 Hz, 2H), 2.75–2.82(m, 2H)3.58(s, 2H), 3.62(s, 2H), 3.69(s, 3H), 7.24–7.28(m, 3H), 7.30–7.38(m, 4H), 7.46–7.49(m, 2H)

Example 302

Methyl 4-(1-benzyl-1,2,5,6-tetrahydropyrid-4-yl)-2-methoxy-phenylacetate 3.41 g of methyl 4-(1-benzyl-4-hydroxypiperidin-4-yl)-2-methoxyphenylacetate was dissolved in 50 ml of toluene. After adding 3.5 g of p-toluenesulfonic acid monohydrate, the mixture was heated under reflux for 1 hour and 45 minutes. After adding water and triethylamine, the reaction mixture was extracted with dichloromethane and the organic layer was dried over anhydrous sodium sulfate. After distilling off the solvent under reduced pressure, 3.6 g of a pale yellow oily substance was obtained.

This product was dissolved in 100 ml of a 10% solution of hydrogen chloride in methanol and heated under reflux for 2 hours. The reaction mixture was concentrated under reduced pressure. After adding an aqueous solution of sodium hydrogencarbonate, the mixture was extracted with ethyl acetate. The organic layer was washed with water and a saturated aqueous solution of sodium chloride and dried over anhydrous sodium sulfate. After distilling off the solvent under reduced pressure, the residue was purified by silica gel column chromatography (eluted with dichloromethane/methanol) to thereby give 2.28 g of the title compound as a pale yellow oily substance.

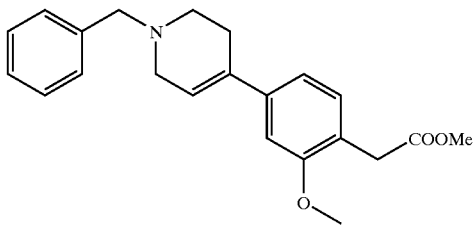

¹H-NMR(CDCl₃) δ ppm: 2.52–2.58(m, 2H), 2.71(t, J=5.9 Hz, 2H), 3.17(dd, J=2.7, 5.9 Hz, 2H), 3.61(s, 2H), 3.64(s, 2H), 3.68(s, 3H), 3.81(s, 3H), 6.04(m, 1H), 6.88(d, J=1.6 Hz, 1H), 6.93(dd, J=1.6, 7.7 Hz, 1H), 7.11(d, J=7.7 Hz, 1H), 7.24–7.40(m, 5H)

Example 303

[1-[1-tert-Butoxycarbonyl)piperidin-4-yl]butan-1-one oxime 3.1 g of [1-(1-tert-butoxycarbonyl)piperidin-4-yl]butan-1-one was dissolved in 20 ml of ethanol. After adding 1 g of hydroxylamine hydrochloride and 1.5 g of sodium acetate, the resulting mixture was heated under reflux for 2.5 hours. The reaction mixture was concentrated under reduced pressure and water was added to the residue followed by extraction with ethyl acetate. The organic layer was washed with water and dried over anhydrous magnesium sulfate. After distilling off the solvent under reduced pressure, the residue was purified by silica gel column chromatography (eluted with n-hexane/ethyl acetate) to thereby give 2.3 g of the title compound as white crystals.

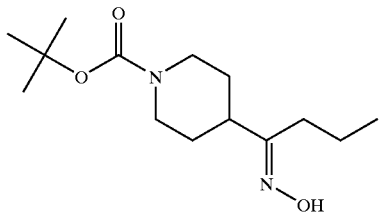

¹H-NMR(CDCl₃) δ ppm: 0.96(t, J=7.2 Hz, 3H), 1.40–1.60(m, 5H), 1.45(s, 9H), 1.69–1.80(m, 2H), 2.22–2.33(m, 2H), 2.62–2.78(m, 2H), 4.03–4.25(m, 2H)

Example 304

Ethyl [(1-(tert-butoxycarbonyl)piperidin-4-yl]butan-1-yl]iminoxyacetate 2.3 g of [1-[1-tert-butoxycarbonyl)piperidin-4-yl]butan-1-one oxime was dissolved in 10 ml of N,N-dimethylformamide and ice-cooled. After adding 0.41 g of 70% sodium hydride, 1.1 ml of ethyl bromoacetate was further added and the resulting mixture was stirred for 1 hour. After adding ice-water, the reaction mixture was extracted with ethyl acetate. The organic layer was washed with water and a saturated aqueous solution of sodium chloride and dried over anhydrous magnesium sulfate. After distilling off the solvent under reduced pressure, the residue was purified by silica gel column chromatography (eluted with n-hexane/ethyl acetate) to thereby give 2.47 g of the title compound as a pale yellow oily substance.

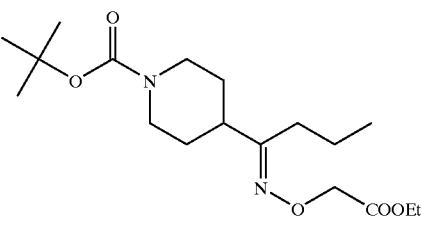

¹H-NMR(CDCl₃) δ ppm: 0.96(t, J=7.6 Hz, 3H), 1.27(t, J=7.2 Hz, 3H), 1.37–1.60(m, 5H), 1.46(s, 9H), 1.65–1.77(m, 2H), 2.23–2.31(m, 2H), 2.64–2.78(m, 2H), 4.04–4.26(m, 2H), 4.20(q, J=7.2 Hz, 2H), 4.55(s, 2H)

Example 305

Ethyl [(1-tert-butoxycarbonyl)piperidin-4-yl]-2-hydroxyacetate

To a solution of 6.1 g of diisopropylamine in tetrahydrofuran (60 ml) was added a 1.6 M solution of 38 ml of n-butyllithium in hexane and the resulting mixture was stirred at 0° C. for 30 minutes. After cooling the reaction mixture to −70° C., a solution of 10.6 g of ethyl [1-(tert-butoxycarbonyl)piperidin-4-yl]acetate in tetrahydrofuran (40 ml) was dropped thereinto. After 1 hour, 26 g of MoPH [peroxymolybdenum(pyridine)(hexamethylphosphorous triamide)]was added thereto and the resulting mixture was slowly heated to room temperature over 5 hours. After adding water, the reaction mixture was extracted with ethyl acetate. The organic layer was washed with water and a saturated aqueous solution of sodium chloride and dried over anhydrous magnesium sulfate. After distilling off the solvent under reduced pressure, the residue was purified by silica gel column chromatography (eluted with n-hexane/ethyl acetate) to thereby give 3.9 g of the title compound as a pale yellow oily substance.

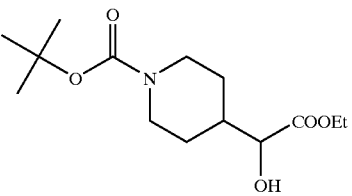

¹H-NMR(CDCl₃) δ ppm: 1.32(t, J=7.2 Hz, 3H), 1.39–1.45(m, 2H), 1.45(s, 9H), 1.60–1.67(m, 2H), 1.82–1.93(m, 1H), 2.59–2.74(m, 2H), 2.75(d, J=6.0 Hz, 1H), 4.05(dd, J=3.5, 6.0 Hz, 1H), 4.08–4.25(m, 2H), 4.27(q, J=7.2 Hz, 2H)

Example 306

Ethyl [(1-(tert-butoxycarbonyl)piperidin-4-yl]-2-oxoacetate

By the same method as the one of Production Example 73, the title compound was obtained as a pale yellow oily substance.

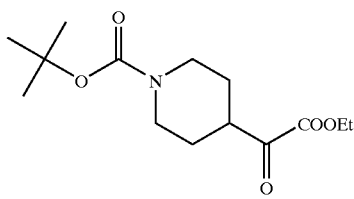

¹H-NMR(CDCl₃) δ ppm: 1.38(t, J=7.2 Hz, 3H), 1.45(s, 9H), 1.47–1.62(m, 2H), 1.84–1.93(m, 2H), 2.79–2.93(m, 2H), 3.16–3.25(m, 1H), 4.03–4.17(m, 2H), 4.33(q, J=7.2 Hz, 2H)

Example 307

Ethyl [(1-benzylpiperidin-4-yl)carbamoyl]aminoacetate 2 g of 4-amino-1-benzylpiperidine was dissolved in 15 ml of tetrahydrofuran. After adding 1.6 g of ethyl isocyanatoacetate, the resulting mixture was heated under reflux for 1 hour. Then the reaction mixture was concentrated under reduced pressure to thereby give 3.15 g of the title compound as white crystals.

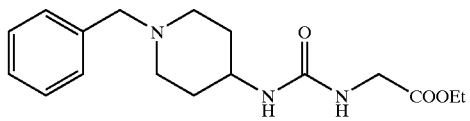

¹H-NMR(CDCl₃) δ ppm: 1.28(t, J=7.2 Hz, 3H), 1.41–1.52(m, 2H), 1.88–1.97(m, 2H), 2.07–2.17(m, 2H), 2.77–2.86(m, 2H), 3.51(s, 2H), 3.52–3.65(m, 1H), 3.97(d, J=5.2 Hz, 2H), 4.20(q, J=7.2 Hz, 2H), 4.52(br.d, J=8.5 Hz, 1H), 5.39(br.t, J=5.2 Hz, 1H), 7.22–7.35(m, 5H)

Example 308

Ethyl [4-(tert-butoxycarbonyl)aminopiperidin-1-yl]acetate 2 g of 4-(tert-butoxycarbonyl)aminopiperidine was dissolved in 50 ml of dichloromethane. After adding 1.6 ml of triethylamine and 1.2 ml of ethyl bromoacetate, the resulting mixture was stirred at room temperature for 5 hours. The reaction mixture was washed with water and dried over anhydrous magnesium sulfate. After distilling off the solvent under reduced pressure, the residue was purified by silica gel column chromatography (eluted with dichloromethane/methanol) to thereby give 3.0 g of the title compound as pale yellow crystals.

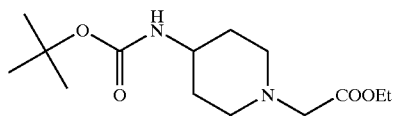

¹H-NMR(CDCl₃) δ ppm: 1.27(t, J=7.2 Hz, 3H), 1.44(s, 9H), 1.44–1.58(m, 2H), 1.88–1.97(m, 2H), 2.21–2.32(m, 2H), 2.85–2.95(m, 2H), 3.20(s, 2H), 3.42–3.53(m, 1H), 4.18(q, J=7.2 Hz, 2H), 4.39–4.49(m, 1H)

Examples 309 to 312

Similar to Example 308, 4-(tert-butoxycarbonyl)aminopiperidine was treated with a halogenated fatty acid ester or an acid halide to thereby give the following compounds.

| Ex. | Structural formula | NMR |
|---|---|---|
| 309 | ethyl 3-[4-(tert-butoxycarbonyl)aminopiperidin-1-yl]propanoate | ¹H-NMR (CDCl₃) δ ppm: 1.25 (t, J = 7.2 Hz, 3H), 1.35–1.52 (m, 2H), 1.45 (s, 9H), 1.87–1.97 (m, 2H), 2.08–2.18 (m, 2H), 2.49 (t, J = 7.4 Hz, 2H), 2.70 (t, J = 7.4 Hz, 2H), 2.78–2.88 (m, 2H), 3.41–3.52 (m, 1H), 4.13 (q, J = 7.2 Hz, 2H), 4.37–4.47 (m, 1H) |
| 310 | ethyl 4-[4-(tert-butoxycarbonyl)aminopiperidin-1-yl]butanoate | ¹H-NMR (CDCl₃) δ ppm: 1.25 (t, J = 7.2 Hz, 3H), 1.37–1.49 (m, 2H), 1.43 (s, 9H), 1.81 (quint, J = 7.4 Hz, 2H), 1.87–1.97 (m, 2H), 2.05–2.14 (m, 2H), 2.32 (t, J = 7.4 Hz, 2H), 2.37 (t, J = 7.4 Hz, 2H), 2.80–2.89 (m, 2H), 3.40–3.54 (m, 1H), 4.11 (q, J = 7.2 Hz, 2H), 4.39–4.49 (m, 1H) |
| 311 | ethyl 3-[4-(tert-butoxycarbonyl)aminopiperidin-1-yl]-3-oxopropanoate | ¹H-NMR (CDCl₃) δ ppm: 1.25–1.40 (m, 2H), 1.29 (t, J = 7.2 Hz, 3H), 1.45 (s, 9H), 1.93–2.07 (m, 2H), 2.73–2.83 (m, 1H), 3.12–3.20 (m, 1H), 3.44 (d, J = 14.7 Hz, 1H), 3.48 (d, J = 14.7 Hz, 1H), 3.62–3.76 (m, 2H), 4.20 (q, J = 7.2 Hz, 2H), 4.43–4.57 (m, 2H) |

| Ex. | Structural formula | NMR |
|---|---|---|
| 312 | 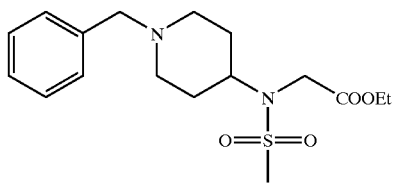

ethyl [4-(tert-butoxycarbonyl)aminopiperidin-1-yl]2-oxoacetate | $^1$H-NMR (CDCl$_3$) δ ppm: 1.33–1.42 (m, 2H), 1.36 (t, J = 7.2 Hz, 3H), 1.44 (s, 9H), 1.97–2.07 (m, 2H), 2.82–2.90 (m, 1H), 3.12–3.20 (m, 1H), 3.61–3.77 (m, 2H), 4.32 (q, J = 7.2 Hz, 2H), 4.36–4.52 (m, 2H) |

Example 313

Ethyl N-(methanesulfonyl)-N-(1-benzylpiperidin-4-yl)aminoacetate

By the same method as those of Examples 308 and 316, the title compound was obtained as a pale yellow oily substance from 1-benzylpiperidine.

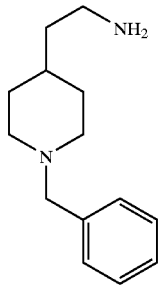

$^1$H-NMR(CDCl$_3$) δ ppm: 1.28(t, J=7.2 Hz, 3H), 1.57–1.70(m, 2H), 1.77–1.84(m, 2H), 2.01–2.11(m, 2H), 2.91–2.98(m, 2H), 3.10(s, 3H), 3.49(br.s, 2H), 3.59–3.69(m, 1H), 4.01(s, 2H), 4.17(q, J=7.2 Hz, 2H), 7.23–7.35(m, 5H)

Example 314

4-Aminomethyl-1-benzylpiperidine

To a solution of 2.2 g of 1-benzylisonipecotamide in 50 ml of tetrahydrofuran was added 1.58 g of lithium aluminum hydride at 0° C. and the resulting mixture was heated under reflux for 2 hours. Then the reaction mixture was cooled to 0° C. After adding water and a 10% aqueous solution of sodium hydroxide, the insoluble matters were filtered off. After distilling off the solvent under reduced pressure, 2.0 g of the title compound was obtained as a brown oily substance.

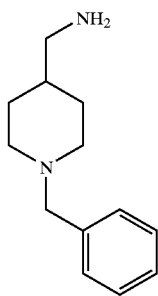

$^1$H-NMR(CDCl$_3$) δ ppm: 1.2–1.4(m, 3H), 1.4–1.8(m, 2H), 1.8–1.9(m, 2H), 1.94(br.t, J=10 Hz, 2H), 2.56(d, J=5 Hz, 2H), 2.90(d, J=10 Hz, 2H), 3.49(s, 2H), 7.2–7.4(m, 5H)

Example 315

2-(1-Benzylpiperidin-4-yl)ethylamine

By the same method of the one of Example 314, 0.5 g of (1-benzylpiperidin-4-ylidene)acetonitrile was treated to thereby give 0.5 g of the title compound as a brown oily substance.

$^1$H-NMR(CDCl$_3$) δ ppm: 1.2–1.4(m, 6H), 1.5–1.7(m, 2H), 1.93(br.t, J=10 Hz, 2H), 2.71(t, J=8 Hz, 1H), 2.87(br.d, J=10 Hz, 2H), 3.46(s, 2H), 7.2–7.4(m, 5H)

Example 316

N-(1-Benzylpiperidin-4-yl)methanesulfonamide

To a solution of 5.0 g of 4-amino-1-benzylpiperidine in 100 ml of dichloromethane were added 4.1 ml of pyridine and 2.2 ml of methanesulfonyl chloride at 0° C. Then the mixture was reacted at the same temperature for 1 hour. The reaction mixture was poured into water, extracted with ethyl acetate, washed with a saturated aqueous solution of sodium chloride and dried over anhydrous magnesium sulfate. After distilling off the solvent under reduced pressure, the crystals thus precipitated were taken up by filtration to thereby give 7.0 g of the title compound as colorless crystals.

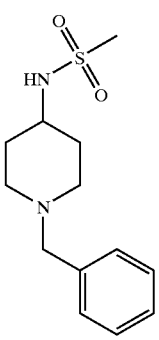

¹H-NMR(DMSO-d₆) δ ppm: 1.36–1.48(m, 2H), 1.77 (br.d, J=11 Hz, 2H), 1.96(t, J=12 Hz, 2H), 2.70(br.d, J=12 Hz, 2H), 2.88(s, 3H), 3.0–3.16(m, 1H), 3.40(s, 2H), 7.03(d, J=7 Hz, 1H), 7.18–7.34(m, 5H)

Examples 317 to 325

The procedure of Example 316 was repeated by using known acid chlorides or acid anhydrides as a substitute for the methanesulfonyl chloride to thereby give the following compounds.

| Ex. | Structural formula | NMR |
| --- | --- | --- |
| 317 | 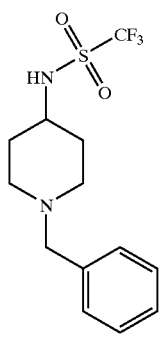<br>N-(1-benzylpiperidin-4-yl)trifluoromethanesulfonamide | ¹H-NMR (DMSO-d₆) δ ppm: 1.5–1.63 (m, 2H), 1.70–1.85 (m, 2H), 2.75–2.95 (m, 2H), 3.20–3.40 (m, 3H), 3.43–3.65 (m, 2H), 7.20–7.40 (m, 5H), 9.45 (s, 1H) |
| 318 | 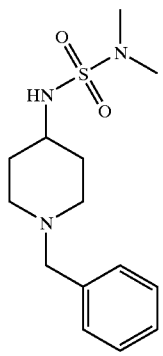<br>N-(1-benzylpiperidin-4-yl)-N',N'-dimethylsulfamide | ¹H-NMR (DMSO-d₆) δ ppm: 1.7–2.2 (m, 4H), 2.61 (s, 6H), 2.9–3.4 (m, 7H), 7.41 (br.s, 4H), 7.58 (br.s, 2H) |

-continued
| Ex. | Structural formula | NMR |
|---|---|---|
| 319 | 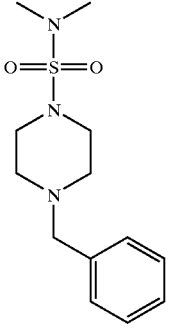<br>N,N-(3-aza-3-benzylpentamethylene)-N,N'-dimethylsulfamide | ¹H-NMR (CDCl₃) δ ppm: 2.46–2.56 (m, 4H), 2.82 (s, 6H), 3.24–3.32 (m, 4H), 3.54 (br.s, 2H), 7.24–7.37 (m, 5H) |
| 320 | 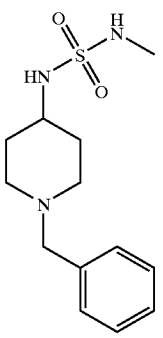<br>N-(1-benzylpiperidin-4-yl)-N'-methylsulfamide | ¹H-NMR (DMSO-d₆) δ ppm: 1.34–1.50 (m, 2H), 1.7–1.84 (m, 2H), 1.84–1.96 (m, 2H), 2.40 (d, J = 5 Hz, 3H), 2.66–2.76 (m, 2H), 2.84–2.96 (m, 1H), 3.40 (s, 2H), 6.58 (d, J = 5 Hz, 1H), 6.85 (d, J = 5 Hz, 1H), 7.18–7.33 (m, 5H) |
| 321 | 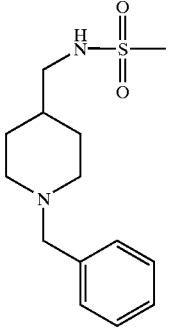<br>N-[(1-benzylpiperidin-4-yl)methyl]methanesulfonamide | ¹H-NMR (CDCl₃) δ ppm: 1.2–1.35 (m, 2H), 1.4–1.6 (m, 1H), 1.71 (d, J = 13 Hz, 2H), 1.95 (t, J = 13 Hz, 2H), 2.90 (d, J = 10 Hz, 2H), 2.94 (s, 3H), 3.00 (t, J = 8 Hz, 2H), 3.49 (s, 2H), 4.4–4.6 (m, 1H), 7.2–7.35 (m, 5H) |

| Ex. | Structural formula | NMR |
|---|---|---|
| 322 | 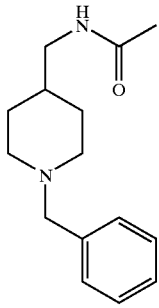<br>N-[(1-benzylpiperidin-4-yl)methyl]acetamide | $^1$H-NMR (CDCl$_3$) δ ppm: 1.2–1.34 (m, 2H), 1.4–1.56 (m, 1H), 1.6–1.7 (m, 2H), 1.88–1.98 (m, 2H), 2.00 (s, 3H), 2.84–2.94 (m, 2H), 3.13 (t, J = 6 Hz, 2H), 3.48 (s, 2H), 5.5–5.6 (m, 1H), 7.2–7.4 (m, 5H) |
| 323 | 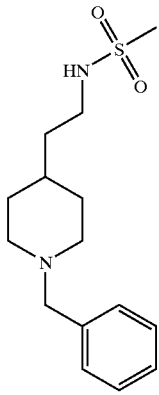<br>N-[2-(1-benzyl piperidin-4-yl)ethyl] methanesulfonamide | $^1$H-NMR (CDCl$_3$) δ ppm: 1.2–1.4 (m, 5H), 1.43–1.55 (m, 2H), 1.64 (br.d, J = 10 Hz, 2H), 1.93 (br.t, J = 10 Hz, 2H), 2.86 (br.d, J = 10 Hz, 2H), 2.93 (s, 3H), 3.15 (t, J = 5 Hz, 1H), 3.46 (s, 2H), 7.2–7.4 (m, 5H) |
| 324 | 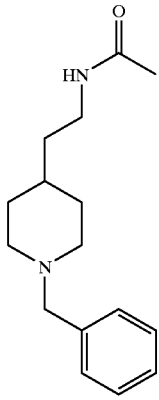<br>N-[2-(1-benzyl piperidin-4-yl)ethyl]acetamide | $^1$H-NMR (CDCl$_3$) δ ppm: 1.1–1.4 (m, 5H), 1.4 (m, 2H), 1.5–1.8 (m, 2H), 1.8–2.2 (m, 2H), 1.95 (s, 3H), 2.87 (br.d, J = 10 Hz, 2H), 3.2–3.3 (m, 1H), 3.48 (s, 2H), 7.2–7.4 (m, 5H) |

| Ex. | Structural formula | NMR |
|---|---|---|
| 325 | 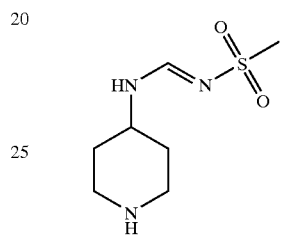<br>N-[1-(diphenyl methylazetidin-3-yl)methyl] methanesulfonamide | $^1$H-NMR (CDCl$_3$) δ ppm: 2.59 (m, 1H), 2.95 (m, 2H), 2.98 (s, 3H), 3.26 (t, J = 7 Hz, 2H), 3.37 (m, 2H), 4.34 (s, 1H), 5.04 (br.s, 1H), 7.07–7.38 (m, 10H) |

Example 326

N-(1-Benzylpiperidin-4-yl)sulfamide

To a solution of 3.0 g of 4-amino-1-benzylpiperidine in dimethoxyethane (20 ml) was added 1.35 g of sulfamide. The resulting mixture was stirred at 100° C. for 10 minutes and then reacted at 130° C. for 1 hour. After distilling off the solvent under reduced pressure, 4.0 g of the title compound was obtained as a brown oily substance.

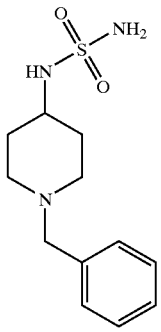

$^1$H-NMR(DMSO-d$_6$) δ ppm: 1.35–1.50(m, 2H), 1.7–1.9 (m, 2H), 1.9–2.1(m, 2H), 2.7–2.85(m, 2H), 3.0–3.1(m, 1H), 3.45(s, 2H), 6.46(s, 2H), 6.54(d, J=6 Hz, 1H), 7.2–7.4(m, 5H)

Example 327

N$^2$-Methanesulfonyl-N$^1$-(piperidin-4-yl) formamidine

Into a solution of 760 mg of ethyl N-methanesulfonyl-formimidate in diethyl ether (20 ml) was dropped 0.95 g of 4-amino-1-benzylpiperidine at room temperature. After stirring for 2 hours, the crystals thus precipitated were filtered and washed with diethyl ether to thereby give 580 mg of N$^2$-methanesulfonyl-N$^1$-(1-benzylpiperidin-4-yl) formamidine as colorless needles. These crystals were dissolved in 30 ml of methanol and 500 mg of 10% palladium-carbon was added thereto. Then the resulting mixture was stirred in a hydrogen atmosphere under atmospheric pressure for 1 hour followed by filtration through celite. After distilling off the solvent under reduced pressure, the residue was recrystallized from acetone/ethyl acetate to thereby give 310 mg of the title compound as colorless needles.

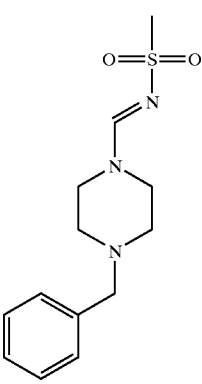

$^1$H-NMR(DMSO-d$_6$) δ ppm: 1.26(dq, J=4.1, 12.5 Hz, 2H), 1.73(br.d, J=12.5 Hz, 2H), 2.44(br.t, J=12.5 Hz, 2H), 2.83(s, 3H), 2.85(br.d, J=12.5 Hz, 2H), 3.60–3.70(br.m, 1H), 7.84(s, 1H), 8.64–8.73(br.s, 1H)

Example 328

N,N-(4-Benzylpiperazin-1-ylmethylene) methanesulfonamide

Into a solution of 1.51 g of ethyl N-methanesulfonyl-formimidate in diethyl ether/tetrahydrofuran (50%, 5 ml) was dropped a solution of 1.76 g of 1-benzylpiperazine in diethyl ether/tetrahydrofuran (50%, 50 ml) and the resulting mixture was reacted at 40° C. for 1 hour. After allowing to cool, the crystals thus precipitated were taken up by filtration and washed with diethyl ether to thereby give 2.7 g of the title compound as colorless crystals.

$^1$H-NMR(CDCl$_3$) δ ppm: 2.48(t, J=5.0 Hz, 2H), 2.52(t, J=5.0 Hz, 2H), 2.95(s, 3H), 3.47(t, J=5.0 Hz, 2H), 3.55(s, 2H), 3.68(t, J=5.0 Hz, 2H), 7.27–7.38(m, 5H), 8.06(s, 1H)

Example 329

N-(1-Benzylpiperidin-4-yl)amidinocarboxylic acid

A solution of 1.9 g of 4-amino-1-benzylpiperidine in dichloromethane (40 ml) was stirred in a nitrogen atmosphere and 20 ml of a solution of benzyl 2-ethylthio-2-iminoacetate in dichloromethane was dropped thereinto. Then the resulting mixture was stirred for 30 minutes and the solvent was distilled off under reduced pressure. To the obtained residue in the form of a colorless oily substance were added 50 ml of methanol and 50 ml of water. Then about 1 g of Dowex ($HCO_3$-form) which had been preliminarily conditioned was added thereto. After stirring for 1 hour, the resulting mixture was filtered and the Dowex-1 was well washed with methanol. After distilling off the solvent under reduced pressure, 2.3 g of the title compound was obtained as a colorless powder.

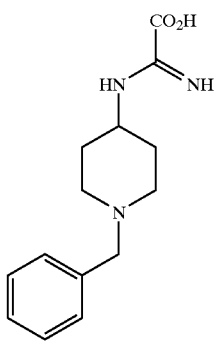

$^1$H-NMR(DMSO-$d_6$) δ ppm: 1.40–1.58(m, 1H), 1.60–1.70(m, 3H), 1.88–2.02(m, 2H), 2.71–2.83(m, 2H), 3.37–3.52(m, 1H), 3.43(s, 2H), 7.19–7.33(m, 5H), 8.62–8.69(br.s, 1H), 8.72–8.79(br.s, 1H), 8.88–8.96(br.s, 1H)

Example 330

Methyl 1-benzylpiperidine-4-carboximidate dihydrochloride

A solution of 20 g of 1-benzylpiperidine-4-carbonitrile in a mixture of dry dichlolomethane (200 ml) with methanol (30 ml) was cooled and saturated with a hydrogen chloride gas while maintaining the reaction system at 0° C. or below. After allowing to stand for 4 hours at 0° C., the solvent was distilled off under reduced pressure at room temperature or below and the residue was diluted with ethyl acetate. The colorless crystals thus obtained were ground, filtered and washed with ethyl acetate to thereby give 23.6 g of the title compound.

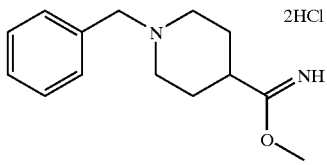

$^1$H-NMR($CD_3OD$) δ ppm: 2.12(br.q, J=13.1 Hz, 2H), 2.23(br.d, J=13.1 Hz, 2H), 3.07–3.16(br.m, 1H), 3.18(br.t, J=13.1 Hz, 2H), 3.58(br.d, J=13.1 Hz, 2H), 4.18(s, 3H), 4.36(s, 2H), 7.46–7.53(m, 3H), 7.55–7.63(m, 2H)

Example 331

$N^2$-methanesulfonyl(piperidin-4-yl)carboxamidine 6.1 g of methyl 1-benzylpiperidine-4-carboximidate dihydrochloride was distributed into an aqueous solution of potassium carbonate and ethyl acetate under ice-cooling. The organic layer was extracted and dried over anhydrous sodium sulfate. After distilling off the solvent under reduced pressure, 4.7 g of free methyl 1-benzylpiperidine-4-carboximidate was obtained as a colorless oily substance. A solution of 2.35 g of methyl 1-benzylpiperidine-4-carboximidate and 0.95 g (10 mmol) of methanesulfonamide in dry methanol was stirred at room temperature for 3 days. Subsequently, 1.0 g of palladium-carbon was added to the reaction mixture and the resulting mixture was stirred in a hydrogen atmosphere under atmospheric pressure for 1 hour. The inorganic matters were eliminated by filtering through celite. After distilling off the solvent under reduced pressure, the residue was recrystallized from methanol to thereby give 1.38 g of the title compound as colorless needles.

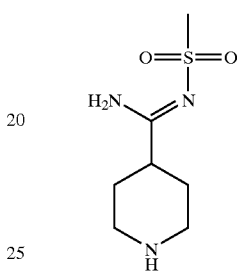

$^1$H-NMR(DMSO-$d_6$) δ ppm: 1.43(dq, J=4.1, 12.8 Hz, 2H), 1.56(br.d, J=12.8 Hz, 2H), 2.21–2.31(m, 1H), 2.38(br.t, J=12.8 Hz, 2H), 2.83(s, 3H), 2.91(br.d, J=12.8 Hz, 2H), 7.51–7.65(br.s, 1H), 8.27–8.39(br.s, 1H)

Example 332

$N^2$-Methanesulfonyl(4-benzylpiperazin-1-yl)carboxamidine

A solution of 2.52 g of 2-methyl-3-methanesulfonylisothiourea and 1.76 g of 1-benzylpiperazine in toluene (10 ml) and tetrahydrofuran (5 ml) was heated under reflux in a nitrogen atmosphere for 5 days. (In the course of this heating treatment, 2.52 g of 2-methyl-3-methanesulfonylisothiourea and 1.76 g of 1-benzylpiperazine were further added thereto). After distilling off the solvent under reduced pressure from the reaction mixture, the obtained residue was purified by silica gel column chromatography (eluted with dichloromethane/methanol). After recrystallizing from diisopropyl ether, 1.7 g of the title compound was obtained as colorless crystals.

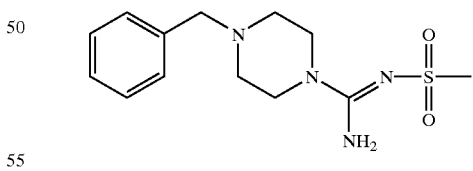

$^1$H-NMR($CDCl_3$) δ ppm: 2.46(t, J=5.0 Hz, 4H), 2.95(s, 3H), 3.48(t, J=5.0 Hz, 4H), 3.53(s, 2H), 6.02–6.16(br.s, 2H), 7.25–7.37(m, 5H)

Example 333

N-(Piperidin-4-yl)benzenesulfonamide

4-Amino-1-benzylpiperidine was treated successively by the same methods as those of Examples 316 and 20 to thereby give 7.0 g of the title compound as a pale yellow oily substance.

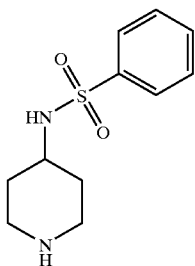

¹H-NMR(DMSO-d₆) δ ppm: 1.43–1.60(m, 2H), 1.60–1.75(m, 2H), 2.78–2.90(m, 2H), 3.05–3.15(m, 2H), 3.2–3.4(m, 1H), 7.55–7.65(m, 3H), 7.81(d, J=8 Hz, 2H), 8.0(m, 1H)

Example 334

4-[1-(tert-Butoxycarbonyl)piperidin-4-yl]-2-butenenitrile

The title compound was obtained as a pale yellow oily substance by the same method as the one of Production Example 25.

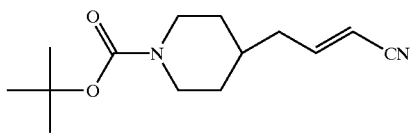

¹H-NMR(CDCl₃) δ ppm: 1.45(s, 9H), 1.62(m, 4H), 2.08 (t, J=7 Hz, 2H), 2.39(m, 1H), 2.70(br.s, 2H), 4.05(br.s, 2H), 5.32 and 5.38(dt, J=2, 16 Hz and 2, 10 Hz, 1H trans/cis≈2:1), 6.50 and 6.66(dt, J=7, 10 Hz and 7, 16 Hz, 1H cis/trans≈1:2)

Example 335

4-[1-(tert-Butoxycarbonyl)piperidin-4-yl]butyronitrile

The title compound was obtained as a pale yellow oily substance by the same method as the one of Example 20.

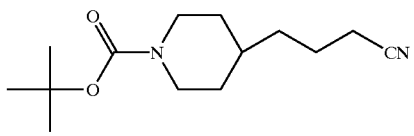

¹H-NMR(CDCl₃) δ ppm: 1.10(m, 2H), 1.41(m, 3H), 1.45(s, 9H), 1.56(m, 4H), 2.34(t, J=7 Hz, 2H), 2.65(m, 2H), 4.08(br.s, 2H)

Example 336

N-Methyl-2-(piperidin-4-yl)ethanesulfonamide acetate 500 mg of N-methyl-2-(piperidin-4-yl)ethanesulfonamide was dissolved in 15 ml of acetic acid. After adding 180 mg of platinum oxide, the resulting mixture was subjected to catalytic reduction at room temperature under a hydrogen pressure of 6 atm. After filtering off the insoluble matters, the acetic acid was distilled off under reduced pressure. The crystals thus precipitated were well washed with diethyl ether and dried under reduced pressure. Thus 664 mg of the title compound was obtained as white crystals almost quantitatively.

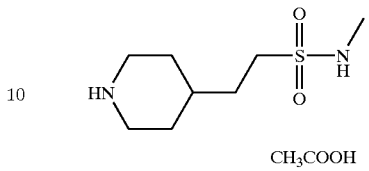

CH₃COOH

¹H-NMR(CDCl₃) δ ppm: 1.55(br.q, J=12 Hz, 2H), 1.72–1.78(m, 3H), 1.84(d, J=12 Hz, 2H), 1.88(s,3H),2.55(s, 3H),2.62(br.s,2H),2.93–3.04(m,4H),6.89(br.s,1H)

Example 337

N,N-Dimethyl-2-(piperidin-4-yl)ethanesulfonamide acetate

The title compound was obtained as white crystals by the same method as the one of Example 336.

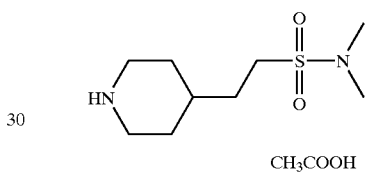

CH₃COOH

¹H-NMR(CDCl₃) δ ppm: 1.18(q, J=12 Hz, 2H), 1.46–1.58(m, 3H), 1.71(br.d, J=12 Hz, 2H), 1.78(s, 3H), 2.58(br.t, J=12 Hz, 2H), 2.74(s, 6H), 3.01(m, 2H), 3.06(m, 2H)

Example 338

[5-[1-(tert-Butoxycarbonyl)piperidin-4-yl]-3-oxo-2-methyl-4-penten-2-yl]acetate

The title compound was obtained as a colorless oily substance by treating [1-(tert-butoxycarbonyl)piperidin-4-yl]carbaldehyde and (4-diethylphosphono-3-oxo-2-methylbutan-2-yl]acetate by the same method as the one of Production Example 25.

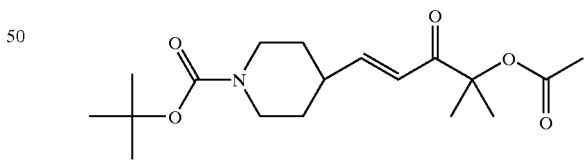

¹H-NMR(CDCl₃) δ ppm: 1.33(br.d, J=13 Hz, 2H), 1.46(s, 9H), 1.48(s, 6H), 1.72(br.d, J=13 Hz, 2H), 2.07(s, 3H), 2.29(m, 1H), 2.76(t, J=12 Hz, 2H), 4.11(br.s, 2H), 6.31(dd, J=2, 16 Hz, 1H), 6.97(dd, J=7, 16 Hz, 1H)

Example 339

[5-[1-(tert-Butoxycarbonyl)piperidin-4-yl]-3-oxo-2-methyl-pentan-2-yl]acetate

The title compound was obtained as a colorless oily substance by treating [5-[1-(tert-butoxycarbonyl)piperidin- 4-yl]-3-oxo-2-methyl-4-penten-2-yl]acetate by the same method as the one of Example 20.

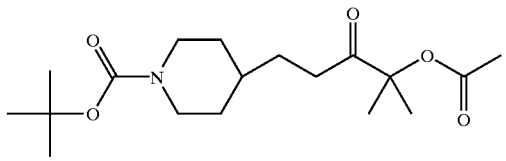

¹H-NMR(CDCl₃) δ ppm: 1.08(qd, J=4, 12 Hz, 2H), 1.34–1.42(m, 1H), 1.45(s, 9H), 1.46(s, 6H), 1.51–1.56(m, 2H), 1.60–1.65(br.d, J=12 Hz, 2H), 2.08(s, 3H), 2.45(t, J=7 Hz, 2H), 2.66(t, J=11 Hz, 2H), 4.06(br.s, 2H)

Example 340

[5-[1-(tert-Butoxycarbonyl)piperidin-4-yl]-2-hydroxy-2-methyl]-3-pentanone

The title compound was obtained as a colorless oily substance by treating [5-[1-(tert-butoxycarbonyl)piperidin-4-yl]-3-oxo-2-methylpentan-2-yl]acetate by the same method as the one of Production Example 96.

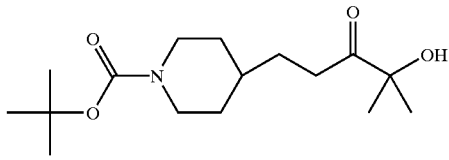

¹H-NMR(CDCl₃) δ ppm: 1.10(qd, J=4, 12 Hz, 2H), 1.37(s, 6H), 1.45(s, 9H), 1.35–1.58(m, 3H)1.64(d, J=12 Hz, 2H), 2.67(t, J=8 Hz, 2H), 2.75(m, 2H), 3.74(s, 1H), 4.08 (br.s, 2H)

Example 341

3-(tert-Butoxycarbonyl)-3-azabicyclo[3.3.0]octan-7-ol 386 mg of ³-(tert-butoxycarbonyl)-3-azabicyclo[3.3.0]-octan-7-one synthesized in accordance with the method described in Tetrahedron, 49, 5047 (1993) was dissolved in 20 ml of ethanol. After adding 65 mg of sodium borohydride, the resulting mixture was stirred at room temperature for 30 minutes. Then the reaction mixture was concentrated under reduced pressure, diluted with ethyl acetate, washed with water and a saturated aqueous solution of sodium chloride and then dried over anhydrous magnesium sulfate. After filtering, the solvent was distilled off under reduced pressure and the residue was purified by silica gel column chromatography (eluted with n-hexane/ethyl acetate) to thereby give 319 mg of the title compound as white crystals.

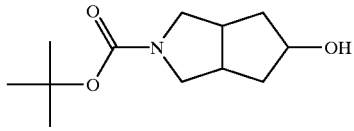

¹H-NMR(CDCl₃) δ ppm: 1.42–1.55(m, 2H), 1.45(s, 9H), 1.69(s, 1H), 2.12–2.22(m, 2H), 2.54–2.66(m, 2H), 3.34(dd, J=3.6, 11.2 Hz, 2H), 3.49(dd, J=8.0, 11.2 Hz, 2H), 4.29(q, J=6.4 Hz, 1H)

Example 342

Methyl 1-(tert-butoxycarbonyl)-1,2,3,6-tetrahydro-4-pyridinecarboxylate 4.62 g of methyl 1-benzyl-1,2,3,6-tetrahydro-4-pyridinecarboxylate was dissolved in 30 ml of dichloromethane. Under ice-cooling, 4.29 g of 1-chloroethyl chloroformate was added thereto and the resulting mixture was heated under reflux for 2 hours. After adding 50 ml of methanol, the mixture was stirred at 70° C. for 1 hour and 20 minutes. Then triethylamine was added to the reaction mixture under ice-cooling until the pH value of the mixture exceeded 7. After further adding 4.37 g of tert-butyl dicarbonate, the resulting mixture was stirred at room temperature for 10 minutes. Then the reaction mixture was concentrated under reduced pressure, diluted with ethyl acetate, washed successively with water and a saturated aqueous solution of sodium chloride and dried over anhydrous magnesium sulfate. After filtration, the solvent was distilled off under reduced pressure and the obtained residue was purified by silica gel column chromatography (eluted with n-hexane/ethyl acetate) to thereby give 4.46 g of the title compound as a yellow oily substance.

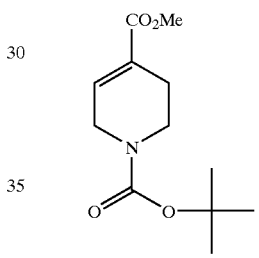

¹H-NMR(CDCl₃) δ ppm: 1.47(s, 9H), 2.40(br.s, 2H), 3.51(t, J=5.6 Hz, 2H), 3.76(s, 3H), 4.07(d, J=2.4 Hz, 2H), 6.88(br.s, 1H)

Example 343

1-(tert-Butoxycarbonyl)-1,2,3,6-tetrahydropyridine-4-methanol 17.6 g of methyl 1-(tert-butoxycarbonyl)-1,2,3,6-tetrahydro-4-pyridinecarboxylate was dissolved in 300 ml of tetrahydrofuran. After adding 4.77 g of lithium tetrahydroborate and then 20 ml of methanol, the resulting mixture was stirred at room temperature for 20 minutes. Saturated ammonium chloride was added to the reaction mixture under ice-cooling and the resulting mixture was concentrated under reduced pressure. The residue was diluted with ethyl acetate, washed successively with water and a saturated aqueous solution of sodium chloride and dried over anhydrous magnesium sulfate followed by filtration. After distilling off the solvent under reduced pressure, the obtained residue was purified by silica gel column chromatography (eluted with n-hexane/ethyl acetate) to thereby give 10.7 g of the title compound as a colorless oily substance.

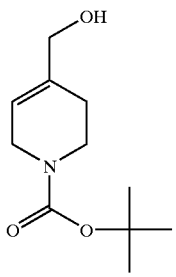

¹H-NMR(CDCl₃) δ ppm: 1.47(s, 9H), 1.64(br.s, 1H), 2.08–2.16(m, 2H), 3.47–3.58(m, 2H), 3.91(br.s, 2H), 4.06(br.s, 2H), 5.64(br.s, 1H)

Example 344

[3-(tert-Butoxycarbonyl)-3-azabicyclo[4.1.0]hept-6-yl]methanol

Under ice-cooling, 15.3 ml of diethylzinc and 6.7 g of diiodomethane were added to 130 ml of dichloromethane. After further adding a solution of 1.07 g of 1-(tert-butoxycarbonyl)-1,2,3,6-tetrahydropyridine-4-methanol in dichloromethane (20 ml), the resulting mixture was stirred at room temperature overnight. Then the reaction mixture was poured into saturated ammonium chloride, extracted with ethyl acetate, washed with a saturated aqueous solution of sodium chloride and dried over anhydrous magnesium sulfate followed by filtration. After distilling off the solvent under reduced pressure, the obtained residue was purified by silica gel column chromatography (eluted with n-hexane/ethyl acetate) to thereby give 90 mg of the title compound as a colorless oily substance.

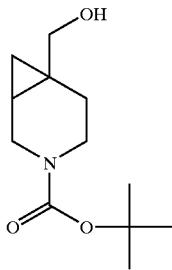

¹H-NMR(CDCl₃) δ ppm: 0.38(t, J=5.2 Hz, 1H), 0.58and0.60(d, J=5.2 Hz, total1H), 0.92–1.00(m, 1H), 1.08–1.20(m, 1H), 1.44(s, 9H), 1.93and1.97(t, J=5.6 Hz, total1H), 3.06and3.09(dd, J=5.2, 8.4 Hz, total1H), 3.37–3.43(m, 2H), 3.51and3.55(d, J=5.2 Hz, total1H), 3.58and3.72(d, J=1.6 Hz, total1H), 4.08–4.17(m, 1H)

Example 345

Ethyl [1-(tert-butoxycarbonyl)piperidin-4-ylidene]acetate 51.0 g of ethyl (1-benzylpiperidin-4-ylidene)acetate was dissolved in 200 ml of dichloroethane. After adding 36.5 g of 1-chloroethyl chloroformate under ice-cooling, the resulting mixture was heated under reflux for 2 hours. After adding 100 ml of methanol, the resulting mixture was further heated under reflux for 40 minutes and then allowed to stand at room temperature overnight. Then 60 g of triethylamine was added to the reaction mixture under ice-cooling. Further, 300 ml of methanol was added thereto and the system was made homogeneous. Next, 47.2 g of tert-butyl dicarbonate was added and the resulting mixture was stirred at room temperature for 20 minutes. The reaction mixture was concentrated under reduced pressure, diluted with ethyl acetate, washed successively with 1 N hydrochloric acid, water, a saturated aqueous solution of sodium chloride and saturated sodium hydrogencarbonate and dried over anhydrous magnesium sulfate followed by filtration. After distilling off the solvent under reduced pressure, the crude crystals thus obtained were ground and washed with hexane to thereby give 15.2 g of the title compound. The filtrate was concentrated and the residue was purified by silica gel column chromatography (eluted with n-hexane/ethyl acetate) to thereby give 37.8 g of the additional title compound as colorless crystals.

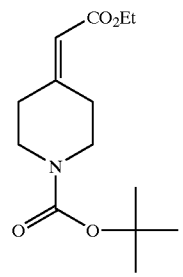

¹H-NMR(CDCl₃) δ ppm: 1.28(t, J=7.2 Hz, 3H), 1.47(s, 9H), 2.25–2.31(m, 2H), 2.91–2.96(m, 2H), 3.45–3.53(m, 4H), 4.15(q, J=7.2 Hz, 2H), 5.71(t, J=1.2 Hz, 1H)

Example 346

Ethyl [1-(tert-buxycarbonyl)-1,2,3,6-tetrahydro-pyridin-4-yl]acetate 53.0 g of ethyl [1-(tert-butoxycarbonyl)-piperidin-4-ylidene]acetate was dissolved in 400 ml of toluene. After adding 3 g of 1,8-diazabicyclo[5.4.0]-7-undecene, the resulting mixture was heated under reflux for 4 days. After concentrating the reaction mixture under reduced pressure, the residue was purified by silica gel column chromatography (eluted with n-hexane/ethyl acetate) to thereby give 31.9 g of the title compound as a colorless oily substance.

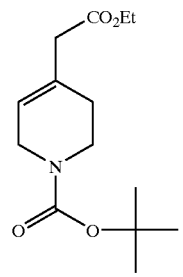

¹H-NMR(CDCl₃) δ ppm: 1.27(t, J=7.2 Hz, 3H), 1.46(s, 9H), 2.12–2.37(m, 2H), 3.02(s, 2H), 3.51(t, J=6.0 Hz, 2H), 3.88–3.92(m, 2H), 4.15(q, J=7.2 Hz, 2H)5.52(br.s, 1H)

Example 347

2-[1-(tert-Butoxycarbonyl)-1,2,3,6-tetrahydropyridin-4-yl]ethanol

The title compound was obtained as a colorless oily substance by treating ethyl [1-(tert-butoxycarbonyl)-1,2,3, 6-tetrahydropyridin-4-yl]acetate by the same method as the one of Example 343.

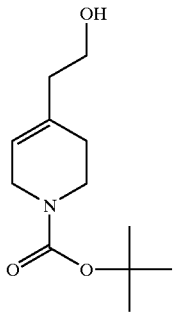

$^1$H-NMR(CDCl$_3$) δ ppm: 1.47(s, 9H), 2.05–2.12(m, 2H), 2.24–2.32(m, 2H), 3.50(t, J=6.0 Hz, 2H), 3.71(t, J=6.0 Hz, 2H), 3.86–3.90(m, 2H), 5.46–5.51(m, 1H)

Example 348

2-[1-(Benzyloxycarbonyl)-1,2,3,6-tetrahydropyridin-4-yl ethanol 11.76 g of 2-(1-benzyl-1,2,3,6-tetrahydropyridin-4-yl) ethanol was dissolved in 100 ml of tetrahydrofuran. After adding 100 ml of a 4 N solution of hydrogen chloride in dioxane, the resulting mixture was stirred at room temperature for 8 hours and 20 minutes. Then the reaction mixture was concentrated under reduced pressure and the residue was dissolved in a mixture of tetrahydrofuran (100 ml) with a 4 N solution of sodium hydroxide (70 ml). Under ice-cooling, 9.7 g of benzyloxycarbonyl chloride was dropped thereinto over 25 minutes and the resulting mixture was stirred for 40 minutes. The reaction mixture was concentrated under reduced pressure, diluted with ethyl acetate, washed with a saturated aqueous solution of sodium chloride and dried over anhydrous magnesium sulfate followed by filtration. After distilling off the solvent under reduced pressure, the obtained residue was purified by silica gel column chromatography (eluted with n-hexane/ethyl acetate) to thereby give 11.4 g of the title compound as a colorless oily substance.

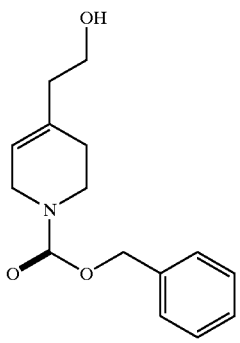

$^1$H-NMR(CDCl$_3$) δ ppm: 1.62(s, 1H), 2.11(br.s, 2H), 2.29(t, J=6.0 Hz, 2H), 3.59(t, J=6.0 Hz, 2H), 3.71(t, J=6.0 Hz, 2H), 3.95–4.00(m, 2H), 5.15(s, 2H), 5.49(br.s, 1H), 7.15–7.20(m, 5H)

Example 349

2-[3-(Benzyloxycarbonyl)-3-azabicyclo[4.1.0]hept-6-yl]ethanol

Under ice-cooling, 75 ml of diethylzinc and 33.5 g of diiodomethane were added to 500 ml of dichloroethane. After further adding a solution of 6.53 g of 2-[1-(benzyloxycarbonyl)-1,2,3,6-tetrahydropyridin-4-yl]ethanol in dichloroethane (20 ml), the resulting mixture was stirred at room temperature for 6 days. Then the reaction mixture was poured into a mixture of saturated ammonium chloride with 1 N hydrochloric acid, washed with a saturated aqueous solution of sodium chloride and dried over anhydrous magnesium sulfate followed by filtration. After distilling off the solvent under reduced pressure, the obtained residue was purified by silica gel column chromatography (eluted with n-hexane/ethyl acetate) to thereby give 1.22 g of the title compound as an oily substance.

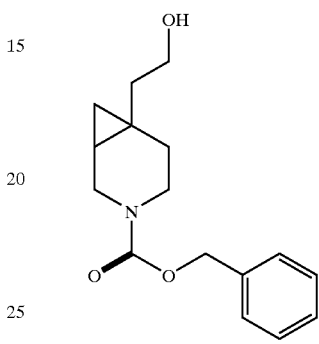

$^1$H-NMR(CDCl$_3$) δ ppm: 0.38–0.40(m, 1H), 0.50–0.54 (m, 1H), 0.84–0.93(m, 1H), 60–1.83(m, 2H), 2.05–2.16(m, 1H), 2.06–2.12(m, 1H), 3.23–3.28(m, 1H), 3.57–3.62(m, 1H), 3.68–3.78(m, 3H), 3.98(s, 1H), 5.12(s, 1H), 5.15(s, 1H), 7.28–7.40(m, 5H)

Example 350

6-(tert-Butoxycarbonyl)-4,5,6,7-tetrahydro-6H-thieno[2,3-c]pyridine

The title compound was obtained as a yellow oily substance by the same method as the one described in Journal of Heterocyclic Chemistry, 27, 1169 (1990).

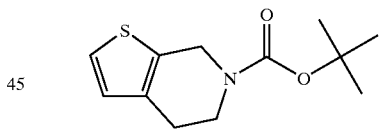

$^1$H-NMR(CDCl$_3$) δ ppm: 1.49(s, 9H), 2.68–2.74(m, 2H), 3.65–3.71(m, 2H), 4.63(br.s, 2H), 6.79(d, J=5.2 Hz, 1H), 7.14(d, J=5.2 Hz, 1H)

Example 351

[6-(tert-Butoxycarbonyl)-4,5,6,7-tetrahydro-6H-thieno[2,3-c]pyridin-2-yl]carbaldehyde To a solution of 0.63 g of diisopropylamine in 10 ml of tetrahydrofuran was added 3.7 ml of a 1.6 M solution of n-butyllithium in hexane and the resulting mixture was stirred at 0° C. for 30 minutes. After cooling the reaction mixture to −70° C., a solution of 1.0 g of 6-(tert-butoxycarbonyl)-4,5,6,7-tetrahydro-6H-thieno[2,3-c] pyridine in 10 ml of tetrahydrofuran was dropped thereinto followed by the addition of N,N,N,N-tetramethylethylenediamine. After stirring for 1 hour, 1.0 ml of N,N-dimethylformamide was added and stirring was continued for additional 2 hours. After adding a saturated aqueous solution of ammonium chloride, the reaction mixture was extracted with ethyl acetate. The organic layer was washed with water and a saturated aqueous solution of sodium chloride and dried over anhydrous magnesium sulfate. After distilling off the solvent under reduced pressure, the residue was purified by silica gel column chromatography (eluted with n-hexane/ethyl acetate) to thereby give 0.35 g of the title compound as a yellow oily substance.

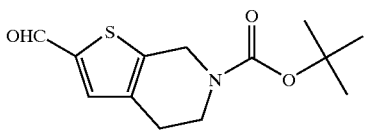

$^1$H-NMR(CDCl$_3$) δ ppm: 1.49(s, 9H), 2.73–2.79(m, 2H), 3.67–3.73(m, 2H), 4.68(br.s, 2H), 7.48(s, 1H), 9.85(s, 1H)

Example 352

2-[(1,3-Dithiacyclohexan-2-ylidene)methyl]-6-(tert-butoxycarbonyl)-4,5,6,7-tetrahydro-6H-thieno[2,3-c]pyridine The title compound was obtained as pale yellow crystals by the same method as the one of Production Example 62.

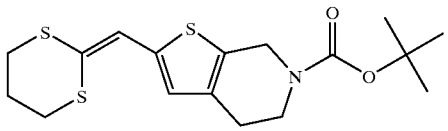

$^1$H-NMR(CDCl$_3$) δ ppm: 1.48(s, 9H), 2.21(quint, J=6.0 Hz, 2H), 2.60–2.69(m, 2H), 2.98(t, J=6.0 Hz, 2H), 3.01(t, J=6.0 Hz, 2H), 3.60–3.70(m, 2H), 4.59(br.s, 2H), 6.76(s, 1H), 6.93(s, 1H)

Example 353

N-[8-Methyl-8-azabicyclo[3.2.1]oct-3-yl]-[7-(tert-butoxy-carbonyl)-7-azaspiro[3.5]non-2-yl]acetamide 1.7 g of [7-(tert-butoxycarbonyl)-7-azaspiro[3.5]non-2-yl]acetic acid was dissolved in 50 ml of dichloromethane. After adding 0.9 ml of triethylamine, the resulting mixture was ice-cooled. After adding 0.95 ml of ethyl chloroformate, the resulting mixture was stirred at room temperature for 30 minutes. Then 1.9 g of 3-amino-8-methyl-8-azabicyclo[3.2.1]octane dihydrochloride and 2.5 ml of triethylamine were added thereto and the resulting mixture was stirred at room temperature for 6 hours. After adding water, the reaction mixture was extracted with ethyl acetate. The organic layer was washed with 1 N sodium hydroxide and dried over anhydrous magnesium sulfate. After distilling off the solvent under reduced pressure, the obtained crystals were washed with ether to thereby give 1.25 g of the title compound as white crystals.

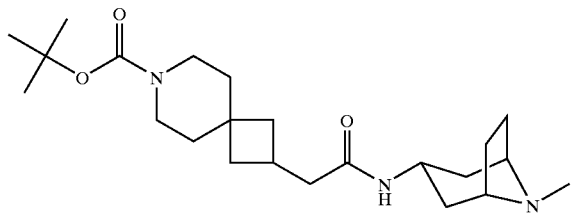

$^1$H-NMR(CDCl$_3$) δ ppm: 1.41–1.52(m, 4H), 1.45(s, 9H), 1.55–1.87(m, 4H), 1.67–1.74(m, 2H), 2.02–2.10(m, 2H), 2.12–2.18(m, 2H), 2.18–2.25(m, 2H), 2.27(d, J=9.0 Hz, 2H), 2.28(s, 3H), 2.56–2.68(m, 1H), 3.12–3.18(m, 2H), 3.22–3.28(m, 2H), 3.31–3.36(m, 2H), 4.02–4.10(m, 1H), 5.75(br.d, J=9.0 Hz, 1H)

Example 354

[2-(Benzyloxycarbonyl)-2-azaspiro[4.5]dec-8-yl]methanol 4.72 g of ethyl[4-(ethoxycarbonyl)-1-(nitromethyl)cyclohex-1-yl]acetate was dissolved in 60 ml of ethanol. After adding 0.5 g of 10% palladium-carbon (moisture content: 50%) and 5.93 g of ammonium formate, the resulting mixture was heated to 60° C. for 1 hour. After allowing to cool, the reaction mixture was filtered and concentrated under reduced pressure. After adding tetrahydrofuran to the residue, the insoluble matters were filtered off. After concentrating under reduced pressure, 4.06 g a slightly pink oily substance was obtained.

This oily substance was heated to 180° C. for 2 hours and purified by silica gel column chromatography (eluted with dichloromethane/methanol) to thereby give 2.19 g of a dark pinky red solid. This product was dissolved in 10 ml of tetrahydrofuran and dropped under ice-cooling into 40 ml of a suspension of 0.69 g of lithium aluminum hydride in tetrahydrofuran. After stirring at room temperature for 30 minutes, the reaction mixture was heated under reflux for 4 hours. Then it was ice-cooled and 0.7 ml of water, 15% sodium hydroxide and 2.1 ml of water were successively added thereto. Further, celite was added thereto and the resulting mixture was stirred at room temperature for 20 minutes. After filtration, it was concentrated under reduced pressure to thereby give 1.73 g of a slightly yellow oily substance.

This product was dissolved in 25 ml of methanol and 0.5 g of 10% palladium-carbon (moisture content: 50%) was added thereto. The resulting mixture was stirred at room temperature under a hydrogen pressure of 1 atm for 4 hours and then heated to 60° C. for 3 hours and 20 minutes. After allowing to cool, the reaction mixture was filtered and concentrated under reduced pressure to thereby give 1.48 g of a colorless oily substance.

This product was dissolved in 14 ml of tetrahydrofuran and added to 14 ml of an aqueous solution of 0.666 g of anhydrous potassium carbonate. Then the mixture was cooled to −2° C. and 1.31 ml of benzyl chloroformate was dropped thereinto while maintaining the bulk temperature at 0° C. or below. After the completion of the addition, the resulting mixture was stirred under ice-cooling for 45 minutes. Then ice-water was added to the reaction mixture followed by the extraction with ethyl acetate. The organic layer was washed with water and a saturated aqueous solution of sodium chloride and dried over anhydrous sodium sulfate. After concentrating under reduced pressure, the residue was purified by silica gel column chromatography (eluted with dichloromethane/methanol) to thereby give 2.21 g of the title compound as a colorless oily substance.

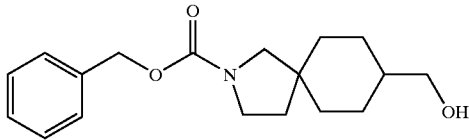

¹H-NMR(CDCl₃) δ ppm: 0.97–1.17(m, 2H), 1.28–1.78 (m, 10H), 3.15–3.28(m, 2H), 3.42–3.52(m, 4H), 5.12, 5.13 (s, total 2H), 7.28–7.40(m, 5H)

Example 355

Methyl[2-(benzyloxycarbonyl)-2-azaspiro[4.5]dec-8-yl]carboxylate

The following compound was obtained as a colorless oily substance by the same method as those of Production Examples 73 and 74.

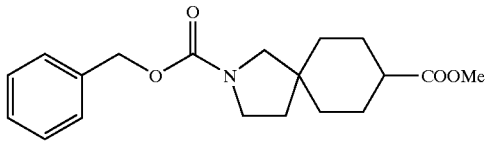

¹H-NMR(CDCl₃) δ ppm: 1.28–1.46(m, 2H), 1.55–1.92 (m, 8H), 2.25–2.38(m, 1H), 3.13–3.31(m, 2H), 3.42–3.51 (m, 2H), 3.67, 3.68(s, total 3H), 5.12, 5.13(s, total 2H), 7.29–7.39(m, 5H)

Example 356

2-Hydroxyphenyl(1-benzylpiperidin-4-yl)sulfamate

To a solution of 9.56 g of 1-benzyl-4-aminopiperidine in N,N-dimethylformamide (125 ml) was added 5.56 g of triethylamine at a temperature of 5° C. or lower. Next, a solution of 9.45 g of catechol sulfate [J. Org. Chem., 45 (26), 5371 (1980)] in dichloromethane (20 ml) was dropped thereinto and the resulting mixture was stirred for 2.5 hours. The reaction mixture was poured into 500 ml of a 1% aqueous solution of sodium chloride and extracted with diethyl ether thrice. The organic layer was washed with water 6 times, dried over anhydrous magnesium sulfate and filtered. After distilling off the solvent under reduced pressure, the residue was purified by silica gel column chromatography (eluted with dichloromethane/methanol) to thereby give 19.08 g of the title compound as a colorless oily substance.

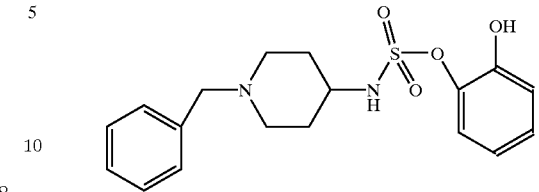

¹H-NMR(CDCl₃) δ ppm: 1.58(dq, J=4, 12 Hz, 2H), 1.96(d, J=12 Hz, 2H), 2.08(t, J=12 Hz, 2H), 2.81(m, 2H), 3.44(m, 1H), 3.48(s, 2H), 4.95(br.s, 2H), 6.83(dt, J=2, 8 Hz, 1H), 6.91(dd, J=2, 8 Hz, 1H), 7.10(dt, J=2, 8 Hz, 1H), 7.22(dd, J=2, 8 Hz, 1H), 7.24–7.32(m, 5H)

Example 357

N-(1-Benzylpiperidin-4-yl)-N',N'-pentamethylenesulfamide

To a solution of 1.81 g of 2-hydroxyphenyl(1-benzylpiperidin-4-yl)sulfamate in 1,4-dioxane (25 ml) was added 0.47 g of piperidine and the resulting mixture was heated under reflux for 4 hours. Then the reaction mixture was poured into 100 ml of water and extracted with ethyl acetate. The organic layer was dried over anhydrous magnesium sulfate, filtered and distilled off under reduced pressure. The residue thus obtained was purified by silica gel column chromatography (eluted with dichloromethane/methanol) to thereby give 0.701 g of the title compound as a colorless oily substance.

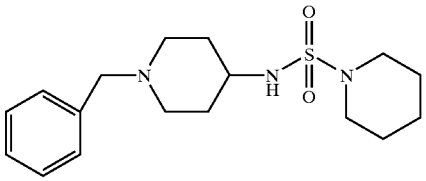

¹H-NMR(CDCl₃) δ ppm: 1.48(m, 4H), 1.58–1.66(m, 4H), 1.96(d, J=12 Hz, 2H), 2.10(t, J=12 Hz, 2H), 2.78(d, J=12 Hz, 2H), 3.14(t, J=5 Hz, 4H), 3.21(m, 1H), 3.48(s, 2H), 3.94(d, J=7 Hz, 1H), 7.22–7.35(m, 5H)

Examples 358 to 361

The following compounds were obtained by the same method as the one of Example 357.

| Ex. | Structural formula | NMR |
|---|---|---|
| 358 | N-(1-benzylpiperidin-4-yl)-N',N'-(3-oxapentamethylene)sulfamide | ¹H-NMR(CDCl₃) δ ppm: 1.64(dq, J=2, 12Hz, 2H), 1.96(br.d, J=12Hz, 2H), 2.09(t, J=12Hz, 2H), 2.80(br.d, J=12Hz, 2H), 3.17(t, J=5Hz, 4H), 3.25(m, 1H), 3.48(s, 2H), 3.74(t, J=5Hz, 4H), 4.07(d, J=8Hz, 1H), 7.22–7.35(m, 5H) |

| Ex. | Structural formula | NMR |
|---|---|---|
| 359 | N-(1-benzylpiperidin-4-yl)-N',N'-[3-(ethoxycarbonyl)pentamethylene]sulfamide | $^1$H-NMR(CDCl$_3$) δ ppm: 1.25(t, J=7Hz, 3H), 1.52(dq, J=4, 11Hz, 2H), 1.75(qd, J=3, 11Hz, 2H), 1.95(br.dt, J=3, 11Hz, 4H), 2.08(t, J=11Hz, 2H), 2.38(tt, J=3, 11Hz, 1H), 2.76–2.82(m, 4H), 3.20(m, 1H), 3.48(s, 2H), 3.62(dt, J=3, 12Hz, 2H), 4.15(d, J=8Hz, 1H), 4.16(q, J=7Hz, 2H), 7.22–7.34(m, 5H) |
| 360 | N-(1-benzylpiperidin-4-yl)-N'-(methoxycarbonyl)methylsulfamide | $^1$H-NMR(CDCl$_3$) δ ppm: 1.53(dq, J=3, 12Hz, 2H), 1.97(br.d, J=12Hz, 2H), 2.09(t, J=12Hz, 2H), 2.79(br.d, 12Hz, 2H), 3.27(m, 1H), 3.48(s, 2H), 3.77(s, 3H), 3.82(s, 2H), 4.31(d, J=8Hz, 1H), 4.89(br.s, 1H), 7.20–7.33(m, 5H) |
| 361 | N-(1-benzylpiperidin-4-yl)-N'-(2-hydroxyethyl)sulfamide | $^1$H-NMR(CDCl$_3$) δ ppm: 1.55(dq, J=3, 12Hz, 2H), 1.98(br.d, J=12Hz, 2H), 2.09(br.t, J=12Hz, 2H), 2.81(br.d, J=12Hz, 2H), 3.19(br.s, 2H), 3.25(m, 1H), 3.48(s, 2H), 3.75(t, J=5Hz, 2H), 4.46(br.s, 1H), 4.83(br.s, 1H), 7.25–7.34(m, 5H) |

Example 362

N-(Tetrazo-5-yl)-4-[1-(tert-butoxycarbonyl)piperidin-4-yl]-butanamide

Into 20 ml of a solution of 0.883 g of 4-[1-(tert-butoxycarbonyl)piperidin-4-yl]butanoic acid in tetrahydrofuran were successively added at 0° C. in a nitrogen atmosphere 0.67 g of triethylamine and 5 ml of a solution of 1.19 g of diethyl chlorophosphate in tetrahydrofuran and the resulting mixture was then stirred at 0° C. for 2 hours. To this reaction mixture were added 0.527 g of 5-aminotetrazole and 10 ml of a solution of 0.54 g of triethylamine in tetrahydrofuran and the resulting mixture was stirred for additional 15 hours. After distilling off the solvent under reduced pressure, ethyl acetate and water were added to the residue and the pH value thereof was adjusted to 4 with formic acid. Then the aqueous layer was extracted with ethyl acetate. The organic layers were combined, dried over anhydrous magnesium sulfate and filtered. After concentrating under reduced pressure, the residue was purified by silica gel column chromatography (eluted with dichloromethane/methanol) to thereby give 0.875 g of the title compound as white crystals.

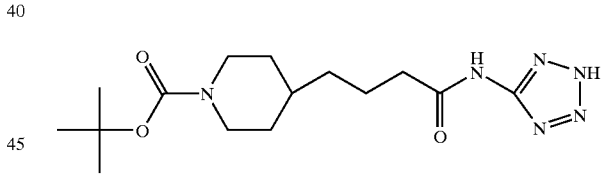

$^1$H-NMR(CDCl$_3$) δ ppm: 1.10(dq, J=5, 12 Hz, 2H), 1.38(m, 3H), 1.45(s, 9H), 1.68(m, 2H), 1.85(m, 2H), 2.67(m, 2H), 2.71(t, J=6 Hz, 2H), 4.08(m, 2H), 12.45(s, 1H)

Example 363

Methyl[3-(benzyloxycarbonyl)-3-azabicyclo[4.1.0]hept-6-yl]-acetate 1.41 g of oxalyl chloride was dissolved in 70 ml of dichloromethane and cooled to −78° C. in a nitrogen atmosphere. Into the solution was dropped a solution of 1.38 g of dimethyl sulfoxide in dichloromethane (3 ml) over 5 minutes. Further, a solution of 1.22 g of 2-[3-(benzyloxycarbonyl)-3-azabicyclo[4.1.0]hept-6-yl]ethanol in dichloromethane (10 ml) was dropped thereinto over 5 minutes. After stirring for 15 minutes, 2.24 g of triethylamine was dropped thereinto over 5 minutes and stirring was continued for additional 30 minutes. Then the reaction mixture was diluted with dichloromethane, washed with 1 N hydrochloric acid and a saturated aqueous solution of sodium chloride and dried over anhydrous magnesium sulfate followed by filtration. After distilling off the solvent under reduced pressure, the obtained residue was purified by silica gel column chromatography (eluted with n-hexane/ethyl acetate) to thereby give 450 mg of a product. Next, this compound was dissolved in 6 ml of dimethyl sulfoxide and 5 ml of an aqueous solution of 257 mg of sodium dihydrogenphosphate was added thereto. After adding 5 ml of an aqueous solution of 496 mg of sodium chlorite over 5 minutes, the resulting mixture was stirred at room temperature for 10 minutes. Then the reaction mixture was diluted with ethyl acetate, washed successively with water and a saturated aqueous solution of sodium chloride, dried over anhydrous magnesium sulfate and filtered. After distilling off the solvent under reduced pressure, the obtained residue was dissolved in 40 ml of toluene. After adding 6 ml of a 2 M solution of trimethylsilyldiazomethane in hexane and 10 ml of methanol, the resulting mixture was stirred at room temperature for 50 minutes. After concentrating the reaction mixture under reduced pressure, the obtained residue was purified by silica gel column chromatography (eluted with n-hexane/ethyl acetate) to thereby give 180 mg of the title compound as an oily substance.

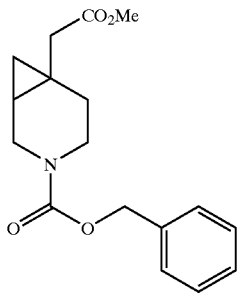

$^1$H-NMR(CDCl$_3$) δ ppm: 0.41–0.48(m, 1H), 0.54–0.66 (m, 1H), 0.88–1.04(m, 1H), 1.76–1.92(m, 2H), 2.16–2.42 (m, 2H), 3.15–3.24(m, 1H), 3.32–3.44(m, 1H), 3.60–3.68 (m, 1H), 3.68(s, 3H), 3.80–3.88(m, 1H), 5.12(s, 2H), 7.28–7.40(m, 5H)

Examples 364 to 386

Starting with known compounds, the following compounds were obtained by the same method as the one of Example 63.

| Ex. | Structural formula | NMR |
|---|---|---|
| 364 | 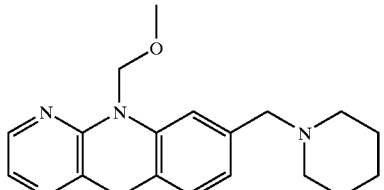<br>8-[(piperidin-1-yl)methyl-10-(methoxymethyl)-10H-pyrazino[2,3-b][1,4]benzothiazine | $^1$H-NMR(CDCl$_3$) δ ppm: 1.34–1.48(br · s, 2H), 1.54–1.62(m, 4H), 2.30–2.45(br · s, 4H), 3.41(s, 2H), 3.54(s, 3H), 5.26(s, 2H), 6.92(s, 2H), 7.12(s, 1H), 7.80(s, 2H) |
| 365 | 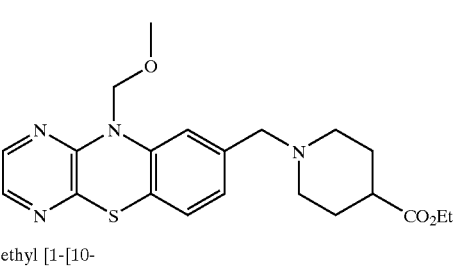<br>ethyl [1-[10-(methoxymethyl)-10H-pyrazino[2,3-b][1,4]benzothiazin-8-ylmethyl] piperidin-4-yl]carboxylate | $^1$H-NMR(CDCl$_3$) δ ppm: 1.23(t, J=6Hz, 3H), 1.60–1.80(m, 2H), 1.82–1.90(m, 2H), 1.92–2.08(m, 2H), 2.20–2.32(m, 1H), 2.75–2.85(m, 2H), 3.41(s, 2H), 3.52(s, 3H), 4.12(q, J=6Hz, 2H), 5.26(s, 2H), 6.92(d, J=8Hz, 1H), 6.94(d, J=8Hz, 1H), 7.10(s, 1H), 7.82(s, 2H) |

| Ex. | Structural formula | NMR |
|---|---|---|
| 366 | 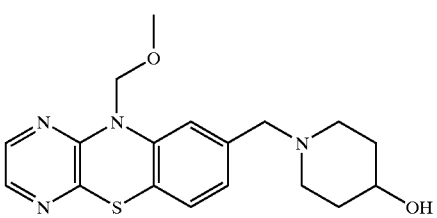<br>[1-[10-(methoxymethyl)-10H-pyrazino[2,3-b][1,4]benzothiazin-8-ylmethyl] piperidin-4-ol | ¹H-NMR(CDCl₃) δ ppm: 1.50–1.62(m, 2H), 1.80–1.90(m, 2H), 2.05–2.16(m, 2H), 2.10–2.30(br · s, 1H), 2.68–2.80(m, 2H), 3.40(s, 2H), 3.52(s, 3H), 3.60–3.70(m, 1H), 5.26(s, 2H), 6.88(d, J=8Hz, 1H), 6.92(d, J=8Hz, 1H), 7.08(s, 1H), 7.80(s, 2H) |
| 367 | 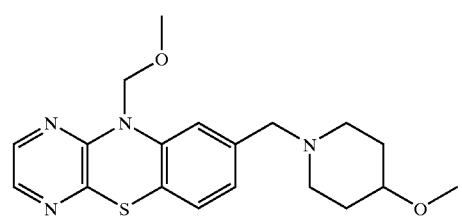<br>8-[(4-methoxypiperidin-1-yl)methyl]-10-(metoxymethyl)-10H-pyrazino[2,3-b][1,4]benzothiazine | ¹H-NMR(CDCl₃) δ ppm: 1.50–1.62(m, 2H), 1.82–1.92(m, 2H), 2.06–2.17(m, 2H), 2.64–2.74(m, 2H), 3.16–3.24(m, 1H), 3.34(s, 3H), 3.42(s, 2H), 3.54(s, 3H), 5.26(s, 2H), 6.92(d, J=8Hz, 1H), 6.94(d, J=8Hz, 1H), 7.10(s, 1H), 7.82(s, 2H) |
| 368 | 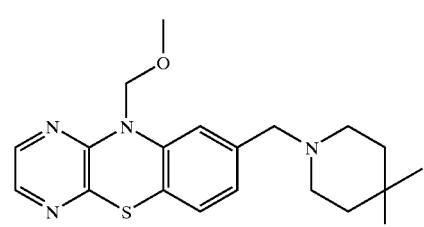<br>[1-[10-(methoxymethyl)-10H-pyrazino[2,3-b][1,4]benzothiazin-8-ylmethyl)-4-methylpiperidin-4-ol | ¹H-NMR(CDCl₃) δ ppm: 1.22(s, 3H), 1.23(s, 1H), 1.50–1.60(m, 2H), 1.60–1.70(m, 2H), 2.45–2.55(m, 2H), 2.32–2.43(m, 2H), 3.43(s, 2H), 3.54(s, 3H), 5.26(s, 2H), 6.94(s, 2H), 7.09(s, 1H), 7.80(s, 2H) |
| 369 | 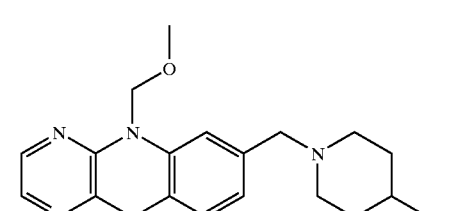<br>[1-[10-(methoxymethyl)-10H-pyrazino[2,3-b][1,4]benzothiazin-8-ylmethyl]piperidin-4-yl]carboxamide | ¹H-NMR(CDCl₃) δ ppm: 1.68–1.82(m, 2H), 1.82–1.89(m, 2H), 1.90–2.30(m, 2H), 2.08–2.20(m, 1H), 2.86–2.95(m, 2H), 3.42(s, 2H), 3.54(s, 3H), 5.26(s, 2H), 5.50–5.62(br · s, 2H), 6.92(d, J=8Hz, 1H), 6.95(d, J=8Hz, 1H), 7.09(s, 1H), 7.80(s, 2H) |

| Ex. | Structural formula | NMR |
|---|---|---|
| 370 | [1-[10-(methoxymethyl)-10H-pyrazino[2,3-b][1,4]benzothiazin-8-ylmethyl]piperidin-4-spiro-4′-(4′-butanolide) | ¹H-NMR(CDCl₃) δ ppm: 1.69–1.80(m, 2H), 1.80–1.90(m, 2H), 2.02(t, J=6Hz, 2H), 2.38–2.50(m, 2H), 2.52–2.62(m, 2H), 2.57(t, J=6Hz, 2H), 3.43(s, 2H), 3.52(s, 3H), 5.26(s, 2H), 6.92(d, J=8Hz, 1H), 6.94(d, J=8Hz, 1H), 7.08(s, 1H), 7.80(s, 2H) |
| 371 | [1-[10-(methoxymethyl)-10H-pyrazino[2,3-b][1,4]benzothiazin-8-ylmethyl]piperidin-3-yl]carboxamide | ¹H-NMR(CDCl₃) δ ppm: 1.50–1.68(m, 2H), 1.68–1.80(m, 1H), 1.78–1.90(m, 1H), 2.10–2.30(m, 1H), 2.30–2.42(m, 1H), 2.42–2.50(m, 1H), 2.58–2.70(m, 1H), 2.70–2.80(br·s, 1H), 3.35(d, J=13Hz, 1H), 3.41(d, J=13Hz, 1H), 3.49(s, 3H), 5.26(s, 2H), 5.80(br·s, 2H), 6.82(d, J=8Hz, 1H), 6.93(d, J=8Hz, 1H), 7.06(s, 1H), 7.80(s, 2H) |
| 372 | [1-[10-(methoxymethyl)-10H-pyrazino[2,3-b][1,4]benzothiazin-8-ylmethyl]piperidin-3-yl]carboxamide | ¹H-NMR(CDCl₃) δ ppm: 1.20–1.40(m, 2H), 1.50–1.70(m, 2H), 1.70–1.80(m, 1H), 1.97–2.08(m, 2H), 2.80–2.92(m, 1H), 2.92–2.97(m, 1H), 3.22(d, J=14Hz, 1H), 3.52(s, 3H), 3.82(d, J=14Hz, 1H), 5.26(s, 2H), 6.60–6.70(br·s, 2H), 6.92(d, J=8Hz, 1H), 6.97(d, J=8Hz, 1H), 7.11(s, 1H), 7.82(d, J=3Hz, 1H) |
| 373 | [1-[10-(methoxymethyl)-10H-pyrazino[2,3-b][1,4]benzothiazin-8-ylmethyl]pyrrolidin-2-yl]carboxamide | ¹H-NMR(CDCl₃) δ ppm: 1.70–1.82(m, 2H), 1.82–2.00(m, 1H), 2.15–2.30(m, 1H), 2.30–2.40(m, 1H), 3.00–3.10(m, 1H), 3.10–3.20(m, 1H), 3.42(d, J=14Hz, 1H), 3.50(s, 3H), 3.82(d, J=14Hz, 1H), 5.26(s, 2H), 5.95–6.15(br·s, 1H), 6.89(d, J=8Hz, 1H), 6.94(d, J=8Hz, 1H), 7.08(s, 1H), 7.10–7.20(br·s, 1H), 7.80(s, 2H) |

-continued

| Ex. | Structural formula | NMR |
|---|---|---|
| 374 | 2-[1-[10-(methoxymethyl)-10H-pyrazino[2,3-b][1,4]benzothiazin-8-ylmethyl]piperidin-4-yl]ethanol | $^1$H-NMR(CDCl$_3$) δ ppm: 1.20–1.36(m, 2H), 1.35–1.45(m, 1H), 1.45–1.55(m, 2H), 1.60–1.70(m, 2H), 1.90–2.00(m, 2H), 2.70–2.80(br·s, 1H), 2.80–2.90(m, 2H), 3.42(s, 2H), 3.54(s, 3H), 3.66(t, J=6Hz, 2H), 5.25(s, 2H), 6.92(s, 2H), 7.08(s, 1H), 7.81(s, 2H) |
| 375 | 8-[(2,6-dimethylpiperidin-1-yl)methyl-10-(methoxymethyl)-10H-pyrazino[2,3-b][1,4]benzothiazine | $^1$H-NMR(CDCl$_3$) δ ppm: 1.02(d, J=7Hz, 3H), 1.04(d, J=7Hz, 3H), 1.20–1.40(m, 2H), 1.50–1.70(m, 4H), 2.40–2.50(m, 2H), 3.53(s, 3H), 3.72(s, 2H), 5.24(s, 2H), 6.92(d, J=8Hz, 1H), 6.97(d, J=8Hz, 1H), 7.24(s, 1H), 7.82(s, 2H) |
| 376 | [1-[10-(methoxymethyl)-10H-pyrazino[2,3-b][1,4]benzothiazin-8-ylmethyl]piperidin-4-yl carbamate | $^1$H-NMR(CDCl$_3$) δ ppm: 1.62–1.76(m, 2H), 1.86–1.96(m, 2H), 2.18–2.30(m, 2H), 2.64–2.74(m, 2H), 3.42(s, 2H), 3.54(s, 3H), 4.50–4.70(m, 3H), 5.32(s, 2H), 6.92(d, J=8Hz, 1H), 6.94(d, J=8Hz, 1H), 7.12(s, 1H), 7.82(s, 2H) |
| 377 | 4-[1-[10-(methoxymethyl)-10H-pyrazino[2,3-b][1,4]benzothiazin-8-ylmethyl]piperidin-4-yl]butanol | $^1$H-NMR(CDCl$_3$) δ ppm: 1.16–1.30(m, 4H), 1.30–1.40(m, 2H), 1.50–1.60(m, 2H), 1.60–1.70(m, 2H), 1.70–1.90(m, 2H), 1.94(m, 2H), 2.82–2.90(m, 2H), 3.44(s, 2H), 3.54(s, 3H), 3.62(t, J=6Hz, 2H) 5.28(s, 2H), 6.92(d, J=8Hz, 1H), 6.94(d, J=8Hz, 1H), 7.09(s, 1H), 7.82(s, 2H) |

| Ex. | Structural formula | NMR |
|---|---|---|
| 378 | 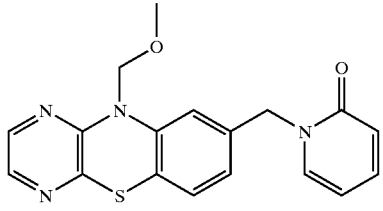<br>[1-[10-(methoxymethyl)-10H-pyrazino[2,3-b][1,4]benzothiazin-8-ylmethyl]-2-pyridone | $^1$H-NMR(CDCl$_3$) δ ppm: 3.49(s, 3H), 5.06(s, 2H), 5.22(s, 2H), 6.16(dt, J=2, 7Hz, 1H), 6.62(ddd, J=1, 2, 9Hz, 1H), 6.87(dd, J=2, 8Hz, 1H), 6.97(d, J=8Hz, 1H), 7.08(d, J=2Hz, 1H), 7.28(ddd, J=1, 2, 7Hz, 1H), 7.34(ddd, J=2, 7, 9Hz, 1H), 7.83(d, J=3Hz, 1H), 7.84(d, J=3Hz, 1H) |
| 379 | 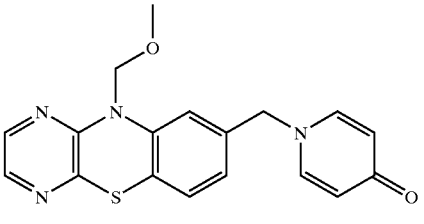<br>[1-[10-(methoxymethyl)-10H-pyrazino[2,3-b]-[1,4]benzo-thiazin-8-ylmethyl]-4-pyridone | $^1$H-NMR(CDCl$_3$) δ ppm: 3.48(s, 3H), 4.88(s, 2H), 5.22(s, 2H), 6.45(d, J=8Hz, 2H), 6.75(dd, J=1, 8Hz, 1H), 6.91(d, J=2Hz, 1H), 7.03(d, J=8Hz, 1H), 7.33(d, J=8Hz, 2H), 7.85(d, J=3Hz, 1H), 7.87(d, J=3Hz, 1H) |
| 380 | 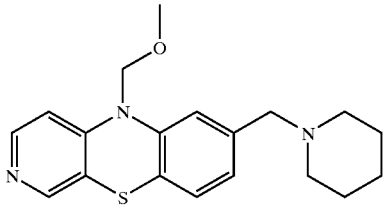<br>7-[(piperidin-1-yl)methyl]-5-(methoxymethyl)-5H-pyrido[3,4-b][1,4]benzothiazine | $^1$H-NMR(CDCl$_3$) δ ppm: 1.44(m, 2H), 1.60(m, 4H), 2.41(br·s, 4H), 3.46(s, 2H), 3.53(s, 3H), 5.03(s, 2H), 6.87(d, J=6Hz, 1H), 6.93(d, J=8Hz, 1H), 7.03(d, J=8Hz, 1H), 7.07(s, 1H), 8.17(s, 1H), 8.25(d, J=6Hz, 1H) |
| 381 | 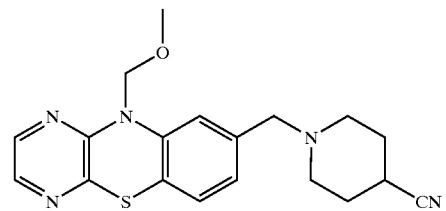<br>[1-[10-(methoxymethyl)-10H-pyrazino[2,3-b][1,4]benzothiazin-8-ylmethyl]piperidin-4-yl]carbonitrile | $^1$H-NMR(CDCl$_3$) δ ppm: 1.81–1.98(m, 4H), 2.26–2.38(m, 2H), 2.60–2.69(m, 3H), 3.43(s, 2H), 3.54(s, 3H), 5.27(s, 2H), 6.91(dd, J=1.5, 7.7Hz, 1H), 6.96(d, J=7.7Hz, 1H), 7.09(d, J=1.5Hz, 1H), 7.83(d, J=2.7Hz, 1H), 7.84(d, J=2.7Hz, 1H) |

| Ex. | Structural formula | NMR |
|---|---|---|
| 382 | 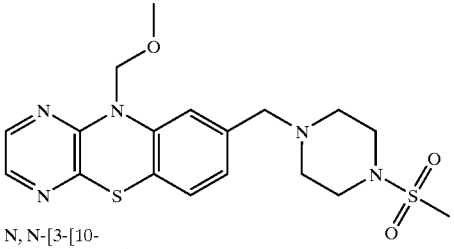<br>N, N-[3-[10-(methoxymethyl)-10H-pyrazino[2,3-b][1,4]benzothiazin-8-ylmethyl]-3-azapentamethylene]methanesulfonamide | ¹H-NMR(CDCl₃) δ ppm: 2.55(br·t, J=4.8Hz, 4H), 2.78(s, 3H), 3.23(br·t, J=4.8Hz, 4H), 3.47(s, 2H), 3.53(s, 3H), 5.28(s, 2H), 6.92(dd, J=1.5, 7.9Hz, 1H), 6.96(d, J=7.9Hz, 1H), 7.09(d, J=1.5Hz, 1H), 7.82(d, J=2.8Hz, 1H), 7.83(d, J=2.8Hz, 1H) |
| 383 | 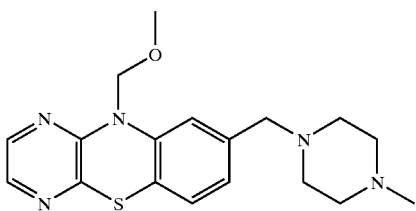<br>8-[(4-methylpiperazin-1-yl)methyl-10-(methoxymethyl)-10H-pyrazino[2,3-b][1,4]benzothiazine | ¹H-NMR(CDCl₃) δ ppm: 1.96–2.23(m, 2H), 2.28(s, 3H), 2.30–2.65(m, 6H), 3.43(s, 2H), 3.53(s, 3H), 5.23(s, 2H), 6.93(dd, J=1.4, 8.3Hz, 1H), 6.95(d, J=8.3Hz, 1H), 7.10(d, J=1.4Hz, 1H), 7.82(d, J=2.8Hz, 1H), 7.83(d, J=2.8Hz, 1H) |
| 384 | 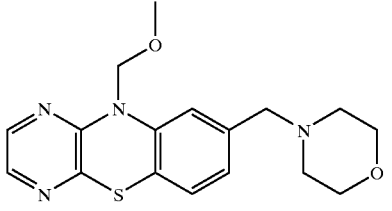<br>8-(morpholinomethyl)-10-(methoxymethyl)-10H-pyrazino[2,3-b][1,4]benzothiazine | ¹H-NMR(CDCl₃) δ ppm: 2.38–2.50(m, 4H), 3.43(s, 2H), 3.53(s, 3H), 3.68–3.75(m, 4H), 5.28(s, 2H), 6.94(dd, J=1.1, 8.0Hz, 1H), 6.96(d, J=8.0Hz, 1H), 7.12(d, J=1.1Hz, 1H), 7.83(d, J=2.8Hz, 1H), 7.84(d, J=2.8Hz, 1H), |
| 385 | 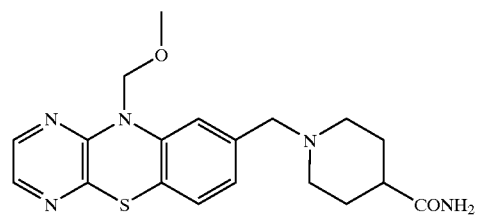<br>[1-(10-methoxymethyl)-10H-pyrazino[2,3-b][1,4]benzoxazin-8-ylmethyl)piperidin-4-yl]carboxamide | ¹H-NMR(CDCl₃) δ ppm: 1.7–1.96(m, 4H), 1.96(m, 2H), 2.1–2.24(m, 1H), 2.93(br·d, J=12Hz, 2H), 3.38(s, 2H), 3.47(s, 3H), 5.32(s, 2H), 5.50(br·s, 1H), 5.60(br·s, 1H), 6.77(s, 2H), 6.89(s, 1H), 7.42(d, J=3Hz, 1H), 7.57(d, J=3Hz, 1H) |

| Ex. | Structural formula | NMR |
|---|---|---|
| 386 | 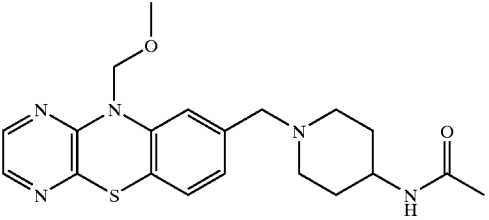<br>N-[1-[10-(methoxymethyl)-10H-pyrazino[2,3-b][1,4]benzo-thiazin-8-ylmethyl]piperidin-4-ylacetamide | ¹H-NMR(CDCl₃) δ ppm: 1.29–1.40(m, 2H), 1.63–1.73(m, 2H), 1.75(s, 3H), 1.92–2.01(m, 2H), 2.68–2.76(m, 2H), 3.37(s, 2H), 3.38(s, 3H), 3.41–3.54(m, 1H), 5.23(s, 2H), 6.92(dd, J=1.2, 7.9Hz, 1H), 7.05(d, J=7.9Hz, 1H), 7.09(d, J=1.2Hz, 1H), 7.75(br·d, J=7.5Hz, 1H), 7.92(d, J=2.7Hz, 1H), 7.95(d, J=2.7Hz, 1H) |

Examples 387 to 392

The following compounds were obtained by the same method as the one of Example 64 by using anhydrous potassium carbonate, sodium hydrogencarbonate or pyridine as a substitute for N,N-diisopropylethylamine.

| Ex. | Structural formula | NMR |
|---|---|---|
| 387 | 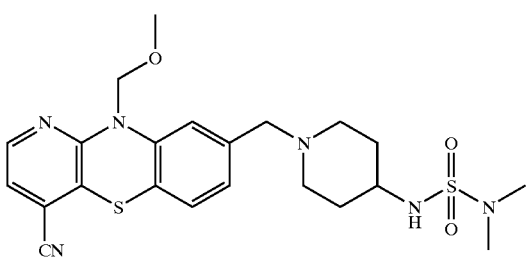<br>N-[1-[4-cyano-10-(methoxymethyl)-10H-pyrido[3,2-b][1,4]benzothiazin-8-ylmethyl]piperidin-4-yl]-N',N'-dimethylsulfamide | ¹H-NMR(CDCl₃) δ ppm: 1.57(m, 2H), 1.99(m, 4H), 2.21(m, 2H), 2.78(s, 6H), 3.24(m, 1H), 3.37(s, 3H), 3.44(s, 2H), 3.96(d, J=4Hz, 1H), 5.24(s, 2H), 7.03(dd, J=2, 8Hz, 1H), 7.10(d, J=8Hz, 1H), 7.11(d, J=2Hz, 1H), 7.22(d, J=5Hz, 1H), 8.16(d, J=5Hz, 1H) |
| 388 | 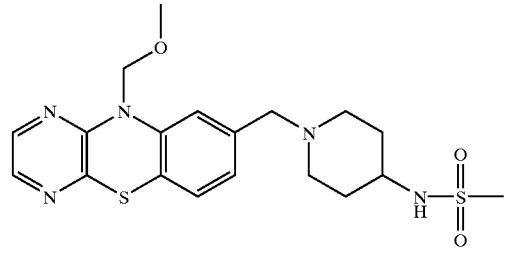<br>N-[1-[10-(methoxymethyl)-10H-pyrazino[2,3-b][1,4]benzoxazin-8-ylmethyl]piperidin-4-yl]methanesulfonamide | ¹H-NMR(CDCl₃) δ ppm: 1.5–1.65(m, 2H), 1.9–2.05(m, 2H), 2.13(t, J=7Hz, 2H), 2.75–2.85(m, 2H), 2.99(s, 3H), 3.30–3.40(m, 1H), 3.44(s, 2H), 3.53(s, 3H), 4.20–4.35(m, 1H), 5.30(s, 2H), 6.93(d, J=8Hz, 1H), 6.97(d, J=8Hz, 1H), 7.10(s, 1H), 7.82–7.87(m, 2H) |

| Ex. | Structural formula | NMR |
|---|---|---|
| 389 | 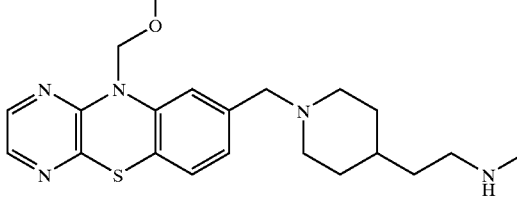<br>N-[2-[1-[10-(methoxymethyl)-10H-pyrazino[2,3-b][1,4]benzothiazin-8-ylmethyl]piperidin-4-yl]ethyl]acetamide | $^1$H-NMR(CDCl$_3$) δ ppm: 1.2–1.4(m, 3H), 1.4–1.5(m, 2H), 1.5–1.8(m, 2H), 1.96(s, 3H), 1.9–2.1(m, 2H), 2.8–2.95(m, 2H), 3.22–3.3(m, 2H), 3.4–3.46(m, 2H), 3.53(s, 3H), 5.28(s, 2H), 5.3–5.4(m, 1H), 6.7–6.96(m, 1H), 6.96(d, J=8Hz, 1H), 7.08–7.12(m, 1H), 7.8–7.86(m, 2H) |
| 390 | 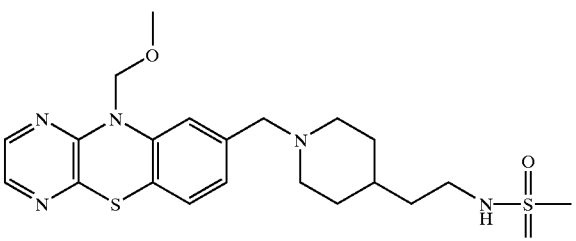<br>N-[2-[1-[10-(methoxymethyl)-10H-pyrazino[2,3-b][1,4]benzothiazin-8-ylmethyl]piperidin-4-yl]ethyl]methanesulfamide | $^1$H-NMR(CDCl$_3$) δ ppm: 1.2–1.4(m, 3H), 1.44–1.54(m, 2H), 1.56–1.68(m, 2H), 1.86–2.00(m, 2H), 2.8–2.9(m, 2H), 2.94(s, 3H), 3.08–3.20(m, 2H), 3.42(s, 2H), 3.53(s, 3H), 4.35(br.s, 1H), 5.28(s, 2H), 6.91(d, J=8Hz, 1H), 6.95(d, J=8Hz, 1H), 7.08(s, 1H), 7.76–7.86(m, 2H) |
| 391 | 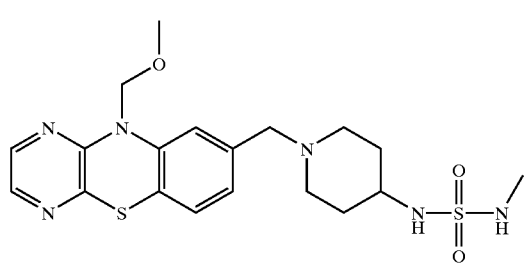<br>N-[1-[10-(methoxymethyl)-10H-pyrazino[2,3-b][1,4]benzothiazin-8-ylmethyl]piperidin-4-yl]-N'-methylsulfamide | $^1$H-NMR(CDCl$_3$) δ ppm: 1.50–1.70(m, 2H), 1.90–2.05(m, 2H), 2.05–2.17(m, 2H), 2.71(d, J=6Hz, 3H), 2.73–2.84(m, 2H), 3.17–3.30(m, 1H), 3.42(s, 2H), 3.53(s, 3H), 4.00–4.15(m, 2H), 5.28(s, 2H), 6.91(dd, J=1, 8Hz, 1H), 6.96(d, J=8Hz, 1H), 7.09(d, J=1Hz, 1H), 7.83(d, J=2Hz, 1H), 7.84(d, J=2Hz, 1H) |

| Ex. | Structural formula | NMR |
|---|---|---|
| 392 | N-[1-[10-(methoxymethyl)-10H-pyrazino[2,3-b][1,4]benzothiazin-8-ylmethyl]piperidin-4-yl]sulfamide | $^1$H-NMR(CDCl$_3$) δ ppm: 1.5–1.63(m, 2H), 1.97–2.08(m, 2H), 2.05–2.18(m, 2H), 2.73–2.85(m, 2H), 3.28–3.40(m, 1H), 3.42(s, 2H), 3.54(s, 3H), 4.34(d, J=10Hz, 1H), 4.6(br.s, 2H), 5.29(s, 2H), 6.91(dd, J=1, 8Hz, 1H), 6.96(d, J=8Hz, 1H), 7.08(d, J=1Hz, 1H), 7.83(d, J=2Hz, 1H), 7.84(J=2Hz, 1H) |

Example 393

N,N-[3-[10-(Methoxymethyl)-10H-pyrazino[2,3-b][1,4]benzo-thiazin-8-ylmethyl]amiono]pentamethylene]methanesulfonamide The title compound was obtained by the same method as the one of Example 66.

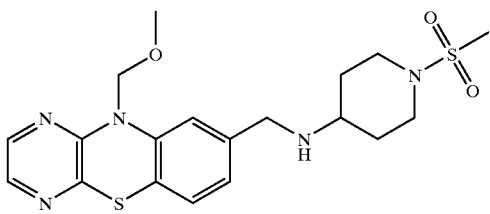

$^1$H-NMR(CDCl$_3$) δ ppm: 1.5–1.65(m, 2H), 1.95–2.05(m, 2H), 2.6–2.7(m, 1H), 2.77(s, 3H), 2.7–2.85(m, 2H), 3.53(s, 3H), 3.6–3.8(m, 2H), 3.77(s, 2H), 5.30(s, 3H), 6.92–7.0(m, 2H), 7.14(s, 1H), 7.83(d, J=3 Hz, 1H), 7.84(d, J=3 Hz, 1H)

Example 394

[1-[10-(Methoxymethyl)-10H-pyrazino[2,3-b][1,4]benzothiazin-8-ylmethyl]-2,3-dehydro-4-piperidone Into a solution of 0.130 g of sodium aluminum hydride in tetrahydrofuran (10 ml) was dropped in a nitrogen atmosphere a solution of 0.858 g of [1-[10-(methoxymethyl)-10H-pyrazino[2,3-b][1,4]benzothiazin-8-ylmethyl]-4-pyridone in tetrahydrofuran (20 ml). After reacting for 16 hours, 0.13 ml of water, 0.13 ml of a 15% aqueous solution of sodium hydroxide and 0.40 ml of water were successively added thereto and the insoluble matters were filtered off. After distilling off the solvent under reduced pressure, the residue was purified by silica gel column chromatography (eluted with dichloromethane/methanol) to thereby give 0.277 g of the title compound as pale yellow crystals.

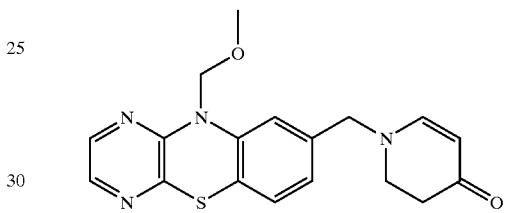

$^1$H-NMR(CDCl$_3$) δ ppm: 2.48(t, J=8 Hz, 2H), 3.38(t, J=8 Hz, 2H), 3.53(s, 3H), 4.29(s, 2H), 5.04(d, J=8 Hz, 1H), 5.26(s, 2H), 6.68(dd, J=2, 8 Hz, 1H), 7.03(d, J=8 Hz, 1H), 7.05(d, J=2 Hz, 1H), 7.14(d, J=8 Hz, 1H), 7.85(d, J=3 Hz, 1H), 7.87(d, J=3 Hz, 1H)

Example 395

[1-[10-(Methoxymethyl)-10H-pyrazino[2,3-b][1,4]benzothiazin-8-ylmethyl]-3-phthalimidomethylpyridinium chloride 0.587 g of 8-chloromethyl-10-(methoxymethyl)-10H-pyrazino[2,3-b][1,4]benzothiazine and a solution of 0.524 g of N-(3-pyridylmethyl)phthalimide in 10 ml of dimethylformamide were heated to 80° C. in a nitrogen atmosphere for 4 hours. After distilling off the solvent under reduced pressure, the residue was purified by silica gel column chromatography (eluted with dichloromethane/methanol) to thereby give 0.489 g of the title compound as yellow crystals.

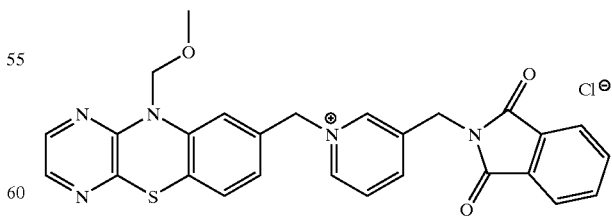

$^1$H-NMR(CDCl$_3$) δ ppm: 3.53(s, 3H), 5.04(s, 2H), 5.32(s, 2H), 6.22(s, 2H), 7.02(d, J=8 Hz, 1H), 7.22(dd, J=2, 8 Hz, 1H), 7.40(d, J=2 Hz, 1H), 7.76(dd, J=3, 6 Hz, 2H), 7.84–7.87(m, 5H), 8.01(dd, J=6, 8 Hz, 1H), 8.30(dd, J=1, 6 Hz, 1H), 9.26(d, J=1Hz, 1H)

Example 396

2-[1-(10-(Methoxymethyl)-10H-pyrazino[2,3-b][1,4]benzothiazin-8-ylmethyl]-3,4-dehydropiperidin-3-ylmethyl]-3-hydroxyiso-indolin-1-one To a solution of 0.486 g of [1-[10-(methoxymethyl)-10H-pyrazino[2,3-b][1,4]benzothiazin-8-ylmethyl]-3-phthalimidomethylpyridinium chloride in methanol (10 ml) was added 0.086 g of sodium borohydride and the resulting mixture was stirred for 30 minutes. Next, 20 ml of tetrahydrofuran and 10 ml of water were further added and the mixture was stirred for additional 1 hour. After neutralizing with sodium dihydrogenphosphate, the mixture was extracted with dichloromethane (50 ml) and the organic layer was dried over anhydrous magnesium sulfate. After filtering and distilling off the solvent under reduced pressure, 0.255 g of the title compound was obtained as pale yellow crystals.

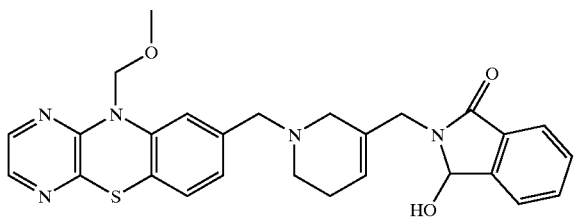

$^1$H-NMR(CDCl$_3$) δ ppm: 2.16(br.s, 2H), 2.42(quint, J=6 Hz, 1H), 2.51–2.56(quint, J=6 Hz, 1H), 2.54(d, J=15 Hz, 1H), 2.98(d, J=15 Hz, 1H), 3.44(d, J=12 Hz, 1H), 3.46(s, 3H), 3.50(d, J=12 Hz, 1H), 3.94(d, J=15 Hz, 1H), 4.20(d, J=15 Hz, 1H), 5.22(d, J=10 Hz, 1H), 5.25(d, J=10 Hz, 1H)5.74(br.s, 1H), 5.78(s, 1H), 6.88(dd, J=1, 8 Hz, 1H), 6.91(d, J=8 Hz, 1H), 7.05(d, J=1 Hz, 1H), 7.48(dt, J=1, 7 Hz, 1H), 7.56(dd, J=1, 7 Hz, 1H), 7.59(dd, J=1, 7 Hz, 1H), 7.76(dt, J=1, 7 Hz, 1H), 7.81(d, J=3 Hz, 1H), 7.83(d, J=3 Hz, 1H)

Example 397

N-[1-[10-(Methoxymethyl)-10H-pyrazino[2,3-b][1,4]benzothiazin-8-ylmethyl]-3,4-dehydropiperidin-3-ylmethyl]-2-hydroxymethyl-benzamide To a solution of 0.255 g of 2-[1-[10-(methoxymethyl)-10H-pyrazino[2,3-b][1,4]benzothiazin-8-ylmethyl]-3,4-dehydropiperidin-3-ylmethyl]-3-hydroxyisoindolin-1-one in 2-propanol (7.7 ml) were added 1.3 ml of water and 0.163 g of sodium borohydride and the resulting mixture was stirred for 16 hours. Then the reaction mixture was naturalized with sodium dihydrogenphosphate and extracted with ethyl acetate. The organic layer was dried over anhydrous magnesium sulfate and filtered. After distilling off the solvent under reduced pressure, 0.235 g of the title compound was obtained as pale yellow crystals.

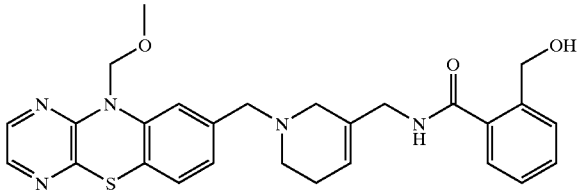

$^1$H-NMR(CDCl$_3$) δ ppm: 2.21(br.s, 1H), 2.58(t, J=6 Hz, 2H), 2.99(br.s, 2H), 3.48(s, 3H), 3.51(s, 3H), 3.99(d, J=5 Hz, 2H), 4.51(s, 2H), 5.26(s, 2H), 5.76(s, 1H), 6.68(br.s, 1H), 6.91(s, 2H), 7.11(s, 1H), 7.32–7.44(m, 3H), 7.52(d, J=8 Hz, 1H), 7.82(d, J=3 Hz, 1H), 7.84(d, J=3 Hz, 1H)

Example 398

[1-[10-(Methoxymethyl)-10H-pyrazino[2,3-b][1,4]benzothiazin-8-ylmethyl]-3-aminomethyl-3,4-dehydropiperidine To a solution of 0.235 g of N-[1-[10-(methoxymethyl)-10H-pyrazino[2,3-b][1,4]benzothiazin-8-ylmethyl]-3,4-dehydropiperidin-3-ylmethyl]-2-hydroxymethylbenzamide in 2-propanol (8 ml) were added 1.5 ml of water and 0.9 ml of acetic acid and the resulting mixture was stirred at 80° C. for 2 hours. After distilling off the solvent under reduced pressure, the residue was purified by silica gel column chromatography (eluted with dichloromethane/methanol) to thereby give 0.120 g of the title compound as a pale yellow oily substance.

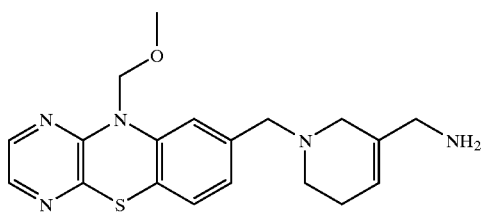

$^1$H-NMR(CDCl$_3$) δ ppm: 2.16(br.s, 2H), 2.52(t, J=6 Hz, 2H), 2.94(br.s, 2H), 3.17(s, 2H), 3.53(s, 3H), 3.55(s, 2H), 5.29(s, 2H), 5.63(m, 1H), 6.96(d, J=8 Hz, 1H), 6.99(dd, J=2, 8 Hz, 1H), 7.11(d, J=2 Hz, 1H), 7.83(d, J=3 Hz, 1H), 7.84(d, J=3 Hz, 1H)

Example 399

N-[1-[10-(Methoxymethyl)-10H-pyrazino[2,3-b][1,4]benzothiazin-8-ylmethyl]-3,4-dehydropiperidin-3-ylmethyl]methanesulfonamide The title compound was obtained as pale yellow crystals by the same method as the one of Example 316.

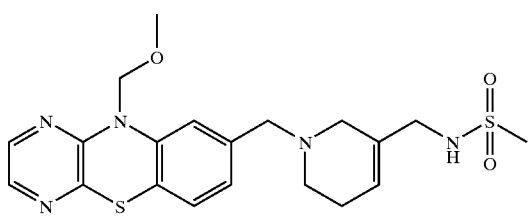

$^1$H-NMR(CDCl$_3$) δ ppm: 2.38(m, 2H), 2.84(m, 2H), 2.96(s, 3H), 3.38(br.s, 2H), 3.54(s, 3H), 3.68(d, J=5 Hz, 2H), 3.88(br.s, 2H), 5.33(s, 2H), 5.49(br.s, 1H), 5.86(m, 1H), 7.00(d, J=8 Hz, 1H), 7.06(br.d, J=8 Hz, 1H), 7.26(br.s, 1H), 7.83(d, J=3 Hz, 1H), 7.84(d, J=3 Hz, 1H)

Example 400

Ethyl N-[1-[10-(methoxymethyl)-10H-pyrazino[2,3-b][1,4]benzothiazin-8-ylmethyl]-2,3-dehydro-3-piperidinecarboxylate To a solution of 0.506 g of diisopropylamine in tetrahydrofuran (16 ml) was added at 0° C. in a nitrogen atmosphere a 1.6 M solution of n-butyllithium in hexane. Further a solution of 0.776 g of ethyl 2,3-dehydro-3-piperidinecarboxylate in tetrahydrofuran (2 ml) was added thereto. In another container, 1.00 g of 8-chloromethyl-10-(methoxymethyl)-10H-pyrazino[2,3-b][1,4]benzothiazine was added at 60° C. in a nitrogen atmosphere to a solution of 1.53 g of sodium iodide in N,N-dimethylformamide (10 ml). After heating for 2 hours, the mixture was brought back to room temperature and then added to the above-mentioned solution of the lithium salt. After stirring at room temperature for 2 hours and concentrating under reduced pressure, the residue was distributed into ethyl acetate and water. The organic layer was concentrated and the residue was purified by silica gel column chromatography (eluted with dichloromethane/methanol) to thereby give 0.375 g of the title compound as pale yellow crystals.

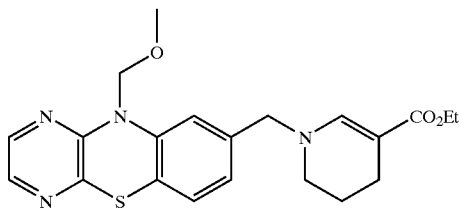

$^1$H-NMR(CDCl$_3$) δ ppm: 1.26(t, J=7 Hz, 3H), 1.52(quint, J=6 Hz, 2H), 2.29(t, J=6 Hz, 2H), 2.98(t, J=6 Hz, 2H), 3.49(s, 3H), 4.15(q, J=7 Hz, 2H), 4.23(s, 2H), 5.22(s, 2H), 6.82(dd, J=2, 7 Hz, 1H), 6.97(d, J=2 Hz, 1H), 6.98(d, J=7 Hz, 1H), 7.51(s, 1H), 7.83(d, J=3 Hz, 1H), 7.84(d, J=3 Hz, 1H)

Example 401

The following compounds were obtained by the same method as the one of Example 8.

| Ex. | Structural formula | MS | M.p. | NMR |
|---|---|---|---|---|
| 401 | N-[2-[1-(10H-pyrazino[2,3-b][1,4]benzothiazin-8-ylmethyl)piperidin-4-yl]ethyl]methanesulfonamide | ESI (+) 420 (MH$^+$) | 168–170° C. | $^1$H-NMR(DMSO-d$_6$) δ ppm: 1.0–1.2(m, 2H), 1.24–1.40(m, 3H), 1.54–1.66(m, 2H), 1.74–1.90(m, 2H), 2.65–2.80(m, 2H), 2.85(s, 3H), 2.92(q, J=7Hz, 2H), 3.23(br · s, 2H), 6.65–6.75(m, 1H), 6.74(s, 1H), 6.82(d, J=8Hz, 1H), 6.89(t, J=6Hz, 1H), 7.62(d, J=3Hz, 1H), 7.63(d, J=3Hz, 1H), 9.43(m, 1H) |
| 402 | N-[1-(10H-pyrazino[2,3-b][1,4]benzothiazin-8-ylmethyl)piperidin-4-yl]methanesulfonamide | ESI (+) 392 (MH$^+$) | 220–223° C. | $^1$H-NMR(DMSO-d$_6$) δ ppm: 1.3–1.5(m, 2H), 1.70–1.80(m, 2H), 1.85–2.00(m, 2H), 2.60–2.75(m, 2H), 2.88(s, 3H), 3.00–3.20(m, 1H), 3.23(s, 2H), 6.63–6.70(m, 1H), 6.73(s, 1H), 6.82(d, J=8Hz, 1H), 7.0–7.1(m, 1H), 7.62(d, J=3Hz, 1H), 7.63(d, J=3Hz, 1H), 9.44(s, 1H) |
| 403 | N-[1-(10H-pyrazino[2,3-b][1,4]benzothiazin-8-ylmethyl)piperidin-4-yl]-N'-methanesulfamide | ESI (+) 407 (MH$^+$) | 209–210° C. | $^1$H-NMR(DMSO-d$_6$) δ ppm: 1.34–1.48(m, 2H), 1.72–1.80(m, 2H), 1.82–1.94(m, 2H), 2.41(d, J=4Hz, 3H), 2.64–2.74(m, 2H), 2.84–2.96(m, 1H), 3.22(s, 2H), 6.55–6.63(m, 1H), 6.67(d, J=8Hz, 1H), 6.73(s, 1H), 6.82(d, J=8Hz, 1H), 6.87 (d, J=8Hz, 1H), 7.62(d, J=3Hz, 1H), 7.62(d, J=3Hz, 1H), 9.44(s, 1H) |

| Ex. | Structural formula | MS | M.p. | NMR |
|---|---|---|---|---|
| 404 | N-[1-(10H-pyrazino[2,3-b][1,4]benzothiazin-8-ylmethyl)piperidin-4-yl]-N'-sulfamide | ESI (+) 393 (MH+) | 196–199° C. | $^1$H-NMR(DMSO-d$_6$) δ ppm: 1.32–1.48(m, 2H), 1.74–1.88(m, 2H), 1.82–1.98(m, 2H), 2.6–2.76(m, 2H), 2.94–3.1(m, 1H), 3.22(s, 2H), 6.45(s, 2H), 6.53(d, J=7Hz, 1H), 6.67(d, J=8Hz, 1H), 6.73(d, J=1Hz, 1H), 6.82(d, J=8Hz, 1H), 7.61(d, J=3Hz, 1H), 7.63(d, J=3Hz, 1H), 9.44(s, 1H) |
| 405 | N-[2-[1-(10H-pyrazino[2,3-b][1,4]benzothiazin-8-ylmethyl)piperidin-4-yl]ethyl]acetamide | ESI (+) 384 (MH+) | 194–196° C. | $^1$H-NMR(DMSO-d$_6$) δ ppm: 1.0–1.36(m, 5H), 1.5–1.66(m, 2H), 1.75(s, 3H), 1.7–1.9(m, 2H), 2.64–2.80(m, 2H), 2.94–3.06(m, 2H), 3.21(m, 2H), 6.6–6.75(m, 1H), 6.73(m, 1H), 6.7–6.88(m, 1H), 7.62(br · s, 2H), 7.75(br · s, 1H), 9.43(m, 1H) |
| 406 | N,N-[3-[(10H-pyrazino[2,3-b][1,4]benzothiazin-8-ylmethyl)amino]pentamethylene]methanesulfonamide | FAB (+) 392 (MH+) | 219–221° C. | $^1$H-NMR(DMSO-d$_6$) δ ppm: 1.24–1.38(m, 2H), 1.80–1.90(m, 2H), 2.06–2.20(m, 1H), 2.75(t, J=7.2Hz, 2H), 2.81(s, 3H), 3.38–3.48(m, 2H), 3.54(s, 2H), 6.75(d, J=8.0Hz, 1H), 6.77(s, 1H), 6.81(d, J=8.0Hz, 1H), 7.61(d, J=2.8Hz, 1H), 7.62(d, J=8.2Hz, 1H), 9.45(s, 1H), |
| 407 | N-[1-(10H-pyrazino[2,3-b][1,4]benzothiazin-8-yl-methyl)piperidin-4-yl]benzenesulfonamide | ESI (+) 454 (MH+) | 157–158° C. | $^1$H-NMR(DMSO-d$_6$) δ ppm: 1.25–1.40(m, 2H), 1.40–1.55(m, 2H), 1.70–1.90(m, 2H), 2.50–2.65(m, 2H), 2.85–2.95(m, 1H), 3.17(s, 2H), 6.60–6.68(m, 1H), 6.68(s, 1H), 6.80(br · d, J=8Hz, 1H), 7.50–7.65(m, 5H), 7.68–7.75(m, 1H), 7.75–7.82(m, 2H), 9.41(s, 1H) |
| 408 | N-[1-(10H-pyrazino[2,3-b][1,4]benzothiazin-8-ylmethyl)3,4-dehydropiperidin-3-yl]methyl]methane-Sulfonamide | FAB (+) 404 (MH+) | 110–112° C. | $^1$H-NMR(DMSO-d$_6$) δ ppm: 2.07(br · s, 2H), 2.42(t, J=3Hz, 2H), 2.79(br · s, 2H), 2.83(s, 3H), 3.36(s, 2H), 3.43(br · d, J=3Hz, 2H), 5.74(br · s, 1H), 6.71(dd, J=1, 8Hz, 1H), 6.77(d, J=1Hz, 1H), 6.84(d, J=8Hz, 1H), 7.24(t, J=3Hz, 1H), 7.63(s, 2H), 9.44(s, 1H) |

-continued

| Ex. | Structural formula | MS | M.p. | NMR |
|---|---|---|---|---|
| 409 | [1-(10H-pyrazino[2,3-b][1,4]benzothiazin-8-yl-methyl)]piperidin-4-yl] carbamate | FAB (+) 358 (MH+) | 139–142° C. | $^1$H-NMR(DMSO-d$_6$) δ ppm: 1.44(m, 2H), 1.70–1.85(m, 2H), 2.50–2.70(m, 2H), 3.15(d, J=10Hz, 1H), 3.20–3.40(m, 2H), 3.25(d, J=10Hz, 1H), 4.30–4.50(br·s, 3H), 6.68(d, J=8Hz, 1H), 6.71(s, 1H), 6.85(d, J=8Hz, 1H), 7.62(s, 2H), 9.45(br·s, 1H) |
| 410 | 4-[N-(10H-pyrazino[2,3-b][1,4]benzothiazin-8-ylmethyl)piperidin-4-yl]butanol | FAB (+) 371 (MH+) | 132–135° C. | $^1$H-NMR(DMSO-d$_6$) δ ppm: 0.95–1.30(m, 7H), 1.30–1.40(m, 2H), 1.50–1.62(m, 2H), 1.70–1.90(m, 2H), 2.70–2.80(m, 2H), 3.21(s, 2H), 3.30–3.40(m, 2H), 4.31(t, J=5Hz, 1H), 6.65(d, J=8Hz, 1H), 6.74(s, 1H), 6.81(d, J=8Hz, 1H), 7.61(s, 2H), 9.42(br·s, 1H) |
| 411 | 1-(10H-pyrido[3,4-b][1,4]benzothiazin-7-yl-methyl)-4-pyridone | FAB (+) 308 (MH+) | 168° C. (decompose) | $^1$H-NMR(DMSO-d$_6$) δ ppm: 4.95(s, 2H), 6.09–6.15(m, 2H), 6.46(d, J=1.5Hz, 1H), 6.52(d, J=5.5Hz, 1H), 6.75(dd, J=1.5, 7.9Hz, 1H), 6.96(d, J=7.9Hz, 1H), 7.66–7.72(m, 2H), 7.88(s, 1H), 7.97(d, J=5.5Hz, 1H), 9.20(s, 1H) |

Examples 412 to 433

The following compounds were obtained by the same method as that of Example 9.

| Ex. | Structural formula | MS | M.p. | NMR |
|---|---|---|---|---|
| 412 | N-[1-(10H-pyrazino[2,3-b][1,4]benzothiazin-8-ylmethyl)-piperidin-4-yl]acetamide | FAB (+) 356 (MH+) | 212–214° C. | $^1$H-NMR (DMSO-d$_6$) δ ppm: 1.25–1.40 (m, 2H), 1.60–1.72 (m, 2H), 1.87–2.02 (m, 2H), 2.48 (s, 3H), 2.60–2.78 (m, 2H), 3.23 (s, 2H), 3.40–3.54 (m, 1H), 6.68 (d, J = 8.3 Hz, 1H), 6.73 (s, 1H), 6.83 (d, J = 8.3 Hz, 1H), 7.62 (s, 2H), 7.73 (d, J = 7.6 Hz, 1H), 9.44 (s, 1H) |

-continued

| Ex. | Structural formula | MS | M.p. | NMR |
|---|---|---|---|---|
| 413 | [1-(10H-pyrazino[2,3-b]1,4]benzoxazin-8-ylmethyl)-piperidin-4-yl]carboxamide | ESI (+) 326 (MH+) | 287–288° C. | $^1$H-NMR (DMSO-d$_6$) δ ppm: 1.40–1.58 (m, 2H), 1.58–1.68 (m, 2H), 1.84 (br.t, J = 11 Hz, 2H), 1.96–2.08 (m, 1H), 2.76 (br.d, J = 11 Hz, 2H), 3.22 (s, 2H), 6.57 (d, J = 8 Hz, 1H), 6.60 (s, 1H), 6.68 (d, J = 8 Hz, 1H), 6.66–6.74 (m, 1H), 7.19 (br.s, 1H), 7.22–7.26 (m, 1H), 7.43–7.46 (m, 1H), 9.57 (s, 1H) |
| 414 | 8-(piperidin-1-ylmethyl)-10H-pyrazino-[2,3-b][1,4]-benzothiazine | FAB (+) 299 (MH+) | | $^1$H-NMR (CDCl$_3$) δ ppm: 1.30–1.27 (m, 2H), 1.50–1.63 (m, 4H), 2.20–2.50 (m, 4H), 3.30 (s, 2H), 6.57 (s, 1H), 6.55–6.60 (br.s, 1H), 6.67 (d, J = 8 Hz, 1H), 6.80 (d, J = 8 Hz, 1H), 7.56 (d, J = 3 Hz, 1H), 7.68 (s, 1H) |
| 415 | 1-(10H-pyrazino[2,3-b][1,4]benzothiazin-8-ylmethyl)-2-pyridone | FAB (+) 308 (M+) | 260–261° C. | $^1$H-NMR (DMSO-d$_6$) δ ppm: 4.90 (s, 2H), 6.23 (t, J = 8 Hz, 1H), 6.40 (d, J = 10 Hz, 1H), 6.65 (s, 1H), 6.66 (d, J = 8 Hz, 1H), 6.86 (d, J = 8 Hz, 1H), 7.43 (ddd, J = 2, 8, 10 Hz, 1H), 7.63 (s, 2H), 7.70 (dd, J = 2, 8 Hz, 1H), 9.52 (s, 1H) |
| 416 | 1-(10H-pyrazino[2,3-b][1,4]benzothiazin-8-ylmethyl)-4-piperidone | FAB (+) 309 (MH+) | >275° C. | $^1$H-NMR (DMSO-d$_6$) δ ppm: 4.92 (s, 2H), 6.09 (d, J = 8 Hz, 2H), 6.58 (d, J = 1 Hz, 1H), 6.66 (dd, J = 1, 8 Hz, 1H), 6.92 (d, J = 8 Hz, 1H), 7.64 (s, 2H), 7.64 (d, J = 8 Hz, 2H), 9.57 (s, 1H) |
| 417 | 1-(10H-pyrazino[2,3-b][1,4]benzothiazin-8-ylmethyl)-2,3-dehydro-4-piperidone | | 233–235° C. | $^1$H-NMR (CDCl$_3$) δ ppm: 2.30 (t, J = 7 Hz, 2H), 3.22 (t, J = 7 Hz, 2H), 4.23 (s, 2H), 5.74 (s, 1H), 6.60 (dd, J = 1, 7 Hz, 1H), 6.68 (d, J = 1 Hz, 1H), 6.82 (d, J = 7 Hz, 1H), 7.21 (s, 1H), 7.62 (s, 2H), 9.43 (s, 1H) |

-continued

| Ex. | Structural formula | MS | M.p. | NMR |
|---|---|---|---|---|
| 418 | 1-(10H-pyrazino[2,3-b][1,4]benzothiazin-8-yl)-2'-piperidin-1-ylmethyl)benzyl alcohol | FAB (+) 405 (MH+) | 219–221° C. | 1H-NMR (CDCl3) δ ppm: 1.58 (m, 6H), 2.34 (m, 4H), 3.25 (d, J = 13 Hz, 1H), 3.31 (d, J = 13 Hz, 1H), 5.65 (s, 1H), 6.36 (s, 1H), 6.58 (s, 1H), 6.59 (d, J = 2 Hz, 1H), 6.80 (dd, J = 2, 8 Hz, 1H), 6.84 (d, J = 8 Hz, 1H), 7.15–7.32 (m, 4H), 7.54 (d, J = 3 Hz, 1H), 7.68 (d, J = 3 Hz, 1H) |
| 419 | 8-(4-methylpiperazin-1-yl)methyl-10H-pyrazino[2,3-b][1,4]benzothiazine | ESI (+) 314 (MH+) | 191–192° C. | 1H-NMR (DMSO-d6) δ ppm: 2.10–2.33 (m, 2H), 2.75 (s, 3H), 2.75–3.05 (m, 6H), 3.33 (s, 2H), 6.68 (s, 1H), 6.71 (d, J = 8.1 Hz, 1H), 6.87 (d, J = 8.1 Hz, 1H), 7.64 (s, 2H), 9.50 (s, 1H) |
| 420 | 8-[(morpholin-4yl)methyl]-10H-pyrazino[2,3-b][1,4]benzothiazine hydrochloride | | | 1H-NMR (DMSO-d6) δ ppm: 2.96–3.10 (m, 2H), 3.15–3.25 (m, 2H), 3.68–3.80 (m, 2H), 3.86–3.94 (m, 2H), 4.11 (d, J = 6.0 Hz, 2H), 6.80 (s, 1H), 7.00 (d, J = 8.3 Hz, 1H), 7.05 (d, J = 8.3 Hz, 1H), 7.66 (s, 2H), 9.74 (s, 1H), 10.95–11.08 (m, 1H) |
| 421 | ethyl [1-(10H-pyrazino[2,3-b][1,4]benzothiazin-8-ylmethyl)piperidin-4-yl]carboxylate | FAB (+) 371 (MH+) | | 1H-NMR (CDCl3) δ ppm: 1.24 (t, J = 7 Hz, 3H), 1.70–1.82 (m, 2H), 1.83–1.95 (m, 2H), 1.95–2.10 (m, 2H), 2.25–2.35 (m, 1H), 2.75–2.84 (m, 2H), 3.34 (s, 2H), 4.14 (q, J = 7 Hz, 2H), 6.54 (s, 1H), 6.64 (d, J = 8 Hz, 1H), 6.82 (d, J = 8 Hz, 1H), 6.95 (s, 1H), 7.58 (d, J = 3 Hz, 1H), 7.68 (d, J = 3 Hz, 1H) |
| 422 | 1-(10H-pyrazino[2,3-b][1,4]benzothiazin-8-ylmethyl)piperidin-4-ol | FAB (+) 315 (MH+) | | 1H-NMR (DMSO-d6) δ ppm: 1.30–1.40 (m, 2H), 1.60–1.70 (m, 2H), 1.90–2.05 (m, 2H), 2.55–2.65 (m, 2H), 3.25 (s, 2H), 3.35–3.45 (m, 1H), 4.53 (m, 1H), 6.68 (d, J = 8 Hz, 1H), 6.73 (s, 1H), 6.82 (d, J = 8 Hz, 1H), 7.62 (s, 2H), 9.42 (br.s, 1H) |

| Ex. | Structural formula | MS | M.p. | NMR |
|---|---|---|---|---|
| 423 | 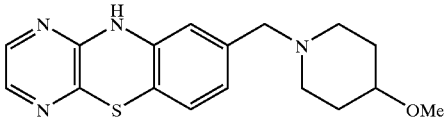<br>1-(10H-pyrazino[2,3-b][1,4]benzothiazin-8-ylmethyl)-4-methoxy piperidine | FAB (+)<br>329 (MH$^+$) | 172–<br>174° C. | $^1$H-NMR (CDCl$_3$) δ ppm: 1.55–1.70 (m, 2H), 1.83–2.00 (m, 2H), 2.10–2.30 (m, 2H), 2.70–2.80 (m, 2H), 3.20–3.30 (m, 1H), 3.35 (s, 3H), 3.40 (s, 2H), 6.58 (s, 1H), 6.62 (s, 1H), 6.78 (d, J = 8 Hz, 1H), 6.82 (d, J = 8 Hz, 1H), 7.57 (s, 1H), 7.68 (s, 1H) |
| 424 | 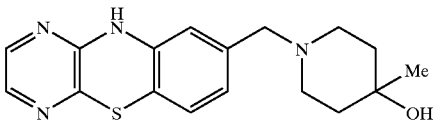<br>1-(10H-pyrazino[2,3-b][1,4]benzothiazin-8-ylmethyl)-4-methyl piperidin-4-ol | FAB (+)<br>329 (MH$^+$) | 176–<br>180° C. | $^1$H-NMR (CDCl$_3$) δ ppm: 1.26 (s, 3H), 1.50–1.80 (m, 4H), 2.10 (s, 1H), 2.30–2.45 (m, 2H), 2.50–2.58 (m, 2H), 3.43 (s, 2H), 6.77 (d, J = 8 Hz, 1H), 6.83 (d, J = 8 Hz, 1H), 7.25 (s, 1H), 7.26 (s, 1H), 7.57 (d, J = 3 Hz, 1H), 7.67 (d, J = 3 Hz, 1H) |
| 425 | 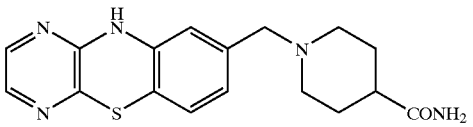<br>1-(10H-pyrazino[2,3-b][1,4]benzothiazin-8-ylmethyl)piperidin-4-yl]carboxamide | FAB (+)<br>342 (MH$^+$) | 225–<br>228° C. | $^1$H-NMR (DMSO-d$_6$) δ ppm: 1.52 (m, 2H), 1.58–1.68 (m, 2H), 1.83 (m, 2H), 2.00–2.10 (m, 1H), 2.70–2.81 (m, 2H), 3.23 (s, 2H), 6.68 (d, J = 8 Hz, 1H), 6.65–6.73 (br.s, 1H), 6.76 (s, 1H), 6.81 (d, J = 8 Hz, 1H), 7.18 (br.s, 1H), 7.61 (d, J = 3 Hz, 2H), 9.42 (br.s, 1H) |
| 426 | 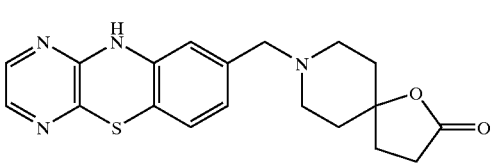<br>1-(10H-pyrazino[2,3-b][1,4]benzothiazin-8-ylmethyl)piperidine-4-spiro-4'-(4'-butanolide) | FAB (+)<br>369 (MH$^+$) | 199–<br>203° C. | $^1$H-NMR (DMSO-d$_6$) δ ppm: 1.60–1.70 (m, 2H), 1.70–1.80 (m, 2H), 1.97 (t, J = 7 Hz, 2H), 2.30–2.38 (m, 2H), 2.38–2.43 (m, 2H), 2.53 (t, J = 7 Hz, 2H), 3.29 (s, 2H), 6.69 (d, J = 8 Hz, 1H), 6.74 (s, 1H), 6.82 (d, J = 8 Hz, 1H), 7.60 (s, 2H), 9.43 (br.s, 1H) |
| 427 | 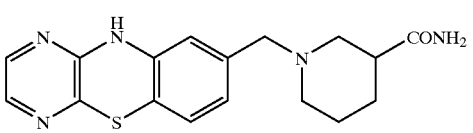<br>[1-(10H-pyrazino[2,3-b][1,4]benzothiazin-8-ylmethyl)piperidine 3-yl]carboxamide | FAB (+)<br>342 (MH$^+$),<br>364 (MNa$^+$) | | $^1$H-NMR (DMSO-d$_6$) δ ppm: 1.50–1.64 (m, 2H), 1.64–1.80 (m, 1H), 1.80–1.90 (m, 1H), 2.10–2.30 (m, 1H), 2.30–2.42 (m, 1H), 2.42–2.50 (m, 1H), 2.48–2.70 (m, 1H), 2.70–2.82 (m, 1H), 3.18 (s, 2H), 5.23 (br.s, 1H), 5.80 (br.s, 1H), 6.68 (d, J = 8 Hz, 1H), 6.73 (s, 1H), 6.81 (d, J = 8 Hz, 1H), 7.80 (s, 2H), 9.40 (br.s, 1H) |

| Ex. | Structural formula | MS | M.p. | NMR |
|---|---|---|---|---|
| 428 | [1-(10H-pyrazino[2,3-b][1,4]benzothiazin-8-ylmethyl)piperidin-2-yl]carboxamide | FAB (+) 342 (MH$^+$) | 209–211° C. | $^1$H-NMR (DMSO-d$_6$) δ ppm: 1.20–1.55 (m, 2H), 1.64–1.80 (m, 1H), 1.96–2.08 (m, 2H), 2.60–2.70 (m, 2H), 2.70–2.80 (m, 2H), 2.90 (d, J = 12 Hz, 1H), 3.56 (d, J = 12 Hz, 1H), 6.77 (s, 1H), 6.78 (d, J = 8 Hz, 1H), 7.82 (d, J = 8 Hz, 1H), 7.00–7.05 (br.s, 1H), 7.05–7.12 (br.s, 1H), 7.62 (s, 2H), 9.40 (br.s, 1H) |
| 429 | [1-(10H-pyrazino[2,3-b][1,4]benzothiazin-8-ylmethyl)pyrrolidin-2-yl]carboxamide | FAB (+) 328 (MH$^+$) | 194–197° C. | $^1$H-NMR (DMSO-d$_6$) δ ppm: 1.60–1.72 (m, 3H), 1.09–1.95 (m, 1H), 1.10–1.22 (m, 1H), 2.80–2.90 (m, 1H), 2.90–2.96 (m, 1H), 3.20 (d, J = 8 Hz, 1H), 3.63 (d, J = 8 Hz, 1H), 6.00–6.15 (br.s, 1H), 6.70 (d, J = 8 Hz, 1H), 6.78 (s, 1H), 6.83 (d, J = 8 Hz, 1H), 7.10–7.20 (br.s, 1H), 7.62 (s, 2H), 9.40 (br.s, 1H) |
| 430 | 2-[1-(10H-pyrazino[2,3-b][1,4]benzothiazin-8-ylmethyl)piperidin-4-yl]ethanol | FAB (+) 343 (MH$^+$) | 148–152° C. | $^1$H-NMR (DMSO-d$_6$) δ ppm: 1.0–1.15 (m, 3H), 1.28–1.35 (m, 2H), 1.50–1.62 (m, 2H), 1.75–1.90 (m, 2H), 2.70–2.80 (m, 2H), 3.15 (s, 2H), 3.30–3.45 (m, J = 6 Hz, 2H), 4.32 (m, J = 6 Hz, 1H), 6.66 (d, J = 8 Hz, 1H), 6.70 (s, 1H), 6.81 (d, J = 8 Hz, 1H), 7.62 (s, 2H), 9.45 (br.s, 1H) |
| 431 | 8-[(2,6-dimethylpiperidin-1-yl)methyl-10H-pyrazino[2,3-b][1,4]benzothiazine | FAB (+) 327 (MH$^+$) | 168–172° C. | $^1$H-NMR (CDCl$_3$) δ ppm: 1.03 (d, J = 8 Hz, 6H), 1.04 (s, 3H), 1.20–1.40 (m, 2H), 1.50–1.70 (m, 4H), 2.40–2.50 (m, 2H), 3.60 (s, 2H), 6.67 (d, J = 8 Hz, 1H), 6.72 (s, 1H), 6.85 (d, J = 8 Hz, 1H), 7.55 (d, J = 3 Hz, 1H), 7.70 (d, J = 3 Hz, 1H), 9.75 (s, 1H) |
| 432 | methyl [1-(10H-pyrazino[2,3-b][1,4]benzothiazin-8-ylmethyl)-3,4-dehydropiperidine-3-yl]carboxylate | FAB (+) 369 (MH$^+$) | 172–175° C. | $^1$H-NMR (CDCl$_3$) δ ppm: 2.37 (m, 2H), 2.59 (t, J = 6 Hz, 2H), 3.24 (br.s, 2H), 3.54 (s, 2H), 3.73 (s, 3H), 6.58 (d, J = 2 Hz, 1H), 6.72 (br.s, 1H), 6.78 (dd, J = 2, 8 Hz, 1H), 6.84 (d, J = 8 Hz, 1H), 7.20 (m, 1H), 7.56 (d, J = 3 Hz, 1H), 7.68 (d, J = 3 Hz, 1H) |

| Ex. | Structural formula | MS | M.p. | NMR |
|---|---|---|---|---|
| 433 | 7-[(piperidin-1-yl)methyl]-5H-pyrido[3,4-b][1,4]benzothiazine | FAB (+) 298 (MH⁺) | 163–166° C. | ¹H-NMR (CDCl₃) δ ppm: 1.46 (m, 2H), 1.62 (m, 4H), 2.42 (br.s, 4H), 3.39 (s, 2H), 6.20 (s, 1H), 6.38 (d, J = 5 Hz, 1H), 6.65 (s, 1H), 6.76 (dd, J = 2, 8 Hz, 1H), 6.88 (d, J = 8 Hz, 1H), 7.98 (s, 1H), 8.05 (d, J = 5 Hz, 1H) |

Example 434

N,N-[3-(10H-Pyrazino[2,3-b][1,4]benzothiazin-8-ylmethyl)-3-azapentamethylene] methanesulfonamide

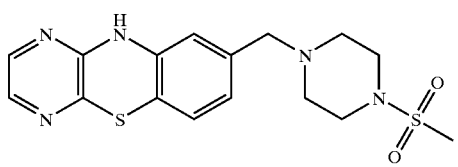

300 mg of N,N-[3-(10-methoxymethyl-10H-pyrazino[2,3-b][1,4]benzothiazin-8-ylmethyl)-3-azapentamethylene]-methanesulfonamide was stirred in glacial acetic acid (20 ml) at 65° C. for 3 hours. After distilling off the solvent under reduced pressure, the residue was crystallized from ethyl acetate/ether to thereby give 240 mg of the title compound as yellow crystals.

¹H-NMR(DMSO-d₆) δ ppm: 2.39–2.44(m, 4H), 2.85(s, 3H), 3.05–3.10(m, 4H), 3.32(s, 2H), 6.71(d, J=7.9 Hz, 1H), 6.74(d, J=1.2 Hz, 1H), 6.85(dd, J=1.2, 7.9 Hz, 1H), 7.61–7.64(m, 2H), 9.44(s, 1H)
m.p.: 221–222° C.
MS: FAB(+)377(M⁺)

Examples 435 and 436

The following compounds were obtained by the same method as the one of Example 434.

| Ex. | Structural formula | MS | M.p. | NMR |
|---|---|---|---|---|
| 435 | 1-(10H-pyrazino[2,3-b][1,4]benzothiazin-8-ylmethyl)-piperidine-4-carbonitrile | FAB (+) 323 (M⁺) | 198–199° C. | ¹H-NMR (DMSO-d₆) δ ppm: 1.61–1.72 (m, 2H), 1.78–1.84 (m, 2H), 2.14–2.26 (m, 2H), 2.41–2.50 (m, 1H), 2.80–2.90 (m, 2H), 3.28 (s, 2H), 6.69 (d, J = 7.9 Hz, 1H), 6.74 (d, J = 1.0 Hz, 1H), 6.83 (dd, J = 1.0, 7.9 Hz, 1H), 7.61–7.64 (m, 2H), 9.44 (s, 1H) |
| 436 | N-[1-(10H-pyrazino[2,3-b][1,4]benzothiazin-7-ylmethyl)piperidin-4-yl]-N′,N′-dimethylsulfamide | FAB (+) 421 (MH⁺) 443 (MNa⁺) | 172–173° C. | ¹H-NMR (DMSO-d₆) δ ppm: 1.34–1.46 (m, 2H), 1.71–1.79 (m, 2H), 1.82–1.93 (m, 2H), 2.60 (s, 6H), 2.64–2.71 (m, 2H), 2.89–2.99 (m, 1H), 3.20 (s, 2H), 6.69 (d, J = 7.6 Hz, 1H), 6.77 (d, J = 1.4 Hz, 1H), 6.85 (dd, J = 1.4, 7.6 Hz, 1H), 7.15 (d, J = 8.6 Hz, 1H), 7.61 (d, J = 2.5 Hz, 1H), 7.62 (d, J = 2.5 Hz, 1H), 9.47 (s, 1H) |

Examples 437 to 465

The following compounds were obtained by the same method as the one of Example 64 by using anhydrous potassium carbonate as a base as a substitute for N,N-diisopropylamine.

| Ex. | Structural formula | MS | M. p. | NMR |
|---|---|---|---|---|
| 437 | N-[1-(10H-pyrazino[2,3-b][1,4]benzothiazin-8-ylmethyl)piperidin-4-yl]-N',N'-pentamethylenesulfamide | FAB (+) 461 (MH⁺) | 56–57° C. | ¹H-NMR(CDCl₃) δ ppm: 1.47–1.58(m, 4H), 1.58–1.65(m, 4H), 1.97(br.d, J=10Hz, 2H), 2.18(br.t, J=10Hz, 2H), 2.77(br.d, J=12Hz, 2H), 3.15(t, 3=6Hz, 4H), 3.22(m, 1H), 3.33(s, 2H), 4.27(d, J=9Hz, 1H), 6.52(d, J=2Hz, 1H), 6.73(dd, J=2, 8Hz, 1H), 6.74(br.s, 1H), 6.82(d, J=8Hz, 1H), 7.56(d, J=3Hz, 1H), 7.68(d, J=3Hz, 1H) |
| 438 | N-[1-(10H-pyrazino[2,3-b][1,4]benzothiazin-8-ylmethyl)piperidin-4-yl]-N',N'-(3-oxapentamethylene)sulfamide | FAB (+) 463 (MH⁺) | 189–190° C. | ¹H-NMR(CDCl₃) δ ppm: 1.54(br.t, J=10Hz, 2H), 1.99(br.d, J=10Hz, 2H), 2.08(br.t, J=10Hz, 2H), 2.69(br.d, J=10Hz, 2H), 3.18(t, J=5Hz, 4H), 3.25(m, 1H), 3.33(s, 2H), 3.74(t, J=5Hz, 4H), 4.35(d, J=9Hz, 1H), 6.52(d, J=2Hz, 1H), 6.69(br.s, 1H), 6.73(dd, J=2, 8Hz, 1H), 6.82(d, J=8Hz, 1H), 7.56(d, J=3Hz, 1H), 7.69(d, J=3Hz, 1H) |
| 439 | N-[(10H-pyrazino[2,3-b][1,4]benzothiazin-8-ylmethyl)piperidin-4-yl]-N'-(2-hydroxyethyl)sulfamide | FAB (+) 437 (MH⁺) | 164–166° C. | ¹H-NMR(CD₃OD) δ ppm: 1.56–1.66(m. 2H), 1.98–2.04(m, 2H), 2.24–2.33(m, 2H), 2.94–2.98(m, 2H), 3.25(t, J=6Hz, 2H), 3.14–3.23(m, 1H), 3.49(s, 2H), 3.62(t, J=6Hz, 2H), 6.67(d, J=2Hz, 1H), 6.79(dd, J=2, 8Hz, 1H), 6.84(d, J=8Hz, 1H), 7.57(d, J=3Hz, 1H), 7.58(d, J=3Hz, 1H) |
| 440 | 2-[1-(10H-pyrazino[2,3-b][1,4]benzothiazin-8-ylmethyl)piperidin-4-yl]-2-methyl-2-propanol | FAB (+) 371 (MH⁺) | 187–188° C. | ¹H-NMR(DMSO-d₆) δ ppm: 1.05(s, 6H), 1.05–1.18(m, 2H), 1.25(d, J=6Hz, 2H), 1.34–1.45(m, 1H), 1.64–1.70(m, 2H), 1.80–1.90(m, 2H), 2.65–2.70(m, 2H), 3.20(s, 2H), 4.12(s, 1H), 6.68(dd, J=1, 7Hz, 1H), 6.74(d, J=1Hz, 1H), 6.82(d, J=7Hz, 1H), 7.62(d, J=3Hz, 1H), 7.63(d, J=3Hz, 1H), 9.43(br.s, 1H) |

| Ex. | Structural formula | MS | M. p. | NMR |
|---|---|---|---|---|
| 441 | 1-(10H-pyrazino[2,3-b][1,4]benzothiazin-8-ylmethyl)piperidin-4-spiro-5'-hydantoin | FAB (+) 383 (MH+) | >275° C. | ¹H-NMR(DMSO-d₆) δ ppm: 1.49(d, J=11Hz, 2H), 1.81(t, J=11Hz, 2H), 2.24(t, J=11Hz, 2H), 2.63(d, J=11Hz, 2H), 3.29(s, 2H), 6.69(dd, J=2, 8Hz, 1H), 6.78(d, J=2Hz, 1H), 6.83(d, J=8Hz, 1H), 7.62(d, J=3Hz, 1H), 7.63(d, J=3Hz, 1H), 8.44(s, 1H), 9.45(s, 1H), 10.62(s, 1H) |
| 442 | N-[1-(10H-pyrazino[2,3-b][1,4]benzothiazin-8-ylmethyl)piperidin-4-yl]-N'-methoxycarbonyl methylsulfamide | FAB (+) 465 (MH+) | 194–196° C. | ¹H-NMR(DMSO-d₆) δ ppm: 1.32–1.42(m, 2H), 1.73–1.78(m, 2H), 1.86–1.92(m, 2H), 2.64–2.72(m, 2H), 2.95–3.00(m, 1H), 3.22(s, 2H), 3.61(s, 3H), 3.62(d, J=7Hz, 2H), 6.67(dd, J=1, 8Hz, 1H), 6.73(d, J=1Hz, 1H), 6.82(d, J=8Hz, 1H), 6.95(d, J=7Hz, 1H), 7.32(t, J=7Hz, 1H), 7.62(d, J=3Hz, 1H), 7.63(d, J=3Hz, 1H), 9.44(s, 1H) |
| 443 | N-[1-(5H-pyrido[3,4-b][1,4]benzothiazin-7-ylmethyl)piperidin-4-yl]-N',N'-dimethylsulfamide | FAB (+) 420 (MH+) | 198–199° C. | ¹H-NMR(CDCl₃) δ ppm: 1.54(dq, J=3, 11Hz, 2H), 1.97(br.d, J=11Hz, 2H), 2.08(t, J=11Hz, 2H), 2.75(br.s, 2H), 2, 78(s, 6H), 3.22(br.s, 1H), 3.34(s, 2H), 4.02(d, J=7Hz, 1H), 6.05(s, 1H), 6.38(d, J=5Hz, 1H), 6.56(s, 1H), 6.77(dd, J=2, 8Hz, 1H), 6.88(d, J=8Hz, 1H), 8.00(s, 1H), 8.24(d, J=5Hz, 1H), |
| 444 | 1-(10H-pyrazino[2,3-b][1,4]benzothiazin-8-ylmethyl)piperidine-4-spiro-3'-(4'-butanolide) | FAB (+) 369 (MH+) | 180–182° C. | ¹H-NMR(CDCl₃) δ ppm: 1.68(m, 4H), 2.32(m, 2H), 2.40(s, 2H), 2.46(m, 2H), 3.33(s, 2H), 4.05(s, 2H), 6.38(s, 1H), 6.50(s, 1H), 6.75(d, J=8Hz, 1H), 6.84(d, J=8Hz, 1H), 7.58(d, J=3Hz, 1H), 7.68(d, J=3Hz, 1H) |
| 445 | 1-(10H-pyrazino[2,3-b][1,4]benzothiazin-8-ylmethyl)piperidine-4-spiro-3'-(4'-butanelactam) | FAB (+) 368 (MH+) | 211–212° C. | ¹H-NMR(CDCl₃) δ ppm: 1.67(t, J=6Hz, 4H), 2.41(s, 2H), 2.35(br.s, 2H), 2.43(br.s, 2H), 3.18(s, 2H), 3.24(s, 2H), 5.47(br.s, 1H), 6.45(br.s, 1H), 6.53(d, J=2Hz, 1H), 6.75(dd, J=2, 8Hz, 1H), 6.83(d, J=8Hz, 1H), 7.57(d, J=3Hz, 1H), 7.69(d, J=3Hz, 1H) |

| Ex. | Structural formula | MS | M. p. | NMR |
|---|---|---|---|---|
| 446 | N-[1-(10H-cyanopyrido[2,3-b][1,4]benzothiazin-8-ylmethyl)piperidin-4-yl]-N',N'-dimethylsulfamide | FAB (+) 444 (MH+) | 155–157° C. | $^1$H-NMR(CDCl$_3$) δ ppm: 1.57(m, 2H), 2.0(m, 4H), 2.2(br.s, 2H), 2.79(s, 6H), 3.25(br.s, 1H), 3.35(s, 2H), 6.64(br.s, 1H), 6.78(dd, J=2, 8Hz, 1H), 6.83(d, J=8Hz, 1H), 6.87(d, J=5Hz, 1H), 7.81(d, J=5Hz, 1H) |
| 447 | N-[1-(10H-pyrazino[2,3-b]pyrido[2,3-e][1,4]thiazin-8-ylmethyl)-piperidin-4-yl]-N',N'-dimethylsulfamide | FAB (+) 422 (MH+) | 205–210° C. | $^1$H-NMR(DMSO-d$_6$) δ ppm: 1.36–1.48(m, 2H), 1.73–1.80(m, 2H), 1.89–1.98(m, 3H), 2.61(s, 6H), 2.64–2.74(m, 2H), 3.24(s, 2H), 6.93(s, 1H), 7.19(s, 1H), 7.64(s, 1H), 7.67(s, 1H), 9.54(s, 1H) |
| 448 | N$^2$-methanesulfonyl-N$^1$-[1-(10H-pyrazino[2,3-b][1,4]benzothiazin-8-ylmethyl)piperidin-4-yl]formamidine | FAB (+) 419 (MH+) | 119–122° C. | $^1$H-NMR(CDCl$_3$) δ ppm: 1.46(m, 2H), 1.86–1.96(m, 1H), 1.96–2.03(m, 2H), 2.05–2.16(m, 2H), 2.76–2.87(m, 2H), 2.96(s, 3H), 3.33(s, 2H), 5.89–5.96(m, 1H), 6.52(d, J=1.7Hz, 1H), 6.69–6.72(br.s, 1H), 6.74(dd, J=1.7, 8.3Hz, 1H), 6.82(d, J=8.3Hz, 1H), 7.56(d, J=3.0Hz, 1H), 7.69(d, J=3.0Hz, 1H), 8.14(d, J=5.6Hz, 1H) |
| 449 | N,N-[[4-(10H-pyrazino[2,3-b][1,4]benzothiazin-8-ylmethyl)piperazin-1-ylmethylene]methylsulfonamide | FAB (+) 404 (M+) 405 (MH+) | 212–214° C. | $^1$H-NMR(DMSO-d$_6$) δ ppm: 2.32–2.37(m, 2H), 2.39–2.44(m, 2H), 2.84(s, 3H), 3.33(s, 2H), 3.48–3.55(m, 4H), 6.71(dd, J=1.6, 8.6Hz, 1H), 6.75(d, J=1.6Hz, 1H), 6.86(d, J=8.6Hz, 1H), 7.61–7.64(m, 2H), 8.07(s, 1H), 9.46(s, 1H) |

| Ex. | Structural formula | MS | M. p. | NMR |
|---|---|---|---|---|
| 450 | N,N-[3-(10H-pyrazino[2,3-b][1,4]benzothiazin-8-ylmethyl)-3-azapentamethylene]-N'-methylsulfamide | FAB (+) 392 (M+) | 208–210° C. | $^1$H-NMR(DMSO-d$_6$) δ ppm: 2.36–2.41(m, 4H), 2.49(d, J=5.1Hz, 3H), 2.99–3.05(m, 4H), 3.30(br.s, 2H), 6.70(d, J=8.0Hz, 1H), 6.77(d, J=2.2Hz, 1H), 6.84(dd, J=2.2, 8.0Hz, 1H), 7.10(q, J=5.1Hz, 1H), 7.63(s, 2H), 9.45(s, 1H) |
| 451 | N,N-[3-(10H-pyrazino[2,3-b][1,4]benzothiazin-8-ylmethyl)-3-azapentamethylene] sulfamide | FAB (+) 378 (M+) | 215–217° C. (decompose) | $^1$H-NMR(DMSO-d$_6$) δ ppm: 2.37–2.43(m, 4H), 2.91–2.96(m, 4H), 3.30(s, 2H), 6.70(d, J=8.4Hz, 1H), 6.75–6.79(m, 3H), 6.84(dd, J=2.0, 8.4Hz, 1H), 7.61–7.64(m, 2H), 9.47(s, 1H) |
| 452 | N-[1-(10H-pyrazino[2,3-b][1,4]benzothiazin-8-ylmethyl)piperidin-4-yl] amidinocarboxylic acid | FAB (+) 385 (MH+) | 186–190° C. | $^1$H-NMR(DMSO-d$_6$) δ ppm: 1.56–1.70(m, 4H), 1.85–1.97(m, 2H), 2.70–2.78(m, 2H), 3.25(s, 2H), 3.36–3.47(m, 1H), 6.68(d, J=7.9Hz, 1H), 6.73(s, 1H), 6.83(d, J=7.9Hz, 1H), 7.60–7.64(m, 2H), 8.60–8.80(br.s, 2H), 8.84–9.02(br.s, 1H), 9.46(s, 1H) |
| 453 | [1-(10H-pyrazino[2,3-b][1,4]benzothiazin-8-ylmethyl)-4-piperidin-4-yl]-(N$^2$-sulfamoyl) carboxamidine | FAB (+) 420 (NH+) | 202–206° C. | $^1$H-NMR(DMSO-d$_6$) δ ppm: 1.56–1.68(m, 4H), 1.80–1.90(m, 2H), 2.07–2.17(m, 1H), 2.77–2.84(m, 2H), 3.25(br.s, 2H), 6.47(br.s, 2H), 6.69(d, J=8.0Hz, 1H), 6.76(s, 1H), 6.83(d, J=8.0Hz, 1H), 7.20(br.s, 1H), 7.62(s, 2H), 8.13(br.s, 1H), 9.45(s, 1H) |

| Ex. | Structural formula | MS | M. p. | NMR |
|---|---|---|---|---|
| 454 | [1-(10H-pyrazino[2,3-b][1,4]benzothiazin-8-ylmethyl)piperidin-4-yl]-(N²-methanesulfonyl)carboxamidine | FAB (+) 419 (MH⁺) | 204–209° C. | ¹H-NMR(DMSO-d₆) δ ppm: 1.56–1.69(m, 4H), 1.80–1.89(m, 2H), 2.14–2.23(m, 1H), 2.76–2.82(m, 2H), 2.84(s, 3H), 3.24(br.s, 2H), 6.68(dd, J=1.3, 8.3Hz, 1H), 6.76(d, J=1.3Hz, 1H), 6.82(d, J=8.3Hz, 1H), 7.62(s, 2H), 7.63(br.s, 1H), 8.38(br.s, 1H), 9.45(s, 1H) |
| 455 | N-[1-(10H-pyrimido[5,4-b][1,4]benzothiazin-8-ylmethyl)piperidin-4-yl]-N′,N′-dimethylsulfamide | FAB (+) 421 (MH⁺) | 198–203° C. | ¹H-NMR(DMSO-d₆) δ ppm: 1.35–1.48(m, 2H), 1.71–1.80(m, 2H), 1.85–1.95(m, 2H), 2.60(s, 6H), 2.65–2.73(m, 2H), 2.90–3.00(m, 1H) 3.23(s, 2H), 6.73(dd, J=1.3, 7.7Hz, 1H), 6.78(d, J=1.3Hz, 1H), 6.86(d, J=7.7Hz, 1H), 7.19(d, J=7.4Hz, 1H), 7.92(s, 1H), 8.22(s, 1H), 9.78(s, 1H) |
| 456 | 8-[(2-isoindolin-2-yl)methyl]-10H-pyrazino[2,3-b][1,4]benzothiazine | FAB (+) 333 (MH⁺) | 219–220° C. | ¹H-NMR(CDCl₃) δ ppm: 3.76(s, 2H), 3.92(s, 4H), 6.58(br.s, 1H), 6.64(br.s, 1H), 6.83–6.88(m, 2H), 7.19(s, 4H), 7.56(d, J=2.9Hz, 1H), 7.63(d, J=2.9Hz, 1H) |
| 457 | N-[1-(10H-pyrazino[2,3-b][1,4]benzoxazin-8-ylmethyl)piperidin-4-yl]methanesulfonamide | ESI (+) 376 (MH⁺) | 241–243° C. | ¹H-NMR(DMSO-d₆) δ ppm: 1.34–1.48(m, 2H), 1.72–1.82(m, 2H), 1.86–1.98(m, 2H), 2.64–2.74(m, 2H), 2.88(s, 3H), 3.20–3.14(m, 1H), 3.21(s, 2H), 6.5–6.65(m, 2H), 6.65–6.70(m, 1H), 7.0–7.1(m, 1H), 7.20–7.28(m, 1H), 7.42–7.48(m, 1H), 9.57(s, 1H) |
| 458 | N-[1-(10H-pyrazino[2,3-b][1,4]benzothiazin-8-ylmethyl)piperidin-4-yl]methylmethanesulfonamide | ESI (+) 406 (MH⁺) | 218–221° C. | ¹H-NMR(DMSO-d₆) δ ppm: 1.0–1.16(m, 2H), 1.30–1.42(m, 1H), 1.58–1.68(m, 2H), 1.78–1.88(m, 2H), 2.7–2.8(m, 2H), 2.78(t, J=7Hz, 2H), 2.84(s, 3H), 3.23(s, 2H), 6.65–6.70(m, 1H), 6.74(s, 1H), 6.82(d, J=8Hz, 1H), 6.96(t, J=6Hz, 1H), 7.60–7.65(m, 2H), 9.43(s, 1H) |

-continued

| Ex. | Structural formula | MS | M. p. | NMR |
|---|---|---|---|---|
| 459 | N-[1-(10H-pyrazino[2,3-b][1,4]benzothiazin-8-ylmethyl)piperidin-4-yl]methylacetamide | ESI (+) 370 (MH$^+$) | 168–170° C. | $^1$H-NMR(DMSO-d$_6$) δ ppm: 1.0–1.2(m, 2H), 1.25–1.45(m, 1H), 1.50–1.65(m, 2H), 1.77(s, 3H), 1.75–1.90(m, 2H), 2.68–2.80(m, 2H), 2.89(t, J=7Hz, 2H), 3.22(br.s, 2H), 6.6–6.75(m, 1H), 6.74(s, 1H), 6.75–6.90(m, 1H), 7.62(d, J=3Hz, 1H), 7.63(d, J=3Hz, 1H), 7.79(m, 1H), 9.43(s, 1H) |
| 460 | N-[1-(10H-pyrazino[2,3-b][1,4]benzothiazin-8-ylmethyl)piperidin-4-yl]-N′,N′-dimethylsulfamide | ESI (+) 421 (MH$^+$) | 202–203° C. | $^1$H-NMR(DMSO-d$_6$) δ ppm: 1.35–1.50(m, 2H), 1.7–1.8(m, 2H), 1.80–1.98(m, 2H), 2.60(s, 6H), 2.6–2.75(m, 2H), 2.9–3.0(m, 1H), 3.21(s, 2H), 6.66(d, J=8Hz, 1H), 6.72(s, 1H), 6.81(d, J=8Hz, 1H), 7.18(d, J=8Hz, 1H), 7.61(d, J=3Hz, 1H), 7.62(d, J=3Hz, 1H), 9.43(s, 1H) |
| 461 | N-[1-(10H-pyrido[2,3-b][1,4]benzoxazin-8-ylmethyl)piperidin-4-yl]-N′-methylsulfamide | ESI (+) 406 (MH$^+$) | 216–218° C. | $^1$H-NMR(DMSO-d$_6$) δ ppm: 1.32–1.48(m, 2H), 1.70–1.80(m, 2H), 1.82–1.94(m, 2H), 2.41(d, J=5Hz, 3H), 2.64–2.74(m, 2H), 2.84–2.96(m, 1H), 3.23(s, 2H), 6.59(q, J=5Hz, 1H), 6.67(dd, J=1, 8Hz, 1H), 6.70(dd, J=1, 8Hz, 1H), 6.78(d, J=1Hz, 1H), 6.83(d, J=8Hz, 1H), 6.87(d, J=8Hz, 1H), 7.25(dd, J=1, 8Hz, 1H), 7.78(dd, J=1, 8Hz, 1H), 9.14(s, 1H) |
| 462 | N-[1-(10H-pyrazino[2,3-b][1,4]benzoxazin-8-ylmethyl)piperidin-4-yl]-N′-methylsulfamide | ESI (+) 391 (MH$^+$) | 219–222° C. | $^1$H-NMR(DMSO-d$_6$) δ ppm: 1.3–1.46(m, 2H), 1.70–1.84(m, 2H), 1.82–1.94(m, 2H), 2.41(d, J=5Hz, 3H), 2.64–2.78(m, 2H), 2.78–2.96(m, 1H), 3.21(s, 2H), 6.5–6.65(m, 3H), 6.68(d, J=8Hz, 1H), 6.87(d, J=7Hz, 1H), 7.24(d, J=3Hz, 1H), 7.44(d, J=3Hz, 1H), 9.57(s, 1H) |

| Ex. | Structural formula | MS | M. p. | NMR |
|---|---|---|---|---|
| 463 | N-[1-(10H-pyrazino[2,3-b][1,4]benzothiazin-8-ylmethyl)piperidin-4-yl]trifluoromethaneulfonamide | ESI (+) 446 (MH⁺) | 199–201° C. | ¹H-NMR(DMSO-$d_6$) δ pm: 1.53–1.60(m, 2H), 1.7–1.8(m, 2H), 1.9–2.3(m, 2H), 2.66–2.80(m, 2H), 3.25(s, 2H), 3.2–3.4(m, 1H), 6.67(d, J=8Hz, 1H), 6.73(s, 1H), 6.83(d, J=8Hz, 1H), 7.62(s, 2H), 9.45(s, 2H) |
| 464 | 2-[1-(10H-pyrazino 2,3-b][1,4]benzothiazin-8-ylmethyl)piperidin-4-ylidene]-4-butanolide | FAB (+) 381 (MH⁺) | 159–162° C. | ¹H-NMR(DMSO-$d_6$) δ pm: 2.29(m, 2H), 2.39(m, 2H), 2.44(m, 2H), 2.85(t, J=7Hz, 2H), 2.94(br.s, 2H), 3.32(s, 2H), 4.22(t, J=7Hz, 2H), 6.72(d, J=8Hz, 1H), 6.76(s, 1H), 6.85(d, J=8Hz, 1H), 7.63(m, 2H), 9.45(s, 1H) |
| 465 | 1-[1-(10H-pyrazino 2,3-b][1,4]benzothiazin-8-ylmethyl)piperidin-4-yl]-1,2-ethanediol | FAB (+) 359 (MH⁺) | 182–185° C. | ¹H-NMR(DMSO-$d_6$) δ pm: 1.16–1.35(m, 3H), 1.44(m, 1H), 1.63(br.d, J=12Hz, 1H), 1.78(br.q, J=8Hz, 2H), 2.77(m, 2H), 3.17–3.38(m, 3H), 3.20(s, 2H), 4.13(d, J=6Hz, 1H), 4.37(t, J=6Hz, 1H), 6.67(d, J=8Hz, 1H), 6.75(s, 1H), 6.81(d, J=8Hz, 1H), 7.63(m, 2H), 9.43(s, 1H) |

Example 466

N,N-[3-(10H-Pyrazino[2,3-b][1,4]benzothiazin-8-ylmethyl)-3-azapentamethylene]-N',N'-dimethylsulfamide The title compound was obtained as yellow crystals by treating 3-benzyl-3-azapentamethylene]-N',N'-dimethylsulfamide and 8-chloromethyl-10H-pyrazino[2,3-b][1,4]benzothiazine by the same method as the one of Example 17.

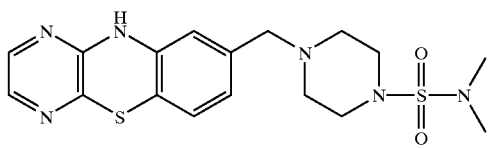

¹H-NMR(CDCl₃) δ ppm: 2.46–2.55(m, 4H), 2.83(s, 6H), 3.25–3.35(m, 4H), 3.38(s, 2H), 6.44(br.s, 1H), 6.54(s, 1H), 6.76(d, J=8.0 Hz, 1H), 6.84(d, J=8.0 Hz, 1H), 7.58(d, J=2.8 Hz, 1H), 7.70(d, J=2.8 Hz, 1H)
m.p.: 171–173° C.

Example 467

N-[1-(10H-Pyrazino[2,3-b][1,4]benzothiazin-8-ylmethyl)-azetidin-3-ylmethyl]methanesulfonamide The title compound was obtained as yellow crystals by treating N-[(1-diphenylmethylazetidin-3-yl)methyl]methanesulfoamide and 8-chloromethyl-10H-pyrazino[2,3-b][1,4]benzothiazine by the same method as the one of Example 64.

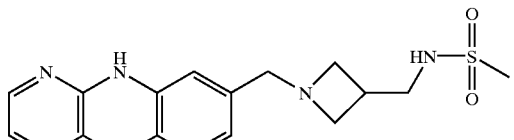

¹H-NMR(DMSO-$d_6$) δ ppm: 2.52(br.s, 1H), 2.87(s, 3H), 2.88(br.s, 2H), 3.10(t, J=7 Hz, 2H), 3.23(br.s, 2H), 3.41(br.s, 2H), 6.68(d, J=8 Hz, 1H), 6.69(s, 1H), 6.82(d, J=8 Hz, 1H), 7.07(t, J=5 Hz, 1H), 7.62(d, J=3 Hz, 1H), 7.63(d, J=3 Hz, 1H), 9.44(s, 1H)
MS: FAB(+)378(MH⁺)
m.p.: 84–88° C.

Examples 468 to 497

The following compound was obtained by the same method as the one of Example 467.

| Ex. | Structural formula | MS | M.p. | NMR |
|---|---|---|---|---|
| 468 | N-[1-(10H-pyrazino[2,3-b][1,4]benzothiazin-8-ylmethyl)azetidin-3-ylmethyl]-N'-methylsulfamide | FAB (+) 393 (MH$^+$) | 173–176° C. | $^1$H-NMR (DMSO-d$_6$) δ ppm: 2.41 (d, J = 5 Hz, 3H), 2.60 (br.s, 3H), 2.96 (t, J = 6 Hz, 2H), 3.44 (br.s, 2H), 3.57 (br.s, 2H), 6.68 (d, J = 8 Hz, 1H), 6.69 (s, 1H), 6.84 (d, J = 8 Hz, 1H), 6.94 (s, 1H), 7.62 (d, J = 3 Hz, 1H), 7.63 (d, J = 3 Hz, 1H), 9.48 (s, 1H) |

Example

The following compounds were obtained by the same method as the one of Example 66.

| Ex. | Structural formula | MS | M.p. | NMR |
|---|---|---|---|---|
| 469 | N-(tetrazol-5-yl)-4-[1-(10H-pyrazino[2,3-b][1,4]benzothiazin-8-ylmethyl)-piperidin-4-yl]butanamide | FAB(+) 452(MH$^+$) | 190–191° C. | $^1$H-NMR (DMSO-d$_6$) δ ppm: 1.10–1.24(m, 6H), 1.54–1.66(m, 4H), 2.0(m, 1H), 2.36(m, 2H), 2.82(d, J=10Hz, 2H), 3.30(s, 2H), 6.72(d, J=8Hz, 1H), 6.75(d, J=2Hz, 1H), 6.85(dd, J=2, 8Hz, 1H), 7.63(m, 2H), 9.48(br.s, 1H), 11.61(br.s, 1H) |
| 470 | N-[8-methyl-8-azabicyclo[3.2.1]oct-3-yl]-[7-[(10H-pyrazino[2,3-b][1,4]benzothiazin-8-ylmethyl)-7-azaspiro[3.5]non-2-yl]acetamide | FAB(+) 519(MH$^+$) | 181–184° C. | $^1$H-NMR (CDCl$_3$) δ ppm: 1.40–1.80(m, 12H), 1.90–2.40(m, 9H), 2.27(d, J=6.8Hz, 2H), 2.34(s, 3H), 2.52–2.64(m, 1H), 3.18–3.27(m, 2H), 3.30(s, 2H), 4.02–4.12(m, 1H), 6.39(br.s, 1H), 6.54(s, 1H), 6.74(d, J=8.0Hz, 1H), 6.82(d, J=8.0Hz, 1H), 7.57(d, J=2.8Hz, 1H), 7.69(d, J=2.8Hz, 1H) |
| 471 | 1-(10H-pyrazino[2,3-b][1,4]benzothiazin-8-ylmethyl)-4-piperidone oxime O-methyl ether | ESI (+) 342(MH$^+$) | 142–143° C. | $^1$H-NMR (CDCl$_3$) δ ppm: 2.31–2.35(m, 2H), 2.44–2.49(m, 2H), 2.51–2.55(m, 2H), 2.55–2.60(m, 2H), 3.36(s, 2H), 3.82(s, 3H), 6.54(d, J=7.9Hz, 1H), 6.65–6.69(br.s, 1H), 6.77(dd, J=1.5, 7.9Hz, 1H), 6.83(d, J=79Hz, 1H), 7.58(d, J=3.1Hz, 1H), 7.69(d, J=3.1Hz, 1H) |

| Ex. | Structural formula | MS | M.p. | NMR |
|---|---|---|---|---|
| 472 | 4-amino-3-[4-(10H-pyrazino[2,3-b][1,4]benzothiazin-8-ylmethyl)piperazino]-3-cyclobutene-1,2-dione | FAB(+) 394(M+) | 285–288° C. (decompose) | $^1$H-NMR (DMSO-$d_6$) δ ppm: 2.46(br.m, 4H), 3.37(s, 2H), 3.68(br.m, 4H), 6.74(d, J=7.9Hz, 1H), 6.77(s, 1H), 6.86(d, J=7.9Hz, 1H), 7.64(d, J=2.9Hz, 1H), 7.65(d, J=2.9Hz, 1H), 7.70(s, 2H), 9.48(s, 1H) |
| 473 | 4-methylamino-3-[4-(10H-pyrazino[2,3-b][1,4]benzothiazin-8-ylmethyl)piperazino]-3-cyclobutene-1,2-dione | FAB(+) 409(MH+) | >300° C. | $^1$H-NMR (DMSO-$d_6$) δ ppm: 2.43(m, 4H), 3.16(d, J=4.6Hz, 3H), 3.35(s, 2H), 3.64(br.s, 4H), 6.73(dd, J=1.5, 7.9Hz, 1H), 6.76(d, J=1.5Hz, 1H), 6.86(d, J=7.9Hz, 1H), 7.61(m, 1H), 7.64(d, J=2.7Hz, 1H), 7.65(d, J=2.7Hz, 1H), 9.48(s, 1H) |
| 474 | 4-dimethylamino-3-[4-(10H-pyrazino[2,3-b][1,4]benzothiazin-8-ylmethyl)piperazino]-3-cyclobutene-1,2-dione | FAB(+) 423(MH+) | 296–300° C. (decompose) | $^1$H-NMR (DMSO-$d_6$) δ ppm: 2.45(m, 4H), 3.15(s, 6H), 3.34(s, 2H), 3.61(m, 4H), 6.73(d, J=7.9Hz, 1H), 6.77(br.s, 1H), 6.86(d, J=7.9Hz, 1H), 7.64(br.s, 2H), 9.47(s, 1H) |
| 475 | [3-(10H-pyrazino[2,3-b][1,4]benzothiazin-8-ylmethyl)-3-azabicyclo[3.3.0]octan-7-ol | ESI(+) 341(MH+) | 192–195°C. | $^1$H-NMR (CDCl$_3$) δ ppm: 1.70(s, 1H), 1.86–1.97(m, 4H), 2.16–2.27(m, 2H), 2.70–2.80(m, 2H), 2.82–2.90(m, 2H), 3.51(s, 2H), 4.05–4.11(m, 1H), 6.54(br.s, 1H), 6.68(dd, J=2, 8Hz, 1H), 6.79(d, J=8Hz, 1H), 7.00(br.s, 1H), 7.55(d, J=2.8Hz, 1H), 7.65(d, J=2.8Hz, 1H) |
| 476 | [3-(10H-pyrazino[2,3-b][1,4]benzothiazin-8-ylmethyl)-3-azabicyclo[4.1.0]hept-6-yl]methanol | | | $^1$H-NMR (CDCl$_3$) δ ppm: 0.53–0.59(m, 2H), 0.97–1.0(m, 1H), 1.80–2.08(m, 2H), 1.95(br.s, 1H), 2.12–2.24(m, 2H), 2.58–2.74(m, 2H), 3.21–3.50(m, 4H), 6.56(s, 1H), 6.71–6.76(m, 2H), 6.81(d, J=8.0Hz, 1H), 7.56(d, J=2.4Hz, 1H), 7.68(d, J=2.4Hz, 1H) |
| 477 | 2-[3-(10H-pyrazino[2,3-b][1,4]benzothiazin-8-ylmethyl)-3-azabicyclo[4.1.0]hept-6-yl]methanol | ESI(+) 355(MH+) | 57–60° C. | $^1$H-NMR (CDCl$_3$) δ ppm: 0.16–0.22(m, 1H), 0.50–0.55(m, 1H), 0.90–1.00(m, 1H), 1.35–1.75(m, 5H), 2.30–2.50(m, 4H), 3.37(s, 2H), 3.50–3.72(m, 2H), 6.59(s, 1H), 6.71(br.s, 1H), 6.77(dd, J=1.6, 8.0Hz, 1H), 6.83(d, J=8.0Hz, 1H), 7.58(d, J=2.8Hz, 1H), 7.69(d, J=2.8Hz, 1H) |

-continued

| Ex. | Structural formula | MS | M.p. | NMR |
|---|---|---|---|---|
| 478 | [3-(10H-pyrazino[2,3-b][1,4]benzothiazin-8-ylmethyl)-3-azabicyclo[3.3.0]oct-7-yl]methanol | ESI(+) 355(MH+) | oil | ¹H-NMR (CDCl₃) δ ppm: 1.20–1.32(m, 1H), 1.35–1.64(m, 1H), 1.82–1.88(m, 1H), 2.00–2.16(m, 3H), 2.31–2.40(m, 2H), 2.57–2.86(m, 4H), 3.40–3.78(m, 4H), 6.60–6.86(m, 4H), 7.56(d, J=2.8Hz, 1H), 7.68–7.69(m, 1H) |
| 479 | 8-[(4,5,6,7-tetrahydrothieno[2,3-c]pyridin-6-yl)methyl]-10H-pyrazino[2,3-b][1,4]benzothiazine | FAB(+) 353(MH+) |  | ¹H-NMR (CDCl₃) δ ppm: 2.71–2.82(m, 4H), 3.56(s, 2H), 3.66(s, 2H), 6.43(s, 1H), 6.62(s, 1H), 6.79(d, J=5.0Hz, 1H), 6.81(d, J=8.0Hz, 1H), 6.85(d, J=8.0Hz, 1H), 7.09(d, J=5.0Hz, 1H), 7.57(d, J=2.8Hz, 1H), 7.68(d, J=2.8Hz, 1H) |
| 480 | 8-[(4,5,6,7-tetrahydrofuro[2,3-c]pyridin-6-yl)methyl]-10H-pyrazino[2,3-b][1,4]benzothiazine | FAB(+) 337(MH+) | 168–172° C. | ¹H-NMR (CDCl₃) δ ppm: 2.54(t, J=5.6Hz, 2H), 2.72(t, J=5.6Hz, 2H), 3.50(s, 2H), 3.56(s, 2H), 6.24(d, J=2.0Hz, 1H), 6.49(br.s, 1H), 6.60(s, 1H), 6.81(d, J=8.0Hz, 1H), 6.85(d, J=8.0Hz, 1H), 7.26(d, J=2.0Hz, 1H), 7.57(d, J=2.8Hz, 1H), 7.68(d, J=2.8Hz, 1H) |

Examples

Starting with known compounds, the following compounds were obtained by the same method as the one of Example 63.

| Ex. | Structural formula | MS | M.p. | NMR |
|---|---|---|---|---|
| 481 | N,N-[3-(10H-pyrazino[2,3-b][1,4]benzothiazin-8-ylmethyl)-3-azapentamethylene]acetamide | FAB(+) 341(M+) |  | ¹H-NMR (DMSO-d₆) δ ppm: 1.95(s, 3H), 2.22–2.27(m, 2H), 2.29–2.34(s, 2H), 3.29(s, 2H), 3.36–3.43(m, 4H), 6.70(d, J=8.2Hz, 1H), 6.75(s, 1H), 6.84(d, J=8.2Hz, 1H), 7.61–7.64(m, 2H), 9.45(s, 1H) |
| 482 | N,N-[4-(10H-pyrazino[2,3-b][1,4]benzothiazin-8-ylmethyl)-4-azahexamethylene]methanesulfonamide | FAB(+) 391(M+) 392(MH+) | 158–160° C. | ¹H-NMR (DMSO-d₆) δ ppm: 1.71–1.80(m, 2H), 2.54–2.59(m, 2H), 2.59–2.63(m, 2H), 2.87(s, 3H), 3.28–3.34(m, 4H), 3.43(s, 2H), 6.71(d, J=8.3Hz, 1H), 6.78(s, 1H), 6.84(d, J=8.3Hz, 1H), 7.61–7.64(m, 2H), 9.47(s, 1H) |

-continued

| Ex. | Structural formula | MS | M.p. | NMR |
|---|---|---|---|---|
| 483 | 8-(1-imidazolinylmethyl)-10H-pyrazino[2,3-b][1,4]benzothiazinehydrochloride | FAB(+) 298(MH+) | 238° C. (decompose) | $^1$H-NMR (DMSO-d$_6$) δ ppm: 1.84–1.92(m, 2H), 2.18–2.24(m, 2H), 2.24–2.29(m, 2H), 4.48(s, 2H), 6.68(d, J=1.3Hz, 1H), 6.76(dd, J=1.3, 8.6Hz, 1H), 6.95(d, J=8.6Hz, 1H), 7.64(s, 2H), 8.43(d, J=6.5Hz, 1H), 9.58(s, 1H), 10.08–10.14(br.s, 1H) |
| 484 | (R*,R*)-1-(10H-pyrazino[2,3-b][1,4]benzothiazin-8-ylmethyl)pyrrolidine-3,4-diol hydrochloride | ESI(+) 317(MH+) | 241–242° C. (decompose) | $^1$H-NMR (DMSO-d$_6$) δ ppm: 2.95–3.04(m, 1H), 3.16–3.25(m, 1H), 3.26–3.35(m, 1H), 3.55–3.65(m, 1H), 4.04–4.23(m, 4H), 5.18–5.26(m, 1H), 5.30–5.39(m, 1H), 6.81(s, 1H), 6.98(d, J=8.5Hz, 1H), 7.02(d, J=8.5Hz, 1H), 7.66(s, 2H), 9.68(s, 1H), 10.67–10.80(br.s, 1H) |
| 485 | [4-(10H-pyrazino[2,3-b][1,4]benzothiazin-8-ylmethyl)piperazin-1-yl]methyleneaminocarbonitrile | FAB(+) 352(MH+) | 238–241° C. (decompose) | $^1$H-NMR (DMSO-d$_6$) δ ppm: 2.31–2.36(m, 2H), 2.38–2.43(m, 2H), 3.29(s, 2H), 3.43–3.49(m, 4H), 6.71(d, J=7.4Hz, 1H), 6.75(s, 1H), 6.85(d, J=7.4Hz, 1H), 7.62(d, J=2.3Hz, 1H), 7.63(d, J=2.3Hz, 1H), 8.40(s, 1H), 9.46(s, 1H) |
| 486 | 1-[4-(10H-pyrazino[2,3-b][1,4]benzothiazin-8-ylmethyl)piperazin-1-yl]ethyleneaminocarbonitrile | ESI(+) 366 (MH+), 388 (MNa+) | 234° C. (decompose) | $^1$H-NMR (DMSO-d$_6$) δ ppm: 2.30–2.36(m, 2H), 2.33(s, 3H), 2.37–2.42(m, 2H), 3.31(s, 2H), 3.49–3.54(m, 2H), 3.58–3.63(m, 2H), 6.70(dd, J=1.8, 7.8Hz, 1H), 6.74(d, J=1.8, Hz, 1H), 6.85(d, J=7.8Hz, 1H), 7.62(d, J=2.7Hz, 1H), 7.63(d, J=2.7Hz, 1H), 9.39–9.53(br.s, 1H) |
| 487 | 8-(heptamethyleneiminomethyl)-10H-pyrazino[2,3-b][1,4]benzothiazine | FAB(+) 327(MH+) | 133–135° C. | $^1$H-NMR (CDCl$_3$) δ ppm: 1.50–1.75(m, 10H), 2.48–2.60(m, 4H), 3.44(s, 2H), 6.49(br.s, 1H), 6.59(s, 1H), 6.80–6.84(m, 2H), 7.56(d, J=2.8Hz, 1H), 7.68(d, J=2.8Hz, 1H) |
| 488 | 8-(hexamethyleneiminomethyl)-10H-pyrazino[2,3-b][1,4]benzothiazine | FAB(+) 313(MH+) | 161–163° C. | $^1$H-NMR (CDCl$_3$) δ ppm: 1.58–1.80(m, 8H), 2.60–2.70(m, 4H), 3.53(s, 2H), 6.57(br.s, 1H), 6.80(s, 1H), 6.77(d, J=8.0Hz, 1H), 6.82(d, J=8.0Hz, 1H), 7.57(d, J=2.8Hz, 1H), 7.68(d, J=2.8Hz, 1H) |

-continued

| Ex. | Structural formula | MS | M.p. | NMR |
|---|---|---|---|---|
| 489 | 8-[(azetidin-1-yl)methyl]-10H-pyrazino[2,3-b][1,4]benzothiazine | FAB(+) 271(MH+) | 158–161° C. | $^1$H-NMR (CDCl$_3$) δ ppm: 2.11(quint, J=6.8Hz, 2H), 3.23(t, J=6.8Hz, 4H), 3.44(s, 2H), 6.49(d, J=1.6Hz, 1H), 6.54(br.s, 1H), 6.72(dd, J=1.6, 8.0Hz, 1H), 6.82(d, J=8.0Hz, 1H), 7.57(d, J=2.8Hz, 1H), 7.68(d, J=2.8Hz, 1H) |
| 490 | 1-(10H-pyrazino[2,3-b][1,4]benzothiazin-8-ylmethyl)pyridinium chloride | FAB(+) 293(M+) | 230–232° C. | $^1$H-NMR (DMSO-d$_6$) δ ppm: 5.67(s, 2H), 6.68(d, J=1Hz, 1H), 6.84(dd, J=1, 7Hz, 1H), 6.98(d, J=7Hz, 1H), 7.65(s, 2H), 8.19(dd, J=6, 7Hz, 2H), 8.64(t, J=7Hz, 1H), 9.11(d, J=6Hz, 2H), 9.61(s, 1H) |
| 491 | 1-(10H-pyrazino[2,3-b][1,4]benzothiazin-8-ylmethyl)-4-piperidone | FAB(+) 312(M+) | 186–188° C. | $^1$H-NMR (DMSO-d$_6$) δ ppm: 2.32(t, J=6Hz, 4H), 2.64(t, J=6Hz, 4H), 3.32(s, 2H), 6.75(d, J=8Hz, 1H), 6.80(s, 1H), 6.86(d, J=8Hz, 1H), 7.63(m, 2H), 9.47(s, 1H) |
| 492 | 4-methyl-4-(10H-pyrazino[2,3-b][1,4]benzothiazin-8-ylmethyl)morpholiniumchloride | FAB(+) 315(M+) | 144–146° C. | $^1$H-NMR (CD$_3$OD) δ ppm: 3.12(s, 3H), 3.34–3.41(br.s, 2H), 3.54–3.61(ddd, J=5, 8, 13Hz, 2H), 4.01–4.07(m, 4H), 4.49(s, 2H), 6.78(d, J=2Hz, 1H), 6.95(dd, J=2, 8Hz, 1H), 7.01(d, J=8Hz, 1H), 7.62(s, 2H) |
| 493 | 1-(10H-pyrazino[2,3-b][1,4]benzothiazin-8-ylmethyl)-4-(hydroxymethyl)piperidin-4-ol | FAB(+) 345(MH+) | 170–173° C. | $^1$H-NMR (DMSO-d$_6$) δ ppm: 1.29(br.d, J=12Hz, 2H), 1.54(br.t, J=12Hz, 2H), 2.22(br.t, J=10Hz, 2H), 2.43(m, 2H), 3.12(s, 2H), 3.23(s, 2H), 4.13(br.s, 1H), 4.51(br.s, 1H), 6.68(d, J=8Hz, 1H), 6.75(s, 1H), 6.82(d, J=8Hz, 1H), 7.62(s, 2H), 9.43(s, 1H) |
| 494 | 8-[(1,2,3,4-tetrahydroquinolin-1-yl)methyl]-10H-pyrazino[2,3-b][1,4]benzothiazine | FAB(+) 347(MH+) | 208–210° C. | $^1$H-NMR (CDCl$_3$) δ ppm: 1.96–2.07(m, 2H), 2.81(t, J=6.0Hz, 2H), 3.30(t, J=6.0Hz, 2H), 4.31(s, 2H), 6.42(br.s, 1H), 6.44(s, 1H), 6.59(d, J=7.2Hz, 1H), 6.61(d, J=7.2Hz, 1H), 6.74(d, J=8.0Hz, 1H), 6.84(d, J=8.0Hz, 1H), 6.96–7.20(m, 2H), 7.50(d, J=2.8Hz, 1H), 7.65(d, J=2.8Hz, 1H) |
| 495 | [4-(10H-pyrazino[2,3-b][1,4]benzothiazin-8-ylmethyl)piperazin-1-yl]amidine | ESI(+) 342(MH+) | 265–271° C. (decompose) | $^1$H-NMR (CD$_3$OD) δ ppm: 2.51(br.t, J=5.1Hz, 4H), 3.41(s, 2H), 3.47(br.t, J=5.1Hz, 4H), 6.70(d, J=1.6Hz, 1H), 6.79(dd, J=1.6, 7.9Hz, 1H), 6.82(d, J=7.9Hz, 1H), 7.57(d, J=2.9Hz, 1H), 7.58(d, J=2.9Hz, 1H) |

| Ex. | Structural formula | MS | M.p. | NMR |
|---|---|---|---|---|
| 496 | 8-[(1,2,3,4-tetrahydroquinolin-2-yl)methyl]-10H-pyrazino[2,3-b][1,4]benzothiazine | FAB(+) 347(MH+) | 188–191° C. | $^1$H-NMR (CDCl$_3$) δ ppm: 2.73(t, J=6.0Hz, 2H), 2.91(t, J=6.0Hz, 2H), 3.52(s, 2H), 3.60(s, 2H), 6.57(br.s, 1H), 6.63(s, 1H), 6.83(d, J=8.0Hz, 1H), 6.85(d, J=8.0Hz, 1H), 6.99(d, J=8.0Hz, 1H), 7.08–7.17(m, 3H), 7.55(d, J=2.8Hz, 1H), 7.63(d, J=2.8Hz, 1H) |
| 497 | 8-[(4,5,6,7-tetrahydrothieno[3,2-c]pyridin-5-yl)methyl]-10H-pyrazino[2,3-b][1,4]benzothiazine | FAB(+) 353(MH+) | 182–184° C. | $^1$H-NMR (CDCl$_3$) δ ppm: 2.79(t, J=6.0Hz, 2H), 2.89(t, J=6.0Hz, 2H), 3.54(s, 2H), 3.55(s, 2H), 6.45(br.s, 1H), 6.62(s, 1H), 6.70(d, J=4.8Hz, 1H), 6.82(d, J=8.0Hz, 1H), 6.86(d, J=8.0Hz, 1H), 7.08(d, J=4.8Hz, 1H), 7.57(d, J=2.8Hz, 1H), 7.67(d, J=2.8Hz, 1H) |

Example 498

N-Methyl-2-[1-(10H-pyrazino[2,3-b][1,4]benzothiazin-8-ylmethyl)piperidin-4-yl]ethanesulfonamide The title compound was obtained as yellow crystals by treating N-methyl-2-(piperidin-4-yl)ethanesulfonamide acetate and 8-chloromethyl-10H-pyrazino[2,3-b][1,4]benzothiazine by the same method as the one of Example 131.

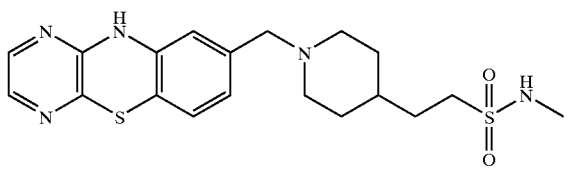

$^1$H-NMR(CDCl$_3$) δ ppm: 1.28(dq, J=3, 11 Hz, 2H), 1.39(m, 1H), 1.67(m, 2H), 1.75(m, 2H), 1.94(dt, J=1, 11 Hz, 2H), 2.81(d, J=6 Hz, 3H), 2.95(br.d, J=11 Hz, 2H), 3.04(m, 2H), 3.32(s, 2H), 4.18(q, J=6 Hz, 1H), 6.51(br.s, 1H), 6.53(d, J=2 Hz, 1H), 6.75(dd, J=2, 8 Hz, 1H), 6.83(d, J=8 Hz, 1H), 7.57(d, J=3 Hz, 1H), 7.69(d, J=3 Hz, 1H)

MS: ESI 420.1(MH+)

m.p.: 195–198° C.

Examples 499 and 500

The following compounds were obtained by the same method as the one of Example 498.

| Ex. | Structural formula | MS | M.p. | NMR |
|---|---|---|---|---|
| 499 | N,N-dimethyl-2-[1-(10H-pyrazino[2,3-b][1,4]benzothiazin-8-ylmethyl)piperidin-4-yl]ethanesulfonamide | FAB(+) 434(MH+) | 188–190° C. | $^1$H-NMR(CDCl$_3$) δ ppm: 1.27(dq, J=3, 11Hz, 2H), 1.39(m, 1H), 1.6(m, 2H), 1.75(m, 2H), 1.92(dt, J=1, 11Hz, 2H), 2.85(br.d, J=11Hz, 2H), 2.86(s, 6H), 2.93(m, 2H), 3.32(s, 2H), 6.51(d, J=2Hz, 1H), 6.60(br.s, 1H), 6.75(dd, J=2, 8Hz, 1H), 6.83(d, J=8Hz, 1H), 7.58(d, J=3Hz, 1H), 7.69(d, J=3Hz, 1H) |

| Ex. | Structural formula | MS | M.p. | NMR |
|---|---|---|---|---|
| 500 N,N-(3-oxapenta methylene)-[1-(10H-pyrazino[2,3-b][1,4] benzothiazin-8-ylmethyl)piperidin-4-yl]ethanesulfonamide | | FAB(+) 476(MH⁺) | 193–194° C. | ¹H-NMR (DMSO-d₆) δ ppm: 1.14(m, 2H), 1.31(m, 1H), 1.53–1.64(m, 4H), 1.83(m, 2H), 2.74(br.d, J=8Hz, 2H), 3.03(m, 2H), 3.12(t, J=6Hz, 4H), 3.23(s, 2H), 3.61(t, J=6Hz, 4H), 6.67(d, J= 8Hz, 1H), 6.74(s, 1H), 6.83(d, J=8Hz, 1H), 7.63(s, 2H), 9.44(s, 1H) |

Example 501

[1-(10H-Pyrazino[2,3-b][1,4]-benzothiazin-8-ylmethyl)-piperidine-4-(N-cyano)carboxamidine To a solution of 450 mg of methyl[1-(10H-pyrazino[2,3-b][1,4]-benzothiazin-8-ylmethyl)-piperidine-4-carboximidate in dry tetrahydrofuran (10 ml) were added 1.0 ml of triethylamine and 1.0 g of cyanamide and the resulting mixture was heated to 45° C. for 2 hours. Then the reaction mixture was distributed into water and ethyl acetate. The organic layer was extracted, washed successively with an aqueous solution of sodium bicarbonate and water and dried over sodium sulfate. After distilling off the solvent under reduced pressure, the residue was purified by silica gel column chromatography (eluted with dichloromethane/methanol) to thereby give 115 mg of the title compound as yellow crystals.

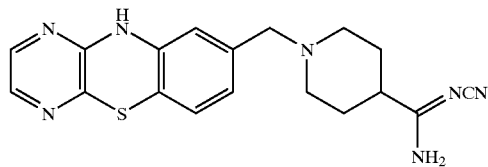

¹H-NMR(DMSO-d₆) δ ppm: 1.49–1.72(m, 4H), 1.79–1.91(m, 2H), 2.08–2.28(m, 1H), 2.74–2.85(m, 2H), 3.25(s, 2H), 6.68(d, J=7.6 Hz, 1H), 6.73(s, 1H), 6.82(d, J=7.6 Hz, 1H), 7.59–7.65(m, 2H), 8.10–8.30(br.s, 1H), 8.40–8.70(br.s, 1H), 9.45(s, 1H)
MS: FAB(+)365(M⁺), 366(MH⁺)

Example 502

4-[1-(10-(Methoxymethyl)-10H-pyrazino[2,3-b][1,4] benzothiazin-8-ylmethyl)piperidin-4-yl]butyronitrile The title compound was obtained as yellow crystals by treating 4-[1-(tert-butoxycarbonyl) piperidin-4-yl] butyronitrile and 8-chloromethyl-10H-pyrazino[2,3-b][1,4] benzothiazine by the same method as the one of Example 66.

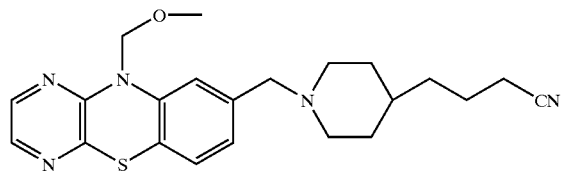

¹H-NMR(CDCl₃) δ ppm: 1.40(m, 2H), 1.65(m, 7H), 1.96(t, J=10 Hz, 2H), 2.34(t, J=7 Hz, 2H), 2.87(t, J=10 Hz, 2H), 3.43(s, 2H), 3.55(s, 3H), 5.31(s, 2H), 6.94(d, J=8 Hz, 1H), 6.96(d, J=8 Hz, 1H), 7.10(s, 1H), 7.83(d, J=3 Hz, 1H), 7.84(d, J=3 Hz, 1H)

Example 503

1-(10H-Pyrazino[2,3-b][1,4]benzothiazin-8-ylmethyl)-4-[2-(tetrazol-5-yl)ethyl]piperidine To a solution of 0.323 g of 4-[1-(10-methoxymethyl)-10H-pyrazino[2,3-b][1,4]benzothiazin-8-ylmethyl) piperidin-4-yl]butyronitrile in 1-methyl-2-pyrrolidone (10 ml) were added in a nitrogen atmosphere 0.354 g of sodium azide and 0.376 g of ammonium chloride. Next, the resulting mixture was stirred under heating to 150° C. for 28 hours. After distilling off the solvent under reduced pressure, the residue was purified by high-porous gel chromatography (CHP20P, 75–150μ; manufactured by Mitsubishi Chemical Industries) (eluted with methanol/water) to thereby give 0.208 g of the title compound as pale yellow crystals.

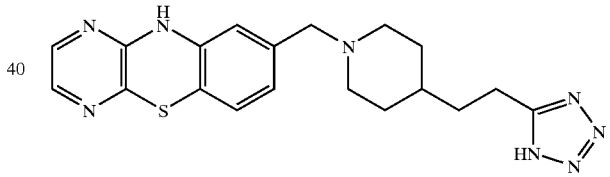

¹H-NMR(DMSO-d₆) δ ppm: 1.10(m, 2H), 1.20(m, 1H), 1.59(br.d, J=11 Hz, 2H), 1.67(quint, J=6 Hz, 2H), 1.99(t, J=11 Hz, 2H), 2.76(br.d, J=11 Hz, 2H), 2.81(t, J=9 Hz, 2H), 3.27(s, 2H), 6.68(dd, J=2, 8 Hz, 1H), 6.74(d, J=2 Hz, 1H), 6.83(d, J=8 Hz, 1H), 7.62(d, J=3 Hz, 1H), 7.63(d, J=3 Hz, 1H), 9.44(s, 1H)
MS: FAB(+)409(MH⁺)
m.p.: 149–152° C.

Example 504

N-[1-(10H-Pyrazino[2,3-b][1,4]benzothiazin-8-ylmethyl)-piperidin-4-yl]-5-methyl-1,2-oxazole-4-carboxamide 50 ml of a solution of 5.7 g of 4-amino-1-benzyl-piperidine in toluene was stirred and 2.5 ml of diketene was carefully dropped thereinto. After the completion of the reaction, the solvent was distilled off under reduced pressure and the residue was allowed to stand at a low temperature. To the crystals thus precipitated was added diethyl ether/isopropyl ether followed by grinding and filtration. Thus 4.95 g of N-(1-benzylpiperidin-4-yl)-3-oxobutanamide was obtained as colorless crystals. Next, this compound was dissolved in a solvent mixture of tetrahydrofuran (25 ml) with methanol (25 ml). After adding 1.0 g of 10% palladium-carbon, the resulting mixture was stirred under atmospheric pressure in a hydrogen atmosphere for 2 hours. After filtering off inorganic matters through celite, the solvent was distilled off under reduced pressure. The oily residue thus obtained was dissolved in 50 ml of N,N-dimethylformamide and 4.1 g of 8-chloromethyl-10-(methoxymethyl)-10H-pyrazino[2,3-b][1,4]benzothiazine and 2.1 g of potassium carbonate were added thereto. The resulting mixture was heated to 100° C. for 1 hour. Then the reaction mixture was brought back to room temperature and distributed into water and ethyl acetate. The organic layer was extracted, washed with water and dried over sodium sulfate. After distilling off the solvent under reduced pressure, the residue was purified by silica gel column chromatography (eluted with dichloromethane/methanol) to thereby give 3.7 g of N-[1-(10H-pyrazino[2,3-b][1,4]benzothiazin-8-ylmethyl)-piperidin-4-yl]-3-oxobutanamide as yellow crystals. Further, 3.7 g of this N-[1-(10H-pyrazino[2,3-b][1,4]benzothiazin-8-ylmethyl)-piperidin-4-yl]-3-oxobutanamide was dissolved in toluene (10 ml). After adding 1.3 ml of N,N-dimethylformamide dimethyl acetal, the mixture was heated to 90° C. for 30 minutes. After distilling off the solvent under reduced pressure, 10 ml of methanol and 800 mg of hydroxylamine hydrochloride were added to the yellow oily residue thus obtained. Then the resulting mixture was heated under reflux for 30 minutes. The reaction mixture was brought back to room temperature and distributed into water and ethyl acetate. The organic layer was extracted, washed with water and dried over sodium sulfate. After distilling off the solvent under reduced pressure, 30 ml of glacial acetic acid was added to the yellow oily residue thus obtained. Then the resulting mixture was heated to 80° C. for 4 hours. After distilling off the solvent under reduced pressure, the residue was purified by silica gel column chromatography (eluted with dichloromethane/methanol) and recrystallized from diethyl ether/ethyl acetate to thereby give 1.6 g of the title compound as yellow crystals.

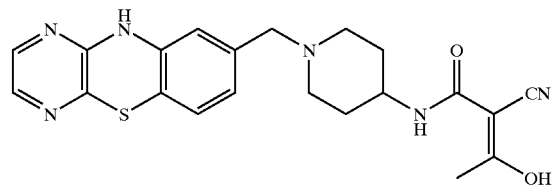

$^1$H-NMR(CDCl$_3$) δ ppm: 1.45–1.57(m, 2H), 1.94–2.02 (m, 2H), 2.07–2.17(m, 2H), 2.70(s, 3H), 2.78–2.87(m, 2H), 3.34(s, 2H), 3.88–4.00(m, 1H), 5.66(br.d, J=7.6 Hz, 1H), 6.53(d, J=1.3 Hz, 1H), 6.68–6.72(br.s, 1H), 6.75(dd, J=1.3, 7.6 Hz, 1H), 6.82(d, J=7.9 Hz, 1H), 7.57(d, J=3.0 Hz, 1H), 7.69(d, J=3.0 Hz, 1H), 8.36(s, 1H)

MS: FAB(+)423(MH$^+$)

Example 505

N-[1-(10H-Pyrazino[2,3-b][1,4]benzothiazin-8-ylmethyl)-piperidin-4-yl]-3-oxo-2-cyanobutanamide To 10 ml of a solution of 500 mg of N-[1-(10H-pyrazino[2,3-b][1,4]benzothiazin-8-ylmethyl)-piperidin-4-yl]-5-methyl-1,2-oxazole-4-carboxamide in tetrahydrofuran was added 400 μl of N,N-dimethylformamide dimethyl acetal and the resulting mixture was heated under reflux for 4 hours. After distributing into water and ethyl acetate, the aqueous layer was extracted and washed with diethyl ether. After distilling off the organic solvent contained therein under reduced pressure, the residue was acidified with dilute hydrochloric acid and purified by high-porous gel chromatography (CHP20P, 75–150μ; manufactured by Mitsubishi Chemical Industries) (eluted with methanol/water) to thereby give 110 mg of the title compound as pale yellow crystals.

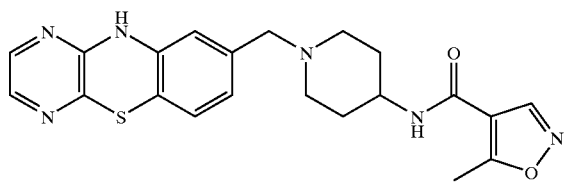

$^1$H-NMR(DMSO-d$_6$) δ ppm: 1.38–1.54(m, 2H), 1.77–2.04(m, 4H), 1.99(br.s, 3H), 2.87–3.07(m, 2H), 3.32(s, 2H), 4.01–4.10(m, 1H), 6.76(s, 1H), 6.77(br.d, J=7.7 Hz, 1H), 7.00(d, J=7.7 Hz, 1H), 7.66(s, 2H), 9.48–9.59(m, 1H), 9.70(br.s, 1H)

MS: FAB(+)423(MH$^+$)

Examples 506 and 507

Starting with known compounds, the following compounds were obtained by the same method as the one of Example 63.

| Ex. | Structural formula | NMR |
|---|---|---|
| 506 | ethyl [1-(10-(methoxymethyl)-10H-pyrazino[2,3-b][1,4]benzoxazin-8-ylmethyl)piperidin-4-yl]carboxylate | $^1$H-NMR (CDCl$_3$) δ ppm: 1.25(t, J=7Hz, 3H), 1.7–1.82(m, 2H), 1.83–1.93(m, 2H), 1.95–2.05(m, 2H), 2.2–2.35(m, 1H), 2.8–2.9(m, 2H), 3.36(s, 2H), 3.46(s, 3H), 4.13(q, J=7Hz, 2H), 5.31(s, 2H), 6.78(s, 2H), 6.88(s, 1H), 7.41(d, J=3Hz, 1H), 7.57(d, J=3Hz, 1H) |

| Ex. | Structural formula | NMR |
|---|---|---|
| 507 | ethyl [1-(10-(methoxymethyl)-10H-pyrazino[2,3-b][1,4]benzothiazin-8-ylmethyl)piperidin-3-yl]carboxylate | $^1$H-NMR (CDCl$_3$) δ ppm: 1.23(t, J=6Hz, 3H), 1.38–1.62(m, 2H), 1.65–1.76(m, 1H), 1.86–1.96(m, 1H), 1.96–2.10(m, 1H), 2.10–2.30(m, 1H), 2.50–2.60(m, 1H), 2.65–2.70(m, 1H), 2.90–2.97(m, 1H), 3.41(d, J=14Hz, 1H), 3.45(d, J=14Hz, 1H), 3.54(s, 3H), 4.10(q, J=6Hz, 2H), 5.28(s, 2H), 6.92(d, J=8Hz, 1H), 6.94(d, J=8Hz, 1H), 7.10(s, 1H), 7.82(s, 2H) |

Example 508

Ethyl 4-[1-(10-(methoxymethyl)-10H-pyrazino[2,3-b][1,4]benzothiazin-8-ylmethyl)piperidin-4-yl]-2-butenoate The title compound was obtained as yellow crystals by the same method as the one of Example 66.

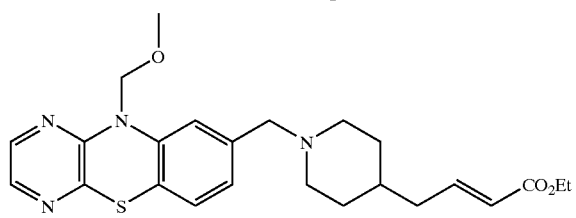

$^1$H-NMR(CDCl$_3$) δ ppm: 1.24(t, J=6 Hz, 3H), 1.36–1.46 (m, 1H), 1.64–1.70(m, 2H), 1.76(br.s, 2H), 1.89–1.94(m, 2H), 2.14(t, J=6 Hz, 2H), 2.80–2.90(m, 2H), 3.39(s, 2H), 3.54(s, 3H), 4.16(q, J=6 Hz, 2H), 5.26(s, 2H), 5.80(d, J=16 Hz, 1H), 6.90(dt, J=6, 16 Hz, 1H), 6.94(d, J=8 Hz, 1H), 6.96(d, J=8 Hz, 1H), 7.08(s, 1H), 7.81(s, 2H)

Examples 509 to 516

The following compounds were obtained by the same method as the one of Example 508.

| Ex. | Structural formula | NMR |
|---|---|---|
| 509 | ethyl 3-[4-[(10-methoxymethyl-10H-pyrazino[2,3-b][1,4]benzothiazin-8-ylmethyl)amino]piperidin-1-yl]propanoate | $^1$H-NMR (CDCl$_3$) δ ppm: 1.25(t, J=7.2Hz, 3H), 1.36–1.51(m, 2H), 1.87–1.95(m, 2H), 2.00–2.12(m, 2H), 2.46–2.58(m, 3H), 2.66–2.74(m, 2H), 2.85–2.93(m, 2H), 3.54(s, 3H), 3.76(s, 2H), 4.13(q, J=7.2Hz, 2H), 5.29(s, 2H), 6.94(d, J=7.4Hz, 1H), 6.97(d, J=7.4Hz, 1H), 7.13(s, 1H), 7.83(s, 2H) |
| 510 | ethyl 4-[4-[(10-methoxymethyl-10H-pyrazino[2,3-b][1,4]benzothiazin-8-ylmethyl)amino]piperidin-1-yl]butanoate | $^1$H-NMR (CDCl$_3$) δ ppm: 1.25(t, J=7.2Hz, 3H), 1.43–1.58(m, 2H), 1.69–1.78(m, 2H), 1.85–1.94(m, 2H), 1.94–2.03(m, 2H), 2.30–2.38(m, 3H), 2.41–2.53(m, 2H), 2.93–3.03(m, 2H), 3.55(s, 3H), 3.76(s, 2H), 4.13(q, J=7.2Hz, 2H), 5.29(s, 2H), 6.93(d, J=8.0Hz, 1H), 6.96(d, J=8.0Hz, 1H), 7.12(s, 1H), 7.83(s, 2H) |

| Ex. | Structural formula | NMR |
|---|---|---|
| 511 | ethyl 4-[4-[(10-methoxymethyl-10H-pyrazino[2,3-b][1,4]benzothiazin-8-ylmethyl)amino]piperidin-1-yl]acetate | $^1$H-NMR (CDCl$_3$) δ ppm:<br>1.26(t, J=7Hz, 3H), 1.42–1.60(m, 2H), 1.84–1.94(m, 2H), 2.16–2.26(m, 2H), 2.44–2.56(m, 1H), 2.84–2.94(m, 2H), 3.20(s, 2H), 3.53(s, 3H), 3.76(s, 2H), 4.17(q, J=7Hz, 2H), 5.30(s, 2H), 6.90–7.00(m, 2H), 7.13(s, 1H), 7.80–7.85(m, 2H) |
| 512 | ethyl 3-[4-[(10-methoxymethyl-10H-pyrazino[2,3-b][1,4]benzothiazin-8-ylmethyl)amino]piperidin-1-yl]-3-oxopropanoate | $^1$H-NMR (CDCl$_3$) δ ppm:<br>1.28(t, J=6.8Hz, 3H), 1.33–1.43(m, 2H), 1.89–1.97(m, 2H), 2.72–2.81(m, 1H), 2.81–2.89(m, 1H), 3.07–3.15(m, 1H), 3.46(s, 2H), 3.53(s, 3H), 3.69–3.79(m, 1H), 3.77(s, 2H), 4.20(q, J=6.8Hz, 2H), 4.37–4.44(m, 1H), 5.29(s, 2H), 6.94(d, J=7.6Hz, 1H), 6.97(d, J=7.6Hz, 1H), 7.13(s, 1H), 7.83(d, J=2.8Hz, 1H), 7.84(d, J=2.8Hz, 1H) |
| 513 | ethyl [4-[(10-methoxymethyl-10H-pyrazino[2,3-b][1,4]enzothiazin-8-ylmethyl)amino]piperidin-1-yl]-2-oxoacetate | $^1$H-NMR (CDCl$_3$) δ ppm:<br>1.30–1.47(m, 2H), 1.36(t, J=7.0Hz, 3H), 1.90–2.00(m, 2H), 2.77–2.85(m, 1H), 2.92–3.00(m, 1H), 3.08–3.17(m, 1H), 3.53(s, 3H), 3.63–3.71(m, 1H), 3.78(s, 2H), 4.24–4.34(m, 1H), 4.32(q, J=7.0Hz, 2H), 5.29(s, 2H), 6.93(dd, J=1.4, 7.6Hz, 1H), 6.97(d, J=7.6Hz, 1H), 7.13(d, J=1.4Hz, 1H), 7.83(d, J=2.6Hz, 1H), 7.84(d, J=2.6Hz, 1H) |
| 514 | ethyl (E)-3[1-(10-methoxymethyl-10H-pyrazino[2,3-b][1,4]enzothiazin-8-ylmethyl)amino]piperidin-4-yl]-2-butenoate | $^1$H-NMR (CDCl$_3$) δ ppm:<br>1.28(t, J=7.2Hz, 3H), 1.52–1.72(m, 4H), 1.91–2.03(m, 3H), 2.15(s, 3H), 2.91–2.97(m, 2H), 3.44(s, 2H), 3.54(s, 3H), 4.14(q, J=7.2Hz, 2H), 5.29(s, 2H), 5.68(s, 1H), 6.94(d, J=8.5Hz, 1H), 6.97(d, J=8.5Hz, 1H), 7.11(s, 1H), 7.84(s, 2H) |
| 515 | ethyl [1-(10-methoxymethyl-10H-pyrazino[2,3-b][1,4]enzothiazin-8-ylmethyl)piperidin-4-yl]-2-oxoacetate | $^1$H-NMR (CDCl$_3$) δ ppm:<br>1.30–1.47(m, 2H), 1.36(t, J=7.0Hz, 3H), 1.90–2.00(m, 2H), 2.77–2.85(m, 1H), 2.92–3.00(m, 1H), 3.08–3.17(m, 1H), 3.53(s, 3H), 3.63–3.71(m, 1H), 3.78(s, 2H), 4.24–4.34(m, 1H), 4.32(q, J=7.0Hz, 2H), 5.29(s, 2H), 6.93(dd, J=1.4, 7.6Hz, 1H), 6.97(d, J=7.6Hz, 1H), 7.13(d, J=1.4Hz, 1H), 7.83(d, J=2.6Hz, 1H), 7.84(d, J=2.6Hz, 1H) |

| Ex. | Structural formula | NMR |
|---|---|---|
| 516 | 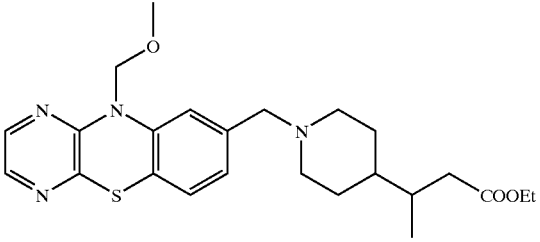<br>ethyl [1-(10-methoxymethyl-10H-pyrazino[2,3-b][1,4]enzothiazin-8-ylmethyl)piperidin-4-yl]butanoate | $^1$H-NMR (CDCl$_3$) δ ppm:<br>0.91(d, J=6.8Hz, 3H), 1.13–1.40(m, 3H), 1.25(t, J=7.2Hz, 3H), 1.54–1.63(m, 2H), 1.85–1.96(m, 3H), 2.08(dd, J=8.4, 14.8Hz, 1H), 2.38(dd, J=4.9, 14.8Hz, 1H), 2.81–2.94(m, 2H), 3.42(s, 2H), 3.54(s, 3H), 4.12(q, J=7.2Hz, 2H), 5.29(s, 2H), 6.93(d, J=7.9Hz, 1H), 6.96(d, J=7.9Hz, 1H), 7.10(br.s, 1H), 7.83(s, 2H) |

Examples 517 and 518

The following compounds were obtained as yellow crystals by the same method as the one of Example 66 by using trifluoroacetic acid as a substitute for hydrochloric acid.

| Ex. | Structural formula | NMR |
|---|---|---|
| 517 | 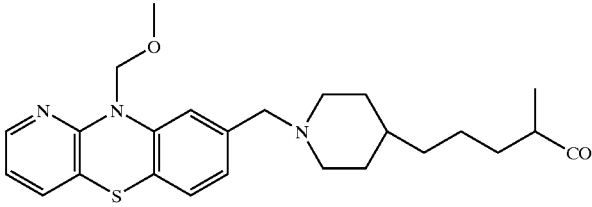<br>ethyl 5-[1-(10-methoxymethyl)-10H-pyrido[2,3-b] [1,4]-benzothiazin-8-ylmethyl]piperidin-4-yl]-2-methylpentanoate | $^1$H-NMR(CDCl$_3$)δppm:<br>1.13(d, J=7Hz, 3H), 1.25(t, J=7Hz, 3H), 1.1–1.45(m, 7H), 1.55–1.70(m, 2H), 1.65–1.80(m, 2H), 1.85–1.95(m, 2H), 2.35–2.45(m, 1H), 2.85(br.d, J=12Hz, 2H), 3.43(s, 2H), 3.55(s, 3H), 4.12(q, J=7Hz, 2H), 5.36(s, 2H), 6.80(dd, J=5, 8Hz, 1H), 6.92(dd, J=2, 8Hz, 1H), 6.97(d, J=8Hz, 1H), 7.11(d, J=2Hz, 1H), 7.28(dd, J=2, 8Hz, 1H), 8.05(dd, J=2, 5Hz, 1H) |
| 518 | 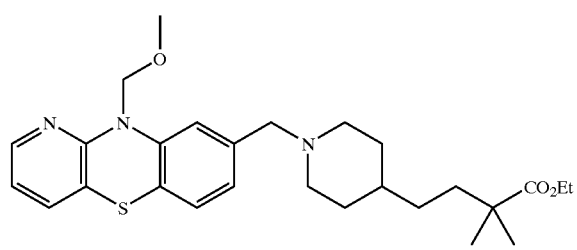<br>ethyl 4-[1-(10-methoxymethyl)-10H-pyrazino[2,3-b] [1,4]-benzothiazin-8-ylmethyl]piperidin-4-yl]-2,2-dimethyl butanoate | $^1$H-NMR(CDCl$_3$)δppm:<br>1.10–1.30(m, 5H), 1.14(s, 6H), 1.26(t, J=6Hz, 3H), 1.48–1.56(m, 2H), 1.58–1.70(m, 2H), 1.84–1.96(m, 2H), 2.80–2.90(m, 2H), 3.40(s, 2H), 3.52(s, 3H), 4.09(q, J=6Hz, 2H), 5.29(s, 2H), 6.93(d, J=8Hz, 1H), 6.96(d, J=8Hz, 1H), 7.09(s, 1H), 7.82(s, 2H) |

Examples 519 to 521

The following compounds were obtained by the same method as the one of Example 64 by using anhydrous potassium carbonate as a substitute for N,N-diisopropylamine.

| Ex. | Structural formula | NMR |
|---|---|---|
| 519 | 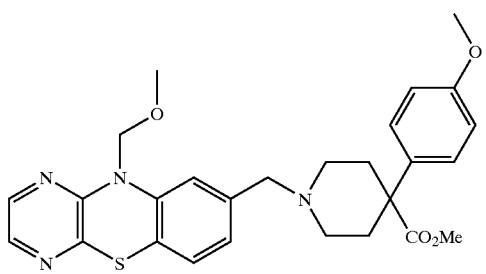<br>methyl [1-(10-methoxymethyl)-10H-pyrido[2,3-b][1,4]benzothiazin-8-ylmethyl]-4-(p-methoxyphenyl)piperidin-4-yl]carboxylate | $^1$H-NMR(CDCl$_3$)δppm:<br>1.87–2.0(m, 2H),<br>2.16(br.t, J=12Hz, 2H),<br>2.53(br.d, J=12Hz, 2H),<br>2.75–2.85(m, 2H),<br>3.39(s, 2H), 3.52(s, 3H), 3.64(s, 3H),<br>3.79(s, 3H), 5.27(s, 2H), 6.85(d, J=9Hz, 2H),<br>6.9–6.96(m, 1H), 6.95(d, J=8Hz, 1H), 7.11(s, 1H),<br>7.29(d, J=9Hz, 2H),<br>7.82(d, J=3Hz, 1H),<br>7.83(d, J=3Hz, 1H) |
| 520 | 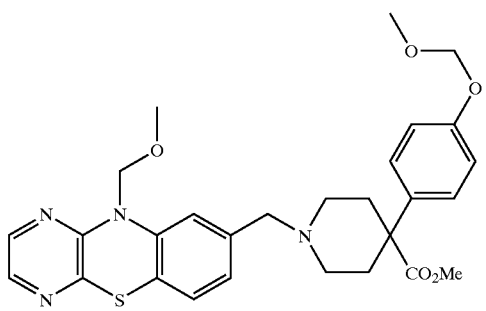<br>methyl [1-(10-methoxymethyl)-10H-pyrazino[2,3-b][1,4]benzothiazin-8-ylmethyl]-4-(p-methoxyphenyl)piperidin-4-yl]carboxylate | $^1$H-NMR(CDCl$_3$)δppm:<br>1.88–2.0(m, 2H),<br>2.15(br.t, J=12Hz, 2H),<br>2.53(br.d, J=12Hz, 2H),<br>2.75–2.84(m, 2H),<br>3.39(s, 2H), 3.47(s, 3H), 3.52(s, 3H),<br>3.64(s, 3H), 5.15(s, 2H), 5.27(s, 2H), 6.9–6.96(m, 1H), 6.95(d, J=8Hz, 1H), 6.98(d, J=9Hz, 2H), 7.10(s, 1H),<br>7.29(d, J=9Hz, 2H),<br>7.82(d, J=3Hz, 1H),<br>7.83(d, J=3Hz, 1H) |
| 521 | 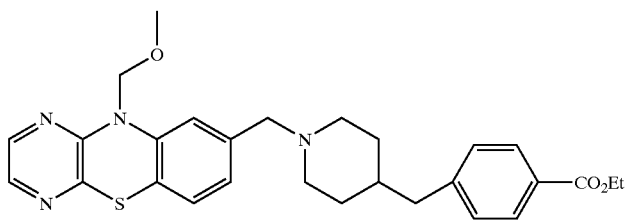<br>ethyl 4-[1-(10-methoxymethyl)-10H-pyrazino[2,3-b][1,4]benzothiazin-8-ylmethyl]piperdin-4-yl]methylbenzoate | $^1$H-NMR(CDCl$_3$)δppm:<br>1.22–1.35(m, 2H),<br>1.36(t, J=6Hz, 3H),<br>1.42–1.60(m, 3H), 1.83–1.93(m, 2H), 2.58(d, J=6Hz, 2H), 2.80–2.90(m, 2H), 3.40(s, 2H),<br>3.52(s, 3H), 4.36(q, J=6Hz, 2H), 5.29(s, 2H),<br>6.92(d, J=8Hz, 1H),<br>6.94(d, J=8Hz, 1H),<br>7.09(s, 1H), 7.19(d, J=9Hz, 2H), 7.82(s, 2H),<br>7.94(d, J=9Hz, 2H) |

Example 522

Methyl[1-(10-methoxymethyl)-10H-pyrazino[2,3-b][1,4]-benzothiazin-8-ylmethyl]-4-phenylpiperidin-4-yl]carboxylate

To a solution of 0.46 g of methyl[(1-benzyl-4-phenylpiperidin)-4-yl]carboxylate in 1,2-dichloroethane (10 ml) was added 0.18 ml of 1-chloroethyl chloroformate at 0° C. After stirring for 15 minutes, the resulting mixture was heated under reflux for additional 1 hour. After distilling off the solvent under reduced pressure, 50 ml of methanol was added to the residue and the resulting mixture was heated under reflux for 1 hour. After distilling off the solvent under reduced pressure, 0.4 g of methyl(4-phenylpiperidin-4-yl)carboxylate was obtained as colorless crystals. 0.4 g of these crystals were dissolved in 20 ml of N,N-dimethylformamide and 0.44 g of 8-(chloromethyl)-10H-(methoxymethyl)-10H-pyrazino[2,3-b][1,4]benzothiazine and 0.62 g of anhydrous potassium carbonate were added thereto. After reacting at 60° C. for 1 hour, water was added to the reaction mixture. The mixture was extracted with ethyl acetate, washed with a saturated aqueous solution of sodium chloride and dried over anhydrous magnesium sulfate. After distilling off the solvent under reduced pressure, the residue was purified by silica gel column chromatography (eluted with n-hexane/ethyl acetate) to thereby give 0.55 g of the title compound as a yellow oily substance.

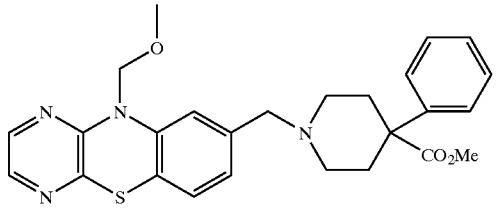

$^1$H-NMR(CDCl$_3$) δ ppm: 1.9–2.05(m, 2H), 2.1–2.25(m, 2H), 2.5–2.6(m, 2H), 2.75–2.85(m, 2H), 3.41(m, 2H), 3.52 (s, 3H), 3.65(s, 3H), 5.28(s, 2H), 6.92–6.96(m, 1H), 6.95(s, 1H), 7.10–7.13(m, 1H), 7.2–7.4(m, 5H), 7.82(d, J=3 Hz, 1H), 7.83(d, J=3 Hz, 1H)

Examples 523 to 525

The following compounds were obtained by the same method as the one of Example 522.

| Ex. | Structural formula | NMR |
|---|---|---|
| 523 | ethyl 4-[1-(10-methoxymethyl)-10H-pyrazino[2,3-b][1,4]benzothiazin-8-ylmethyl]piperdin-4-ylidene]-4-cyanobutanoate | $^1$H-NMR(CDCl$_3$)δppm: 1.26(t, J=7Hz, 3H), 2.4–2.5(m, 4H), 2.5–2.58(m, 6H), 2.58–2.66(m, 2H), 3.46(s, 2H), 3.53(s, 3H), 4.13(q, J=7Hz, 2H), 5.29(s, 2H), 6.90–6.96(m, 1H), 6.97(d, J=8Hz, 1H), 7.12(s, 1H), 7.83(d, J=3Hz, 1H), 7.84(d, J=3Hz, 1H) |
| 524 | methyl 2,2-dimethyl-4-[4-(10-methoxymethyl)-10H-pyrazino[2,3-b][1,4]benzothiazin-8-ylmethyl]piperazin-1-yl]pentanoate | $^1$H-NMR(CDCl$_3$)δppm: 1.17(s, 6H), 1.38–1.56(m, 4H), 2.30(m, 2H), 2.39–2.54(br.s, 8H), 3.44(s, 2H), 3.53(s, 3H), 3.65(s, 3H), 5.26(s, 2H), 6.94(s, 2H), 7.10(s, 1H), 7.82(m, 2H) |

| Ex. | Structural formula | NMR |
|---|---|---|
| 525 | 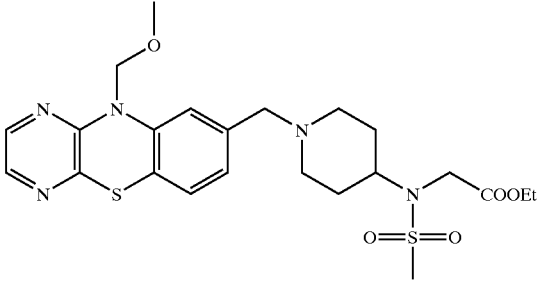<br>ethyl N-(methanesulfonyl)-N-[1-(10-methoxymethyl)-10H-pyrazino[2,3-b][1,4]benzothiazin-8-ylmethyl]piperidin-4-yl]aminoacetate | NMR(CDCl$_3$)<br>1.29(t, J=6.8Hz, 3H), 1.56–1.70(m, 2H), 1.77–1.85(m, 2H), 2.02–2.11(m, 2H), 2.87–2.98(m, 2H), 3.10(s, 3H), 3.42(br.s, 2H), 3.54(s, 3H), 3.58–3.69(m, 1H), 4.06(s, 2H), 4.18(q, J=6.8Hz, 2H), 5.29(s, 2H), 6.92(dd, J=1.2, 7.6Hz, 1H), 6.97(d, J=7.6Hz, 1H), 7.07(br.d, J=1.2Hz, 1H), 7.84(d, J=2.8Hz, 1H), 7.85(d, J=2.8Hz, 1H) |

Example 526

Ethyl 4-[1-(10-methoxymethyl)-10H-pyrazino[2,3-b][1,4]-benzothiazin-8-ylmethyl]piperidin-4-yl]-2-methylbutanoate To a solution of 15.7 g of ethyl 4-[1-benzyloxycarbonyl]piperidin-4-yl]-2-methyl-2-butenoate in ethanol (200 ml) was added 3.1 g of 10% palladium-carbon (moisture content: 50%) and hydrogenation reaction was effected at ordinary temperature under atmospheric pressure for 8 hours and 40 minutes. After filtering off the palladium-carbon, the solvent was concentrated under reduced pressure to thereby give 10.06 g of crude ethyl 4-(piperidin-4-yl)-2-methyl-2-butanoate as a pale yellow oily substance. A 3.74 g portion of this product was dissolved in 50 ml of N,N-dimethylformamide. After adding 4.06 g of 8-(chloromethyl)-10H-(methoxymethyl)-10H-pyrazino[2,3-b][1,4]benzothiazine and 20 ml of pyridine, the resulting mixture was reacted at 70° C. for 11 hours. After adding water, the reaction mixture was extracted with ethyl acetate, washed with a saturated aqueous solution of sodium chloride and dried over anhydrous magnesium sulfate. After distilling off the solvent under reduced pressure, the residue was purified by silica gel column chromatography (eluted with toluene/ethyl acetate) to thereby give 4.5 g of the title compound as a yellow oily substance.

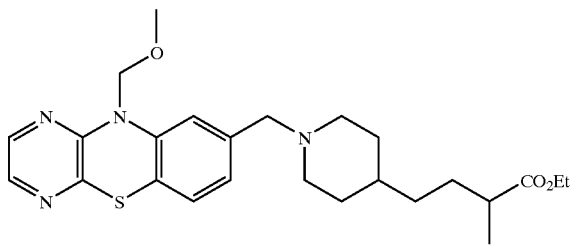

$^1$H-NMR(CDCl$_3$) δ ppm: 1.07(d, J=7 Hz, 3H), 1.10–1.30 (m, 4H), 1.13(t, J=6 Hz, 3H), 1.58–1.70(m, 3H), 1.70–1.82 (m, 2H), 1.88–1.98(m, 2H), 2.32–2.41(m, 1H), 2.80–2.88 (m, 2H), 3.42(s, 2H), 3.52(s, 3H), 4.11(q, J=6 Hz, 2H), 5.30(s, 2H), 6.90(d, J=8 Hz, 1H), 6.92(d, J=8 Hz, 1H), 7.09(s, 1H), 7.82(s, 2H)

Examples 527 to 530

The following compounds were obtained by the same method as the one of Example 526.

| Ex. | Structural formula | NMR |
|---|---|---|
| 527 | 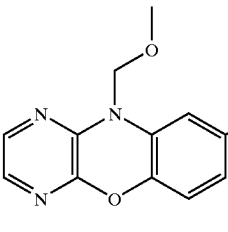<br>ethyl 4-[1-(10-methoxymethyl)-10H-pyrazino[2,3-b][1,4]benzoxazin-8-ylmethyl]piperidin-4-yl]-2-methylbutanoate | $^1$H-NMR(CDCl$_3$)δppm:<br>1.13(d, J=7Hz, 3H), 1.1–1.3(m, 3H), 1.24(t, J=7Hz, 3H), 1.3–1.5(m, 1H), 1.6–1.7(m, 3H), 1.7–1.85(m, 2H), 1.85–1.95(m, 2H), 2.3–2.43(m, 1H), 2.83(br.d, J=9Hz, 2H), 3.35(s, 2H), 3.45(s, 3H), 4.11(q, J=7Hz, 2H), 5.29(m, 2H), 6.77(s, 2H), 6.87(s, 1H), 7.40(d, J=3Hz, 1H), 7.55(d, J=3Hz, 1H) |

-continued

| Ex. | Structural formula | NMR |
|---|---|---|
| 528 | ethyl 4-[1-[5-(methoxymethyl)-5H-pyrido[3,4-b][1,4]benzothiazin-7-ylmethyl]-piperidin-4-yl]-2-methylbutanoate | $^1$H-NMR(CDCl$_3$)δppm: 1.13(d, J=7Hz, 3H), 1.21(m, 4H), 1.24(t, J=7Hz, 3H), 1.41(m, 1H), 1.65(m, 4H), 1.92(t, J=11Hz, 2H), 2.37(sext, J=7Hz, 1H), 2.83(d, J=11Hz, 2H), 3.42(s, 2H), 3.53(s, 3H), 4.12(q, J=7Hz, 2H), 5.03(s, 2H), 6.87(d, J=6Hz, 1H), 6.96(dd, J=2, 8Hz, 1H), 7.02(d, J=2Hz, 1H), 7.04(d, J=8Hz, 1H), 8.18(s, 1H), 8.26(d, J=6Hz, 1H) |
| 529 | ethyl [4-[[10-(methoxymethyl)-10H-pyrazino[2,3-b][1,4]benzothiazin-8-ylmethyl]amino]piperidin-1-yl]acetate | $^1$H-NMR(CDCl$_3$)δppm: 1.26(t, J=8Hz, 3H), 1.42–1.60(m, 2H), 1.84–1.94(m, 2H), 2.16–2.26(m, 2H), 2.44–2.56(m, 1H), 2.84–2.94(m, 2H), 3.20(s, 2H), 3.53(br.s, 3H), 3.76(s, 2H), 4.17(q, J=8Hz, 2H), 5.2–5.35(m, 3H), 6.9–7.0(m, 2H), 7.13(s, 1H), 7.8–7.85(m, 2H) |
| 530 | ethyl 4-[1-(10-methoxymethyl)-10H-pyrazino[2,3-b]pyrido[2,3-e][1,4]thiazin-8-ylmethyl]piperidin-4-yl]-2-methylbutanoate | $^1$H-NMR(CDCl$_3$)δppm: 1.13(d, J=6.8Hz, 3H), 1.15–1.30(m, 5H), 1.25(t, J=7.2Hz, 3H), 1.35–1.47(m, 1H), 1.57–1.69(m, 3H), 1.88–1.98(m, 2H), 2.33–2.42(m, 1H), 2.79–2.86(m, 2H), 3.40(s, 2H), 3.52(s, 3H), 4.12(q, J=6.8Hz, 2H), 5.26(s, 2H), 7.28(br.d, J=1.6Hz, 1H), 7.80(d, J=2.8Hz, 1H), 7.84(d, J=2.8Hz, 1H), 7.95(d, J=1.6Hz, 1H) |

Example 531

Ethyl [4-1-[10-(methoxymethyl)-7-methoxy-10H-pyrazino[2,3-b][1,4]benzothiazin-8-ylmethyl]piperidin-4-yl]-2-methyl-butanoate To a solution of 0.7 g of 7-methoxy-10-(methoxymethyl)-10H-pyrazino[2,3-b][1,4]benzothiazine-8-carboxaldehyde and 0.98 g of ethyl 4-(piperidin-4-yl)-2-methylbutanoate in acetonitrile (50 ml) was added 0.29 g of sodium cyanoborohydride. After stirring at room temperature for 10 minutes, 0.4 ml of acetic acid was dropped thereinto and the resulting mixture was reacted for 12 hours. After adding water, the reaction mixture was extracted with ethyl acetate, washed with a saturated aqueous solution of sodium chloride and dried over anhydrous magnesium sulfate. After distilling off the solvent under reduced pressure, the residue was purified by silica gel column chromatography (eluted with n-hexane/ethyl acetate) to thereby give 0.2 g of the title compound as a pale yellow oily substance.

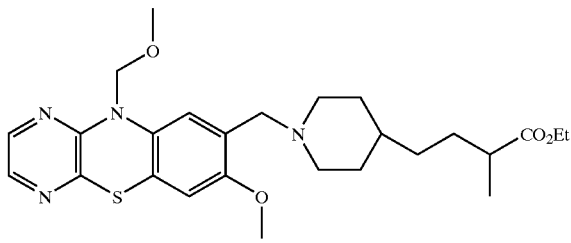

¹H-NMR(CDCl₃) δ ppm: 1.15(d, J=7 Hz, 3H), 1.26(t, J=7 Hz, 3H), 1.2–1.3(m, 2H), 1.35–1.50(m, 3H), 1.55–1.80(m, 6H), 2.2–2.40(m, 2H), 2.3–2.43(m, 1H), 3.0–3.15(m, 2H), 3.56(s, 3H), 3.79(s, 3H), 4.13(q, J=7 Hz, 2H), 5.28(s, 2H), 6.55(s, 1H), 7.26(s, 1H), 7.83(d, J=3 Hz, 1H), 7.85(d, J=3 Hz, 1H)

Example 532

10H-Pyrazino[2,3-b][1,4]benzothiazine-8-carboxylic acid

To 50 ml of a solution of 2 g of methyl 10H-pyrazino[2,3-b][1,4]benzothiazine-8-carboxylate in methanol was added 0.8 g of sodium hydroxide and the resulting mixture was heated under reflux for 1 hour. After distilling off the methanol under reduced pressure, a 1 N aqueous solution of hydrochloric acid was added thereto so as to adjust the pH value to 5 to 6. Then the mixture was extracted with ethyl acetate/dichloromethane and the organic layer was dried over anhydrous magnesium sulfate. After distilling off the solvent under reduced pressure, 1.9 g of the title compound was obtained as a yellow solid.

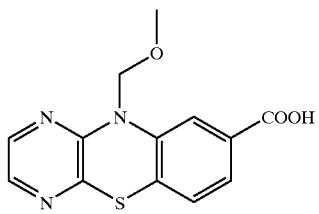

¹H-NMR(DMSO-d₆) δ ppm: 3.40(s, 3H), 5.26(s, 2H), 7.22(d, J=8.1 Hz, 1H), 7.52(dd, J=1.7, 8.1 Hz, 1H), 7.64(d, J=1.7 Hz, 1H), 7.94(d, J=2.6 Hz, 1H), 7.87(d, J=2.6 Hz, 1H), 13.05–13.25(br.s, 1H)

Example 533

Ethyl 4-[1-[(10H-pyrazino[2,3-b][1,4]benzothiazin-8-yl)carbonyl]piperidin-4-yl]-2-methylbutanoate To a solution of 1 g of 10H-pyrazino[2,3-b][1,4]-benzothiazine-8-carboxylic acid in tetrahydrofuran (50 ml) were added under ice-cooling 0.6 ml of triethylamine and 0.55 ml of diethyl chlorophosphate. The resulting mixture was reacted at room temperature for 0.5 hour. Next, 0.66 g of ethyl 4-(piperidin-4-yl)-2-methylbutanoate was added thereto and the resulting mixture was stirred at room temperature for 12 hours. After adding ethyl acetate to the reaction mixture, the organic layer was washed with water and dried over anhydrous magnesium sulfate. After distilling off the solvent under reduced pressure, the residue was purified by silica gel column chromatography (eluted with n-hexane/ethyl acetate) to thereby give 1.0 g of the title compound as a yellow oily substance.

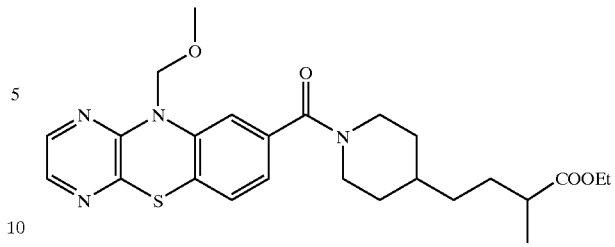

¹H-NMR(CDCl₃) δ ppm: 1.0–1.8(m, 9H), 1.15(d, J=7 Hz, 3H), 1.26(t, J=7 Hz, 3H), 2.3–2.45(m, 1H), 2.6–2.7(m, 1H), 2.9–3.3(m, 1H), 3.51(s, 3H), 3.6–3.8(m, 1H), 3.95–4.10(m, 1H), 4.13(q, J=7 Hz, 2H), 5.26(s, 2H), 6.99(dd, J=2, 8 Hz, 1H), 7.04(d, J=8 Hz, 1H), 7.18(d, J=2 Hz, 1H), 7.85(d, J=3 Hz, 1H), 7.87(d, J=3 Hz, 1H)

Example 534

10H-Pyrazino[2,3-b][1,4]benzothiazine-8-acetonitrile

To 50 ml of a solution of 5 g of 8-(chloromethyl)-10H-pyrazino[2,3-b][1,4]benzothiazine in dimethyl sulfoxide was added 0.92 g of sodium cyanide and the resulting mixture was reacted at 60° C. for 1 hour. After adding ethyl acetate, the organic layer was washed with water and dried over anhydrous magnesium sulfate. After distilling off the solvent under reduced pressure, 4.7 g of the title compound was obtained as a yellow solid.

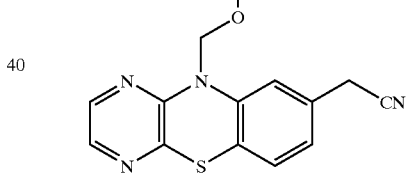

¹H-NMR(DMSO-d₆) δ ppm: 3.38(s, 3H), 4.00(s, 2H), 5.24(s, 2H), 6.99(dd, J=1.8, 8.0 Hz, 1H), 7.09(d, J=1.8 Hz, 1H), 7.15(d, J=8.0 Hz, 1H), 7.94(d, J=2.4 Hz, 1H), 7.97(d, J=2.4 Hz, 1H)

Example 535

10H-Pyrazino[2,3-b][1,4]benzothiazine-8-acetic acid 4.7 g of 10H-pyrazino[2,3-b][1,4]benzothiazine-8-acetonitrile was dissolved in 100 ml of ethanol. After adding 2.8 g of potassium hydroxide, the resulting mixture was heated under reflux for 16 hours. After distilling off the ethanol, water was added and the mixture was made weakly acidic with dilute hydrochloric acid followed by the extraction with ethyl acetate and dichloromethane. The organic layer was dried over anhydrous magnesium sulfate. After distilling off the solvent under reduced pressure, 3.85 g of the title compound was obtained as yellow crystals.

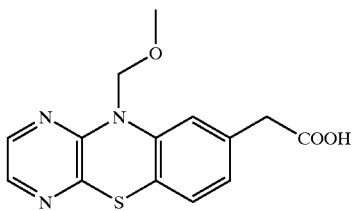

¹H-NMR(CDCl₃) δ ppm: 3.53(s, 3H), 3.60(s, 2H), 5.27(s, 2H), 6.90(dd, J=2, 8 Hz, 1H), 6.98(d, J=8 Hz, 1H), 7.08(d, J=2 Hz, 1H), 7.83(d, J=3 Hz, 1H), 7.85(d, J=3 Hz, 1H)

Example 536

Ethyl 4-[1-[(10-(methoxymethyl)-10H-pyrazino[2,3-b][1,4]benzothiazin-8-ylmethyl]carbamoyl]piperidin-4-yl]-2-methylbutanoate To a solution of 0.7 g of 10H-pyrazino[2,3-b][1,4]benzothiazine-8-acetic acid in tetrahydrofuran (50 ml) were added 0.35 ml of triethylamine and 0.55 ml of diphenyl phosphate azide and the resulting mixture was stirred at room temperature for 3 hours. Next, it was heated under reflux for 1.5 hours. After adding 0.55 g of ethyl 4-(piperidin-4-yl)-2-methylbutanoate, the resulting mixture was reacted at room temperature for 1 hour. After adding ethyl acetate, the reaction mixture was washed with water and dried over anhydrous magnesium sulfate. After distilling off the solvent under reduced pressure, the residue was purified by silica gel column chromatography (eluted with dichloromethane/methanol) to thereby give 0.66 g of the title compound as a yellow oily substance.

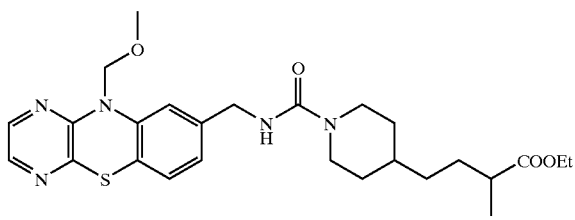

¹H-NMR(CDCl₃) δ ppm: 1.14(d, J=7 Hz, 3H), 1.1–1.2(m, 1H), 1.25(t, J=7 Hz, 3H), 1.25–1.35(m, 2H), 1.3–1.5(m, 2H), 1.6–1.75(m, 4H), 2.3–2.45(m, 1H), 2.7–2.8(m, 2H), 3.52(s, 3H), 3.85–3.95(m, 2H), 4.12(q, J=7 Hz, 2H), 4.35(d, J=6 Hz, 2H), 4.73(br.t, J=6 Hz, 1H), 5.26(s, 2H), 6.91(dd, J=1, 8 Hz, 1H), 6.96(d, J=8 Hz, 1H), 7.08(d, J=1 Hz, 1H), 7.8–7.86(m, 2H)

Example 537

Ethyl 1-[(10-(methoxymethyl)-10H-pyrazino[2,3-b][1,4]-benzothiazin-8-ylmethyl]-2,3-dehydro-3-piperidinecarboxylate To a solution of 0.506 g of diisopropylamine in tetrahydrofuran (10 ml) was added in a nitrogen atmosphere at 0° C. 3.14 ml of a 1.6 M solution of n-butyllithium in hexane. Further, a solution of 0.776 g of ethyl 2,3-dehydro-3-piperidinecarboxylate in tetrahydrofuran (2 ml) was added thereto to thereby prepare a lithium salt. In another container, 1.00 g of 8-(chloromethyl)-10-methoxymethyl-10H-pyrazino[2,3-b][1,4]benzothiazine was added to a solution of 1.53 g of sodium iodide in N,N-dimethylformamide (10 ml). After heating for 2 hours, the mixture was brought back to room temperature. The solution thus obtained was added to the solution of the lithium salt as described above and the resulting mixture was stirred at room temperature for 2 hours. After concentrating under reduced pressure, the residue was dissolved in ethyl acetate and water. The organic layer was concentrated and the residue was purified by silica gel column chromatography (eluted with dichloromethane/methanol) to thereby give 0.375 g of the title compound as pale yellow crystals.

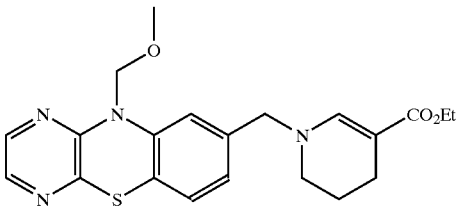

¹H-NMR(CDCl₃) δ ppm: 1.26(t, J=7 Hz, 3H), 1.52(quint, J=6 Hz, 2H), 2.29(t, J=6 Hz, 2H), 2.98(t, J=6 Hz, 2H), 3.49(s, 3H), 4.15(q, J=7 Hz, 2H), 4.23(s, 2H), 5.22(s, 2H), 6.82(dd, J=2, 7 Hz, 1H), 6.97(d, J=2 Hz, 1H), 6.98(d, J=1, 7 Hz, 1H), 7.51(s, 1H), 7.83(d, J=3 Hz, 1H), 7.84(d, J=3 Hz, 1H)

Example 538

1-[10-(Methoxymethyl)-10H-pyrazino[2,3-b][1,4]-benzothiazin-8-ylmethyl]-3-(tert-butyldimethylsilyloxymethyl)pyridinium chloride

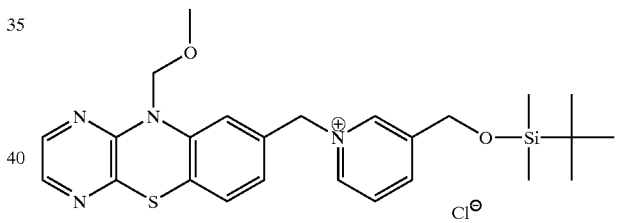

¹H-NMR(DMSO-d₆) δ ppm: 0.00(s, 6H), 0.75(s, 9H), 3.35(s, 3H), 4.84(s, 2H), 5.20(s, 2H), 5.75(s, 2H), 7.05(dd, J=2, 8 Hz, 1H), 7.16(d, J=8 Hz, 1H), 7.18(d, J=2 Hz, 1H), 7.88(d, J=3 Hz, 1H), 7.94(d, J=3 Hz, 1H), 8.20(t, J=7 Hz, 1H), 8.44(d, J=7 Hz, 1H), 8.80(s, 1H), 9.06(d, J=7 Hz, 1H)

Example 539

1-[10-(Methoxymethyl)-10H-pyrazino[2,3-b][1,4]-benzothiazin-8-ylmethyl]-3,4-dehydro-3-(tert-butyldimethylsilyloxymethyl)piperidine To a solution of 0.326 g of 1-[10-(methoxymethyl)-10H-pyrazino[2,3-b][1,4]benzothiazin-8-ylmethyl]-3-(tert-butyldimethylsilyloxymethyl)pyridinium chloride in methanol (10 ml) was added at room temperature in a nitrogen atmosphere 0.06 g of sodium borohydride. After stirring for 18 hours, water and ethyl acetate were added thereto. The organic layer was dried over anhydrous magnesium sulfate, filtered and concentrated under reduced pressure. The residue was purified by silica gel column chromatography (eluted with n-hexane/ethyl acetate) to thereby give 0.176 g of the title compound as pale yellow crystals.

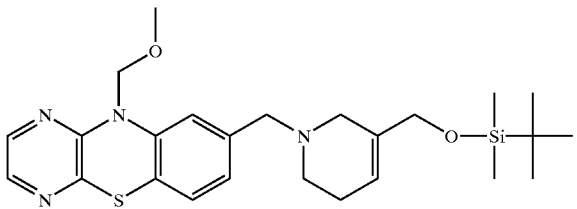

¹H-NMR(CDCl₃) δ ppm: 0.05(s, 6H), 0.83(s, 9H), 2.10–2.15(m, 2H), 2.46(t, J=6 Hz, 2H), 2.86(br.s, 2H), 3.41(s, 3H), 3.49(s, 2H), 3.90(br.s, 2H), 5.25(s, 2H), 5.65(m, 1H), 6.92(d, J=8 Hz, 1H), 6.95(dd, J=2, 8 Hz, 1H), 7.08(d, J=8 Hz, 1H), 7.79(d, J=3 Hz, 1H), 7.80(d, J=3 Hz, 1H)

Example 540

1-[10-(Methoxymethyl)-10H-pyrazino[2,3-b][1,4]-benzothiazin-8-ylmethyl]-3,4-dehydro-3-piperidinemethanol To a solution of 0.176 g of 1-[10-(methoxymethyl)-10H-pyrazino[2,3-b][1,4]-benzothiazin-8-ylmethyl]-3,4-dehydro-3-(tert-butyldimethylsilyloxymethyl)piperidine in tetrahydrofuran (5 ml) was added at 0° C. in a nitrogen atmosphere 1 ml of a 1 M solution of tetra-n-butylammonium fluoride in tetrahydrofuran and the resulting mixture was stirred at room temperature for 3 hours. After distilling off the solvent under reduced pressure, the residue was purified by silica gel column chromatography (eluted with dichloromethane/methanol) to thereby give 0.100 g of the title-compound as pale yellow crystals.

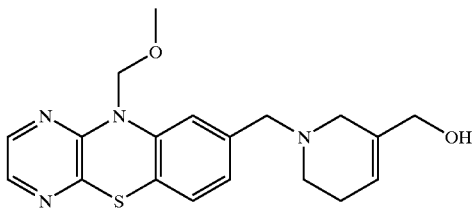

¹H-NMR(CDCl₃) δ ppm: 2.18(m, 2H), 2.54(t, J=6 Hz, 2H), 3.04(br.s, 2H), 3.53(s, 3H1), 3.57(s, 2H), 4.00(s, 2H), 5.30(s, 2H), 5.64(br.s, 1H), 6.95(s, 2H), 7.13(s, 1H), 7.81(d, J=3 Hz, 1H), 7.83(d, J=3 Hz, 1H)

Example 541

1-[10-(Methoxymethyl)-10H-pyrazino[2,3-b][1,4]benzothiazin-8-ylmethyl]-3,4-dehydro-3-piperidinecarbaldehyde To a solution of 0.150 g of 1-[10-(methoxymethyl)-10H-pyrazino[2,3-b][1,4]benzothiazin-8-ylmethyl]-3,4-dehydro-3-piperidinemethanol in dichloromethane (4 ml) was added 1.00 g of manganese dioxide. After stirring for 3 hours, the mixture was filtered. After distilling off the solvent under reduced pressure, 0.108 g of the title compound was obtained as pale yellow crystals.

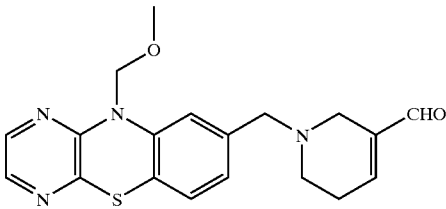

¹H-NMR(CDCl₃) δ ppm: 2.47(m, 2H), 2.58(t, J=7 Hz, 2H), 3.20(m, 2H), 3.53(s, 3H), 3.59(s, 2H), 5.30(s, 2H), 6.86(m, 1H), 6.96(s, 2H), 7.11(s, 1H), 7.83(d, J=3 Hz, 1H), 7.84(d, J=3 Hz, 1H), 9.42(s, 1H)

Example 542

Methyl 1-[10-(methoxymethyl)-10H-pyrazino[2,3-b][1,4]benzothiazin-8-ylmethyl]-3,4-dehydro-3-piperidinecarboxylate To a solution of 0.108 g of 1-[10-(methoxymethyl)-10H-pyrazino[2,3-b][1,4]-benzothiazin-8-ylmethyl]-3,4-dehydro-3-piperidinecarbaldehyde in methanol (5 ml) were added 0.096 g of potassium cyanide, 0.504 g of manganese dioxide and 0.070 g of acetic acid and the resulting mixture was stirred for 12 hours. Then the reaction mixture was filtered through celite and the celite was extracted with dichloromethane. The organic layer was washed with a dilute aqueous solution of potassium hydroxide and concentrated under reduced pressure. The residue was purified by silica gel column chromatography (eluted with dichloromethane/methanol) to thereby give 0.080 g of the title compound as pale yellow crystals.

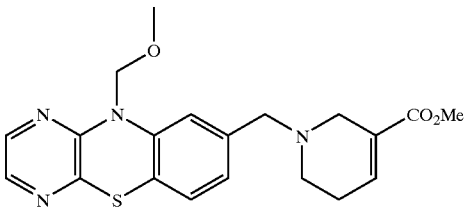

¹H-NMR(CDCl₃) δ ppm: 2.34(m, 2H), 2.54(t, J=7 Hz, 2H), 3.22(br.s, 2H), 3.53(s, 3H), 3.58(s, 2H), 3.73(s, 3H), 5.28(s, 2H), 6.96(s, 2H), 7.01(m, 1H), 7.12(s, 1H), 7.83(s, 2H)

Example 543

Ethyl N-[10-(methoxymethyl)-10H-pyrazino[2,3-b][1,4]benzothiazin-8-ylmethyl]-N-(1-methanesulfonylpiperidin-4-yl)-aminoacetate To a solution of 1.1 g of N,N-[3-[[(10-(methoxymethyl)-10H-pyrazino[2,3-b][1,4]benzothiazin-8-ylmethyl]-amino]penta-methylene]methanesulfonamide in 30 ml of N,N-dimethylformamide were added 0.42 g of anhydrous potassium carbonate and 0.34 ml of ethyl bromoacetate. Then the resulting mixture was reacted at 60° C. for 2 hours. After adding ethyl acetate, the reaction mixture was washed with water and a saturated aqueous solution of sodium chloride and dried over anhydrous magnesium sulfate. After distilling off the solvent under reduced pressure, the residue was purified by silica gel column chromatography (eluted with methanol/dichloromethane) to thereby give 0.34 g of the title compound as a yellow oily substance.

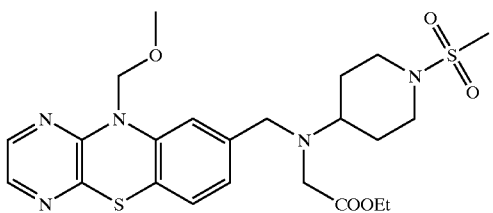

¹H-NMR(CDCl₃) δ ppm: 1.25(t, J=7 Hz, 3H), 1.5–1.7(m, 2H), 1.9–2.0(m, 2H), 2.6–2.7(m, 2H), 2.75(s, 3H), 2.7–2.8 (m, 1H), 3.35(s, 2H), 3.53(s, 3H), 3.78(s, 2H), 3.75–3.85(m, 2H), 4.13(q, J=7 Hz, 2H), 5.27(s, 2H), 6.9–7.0(m, 2H), 7.20(s, 1H), 7.8–7.9(m, 2H)

Example 544

Ethyl [[4-[N-[10-(methoxymethyl)-10H-pyrazino[2,3-b][1,4]-benzothiazin-8-ylmethyl]-N-acetyl]amino] piperidin-1-yl]-acetate To a solution of 1.1 g of ethyl[4-[[10-(methoxymethyl)-10H-pyrazino[2,3-b][1,4]benzothiazin-8-ylmethyl]amino]-piperidin-1-yl]acetate in dichloromethane (30 ml) were added 0.4 ml of triethylamine and 0.2 ml of acetyl chloride and the resulting mixture was reacted at room temperature for 0.5 hour. Then the reaction mixture was washed with water, dried over anhydrous magnesium sulfate and concentrated. The residue was purified by silica gel column chromatography (eluted with methanol/dichloromethane) to thereby give 1.0 g of the title compound as a yellow oily substance.

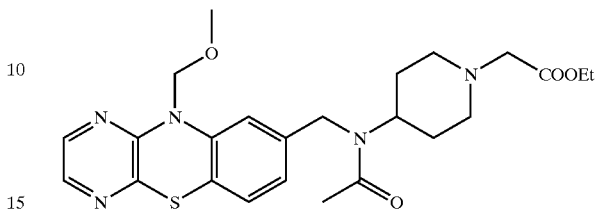

¹H-NMR(CDCl₃) δ ppm: 1.2–1.3(m, 5H), 1.5–1.7(m, 2H), 1.8–1.9(m, 1H), 2.2–2.3(m, 1H), 2.25(s, 3H), 2.9–3.0 (m, 2H), 3.15and3.89(s, total2H), 3.51(s, 3H), 4.16(q, J=7 Hz, 2H), 4.45and4.50(s, total2H), 4.40–4.60(m, 1H), 5.23 (m, 2H), 6.78(d, J=8 Hz, 1H), 6.85–7.00(m, 2H), 7.8–7.9(m, 2H)

Examples 545 to 551

The following compounds were obtained by the same method as the one of Example 18.

| Ex. | Structural formula | NMR |
|---|---|---|
| 545 | 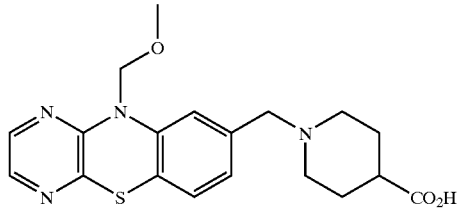<br>[1-[10-(methoxymethyl)-10H-pyrazino[2,3-b] [1,4] benzo-thiazin-8-ylmethyl]piperidin-4-yl]carboxylic acid | ¹H-NMR(CDCl₃)δppm: 1.90–2.06(br.s, 2H), 2.06–2.16(br.s, 2H) 2.38–2.43(br.s, 1H), 2.58–2.70(br.s, 2H), 3.18–3.30(br.s, 2H), 3.48(s, 3H), 3.94(s, 2H), 5.28(s, 2H), 6.96(d, J=8Hz, 1H), 6.98(s, 1H), 7.02(d, J=8Hz, 1H), 7.79(d, J=3Hz, 1H), 7.80(d, J=3Hz, 1H) |
| 546 | 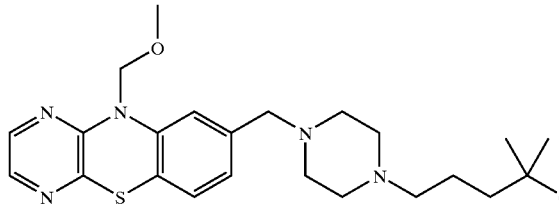<br>4-[4-[10-(methoxymethyl)-pyrazino[2,3-b] [1,4] benzothiazin-8-ylmethyl] piperazin-1-yl]-2,2-dimethylpentanoic acid | ¹H-NMR(CDCl₃)δppm: 1.01(s, 6H), 1.38(br.s, 4), 2.44(br.s, 2H), 2.31–2.50(br.s, 8H), 3.38(s, 2H), 3.51(s, 3H), 5.25(s, 2H), 6.89(d, J=8Hz, 1H), 6.91(d, J=1, 8Hz, 1H), 7.08(s, 1H), 7.81(d, J=3Hz, 1H), 7.83(d, J=3Hz, 1H) |

| Ex. | Structural formula | NMR |
|---|---|---|
| 547 | 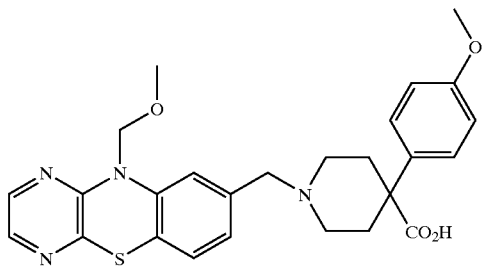<br>[1-[10-(methoxymethyl)-10H-pyrazino[2,3-b] [1,4]benzothiazin-8-ylmethyl]-4-(p-methoxyphenyl)piperidin-4-yl]carboxylic acid | $^1$H-NMR(CD$_3$OD)δppm: 2.0–2.2(m, 2H), 2.4–2.6(m, 2H), 2.8–3.0(m, 2H), 3.0–3.2(m, 2H), 3.30(s, 2H), 3.51(s, 3H), 3.78(s, 3H), 5.38(s, 2H), 6.78–7.0(m, 2H), 7.1–7.2(m, 2H), 7.3–7.4(m, 3H), 7.88(s, 1H), 7.93(s, 1H) |
| 548 | 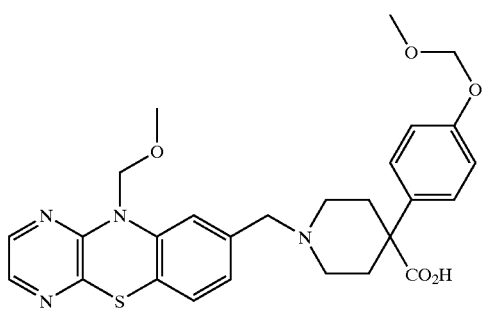<br>[1-[10-(methoxymethyl)-10H-pyrazino[2,3-b] [1,4]benzothiazin-8-ylmethyl]-4-(p-methoxymethoxyphenyl)piperidin-4-yl]carboxylic acid | $^1$H-NMR(DMSO-d$_6$)δppm: 1.6–1.75(m, 2H), 2.13(br.t, J=12Hz, 2H), 2.38(br.d, J=12Hz, 2H), 2.6–2.7(m, 2H), 3.34(s, 3H), 3.35(s, 2H), 3.36(s, 3H), 5.13(s, 2H), 5.23(s, 2H), 6.93(d, J=9Hz, 3H), 7.04(d, J=8Hz, 1H), 7.08–7.11(m, 1H), 7.28(d, J=8Hz, 2H), 7.91(d, J=3Hz, 1H), 7.95(d, J=3Hz, 1H) |
| 549 | 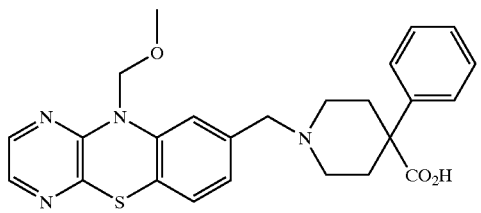<br>[1-[10-(methoxymethyl)-10H-pyrazino[2,3-b] [1,4]benzothiazin-8-ylmethyl]-4-phenylpiperidin-4-yl]carboxylic acid | $^1$H-NMR(DMSO-d$_6$)δppm: 1.65–1.80(m, 2H), 2.08–2.20(m, 2H), 2.35–2.45(m, 2H), 2.6–2.75(m, 2H), 3.36(s, 5H), 5.23(s, 2H), 6.94(d, J=8Hz, 1H), 7.04(d, J=8Hz, 1H), 7.09(s, 1H), 7.20(t, J=8Hz, 1H), 7.30(t, J=8Hz, 2H), 7.37(d, J=8Hz, 2H), 7.9–7.93(m, 1H), 7.93–7.97(m, 1H) |

| Ex. | Structural formula | NMR |
|---|---|---|
| 550 | [1-[10-(methoxymethyl)-10H-pyrazino[2,3-b][1,4]benzothiazin-8-ylmethyl]piperidin-4-yl]acetic acid | $^1$H-NMR(CDCl$_3$)δppm: 1.50–1.80(m, 5H), 2.00–2.30(m, 4H), 3.10–3.20(m, 2H), 3.49(s, 3H), 3.64(s, 2H), 5.23(s, 2H), 6.91(d, J=8Hz, 1H), 6.94(d, J=8Hz, 1H), 7.09(s, 1H), 7.81(s, 2H) |
| 551 | 4-[1-[10-(methoxymethyl)-10H-pyrazino[2,3-b][1,4]benzothiazin-8-ylmethyl]piperidin-4-yl]butanoic acid | $^1$H-NMR(CDCl$_3$)δppm: 1.20–1.30(m, 4H), 1.44–1.58(m, 4H), 1.74–1.82(m, 2H), 2.23–2.28(m, 3H), 2.42–2.56(m, 2H), 3.48(s, 3H), 4.02(s, 2H), 5.23(s, 2H), 6.96(d, J=8Hz, 1H), 6.98(d, J=8Hz, 1H), 7.16(s, 1H), 7.82(s, 2H), 10.20–11.00(br.s, H) |

Example 552
[[1-[10-(Methoxymethyl)-10H-pyrazino[2,3-b][1,4]benzothiazin-8-ylmethyl]piperidin-4-yl]carbamoyl]aminoacetic acid The title compound was obtained by treating ethyl[(1-benzylpiperidin-4-yl)carbamoyl]aminoacetate by the same methods as those of Examples 64 and 18.

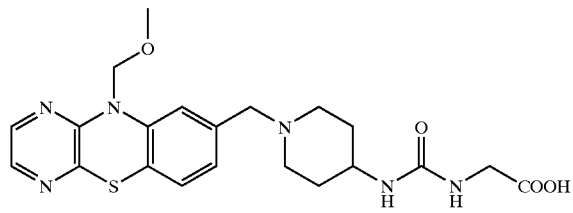

$^1$H-NMR(CDCl$_3$) δ ppm: 1.57–1.68(m, 2H), 2.00–2.10 (m, 2H), 2.44–2.57(m, 2H), 2.93–2.99(m, 2H), 3.45(s, 2H), 3.56(s, 3H), 3.88–3.99(m, 1H), 3.91(s, 2H), 5.25–5.35(br.s, 1H), 5.28(s, 2H), 5.33(br.s, 1H), 6.96(s, 2H), 7.14(s, 1H), 7.83(s, 2H)

Examples 553 to 574

The following compounds were obtained by the same method as the one of Example 64 by using N,N-diisopropylethylamine or anhydrous potassium carbonate as a base.

| Ex. | Structural formula | NMR |
|---|---|---|
| 553 | methyl 4-[[4-hydroxy-(10H-pyrazino[2,3-b][1,4]benzothiazin-8-ylmethyl)piperidin]-4-yl]phenylacetate | $^1$H-NMR(CDCl$_3$) δ ppm: 1.56(br.s, 1H), 1.71–1.78(m, 2H), 2.08–2.20(m, 2H), 2.42–2.53(m, 2H), 2.73–2.81(m, 2H), 3.43(br.s, 2H), 3.63(s, 2H), 3.70(s, 3H), 6.46(br.s, 1H), 6.59(br.s, 1H), 6.81(dd, J=1.5, 7.8Hz, 1H), 6.85(d, J=7.8Hz, 1H), 7.25–7.30(m, 2H), 7.45–7.49(m, 2H), 7.58(d, J=2.9Hz, 1H), 7.69(d, J=2.9Hz, 1H) |

-continued

| Ex. | Structural formula | NMR |
|---|---|---|
| 554 | 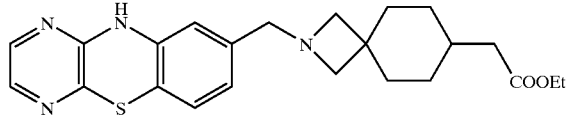<br>ethyl [2-(10H-pyrazino[2,3-b][1,4]benzothiazin-8-ylmethyl)-2-azaspiro[3.5]non-7-yl]acetate | $^1$H-NMR(CDCl$_3$) δ ppm: 0.91–1.03(m, 2H), 1.25(t, J=7.1Hz, 3H), 1.41–1.51(m, 2H), 1.63–1.79(m, 3H), 1.94–2.02(m, 2H), 2.15(d, J=7.0Hz, 2H), 3.12(s, 2H), 3.15(s, 2H), 3.61(s, 2H), 4.12(q, J=7.1Hz, 2H), 6.64(br.s, 1H), 6.67(br.s, 1H), 6.74(dd, J=1.6, 7.9Hz, 1H), 6.82(d, J=7.9Hz, 1H), 7.57(d, J=2.7Hz, 1H), 7.68(d, J=2.7Hz, 1H) |
| 555 | 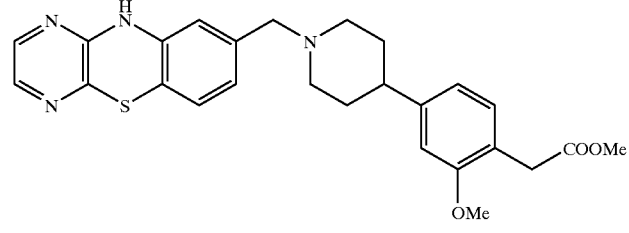<br>methyl 2-methoxy-4-[1-(10H-pyrazino[2,3-b][1,4]benzothiazin-8-yl-methyl)piperidin-4-yl]phenylacetate | $^1$H-NMR(CDCl$_3$) δ ppm: 1.72–1.86(m, 4H), 2.02–2.10(m, 2H), 2.49(m, 1H), 2.95–3.02(m, 2H), 3.38(s, 2H), 3.60(s, 2H), 3.69(s, 3H), 3.81(s, 3H), 6.49(br.s, 1H), 6.58(d, J=1.5Hz, 1H), 6.74(d, J=1.5Hz, 1H), 6.78(dd, J=1.5, 7.5Hz, 1H), 6.79(dd, J=1.5, 7.9Hz, 1H), 6.85(d, J=7.9Hz, 1H), 7.10(d, J=7.5Hz, 1H), 7.58(d, J=2.9Hz, 1H), 7.70(d, J=2.9Hz, 1H) |
| 556 | 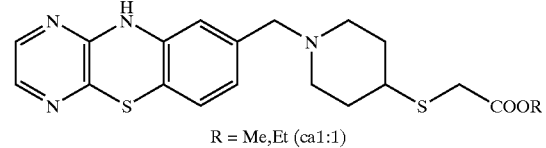<br>R = Me,Et (ca1:1)<br>methyl 1-[2-(10H-pyrazino[2,3-b][1,4]benzothiazin-8-ylmethyl)piperidin-4-yl]thioacetate and ethyl 1-[2-(10H-pyrazino[2,3-b][1,4]benzothiazin-8-ylmethyl)piperidin-4-yl]thioacetate (mixture of about 1 : 1) | $^1$H-NMR(CDCl$_3$) δ ppm: 1.28(t, J=7.1Hz, 1.5H), 1.54–1.66(m, 2H), 1.93–2.00(m, 2H), 2.01–2.10(m, 2H), 2.78–2.87(m, 3H), 3.25(s, 1H), 3.27(s, 1H), 3.32(s, 2H), 3.74(s, 1.5H), 4.19(q, J=7.1Hz, 1H), 6.54(d, J=1.5Hz, 1H), 6.73(dd, J=1.5, 7.9Hz, 1H), 6.81(d, J=7.9Hz, 1H), 7.18(br.s, 1H), 7.59(d, J=2.9Hz, 1H), 7.69(d, J=2.9Hz, 1H) |
| 557 | 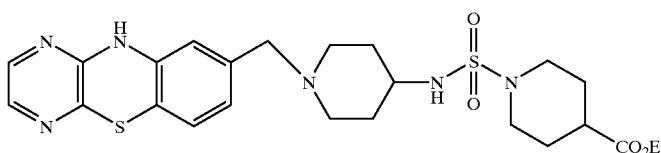<br>N-[1-(10H-pyrazino[2,3-b][1,4]benzothiazin-8-ylmethyl)-piperidin-4-yl]-N',N'-[(3-ethoxycarbonyl)pentamethylene]sulfamide | $^1$H-NMR(CDCl$_3$) δ ppm: 1.26(t, J=7Hz, 3H), 1.38(dq, J=3, 12Hz, 2H), 1.76(dq, J=3, 12Hz, 2H), 1.99(br.d, J=12Hz, 4H), 2.41(m, 5H), 2.83(m, 4H), 3.22(m, 1H), 3.38(s, 2H), 4.14(q, J=7Hz, 2H), 6.55(d, J=1Hz, 1H), 6.74(dd, J=1, 8Hz, 1H), 6.82(d, J=8Hz, 1H), 7.40(br.s, 1H), 7.48(d, J=3Hz, 1H), 7.67(d, J=3Hz, 1H), 8.20(s, 1H) |
| 558 | 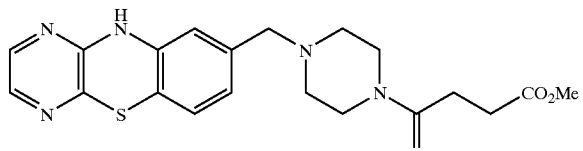<br>methyl 4-oxo-4-[4-(10H-pyrazino[2,3-b][1,4]benzothiazin-8-ylmethyl)piperazin-1-yl]butanoate | $^1$H-NMR(CDCl$_3$) δ ppm: 2.41(m, 4H), 2.60–2.69(m, 4H), 3.35(s, 2H), 3.48(t, J=5Hz, 2H), 3.61(t, J=5Hz, 2H), 3.69(s, 3H), 6.41(s, 1H), 6.53(d, J=2Hz, 1H), 6.77(dd, J=2, 8Hz, 1H), 6.85(d, J=8Hz, 1H), 7.58(d, J=3Hz, 1H), 7.70(d, J=3Hz, 1H) |

| Ex. | Structural formula | NMR |
|---|---|---|
| 559 | (2-trimethylsilylethyl) N-[1-(10H-pyrazino[2,3-b][1,4]benzothiazin-8-ylmethyl]piperidin-4-ylsulfamoylacetate | $^1$H-NMR(CDCl$_3$) δ ppm: 0.00(s, 9H), 0.99(m, 2H), 1.61(br.d, 2H), 1.95(br.d, J=12Hz, 2H), 2.07(br.s, 2H), 2.73(br.s, 2H), 3.29(s, 2H), 3.33(m, 1H), 3.93(s, 2H), 4.22(m, 2H), 6.46 (br.s, 1H), 6.58(br.s, 1H), 6.69(dd, J=2, 8Hz, 1H), 6.78(d, J=8Hz, 1H), 7.52(d, J=3Hz, 1H), 7.64(d, J=3Hz, 1H) |
| 560 | methyl [1-(10H-pyrazino [2,3-b][1,4]benzothiazin-8-ylmethyl)-4-ethyl piperidin-4-yl]acetate | $^1$H-NMR(CDCl$_3$) δ ppm: 0.84(t, J=7Hz, 3H), 1.44(q, J=7Hz, 2H), 1.47–1.61(m, 4H), 2.30(s, 2H), 2.33–2.40(m, 2H), 2.41–2.49(m, 2H), 3.35(s, 2H), 3.54(s, 3H), 6.55(d, J=2Hz, 1H), 6.72(br.s, 1H), 6.74(dd, J=2, 8Hz, 1H), 6.81(d, J=8Hz, 1H), 7.57(d, J=3Hz, 1H), 7.68(d, J=3Hz, 1H) |
| 561 | ethyl [1-(10H-pyrazino [2,3-b][1,4]benzothiazin-8-ylmethyl)piperidin-3-yl]acetate | $^1$H-NMR(CDCl$_3$) δ ppm: 1.22(t, J=7Hz, 3H), 1.5–1.7(m, 3H), 1.7–1.8(m, 2H), 1.9–2.15(m, 2H), 2.15–2.28(m, 2H), 2.65–2.75(m, 2H), 3.29(d, J=9Hz, 1H), 3.33(d, J=9Hz, 1H), 4.10(q, J=7Hz, 2H), 6.51(br.s, 1H), 6.54(d, J=2Hz, 1H), 6.74(dd, J=2, 8Hz, 1H), 6.81(d, J=8Hz, 1H), 7.57(d, J=3Hz, 1H), 7.68(d, J=3Hz, 1H) |
| 562 | methyl [7-(10H-pyrazino[2,3-b][1,4] enzothiazin-8-ylmethyl)-7-azaspiro[3.5]non-2-yl] arboxylate | $^1$H-NMR(CDCl$_3$) δ ppm: 1.58(t, J=5Hz, 2H), 1.64(t, J=5Hz, 2H), 2.01(s, 2H), 2.03(s, 2H), 2.25(br.s, 2H), 2.23(br.s, 2H), 3.05(quint, J=9Hz, 1H), 3.28(s, 2H), 3.67(s, 3H), 6.39(br.s, 1H), 6.53(br.s, 1H), 6.74(dd, J=2, 8Hz, 1H), 6.82(d, J=8Hz, 1H), 7.57(d, J=3Hz, 1H), 7.68(d, J=3Hz, 1H) |
| 563 | ethyl 3-[1-(10H-pyrazino[2,3-b][1,4] enzothiazin-8-ylmethyl)piperidin-4-yl]-2,2,-dimethyl propanoate | $^1$H-NMR(CDCl$_3$) δ ppm: 1.15(s, 6H), 1.23(t, J=7Hz, 3H), 1.1–1.4(m, 3H), 1.52(d, J=6Hz, 2H), 1.50–1.60(m, 2H), 1.8–1.95(m, 2H), 2.78(br.d, J=12Hz, 2H), 3.28(s, 2H), 4.08(q, J=7Hz, 2H), 6.53(d, J=1Hz, 1H), 6.68–6.76(m, 2H), 6.81(d, J=8Hz, 1H), 7.57(d, J=3Hz, 1H), 7.68(d, J=3Hz, 1H) |
| 564 | ethyl [1-(10H-pyrazino [2,3-b][1,4]benzo thiazin-8-ylmethyl) pyrrolidin-3-yl]acetate | $^1$H-NMR(CDCl$_3$) δ ppm: 1.24(t, J=7Hz, 3H), 1.4–1.6(m, 1H), 2.02–2.14(m, 1H), 2.14–2.24 (m, 1H), 2.4(d, J=8Hz, 2H), 2.46–2.64(m, 3H), 2.80(t, J=8Hz, 1H), 3.44(d, J=13Hz, 1H), 3.48(d, J=13Hz, 1H), 4.11(q, J=7Hz, 2H), 6.44–6.50(m, 1H), 6.56(br.s, 1H), 6.74–6.78(m, 1H), 6.82(d, J=8Hz, 1H), 7.57 (d, J=3Hz, 1H), 7.68(d, J=3Hz, 1H) |

| Ex. | Structural formula | NMR |
|---|---|---|
| 565 | ethyl 2-[1-(10H-pyrazino[2,3-b][1,4]benzothiazin-8-ylmethyl)piperidin-4-yl]propanoate | $^1$H-NMR(CDCl$_3$) δ ppm: 1.12(d, J=7Hz, 3H), 1.25(t, J=7Hz, 3H), 1.2–1.45(m, 2H), 1.48–1.60(m, 2H), 1.60–1.75(m, 1H), 1.92(t, J=10Hz, 2H), 2.25(quint, J=7Hz, 1H), 2.8–2.93(m, 2H), 3.31(s, 2H), 4.12(q, J=7Hz, 2H), 6.50–6.56(m, 1H), 6.53(d, J=1Hz, 1H), 6.75(dd, J=1, 8Hz, 1H), 6.82(d, J=8Hz, 1H), 7.57(d, J=3Hz, 1H), 7, 68(d, J=3Hz, 1H) |
| 566 | ethyl 2-[1-(10H-pyrazino[2,3-b][1,4]benzothiazin-8-ylmethyl)piperidin-4-yl]-2-methylpropanoate | $^1$H-NMR(CDCl$_3$) δ ppm: 1.11(s, 6H), 1.24(t, J=7Hz, 3H), 1.3–1.45(m, 2H), 1.45–1.55(m, 2H), 1.50–1.65(m, 1H), 1.85–1.95(m, 2H), 2.85–2.9(m, 2H), 3.31(m, 2H), 4.11(q, J=7Hz, 2H), 6.38–6.44(m, 1H), 6.52(br.s, 1H), 6.75(dd, J=1, 8Hz, 1H), 6.82(d, J=8Hz, 1H), 7.57(d, J=2Hz, 1H), 7.69(d, J=2Hz, 1H) |
| 567 | ethyl 3-[1-(10H-pyrazino[2,3-b][1,4]benzothiazin-8-ylmethyl)piperidin-4-yl]propanoate | $^1$H-NMR(CDCl$_3$) δ ppm: 1.25(t, J=7Hz, 3H), 1.28–1.45(m, 1H), 1.53–1.65(m, 2H), 1.6–1.70(m, 2H), 1.70–1.90(m, 2H), 1.85–2.0(m, 2H), 2.30(t, J=8Hz, 2H), 2.8–2.9(m, 2H), 3.23(s, 2H), 4.12(q, J=7Hz, 2H), 6.55(br.s, 1H), 6.57(br.s, 1H), 6.74(dd, J=1, 8Hz, 1H), 6.82(d, J=8Hz, 1H), 7.57(d, J=3Hz, 1H), 7.68(d, J=3Hz, 1H) |
| 568 | ethyl N-[1-(10H-pyrazino[2,3-b][1,4]benzothiazin-8-ylmethyl)piperidin-4-yl]aminoacetate | $^1$H-NMR(CDCl$_3$) δ ppm: 1.25(t, J=7.2Hz, 3H), 1.33–1.45(m, 2H), 1.75–1.83(m, 2H), 1.93–2.03(m, 2H), 2.41–2.50(m, 1H), 2.75–2.84(m, 2H), 3.29(s, 2H), 3.40(s, 2H), 4.16(q, J=7.2Hz, 2H), 6.53(d, J=1.6Hz, 1H), 6.70(dd, J=1.6, 7.7Hz, 1H), 6.77(d, J=7.7Hz, 1H), 7.37(br.s, 1H), 7.55(d, J=2.8Hz, 1H), 7.64(d, J=2.8Hz, 1H) |
| 569 | ethyl 1-[1-(10H-pyrazino[2,3-b][1,4]benzothiazin-8-ylmethyl)piperidin-4-yl]cyclopropanecarboxylate | $^1$H-NMR(CDCl$_3$) δ ppm: 0.73(dd, J=4.6, 6.5Hz, 2H), 1.10(dd, J=4.6, 6.5Hz, 2H), 1.22(t, J=7.1Hz, 3H), 1.35–1.48(m, 2H), 1.53–1.60(m, 2H), 1.63–1.73(m, 1H), 1.86–1.96(m, 2H), 2.83–2.90(m, 2H), 3.30(s, 2H), 4.09(q, J=7.1Hz, 2H), 6.48–6.53(br.s, 1H), 6.54(d, J=1.4Hz, 1H), 6.75(dd, J=1.4, 8.0Hz, 1H), 6.82(d, J=8.0Hz, 1H), 7.57(d, J=2.7Hz, 1H), 7.68(d, J=2.7Hz, 1H) |
| 570 | methyl [1-(10H-pyrazino[2,3-b][1,4]benzothiazin-8-ylmethyl)piperidin-4-yl]methoxyacetate | $^1$H-NMR(CDCl$_3$) δ ppm: 1.21–1.35(m, 2H), 1.60–1.70(m, 1H), 1.70–1.77(m, 2H), 1.88–1.98(m, 2H), 2.82–2.88(m, 2H), 3.31(s, 2H), 3.37(d, J=6.7Hz, 2H), 3.75(s, 3H), 4.08(s, 2H), 6.51–6.56(br.s, 1H), 6.54(d, J=1.7Hz, 1H), 6.75(dd, J=1.7, 7.8Hz, 1H), 6.82(d, J=7.8Hz, 1H), 7.57(d, J=3.2Hz, 1H), 7.68(d, J=3.2Hz, 1H) |

| Ex. | Structural formula | NMR |
|---|---|---|
| 571 | ethyl 4-[1-(10H-pyrazino[2,3-b][1,4]benzothiazin-8-ylmethyl)piperidin-4-yl]phenoxyacetate | $^1$H-NMR(CDCl$_3$) δ ppm: 1.30(t, J=7Hz, 3H), 1.7–1.85(m, 4H), 2.0–2.1(m, 2H), 2.4–2.5(m, 1H), 2.9–3.0(m, 2H), 3.38(s, 2H), 4.27(q, J=7Hz, 2H), 4.60(s, 2H), 6.59(s, 1H), 6.56–6.66(m, 1H), 6.79(dd, J=1, 8Hz, 1H), 6.84(d, J=8Hz, 1H), 6.85(d, J=9Hz, 2H), 7.14(d, J=9Hz, 2H), 7.58(d, J=3Hz, 1H), 7.69(d, J=3Hz, 1H) |
| 572 | ethyl 4-[1-(10H-pyrazino[2,3-b][1,4]benzothiazin-8-ylmethyl)piperidin-4-yl]benzoate | $^1$H-NMR(CDCl$_3$) δ ppm: 1.38(t, J=7Hz, 3H), 1.7–1.88(m, 4H), 2.07(dt, J=4, 12Hz, 2H), 2.5–2.64(m, 1H), 2.99(br.d, J=12Hz, 2H), 3.39(s, 2H), 4.36(q, J=7Hz, 2H), 6.56(s, 1H), 6.58(d, J=1Hz, 1H), 6.79(dd, 1, 8Hz, 1H), 6.85(d, J=8Hz, 1H), 7.29(d, J=8Hz, 2H), 7.58(d, J=3Hz, 1H), 7.70(d, J=3Hz, 1H), 7.98(d, J=8Hz, 2H) |
| 573 | ethyl 3-[1-(10H-pyrazino[2,3-b][1,4]benzothiazin-8-ylmethyl)azetidin-3-yl]-2-methylpropanoate | $^1$H-NMR(CDCl$_3$) δ ppm: 1.12(d, J=7Hz, 3H), 1.24(t, J=7Hz, 3H), 1.65(m, 1H), 1.89(dt, J=7, 13Hz, 1H), 2.35(sex, J=7Hz, 1H), 2.52(m, 1H), 2.75(dt, J=3, 7Hz, 2H), 3.42(s, 2H), 3.46(m, 2H), 4.10(q, J=7Hz, 2H), 6.43(br.s, 1H), 6.46(d, J=2Hz, 1H), 6.71(dd, J=2, 8Hz, 1H), 6.81(d, J=8Hz, 1H), 7.56(d, J=3Hz, 1H), 7.68(d, J=3Hz, 1H) |
| 574 | ethyl [1-(10H-pyrazino[2,3-b][1,4]benzothiazin-8-ylmethyl)piperidin-4-yl]carbamoylformate | $^1$H-NMR(DMSO-d$_6$) δ ppm: 1.25(t, J=7.2Hz, 3H), 1.47–1.59(m, 2H), 1.60–1.68(m, 2H), 1.88–1.97(m, 2H), 2.69–2.78(m, 2H), 3.24(s, 2H), 3.48–3.60(m, 1H), 4.19(q, J=7.2Hz, 2H), 6.69(d, J=7.8Hz, 1H), 6.73(s, 1H), 6.84(d, J=7.8Hz, 1H), 7.63(s, 2H), 8.80(d, J=8.4Hz, 1H), 9.45(s, 1H) |

Example 575

Methyl 4-[1-(10H-pyrazino[2,3-b][1,4]benzothiazin-8-ylmethyl)-piperidin-4-yl]phenylacetate To a solution of 1.0 g of methyl 4-[1-(benzyloxycarbonyl)piperidin-4-yl]phenylacetate in ethanol (100 ml) was added 1.0 g of 10% palladium-carbon (moisture content: 50%) and a hydrogenation reaction was effected under atmospheric pressure for 12 hours. Then the palladium-carbon was filtered off and the solvent was concentrated under reduced pressure to thereby give 0.5 g of crude methyl 4-(piperidin-4-yl)phenylacetate. To a solution of 0.5 g of this crude product and 0.5 g of 8-(chloroethyl)-10H-pyrazino[2,3-b][1,4]benzothiazine in N,N-dimethylformamide (30 ml) was added 0.87 g of anhydrous potassium carbonate and the resulting mixture was stirred under heating to 60° C. for 40 minutes. After adding water, the reaction mixture was extracted with ethyl acetate, washed with a saturated aqueous solution of sodium chloride and dried over anhydrous magnesium sulfate. After distilling off the solvent under reduced pressure, the residue was purified by silica gel column chromatography (eluted with n-hexane/ethyl acetate) to thereby give 0.6 g of the title compound as a yellow oily substance.

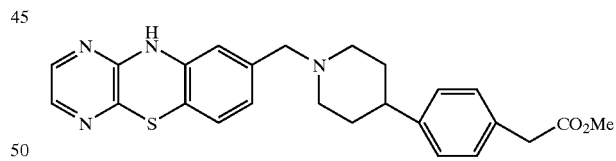

$^1$H-NMR(CDCl$_3$) δ ppm: 1.7–1.85(m, 4H), 2.0–2.1(m, 2H), 2.4–2.54(m, 1H), 2.94–3.0(m, 2H), 3.37(s, 2H), 3.59(s, 2H), 3.69(s, 3H), 6.38–6.43(m, 1H), 6.55–6.58(m, 1H), 6.76–6.80(m, 1H), 6.84(d, J=8 Hz, 1H), 7.18(d, J=8 Hz, 2H), 7.21(d, J=8 Hz, 2H), 7.57(d, J=3 Hz, 1H), 7.69(d, J=3 Hz, 1H)

Examples 576 to 582

The following compounds were obtained by the same method as the one of Example 575.

| Ex. | Structural formula | NMR |
|---|---|---|
| 576 | 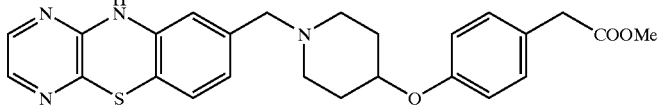<br>methyl 4-[1-(10H-pyrazino[2,3-b][1,4]benzothiazin-8-ylmethyl)piperidin-4-yloxy]phenylacetate | $^1$H-NMR(CDCl$_3$) δ ppm: 1.76–1.88(m, 2H), 1.92–2.04(m, 2H), 2.20–2.36(m, 2H), 2.65–2.76(m, 2H), 3.37(s, 2H), 3.56(s, 2H), 3.69(s, 3H), 4.31(m, 1H), 6.52(br.s, 1H), 6.56(br.s, 1H), 6.77(dd, J=1.6, 7.9Hz, 1H), 6.82–6.88(m, 3H), 7.15–7.20(m, 2H), 7.58(d, J=2.7Hz, 1H), 7.69(d, J=2.7Hz, 1H) |
| 577 | 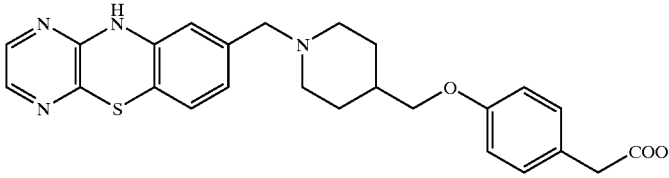<br>methyl 4-[[1-(10H-pyrazino[2,3-b][1,4]benzothiazin-8-ylmethyl)piperidin-4-yl]methyloxy]phenylacetate | $^1$H-NMR(CDCl$_3$) δ ppm: 1.32–1.46(m, 2H), 1.74–1.86(m, 2H), 1.93–2.04(m, 3H), 2.86–2.94(m, 2H), 3.35(s, 2H), 3.56(s, 2H), 3.68(s, 3H), 3.78(d, J=5.9Hz, 2H), 6.56(br.s, 1H), 6.64(br.s, 1H), 6.77(dd, J=1.5, 8.0Hz, 1H), 6.81–6.86(m, 3H), 7.15–7.20(m, 2H), 7.58(d, J=2.7Hz, 1H), 7.69(d, J=2.7Hz, 1H) |
| 578 | 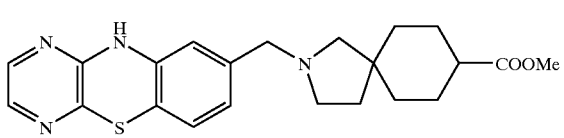<br>methyl [2-(10H-pyrazino[2,3-b][1,4]benzothiazin-8-ylmethyl)-2-azaspiro[4.5]dec-8-yl]carboxylate | $^1$H-NMR(CDCl$_3$) δ ppm: 1.24–1.88(m, 10H), 2.20–2.30(m, 1H), 2.34, 2.43(m, total2H), 2.58–2.69(m, 2H), 3.46, 3.49(m, total2H), 3.65, 3.67(s, total3H), 6.50(m, 1H), 6.62(m, 1H), 6.67, 6.78(dd, J=1.6, 7.9Hz, total1H), 6.83, 6.40(d, J=7.9Hz, total1H), 7.57(d, J=2.9Hz, 1H), 7.69(d, J=2.9Hz, 1H) |
| 579 | 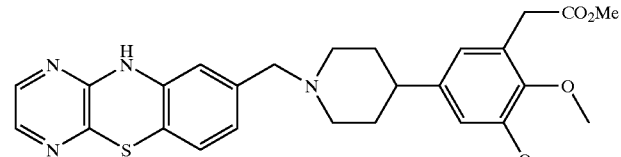<br>methyl 2,3-dimethoxy-5-[1-(10H-pyrazino[2,3-b][1,4]benzothiazin-8-ylmethyl)piperidin-4-yl]phenylacetate | $^1$H-NMR(CDCl$_3$) δ ppm: 1.5–1.9(m, 4H), 2.0–2.1(m, 2H), 2.38–2.48(m, 1H), 2.9–3.0(m, 2H), 3.38(s, 2H), 3.63(s, 2H), 3.70(s, 3H), 3.80(s, 3H), 3.84(s, 3H), 6.42–6.46(m, 1H), 6.58(d, J=1Hz, 1H), 6.68(d, J=2Hz, 1H), 6.72(d, J=2Hz, 1H), 6.79(dd, J=2, 8Hz, 1H), 6.85(d, J=8Hz, 1H), 7.58(d, J=3Hz, 1H), 7.70(d, J=3Hz, 1H) |
| 580 | 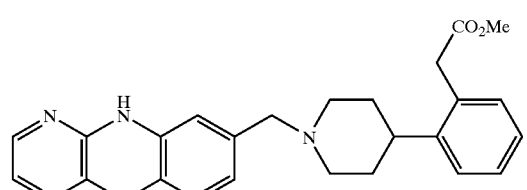<br>ethyl 2-[1-(10H-pyrazino[2,3-b][1,4]benzothiazin-8-ylmethyl)piperidin-4-yl]phenylacetate | $^1$H-NMR(DMSO-d$_6$) δ ppm: 1.5–1.7(m, 4H), 1.9–2.0(m, 2H), 2.5–2.66(m, 1H), 2.86(br.d, J=12Hz, 2H), 3.30(s, 2H), 3.57(s, 3H), 3.72(s, 2H), 6.72(d, J=8Hz, 1H), 6.79(s, 1H), 6.84(d, J=8Hz, 1H), 7.06–7.18(m, 2H), 7.18–7.28(m, 2H), 7.56–7.66(m, 2H), 9.44(s, 1H) |

-continued

| Ex. | Structural formula | NMR |
|---|---|---|
| 581 | methyl 3-[1-(10H-pyrazino[2,3-b][1,4]benzothiazin-8-ylmethyl)piperidin-4-yl]phenylacetate | ¹H-NMR(CDCl₃) δ ppm: 1.7–1.86(m, 4H), 2.0–2.1(m, 2H), 2.44–2.56(m, 1H), 2.94–3.0(m, 2H), 3.38(s, 2H), 3.61(s, 2H), 3.69(s, 3H), 6.40–6.48(m, 1H), 6.58(d, J=1Hz, 1H), 6.80(dd, J=1, 8Hz, 1H), 6.85(d, J=8Hz, 1H), 7.1–7.18(m, 3H), 7.22–7.3(m, 1H), 7.58(d, J=3Hz, 1H), 7.69(d, J=3Hz, 1H) |
| 582 | ethyl 4-[1-(10H-pyrimido[5,4-b][1,4]benzothiazin-8-ylmethyl)piperidin-4-yl]-2-methylbutanoate | ¹H-NMR(DMSO-d₆) δ ppm: 1.00–1.09(m, 5H), 1.03(d, J=7.1Hz, 3H), 1.14(t, J=7.3Hz, 3H), 1.29–1.40(m, 1H), 1.55–1.60(m, 3H), 1.77–1.87(m, 2H), 2.28–2.37(m, 1H), 2.66–2.75(m, 2H), 3.23(s, 2H), 4.03(q, J=7.3Hz, 2H), 6.74(dd, J=1.6, 7.9Hz, 1H), 6.79(d, J=1.6Hz, 1H), 6.85(d, J=7.9Hz, 1H), 7.93(s, 1H), 8.22(s, 1H), 9.76(s, 1H) |

Example 583

Ethyl(E)-3-[1-(10H-pyrazino[2,3-b][1,4]benzothiazin-8-ylmethyl)piperidin-4-yl]propanoate To a solution of 1.6 g of ethyl 3-(1-benzylpiperidin-4-yl)propenoate in 1,2-dichloroethane (30 ml) was added at 0° C. 0.74 ml of 1-chloroethyl chloroformate and the resulting mixture was stirred at the same temperature for 15 minutes and then heated under reflux for 1 hour. After distilling off the solvent under reduced pressure, 50 ml of methanol was added to the residue and the resulting mixture was heated under reflux for 1 hour. Then the mixture was made weakly alkaline with a dilute aqueous solution of sodium hydroxide and the solvent was distilled off under reduced pressure. To a solution of 1.0 g of ethyl 3-(piperidin-4-yl)propenoate thus obtained and 0.64 g of 8-(chloroethyl)-10H-pyrazino[2,3-b][1,4]benzothiazine in N,N-dimethylformamide (30 ml) was added 1.1 g of anhydrous potassium carbonate and the resulting mixture was stirred by heating to 60° C. for 1 hour. After adding water, the reaction mixture was extracted with ethyl acetate, washed with a saturated aqueous solution of sodium chloride and dried over anhydrous magnesium sulfate. After distilling off the solvent under reduced pressure, the residue was purified by silica gel column chromatography (eluted with methanol/dichloromethane) to thereby give 0.6 g of the title compound as yellow crystals.

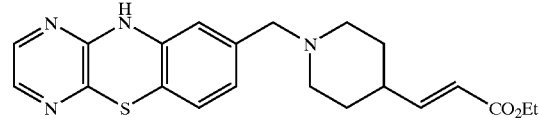

¹H-NMR(CDCl₃) δ ppm: 1.29(t, J=3 Hz, 3H), 1.4–1.55(m, 2H), 1.65–1.78(m, 2H), 1.93–2.05(m, 2H), 2.07–2.2(m, 1H), 2.8–2.90(m, 2H), 3.33(s, 2H), 4.18(q, J=7 Hz, 2H), 5.79(dd, J=1, 16 Hz, 1H), 6.48(s, 1H), 6.52(d, J=, 2 Hz, 1H), 6.75(dd, J=2, 8 Hz, 1H), 6.83(d, J=8 Hz, 1H), 6.91(dd, J=6, 16 Hz, 1H), 7.57(d, J=3 Hz, 1H), 7.69(d, J=3 Hz, 1H)

Examples 584 to 601

The following compounds were obtained by the same method as the one of Example 583.

| Ex. | Structural formula | NMR |
|---|---|---|
| 584 | ethyl [1-(10H-pyrazino[2,3-b][1,4]benzothiazin-8-ylmethyl)-pyrrolidin-3-ylidene]acetate | ¹H-NMR(CDCl₃)δppm: 1.27(t, J=7Hz, 3H), 2.71(t, J=7Hz, 2H), 2.92–3.0(m, 2H), 3.24(d, J=1Hz, 2H), 3.49(s, 2H), 4.15(q, J=7Hz, 2H), 5.75(t, J=2Hz, 1H), 6.47(s, 1H), 6.53(d, J=1Hz, 1H), 6.77(dd, J=1, 8Hz, 1H), 6.84(d, J=8Hz, 1H), 7.57(d, J=3Hz, 1H), 7.69(d, J=3Hz, 1H) |

| Ex. | Structural formula | NMR |
|---|---|---|
| 585 | ethyl 3-[1-(10H-pyrazino[2,3-b][1,4]benzothiazin-8-ylmethyl)piperidin-4-yl]-2-methylpropenoate (cis:trans = 2.7:1) | $^1$H-NMR(CDCl$_3$)δppm: 1.29(t, J=7Hz, 3H, E), 1.30(t, J=7Hz, 3H, Z), 1.34–1.48(m, 2H, Z), 1.44–1.56(m, 2H, E), 1.56–1.63(m, 2H, E), 1.63–1.72(m, 2H, Z), 1.84(d, J=2Hz, 3H, E), 1.87(d, J=1Hz, 3H, Z), 1.94–2.06(m, 2H, Z+E), 2.24–2.36(m, 1H, E), 2.84–2.96(m, 2H, E+Z), 2.84–2.96(m, 1H, Z), 3.48(s, 3H, Z), 3.50(s, 3H, E), 4.18(q, J=7Hz, 2H, E), 4.18(q, J=7Hz, 2H, Z), 5.73(d, J=9Hz, 1H, Z), 6.59(d, J=9Hz, 1H, E), 7.2–7.38(m, 5H, E+Z) |
| 586 | ethyl 3-[1-(10H-pyrazino[2,3-b][1,4]benzothiazin-8-ylmethyl)piperidin-4-yl]-2-methylpropanoate | $^1$H-NMR(CDCl$_3$)δppm: 1.13(d, J=7Hz, 3H), 1.24(t, J=7Hz, 3H), 1.1–1.3(m, 3H), 1.55–1.80(m, 4H), 1.89(br.t, J=13Hz, 2H), 2.45–2.55(m, 1H), 2.77–2.8(m, 2H), 3.30(s, 2H), 4.05–4.18(m, 2H), 6.53(d, J=1Hz, 1H), 6.64–6.72(m, 1H), 6.74(dd, J=1, 8Hz, 1H), 6.81(d, J=8Hz, 1H), 7.57(d, J=3Hz, 1H), 7.68(d, J=3Hz, 1H) |
| 587 | methyl 4-[1-(10H-pyrazino[2,3-b][1,4]benzothiazin-8-ylmethyl)piperidin-4-yl]-3,3-dimethyl butanoate | $^1$H-NMR(CDCl$_3$)δppm: 1.0(s, 6H), 1.24–1.38(m, 5H), 1.6–1.7(m, 2H), 1.94(br.t, J=12Hz, 2H), 2.21(s, 2H), 2.78(br.d, J=12Hz, 2H), 3.30(s, 2H), 3.64(s, 3H), 6.45(s, 1H), 6.53(d, J=1Hz, 1H), 6.75(dd, J=1, 8Hz, 1H), 6.83(d, J=8Hz, 1H), 7.57(d, J=3Hz, 1H), 7.69(d, J=3Hz, 1H) |
| 588 | ethyl (E)-[1-(10H-pyrazino[2,3-b][1,4]benzothiazin-8-ylmethyl)piperidin-3-ylidene]acetate | $^1$H-NMR(CDCl$_3$)δppm: 1.00(t, J=7Hz, 3H), 1.4–1.5(m, 2H), 2.28(t, J=6Hz, 2H), 2.59(t, J=6Hz, 2H), 2.66(s, 2H), 3.11(s, 2H), 3.88(q, J=7Hz, 2H), 5.38(s, 1H), 6.28(d, J=2Hz, 1H), 6.48(dd, J=2, 8Hz, 1H), 6.55(s, 1H), 6.56(d, J=8Hz, 1H), 7.32(d, J=3Hz, 1H), 7.41(d, J=3Hz, 1H) |

| Ex. | Structural formula | NMR |
|---|---|---|
| 589 | 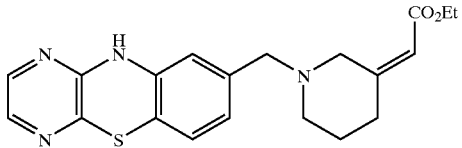<br>ethyl (Z)-[1-(10H-pyrazino[2,3-b][1,4]benzothiazin-8-ylmethyl)piperidin-3-ylidene]acetate | $^1$H-NMR(CDCl$_3$)δppm: 1.23(t, J=7Hz, 3H), 1.67–1.8(m, 2H), 2.2–2.28(m, 2H), 2.49(t, J=5Hz, 2H), 3.43(s, 2H), 3.66(s, 2H), 4.11(q, J=7Hz, 2H), 5.68(s, 1H), 6.56(d, J=2Hz, 1H), 6.74(dd, J=2, 8Hz, 1H), 6.81(d, J=8Hz, 1H), 6.82–6.94(m, 1H), 7.57(d, J=3Hz, 1H), 7.66(d, J=3Hz, 1H) |
| 590 | 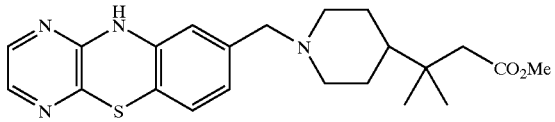<br>methyl 3-[1-(10H-pyrazino[2,3-b][1,4]benzothiazin-8-ylmethyl)piperidin-4-yl]-3-methylbutanoate | $^1$H-NMR(CDCl$_3$)δppm: 0.96(s, 6H), 1.15–1.4(m, 3H), 1.6–1.72(m, 2H), 1.87(br.t, J=12Hz, 2H), 2.23(s, 2H), 2.92(br.d, J=12Hz, 2H), 3.31(s, 2H), 3.65(s, 3H), 6.53(d, J=1Hz, 1H), 6.55(m, 1H), 6.75(dd, J=2, 8Hz, 1H), 6.82(d, J=8Hz, 1H), 7.57(d, J=3Hz, 1H), 7.69(d, J=3Hz, 1H) |
| 591 | 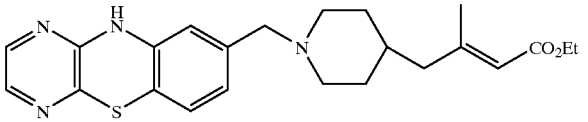<br>ethyl (E)-4-[1-(10H-pyrazino[2,3-b][1,4]benzothiazin-8-ylmethyl)piperidin-4-yl]-3-methylbutenoate | $^1$H-NMR(CDCl$_3$)δppm: 1.28(t, J=7Hz, 3H), 1.17–1.35(m, 2H), 1.47–1.70(m, 3H), 1.85–1.95(m, 2H), 2.06(d, J=7Hz, 2H), 2.14(d, J=1Hz, 3H), 2.84(br.d, J=12Hz, 2H), 3.32(s, 2H), 4.14(q, J=7Hz, 2H), 5.63(d, J=1Hz, 1H), 6.43(s, 1H), 6.53(d, J=1Hz, 1H), 6.75(dd, J=1, 8Hz, 1H), 6.83(d, J=8Hz, 1H), 7.57(d, J=3Hz, 1H), 7.69(d, J=3Hz, 1H) |
| 592 | 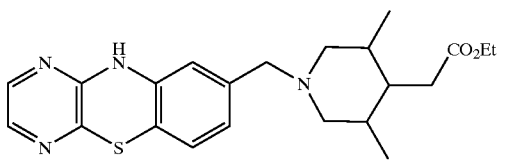<br>ethyl [1-(10H-pyrazino[2,3-b][1,4]benzothiazin-8-ylmethyl)-3,5-dimethylpiperidin-4-yl]acetate | $^1$H-NMR(CDCl$_3$)δppm: 0.85(d, J=7Hz, 6H), 1.25(t, J=7Hz, 3H), 1.7–1.9(m, 1H), 2.0–2.15(m, 2H), 2.16(d, J=6Hz, 2H), 2.25–2.35(m, 2H), 2.50–2.60(m, 2H), 3.3–3.45(m, 2H), 4.12(q, J =7Hz, 2H), 6.4–6.5(m, 1H), 6.5–6.7(m, 1H), 6.73–6.78(m, 1H), 6.83(d, J=8Hz, 1H), 7.57(d, J=3Hz, 1H), 7.69(d, J=3Hz, 1H) |
| 593 | 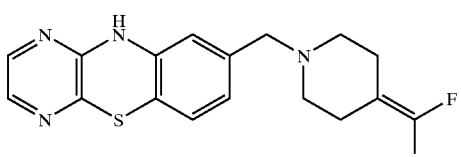<br>ethyl [1-(10H-pyrazino[2,3-b][1,4]benzothiazin-8-ylmethyl)piperidin-4-ylidene]flouroacetate | $^1$H-NMR(DMSO-d$_6$)δppm: 1.21(t, J=7.1Hz, 3H), 2.35–2.45(m, 4H), 2.41(br.t, J=5.1Hz, 2H), 2.78(br.t, J=5.1Hz, 2H), 3.29(s, 2H), 4.19(q, J=7.1Hz, 2H), 6.71(d, J=7.5Hz, 1H), 6.76(s, 1H), 6.84(d, J=7.5Hz, 1H), 7.63(s, 2H), 9.44(s, 1H) |

-continued

| Ex. | Structural formula | NMR |
|---|---|---|
| 594 | 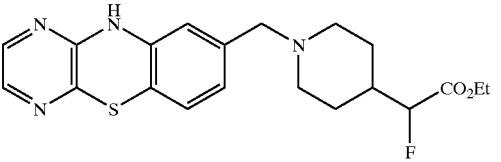<br>ethyl [1-(10H-pyrazino[2,3-b][1,4]benzothiazin-8-ylmethyl)piperidin-4-ylidene]flouroacetate | $^1$H-NMR(DMSO-d$_6$)δppm: 1.20(t, J=7.3Hz, 3H), 1.30–1.48(m, 3H), 1.56–1.64(m, 1H), 1.70–1.92(m, 3H), 2.74–2.84(m, 2H), 3.24(s, 2H), 4.16(q, J=7.3Hz, 2H), 4.95(dd, J=4.7, 48.8Hz, 1H), 6.67(d, J=7.6Hz, 1H), 6.75(s, 1H), 6.82(d, J=7.6Hz, 1H), 7.62(s, 2H), 9.44(s, 1H) |

Examples

The following compounds were obtained by the same method as the one of Example 66 by using trifluoroacetic acid as a substitute for hydrochloric acid.

| Ex. | Structural formula | NMR |
|---|---|---|
| 595 | 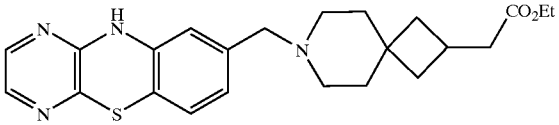<br>ethyl [7-(10H-pyrazino[2,3-b][1,4]benzothiazin-8-ylmethyl)-7-azaspiro[3.5]non-2-yl]acetate | $^1$H-NMR(CDCl$_3$)δppm: 1.25(t, J=7Hz, 3H), 1.44(dd, J=8, 12Hz, 2H), 1.52(t, J=3Hz, 2H), 1.64(t, J=3Hz, 2H), 2.00(dd, J=8, 12Hz, 2H), 2.22(br.s, 2H), 2.32(br.s, 2H), 2.39(d, J=8Hz, 2H), 2.59(sept, J=8Hz, 1H), 3.28(s, 2H), 4.10(q, J=7Hz, 2H), 6.51(br.s, 1H), 6.56(d, J=2Hz, 1H), 6.74(dd, J=2, 8Hz, 1H), 6.81(d, J=8Hz, 1H), 7.57(d, J=3Hz, 1H), 7.68(d, J=3Hz, 1H) |
| 596 | 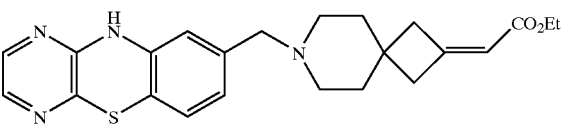<br>ethyl [7-(10H-pyrazino[2,3-b][1,4]benzothiazin-8-ylmethyl)-7-azasprio[3.5]non-2-ylidene]acetate | $^1$H-NMR(CDCl$_3$)δppm: 1.27(t, J=7Hz, 3H), 1.65(t, J=5Hz, 4H), 2.32(br.s, 4H), 2.54(br.s, 2H), 2.84(d, J=2Hz, 2H), 3.31(s, 2H), 4.14(q, J=7Hz, 2H), 5.67(quint, J=2Hz, 1H), 6.42(br.s, 1H), 6.54(d, J=2Hz, 1H), 6.75(dd, J=2, 8Hz, 1H), 6.82(d, J=8Hz, 1H), 7.57(d, J=3Hz, 1H), 7.68(d, J=3Hz, 1H) |
| 597 | 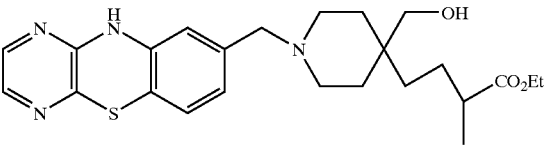<br>ethyl 4-[1-(10H-pyrazino[2,3-b][1,4]benzothiazin-8-ylmethyl)-4-hydroxy methylpiperin-4-yl]-2-methylbutanoate | $^1$H-NMR(CDCl$_3$)δppm: 1.11(d, J=7Hz, 3H), 1.20(t, J=7Hz, 3H), 1.17–1.64(m, 8H), 2.25–2.42(m, 5H), 3.28(s, 2H), 3.38(d, J=11Hz, 1H), 3.44(d, J=11Hz, 1H), 4.07(q, J=7Hz, 2H), 6.45(s, 1H), 6.50(br.s, 1H), 6.68(dd, J=2, 8Hz, 1H), 6.76(d, J=8Hz, 1H), 7.50(d, J=3Hz, 1H), 7.62(d, J=3Hz, 1H) |

-continued

| Ex. | Structural formula | NMR |
|---|---|---|
| 598 | ethyl [2-methyl-7-(10H-pyrazino[2,3-b][1,4]benzothiazin-8-ylmethyl)-7-azaspiro[3.5]non-2-yl]acetate | $^1$H-NMR(CDCl$_3$)δppm: 1.20(s, 3H), 1.25(t, J=7Hz, 3H), 1.62(m, 4H), 1.67(d, J=13Hz, 2H), 1.85(d, J=13Hz, 2H), 2.31(br.s, 4H), 2.37(s, 2H), 3.30(s, 2H), 4.13(q, J=7Hz, 2H), 6.42(br.s, 1H), 6.55(br.s, 1H), 6.74(dd, J=1, 8Hz, 1H), 6.82(d, J=8Hz, 1H), 7.57(d, J=3Hz, 1H), 7.68(d, J=3Hz, 1H) |
| 599 | methyl [7-(10H-pyrazino[2,3-b][1,4]benzothiazin-8-ylmethyl)-1-oxa-7-azaspiro[3.5]non-2-yl]carboxylate | $^1$H-NMR(CDCl$_3$)δppm: 1.86(m, 2H), 2.01(m, 2H), 2.35(m, 2H), 2.44(dd, J=7, 11Hz, 1H), 2.52(m, 2H), 2.64(dd, J=9, 11Hz, 1H), 3.32(s, 2H), 3.79(s, 3H), 4.98(dd, J=7, 9Hz, 1H), 6.53(br.s, 1H), 6.58(br.s, 1H), 6.74(dd, J=2, 8Hz, 1H), 6.82(d, J=8Hz, 1H), 7.57(d, J=3Hz, 1H), 7.68(d, J=3Hz, 1H) |
| 600 | ethyl 5-[1-(10H-pyrazino[2,3-b][1,4]benzothiazin-8-yl-methyl)-7-azaspiro[3.5]non-2-ylidene]propanoate | $^1$H-NMR(CDCl$_3$)δppm: 1.27(t, J=7Hz, 3H), 1.61(m, 4H), 1.70(t, J=1Hz, 3H), 2.32(br.s, 4H), 2.47(s, 2H), 2.76(s, 2H), 3.31(s, 2H), 4.16(q, J=7Hz, 2H), 6.41(br.s, 1H), 6.54(d, J=2Hz, 1H), 6.76(dd, J=2, 8Hz, 1H), 6.83(d, J=8Hz, 1H), 7.57(d, J=3Hz, 1H), 7.69(d, J=3Hz, 1H) |
| 601 | ethyl 5-[1-(10H-pyrazino[2,3-b][1,4]benzothiazin-8-yl-methyl)-piperidin-4-yl]-2-methylpentanoate | $^1$H-NMR(CDCl$_3$)δppm: 1.13(d, J=7Hz, 3H), 1.25(t, J=7Hz, 3H), 1.1–1.45(m, 7H), 1.57–1.70(m, 2H), 1.7–1.83(m, 1H), 1.83–1.95(m, 2H), 2.35–2.46(m, 1H), 2.83(br.d, J=12Hz, 2H), 3.31(s, 2H), 4.12(q, J=7Hz, 2H), 6.54(s, 1H), 6.6–6.74(m, 1H), 6.75(dd, J=1, 8Hz, 1H), 6.82(d, J=3Hz, 1H), 7.58(d, J=3Hz, 1H), 7.68(d, J=3Hz, 1H), 8.02(s, 1H) |

Examples 602 to 610

The following compounds were obtained by the same method as the one of Example 66.

| Ex. | Structural formula | NMR |
|---|---|---|
| 602 | 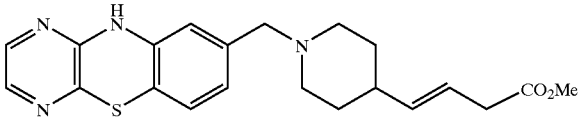<br>methyl 4-[1-(10H-pyrazino[2,3-b][1,4]benzothiazin-8-ylmethyl)piperin-4-yl]-3-butenoate | $^1$H-NMR(CDCl$_3$)δppm: 1.20–1.48(m, 2H), 1.60–2.18(m, 6H), 2.78–2.88(m, 2H), 3.00–3.06(m, 1H), 3.28–3.34(m, 2H), 3.67(s, 2H), 3.72(s, 1H), 5.49–5.54(m, 1H), 6.50–6.56(m, 1H), 6.63–6.98(m, 4H), 7.57(d, J=3Hz, 1H), 7.66–7.70(m, 1H) |
| 603 | 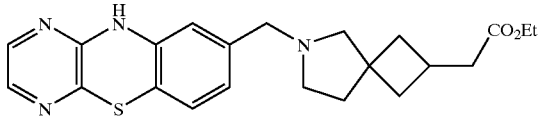<br>ethyl [6-(10H-pyrazino[2,3-b][1,4]benzothiazin-8-ylmethyl)-6-azaspiro[3.4]oct-2-yl]acetate | $^1$H-NMR(CDCl$_3$)δppm: 1.21–1.28(m, 3H), 1.68–1.88(m, 6H), 2.11–2.24(m, 2H), 2.33–2.68(m, 5H), 3.46(s, 2H), 4.06–4.13(m, 2H), 6.57–6.61(m, 2H), 6.72–6.79(m, 1H), 6.79–6.84(m, 1H), 7.55–7.59(m, 1H), 7.67–7.69(m, 1H) |
| 604 | 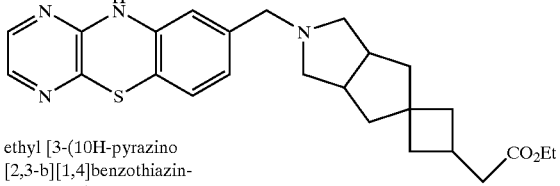<br>ethyl [3-(10H-pyrazino[2,3-b][1,4]benzothiazin-8-ylmethyl)-3-azabicyclo[3.3.0]octane-7-spirocyclobut-3'-yl]acetate | $^1$H-NMR(CDCl$_3$)δppm: 1.24(t, J=7.2Hz, 3H), 1.37–1.53(m, 3H), 1.69–1.78(m, 2H), 1.93–2.10(m, 2H), 2.12–2.20(m, 1H), 2.29–2.61(m, 9H), 3.39(s, 2H), 4.11(q, J=7.2Hz, 2H), 6.56(d, J=1.2Hz, 1H), 6.65(s, 1H), 6.74(dd, J=1.2, 8.0Hz, 1H), 6.80(d, J=8.0Hz, 1H), 7.55–7.58(m, 1H), 7.66–7.69(m, 1H) |
| 605 | 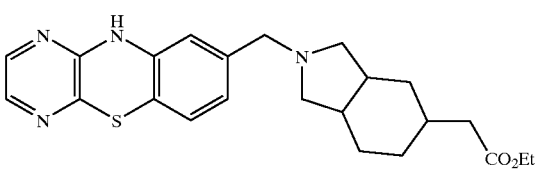<br>ethyl [8-(10H-pyrazino[2,3-b][1,4]benzothiazin-8-ylmethyl)-8-azabicyclo[4.3.0]non-3-yl]acetate | $^1$H-NMR(CDCl$_3$)δppm: 1.06–1.20(m, 2H), 1.22–1.30(m, 3H), 1.50–2.47(m, 10H), 2.56–2.72(m, 2H), 2.83–2.92(m, 1H), 3.51–3.63(m, 2H), 4.09–4.18(m, 2H), 6.58(s, 1H), 6.60(br.s, 1H), 6.77(dd, J=1.2, 8.0Hz, 1H), 6.82(d, J=8.0Hz, 1H), 7.57(d, J=3.2Hz, 1H), 7.67–7.70(m, 1H) |
| 606 | 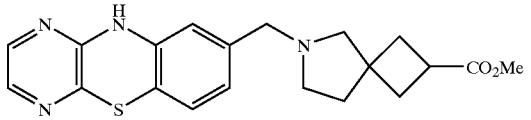<br>methyl [6-(10H-pyrazino[2,3-b][1,4]benzothiazin-8-ylmethyl)-6-azaspiro[3.4]oct-2-yl]carboxylate | $^1$H-NMR(CDCl$_3$)δppm: 1.89(t, J=7.2Hz, 1H), 1.99(t, J=6.8Hz, 1H), 2.16–2.36(m, 4H), 2.54–2.68(m, 4H), 2.88–3.31(m, 1H), 3.48(s, 2H), 3.67(s, 3H), 6.45–6.51(m, 1H), 6.59(br.s, 1H), 6.73–6.80(m, 1H), 6.81–6.86(m, 1H), 7.56–7.59(m, 1H), 7.68–7.71(m, 1H) |

-continued

| Ex. | Structural formula | NMR |
|---|---|---|
| 607 | methyl [3-(10H-pyrazino[2,3-b][1,4]benzothiazin-8-ylmethyl)-3-azabicyclo[4.1.0]hept-6-yl] acetate | $^1$H-NMR(CDCl$_3$)δppm: 0.52–0.58(m, 1H), 0.63(t, J=4.8Hz, 1H), 0.92–1.00(m, 1H), 1.74–1.96(m, 2H), 2.02–2.12(m, 1H), 2.18–2.32(m, 3H), 2.55–2.73(m, 2H), , 3.26(s, 2H), 3.68(s, 3H), 6.52(s, 1H), 6.62(s, 1H), 6.74(dd, J=2.8, 8.0Hz, 1H), 6.81(d, J=8.0Hz, 1H), 7.57(d, J=2.8Hz, 1H), 7.69(d, J=2.8Hz, 1H) |
| 608 | ethyl [7-(10H-pyrazino[2,3-b][1,4]benzothiazin-8-ylmethyl)-2-methyl-7-azaspiro[3.5]non-2-yl] acetate | $^1$H-NMR(CDCl$_3$)δppm: 1.05–1.20(m, 3H), 1.24(t, J=7.2Hz, 3H), 1.26–2.13(m, 10H), 2.30–2.42(m, 2H), 2.45–2.70(m, 2H), 2.80–2.95(m, 1H), 3.70–4.00(m, 1H), 4.10(q, J=7.2Hz, 2H), 6.52–6.64(m, 2H), 6.72–6.77(m, 1H), 6.78–6.84(m, 1H), 7.56–7.60(m, 1H), 7.67–7.70(m, 1H) |
| 609 | methyl [7-(10H-pyrazino[2,3-b][1,4]benzothiazin-8-ylmethyl)-2-methyl-7-azaspiro[3.5]non-2-yl] carboxylate | $^1$H-NMR(CDCl$_3$)δppm: 1.10–1.24(m, 3H), 1.34–2.13(m, 10H), 2.56–2.72(m, 1H), 2.84–3.12(m, 2H), 3.67(s, 3H), 3.84–4.01(m, 1H), 6.50–6.64(m, 2H), 6.73–6.77(m, 1H), 6.79–6.84(m, 1H), 7.56–7.60(m, 1H), 7.67–7.70(m, 1H) |
| 610 | ethyl 3-[1-(10H-pyrazino[2,3-b][1,4]benzothiazin-8-ylmethyl)piperin-4-yl]cyclobutanoate | $^1$H-NMR(CDCl$_3$)δppm: 1.03–1.18(m, 2H), 1.21–1.36(m, 1H), 1.25(t, J=7.0Hz, 3H), 1.52–1.82(m, 5H), 1.82–2.07(m, 3H), 2.15–2.24(m, 1H), 2.35(t, J=7.5Hz, 1H), 2.40–2.60(m, 1H), 2.47(t, J=7.5Hz, 1H), 2.80–2.90(m, 2H), 3.20(s, 2H), 4.12(q, J=7.0Hz, 2H), 6.51(br.s, 1H), 6.56(s, 1H), 6.75(d, J=8.4Hz, 1H), 6.82(d, J=8.4Hz, 1H), 7.57(d, J=2.4Hz, 1H), 7.68(d, J=2.4Hz, 1H) |

Examples 611 and 612

The following compounds were obtained by the same method as the one of Example 8.

| Ex. | Structural formula | NMR |
|---|---|---|
| 611 | ethyl 4-[1-(10H-7-methoxypyrazino[2,3-b][1,4]benzothiazin-8-ylmethyl)piperin-4-yl]-2-methylbutanoate | $^1$H-NMR(CDCl$_3$)δppm: 1.14(d, J=7Hz, 3H), 1.25(t, J=7Hz, 3H), 1.3–1.7(m, 7H), 1.7–1.8(m, 2H), 2.2–2.4(m, 2H), 2.30–2.4(m, 1H), 3.08–3.2(m, 2H), 3.66–3.76(m, 2H), 3.75(s, 3H), 4.12(q, J=7Hz, 2H), 6.42(s, 1H), 6.76–6.86(m, 1H), 6.92–7.00(m, 1H), 7.57(d, J=3Hz, 1H), 7.65(d, J=3Hz, 1H) |
| 612 | ethyl 5-[1-(10H-pyrido[3,2-b][1,4]benzothiazin-8-ylmethyl)piperin-4-yl]-2-methylpentatoate | $^1$H-NMR(CDCl$_3$)δppm: 1.14(d, J=7Hz, 3H), 1.26(t, J=7Hz, 3H), 1.0–1.45(m, 8H), 1.55–1.70(m, 2H), 1.65–1.80(m, 1H), 1.80–1.95(m, 2H), 2.35–2.45(m, 1H), 2.83(br.d, J=12Hz, 2H), 3.30(s, 2H), 4.13(q, J=7Hz, 2H), 6.58(s, 1H), 6.67(s, 1H), 6.71(dd, J=5, 8Hz, 1H), 6.87(d, J=8Hz, 1H), 6.87(d, J=8Hz, 1H), 7.18(dd, J=2, 8Hz, 1H), 7.84(dd, J=2, 5Hz, 1H) |

Example 613

Ethyl 3-[1-[3-(10H-pyrazino[2,3-b][1,4]benzothiazin-8-yl)propyl]piperidin-4-yl]-2-methylbutanoate

To a solution of 2.7 g of 3-[10-(methoxymethyl)-10H-pyrazino[2,3-b][1,4]benzothiazin-8-yl]propyl methanesulfonate in methyl ethyl ketone (50 ml) was added 1.6 g of sodium iodide and the resulting mixture was reacted at 80° C. for 2 hours. After adding ice-water, the reaction mixture was extracted with ethyl acetate, washed with a saturated aqueous solution of sodium chloride and dried over anhydrous magnesium sulfate. After distilling off the solvent under reduced pressure, a 0.5 g portion of the obtained brown oily substance was dissolved in 20 ml of N,N-dimethylformamide. After adding 0.5 g of ethyl 4-(piperidin-4-yl)-2-methylbutanoate and 0.44 g of anhydrous potassium carbonate, the resulting mixture was reacted at 90° C. for 3 hours. After adding water, the reaction mixture was extracted with ethyl acetate, washed with a saturated aqueous solution of sodium chloride and dried over anhydrous magnesium sulfate. After distilling off the solvent under reduced pressure, the residue was purified by silica gel column chromatography (eluted with methanol/dichloromethane) to thereby give 0.1 g of the title compound as a yellow oily substance.

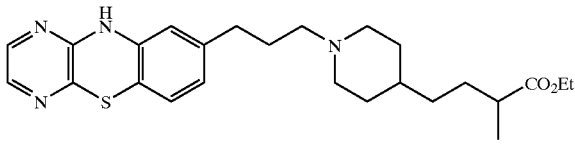

$^1$H-NMR(CDCl$_3$) δ ppm: 1.13(d, J=7 Hz, 3H), 1.25(t, J=7 Hz, 3H), 1.14–1.3(m, 6H), 1.36–1.46(m, 1H), 1.5–1.7(m, 2H), 1.72–1.84(m, 2H), 1.84–1.96(m, 2H), 2.28–2.42(m, 3H), 2.47(t, J=8 Hz, 2H), 2.86–2.96(m, 2H), 4.12(q, J=7 Hz, 2H), 6.35(s, 1H), 6.3–6.4(m, 1H), 6.63–6.68(m, 1H), 6.79(d, J=8 Hz, 1H), 7.56(d, J=3 Hz, 1H), 7.68(d, J=3 Hz, 1H)

Example 614

Ethyl[1-[3-(10H-pyrazino[2,3-b][1,4]benzothiazin-8-yl)-propyl]piperidin-4-yl]carboxylate

To a solution of 0.6 g of 3-[10-(methoxymethyl)-10H-pyrazino[2,3-b][1,4]benzothiazin-8-yl]propionaldehyde and 0.31 g of ethyl isonipecotate in acetonitrile (50 ml) was added 0.2 g of sodium borohydride cyanide. Further, acetic acid was added so as to maintain the pH value at 4. Then the resulting mixture was reacted at room temperature for 12 hours. After adding an aqueous solution of sodium hydroxide, the reaction mixture was extracted with ethyl acetate, washed with a saturated aqueous solution of sodium chloride and dried over anhydrous magnesium sulfate. After distilling off the solvent under reduced pressure, the crude product thus obtained was dissolved in 30 ml of tetrahydrofuran. After adding 1 ml of 6 N hydrochloric acid, the resulting mixture was reacted for 1 hour. After adding an aqueous solution of sodium bicarbonate, the reaction mixture was extracted with ethyl acetate, washed with a saturated aqueous solution of sodium chloride and dried over anhydrous magnesium sulfate. After distilling off the solvent under reduced pressure, the residue was purified by silica gel column chromatography (eluted with methanol/dichloromethane) to thereby give 0.39 g of the title compound as a brown oily substance.

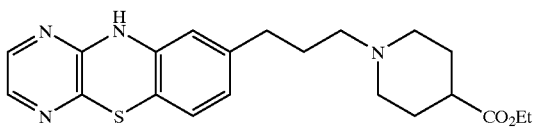

¹H-NMR(CDCl₃) δ ppm: 1.25(t, J=7 Hz, 3H), 1.7–1.85 (m, 4H), 1.88–2.0(m, 2H), 2.0–2.15(m, 2H), 2.25–2.4(m, 1H), 2.36(t, J=8 Hz, 2H), 2.49(t, J=8 Hz, 2H), 2.85–2.95(m, 2H), 4, 13(q, J=7 Hz, 2H), 6.34(d, J=2 Hz, 1H), 6.46–6.54 (m, 1H), 6.56(dd, J=1, 8 Hz, 1H), 6.79(d, J=8 Hz, 1H), 7.56(d, J=3 Hz, 1H), 7.68(d, J=3 Hz, 1H)

Example 615

Ethyl 4-[1-[2-(10H-pyrazino[2,3-b][1,4] benzothiazin-8-yl)ethyl]piperidin-4-yl]-2-methylbutanoate Starting with 2-[10-(methoxymethyl)-10H-pyrazino[2,3-b][1,4]benzothiazin-8-yl]ethyl methanesulfonate and ethyl 4-(piperidin-4-yl)-2-methylbutanoate, ethyl 4-[1-[2-10-(methoxymethyl)-10H-pyrazino[2,3-b][1,4]benzothiazin-8-yl)-ethyl]piperidin-4-yl]-2-methylbutanoate was obtained by the same method as the one of Example 63. Next, this product was treated by the same method as the one of Example 8 to thereby give the title compound.

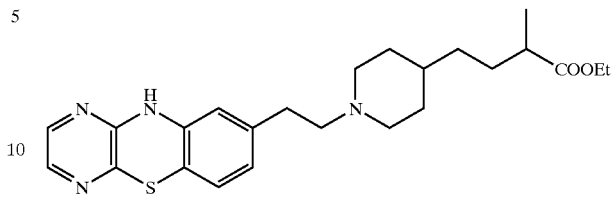

¹H-NMR(CDCl₃) δ ppm: 1.14(t, J=7.0 Hz, 3H), 1.20–1.48(m, 9H), 1.61–1.77(m, 3H), 2.05–2.14(m, 2H), 2.39(m, 1H), 2.57–2.65(m, 2H), 2.69–2.76(m, 2H), 3.03–3.10(m, 2H), 4.13(q, J=7.0 Hz, 2H), 6.40(d, J=1.6 Hz, 1H), 6.66(dd, J=1.6, 8.1 Hz, 1H), 6.79(d, J=8.1 Hz, 1H), 6.80(br.s, 1H), 7.56(d, J=2.9 Hz, 1H), 7.68(d, J=2.9 Hz, 1H)

Examples 616 to 619

The following compounds were obtained by the same method as the one of Example 9.

| Ex. | Structural formula | NMR |
|---|---|---|
| 616 | ethyl [1-(10H-pyrazino[2,3-b][1,4]benzothiazin--8-yl)methyl]piperin-3-yl] carboxylate | ¹H-NMR(CDCl₃)δppm: 1.22(t, J=6Hz, 3H), 1.34–1.62(m, 2H), 1.64–1.76(m, 1H), 1.90–2.00(m, 1H), 1.98–2.06(m, 1H), 2.10–2.24(m, 1H), 2.50–2.60(m, 1H), 2.60–2.80(m, 1H), 2.86–2.96(m, 1H), 3.35(d, J=12Hz, 1H), 3.38(d, J=12Hz, 1H), 4.10(q, J=6Hz, 2H), 4.05–4.15(m, 1H), 6.54(s, H), 6.76(d, J=8Hz, 1H), 6.93(d, J=8Hz, 1H), 7.55(s, 1H), 7.66(s, 1H) |
| 617 | ethyl 4-[1-(10H-pyrazino[2,3-b][1,4]enzothiazin-8-yl)methyl)piperidin-4-yl]-2-butenoate | ¹H-NMR(CDCl₃)δppm: 1.09(t, J=6Hz, 3H), 1.30–1.40(m, 1H), 1.50–1.64(m, 2H), 1.60–1.80(m, 2H), 1.80–1.90(m, 2H), 2.08(t, J=6Hz, 2H), 2.70–2.82(m, 2H), 3.25(s, 2H), 4.08(q, J=6Hz, 2H), 5.73(d, J=16Hz, 1H), 6.46(s, 1H), 6.50(s, 1H), 6.68(d, J=8Hz, 1H), 7.76(d, J=8Hz, 1H), 6.83 (dt, J=6, 16Hz, 1H), 7.49(s, 1H), 7.60(s, 1H) |
| 618 | methyl [1-(10H-pyrazino[2,3-b][1,4]benzothiazin-8-yl)methyl]-3,4-dehydropiperin-3-yl] carboxylate | ¹H-NMR(CDCl₃)δppm: 2.37(m, 2H), 2.59(t, J=6Hz, 2H), 3.24(br.s, 2H), 3.54(s, 2H), 3.73(s, 3H), 6.58(d, J=2Hz, 1H), 6.72(br.s, 1H), 6.78(dd, J=2, 8Hz, 1H), 6.84(d, J=8Hz, 1H), 7.20(m, 1H), 7.56(d, J=3Hz, 1H), 7.68(d, J=3Hz, 1H) |

| Ex. | Structural formula | NMR |
|---|---|---|
| 619 | ethyl 4-[1-(10H-pyrazino[2,3-b][1,4]benzoxazin-8-ylmethyl]piperidin-4-yl]-2-methylbutanoate | ¹H-NMR(CDCl₃)δppm: 1.13(d, J=7Hz, 3H), 1.24(t, J=7Hz, 3H), 1.1–1.3(m, 6H), 1.35–1.45(m, 1H), 1.6–1.7(m, 2H), 1.85–2.00(m, 2H), 2.3–2.43(m, 1H), 2.86(br.d, J=11Hz, 2H), 3.32(s, 2H), 4.12(q, J=7Hz, 2H), 6.57(br.s, 1H), 6.65(dd, J=2, 8Hz, 1H), 6.73(d, J=8Hz, 1H), 6.9–7.06(m, 1H), 7.36(d, J=3Hz, 1H), 7.45(d, J=3Hz, 1H) |

Example 620

Ethyl[1-(10H-pyrazino[2,3-b][1,4]benzothiazin-8-ylmethyl)piperidin-4-yl]propiolate 200 ml of a solution of 19.7 g of triphenylphosphine and 12.4 g of carbon tetrabromide in dichloromethane was stirred under ice-cooling and 20 ml of a solution of 4.0 g of 1-(tert-butoxycarbonyl)piperidine-4-carbaldehyde in dichloromethane was dropped thereinto. After stirring for 1 hour, the reaction mixture was diluted with diethyl ether and filtered through celite to thereby remove the insoluble residue. After distilling off the solvent under reduced pressure, the residue was purified by silica gel column chromatography (eluted with ethyl acetate/n-hexane) to thereby give 5.7 g of 4-(2,2-dibromovinyl)-1-(tert-butoxycarbonyl)piperidine as a colorless oily component. Next, 2.72 g of this product was dissolved in 50 ml of dry tetrahydrofuran in a nitrogen atmosphere and cooled to −78° C. A 1.0 M solution of n-buthyllithium (15 ml; 15 mmol) in hexane was dropped thereinto and the resulting mixture was stirred for 1 hour and then at room temperature for additional 1 hour. After cooling to −78° C. again, ethyl chloroformate was dropped into the reaction mixture. Then the reaction mixture was brought back to room temperature and distributed into water and ethyl acetate. The organic layer was extracted, washed with water and dried over magnesium sulfate. After distilling off the solvent under reduced pressure, the residue was purified by silica gel column chromatography (eluted with ethyl acetate/n-hexane) to thereby give 2.2 g of ethyl(1-(tert-butoxycarbonyl)piperidin-4-yl)propionate as a colorless oily component. A 1.1 g portion of this product was dissolved in a mixture of anisole (5 ml) with dichloromethane (5 ml). To this solution was added trifluoroacetic acid until the material disappeared. The reaction mixture was distributed into an aqueous solution of potassium carbonate and ethyl acetate. The organic layer was extracted and dried over potassium carbonate. After distilling off the solvent under reduced pressure, the residue was dissolved in 20 ml of N,N-dimethylformamide. After adding 350 mg of potassium carbonate and 630 mg of 8-chloromethyl-10H-pyrazino[2,3-b][1,4]benzothiazine, the resulting mixture was heated to 80° C. for 1 hour. Then the reaction mixture was brought back to room temperature and distributed into water and ethyl acetate. The organic layer was extracted, washed with water and dried over sodium sulfate. After distilling off the solvent under reduced pressure, the residue was purified by silica gel column chromatography (eluted with dichloromethane/methanol) to thereby give 550 mg of yellow crystals of ethyl[1-(10H-pyrazino[2,3-b][1,4]benzothiazin-8-ylmethyl)piperidin-4-yl]propiolate.

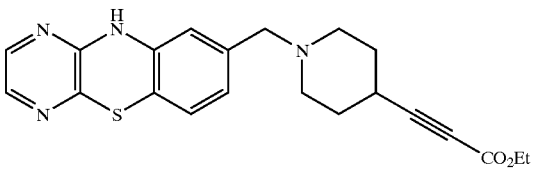

1H-NMR(DMSO-d6): 1.19(t, J=6.9 Hz, 3H), 1.48–1.60 (m, 2H), 1.75–1.84(m, 2H), 2.03–2.13(m, 2H), 2.51–2.68 (m,.3H), 3.24(s, 2H), 4.12(g, J=6.9 Hz, 2H), 6.68(d, J=8.0 Hz, 1H), 6.74(d, J=1.8 Hz, 1H), 6.83(dd, J=1.8, 8.0 Hz, 1H), 7.62(s, 2H), 9.44(s, 1H)

Example 621

Ethyl[3-(10H-pyrazino[2,3-b][1,4]benzothiazin-8-ylmethyl)-3-azabicyclo[3.1.0]hex-6-yl]carboxylate To a solution of 1.523 g of ethyl(3-azabicyclo[3.1.0]hex-6-yl)carboxylate in N,N-dimethylformamide (30 ml) were added 2.30 g of sodium hydrogencarbonate and 1.39 g of 8-chloromethyl-10H-pyrazino[2,3-b][1,4]benzothiazine and the resulting mixture was heated to 80° C. for 2 hours. After adding water and ethyl acetate, the organic layer was washed with water, dried over magnesium sulfate and concentrated under reduced pressure. Then the residue was purified by silica gel column chromatography (eluted with dichloromethane/methanol) to thereby give 0.574 g of the title compound as pale yellow crystals.

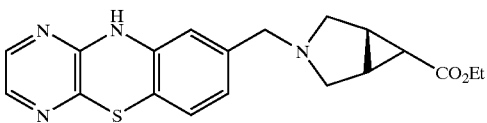

¹H-NMR(CDCl₃) δ ppm: 1.27(t, J=7 Hz, 3H), 1.95(m, 2H), 2.07(t, J=3 Hz, 1H), 2.38(d, J=10 Hz, 2H), 3.03(d, J=10 Hz, 2H), 3.44(s, 2H), 4.14(q, J=7 Hz, 2H), 6.41(br.s, 1H), 6.45(d, J=1 Hz, 1H), 6.71(dd, J=1, 8 Hz, 1H), 6.81(d, J=8 Hz, 1H), 7.57(d, J=3 Hz, 1H), 7.69(d, J=3 Hz., 1H)

Example 622

N-(10-methoxymethyl-10H-Pyrazino[2,3-b][1,4]benzothiazin-8-ylmethyl) chloro-acetamide 1.25 g of 8-aminomethyl-10-methoxymethyl-10H-pyrazino[2,3-b][1,4]benzothiazine and 0.7 ml of triethylamine were dissolved in N,N-dimethylformamide (15 ml). Under ice-cooling, 2 ml of a solution of 0.4 ml of chloroacetyl chloride in dichloromethane was dropped thereinto and the resulting mixture was stirred for 1 hour. After adding water, the reaction mixture was extracted with ethyl acetate. The ethyl acetate layer was washed with water and a saturated aqueous solution of sodium chloride and dried over anhydrous sodium sulfate. After concentrating under reduced pressure, the residue was purified by silica gel column chromatography (eluted with n-hexane/ethyl acetate). The crystals thus obtained were washed with n-hexane and thus 1.28 g of the title compound was obtained as a yellow powder.

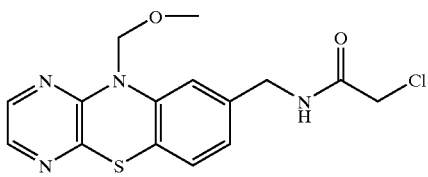

$^1$H-NMR(CDCl$_3$) δ ppm: 3.54(s, 3H), 4.11(s, 2H), 4.43(d, J=5.9 Hz, 2H), 5.27(s, 2H), 6.89(br.s, 1H), 6.91(dd, J=1.6, 7.9 Hz, 1H), 7.00(d, J=7.9 Hz, 1H), 7.08(d, J=1.6 Hz, 1H), 7.84(d, J=2.7 Hz, 1H), 7.85(d, J=2.7 Hz, 1H)

Example 623

Ethyl[1-[[(10H-pyrazino[2,3-b][1,4]benzothiazin-8-ylmethyl)-carbamoyl]methyl]piperidin-4-yl]carboxylate 0.6 g of N-(10H-pyrazino[2,3-b][1,4]benzothiazin-8-ylmethyl)chloroacetamide was dissolved in 9 ml of N,N-dimethylformamide. After adding 0.26 g of anhydrous sodium carbonate and 0.3 g of isonipecotic acid, the resulting mixture was stirred at room temperature for 13 hours. After adding water, the reaction mixture was extracted with ethyl acetate. The ethyl acetate layer was washed with water and a saturated aqueous solution of sodium chloride, dried over anhydrous sodium sulfate and concentrated under reduced pressure to thereby give a yellow oily substance.

This oily substance was dissolved in 10 ml of ethanol. After adding 5 ml of 6 N hydrochloric acid, the resulting mixture was stirred for 30 minutes. After adding an aqueous solution of sodium carbonate, the reaction mixture was extracted with ethyl acetate. The ethyl acetate layer was washed with water and a saturated aqueous solution of sodium chloride, dried over anhydrous sodium sulfate and concentrated under reduced pressure. The obtained residue was purified by silica gel column chromatography (eluted with dichloromethane/methanol). The crystals thus obtained were washed with ether and thus 0.64 g of the title compound was obtained as a yellow powder.

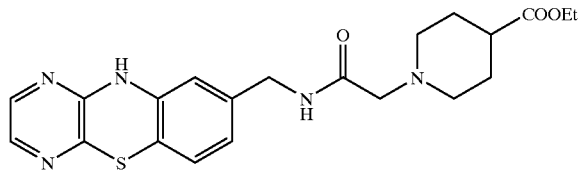

$^1$H-NMR(CDCl$_3$) δ ppm: 1.25(t, J=7.1 Hz, 3H), 1.65–1.78(m, 2H), 1.87–1.95(m, 2H), 2.18–2.33(m, 3H), 2.78–2.85(m, 2H), 3.04(s, 2H), 4.14(q, J=7.1 Hz, 2H), 4.30(d, J=6.2 Hz, 2H), 6.45(d, J=1.6 Hz, 1H), 6.61(br.s, 1H), 6.72(dd, J=1.6, 8.1 Hz, 1H), 6.84(d, J=8.1 Hz, 1H), 7.51(m, 1H), 7.57(d, J=2.7 Hz, 1H), 7.69(d, J=2.7 Hz, 1H)

Example 624

Ethyl[1-[3-[(10H-pyrazino[2,3-b][1,4]benzothiazin-8-yl)acetylamino]propyl]piperidin-4-yl]carboxylate To 10 ml of N,N-dimethylformamide were added 0.6 g of 10H-pyrazino[2,3-b][1,4]benzothiazine-8-acetic acid, 0.8 g of ethyl 1-(3-aminopropyl)piperidine-4-carboxylate dihydrochloride, 0.38 g of 1-hydroxybenzotriazole, 1.07 ml of triethylamine and 0.53 g of 1-(3-dimethylaminopropyl)-3-ethylcarbodiimide and the resulting mixture was stirred at room temperature for 22 hours. After adding water, the reaction mixture was extracted with ethyl acetate. The ethyl acetate layer was washed with water and a saturated aqueous solution of sodium. chloride, dried over anhydrous sodium sulfate and concentrated under reduced pressure. The obtained residue was purified by silica gel column chromatography (eluted with dichloromethane/methanol). The crystals thus obtained were washed with ether and thus 0.72 g of the title compound was obtained as a pale brown powder.

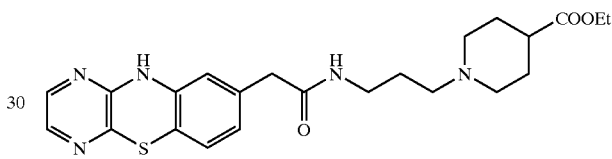

$^1$H-NMR(CDCl$_3$) δ ppm: 1.28(t, J=7.1 Hz, 3H), 1.60–1.77(m, 4H), 1.86–2.05(m, 4H), 2.34(m, 1H), 2.40–2.46(m, 2H), 2.87–2.96(m, 2H), 3.30–3.46(m, 2H), 3.34(s, 2H), 4.19(q, J=7.1 Hz, 2H), 6.58(d, J=1.6 Hz, 1H), 6.76(dd, J=1.6, 7.9 Hz, 1H), 6.82(d, J=7.9 Hz, 1H), 7.13 (br.s, 1H), 7.37(m, 1H), 7.55(d, J=2.9 Hz, 1H), 7.66(d, J=2.9 Hz, 1H)

Example 625

[10-(Methoxymethyl)-10H-pyrazino[2,3-b][1,4]benzothiazin-8-yl] methyl ketone

Into a solution of 16 g of 10-(methoxymethyl)-10H-pyrazino[2,3-b][1,4]benzothiazine-8-carboxaldehyde in 200 ml of tetrahydrofuran was dropped at −78° C. 60 ml of a 1.4 M solution of methyllithium in diethyl ether. Next, the resulting mixture was heated to room temperature over 2 hours. The reaction mixture was poured into ice-water and extracted with ethyl acetate. The organic layer was washed with a saturated aqueous solution of sodium chloride and dried over anhydrous magnesium sulfate. After distilling off the solvent under reduced pressure, 16 g of a yellow oily substance was obtained. To a solution of 16 g of this oily substance in dichloromethane (300 ml) was added 100 g of manganese dioxide and the resulting mixture was stirred at room temperature for 17 hours. After the completion of the reaction, the manganese dioxide was filtered off. The filtrate was concentrated and the residue thus obtained was purified by silica gel column chromatography (eluted with n-hexane/ethyl acetate) to thereby give 9. 4 g of the title compound. as yellow. crystals.

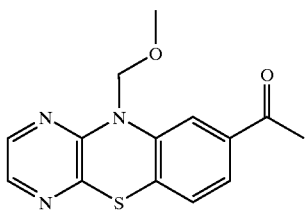

¹H-NMR(CDCl₃) δ ppm: 2.55(s, 3H), 3.55(s, 3H), 5.31(s, 2H), 7.18(d, J=8 Hz, 1H), 7.53(d, J=8 Hz, 1H), 7.69(s, 1H), 7.85(s, 2H)

Example 626

[10-(Methoxymethyl)-10H-pyrazino[2,3-b][1,4]benzothiazin-8-yl]bromomethyl ketone To a solution of 1.5 g of [10-(methoxymethyl)-10H-pyrazino[2,3-b][1,4]benzothiazin-8-yl]methyl ketone in a mixture of methanol (50 ml) with dichloromethane (100 ml) was added 3.0 g of tetra-n-butylammonium tribromide and the resulting mixture was stirred at room temperature for 4 hours. After distilling off the solvent, the residue was purified by silica gel column chromatography (eluted with n-hexane/ethyl acetate) to thereby give 0.9 g of the title compound as a yellow oily substance.

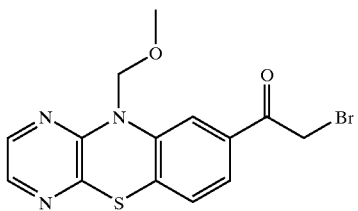

¹H-NMR(CDCl₃) δ ppm: 3.56(s, 3H), 4.38(s, 2H), 5.30(s, 2H), 7.10(d, J=8 Hz, 1H), 7.54(dd, J=2, 8 Hz, 1H), 7.72(d, J=2 Hz, 1H), 7.87(s, 2H)

Example 627

Ethyl 4-[1-[2-oxo-2-(10H-pyrazino[2,3-b][1,4]benzothiazin-8-yl]ethyl]piperidin-4-yl]-2-methylbutanoate To a solution of 2.6 g of [10-(methoxymethyl)-10H-pyrazino[2,3-b][1,4]benzothiazin-8-yl]bromomethyl ketone and 3.0 g of ethyl 4-(piperidin-4-yl)-2-methylbutanoate in N,N-dimethylformamide (50 ml) was added 2.9 g of anhydrous potassium carbonate and the resulting mixture was reacted at room temperature for 1.5 hours. After the completion of the reaction, ethyl acetate was added thereto. The reaction mixture was washed with water and a saturated aqueous solution of sodium chloride and dried over anhydrous magnesium sulfate. After concentrating the solvent, the residue was purified by silica gel column chromatography (eluted with n-hexane/ethyl acetate) to thereby give 2.7 g of ethyl 4-1-[2-oxo-2-[10-(methoxymethyl)-10H-pyrazino[2,3-b][1,4]benzothiazin-8-yl]ethyl]piperidin-4-yl]-2-methylbutanoate as a brown oily substance.

To a solution of 1.7 g of this oily substance in tetrahydrofuran (50 ml) was added 4 ml of 6 N hydrochloric acid and the resulting mixture was reacted for 1 hour. After adding ethyl acetate, the reaction mixture was washed with water and a saturated aqueous solution of sodium chloride and dried over anhydrous magnesium sulfate. After distilling off the solvent under reduced pressure, the residue was purified by silica gel column chromatography (eluted with n-hexane/ethyl acetate) to thereby give 1.0 g of the title compound as a brown oily substance.

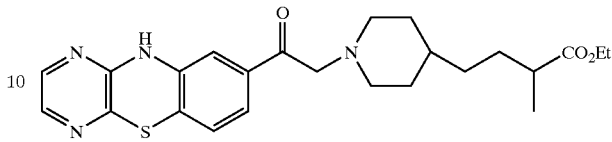

¹H-NMR(CDCl₃) δ ppm: 1.14(d, J=7 Hz, 3H), 1.24(t, J=7 Hz, 3H), 1.0–1.4(m, 4H), 1.3–1.5(m, 1H), 1.5–1.8(m, 4H), 2.0–2.1(m, 2H), 2.3–2.43(m, 1H), 2.91(br.d, J=10 Hz, 2H), 3.63(s, 2H), 4.11(q, J=7 Hz, 2H), 6.52–6.60(m, 1H), 6.93(d, J=8 Hz, 1H), 7.15(d, J=2 Hz, 1H), 7.46(dd, J=2, 8 Hz, 1H), 7.60(d, J=3 Hz, 1H), 7.70(d, J=3 Hz, 1H)

Example 628

Ethyl 4-[1-[2-hydroxy-2-(10H-pyrazino[2,3-b][1,4]benzothiazin-8-yl]ethyl]piperidin-4-yl]-2-methylbutanoate To a solution of 0.8 g of ethyl 4-[1-[2-oxo-2-(10H-pyrazino[2,3-b][1,4]benzothiazin-8-yl]ethyl]piperidin-4-yl]-2-methylbutanoate in ethanol (30 ml) was added 70 mg of sodium borohydride and the resulting mixture was reacted at room temperature for 30 minutes. After adding ethyl acetate, the reaction mixture was washed with water and a saturated aqueous solution of sodium chloride and dried over anhydrous magnesium sulfate. After distilling off the solvent under reduced pressure, the residue was purified by silica gel column chromatography (eluted with n-hexane/ethyl acetate) to thereby give 0.53 g of the title compound as a yellow oily substance.

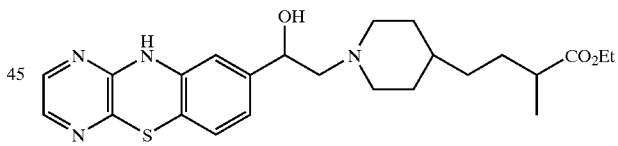

¹H-NMR(CDCl₃) δ ppm: 1.14(d, J=7 Hz, 3H), 1.25(t, J=7 Hz, 3H), 1.0–1.5(m, 6H), 1.5–1.8(m, 3H), 2.05–2.2(m, 1H), 2.3–2.6(m, 3H), 2.4–2.6(m, 2H), 2.9–3.0(m, 1H), 3.15–3.25(m, 1H), 4.13(q, J=7 Hz, 2H), 4.65–4.75(m, 1H), 6.63(s, 1H), 6.4–6.8(m, 1H), 6.7–6.8(m, 1H), 6.83(dd, J=2, 8 Hz, 1H), 7.55(d, J=3 Hz, 1H), 7.66–7.7(m, 1H)

Example 629

Ethyl[2-butyl-7-(10H-pyrazino[2,3-b][1,4]benzothiazin-8-ylmethyl)-7-azaspiro[3.5]non-2-yl]acetate Ethyl[7-(tert-butoxycarbonyl)-7-azaspiro [3.5]non-2-ylidene]acetate was treated successively by the same methods as those of Examples 66 and 9 to thereby give the title compound.

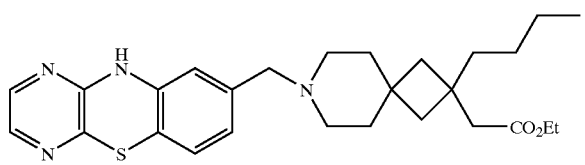

¹H-NMR(CDCl₃) δ ppm: 0.75(t, J=7 Hz, 3H), 1.07(m, 2H), 1.10(t, J=7 Hz, 3H), 1.35(m, 2H), 1.47(m, 6H), 1.54(d, J=13 Hz, 2H)1.65(d, J=13 Hz, 2H), 2.16(br.s, 4H), 2.25(s, 2H), 3.15(s, 2H), 3.95(q, J=7 Hz, 2H), 6.33(br.s, 1H), 6.41(br.s, 1H), 6.59(dd, J=1, 8 Hz, 1H), 6.65(d, J=8 Hz, 1H), 7.42(d, J=3 Hz, 1H), 7.53(d, J=3 Hz, 1H)

Example 630

Ethyl[1-(10H-pyrazino[2,3-b][1,4]benzothiazin-8-ylmethyl)piperidin-4-yl]butan-1-yl]iminoxyacetate 2.47 g of ethyl[(1-(tert-butoxycarbonyl)piperidin-4-yl] butan-1-yl]iminoxyacetate was dissolved in 20 ml of dichloromethane and ice-cooled. After adding 1.1 ml of iodotrimethylsilane, the resulting mixture was stirred and then heated to room temperature over 16 hours and 30 minutes. After adding 1.0 ml of iodotrimethylsilane, stirring was continued for additional 1 hour. The reaction mixture was concentrated under reduced pressure and thus a pale brown oily substance was obtained.

The obtained product was dissolved in 20 ml of N,N-dimethylformamide. After adding 1.7 g of 8-chloromethyl-10H-pyrazino[2,3-b][1,4]benzothiazine and 9.7 g of anhydrous potassium carbonate, the resulting mixture was stirred at 80° C. for 2 hours. After adding ethyl acetate, the reaction mixture was washed with water and a saturated aqueous solution of sodium chloride and dried over anhydrous magnesium sulfate. After concentrating the solvent, the residue was purified by silica gel column chromatography (eluted with dichloromethane/methanol) to thereby give 2.8 g of the title compound as a yellow oily substance.

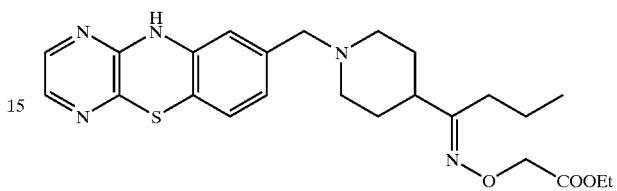

¹H-NMR(CDCl₃) δ ppm: 0.95(t, J=7.6 Hz, 3H), 1.27(t, J=7.2 Hz, 3H), 1.50–1.75(m, 8H), 2.06–2.20(m, 1H), 2.22–2.32(m, 2H), 2.86–2.93(m, 2H), 3.23(s, 2H), 4.20(q, J=7.2 Hz, 2H), 4.55(s, 2H), 6.48(br.s, 1H), 6.55(br.d, J=1.6 Hz, 1H), 6.76(dd, J=1.6, 7.6 Hz, 1H), 6.83(d, J=7.6 Hz, 1H), 7.58(d, J=2.4 Hz, 1H), 7.69(d, J=2.4 Hz, 1H)

Examples 631 to 734

The following compounds were obtained by the same method as the one of Example 18.

| Ex. | Structural formula | MS | M.p. | NMR |
|---|---|---|---|---|
| 631 | ![structure] [1-[2-(10H-pyrazino[2,3-b][1,4]benzothiazin-8-ylmethyl)amino-2-oxoethyl]piperidin-4-yl]carboxylic acid | FAB(+) 400(MH⁺) | 226–230° C. (decompose) | ¹H-NMR (DMSO-d₆) δ ppm: 1.58–1.72(m, 2H), 1.74–1.83(m, 2H), 2.07–2.23(m, 3H), 2.27–2.80(m, 2H), 2.94(s, 2H), 4.11(d, J=6.0Hz, 2H), 6.66(d, J=1.3Hz, 1H), 6.68(dd, J=1.3, 7.9Hz, 1H), 6.85(d, J=7.9Hz, 1H), 7.63(d, J=2.7Hz, 1H), 7.65(d, J=2.7Hz, 1H), 8.25(t, J=6.0Hz, 1H), 9.55(s, 1H) |
| 632 | ![structure] 3-[1-(10H-pyrazino[2,3-b][1,4]benzothiazin-8-ylmethyl)piperidin-4-yl] cyclobutaneacetic acid | FAB(+) 411(MH⁺) | 215–220° C. | ¹H-NMR (DMSO-d₆) δ ppm: 0.90–1.34(m, 3H), 1.48–1.90(m, 8H), 2.02–2.14(m, 1H), 2.22–2.60(m, 3H), 2.70–2.82(m, 2H), 3.26(s, 2H), 6.67(d, J=8Hz, 1H), 6.74(s, 1H), 6.81(d, J=8Hz, 1H), 7.61(d, J=2.8Hz, 1H), 7.62(d, J=2.8Hz, 1H), 9.34(s, 1H) |
| 633 | ![structure] [1-(10H-pyrazino[2,3-b][1,4]benzothiazin-8-ylmethyl)piperidin-4-yl]butan-1-yl] iminoxyacetic acid | FAB(+) 442(MH⁺) | 193–195° C. | ¹H-NMR (DMSO-d₆) δ ppm: 0.86(t, J=6.4Hz, 3H), 1.38–1.52(m, 4H), 1.60–1.70(m, 2H), 1.82–1.92(m, 2H), 1.95–2.10(m, 1H), 2.10–2.20(m, 2H), 2.75–2.82(m, 2H), 3.24(s, 2H), 4.00(s, 2H), 6.68(d, J=8.0Hz, 1H), 6.78(s, 1H), 6.81(d, J=8.0Hz, 1H), 7.61(d, J=2.8Hz, 1H), 7.62(d, J=2.8Hz, 1H), 9.47(s, 1H) |

| Ex. | Structural formula | MS | M.p. | NMR |
|---|---|---|---|---|
| 634 | (E)-3-[1-(10H-pyrazino[2,3-b][1,4]benzothiazin-8-ylmethyl)piperidin-4-yl]-2-butenoic acid | FAB(+) 383(MH⁺) | 207–209° C. | ¹H-NMR (DMSO-d₆) δ ppm: 1.50–2.04(m, 7H), 2.05(s, 3H), 2.75–2.90(m, 2H), 3.18(s, 2H), 5.57(s, 1H), 6.70(d, J=8.0Hz, 1H), 6.75(s, 1H), 6.83(d, J=8.0Hz, 1H), 7.61(d, J=2.8Hz, 1h), 7.63(d, J=2.8Hz, 1H), 9.45(s, 1H) |
| 635 | [1-3-[(10H-pyrazino[2,3-b][1,4]benzothiazin-8-yl)acetylaminopropyl]piperidin-4-yl]carboxylic acid | FAB(+) 428(MH⁺) | 143° C. (decompose) | ¹H-NMR (DMSO-d₆) δ ppm: 1.45–1.58(m, 4H), 1.72–1.80(m, 2H), 1.86–1.95(m, 2H), 2.16(m, 1H), 2.20–2.27(m, 2H), 2.72–2.80(m, 2H), 3.00–3.07(m, 2H), 3.21(s, 2H), 6.65–6.70(m, 2H), 6.83(d, J=8.2Hz, 1H), 7.64(d, J=2.7Hz, 1H), 7.65(d, J=2.7Hz, 1H), 8.00(t, J=5.0Hz, 1H), 9.52(s, 1H) |
| 636 | 3-[4-[(10H-pyrazino[2,3-b][1,4]benzothiazin-8-ylmethyl)amino]piperidin-1-yl]-3-oxopropanoic acid | FAB(+) 400(MH⁺) | 167–170° C. | ¹H-NMR (DMSO-d₆) δ ppm: 1.04–1.15(m, 1H), 1.18–1.30(m, 1H), 1.70–1.81(m, 2H), 2.50–2.62(m, 1H), 2.68(t, J=11.2Hz, 2H), 2.97(t, J=11.2Hz, 1H), 3.23(s, 2H), 3.55(s, 2H), 3.70(d, J=12Hz, 1H), 4.10(d, J=12Hz, 1H), 6.75(d, J=8.0Hz, 1H), 6.80(s, 1H), 6.81(d, J=8.0Hz, 1H), 7.60–7.66(m, 2H), 9.45(s, 1H) |
| 637 | [4-[10H-pyrazino[2,3-b][1,4]benzothiazin-8-ylmethyl)amino]piperidin-1-yl]-2-oxoacetic acid | FAB(+) 371(MH⁺) | 200–204° C. | ¹H-NMR (DMSO-d₆) δ ppm: 1.38–1.50(m, 3H), 1.65–1.78(m, 2H), 1.92–2.06(m, 2H), 2.70–2.80(m, 2H), 3.17(s, 2H), 6.69(d, J=8.0Hz, 1H), 6.76(s, 1H), 6.82(d, J=8.0Hz, 1H), 7.61(d, J=2.8Hz, 1H), 7.63(d, J=2.8Hz, 1H), 9.46(s, 1H) |
| 638 | 4-[4-[(10H-pyrazino[2,3-b][1,4]benzothiazin-8-ylmethyl)amino]piperidin-1-yl]butanoic acid | FAB(+) 400(MH⁺) | 121–124° C. | ¹H-NMR (DMSO-d₆) δ ppm: 1.20–1.35(m, 2H), 1.56–1.66(m, 2H), 1.72–1.82(m, 2H), 2.02–2.10(m, 2H), 2.23(t, J=6.8Hz, 2H), 2.37(t, J=6.8Hz, 2H), 2.42–2.50(m, 1H), 2.82–2.90(m, 2H), 3.15(s, 2H), 6.74(d, J=8.0Hz, 1H), 6.76(s, 1H), 6.81(d, J=8.0Hz, 1H), 7.61(d, J=2.8Hz, 1H), 7.63(d, J=2.8Hz, 1H), 9.45(s, 1H) |
| 639 | 3-[4-[(10H-pyrazino[2,3-b][1,4]benzothiazin-8-ylmethyl)amino]piperidin-1-yl]propanoic acid | FAB(+) 386(MH⁺) | 130–134° C. | ¹H-NMR (DMSO-d₆) δ ppm: 1.20–1.34(m, 2H), 1.76–1.87(m, 2H), 2.04–2.14(m, 2H), 2.32(t, J=6.8Hz, 2H), 2.40–2.50(m, 1H), 2.59(t, J=6.8Hz, 2H), 2.83–2.92(m, 2H), 3.15(s, 2H), 6.76(s, J=8.0Hz, 1H), 6.77(s, 1H), 6.83(d, J=8.0Hz, 1H), 7.61(d, J=2.8Hz, 1H), 7.63(d, J=2.8Hz, 1H), 9.48(s, 1H) |

-continued

| Ex. | Structural formula | MS | M.p. | NMR |
|---|---|---|---|---|
| 640 | 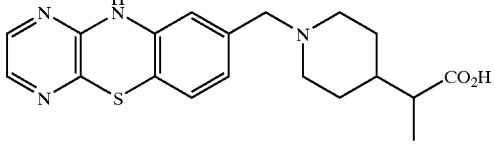<br>2-[1-(10H-pyrazino[2,3-][1,4]benzothiazin-8-ylmethyl)piperidin-4-yl] propanoic acid | ESI(+)<br>371(MH+) | 240–243° C. | $^1$H-NMR (DMSO-d$_6$) δ ppm: 0.99(d, J=6Hz, 3H), 1.1–1.3(m, 2H), 1.3–1.6(m, 3H), 1.81(br.t, J=10Hz, 2H), 2.1–2.2(m, 1H), 2.7–2.8(m, 2H), 3.23(s, 2H), 6.65–6.70(m, 1H), 6.74(s, 1H), 6.81(d, J=8Hz, 1H), 7.62(d, J=3Hz, 1H), 7.63(d, J=3Hz, 1H), 9.43(s, 1H) |
| 641 | 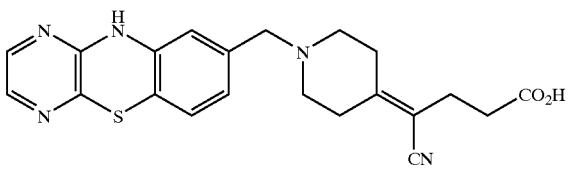<br>4-[1-(10H-pyrazino[2,3-b][1,4]benzothiazin-8-ylmethyl)piperidin-4-ylidene]-4-cyanobutanoic acid | ESI(+)<br>408(MH+) | 114–116° C. | $^1$H-NMR (DMSO-d$_6$) δ ppm: 2.34–2.60(m, 12H), 3.33(s, 2H), 6.71(dd, J=2, 8Hz, 1H), 6.76(d, J=2Hz, 1H), 6.84(d, J=8Hz, 1H), 7.62(d, J=3Hz, 1H), 7.63(d, J=3Hz, 1H), 9.45(s, 1H) |
| 650 | 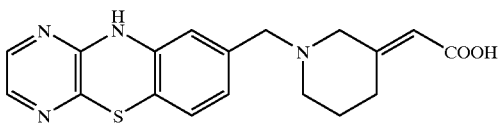<br>(E)-[1-(10H-pyrazino[2,3-b][1,4]benzothiazin-8-ylmethyl)piperidin-3-ylidene] acetic acid | ESI(+)<br>355(MH+) | 200–203° C. | $^1$H-NMR (DMSO-d$_6$) δ ppm: 1.50–1.60(m, 2H), 2.02(br.t, J=5Hz, 2H), 2.72(br.t, J=6Hz, 2H), 2.89(s, 2H), 3.30(s, 2H), 5.56(s, 1H), 6.68(d, J=8Hz, 1H), 6.74(s, 1H), 6, 83(d, J=8Hz, 1H), 7.61(d, J=2Hz, 1H), 7.62(d, J=2Hz, 1H), 9.44(s, 1H), 12.2 (br.s, 1H) |
| 651 | 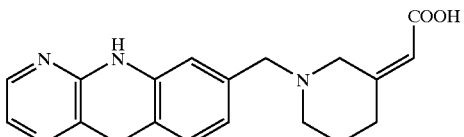<br>(Z)-[1-(10H-pyrazino[2,3-b][1,4]benzothiazin-8-ylmethyl)piperidin-3-ylidene] acetic acid | ESI(+)<br>355(MH+) | 216–220° C. | $^1$H-NMR (DMSO-d$_6$) δ ppm: 1.56–1.66(m, 2H), 2.19(t, J=6Hz, 2H), 2.36–2.44(m, 2H), 3.32(s, 2H), 3.51(s, 2H), 5.60(s, 1H), 6.68(dd, J=2, 8Hz, 1H), 6.74(d, J=2Hz, 1H), 6.82(d, J=8Hz, 1H), 7.61(d, J=3Hz, 1H), 7.62(d, J=3Hz, 1H), 9.42(s, 1H) |
| 652 | 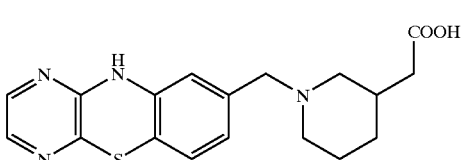<br>[1-(10H-pyrazino[2,3-b][1,4]benzothiazin-8-ylmethyl)piperidin-3-yl] acetic acid | ESI(+)<br>357(MH+) | amorphous | $^1$H-NMR (DMSO-d$_6$) δ ppm: 0.84–0.98(m, 1H), 1.36–1.48(m, 1H), 1.50–1.60(m, 1H), 1.60–1.70(m, 2H), 1.80–1.92(m, 2H), 2.06–2.12(m, 2H), 2.56–2.70(m, 2H), 3.23(s, 2H), 6.68(dd, J=1, 8Hz, 1H), 6.74(d, J=1Hz, 1H), 6.82(d, J=8Hz, 1H), 7.62(d, J=3Hz, 1H), 7.63(d, J=3Hz, 1H), 9.45(s, 1H) |
| 653 | 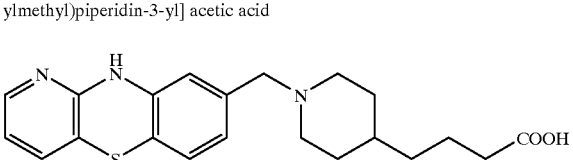<br>4-[1-(10H-pyrido[3,2-b][1,4]benzothiazin-8-ylmethyl)piperidin-4-yl]-2-methylbutanoic acid | ESI(+)<br>398(MH+) | 113–115° C. | $^1$H-NMR (DMSO-d$_6$) δ ppm: 1.01(d, J=7Hz, 3H), 0.94–1.22(m, 5H), 1.20–1.40(m, 1H), 1.46–1.62(m, 3H), 1.78–1.88(m, 2H), 2.24(q, J=7Hz, 1H), 2.72(br.d, J=12Hz, 2H), 3.23(s, 2H), 6.6–6.74(m, 2H), 6.72(s, 1H), 6.82(d, J=8Hz, 1H), 7.2–7.28(m, 1H), 7.78(dd, J=1, 4Hz, 1H), 9.12(s, 1H) |
| 654 | 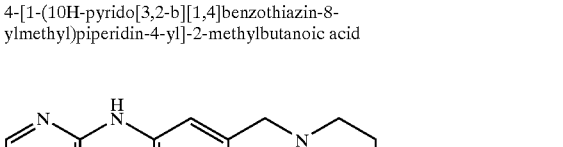<br>4-[1-(10H-pyrazino[2,3-b][1,4]benzoxazin-8-ylmethyl)piperidin-4-yl]-2-methylbutanoic acid | ESI(+)<br>383(MH+) | 238–240° C. | $^1$H-NMR (DMSO-d$_6$) δ ppm: 1.01(d, J=7Hz, 3H), 0.96–1.24 (m, 5H), 1.24–1.38(m, 1H), 1.44–1.60(m, 1H), 1.57(br.d, J=11Hz, 2H), 1.82(t, J=12Hz, 2H), 2.16–2.30(m, 1H), 2.72(br.d, J=11Hz, 2H), 3.20(s, 2H), 6.56(dd, J=2, 8Hz, 1H), 6.58(d, J=2Hz, 1H), 6.67(J=8Hz, 1H), 7.23(d, J=3Hz, 1H), 7.44(d, J=3Hz, 1H), 9.55(br.s, 1H) |

| Ex. | Structural formula | MS | M.p. | NMR |
|---|---|---|---|---|
| 655 | 4-[1-(10H-pyrimido[5,4-b][1,4]benzothiazin-8-ylmethyl)piperidin-4-yl]-2-methylbutanoic acid | FAB(+) 399(MH+) | 219–220° C. | $^1$H-NMR (DMSO-d$_6$) δ ppm: 1.01(d, J=7.1Hz, 3H), 1.01–1.19(m, 5H), 1.25–1.36(m, 1H), 1.45–1.60(m, 3H), 1.77–1.86(m, 2H), 2.18–2.28(m, 1H), 2.67–2.75(m, 2H), 3.14(s, 2H), 6.73(dd, J=1.5, 7.9Hz, 1H), 6.79(d, J=7.9Hz, 1H), 6.85(d, J=1.5Hz, 1H), 7.95(s, 1H), 8.22(s, 1H), 9.76(s, 1H) |
| 656 | 4-[1-[2-hydroxy-2-(10H-pyrazino[2,3-b] [1,4] benzothiazin-8-yl] ethyl)]piperidin-4-yl]-2-methylbutanoic acid | FAB(+) 429(MH+) | 239–242° C. | $^1$H-NMR (DMSO-d$_6$) δ ppm: 0.9–1.3(m, 5H), 1.01(d, J=7Hz, 3H), 1.2–1.4(m, 1H), 1.4–1.75(m, 3H), 1.8–2.1(m, 2H), 2.1–2.4(m, 3H), 2.8–2.95(m, 2H), 4.2–4.35(m, 1H), 6.72(d, J=8Hz, 1H), 6.78(d, J=2Hz, 1H), 6.81(d, J=8Hz, 1H), 7.60(d, J=3Hz, 1H), 7.62(d, J=3Hz, 1H), 9.44(s, 1H) |
| 657 | 4-[1-[3-(10H-pyrazino[2,3-b][1,4]benzothiazin-8-yl) propyl]piperidin-4-yl]-2-methylbutanoic acid | ESI(+) 427(MH+) | 235–238° C. | $^1$H-NMR (DMSO-d$_6$) δ ppm: 1.01(d, J=7Hz, 3H), 1.0–1.2(m, 5H), 1.26–1.36(m, 1H), 1.46–1.60(m, 1H), 1.50–1.68(m, 4H), 1.74–1.90(m, 2H), 2.16–2.30(m, 3H), 2.37(t, J=9Hz, 2H), 2.76–2.86(m, 2H), 6.60(s, 1H), 6.61(d, J=8Hz, 1H), 6.78(d, J=8Hz, 1H), 7.61(d, J=2Hz, 1H), 7.62(d, J=2Hz, 1H), 9.40(s, 1H) |
| 658 | [1-(10H-pyrazino[2,3-b][1,4]benzothiazin-8-ylmethyl)piperidin-4-yl] carboxylic acid | ESI(+) 327(MH+) | 242–244° C. | $^1$H-NMR (DMSO-d$_6$) δ ppm: 1.42–1.58(m, 2H), 1.70–1.80(m, 2H), 1.84–2.0(m, 2H), 2.10–2.25(m, 1H), 2.64–2.76(m, 2H), 3.24(s, 2H), 6.57(dd, J=1, 8Hz, 1H), 6.60(s, 1H), 6.68(d, J=8Hz, 1H), 7.24(d, J=3Hz, 1H), 7.44(d, J=3Hz, 1H), 9.57 (s, 1H) |
| 659 | 4-[1-(10H-pyrazino[2,3-b][1,4]benzothiazin-8-ylmethyl)piperidin-4-yl] phenylacetic acid | ESI(+) 432(MH+) | 266–269° C. | $^1$H-NMR (DMSO-d$_6$) δ ppm: 1.84–2.08(m, 4H), 2.68–2.80(m, 1H), 2.90–3.08(m, 2H), 3.28–3.42(m, 2H), 3.51(s, 2H), 4.06–4.16(m, 2H), 6.82(s, 1H), 7.00(d, J=8Hz, 1H), 7.0–7.1(m, 1H), 7.14(d, J=8Hz, 2H), 7.19(d, J=8Hz, 2H), 7.65(d, J=3Hz, 1H), 7.66(d, J=3Hz, 1H), 9.73(s, 1H) |
| 660 | 5-[1-(10H-pyrazino 2,3-b][1,4]benzothiazin-8-ylmethyl)piperidin-4-yl]-2-methylpentanoic acid | ESI(+) 413(MH+) | Amorphous | $^1$H-NMR (DMSO-d$_6$) δ ppm: 1.01(d, J=7Hz, 3H), 0.98–1.38(m, 8H), 1.42–1.54(m, 1H), 1.58(br.d, J=12Hz, 2H), 1.82–1.94(m, 2H), 2.22–2.34(m, 1H), 2.74(br.d, J=18Hz, 2H), 3.25(s, 2H), 6.68(d, J=8Hz, 1H), 6.74(s, 1H), 6.82(d, J=8Hz, 1H), 7.58–7.66(m, 2H), 9.44(s, 1H) |

| Ex. | Structural formula | MS | M.p. | NMR |
|---|---|---|---|---|
| 661 | 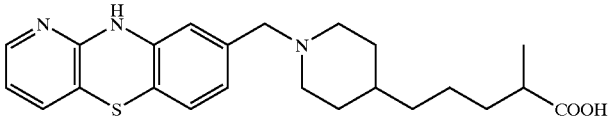<br>5-[1-(10H-pyrido[3,2-b][1,4]benzothiazin-8-ylmethyl)piperidin-4-yl]-2-methylpentanoic acid | ESI(+)<br>412(MH⁺) | oily<br>substance | ¹H-NMR (DMSO-d₆) δ ppm:<br>0.95–1.36(m, 8H), 1.01(d,<br>J=7Hz, 3H), 1.40–1.62(m,<br>3H), 1.80–1.90(m, 2H),<br>2.20–2.32(m, 1H), 2.70–<br>2.80(m, 2H), 3.26(s, 2H),<br>6.66–6.72(m, 2H), 6.79(s,<br>1H), 6.83(d, J=8Hz, 1H),<br>7.25(d, J=7Hz, 1H),<br>7.78(d, J=5Hz, 1H),<br>9.13(s, 1H) |
| 662 | 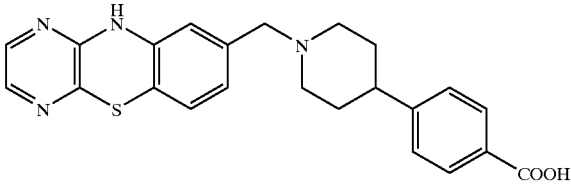<br>4-[1-(10H-pyrazino 2,3-b] [1,4]benzothiazin-8-ylmethyl)piperidin-4-yl] benzoic acid | ESI(+)<br>419(MH⁺) | 265–<br>268° C. | ¹H-NMR (DMSO-d₆) δ ppm:<br>1.9–2.1(m, 4H), 2.85(br.s,<br>1H), 3.00(br.s, 2H),<br>3.39(br.s, 2H), 4.10(br.s,<br>2H), 6.82(br.s, 1H), 6.97–<br>7.06(m, 1H), 6.97–7.12(m,<br>1H), 7.33(d, J=8Hz, 2H),<br>7.65(d, J=2Hz, 1H),<br>7.66(d, J=2Hz, 1H),<br>7.89(d, J=8Hz, 2H),<br>9.73(br.s, 1H), 12.9(br.s, 1H) |
| 663 | 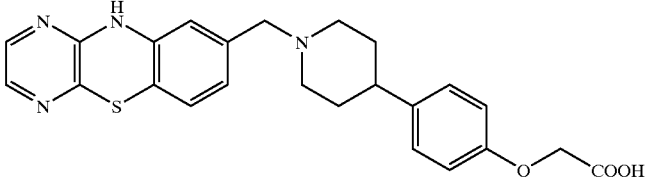<br>4-[1-(10H-pyrazino[2,3-b][1,4]benzothiazin-8-ylmethyl)piperidin-4-yl] phenoxyacetic acid | ESI(+)<br>449(MH⁺) | 258–<br>262° C. | ¹H-NMR (DMSO-d₆) δ ppm:<br>1.50–1.75(m, 4H), 1.95–<br>2.10(m, 2H), 2.35–2.55(m,<br>2H), 2.87(br.d, J=11Hz, 1H),<br>3.32(s, 2H), 4.53(s, 2H),<br>6.72(d, J=8Hz, 1H), 6.78(d,<br>J=8Hz, 2H), 6.79(s, 1H),<br>6.84(d, J=8Hz, 1H), 7.11(d,<br>J=8Hz, 2H), 7.62(d, J= 3Hz,<br>1H), 7.63(d, J=3Hz, 1H),<br>9.46(s, 1H) |
| 664 | 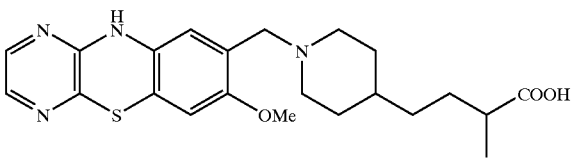<br>4-[1-(10H-methoxypyrazino[2,3-b][1,4] benzothiazin-8-ylmethyl)piperidin-4-yl]-2-methylbutanoic acid | ESI(+)<br>429(MH⁺) | 155–<br>160° C. | ¹H-NMR (DMSO-d₆) δ ppm:<br>1.02(d, J=7Hz, 3H), 1.10–<br>1.25(m, 5H), 1.45–1.65(m,<br>4H), 1.88–2.00(m, 2H), 2.20–<br>2.32(m, 1H), 2.78(br.d,<br>J=12Hz, 2H), 3.30(s, 2H),<br>3.65(s, 3H), 6.57(s, 1H),<br>6.83(s, 1H), 7.57(d, J=3Hz, 1H),<br>7.60(d, J=3Hz, 1H), 9.28(s, 1H) |
| 665 | 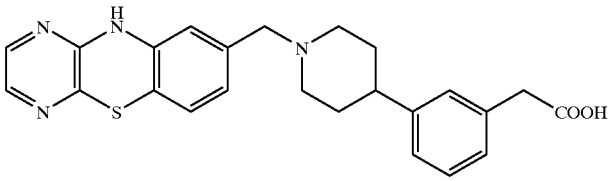<br>3-[1-(10H-pyrazino[2,3-b][1,4]benzothiazin-8-yl-methyl)piperidin-4-yl] phenylacetic acid | ESI(+)<br>433(MH⁺) | 130–<br>132° C. | ¹H-NMR (DMSO-d₆) δ ppm:<br>1.50–1.76(m, 4H), 1.96–<br>2.08(m, 2H), 2.40–2.52(m,<br>1H), 2.88(br.d, J=11Hz, 2H),<br>3.32(s, 2H), 3.51(s, 2H),<br>6.72(dd, J=1, 8Hz, 1H),<br>6.79(s, 1H), 6.84(d, J=8Hz,<br>1H), 7.05(d, J=8Hz, 1H),<br>7.09(d, J=8Hz, 1H), 7.10(s,<br>1H), 7.21(t, J=8Hz, 1H),<br>7.62(d, J=3Hz, 1H), 7.63(d,<br>J=3Hz, 1H), 9.45(s, 1H) |
| 666 | 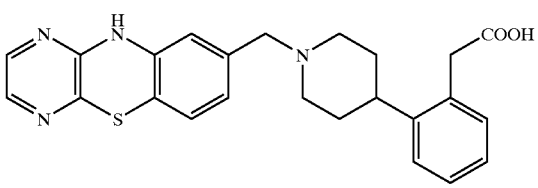<br>2-[1-(10H-pyrazino[2,3-b] [1,4]benzothiazin-8-yl-methyl)piperidin-4-yl] phenylacetic acid | ESI(+)<br>433(MH⁺) | 152–<br>154° C. | ¹H-NMR (DMSO-d₆) δ ppm:<br>1.56–1.80(m, 4H), 1.96–2.20(m,<br>2H), 2.58–2.72(m, 1H), 2.84–<br>2.96(m, 2H), 3.38(s, 2H), 3.61<br>(s, 2H), 6.74(d, J=8Hz, 1H),<br>6.79(s, 1H), 6.86(d, J=8Hz, 1H),<br>7.10(t, J=7Hz, 1H), 7.15(d, J=<br>7Hz, 1H), 7.21(t, J=7Hz, 1H),<br>7.24(d, J=7Hz, 1H), 7.62(d, J=<br>2Hz, 1H), 7.63(d, J=2Hz, 1H),<br>9.47(s, 1H) |

| Ex. | Structural formula | MS | M.p. | NMR |
|---|---|---|---|---|
| 667 | 2-methoxy-5-[1-(10H-pyrazino[2,3-b][1,4]benzothiazin-8-ylmethyl)piperidin-4-yl] phenylacetic acid | ESI(+) 463(MH$^+$) | 174–176° C. | $^1$H-NMR (DMSO-d$_6$) δ ppm: 1.53–1.68(m, 4H), 1.96–2.08(m, 2H), 2.80–2.92(m, 3H), 3.33(s, 2H), 3.45(s, 2H), 3.74(s, 3H), 6.72(dd, J=1, 8Hz, 1H), 6.80(d, J=1Hz, 1H), 6.84(d, J=8Hz, 1H), 6.86(d, J=8Hz, 1H), 7.00–7.08(m, 1H), 7.04(s, 1H), 7.62(d, J=3Hz, 1H), 7.63(d, J=3Hz, 1H), 9.45(s, 1H) |
| 668 | 2,3-dimethoxy-5-[1-(10H-pyrazino[2,3-b][1,4]benzothiazin-8-ylmethyl)piperidin-4-yl] phenylacetic acid | ESI(+) 493(MH$^+$) | 138–140° C. | $^1$H-NMR (DMSO-d$_6$) δ ppm: 1.55–1.75(m, 4H), 1.93–2.05(m, 2H), 2.35–2.48(m, 1H), 2.83–2.93(m, 2H), 3.29(s, 2H), 3.46(s, 2H), 3.63(s, 3H), 3.77(s, 3H), 6.64(d, J=2Hz, 1H), 6.72(dd, J=2, 8Hz, 1H), 6.78(s, 1H), 6.79(s, 1H), 6.84(d, J=8Hz, 1H), 7.62(d, J=3Hz, 1H), 7.63(d, J=3Hz, 1H), 9.44(s, 1H) |
| 669 | 3-[1-(10H-pyrazino[2,3-b][1,4]benzothiazin-8-ylmethyl)piperidin-4-yl]-3-methylbutanoic acid | ESI(+) 399(MH$^+$) | 272–275° C. | $^1$H-NMR (CD$_3$OD) δ ppm: 1.02(s, 6H), 1.50–1.75(m, 3H), 1.95–2.05(m, 2H), 2.24(s, 2H), 2.85–2.98(m, 2H), 3.45–3.55(m, 2H), 4.09(s, 2H), 6.77(d, J=2Hz, 1H), 6.91(dd, J=2, 8Hz, 1H), 6.96(d, J=8Hz, 1H), 7.61(d, J=3Hz, 1H), 7.61(d, J=3Hz, 1H) |
| 670 | 4-[1-(10H-pyrazino[2,3-b][1,4]benzothiazin-8-ylmethyl)piperidin-4-yl]-3,3-dimethylbutanoic acid | ESI(+) 413(MH$^+$) | 230–232° C. | $^1$H-NMR (CD$_3$OD) δ ppm: 1.04(s, 6H), 1.38(d, J=5Hz, 2H), 1.45–1.60(m, 2H), 1.65–1.70(m, 1H), 1.92–2.03(m, 2H), 2.20(s, 2H), 2.78–3.00(m, 2H), 3.36(br.d, J=8Hz, 2H), 4.05(s, 2H), 6.76(d, J=2Hz, 1H), 6.90(dd, J=2, 8Hz, 1H), 6.95(d, J=8Hz, 1H), 7.60(d, J=3Hz, 1H), 7.61(d, J=3Hz, 1H) |
| 671 | [1-[N-[1-(10H-pyrazino[2,3-b][1,4]benzothiazin-8-ylmethyl)piperidin-4-yl]sulfamoyl]piperidin-4-yl] carboxylic acid | FAB(+) 505(MH$^+$) | 54–55° C. | $^1$H-NMR (DMSO-d$_6$) δ ppm: 1.41–1.56(m, 4H), 1.75–1.89(m, 4H), 2.05–2.16(m, 2H), 2.31–2.38(m, 1H), 2.65–2.72(m, 2H), 2.74–2.82(m, 2H), 2.96–3.04(m, 1H), 3.30(s, 2H), 3.31–3.42(m, 2H), 6.71(s, 1H), 6.72(d, J=8Hz, 1H), 6.86(d, J=8Hz, 1H), 7.26(s, 1H), 7.64(s, 2H), 9.45(s, 1H) |
| 672 | [N-[1-(10H-pyrazino[2,3-b][1,4]benzothiazin-8-yl-methyl)piperidin-4-yl]sulfamoyl] aminoacetic acid | FAB(+) 451(MH$^+$) | 195–196° C. | $^1$H-NMR (CD$_3$OD) δ ppm: 1.50–1.61(m, 2H), 1.82–1.98(m, 2H), 2.07–2.15(m, 2H), 2.79–2.85(m, 2H), 3.14–3.21(m, 1H), 3.35(s, 2H), 3.50(s, 2H), 6.66(d, J=2Hz, 1H), 6.76(dd, J=2, 8Hz, 1H), 6.80(d, J=8Hz, 1H), 7.55(d, J=3Hz, 1H), 7.57(d, J=3Hz, 1H) |

-continued

| Ex. | Structural formula | MS | M.p. | NMR |
|---|---|---|---|---|
| 673 | 4-oxo-4-[4-(10H-pyrazino[2,3-b][1,4]benzothiazin-8-ylmethyl)piperazin-1-yl] butanoic acid | FAB(+) 399(M+) | 240–242° C. | $^1$H-NMR (DMSO-d$_6$) δ ppm: 1.95(dd, J=6, 7Hz, 2H), 2.22–2.26(br.s, 2H), 2.27–2.32(br.s, 2H), 2.35(dd, J=7, 9Hz, 2H), 3.28(s, 2H), 3.34–3.42(m, 4H), 6.70(dd, J=1, 8Hz, 1H), 6.77(d, J=1Hz, 1H), 6.83(d, J=8Hz, 1H), 7.62(d, J=3Hz, 1H), 7.63(d, J=3Hz, 1H), 9.52(s, 1H) |
| 674 | 1-(10H-pyrazino[2,3-b][1,4]benzothiazin-8-ylmethyl)-3-azetidinecarboxylic acid | FAB(+) 315(MH+) | 181–183° C. | $^1$H-NMR (CD$_3$OD) δ ppm: 3.65–3, 72(m, 1H), 4.25–4.35(m, 6H), 6.71(s, 1H), 6.86(d, J=8Hz, 1H), 6.96(d, J=8Hz, 1H), 7.62(s, 2H) |
| 675 | 3-[1-(10H-pyrazino[2,3-b][1,4]benzothiazin-8-ylmethyl)azetidin-3-yl]-2-methylpropanoic acid | FAB(+) 357(MH+) | Amorphous | $^1$H-NMR (DMSO-d$_6$) δ ppm: 0.80(d, J=7Hz, 3H), 1.24–1.31(m, 1H), 1.65–1.74(m, 2H), 2.38–2.45(m, 1H), 2.59(t, J=7Hz, 2H), 3.20–3.27(m, 2H), 3.28(s, 2H), 6.64(dd, J=2, 7Hz, 1H), 6.71(d, J=2Hz, 1H), 6.78(d, J=7Hz, 1H), 7.61(d, J=3Hz, 1H), 7.62(d, J=3Hz, 1H), 9.53(s, 1H) |
| 676 | [4-ethyl-1-(10H-pyrazino[2,3-b][1,4]benzothiazin-8-ylmethyl)piperidin-4-yl] acetic acid | FAB(+) 385(MH+) | 225–226° C. | $^1$H-NMR (DMSO-d$_6$) δ ppm: 0.80(t, J=7Hz, 3H), 1.43(br.s, 2H), 1.70(br.s, 4H), 2.25(br.s, 2H), 2.80(br.s, 4H), 3.80(s, 2H), 6.84(s, 1H), 6.89(d, J=8Hz, 1H), 6.96(br.s, 1H), 7.63(s, 2H), 9.42(br.s, 1H) |
| 677 | [7-(10H-pyrazino[2,3-b][1,4]benzothiazin-8-ylmethyl)-7-azaspiro[3.5]non-2-yl] acetic acid | FAB(+) 397(MH+) | 207–209° C. | $^1$H-NMR (DMSO-d$_6$) δ ppm: 1.36(dd, J=10, 11Hz, 2H), 1.42(t, J=5Hz, 2H), 1.52(m, 2H), 1.87(t, J=10Hz, 2H), 2.14(br.s, 2H), 2.22(br.s, 2H), 2.28(d, J=8Hz, 2H), 2.46(m, 1H), 3.18(s, 2H), 6.67(dd, J=2, 8Hz, 1H), 6.74(d, J=2Hz, 1H), 6.81(d, J=8Hz, 1H), 7.61(d, J=3Hz, 1H), 7.62(d, J=3Hz, 1H), 9.41(s, 1H) |
| 678 | 4-[1-(5H-pyrido[3,4-b][1,4]benzothiazin-7-ylmethyl)piperidin-4-yl]-2-methylbutanoic acid | FAB(+) 398(MH+) | 210–215° C. | $^1$H-NMR (DMSO-d$_6$) δ ppm: 0.95(d, J=8Hz, 3H), 1.02–1.21(m, 5H), 1.44–1.58(m, 4H), 1.79(m, 2H), 2.09(m, 1H), 2.70(d, J=10Hz, 2H), 3.21(s, 2H), 6.51(d, J=5Hz, 1H), 6.65(s, 1H), 6.66(d, J=8Hz, 1H), 6.81(d, J=8Hz, 1H), 7.84(s, 1H), 7.94(d, J=5Hz, 1H), 9.10(s, 1H) |
| 679 | [7-(10H-pyrazino[2,3-b][1,4]benzothiazin-8-ylmethyl)-7-azaspiro[3.5]non-2-ylidene] acetic acid | FAB(+) 395(MH+) | 238–241° C. | $^1$H-NMR (DMSO-d$_6$) δ ppm: 1.54(m, 4H), 2.22(br.s, 4H), 2.49(br.s, 2H), 2.71(br.s, 2H), 3.24(s, 2H), 5.57(br.s, 1H), 6.68(d, J=8Hz, 1H), 6.75(s, 1H), 6.82(d, J=8Hz, 1H), 7.62(d, J=3Hz, 1H), 7.63(d, J=3Hz, 1H), 9.44(s, 1H), 11.85(br.s, 1H) |

-continued

| Ex. | Structural formula | MS | M.p. | NMR |
|---|---|---|---|---|
| 680 | [2-ethoxy-7-(10H-pyrazino[2,3-b][1,4]benzothiazin-8-ylmethyl)-7-azaspiro[3.5]non-2-yl] acetic acid | FAB(+) 441(MH+) | 226–227° C. | $^1$H-NMR (DMSO-d$_6$) δ ppm: 1.02(t, J=7Hz, 3H), 1.47(m, 2H), 1.54(m, 2H), 1.81(d, J=13Hz, 2H), 1.90(d, J=13Hz, 2H), 2.29(br.s, 4H), 2.46(s, 2H), 3.18(s, 2H), 3.30(q, J=7Hz, 2H), 6.67(dd, J=2, 8Hz, 1H), 6.73(d, J=2Hz, 1H), 6.81(d, J=8Hz, 1H), 7.62(d, J=3Hz, 1H), 7.63(d, J=3Hz, 1H), 9.42(s, 1H) |
| 681 | 4-[1-(10H-pyrazino[2,3-b][1,4]benzothiazin-8-ylmethyl)-4-(hydroxymethyl)piperidin-4-yl]-2-methylbutanoic acid | FAB(+) 429(MH+) | 105–110° C. | $^1$H-NMR (CD$_3$OD) δ ppm: 1.04(d, J=7Hz, 3H), 1.2–1.5(m, 8H), 2.21(m, 3H), 2.29(m, 2H), 3.16(s, 2H), 3.42(s, 2H), 5.74(s, 1H), 6.67(dd, J=2, 8Hz, 1H), 6.75(d, J=2Hz, 1H), 6.81(d, J=8Hz, 1H), 7.62(d, J=3Hz, 1H), 7.63(d, J=3Hz, 1H), 9.43 (br.s, 1H) |
| 682 | sodium 2-[7-(10H-pyrazino[2,3-b][1,4]benzothiazin-8-ylmethyl)-7-azaspiro[3.5]non-2-yl]carboxylate | FAB(+) 405(MH+) | 230–232° C. | $^1$H-NMR (CD$_3$OD) δ ppm: 1.61(t, J=11Hz, 2H), 1.68(t, 11Hz, 2H), 1.96(s, 2H), 1.98(s, 2H), 2.4–2.8(br.m, 5H), 3.41(s, 2H), 6.66(d, J=2Hz, 1H), 6.78(dd, J=2, 8Hz, 1H), 6.83(d, J=8Hz, 1H), 7.56(d, J=3Hz, 1H), 7.58(d, J=3Hz, 1H) |
| 683 | 2-[7-(10H-pyrazino[2,3-b][1,4]benzothiazin-8-ylmethyl)-7-azaspiro[3.5]non-2-ylidene] propanoic acid | FAB(+) 409(MH+) | 251–252° C. | $^1$H-NMR (DMSO-d$_6$) δ ppm: 1.51(m, 4H), 1.58(s, 3H), 2.2(br.s, 4H), 2.43(s, 2H), 2.66(s, 2H), 3.22(s, 2H), 6.68(d, J=8Hz, 1H), 6.75(d, J=2Hz, 1H), 6.82(dd, J=2, 8Hz, 1H), 7.62(m, 2H), 9.42(br.s, 1H) |
| 684 | 2-[7-(10H-pyrazino 2,3-b][1,4]benzothiazin-8-ylmethyl)-7-azaspiro3.5]non-2-yl] propanoic acid | FAB(+) 410(M+) | 169–172° C. | $^1$H-NMR (DMSO-d$_6$) δ ppm: 0.92(d, J=7Hz, 3H), 1.3–1.42(m, 5H), 1.52(br.s, 2H), 1.74–1.85(m, 2H), 2.10–2.26(m, 5H), 3.22(s, 2H), 6.69(d, J=8Hz, 1H), 6.75(s, 1H), 6.83(d, J=8Hz, 1H), 7.63(m, 2H), 9.43(br.s, 1H) |
| 685 | [2-methyl-7-(10H-pyrazino[2,3-b][1,4]enzothiazin-8-ylmethyl)-7-azaspiro[3.5]non-2-yl] acetic acid | FAB(+) 411(MH+) | 149–151° C. | $^1$H-NMR (DMSO-d$_6$) δ ppm: 1.25(s, 3H), 1.72(d, J=13Hz, 2H), 1.78(br.s, 4H), 2.02(d, J=13Hz, 2H), 2.33(s, 2H), 2.88(br.s, 4H), 3.84(s, 2H), 6.69(d, J=2Hz, 1H), 6.85(dd, J=2, 8Hz, 1H), 6.92(d, J=8Hz, 1H), 7.60(d, J=3Hz, 1H), 7.61(d, J=3Hz, 1H), 9.42(s, 1H) |

-continued

| Ex. | Structural formula | MS | M.p. | NMR |
|---|---|---|---|---|
| 686 | [7-(10H-pyrazino[2,3-b][1,4]benzothiazin-8-ylmethyl)-7-azaspirol[3.5]non-2-yl] carboxylic acid | FAB(+) 383(MH$^+$) | 265–268° C. | $^1$H-NMR (CD$_3$OD) δ ppm: 1.71(m, 2H), 1.87(s, 2H), 2.05–2.15(m, 4H), 2.95–3.10(m, 5H), 3.97(s, 2H), 6.74(d, J=2Hz, 1H), 6.89(dd, J=2, 8Hz, 1H), 6.96(d, J=8Hz, 1H), 7.61(s, 2H) |
| 687 | [2-butyl-7-(10H-pyrazino[2,3-b][1,4]benzothiazin-8-yl-methyl)-7-azaspiro[3.5]non-2-yl] acetic acid | FAB(+) 453(MH$^+$) | 133–135° C. | $^1$H-NMR (CD$_3$OD) δ ppm: 0.92(t, J=7Hz, 3H), 1.21–1.33(m, 4H), 1.55(m, 2H), 1.67(d, J=13Hz, 2H), 1.75(m, 4H), 1.95(d, J=13Hz, 2H), 2.32(s, 2H), 2.50(br.s, 2H), 2.75(br.s, 2H), 3.68(s, 2H), 6.67(d, J=2Hz, 1H), 6.82(dd, J=2, 8Hz, 1H), 6.88(d, J=8Hz, 1H), 7.58(d, J=3Hz, 1H), 7.59(d, J=3Hz, 1H) |
| 688 | 1-(10-pyrazino[2,3-b][1,4]benzothiazin-8-ylmethyl-1-azoniabicyclo[2.2.2]octane-4-carboxylate | FAB(+) 369(MH$^+$) | 229–230° C. | $^1$H-NMR (CD$_3$OD) δ ppm: 2.19(t, J=8Hz, 6H), 3.43(t, J=8Hz, 6H), 4.19(s, 2H), 6.71(d, J=2Hz, 1H), 6.88(dd, J=2, 8Hz, 1H), 6.99(d, J=8Hz, 1H), 7.62(s, 2H) |
| 689 | [3-(10H-pyrazino[2,3-b][1,4]benzothiazin-8-ylmethyl)-3-azabicyclo[3.1.0]hexa-6-yl] carboxylic acid | FAB(+) 341(MH$^+$) | >275° C. | $^1$H-NMR (DMSO-d$_6$) δ ppm: 1.83(s, 2H), 2.31(d, J=10Hz, 2H), 2.91(d, J=10Hz, 2H), 3.29(s, 2H), 3.38(s, 1H), 6.64(d, J=7Hz, 1H), 6.72(s, 1H), 6.81(d, J=7Hz, 1H), 7.62(d, J=3Hz, 1H), 7.63(d, J=3Hz, 1H), 9.44(s, 1H) |
| 690 | [7-(10H-pyrazino[2,3-b][1,4]benzothiazin-8-ylmethyl)-1-oxa-7-azaspiro[3,5]non-2-yl] carboxylic acid | FAB(+) 385(MH$^+$) | 178–180° C. | 1H-NMR (CD$_3$OD) δ: 1.81–1.95(m, 3H), 2.00–2.09(m, 1H), 2.31(dd, J=7, 11Hz, 1H), 2.66(dd, J=9, 11Hz, 1H), 2.78(br.s, 2H), 3.31(s, 2H), 3.58(br.s, 2H), 4.74(dd, J=7, 9Hz, 1H), 6.68(d, J=2Hz, 1H), 6.81(dd, J=2, 8Hz, 1H), 6.86(d, J=8Hz, 1H), 7.57 (d, J=3Hz, 1H), 7.59(d, J=3Hz, 1H) |
| 691 | [1-(10H-pyrazino[2,3-b][1,4]benzothiazin-8-ylmethyl)-piperidin-4-yl] aminoacetic acid | ESI(+) 372(MH$^+$) | 206–208° C. | $^1$H-NMR (DMSO-d$_6$) δ ppm: 1.43–1.53(m, 2H), 1.80–1.92(m, 4H), 2.73–2.86(m, 3H), 3.11(s, 2H), 3.24(s, 2H), 6.67(dd, J=1.9, 7.4Hz, 1H), 6.72(d, J=1.9Hz, 1H), 6.83(d, J=7.4Hz, 1H), 7.62(s, 2H), 9.46(s, 1H) |

| Ex. | Structural formula | MS | M.p. | NMR |
|---|---|---|---|---|
| 692 | [1-(10H-pyrazino[2,3-][1,4]benzothiazin-8-ylmethyl)-piperidin-4-yl] methoxyacetic acid | ESI(+) 387(MH⁺) | 146–148° C. | ¹H-NMR (DMSO-d₆) δ ppm: 1.59–1.72(m, 2H), 1.43–1.57(m, 1H), 1.57–1.66(m, 2H), 1.82–1.92(m, 2H), 2.71–2.79(m, 2H), 3.14(s, 2H), 3.27(d, J=6.3Hz, 2H), 3.94(s, 2H), 6.68(dd, J=2.0, 8.7Hz, 1H), 6.75(d, J=2.0Hz, 1H), 6.82(d, J=8.7Hz, 1H), 7.61(d, J=2.7Hz, 1H), 7.63(d, J=2.7Hz, 1H), 9.43(s, 1H) |
| 693 | [1-(10H-pyrazino[2,3-b][1,4]benzothiazin-8-ylmethyl)piperidin-4-yl] carbamoylacetic acid | FAB(+) 400(MH⁺) | 149–151° C. | ¹H-NMR (DMSO-d₆) δ ppm: 1.28–1.41(m, 2H), 1.65–1.73(m, 2H), 1.93–2.02(m, 2H), 2.65–2.73(m, 2H), 3.07(s, 2H), 3.25(s, 2H), 3.43–3.55(m, 1H), 6.67(dd, J=1.3, 7.4Hz, 1H), 6.74(d, J=1.3Hz, 1H), 6.83(d, J=7.4Hz, 1H), 7.62(d, J=2.9Hz, 1H), 7.63(d, J=2.9Hz, 1H), 8.00(d, J=8.0Hz, 1H), 9.45(s, 1H) |
| 694 | [1-(10H-pyrazino[2,3-b][1,4]benzothiazin-8-ylmethyl)piperidin-4-ylidene] fluoroacetic acid | ESI(+) 373(MH⁺) | 167–173° C. | ¹H-NMR (DMSO-d₆) δ ppm: 2.34–2.39(m, 2H), 2.39–2.45(m, 4H), 2.75–2.81(m, 2H), 3.32(s, 2H), 6.71(d, J=7.9Hz, 1H), 6.76(s, 1H), 6.85(d, J=7.9Hz, 1H), 7.62(s, 2H), 9.46(s, 1H) |
| 695 | [1-(10H-pyrazino[2,3-b][1,4]benzothiazin-8-ylmethyl)piperidin-4-yl] fluoroacetic acid | ESI(+) 375(MH⁺) | 163° C. (decompose) | ¹H-NMR (DMSO-d₆) δ ppm: 1.35–1.52(m, 3H), 1.59–1.67(m, 1H), 1.70–1.88(m, 1H), 1.92–2.07(m, 2H), 2.83–2.91(m, 2H), 3.34(s, 2H), 4.77(dd, J=4.5, 49.2Hz, 1H), 6.70(d, J=7.7Hz, 1H), 6.74(s, 1H), 6.83(d, J=7.7Hz, 1H), 7.61(d, J=2.8Hz, 1H), 7.62(d, J=2.8Hz, 1H), 9.46(s, 1H) |
| 696 | [1-(10H-pyrazino[2,3-b][1,4]benzothiazin-8-ylmethyl)piperidin-4-yl] propiolic acid | ESI(+) 367(MH⁺) | 155–156° C. | ¹H-NMR (DMSO-d₆) δ ppm: 1.50–1.61(m, 2H), 1.76–1.85(m, 2H), 2.15–2.25(m, 2H), 2.54–2.72(m, 3H), 3.14(s, 2H), 6.71(dd, J=1.2, 7.7Hz, 1H), 6.74(d, J=1.2Hz, 1H), 6.84(d, J=7.7Hz, 1H), 7.61(d, J=2.5Hz, 1H), 7.63(d, J=2.5Hz, 1H), 9.47(s, 1H) |
| 697 | 4-[1-(10H-pyrazino[2,3-b][1,4]benzothiazin-7-ylmethyl)piperidin-4-yl]-2-methylbutanoic acid | ESI(+) 399(MH⁺) | 221–222° C. | ¹H-NMR (DMSO-d₆) δ ppm: 1.01(d, J=6.5Hz, 3H), 1.02–1.21(m, 5H), 1.24–1.38(m, 1H), 1.44–1.65(m, 3H), 1.79–1.99(m, 2H), 2.20–2.27(m, 1H), 2.69–2.82(m, 2H), 3.15(s, 2H), 6.69(d, J=7.9Hz, 1H), 6.80(br.s, 1H), 6.87(br.d, J=7.9Hz, 1H), 7.60(d, J=2.6Hz, 1H), 7.62(d, J=2.6Hz, 1H), 9.48(s, 1H) |

| Ex. | Structural formula | MS | M.p. | NMR |
|---|---|---|---|---|
| 698 | 1-[1-(10H-pyrazino[2,3-b][1,4]benzothiazin-7-ylmethyl)-4-piperidin-4-yl]cyclopropanecarboxylic acid | ESI(+) 383(MH+) | 228–231° C. | $^1$H-NMR (DMSO-d$_6$) δ ppm: 0.63–0.69(m, 2H), 0.90–0.95(m, 2H), 1.31–1.51(m, 5H), 1.71–1.84(m, 2H), 2.71–2.81(m, 2H), 3.20(s, 2H), 6.67(dd, J=1.6, 8.7Hz, 1H), 6.74(d, J=1.6Hz, 1H), 6.81(d, J=8.7Hz, 1H), 7.61(d, J=2.5Hz, 1H), 7.62 (d, J=2.5Hz, 1H), 9.43(s, 1H) |
| 699 | [1-(10H-pyrazino[2,3-b][1,4]benzothiazin-7-ylmethyl) piperidin-4-yl] carbamoylformic acid | FAB(+) 386(MH+) | 222–226° C. | $^1$H-NMR (DMSO-d$_6$) δ ppm: 1.52–1.66(m, 2H), 1.66–1.76(m, 2H), 2.21–2.35(m, 2H), 2.85–2.96(m, 2H), 3.51(s, 2H), 3.55–3.65(m, 1H), 6.74(d, J=7.7Hz, 1H), 6.85(s, 1H), 6.87(d, J=7.7Hz, 1H), 7.63(s, 2H), 8.48(d, J=9.0Hz, 1H), 9.52(s, 1H) |
| 700 | (E)-4-[1-(10H-pyrazino[2,3-b][1,4] benzothiazin-8-ylmethyl)piperidin-4-yl]-3-methyl-2-butenoic acid | ESI(+) 397(MH+) | 126–130° C. | $^1$H-NMR (CD$_3$OD) δ ppm: 1.30–1.45(m, 2H), 1.70–1.88(m, 3H), 2.07(d, J=1Hz, 3H), 2.09 (d, J=8Hz, 2H), 2.55–2.65(m, 2H), 3.20–3.30(m, 2H), 3.82(s, 2H), 5.66(d, J=1Hz, 1H), 6.70 (d, J=2Hz, 1H), 6.85(dd, J=2, 8Hz, 1H), 6.90(d, J=8Hz, 1H), 7.59(d, J=3Hz, 1H), 7.60(d, J=3Hz, 1H) |
| 701 | [1-(10H-pyrazino[2,3-b][1,4]benzothiazin-8-ylmethyl)-3,5-dimethylpiperidin-4-yl] acetic acid | ESI(+) 385(MH+) | 200° C. (decompose) | $^1$H-NMR (DMSO-d$_6$) δ ppm: 0.77(d, J=7Hz, 6H), 1.69(m, 2H), 1.82(m, 2H), 2.01(m, 2H), 2.09(m, 1H), 2.34(d, J=10Hz, 2H), 3.20(s, 2H), 6.67(d, J=8Hz, 1H), 6.73(s, 1H), 6.81(d, J=8Hz, 1H), 7.55–7.70(m, 2H), 9.45(s, 1H) |
| 702 | 4-[4-hydroxy-1-(10H-pyrazino[2,3-b][1,4] benzothiazin-8-ylmethyl)piperidin-4-yl] phenylacetic acid | FAB(+) 449(MH+) | 192° C. (decompose) | $^1$H-NMR (CD$_3$OD) δ ppm: 1.81–1.89(m, 2H), 2.15–2.28(m, 2H), 3.30–3.40(m, 4H), 3.56(s, 2H), 4.15(s, 2H), 6.82(s, 1H), 6.95–6.98(m, 2H), 7.28–7.32(m, 2H), 7.36–7.40(m, 2H), 7.61(d, J=2.9Hz, 1H), 7.62(d, J=2.9Hz, 1H) |
| 703 | [2-(10H-pyrazino[2,3-b][1,4] benzothiazin-8-ylmethyl)-2-azaspiro[3.5] non-7-yl] acetic acid | FAB(+) 397(MH+) | 145° C. (decompose) | $^1$H-NMR (CD$_3$OD) δ ppm: 0.93–1.06(m, 2H), 1.49–1.58(m, 2H), 1.64–1.77(m, 3H), 1.97–2.04(m, 2H), 2.08(d, J=6.8Hz, 2H), 3.67(s, 2H), 3.76(m, 2H), 4.07(s, 2H), 6.69(d, J=1.6Hz, 1H), 6.85(dd, J=1.6, 7.9Hz, 1H), 6.92(d, J=7.9Hz, 1H), 7.60(d, J=2.9Hz, 1H), 7.10(d, J=2.9Hz, 1H) |
| 704 | [2-(10H-pyrazino[2,3-b][1,4] benzothiazin-8-ylmethyl)-2-azaspiro[4.5]dec-8-yl]carboxlic acid | FAB(+) 397(MH+) | 146° C. (decompose) | $^1$H-NMR (CD$_3$OD) δ ppm: 1.39–1.62(m, 4H), 1.68–1.94(m, 6H), 2.12–2.23(m, 1H), 2.90, 3.04(s, total 2H), 3.16–3.24(m, 2H), 3.98, 4.02(s, total 2H), 6.72–6.76(m, 1H), 6.86–6.94(m, 2H), 7.58–7.63(m, 2H) |

-continued

| Ex. | Structural formula | MS | M.p. | NMR |
|---|---|---|---|---|
| 705 | sodium 4-[1-(10H-pyrazino[2,3-b][1,4]benzothiazin-8-ylmethyl)piperidin-4-yloxy] phenylacetate | FAB(+) 471(MH+) | 261–265° C. (decompose) | $^1$H-NMR (DMSO-d$_6$) δ ppm: 1.52–1.62(m, 2H), 1.83–1.92(m, 2H), 2.11–2.20(m, 2H), 2.56–2.66(m, 2H), 3.13(s, 2H), 3.27(s, 2H), 4.26(m, 1H), 6.69(d, J=7.9Hz, 1H), 6.72–6.83(m, 4H), 7.05–7.11(m, 2H), 7.59–7.63(m, 2H), 9.49(br.s, 1H) |
| 706 | 4-[[1-(10H-pyrazino[2,3-b][1,4]benzothiazin-8-ylmethyl)-piperidin-4-yl) methyloxy] phenylacetic acid | FAB(+) 463(MH+) | 225–230° C. | $^1$H-NMR (DMSO-d$_6$) δ ppm: 1.20–1.34(m, 2H), 1.52–1.62(m, 3H), 1.83–1.92(m, 2H), 2.75–2.82(m, 2H), 3.25(s, 2H), 3.38(s, 2H), 3.76(d, J=5.9Hz, 2H), 6.69(dd, J=1.5, 7.9Hz, 1H), 6.76(d, J=1.5Hz, 1H), 6.78–6.83(m, 3H), 7.08–7.13(m, 2H), 7.61(d, J=2.7Hz, 1H), 7.62(d, J=2.7Hz, 1H), 9.49(br.s, 1H) |
| 707 | 2-methoxy-4-[[1-(10H-pyrazino [2,3-b][1,4]benzothiazin-8-ylmethyl)piperidin-4-yl] phenylacetic acid | FAB(+) 463(MH+) | 171–177° C. (decompose) | $^1$H-NMR (CD$_3$OD) δ ppm: 1.86–2.00(m, 4H), 2.76(m, 1H), 2.88–2.97(m, 2H), 3.41–3.48(m, 2H), 3.52(s, 2H), 3.76(s, 3H), 4.04(s, 2H), 6.71(dd, J=1.6, 7.7Hz, 1H), 6.77(d, J=1.6Hz, 1H), 6.81(m, 1H), 6.91–6.96(m, 2H), 7.12 (d, J=7.7Hz, 1H), 7.60(d, J=2.9Hz, 1H), 7.61(d, J=2.9Hz, 1H) |
| 708 | 4-[1-[2-(10H-pyrazino[2,3-b][1,4]benzothiazin-8-yl) ethyl]piperidin-4-yl]-2-methylbutanoic acid | FAB(+) 413(MH+) | 229–230° C. (decompose) | $^1$H-NMR (DMSO-d$_6$) δ ppm: 0.95–1.21(m, 8H), 1.33(m, 1H), 1.48–1.64(m, 3H), 1.88(m, 2H), 2.26(m, 1H), 2.40(m, 2H), 2.46–2.56(m, 2H), 2.82–2.90(m, 2H), 6.24(s, 1H), 6.64(d, J=7.9Hz, 1H), 6.79(d, J=7.9Hz, 1H), 7.62(d, J=2.9Hz, 1H), 7.63(d, J=2.9Hz, 1H), 9.43(s, 1H) |
| 709 | [1-(10H-pyrazino[2,3-b][1,4]benzothiazin-8-ylmethyl)piperidin-4-yl] thioacetic acid | FAB(+) 389(MH+) | 148–152° C. | $^1$H-NMR (DMSO-d$_6$) δ ppm: 1.38–1.49(m, 2H), 1.86–2.04(m, 4H), 2.67–2.84(m, 3H), 3.23(s, 2H), 3.27(s, 2H), 6.70(dd, J=1.5, 7.7Hz, 1H), 6.77(d, J=1.5Hz, 1H), 6.84(d, J=7.7Hz, 1H), 7.64(d, J=2.7Hz, 1H), 7.65(d, J=2.7Hz, 1H), 9.46(s, 1H) |
| 710 | (E)-4-[1-(10H-pyrazino[2,3-b][1,4]benzothiazin-8-ylmethyl)piperidin-4-yl]-3-butenoic acid | | | $^1$H-NMR (CD$_3$OD) δ ppm: 1.42–1.56(m, 2H), 1.73–1.82(m, 2H), 2.00–2.20(m, 1H), 2.24–2.30(m, 2H), 2.84–2.88(m, 2H), 3.02—3.08(m, 2H), 3.58(s, 2H), 5.43(dd, J=6, 16Hz, 1H), 5.61–5.71(m, 1H), 6.68(s, 1H), 6.78–6.88(m, 2H), 7.56(d, J=3Hz, 1H), 7.58(d, J=3Hz, 1H) |

-continued

| Ex. | Structural formula | MS | M.p. | NMR |
|---|---|---|---|---|
| 711 | [3-(10H-pyrazino[2,3-b][1,4]benzothiazin-8-ylmethyl)-3-azabicyclo[3.3.0]oct-7-yl] acetic acid | ESI(+) 383(MH$^+$) | 112–117° C. | 1H-NMR (D$_2$O) δ ppm: 1.35–1.45(m, 2H), 1.90–2.10(m, 5H), 2.66–2.80(m, 2H), 2.92–3.03(m, 2H), 3.13–3.23(m, 2H), 3.80–3.90(m, 2H), 6.37–6.39(m, 1H), 6.50–6.59(m, 2H), 7.19–7.26(m, 2H) |
| 712 | [3-(10H-pyrazino[2,3-b][1,4]benzothiazin-8-ylmethyl)-3-azabicyclo[3.30]oct-7-yl] carboxylic acid | | | $^1$H-NMR (D$_2$O) δ ppm: 1.58–1.76(m, 4H), 2.65–2.70(m, 3H), 2.74–2.82(m, 2H), 3.39–3.48(m, 2H), 3.84(s, 2H), 6.35(d, J=1.6Hz, 1H), 6.51(d, J=8.0Hz, 1H), 6.56(dd, J=1.6, 8.0Hz, 1H), 7.18(d, J=2.0Hz, 1H), 7.22(d, J=2.0Hz, 1H) |
| 713 | [3-(10H-pyrazino[2,3-b][1,4]benzothiazin-8-ylmethyl)-3-azabicyclo[3.3.0]oct-7-yl] carboxylic acid | | | $^1$H-NMR (D$_2$O) δ ppm: 1.44–1.54(m, 2H), 2.06(dt, J=8.0, 13.6Hz, 2H), 2.59(quint, J=7.2Hz, 1H), 2.84(br.s, 2H), 3.08(br.s, 4H), 3.80(s, 2H), 6.32(d, J=1.6Hz, 1H), 6.39(d, J=8.0Hz, 1H), 6.48(dd, J=1.6, 8.0Hz, 1H), 7.11(d, J=3.2Hz, 1H), 7.16(d, J=3.2Hz, 1H) |
| 714 | [3-(10H-pyrazino[2,3-b][1,4]benzothiazin-8-ylmethyl)-3-azabicyclo[3.3.0]oct-7-yl] acetic acid | ESI(+) 383(MH$^+$) | 110–115° C. | $^1$H-NMR (D$_2$O) δ ppm: 0.82–0.95(m, 2H), 1.86–2.10(m, 5H), 2.65–2.80(m, 2H), 2.88–3.03(m, 2H), 3.07–3.23(m, 2H), 3.85(s, 2H), 6.37(d, J=1.6Hz, 1H), 6.51(d, J=8.0Hz, 1H), 6.56(dd, J=1.6, 8.0Hz, 1H), 7.17–7.21(m, 1H), 7.21–7.26(m, 1H) |
| 715 | sodium [6-(10H-pyrazino[2,3-b][1,4]benzothiazin-8-ylmethyl)-6-azaspiro[3.4]oct-2-yl] acetate | ESI(+) 383(M − Na + 2H)$^+$ | 203–214° C. (decompose) | $^1$H-NMR (D$_2$O) δ ppm: 1.60–1.72(m, 2H), 1.90–2.15(m, 6H), 2.25–2.48(m, 1H), 3.00–3.28(m, 4H), 3.85(s, ⅞H), 3.88(s, ⅜H), 6.34–6.39(m, 1H), 6.50–6.59(m, 2H), 7.17–7.20(m, 1H), 7.21–7.25(m, 1H) |
| 716 | sodium [3-(10H-pyrazino[2,3-b][1,4]benzothiazin-8-yl-methyl)-3-azabicyclo[3.3.0]octane-7-spirocyclobut-3′-yl] acetate | ESI(+) 423(M − Na + 2H)$^+$ | 231–235° C. | $^1$H-NMR (D$_2$O) δ ppm: 1.02–1.28(m, 3H), 1.36–1.56(m, 2H), 1.62–1.84(m, 3H), 1.94–2.08(m, 2H), 2.12–2.48(m, 5H), 2.56–2.74(m, 2H), 3.35(s, 2H), 6.34(s, 1H), 6.39(s, 2H), 7.25(d, J=2.4Hz, 1H), 7.30(d, J= 2.4Hz, 1H) |
| 717 | sodium [8-(10H-pyrazino[2,3-b][1,4]benzothiazin-8-ylmethyl)-8-azabicyclo[4.3.0]non-3-yl] acetate | ESI(+) 397(M − Na + 2H)$^+$ | 126–130° C. | $^1$H-NMR (D$_2$O) δ ppm: 0.63—0.90(m, 2H), 1.25–1.55(m, 5H), 1.80–2.35(m, 4H), 2.68(d, J=10.8Hz, 1H), 2.80–3.13(m, 2H), 2.88(d, J=10.4Hz, 1H), 3.68(dd, J=13.2, 22.4Hz, 2H), 6.31(s, 1H), 6.38(d, J= 8.0Hz, 1H), 6.48(d, J=8.0Hz, 1H), 7.13–7.16(m, 1H), 7.16–7.21(m, 1H) |

-continued

| Ex. | Structural formula | MS | M.p. | NMR |
|---|---|---|---|---|
| 718 | sodium [3-(10H-pyrazino[2,3-b][1,4]benzothiazin-8-ylmethyl)-3-azabicyclo[3.3.0]octane-7-spirocyclobut-3'-yl] carboxylate | ESI(+) 409(M − Na + 2H)$^+$ | 232–243° C. (decompose) | $^1$H-NMR (D$_2$O) δ ppm: 1.08–1.10(m, 2H), 1.44–1.54(m, 1H), 1.60–2.02(m, 7H), 2.18–2.40(m, 4H), 2.66(quint, J=8.8Hz, 1H), 3.09(br.s, 2H), 6.28(s, 1H), 6.31(d, J=7.6Hz, 1H), 6.35(d, J=7.6Hz, 1H), 7.25(d, J=2.8Hz, 1H), 7.31(d, J=2.8Hz, 1H) |
| 719 | sodium [6-(10H-pyrazino[2,3-b][1,4]benzothiazin-8-ylmethyl)-6-azaspiro[3.4]oct-2-yl] carboxylate | | | $^1$H-NMR (D$_2$O) δ ppm: 1.60–1.68(m, 1H), 1.73–1.82(m, 1H), 1.88–2.03(m, 4H), 2.32–2.48(m, 4H), 2.58–2.82(m, 1H), 3.12–3.20(m, 2H), 6.21–6.26(m, 1H), 6.37–6.45(m, 2H), 7.14–7.20(m, 2H) |
| 720 | sodium [8-(10H-pyrazino[2,3-b][1,4]benzothiazin-8-ylmethyl)-8-azabicyclo[4.3.0]non-3-yl] carboxylate | | | $^1$H-NMR (DMSO-d$_6$) δ ppm: 1.18–1.82(m, 8H), 2.10–2.20(m, 1H), 2.28(dd, J=2.4, 8.8Hz, ⅔H), 2.34(dd, J=2.4, 8.8Hz, ⅓H), 2.44–2.57(m, 2H), 2.67(dd, J=6.0, 8.8Hz, ⅓H), 2.74(dd, J=6.0, 8.8Hz, ⅔H), 3.40–3.54(m, 2H), 6.70(dd, J=1.6, 8.0Hz, ⅓H), 6.71(dd, J=1.6, 8.0Hz, ⅔H), 6.78–6.81(m, 1H), 6.82(d, J=8.0Hz, ⅓H), 6.82(d, J=8.0Hz, ⅔H), 7.63(d, J=2.8Hz, 1H), 7.64(d, J=2.8Hz, 1H), 9.54(s, 1H) |
| 721 | sodium [3-(10H-pyrazino[2,3-b][1,4]benzothiazin-8-yl-methyl)-3-azabicyclo[4.1.0]hept-6-yl] acetate | ESI(+) 369(M − Na + 2H)$^+$ | 152–156° C. (decompose) | $^1$H-NMR (CD$_3$OD) δ ppm: 0.50(t, J=4.8Hz, 1H), 0.60–0.66(m, 1H), 0.96–1.04(m, 1H), 1.84–2.28(m, 6H), 2.52–2.59(m, 1H), 2.78(dd, J=6.0, 11.6Hz, 1H), 3.25(d, J=13.2Hz, 1H), 3.27(d, J=13.2Hz, 1H), 6.67(d, J=1.2Hz, 1H), 6.72–6.80(m, 2H), 7.54(d, J=2.8Hz, 1H), 7.57(d, J=2.8Hz, 1H) |
| 722 | sodium [7-(10H-pyrazino[2,3-b][1,4]benzothiazin-8-ylmethyl)-6-methyl-7-azaspiro[5.3]non-2-yl] acetate | ESI(+) 411(M − Na + 2H)$^+$ | 226–234° C. (decompose) | $^1$H-NMR (CD$_3$OD) δ ppm: 1.13–1.24(m, 3H), 1.28–1.58(m, 5H), 1.66–2.10(m, 4H), 2.18–2.36(m, 3H), 2.51–2.72(m, 2H), 3.03(d, J=13.2Hz, ½H), 3.04(d, J=13.2Hz, ½H), 3.87(d, J=13.2Hz, ½H), 3.89(d, J=13.2Hz, ½H), 6.64(m, 1H), 6.72–6.80(m, 2H), 7.53–7.58(m, 2H) |
| 723 | sodium [7-(10H-pyrazino[2,3-b][1,4]benzothiazin-8-ylmethyl)-6-methyl-7-azaspiro[5.3]non-2-yl]carboxylate | ESI(+) 397(M − Na + 2H)$^+$ | 253–265° C. (decompose) | $^1$H-NMR (CD$_3$OD) δ ppm: 1.15(d, J=6.0Hz, 1H), 1.21(d, J=6.0Hz, 2H), 1.26–2.07(m, 9H), 2.18–2.33(m, 1H), 2.57–2.71(m, 1H), 2.82–2.94(m, 1H), 3.02(d, J=13.2Hz, ⅔H), 3.86(d, J=13.6Hz, ⅓H), 3.87(d, J=13.2Hz, ⅔H), 6.64–6.67(m, 1H), 6.73–6.81(m, 2H), 7.53–7.58(m, 2H) |

| Ex. | Structural formula | MS | M.p. | NMR |
|---|---|---|---|---|
| 724 | 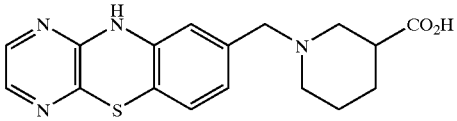<br>[1-(10H-pyrazino[2,3-b][1,4]benzothiazin-8-ylmethyl)piperidin-4-yl] carboxylic acid | | | $^1$H-NMR (DMSO-d$_6$) δ ppm: 1.00–1.20(m, 1H), 1.30–1.40(m, 1H), 1.45–1.60(m, 1H), 1.60–1.85(m, 2H), 1.95–2.10(m, 1H), 2.30–2.50(m, 1H), 2.50–2.70(m, 1H), 2.70–2.90(m, 1H), 3.15(d, J=10Hz, 1H), 3.24(d, J=10Hz, 1H), 6.65(d, J=8Hz, 1H), 6.70(s, 1H), 6.80(d, J=8Hz, 1H), 7.60(s, 2H), 9.47(s, 1H) |
| 725 | 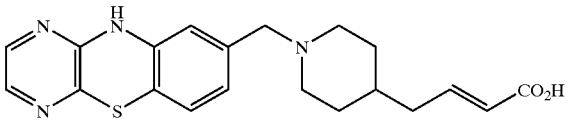<br>4-[1-(10H-pyrazino[2,3-b][1,4]benzothiazin-8-ylmethyl)piperidin-4-yl]-2-butenoic acid | FAB(+)<br>383(MH$^+$) | | $^1$H-NMR (DMSO-d$_6$) δ ppm: 1.05–1.20(m, 2H), 1.25–1.40(m, 1H), 1.50–1.60(m, 2H), 1.75–1.90(m, 4H), 2.00–2.10(m, 2H), 3.15(s, 2H), 5.70(d, J=16Hz, 1H), 6.65(d, J=8Hz, 1H), 6.75(s, 1H), 6.80(d, J=8Hz, 1H), 6.82(dt, J=6, 16Hz, 1H), 7.60(s, 2H), 9.42(br.s, 1H) |
| 726 | 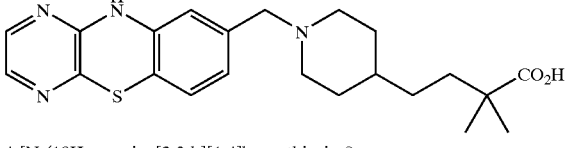<br>4-[N-(10H-pyrazino[2,3-b][1,4]benzothiazin-8-ylmethyl) piperidine-2,2-dimethylbutanoic acid | FAB(+)<br>413(MH$^+$) | 180–185° C. | $^1$H-NMR (DMSO-d$_6$) δ ppm: 1.10(s, 6H), 1.00–1.30(m, 5H), 1.30–1.40(m, 2H), 1.45–1.60(m, 2H), 1.75–1.85(m, 2H), 3.20(s, 2H), 3.20–3.30(m, 2H), 6.67(d, J=8Hz, 1H), 6.72(s, 1H), 6.82(d, J=8Hz, 1H), 7.60(br.s, 2H), 9.42(br.s, 1H) |
| 727 | 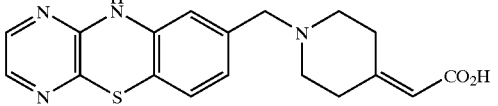<br>[1-(10H-pyrazino[2,3-b][1,4]benzothiazin-8-ylmethyl)piperidin-4-ylidenle] acetic acid | FAB(+)<br>355(MH$^+$) | 214–216° C. | $^1$H-NMR (DMSO-d$_6$) δ ppm: 2.24(br.m, 2H), 2.42(br.s, 4H), 2.83(br.s, 2H), 3.33(s, 2H), 5.59(s, 1H), 6.72(d, J=8Hz, 1H), 6.77(s, 1H), 6.85(d, J=8Hz, 1H), 7.63(s, 2H), 9.45(s, 1H), 12.01(br.s, 1H) |
| 728 | 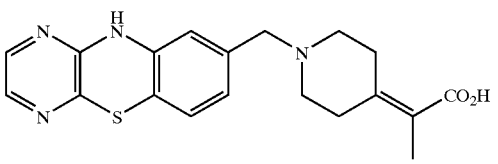<br>2-[1-(10H-pyrazino[2,3-b][1,4]benzothiazin-8-ylmethyl)piperidin-4-ylidene] propanoic acid | FAB(+)<br>369(MH$^+$) | 125–127° C. | $^1$H-NMR (DMSO-d$_6$) δ ppm: 1.34(s, 3H), 2.26(m, 2H), 2.34(m, 4H), 2.53(m, 2H), 3.26(s, 2H), 6.70(d, J=8Hz, 1H), 6.77(s, 1H), 6.84(d, J=8Hz, 1H), 7.63(s, 2H), 9.44(s, 1H) |
| 729 | 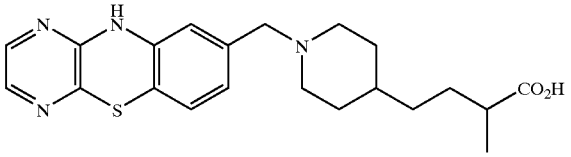<br>4-[1-(10H-pyrazino[2,3-b][1,4]benzothiazin-8-ylmethyl)piperidin-4-yl]-2-methylbutanoic acid | FAB(+)<br>399 (MH$^+$),<br>421(M + Na$^+$) | 149–152° C. | $^1$H-NMR (DMSO-d$_6$) δ ppm: 1.00–1.20(m, 4H), 1.14(d, J=6Hz, 3H), 1.21–1.40(m, 1H), 1.42–1.60(m, 4H), 1.78–1.90(m, 2H), 2.20–2.30(m, 1H), 2.68–2.78(m, 2H), 3.22(s, 2H), 6.67(d, J=8Hz, 1H), 6.74(s, 1H), 6.80(d, J=8Hz, 1H), 7.62(s, 2H), 9.43(s, 1H) |
| 730 | 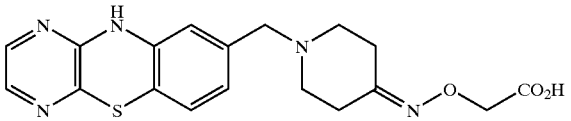<br>N-[1-(10H-pyrazino[2,3-b][1,4]benzothiazin-8-ylmethyl)piperidin-4-ylidene] aminoxyacetic acid | FAB(+)<br>368(MH$^+$) | 128–131° C. | $^1$H-NMR (DMSO-d$_6$) δ ppm: 2.21(m, 2H), 2.38(m, 2H), 2.45(m, 2H), 2.50(m, 2H), 3.33(s, 2H), 4.43(s, 2H), 6.72(dd, J=1, 8Hz, 1H), 6.77(d, J=1Hz, 1H), 6.83(d, J=8Hz, 1H), 7.63(s, 2H), 9.45(br.s, 1H) |

| Ex. | Structural formula | MS | M.p. | NMR |
|---|---|---|---|---|
| 731 | 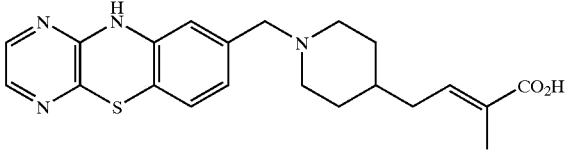<br>(E)-4-[1-(10H-pyrazino[2,3-b][1,4]benzothiazin-8-ylmethyl)piperidin-4-yl]-2-methyl-2-butenoic acid | FAB(+) 397(MH⁺) | 91–93° C. | ¹H-NMR (CD₃OD) δ ppm: 1.48(m, 1H), 1.72(m, 1H), 1.81(s, 3H), 1.85–1.95(m, 3H), 2.21(m, 2H), 2.79(br.t, J=12Hz, 2H), 3.35(m, 2H), 3.98(s, 2H), 6.70(t, J=7Hz, 1H), 6.74(d, J=2Hz, 1H), 6.88(dd, J=2, 8Hz, 1H), 6.92(s, 1H), 6.93(d, J= 8Hz, 1H), 7.60(s, 2H) |
| 732 | 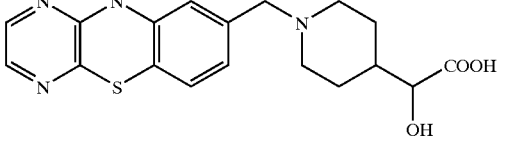<br>2-hydroxy-[1-(10H-pyrazino[2,3-b][1,4]benzothiazin-8-ylmethyl)piperidin-4-yl] acetic acid | | 98–99° C. | ¹H-NMR (DMSO-d₆) δ ppm: 1.26–1.59(m, 5H), 1.71–1.85(m, 2H), 2.77(m, 2H), 3.22(s, 2H), 3.46(m, 1H), 6.67(d, J=8Hz, 1H), 6.75(s, 1H), 6.81(d, J=8Hz, 1H), 7.61(s, 2H), 9.45(s, 1H) |
| 733 | 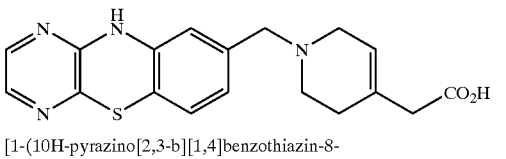<br>[1-(10H-pyrazino[2,3-b][1,4]benzothiazin-8-ylmethyl)-3,4-dehydropiperidin-4-yl] acetic acid | | 124–128° C. | ¹H-NMR (DMSO-d₆) δ ppm: 2.11(br.s, 2H), 2.56(br.s, 1H), 2.91(s, 2H), 2.94(br.s, 1H), 3.32(br.s, 4H), 5.48(s, 1H), 6.77(d, J=8Hz, 1H), 6.78(s, 1H), 6.86(d, J=8Hz, 1H), 7.63(s, 2H), 9.49(br.s, 1H) |
| 734 | 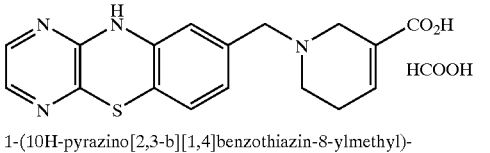<br>1-(10H-pyrazino[2,3-b][1,4]benzothiazin-8-ylmethyl)-3,4-dehydro-3-piperidinecarboxylic acid formate acid | FAB(+) 341(MH⁺) | 178–180° C. | ¹H-NMR (DMSO-d₆) δ ppm: 2.24(br.m 2H), 2.43(t, J=3Hz, 2H), 2.95(br.s, 2H), 3.39(s, 2H), 6.72(d, J=4Hz, 1H), 6.78(s, 1H), 6.81(br.m, 1H), 6.84(d, J=4Hz, 1H), 7.63(s, 2H), 8.33(s, 1H), 9.46(s, 1H) |

Example 735

1-(10H-Pyrazino[2,3-b][1,4]benzothiazin-8-ylmethyl)-2,3-dehydro-3-piperidinecarboxylic acid To a solution of 0.126 g of ethyl 1-(10H-pyrazino[2,3-b][1,4]benzothiazin-8-ylmethyl)-2,3-dehydro-3-piperidinecarboxylate in dimethyl sulfoxide (6 ml) were added in a nitrogen atmosphere 0.018 g of water and 0.448 g of tert-butoxypotassium and the resulting mixture was reacted for 16 hours. After pouring into water, the solution was neutralized with sodium dihyrogenphosphate. The precipitate thus formed was taken up by filtration, washed successively with a small portion of water and dichloromethane and dissolved in dichloromethane. The obtained solution was dried over magnesium sulfate. After filtering off the insoluble matters, the solution was concentrated to 5 ml under reduced pressure. Then diethyl ether (10 ml) was added thereto and the crystals thus precipitated were taken up by filtration to thereby give 0.035 g of the title compound as pale yellow crystals.

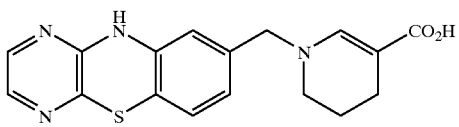

¹H-NMR(CD₃OD) δ ppm: 1.81(quint, J=6 Hz, 2H), 2.23 (t, J=6 Hz, 2H), 3.19(t, J=6 Hz, 2H), 4.20(s, 2H), 6.59(d, J=1 Hz, 1H), 6.71(dd, J=1, 7 Hz, 1H), 6.85(d, J=7 Hz, 1H), 7.57(d, J=3 Hz, 1H), 7.57(d, J=3 Hz, 1H), 7.58(1H, s)

MS: FAB(+)340(MH⁺⁾ m.p.: 158–160° C.

Example 736

N-[1-(10H-Pyrazino[2,3-b][1,4]benzothiazin-8-ylmethyl)-piperidin-4-yl)sulfamoylacetic acid To a solution of (2-trimethylsilylethyl) N-[1-(10H-pyrazino[2,3-b][1,4]benzothiazin-8-ylmethyl)piperidin-4-yl)sulfamoylacetate in tetrahydrofuran (30 ml) was added in a nitrogen atmosphere at 0° C. 5.4 ml of a 1 M solution of tetra-n-butylammonium fluoride in tetrahydrofuran and the resulting mixture was stirred at 0° C. for 1 hour and then at room temperature for 2 hours. The reaction mixture was concentrated under reduced pressure and the residue was purified by High-porous gel chromatography (CHP20P, mfd. by Mitsubishi Chemical Industries, 45–150μ) (eluted with methanol/water). The compound thus obtained was dissolved again in a 5 N aqueous solution of sodium hydroxide (100 ml) and washed with dichloromethane. Then the aqueous layer was neutralized with sodium dihydrogenphosphate and treated by High-porous gel chromatography (CHP20P, mfd by Mitsubishi Chemical Industries, 75–150μ) (eluted with methanol/water) again. Thus 0.190 g of the title compound was obtained as pale yellow crystals.

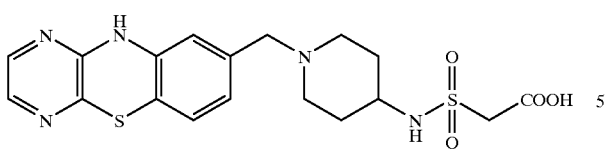

$^1$H-NMR(CD$_3$OD) δ ppm: 1.55–1.62(m, 4H), 1.98(d, J=10 Hz, 2H), 2.15(d, J=10 Hz, 2H), 2.81(d, J=10 Hz, 1H), 3.2(m, 1H), 3.35(s, 2H), 3.85(s, 2H), 6.66(d, J=1 Hz, 1H), 6.76(dd, J=1, 8 Hz, 1H), 6.80(d, J=8 Hz, 1H), 7.55(d, J=3 Hz, 1H), 7.57(d, J=3 Hz, 1H)

MS: FAB(+)436(MH$^+$)

m.p.: 200–210° C.

Examples 737 to

The following compounds were obtained by the same method as the one of Example 8.

| Ex. | Structural formula | MS | M.p. | NMR |
|---|---|---|---|---|
| 737 | 3-[1-(10H-pyrazino[2,3-b][1,4]benzothiazin-8-ylmethyl)piperidin-4-yl]butanoic acid | FAB (+) 385 (MH+) | 218–220° C. | $^1$H-NMR (DMSO-d$_6$) δ ppm: 0.82 (d, J = 6.8 Hz, 3H), 1.48–1.55 (m, 3H), 1.69–1.95 (m, 5H), 2.24–2.30 (m, 2H), 2.75–2.82 (m, 2H), 3.22 (s, 2H), 6.67 (d, J = 8.0 Hz, 1H), 6.75 (s, 1H), 6.81 (d, J = 8.0 Hz, 1H), 7.61 (d, J = 2.8 Hz, 1H), 7.63 (d, J = 2.8 Hz, 1H), 9.43 (s, 1H) |
| 738 | [1-(10H-pyrazino[2,3-b][1,4]benzothiazin-8-ylmethyl)-4-phenylpiperidin-4-yl]carboxylic acid | ESI (+) 419 (MH$^+$) | >297° C. | $^1$H-NMR (DMSO-d$_6$) δ ppm: 1.78–1.90 (m, 2H), 2.14–2.26 (m, 2H), 2.36–2.46 (m, 2H), 2.68–2.80 (m, 2H), 3.30–3.40 (m, 2H), 6.73 (d, J = 8 Hz, 1H), 6.76 (s, 1H), 6.84 (d, J = 8 Hz, 1H), 7.24 (t, J = 7 Hz, 1H), 7.33 (t, J = 7 Hz, 2H), 7.37 (d, J = 7 Hz, 2H), 7.62 (d, J = 2 Hz, 1H), 7.63 (d, J = 2 Hz, 1H), 9.46 (s, 1H) |
| 739 | [1-(10H-pyrazino[2,3-b][1,4]benzothiazin-8-ylmethyl)-4-(p-methoxyphenyl)piperidin-4-yl]carboxylic acid | FAB (+) 499 (MH$^+$) | >295° C. | $^1$H-NMR (DMSO-d$_6$) δ ppm: 1.70–1.90 (m, 2H), 2.10–2.20 (m, 2H), 2.30–2.45 (m, 2H), 2.60–2.80 (m, 2H), 3.30 (m, 2H), 3.71 (s, 3H), 6.68–6.74 (m, 1H), 6.76 (d, J = 2 Hz, 1H), 6.84 (d, J = 8 Hz, 1H), 6.88 (d, J = 9 Hz, 2H), 7.28 (d, J = 9 Hz, 2H), 7.62 (d, J = 3 Hz, 1H), 7.63 (d, J = 3 Hz, 1H), 9.45 (s, 1H) |
| 740 | [1-(10H-pyrazino[2,3-b][1,4]benzothiazin-8-ylmethyl)-4-(p-hydroxyphenyl)piperidin-4-yl]carboxylic acid | FAB (+) 435 (MH$^+$) | 260–262° C. | $^1$H-NMR (DMSO-d$_6$) δ ppm: 1.60–1.80 (m, 2H), 1.90–2.12 (m, 2H), 2.20–2.40 (m, 2H) 2.54–2.72 (m, 2H), 3.23 (m, 2H), 6.69 (d, J = 8 Hz, 1H), 6.69 (d, J = 9 Hz, 2H), 6.75 (s, 1H), 6.82 (d, J = 8 Hz, 1H), 7.15 (d, J = 9 Hz, 2H), 7.62 (s, 2H), 9.32 (s, 1H), 9.42 (s, 1H) |

| Ex. | Structural formula | MS | M.p. | NMR |
|---|---|---|---|---|
| 741 | [1-[3-(10H-pyrazino[2,3-b][1,4]benzothiazin-8-yl)propyl]piperidin-4-yl]carboxylic acid | ESI (+) 371 (MH$^+$) | 262–264° C. | $^1$H-NMR (DMSO-d$_6$) δ ppm: 1.46–1.66 (m, 4H), 1.70–1.80 (m, 2H), 1.84–1.96 (m, 2H), 2.10–2.20 (m, 1H), 2.21 (t, J = 7 Hz, 2H), 2.38 (t, J = 8 Hz, 2H), 2.7–2.8 (m, 2H), 6.60 (s, 1H), 6.62 (d, J = 8 Hz, 1H), 6.78 (d, J = 8 Hz, 1H), 7.60 (d, J = 3 Hz, 1H), 7.62 (d, J = 3 Hz, 1H), 9.41 (s, 1H) |
| 742 | 4-[1-[(10H-pyrazino[2,3-b][1,4]benzothiazin-8-yl)carbonyl]piperidin-4-yl]-2-methylbutanoic acid | FAB (+) 427 (MH$^+$) | 275–280° C. | $^1$H-NMR (DMSO-d$_6$) δ ppm: 0.93–1.08 (m, 2H), 1.02 (d, J = 8 Hz, 3H), 1.13–1.23 (m, 2H), 1.28–1.40 (m, 1H), 1.40–1.76 (m, 4H), 2.21–2.32 (m, 1H), 2.58–2.73 (m, 1H), 2.86–3.01 (m, 1H), 3.50–3.65 (m, 1H), 4.27–4.43 (m, 1H), 6.71 (d, J = 1.7 Hz, 1H), 6.74 (dd, J = 1.7, 7.7 Hz, 1H), 6.94 (d, J = 7.7 Hz, 1H), 7.64 (d, J = 2.9Hz, 1H), 9.58 (s, 1H) |
| 743 | 4-[1-(10H-pyrazino[2,3-b]pyrido[3,2-e][1,4]thiazin-8-ylmethyl)piperidin-4-yl]-2-methylbutanoic acid | FAB (+) 400 (MH$^+$) | 115–118° C. | $^1$H-NMR (DMSO-d$_6$) δ ppm: 1.01 (d, J = 7.1 Hz, 3H), 1.03–1.22 (m, 5H), 1.25–1.37 (m, 1H), 1.44–1.55 (m, 1H), 1.55–1.66 (m, 2H), 1.78–2.01 (m, 2H), 2.18–2.29 (m, 1H), 2.68–2.83 (m, 2H), 3.32 (s, 2H), 6.94 (br.d, J = 1.9 Hz, 1H), 7.63 (s, 2H), 7.69 (br.d, J = 1.9 Hz, 1H), 9.49–9.60 (br.s, 1H) |
| 744 | [4-[(10H-pyrazino[2,3-b][1,4]benzothiazin-8-ylmethyl)amino]piperidin-1-yl]acetic acid | FAB (+) 372 (MH$^+$) | 148–152° C. | $^1$H-NMR (DMSO-d$_6$) δ ppm: 1.38–1.54 (m, 2H), 1.80–1.90 (m, 2H), 2.40–2.50 (m, 1H), 2.60–2.70 (m, 2H), 3.10–3.22 (m, 2H), 3.14 (s, 2H), 3.51 (s, 2H), 6.74 (d, J = 8.0 Hz, 1H), 6.75 (s, 1H), 6.81 (d, J = 8.0 Hz, 1H), 7.60 (d, J = 2.8 Hz, 1H), 7.62 (d, J = 2.8 Hz, 1H), 9.45 (s, 1H) |

| Ex. | Structural formula | MS | M.p. | NMR |
|---|---|---|---|---|
| 745 | 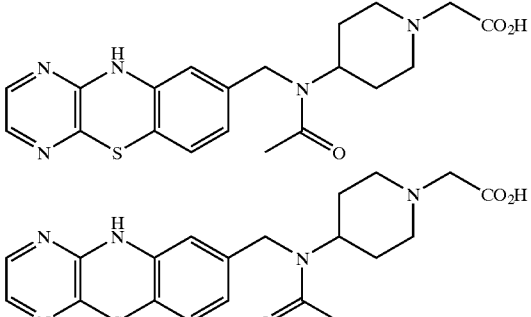<br>[4-[(10H-pyrazino[2,3-b][1,4]benzothiazin-8-ylmethyl)acetylamino]piperidin-1-yl]acetic acid (1:1 mixture) | FAB (+) 400 (MH+) | 185–191° C. | $^1$H-NMR (DMSO-$d_6$) δ ppm: 1.45–1.53 and 1.53–1.61 (m, total 2H), 1.63–1.79 (m, total 2H), 2.01 and 2.14 (s, total 3H), 2.40–2.49 (m, total 2H), 2.981–3.08 (m, total 2H), 3.09 and 3.10 (s, total 2H), 3.68–3.82 and 4.24–4.38 (m, total 1H), 4.28 and 4.35 (s, 2H), 6.61 and 6.65 (dd, J = 1.7, 8.0 Hz, total 1H), 6.62 and 6.70 (d, J = 1.7 Hz, total 1H), 6.80 and 6.88 (d, J = 8.0 Hz, total 1H), 7.61 and 7.62 (d, J = 3.0 Hz, total 1H), 7.62 and 7.63 (d, J = 3.0 Hz, total 1H), 9.44 and 9.49 (s, total 1H) |
| 746 | 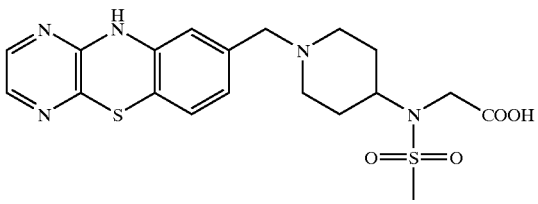<br>N-(methanesulfonyl)-N-[1-(10H-pyrazino[2,3-b][1,4]benzothiazin-8-ylmethyl)piperidin-4-yl]aminoacetic acid | FAB (+) 450 (MH+) | 210–215° C. | $^1$H-NMR (DMSO-$d_6$) δ ppm: 1.52–1.70 (m, 4H), 1.86–1.98 (m, 2H), 2.72–2.80 (m, 2H), 3.08 (s, 3H), 3.23 (s, 2H), 3.38–3.48 (m, 1H), 3.68 (s, 2H), 6.66 (d, J = 8.0 Hz, 1H), 6.75 (s, 1H), 6.81 (d, J = 8.0 Hz, 1H), 7.61 (d, J = 2.8 Hz, 1H), 7.62 (d, J = 2.8 Hz, 1H), 9.44 (s, 1H) |
| 747 | 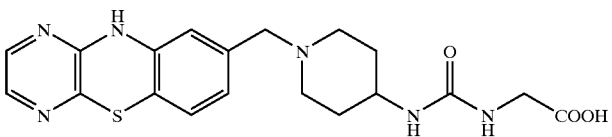<br>[1-(10H-pyrazino[2,3-b][1,4]benzothiazin-8-ylmethyl)piperidin-4-yl]carbamoyl]aminoacetic acid | FAB (+) 415 (MH+) | 207–210° C. | $^1$H-NMR (DMSO-$d_6$) δ ppm: 1.20–1.35 (m, 3H), 1.66–1.75 (m, 2H), 1.94–2.04 (m, 2H), 2.60–2.69 (m, 2H), 3.24 (s, 2H), 3.64 (d, J = 5.6 Hz, 2H), 5.93 (t, J = 5.6 Hz, 1H), 6.10 (d, J = 7.2 Hz, 1H), 6.68 (d, J = 8.0 Hz, 1H), 6.74 (s, 1H), 6.82 (d, J = 8.0 Hz, 1H), 7.61 (d, J = 2.8 Hz, 1H), 7.63 (d, J = 2.8 Hz, 1H), 9.43 (s, 1H) |
| 748 | 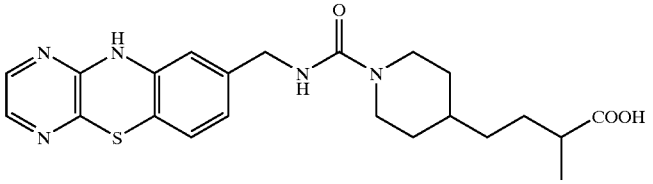<br>4-[1-[(10H-pyrazino[2,3-b][1,4]benzothiazin-8-ylmethyl)carbamoyl]piperidin-4-yl]-2-butanoic acid | FAB (+) 442 (MH+) | 94–98° C. | $^1$H-NMR (DMSO-$d_6$) δ ppm: 0.85–1.00 (m, 2H), 1.02 (d, J = 6.0 Hz, 3H), 1.10–1.22 (m, 3H), 1.26–1.40 (m, 2H), 1.50–1.62 (m, 2H), 2.20–2.32 (m, 1H), 2.55–2.65 (m, 2H), 3.85–3.95 (m, 2H), 4.02 (d, J = 5.2 Hz, 2H), 6.62–6.68 (m, 1H), 6.65 (s, 1H), 6.81 (d, J = 8.0 Hz, 1H), 6.93 (d, J = 8.0 Hz, 1H), 7.61 (d, J = 2.8 Hz, 1H), 7.63 (d, J = 2.8 Hz, 1H), 9.51 (s, 1H) |

-continued

| Ex. | Structural formula | MS | M.p. | NMR |
|---|---|---|---|---|
| 749 | N-(10H-pyrazino[2,3-b][1,4]benzothiazin-8-ylmethyl)-N-[1-(methanesulfonyl)piperidin-4-yl]aminoacetic acid | FAB (+) 450 (MH$^+$) | 185–189° C. (decompose) | $^1$H-NMR (DMSO-d$_6$) δ ppm: 1.32–1.45 (m, 3H), 1.82–1.90 (m, 2H), 2.57–2.70 (m, 2H), 2.80 (s, 3H), 3.15 (s, 2H), 3.44–3.56 (m, 2H), 3.62 (s, 2H), 6.74 (d, J = 8.0 Hz, 1H), 6.78 (d, J = 8.0 Hz, 1H), 6.79 (s, 1H), 7.59 (d, J = 2.8 Hz, 1H), 7.61 (d, J = 2.8 Hz, 1H), 9.45 (s, 1H) |
| 750 | 2,2-dimethyl-5-[4-(10H-pyrazino[2,3-b][1,4]benzothiazin-8-ylmethyl)piperazin-1-yl]pentanoic acid | FAB (+) 428 (MH$^+$) | 240–242° C. | $^1$H-NMR (DMSO-d$_6$) δ ppm: 1.05 (s, 6H), 1.26–1.35 (m, 2H), 1.38–1.42 (m, 2H), 2.18 (t, J = 7 Hz, 2H), 2.30 (br.s, 8H), 3.23 (s, 2H), 6.68 (dd, J = 1, 8 Hz, 1H), 6.74 (d, J = 1 Hz, 1H), 6.83 (d, J = 8 Hz, 1H), 7.62 (d, J = 3 Hz, 1H), 7.63 (d, J = 3 Hz, 1H), 9.44 (s, 1H) |
| 751 | 2,2-dimethyl-4-[4-(10H-pyrazino[2,3-b][1,4]benzothiazin-8-ylmethyl)piperazin-1-yl]pentanoic acid dihydrochloride 2HCl | FAB (+) 428 (MH$^+$) | >275° C. | $^1$H-NMR (DMSO-d$_6$) δ ppm: 1.06 (s, 6H), 1.43 (m, 2H), 1.65 (m, 2H), 3.05 (br.s, 2H), 3.44 (br.s, 4H), 3.50 (br.s, 4H), 4.16 (s, 2H), 6.86 (br.s, 1H), 6.98 (d, J = 8 Hz, 1H), 7.12 (br.d, J = 8 Hz, 1H), 7.64 (d, J = 3 Hz, 1H), 7.65 (d, J = 3 Hz, 1H), 9.70 (s, 1H) |

Examples

The following compounds were obtained by the same method as the one of Example 9.

| Ex. | Structural formula | MS | M.p. | NMR |
|---|---|---|---|---|
| 752 | [1-(10H-pyrazino[2,3-b][1,4]benzothiazin-8-ylmethyl)piperidin-4-yl]acetic acid | FAB (+) 357 (MH$^+$), 379 (MNa$^+$) | 142–146° C. | $^1$H-NMR (DMSO-d$_6$) δ ppm: 1.05–1.25 (m, 2H), 1.50–1.65 (m, 3H), 1.83–1.90 (m, 2H), 2.03 (d, J = 6 Hz, 2H), 2.70–2.75 (m, 2H), 3.22 (s, 2H), 6.66 (d, J = 8 Hz, 1H), 6.74 (s, 1H), 6.80 (d, J = 8 Hz, 1H), 7.62 (s, 2H), 9.40 (s, 1H) |
| 753 | 4-[1-(10H-pyrazino[2,3-b][1,4]benzothiazin-8-ylmethyl)piperidin-4-yl]methylbenzoic acid | FAB (+) 433 (MH$^+$) | 158–161° C. | $^1$H-NMR (DMSO-d$_6$) δ ppm: 1.10–1.19 (m, 2H), 1.19–1.30 (m, 3H), 1.50–1.70 (m, 2H), 2.40–2.52 (m, 2H), 2.50–2.60 (m, 2H), 3.30 (s, 2H), 6.64 (s, 2H), 6.83 (s, 1H), 7.26 (d, J = 8 Hz, 2H), 7.63 (s, 2H), 7.82 (d, J = 8 Hz, 2H), 9.50 (s, 1H) |

| Ex. | Structural formula | MS | M.p. | NMR |
|---|---|---|---|---|
| 754 | 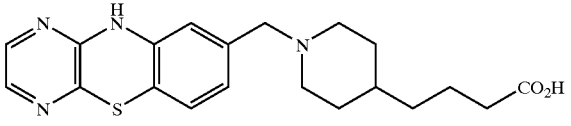<br>4-[1-(10H-pyrazino[2,3-b][1,4]benzothiazin-8-ylmethyl)piperidin-4-yl]butanoic acid | FAB (+)<br>384 (MH$^+$) | | $^1$H-NMR (DMSO-d$_6$) δ ppm: 1.00–1.30 (m, 5H), 1.40–1.55 (m, 2H), 1.55–1.62 (m, 2H), 1.70–1.90 (m, 2H), 2.12 (t, J = 6 Hz, 2H), 2.70–2.80 (m, 2H), 3.22 (s, 2H), 6.65 (d, J = 8 Hz, 1H), 6.73 (s, 1H), 6.80 (d, J = 8 Hz, 1H), 7.60 (s, 2H), 9.43 (br.s, 1H) |
| 755 | 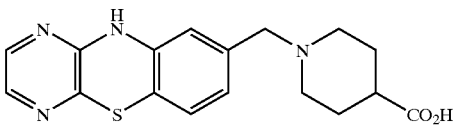<br>[1-(10H-pyrazino[2,3-b][1,4]benzothiazin-8-ylmethyl)piperidin-4-yl]carboxylic acid | FAB (+)<br>343 (MH$^+$) | | $^1$H-NMR (DMSO-d$_6$) δ ppm: 1.40–1.60 (m, 2H), 1.65–1.80 (m, 2H), 1.80–1.95 (m, 2H), 2.0–2.13 (m, 1H), 2.60–2.75 (m, 2H), 3.20 (s, 2H), 6.66 (d, J = 8 Hz, 1H), 6.78 (s, 1H), 6.82 (d, J = 8 Hz, 1H), 7.62 (s, 2H), 9.43 (br.s, 1H) |

Example 756

[5-[1-(10H-Pyrazino[2,3-b][1,4]benzothiazin-8-ylmethyl)piperidin-4-yl]-2-hydroxy-3-oxo-2-methyl-4-pentan-5-yl]thioacetic acid To a solution of 0.240 g of [5-[1-(10H-pyrazino[2,3-b][1,4]benzothiazin-8-ylmethyl)piperidin-4-yl]-2-hydroxy-2-methyl-4-penten-3-one in tetrahydrofuran (20 ml) was added at 0° C. a solution of 0.18 g of mercaptoacetic acid in water (10 ml). After adding 0.18 g of sodium hydroxide, the resulting mixture was stirred at room temperature for 30 minutes and then concentrated under reduced pressure. Next, the residue was purified by High-porous gel chromatography (CHP20P, mfd by Mitsubishi Chemical Industries, 75–150μ) (eluted with methanol/water) to thereby give 0.165 g of the title compound as pale yellow crystals.

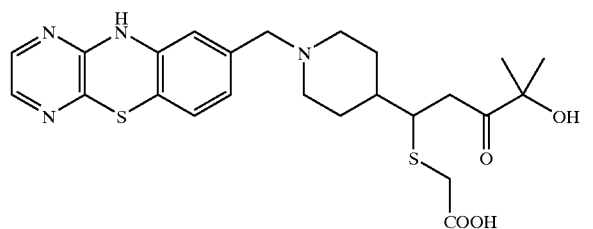

$^1$H-NMR(DMSO-d$_6$) δ ppm: 1.15(s, 6H), 1.18–1.23(m, 1H), 1.36–1.46(m, 2H), 1.53(br.d, J=13 Hz, 1H), 1.61(br.d, J=13 Hz, 1H), 1.74–1.83(m, 2H), 2.78(d, J=11 Hz, 2H), 2.87–2.98(m, 2H), 3.08(m, 1H), 3.17(d, J=4 Hz, 2H), 3.22(s, 2H), 6.67(d, J=8 Hz, 1H), 6.75(d, J=2 Hz, 1H), 6.82(dd, J=2, 8 Hz, 1H), 7.62(m, 2H), 9.42(s, 1H)
MS: FAB(+)503(MH$^+$)
m.p.: 130–132° C.

Example 757

[1-(10H-Pyrazino[2,3-b][1,4]benzothiazin-8-ylmethyl)-1-azoniabicyclo[2.2.2]octane-4-carboxylate 0.620 g of 1-azabicyclo[2.2.2]octane-4-carboxylic acid was dissolved in 40 ml of acetonitrile. After adding 3.98 g of N-methyl-N-(trimethylsilyl)trifluoroacetamide, the resulting mixture was stirred for 2 hours. Next, 0.998 g of 8-chloromethyl-10H-pyrazino[2,3-b][1,4]benzothiazine was added thereto and the resulting mixture was heated under reflux for 4 hours. After distilling off the solvent under reduced pressure, the residue was dissolved in methanol/dichloromethane. After adding diethyl ether, the mixture was filtered and the residue was purified by High-porous gel chromatography (CHP20P, mfd by Mitsubishi Chemical Industries, 75–150μ) (eluted with methanol/water) to thereby give 0.21 g of the title compound as a yellow powder.

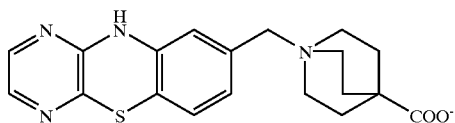

$^1$H-NMR(DMSO-d$_6$) δ ppm: 2.19(t, J=8 Hz, 6H), 3.43(t, J=8 Hz, 6H), 4.19(s, 2H), 6.71(d, J=2 Hz, 1H), 6.88(dd, J=2, 8 Hz, 1H), 6.99(d, J=8 Hz, 1H), 7.62(s, 2H)
MS: FAB(+)369(MH$^+$)
m.p.: 229–230° C.

Example 758

[1-(10H-Pyrazino[2,3-b][1,4]benzothiazin-8-ylmethyl)piperidin-4-yl]oxyacetic acid Ethyl(piperidin-4-yl)oxyacetate was treated by the same methods as those of Examples 63 and 18 to thereby give the title compound as yellow crystals.

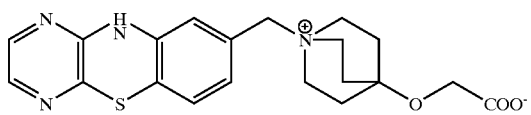

$^1$H-NMR(DMSO-d$_6$) δ ppm: 1.35–1.47(m, 2H), 1.76–1.84(m, 2H), 1.95–2.06(m, 2H), 2.56–2.64(m, 2H), 3.24(s, 2H), 3.29–3.38(m, 1H), 3.98(s, 2H), 6.68(dd, J=1.8, 7.8 Hz, 1H), 6.74(d, J=1.8 Hz, 1H), 6.82(d, J=7.8 Hz, 1H), 7.61(d, J=2.8 Hz, 1H), 7.62(d, J=2.8 Hz, 1H), 9.43(s, 1H)
MS: ESI(+)373(MH+)
m.p.: 204–207° C.

Example 759

[1-(10H-Pyrazino[2,3-b][1,4]benzothiazin-8-ylmethyl)-piperidin-4-yl]methylthioacetic acid Ethyl[1-(tert-butoxycarbonyl)piperidin-4-yl)methylthioacetate was treated successively by the same methods as those of Examples 66 and 18 to thereby give the title compound.

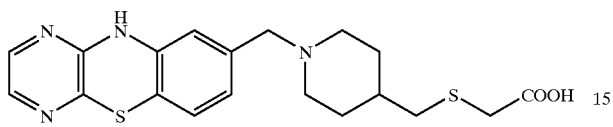

$^1$H-NMR(DMSO-d$_6$) δ ppm: 1.10–1.20(m, 2H), 1.36–1.48(m, 1H), 1.63–1.72(m, 2H), 1.82–1.91(m, 2H), 2.48(d, J=7.2 Hz, 2H), 2.71–2.78(m, 2H), 3.17(s, 2H), 3.24(s, 2H), 6.68(d, J=7.9 Hz, 1H), 6.74(s, 1H), 6.82(d, J=7.9 Hz, 1H), 7.62(s, 2H), 9.43(s, 1H)

MS: FAB(+)403(MH$^+$)

m.p.: 110–113° C.

Example 760

8-[2-[(1,3-Dithiacyclohexan-2-ylidene)methyl]-4,5,6,7-tetrahydro-6H-thieno[2,3-c]pyridin-6-ylmethyl]-10H-pyrazino[2,3-b][1,4]benzothiazine 2-[(1,3-Dithiacyclohexan-2-ylidene)methyl]-6-(tert-butoxycarbonyl)-4,5,6,7-tetrahydro-6H-thieno[2,3-c]pyridine was treated by the same method as the one of Example 66 to thereby give the title compound as orange crystals.

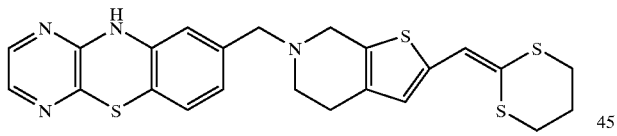

$^1$H-NMR(CDCl$_3$) δ ppm: 2.20(quint, J=6.0 Hz, 2H), 2.72(br.t, J=5.4 Hz, 2H), 2.84(br.t, J=5.4 Hz, 2H), 2.98(t, J=6.0 Hz, 2H), 3.00(t, J=6.0 Hz, 2H), 3.60(s, 2H), 3.70(br.s, 2H), 6.51–6.58(br.s, 1H), 6.68(br.d, J=1.6 Hz, 1H), 6.77(s, 1H), 6.79(dd, J=1.6, 8.0 Hz, 1H), 6.85(d, J=8.0 Hz, 1H), 6.92(s, 1H), 7.57(d, J=2.8 Hz, 1H), 7.68(d, J=2.8 Hz, 1H)

Example 761

[6-(10H-Pyrazino[2,3-b][1,4]benzothiazin-8-ylmethyl)-4,5,6,7-tetrahydro-6H-thieno[2,3-c]pyridin-2-yl]acetic acid 8-[2-[(1,3-Dithlacyclohexan-2-ylidene)methyl]-4,5,6,7-tetrahydro-6H-thieno[2,3-c]pyridin-6-ylmethyl]-10H-pyrazino[2,3-b][1,4]benzothiazine was treated successively by the same methods as those of Production Example 63 and Example 18 to thereby give the title compound as yellow crystals.

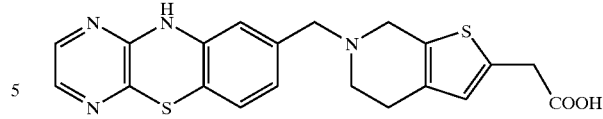

$^1$H-NMR(DMSO-d$_6$) δ ppm: 2.56(t, J=6.8 Hz, 2H), 2.65 (t, J=6.8 Hz, 2H), 3.47(s, 4H), 3.64(s, 2H), 6.59(s, 1H), 6.73(d, J=8.0 Hz, 1H), 6.81(s, 1H), 6.84(d, J=8.0 Hz, 1H), 7.61 (d, J=2.8 Hz, 1H), 7.62(d, J=2.8 Hz, 1H), 9.45(s, 1H)

MS: FAB(+)411(MH$^+$)

m.p.: 98–105° C.

Example 762

4-[1-(10H-Pyrazino[2,3-b][1,4]benzothiazin-8-yl]acetyl]-piperidin-4-yl]-2-methylbutanoic acid 10-(Methoxymethyl)-10H-pyrazino[2,3-b][1,4]benzothiazine-8-acetic acid was treated successively by the same methods as those of Examples 362, 18 and 8 to thereby give the title compound as yellow crystals.

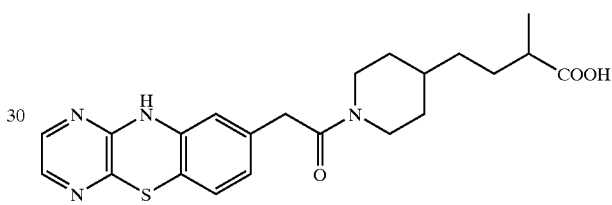

$^1$H-NMR(DMSO-d$_6$) δ ppm: 0.82–0.94(m, 2H), 1.01(d, J=7.1 Hz, 3H), 1.10–1.19(m, 2H), 1.26–1.46(m, 2H), 1.46–1.56(m, 1H), 1.56–1.66(m, 2H), 2.19–2.30(m, 1H), 2.43–2.53(m, 1H), 2.86–2.96(m, 1H), 3.50(s, 2H), 3.82(br.d, J=13.0 Hz, 1H), 4.33(br.d, J=13 Hz, 1H), 6.62(s, 1H), 6.63(d, J=8.3 Hz, 1H), 6.82(d, J=8.3 Hz, 1H), 7.62(d, J=2.7 Hz, 1H), 7.63(d, J=2.7 Hz, 1H), 9.48(s, 1H)

MS: FAB(+)427(MH$^+$)

m.p.: 84–89° C.

Production Example 120

2-[N-Methyl-(2-nitrophenyl)amino]-3-chloropyrazine

To a solution of 1.52 g of N-methyl-2-nitroaniline in N,N-dimethylformamide (50 ml) was added in a nitrogen atmosphere 0.44 g of sodium hydride. After stirring for 30 minutes, 1.75 g of 2,3-dichloropyrazine was added thereto and the resulting mixture was stirred at room temperature for additional 6 hours. Then the reaction mixture was distributed into ethyl acetate and a saturated aqueous solution of sodium dihydrogenphosphate and the aqueous layer was extracted with ethyl acetate. The organic layers were combined, washed successively with water and a saturated aqueous solution of sodium chloride and dried over anhydrous magnesium sulfate. After distilling off the solvent under reduced pressure, the residue was purified by silica gel column chromatography (eluted with n-hexane/ethyl acetate) to thereby give 0.586 g of the title compound as an oily substance.

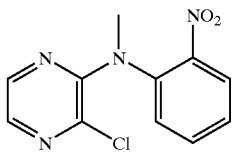

¹H-NMR(CDCl₃) δ ppm: 3.45(s, 3H), 7.08(dd, J=1, 7 Hz, 1H), 7.39(dt, J=1, 7 Hz, 1H), 7.58(dt, J=1, 7 Hz, 1H), 7.89(d, J=2 Hz, 1H), 7.97(dd, J=1, 7 Hz, 1H), 8.17(d, J=2 Hz, 1H)

Production Example 121

2-[(2-Nitrophenyl)amino]-3-chloropyrazine

Starting with 41.4 g of 2-nitroaniline and 35.0 g of 2,3-dichloropyrazine, 39.8 g of the title compound was obtained by the same method as the one described in Production Example 120.

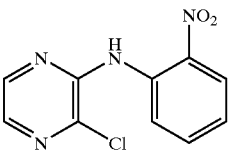

¹H-NMR(CDCl₃) δ ppm: 7.13(dt, J=1, 7 Hz, 1H), 7.67(dt, J=1, 7 Hz, 1H), 7.96(d, J=2 Hz, 1H), 8.18(d, J=2 Hz, 1H), 8.31(dd, J=1,7 Hz, 1H), 9.02(dd, J=1, 7 Hz, 1H), 11.00(br.s, 1H)

Production Examples

The following compounds were obtained from various anilines and 2,3-dichloropyrazine by the same procedure as the one of Production Example 121.

| Prodn. Ex. | Structural formula | NMR |
|---|---|---|
| 122 | 2-[[2-nitro-4-(methoxymethoxy)phenyl]amino]-3-chloropyrazine | ¹H-NMR (CDCl₃) δ ppm: 3.50 (s, 3H), 5.22 (s, 2H), 7.39 (dd, J = 3, 9 Hz, 1H), 7.91 (d, J = 3 Hz, 1H), 7.95 (d, J = 3 Hz, 1H), 8.12 (d, J = 3 Hz, 1H), 8.88 (d, J = 9 Hz, 1H), 10.70 (br.s, 1H) |
| 123 | 2-[(2-nitro-5-methoxyphenyl)amino]-3-chloropyrazine | ¹H-NMR (CDCl₃) δ ppm: 3.87 (s, 3H), 7.28 (dd, J = 3, 10 Hz, 1H), 7.75 (d, J = 3 Hz, 1H), 7.90 (d, J = 3 Hz, 1H), 8.12 (d, J = 3 Hz, 1H), 8.88 (d, J = 10 Hz, 1H), 10.70 (br.s, 1H) |
| 124 | ethyl 3-nitro-4-[(3-chloropyrazin-2-yl)amino]benzoate | ¹H-NMR (CDCl₃) δ ppm: 1.42 (t, J = 7 Hz, 3H), 4.42 (q, J = 7 Hz, 2H), 8.14 (d, J = 3 Hz, 1H), 8.24 (d, J = 3 Hz, 1H), 8.29 (dd, J = 2, 8 Hz, 1H), 8.98 (d, J = 2 Hz, 1H), 9.16 (d, J = 8 Hz, 1H), 11.30 (s, 1H) |
| 125 | 3-nitro-4-[(3-chloropyrazin-2-yl)amino]benzonitrile | ¹H-NMR (CDCl₃) δ ppm: 7.87 (dd, J = 2, 8 Hz, 1H), 8.10 (d, J = 3 Hz, 1H), 8.26 (d, J = 3 Hz, 1H), 8.65 (d, J = 2 Hz, 1H), 9.30 (d, J = 8 Hz, 1H), 11.34 (s, 1H) |

| Prodn. Ex. | Structural formula | NMR |
|---|---|---|
| 126 | 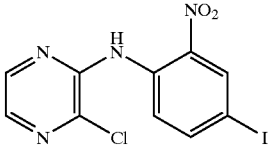<br>2-[(4-iodo-2-nitrophenyl)amino]-3-chloropyrazine | $^1$H-NMR (CDCl$_3$) δ ppm: 7.90 (dd, J = 2, 8 Hz, 1H), 7.98 (d, J = 3 Hz, 1H), 8.18 (d, J = 3 Hz, 1H), 8.60 (d, J = 2 Hz, 1H), 8.84 (d, J = 8 Hz, 1H), 10.95 (br.s, 1H) |

Production Example 127

2-[(2-Aminophenyl)amino]-3-chloropyrazine

To a solution of 1.1 g of 2-[(2-nitrophenyl)-1-amino)]-3-chloropyrazine in tetrahydrofuran (35 ml) was added an aqueous solution (14 ml) of 7 g of sodium hydrosulfide. After adding 14 ml of 50% aqueous ammonia thereto, the resulting mixture was vigorously stirred at room temperature for 16 hours. Then the reaction mixture was distributed into ethyl acetate and water and the organic layer was dried over anhydrous magnesium sulfate. After distilling off the solvent under reduced pressure, the residue was purified by silica gel column chromatography (eluted with n-hexane/ethyl acetate) to thereby give 0.28 g of the title compound as yellow crystals.

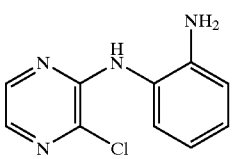

$^1$H-NMR(CDCl$_3$) δ ppm: 3.73(br.s, 2H), 6.79(br.s, 1H), 6.83–6.87(m, 2H), 7.10(t, J=7 Hz, 1H), 7.38(d, J=7 Hz, 1H), 7.74(d, J=2 Hz, 1H), 8.00(d, J=2 Hz, 1H)

Production Examples

The following compounds were obtained by reducing nitro groups by the same procedure as the one of Production Example 127.

| Prodn. Ex. | Structural formula | NMR |
|---|---|---|
| 128 | 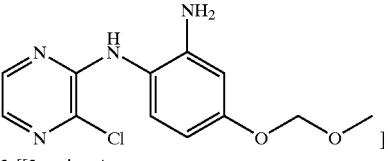<br>2-[[2-amino-4-(methoxymethoxy)phenyl]amino]-3-chloropyrazine | $^1$H-NMR (CDCl$_3$) δ ppm: 3.48 (s, 3H), 3.79 (br.s, 2H), 5.14 (s, 2H), 6.51 (dd, J = 3, 8 Hz, 1H), 6.54 (br.s, 1H), 6.56 (d, J = 3 Hz, 1H), 7.14 (d, J = 8 Hz, 1H), 7.70 (d, J = 3 Hz, 1H), 7.98 (d, J = 3 Hz, 1H) |
| 129 | 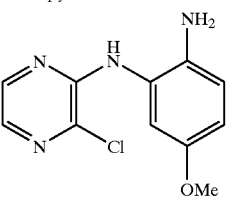<br>2-[(2-amino-5-(methoxyphenyl]amino]-3-chloropyrazine | $^1$H-NMR (CDCl$_3$) δ ppm: 3.78 (s, 3H), 3.80 (br.s, 2H), 6.37–6.40 (m, 2H), 6.53 (br.s, 1H), 7.12 (d, J = 9 Hz, 1H), 7.69 (d, J = 3 Hz, 1H), 7.98 (d, J = 3 Hz, 1H) |
| 130 | 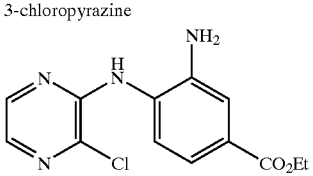<br>ethyl 3-amino-4-[(3-chloropyrazin-2-yl)amino]benzoate | $^1$H-NMR (CDCl$_3$) δ ppm: 1.39 (t, J = 7 Hz, 3H), 3.69 (br.s, 2H), 4.35 (q, J = 7 Hz, 2H), 7.20 (br.s, 1H), 7.58–7.62 (m, 2H), 7.80 (d, J = 3 Hz, 1H), 7.81 (d, J = 8 Hz, 1H), 8.06 (d, J = 3 Hz, 1H) |

| Prodn. Ex. | Structural formula | NMR |
|---|---|---|
| 131 | 3-amino-4-[(3-chloropyrazin-2-yl)amino]benzonitrile | $^1$H-NMR (CDCl$_3$) δ ppm: 3.75 (br.s, 2H), 7.14 (d, J = 2 Hz, 1H), 7.17 (br.s, 1H), 7.20 (dd, J = 2, 8 Hz, 1H), 7.85 (d, J = 3 Hz, 1H), 7.90 (d, J = 8 Hz, 1H), 8.08 (d, J = 3 Hz, 1H) |

Production Example 132

2-[N-Allyl-(2-nitrophenyl)amino]-3-chloropyrazine

A solution of 5.01 g of 2-[(2-nitrophenyl)amino]-3-chloropyrazine in N,N-dimethylformamide (200 ml) was degassed in a nitrogen atmosphere and then 0.92 g of sodium hydride (60% oily) was added thereto at 0° C. After stirring for 30 minutes, 4.84 g of allyl bromide was added and the resulting mixture was stirred at ordinary temperature for 16 hours. Then the reaction mixture was distributed into ethyl acetate and water and the aqueous layer was extracted with ethyl acetate. The organic layers were combined, washed successively with water and a saturated aqueous solution of sodium chloride and dried over anhydrous magnesium sulfate. After distilling off the solvent under reduced pressure, the residue was purified by silica gel column chromatography (eluted with n-hexane/ethyl acetate) to thereby give 4.78 g of the title compound as a colorless oily substance.

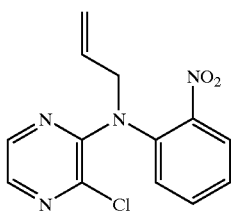

$^1$H-NMR(CDCl$_3$) δ ppm: 4.54(d, J=7 Hz, 2H), 5.11–5.16 (m, 2H), 5.99–6.09(m, 1H), 7.19(dd, J=1, 7 Hz, 1H), 7.38(dt, J=1, 7 Hz, 1H), 7.57(dt, J=1, 7 Hz, 1H), 7.91(d, J=3 Hz, 1H), 7.95(dd, J=1, 7 Hz, 1H), 8.16(d, J=3 Hz, 1H)

Production Examples

The following compounds were obtained by treating 2-[(2-nitrophenyl)amino]-3-chloropyrazine with various halides by the same procedure as the one of Production Example 132.

| Prodn. Ex. | Structural formula | NMR |
|---|---|---|
| 133 | t-butyl N-(3-chloropyrazin-2-yl)-N-(2-nitrophenyl)minoacetate | $^1$H-NMR (CDCl$_3$) δ ppm: 1.45 (s, 9H), 4.40 (s, 2H), 7.45 (dt, J = 2, 8 Hz, 1H), 7.51 (dd, J = 2, 8 Hz, 1H), 7.60 (dt, J = 2, 8 Hz, 1H), 7.91 (d, J = 2 Hz, 1H), 8.03 (dd, J = 2, 8 Hz, 1H), 8.12 (d, J = 2 Hz, 1H) |
| 134 | methyl 4-[N-(3-chloropyrazin-2-yl)-N-(2-nitrophenyl)minomethyl]benzoate | $^1$H-NMR (CDCl$_3$) δ ppm: 3.88 (s, 3H), 5.22 (s, 2H), 7.11 (dd, J = 1, 7 Hz, 1H), 7.37 (dt, J = 1, 7 Hz, 1H), 7.42 (d, J = 8 Hz, 2H), 7.51 (dt, J = 1, 7 Hz, 1H), 7.91–7.94 (m, 4H), 8.12 (d, J = 3 Hz, 1H) |
| 135 | methyl (E)-4-[N-(3-chloropyrazin-2-yl)-N-(2-nitrophenyl)amino]-2-butenoate | $^1$H-NMR (CDCl$_3$) δ ppm: 3.71 (s, 3H), 4.66 (d, J = 6 Hz, 2H), 5.93 (d, J = 16 Hz, 1H), 7.10 (td, J = 6, 16 Hz, 1H), 7.14 (d, J = 8 Hz, 1H), 7.42 (t, J = 8 Hz, 1H), 7.57 (t, J = 8 Hz, 1H), 7.95 (s, 1H), 7.97 (d, J = 8 Hz, 1H), 8.17 (s, 1H) |

Production Examples

The following compounds were obtained by the same method as the one of Production Example 132 by replacing the allyl bromide by methyl iodide.

| Prodn. Ex. | Structural formula | NMR |
|---|---|---|
| 136 | 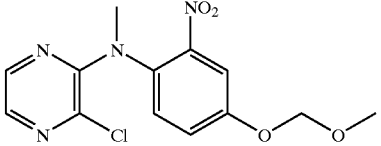<br>2-[N-(4-methoxymethoxy-2-nitrophenyl)-N-methylamino]-3-chloropyrazine | ¹H-NMR (CDCl₃) δ ppm: 3.42 (s, 3H), 3.50 (s, 3H), 5.23 (s, 2H), 7.10 (d, J = 9 Hz, 1H), 7.24 (dd, J = 3, 9 Hz, 1H), 7.65 (s, 1H), 7.85 (s, 1H), 8.15 (d, J = 3 Hz, 1H) |
| 137 | 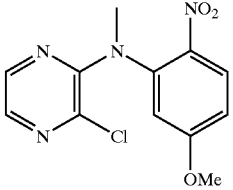<br>2-[N-(5-methoxy-2-nitrophenyl)-N-methylamino]-3-chloropyrazine | ¹H-NMR (CDCl₃) δ ppm: 3.42 (s, 3H), 3.88 (s, 3H), 7.05 (m, 2H), 7.49 (m, 1H), 7.84 (d, J = 3 Hz, 1H), 8.15 (d, J = 3 Hz, 1H) |
| 138 | 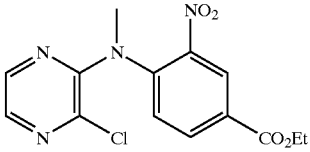<br>ethyl 4-[N-methyl-N-(3-chloropyrazin-2-yl)amino]-3-nitrobenzoate | ¹H-NMR (CDCl₃) δ ppm: 1.41 (t, J = 7 Hz, 3H), 3.51 (s, 3H), 4.42 (q, J = 7 Hz, 2H), 7.25 (d, J = 8 Hz, 1H), 8.02 (d, J = 2 Hz, 1H), 8.20 (d, J = 2 Hz, 1H), 8.21 (dd, J = 2, 8 Hz, 1H), 8.58 (d, J = 2 Hz, 1H) |
| 139 | 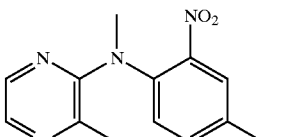<br>3-nitro-4-[N-methyl-N-(3-chloropyrazin-2-yl)amino]benzonitrile | ¹H-NMR (CDCl₃) δ ppm: 3.53 (s, 3H), 7.33 (d, J = 8 Hz, 1H), 7.83 (dd, J = 2, 8 Hz, 1H), 8.12 (d, J = 3 Hz, 1H), 8.20 (d, J = 2 Hz, 1H), 8.21 (d, J = 3 Hz, 1H) |
| 140 | 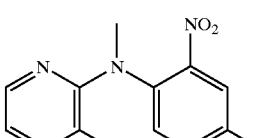<br>2-[N-(4-iodo-2-nitrophenyl)-N-methylamino]-3-chloropyrazine | ¹H-NMR (CDCl₃) δ ppm: 3.37 (s, 3H), 6.86 (d, J = 8 Hz, 1H), 7.80 (d, J = 8 Hz, 1H), 7.88 (s, 1H), 8.12 (s, 1H), 8.19 (s, 1H) |

Production Examples

The following compounds were obtained by the same method as the one of Production Example 132 by replacing the allyl bromide by chloromethyl methyl ether.

| Prodn. Ex. | Structural formula | NMR |
|---|---|---|
| 141 | 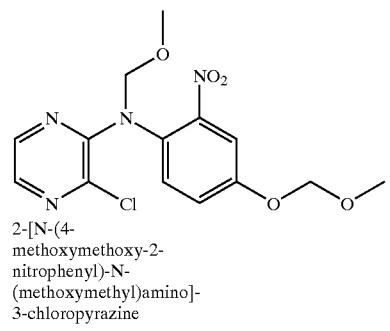<br>2-[N-(4-methoxymethoxy-2-nitrophenyl)-N-(methoxymethyl)amino]-3-chloropyrazine | $^1$H-NMR (CDCl$_3$) δ ppm: 3.38 (s, 3H), 3.50 (s, 3H), 5.23 (s, 2H), 5.27 (s, 2H), 7.26 (d, J = 9 Hz, 1H), 7.32 (d, J = 9 Hz, 1H), 7.62 (s, 1H), 7.94 (s, 1H), 8.18 (s, 1H) |
| 142 | 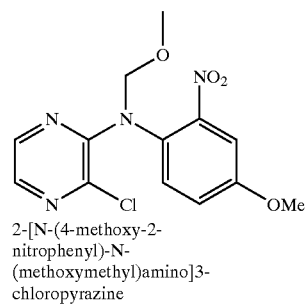<br>2-[N-(4-methoxy-2-nitrophenyl)-N-(methoxymethyl)amino]3-chloropyrazine | $^1$H-NMR (CDCl$_3$) δ ppm: 3.39 (s, 3H), 3.88 (s, 3H), 5.27 (s, 2H), 7.14 (dd, J = 3, 9 Hz, 1H), 7.33 (d, J = 9 Hz, 1H), 7.46 (d, J = 3 Hz, 1H), 7.94 (d, J = 3 Hz, 1H), 8.18 (d, J = 3 Hz, 1H) |
| 143 | 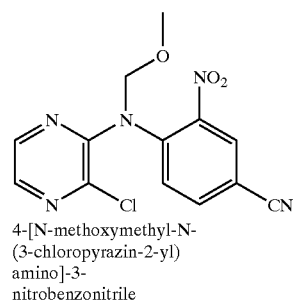<br>4-[N-methoxymethyl-N-(3-chloropyrazin-2-yl)amino]-3-nitrobenzonitrile | $^1$H-NMR (CDCl$_3$) δ ppm: 3.35 (s, 3H), 5.39 (s, 2H), 7.75 (d, J = 8 Hz, 1H), 7.87 (d, J = 2, 8 Hz, 1H), 8.15 (d, J = 2 Hz, 1H), 8.17 (d, J = 3 Hz, 1H), 8.25 (d, J = 3 Hz, 1H) |
| 144 | 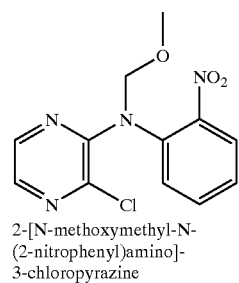<br>2-[N-methoxymethyl-N-(2-nitrophenyl)amino]-3-chloropyrazine | $^1$H-NMR (CDCl$_3$) δ ppm: 3.38 (s, 3H), 5.32 (s, 2H), 7.42 (dt, J = 1, 8 Hz, 1H), 7.47 (dd, J = 1, 8 Hz, 1H), 7.62 (dt, J = 1, 8 Hz, 1H), 7.94 (dd, J = 1, 8 Hz, 1H), 8.00 (d, J = 2 Hz, 1H), 8.21 (d, J = 2 Hz, 1H) |

Production Example 145

(E)-2-[N-(4-Bromo-2-buten-1-yl)-N-(2-nitrophenyl)amino]-3-chloropyrazine

Similar to Production Example 132, 5.04 g of 2-[(2-nitrophenyl)amino]-3-chloropyrazine was treated with (E)-1,4-dibromo-2-butene to thereby give 0.34 g of the title compound.

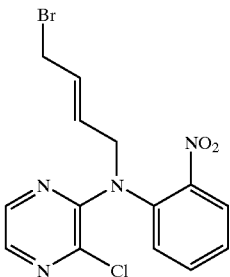

$^1$H-NMR(CDCl$_3$) δ ppm: 3.86(d, J=7 Hz, 2H), 4.51(d, J=6 Hz, 2H), 5.76(td, J=7, 14 Hz, 1H), 6.01(td, J=6, 14 Hz, 1H), 7.15(dd, J=1, 8 Hz, 1H), 7.41(dt, J=1, 8 Hz, 1H), 7.57(dt, J=1, 8 Hz, 1H), 7.92(d, J=2 Hz, 1H), 7.97(dd, J=1, 8 Hz, 1H), 8.17(d, J=2 Hz, 1H)

Production Example 146

(E)-2-[N-(4-Dimethylamino-2-buten-1-yl)-N-(2-nitrophenyl)amino]-3-chloropyrazine Similar to Example 1094, 0.34 g of (E)-2-[N-(4-bromo-2-buten-1-yl)-N-(2-nitrophenyl)amino]-3-chloropyrazine was treated with 20 ml of a 0.86 M ethanol solution of dimethylamine in 5 ml of ethanol to thereby give 0.17 g of the title compound as a yellow oily substance.

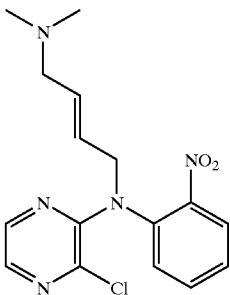

$^1$H-NMR(CDCl$_3$) δ ppm: 2.65(s, 6H), 3.57(d, J=7 Hz, 2H), 4.53(d, J=6 Hz, 2H), 5.90(td, J=7, 16 Hz, 1H), 6.16(td, J=6, 16 Hz, 1H), 7.17(dd, J=1, 8 Hz, 1H), 7.41(dt, J=1, 8 Hz, 1H), 7.60(dt, J=1, 8 Hz, 1H), 7.92(dd, J=1, 8 Hz, 1H), 7.93(d, J=2 Hz, 1H), 8.19(d, J=2 Hz, 1H)

Production Example 147

3-[[N-(3-Chloropyrazin-2-yl)-N-(2-nitrophenyl)]amino]-1,2-propanediol 1.16 g of 2-[N-[allyl-N-(2-nitrophenyl)amino]-3-chloropyrazine was treated in the same manner as that of Example 1195 to thereby give 0.716 g of the title compound.

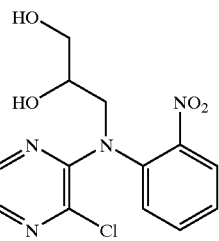

$^1$H-NMR(CDCl$_3$) δ ppm: 3.55–3.60(m, 1H), 3.62–3.68(m, 1H), 3.93(br.s, 1H), 3.98–4.03(m, 1H), 4.08–4.20(m, 2H), 4.43(br.s, 1H), 7.36(d, J=7 Hz, 1H), 7.45(t, J=7 Hz, 1H), 7.63(t, J=7 Hz, 1H), 7.98(d, J=2 Hz, 1H), 8.00(d, J=7 Hz, 1H), 8.14(d, J=2 Hz, 1H)

Production Example 148

2-(6-Methyl-2-nitrophenyl)thio-3-chloropyrazine

To a solution of 1.254 g of 6-methyl-2-nitrobenzenethiol in tetrahydrofuran (10 ml) was added 0.326 g of sodium hydride under ice-cooling in a nitrogen atmosphere. After stirring for 10 minutes, 1.67 g of dichloropyrazine was added thereto and the resulting mixture was stirred at room temperature for 1 hour and heated under reflux for 1.5 hour. Then the reaction mixture was poured into a saturated aqueous solution of sodium dihydrogenphosphate and extracted with ethyl acetate. The organic layer was dried over anhydrous magnesium sulfate and distilled under reduced pressure. Then the residue was purified by silica gel column chromatography (eluted with n-hexane/ethyl acetate) to thereby give 0.737 g of the title compound as a red oily substance.

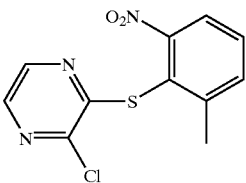

$^1$H-NMR(CDCl$_3$) δ ppm: 2.46(s, 3H), 7.53(t, J=8 Hz, 1H), 7.58(dd, J=2, 8 Hz, 1H), 7.68(dd, J=2, 8 Hz, 1H), 8.06(d, J=3 Hz, 1H), 8.10(d, J=3 Hz, 1H)

Production Example 149

Diethyl 2-phenyl-2-(5-nitropyridin-2-yl)malonate 14.9 g of diethyl phenylmalonate was dissolved in 50 ml of N,N-dimethylformamide and 2.52 g of sodium hydride (60% oily) was added thereto at room temperature. Next, 5.0 g of 2-chloro-5-nitropyridine was added thereto and the resulting mixture was stirred at 80° C. for 2 hours. After the completion of the reaction, the reaction mixture was poured into ice-water/ethyl acetate and neutralized with dilute hydrochloric acid. After extracting with ethyl acetate, the extract was dried over anhydrous sodium sulfate and filtered. The filtrate was distilled under reduced pressure and the obtained residue was purified by silica gel column chromatography (eluted with ethyl acetate/n-hexane) to thereby give 16.55 g of the title compound as a reddish brown oily substance.

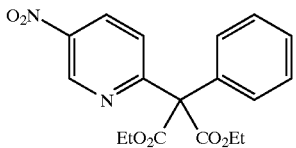

¹H-NMR(CDCl₃) δ ppm: 1.23(t, J=7 Hz, 6H), 4.15(q, J=7 Hz, 4H), 7.20–7.45(m, 6H), 8.25(d, J=7 Hz, 1H), 9.38(s, 1H)

Production Example 150

2-Benzyl-5-nitropyridine 1.5 g of diethyl 2-phenyl-2-(5-nitropyridin-2-yl)malonate was dissolved in 50 ml of ethanol. After adding 10 ml of water and 10 ml of conc. sulfuric acid, the mixture was heated under reflux for 8 hours. After the completion of the reaction, the reaction mixture was poured into a saturated aqueous solution of sodium hydrogencarbonate and extracted with ethyl acetate. The extract was dried over anhydrous sodium sulfate and filtered. The filtrate was distilled under reduced pressure and the obtained residue was purified by silica gel column chromatography (eluted with ethyl acetate/n- hexane) to thereby give 632 mg of the title compound as reddish brown crystals.

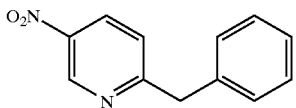

¹H-NMR(CDCl₃) δ ppm: 4.28(s, 2H), 7.20–7.43(m, 6H), 8.33(d, J=7 Hz, 1H), 9.36(s, 1H)

Production Example 151

2-Benzyl-5-aminopyridine 389 mg of 2-benzyl-5-nitropyridine was dissolved in ethyl acetate and 153 mg of 10% palladium carbon was added thereto. Then the resulting mixture was stirred under a hydrogen gas stream at room temperature under atmospheric pressure for 30 minutes. Then the reaction mixture was filtered through celite. After distilling off the solvent under reduced pressure, 333 mg of the title compound was obtained as an amber oily substance.

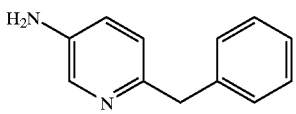

¹H-NMR(CDCl₃) δ ppm: 3.65(br.s, 2H), 4.02(s, 2H), 6.82(d, J=7 Hz, 1H), 6.85(d, J=7 Hz, 1H), 7.13–7.36(m, 5H), 7.97(s, 1H)

Production Examples

The following compounds were obtained by successively treating diethyl benzylmalonate and diethyl methylmalonate in the same manner as those of Production Examples 149, 150 and 151.

| Prodn. Ex. | Structural formula | NMR |
|---|---|---|
| 152 | ![2-phenethyl-5-aminopyridine] 2-phenethyl-5-aminopyridine | ¹H-NMR (CDCl₃) δ ppm: 2.92 (s, 4H), 3.90 (br.s, 2H), 6.72–6.83 (m, 2H), 7.08–7.20 (m, 2H), 7.20–7.30 (m, 3H), 7.96 (br.s, 1H) |
| 153 | ![2-ethyl-5-aminopyridine] 2-ethyl-5-aminopyridine | ¹H-NMR (CDCl₃) δ ppm: 1.23 (t, J = 7 Hz, 3H), 2.72 (q, J = 7 Hz, 2H), 3.58 (br.s, 2H), 6.92 (s, 2H), 8.00 (s, 1H) |

Production Example 154

Triethyl 5-methyl-1-(5-nitropyridin-2-yl)hexane-1,1,5-tricarboxylate 5 g of diethyl malonate was dissolved in 30 ml of N,N-dimethylformamide and 1.550 g of sodium hydride (60% oily) was added thereto under ice-cooling. Next, 7.04 g of ethyl 2,2-dimethyl-5-bromopentanoate was added to the reaction mixture and the resulting mixture was stirred at 80° C. for 2 hours. After ice-cooling the reaction mixture again, 1.550 g of sodium hydride (60% oily) was added thereto. After stirring for 25 minutes, 7.4 g of 2-chloro-5-nitropyridine was added and the resulting mixture was stirred at 80° C. for 1.5 hours. After the completion of the reaction, the reaction mixture was poured into a saturated aqueous solution of sodium chloride and repeatedly extracted with ethyl acetate. The extracts were dried over anhydrous sodium sulfate and filtered. The filtrate was distilled under reduced pressure and the obtained residue was purified by silica gel column chromatography (eluted with ethyl acetate/n-hexane) to thereby give 9.71 g of the title compound as a yellow oily substance.

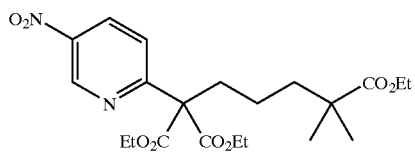

¹H-NMR(CDCl₃) δ ppm: 1.12(s, 6H), 1.13(t, J=7 Hz, 3H), 1.14(t, J=7 Hz, 6H), 1.43–1.60(m, 2H), 2.25–2.38(m, 4H), 4.10(q, J=7 Hz, 2H), 4.21(q, J=7 Hz, 2H), 4.23(q, J=7 Hz, 2H), 8.00(d, J=8 Hz, 1H), 8.49(d, J=8 Hz, 1H), 9.33(s, 1H)

Production Example 155

Ethyl 6-(5-nitropyridin-2-yl)-2,2-dimethylhexanoate 9.71 g of triethyl 5-methyl-1-(5-nitropyridin-2-yl)hexane-1,1,5-tricarboxylate was treated in the same manner as the one of Production Example 149 to thereby give 2.87 g of a yellow oily substance. A 1.82 g portion of this product was dissolved in 30 ml of ethanol. After adding 3 ml of conc. sulfuric acid, the resulting mixture was heated under reflux for 7 hours. After the completion of the reaction, the reaction mixture was poured into a saturated aqueous solution of sodium chloride and extracted with ethyl acetate. The extract was dried over anhydrous sodium sulfate and filtered. The filtrate was distilled under reduced pressure and the obtained residue was purified by silica gel column chromatography (eluted with ethyl acetate/n-hexane) to thereby give 1.0 g of the title compound as a yellow oily substance.

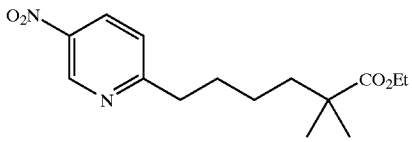

¹H-NMR(CDCl₃) δ ppm: 1.12(s, 6H), 1.22(t, J=7 Hz, 3H), 1.60–1.80(m, 4H), 2.30(t, J=6 Hz, 2H), 2.60(t, J=6 Hz, 2H), 4.13(q, J=7 Hz, 2H), 7.35(d, J=8 Hz, 1H), 8.37(dd, J=2, 8 Hz, 1H), 9.28(d, J=2 Hz, 1H)

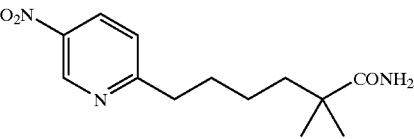

¹H-NMR(CDCl₃) δ ppm: 1.13(s, 6H), 1.30–1.40(m, 2H), 1.50–1.60(m, 2H), 1.70–1.80(m, 2H), 2.90(t, J=7 Hz, 2H), 5.55–5.80(br.s, 2H), 7.16(d, J=7 Hz, 1H), 8.37(d, J=7 Hz, 1H), 9.33(s, 1H)

Production Examples

Ethyl 6-(5-nitropyridin-2-yl)-2,2-dimethylhexanoate and 6-(5-nitropyridin-2-yl)-2,2-dimethylhexanamide were hydrogenated in the same manner as the one of Production Example 151 to thereby give the following compounds.

| Prodn. Ex. | Structural formula | NMR |
|---|---|---|
| 157 | ethyl 6-(5-aminopyridin-2-yl)-2,2-dimethylhexanoate | ¹H-NMR (CDCl₃) δ ppm: 1.13 (s, 6H), 1.23 (t, J = 7 Hz, 3H), 1.60–1.80 (m, 4H), 2.32 (t, J = 6 Hz, 2H), 2.60 (t, J = 6 Hz, 2H), 3.40–3.60 (br.s, 2H), 4.12 (q, J = 7 Hz, 2H), 6.92 (s, 2H), 8.01 (s, 1H) |
| 158 | 6-(5-aminopyridin-2-yl)-2,2-dimethylhexanamide | ¹H-NMR (CDCl₃) δ ppm: 1.13 (s, 6H), 1.22–1.36 (m, 2H), 1.50–1.58 (m, 2H), 1.60–1.70 (m, 2H), 2.63 (t, J = 7 Hz, 2H), 3.60 (br.s, 2H), 5.62 (br.s, 2H), 6.92 (s, 2H), 7.99 (s, 1H) |

Production Example 156

6-(5-Nitropyridin-2-yl)-2,2-dimethylhexanamide

Ethyl 6-(5-nitropyridin-2-yl)-2,2-dimethylhexanoate was treated in the same manner as the one of Example 18 and 661 mg of 6-(5-nitropyridin-2-yl)-2,2-dimethylhexanoic acid thus obtained was dissolved in 15 ml of tetrahydrofuran. After adding 695 mg of carbonyldiimidazole, the resulting mixture was heated under reflux for 2 hours. Then the reaction mixture was cooled to room temperature and 25 ml of saturated aqueous ammonia was added thereto followed by stirring over day and night. After the completion of the reaction, the reaction mixture was poured into a saturated aqueous solution of sodium chloride and repeatedly extracted with ethyl acetate. The extracts were dried over anhydrous sodium sulfate and filtered. The filtrate was distilled under reduced pressure and the residue was purified by silica gel column chromatography (eluted with toluene/acetone) to thereby give 453 mg of the title compound as white crystals.

Production Example 159

Mixture of 2-methyl-5-aminopyridine with ethyl(5-aminopyridin-2-yl)acetate 3.131 g of diethyl 2-(5-nitropyridin-2-yl)malonate, 476 mg of lithium chloride and 0.2 ml of water were dissolved in 10 ml of N,N-dimethylformamide and heated at 120° C. for 3 hours. Then the reaction mixture was distilled under reduced pressure and the residue thus obtained was purified by silica gel column chromatography (eluted with ethyl acetate/n-hexane) to thereby give 803 mg of a mixture of 2-methyl-5-nitropyridine with ethyl(5-nitropyridin-2-yl)acetate as a reddish brown crystalline substance. 803 mg of these crystals were hydrogenated in the same manner as the one of Production Example 151 to thereby give as a pale yellow oily substance 614 mg of a mixture of the title compounds which could be hardly separated. 2-methyl-5-aminopyridine:

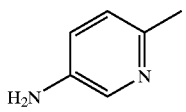

¹H-NMR(CDCl₃) δ ppm: 2.27(s, 3H), 3.70–3.90(br.s, 2H), 6.82(d, J=2 Hz, 1H), 6.98(d, J=7 Hz, 1H), 7.93(dd, J=2, 7 Hz, 1H) ethyl(5-aminopyridin-2-yl)acetate

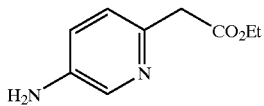

¹H-NMR(CDCl₃) δ ppm: 1.18(t, J=7 Hz, 3H), 3.65(s, 2H), 3.70–3.90(br.s, 2H), 4.10(q, J=7 Hz, 2H), 6.82(d, J=2 Hz, 1H), 6.98(d, J=7 Hz, 1H), 7.93(dd, J=2, 7 Hz, 1H)

Production Example 160

N-(Imidazol-2-ylmethyl)acetamide 0.34 g of 2-aminomethylimidazole dihydrochloride was added to 20 ml of N,N-dimethylformamide in a nitrogen atmosphere. Under ice-cooling, 0.40 g of sodium hydride (60% oily) was added thereto and the resulting mixture was subjected to ultrasonication for 30 minutes. To the reaction mixture were added 20 ml of pyridine and 10 ml of acetic anhydride and the obtained mixture was stirred at room temperature for 2 days. After concentrating under reduced pressure, the residue was distributed into water and ethyl acetate. The organic layer was washed with water and dried over anhydrous sodium sulfate. The extract was concentrated under reduced pressure to thereby give 0.24 g of the title compound as a pale brown solid.

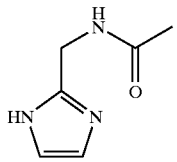

¹H-NMR(CDCl₃) δ ppm: 1.99(s, 3H), 4.44(d, J=7 Hz, 2H), 6.96(s, 2H), 8.25(br.s, 1H), 8.39(br.m, 1H)

Production Example 161

N-[1-[2-(Trimethylsilyl)ethoxymethyl]imidazol-2-ylmethyl]-acetamide

Under ice-cooling, 0.08 g of sodium hydride (60% oily) was added to a solution of 0.31 g of N-(imidazol-2-ylmethyl)acetamide in N,N-dimethylformamide (10 ml). After stirring for 15 minutes, a solution of 0.35 ml of 2-(trimethylsilyl)ethoxymethyl chloride in N,N-dimethylformamide (1 ml) was dropped thereinto and the resulting mixture was stirred at room temperature for additional 16 hours. Then the reaction mixture was distributed into water and ethyl acetate. The organic layer was washed with water and dried over anhydrous magnesium sulfate. After concentrating under reduced pressure, the residue was purified by silica gel column chromatography (eluted with dichloromethane/methanol) to thereby give 0.16 g of the title compound as a colorless oily substance.

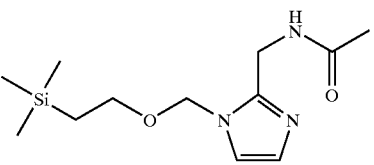

¹H-NMR(CDCl₃) δ ppm: 0.01(s, 9H), 0.92(t, J=8 Hz, 2H), 2.05(s, 3H), 3.51(t, J=8 Hz, 2H), 4.54(d, J=7 Hz, 2H), 5.30(s, 2H), 6.53(br.s, 1H), 6.99(d, J=1 Hz, 1H), 7.01(d, J=1 Hz, 1H)

Production Example 162

2-[N-(tert-Butoxycarbonyl)aminomethyl]imidazole

To an aqueous solution (10 ml) of 0.34 g of 2-aminomethylimidazole dihydrochloride were added 0.32 g of sodium hydroxide and 0.34 g of sodium hydrogencarbonate. Then a tetrahydrofuran solution (10 ml) of 1.05 g of di-tert-butyl dicarbonate was added thereto and the resulting mixture was stirred at room temperature for 16 hours. After adding an aqueous solution of disodium hydrogenphosphate, the resulting mixture was extracted with ethyl acetate. The organic layer was washed successively with water and a saturated aqueous solution of sodium chloride and dried over anhydrous magnesium sulfate. After concentrating under reduced pressure, the residue was purified by silica gel column chromatography (eluted with n-hexane/ethyl acetate) to thereby give 0.20 g of the title compound as a colorless powder.

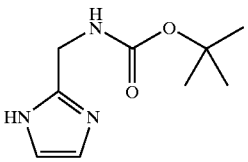

¹H-NMR(CDCl₃) δ ppm: 1.43(s, 9H), 4.32(d, J=7 Hz, 2H), 5.43(br.s, 1H), 6.96(s, 2H)

Production Example 163

1-[2-(Trimethylsilyl)ethoxymethyl-2-[N-(tert-butoxycarbonyl)-aminomethyl]imidazole Starting with 2-[N-(tert-butoxycarbonyl)aminomethyl]-imidazole, the title compound was obtained by the same procedure as that of Production Example 161.

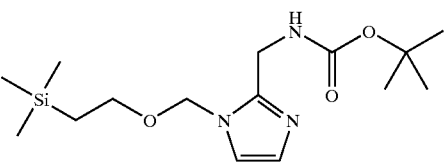

¹H-NMR(CDCl₃) δ ppm: 0.01(s, 9H), 0.92(t, J=8 Hz, 2H), 1.46(s, 9H), 3.49(t, J=8 Hz, 2H), 4.46(d, J=5 Hz, 2H), 5.33(br.s, 2H), 7.00(br.s, 2H), 8.03(br.s, 1H)

Production Example 164

N,N-Dimethyl-[2-[(pyridin-2-yl)hydroxymethyl]imidazol-1-yl]-sulfonamide

To a solution of 4.37 g of 2-bromopyridine in diethyl ether (40 ml) was added 16.5 ml of a 1.6 M hexane solution of n-butyllithium at −78° C. in a nitrogen atmosphere. After stirring for 30 minutes, a tetrahydrofuran solution (20 ml) of 4.34 g of N,N-dimethyl-2-formylimidazole-1-sulfonamide was added thereto. Then the reaction mixture was brought back to room temperature and distributed into ethyl acetate and an aqueous solution of ammonium chloride. The organic layer was extracted and washed successively with water and a saturated aqueous solution of sodium chloride and dried over anhydrous sodium sulfate. After distilling off the solvent under reduced pressure, the residue was purified by silica gel column chromatography (eluted with dichloromethane/methanol) to thereby give 2.02 g of the title compound as a pale yellow oily substance.

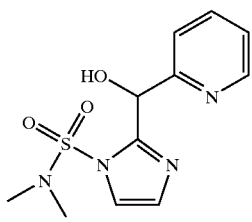

$^1$H-NMR(CDCl$_3$) δ ppm: 2.99(s, 6H), 5.32(d, J=7 Hz, 1H), 6.30(d, J=7 Hz, 1H), 7.00(d, J=1 Hz, 1H), 7.29(d, J=1 Hz, 1H), 7.26–7.31(m, 2H), 7.71(dt, J=2, 8 Hz, 1H), 8.61(dt, J=1, 5 Hz, 1H Production Example 165

[(Pyridin-2-yl)[1-(N,N-dimethylsulfonamido)imidazol-1-yl]methyl acetate 0.93 g of N,N-dimethyl-[2-[(pyridin-2-yl)hydroxymethyl]-imidazol-1-yl]-sulfonamide was dissolved in 20 ml of pyridine and 1.0 ml of acetic anhydride and 0.44 g of 4-dimethylaminopyridine were added thereto. After stirring at room temperature for 48 hours, the solvent was distilled off under reduced pressure. Then the residue was purified by silica gel column chromatography (eluted with dichloromethane/methanol) to thereby give 0.976 g of the title compound as an orange oily substance.

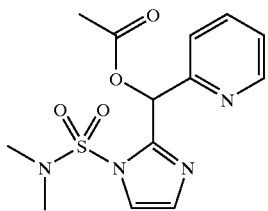

$^1$H-NMR(CDCl$_3$) δ ppm: 2.20(s, 3H), 3.00(s, 6H), 7.08(d, J=2 Hz, 1H), 7.22(s, 1H), 7.25(ddd, J=2, 5, 8 Hz, 1H), 7.30(d, J=2 Hz, 1H), 7.40(br.d, J=8 Hz, 1H), 7.73(dt, J=2, 8 Hz, 1H), 8.58(ddd, J=1, 2, 5 Hz, 1H)

Production Example 166

N,N-Dimethyl[2-(pyridin-2-ylmethyl)imidazol-1-yl]sulfonamide

A solution of 0.97 g of [(pyridin-2-yl)[1-(N,N-dimethylsulfonamido)imidazol-1-yl]methyl acetate in ethanol (30 ml) was stirred in the presence of 0.20 g of palladium carbon (containing 50% of moisture) in a hydrogen gas stream at room temperature for 20 hours. After filtering off the catalyst, the residue was concentrated under reduced pressure to thereby give 0.21 g of the title compound as a colorless oily substance.

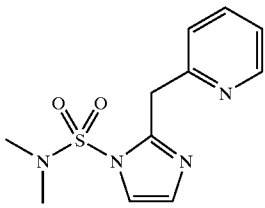

$^1$H-NMR(CDCl$_3$) δ ppm: 2.81(s, 6H), 4.54(s, 2H), 7.03(d, J=2 Hz, 1H), 7.16(ddd, J=1, 5, 8 Hz, 1H), 7.21(br.d, J=8 Hz, 1H), 7.28(d, J=2 Hz, 1H), 7.64(dt, J=2, 8 Hz, 1H), 8.54(ddd, J=1, 2, 5 Hz, 1H)

Production Example 167

2-(Pyridin-2-ylmethyl)imidazole

To a solution of 0.21 g of N,N-dimethyl[2-(pyridin-2-ylmethyl)imidazol-1-yl]sulfonamide in ethanol (2 ml) was added a 2% aqueous solution (20 ml) of potassium hydroxide and the resulting mixture was heated under reflux for 11 hours. After distilling off the solvent under reduced pressure, the residue was purified by silica gel column chromatography (eluted with dichloromethane/methanol) to thereby give 0.053 g of the title compound as a colorless oily substance.

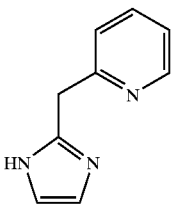

$^1$H-NMR(CDCl$_3$) δ ppm: 4.22(s, 2H), 7.02(s, 2H), 7.13 (ddd, J=1, 5, 8 Hz, 1H), 7.25(br.d, J=8 Hz, 1H), 7.59(dt, J=2, 8 Hz, 1H), 8.51(ddd, J=1, 2, 5 Hz, 1H)

Production Example 168

2-Pyridyl 2-imidazolyl ketone

To an ethanol solution (5 ml) of 1.41 g of N,N-dimethyl[2-(pyridin-2-yl)hydroxymethyl)imidazol-1-yl]sulfonamide was added 50 ml of a 2% aqueous solution of potassium hydroxide and the resulting mixture was heated under reflux for 9 hours. After distilling off the solvent under reduced pressure, the residue was purified by silica gel column chromatography (eluted with dichloromethane/methanol) to thereby give 0.441 g of the title compound as a colorless oily substance.

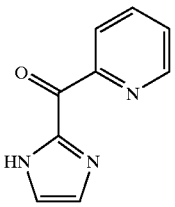

$^1$H-NMR(CDCl$_3$) δ ppm: 7.32(br.s, 1H), 7.47(br.s, 1H), 7.58(ddd, J=2, 5, 8 Hz, 1H), 7.98(dt, J=2, 8 Hz, 1H), 8.46(br.d, J=8 Hz, 1H), 8.76(br.d, J=5 Hz, 1H)

Production Example 169

N,N-Dimethyl-2-[[4-(4,4-dimethyl-2-oxazolin-2-yl)phenyl]hydroxymethyl]imidazole-1-sulfonamide Similar to Production Example 164, 4.54 g of N,N-dimethyl-2-formylimidazole-1-sulfonamide was treated with 7.0 g of 2-(4-bromophenyl)-4,4-dimethyl-2-oxazoline to thereby give 3.41 g of the title compound.

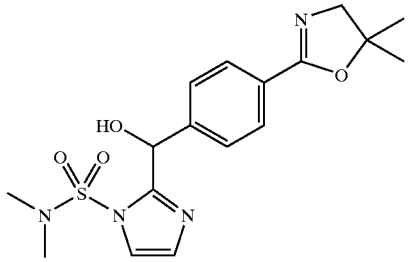

$^1$H-NMR(CDCl$_3$) δ ppm: 1.36(s, 6H), 2.72(s, 6H), 3.98(d, J=7 Hz, 1H), 4.08(s, 2H), 6.21(d, J=7 Hz, 1H), 7.08(d, J=2 Hz, 1H), 7.24(d, J=2 Hz, 1H), 7.41(d, J=8 Hz, 2H), 7.91(d, J=8 Hz, 2H)

Production Example 170

Methyl 4-[(imidazol-2-yl)carbonyl]benzoate and methyl 4-[(imidazol-2-yl)hydroxymethyl]benzoate To a solution of 1.70 g of N,N-dimethyl-2-[[4-(4,4-dimethyl-2-oxazolin-2-yl)phenyl]hydroxymethyl]imidazole-1-sulfonamide in ethanol was added 50 ml of a 2% aqueous solution of potassium hydroxide and the resulting mixture was heated under reflux for 15 hours. After distilling off the solvent under reduced pressure, 50 ml of methanol and 5 ml of conc. sulfuric acid were added to the residue and the resulting mixture was heated under reflux for 10 hours. After distilling off methanol under reduced pressure, the residue was distributed into ethyl acetate and an aqueous solution of sodium bicarbonate. The organic layer was extracted, washed successively with water and a saturated aqueous solution of sodium chloride and dried over anhydrous sodium sulfate. After distilling off the solvent under reduced pressure, the residue was purified by silica gel column chromatography (eluted with dichloromethane/methanol) to thereby give 0.38 g of methyl 4-[(imidazol-2-yl)carbonyl]benzoate and 0.21 g of methyl 4-[(imidazol-2-yl)hydroxymethyl]benzoate each as a colorless oily substance.

methyl 4-[(imidazol-2-yl)carbonyl]benzoate

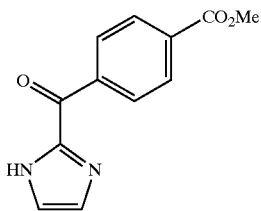

$^1$H-NMR(CDCl$_3$) δ ppm: 3.89(s, 3H), 7.27(d, J=1 Hz, 1H), 7.35(d, J=1 Hz, 1H), 8.11(d, J=8 Hz, 2H), 8.57(d, J=8 Hz, 2H)

methyl 4-[(imidazol-2-yl)hydroxymethyl]benzoate

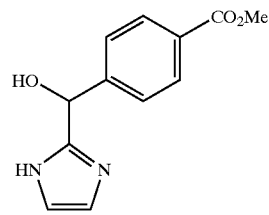

$^1$H-NMR(CDCl$_3$) δ ppm: 3.91(s, 3H), 5.98(s, 1H), 6.99(s, 2H), 7.50(d, J=8 Hz, 2H), 8.02(d, J=8 Hz, 2H)

Production Example 171

Methyl 4-[(1-acetylimidazol-2-yl)acetoxymethyl]benzoate

To a pyridine solution (16 ml) of 0.21 g of methyl 4-[(imidazol-2-yl)hydroxymethyl]benzoate was added 0.5 ml of acetic anhydride and the resulting mixture was stirred at room temperature for 20 hours. After distilling off the solvent under reduced pressure, 0.25 g of the title compound was obtained as an orange oily substance.

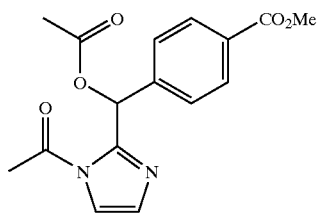

$^1$H-NMR(CDCl$_3$) δ ppm: 2.15(s, 3H), 2.54(s, 3H), 3.79(s, 3H), 7.06(s, 1H), 7.23(s, 1H), 7.35(s, 1H), 7.56(d, J=8 Hz, 2H), 8.02(d, J=8 Hz, 2H)

Production Example 172

Methyl 4-[(imidazol-2-yl)methyl]benzoate 0.25 g of methyl 4-[(1-acetylimidazol-2-yl)acetoxymethyl]benzoate was treated in the same manner as the one of Production Example 166 to thereby give the title compound.

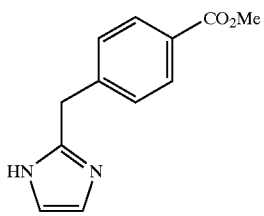

$^1$H-NMR(CDCl$_3$) δ ppm: 3.90(s, 3H), 4.17(s, 2H), 6.99(s, 2H), 7.32(d, J=8 Hz, 2H), 7.99(d, J=8 Hz, 2H)

Production Example 173

8-Trifluoromethyl-6-dimethylaminopurine 0.306 g of 4,5-diamino-6-dimethylaminopyrimidine was dissolved in 20 ml of trifluoroacetic anhydride. Then the reaction mixture was introduced into a steel container. After sealing, it was heated to 100° C. for 14 hours. The reactor was opened at room temperature and the solvent was distilled off under reduced pressure. The residue was purified by silica gel column chromatography (eluted with n-hexane/ethyl acetate) to thereby give 0.073 g of the title compound as white crystals.

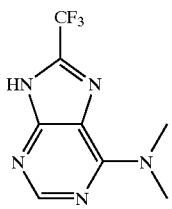

$^1$H-NMR(CDCl$_3$) δ ppm: 3.47(br.s, 3H), 3.99(br.s, 3H), 8.39(s, 1H)

Production Example 174

6-Dimethylamino-8-oxo-7(H),8(H)-purine

To an acetonitrile solution (30 ml) of 0.306 g of 4,5-diamino-6-dimethylaminopyrimidine was added 30 ml of an acetonitrile solution of 0.512 g of N,N'-disuccinimidyl carbonate and the resulting mixture was stirred for 24 hours. Further, 0.256 g of N,N'-disuccinimidyl carbonate was added thereto and the resulting mixture was stirred at room temperature for 24 hours. Next, the reaction mixture was concentrated under reduced pressure and the crystals thus precipitated were collected by filtration and washed successively with water and methanol. Thus 0.128 g of the title compound was obtained as brown crystals.

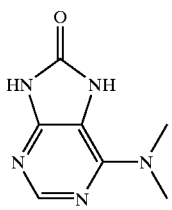

$^1$H-NMR(CDCl$_3$) δ ppm: 3.08(s, 6H), 7.99(s, 1H), 10.54 (br.s, 1H), 11.34(br.s, 1H)

Production Example 175

(Purin-6-yl)ethanone 1.04 g of 6-(ethoxyvinyl)purine was dissolved in 80 ml of 1 N hydrochloric acid and stirred at room temperature for 15 hours. After neutralizing with a saturated aqueous solution of sodium bicarbonate, it was extracted with dichloromethane and the organic layer was dried over anhydrous sodium sulfate. After distilling off the solvent under reduced pressure, 0.70 g of crude title compound was obtained as a colorless oily substance.

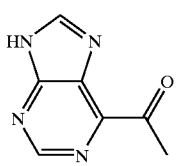

$^1$H-NMR(DMSO-d$_6$) δ ppm: 2.75(s, 3H), 8.80(s, 1H), 9.14(s, 1H)

Production Example 176

1-(Purin-6-yl)ethanol

To an ethanol solution (80 ml) of 0.70 g of (purin-6-yl) ethanone was added 0.70 g of sodium borohydride and the resulting mixture was stirred at room temperature for 4 hours. The excessive reagent was decomposed by adding water and 4 N hydrochloric acid and distilled off under reduced pressure. The residue was purified by silica gel column chromatography (eluted by dichloromethane/methanol) to thereby give 0.57 g of the title compound as a white solid.

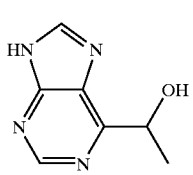

$^1$H-NMR(CDCl$_3$) δ ppm: 1.48(d, J=7 Hz, 3H), 5.05(m, 1H), 5.78(br.s, 1H), 8.58(s, 1H), 8.82(s, 1H)

Production Example 177

6-[1-(tert-Butyldimethylsiloxy)ethyl]purine

To a solution of 0.543 g of 1-(purin-6-yl)ethanol in N,N-dimethylformamide (10 ml) were added 0.27 g of imidazole and 0.598 g of tert-butyldimethylsilyl chloride and the resulting mixture was stirred at room temperature for 15 hours. After distilling off the solvent under reduced pressure, the residue was purified by silica gel column chromatography (eluted with dichloromethane/methanol) to thereby give 0.793 g of the title compound as a white solid.

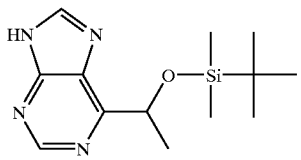

$^1$H-NMR(CDCl$_3$) δ ppm: 0.08(s, 3H), 0.01(s, 3H), 0.77(s, 9H), 1.53(d, J=7 Hz, 3H), 5.23(q, J=7 Hz, 1H), 8.37(s, 1H), 9.03(s, 1H)

Example 763

5,10-Dihydro-5-methyl-10H-pyrazino[2,3-b][1,4]quinoxaline

To a solution of 0.586 g of 2-[N-methyl-N-(2-nitrophenyl)amino]-3-chloropyrazine in tetrahydrofuran (20 ml) was added 4 g of hydrosulfite sodium in water (8 ml). After adding 8 ml of 50% aqueous ammonia/water, the resulting mixture was vigorously stirred at room temperature for 6 hours. Then the reaction mixture was distributed into ethyl acetate and water and the organic layer was dried over anhydrous magnesium sulfate. After distilling off the solvent under reduced pressure, the residue was purified by silica gel column chromatography (eluted with n-hexane/ethyl acetate) to thereby give 0.32 g of the title compound as yellow crystals.

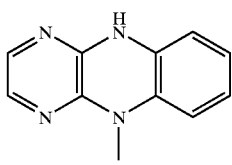

$^1$H-NMR(CDCl$_3$) δ ppm: 2.93(s, 3H), 6.33(m, 1H), 6.42(m, 1H), 6.50–6.56(m, 2H), 6.83(d, J=3 Hz, 1H), 6.93(d, J=3 Hz, 1H), 9.04(s, 1H)

m.p.: 229–231° C.

MS: FAB(+)198(M$^+$)

Example 764

5,10-Dihydro-10H-pyrazino[2,3-b][1,4]quinoxaline

A solution of 0.28 g of 2-[(2-aminophenyl)amino]-3-chloropyrazine in N,N-dimethylformamide (15 ml) was degassed and then heated to 100° C. for 30 minutes. Next, the reaction mixture was brought back to room temperature and poured into water. The precipitate was taken up by filtration and dissolved in 2 N hydrochloric acid. After filtering off the insoluble matters, the hydrochloric acid solution was neutralized with potassium hydroxide. The crystals thus precipitated were taken up by filtration to thereby give 0.10 g of the title compound as greenish yellow crystals.

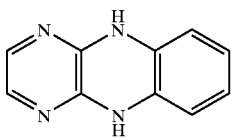

$^1$H-NMR(DMSO-d$_6$) δ ppm: 6.23(dd, J=3, 6 Hz, 2H), 6.39(dd, J=3, 6 Hz, 2H), 6.75(s, 2H), 8.75(s, 2H)

m.p.: 215–217° C.

MS: FAB(+)184(M$^+$)

Example 765

5,10-Dihydro-5-allyl-10H-pyrazino[2,3-b][1,4]quinoxaline 2.91 g of 2-[N-allyl-N-(2-nitrophenyl)amino]-3-chloropyrazine was treated by the same method as the one of Example 985 to thereby give 1.26 g of the title compound as a yellow powder.

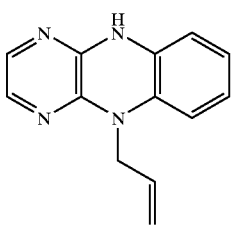

$^1$H-NMR(CDCl$_3$) δ ppm: 4.28(d, J=5 Hz, 2H), 5.23(d, J=11 Hz, 1H), 5.30(d, J=16 Hz, 1H), 5.79–5.91(tdd, J=5, 11, 16 Hz, 1H), 6.21(d, J=8 Hz, 1H), 6.36(d, J=8 Hz, 1H), 6.54–6.63(m, 2H), 6.91(d, J=3 Hz, 1H), 7.04(d, J=3 Hz, 1H)

m.p.: 173–175° C.

MS: ESI(+)225(MH$^+$)

Examples

The following compounds were obtained by reacting analogs of 2-[(2-nitrophenyl)amino]-3-chloropyrazine by the same method as the one of Example 763.

| Ex. | Structural formula | MS | M.p. | NMR |
|---|---|---|---|---|
| 766 | tert-butyl (5,10-dihydro-10H-pyrazino[2,3-b][1,4quinoxalin-5-yl)acetate | ESI (+) 299 (MH$^+$) | 199–201° C. | $^1$NMR(CDCl$_3$) δ ppm: 1.40(s, 9H), 4.25(s, 2H), 6.13–6.15(m, 1H), 6.17–6.19(m, 1H), 6.52–6.58(m, 2H), 6.91(d, J=3Hz, 1H), 6.99(d, J=3Hz, 1H) |

| Ex. | Structural formula | MS | M.p. | NMR |
|---|---|---|---|---|
| 767 | methyl 4-[(5,10-dihydro-10H-pyrazino[2,3-b][1,4]quinoxalin-5-yl)methyl]benzoate | ESI (+) 333 (MH+) | 232–234° C. | $^1$NMR(CDCl$_3$) δ ppm: 3.90(s, 3H), 4.96(br · s, 2H), 6.15(dd, J=1, 8Hz, 1H), 6.24(dd, J=1, 8Hz, 1H), 6.48(dt, J=1, 8Hz, 1H), 6.57(dt, J=1, 8Hz, 1H), 6.98(d, J=3Hz, 1H), 7.04(d, J=3Hz, 1H), 7.41(d, J=8Hz, 2H), 8.01(d, J=8Hz, 2H) |
| 768 | methyl (E)4-(5,10-dihydro-10H-pyrazino[2,3-b][1,4]quinoxalin-5-yl)-2-butenoate | ESI (+) 287 (MH+) | 195–197° C. | $^1$NMR(CDCl$_3$) δ ppm: 3.72(s, 3H), 4.44(m, 2H), 6.06(d, J=16Hz, 1H), 6.24(m, 2H), 6.60(m, 2H), 6.95–7.05(m, 3H) |
| 769 | 5,10-dihydro-5-methoxymethyl-10H-pyrazino[2,3-b][1,4]quinoxaline | ESI (+) 229 (MH+) | 185–188° C. | $^1$NMR(CDCl$_3$) δ ppm: 3.45(s, 3H), 5.13(s, 2H), 6.14(br · s, 1H), 6.26(m, 1H), 6.65–6.71(m, 3H), 7.05(d, J=3Hz, 1H), 7.13(d, J=3Hz, 1H) |
| 770 | 5,10-dihydro-5-benzyl-10H-pyrazino[2,3-b][1,4]quinoxaline | ESI (+) 275 (MH+) | 194–196° C. | $^1$NMR(CDCl$_3$) δ ppm: 4.85(s, 2H), 6.13–6.17(m, 2H), 6.41(dt, J=2, 8Hz, 1H), 6.48(dt, J=2, 8Hz, 1H), 6.87(d, J=3Hz, 1H), 6.97(d, J=3Hz, 1H), 7.16–7.28(m, 5H), 7.46(br · s, 1H) |

-continued

| Ex. | Structural formula | MS | M.p. | NMR |
|---|---|---|---|---|
| 771 | 3-(5,10-dihydro-10H-pyrazino[2,3-b][1,4]quinoxalin-5-yl)-1,2-propanediol | ESI (+) 281 (MNa⁺) | 191–194° C. | ¹NMR(CDCl₃) δ ppm: 3.34(m, 2H), 3.53–3.64(m, 2H), 3.71–3.76(m, 1H), 4.64(t, J=6Hz, 1H), 4.90(d, J=6Hz, 1H), 6.29–6.31(m, 1H), 6.46–6.52(m, 2H), 6.55–6.59(m, 1H), 6.81(d, J=3Hz, 1H), 6.87(d, J=3Hz, 1H), 9.02(s, 1H) |

Examples

The following compounds were obtained by reacting analogs of 2-[1-(2-amino-4-substituted phenyl)amino]-3-chloropyrazine by the same method as the one of Example 764.

| Ex. | Structural formula | MS | M.p. | NMR |
|---|---|---|---|---|
| 772 | 5,10-dihydro-7-methoxymethoxy-10H-pyrazino[2,3-b][1,4]quinoxaline | FAB (+) 244 (MH⁺) | | ¹NMR(CDCl₃) δ ppm: 3.38(s, 3H), 4.94(s, 2H), 6.03(s, 1H), 6.07(d, J=8Hz, 1H), 6.15(d, J=8Hz, 1H), 6.74(m, 2H), 8.65(s, 1H), 8.79(s, 1H) |
| 773 | 5,10-dihydro-7-methoxy-10H-pyrazino[2,3-b][1,4]quinoxaline | | | ¹NMR(CDCl₃) δ ppm: 3.54(s, 3H), 5.92(d, J=2Hz, 1H), 5.99(dd, J=2, 8Hz, 1H), 6.17(d, J=8Hz, 1H), 6.74(d, J=3Hz, 1H), 6.76(d, J=3Hz, 1H), 8.64(s, 1H), 8.77(s, 1H) |
| 774 | ethyl (5,10-dihydro-10H-pyrazino[2,3-b][1,4]quinoxalin-7-yl)carboxylate | ESI (+) 257 (MH⁺) | >275° C. | ¹NMR(DMSO-d₆) δ ppm: 1.21(t, J=7Hz, 3H), 4.16(q, J=7Hz, 2H), 6.26(d, J=8Hz, 1H), 6.79–6.85(m, 3H), 7.05(dd, J=1, 8Hz, 1H), 8.94(s, 1H), 9.23(s, 1H) |

-continued

| Ex. | Structural formula | MS | M.p. | NMR |
|---|---|---|---|---|
| 775 | (5,10-dihydro-10H-pyrazino[2,3-b][1,4]quinoxalin-7-yl)carbonitrile | EI (+) 209 (M+) | >275° C. | ¹NMR(DMSO-d₆) δ ppm: 6.26(d, J=8Hz, 1H), 6.37(d, J=1Hz, 1H), 6.83–6.88(m, 3H), 9.05(s, 1H), 9.30(s, 1H) |

Examples

The following compounds were obtained by reacting analogs of 2-[(nitrophenyl)amino]-3-chloropyrazine by the same method as the one of Example 763.

| Ex. | Structural formula | MS | M.p. | NMR |
|---|---|---|---|---|
| 776 | 5,10-dihydro-8-methoxy-5-methyl-10H-pyrazino[2,3-b][1,4]quinoxaline | ESI (+) 228 (M+) | 198–201° C. | ¹NMR(CDCl₃) δ ppm: 3.06(s, 3H), 3.68(s, 3H), 5.87(d, J=1Hz, 1H), 6.17(dd, J=1, 8Hz, 1H), 6.31(d, J=8Hz, 1H), 6.54(br · s, 1H), 6.89(d, J=3Hz, 1H), 7.08(d, J=3Hz, 1H) |
| 777 | 5,10-dihydro-8-methoxymethoxy-5-methyl-10H-pyrazino[2,3-b][1,4]quinoxaline | ESI (+) 259 (MH+) | 197–198° C. | ¹NMR(CDCl₃) δ ppm: 2.92(s, 3H), 3.32(s, 3H), 4.98(s, 2H), 6.11(d, J=2Hz, 1H), 6.21(dd, J=2, 8Hz, 1H), 6.34(d, J=8Hz, 1H), 6.83(d, J=3Hz, 1H), 6.95(d, J=3Hz, 1H), 9.07(s, 1H) |
| 778 | (5,10-dihydro-5-methyl-10H-pyrazino[2,3-b][1,4]quinoxalin-8-yl)carbonitrile | ESI (+) 224 (MH+) | 274–275° C. | ¹NMR(DMSO-d₆) δ ppm: 2.94(s, 3H), 6.45(d, J=2Hz, 1H), 6.48(d, J=8Hz, 1H), 6.95(d, J=3Hz, 1H), 6.98(dd, J=2, 8Hz, 1H), 7.01(d, J=3Hz, 1H), 9.33(s, 1H) |

| Ex. | Structural formula | | NMR |
|---|---|---|---|
| 779 | 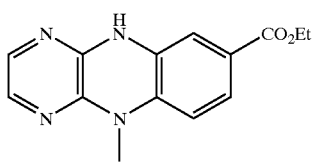<br>ethyl (5,10-dihydro-5-methyl-10H-pyrazino[2,3-b][1,4]quinoxalin-8-yl)carboxylate | ESI (+) 271 (MH⁺)    239–242° C. | ¹NMR(DMSO-d$_6$) δ ppm: 1.23(t, J=7Hz, 3H), 2.96(s, 3H), 4.18(q, J=7Hz, 2H), 6.47(d, J=8Hz, 1H), 6.86(d, J=2Hz, 1H), 6.91(d, J=3Hz, 1H), 6.99(d, J=3Hz, 1H), 7.16(dd, J=2, 8Hz, 1H), 9.20(s, 1H) |
| 780 | 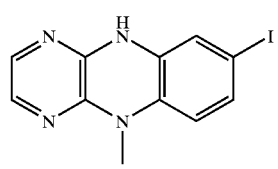<br>5,10-dihydro-8-iodo-5-methyl-10H-pyrazino[2,3-b][1,4]quinoxaline | ESI (+) 325 (MH⁺)    >275° C. | ¹NMR(DMSO-d$_6$) δ ppm: 2.88(s, 3H), 6.20(d, J=8Hz, 1H), 6.58(d, J=2Hz, 1H), 6.83(dd, J=2, 8Hz, 1H), 6.87(d, J=3Hz, 1H), 6.96(d, J=3Hz, 1H), 9.13(s, 1H) |
| 781 | 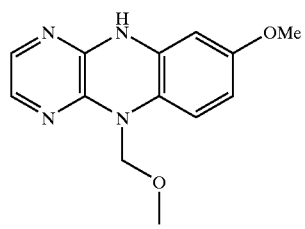<br>5,10-dihydro-5-methoxymethyl-8-methoxy-10H-pyrazino[2,3-b][1,4]quinoxaline | ESI (+) 259 (MH⁺)    244–251° C. | ¹NMR(DMSO-d$_6$) δ ppm: 3.26(s, 3H), 3.59(s, 3H), 4.99(s, 3H), 6.06(d, J=3Hz, 1H), 6.14(dd, J=3, 9Hz, 1H), 6.48(d, J=9Hz, 1H), 6.99(d, J=3Hz, 1H), 7.12(d, J=3Hz, 1H) |

| Ex. | Structural formula | NMR |
|---|---|---|
| 782 | 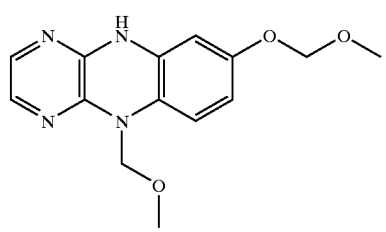<br>5,10-dihydro-8-methoxymethoxy-5-methoxymethyl-10H-pyrazino[2,3-b][1,4]quinoxaline | ¹NMR(CDCl$_3$) δ ppm: 3.43(s, 3H), 3.45(s, 3H), 5.03(s, 2H), 5.11(s, 2H), 6.05(s, 1H), 6.33(d, J=8Hz, 1H), 6.60(d, J=8Hz, 1H), 6.79(br · s, 1H), 7.05(d, J=3Hz, 1H), 7.13(d, J=3Hz, 1H) |

| | | | |
|---|---|---|---|
| 783 | 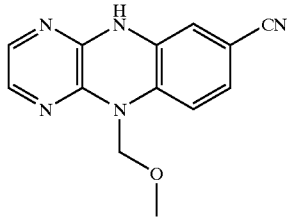<br>(5,10-dihydro-5-methoxymethyl-10H-pyrazino[2,3-b][1,4]quinoxalin-8-yl) carbonitrile | | ¹NMR(CDCl₃) δ ppm: 3.38(s, 3H), 5.07(s, 2H), 6.36(s, 1H), 6.61(d, J=8Hz, 1H), 6.89(d, J=8Hz, 1H), 7.08(d, J=3Hz, 1H), 7.14(d, J=3Hz, 1H) |

Example 784

5,10-Dihydro-7-hydroxy-10H-pyrazino[2,3-b][1,4]quinoxaline hydrochloride 5,10-Dihydro-5-methoxymethyl-8-methoxymethoxy-10H-pyrazino[2,3-b][1,4]quinoxaline was treated by the same method as the one of Example 8 to thereby give the title compound.

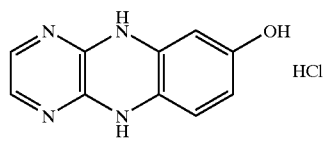

¹H-NMR(DMSO-d₆) δ ppm 6.07(d, J=8 Hz, 1H), 6.11(s, 1H), 6.46(d, J=8 Hz, 1H), 6.49(br.s, 1H), 6.56(br.s, 1H)

m.p.: >275° C.

MS: ESI(+)201(MH⁺)

Examples

The compounds obtained in Examples 767 and 779 were treated by the same method as the one of Example 8 to thereby give the following compounds.

| Ex. | Structural formula | MS | M.p. | NMR |
|---|---|---|---|---|
| 785 | 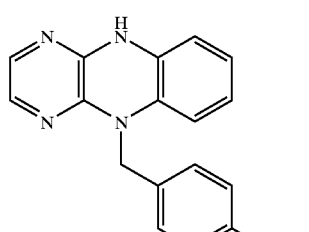<br>[4-(5,10-dihydro-10H-pyrazino[2,3-b][1,4]quinoxalin-5-yl)methyl]benzoic acid | ESI (+) 319 (MH⁺) | 253–255° C. | ¹NMR(DMSO-d₆) δ ppm: 4.90(s, 2H), 6.15(d, J=8Hz, 1H), 6.36(d, J=8Hz, 1H), 6.39(t, J=8Hz, 1H), 6.49(t, J=8Hz, 1H), 6.88(d, J=3Hz, 1H), 6.90(d, J=3Hz, 1H), 7.43(d, J=9Hz, 2H), 7.88(d, J=8Hz, 2H), 9.18(s, 1H) |
| 786 | 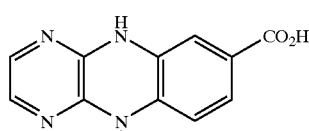<br>5,10-dihydro-5-methyl-10H-pyrazino[2,3-b][1,4]quinoxaline-7-carboxylic acid | | | ¹NMR(DMSO-d₆) δ ppm: 2.96(s, 3H), 6.47(d, J=8Hz, 1H), 6.85(d, J=2Hz, 1H), 6.91(d, J=3Hz, 1H), 6.98(d, J=3Hz, 1H), 7.15(dd, J=2, 8Hz, 1H), 9.23(s, 1H) |

Example 787

(5,10-Dihydro-10H-pyrazino[2,3-b][1,4]quinoxalin-5-yl)acetic acid

The title compound was obtained by treating tert-butyl (5,10-dihydro-10H-pyrazino[2,3-b][1,4]quinoxalin-5-yl) acetate by the same method as the one of Example 9.

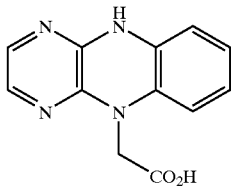

$^1$H-NMR(DMSO-$d_6$) δ ppm: 4.26(s, 2H), 6.33(dd, J=2, 8 Hz, 1H), 6.37(dd, J=2, 8 Hz, 1H), 6.51(dt, 2, 8 Hz, 1H), 6.54(dt, J=2, 8 Hz, 1H), 6.91(d, J=3 Hz, 1H), 6.93(d, J=3 Hz, 1H), 9.14(s, 1H)
m.p.: 210–212° C.
MS: ESI(+)243(MH$^+$)

Example 788

5,10-Dihydro-7-methoxy-5-methyl-10-methoxymethyl-10H-pyrazino[2,3-b][1,4]quinoxaline 0.258 g of 5,10-dihydro-5-methoxymethyl-8-methoxy-10H-pyrazino[2,3-b][1,4]quinoxaline in N,N-dimethylformamide (20 ml) was degassed at 0° C. in a nitrogen atmosphere. After adding 0.050 g of sodium hydride (60% or above), the resulting mixture was stirred for 30 minutes. Then a solution of 0.13 ml of methyl iodide in N,N-dimethylformamide (5 ml) was dropped thereinto at the same temperature and the resulting mixture was stirred at room temperature for 16 hours. The reaction mixture was distributed into ethyl acetate and water and the aqueous layer was extracted with ethyl acetate. Then the organic layers were combined, washed successively with water and a saturated aqueous solution of sodium chloride and dried over magnesium sulfate. After distilling off the solvent under reduced pressure, the residue was purified by silica gel column chromatography (eluted with n-hexane/ethyl acetate) to thereby give 0.234 g of the title compound as a yellow solid.

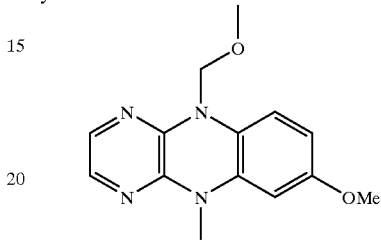

$^1$H-NMR(CDCl$_3$) δ ppm: 3.13(s, 3H), 3.44(s, 3H), 3.75(s, 3H), 5.16(s, 2H), 6.13(s, 1H), 6.21(d, J=8 Hz, 1H), 6.65(d, J=8 Hz, 1H), 7.14(s, 1H), 7.18(s, 1H)

Examples

The compounds obtained in Examples 783 and 782 were treated by the same method as the one of Example 788 to thereby give the following compounds.

| Ex. | Structural formula | NMR |
|---|---|---|
| 789 | 5,10-dihydro-7-methoxymethoxy-10-methoxymethyl-5-methyl-10H-pyrazino[2,3-b][1,4]quinoxaline | $^1$NMR(CDCl$_3$) δ ppm: 3.13(s, 3H), 3.43(s, 3H), 3.47(s, 3H), 5.08(s, 2H), 5.13(s, 2H), 6.23(d, J=2Hz, 1H), 6.40(dd, J=2, 8Hz, 1H), 6.63(d, J=8Hz, 1H), 7.10(d, J=3Hz, 1H), 7.17(d, J=3Hz, 1H) |
| 790 | 5,10-dihydro-10-methoxymethyl-5-methyl-10H-pyrazino[2,3-b][1,4]quinoxaline-7-carbonitrile | $^1$NMR(CDCl$_3$) δ ppm: 3.04(s, 3H), 3.38(s, 3H), 5.09(s, 2H), 6.49(s, 1H), 6.62(d, J=8Hz, 1H), 6.93(d, J=8Hz, 1H), 7.10(s, 1H), 7.19(s, 1H) |

Examples

The compounds obtained in Examples 782, 790 and 788 were treated by the same method as the one of Example 8 to thereby give the following compounds.

| Ex. | Structural formula | MS | M.p. | NMR |
|---|---|---|---|---|
| 791 | 5,10-dihydro-5-methyl-7-hydroxy-10H-pyrazino[2,3-b][1,4]quinoxaline | ESI (+) 215 (MH$^+$) | >275° C. | $^1$NMR(DMSO-d$_6$) δ ppm: 3.02(s, 3H), 6.25(br · s, 2H), 6.59(br · s, 2H), 6.81(br · s, 1H) |
| 792 | 5,10-dihydro-5-methyl-10H-pyrazino[2,3-b][1,4]quinoxaline-7-carbonitrile | FAB (+) 223 (M$^+$) | >275° C. | $^1$NMR(DMSO-d$_6$) δ ppm: 2.92(s, 3H), 6.34(d, J=8Hz, 1H), 6.69(s, 1H), 6.94(d, J=3Hz, 1H), 6.98(d, J=8Hz, 1H), 7.05(d, J=3Hz, 1H), 9.58(s, 1H) |
| 793 | 5,10-dihydro-5-methyl-7-methoxy-10H-pyrazino[2,3-b][1,4]quinoxaline | ESI (+) 228 (M$^+$) | 195–197° C. | $^1$NMR(DMSO-d$_6$) δ ppm: 2.95(s, 3H), 3.61(s, 3H), 6.07(br · s, 1H), 6.12(br · d, J=8Hz, 1H), 6.25(br · d, J=8Hz, 1H), 684(br · s, 1H), 6.91(br · s, 1H), 8.92(br · s, 1H) |

Examples

The following compounds were obtained by treating 5,10-dihydro-5-methoxymethyl-10H-pyrazino[2,3-b][1,4]quinoxaline by the same method as the one of Example 788 by using appropriate halides as a substitute for methyl iodide.

| Ex. | Structural formula | NMR |
|---|---|---|
| 794 | ethyl 3-(5,10-dihydro-10-methoxymethyl-10H-pyrazino[2,3-b][1,4]quinoxalin-5-yl) propanoate | $^1$NMR(CDCl$_3$) δ ppm: 1.20(t, J=7Hz, 3H), 2.57(t, J=8Hz, 2H), 3.38(s, 3H), 3.95(t, J=8Hz, 2H), 4.09(q, J=7Hz, 2H), 5.07(s, 2H), 6.45(dd, J=2, 8Hz, 1H), 6.63–6.70(m, 3H), 7.04(d, J=2Hz, 1H), 7.10(d, J=2Hz, 1H) |

| Ex. | Structural formula | NMR |
|---|---|---|
| 795 | 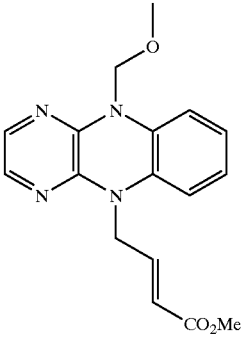  methyl (E)-4-(5,10-dihydro-10-methoxymethyl-10H-pyrazino[2,3-b][1,4]quinoxalin-5-yl)-2-butenoate | $^1$NMR(CDCl$_3$) δ ppm: 3.47(s, 3H), 3.72(s, 3H), 4.50(br · m, 2H), 5.09(s, 2H), 6.02(br · d, J=16Hz, 1H), 6.28(br · d, J=8Hz, 1H), 6.67–6.77(m, 3H), 6.92(td, J=6, 16Hz, 1H), 7.14(s, 2H) |

Example 796

Ethyl 3-(5,10-dihydro-10H-pyrazino[2,3-b][1,4]quinoxalin-5-yl)propanoate

The title compound was obtained by treating ethyl 3-(5,10-dihydro-10-methoxymethyl-10H-pyrazino[2,3-b][1,4]quinoxalin-5-yl)propanoate by the same method as the one of Example 8.

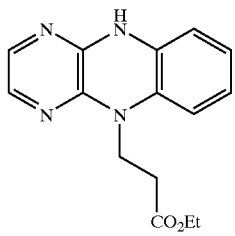

$^1$H-NMR(CDCl$_3$) δ ppm: 1.20(t, J=7 Hz, 3H), 2.55(t, J=7 Hz, 2H), 3.88(t, J=7 Hz, 2H), 4.09(q, J=7 Hz, 2H), 6.14(d, J=8 Hz, 1H), 6.38(d, J=8 Hz, 1H), 6.42(t, J=8 Hz, 1H), 6.56(t, J=8 Hz, 1H), 6.84(d, J=3 Hz, 1H), 6.98(d, J=3 Hz, 1H)

MS: ESI(+)285(MH$^+$)

m.p.:

Example 797

5,10-Dihydro-5-[4-(N,N-dimethylamino)-2-buten-1-yl)]-10H-pyrazino[2,3-b][1,4]quinoxaline 0.0060 g of the title compound was obtained by treating 0.170 g of (E)-2-[N-(4-dimethylamino-2-buten-1-yl)-N-(2-nitrophenyl)amino]-3-chloropyrazine by the same method as the one of Example 763.

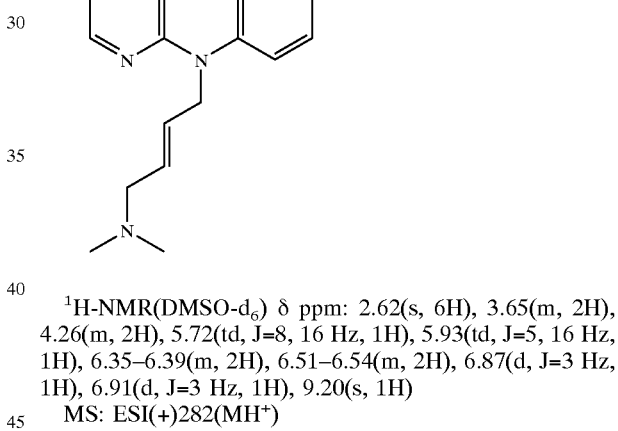

$^1$H-NMR(DMSO-d$_6$) δ ppm: 2.62(s, 6H), 3.65(m, 2H), 4.26(m, 2H), 5.72(td, J=8, 16 Hz, 1H), 5.93(td, J=5, 16 Hz, 1H), 6.35–6.39(m, 2H), 6.51–6.54(m, 2H), 6.87(d, J=3 Hz, 1H), 6.91(d, J=3 Hz, 1H), 9.20(s, 1H)

MS: ESI(+)282(MH$^+$)

Example 798

5,10-Dihydro-5-propyl-10H-pyrazino[2,3-b][1,4]quinoxaline 0.188 g of the title compound was obtained as yellow crystals by treating 0.224 g of 5,10-dihydro-5-allyl-10H-pyrazino[2,3-b][1,4]quinoxaline by the same method as the one of Example 20.

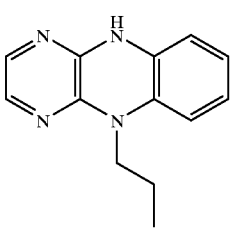

$^1$H-NMR(CDCl$_3$) δ ppm: 0.98(t, J=7 Hz, 3H), 1.55–1.68 (m, 2H), 3.56(t, J=8 Hz, 2H), 6.18(d, J=8 Hz, 1H), 6.35(d, J=8 Hz, 1H), 6.55(t, J=8 Hz, 1H), 6.62(t, J=8 Hz, 1H), 6.86(d, J=3 Hz, 1H), 7.03(d, J=3 Hz, 1H)

m.p.: 190–192° C.
MS: ESI(+)227(MH⁺)

Example 799

Methyl 4-(5,10-dihydro-10-methoxymethyl-10H-pyrazino[2,3-b][1,4]quinoxalin-5-yl)butanoate The title compound was obtained by treating methyl 4-(5,10-dihydro-10-methoxymethyl-10H-pyrazino[2,3-b][1,4]quinoxalin-5-yl)-2-butenoate by the same method as the one of Example 20.

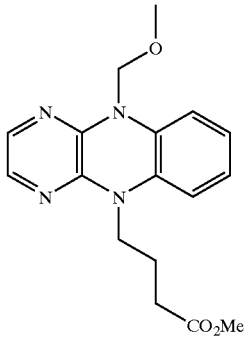

$^1$H-NMR(CDCl$_3$) δ ppm: 1.87(quint, J=7 Hz, 2H), 2.38(t, J=7 Hz, 2H), 3.38(s, 3H), 3.63(s, 3H), 3.67(t, J=7 Hz, 2H), 5.06(s, 2H), 6.55(d, J=8 Hz, 1H), 6.61–6.65(m, 2H), 6.69 (ddd, J=2, 6, 8 Hz, 1H), 7.00(d, J=3 Hz, 1H), 7.06(d, J=3 Hz, 1H)

Example 800

Methyl 4-(5,10-dihydro-10H-pyrazino[2,3-b][1,4]quinoxalin-5-yl)butanoate

The title compound was obtained by treating methyl 4-(5,10-dihydro-10-methoxymethyl-10H-pyrazino[2,3-b][1,4]quinoxalin-5-yl)-2-butenoate by the same method as the one of Example 8.

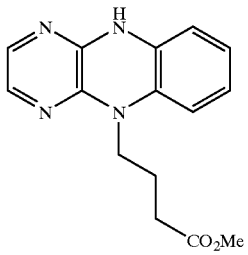

$^1$H-NMR(CDCl$_3$) δ ppm: 1.92.(quint, J=7 Hz, 2H), 2.44(t, J=7 Hz, 2H), 3.68(t, J=7 Hz, 2H), 3.70(s, 3H), 6.18(d, J=8 Hz, 1H), 6.53–6.59(m, 2H), 7.05(t, J=8 Hz, 1H), 6.87(d, J=3 Hz, 1H), 7.00(d, J=3 Hz, 1H)

m.p.: 189–190° C.
MS: ESI(+)285(MH⁺)

Example 801

5,10-Dihydro-5-methoxymethyl-10-methyl-10H-pyrazino[2,3-b][1,4]quinoxaline-7-carbonitrile 2.43 g of the title compound was obtained as yellow crystals by reacting 3.14 g of 5,10-dihydro-10-methyl-10H-pyrazino[2,3-b][1,4]quinoxaline-7-carbonitrile with chloromethyl methyl ether by the same method as the one of Example 788.

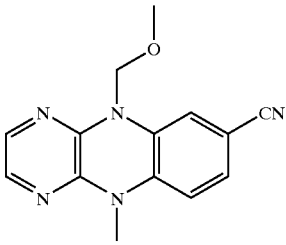

$^1$H-NMR(CDCl$_3$) δ ppm: 3.16(s, 3H), 3.45(s, 3H), 5.11(s, 2H), 6.42(d, J=8 Hz, 1H), 6.86(d, J=2 Hz, 1H), 7.05(dd, J=2, 8 Hz, 1H), 7.21(d, J=3 Hz, 1H), 7.26(d, J=3 Hz, 1H)

Example 802

5,10-Dihydro-5-methoxymethyl-10-methyl-10H-pyrazino[2,3-b][1,4]quinoxaline-7-carboxamide 0.267 g of 5,10-dihydro-5-methoxymethyl-10-methyl-10H-pyrazino[2,3-b][1,4]quinoxaline-7-carbonitrile was dissolved at 0° C. in 20 ml of ethanol and 20 ml of dimethyl sulfoxide. After adding 0.36 ml of a 30% aqueous solution of hydrogen peroxide and 0.36 ml of 6 N sodium hydroxide, the resulting mixture was stirred at room temperature for 16 hours. Then the reaction mixture was poured into water. The precipitate was taken up by filtration. and washed with water to thereby give 0.271 g of the title compound as a yellow powder.

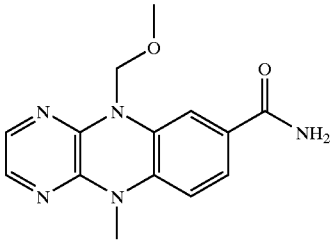

$^1$H-NMR(CDCl$_3$) δ ppm: 3.07(s, 3H), 3.31(s, 3H), 5.12(s, 2H), 6.61(d, J=8 Hz, 1H), 7.12(d, J=1 Hz, 1H), 7.15(d, J=3 Hz, 1H), 7.16(br.s, 1H), 7.22(d, J=3 Hz, 1H), 7.29(dd, J=1, 8 Hz, 1H), 7.77(br.s, 1H)

Example 803

5,10-Dihydro-10-methyl-10H-pyrazino[2,3-b][1,4]quinoxaline-7-carboxamide

The title compound was obtained by treating 5,10-dihydro-5-methoxymethyl-10-methyl-10H-pyrazino[2,3-b][1,4]quinoxaline-7-carboxamide by the same method as the one of Example 8.

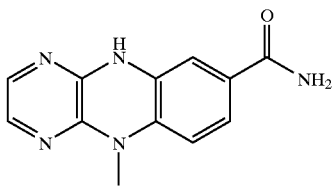

¹H-NMR(DMSO-d₆) δ ppm: 2.95(s, 3H), 6.43(d, J=8 Hz, 1H), 6.81(s, 1H), 6.89(d, J=3 Hz, 1H), 6.97(d, J=3 Hz, 1H), 7.06(br.s, 1H), 7.09(d, J=8 Hz, 1H), 7.65(br.s, 1H), 9.18(s, 1H)

MS: ESI(+)263.9(MNa⁺)

Example 804

5,10-Dihydro-5-methoxymethyl-10-methyl-10H-pyrazino[2,3-b][1,4]quinoxaline-7-carbaldehyde A solution of 1.068 g of 5,10-dihydro-5-methoxymethyl-10-methyl-10H-pyrazino[2,3-b][1,4]quinoxaline-7-carbonitrile in toluene (100 ml) was degassed in a nitrogen atmosphere and cooled to −78° C. After dropping 9.6 ml of a 1.0 M solution of diisobutylaluminum hydride in toluene thereinto, the resulting mixture was heated to room temperature over 15 hours. Then the reaction mixture was cooled to 0° C. and the excessive reagent was decomposed with methanol. The reaction mixture was distributed into ethyl acetate and water. After filtering off the insoluble matters, the aqueous layer was extracted with ethyl acetate. The organic layers were combined, washed successively with water and a saturated aqueous solution of sodium chloride and dried over anhydrous magnesium sulfate. After distilling off the solvent under reduced pressure, the residue was purified by silica gel column chromatography (eluted with n-hexane/ethyl acetate) to thereby give 0.519 g of the title compound as a yellow solid.

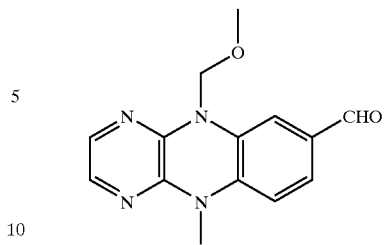

¹H-NMR(CDCl₃) δ ppm:
3.13(s, 3H), 3.33(s, 3H), 5.13(s, 2H), 6.75(d, J=8 Hz, 1H), 7.01(d, J=2 Hz, 1H), 7.24(d, J=3 Hz, 1H), 7.28(d, J=3 Hz, 1H), 7.35(dd, J=2, 8 Hz, 1H), 9.67(s, 1H)

Example 805

Ethyl(E)-3-(5,10-dihydro-5-methoxymethyl-10-methyl-10H-pyrazino[2,3-b][1,4]quinoxalin-7-yl)propenoate The title compound was obtained by treating 5,10-dihydro-10-methyl-5-methoxymethyl-10H-pyrazino[2,3-b][1,4]quinoxaline-7-carbaldehyde by the same method as the one of Production Example 25.

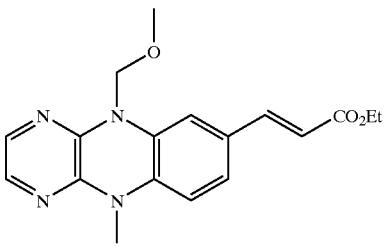

¹H-NMR(CDCl₃) δ ppm: 1.26(t, J=7 Hz, 3H), 3.09(s, 3H), 3.40(s, 3H), 4.18(q, J=7 Hz, 2H), 5.11(s, 2H), 6.18(d, J=16 Hz, 1H), 6.38(d, J=8 Hz, 1H), 6.91(d, J=2 Hz, 1H), 6.86(dd, J=2, 8 Hz, 1H), 7.09(d, J=3 Hz1H), 7.16(d, J=3 Hz, 1H), 7.43(d, J=16 Hz, 1H)

Examples

The following compounds were obtained by hydrolyzing the compounds obtained in Examples 805 and 799 by the same method as the one of Example 18.

| Ex. | Structural formula | NMR |
|---|---|---|
| 806 | (E)-3-(5,10-dihydro-5-methoxymethyl-10-methyl-10H-pyrazino[2,3-b][1,4]quinoxalin-7-yl)propenoic acid | ¹NMR(DMSO-d₆) δ ppm: 3.07(s, 3H), 3.42(s, 3H), 5.17(s, 2H), 6.26(d, J=16Hz, 1H), 6.61(d, J=8Hz, 1H), 6.88(d, J=1Hz, 1H), 7.07(dd, J=1, 8Hz, 1H), 7.16(d, J=3Hz, 1H), 7.24(d, J=3Hz, 1H), 7.38(d, J=16Hz, 1H), 12.20(br · s, 1H) |

-continued

| Ex. | Structural formula | NMR |
|---|---|---|
| 807 | 4-(5,10-dihydro-10-methoxymethyl-10H-pyrazino[2,3-b][1,4]quinoxalin-5-yl)butanoic acid | $^1$NMR(CDCl$_3$) δ ppm: 1.89(quint, J=7Hz, 2H), 2.42(t, J=7Hz, 2H), 3.38(s, 3H), 3.69(br · t, J=7Hz, 2H), 5.06(s, 2H), 6.52(d, J=8Hz, 1H), 6.60–6.71(m, 3H), 7.01–7.04(m, 2H) |

Examples 25

The following compounds were obtained by treating the compounds obtained in Examples 806 and 807 by the same method as the one of Example 8.

| Ex. | Structural formula | MS | M.p. | NMR |
|---|---|---|---|---|
| 808 | (E)-3-(5,10-dihydro-5-methyl-10H-pyrazino[2,3-b][1,4]quinoxalin-8-yl)propenoic acid | ESI (+) 269 (MH$^+$) | 275° C. | $^1$NMR(DMSO-d$_6$) δ ppm: 2.97(s, 3H), 6.05(d, J=16Hz, 1H), 6.46(d, J=8Hz, 1H), 6.55(d, J=1Hz, 1H), 6.87(dd, J=1, 8Hz, 1H), 6.90(d, J=3Hz, 1H), 6.99(d, J=3Hz, 1H), 7.27(d, J=16Hz, 1H), 9.13(s, 1H) |
| 809 | 4-(5,10-dihydro-10H-pyrazino[2,3-b][1,4]quinoxalin-5-yl)butanoic acid | ESI (+) 271 (MH$^+$) | 273–274° C. | $^1$NMR(DMSO-d$_6$) δ ppm: 1.66(quint, J=7Hz, 2H), 2.28(t, J=7Hz, 2H), 3.53(t, J=7Hz, 2H), 6.31(d, J=8Hz, 1H), 6.49–6.55(m, 3H), 6.81(d, J=3Hz, 1H), 6.90(d, J=3Hz, 1H), 9.03(s, 1H) |

Example 810

5,10-Dihydro-5-methoxymethyl-10-methyl-7-(oxazol-5-yl)-10H-pyrazino[2,3-b][1,4]quinoxaline To 15 ml of methanol were added 0.166 g of 5,10-dihydro-10-methyl-5-methoxymethyl-10H-pyrazino[2,3-b][1,4]quinoxaline-7-carbaldehyde, 0.120 g of p-toluenesulfonylmethyl isocyanide and 0.081 g of potassium carbonate and the resulting mixture was heated under reflux for 90 minutes. After distilling off the solvent under reduced pressure, the residue was dissolved in ethyl acetate, washed successively with a 1 N aqueous solution of sodium hydroxide, water and a saturated aqueous solution of sodium chloride and dried over anhydrous magnesium sulfate. After distilling off the solvent under reduced pressure, the residue was purified by silica gel column chromatography (eluted with n-hexane/ethyl acetate) to thereby give 0.134 g of the title compound as a yellow solid.

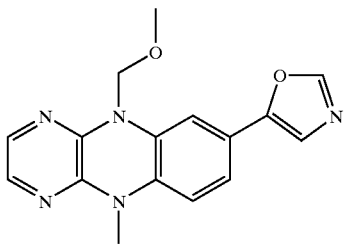

$^1$H-NMR(CDCl$_3$) δ ppm: 3.16(s, 3H), 3.47(s, 3H), 5.22(s, 2H), 6.49(d, J=8 Hz, 1H), 6.97(d, J=2 Hz, 1H), 7.05(dd, J=2, 8 Hz, 1H), 7.15(d, J=3 Hz, 1H), 7.21(s, 1H), 7.22(d, J=3 Hz, 1H), 7.86(s, 1H)

Example 811

5,10-Dihydro-10-methyl-5-methoxymethyl-10H-pyrazino[2,3-b][1,4]quinoxaline-7-methanol The title compound was obtained by treating 5,10-dihydro-10-methyl-5-methoxymethyl-10H-pyrazino[2,3-b][1,4]quinoxaline-7-carbaldehyde by the same method as the one of Example 2.

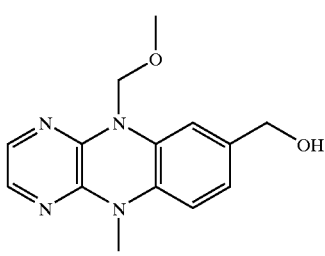

$^1$H-NMR(CDCl$_3$) δ ppm: 3.12(s, 3H), 3.35(s, 3H), 3.46(s, 3H), 4.27(s, 2H), 5.17(s, 2H), 6.45(d, J=8 Hz, 1H), 6.70(s, 1H), 6.74(d, J=8 Hz, 1H), 7.10(d, J=3 Hz, 1H), 7.18(d, J=3 Hz, 1H)

Example 812

5,10-Dihydro-10-methyl-5,7-dimethoxymethyl-7-10H-pyrazino[2,3-b][1,4]quinoxaline The title compound was obtained by treating 5,10-dihydro-10-methyl-5-methoxymethyl-10H-pyrazino[2,3-b][1,4]quinoxaline-7-methanol by the same method as the one of Example 788.

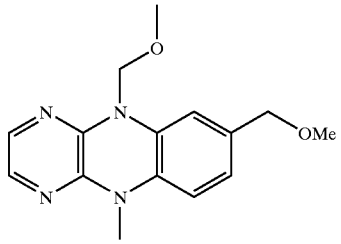

$^1$H-NMR(CDCl$_3$) δ ppm: 3.12(s, 3H), 3.45(s, 3H), 4.50(d, J=6 Hz, 2H), 5.17(s, 2H), 6.44(d, J=8 Hz, 1H), 6.72(d, J=2 Hz, 1H), 6.76(dd, J=2, 8 Hz, 1H), 7.11(d, J=3 Hz, 1H), 7.19(d, J=3 Hz, 1H)

Examples

The following compounds were obtained by treating the compounds obtained in Examples 804, 805, 810, 811 and 812 by the same method as the one of Example 8.

| Ex. | Structural formula | MS | M.p. | NMR |
|---|---|---|---|---|
| 813 | 5,10-dihydro-5-methyl-10H-pyrazino[2,3-b][1,4]quinoxaline-8-carbaldehyde | ESI (+) 227 (MH$^+$) | 215–219° C. | $^1$NMR(DMSO-d$_6$) δ ppm: 3.00(s, 3H), 6.58(d, J=8Hz, 6.70(s, 1H), 6.97(d, J=3Hz, 1H), 7.02(d, J=3Hz, 1H), 7.15(d, J=8Hz, 1H), 9.36(s, 1H), 9.55(s, 1H) |

| Ex. | Structural formula | MS | M.p. | NMR |
|---|---|---|---|---|
| 814 | 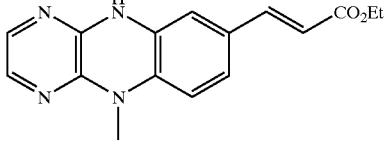<br>ethyl (E)-3-(5,10-dihydro-5-methyl-10H-pyrazino[2,3-b][1,4]quinoxalin-8-yl)propenoate | ESI (+) 297 (MH+) | 190–191° C. | $^1$NMR(CDCl$_3$) δ ppm: 1.33(t, J=7Hz, 3H), 3.20(s, 3H), 4.24(q, J=7Hz, 2H), 6.31(d, J=16Hz, 1H), 6.45(d, J=3Hz, 1H), 6.60(d, J=8Hz, 1H), 6.85(d, J=2Hz, 1H), 6.97(d, J=3Hz, 1H), 7.04(dd, J=2, 8Hz, 1H), 7.45(d, J=16Hz, 1H) |
| 815 | 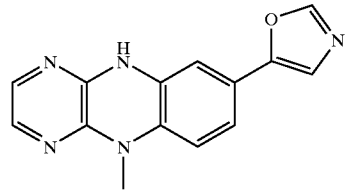<br>5,10-dihydro-5-methyl-8-(oxazol-5-yl)-10H-pyrazino[2,3-b][1,4]quinoxaline | ESI (+) 266 (MH+) | 268–269° C. | $^1$NMR(DMSO-d$_6$) δ ppm: 2.98(s, 3H), 6.51(d, J=8Hz, 1H), 6.64(d, J=2Hz, 1H), 6.90(d, J=4Hz, 1H), 6.93(dd, J=2, 8Hz, 1H), 6.98(d, J=4Hz, 1H), 7.37(s, 1H), 8.33(s, 1H), 9.23(s, 1H) |
| 816 | 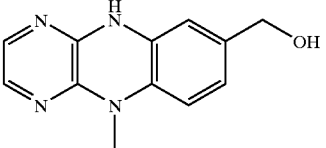<br>5,10-dihydro-5-methyl-10H-pyrazino[2,3-b][1,4]uinoxaline-8-methanol | ESI (+) 229 (MH+) | 215–218° C. | $^1$NMR(DMSO-d$_6$) δ ppm: 2.93(s, 3H), 4.18(d, J=6Hz, 2H), 4.97(t, J=6Hz, 1H), 6.33(s, 1H), 6.37(d, J=8Hz, 1H), 6.47(d, J=8Hz, 1H), 6.82(d, J=3Hz, 1H), 6.92(d, J=3Hz, 1H), 9.07(s, 1H) |
| 817 | 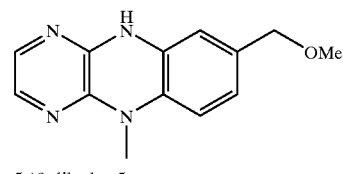<br>5,10-dihydro-5-methyl-8-methoxymethyl-7-10H-pyrazino[2,3-b][1,4]uinoxaline | ESI (+) 243 (MH+) | 169–172° C. | $^1$NMR(DMSO-d$_6$) δ ppm: 2.94(s, 3H), 3.19(s, 3H), 4.08(s, 2H), 6.30(s, 1H), 6.36(d, J=8Hz, 1H), 6.48(d, J=8Hz, 1H), 6.84(d, J=4Hz, 1H), 6.94(d, J=4Hz, 1H), 9.08(s, 1H) |

Example 818

(5,10-Dihydro-5-methoxymethyl-10-methyl-10H-pyrazino[2,3-b]-[1,4]quinoxalin-7-yl)-(pyridin-3-yl)methanol Into a solution of 0.22 g of 3-bromopyridine in dry diethyl ether (10 ml) was dropped 0.7 ml of a 1.6 M solution of n-butyllithium in hexane at −78° C. in a nitrogen atmosphere. After stirring for 1 hour, a solution of 0.126 g of 5,10-dihydro-5-methoxymethyl-10-methyl-10H-pyrazino[2,3-b][1,4]quinoxaline-7-carbaldehyde in tetrahydrofuran (3 ml) was dropped into the reaction mixture and then the bulk temperature was elevated to −20° C. After adding a saturated aqueous solution of sodium dihydrogenphosphate, the resulting mixture was extracted with ethyl acetate. The organic layers were combined, washed successively with water and a saturated aqueous solution of sodium chloride and dried over anhydrous magnesium sulfate. After distilling off the solvent under reduced pressure, the residue was purified by silica gel column chromatography (eluted with n-hexane/ethyl acetate) to thereby give 0.100 g of the title compound as a yellow solid.

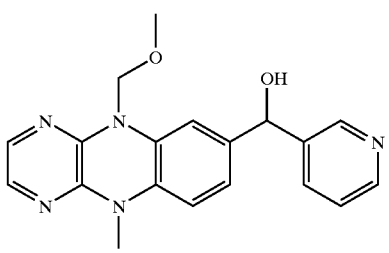

¹H-NMR(CDCl₃) δ ppm: 3.10(s, 3H), 3.41(s, 3H), 5.12(s, 2H), 5.70(s, 1H), 6.42(d, J=8 Hz, b 1H), 6.71(dd, J=2, 8 Hz, 1H), 6.72(d, J=2 Hz, 1H), 7.11(d, J=3 Hz, 1H), 7.19(d, J=3 Hz, 1H) 7.27(dd, J=5, 8 Hz, 1H) 7.71(td, J=2, 8 Hz, 1H), 8.51(dd, J=2, 5 Hz, 1H), 8.62(d, J=2 Hz, 1H)

Examples

The following compounds were obtained by treating 5,10-dihydro-5-methoxymethyl-10-methyl-10H-pyrazino[2,3-b][1,4]quinoxaline-7-carbaldehyde with appropriate alkyl-metals or arylmetals by the same method as the one of Example 818.

| Ex. | Structural formula | NMR |
|---|---|---|
| 819 | (5,10-dihydro-5-methoxymethyl-10-methyl-10H-pyrazino[2,3-b][1,4]quinoxalin-7-yl)-(thiazol-2-yl)methanol | ¹H-NMR(CDCl₃) δ ppm: 3.11(s, 3H), 3.42(s, 3H), 3.43(br.s, 1H), 5.12(s, 2H), 5.88(s, 1H), 6.43(d, J=8Hz, 1H), 6.80(d, J=2Hz, 1H), 6.83(dd, J=2, 8Hz, 1H), 7.11(d, J=3Hz, 1H), 7.19(d, J=3Hz, 1H), 7.31(d, J=3Hz, 1H), 7.74(d, J=3Hz, 1H) |
| 820 | (5,10-dihydro-5-methoxymethyl-10-methyl-10H-pyrazino[2,3-b][1,4]quinoxalin-7-yl)-(thiophen-2-yl)methanol | ¹H-NMR(CDCl₃) δ ppm: 2.37(s, 1H), 3.12(s, 3H), 3.41(s, 3H), 5.11(d, J=11Hz, 1H), 5.15(d, J=11Hz, 1H), 5.89(s, 1H), 6.44(d, J=8Hz, 1H), 6.79(d, J=2Hz, 1H), 6.83(dd, J=2, 8Hz, 1H), 6.92–6.96(m, 2H), 7.11(d, J=3Hz, 1H), 7.19(d, J=3Hz, 1H), 7.25–7.28(m, 1H) |
| 821 | (5,10-dihydro-5-methoxymethyl-10-methyl-10H-pyrazino[2,3-b][1,4]quinoxalin-7-yl)-(pyridin-2-yl)methanol | ¹H-NMR(CDCl₃) δ ppm: 3.11(s, 3H), 3.40(s, 3H), 5.12(s, 2H), 5.15(d, J=4Hz, 1H), 5.59(d, J=4Hz, 1H), 6.42(d, J=8Hz, 1H), 6.73(d, J=2Hz, 1H), 6.75(dd, J=2, 8Hz, 1H), 7.09(d, J=3Hz, 1H), 7.16–7.24(m, 3H), 7.65(dt, J=1, 8Hz, 1H), 8.56(ddd, J=1, 2, 6Hz, 1H) |

-continued

| Ex. | Structural formula | NMR |
|---|---|---|
| 822 | α-(5,10-dihydro-5-methoxymethyl-10-methyl-10H-pyrazino[2,3-b][1,4]quinoxalin-7-yl)benzyl alcohol | $^1$H-NMR(CDCl$_3$) δ ppm: 2.21(s, 1H), 3.09(s, 3H), 3.39(s, 3H), 5.16(d, J=9Hz, 1H), 5.22(d, J=9Hz, 1H), 5.78(s, 1H), 6.41(d, J=8Hz, 1H), 6.73(d, J=8Hz, 1H), 6.74(s, 1H), 7.09(d, J=3Hz, 1H), 7.18(d, J=3Hz, 1H), 7.25–7.39(m, 5H) |
| 823 | (5,10-dihydro-5-methoxymethyl-10-methyl-10H-pyrazino[2,3-b][1,4]quinoxalin-7-yl)-3-phenylpropynol | $^1$H-NMR(CDCl$_3$) δ ppm: 2.36(br.s, 1H), 3.13(s, 3H), 3.45(s, 3H), 5.18(s, 2H), 5.51(d, J=5Hz, 1H), 6.47(d, J=8Hz, 1H), 6.98(d, J=2Hz, 1H), 7.00(dd, J=2, 8Hz, 1H), 7.12(d, J=3Hz, 1H), 7.20(d, J=3Hz, 1H), 7.29–7.34(m, 3H), 7.45–7.48(m, 2H) |
| 824 | N,N-dimethyl-[2-(5,10-dihydro-5-methoxymethyl-10-methyl-10H-pyrazino[2,3-b][1,4]quinoxalin-7-yl)(hydroxymethyl)]imadazole-1-sulfonamide | $^1$H-NMR(CDCl$_3$) δ ppm: 2.79(s, 6H), 3.07(s, 3H), 3.38(s, 3H), 5.01(d, J=11Hz, 1H), 5.10(d, J=11Hz, 1H), 6.04(s, 1H), 6.39(d, J=8Hz, 1H), 6.68(d, J=2Hz, 1H), 6.75(dd, J=2, 8Hz, 1H), 7.06(d, J=2Hz, 1H), 7.09(d, J=3Hz, 1H), 7.16(d, J=3Hz, 1H), 7.23(d, J=2Hz, 1H) |

Example 825

(5,10-Dihydro-10-methyl-5-methoxymethyl-10H-pyrazino[2,3-b][1,4]quinoxalin-7-yl)-(1,2,4-triazol-3-yl)methanol To a solution of 0.404 g of 1-diethoxymethyl-1,2,4-triazole in dry tetrahydrofuran (10 ml) was added at 0° C. in a nitrogen atmosphere 1.5 ml of a 1.5 M solution of n-butyllithium in hexane. After stirring for 1 hour, the resulting mixture was cooled to −78° C. Then a solution of 0.270 g of 5,10-dihydro-5-methoxymethyl-10-methyl-10H-pyrazino[2,3-b][1,4]quinoxaline-7-carbaldehyde in dry tetrahydrofuran (10 ml) was dropped thereinto and the bulk temperature was elevated to room temperature. After stirring for 16 hours, a saturated aqueous solution of sodium dihydrogenphosphate was added and the resulting mixture was extracted with ethyl acetate. The organic layers were combined, washed successively with water and a saturated aqueous solution of sodium chloride and dried over anhydrous magnesium sulfate. After distilling off the solvent under reduced pressure, the residue was purified by silica gel column chromatography (eluted with n-hexane/ethyl acetate) to thereby give 0.170 g of the title compound as a yellow solid.

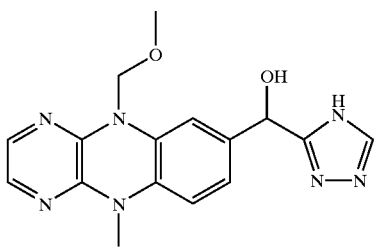

¹H-NMR(CDCl₃) δ ppm: 3.02(s, 3H), 3.29(s, 3H), 5.04(s, 2H), 5.53 and 5.64(s, total 1H), 5.64(s, 1H), 6.55(d, J=8 Hz, 1H), 6.73–6.89(m, 2H), 7.10(d, J=3 Hz, 1H), 7.18(d, J=3 Hz, 1H), 7.79 and 8.43(s, total 1H), 13.90(s, 1H)

Examples

The following compounds were obtained by the same method as the one of Example 8.

| Ex. | Structural formula | MS | M. p. | NMR |
|---|---|---|---|---|
| 826 | (5,10-dihydro-5-methyl-10H-pyrazino[2,3-b][1,4]quinoxalin-8-yl)-(pyridin-3-yl)methanol | ESI (+) 306 (MH⁺) | 131–134° C. | ¹H-NMR(DMSO-d₆) δ ppm: 2.91(s, 3H), 5.46(d, J=5Hz, 1H), 5.88(d, J=5Hz, 1H), 6.36(d, J=2Hz, 1H), 6.36(d, J=8Hz, 1H), 6.55(dd, J=2, 8Hz, 1H), 6.83(d, J=4Hz, 1H), 6.92(d, J=4Hz, 1H), 7.31(dd, J=6, 8Hz, 1H), 7.63(td, J=2, 8Hz, 1H), 8.40(dd, J=2, 6Hz, 1H), 8.50(d, J=2Hz, 1H), 9.01(s, 1H) |
| 827 | (5,10-dihydro-5-methyl-10H-pyrazino[2,3-b][1,4]quinoxalin-8-yl)-(thiazol-2-yl)methanol | ESI (+) 334 (MNa⁺) | 203–204° C. | ¹H-NMR(DMSO-d₆) δ ppm: 2.92(s, 3H), 5.62(d, J=5Hz, 1H), 6.38(d, J=8Hz, 1H), 6.43(s, 1H), 6.57(d, J=5Hz, 1H), 6.60(d, J=8Hz, 1H), 6.83(d, J=3Hz, 1H), 6.93(d, J=3Hz, 1H), 7.59(d, J=4Hz, 1H), 7.66(d, J=4Hz, 1H), 9.05(s, 1H) |
| 828 | (5,10-dihydro-5-methyl-10H-pyrazino[2,3-b][1,4]quinoxalin-8-yl)-(thiazol-2-yl)methanol | ESI (+) 311 (MH⁺) | >275° C. | ¹H-NMR(DMSO-d₆) δ ppm: 2.93(s, 3H), 5.62(d, J=5Hz, 1H), 6.02(d, J=5Hz, 1H), 6.37(d, J=8Hz, 1H), 6.43(s, 1H), 6.56(d, J=8Hz, 1H), 6.82(d, J=4Hz, 1H), 6.83(d, J=6Hz, 1H), 6.90(d, J=6Hz, 1H), 6.93(d, J=4Hz, 1H), 7.36(d, J=6Hz, 1H), 9.05(s, 1H) |

| Ex. | Structural formula | MS | M. p. | NMR |
|---|---|---|---|---|
| 829 | (5,10-dihydro-5-methyl-10H-pyrazino[2,3-b][1,4]quinoxalin-8-yl)-(pyridin-2-yl)methanol | ESI (+) 328 (MH+) | 171–173° C. | $^1$H-NMR(DMSO-d$_6$) δ ppm: 2.90(s, 3H), 5.39(d, J=5Hz, 1H), 5.89(d, J=5Hz, 1H), 6.35(d, J=8Hz, 1H), 6.40(d, J=2Hz, 1H), 6.56(dd, J=2, 8Hz, 1H), 6.81(d, J=4Hz, 1H), 6.92(d, J=4Hz, 1H), 7.21(dd, J=5, 8Hz, 1H), 7.45(d, J=8Hz, 1H), 7.75(t, J=8Hz, 1H), 8.42(d, J=5Hz, 1H), 9.00(s, 1H) |
| 830 | α-(5,10-dihydro-5-methyl-10H-pyrazino[2,3-b][1,4]quinoxalin-8-yl)benzyl alcohol | ESI (+) 305 (MH+) | 127–132° C. | $^1$H-NMR(DMSO-d$_6$) δ ppm: 2.90(s, 3H), 5.38(d, J=5Hz, 1H), 5.69(d, J=5Hz, 1H), 6.35(d, J=8Hz, 1H), 6.37(s, 1H), 6.53(d, J=8Hz, 1H), 6.82(d, J=4Hz, 1H), 6.92(d, J=4Hz, 1H), 7.15–7.21(m, 2H), 7.23–7.28(m, 3H), 9.00(s, 1H) |
| 831 | 1-(5,10-dihydro-5-methyl-10H-pyrazino[2,3-b][1,4]quinoxalin-8-yl)-3-phenylpropynol | ESI (+) 329 (MH+) | 204–208° C. | $^1$H-NMR(CDCl$_3$) δ ppm: 3.11(s, 3H), 5.29(s, 1H), 5.30(d, J=6Hz, 1H), 5.95(d, J=6Hz, 1H), 6.42(d, J=8Hz, 1H), 6.58(d, J=2Hz, 1H), 6.69(dd, J=2, 8Hz, 1H), 6.85(dd, J=1, 3Hz, 1H), 6.95(dd, J=1, 3Hz, 1H), 7.37(m, 3H), 7.42(m, 2H) |
| 832 | N,N-dimethyl-[2-(5,10-dihydro-5-methyl-10H-pyrazino[2,3-b][1,4]quinoxalin-8-yl)-hydroxymethyl]imidazole-1-sulfonamide | ESI (+) 424 (MNa+) | 185–190° C. | $^1$H-NMR(DMSO-d$_6$) δ ppm: 2.84(s, 6H), 2.93(s, 3H), 5, 83(s, 1H), 5.89(br.s, 1H), 6.37(d, J=8Hz, 1H), 6.46(d, J=2Hz, 1H), 6.52(dd, J=2, 8Hz, 1H), 6.83(d, J=4Hz, 1H), 6.94(d, J=4Hz, 1H), 7.00(d, J=2Hz, 1H), 7.50(d, J=2Hz, 1H), 9.06(s, 1H) |

-continued

| Ex. | Structural formula | MS | M. p. | NMR |
|---|---|---|---|---|
| 833 | <br>(5,10-dihydro-5-methyl-10H-pyrazino[2,3-b][1,4]quinoxalin-8-yl)-(1,2,4-triazol-3-yl) methanol | FAB (+)<br>296 (MH$^+$) | >275° C. | $^1$H-NMR(DMSO-d$_6$) δ ppm:<br>2.92(s, 3H), 5.54(s, 1H), 6.37(m, 2H), 6.54(d, J=8Hz, 1H), 6.83(s, 1H), 6.93(s, 1H), 7.79(s, 1H), 9.09(br.s, 1H), 13.86(br.s, 1H) |

Example 834

(5,10-Dihydro-5-methyl-10H-pyrazino[2,3-b][1,4]quinoxalin-8-yl)-(imidazol-2-yl)methanol 0.084 g of N,N-dimethyl-[2-(5,10-dihydro-5-methyl-10H-pyrazino[2,3-b][1,4]quinoxalin-8-yl) hydroxymethyl]imidazole-1-sulfonamide was dissolved in 4.5 ml of 35% hydrochloric acid in a nitrogen atmosphere and heated to 50° C. for 30 hours. Then the reaction mixture was neutralized with a saturated aqueous solution of sodium hydrogencarbonate and the solid thus precipitated was taken up by filtration. This solid was dissolved in 6 N hydrochloric acid. After filtering off the insoluble, matters, the solution was neutralized again with a saturated aqueous solution of sodium hydrogencarbonate. The crystals thus precipitated were taken up by filtration to thereby give 0.060 g of the title compound as a yellowish green solid.

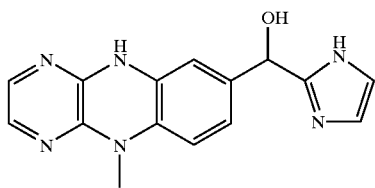

$^1$H-NMR(DMSO-d$_6$) δ ppm: 2.92(s, 3H), 5.46(s, 1H), 6.10(br.s, 1H), 6.37(d, J=8 Hz, 1H), 6.38(s, 1H), 6.55(d, J=8 Hz, 1H), 6.83(d, J=3 Hz, 1H), 6.94(d, J=3 Hz, 1H), 6.96(br.s, 2H), 9.08(br.s, 1H)

MS: ESI(+)295(MH$^+$)

Example 835

(5,10-Dihydro-5-methoxymethyl-10-methyl-10H-pyrazino[2,3-b][1,4]quinoxalin-7-yl)(pyridin-2-yl) ketone The title compound was obtained by oxidizing (5,10-dihydro-5-methoxymethyl-10-methyl-10H-pyrazino 2,3-b][1,4]quinoxalin-7-yl)-(pyridin-2-yl)methanol with manganese dioxide by the same method as the one of Example 625.

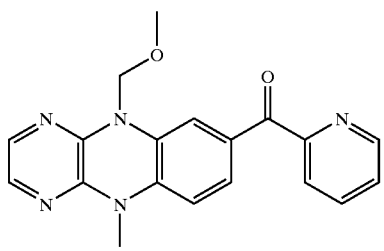

$^1$H-NMR(CDCl$_3$) δ ppm: 3.19(s, 3H), 3.45(s, 3H), 5.20(s, 2H), 6.50(d, J=8 Hz, 1H), 7.20(d, J=3 Hz, 1H), 7.24(d, J=3 Hz, 1H), 7.46(ddd, J=1, 5, 8 Hz, 1H), 7.49(d, J=2 Hz, 1H), 7.61(dd, J=2, 8 Hz, 1H), 7.86(dt, J=2, 8 Hz, 1H), 7.77(td, J=1, 8 Hz, 1H), 8.69(ddd, J=1, 2, 5 Hz, 1H)

Example 836

1-(5,10-Dihydro-5-methoxymethyl-10-methyl-10H-pyrazino[2,3-b][1,4]quinoxalin-7-yl)-1-(pyridin-2-yl)ethanol The title compound was obtained by treating (5,10-dihydro-5-methoxymethyl-10-methyl-10H-pyrazino[2,3-b][1,4]quinoxalin-7-yl)(pyridin-2-yl) ketone with methyllithium by the same method as the one of Example 818.

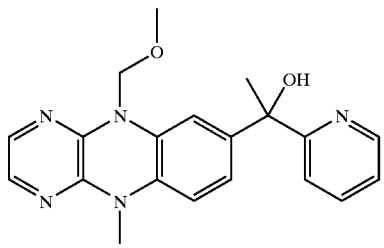

$^1$H-NMR(CDCl$_3$) δ ppm: 1.85(s, 3H), 3.08(s, 3H), 3.38(s, 3H), 5.09(s, 2H), 5.75(s, 1H), 6.49(d, J=8 Hz, 1H), 6.82(d, J=2 Hz, 1H), 6.86(dd, J=2, 8 Hz, 1H), 7.09(d, J=3 Hz, 1H), 7.16(d, J=3 Hz, 1H), 7.17(dd, J=5, 8 Hz, 1H), 7.31(d, J=8 Hz, 1H), 7.66(dt, J=1, 8 Hz, 1H), 8.52(dd, J=1, 5 Hz, 1H)

Example 837

[(5,10-Dihydro-5-methoxymethyl-10-methyl-10H-pyrazino[2,3-b][1,4]quinoxalin-7-yl)-(pyridin-2-yl)methyl] acetate 0.192 g of the title compound was obtained as a yellow solid by treating 0.202 g of (5,10-dihydro-5-methoxymethyl-10-methyl-10H-pyrazino[2,3-b][1,4]quinoxalin-7-yl)-(pyridin-2-yl)methanol with 0.5 ml of acetic anhydride in the presence of 5 ml of pyridine by the same method as the one of Production Example 165.

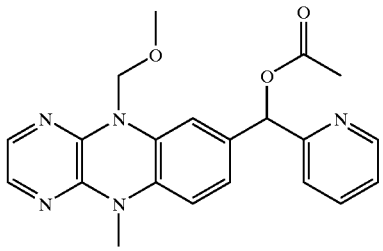

$^1$H-NMR(CDCl$_3$) δ ppm: 2.19(s, 3H), 3.08(s, 3H), 3.40(s, 3H), 5.09(s, 2H), 6.40(d, J=8 Hz, 1H), 6.68(s, 1H), 6.75(d, J=2 Hz, 1H), 6.80(dd, J=2, 8 Hz, 1H), 7.09(d, J=3 Hz, 1H), 7.17(d, J=3 Hz, 1H), 7.19(ddd, J=1, 5, 8 Hz, 1H), 7.40(br.t, J=8 Hz, 1H), 7.67(dt, J=2, 8 Hz, 1H), 8.58(ddd, J=1, 2, 5 Hz, 1H)

Example 838

5,10-Dihydro-5-methoxymethyl-10-methyl-7-[(piperidin-2-yl)methyl]-10H-pyrazino[2,3-b][1,4]quinoxaline 0.019 g of the title compound was obtained as a yellow solid by hydrogenating 0.096 g of [(5,10-dihydro-5-methoxymethyl-10-methyl-10H-pyrazino[2,3-b][1,4]quinoxalin-7-yl)-(pyridin-2-yl)methyl) acetate in a solvent [ethanol (10 ml)/acetic acid (0.2 ml)] in the presence of 0.12 g of a 10% palladium-carbon powder (moisture content: 50%) by the same method as the one of Example 20.

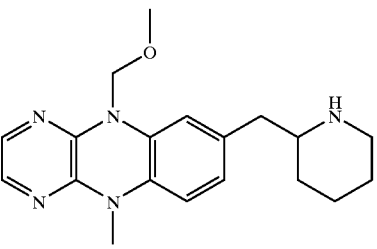

$^1$H-NMR(CDCl$_3$) δ ppm: 1.30–1.41(m, 1H), 1.48–1.60 (m, 1H), 1.74–1.87(m, 4H), 2.65(dd, J=9, 13 Hz, 1H), 2.79(dd, J=5, 13 Hz, 1H), 2.95–3.07(m, 3H), 3.07(s, 3H), 3.36–3.42(m, 1H), 3.44(s, 3H), 5.12(s, 2H), 6.36(d, J=8 Hz, 1H), 6.53(d, J=2 Hz, 1H), 6.60(dd, J=2, 8 Hz, 1H), 7.08(d, J=3 Hz, 1H), 7.17(d, J=3 Hz, 1H)

Example 839

5,10-Dihydro-5-methoxymethyl-10-methyl-7-[(pyridin-2-yl)methyl]-10H-pyrazino[2,3-b][1,4]quinoxaline 0.160 g of the title compound was obtained as a yellow solid by hydrogenating 0.194 g of [(5,10-dihydro-5-methoxymethyl-10-methyl-10H-pyrazino[2,3-b][1,4]quinoxalin-7-yl)-(pyridin-2-yl)methyl] acetate in a mixture (15 ml) of tetrahydrofuran with ethanol (1:1) in the presence of 0.12 g of a 10% palladium-carbon powder (moisture content: 50%) by the same method as the one of Example 20.

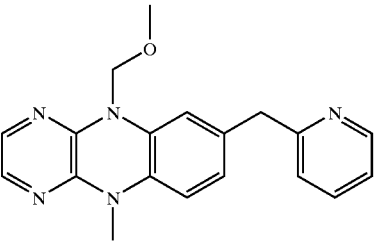

$^1$H-NMR(CDCl$_3$) δ ppm: 3.03(s, 3H), 3.46(s, 3H), 4.05(s, 2H), 5.10(s, 2H), 6.37(d, J=8 Hz, 1H), 6.61(m, 2H), 7.01(d, J=3 Hz, 1H), 7.09(d, J=3 Hz, 1H), 7.21(m, 1H), 7.62(dt, J=2, 8 Hz, 1H), 7.70(br.t, J=8 Hz, 1H), 8.51(m, 1H)

Examples

The following compounds were obtained by treating the compounds obtained in Examples 835, 836, 838 and 839 by the same method as the one of Example 8.

| Ex. | Structural formula | MS | M. p. | NMR |
|---|---|---|---|---|
| 840 | (5,10-dihydro-5-methyl-10H-pyrazino[2,3-b][1,4]quinoxalin-8-yl)-(pyridin-2-yl)ketone | ESI (+) 326 (MNa$^+$) | 261–262° C. | $^1$H-NMR(DMSO-d$_6$) δ ppm: 3.01(s, 3H), 6.52(d, J=8Hz, 1H), 6.95(d, J=4Hz, 1H), 6.98(d, J=2Hz, 1H), 7.02(d, J=4Hz, 1H), 7.28(dd, J=2, 8Hz, 1H), 7.60(dd, J=5, 8Hz, 1H), 7.82(d, J=8Hz, 1H), 8.00(dt, J=1, 8Hz, 1H), 8.57(dd, J=1, 5Hz, 1H), 9.28(s, 1H) |

-continued

| Ex. | Structural formula | MS | M. p. | NMR |
|---|---|---|---|---|
| 841 | 1-(5,10-dihydro-5-methyl-10H-pyrazino[2,3-b][1,4]quinoxalin-8-yl)-1-(pyridin-2-yl)ethanol | ESI (+) 342 (MH⁺) | 185–187° C. | ¹H-NMR(DMSO-d₆) δ ppm: 1.71(s, 3H), 2.89(s, 3H), 5.74(s, 1H), 6.32(d, J=8Hz, 1H), 6.53(d, J=2Hz, 1H), 6.62(dd, J=2, 8Hz, 1H), 6.80(d, J=4Hz, 1H), 6.90(d, J=4Hz, 1H), 7.18(dd, J=6, 8Hz, 1H), 7.56(d, J=8Hz, 1H), 7.71(dt, J=2, 8Hz, 1H), 8.44(dd, J=2, 6Hz, 1H), 8.95(s, 1H) |
| 842 | (5,10-dihydro-5-methyl-8-[(piperidin-2-yl)methyl]-10H-pyrazino[2,3-b][1,4]quinoxaline | | | ¹H-NMR(CDCl₃) δ ppm: 0.84–0.88(m, 1H), 1.04–1.12(m, 1H), 1.16–1.28(m, 3H), 2.19–2.30(m, 1H), 2.36–2.50(m, 3H), 2.92–3.05(m, 2H), 3.00(s, 3H), 5.95(br.s, 1H), 6.01(d, J=2Hz, 1H), 6.25(d, J=8Hz, 1H), 6.43(dd, J=2, 8Hz, 1H), 6.84(d, J=3Hz, 1H), 7.01(d, J=3Hz, 1H) |
| 843 | (5,10-dihydro-5-methyl-8-[(pyridin-2-yl)methyl]-10H-pyrazino[2,3-b][1,4]quinoxaline | ESI (+) 290 (MH⁺) | | ¹H-NMR(CDCl₃) δ ppm: 3.05(s, 3H), 3.88(s, 2H), 6.13(d, J=2Hz, 1H), 6.34(d, J=8Hz, 1H), 6.55(dd, J=2, 8Hz, 1H), 6.88(d, J=4Hz, 1H), 7.06(d, J=4Hz, 1H), 7.12(d, J=8Hz, 1H), 7.12(dd, J=6, 8Hz, 1H), 7.59(dt, J=2, 8Hz, 1H), 8.54(dd, J=2, 6Hz, 1H) |

Example 844

Methyl(5,10-dihydro-10-methoxymethyl-10H-pyrazino[2,3-b][1,4]quinoxalin-5-yl)acetate

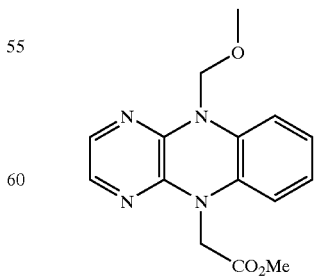

1.71 g of the title compound was obtained by treating 2.28 g of 5,10-dihydro-5-methoxymethyl-10H-pyrazino[2,3-b][1,4]quinoxaline with ethyl bromoacetate by the same method as the one of Example 788.

¹H-NMR(CDCl₃) δ ppm: 3.46(s, 3H), 3.78(s, 3H), 4.49(s, 2H), 5.18(s, 2H), 6.26(m, 1H), 6.70–6.79(m, 3H), 7.16(s, 2H)

Examples

The following compounds were obtained by treating the compounds obtained in Examples 844, 794 and 795 by the same method as the one of Example 2.

| Ex. | Structural formula | NMR |
|---|---|---|
| 845 | (5,10-dihydro-10-methoxymethyl-10H-pyrazino[2,3-b][1,4]quinoxaline-5-yl)ethanol | $^1$H-NMR(DMSO-d$_6$) δ ppm: 3.29(s, 3H), 3.52(q, J=7Hz, 2H), 3.74(t, J=7Hz, 2H), 4.84(t, J=7Hz, 1H), 5.05(s, 2H), 6.61–6.72(m, 4H), 7.08(s, 1H), 7.16(s, 1H) |
| 846 | 4-(5,10-dihydro-10-methoxymethyl-10H-pyrazino[2,3-b][1,4]quinoxaline-5-yl)-1-butanol | $^1$H-NMR(CDCl$_3$) δ ppm: 1.60–1.79(m, 4H), 2.64(br.s, 1H), 3.43(s, 3H), 3.68–3.78(m, 4H), 5.13(s, 2H), 6.48(d, J=8Hz, 1H), 6.66–6.76(m, 3H), 7.07(d, J=3Hz, 1H), 7.12(d, J=3Hz, 1H) |
| 847 | (E)-4-(5,10-dihydro-10-methoxymethyl-10H-pyrazino[2,3-b][1,4]quinoxaline-5-yl)-2-buten-1-ol | $^1$H-NMR(CDCl$_3$) δ ppm: 3.45(s, 3H), 4.15(br.m, 2H), 4.37(br.s, 2H), 5.13(s, 2H), 5.75(ttd, J=1, 4, 16Hz, 1H), 5.90(ttd, J=1, 5, 16Hz, 1H), 6.43(m, 1H), 6.68(m, 3H), 7.11(d, J=3Hz, 1H), 7.16(d, J=3Hz, 1H) |

Examples

The following compounds were obtained by treating the compounds obtained in Examples 845, 846 and 847 by the same method as the one of Example 8.

| Ex. | Structural formula | MS | M. p. | NMR |
|---|---|---|---|---|
| 848 | 2-(5,10-dihydro-10H-pyrazino[2,3-b][1,4]quinoxaline-5-yl)ethanol | ESI (+) 229 (MH$^+$) | 197–204° C. | $^1$H-NMR(DMSO-d$_6$) δ ppm: 3.46(t, J=7Hz, 2H), 3.62(t, J=7Hz, 2H), 6.30(d, J=8Hz, 1H), 6.47–6.55(m, 3H), 6.83(d, J=3Hz, 1H), 6.90(d, J=3Hz, 1H), 9.03(s, 1H) |

-continued

| Ex. | Structural formula | MS | M. p. | NMR |
|---|---|---|---|---|
| 849 | 4-(5,10-dihydro-10H-pyrazino[2,3-b][1,4]quinoxaline-5-yl)-2-buten-1-ol | ESI (+) 257 (MH⁺) | 138–139° C. | ¹H-NMR(CDCl₃) δ ppm: 1.51–1.69(m, 4H), 2.58(br.s, 1H), 3.59(t, J=7Hz, 2H), 3.68(m, 2H), 6.14(d, J=8Hz, 1H), 6.35(d, J=8Hz, 1H), 6.48–6.60(m, 2H), 6.80(s, 1H), 6.93(s, 1H) |
| 850 | 4-(5,10-dihydro-10H-pyrazino[2,3-b][1,4]quinoxaline-5-yl)-2-buten-1-ol | ESI (+) 255 (MH⁺) | 197–199° C. | ¹H-NMR(CDCl₃) δ ppm: 3.88(dd, J=5, 6Hz, 2H), 4.16(d, J=4Hz, 2H), 4.69(d, J=6Hz, 1H), 5.43(td, J=5, 16Hz, 1H), 5.77(td, J=4, 16Hz, 1H), 6.30–6.38(m, 2H), 6.47–6.52(m, 2H), 6.84(d, J=3Hz, 1H), 6.90(d, J=3Hz, 1H) |

Example 851

5,10-Dihydro-10-(3-chloropropan-1-yl)-5-methoxymethyl-10H-pyrazino[2,3-b][1,4]quinoxaline 0.607 g of the title compound was obtained by treating 0.684 g of 5,10-dihydro-5-methoxymethoxy-10H-pyrazino[2,3-b][1,4]quinoxaline with 3-bromo-1-chloropropane by the same method as the one of Example 788.

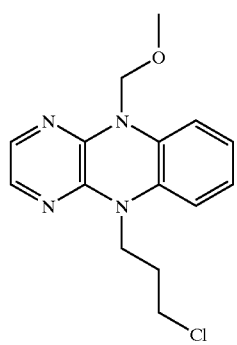

¹H-NMR(CDCl₃) δ ppm: 2.33(quint, J=7 Hz, 2H), 3.45(s, 3H), 3.67(t, J=7 Hz, 2H), 3.86(t, J=7 Hz, 2H), 5.13(s, 2H), 6.55(d, J=8 Hz, 1H), 6.70–6.78(m, 3H), 7.08–7.15(m, 2H)

Example 852

5,10-Dihydro-10-(3-azidopropai-1-yl)-5-methoxymethyl-10H-pyrazino[2,3-b][1,4]quinoxaline To a solution of 0.082 g of 5,10-dihydro-10-(3-chloropropan-1-yl)-5-methoxymethyl-10H-pyrazino[2,3-b][1,4]quinoxaline in N,N-dimethylformamide (5 ml) was added in a nitrogen atmosphere 0.035 g of sodium azide and the resulting mixture was heated to 80° C. for 1 hour. Then the reaction mixture was distributed into ethyl acetate and water and the aqueous layer was extracted with ethyl acetate. The organic layers were combined, washed with water and dried over anhydrous magnesium sulfate. After distilling off the solvent under reduced pressure, the residue was purified by silica gel column chromatography (eluted with n-hexane/ethyl acetate) to thereby give 0.045 g of the title compound as a yellow solid.

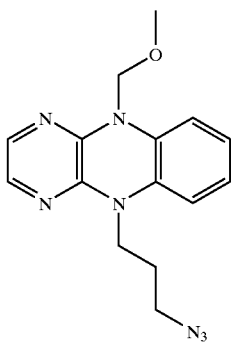

¹H-NMR(CDCl₃) δ ppm: 1.83(quint, J=7 Hz, 2H), 3.38(s, 3H), 3.39(t, J=7 Hz, 2H), 3.73(t, J=7 Hz, 2H), 5.07(s, 2H), 6.43(d, J=8 Hz, 1H), 6.61(m, 3H), 7.02(s, 1H), 7.08(s, 1H)

Example 853

5,10-Dihydro-10-(3-aminopropan-1-yl)-5-methoxymethyl-10H-pyrazino[2,3-b][1,4]quinoxaline 0.045 g of 5,10-dihydro-10-(3-azidopropan-1-yl)-5-methoxymethyl-10H-pyrazino[2,3-b][1,4]quinoxaline was dissolved in ethanol (10 ml) and 0.020 g of 10% palladium-carbon was added thereto. Then the mixture was subjected to a hydrogenation reaction at room temperature under atmospheric pressure for 24 hours. Next, the reaction mixture was filtered through celite and concentrated under reduced pressure to thereby give 0.018 g of the title compound as a yellow solid.

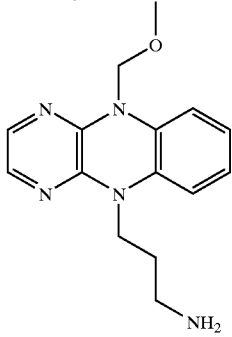

¹H-NMR(CDCl₃) δ ppm: 2.15(quint, J=7 Hz, 2H), 2.89(t, J=7 Hz, 2H), 3.44(s, 3H), 3.83(br.m, 2H), 5.13(s, 2H), 6.45(dd, J=2, 8 Hz, 1H), 6.90–6.97(m, 3H), 7.02(d, J=2 Hz, 1H), 7.10(d, J=2 Hz, 1H)

Example 854

5,10-Dihydro-5-(3-aminopropan-1-yl)-10H-pyrazino[2,3-b][1,4]quinoxaline 0.011 g of the title compound was obtained as a yellowish green solid by treating 0.018 g of 5,10-dihydro-5-methoxymethyl-10-(3-aminopropan-1-yl)-10H-pyrazino[2,3-b][1,4]quinoxaline by the same method as the one of Example 8.

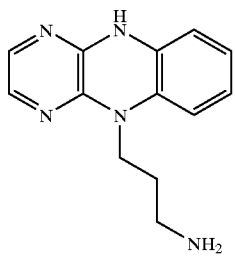

¹H-NMR(DMSO-d₆) δ ppm: 1.51(quint, J=7 Hz, 2H), 2.58(t, J=7 Hz, 2H), 3.59(t, J=7 Hz, 2H), 6.30(d, J=8 Hz, 1H), 6.47–6.52(m, 3H), 6.80(d, J=3 Hz, 1H), 6.89(d, J=3 Hz, 1H), 9.00(s, 1H)

Examples

The following compounds were obtained by treating the compounds obtained in Examples 811 and 845 by the same method as the one of Example 1237.

| Ex. | Structural formula | NMR |
|---|---|---|
| 855 | N-(5,10-dihydro-5-methoxymethyl-10-methyl-10H-pyrazino[2,3-b][1,4]quinoxalin-7-yl)methylphthalimide | ¹H-NMR(CDCl₃) δ ppm: 3.05(s, 3H), 3.38(s, 3H), 4.60(s, 2H), 5.08(s, 2H), 6.32(d, J=8Hz, 1H), 6.74–6.77(m, 2H), 7.03(s, 1H), 7.10(s, 1H), 7.36–7.66(m, 2H), 7.75–7.79(m, 2H) |

| Ex. | Structural formula | NMR |
|---|---|---|
| 856 | 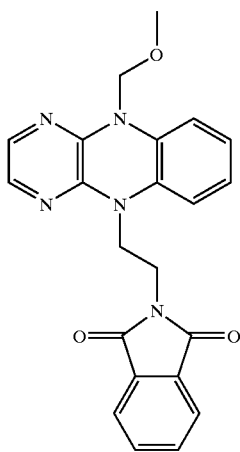<br>N-[2-(5,10-dihydro-5-methoxymethyl-10-methyl-10H-pyrazino[2,3-b][1,4]quinoxalin-7-yl)ethyl]phthalimide | $^1$H-NMR(CDCl$_3$) δ ppm: 3.38(s, 3H), 3.92(m, 2H), 3.96(m, 2H), 5.07(s, 2H), 6.66–6.71(m, 4H), 6.95(d, J=3Hz, 1H), 6.97(d, J=3Hz, 1H), 7.64(dd, J=2, 5Hz, 2H), 7.75(dd, J=2, 5Hz, 2H) |

Examples

The following compounds were obtained by treating the compounds obtained in Examples 855 and 856 by the same method as the one of Example 1239.

| Ex. | Structural formula | NMR |
|---|---|---|
| 857 | 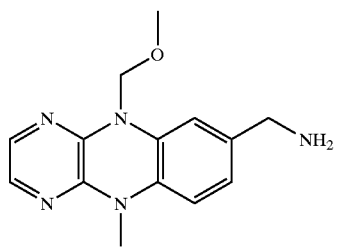<br>5,10-dihydro-7-aminomethyl-5-methoxymethyl-10-methyl-10H-pyrazino[2,3-b][1,4]quinoxaline | $^1$H-NMR(CDCl$_3$) δ ppm: 3.12(s, 3H), 3.46(s, 3H), 3.70(s, 2H), 5.17(s, 2H), 6.42(d, J=8Hz, 1H), 6.68(d, J=2Hz, 1H), 6.71(dd, J=2, 8Hz, 1H), 7.09(d, J=3Hz, 1H), 7.18(d, J=3Hz, 1H) |

-continued

| Ex. | Structural formula | NMR |
|---|---|---|
| 858 | 5,10-dihydro-5-(2-aminoethan-1-yl)-10-methoxymethyl-10H-pyrazino[2,3-b][1,4]quinoxaline | $^1$H-NMR(CDCl$_3$) δ ppm: 2.15(quint, J=7Hz, 2H), 2.89(t, J=7Hz, 2H), 3.44(s, 3H), 3.83(br.m, 2H), 5.13(s, 2H), 6.45(dd, J=2, 8Hz, 1H), 6.90–6.97(m, 3H), 7.02(d, J=2Hz, 1H), 7.10(d, J=2Hz, 1H) |

Examples 25

The following compounds were obtained by treating the compounds obtained in Examples 857 and 858 by the same method as the one of Example 8.

| Ex. | Structural formula | MS | M. p. | NMR |
|---|---|---|---|---|
| 859 | 5,10-dihydro-10-methyl-7-aminomethyl-10H-pyrazino[2,3-b][1,4]quinoxaline | ESI (+) 228 (MH$^+$) | 117–122° C. | $^1$H-NMR(DMSO-d$_6$) δ ppm: 2.93(s, 3H), 3.54(s, 2H), 6.33(d, J=2Hz, 1H), 6.41(d, J=8Hz, 1H), 6.56(dd, J=2, 8Hz, 1H), 6.85(d, J=3Hz, 1H), 6.94(d, J=3Hz, 1H), 9.16(s, 1H) |
| 860 | 5,10-dihydro-5-(2-aminoethan-1-yl)-10H-pyrazino[2,3-b][1,4]quinoxaline | ESI (+) 228 (MH$^+$) | | $^1$H-NMR(DMSO-d$_6$) δ ppm: 2.86–2.94(m, 2H), 3.85(t, J=7Hz, 2H), 6.42(dd, J=4, 7Hz, 1H), 6.56–6.60(m, 2H), 6.67(dd, J=4, 7Hz, 1H), 6.86(d, J=3Hz, 1H), 6.92(d, J=3Hz, 1H), 8.02(br.s, 2H), 9.47(br.s, 1H) |

Example 861

N-[(5,10-Dihydro-10-methyl-10H-pyrazino[2,3-b][1,4]quinoxalin-7-yl)-(piperidin-2-yl)methyl]phthalimide The title compound was obtained by treating (5,10-dihydro-5-methoxymethyl-10-methyl-10H-pyrazino[2,3-b][1,4]quinoxalin-7-yl)-(pyridin-2-yl)methanol with phthalimide by the same method as the one of Example 1237 followed by the same treatment as the one of Example 8.

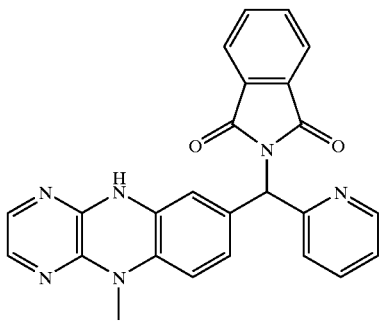

¹H-NMR(CDCl₃) δ ppm: 2.93(s, 3H), 6.30(s, 1H), 6.42–6.45(m, 2H), 6.61(d, J=8 Hz, 1H), 6.84(d, J=3 Hz, 1H), 6.95(d, J=3 Hz, 1H), 7.23(d, J=8 Hz, 1H), 7.28(dd, J=5, 8 Hz,1H), 7.52–7.63(m, 2H), 7.77(t, J=8 Hz, 1H), 7.87(m, 2H), 8.45(d, J=5 Hz, 1H), 9.02(s, 1H)

Example 862

5,10-Dihydro-5-methyl-8-[(pyridin-2-yl)(amino)methyl]-10H-pyrazino[2,3-b][1,4]quinoxaline The title compound was obtained by treating N-[(5,10-dihydro-10-methyl-10H-pyrazino[2,3-b][1,4]quinoxalin-7-yl)-(pyridin-2-yl)methyl]phthalimide with hydrazine by the same method as the one of Example 1239.

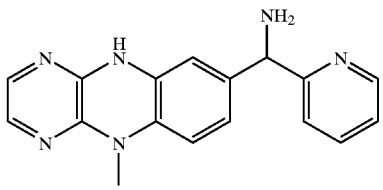

¹H-NMR(DMSO-d₆) δ ppm: 2.22(br.s, 2H), 2.91(s, 3H), 4.81(s, 1H), 6.35(d, J=8 Hz, 1H), 6.40(s, 1H), 6.58(d, J=8 Hz, 1H), 6.81(d, J=4 Hz, 1H), 6.91(d, J=4 Hz, 1H), 7.19(dd, J=6, 8 Hz, 1H), 7.38(d, J=8 Hz, 1H), 7.70(t, J=8 Hz, 1H), 8.44(d, J=6 Hz, 1H), 8.99(s, 1H)
MS: ESI(+)305(MH⁺)
m.p.: >275° C.

Example 863

N-[2-(5,10-Dihydro-10-methoxymethyl-10H-pyrazino[2,3-b][1,4]quinoxalin-5-yl)ethyl]urea To a solution of 0.081 g of 5,10-dihydro-5-(2-aminoethan-1-yl)-10-methoxymethyl-10H-pyrazino [2,3-b][1,4]quinoxaline in dry tetrahydrofuran (10 ml) were added in a nitrogen atmosphere 0.081 ml of triethylamine and 0.061 ml of trimethylsilyl isocyanate and the resulting mixture was stirred at room temperature for 16 hours. Next, the reaction mixture was distributed into ethyl acetate and water. The organic layer was washed with a saturated aqueous solution of sodium chloride and dried over anhydrous magnesium sulfate. After distilling off the solvent under reduced pressure, the residue was purified by silica gel column chromatography (eluted with dichloromethane/methanol) to thereby give 0.057 g of the title compound as a yellow solid.

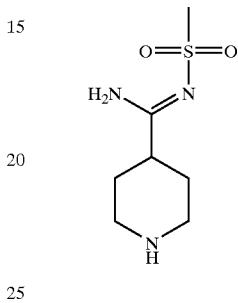

¹H-NMR(CDCl₃) δ ppm: 3.40(m, 2H), 3.46(s, 3H), 3.84 (t, J=7 Hz, 2H), 5.14(s, 2H), 6.64–6.68(m, 1H), 6.73–6.80 (m, 3H), 7.10(d, J=3 Hz, 1H), 7.14(d, J=3 Hz, 1H)

Example 864

N-[(5,10-Dihydro-5-methoxymethyl-10-methyl-10H-pyrazino[2,3-b][1,4]quinoxalin-7-yl)methyl]urea 0.034 g of the title compound was obtained by treating 0.041 g of 5,10-dihydro-5-methoxymethyl-10-methyl-7-aminomethyl-10H-pyrazino[2,3-b][1,4]quinoxaline by the same method as the one of Example 863.

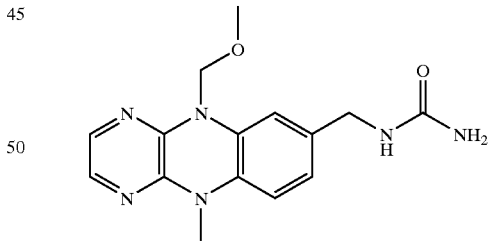

¹H-NMR(DMSO-d₆) δ ppm: 3.02(s, 3H), 3.30(s, 3H), 3.96(d, J=6 Hz, 2H), 5.06(s, 2H), 5.48(s, 2H), 6.28(t, J=6 Hz, 1H), 6.54(d, J=8 Hz, 1H), 6.56(d, J=2 Hz, 1H), 6.65(dd, J=2, 8 Hz, 1H), 7.09(d, J=3 Hz, 1H), 7.18(d, J=3 Hz, 1H)

Examples

The following compounds were obtained by treating the compounds obtained in Examples 863 and 864 by the same method as the one of Example 8.

| Ex. | Structural formula | MS | M. p. | NMR |
|---|---|---|---|---|
| 865 | N-[(5,10-dihydro-10-methyl-10H-pyrazino[2,3-b][1,4]quinoxalin-7-yl)methyl]urea | ESI (+) 271 (MH⁺) | >275° C. | ¹H-NMR(DMSO-d₆) δ ppm: 2.94(s, 3H), 3.85(d, J=6Hz, 2H), 5.46(s, 2H), 6.21(t, J=6Hz, 1H), 6.26(s, 1H), 6.35(d, J=8Hz, 1H), 6.43(d, J=8Hz, 1H), 6.83(d, J=4Hz, 1H), 6.93(d, J=4Hz, 1H), 9.08(s, 1H) |
| 866 | N-[2-(5,10-dihydro-10H-pyrazino[2,3-b][1,4]quinoxalin-5-yl)ethyl]urea | ESI (+) 293 (MNa⁺) | 231–233° C. | ¹H-NMR(DMSO-d₆) δ ppm: 3.04(q, J=7Hz, 2H), 3.54(t, J=7Hz, 2H), 5.49(s, 2H), 6.19(t, J=7Hz, 1H), 6.32(m, 1H), 6.51(m, 2H), 6.72(m, 1H), 6.84(d, J=4Hz, 1H), 6.90(d, J=4Hz, 1H), 9.03(s, 1H) |

Example 867

N-[(5,10-Dihydro-5-methyl-10H-pyrazino[2,3-b][1,4]quinoxalin-8-yl)methyl]guanidine To a solution of 0.084 g of 5,10-dihydro-5-methyl-8-aminomethyl-10H-pyrazino[2,3-b][1,4]quinoxaline in methanol (10 ml) was added 0.046 g of formamidinesulfonic acid and the resulting mixture was stirred at room temperature for 40 hours. After adding water, the precipitate thus formed was taken up by filtration to thereby give 0.066 g of the title compound as a yellow solid.

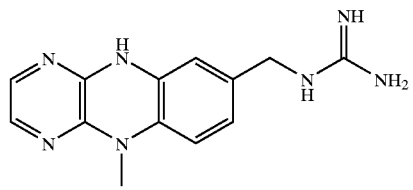

¹H-NMR(DMSO-d₆) δ ppm: 2.92(s, 3H), 4.03(s, 2H), 6.26(d, J=1 Hz, 1H), 6.40(d, J=8 Hz, 1H), 6.48(dd, J=1, 8 Hz, 1H), 6.85(d, J=3 Hz, 1H), 6.94(d, J=3 Hz, 1H)
m.p.: >275° C.
MS: ESI(+)270(MH⁺)

Example 868

N-[2-(5,10-Dihydro-10H-pyrazino[2,3-b][1,4]quinoxalin-5-yl)ethyl]guanidine

Starting with 0.064 g of 5,10-dihydro-5-(2-aminoethan-1-yl)-10-methoxymethyl-10H-pyrazino[2,3-b][1,4]quinoxaline, 0.030 g of the title compound was obtained by the same method as the one of Example 867.

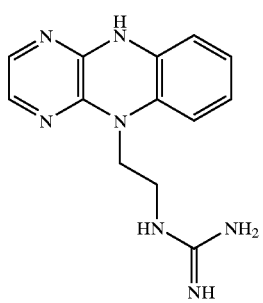

¹H-NMR(DMSO-d₆) δ ppm: 3.22(t, J=7 Hz, 2H), 3.66(t, J=7 Hz, 2H), 6.33(m, 1H), 6.50–6.62(m, 3H), 6.81(d, J=4 Hz, 1H), 6.92(d, J=4 Hz, 1H)

MS: ESI(+)270(MH⁺)

Examples

The following compounds were obtained by the same method as the one of Production Example 165.

| Ex. | Structural formula | NMR |
|---|---|---|
| 869 | N-[(5,10-dihydro-5-methoxymethyl-10-methyl-10H-pyrazino[2,3-b][1,4]quinoxalin-7-yl)methyl]acetamide | ¹H-NMR(CDCl₃) δ ppm: 1.83(s, 3H), 3.03(s, 3H), 3.31(s, 3H), 4.03(d, J=6Hz, 2H), 5.06(s, 2H), 6.54(d, J=8Hz, 1H), 6.56(d, J=2Hz, 1H), 6.63(dd, J=2, 8Hz, 1H), 7.10(d, J=3Hz, 1H), 7.18(d, J=3Hz, 1H), 8.24(br.s, 1H) |
| 870 | (E)-N-[4-(5,10-dihydro-5-methoxymethyl-10H-pyrazino[2,3-b][1,4]quinoxalin-5-yl)-2-buten-1-yl]acetamide | ¹H-NMR(CDCl₃) δ ppm: 1.90(s, 3H), 3.39(s, 3H), 3.81(br.t, J=6Hz, 2H), 4.25(br.t, J=4Hz, 2H), 5.07(s, 2H), 5.55–5.67(m, 2H), 6.53(m, 1H), 6.61–6.66(m, 3H), 7.04(d, J=3Hz, 1H), 7.08(d, J=3Hz, 1H) |

Examples

The following compounds were obtained by the same method as the one of Example 8.

| Ex. | Structural formula | MS | M.p. | NMR |
|---|---|---|---|---|
| 871 | N-[(5,10-dihydro-5-methyl-10H-pyrazino[2,3-b][1,4]quinoxalin-8-yl)methyl]acetamide | ESI (+) 270 (MH⁺) | 247–249° C. | ¹H-NMR(DMSO-d₆) δ ppm: 2.48(s, 3H), 2.93(s, 3H), 3.93(d, J=6Hz, 2H), 6.25(s, 1H), 6.37(d, J=8Hz, 1H), 6.43(d, J=8Hz, 1H), 6.85(d, J=4Hz, 1H), 6.92(d, J=4Hz, 1H), 8.19(br.s, 1H), 9.05(s, 1H) |

| Ex. | Structural formula | MS | M.p. | NMR |
|---|---|---|---|---|
| 872 | (E)-N-[4-(5,10-dihydro-10H-pyrazino [2,3-b][1,4] quinoxalin-5-yl)-2-buten-1-yl]acetamide | ESI (+) 318 (MH⁺) | 225–227° C. | ¹H-NMR(DMSO-d₆) δ ppm: 1.77(s, 3H), 3.63(t, J=6Hz, 2H), 4.16(d, J=3Hz, 2H), 5.49(td, J=3, 15Hz, 1H), 5.53(td, J=6, 15Hz, 1H), 6.31–6.36(m, 2H), 6.47–6.51(m, 2H), 6.85(d, J=3Hz, 1H), 6.91(d, J=3Hz, 1H), 7.96(t, J=6Hz, 1H), 9.06(s, 1H) |

Example 873

N-[2-(5,10-Dihydro-10H-pyrazino[2,3-b][1,4]quinoxalin-5-yl)ethyl]methylsulfonamide The title compound was obtained by successively treating 5,10-dihydro-5-(2-aminoethan-1-yl)-10-methoxymethyl-10H-pyrazino[2,3-b][1,4]quinoxaline by the same methods as those of Examples 316 and 8.

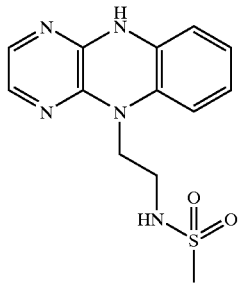

¹H-NMR(DMSO-d₆) δ ppm: 2.92(s, 3H), 3.06(q, J=7 Hz, 2H), 3.65(t, J=7 Hz, 2H), 6.34(m, 1H), 6.53(m, 3H), 6.86(d, J=3 Hz, 1H), 6.93(d, J=3 Hz, 1H), 7.26(t, J=7 Hz, 1H), 9.07(s, 1H)

MS: ESI(+)306(MH⁺)

m.p.: 218–222° C.

Example 874

[4-(5,10-Dihydro-10-methoxymethyl-10H-pyrazino[2,3-b][1,4]-quinoxalin-5-yl)butan-1-yl]methylsulfonate Starting with 0.195 g of 4-(5,10-dihydro-10-methoxymethyl-10H-pyrazino[2,3-b][1,4]-quinoxalin-5-yl)butan-1-ol, 0.247 g of the title compound was obtained as a yellow oily substance by the same method as the one of Production Example 52.

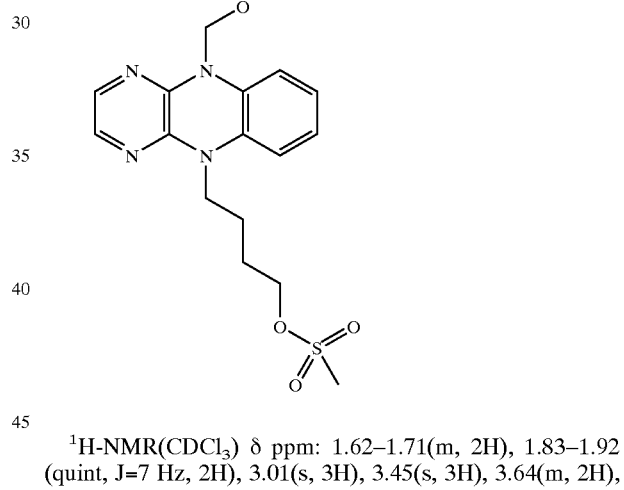

¹H-NMR(CDCl₃) δ ppm: 1.62–1.71(m, 2H), 1.83–1.92 (quint, J=7 Hz, 2H), 3.01(s, 3H), 3.45(s, 3H), 3.64(m, 2H), 4.30(t, J=7 Hz, 2H), 5.13(s, 2H), 6.43(d, J=8 Hz, 1H), 6.65–6.77(m, 3H), 7.08(d, J=3 Hz, 1H), 7.12(d, J=3 Hz, 1H)

Example 875

N-[4-(5,10-Dihydro-10-methoxymethyl-10H-pyrazino[2,3-b][1,4]-quinoxalin-5-yl)butyl]-p-toluenesulfonamide A solution of 0.089 g of p-toluenesulfonamide in N,N-dimethylformamide (5 ml) was cooled to 0° C. in a nitrogen atmosphere. After adding 0.023 g of sodium hydride (60% oily), 0.131 g of [4-(5,10-dihydro-10-methoxymethyl-10H-pyrazino[2,3-b][1,4]-quinoxalin-5-yl)butan-1-yl]methanesulfonate was further added thereto and the resulting mixture was heated to 60° C. for 16 hours. Then the reaction mixture was distributed into ethyl acetate and water. The organic layer was washed with a saturated aqueous solution of sodium chloride and dried over anhydrous magnesium sulfate. After distilling off the solvent under reduced pressure, the residue was purified by silica gel column chromatography (eluted with dichloromethane/methanol) to thereby give 0.094 g of the title compound as a yellow solid.

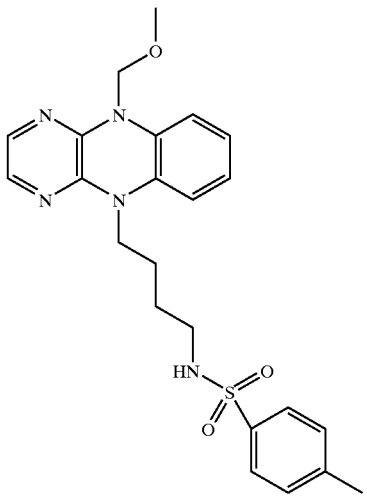

¹H-NMR(CDCl₃) δ ppm: 2.41(s, 3H), 3.05(quint, J=7 Hz, 2H), 3.44(s, 3H), 3.55(m, 2H), 3.74(m, 1H), 4.71(br.s, 4H), 5.13(s, 2H), 6.41(d, J=8 Hz, 1H), 6.68–6.75(m,3H), 7.25–7.30(m,4H),7.64(d, J=8 Hz,2H)

Example 876

N-[4-(5,10-Dihydro-10H-pyrazino[2,3-b][1,4]quinoxalin-5-yl)butyl]-p-toluenesulfonamide 0.051 g of the title compound was obtained as a yellow solid by treating 0.094 g of N-[4-(5,10-dihydro-10-methoxymethyl-10H-pyrazino[2,3-b]1,4]quinoxalin-5-yl)butyl]-p-toluenesulfonamide by the same method as the one of Example 8.

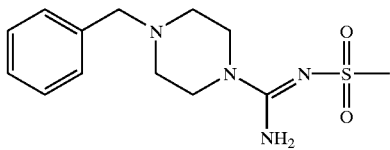

¹H-NMR(DMSO-d₆) δ ppm: 1.39(m, 4H), 2.35(s, 3H), 2.71(m, 2H), 3.47(m, 2H), 6.32(m, 1H), 6.41(m, 1H), 6.48–6.54(m,2H), 6.80(d, J=3 Hz, 1H), 6.88(d, J=3 Hz, 1H), 7.35(d, J=8 Hz, 2H), 7.52(t, J=6 Hz, 1H), 7.63(d, J=8 Hz, 2H), 9.10(br.s, 1H) m.p.: 124–128° C.

Example 877

5-Methoxymethyl-5,10-dihydro-7-iodo-10-methyl-10H-pyrazino-[2,3-b][1,4]quinoxaline 7.3 g of the title compound was obtained as a yellow solid by reacting 10.0 g of 5,10-dihydro-7-iodo-10-methyl-10H-pyrazino[2,3-b][1,4]quinoxaline with chloromethyl methyl ether by the same method as the one of Example 788.

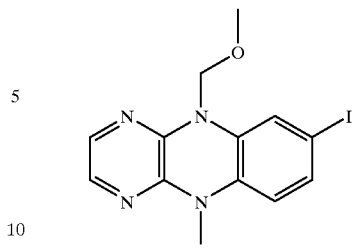

¹H-NMR(CDCl₃) δ ppm: 3.08(s, 3H), 3.44(s, 3H), 5.10(s, 2H), 6.17(d, J=9 Hz, 1H), 6.95(d, J=2 Hz, 1H), 7.05(dd, J=2, 9 Hz, 1H), 7.12(d, J=3 Hz, 1H), 7.21(d, J=3 Hz, 1H)

Example 878

5,10-Dihydro-5-methoxymethyl-10-methyl-7-(pyridin-2-yl)-10H-pyrazino[2,3-b][1,4]quinoxaline To a solution of (pyridin-2-yl)copper in toluene (20 ml) were added 0.423 g of 5,10-dihydro-7-iodo-5-methoxymethyl-10-methyl-10H-pyrazino[2,3-b][1,4]quinoxaline and 1.68 g of triphenylphosphine and the resulting mixture was heated to 100° C. in a nitrogen atmosphere for 14 hours. After cooling to room temperature, the reaction mixture was filtered and distributed into ethyl acetate and water. After filtering off the insoluble matters, the organic layer was washed with aqueous ammonia and dried over anhydrous magnesium sulfate. After distilling off the solvent under reduced pressure, the residue was purified by silica gel column chromatography (eluted with n-hexane/ethyl acetate) to thereby give 0.224 g of the title compound as a yellow solid.

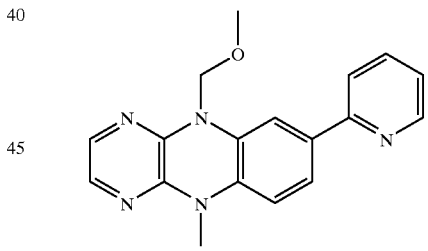

¹H-NMR(CDCl₃) δ ppm: 3.18(s, 3H), 3.50(s, 3H), 5.28(s, 2H), 6.55(d, J=9 Hz, 1H), 7.14(d, J=3 Hz, 1H), 7.10(ddd, J=1, 4, 7 Hz, 1H), 7.14(d, J=3 Hz, 1H), 7.33–7.36(m, 2H), 7.54(d, J=8 Hz, 1H), 7.63(dt, J=2, 8 Hz, 1H), 8.56(ddd, J=1, 2, 8 Hz, 1H)

Example 879

5,10-Dihydro-5-methyl-8-(pyridin-2-yl)-10H-pyrazino[2,3-b][1,4]quinoxaline

The title compound was obtained by treating 5,10-dihydro-5-methoxymethyl-10-methyl-7-(pyridin-2-yl)-10H-pyrazino[2,3-b][1,4]quinoxaline by the same method as the one of Example 8.

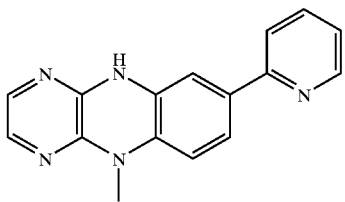

¹H-NMR(DMSO-d₆) δ ppm: 2.99(s,3H),6.53(d,J=8 Hz,1H),6.89(d,J=4 Hz,1H),6.98(d,J=4 Hz,1H),7.16(d,J=2 Hz,1H),7.24(dd,J=5,8 Hz,1H),7.28(dd,J=2,8 Hz,1H),7.69(d, J=8 Hz,1H),7.78(dt,J=2,8 Hz,1H),8.54(dd,J=2,5 Hz,1H), 9.20(s,1 H)

MS: FAB(+)275(M⁺)

Example 880

5,10-Dihydro-5-methoxymethyl-10-methyl-7-trimethylsilyl-ethynyl-10H-pyrazino[2,3-b][1,4]quinoxaline To a solution of 1.445 g of 5,10-dihydro-7-iodo-5-methoxymethyl-10-methyl-10H-pyrazino[2,3-b][1,4] quinoxaline in N,N-dimethylformamide (40 ml) were added 0.28 g of dichlorobis(triphenylphosphine)palladium, 0.090 g of cuprous iodide, 0.86 ml of triethylamine and 1.10 ml of trimethylsilylacetylene. Then this mixture was treated by the same method as the one of Example 1386-3 to thereby give 1.329 g of the title compound as a yellow solid.

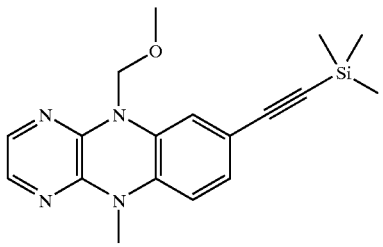

¹H-NMR(CDCl₃) δ ppm: 0.23(s, 9H), 3.12(s, 3H), 3.46(s, 3H), 5.15(s, 2H), 6.36(d, J=8 Hz, 1H), 6.78(d, J=2 Hz, 1H), 6.89(dd, J=2, 8 Hz, 1H), 7.12(d, J=3 Hz, 1H), 7.20(d, J=3 Hz, 1H)

Example 881

5,10-Dihydro-7-ethynyl-5-methoxymethyl-10-methyl-10H-pyrazino[2,3-b][1,4]quinoxaline Similar to Example 1418, a solution of 0.338 g of 5,10-dihydro-5-methoxymethyl-10-methyl-7-trimethylsilyl-ethynyl-10H-pyrazino[2,3-b][1,4]quinoxaline in dry tetrahydrofuran was treated with 1.5 ml of a 1 M solution of tetra-n-butylammonium fluoride in tetrahydrofuran. Thus 0.250 g of the title compound was obtained as a yellow solid.

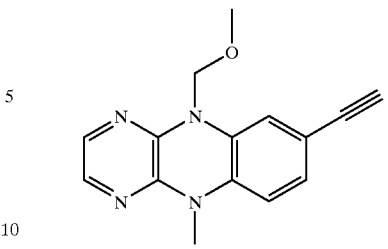

¹H-NMR(CDCl₃) δ ppm: 3.00(s, 1H), 3.12(s, 3H), 3.45(s, 3H), 5.12(s, 2H), 6.38(d, J=8 Hz, 1H), 6.80(s, 1H), 6.91(d, J=8 Hz, 1H), 7.13(s, 1H), 7.20(s, 1H)

Example 882

N,N-Dimethyl-3-(5,10-dihydro-5-methyl-10H-pyrazino [2,3-b][1,4]quinoxalin-8-yl)propynylamide To 5 ml of triethylamine were added in a nitrogen atmosphere 0.115 g of 5,10-dihydro-7-ethynyl-5-methoxymethyl-10-methyl-10H-pyrazino[2,3-b][1,4] quinoxaline, 0.020 g of dichlorobis (triphenylphosphine) palladium, 0.020 g of cuprous iodide, 0.026 g of triphenylphosphine and 0.044 ml of dimethylcarbamoyl chloride and the resulting mixture was heated to 90° C. for 6 hours. After distilling off the solvent under reduced pressure, the residue was distributed into ethyl acetate and water and the insoluble matters were filtered off. After distilling off the solvent under reduced pressure, the residue was purified by silica gel column chromatography (eluted with dichloromethane/methanol) to thereby give 0.081 g of the title compound as a yellow solid.

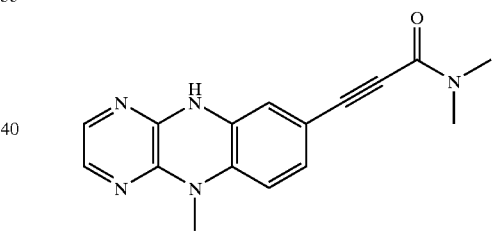

¹H-NMR(DMSO-d₆) δ ppm: 2.86(s,3H),2.95(s,3H),3.15 (s,3H),6.41(d,J=2 Hz,1H),6.45(d,J=8 Hz,1H),6.82(dd,J=2,8 Hz,1H),6.92(d,J=3 Hz,1H),6.99(d,J=3 Hz,1H),9.25(s,1H)
m.p.: 203–205° C.
MS: ESI(+)316(MNa⁺)

Example 883

(5,10-Dihydro-5-methoxymethyl-10-methyl-10H-pyrazino[2,3-b][1,4]quinoxalin-7-yl)propynoic acid Into a solution of 0.266 g of 5,10-dihydro-7-ethynyl-5-methoxymethyl-10-methyl-10H-pyrazino[2,3-b][1,4] quinoxaline in dry tetrahydrofuran (15 ml) was dropped at −78° C. in a nitrogen atmosphere 1.6 ml of a 1.6 M solution of n-butyllithium in hexane. After stirring for 1 hour, dry ice was added to the mixture. Then the bulk temperature was elevated to room temperature and the reaction mixture was distributed into 6 N potassium hydroxide and ethyl acetate. The pH value of the aqueous layer was adjusted to 4 with hydrochloric acid followed.by extraction with ethyl acetate. The extractant was distilled off under reduced pressure to thereby give 0.180 g of the title compound as a yellow solid.

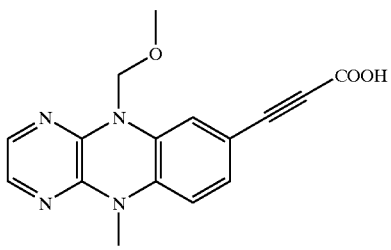

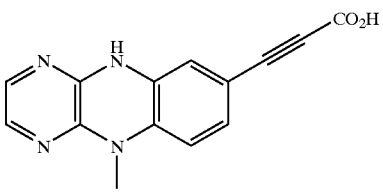

¹H-NMR(CDCl₃) δ ppm: 3.06(s, 3H), 3.32(s, 3H), 5.11(s, 2H), 6.61(d, J=9 Hz, 1H), 6.73(d, J=2 Hz, 1H), 7.04(dd, J=2, 9 Hz, 1H), 7.19(d, J=3 Hz, 1H), 7.25(d, J=3 Hz, 1H)

Example 884

(5,10-Dihydro-10-methyl-10H-pyrazino[2,3-b][1,4]quinoxalin-7-yl)propynoic acid

The title compound was obtained by treating (5,10-dihydro-5-methoxymethyl-10-methyl-10H-pyrazino[2,3-b][1,4]quinoxalin-7-yl)propynoic acid by the same method as the one of Example 9.

¹H-NMR(DMSO-d₆) δ ppm: 2.95(s, 3H), 6.41(d, J=2 Hz, 1H), 6.45(d, J=8 Hz, 1H), 6.84(dd, J=2, 8 Hz, 1H), 6.93(d, J=3 Hz, 1H), 7.00(d, J=3 Hz, 1H)

MS: ESI(+)267(MH⁺)

m.p.: >275° C.

Examples

The following compounds were synthesized by treating 5,10-dihydro-5-methoxymethyl-7-iodo-10-methyl-10H-pyrazino[2,3-b][1,4]quinoxaline by the same method as the one of Example 883.

| Ex. | Stuctural formula | NMR |
|---|---|---|
| 885 | <br>3-(5,10-dihydro-5-methoxymethyl-10-methyl-10H-pyrazino[2,3-b][1,4]quinoxalin-7-yl)-2-propyn-1-ol | ¹H-NMR(CDCl₃) δ ppm: 3.06(s, 3H), 3.38(s, 3H), 4.40(s, 2H), 5.06(s, 2H), 6.38(d, J=8Hz, 1H), 6.77(d, J=2Hz, 1H), 6.86(dd, J=2, 8Hz, 1H), 7.14(d, J=3Hz, 1H), 7.21(d, J=3Hz, 1H) |
| 886 | <br>5,10-dihydro-5-methoxymethyl-10-methyl-7-phenylethynyl-10H-pyrazino[2,3-b][1,4]quinoxaline | ¹H-NMR(CDCl₃) δ ppm: 3.12(s, 3H), 3.48(s, 3H), 5.17(s, 2H), 6.42(d, J=8Hz, 1H), 6.86(d, J=2Hz, 1H), 6.96(dd, J=2, 8Hz, 1H), 7.14(d, J=3Hz, 1H), 7.21(d, J=3Hz, 1H), 7.30–7.35(m, 3H), 7.49–7.52(m, 2H) |

-continued

| Ex. | Stuctural formula | NMR |
|---|---|---|
| 887 | (5,10-dihydro-7-[3-(N,N-dimethylamino)-1-propyn-1-yl]-5-methoxymethyl-10-methyl-10H-pyrazino[2,3-b][1,4]quinoxaline | $^1$H-NMR(CDCl$_3$) δ ppm: 2.37(s, 6H), 3.12(s, 3H), 3.42(s, 2H), 3.44(s, 3H), 5.13(s, 2H), 6.37(d, J=8Hz, 1H), 6.77(d, J=2Hz, 1H), 6.86(dd, J=2, 8Hz, 1H), 7.12(d, J=3Hz, 1H), 7.20(d, J=3Hz, 1H) |
| 888 | ethyl (5,10-dihydro-5-methoxymethyl-10-methyl-10H-pyrazino[2,3-b][1,4]quinoxalin-7-yl)propynoate | $^1$H-NMR(CDCl$_3$) δ ppm: 1.25(t, J=7Hz, 3H), 3.13(s, 3H), 3.43(s, 3H), 4.09(q, J=7Hz, 2H), 5.10(s, 2H), 6.40(d, J=8Hz, 1H), 6.66(s, 1H), 7.02(d, J=8Hz, 1H), 7.16(d, J=3Hz, 1H), 7.22(d, J=3Hz, 1H) |

Examples

The following compounds were obtained by treating the compounds obtained in Examples 885, 886 and 887 by the same method as the one of Example 8.

| Ex. | Structural formula | Ms | M.p. | NMR |
|---|---|---|---|---|
| 889 | 3-(5,10-dihydro-5-methyl-10H-pyrazino[2,3-b][1,4]quinoxalin-8-yl)-2-propyn-1-ol | ESI (+) 253 (MH$^+$) | 241–243° C. | $^1$H-NMR(DMSO-d$_6$) δ ppm: 2.93(s, 3H), 4.21(d, J=7Hz, 2H), 5.24(t, J=7Hz, 1H), 6.31(d, J=2Hz, 1H), 6.38(d, J=8Hz, 1H), 6.61(dd, J=2, 8Hz, 1H), 6.88(d, J=3Hz, 1H), 6.97(d, J=3Hz, 1H), 9.16(s, 1H) |

| Ex. | Structural formula | Ms | M.p. | NMR |
|---|---|---|---|---|
| 890 | 5,10-dihydro-5-methyl-8-phenylethynyl-10H-pyrazino[2,3-b][1,4]quinoxaline | ESI (+) 299 (MH⁺) | 245–247° C. | ¹H-NMR(CDCl₃) δ ppm: 3.09(s, 3H), 6.24(br.s, 1H), 6.35(d, J=2Hz, 1H), 6.35(d, J=8Hz, 1H), 6.85(dd, J=2, 8Hz, 1H), 6.96(d, J=4Hz, 1H), 7.11(d, J=4Hz, 1H), 7.30–7.35(m, 3H), 7.46–7.49(m, 2H) |
| 891 | 5,10-dihydro-8-[3-(N,N-dimethylamino)-1-propyn-1-yl]-5-methyl-10H-pyrazino[2,3-b][1,4]quinoxaline | ESI (+) 280 (MH⁺) | 188–189° C. | ¹H-NMR(DMSO-d₆) δ ppm: 2.19(s, 6H), 2.92(s, 3H), 3.38(s, 2H), 6.32(s, 1H), 6.39(d, J=8Hz, 1H), 6.63(d, J=8Hz, 1H), 6.87(d, J=3Hz, 1H), 6.93(d, J=3Hz, 1H), 9.12(s, 1H) |

Example 892

Ethyl(5,10-dihydro-50-methyl-10H-pyrazino[2,3-b][1,4]quinoxalin-8-yl)propynoate

The following compound was obtained by treating ethyl (5,10-dihydro-5-methoxymethyl-10-methyl-10H-pyrazino[2,3-b][1,4]quinoxalin-7-yl)propynoate by the same method as the one of Example 9.

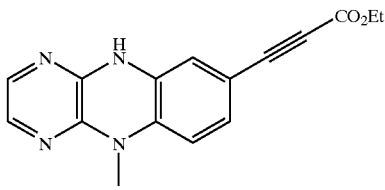

¹H-NMR(DMSO-d₆) δ ppm: 1.24(t, J=7 Hz, 3H), 2.95(s, 3H), 4.18(q, J=7 Hz, 2H), 6.41(d, J=2 Hz, 1H), 6.45(d, J=8 Hz, 1H), 6.87(dd, J=2, 8 Hz, 1H), 6.93(d, J=3 Hz, 1H), 7.00(d, J=3 Hz, 1H), 9.27(s, 1H)

MS: ESI(+)295(MH⁺)
m.p.: 232–235° C.

Example 893

Ethyl 3-(5,10-dihydro-5-methoxymethyl-10-methyl-10H-pyrazino[2,3-b][1,4]quinoxalin-7-yl)-3-oxopropanoate 0.150 g of ethyl 3-(5,10-dihydro-5-methoxymethyl-10-methyl-10H-pyrazino[2,3-b][1,4]quinoxalin-7-yl)propynoate was dissolved in a saturated solution of dimethylamine in ethanol (25 ml) and heated under reflux for 1 hour. After distilling off the solvent under reduced pressure, the residue was purified by silica gel column chromatography (eluted with n-hexane/ethyl acetate) to thereby give 0.080 g of the title compound as a yellow solid.

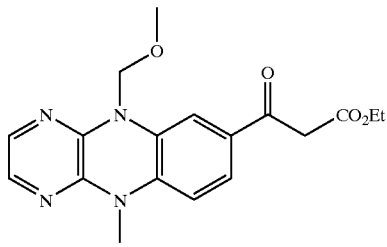

¹H-NMR(CDCl₃) δ ppm: 1.27(t, J=7 Hz, 3H), 3.18(s, 3H), 3.46(s, 3H), 3.86(s, 2H), 4.20(q, J=7 Hz, 2H), 5.17(s, 2H), 6.46(d, J=8 Hz, 1H), 7.21(d, J=3 Hz, 1H), 7.24–7.26(m, 2H), 7.37(dd, J=2, 8 Hz, 1H)

Example 894

Ethyl 3-(5,10-dihydro-5-methoxymethyl-10-methyl-10H-pyrazino-[2,3-b][1,4]quinoxalin-7-yl)-3-(methylthio)propenoate To a solution of 0.205 g of ethyl 3-(5,10-dihydro-5-methoxymethyl-10-methyl-10H-pyrazino[2,3-b][1,4]quinoxalin-7-yl)propynoate in N,N-dimethylformamide (10 ml) were added 1 ml of methanol and 0.063 g of methylmercaptane sodium salt and the resulting mixture was stirred at room temperature for 1 hour. After distilling off the solvent under reduced pressure, the residue was purified by silica gel column chromatography (eluted with n-hexane/ ethyl acetate) to thereby give 0.136 g of the title compound as a reddish oily substance.

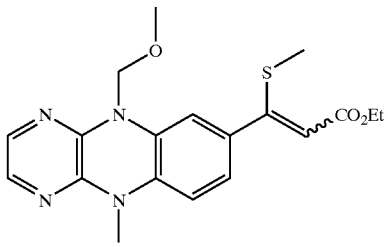

¹H-NMR(DMSO-d₆) δ ppm: 1.12 and 1.29(t, J=7 Hz, total 3H), 2.13 and 2.37(s, total 3H), 3.07(s, 3H), 3.30 and 3.32(s, total 3H), 3.94 and 4.07(q, J=7 Hz, total 2H), 5.03 and 5.13(s, total 2H), 5.53 and 5.87(s, total 1H), 6.52–6.73 (m, 3H), 7.15 and 7.16(d, J=3 Hz, total 1H), 7.23(d, J=3 Hz, 1H)

Example 895

Ethyl 3-(5,10-dihydro-5-methoxymethyl-10-methyl-10H-pyrazino-[2,3-b][1,4]quinoxalin-7-yl)-3-(methylsulfinyl)propenoate To a solution of 102 mg of ethyl 3-(5,10-dihydro-5-methoxymethyl-10-methyl-10H-pyrazino[2,3-b][1,4]quinoxalin-7-yl)-3-(methylthio)propenoate in dichloromethane (10 ml) were added 0.120 g of m-chloroperbenzoic acid and 0.025 g of sodium hydrogencarbonate and the resulting mixture was stirred at room temperature for 20 hours. Then the reaction mixture was distributed into ethyl acetate and water. Next, the organic layer was dried over anhydrous magnesium sulfate and distilled off under reduced pressure to thereby give 0.150 g of the crude title compound as a red oily substance.

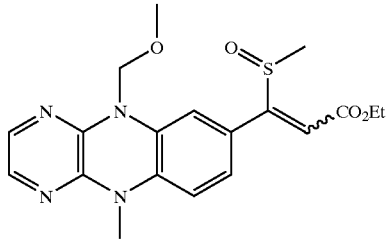

¹H-NMR(CDCl₃) δ ppm: 1.18 and 1.26(t, J=7 Hz, total 3H), 2.42 and 2.80(s, total 3H), 3.06(s, 3H), 3.37 and 3.38(s, total 3H), 4.10 and 4.17(q, J=7 Hz, total 2H), 4.98–5.13(m, 2H), 6.21 and 6.22(s, total 1H), 6.40 and 6.41(d, J=8 Hz, total 1H), 6.57 and 6.73(d, J=2 Hz, total 1H), 6.67 and 6.85(dd, J=2, 8 Hz, total 1H), 7.08 and 7.10(d, J=3 Hz, total 1H), 7.15 and 7.17(d, J=3 Hz, total 1H)

Examples

The following compounds were obtained by treating the compounds obtained in Examples 893 and 895 by the same method as the one of Example 9.

| Ex. | Structural formula | MS | M.p. | NMR |
|---|---|---|---|---|
| 896 | ethyl 3-(5,10-dihydro-5-methyl-10H-pyrazino[2,3-b][1,4]quinoxalin-8-yl)-3-oxopropanoate | | 88–89° C. | ¹H-NMR(CDCl₃) δ ppm: 1.16(t, J=7Hz, 3H), 3.11(s, 3H), 3.80(s, 2H), 4.20(q, J=7Hz, 2H), 6.35(d, J=8Hz, 1H), 6.77(d, J=2Hz, 1H), 7.01(d, J=3Hz, 1H), 7.11(d, J=3Hz, 1H), 7.21(dd, J=2, 8Hz, 1H), 7.25(br.s, 1H) |
| 897 | ethyl 3-(5,10-dihydro-5-methyl-10H-pyrazino-[2,3-b][1,4]quinoxalin-8-yl)-3-methylsulfinyl propenoate | FAB (+) 359 (MH⁺) | | ¹H-NMR(CDCl₃) δ ppm: 1.25 and 1.32(t, J=7Hz, total 3H), 2.47 and 2.86(s, total 3H), 3.06 and 3.07(s, total 3H), 4.17 and 4.23(q, J=7Hz, total 2H), 6.16 and 6.24(s, total 1H), 6.35–6.41(m, 2H), 6.62 and 6.71(m, 1H), 6.95 and 6.98(d, J=3Hz, total 1H), 7.09 and 7.12(d, J=3Hz, total 1H) |

Example 898

Ethyl 3-(5,10-dihydro-5-methyl-10H-pyrazino[2,3-b][1,4]quinoxalin-8-yl)-3-(methylthio)propenoate The title compound was obtained by treating ethyl 3-(5,10-dihydro-5-methoxymethyl-10-methyl-10H-pyrazino[2,3-b][1,4]quinoxalin-7-yl)-3-(methylthio)propenoate by the same method as the one of Example 8.

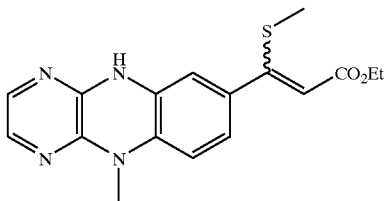

$^1$H-NMR(CDCl$_3$) δ ppm: 1.20 and 1.27(t, J=7 Hz, total 3H), 2.05 and 2.36(s, total 3H), 3.07 and 3.08(s, total 3H), 4.06 and 4.21(q, J=7 Hz, total 2H), 5.53 and 5.59(s, total 1H), 6.15 and 6.19(d, J=2 Hz, total 1H), 6.38(d, J=2 Hz, 1H), 6.59 and 6.64(dd, J=2, 8 Hz, total 1H), 6.91 and 6.95(d, J=3 Hz, total 1H), 7.07 and 7.11(d, J=3 Hz, total 1H)

Example 899

6-Methyl-10H-pyrazino[2,3-b][1,4]benzothiazine

To a solution of 0.737 g of 2-(6-methyl-2-nitrophenyl)thio-3-chloropyrazine in 15 ml of tetrahydrofuran was added a solution of 4.2 g of hydrosulfite sodium in water (8.4 ml). Into the reaction mixture was dropped a solution of 4.2 ml of aqueous ammonia with 4.2 ml of water under ice-cooling. After stirring at room temperature for 20 hours, the reaction mixture was distributed into ethyl acetate and water and the organic layer was dried over anhydrous magnesium sulfate. After distilling off the solvent under reduced pressure, 0.676 g of a crude amine was obtained. This amine was dissolved in 10 ml of N,N-dimethylformamide. The reaction mixture was degassed and heated to 80° C. for 2 hours. Then the reaction mixture was distributed into ethyl acetate and water. The organic layer was washed with water and dried over anhydrous magnesium sulfate. After distilling off the solvent under reduced pressure, the residue was purified by silica gel column chromatography (eluted with n-hexane/ethyl acetate) to thereby give 0.105 g of the title compound as a yellow solid.

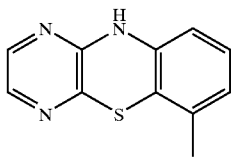

$^1$H-NMR(DMSO-d$_6$) δ ppm: 2.07(s, 3H), 6.58(d, J=8 Hz, 1H), 6.65(d, J=8 Hz, 1H), 6.85(t, J=8 Hz, 1H), 7.60(d, J=3 Hz, 1H), 7.61(d, J=3 Hz, 1H), 9.40(s, 1H)
MS: FAB(+)215(M$^+$)
m.p.: 165–166° C.

Example 900

10-Methoxymethyl-8-[N-(pyridin-3-yl)aminomethyl]-10H-pyrazino-[2,3-b][1,4]benzothiazine 3 g of (10-methoxymethyl-10H-pyrazino[2,3-b][1,4]benzothiazin-8-yl)carbaldehyde and 3.4 g of 3-aminopyridine were dissolved in toluene and heated under reflux for 2 hours. During this period, the water formed in the reaction system was eliminated by using a Dean-Stark tube. After the completion of the reaction, the toluene was distilled off under reduced pressure and the residue was dissolved in ethanol and tetrahydrofuran newly added thereto. After adding 4.06 g of sodium borohydride under ice-cooling, the resulting mixture was stirred at room temperature. After the completion of the reaction, the reaction mixture was poured into a saturated aqueous solution of sodium chloride and repeatedly extracted with ethyl acetate. The extract thus obtained was dried over anhydrous sodium sulfate and filtered. The filtrate was distilled off under reduced pressure and the residue was purified by silica gel column chromatography (eluted with toluene/acetone) to thereby give 1.35 g of the title compound as a yellow oily substance.

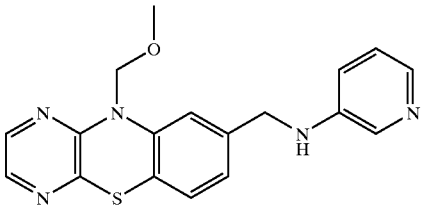

$^1$H-NMR(CDCl$_3$) δ ppm: 3.46(s, 3H), 4.28(s, 2H), 4.30(s, 2H), 5.22(s, 2H), 6.83(dd, J=2, 5 Hz, 1H), 6.95(d, J=8 Hz, 1H), 6.97(d, J=8 Hz, 1H), 7.12(s, 1H), 7.83(d, J=3 Hz, 2H), 7.98(d, J=5 Hz, 1H), 8.04–8.09(m, 1H)

Example 901

8-[N-(Pyridin-3-yl)aminomethyl]-10H-pyrazino[2,3-b][1,4]benzothiazine 0.99 g of the title compound was obtained as yellow crystals by deblocking 1.35 g of 10-methoxymethyl-8-[N-(pyridin-3-yl)aminomethyl]-10H-pyrazino[2,3-b][1,4]benzothiazine obtained in Example 900 by the same method as the one of Example 9.

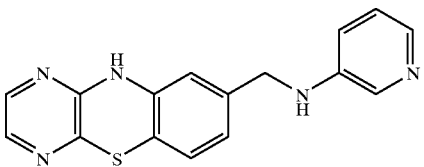

$^1$H-NMR(DMSO-d$_6$) δ ppm: 4.08(d, J=6 Hz, 2H), 6.45(t, J=6 Hz, 1H), 6.74(s, 1H), 6.78(d, J=8 Hz, 1H), 6.80(d, J=8 Hz, 1H), 6.84(d, J=8 Hz, 1H), 7.02(dd, J=5, 8 Hz, 1H), 7.60(s, 2H), 7.70(d, J=5 Hz, 1H), 7.90(s, 1H), 9.49(br.s, 1H)
MS: FAB(+)308(MH$^+$)
m.p.: 168–172° C.

Examples

Similar to Example 900, (10-methoxymethyl-10H-pyrazino[2,3-b][1,4]-benzothiazin-8-yl)carbaldehyde was treated with readily available various amines. Then, the products thus obtained were deblocked by the same method as the one of Example 9 to thereby give the following compounds.

| Ex. | Amine | Structural formula | MS | M.p. | NMR |
|---|---|---|---|---|---|
| 902 |  | 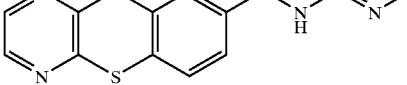<br>8-[N-(pyridin-2-yl)aminomethyl]-10H-pyrazino[2,3-b][1,4]benzothiazine | ESI(+) 308 (MH$^+$) | 208–212° C. | $^1$H-NMR(DMSO-d$_6$) δ ppm: 4.25(d, J=6Hz, 2H), 6.42–6.48(m, 1H), 6.47(t, J=6Hz, 1H), 6.74(d, J=8Hz, 1H), 6.76(s, 1H), 6.82(d, J=8Hz, 1H), 6.94–7.02(m, 1H), 7.34(d, J=8Hz, 1H), 7.62(s, 2H), 7.90(d, J=5Hz, 1H), 9.50(br.s, 1H) |
| 903 |  | <br>8-[N-(pyridin-4-yl)aminomethyl]-10H-pyrazino[2,3-b][1,4]benzothiazine | ESI(+) 308 (MH$^+$) | 194–196° C. | $^1$H-NMR(DMSO-d$_6$) δ ppm: 4.13(d, J=6Hz, 2H), 6.44(d, J=6Hz, 2H), 6.72(s, 1H), 6.74(d, J=8Hz, 1H), 7.17(t, J=6Hz, 1H), 7.62(s, 2H), 7.87(d, J=8Hz, 1H), 7.98(d, J=5Hz, 2H), 9.52(br.s, 1H) |
| 904 |  | 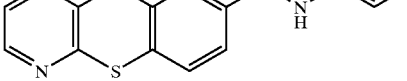<br>8-[N-(pyrazin-2-yl)aminomethyl]-10H-pyrazino[2,3-b][1,4]benzothiazine | | | $^1$H-NMR(DMSO-d$_6$) δ ppm: 4.28(d, J=5Hz, 2H), 6.72(s, 1H), 6.73(d, J=8Hz, 1H), 6.82(d, J=8Hz, 1H), 7.53(t, J=5Hz, 1H), 7.61(s, 1H), 7.60(d, J=2Hz, 1H), 7.64(d, J=2Hz, 1H), 7.88(s, 1H), 7.92(s, 1H), 9.48(br.s, 1H) |
| 905 |  | <br>8-[N-(pyrimidin-2-yl)aminomethyl]-10H-pyrazino[2,3-b][1,4]benzothiazine | | 232–235° C. | $^1$H-NMR(CDCl$_3$) δ ppm: 4.48(d, J=5Hz, 1H), 5.70(br.s, 1H), 6.52(s, 1H), 6.59(d, J=8Hz, 1H), 6.81(d, J=8Hz, 1H), 6.82(d, J=8Hz, 1H), 7.25(d, J=4Hz, 1H), 7.50(d, J=3Hz, 1H), 7.65(d, J=3Hz, 1H), 8.30(d, J=4Hz, 2H), 8.75(br.s, 1H) |
| 906 |  | 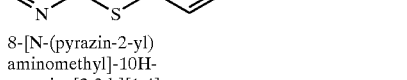<br>8-[N-(thiazol-2-yl)aminomethyl]-10H-pyrazino[2,3-b][1,4]benzothiazine | FAB(+) 313 (M$^+$) | 230–235° C. | $^1$H-NMR(DMSO-d$_6$) δ ppm: 4.22(d, J=6Hz, 2H), 6.60(d, J=5Hz, 1H), 6.66(d, J=8Hz, 1H), 6.67(s, 1H), 6.84(d, J=8Hz, 1H), 6.98(d, J=5Hz, 1H), 7.60(d, J=3Hz, 1H), 7.61(d, J=3Hz, 1H), 7.99(t, J=6Hz, 1H), 9.50(br.s, 1H) |

-continued

| Ex. | Amine | Structural formula | MS | M.p. | NMR |
|---|---|---|---|---|---|
| 907 | H₂N-C₆H₄-NH₂ (1,4-diaminobenzene) | 8-[N-(pyrazin-2-yl)aminomethyl]-10H-pyrazino[2,3-b][1,4]benzothiazine | ESI(+) 322 (MH⁺) | | ¹H-NMR(DMSO-d₆) δ ppm: 3.92(s, 2H), 4.20(br.s, 2H), 5.28–5.33(m, 1H), 6.32(d, J=8Hz, 2H), 6.37(d, J=8Hz, 2H), 6.77(s, 1H), 6.73–6.82(m, 2H), 7.62(s, 2H), 9.46(s, 1H) |
| 908 | 3-aminoquinoline | 8-[N-(quinolin-3-yl)aminomethyl]-10H-pyrazino[2,3-b][1,4]benzothiazine | ESI(+) 358 (MH⁺) | 160–164° C. | ¹H-NMR(DMSO-d₆) δ ppm: 4.21(d, J=5Hz, 2H), 6.80(s, 1H), 6.82(d, J=8Hz, 1H), 6.87(s, 1H), 6.88(d, J=8Hz, 1H), 6.84–6.92(m, 1H), 7.26–7.40(m, 2H), 7.58(d, J=5Hz, 1H), 7.60(s, 2H), 7.77(d, J=5Hz, 1H), 8.50(br.s, 1H), 9.50(br.s, 1H) |
| 909 | 1-aminoisoquinoline | 8-[N-(isoquinolin-1-yl)aminomethyl]-10H-pyrazino[2,3-b][1,4]benzothiazine | ESI(+) 358 (MH⁺) | 222–225° C. | ¹H-NMR(DMSO-d₆) δ ppm: 4.53(d, J=5Hz, 2H), 6.75–6.80(m, 1H), 6.78(s, 1H), 6.79(d, J=8Hz, 1H), 6.88(d, J=8Hz, 1H), 7.48(t, J=10Hz, 1H), 7.58(s, 2H), 7.55–7.63(m, 1H), 7.69(d, J=10Hz, 1H), 7.79(d, J=8Hz, 1H), 7.92(t, J=8Hz, 1H), 8.24(d, J=10Hz, 1H), 9.45(br.s, 1H) |
| 910 | 2-(aminomethyl)pyridine | 8-[N-(2-pyridylmethyl)aminomethyl]-10H-pyrazino[2,3-b][1,4]benzothiazine | ESI(+) 322 (MH⁺) | | ¹H-NMR(CDCl₃) δ ppm: 3.62(s, 2H), 3.82(s, 2H), 6.30(br.s, 1H), 6.53(s, 1H), 6.77(d, J=8Hz, 1H), 6.85(d, J=8Hz, 1H), 7.12–7.15(m, 1H), 7.26(d, J=7Hz, 1H), 7.62(t, J=7Hz, 1H), 7.70(d, J=3Hz, 2H), 8.55(d, J=5Hz, 1H), 9.52(br.s, 1H) |
| 911 | 3-(aminomethyl)pyridine | 8-[N-(3-pyridylmethyl)aminomethyl]-10H-pyrazino[2,3-b][1,4]benzothiazine | ESI(+) 322 (MH⁺) | 104–106° C. | ¹H-NMR(CDCl₃) δ ppm: 3.68(s, 2H), 3.80(s, 2H), 6.52(br.s, 1H), 6.54(s, 1H), 6.78(d, J=8Hz, 1H), 6.83(d, J=8Hz, 1H), 7.25–7.28(m, 2H), 7.57(d, J=3Hz, 1H), 7.69(d, J=3Hz, 1H), 7.66–7.70(m, 1H), 8.52–8.55(m, 1H), 8.59(br.s, 1H) |
| 912 | 4-(aminomethyl)pyridine | 8-[N-(4-pyridylmethyl)aminomethyl]-10H-pyrazino[2,3-b][1,4]benzothiazine | ESI(+) 322 (MH⁺) | 174–176° C. | ¹H-NMR(CDCl₃) δ ppm: 3.65(s, 2H), 3.80(s, 2H), 6.54(s, 1H), 6.67(br.s, 1H), 6.79(d, J=8Hz, 1H), 6.83(d, J=8Hz, 1H), 7.22–7.30(m, 3H), 7.55(d, J=3Hz, 1H), 7.68(d, J=3Hz, 1H), 8.58(d, J=5Hz, 2H) |

-continued

| Ex. | Amine | Structural formula | MS | M.p. | NMR |
|---|---|---|---|---|---|
| 913 | H₂N-CH₂-(piperidin-4-yl) | 8-[N-(piperidin-4-ylmethyl)aminomethyl]-10H-pyrazino[2,3-b][1,4]benzothiazine | ESI(+) 328 (MH⁺) | 173–175° C. | ¹H-NMR(DMSO-d₆) δ ppm: 0.83–1.00(m, 2H), 1.30–1.50(m, 1H), 1.60(d, J=8Hz, 2H), 2.28(d, J=5Hz, 2H), 2.38(d, J=2, 8Hz, 2H), 2.87(d, J=7Hz, 2H), 3.25(br.s, 2H), 3.44(s, 2H), 6.74(d, J=7Hz, 1H), 6.75(s, 1H), 6.80(d, J=7Hz, 1H), 7.60(d, J=2Hz, 1H), 7.61(d, J=2Hz, 1H), 9.48(br.s, 1H) |
| 914 | H₂N-CH₂CH₂-(2-pyridyl) | 8-[N-[2-(2-piperidyl)ethyl]aminomethyl]-10H-pyrazino[2,3-b][1,4]benzothiazine | ESI(+) 336 (MH⁺) | 179–182° C. | ¹H-NMR(DMSO-d₆) δ ppm: 3.03(t, J=7Hz, 2H), 3.10–3.20(m, 2H), 3.30(br.s, 1H), 3.86(br.s, 2H), 6.78(s, 1H), 6.88(d, J=8Hz, 1H), 6.92(d, J=8Hz, 1H), 7.20–7.32(m, 2H), 7.63(s, 2H), 7.68–7.78(m, 1H), 8.50(d, J=5Hz, 1H), 9.63(br.s, 1H) |
| 915 | H₂N-(4,6-dimethylpyridin-2-yl) | 8-[N-(2,4-dimethylaminopyridin-6-yl)aminomethyl]-10H-pyrazino[2,3-b][1,4]benzothiazine | ESI(+) 336 (MH⁺) | 162–165° C. | ¹H-NMR(DMSO-d₆) δ ppm: 2.08(s, 3H), 2.17(s, 3H), 4.24(d, J=5Hz, 2H), 6.03(s, 1H), 6.18(s, 1H), 6.70(br.s, 1H), 6.73(d, J=8Hz, 1H), 6.75(s, 1H), 6.82(d, J=8Hz, 1H), 7.62(s, 2H), 9.48(br.s, 1H) |
| 916 | H₂N-(3-benzyloxypyridin-2-yl) | 8-[N-(3-benzyloxypyridin-2-yl)aminomethyl]-10H-pyrazino[2,3-b][1,4]benzothiazine | ESI(+) 413 (MH⁺) | 180–184° C. | ¹H-NMR(DMSO-d₆) δ ppm: 4.35(d, J=5Hz, 2H), 5.12(s, 2H), 6.42–6.48(m, 1H), 6.53(t, J=5Hz, 1H), 6.72(d, J=8Hz, 1H), 6.74(s, 1H), 6.79(d, J=8Hz, 1H), 7.04(d, J=5Hz, 1H), 7.30–7.36(m, 1H), 7.38–7.42(m, 2H), 7.48–7.52(m, 3H), 7.60(s, 2H), 9.48(br.s, 1H) |

| Ex. | Amine | Structural formula | MS | M.p. | NMR |
|---|---|---|---|---|---|
| 917 | (3-chloro-5-(trifluoromethyl)pyridin-2-yl)amine | 8-[N-(3-chloro-5-(trifluoromethyl)pyridin-2-yl)aminomethyl]-10H-pyrazino[2,3-b][1,4]benzothiazine | FAB(+) 409 (M⁺) | 158–161° C. | ¹H-NMR(CDCl₃) δ ppm: 4.60(d, J=5Hz, 2H), 5.64(t, J=5Hz, 1H), 6.50(s, 1H), 6.55(br.s, 1H), 6.80(d, J=8Hz, 1H), 6.88(d, J=8Hz, 1H), 7.58(s, 1H), 7.67(s, 1H), 7.69(s, 1H), 8.30(s, 1H) |
| 918 | 6-aminopyridine-3-carboxamide | 2-(10H-pyrazino[2,3-b][1,4]benzothiazin-8-ylmethyl)aminopyridine-5-carboxamide | | 245–250° C. | ¹H-NMR(CD₃OD) δ ppm: 4.52(s, 2H), 4.90(br.s, 2H), 6.55(d, J=8Hz, 1H), 6.92(d, J=8Hz, 1H), 6.95(s, 1H), 6.96(s, 1H), 6.97(d, J=8Hz, 1H), 7.72(s, 1H), 7.82(d, J=3Hz, 1H), 7.86(d, J=3Hz, 1H), 7.87(d, J=8Hz, 1H), 8.53(s, 1H) |
| 919 | methyl 6-aminopyridine-3-carboxylate | methyl 2-(10H-pyrazino[2,3-b][1,4]benzothiazin-8-ylmethylamino)pyridine-5-carboxylate | ESI(+) 366 (MH⁺) | 140–148° C. | ¹H-NMR(DMSO-d₆) δ ppm: 3.73(s, 3H), 4.16(d, J=5Hz, 2H), 6.71(d, J=8Hz, 1H), 6.74(s, 1H), 6.83(d, J=8Hz, 1H), 7.62(s, 2H), 7.82(d, J=8Hz, 2H), 7.85(t, J=5Hz, 1H), 8.55(s, 1H), 9.50(br.s, 1H) |
| 920 | 2-ethylpyridin-4-amine | 8-[N-(2-ethylpyridin-4-yl)aminomethyl-10H-pyrazino[2,3-b][1,4]benzothiazine | ESI(+) 336 (MH⁺) | 148–152° C. | ¹H-NMR(DMSO-d₆) δ ppm: 1.14(t, J=6Hz, 3H), 2.55(q, J=6Hz, 2H), 3.30(s, 2H), 4.20(d, J=5Hz, 2H), 6.42(d, J=3Hz, 1H), 6.46(s, 1H), 6.72(s, 1H), 6.73(d, J=8Hz, 1H), 6.88(d, J=8Hz, 1H), 7.60(s, 2H), 7.94(d, J=3Hz, 1H), 9.53(s, 1H) |
| 921 | (4-aminopyridin-2-yl)methanol | [4-(10H-pyrazino[2,3-b][1,4]benzothiazin-8-ylmethyl)aminopyridin-2-yl]methanol | ESI(+) 338 (MH⁺) | 156–160° C. | ¹H-NMR(DMSO-d₆) δ ppm: 3.30(t, J=5Hz, 1H), 4.15(d, J=5Hz, 2H), 4.36(s, 2H), 6.34(m, 1H), 6.62(s, 1H), 6.65(s, 1H), 6.66(d, J=8Hz, 1H), 6.82(d, J=8Hz, 1H), 7.31(m, 1H), 1H), 7.61(s, 2H), 7.92(d, J=5Hz, 1H), 9.52(s, 1H) |

-continued

| Ex. | Amine | Structural formula | MS | M.p. | NMR |
|---|---|---|---|---|---|
| 922 | (structure: H₂N-2,6-dimethylpyridin-4-yl) 8-[N-(2,6-dimethylpyridin-4-yl)aminomethyl]-10H-pyrazino[2,3-b][1,4]benzothiazine | | ESI(+) 336 (MH⁺) | 230–235° C. | ¹H-NMR(DMSO-d₆) δ ppm: 2.48(s, 6H), 4.05(d, J=6Hz, 2H), 6.14(s, 2H), 6.68(s, 1H), 6.69(d, J=8Hz, 1H), 6.84(d, J=8Hz, 1H), 7.62(s, 2H), 7.85(br.s, 1H), 9.50(br.s, 1H) |

Examples

The following compounds were obtained by treating (10-methoxymethyl-10H-pyrazino[2,3-b][1,4]benzothiazin-8-yl)carbaldehyde with various aminopyridines by the same method as the one of Example 900.

| Ex. | Amino-pyridine | Structural formula | NMR |
|---|---|---|---|
| 923 | (H₂N-pyridin-5-yl with 2-N,N-dimethylamino) | 10-methoxymethyl-8-[N-[2-N',N'-dimethyl amino)pyridin-5-yl]aminomethyl-10H-pyrazino[2,3-b][1,4]benzothiazine | ¹H-NMR(CDCl₃) δ ppm: 2.95(s, 6H), 3.43(s, 3H), 4.17(s, 2H), 5.18(s, 2H), 6.43(d, J=8Hz, 1H), 6.85–6.90(m, 2H), 6.89(s, 2H), 7.08(s, 1H), 7.66(d, J=2Hz, 1H), 7.77–7.82(m, 2H) |
| 924 | (H₂N-pyridin-5-yl with 2-N'-benzylamino) | 10-methoxymethyl-8-[N-[2-N'-benzylamino)pyridin-5-yl]amino methyl-10H-pyrazino[2,3-b][1,4]benzothiazine | ¹H-NMR(CDCl₃) δ ppm: 3.48(s, 3H), 4.18(s, 2H), 4.40(s, 1H), 4.50(br.s, 2H), 5.22(s, 2H), 6.28(d, J=8Hz, 1H), 6.82(dd, J=2, 5Hz, 1H), 6.93(s, 2H), 7.10(s, 1H), 7.20–7.40(m, 2H), 7.60(d, J=2Hz, 1H), 7.81(d, J=3Hz, 1H), 7.83(d, J=3Hz, 1H) |

Examples

The following compounds were obtained by treating the compounds in the above table by the same method as the one of Example 9.

| Ex. | Structural formula | MS | M.p. | NMR |
|---|---|---|---|---|
| 925 | 8-[N-[2-N',N'-dimethylamino)pyridin-5-yl]aminomethyl-10H-pyrazino[2,3-b][1,4]benzothiazine | ESI (+) 351 (MH$^+$) | 244–247° C. | $^1$H-NMR(CDCl$_3$) δ ppm: 2.95(s, 6H), 4.13(s, 2H), 6.45(d, J=7Hz, 1H), 6.45(br.s, 1H), 6.52(s, 1H), 6.80(d, J=8Hz, 1H), , 6.83(d, J=8Hz, 1H), 6.92(dd, J=2, 7Hz, 1H), 7.55(d, J=2Hz, 1H), 7.71(d, J=2Hz, 1H), 7.72(d, J=2Hz, 1H), 9.50(s, 1H) |
| 926 | 8-[N-[2-N',N'-(benzyl amino)pyridin-5-yl]aminomethyl-10H-pyrazino[2,3-b][1,4]benzothiazine | FAB (+) 413 (MH$^+$) | 208–211° C. | $^1$H-NMR(CDCl$_3$) δ ppm: 4.20(s, 2H), 4.42(s, 2H), 4.55(br.s, 2H), 6.30(d, J=8Hz, 1H), 6.82(d, J=5Hz, 1H), 6.95(s, 2H), 7.12(s, 1H), 7.20–7.40(m, 5H), 7.62(d, J=2Hz, 1H), 7.81(d, J=3Hz, 1H), 7.83(d, J=3Hz, 1H), 9.50(s, 1H) |
| 927 | 8-[N-[2-aminopyridin-3-yl]aminomethyl]-10H-pyrazino[2,3-b][1,4]benzothiazine | ESI (+) 323 (MH$^+$) | 225–228° C. | $^1$H-NMR(DMSO-d$_6$) δ ppm: 4.09(d, J=6Hz, 2H), 5.39(t, J=6Hz, 1H), 5.50(s, 2H), 6.34–6.39(m, 2H), 6.75(s, 1H), 6.76(d, J=8Hz, 1H), 6.85(d, J=8Hz, 1H), 7.24(br.d, J=4Hz, 1H), 7.62(s, 2H), 9.52(s, 1H) |

Examples

The following compounds were obtained by treating (10-methoxymethyl-10H-pyrazino[2,3-b][1,4]benzothiazin-8-yl)carbaldehyde with various aminopyridines by the same method as the one of Example 900.

| Ex. | Amine | Structural formula | NMR |
|---|---|---|---|
| 928 | H$_2$N-pyridine-OMe | 10-methoxymethyl-8-[N-(2-methoxypyridin-5-yl]aminomethyl]-10H-pyrazino[2,3-b][1,4]benzothiazine | $^1$H-NMR(CDCl$_3$) δ ppm: 3.46(s, 3H), 3.87(s, 3H), 4.22(s, 2H), 5.22(s, 2H), 6.58(d, J=8Hz, 1H), 6.60(d, J=8Hz, 1H), 6.97(s, 1H), 7.02(d, J=8Hz, 1H), 7.03(d, J=8Hz, 1H), 7.12(s, 1H), 7.55(d, J=2Hz, 1H), 7.82(d, J=3Hz, 1H), 7.84(d, J=3Hz, 1H) |

-continued

| Ex. | Amine | Structural formula | NMR |
|---|---|---|---|
| 929 |  | 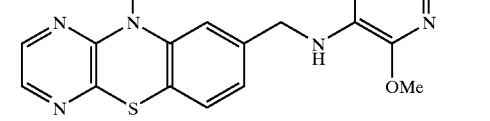

10-methoxymethyl-8-[N-(2,6-dimethoxypyridin-3-yl)aminomethyl]-10H-pyrazino[2,3-b][1,4]benzothiazine | $^1$H-NMR(CDCl$_3$) δ ppm: 3.34(s, 3H), 3.85(s, 3H), 3.88(s, 3H), 4.10(s, 2H), 5.10(s, 2H), 6.03(d, J=8Hz, 1H), 6.05(d, J=8Hz, 1H), 6.62(d, J=8Hz, 1H), 6.82(d, J=8Hz, 1H), 6.83(s, 1H), 7.00(s, 1H), 7.52(s, 2H) |
| 930 |  | 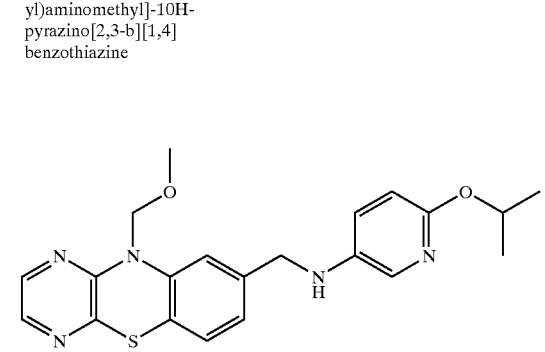

8-[N-(2-isopropoxypyridin-5-yl)aminomethyl]-10-methoxymethyl-10H-pyrazino[2,3-b][1,4]benzothiazine | $^1$H-NMR(CDCl$_3$) δ ppm: 1.29(d, J=6Hz, 6H), 3.42(s, 3H), 3.90(br.s, 1H), 4.18(s, 2H), 5.02–5.17(m, 1H), 5.18(s, 2H), 6.52(d, J=8Hz, 1H), 6.87(s, 2H), 6.88(d, J=8Hz, 1H), 7.06(s, 1H), 7.52(d, J=2Hz, 1H), 7.78(s, 2H) |
| 931 |  | 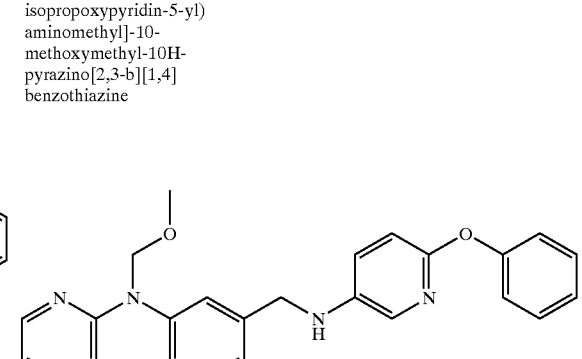

8-[N-(2-phenoxypyridin-5-yl)aminomethyl]-10-methoxymethyl-10H-pyrazino[2,3-b][1,4]benzothiazine | $^1$H-NMR(CDCl$_3$) δ ppm: 3.47(s, 3H), 4.22(s, 2H), 5.22(s, 2H), 6.73(d, J=7Hz, 1H), 6.95(s, 1H), 6.97(d, J=7Hz, 1H), 7.09(s, 1H), 6.90–7.12(m, 5H), 7.32(t, J=7Hz, 2H), 7.62(d, J=2Hz, 1H), 7.82(d, J=3Hz, 1H), 7.83(d, J=3Hz, 1H) |
| 932 |  | 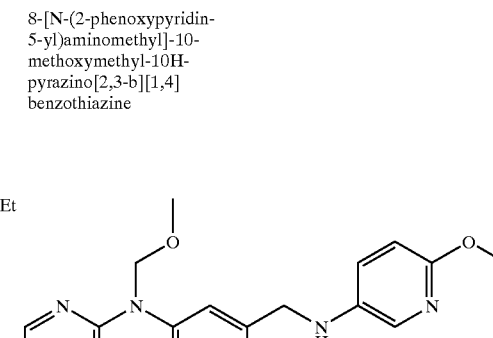

ethyl [5-[N-(10-methoxymethyl-10H-pyrazino[2,3-b][1,4]benzothiazin-8-ylmethyl)amino]pyridin-2-yloxy]acetate | $^1$H-NMR(CDCl$_3$) δ ppm: 1.23(t, J=7Hz, 3H), 3.43(s, 3H), 3.90(br.s, 1H), 4.20(q, J=7Hz, 2H), 4.20(s, 2H), 4.77(s, 2H), 5.21(s, 2H), 6.70(d, J=8Hz, 1H), 6.90(s, 2H), 6.92(dd, J=2, 8Hz, 1H), 7.08(s, 1H), 7.48(d, J=2Hz, 1H), 7.78(d, J=3Hz, 1H), 7.80(d, J=3Hz, 1H) |

Examples

The following compounds were obtained by treating the compounds in the above table by the same method as the one of Example 9.

| Ex. | Structural formula | MS | M.p. | NMR |
|---|---|---|---|---|
| 933 | 8-[N-(2-methoxypyridin-5-yl)aminomethyl]-10H-pyrazino[2,3-b][1,4]benzothiazine | ESI (+) 338 (MH$^+$) | 168–172° C. | $^1$H-NMR(DMSO-d$_6$) δ ppm: 3.67(s, 3H), 4.02(d, J=5Hz, 2H), 5.93(t, J=5Hz, 1H), 6.56(d, J=7Hz, 1H), 6.77(s, 1H), 6.78(d, J=8Hz, 1H), 6.84(d, J=8Hz, 1H), 6.98(d, J=8Hz, 1H), 7.38(s, 1H), 7.60(s, 2H), 9.48(br.s, 1H) |
| 934 | 8-[N-(2,6-dimethoxypyridin-3-yl)aminomethyl]-10H-pyrazino[2,3-b][1,4]benzothiazine | ESI (+) 368 (MH$^+$) | 160–164° C. | $^1$H-NMR(CDCl$_3$) δ ppm: 3.82(s, 3H), 3.98(s, 3H), 4.15(br.s, 1H), 4.18(s, 2H), 6.17(d, J=7Hz, 1H), 6.47(br.s, 1H), 6.52(s, 1H, 6.70(d, J=7Hz, 1H), 6.82(d, J=8Hz, 1H), 6.84(d, J=8Hz, 1H), 7.55(s, 1H), 7.68(s, 1H) |
| 935 | 8-[N-(2-isopropoxypyridin-1-yl)aminomethyl]-10H-pyrazino[2,3-b][1,4]benzothiazine | ESI (+) 366 (MH$^+$) | 145–148° C. | $^1$H-NMR(CDCl$_3$) δ ppm: 1.30(d, J=6Hz, 6H), 3.70–3.80(m, 1H), 4.18(s, 2H), 5.12(m, 1H), 6.43(br.s, 1H), 6.52(d, J=2Hz, 1H), 6.56(d, J=6Hz, 1H), 6.82(d, (J=8Hz, 1H), 6.85(d, J=8Hz, 1H), 6.90–6.95(m, 1H), 7.54(d, J=3Hz, 1H), 7.58(d, J=3Hz, 1H), 7.69(s, 1H) |
| 936 | 8-[N-(2-phenoxypyridin-5-yl)aminomethyl]-10H-pyrazino[2,3-b][1,4]benzothiazine | ESI (+) 400 (MH$^+$) | 162–165° C. | $^1$H-NMR(CDCl$_3$) δ ppm: 4.13(s, 2H), 6.48(br.s, 1H), 6.74(d, J=8Hz, 1H), 6.76(s, 1H), 6.80(d, J=8Hz, 1H), 6.90–7.10(m, 5H), 7.15(br.s, 1H) 7.30(t, J=6Hz, 2H), 7.48(d, J=3Hz, 1H), 7.60(d, J=3Hz, 1H), 7.63(d, J=3Hz, 1H) |
| 937 | ethyl[5-[10H-pyrazino[2,3-b][1,4]benzothiazin-8-ylmethyl)amino]pyridin-2-yloxy]acetate | ESI (+) 410 (MH$^+$) | 230–235° C. | $^1$H-NMR(CDCl$_3$) δ ppm: 1.25(t, J=6Hz, 3H), 4.14(s, 2H), 4.21(q, J=6Hz, 2H), 4.79(s, 2H), 6.44(br.s, 1H), 6.51(s, 1H), 6.72(d, J=8Hz, 1H), 6.81(d, J=7Hz, 1H), 6.86(d, J=8Hz, 1H), 6.95(dd, J=3, 7Hz, 1H), 7.25–7.28(m, 1H), 7.42(d, J=3Hz, 1H), 7.55(d, J=3Hz, 1H), 7.68(d, J=3Hz, 1H) |

Examples

The following compounds were obtained by treating (10-methoxymethyl-10H-pyrazino[2,3-b][1,4]benzothiazin-8-yl) carbaldehyde with various aminopyridines by the same method as the one of Example 900.

| Ex. | Aminopyridine | Structural formula | NMR |
|---|---|---|---|
| 938 | (5-amino-2-benzylpyridine) | 8-[N-(2-benzylpyridin-5-yl)aminomethyl]-10-methoxymethyl-10H-pyrazino[2,3-b][1,4]benzothiazine | ¹H-NMR(CDCl₃) δ ppm: 3.37(s, 3H), 4.00 (s, 2H), 4.20(s, 2H), 4.23–4.37(br.s, 1H), 5.17(s, 1H), 6.77 (d, J=8Hz, 1H), 6.87(d, J=8Hz, 1H), 7.07(s, 1H), 7.10–7.30(m, 7H), 7.79 (s, 2H), 7.88(d, J=8Hz, 1H), 7.97 (s, 1H) |
| 939 | (5-amino-2-phenethylpyridine) | 8-[N-(2-phenethylpyridin-5-yl)aminomethyl]-10-methoxymethyl-10H-pyrazino[2,3-b][1,4]benzothiazine | ¹H-NMR(CDCl₃) δ ppm: 2.95(s, 4H), 3.42(s, 3H), 4.20(s, 2H), 4.36 (br.s, 1H), 5.18(s, 2H), 6.75(dd, J=2, 8Hz, 1H), 6.85(d, J=8Hz, 1H), 6.85–7.00(m, 2H), 7.07 (s, 1H), 7.10–7.30(m, 5H), 7.78 (s, 2H), 7.97(s, 1H) |
| 940 | (5-amino-2-ethylpyridine) | 8-[N-(2-ethylpyridin-5-yl)aminomethyl]-10-methoxymethyl-10H-pyrazino[2,3-b][1,4]benzothiazine | ¹H-NMR(CDCl₃) δ ppm: 1.23(t, J=6Hz, 3H), 2.68(q, J=6Hz, 2H), 3.42(s, 3H), 4.20 (s, 2H), 5.18(s, 2H), 6.78(d, J=8Hz, 1H), 6.82(d, J=8Hz, 1H), 7.09(s, 1H), 7.16(d, J=8Hz, 1H), 7.22(d, J=8Hz, 1H), 7.78(s, 2H), 7.82(s, 1H), 7.95(s, 1H) |

Examples

The following compounds were obtained by treating the compounds in the above table by the same method as the one of Example 9.

| Ex. | Structural formula | MS | M.p. | NMR |
|---|---|---|---|---|
| 941 | 8-[N-(2-benzylpyridin-5-yl)aminomethyl]-10H-pyrazino[2,3-b][1,4]benzothiazine | ESI (+) 398 (MH⁺) | 162–164° C. | ¹H-NMR(CDCl₃) δ ppm: 4.02(s, 2H), 4.18(d, J=5Hz, 2H, 6.75(d, J=8Hz, 1H), 6.86(d, J=8Hz, 1H), 6.89(s, 1H), 6.90(d, J=8Hz, 1H), 7.08(s, 1H), 7.10–7.40(m, 7H), 7.56(s, 1H), 7.69(s, 1H), 7.96(s, 1H) |

| Ex. | Structural formula | MS | M.p. | NMR |
|---|---|---|---|---|
| 942 | 8-[N-(2-phenethyl pyridin-5-yl)amino methyl]-10H-pyrazino[2,3-b][1,4] benzothiazine | | | $^1$H-NMR(CDCl$_3$) δ ppm: 2.95(br.s, 4H), 4.13(s, 2H), 4.28(br.s, 1H), 6.46(s, 1H), 6.73(d, J=8Hz, 1H), 6.78(s, 1H), 6.70–6.80(m, 2H), 6.83(d, J=8Hz, 1H), 7.12–7.21(m, 3H), 7.23(m, 2H), 7.37(s, 1H), 7.58(s, 1H), 7.73(s, 1H) |
| 943 | 8-[N-(2-ethylpyridin-5-yl)aminomethyl]-10H-pyrazino[2,3-b][1,4] benzothiazine | ESI (+) 336 (MH$^+$) | 202–204° C. | $^1$H-NMR(CDCl$_3$) δ ppm: 1.10(t,J=6Hz, 3H), 2.54(q, J=6Hz, 2H), 4.06(d, J=3Hz, 2H), 6.23(t, J=3Hz, 1H), 6.72(s, 1H), 6.73(d, J=8hz, 1H), 6.76(br.s, 1H), 6.83(d, J=8Hz, 1H), 6.88(br.s, 1H), 7.62(s, 2H), 7.80(br.s, 1H), 9.50(s, 1H) |

Examples

The following compounds were obtained by treating (10-methoxymethyl-10H-pyrazino[2,3-b][1,4]benzothiazin-8-yl)carbaldehyde with various amines by the same method as the one of Example 900 and then treating the obtained products by the same method as the one of Example 9.

| Ex. | Amine | Structural formula | MS | M.p. | NMR |
|---|---|---|---|---|---|
| 944 | 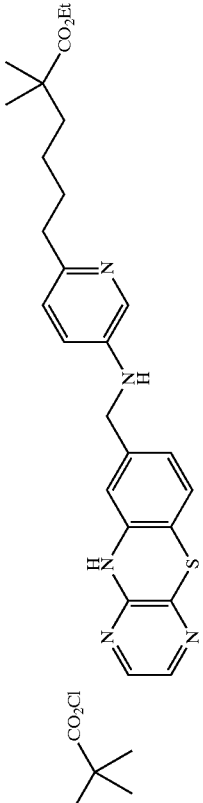 | ethyl 6-[5-(10H-pyrazino[2,3-b][1,4]benzothiazin-8-ylmethylamino)pyridin-2-yl]-2,2-dimethylhexanoate | | 160–164° C. | ¹H-NMR(CDCl₃) δ ppm: 1.15(s, 6H), 1.21(t, J=6Hz, 3H), 1.20–1.30(m, 2H), 1.45–1.55(m, 2H), 1.60–1.70(m, 2H), 2.60–2.75(m, 2H), 3.62(s, 2H), 4.08(q, J=6Hz, 2H), 4.20 (br.s, 1H), 6.54(br.s, 1H), 6.80(d, J=8Hz, 1H), 6.81(d, J=7Hz, 1H), 6.83(d, J=8Hz, 1H), 6.83(s, 1H), 6.95(d, J=7Hz, 1H), 7.55(s, 1H), 7.70(d, J=3Hz, 2H) |
| 945 | 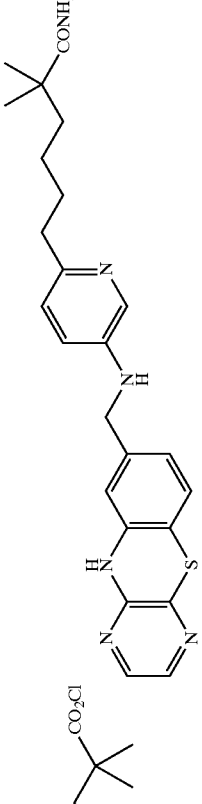 | 6-[5-(10H-pyrazino[2,3-b][1,4]benzothiazin-8-ylmethylamino)pyridin-2-yl]-2,2-dimethylhexanamide | ESI (+) 449 (MH⁺) | | ¹H-NMR(CD₃OD) δ ppm: 1.05(s, 6H), 1.25–1.35(m, 2H), 1.40–1.50(m, 2H), 1.50–1.62(m, 2H), 2.50–2.65(m, 2H), 4.13(s, 2H), 4.10(br.s, 2H), 4.25(br.s, 1H), 6.65(d, J=8Hz, 1H), 6.75(s, 1H), 6.76(d, J=8Hz, 1H), 6.89(d, J=7Hz, 1H), 6.95(d, J=7Hz, 1H), 7.50(s, 2H), 7.67(s, 1H), 9.50(s, 1H) |

Example 946

Ethyl 5-[5-(10H-pyrazino[2,3-b][1,4]benzothiazin-8-yl-methylamino)pyridin-2-yl]pentanoate

The title compound was obtained by treating (10-methoxymethyl-10H-pyrazino[2,3-b][1,4]benzothiazin-8-yl)carbaldehyde with ethyl 5-(5-aminopyridin-2-yl)pentanoate by the same method as the one of Example 900 and then treating the obtained product by the same method as the one of Example 9.

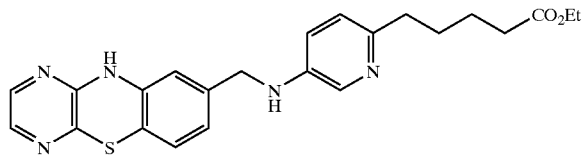

1.23(t, J=6 Hz, 3H), 1.58–1.72(m, 4H), 2.30(t, J=6 Hz, 2H), 2.67(t, J=6 Hz, 2H), 4.09(q, J=6 Hz, 2H), 4.14(s, 2H), 4.24(br.s, 1H), 6.48(s, 1H), 6.73(d, J=8 Hz, 1H), 6.74(d, J=7 Hz, 1H), 6.90(d, J=8 Hz, 1H), 7.40(s, 1H), 7.46(br.s, 1H), 7.59(s, 1H), 7.78(d, J=7 Hz, 1H), 7.90(m, 1H)

Example 947

2-[5-(10-Methoxymethyl-10H-pyrazino[2,3-b][1,4]benzothiazin-8-yl)methylamino]pyridin-2-yl]ethanol and 8-[N-(2-methylpyridin-5-yl)aminomethyl]-10-methoxymethyl-10H-pyrazino[2,3-b][1,4]-benzothiazine

By the same method as the one of Example 900, (10-methoxymethyl-10H-pyrazino[2,3-b][1,4 ]benzothiazin-8-yl)carbaldehyde was treated with 290 mg of a mixture of 2-methyl-5-aminopyridine with ethyl(5-aminopyridin-2-yl)acetate and then the obtained product was reduced with sodium borohydride by heating under reflux to thereby give 230 mg of 2-[5-[(10-methoxymethyl-10H-pyrazino[2,3-b][1,4]benzothiazin-8-yl)methylamino]pyridin-2-yl]ethanol and 173 mg of 8-[N-(2-methylpyridin-5-yl)aminomethyl]-10-methoxymethyl-10H-pyrazino[2,3-b][1,4]benzothiazine each as a yellow oily substance.

2-[5-[(10-methoxymethyl-10H-pyrazino[2,3-b][1,4]benzothiazin-8-yl)methylamino]pyridin-2-yl]ethanol

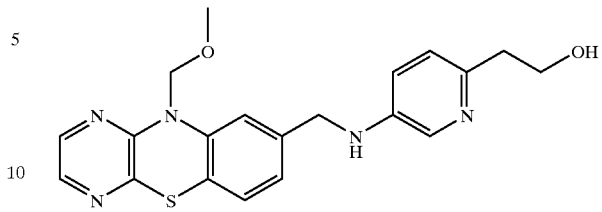

$^1$H-NMR(CDCl$_3$) δ ppm: 2.85(t, J=6 Hz, 2H), 3.45(br.s, 1H), 3.42(s, 3H), 3.92(t, J=6 Hz, 2H), 4.20(s, 2H), 4.35(br.s, 1H), 5.20(s, 2H), 6.80(dd, J=2, 5 Hz, 1H), 6.85–6.98(m, 3H), 7.07(s, 1H), 7.80(s, 2H), 7.90(d, J=2 Hz, 1H)

8-[N-(2-methylpyridin-5-yl)aminomethyl]-10-methoxymethyl-10H-pyrazino[2,3-b][1,4]benzothiazine

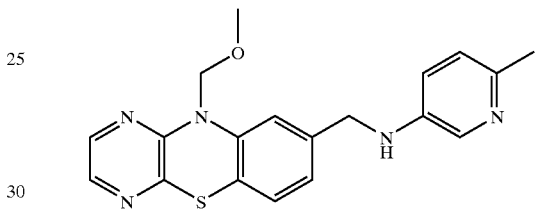

$^1$H-NMR(CDCl$_3$) δ ppm: 2.37(s, 3H), 3.41(s, 3H), 4.21(s, 2H), 4.25(br.s, 1H), 5.17(s, 2H), 6.73(dd, J=2, 5 Hz, 1H), 6.88(d, J=5 Hz, 1H), 6.90(s, 2H), 7.08(s, 1H), 7.78(s, 2H), 7.92(d, J=2 Hz, 1H)

Examples

The following compounds were obtained by treating (10-methoxymethyl-10H-pyrazino[2,3-b][1,4]benzothiazin-8-yl)carbaldehyde with aminopyridines by the same method as the one of Example 947.

| Ex. | Amine | Structural formula | NMR |
|---|---|---|---|
| 948 | (structure: 5-amino-2-[(2-ethoxycarbonylethyl)thio]pyridine) | 2-[5-[(10-methoxymethyl-10H-pyrazino[2,3-b][1,4]benzothiazin-8-yl)methylamino]pyridin-2-ylthio]ethanol | ¹H-NMR(CDCl₃) δ ppm: 1.70(br.s, 1H), 3.18(t, J=6Hz, 2H), 3.45(s, 3H), 3.90(t, J=6Hz, 2H), 4.25(s, 2H), 5.22(s, 2H), 5.57(br.s, 1H), 6.80(dd, J=2, 5Hz, 1H), 6.92(d, J=8Hz, 1H), 6.97(d, J=8Hz, 1H), 7.10(d, J=5Hz, 1H), 7.13(s, 1H), 7.22(s, 1H), 7.82(d, J=3Hz, 1H), 7.84(d, J=3Hz, 1H) |
| 949 | (structure: 5-amino-2-[(6-chlorocarbonylhexyl)oxy]pyridine) | 6-[5-[(10-methoxymethyl-10H-pyrazino[2,3-b][1,4]benzothiazin-8-yl)methylamino]pyridin-2-yl]hexan-1-ol | ¹H-NMR(CDCl₃) δ ppm: 1.30–1.48(m, 4H), 1.49–1.60(m, 2H), 1.60–1.80(m, 2H), 3.43(s, 3H), 3.58(t, J=6Hz, 2H), 4.13(t, J=6Hz, 2H), 4.18(s, 2H), 4.19(s, 2H), 5.18(s, 2H), 6.57(d, J=8hz, 1H), 6.91(s, 2H), 6.92(d, J=8Hz, 1H), 7.08(s, 1H), 7.50(d, J=2Hz, 1H), 7.78(s, 2H) |

Examples

The following compounds were obtained by treating (10-methoxymethyl-10H-pyrazino[2,3-b][1,4]benzothiazin-8-yl)carbaldehyde with various aminopyridines by the same method as the one of Example 900.

| Ex | Amine | Structural formula | | NMR |
|---|---|---|---|---|
| 950 | (pyridine with CH2CO2Et at 2-position, NH2 at 5-position) | (phenothiazine-pyrazine tricyclic with OCH2OCH3, CH2NH linked to pyridine-CH2CO2Et) | ethyl [5-[(10-methoxymethyl-10H-pyrazino[2,3-b][1,4]benzothiazin-8-yl)methylamino]pyridin-2-yl]acetate | ¹H-NMR(CDCl₃) δ ppm: 1.23(t, J=6Hz, 3H), 3.42(s, 3H), 3.70(s, 2H), 4.13(q, J=6Hz, 2H), 4.23(s, 2H), 4.30(br.s, 1H), 5.20(s, 2H), 6.82(dd, J=2, 5Hz, 1H), 6.92(d, J=8Hz, 1H), 6.95(d, J=8Hz, 1H), 7.05(d, J=5Hz, 1H), 7.08(s, 1H), 7.79(d, J=3Hz, 1H), 7.81(d, J=3Hz, 1H), 7.98(d, J=2Hz, 1H) |
| 951 | (pyridine with SCH2CO2Et at 2-position, NH2 at 5-position) | (phenothiazine-pyrazine tricyclic with OCH2OCH3, CH2NH linked to pyridine-SCH2CO2Et) | ethyl [5-[(10-methoxymethyl-10H-pyrazino[2,3-b][1,4]benzothiazin-8-yl)methylamino]pyridin-2-ylthio]acetate | ¹H-NMR(CDCl₃) δ ppm: 1.22(t, J=6Hz, 3H), 3.42(s, 3H), 3.82(s, 2H), 4.22(s, 2H), 4.10(q, J=6Hz, 2H), 4.25(br.s, 1H), 5.18(s, 2H), 6.75(dd, J=2, 5Hz, 1H), 6.90(d, J=8Hz, 1H), 6.92(d, J=8Hz, 1H), 7.06(d, J=5Hz, 1H), 7.07(s, 1H), 7.80(d, J=3Hz, 1H), 7.82(d, J=3Hz, 1H), 7.88(d, J=2Hz, 1H) |
| 952 | (pyridine with O-(CH2)5-CO2Et at 2-position, NH2 at 5-position) | (phenothiazine-pyrazine tricyclic with OCH2OCH3, CH2NH linked to pyridine-O(CH2)5CO2Et) | ethyl 6-[5-[(10-methoxymethyl-10H-pyrazino[2,3-b][1,4]benzothiazin-8-yl)methylamino]pyridin-2-yloxy]hexanoate | ¹H-NMR(CDCl₃) δ ppm: 1.22(t, J=6Hz, 3H), 1.38–1.50(m, 2H), 1.60–1.70(m, 2H), 1.70–1.80(m, 2H), 2.28(t, J=6Hz, 2H), 3.42(s, 3H), 4.10(q, J=6Hz, 2H), 4.20(s, 2H), 4.13(t, J=6Hz, 2H), 5.20(s, 2H), 6.57(d, J=8Hz, 1H), 6.90(d, J=8Hz, 1H), 6.92(d, 2H), 7.08(s, 1H), 7.52(d, J=2Hz, 1H), 7.80(s, 2H) |

Examples

The following compounds were obtained by treating the compounds obtained in Examples 947, 950, 952, 949, 951 and 948 by the same method as the one of Example 9.

| Ex. | Structural formula | MS | M.p. | NMR |
|---|---|---|---|---|
| 953 | 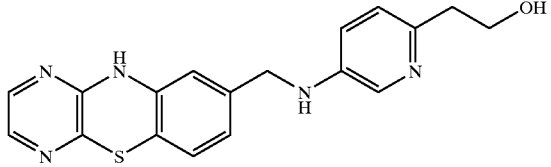<br>2-[5-[(10H-pyrazino[2,3-b][1,4]benzothiazin-8-yl)methylamino]pyridin-2-yl]ethanol | ESI (+) 352 (MH+) | 138–142° C. | $^1$H-NMR(CDCl$_3$) δ ppm: 2.86(t, J=5Hz, 2H), 3.92(t, J=5Hz, 2H), 4.18(s, 2H), 4.20(br.s, 1H), 6.52(s, 1H), 6.78(d, J=8Hz, 1H), 6.80–6.86(m, 2H), 6.96(s, 1H), 6.97(d, J=8Hz, 1H), 6.82(s, 1H), 7.52(d, J=2Hz, 1H), 7.63(d, J=2Hz, 1H), 7.90(d, J=2Hz, 1H) |
| 954 | 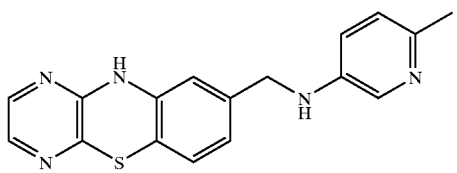<br>8-[N-(2-methylpyridin-5-yl)aminomethyl]-10H-pyrazino[2,3-b][1,4]benzothiazine | ESI (+) 322 (MH+) | 205–208° C. | $^1$H-NMR(CDCl$_3$) δ ppm: 2.42(s. 3H), 3.97(br.s, 1H), 3.98(t, J=5Hz, 1H), 4.18(d, J=5Hz, 1H), 6.48(br.s, 1H), 6.52(s, 1H), 6.75–7.82(m, 2H), 6.86(d, J=8Hz, 1H), 6.92(d, J=8Hz, 1H), 7.54(d, J=3Hz, 1H), 7.68(d, J=3Hz, 1H), 7.94(d, J=3Hz, 1H) |
| 955 | 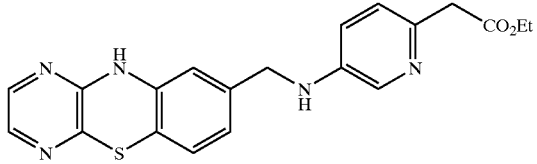<br>ethyl [5-[(10H-pyrazino[2,3-b][1,4]benzothiazin-8-yl)methylamino]pyridin-2-yl]acetate | ESI (+) 394 (MH+) | amorphous | $^1$H-NMR(CDCl$_3$) δ ppm: 1.12(t, J=6Hz, 3H), 3.69(s, 2H), 4.10(q, J=6Hz, 2H), 4.13(s, 2H), 4.30(br.s, 1H), 6.46(s, 1H), 6.72(d, J=8Hz, 1H), 6.76(s, 1H), 6.78(d, J=8Hz, 1H), 7.03(d, J=7Hz, 1H), 7.42(d, J=7Hz, 1H), 7.43(d, J=3Hz, 1H), 760(d, J=3Hz, 1H), 7.90(s, 1H) |
| 956 | 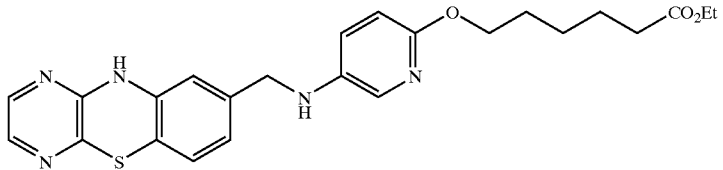<br>ethyl 6-[5-[(10H-pyrazino[2,3-b][1,4]benzothiazin-8-yl)-methylamino]pyridin-2-yloxy]hexanoate | ESI (+) 466 (MH+) | 105–108° C. | $^1$H-NMR(CDCl$_3$) δ ppm: 1.23(t, J=6Hz, 3H), 1.40–1.50(m, 2H), 1.60–7.70(m, 2H), 1.70–1.80(m, 2H), 2.30(t, J=6Hz, 2H), 4.10(br.s, 1H), 4.13(q J=6Hz, 2H), 4.15(q, J=6Hz, 2H), 4.18(s, 2H), 6.57(br.s, 1H), 6.60(d, J=8Hz, 1H), 6.65–6.70(m, 1H), 6.81(s, 1H), 6.82(s, 1H), 7.00(d, J=7Hz, 1H), 7.52(s, 1H), 7.58(br.s, 1H), 7.68(s, 1H) |
| 957 | <br>6-[5-[(10H-pyrazino-2,3-b][1,4]benzohiazin-8-yl)methylmino]yridin-2-yloxy]hexan-1-ol | ESI (+) 424 (MH+) | 124–128° C. | $^1$H-NMR(CDCl$_3$) δ ppm: 1.16(br.s, 1H), 1.30–1.42(m, 4H), 1.42–1.60(m, 2H), 1.60–1.75(m, 2H), 3.58(t, J=6Hz, 2H), 4.10(t, J=6Hz, 2H), 4.12(s, 2H), 4.10(br.s, 1H), 6.45(s, 1H), 6.54(d, J=7Hz, 1H), 6.66(br.s, 1H), 6.72(d, J=7Hz, 1H), 6.78(d, J=8Hz, 1H), 6.85(d, J=8Hz, 1H), 7.48(d, J=3Hz, 2H), 7.60(s, 1H) |

-continued

| Ex. | Structural formula | MS | M.p. | NMR |
|---|---|---|---|---|
| 958 | 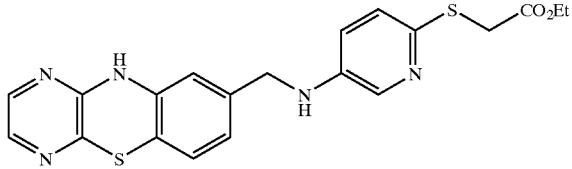<br>ethyl [5-[(10H-pyrazino[2,3-b][1,4]enzothiazin-8-yl)methylamino]pyridin-2-ylthio]acetate | ESI (+) 426 (MH⁺) | 118–122° C. | ¹H-NMR(CDCl₃) δ ppm: 1.24(t, J=6Hz, 3H), 3.85(s, 2H), 4.19(q J=6Hz, 2H), 4.21(s, 2H), 6.47(d, J=8Hz, 1H), 6.49(s, 1H), 6.76–6.82(m, 1H), 6.80(br.s, 1H), 6.80(d, J=8Hz, 1H), 6.85(d, J=6Hz, 1H), 7.09(d, J=6Hz, 1H), 7.58(d, J=3Hz, 1H), 7.71(dd, J=2, 6Hz, 1H), 7.90(s, 1H) |
| 959 | 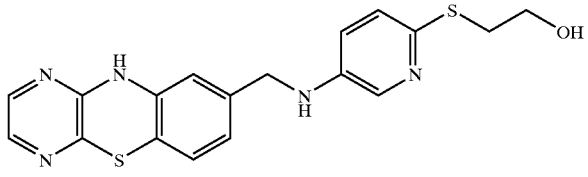<br>2-[5-[(10H-pyrazino[2,3-b][1,4]benzothiazin-8-yl)methylamino]pyridin-2-ylthio]ethanol | ESI (+) 384 (MH⁺) | 138–142° C. | ¹H-NMR(CDCl₃) δ ppm: 1.60(br.s, 1H), 3.19(t, J=6Hz, 2H), 3.93(t, J=6Hz, 2H), 4.19(s, 2H), 6.48(s, 1H), 6.50(s, 1H), 6.80(br.s, 1H), 6.80(d, J=8Hz, 2H), 6.86(d, J=8hz, 1H), 7.15(d, J=8Hz, 1H), 7.57(s, 1H), 7.70(s, 1H), 7.83(s, 1H) |

Example 960

[5-[(10H-Pyrazino[2,3-b][1,4]benzothiazin-8-ylmethyl)amino]pyridin-2-yloxy]acetic acid The title compound was obtained by treating ethyl[5-[(10-methoxymethyl-10H-pyrazino[2,3-b][1,4]benzothiazin-8-ylmethyl)amino]pyridin-2-yloxy]acetate successively by the same methods as those of Examples 18 and 9.

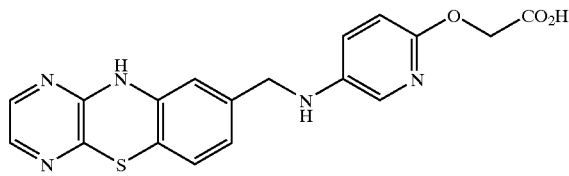

¹H-NMR(DMSO-d₆) δ ppm: 4.14(s, 2H), 4.80(s, 2H), 6.49(br.s, 1H), 6.52(s, 1H), 6.75(d, J=8 Hz, 1H), 6.78(s, 1H), 6.80(d, J=8 Hz, 1H), 6.84(d, J=7 Hz, 1H), 7.12(d, J=7 Hz, 1H), 7.43(d, J=3 Hz, 1H), 7.56(d, J=3 Hz, 1H), 7.62((d, J=3 Hz, 1H), 9.50(br.s, 1H)

MS: FAB(+)382(MH⁺)

m.p.: 170° C.

Examples

The following compounds were obtained by successively treating by the same methods as those of Examples 18 and 9.

| Ex. | Structural formula | MS | M.p. | NMR |
|---|---|---|---|---|
| 961 | 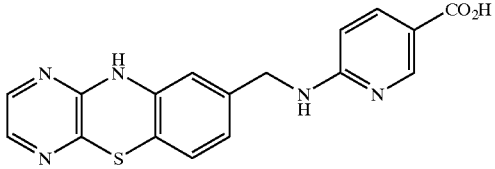<br>[2-[(10H-pyrazino[2,3-b][1,4]benzothiazin-8-yl)methylamino]pyridin-5-yl]carboxylic acid | ESI (+) 352 (MH⁺) | 215–220° C. | ¹H-NMR(DMSO-d₆) δ ppm: 4.20(br.s, 1H), 3.35(d, J=5Hz, 2H), 6.50(d, J=8Hz, 1H), 6.70–6.72(m, 1H), 6.70(d, J=8Hz, 1H), 6.73(s, 1H), 6.82(d, J=8Hz, 1H), 7.62(s, 2H), 7.80(d, J=8Hz, 1H), 9.50(br.s, 1H) |

-continued

| Ex. | Structural formula | MS | M.p. | NMR |
|---|---|---|---|---|
| 962 | [5-[(10H-pyrazino[2,3-b][1,4]benzothiazin-8-yl)methylamino]pyridin-2-ylthio]acetic acid | ESI (+) 398 (MH+) | 114–116° C. | $^1$H-NMR(DMSO-d$_6$) δ ppm: 3.78(s, 2H), 4.10(s, 2H), 6.72(s, 1H), 6.75(d, J=8Hz, 1H), 6.85(d, J=8Hz, 1H), 6.90(br.s, 1H), 6.95(dd, J=2, 7Hz, 1H), 7.12(d, J=7Hz, 1H), 7.60(s, 2H),7;80 (d, J=2Hz, 1H), 9.50(s, 1H) |
| 963 | [5-[(10H-pyrazino[2,3-b][1,4]benzothiazin-8-yl)methylamino]pyridin-2-yl]acetic acid | | | $^1$H-NMR(DMSO-d6) δ ppm: 3.50(s, 2H), 4.05(d, J=5Hz, 2H), 6.42(t, J=5Hz, 1H), 6.70–6.84(m, 2H), 6.78(s, 1H), 6.84(d, J=8Hz, 1H), 6.99(d, J=8Hz, 1H), 7.62(s, 2H), 7.82(d, J=3Hz, 1H), 9.54(br.s, 1H) |
| 964 | 6-[5-[(10H-pyrazino[2,3-b][1,4]benzothiazin-8-yl)methylamino]pyridin-2-yloxy]hexanoic acid | ESI (+) 438 (MH+) | | $^1$H-NMR(DMSO-d$_6$) δ ppm: 1.20–1.23(m, 2H), 1.40–1.55(m, 2H), 1.55–1.70(m, 2H), 2.18(t, J=6Hz, 2H), 3.97(br.s, 1H), 3.98(t, J=6Hz, 2H), 4.08(s, 2H), 6.60(d, J=8Hz, 1H), 6.75(s, 1H), 6.76(d, J=7Hz, 1H), 6.81(d, J=8Hz, 1H), 7.05(d, J=7Hz, 1H), 7.40(s, 1H), 7.60(s, 2H), 9.50(s, 1H) |
| 965 | 5-[5-[(10H-pyrazino[2,3-b][1,4]benzothiazin-8-yl)methylamino]pyridin-2-yl)pentanoic acid | | | $^1$H-NMR(DMSO-d$_6$) δ ppm: 1.40–1.50(m, 2H), 1.50–1.60(m, 2H), 2.18(t, J=6Hz, 2H), 2.50(m, 2H), 4.08(d, J=5Hz, 2H), 6.28(t, J=5Hz, 1H), 6.68(m, 3H), 6.80(d, J=8Hz, 1H), 6.83(d, J=8Hz, 1H), 7.60(s, 2H), 7.81(s, 1H), 9.50(s, 1H) |
| 966 | 6-5-[(10H-pyrazino[2,3-b][1,4]benzothiazin-8-yl)methylamino]pyridin-2-yl]-2,2-dimethylhexanoic acid | ESI (+) 450 (MH+) | 158–161° C. | $^1$H-NMR(DMSO-d$_6$) δ ppm: 1.02(s, 6H), 1.10–1.20(m, 2H), 1.40–1.48(m, 2H), 1.48–1.55(m, 2H), 2.40–2.50(m, 2H), 4.08(d, J=5Hz, 1H), 6.23(t, J=5Hz, 1H), 6.70–6.80(m, 1H), 6.72(s, 1H), 6.73(d, J=8Hz, 1H), 6.74(d, J=7Hz, 1H), 6.85(d, J=8Hz, 1H), 6.89(d, J=7Hz, 1H), 7.60(s, 2H), 7.80(s, 1H), 9.50(s, 1H) |

Example 967

8-[(2-Methylquinolin-4-yl)aminomethyl]-[(10H-pyrazino[2,3-b][1,4]benzothiazine

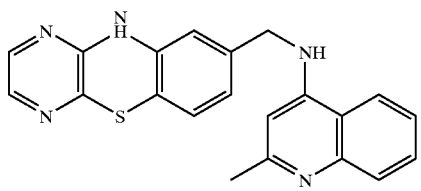

Similar to Example 1094, 307 mg of 8-chloromethyl-10-methoxymethyl-10H-pyrazino[2,3-b][1,4]benzothiazine was treated with 354 mg of 2-methyl-4-aminoquinoline in the presence of 91 mg of sodium hydride (60% oily) to thereby give 413 mg of 8-[(2-methylquinolin-4-yl)aminomethyl]-10-methoxymethyl-10H-pyrazino[2,3-b][1,4]benzothiazine as a yellow oily substance. Then this product was deblocked by the same method as the one of Example 9 to thereby give 114 mg of the title compound as, yellow crystals.

$^1$H-NMR(DMSO-d$_6$) δ ppm: 3.53(s, 3H), 4.22(s, 2H), 6.74(d, J=8 Hz, 1H), 6.79(s, 1H), 6.82(d, J=8 Hz, 1H), 6.82(s, 1H), 7.50(t, J=7 Hz, 1H), 7.60(s, 2H), 7.64(t, J=7 Hz, 1H), 7.84(d, J=7 Hz, 1H), 8.14(d, J=7 Hz, 1H), 9.48(br.s, 2H)

MS: ESI(+)372(MH$^+$)

m.p.: 290–300° C.

Examples

The following compounds were synthesized by treating 8-chloromethyl-10-methoxymethyl-10H-pyrazino[2,3-b][1,4]-benzothiazine with amines by the same method as the one of Example 967 and then treating by the same method as the one of Example 9.

| Ex. | Amino | Structural formula | MS | M.p. | NMR |
|---|---|---|---|---|---|
| 968 | (2-amino-5-chloropyridine structure) | 8-[N-(5-chloropyridin-2-yl)aminomethyl]-10H-pyrazino[2,3-b][1,4]benzothiazine | ESI (+) 342 (MH$^+$) | 200–203° C. | $^1$H-NMR(CDCl$_3$) δ ppm: 4.30(d, J=5Hz, 2H), 6.50(d, J=8Hz, 1H), 6.70(d, J=8Hz, 1H), 6.72(s, 1H), 6.82(d, J=8Hz, 1H), 7.25(t, J=5Hz, 1H), 7.42(d, J=8Hz, 1H), 7.61(s, 2H), 7.92(s, 1H), 9.50(br.s, 1H) |
| 969 | (2-amino-5-bromopyridine structure) | 8-[N-(5-bromopyridin-2-yl)aminomethyl]-10H-pyrazino[2,3-b][1,4]benzothiazine | FAB (+) 386 (MH$^+$), 388 (MH$^+$) | 265–268° C. | $^1$H-NMR(DMSC-d$_6$) δ ppm: 4.52(d, J=5Hz, 2H), 6.51(d, J=8Hz, 1H), 6.72(d, J=8Hz, 1H), 6.73(s, 1H), 6.85(d, J=8Hz, 1H), 7.00(t, J=5Hz, 1H), 7.45(d, J=8Hz, 1H), 7.62(s, 2H), 7.92(s, 1H), 9.50(br.s, 1H) |

Examples

Similar to Example 10947, N-[1-(2-trimethylsilylethoxymethyl)imidazol-2-ylmethyl]acetamide and 1-(2-trimethylsilylethoxymethyl)-2-(N-tert-butoxycarbonyl-aminomethyl)imidazole were treated with 8-chloromethyl-10-methoxy-10H-pyrazino[2,3-b][1,4]benzothiazine in the presence of sodium hydride to thereby give the following compounds.

| Ex. | Aminopyridine | Structural formula | NMR |
|---|---|---|---|
| 970 | | 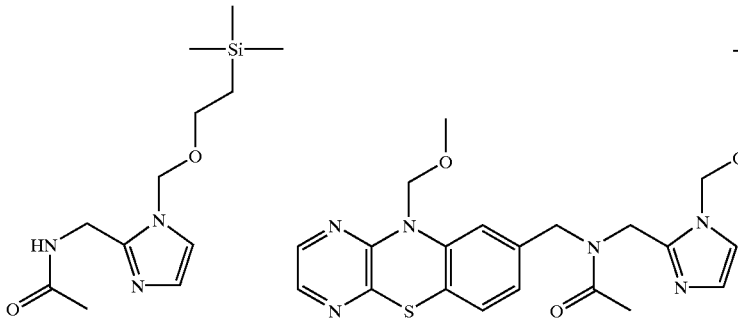<br>N-(10-methoxymethyl-10H-pyrazino[2,3-b][1,4]benzothiazin-8-ylmetmhyl)-N-[1-[2-(trimethylsilyl)ethoxymethyl]imidazol-2-ylmethyl]acetamide | $^1$H-NMR(CDCl$_3$) δ ppm: 0.02(s, 9H), 0.93(t, J=9Hz, 2H), 2.16(s, 3H), 3.44(t, J=9Hz, 2H), 3.46(s, 3H), 4.64(s. 2H), 4.73(s, 2H), 5.29(s, 2H), 5.44(s, 2H), 6.83(d, J=8Hz, 1H) 7.01–7.05(m, 4H), 7.88–7.90(m, 2H) |
| 971 | | 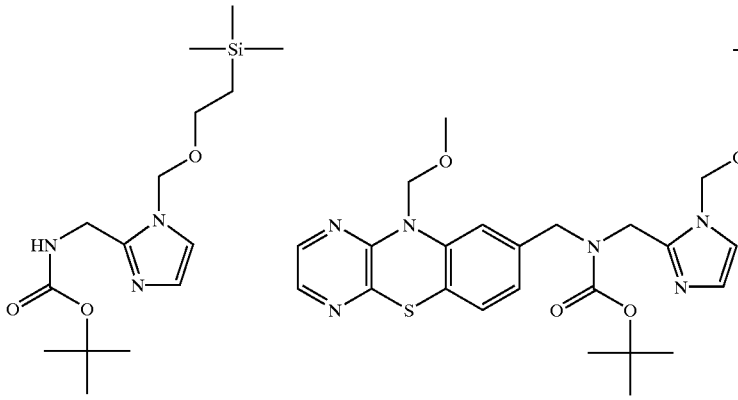<br>N-[2-(trimethylsilyl)ethoxymethylimidazol-2-ylmethyl]-N-(10-methoxymethyl-10H-pyrazino[2,3-b][1,4]benzothiazin-8-ylmethyl)-tert-butylcarbamate | $^1$H-NMR(CDCl$_3$) δ ppm: 0.00(s, 9H), 0.92(m, 2H), 1.52(s, 9H), 3.49(m, 2H), 3.57(s, 3H), 4.41(s, 2H), 4.62(br.s, 2H), 5.31(s, 2H), 5.39(s, 2H), 6.90(d, J=8Hz, 1H), 6.97–7.12 (m, 4H), 7.86(m, 2H) |

Examples

The following compounds were obtained by treating the compounds obtained in Examples 970 and 971 by the same method as the one of Example 9.

| Ex. | Structural formula | MS | M.p. | NMR |
|---|---|---|---|---|
| 972 | N-(10H-pyrazino[2,3-b][1,4]benzothiazin-8-ylmethyl)-N-(imidazol-2-ylmethyl)acetamide | FAB (+) 353 (MH+) | | $^1$H-NMR(CDCl$_3$) δ ppm: 2.10(s, 3H), 4.39(s, 2H), 4.43(s, 2H), 6.25(s, 1H), 6.57(d, J=8Hz, 1H), 6.79(d, J=8Hz, 1H), 6.92(s, 3H), 7.41(d, J=3Hz, 1H), 7.63(d, J=3Hz, 1H) |
| 973 | 8-[N-(imidazol-2-ylmethyl)aminomethyl]-10H-pyrazino[2,3-b][1,4]benzothiazine | | | $^1$H-NMR(DMSO-d$_6$) δ ppm: 3.52(s, 2H), 3.66(s, 2H), 6.74(d, J=1Hz, 1H), 6.78(d, J=1Hz, 1H), 6.85(d, J=8Hz, 1H), 6.91(s, 2H), 7.62(d, J=3Hz, 1H), 7.63(d, J=3Hz, 1H), 9.47(s, 1H) |

Example 974

N-(10-Methoxymethyl-10H-pyrazino[2,3-b][1,4]benzothiazin-8-ylmethyl)-N-(pyridin-3-yl)acetamide The title compound was obtained by treating 10-methoxymethyl-8-[N-(pyridin-3-yl)aminomethyl]-10H-pyrazino[2,3-b][1,4]-benzothiazine by the same method as the one of Production Example 85.

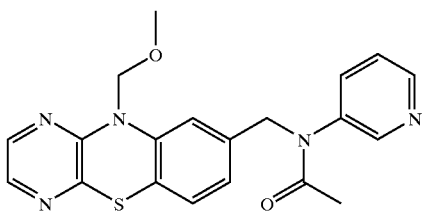

$^1$H-NMR(CDCl$_3$) δ ppm: 1.90(s, 3H), 3.42(s, 3H), 4.80(s, 2H), 5.19(s, 2H), 6.78(d, J=8 Hz, 1H), 6.92(d, J=8 Hz, 1H), 6.97(s, 1H), 7.30–7.42(m, 2H), 7.83(d, J=3 Hz, 2H), 8.38 (br.s, 1H), 8.58(br.s, 1H)

Example 975

N-(10H-Pyrazino[2,3-b][1,4]benzothiazin-8-ylmethyl)-N-(3-pyridyl)acetamide

The title compound was obtained by treating N-(10-methoxymethyl-10H-pyrazino[2,3-b][1,4]benzothiazin-8-ylmethyl)-N-(pyridin-3-yl)acetamide by the same method as the one of Example 9.

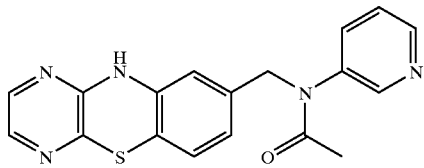

$^1$H-NMR(DMSO-d$_6$) δ ppm: 1.82(s, 3H), 4.88(s, 2H), 6.58(d, J=8 Hz, 1H), 6.63(s, 1H), 6.80(d, J=8 Hz, 1H), 7.45(br.s, 1H), 7.60(s, 2H), 7.68–7.70(m, 1H), 8.43–8.50(m, 2H), 9.41(s, 1H)

MS: ESI(+)350(MH+)

m.p.: 212–214° C.

Example 976

N-(10-Methoxymethyl-10H-pyrazino[2,3-b][1,4]benzothiazin-8-ylmethyl)-N-(pyridin-3-yl)-N'-ethylurea 341 mg of 10-methoxymethyl-8-[N-(pyridin-3-yl)aminomethyl]-10H-pyrazino[2,3-b][1,4]benzothiazine was dissolved in 5 ml of toluene. After adding 3 ml of pyridine and 1.9 ml of ethyl isocyanate, the reaction mixture was heated under reflux for 3 days. After the completion of the reaction, the reaction mixture was poured into a saturated aqueous solution of sodium chloride and extracted repeatedly with ethyl acetate. After distilling off the solvent under reduced pressure, the residue was purified by silica gel column chromatography (eluted with toluene/acetone) to thereby give 350 mg of the title compound as a yellow oily substance.

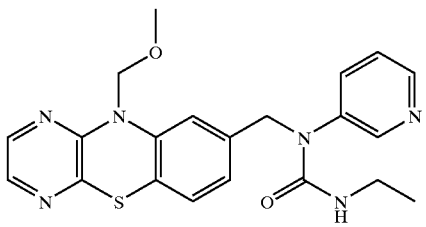

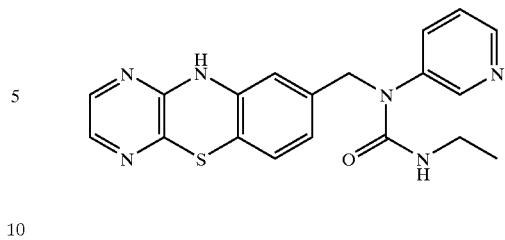

¹H-NMR(CDCl₃) δ ppm: 1.03(t, J=6 Hz, 3H), 3.17(q, J=6 Hz, 2H), 3.42(s, 3H), 4.29(br.s, 1H), 4.75(s, 2H), 5.14(s, 2H), 6.80(d, J=8 Hz, 1H), 6.86(d, J=8 Hz, 1H), 6.97(s, 1H), 7.18–7.23(m, 1H), 7.23(d, J=5 Hz, 1H), 7.42(d, J=5 Hz, 1H), 7.77(s, 2H), 8.40(s, 1H)

Example 977

N-(10H-Pyrazino[2,3-b][1,4]benzothiazin-8-ylmethyl)-N-(pyridin-3-yl)-N'-ethylurea The title compound was obtained by treating N-(10-methoxymethyl-10H-pyrazino[2,3-b][1,4]benzothiazin-8-ylmethyl)-N-(pyridin-3-yl)-N'-ethylurea by the same method as the one of Example 9.

¹H-NMR(DMSO-d₆) δ ppm: 0.96(t, J=6 Hz, 3H), 3.06(q, J=6 Hz, 2H), 4.68(s, 2H), 6.26(t, J=7 Hz, 1H), 6.58(d, J=8 Hz, 1H), 6.69(s, 1H), 6.79(d, J=8 Hz, 1H), 7.30–7.40(m, 1H), 7.53–7.62(m, 1H), 7.60(s, 2H), 8.16(m, 1H), 8.20(m, 1H), 9.48(s, 1H)

MS: ESI(+)379(MH⁺)

m.p.: 210–212° C.

Examples

The following compounds were obtained by treating 10-methoxymethyl-8-[N-(pyridin-3-yl)aminomethyl]-10H-pyrazino[2,3-b][1,4]benzothiazine by the same method as the one of Example 974 or 976 followed by the same treatment as the one of Example 9.

| Ex. | Structural formula | MS | M.p. | NMR |
|---|---|---|---|---|
| 978 | N-(10H-pyrazino[2,3-b][1,4]benzothiazin-8-ylmethyl)-N-(pyridin-3-yl)benzenesulfonamide | ESI (+) 448 (MH⁺) | 205–260° C. | ¹H-NMR(DMSO-d₆) δ ppm: 4.68(s, 2H), 6.60(d, J=8Hz, 1H), 6.77(d, J=8Hz, 1H), 6.79(s, 1H), 7.32(dd, J=2, 5Hz, 1H), 7.47–7.56(m, 1H), 7.58–7.62(m, 6H), 7.70–7.76(m, 1H), 8.30(d, J=3Hz, 1H), 8.42(d, J=3Hz, 1H), 9.50(br.s, 1H) |
| 979 | N-(10H-pyrazino[2,3-b][1,4]benzothiazin-8-ylmethyl)-N-(pyridyl)benzamide | FAB (+) 411 (M⁺) | 178–182° C. | ¹H-NMR(CDCl₃) δ ppm: 4.92(s, 2H), 6.60(d, J=8Hz, 1H), 6.61(s, 1H), 6.72(d, J=8Hz, 1H), 7.05–7.20(m, 3H), 7.20–7.40(m, 5H), 7.53(d, J=3Hz, 1H), 7.60(d, J=3Hz, 1H), 8.24(s, 1H), 8.36(d, J=2Hz, 1H) |

-continued

| Ex. | Structural formula | MS | M.p. | NMR |
|---|---|---|---|---|
| 980 | N-(10H-pyrazino[2,3-b][1,4]benzothiazin-8-ylmethyl)-N-(pyridin-3-yl)methanesulfonamide | FAB (+) 385 (M+) | 208–210° C. | $^1$H-NMR(DMSO-$d_6$) δ ppm: 3.14(s, 3H), 4.73(s, 2H), 6.62(d, J=8Hz, 1H), 6.73(s, 1H), 6.78(d, J=8Hz, 1H), 7.40(m, 1H), 7.60(m, 2H), 7.84(dd, J=2, 8Hz, 1H), 8.43(d, J=4Hz, 1H), 8.54(s, 1H), 9.50(s, 1H) |
| 981 | N-(10H-pyrazino[2,3-b][1,4]benzothiazin-8-ylmethyl)-N-(pyridin-3-yl)-N′-phenylurea | ESI (+) 427 (MH+) | 208–210° C. | $^1$H-NMR(DMSO-$d_6$) δ ppm: 4.78(s, 2H), 6.65(d, J=8Hz, 1H), 6.77(s, 1H), 6.81(d, J=8Hz, 1H), 6.95(t, J=7Hz, 2H), 7.22(t, J=7Hz, 2H), 7.22(t, J=7Hz, 2H), 7.42(d, J=7Hz, 2H), 7.60(d, J=2Hz, 1H), 7.61(d, J=2Hz, 1H), 7.69(m, 1H), 8.38(d, J=2Hz, 1H), 8.42(s, 1H), 8.48(s, 1H), 9.52(s, 1H) |

Examples

The following compounds were obtained by treating 10-methoxymethyl-8-chloromethyl-10H-pyrazino([2,3-b][1,4]-benzothiazine with various imidazoles by the same method as the one of Example 1094.

| Ex. | Imidazole | Structural formula | NMR |
|---|---|---|---|
| 982 | 2-methylimidazole | 8-(2-methylimidazol-1-ylmethyl)-10-methoxymethyl-10H-pyrazino[2,3-b][1,4]enzothiazine | $^1$H-NMR(CDCl$_3$) δ ppm: 2.34(s, 3H), 3.45(s, 3H), 4.98(s, 2H), 5.16(s, 2H), 6.64(dd, J=1, 8Hz, 1H), 6.77(d, J=1Hz, 1H), 6.84(d, J=1Hz, 1H), 6.96(d, J=1Hz, 1H), 6.97(d, J=8Hz, 1H), 7.84(d, J=3Hz, 1H), 7.85(d, J=3Hz, 1H) |
| 983 | 2-ethylimidazole | 8-(2-ethylimidazol-1-ylmethyl)-10-methoxymethyl-10H-pyrazino[2,3-b][1,4]benzothiazine | $^1$H-NMR(CDCl$_3$) δ ppm: 1.27(t, J=7Hz, 3H), 2.61(q, J=7Hz, 2H), 3.42(s, 2H), 4.98(s, 2H), 5.12(s, 2H), 6.61(d, J=8Hz, 1H), 6.71(s, 1H), 6.82(s, 1H), 6.94(d, J=8Hz, 1H), 6.98(s, 1H), 7.82(m, 2H) |

-continued

| Ex. | Imidazole | Structural formula | NMR |
| --- | --- | --- | --- |
| 984 | 2-isopropylimidazole | 8-(2-isopropylimidazol-1-ylmethyl)-10-methoxymethyl-10H-pyrazino[2,3-b][1,4]benzothiazine | $^1$H-NMR(CDCl$_3$) δ ppm: 1.27(d, J=7Hz, 6H), 2.93(sept, J=7Hz, 1H), 3.42(s, 3H), 5.03(s, 2H), 5.13(s, 2H), 6.63(d, J=8Hz, 1H), 6.70(s, 1H), 6.78(s, 1H), 6.96(d, J=8Hz, 1H), 7.02(s, 1H), 7.83(m, 2H) |
| 985 | 2-chloroimidazole | 8-(2-chloroimidazol-1-ylmethyl)-10-methoxymethyl-10H-pyrazino[2,3-b][1,4]benzothiazine | $^1$H-NMR(CDCl$_3$) δ ppm: 3.48(s, 3H), 5.03(s, 2H), 5.19(s, 2H), 6.73(dd, J=2, 8Hz, 1H), 6.89(d, J=2Hz, 1H), 6.91(d, J=1Hz, 1H), 6.99(d, J=1Hz, 1H), 7.00(d, J=8Hz, 1H), 7.84(d, J=3Hz, 1H), 7.86(d, J=3Hz, 1H) |
| 986 | 2-bromoimidazole | 8-(2-bromoimidazol-1-ylmethyl)-10-methoxymethyl-10H-pyrazino[2,3-b][1,4]benzothiazine | $^1$H-NMR(CDCl$_3$) δ ppm: 3.47(s, 3H), 5.05(s, 2H), 5.19(s, 2H), 6.74(dd, J=2, 8Hz, 1H), 6.89(d, J=2Hz, 1H), 6.97(d, J=1Hz, 1H), 6.99(d, J=8Hz, 1H), 7.06(d, J=1Hz, 1H), 7.84(d, J=3Hz, 1H), 7.86(d, J=3Hz, 1H) |
| 987 | 2-(trifluoromethyl)imidazole | 8-[2-(trifluoromethyl)imidazol-1-ylmethyl)-10-methoxymethyl-10H-pyrazino[2,3-b][1,4]benzothiazine | $^1$H-NMR(CDCl$_3$) δ ppm: 3.46(s, 3H), 5.17(s, 2H), 5.18(s, 2H), 6.75(dd, J=1, 8Hz, 1H), 6.88(br.s, 1H), 6.98(s, 1H), 7.00(d, J=8Hz, 1H), 7.13(s, 1H), 7.83–7.88(m, 2H) |

-continued

| Ex. | Imidazole | Structural formula | NMR |
|---|---|---|---|
| 988 | 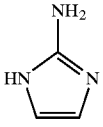 | 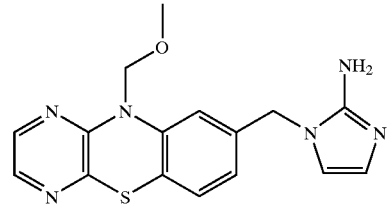  8-(2-aminoimidazol-1-ylmethyl)-10-methoxymethyl-10H-pyrazino[2,3-b][1,4]benzothiazine | ¹H-NMR(CDCl₃) δ ppm: 3.46(s, 3H), 4.86(s, 2H), 5.19(s, 2H), 6.59(d, J=2Hz, 1H), 6.70(d, J=2Hz, 1H), 6.72(d, J=2Hz, 1H), 6.87(d, J=2Hz, 1H), 7.00(d, J=8Hz, 1H), 7.84(d, J=3Hz, 1H), 7.86(d, J=3Hz, 1H) |
| 989 | 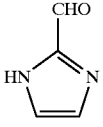 | 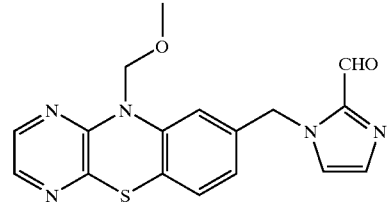  1-(10-methoxymethyl-10H-pyrazino[2,3-b][1,4]benzothiazin-8-ylmethyl)imidazole-2-carbaldehyde | ¹H-NMR(CDCl₃) δ ppm: 3.48(s, 3H), 5.19(s, 2H), 5.53(s, 2H), 6.78(d, J=8Hz, 1H), 6.97(s, 2H), 7.17(s, 1H), 7.28(s, 1H), 7.83(m, 2H), 9.84(s, 1H) |
| 990 | 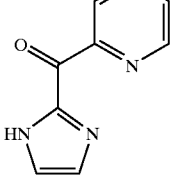 | 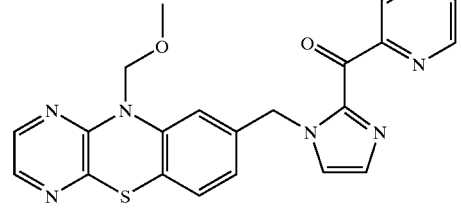  1-(10-methoxymethyl-10H-pyrazino[2,3-b][1,4]benzothiazin-8-ylmethyl)imidazol-2-yl 2-pyridyl ketone | ¹H-NMR(CDCl₃) δ ppm: 3.48(s, 3H), 5.20(s, 2H), 5.64(s, 2H), 6.87(dd, J=2, 8Hz, 1H), 6.99(d, J=8Hz, 1H), 7.05(d, J=2Hz, 1H), 7.20(d, J=1Hz, 1H), 7.33(d, J=1Hz, 1H), 7.47(ddd, J=2, 5, 8Hz, 1H), 7.83–7.88(m, 3H), 8.26(dd, J=2, 8Hz, 1H), 8.81(dd, J=1, 5Hz, 1H) |
| 991 | 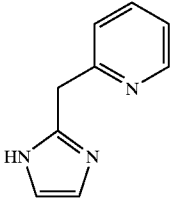 | 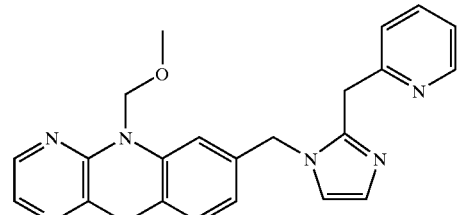  8-[2-(pyridin-2-ylmethyl)imidazol-1-ylmethyl)-10-methoxymethyl-10H-pyrazino[2,3-b][1,4]benzothiazine | ¹H-NMR(CDCl₃) δ ppm: 3.42(s, 3H), 4.24(s, 2H), 5.08(s, 2H), 5.12(s, 2H), 6.54(dd, J=2, 8Hz, 1H), 6.69(d, J=2Hz, 1H), 6.85(d, J=1Hz, 1H), 6.88(d, J=8Hz, 1H), 7.03(d, J=1Hz, 1H), 7.07(ddd, J=2, 5, 8Hz, 1H), 7.19(br.d, J=8Hz, 1H), 7.54(dt, J=2, 8Hz, 1H), 7.83(d, J=3Hz, 1H), 7.84(d, J=3Hz, 1H), 8.42(ddd, J=1, 2, 5Hz, 1H) |

-continued

| Ex. | Imidazole | Structural formula | NMR |
|---|---|---|---|
| 992 | 4-phenylimidazole | 8-(4-phenylimidazol-1-ylmethyl)-10-methoxymethyl-10H-pyrazino[2,3-b][1,4]benzothiazine | ¹H-NMR(CDCl₃) δ ppm: 3.43(s, 3H), 5.08(s, 2H), 5.19(s, 2H), 6.79(dd, J=2, 8Hz, 1H), 6.92(d, J=2Hz, 1H), 7.00(d, J=8Hz, 1H), 7.19(d, J=2Hz, 1H), 7.23(t, J=8Hz, 1H), 7.36(t, J=8Hz, 2H), 7.60(d, J=2Hz, 1H), 7.75(d, J=8Hz, 2H), 7.83(d, J=3Hz, 1H), 7.85(d, J=3Hz, 1H), |
| 993 | 4-(pyridin-4-yl)imidazole | 8-[4-(pyridin-4-yl)imidazol-1-ylmethyl]-10-methoxymethyl-10H-pyrazino[2,3-b][1,4]benzothiazine | ¹H-NMR(CDCl₃) δ ppm: 3.43(s, 3H), 5.10(s, 2H), 5.20(s, 2H), 6.80(dd, J=2, 8Hz, 1H), 6.94(d, J=2Hz, 1H), 7.02(d, J=8Hz, 1H), 7.35(d, J=1Hz, 1H), 7.62(dd, J=2, 5Hz, 2H), 7.64(t, J=1Hz, 1H), 7.84(d, J=3Hz, 1H), 7.87(d, J=3Hz, 1H), 8.57(dd, J=2, 5Hz, 2H) |
| 994 | 4-hydroxymethylimidazole | [1-(10-methoxymethyl-10H-pyrazino[2,3-b][1,4]benzothiazin-8-ylmethyl)imidazol-4(5)-yl]methanol (4,5-mix) | ¹H-NMR(DMSO-d₆) δ ppm: 3.0–3.4(br.s, total 1H), 3.43 and 3.47(s, total 3H, 3:4), 4.50 and 4.54(s, total 2H, 3:4), 5.00 and 5.16(s, total 2H, 4:3), 5.16 and 5.20(s, total 2H, 4:3), 6.70 and 6.73(dd, J=1.8, 8.1Hz, total 1H, 3:4), 6.84 and 6.90(d, J=1.8Hz, total 1H, 3:4), 6.85 and 6.94(s, total 1H, 4:3), 6.95 and 6.97(d, J=8.1Hz, total 1H, 3:4), 7.48(s, total 1H), 7.83 and 7.84(d, J=2.5Hz, total 1H, 3:4), 7.84 and 7.85(d, J=8.1Hz, total 1H, 3:4) |
| 995 | 4,5-dicyanoimidazole | 1-(10-methoxymethyl-10H-pyrazino[2,3-b][1,4]benzothiazin-8-ylmethyl)imidazol-4,5-dicarbonitrile | ¹H-NMR(CDCl₃) δ ppm: 3.52(s, 3H), 5.20(s, 2H), 5.26(s, 2H), 6.85(dd, J=2, 8Hz, 1H), 7.06(d, J=8Hz, 1H), 7.09(d, J=2Hz, 1H), 7.72(s, 1H), 7.86(d, J=3Hz, 1H), 7.88(d, J=3Hz, 1H) |

| Ex. | Imidazole | Structural formula | NMR |
|---|---|---|---|
| 996 | 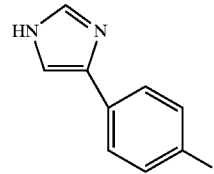 | 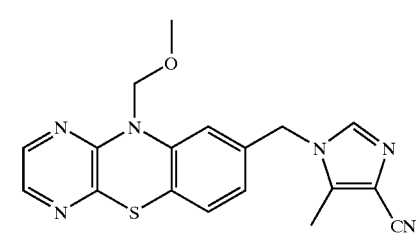<br>4-[1-(10-methoxymethyl-10H-pyrazino[2,3-b][1,4]benzothiazin-8-ylmethyl)imidazol-4-yl]benzonitrile | ¹H-NMR(CDCl₃) δ ppm: 3.44(s, 3H), 5.09(s, 2H), 5.21(s, 2H), 6.79(dd, J=2, 8Hz, 1H), 6.94(d, J=2Hz, 1H), 7.01(d, J=8Hz, 1H), 7.29(d, J=1Hz, 1H), 7.62–7.65(m, 3H), 7.83–7.87(m, 4H) |
| 997 | 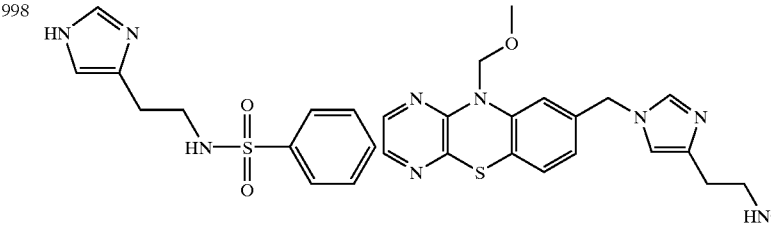 | 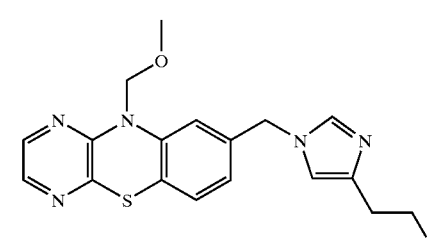<br>1-(10-methoxymethyl-10H-pyrazino[2,3-b][1,4]benzothiazin-8-ylmethyl)-5-methylimidazol-4-carbonitrile | ¹H-NMR(CDCl₃) δ ppm: 2.30(s, 3H), 3.46(s, 3H), 5.01(s, 2H), 5.17(s, 2H), 6.62–6.67(m, 1H), 6.77(d, J=2Hz, 1H), 7.01(d, J=8Hz, 1H), 7.48(s, 1H), 7.84(d, J=3Hz, 1H), 7.87(d, J=3Hz, 1H) |
| 998 | | N-[2-[1-[10-(methoxymethyl)-10H-pyrazino[2,3-b][1,4]benzothiazin-8-ylmethyl]imidazol-4-yl]ethyl]benzenesulfonamide | ¹H-NMR(CDCl₃) δ ppm: 2.68(t, J=8Hz, 2H), 3.25(q, J=8Hz, 2H), 3.46(s, 3H), 4.96(s, 2H), 5.20(s, 2H), 5.86(br.s, 1H), 6.62(s, 1H), 6.73(d, J=8Hz, 1H), 6.88(s, 1H), 6.97(d, J=8Hz, 1H), 7.43(s, 1H), 7.48(t, J=8Hz, 2H), 7.50–7.58(d, 1H), 7.80–7.90(m, 4H) |
| 999 | | N-[2-[1-[10-(methoxymethyl)-10H-pyrazino[2,3-b][1,4]benzothiazin-8-ylmethyl]imidazol-4-yl]ethyl]benzamide | ¹H-NMR(CDCl₃) δ ppm: 2.86(t, J=6Hz, 2H), 3.45(s, 3H), 3.68–3.76(m, 2H), 5.00(s, 2H), 5.19(s, 2H), 6.73(s, 1H), 6.70–6.76(m, 1H), 6.89(s, 1H), 6.97(d, J=8Hz, 1H), 7.40(t, J=8Hz, 2H), 7.44–7.49(m, 1H), 7.51(s, 1H), 7.52–7.60(m, 1H), 7.80(d, J=8Hz, 2H), 7.80–7.88(m, 2H) |

Examples

The following compounds were obtained by the same method as the one of Example 8.

| Ex. | Structural formula | MS | M.p. | NMR |
|---|---|---|---|---|
| 1000 | 8-(2-methylimidazol-1-ylmethyl)-10H-pyrazino[2,3-b][1,4]benzothiazine | ESI(+) 296.2 (MH$^+$) | 244–246° C. | $^1$H-NMR(DMSO-d$_6$) δ ppm: 2.27(s, 3H), 5.01(s, 2H), 6.53(s, 1H), 6.56(d, J=8Hz, 1H), 6.89(d, J=8Hz, 1H), 6.93(s, 1H), 7.16(s, 1H), 7.63(s, 2H), 9.53(s, 1H) |
| 1001 | 8-(2-ethylimidazol-1-ylmethyl)-10H-pyrazino[2,3-b][1,4]benzothiazine | ESI(+) 310.2 (MH$^+$) | 230–231° C. | $^1$H-NMR(CDCl$_3$) δ ppm: 1.27(t, J=7Hz, 3H), 2.61(q, J=7Hz, 2H), 4.90(s, 2H), 6.09(d, J=2Hz, 1H), 6.55(dd, J=2, 8Hz, 1H), 6.79(br.s, 1H), 6.82(d, J=1Hz, 1H), 6.85(d, J=8Hz, 1H), 6.99(d, J=1Hz, 1H), 7.56(d, J=3Hz, 1H), 7.69(d, J=3Hz, 1H) |
| 1002 | 8-(2-isopropyl imidazol-1-ylmethyl)-10H-pyrazino[2,3-b][1,4]benzothiazine | ESI(+) 324.0 (MH$^+$) | 241–242° C. | $^1$H-NMR(CDCl$_3$) δ ppm: 1.26(d, J=7Hz, 6H), 2.90(septet, J=7Hz, 1H), 4.94(s, 2H), 6.09(d, J=2Hz, 1H), 6.55(dd, J=2, 8Hz, 1H), 6.76(d, J=1Hz, 1H), 6.85(d, J=8Hz, 1H), 6.98(d, J=1Hz, 1H), 7.18(br.s, 1H), 7.52(d, J=3Hz, 1H), 7.68(d, J=3Hz, 1H) |
| 1003 | N-[2-[1-(10H-pyrazino[2,3-b][1,4]benzothiazin-8-ylmethyl]imidazol-4-yl]ethyl]benzenesulfonamide | ESI (+) 465 (MH$^+$) | 127–130° C. | $^1$H-NMR(CDCl$_3$) δ ppm: 2.70(t, J=6Hz, 2H), 3.27(q, J=6Hz, 2H), 4.88(s, 2H), 6.21(s, 1H), 6.64(s, 1H), 6.63(dd, J=2, 8Hz, 1H), 6.86(d, J=8Hz, 1H), 7.40(s, 1H), 7.48(t, J=8Hz, 2H), 7.52–7.58(m, 2H), 7.68(d, J=3Hz, 1H), 7.85(d, J=8Hz, 2H) |

-continued

| Ex. | Structural formula | MS | M.p. | NMR |
|---|---|---|---|---|
| 1004 | N-[2-[1-[10H-pyrazino[2,3-b][1,4]benzothiazin-8-ylmethyl]imidazol-4-yl]ethyl]benzamide | ESI (+) 429 (MH⁺) | 231–233° C. | ¹H-NMR(DMSO-d₆) δ ppm: 2.97(t, J=6Hz, 2H), 3.62(q, J=6Hz, 2H), 5.29(s, 2H), 6.75(d, J=1Hz, 1H), 6.76(dd, J=1, 8Hz, 1H), 6.91(d, J=8Hz, 1H), 7.47(t, J=7Hz, 2H), 7.53(t, J=7Hz, 1H), 7.55(s, 1H), 7.72(s, 2H), 7.85(d, J=7Hz, 2H), 8.78(t, J=6Hz, 1H), 9.27(s, 1H), 9.66(s, 1H) |

Examples

The following compounds were obtained by the same method as the one of Example 9.

| Ex. | Structural formula | MS | M.p. | NMR |
|---|---|---|---|---|
| 1005 | 8-(2-chloroimidazol-1-ylmethyl)-10H-pyrazino[2,3-b][1,4]benzothiazine | FAB (+) 316 (MH⁺) | 231–232° C. | ¹H-NMR(DMSO-d₆) δ ppm: 5.01(s, 2H), 6.55(d, J=1Hz, 1H), 6.59(dd, J=1, 8Hz, 1H), 6.90(d, J=8Hz, 1H), 6.92(d, J=2Hz, 1H), 7.34(d, J=2Hz, 1H), 7.63(s, 2H), 9.55(s, 1H) |
| 1006 | 8-(2-bromoimidazol-1-ylmethyl)-10H-pyrazino[2,3-b][1,4]benzothiazine | FAB (+) 361 (M⁺) | 256–258° C. | ¹H-NMR(DMSO-d₆) δ ppm: 5.00(s, 2H), 6.54(s, 1H), 6.56(d, J=8Hz, 1H), 6.90(d, J=8Hz, 1H), 6.97(d, J=2Hz, 1H), 7.39(d, J=2Hz, 1H), 7.63(s, 2H), 9.45(s, 1H) |
| 1007 | 8-[2-(trifluoromethyl)imidazol-1-ylmethyl]-10H-pyrazino[2,3-b][1,4]benzothiazine | FAB (+) 350 (MH⁺) | 231–233° C. | ¹H-NMR(DMSO-d₆) δ ppm: 5.20(s, 2H), 6.50(d, J=1Hz, 1H), 6.57(dd, J=1, 8Hz, 1H), 6.90(d, J=8Hz, 1H), 7.15(d, J=1Hz, 1H), 7.54(d, J=1Hz, 1H), 7.63(s, 2H), 9.55(s, 1H) |

-continued

| Ex. | Structural formula | MS | M.p. | NMR |
|---|---|---|---|---|
| 1008 | 8-(2-aminoimidazol-1-ylmethyl)-10H-pyrazino[2,3-b][1,4]benzothiazine | FAB (+) 297 (MH$^+$) | 286–287° C. | $^1$H-NMR(DMSO-d$_6$) δ ppm: 4.87(s, 2H), 6.56(s, 1H), 6.59(d, J=8Hz, 1H), 6.74(s, 1H), 6.77(s, 1H), 6.90(d, J=8Hz, 1H), 6.92(br.s, 2H), 7.63(s, 2H), 9.57(s, 1H) |
| 1009 | 1-(10H-pyrazino[2,3-b][1,4]benzothiazin-8-ylmethyl)imidazol-2-yl 2-pyridyl ketone | FAB (+) 387 (MH$^+$) | 191–193° C. | $^1$H-NMR(CDCl$_3$) δ ppm: 5.52(s, 2H), 6.43(s, 1H), 6.72(d, J=8Hz, 1H), 6.84(d, J=8Hz, 1H), 6.95(s, 1H), 7.19(s, 1H), 7.32(s, 1H), 7.47(dd, J=5, 8Hz, 1H), 7.53(d, J=3Hz, 1H), 7.65(d, J=3Hz, 1H), 7.85(td, J=1, 8Hz, 1H), 8.15(d, J=8Hz, 1H), 8.78(d, J=5Hz, 1H) |
| 1010 | 8-[2-(pyridin-2-ylmethyl)imidazol-1-ylmethyl]-10H-pyrazino[2,3-b][1,4]-benzothiazine | FAB (+) 373 (MH$^+$) | 216–219° C. | $^1$H-NMR(DMSO-d$_6$) δ ppm: 4.10(s, 2H), 5.04(s, 2H), 6.45(d, J=8Hz, 1H), 6.48(s, 1H), 6.81(d, J=8Hz, 1H), 6.82(s, 1H), 7.09(s, 1H), 7.14(d, J=9Hz, 1H), 7.16(dd, J=6, 9Hz, 1H), 7.63(s, 2H), 7.64(dt, J=2, 9Hz, 1H), 8.41(dd, J=2, 6Hz, 1H), 9.49(s, 1H) |
| 1011 | 8-(4-phenylimidazol-1-ylmethyl)-10H-pyrazino[2,3-b][1,4]benzothiazine | FAB (+) 358 (MH$^+$) | 216–218° C. | $^1$H-NMR(DMSO-d$_6$) δ ppm: 5.05(s, 2H), 6.62(d, J=1Hz, 1H), 6.68(dd, J=1, 8Hz, 1H), 6.90(d, J=8Hz, 1H), 7.16(t, J=8Hz, 1H), 7.31(t, J=8Hz, 2H), 7.59(s, 1H), 7.62(s, 2H), 7.73(d, J=8Hz, 2H), 7.75(s, 1H), 9.53(s, 1H) |
| 1012 | 8-[4-(pyridin-4-yl)imidazol-1-ylmethyl]-10H-pyrazino[2,3-b][1,4]benzothiazine bistrifluoroacetate · 2CF$_3$CO$_2$H | FAB (+) 359 (MH$^+$) | 157–158° C. | $^1$H-NMR(DMSO-d$_6$) δ ppm: 5.17(s, 2H), 6.63(d, J=1Hz, 1H), 6.73(dd, J=1, 7Hz, 1H), 6.94(d, J=7Hz, 1H), 7.64(s, 2H), 8.20(d, J=1Hz, 1H), 8.24(d, J=6Hz, 2H), 8.38(s, J=1Hz, 1H), 8.75(d, J=6Hz, 2H), 9.54(s, 1H) |

-continued

| Ex. | Structural formula | MS | M.p. | NMR |
|---|---|---|---|---|
| 1013 | 4-[1-(10H-pyrazino[2,3-b][1,4]benzothiazin-8-ylmethyl)imidazol-4-yl]benzonitrile | FAB (+) 383 (M⁺) | 262–264° C. | ¹H-NMR(DMSO-d₆) δ ppm: 5.09(s, 2H), 6.60(d, J=1Hz, 1H), 6.69(dd, J=1, 8Hz, 1H), 6.91(d, J=8Hz, 1H), 7.62(s, 2H), 7.77(d, J=8Hz, 2H), 7.85(d, J=1Hz, 1H), 7.86(d, J=1Hz, 1H), 7.91(d, J=8Hz, 2H), 9.52(s, 1H) |

Examples

The following compounds were obtained by the same treatment as the one of Example 434.

| Ex. | Structural formula | MS | M.p. | NMR |
|---|---|---|---|---|
| 1014 | 1-(10H-pyrazino[2,3-b][1,4]benzothiazin-8-ylmethyl)imidazole-2-carbaldehyde | | 218–219° C. | ¹H-NMR(DMSO-d₆) δ ppm: 5.41(s, 2H), 6.53(d, J=1Hz, 1H), 6.57(dd, J=1, 9Hz, 1H), 6.86(d, J=9Hz, 1H), 7.33(s, 1H), 7.63(s, 2H), 7.69(s, 1H), 9.49(s, 1H), 9.68(s, 1H) |
| 1015 | [1-(10H-pyrazino[2,3-b][1,4]benzothiazin-8-ylmethyl)imidazol-4(5)-yl]methanol (4,5-mix) | ESI (+) 312.0 (M⁺) | 208–215° C. | ¹H-NMR(DMSO-d₆) δ ppm: 4.38(m, 2H), 4.79 and 5.08(t, J=6Hz, 1H), 4.79 and 5.06(s, 2H), 6.54–6.65(m, 2H), 6.85–6.90(m, 1H), 6.82 and 6.91(s, 1H), 7.59 and 7.63(s, 1H), 7.63–7.65(m, 2H), 9.51 and 9.53(s, 1H) |
| 1016 | 1-(10H-pyrazino[2,3-b][1,4]benzothiazin-8-ylmethyl)imidazole-4,5-dicarbonitrile | | | ¹H-NMR(DMSO-d₆) δ ppm: 5.34(s, 2H), 6.56(d, J=2Hz, 1H), 6.73(dd, J=2, 8Hz, 1H), 6.96(d, J=8Hz, 1H), 7.66(s, 2H), 8.48(s, 1H), 9.54(s, 1H) |
| 1017 | 1-(10H-pyrazino[2,3-b][1,4]benzothiazin-8-ylmethyl)-5-methylimidazole-4-carbonitrile | | | ¹H-NMR(DMSO-d₆) δ ppm: 2.24(s, 3H), 5.12(s, 2H), 6.47(d, J=2Hz, 1H), 6.62(dd, J=2, 8Hz, 1H), 6.92(d, J=8Hz, 1H), 7.65(s, 2H), 7.90(s, 1H), 9.50(s, 1H) |

Examples 280 mg portions of the following compounds were obtained by the same method as the one of Example 1094 by starting with 0.55 g of ethyl(5-methylimidazol-4-yl) carboxylate and 0.7 g of 10-methoxymethyl-8-chloromethyl-10H-pyrazino[2,3-b][1,4]benzothiazine.

| Ex. | Structural formula | NMR |
|---|---|---|
| 1018 | 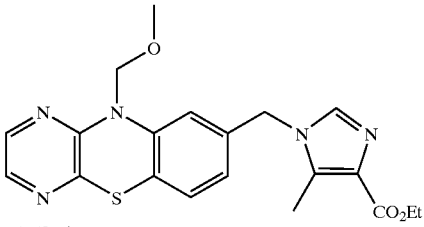<br>ethyl[1-(10-(methoxymethyl)-10H-pyrazino[2,3-b][1,4]-benzothiazin-8-ylmethyl)-5-methylimidazol-4-yl]carboxylate | $^1$H-NMR(CDCl$_3$) δ ppm: 1.40(t, J=7Hz, 3H), 2.47(s, 3H), 3.45(s, 3H), 4.37(q, J=7Hz, 2H), 5.02(s, 2H), 5.17(s, 2H), 6.62(dd, J=2, 8Hz, 1H), 6.80(d, J=2Hz, 1H), 6.98(d, J=8Hz, 1H), 7.48(s, 1H), 7.84(d, J=3Hz, 1H), 7.86(d, J=3Hz, 1H) |
| 1019 | 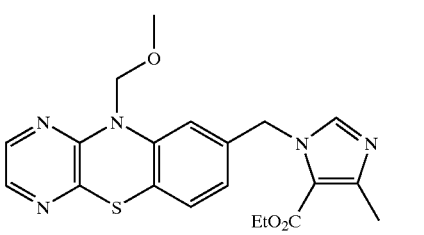<br>ethyl[1-(10-(methoxymethyl)-10H-pyrazino[2,3-b][1,4]-benzothiazin-8-ylmethyl)-4-methylimidazol-5-yl]carboxylate | $^1$H-NMR(CDCl$_3$) δ ppm: 1.33(t, J=7Hz, 3H), 2.51(s, 3H), 3.46(s, 3H), 4.28(q, J=7Hz, 2H), 5.18(s, 2H), 5.40(s, 2H), 6.73(dd, J=2, 8Hz, 1H), 6.87(d, J=8Hz, 1H), 6.96(d, J=8Hz, 1H), 7.53(s, 1H), 7.83(d, J=3Hz, 1H), 7.85(d, J=3Hz, 1H) |

Examples

The following compounds were obtained by the same method as the one of Example 1094 by starting with 10-methoxymethyl-8-chloromethyl-10H-pyrazino[2,3-b][1,4]benzothiazine and various imidazoles.

| Ex. | Imidazole | Structural formula | NMR |
|---|---|---|---|
| 1020 | | 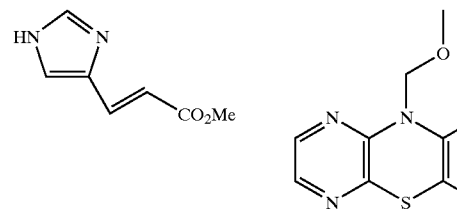<br>methyl (E)-3-[1-[10-(methoxymethyl)-10H-pyrazino[2,3-b][1,4]benzothiazin-8-ylmethyl]imidazol-4-yl]propenoate | $^1$H-NMR(DMSO-d$_6$) δ ppm: 3.33(s, 3H), 3.65(s, 3H), 5.66(s, 2H), 5.70(s, 2H), 6.33(d, J=15.5Hz, 1H), 6.88(dd, J=1.7, 8.3Hz, 1H), 6.97(d, J=1.7Hz, 1H), 7.12(d, J=8.3Hz, 1H), 7.48(d, J=15.5Hz, 1H), 7.62(s, 1H), 7.86(s, 1H), 7.93(d, J=3.0Hz, 1H), 7.96(d, J=3.0Hz, 1H) |

-continued

| Ex. | Imidazole | Structural formula | NMR |
|---|---|---|---|
| 1021 | 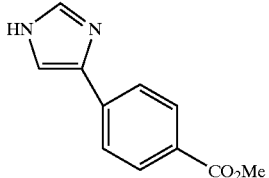 | 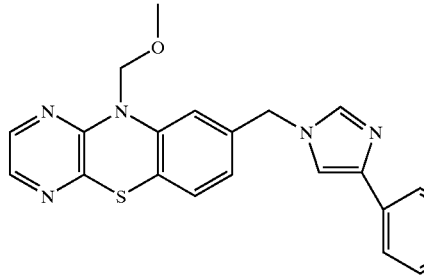  methyl 4-[1-[10 (methoxymethyl)-10H-pyrazino[2,3-b][1,4] benzothiazin-8-ylmethyl] imidazol-4-yl]benzoate | $^1$H-NMR(CDCl$_3$) δ ppm: 3.42(s, 3H), 3.81(s, 3H), 5.09(s, 2H), 5.20(s, 2H), 6.80(dd, J=2, 8Hz, 1H), 6.93(d, J=2Hz, 1H), 7.01(d, J=8Hz, 1H), 7.29(d, J=1Hz, 1H), 7.63(d, J=1Hz, 1H), 7.82(d, J=8Hz, 2H), 7.83(d, J=3Hz, 1H), 7.86(d, J=3Hz, 1H), 8.03(d, J=8Hz, 2H) |
| 1022 | 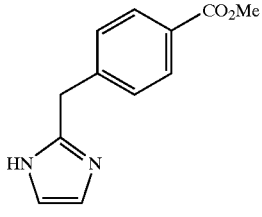 | 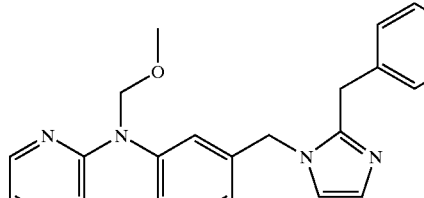  methyl 4-[1-[10-(methoxymethyl)-10H-pyrazino[2,3-b][1,4] benzothiazin-8-ylmethyl] imidazol-2-yl]benzoate | $^1$H-NMR(CDCl$_3$) δ ppm: 3.43(s, 3H), 3.87(s, 3H), 4.08(s, 2H), 4.83(s, 2H), 5.10(s, 2H), 6.63(s, 1H), 6.76(d, J=8Hz, 1H), 6.90(d, J=8Hz, 1H), 6.99(s, 1H), 7.16(d, J=8Hz, 2H), 7.78(s, 1H), 7.87–7.93(m, 4H) |
| 1023 | 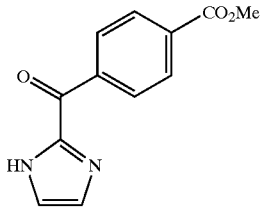 | 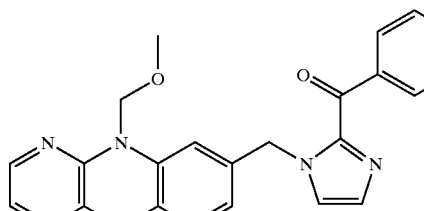  methyl 4-[1-[10-(methoxymethyl)-10H-pyrazino[2,3-b][1,4] benzothiazin-8-ylmethyl] imidazol-2-ylcarbonyl] benzoate | $^1$H-NMR(CDCl$_3$) δ ppm: 3.43(s, 3H), 3.94(s, 3H), 5.18(s, 2H), 5.63(s, 2H), 6.83(dd, J=2, 8Hz, 1H), 6.99(d, J=8Hz, 1H), 7.01(d, J=2Hz, 1H), 7.20(d, J=1Hz, 1H), 7.30(d, J=1Hz, 1H), 7.83(d, J=3Hz, 1H), 7.84(d, J=3Hz, 1H), 8.13(d, J=8Hz, 2H), 8.30(d, J=8Hz, 2H) |

Examples

The following compounds were obtained by treating the starting compounds by the same method as the one of Example 434.

| Ex. | Structural formula | MS | M. p. | NMR |
|---|---|---|---|---|
| 1024 | ethyl [1-(10H-pyrazino[2,3-b][1,4]benzothiazin-8-ylmethyl)-5-methylimidazol-4-yl]carboxylate | ESI (+) 368 (MH$^+$) | 222–224° C. | $^1$H-NMR (DMSO-d$_6$) δ ppm: 1.25(q, J=7Hz, 3H), 2.33(s, 3H), 4.19(q, J=7Hz, 2H), 5.09(s, 2H), 6.45(d, J=2Hz, 1H), 6.56(dd, J=2, 8Hz, 1H), 6.89(d, J=8Hz, 1H), 7.62(s, 2H), 7.84(s, 1H), 9.48(s, 1H) |
| 1025 | ethyl [1-(10H-pyrazino[2,3-b][1,4]benzothiazin-8-ylmethyl)-4-methylimidazol-5-yl]carboxylate | ESI (+) 368 (MH$^+$) | 194–196° C. | $^1$H-NMR (DMSO-d$_6$) δ ppm: 1.23(t, J=7Hz, 3H), 2.38(s, 3H), 4.18(q, J=7Hz, 2H), 5.30(s, 2H), 6.48(s, 1H), 6.45–6.54(m, 1H), 6.86(d, J=8Hz, 1H), 7.64(s, 2H), 7.94(s, 1H), 9.52(s, 1H) |
| 1026 | methyl (E)-3-[1-(10H-pyrazino[2,3-b][1,4]benzothiazin-8-ylmethyl)imidazol-4-yl]propenoate | ESI (+) 366.1 (MH$^+$) | 248–250° C. | $^1$H-NMR (DMSO-d$_6$) δ ppm: 3.65(s, 3H), 5.05(s, 2H), 6.33(d, J=15.6Hz, 1H), 6.56(s, 1H), 6.66(d, J=7.9Hz, 1H), 6.90(d, J=7.9Hz, 1H), 7.49(d, J=15.6Hz, 1H), 7.56(s, 1H), 7.63(s, 2H), 7.81(s, 1H), 9.52(s, 1H) |

Example 1027

Methyl 4-[1-(10H-pyrazino[2,3-b][1,4]benzothiazin-8-ylmethyl)imidazol-4-yl]benzoate trifluoroacetate The title compound was obtained by treating methyl 4-[1-[10-(methoxymethyl)-10H-pyrazino[2,3-b][1,4]benzothiazin-8-ylmethyl)imidazol-4-yl]benzoate by the same method as the one of Example 9.

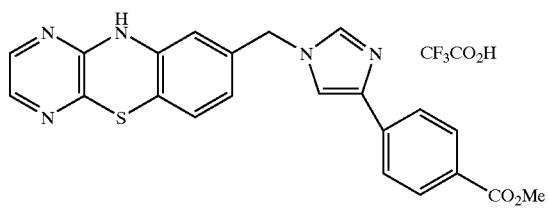

$^1$H-NMR(DMSO-d$_6$) δ ppm: 3.83(s, 3H), 5.19(s, 2H), 6.64(d, J=1 Hz, 1H), 6.76(dd, J=1, 7 Hz, 1H), 6.95(d, J=7 Hz, 1H), 7.64(s, 2H), 7.90(d, J=8 Hz, 2H), 8.00(d, J=8 Hz, 2H), 8.06(s, 1H), 8.75(s, 1H), 9.54(s, 1H)
MS: FAB(+)416(MH$^+$)
m.p.: 161–162° C.

Example 1028

(E)-3-[1-(10H-Pyrazino[2,3-b][1,4]benzothiazin-8-ylmethyl)imidazol-4-yl]-2-propenoic acid The title compound was obtained as yellow crystals by treating methyl(E)-3-[1-[10-(methoxymethyl)-10H-pyrazino[2,3-b][1,4]benzothiazin-8-ylmethyl)imidazol-4-yl]propenoate successively by the same methods as those of Examples 434 and 18.

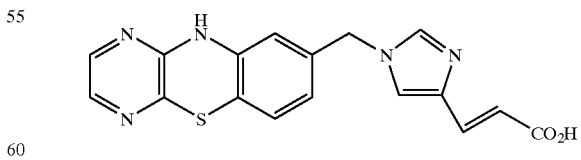

$^1$H-NMR(DMSO-d$_6$) δ ppm: 5.04(s, 2H), 6.26(d, J=15.4 Hz, 1H), 6.56(s, 1H), 6.65(d, J=7.9 Hz, 1H), 6.90(d, J=7.9 Hz, 1H), 7.41(d, J=15.4 Hz, 1H), 7.52(s, 1H), 7.63(s, 2H), 7.89(s, 1H), 9.52(s, 1H)
MS: ESI(+)352.2(MH$^+$)
m.p.: 275–276° C.

Examples

The following compounds were obtained by treating the compounds obtained in Examples 1021, 1022 and 1023 successively by the same methods as those of Examples 9 and 18.

| Ex. | Structural formula | MS | M. p. | NMR |
|---|---|---|---|---|
| 1029 | 4-[1-(10H-pyrazino-[2,3-b][1,4]benzo-thiazin-8-ylmethyl)-imidazol-4-yl]benzoic acid trifluoroacetate · CF$_3$CO$_2$H | FAB (+) 402 (M$^+$) | 264–266° C. | $^1$H-NMR (DMSO-d$_6$) δ ppm: 5.20(s, 2H), 6.64(d, J=1Hz, 1H), 6.77(dd, J=1, 7Hz, 1H), 6.94(d, J=7Hz, 1H), 7.64(s, 2H), 7.86(d, J=8Hz, 2H), 7.97(d, J=8Hz, 2H), 8.18(s, 1H), 8.65(s, 1H), 9.54(s, 1H) |
| 1030 | 4-[1-(10H-pyrazino[2,3-b][1,4]benzothiazin-8-ylmethyl)imidazol-2-ylmethyl]benzoic acid | FAB (+) 416 (MH$^+$) | 185–188° C. | $^1$H-NMR (DMSO-d$_6$) δ ppm: 4.03(s, 2H), 4.94(s, 2H), 6.42(s, 1H), 6.44(d, J=8Hz, 1H), 6.78(d, J=8Hz, 1H), 6.85(s, 1H), 7.11(s, 1H), 7.20(d, J=8Hz, 2H), 7.63(s, 2H), 7.78(d, J=8Hz, 2H), 9.45(s, 1H), 13.50(br.s, 1H) |
| 1031 | 4-[1-[10H-pyrazino[2,3-b][1,4]benzothiazin-8-ylmethyl]imidazol-2-ylcarbonyl]benzoic acid | FAB (+) 430 (MH$^+$) | 242–246° C. | $^1$H-NMR (DMSO-d$_6$) δ ppm: 5.53(s, 2H), 6.55(d, J=1Hz, 1H), 6.62(dd, J=1, 8Hz, 1H), 6.87(d, J=8Hz, 1H), 7.33(s, 1H), 7.62(s, 2H), 7.75(s, 1H), 8.04(d, J=8Hz, 2H), 8.25(d, J=8Hz, 2H), 9.51(s, 1H) |

Example 1032

[1-[10-(Methoxymethyl)-10H-pyrazino[2,3-b][1,4] benzothiazin-8-ylmethyl]-5-methylimidazol-4-yl] carboxamide To a solution of 0.7 g of ethyl[1-[10-(methoxymethyl)-10H-pyrazino[2,3-b][1,4]benzothiazin-8-ylmethyl]-5-methylimidazol-4-yl]carboxylate in tetrahydrofuran (10 ml) was added 50 ml of aqueous ammonia. After sealing, the resulting mixture was heated to 100° C. for 24 hours. Then the reaction mixture was concentrated, extracted with dichloromethane, washed with a saturated aqueous solution of sodium chloride and dried over anhydrous magnesium sulfate. After distilling off the solvent under reduced pressure, the residue was purified by silica gel column chromatography (eluted with ethanol/dichloromethane) to thereby give 0.31 g of the title compound as pale yellow crystals.

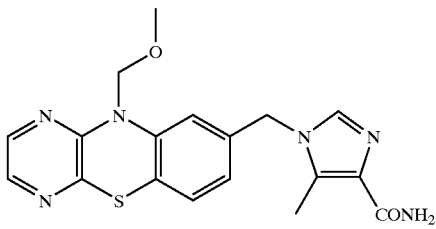

¹H-NMR(DMSO-d₆) δ ppm: 2.35(s, 3H), 3.29(s, 3H), 5.15(s, 4H), 6.73(dd, J=2, 8 Hz, 1H), 6.82(d, J=2 Hz, 1H), 6.92–6.97(m, 1H), 7.11(d, J=8 Hz, 1H), 7.16–7.22(m, 1H), 7.72(s, 1H), 7.92(d, J=3 Hz, 1H), 7.95(d, J=3 Hz, 1H)

Example 1033

[1-[10-(Methoxymethyl)-10H-pyrazino[2,3-b][1,4]benzothiazin-8-ylmethyl]-4-methylimidazol-5-yl] carboxylic acid 0.4 g of the title compound was obtained as a yellow oily substance by treating 0.5 g of ethyl[1-[10-(methoxymethyl)-10H-pyrazino[2,3-b][1,4]benzothiazin-8-ylmethyl]-4-methylimidazol-5-yl]carboxylate by the same method as the one of Example 1032 by conducting the reaction for 60 hours.

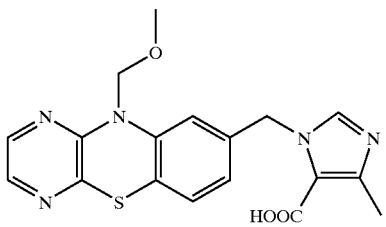

¹H-NMR(DMSO-d₆) δ ppm: 2.34(s, 3H), 3.32(s, 3H), 5.13(s, 2H), 5.47(s, 2H), 6.73(dd, J=2, 8 Hz, 1H), 6.88(d, J=2 Hz, 1H), 7.06(d, J=8 Hz, 1H), 7.73(s, 1H), 7.93(d, J=3 Hz, 1H), 7.97(d, J=3 Hz, 1H)

Example 1034

(E)-3-[1-[10-(Methoxymethyl)-10H-pyrazino[2,3-b][1,4]benzothiazin-8-ylmethyl]-5-methylimidazol-4-yl]-2-methylpropenamide 0.9 g of ethyl(E)-3-[1-[10-(methoxymethyl)-10H-pyrazino[2,3-b][1,4]benzothiazin-8-ylmethyl]-5-methylimidazol-4-yl]-2-methylpropenoate was treated by the same method as the one of Example 18 to thereby give 0.9 g of (E)-3-[1-[10-(methoxymethyl)-10H-pyrazino[2,3-b][1,4]benzothiazin-8-ylmethyl]-5-methylimidazol-4-yl]-2-methylpropenoic acid as yellow crystals. To a solution of 0.9 g of these crystals in tetrahydrofuran (30 ml) were added at, 0° C. 0.83 ml of triethylamine and 0.57 ml of diethyl chlorophosphate. After stirring for 30 minutes, 5 ml of an ammonia-methanol solution was added and the resulting mixture was reacted at room temperature for 2 hours. Then the reaction mixture was poured into water, extracted with ethyl acetate, washed with a saturated aqueous solution of sodium chloride and dried over anhydrous magnesium sulfate. After concentrating under reduced pressure, the residue was purified by silica gel column chromatography (eluted with methanol/dichloromethane) to thereby give 0.27 of the title compound as a yellow oily substance.

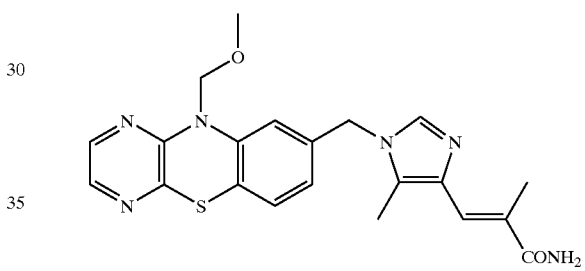

¹H-NMR(CDCl₃) δ ppm: 2.22(s, 3H), 2.51(d, J=1 Hz, 3H), 3.43(s, 3H), 5.02(s, 2H), 5.16(s, 2H), 6.62(dd, J=2, 8 Hz, 1H), 6.78(d, J=2 Hz, 1H), 6.98(d, J=8 Hz, 1H), 7.40–7.43(m, 1H), 7.57(s, 1H), 7.84(d, J=3 Hz, 1H), 7.86(d, J=3 Hz, 1H)

Examples

The following compounds were obtained by treating the compounds obtained in Examples 1032, 1033 and 1034 by the same method as the one of Example 8.

| Ex. | Structural formula | MS | M. p. | NMR |
|---|---|---|---|---|
| 1035 | [1-[10H-pyrazino[2,3-b][1,4]benzothiazin-8-ylmethyl]-5-methylimidazol-4-yl] carboxamide | ESI (+) 339 (MH⁺) | >298° C. | ¹H-NMR (DMSO-d₆) δ ppm: 2.33(s, 3H), 5.03(s, 2H), 6.47(s, 1H), 6.54(d, J=8Hz, 1H), 6.89(d, J=8Hz, 1H), 6.96(br.s, 1H), 7.13–7.25(m, 1H), 7.62(s, 2H), 7.68(br.s, 1H), 9.50(s, 1H) |

| Ex. | Structural formula | MS | M. p. | NMR |
|---|---|---|---|---|
| 1036 | [1-[10H-pyrazino[2,3-b][1,4]benzothiazin-8-ylmethyl]-4-methyl-imidazol-5-yl]-carboxylic acid | ESI (+) 340 (MH⁺) | 235° C. (decompose) | ¹H-NMR (DMSO-d₆) δ ppm: 2.37(s, 3H), 5.32(s, 2H), 6.49(s, 1H), 6.47–6.52(m, 1H), 6.86(d, J=8Hz, 1H), 7.64(s, 2H), 7.97(s, 1H), 9.51(s, 1H) |
| 1037 | (E)-3-[1-(10H-pyrazino[2,3-b][1,4]benzothiazin-8-ylmethyl]-5-methylimidazol-4-yl]-2-methylpropenamide | ESI (+) 379 (MH⁺) | 280° C. (decompose) | ¹H-NMR (DMSO-d₆) δ ppm: 2.11(s, 3H), 2.28(s, 3H), 5.03(s, 2H), 6.49(s, 1H), 6.53(d, J=8Hz, 1H), 6.75–6.90(m, 1H), 6.88(d, J=8Hz, 1H), 7.06(s, 1H), 7.35–7.40(m, 1H), 7.62(s, 2H), 7.74(s, 1H), 9.51(s, 1H) |

Example 1038

[1-[10-(Methoxymethyl)-10H-pyrazino[2,3-b][1,4]benzothiazin-8-ylmethyl]-5-methylimidazol-4-yl]carbaldehyde 0.22 g of the title compound was obtained as yellow crystals by treating 0.68 g of [1-[10-(methoxymethyl)-10H-pyrazino[2,3-b][1,4]benzothiazin-8-ylmethyl]-5-methylimidazol-4-yl]methanol with manganese dioxide by the same method as the one of Example 173.

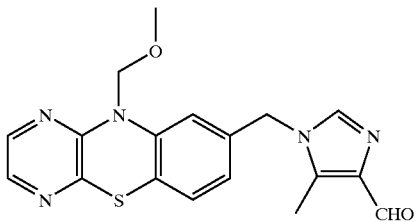

¹H-NMR(CDCl₃) δ ppm: 2.49(s, 3H), 3.45(s, 3H), 5.04(s, 2H), 5.18(s, 2H), 6.63–6.69(m, 1H), 6.80(m, 1H), 7.01(d, J=8 Hz, 1H), 7.53(s, 1H), 7.85(d, J=3 Hz, 1H), 7.87(d, J=3 Hz, 1H), 9.98(s, 1H)

Examples

The following compounds were obtained by the same method as the one of Production Example 25 by starting with [1-[10-(methoxymethyl)-10H-pyrazino[2,3-b][1,4]benzothiazin-8-ylmethyl]-5-methylimidazol-4-yl]carbaldehyde and various Wittig-Horner-Emmons reagents.

| Ex. | Structural formula | NMR |
|---|---|---|
| 1039 | ethyl (E)-3-[1-[10-(methoxymethyl)-10H-pyrazino[2,3-b][1,4]benzothiazin-8-ylmethyl]-5-methylimidazol-4-yl]-2-methylpropenoate | ¹H-NMR (CDCl₃) δ ppm: 1.33(t, J=7Hz, 3H), 2,21(s, 3H), 2.49(d, J=1Hz, 3H), 3.43(s, 3H), 4.25(q, J=7Hz, 2H), 5.03(s, 2H), 5.15(s, 2H), 6.61–6.50(m, 1H), 6.72–6.76(m, 1H), 6.98(d, J=8Hz, 1H), 7.46–7.48(m, 1H), 7.59(s, 1H), 7.85(d, J=3Hz, 1H), 7.86(d, J=3Hz, 1H) |

-continued

| Ex. | Structural formula | NMR |
|---|---|---|
| 1040 | 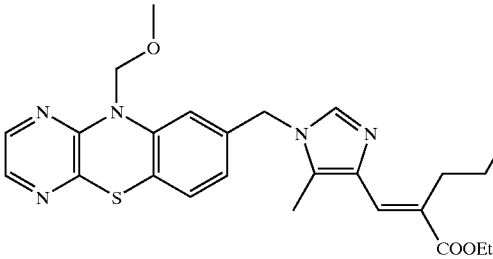<br>ethyl (E)-2-[[1-[10-(methoxymethyl)-10H-pyrazino[2,3-b][1,4]benzothiazin-8-ylmethyl]-5-methylimidazol-4-yl]-methylene]undecanoate | $^1$H-NMR (CDCl$_3$) δ ppm: 0.87(t, J=7Hz, 3H), 1.2–1.4(m, 15H), 1.45–1.57(m, 2H), 2.20(s, 3H), 3.0–3.1(m, 2H), 3.42(s, 3H), 4.24(q, J=7Hz, 2H), 5.01(s, 2H), 5.15(s, 2H), 6.63(dd, J=1, 8Hz, 1H), 6.74(d, J=1Hz, 1H), 6.98(d, J=8Hz, 1H), 7.42(s, 1H), 7.54(s, 1H), 7.84(d, J=3Hz, 1H), 7.86(d, J=3Hz, 1H) |

Examples 1.2 g of [1-[10-(methoxymethyl)-10H-pyrazino[2,3-b][1,4]benzothiazin-8-ylmethyl]-4-methylimidazol-5-yl]carbaldehyde was obtained from 1.6 g of [1-[10-(methoxymethyl)-10H-pyrazino[2,3-b][1,4]benzothiazin-8-ylmethyl]-4-methylimidazol-5-yl]methanol by the same method as the one of Example 173. Next, the obtained product was treated with various Wittig-Horner-Emmons reagents similar to Production Example 25 to thereby give the following compounds.

| Ex. | Structural formula | NMR |
|---|---|---|
| 1041 | 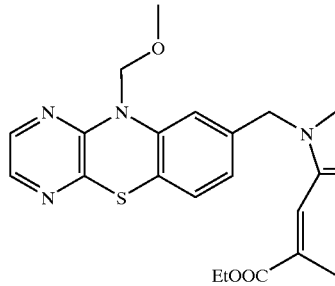<br>ethyl (E)-3-[1-[10-(methoxymethyl)-10H-pyrazino[2,3-b][1,4]benzothiazin-8-ylmethyl]-4-methylimidazol-5-yl]-2-methylpropenoate | $^1$H-NMR (DMSO-d$_6$) δ ppm: 1.17(t, J=7Hz, 3H), 1.74(s, 3H), 1.99(s, 3H), 3.29(s, 3H), 4.10(q, J=7Hz, 2H), 5.08(s, 2H), 5.12(s, 2H), 6.69(dd, J=1, 8Hz, 1H), 6.78(d, J=1Hz, 1H), 7.08(d, J=8Hz, 1H), 7.21(s, 1H), 7.83(s, 1H), 7.92(d, J=3Hz, 1H), 7.95(d, J=3Hz, 1H) |

-continued

| Ex. | Structural formula | NMR |
|---|---|---|
| 1042 | ethyl (E)-2-[1-[10-(methoxymethyl)-10H-pyrazino[2,3-b][1,4]benzothiazin-8-ylmethyl]-4-methylimidazol-5-yl]methylene]butanoate | $^1$H-NMR (DMSO-$d_6$) δ ppm: 0.73(t, J=7Hz, 3H), 1.18(t, J=8Hz, 3H), 1.99(s, 3H), 2.13(q, J=8Hz, 2H), 3.30(s, 3H), 4.12(q, J=8Hz, 2H), 5.07(s, 2H), 5.13(s, 2H), 6.68(d, J=8Hz, 1H), 6.80(s, 1H), 7.07(dd, J=1, 8Hz, 1H), 7.11(s, 1H), 7.83(s, 1H), 7.90–7.94 (m, 1H), 7.94–7.98(m, 1H) |

Example 1043

(E)-2-Hydroxy-5-[1-[10-(methoxymethyl)-10H-pyrazino[2,3-b][1,4]benzothiazin-8-ylmethyl]-5-methylimidazol-4-yl]-2-methyl-4-penten-3-one 0.7 g of the title compound was obtained as a yellow oily substance by reacting 0.5 g of [1-[10-(methoxymethyl)-10H-pyrazino[2,3-b][1,4]benzothiazin-8-ylmethyl]-5-methylimidazol-4-yl]carbaldehyde with 2.1 ml of 3-hydroxy-3-methyl-2-butanone in the presence of lithium hydroxide by the same method as the one of Example 1203.

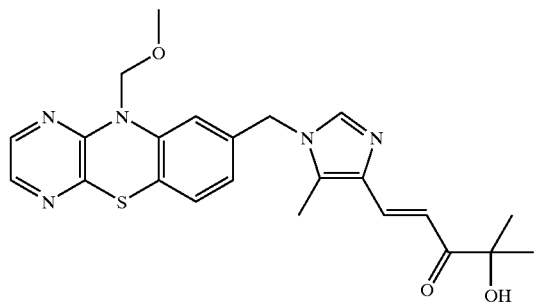

$^1$H-NMR(CDCl$_3$) δ ppm: 1.45(s, 6H), 2.25(s, 3H), 3.43(s, 3H), 5.01(s, 2H), 5.17(s, 2H), 6.60–6.65(m, 1H), 6.80(s, 1H), 6.98(d, J=8 Hz, 1H), 7.15(d, J=16 Hz, 1H), 7.55(s, 1H), 7.77(d, J=16 Hz, 1H), 7.80–7.88(m, 2H)

Example 1044

2-Hydroxy-5-[1-[10-(methoxymethyl)-10H-pyrazino[2,3-b][1,41-benzothiazin-8-ylmethyl]-5-methylimidazol-4-yl]-2-methyl-4-pentan-3-one The title compound was obtained by hydrogenating (E)-2-Hydroxy-5-[1-[10-(methoxymethyl)-10H-pyrazino[2,3-b][1,4]benzothiazin-8-ylmethyl]-5-methylimidazol-4-yl]-2-methyl-4-penten-3-one by the same method as the one of Example 20.

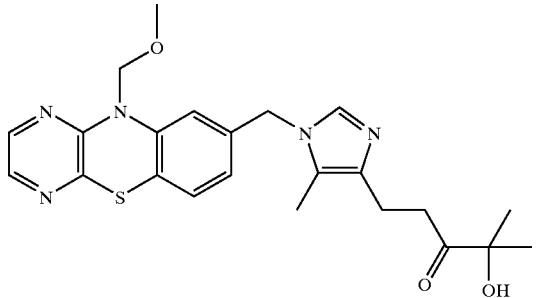

$^1$H-NMR(CDCl$_3$) δ ppm: 1.33(s, 6H), 2.04(s, 3H), 2.86(t, J=7 Hz, 2H), 2.99(t, J=7 Hz, 2H), 3.45(s, 3H), 3.49(s, 1H), 4.94(s, 2H), 5.17(s, 2H), 6.60(dd, J=2, 8 Hz, 1H), 6.78(d, J=2 Hz, 1H), 6.97(d, J=8 Hz, 1H), 7.39(s, 1H), 7.84(d, J=3 Hz, 1H), 7.86(d, J=3 Hz, 1H)

Example 1045

Ethyl(E)-3-[1-(10H-pyrazino[2,3-b][1,4]benzothiazin-8-yl-methyl)imidazol-2-yl]propenoate The title compound was obtained by treating 1-(10-methoxymethyl-10H-pyrazino[2,3-b][1,4]benzothiazin-8-ylmethyl)imidazol-2-carbaldehyde successively by the same methods as those described in Production Example 25 and Example 9.

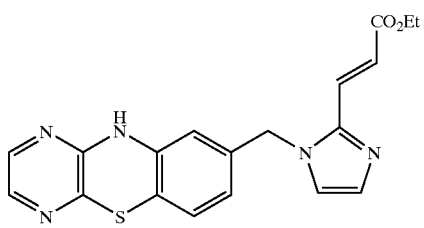

$^1$H-NMR(DMSO-$d_6$) δ ppm: 1.20(t, J=7 Hz, 3H), 4.11(q, J=7 Hz, 2H), 5.25(s, 2H), 6.50(d, J=1 Hz, 1H), 6.52(dd, J=1, 8 Hz, 1H), 6.56(d, J=16 Hz, 1H), 6.87(d, J=8 Hz, 1H), 7.12(s, 1H), 7.34(s, 1H), 7.47(d, J=16 Hz, 1H), 7.63(s, 2H), 9.55(s, 1H)

MS: ESI(+)402.1(MNa$^+$)

m.p.: 213–215° C.

Examples

The following compounds were obtained by the same treatments as those of Examples 18 and 8.

| Ex. | Structural formula | MS | M. p. | NMR |
|---|---|---|---|---|
| 1046 | (E)-3-[1-(10H-pyrazino[2,3-b][1,4]benzothiazin-8-ylmethyl)-5-methylimidazol-4-yl]-2-methyl-2-propenoic acid | ESI (+) 380 (MH$^+$) | >290° C. | $^1$H-NMR (DMSO-d$_6$) δ ppm: 2.12(s, 3H), 2.27(s, 3H), 5.04(s, 2H), 6.48(s, 1H), 6.50–6.60(m, 1H), 6.88(d, J=8Hz, 1H), 7.32(s, 1H), 7.62(s, 2H), 7.79(s, 1H), 9.49(s, 1H) |
| 1047 | (E)-2-[[1-(10H-pyrazino[2,3-b][1,4]benzothiazin-8-ylmethyl)-4-methylimidazol-5-yl]methylene]butanoic acid | ESI (+) 394 (MH$^+$) | >288° C. (decompose) | $^1$H-NMR (DMSO-d$_6$) δ ppm: 0.99(t, J=8Hz, 3H), 2.13(s, 3H), 2.90(q, J=8Hz, 2H), 5.04(s, 2H), 6.50(s, 1H), 6.57(d, J=8Hz, 1H), 6.89(dd, J=2, 8Hz, 1H), 7.28(d, J=2Hz, 1H), 7.60–7.64(m 2H), 7.79(d, J=2Hz, 1H), 9.50(s, 1H) |
| 1048 | (E)-5-methoxy-5-methyl-2-[[1-(10H-pyrazino[2,3-b][1,4]benzothiazin-8-ylmethyl)-5-methylimidazol-4-yl]methylene]hexanoic acid | ESI (+) 466 (MH$^+$) | 202–204° C. | $^1$H-NMR (DMSO-d$_6$) δ ppm: 1.11(s, 6H), 1.48–1.60(m, 2H), 2.13(s, 3H), 2.8–2.93(m, 2H), 3.12(s, 3H), 5.03(s, 2H), 6.51(d, J=2Hz, 1H), 6.58(dd, J=2, 8Hz, 1H), 6.89(d, J=8Hz, 1H), 7.30(s, 1H), 7.62(s, 2H), 7.77(s, 1H), 9.50(s, 1H) |

| Ex. | Structural formula | MS | M. p. | NMR |
|---|---|---|---|---|
| 1049 | (E)-2-[[1-(10H-pyrazino[2,3-b][1,4]benzothiazin-8-ylmethyl)-5-methylimidazol-4-yl]methylene]undecanoic acid | ESI (+) 492 (MH$^+$) | 194–197° C. | $^1$H-NMR (DMSO-d$_6$) δ ppm: 0.81(t, J=8Hz, 3H), 1.18(br.s, 13H), 1.3–1.43(m, 2H), 2.13(s, 3H), 2.6–2.78(m, 2H), 5.13(s, 2H), 6.53(d, J=1Hz, 1H), 6.61(d, J=8Hz, 1H), 6.89(d, J=8Hz, 1H), 7.26(s, 1H), 7.62(s, 2H), 8.2–8.5(m, 1H), 9.52(s, 1H) |
| 1050 | (E)-3-[1-(10H-pyrazino[2,3-b][1,4]benzothiazin-8-ylmethyl)-4-methylimidazol-5-yl]-2-methylpropenoic acid | ESI (+) 380 (MH$^+$) | >298° C. | $^1$H-NMR (DMSO-d$_6$) δ ppm: 1.71(d, J=1Hz, 3H), 1.99(s, 3H), 4.96(s, 2H), 6.41(s, 1H), 6.38–6.46(m, 1H), 6.84(d, J=8Hz, 1H), 7.12(s, 1H), 7.61(s, 2H), 7.75(s, 2H), 9.51(s, 1H) |
| 1051 | (E)-2-[[1-(10H-pyrazino[2,3-b][1,4]benzothiazin-8-ylmethyl)-4-methylimidazol-5-yl]methylene]butanoic acid | ESI (+) 394 (MH$^+$) | 172° C. | $^1$H-NMR (DMSO-d$_6$) δ ppm: 0.78(t, J=8Hz, 3H), 2.00–2.20(m, 2H), 2.13(s, 3H), 5.15(s, 2H), 6.40–6.45(m, 1H), 6.55–6.63(m, 1H), 6.88(d, J=8Hz, 1H), 7.00(s, 1H), 7.63(s, 2H), 8.90(m, 1H), 9.49(s, 1H) |

Example 1052

(E)-3-[1-(10H-Pyrazino[2,3-b][1,4]benzothiazin-8-ylmethyl)imidazol-2-yl]propenoic acid The title compound was obtained by treating ethyl(E)-3-[1-(10H-Pyrazino[2,3-b][1,4]benzothiazin-8-ylmethyl)imidazol-2-yl]propenoate by the same method as the one of Example 18.

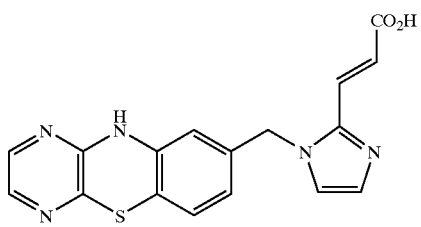

$^1$H-NMR(DMSO-d$_6$) δ ppm: 5.26(s, 2H), 6.46(d, J=1 Hz, 1H), 6.50(dd, J=1, 8 Hz, 1H), 6.52(d, J=16 Hz, >1H), 6.88(d, J=8 Hz, 1H), 7.12(s, 1H), 7.37(d, J=16 Hz, 1H), 7.39(s, 1H), 7.62(s, 2H), 9.52(s, 1H)

MS: ESI(+)352.2(MH⁺)

m.p.: 243–244° C.

Example 1053

1-(10H-Pyrazino[2,3-b][1,4]benzothiazin-8-ylmethyl)imidazol-2-carboxylic acid

To a solution of 177 mg of 1-(10-methoxymethyl-10H-pyrazino[2,3-b][1,4]benzothiazin-8-ylmethyl)imidazol-2-carbaldehyde in a mixture of tetrahydrofuran (10 ml) with ethanol (10 ml) were added 0.5 ml of an aqueous solution of 0.24 g of silver nitrate and 1.5 N sodium hydroxide (4 ml) and the resulting mixture was stirred at room temperature for 15 hours. After filtering off the insoluble matters, the solution was concentrated under reduced pressure and the crystals of 1-(10-methoxymethyl-10H-pyrazino[2,3-b][1,4]benzothiazin-8-ylmethyl)imidazol-2-carboxylic acid thus precipitated were taken up by filtration. Next, the crystals were treated by the same method as the one of Example 9 to thereby give 55 mg of the title compound as orange crystals.

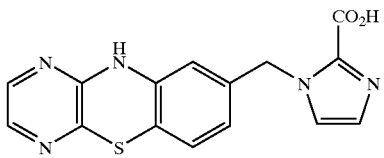

$^1$H-NMR(DMSO-d$_6$) δ ppm: 5.61(s, 2H), 6.56(d, J=8 Hz, 1H), 6.65(s, 1H), 6.78(s, 1H), 6.81(d, J=8 Hz, 1H), 7.05(s, 1H), 7.61(s, 2H), 9.55(s, 1H)

MS: ESI(+)281(M⁺–CO$_2$)

m.p.: 219–220° C.

Example 1054

N-[2-[1-(10H-Pyrazino[2,3-b][1,4]benzothiazin-8-ylmethyl)-imidazol-4-yl]ethyl]methanesulfonamide 0.5 g of 10-methoxymethyl-8-chloromethyl-10H-pyrazino-[2,3-b][1,4]benzothiazine and 1.0 g of 4-(2-aminoethyl)imidazole dihydorchloride were treated by the same method as the one of Example 1094 to thereby give 0.7 g of crude 8-[4-(2-aminoethyl)imidazol-1-yl]-10-methoxymethyl-10H-pyrazino[2,3-b][1,4]benzothiazine as a brown solid. This crude product was then treated by the same method as the one of Example 316 to thereby give 0.1 g of N-[2-[1-(10-methoxymethyl-10H-pyrazino[2,3-b][1,4benzothiazin-8-ylmethyl)imidazol-4-yl]ethyl] methanesulfonamide. Further, it was treated by the same method as the one of Example 8 to thereby give 50 mg of the title compound as yellow crystals.

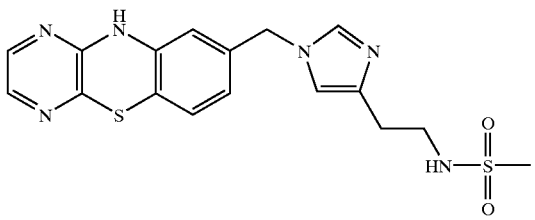

$^1$H-NMR(CDCl$_3$) δ ppm: 2.80(t, J=6 Hz, 2H), 2.94(s, 3H), 3.44(q, J=6 Hz, 2H), 4.92(s, 2H), 5.40–5.50(m, 1H), 6.20(d, J=2 Hz, 1H), 6.64(dd, J=2, 8 Hz, 1H), 6.73(d, J=1 Hz, 1H), 6.86(d, J=8 Hz, 1H), 6.90–6.98(m, 1H), 7.44(d, J-1 Hz, 1H), 7.56(d, J=3 Hz, 1H), 7.68(d, J=3 Hz, 1H)

MS: ESI(+)403(MH⁺)

m.p.: 173–176° C.

Example 1055

N-[2-[1-[10-(Methoxymethyl)-10H-pyrazino[2,3-b][1,4]-benzothiazin-8-ylmethyl]imidazol-4-yl]ethyl] sulfamide 0.25 g of the title compound was obtained as yellow crystals by treating 1.0 g of 8-[4-(2-aminoethyl)imidazol-1-yl]-10-(methoxymethyl)-10H-pyrazino[2,3-b][1,4]-benzothiazine and 0.23 g of sulfamide by the same method as the one of Example 326.

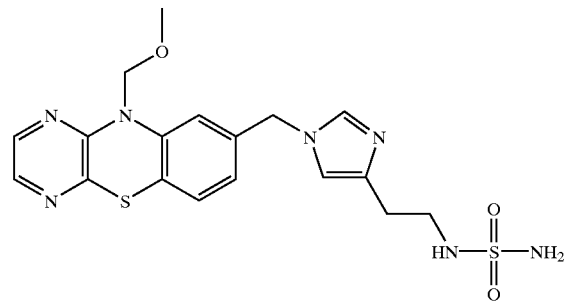

$^1$H-NMR(DMSO-d6) δ ppm: 2.62(t, J=BHz, 2H), 3.02–3.10(m, 2H), 3.33(s, 3H), 5.06(s, 2H), 5.19(s, 2H), 6.50(s, 3H), 6.85(dd, J=1, 8 Hz, 1H), 6.92(s, 1H), 6.95(m, 1H), 7.10(d, J=8 Hz, 1H), 7.63(s, 1H), 7.92(d, J=3 Hz, 1H), 7.95(d, J=3 Hz, 1H)

Example 1056

N-[2-[1-(10H-Pyrazino[2,3-b][1,4]benzothiazin-8-ylmethyl)-imidazol-4-yl]ethyl]sulfamide The title compound was obtained as yellow crystals by treating N-[2-[1-[10-(methoxymethyl)-10H-pyrazino[2,3-b][1,4]-benzothiazin-8-ylmethyl]imidazol-4-yl]ethyl] sulfamide by the same method as the one of Example 8.

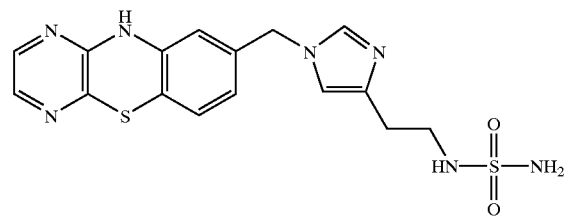

$^1$H-NMR(DMSO-d$_6$) δ ppm: 2.58–2.65(m, 3H), 3.02–3.10(m, 2H), 4.95(s, 2H), 6.50(br.s, 3H), 6.58(d, J=2 Hz, 1H), 6.60–6.65(m, 1H), 6.85(s, 1H), 6.88(d, J=8 Hz, 1H), 7.59(s, 1H), 7.63(s, 2H)

MS: ESI(+)404(MH⁺)

m.p.: 187–189° C.

Example 1057

8-[4-(4-Nitrophenyl)imidazol-1-ylmethyl]-10-methoxymethyl-10H-pyrazino[]2,3-b][1,4] benzothiazine The title compound was synthesized by treating 8-chloromethyl-10-methoxymethyl-10H-pyrazino[2,3-b][1, 4]benzothiazine and 4-(4-nitrophenyl)imidazole by the same method as the one of Example 1094.

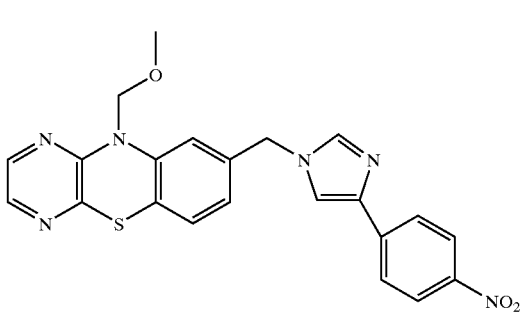

¹H-NMR(CDCl₃) δ ppm: 3.43(s, 3H), 5.09(s, 2H), 5.22(s, 2H), 6.81(dd, J=2, 8 Hz, 1H), 6.96(d, J=2 Hz, 1H), 7.03(d, J=8 Hz, 1H), 7.34(d, J=1 Hz, 1H), 7.65(d, J=1 Hz, 1H), 7.84(d, J=3 Hz, 1H), 7.87(d, J=3 Hz, 1H), 7.89(m, 2H), 8.22(m, 2H)

Example 1058

8-[4-(4-Aminophenyl)imidazol-1-ylmethyl]-10-methoxymethyl-10H-pyrazino[2,3-b][1,4]benzothiazine The title compound was obtained by hydrogenating 8-[4-(4-nitrophenyl)imidazol-1-ylmethyl]-10-methoxymethyl-10H-pyrazino[2,3-b][1,4]benzothiazine by the same method as the one of Example 20.

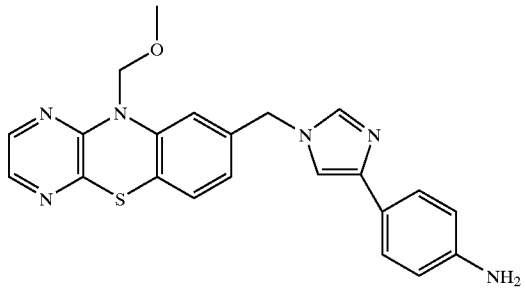

¹H-NMR(CDCl₃) δ ppm: 3.42(s, 3H), 3.67(br.s, 2H), 5.05(s, 2H), 5.18(s, 2H), 6.69(m, 2H), 6.78(dd, J=2, 8 Hz, 1H), 6.89(d, J=2 Hz, 1H), 6.99(d, J=8 Hz, 1H), 7.04(d, J=2 Hz, 1H), 7.54(d, J=2 Hz, 1H), 7.55(m, 2H), 7.83(d, J=3 Hz, 1H), 7.85(d, J=3 Hz, 1H)

Examples

The following compounds were obtained by treating 8-[4-(4-aminophenyl)imidazol-1-ylmethyl]-10-methoxymethyl-10H-pyrazino[2,3-b][1,4]benzothiazine by the same method as the one of Example 316.

| Ex. | Structural formula | NMR |
|---|---|---|
| 1059 N-[4-[1-(10-methoxymethyl-10H-pyrazino[2,3-b][1,4]benzothiazin-8-ylmethyl)imidazol-4-yl]phenyl]methanesulfonamide | | ¹H-NMR (CDCl₃) δ ppm: 2.99(s, 3H), 3.43(s, 3H), 5.08(s, 2H), 5.20(s, 2H), 6.51(br.s, 1H), 6.79(dd, J=2, 8Hz, 1H), 6.93(d, J=2Hz, 1H), 7.01(d, J=8Hz, 1H), 7.16(d, J=1Hz, 1H), 7.21(d, J=8Hz, 2H), 7.61(d, J=1Hz, 1H), 7.73(d, J=8Hz, 2H), 7.84(d, J=3Hz, 1H), 7.86(d, J=3Hz, 1H) |

| Ex. | Structural formula | NMR |
|---|---|---|
| 1060 | 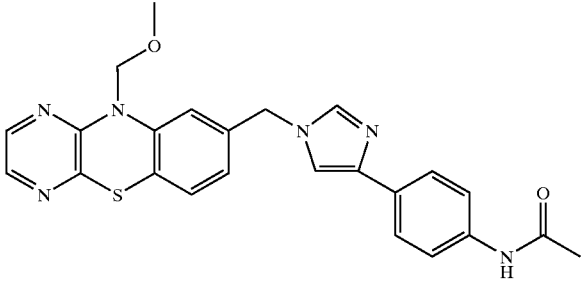<br>N-[4-[1-(10-methoxymethyl-10H-pyrazino[2,3-b][1,4]benzothiazin-8-ylmethyl)imidazol-4-yl]phenyl]acetamide | $^1$H-NMR (CDCl$_3$) δ ppm: 2.18(s, 3H), 3.42 (s, 3H), 5.07(s, 2H), 5.19(s, 2H), 6.80(dd, J=2, 8Hz, 1H), 6.92(d, J=2Hz, 1H), 7.02(d, J=8Hz, 1H), 7.04(m, 2H), 7.19(d, J=1Hz, 1H), 7.62(d, J=1Hz, 1H), 7.76(m, 2H), 7.83–7.85(m, 2H) |

Example 1061

$^1$N-[4-[1-(10-Methoxymethyl-10H-pyrazino[2,3-b][1,4]-benzothiazin-8-ylmethyl)imidazol-4-yl]phenyl]-N$^2$-methanesulfonyl-formamidine The title compound was obtained by treating 8-[4-(4-aminophenyl)imidazol-1-ylmethyl]-10-methoxymethyl-10H-pyrazino[2,3-b][1,4]benzothiazine by the same method as the one of Example 328.

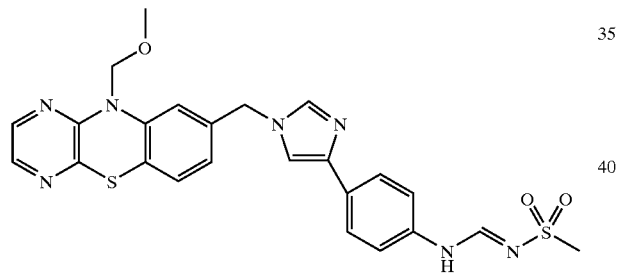

$^1$H-NMR(CDCl$_3$) δ ppm: 3.03 and 3.05(s, total 3H), 3.43(s, 3H), 5.07(s, 2H), 5.20(s, 2H), 6.80(dd, J=2, 8 Hz, 1H), 6.84(d, J=2 Hz, 1H), 7.01(d, J=8 Hz, 1H), 7.11 and 7.65(d, J=8 Hz, total 2H), 7.18(d, J=1 Hz, 1H), 7.61(d, J=1 Hz, 1H), 7.75 and 7.77(d, J=8 Hz, total 2H), 7.84(d, J=3 Hz, 1H), 7.86(d, J=3 Hz, 1H), 7.98 and 8.01(s, total 1H), 8.67 and 8.71(s, total 1H)

Examples

The following compounds were obtained by treating the compounds obtained in Examples 1059, 1060 and 1061 by the same method as the one of Example 9.

| Ex. | Structural formula | MS | M. p. | NMR |
|---|---|---|---|---|
| 1062 | 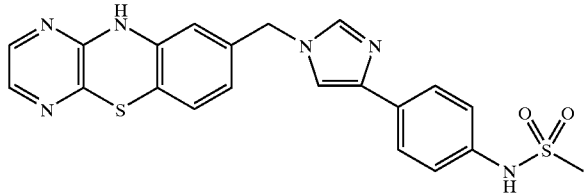<br>N-[4-[1-(10H-pyrazino[2,3-b][1,4]benzothiazin-8-ylmethyl)imidazol-4-yl]phenyl]methanesulfonamide | ESI (+) 451.1 (MH$^+$) | 253–255° C. | $^1$H-NMR (DMSO-d$_6$) δ ppm: 2.97(s, 3H), 5.05(s, 2H), 6.62(d, J=1Hz, 1H), 6.67(dd, J=1, 7Hz, 1H), 6.90(d, J=7Hz, 1H), 7.16(d, J=8Hz, 2H), 7.53(d, J=1Hz, 1H), 7.63(s, 2H), 7.68(d, J=8Hz, 2H), 7.74(d, J=1Hz, 1H), 9.53(s, 1H), 9.65(s, 1H) |

| Ex. | Structural formula | MS | M. p. | NMR |
|---|---|---|---|---|
| 1063 | N-[4-[1-(10H-pyrazino[2,3-b][1,4]benzothiazin-8-ylmethyl)imidazol-4-yl]phenyl]acetamide | FAB (+) 415 (M+) | 261–263° C. | $^1$H-NMR (DMSO-$d_6$) δ ppm: 2.02(s, 3H), 5.04(s, 2H), 6.62(d, J=1Hz, 1H), 6.68(dd, J=1, 7Hz, 1H), 6.90(d, J=7Hz, 1H), 7.49(s, 1H), 7.53(d, J=8Hz, 2H), 7.63(s, 2H), 7.64(d, J=8Hz, 2H), 7.74(s, 1H), 9.53(s, 1H), 9.79(s, 1H) |
| 1064 | $^1$N-[4-[1-(10H-pyrazino[2,3-b][1,4]-benzothiazin-8-ylmethyl)imidazol-4-yl]phenyl]-N$^2$-methanesulfonyl-formamidine | FAB (+) 478 (M+) | 159–162° C. | $^1$H-NMR (DMSO-$d_6$) δ ppm: 3.30(s, 3H), 5.06(s, 2H), 6.61(d, J=1Hz, 1H), 6.69(dd, J=1, 7Hz, 1H), 6.91(d, J=7Hz, 1H), 7.24(d, J=8Hz, 1H), 7.57(s, 1H), 7.62(s, 2H), 7.65(d, J=8Hz, 2H), 7.74(d, J=8Hz, 2H), 7.75(d, J=8Hz, 1H), 8.08(s, 1H), 9.52(s, 1H) |

Example 1065

N-[$^4$-[1-(10-Methoxymethyl-10H-pyrazino[2,3-b][1,4]benzothiazin-8-ylmethyl)imidazol-4-yl]phenyl]hexahydro-2-oxo-1H-thieno[3,4-d]imidazole-4-pentanamide 104 mg of 8-[4-(4-aminophenyl)imidazol-1-ylmethyl3-10-methoxymethyl-10H-pyrazino[2,3-b][1,4]benzothiazine and 91 mg of hexahydro-2-oxo-1H-thieno(3,4-d]imidazole-4-pentanoic acid were treated by the same method as the one of Example 1294. Then the obtained product was purified by using a preparative silica gel plate to thereby give 72 mg of the title compound as yellow crystals.

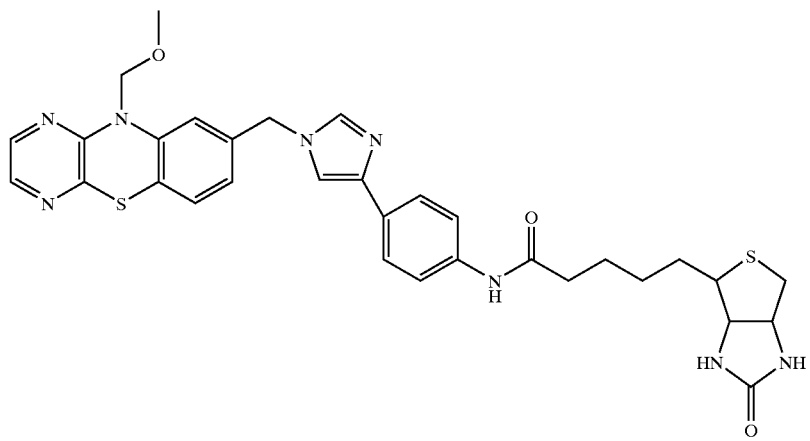

¹H-NMR(DMSO-d₆) δ ppm: 1.4–1.6(m, 6H), 2.28(t, J=6 Hz, 2H), 2.56(d, J=7 Hz, 1H), 2.80(dd, J=3, 7 Hz, 1H), 3.10(m, 1H), 3.30(s, 3H), 4.12(m, 1H), 4.28(m, 1H), 5.15(s, 2H), 5.20(s, 2H), 6.35(s, 1H), 6.43(s, 1H), 6.91(dd, J=2, 8 Hz, 1H), 7.00(d, J=2 Hz, 1H), 7.12(d, J=8 Hz, 1H), 7.54(d, J=8 Hz, 2H), 7.55(d, J=1 Hz, 1H), 7.63(d, J=8 Hz, 2H), 7.77(d, J=1 Hz, 1H), 7.92(d, J=3 Hz, 1H), 7.98(d, J=3 Hz, 1H), 9.84(s, 1H)

Example 1066

N-[4-[1-(10H-Pyrazino[2,3-b][1,4]benzothiazin-8-ylmethyl)imidazol-4-yl]phenyl]-hexahydro-2-oxo-1H-thieno[3,4-d]-imidazole-4-pentanamide The title compound was obtained by treating N-[4-[1-(10-methoxymethyl-10H-pyrazino[2,3-b][1,4]benzothiazin-8-ylmethyl)imidazol-4-yl]phenyl]-hexahydro-2-oxo-1H-thieno[3,4-d]imidazole-4-pentanamide by the same method as the one of Example 9.

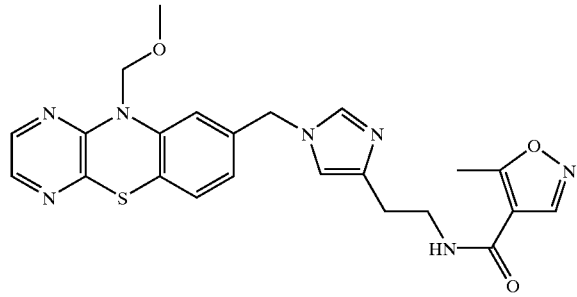

¹H-NMR(DMSO-d₆) δ ppm: 2.58(s, 3H), 2.64(t, J=6 Hz, 2H), 3.32(s, 3H), 3.34–3.42(m, 2H), 5.07(s, 2H), 5.19(s, 2H), 6.80–6.86(m, 1H), 6.90–6.96(m, 2H), 7.07(d, J=8 Hz, 1H), 7.62–7.66(m, 1H), 7.92(d, J=3 Hz, 1H), 7.95(d, J=3 Hz, 1H), 8.33(t, J=6 Hz, 1H), 8.80(s, 1H)

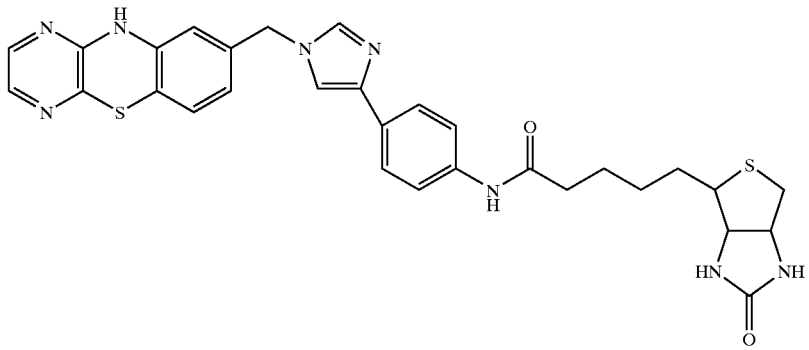

¹H-NMR(DMSO-d₆) δ ppm: 1.4–1.6(m, 6H), 2.28(t, J=6 Hz, 2H), 2.46(d, J=7 Hz, 1H), 2.80(dd, J=3, 7 Hz, 1H), 3.10(m, 1H), 4.09(m, 1H), 4.28(m, 1H), 5.15(s, 2H), 6.35(s, 1H), 6.43(s, 1H), 6.91(dd, J=1, 6 Hz, 1H), 7.00(d, J=1 Hz, 1H), 7.12(d, J=6 Hz, 1H), 7.54(d, J=5 Hz, 2H), 7.54(s, 1H), 7.63(d, J=5 Hz, 2H), 7.77(d, J=1 Hz, 1H), 7.92(d, J=2 Hz, 1H), 7.95(d, J=2 Hz, 1H), 9.53(s, 1H), 9.85(s, 1H)

MS: FAB(+)599(M⁺)

Example 1067

N-[2-[1-[10-(Methoxymethyl)-10H-pyrazino[2,3-b][1,4]benzothiazin-8-ylmethyl)imidazol-4-yl]ethyl]-5-methyl-1,2oxazole-4-carboxamide 0.5 g of the title compound was obtained as a yellow oily substance by dehydrating/condensing 1.5 g of 8-[4-(4-aminoethyl)imidazol-1-ylmethyl]-10H-pyrazino[2,3-b][1,4]benzothiazine with 1.5 g of 5-methyl-1,2-oxazole-4-carboxylic acid by the same method as the one of Example 1294.

Example 1068

N-[2-[1-(10H-Pyrazino[2,3-b][1,4]benzothiazin-8-ylmethyl)imidazol-4-yl]ethyl]-5-methyl-1,2-oxazole-4-carboxamide The title compound was obtained by treating N-[2-[1-[10-(methoxymethyl)-10H-pyrazino[2,3-b][1,4]benzothiazin-8-ylmethyl)imidazol-4-yl]ethyl]-5-methyl-1,2-oxazole-4-carboxamide by the same method as the one of Example 8.

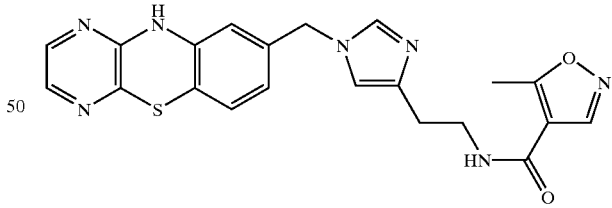

¹H-NMR(DMSO-d₆) δ ppm: 2.59(s, 3H), 2.64(t, J=8 Hz, 2H), 3.3–3.45(m, 2H), 4.95(s, 2H), 6.56(m, 1H), 6.6–6.65(m, 1H), 6.85(d, J=8 Hz, 1H), 6.88(br.s, 1H), 7.63(s, 3H), 8.33(t, J=6 Hz, 1H), 8.90(s, 1H), 9.51(s, 1H)
MS: ESI(+)434(MH⁺)
m.p.: 165–167° C.

Example 1069

N-[2-[1-[10-(Methoxymethyl)-10H-pyrazino[2,3-b][1,4]-benzothiazin-8-ylmethyl]imidazol-4-yl]phenyl]-5-methyl-1,2-oxazole-4-carboxamide The title compound was obtained as a yellow oily substance by dehydrating/condensing 1.5 g of 8-[4-(4- aminophenyl)imidazol-1-ylmethyl]-10H-pyrazino[2,3-b][1,4]benzothiazine with 5-methyl-1,2-oxazole-4-carboxylic acid by the same method as the one of Example 1294.

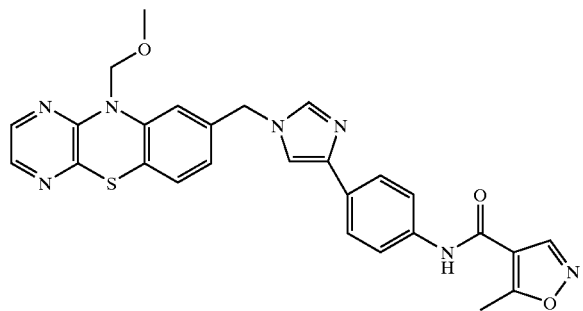

¹H-NMR(CDCl₃) δ ppm: 2.77(s, 3H), 3.43(s, 3H), 5.07(s, 2H), 5.19(s, 2H), 6.80(dd, J=2, 8 Hz, 1H), 6.93(d, J=2 Hz, 1H), 7.01(d, J=8 Hz, 1H), 7.17(d, J=1 Hz, 1H), 7.49(br.s, 1H), 7.56(br.d, J=8 Hz, 2H), 7.59(d, J=1 Hz, 1H), 7.75(d, J=8 Hz, 2H), 7.84(d, J=3 Hz, 1H), 7.86(d, J=3 Hz, 1H), 8.46(br.s, 1H)

Example 1070

N-[2-[1-(10H-Pyrazino[2,3-b][1,4]benzothiazin-⁸-ylmethyl)-imidazol-4-yl]phenyl]-2-cyano-3-oxobutanamide The title compound was obtained by treating N-[2-[1-[10-(methoxymethyl)-10H-pyrazino[2,3-b][1,4]-benzothiazin-8-ylmethyl]imidazol-4-yl]phenyl]-5-methyl-1,2-oxazole-4-carboxamide successively by the same methods as those of Examples 9 and 505.

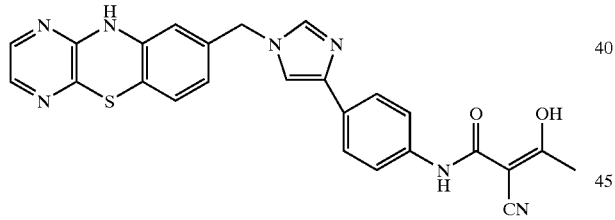

¹H-NMR(DMSO-d₆) δ ppm: 2.66(s, 3H), 5.05(s, 2H), 6.62(d, J=1 Hz, 1H), 6.70(d, J=1, 7 Hz, 1H), 6.91(d, J=7 Hz, 1H), 7.54(d, J=1 Hz, 1H), 7.62(s, 2H), 7.64(d, J=8 Hz, 2H), 7.72(d, J=8 Hz, 2H), 7.75(d, J=1 Hz, 1H), 9.05(s, 1H), 9.52(s, 1H), 10.00(s, 1H)

MS: FAB(+)482(M⁺)

m.p.: 259–261° C.

Example 1071

[1-(10-Methoxymethyl-10H-pyrazino[2,3-b][1,4]benzothiazin-8-ylmethyl)imidazol-2-yl]-(2-pyridyl)methanol The title compound was obtained by treating [1-(10-methoxymethyl-10H-pyrazino[2,3-b][1,4]benzothiazin-8-ylmethyl)imidazol-2-yl](2-pyridyl)ketone by the same method as the one of Example 628.

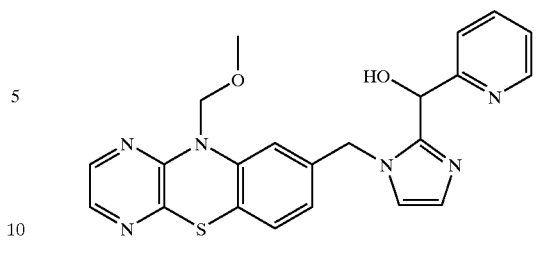

¹H-NMR(CDCl₃) δ ppm: 3.43(s, 3H), 5.12(s, 4H), 5.40 (br.s, 1H), 6.00(s, 1H), 6.64(dd, J=2, 8 Hz, 1H), 6.67(d, J=2 Hz, 1H), 6.85(d, J=8 Hz, 1H), 6.85(d, J=1 Hz, 1H), 7.04(d, J=1 Hz, 1H), 7.13(ddd, J=2, 5, 8 Hz, 1H), 7.23-7.25(m, 1H), 7.59(dt, J=2, 8 Hz, 1H), 7.84(d, J=3 Hz, 1H), 7.85(d, J=3 Hz, 1H), 8.45(ddd, J=1, 2, 5 Hz, 1H)

Example 1072

[1-(10-Methoxymethyl-10H-pyrazino[2,3-b][1,4]benzothiazin-8-ylmethyl)imidazol-2-yl]methanol The title compound was obtained by treating 1-(10-methoxymethyl-10H-pyrazino[2,3-b][1,4]benzothiazin-8-ylmethyl)imidazole-2-carbaldehyde by the same method as the one of Example 628.

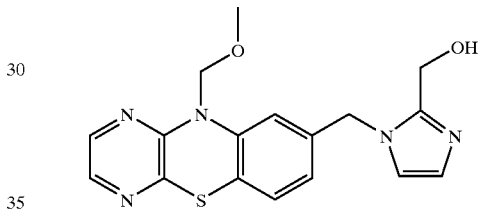

¹H-NMR(CDCl₃) δ ppm: 1.80(br.s, 1H), 3.48(s, 3H), 4.66(s, 2H), 5.14(s, 2H), 5.19(s, 2H), 6.73(dd, J=2, 8 Hz, 1H)., 6.88(d, J=2 Hz, 1H), 6.89(s, 1H), 6.98(d, J=8 Hz, 1H), 6.99(s, 1H), 7.83(d, J=3 Hz, 1H), 7.85(d, J=3 Hz, 1H)

Example 1073

Methyl 4-[[1-(10-methoxymethyl-10H-pyrazino[2,3-b][1,4]benzothiazin-8-ylmethyl)imidazol-2-yl]hydroxymethyl]benzoate The title compound was obtained by treating methyl 4-[1-(10-methoxymethyl-10H-pyrazino[2,3-b][1,4]benzothiazin-8-ylmethyl)imidazol-2-ylcarbonyl]benzoate by the same method as the one of Example 628.

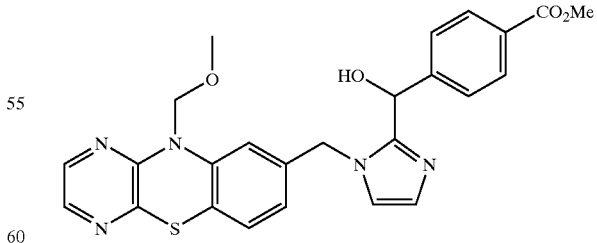

¹H-NMR(CDCl) δ ppm: 3.43(s, 3H), 3.87(s, 3H), 4.80(d, J=16 Hz, 1H), 4.91(d, J=16 Hz, 1H), 5.09(d, J=10Hz, 1H), 5.13(d, J=10Hz, 1H), 5.90(s, 1H), 6.48(dd, J=2, 8 Hz, 1H), 6.61(d, J=2 Hz, 1H), 6.86(d, J=8 Hz, 1H), 6.87(d, J=1 Hz, 1H), 7.06(d, J=1 Hz, 1H), 7.36(d, J=8 Hz, 2H), 7.83(d, J=3 Hz, 1H), 7.85(d, J=3 Hz, 1H), 7.94(d, J=8 Hz, 2H)

Example 1074

4-[[1-(10-Methoxymethyl-10H-pyrazino[2,3-b][1,4]benzothiazin-8-ylmethyl)imidazol-2-yl]hydroxymethyl]benzoic acid The title compound was obtained by treating methyl 4-[[1-(10-methoxymethyl-10H-pyrazino[2,3-b][1,4]benzothiazin-8-ylmethyl)imidazol-2-yl]hydroxymethyl]benzoate by the same method as the one of Example 18.

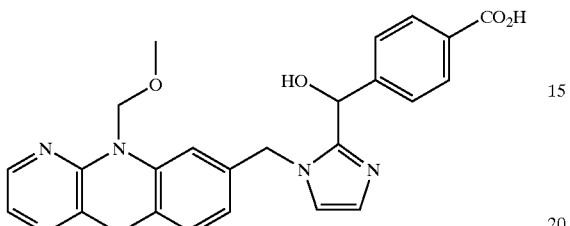

¹H-NMR(CDCl₃) δ ppm: 3.48(s, 3H), 4.95(d, J=16 Hz, 1H), 5.04(d, J=16 Hz, 1H), 5.13(d, J=10Hz, 1H), 5.17(d, J=10Hz, 1H), 5.98(s, 1H), 6.58(dd, J=2, 8 Hz, 1H), 6.72(s, 1H), 6.89–6.91(m, 2H), 7.13(s, 1H), 7.36(d, J=8 Hz, 2H), 7.83(s, 2H), 7.89(d, J=8 Hz, 2H)

Examples

The following compounds were obtained by treating the compounds obtained in Examples 1071, 1072 and 1074 by the same method as the one of Example 9.

| Ex. | Structural formula | MS | M. p. | NMR |
|---|---|---|---|---|
| 1075 | [1-(10H-pyrazino[2,3-b][1,4]benzothiazin-8-ylmethyl)imidazol-2-yl]-(2-pyridyl)methanol | FAB (+) 389 (MH⁺) | 95–98° C. | ¹H-NMR (DMSO-d₆) δ ppm: 5.09(s, 2H), 5.78(d, J=6Hz, 1H), 6.26(d, J=6Hz, 1H), 6.46(dd, J=1, 8Hz, 1H), 6.54(d, J=1Hz, 1H), 6.78(s, 1H), 6.82(d, J=8Hz, 1H), 7.04(s, 1H), 7.22(dd, J=6, 9Hz, 1H), 7.57(d, J=9Hz, 1H), 7.63(s, 2H), 7.75(dt, J=2, 9Hz, 1H), 8.48(dd, J=2, 6Hz, 1H), 9.51(s, 1H) |
| 1076 | [1-(10H-pyrazino[2,3-b][1,4]benzothiazin-8-ylmethyl)imidazol-2-yl]methanol | ESI (+) 312.2 (MH⁺) | 247–250° C. | ¹H-NMR (DMSO-d₆) δ ppm: 4.41(d, J=6Hz, 2H), 5.06(s, 2H), 5.31(t, J=6Hz, 1H), 6.57(d, J=9Hz, 1H), 6.58(s, 1H), 6.80(s, 1H), 6.87(d, J=9Hz, 1H), 7.07(s, 1H), 7.63(s, 2H), 9.51(s, 1H) |

-continued

| Ex. | Structural formula | MS | M. p. | NMR |
|---|---|---|---|---|
| 1077 | 4-[[1-(10H-pyrazino[2,3-b][1,4]benzothiazin-8-ylmethyl)imidazol-2-yl]hydroxymethyl]benzoic acid | FAB (+) 432 (MH+) | 240–241° C. | ¹H-NMR (DMSO-$d_6$) δ ppm: 4.98(d, J=15Hz, 1H), 5.05(d, J=15Hz, 1H), 5.88(d, J=6Hz, 1H), 6.36(d, J=6Hz, 1H), 6.44(d, J=8Hz, 1H), 6.45(s, 1H), 6.78(d, J=8Hz, 1H), 6.84(s, 1H), 7.05(s, 1H), 7.35(d, J=9Hz, 2H), 7.63(s, 2H), 7.81(d, 2H), J=9Hz, 2H), 9.45(s, 1H) |

Example 1078

[1-[10-(Methoxymethyl)-10H-pyrazino[2,3-b][1,4]benzothiazin-8-ylmethyl]-5-methylimidazol-4-yl]methanol The title compound was obtained by treating ethyl[1-[10-(methoxymethyl)-10H-pyrazino[2,3-b][1,4]benzothiazin-8-ylmethyl]-5-methylimidazol-4-yl]carboxylate by the same method as the one of Example 3.

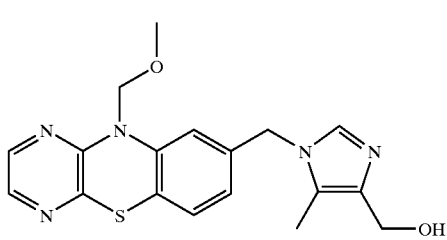

¹H-NMR(CDCl₃) δ ppm: 2.13(s, 3H), 3.46(s, 3H), 4.58(s, 2H), 4.98(s, 2H), 5.18(s, 2H), 6.64(dd, J=2, 8 Hz, 1H), 6.77(d, J=2 Hz, 1H), 6.98(d, J=8 Hz, 1H), 7.45–7.51(m, 1H), 7.84(d, J=3 Hz, 1H), 7.86(d, J=3 Hz, 1H)

Example 1079

[1-[10-(Methoxymethyl)-10H-pyrazino[2,3-b][1,4]benzothiazin-8-ylmethyl]-4-methylimidazol-5-yl]methanol The title compound was obtained by treating ethyl[1-[10-(methoxymethyl)-10H-pyrazino[2,3-b][1,4]benzothiazin-8-ylmethyl]-4-methylimidazol-5-yl]carboxylate by the same method as the one of Example 3.

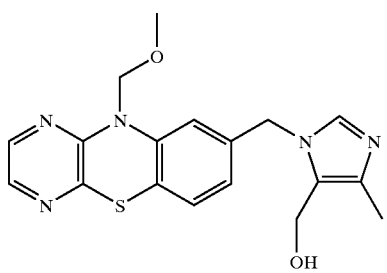

¹H-NMR(CDCl₃) δ ppm: 2.25(s, 3H), 3.46(s, 3H), 4.51(s, 2H), 5.14(s, 2H), 5.19(s, 2H), 6.70–6.76(m, 1H), 6.84–6.87(m, 1H), 6.98–7.00(m, 2H), 7.84(d, J=3 Hz, 1H), 7.86(d, J=3 Hz, 1H)

Examples

The following compounds were obtained by treating the compounds obtained in Examples 1078 and 1079 by the same method as the one of Example 434.

| Ex. | Structural formula | MS | M. p. | NMR |
|---|---|---|---|---|
| 1080 | [1-(10H-pyrazino[2,3-b][1,4]benzothiazin-8-ylmethyl)-5-methylimidazol-4-yl]methanol | ESI (+) 326 (MH$^+$) | >270° C. (decompose) | $^1$H-NMR (DMSO-d$_6$) δ ppm: 2.04(s, 3H), 4.28(s, 2H), 4.60(s, 1H), 4.96(s, 2H), 6.54(d, J=8Hz, 1H), 6.55(s, 1H), 6.89(d, J=8Hz, 1H), 7.55(s, 1H), 7.64(s, 2H), 9.54(s, 1H) |
| 1081 | [1-(10H-pyrazino[2,3-b][1,4]benzothiazin-8-ylmethyl)-4-methylimidazol-5-yl]methanol | ESI (+) 326 (MH$^+$) | 188–192° C. | $^1$H-NMR (DMSO-d$_6$) δ ppm: 2.08(s, 3H), 4.25(d, J=5Hz, 2H), 4.91(t, J=5Hz, 1H), 5.02(s, 2H), 6.50–6.60(m, 2H), 6.88(d, J=8Hz, 1H), 7.53(s, 1H), 7.64(s, 2H), 9.57(s, 1H) |

Example 1082

2-[1-[10-(Methoxymethyl)-10H-pyrazino[2,3-b][1,4]benzothiazin-8-ylmethyl]-5-methylimidazol-4-yl]-2-propanol 0.49 g of the title compound was obtained as a yellow oily substance by treating 0.7 g of ethyl [1-[10-(methoxymethyl)-10H-pyrazino[2,3-b][1,4]benzothiazin-8-ylmethyl]-5-methylimidazol-4-yl]carboxylate with methylmagnesium bromide by the same method as the one of Production Example 86.

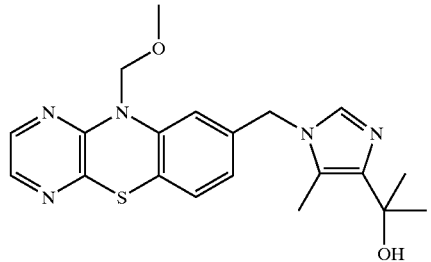

$^1$H-NMR(CDCl$_3$) ppm: 1.58(s, 6H), 2.21(s, 3H), 3.46(s, 3H), 4.97(s, 2H), 5.17(s, 2H), 6.64(d, J=8 Hz, 1H), 6.75(d, J=1 Hz, 1H), 6.98(dd, J=1, 8 Hz, 1H), 7.40(s, 1H), 7.84(dd, J=1, 3 Hz, 1H), 7.85(dd, J=1, 3 Hz, 1H)

Example 1083

2-[1-[10-(Methoxymethyl)-10H-pyrazino[2,3-b][1,4]benzothiazin-8-ylmethyl]-4-methylimidazol-5-yl]-2-propanol and [1-[10-(methoxymethyl)-10H-pyrazino(2,3-b][1,4]benzothiazin-8-ylmethyl]-4-methylimidazol-5-yl]methyl ketone 0.7 g of ethyl[1-[10-(methoxymethyl)-10H-pyrazino[2,3-b][1,4]benzothiazin-8-ylmethyl]-4-methylimidazol-5-yl]-carboxylate was treated with methylmagnesium bromide by the same method as the one of Production Example 86. Thus, 0.4 g of 2-[1-[10-(methoxymethyl)-10H-pyrazino[2,3-b][1,4]benzothiazin-8-ylmethyl]-4-methylimidazol-5-yl]-2-propanol and 80 mg of [1-[10-(methoxymethyl)-10H-pyrazino[2,3-b][1,4]benzothiazin-8-ylmethyl]-4-methylimidazol-5-yl]methyl ketone were obtained each as yellow crystals.

2-[1-[10-(methoxymethyl)-10H-pyrazino[2,3-b][1,4]benzothiazin-8-ylmethyl]-4-methylimidazol-5-yl]-2-propanol

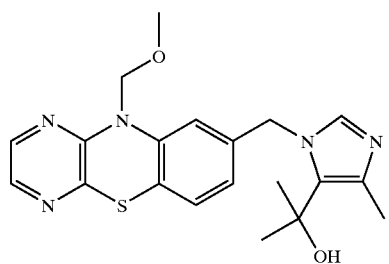

$^1$H-NMR(CDCl$_3$) δ ppm: 1.59(s, 6H), 2.34(s, 3H), 3.48(s, 3H), 5.15(s, 2H), 5.39(s, 2H), 6.64(dd, J=2, 8 Hz, 1H), 6.69(d, J=2 Hz, 1H), 6.95(d, J=8 Hz, 1H), 7.30(s, 1H), 7.83(d, J=3 Hz, 1H), 7.84(d, J=3 Hz, 1H)

[1-[10-(methoxymethyl)-10H-pyrazino[2,3-b][1,4]
benzothiazin-8-ylmethyl]-4-methylimidazol-5-yl]
methyl ketone

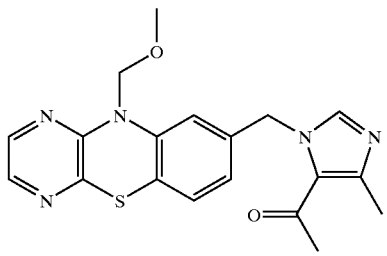

$^1$H-NMR(DMSO-d$_6$) δ ppm: 2.40(s, 3H), 2.48(s, 3H), 3.33(s, 3H), 5.13(s, 2H), 5.42(s, 2H), 6.73(dd, J=2, 8 Hz, 1H), 6.82(d, J=2 Hz, 1H), 7.06(d, J=8 Hz, 1H), 7.93(d, J=3 Hz, 1H), 7.97(d, J=3 Hz, 1H), 7.98(s, 1H)

Example 1084

1-[1-[10-(Methoxymethyl)-10H-pyrazino[2,3-b][1,4]
benzothiazin-8-ylmethyl]-4-methylimidazol-5-yl]
ethanol The title compound was obtained by treating [1-[10-(methoxymethyl)-10H-pyrazino[2,3-b][1,4]benzothiazin-8-ylmethyl]-4-methylimidazol-5-yl]methyl ketone by the same method as the one of Example 628.

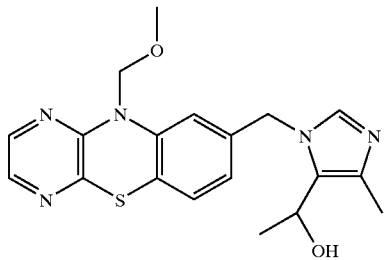

$^1$H-NMR(CDCl1) δ ppm: 1.46(d, J=7 Hz, 3H), 2.30(s, 3H), 3.44(s, 3H), 4.94(q, J=7 Hz, 1H), 5.1–5.25(m, 4H), 6.68–6.74(m, 1H), 6.72(s, 1H), 6.98(d, J=8 Hz, 1H), 7.40(s, 1H), 7.82(d, J=3 Hz, 1H), 7.85(d, J=3 Hz, 1H)

Examples

The following compounds were obtained by treating the compounds obtained in Examples 1082, 1083 and 1084 by the same method as the one of Example 8.

| Ex. | Structural formula | MS | M.p. | NMR |
|---|---|---|---|---|
| 1085 | ![structure] 2-[1-(10H-pyrazino[2,3-b][1,4]benzothiazin-8-ylmethyl)-5-methylimidazol-4-yl]-2-propanol | ESI (+) 354 (MH$^+$) | 264–266° C. | $^1$H-NMR(DMSO-d$_6$) δ ppm: 1.34(s, 6H), 2.18(s, 3H), 4.60(s, 1H), 4.93(s, 2H), 6.54(d, J=7Hz, 1H), 6.57(s, 1H), 6.89(d, J=8Hz, 1H), 7.49(s, 1H), 7.65(s, 2H), 9.55(s, 1H) |
| 1086 | ![structure] 2-[1-(10H-pyrazino[2,3-b][1,4]benzothiazin-8-ylmethyl)-4-methylimidazol-5-yl]-2-propanol | ESI (+) 354 (MH$^+$) | 199–202° C. | $^1$H-NMR(DMSO-d$_6$) δ ppm: 1.41(s, 6H), 2.20(s, 3H), 5.12(s, 1H), 5.30(s, 2H), 6.46(dd, J=2, 8Hz, 1H), 6.53(d, J=2Hz, 1H), 6.87(d, J=8Hz, 1H), 7.38(s, 1H), 7.64(s, 2H), 9.52(s, 1H) |

| Ex. | Structural formula | MS | M.p. | NMR |
|---|---|---|---|---|
| 1087 | ![structure] 1-[1-(10H-pyrazino[2,3-b][1,4]benzothiazin-8-ylmethyl)-4-methylimidazol-5-yl]ethanol | ESI (+) 340 (MH⁺) | 178–182° C. | ¹H-NMR(DMSO-d₆) δ ppm: 1.23(d, J=7Hz, 3H), 2.15(s, 3H), 4.75(br.s, 1H), 5.00–5.20(m, 2H), 6.48–6.56(m, 2H), 6.84–6.92(m, 1H), 7.50(m, 1H), 7.64(s, 2H), 9.52(s, 1H) |

Example 1088

(E)-8-(3-Chloro-1-propen-1-yl)-10-methoxymethyl-10H-pyrazino-[2,3-b][1,4]benzothiazine 2.9 g of ethyl(E)-3-[10-(methoxymethyl)-10H-pyrazino-[2,3-b][1,4]benzothiazin-8-ylmethyl]propenoate was dissolved in 20 ml of dry dichloromethane in a nitrogen atmosphere and ice-cooled. The reaction mixture was stirred and 5.8 ml of a 1.5 M solution of isobutylalminum hydride in toluene was dropped thereinto. After stirring for 2 hours, the reaction mixture was poured into ice-ethyl acetate and stirred for 30 minutes. The insoluble matters were removed by filtering the reaction mixture thorough celite. Then the organic layer was extracted, washed with water and dried over anhydrous sodium sulfate. After distilling off the solvent under reduced pressure, the residue was purified by silica gel column chromatography (eluted with ethyl acetate/n-hexane) to thereby give 1.4 g of 3-[10-(methoxymethyl)-10H-pyrazino-[2,3-b][1,4]benzothiazin-8-ylmethyl]-2-propen-1-ol as a pale yellow oily substance. The obtained compound was dissolved in 10 ml of hexachloroacetone and 1.34 g of triphenylphosphine was added in several portions thereto under ice-cooling. After stirring at room temperature for 30 minutes, the reaction mixture was distributed into an aqueous solution of sodium bicarbonate and diethyl ether and extracted with ether. After drying over anhydrous sodium sulfate and distilling off the solvent under reduced pressure, the residue was purified by silica gel column chromatography (eluted with ethyl acetate/n-hexane) to thereby give 230 mg of the title compound as yellow crystals.

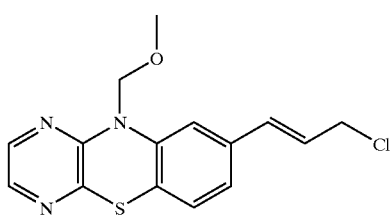

¹H-NMR(CDCl₃) δ ppm: 3.53(s, 3H), 4.23(d, J=7.1 Hz, 2H), 5.27(s, 2H), 6.28(dt, J=7.1, 15.6 Hz, 1H), 6.57(d, J=15.6 Hz, 1H), 6.95(d, J=8.1 Hz, 1H), 7.00(dd, J=1.7, 8.1 Hz, 1H), 7.15(d, J=1.7 Hz, 1H), 7.83(d, J=3.0 Hz, 1H), 7.84(d, J=3.0 Hz, 1H)

Example 1089

(E)-8-[3-(1-Imidazolyl)-1-propen-1-yl]-10-methoxymethyl-10H-pyrazino[2,3-b][1,4]benzothiazine 150 mg of the title compound was obtained as yellow crystals by treating 200 mg of (E)-8-(3-chloro-1-propen-1-yl)-10-methoxymethyl-10H-pyrazino[2,3-b][1,4]benzothiazine with imidazole by the same method as the one of Example 1094.

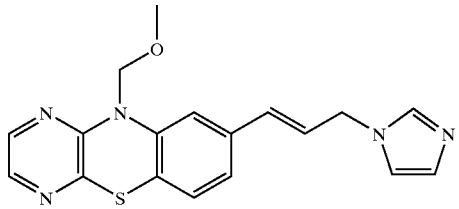

¹H-NMR(CDCl₃) δ ppm: 3.54(s, 3H), 4.72(d, J=6.1 Hz, 2H), 5.28(s, 2H), 6.25(dt, J=6.1, 15.9 Hz, 1H), 6.43(d, J=15.9 Hz, 1H), 6.95(d, J=8.0 Hz, 1H), 6.97(s, 1H), 6.98(dd, J=1.6, 8.0 Hz, 1H), 7.11(s, 1H), 7.13(d, J=1.6 Hz, 1H), 7.56(s, 1H), 7.83(d, J=2.6 Hz, 1H), 7.84(d, J=2.6 Hz, 1H)

Example 1090

(E)-8-[3-(1-Imidazolyl)-1-propen-1-yl]-10H-pyrazino[2,3-b][1,4]benzothiazine

The following compound was obtained by treating (E)-8-[3-imidazolyl)-1-propen-1-yl]-10-methoxymethyl-10H-pyrazino[2,3-b][1,4]benzothiazine by the same method as the one of Example 434.

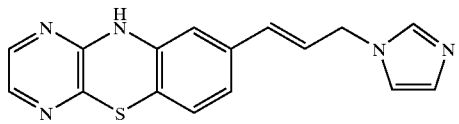

¹H-NMR(DMSO-d₆) δ ppm: 4.73(d, J=5.3 Hz, 2H), 6.26 (td, J=5.3, 15.8 Hz, 1H), 6.30(d, J=15.8 Hz, 1H), 6.75(s, 1H), 6.85(d, J=7.8 Hz, 1H), 6.87(d, J=7.8 Hz, 1H), 6.91(s, 1H), 7.16(s, 1H), 7.61–7.63(m, 2H), 7.65(s, 1H), 9.45(s, 1H)

Example 1091

8-[3-(1-Imidazolyl)-1-propyl]-10H-pyrazino[2,3-b][1,4]benzothiazine

Similar to Example 1094, 3-[10-methoxymethyl-10H-pyrazino[2,3-b][1,4]benzothiazin-8-yl]propyl methanesulfonate was reacted with imidazole and then treated by the same method as the one of Example 434 to thereby give the following compound.

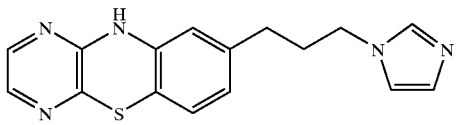

¹H-NMR(CDCl₃) δ ppm: 2.06(quintet, J=7.0 Hz, 2H), 2.44(t, J=7.0 Hz, 2H), 3.93(t, J=7.0 Hz, 2H), 6.30(d, J=1.8 Hz, 1H), 6.63(dd, J=1.8, 8.0 Hz, 1H), 6.82(d, J=8.0 Hz, 1H), 6.86–6.93(br.s, 1H), 6.91(s, 1H), 7.09(s, 1H), 7.50(s, 1H), 7.55(d, J=2.9 Hz, 1H), 7.69(d, J=2.9 Hz, 1H)
MS: ESI(+)310.2(MH⁺)
m.p.: 139–141° C.

Example 1092

8-(Imidazol-1-yl)-10H-pyrazino[2,3-b][1,4]benzoxazine

The following compound was obtained by reacting 8-chloromethyl-10-methoxymethyl-10H-pyrazino[2,3-b][1,4]-benzoxazine with imidazole and then treating by the same method as the one of Example 8.

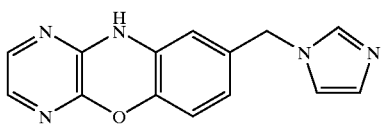

¹H-NMR(DMSO-d₆) δ ppm: 5.04(s, 2H), 6.46(d, J=2 Hz, 1H), 6.59(dd, J=2, 8 Hz, 1H), 6.75(d, J=8 Hz, 1H), 6.87–6.98(m, 1H), 7.10-7.20(m, 1H), 7.27(d, J=3 Hz, 1H), 7.47(d, J=3 Hz, 1H), 7.65–7.78(m, 1H), 9.66(s, 1H)
MS: ESI(+)266(MH⁺)
m.p.: 252–255° C.

Example 1093

4-[1-(10H-Pyrazino[2,3-b][1,4]benzothiazin-8-ylmethyl)imidazol-4-yl]benzamidine 0.092 g of the title compound was obtained by treating 0.44 g of 4-[1-(10H-pyrazino[2,3-b][1,4]benzothiazin-8-ylmethyl)imidazol-4-yl]benzonitrile by the same method as the one of Example 1479.

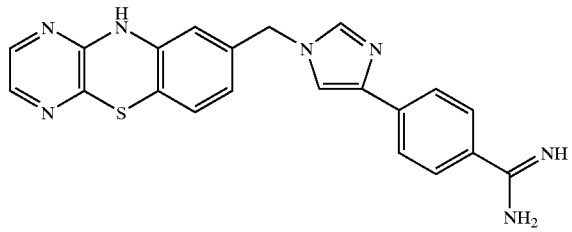

¹H-NMR(DMSO-d,) δ ppm: 5.10(s, 2H), 6.64(d, J=1 Hz, 1H), 6.72(dd, J=1, 7 Hz, 1H), 6.93(d, J=7 Hz, 1H), 7.60(d, J=8 Hz, 2H), 7.64(s, 2H), 7.87(s, 2H), 7.96(d, J=8 Hz, 2H), 9.51(s, 1H)
MS: FAB(+)399(M⁺)

Example 1094

10-Methoxymethyl-8-(pyrazol-1-ylmethyl)-10H-pyrazino[2,3-b][1,4]benzothiazine

To a solution of 100 mg of pyrazole in N,N-dimethylformamide was added in a nitrogen atmosphere 60 mg of sodium hydride (oily 60%) under ice cooling and the resulting mixture was stirred for 10 minutes. Subsequently, 240 mg of 10-methoxymethyl-8-chloromethyl-10H-pyrazino[2,3-b][1,4]benzothiazine was added to the reaction mixture, which was then heated to 80° C. for 10 minutes. Then the reaction mixture was brought back to room temperature and distributed into water and ethyl acetate. The organic layer was extracted, washed with water and dried over anhydrous sodium sulfate. After distilling off the solvent under reduced pressure, the residue thus obtained was purified by silica gel column chromatography (eluted with ethyl acetate/n-hexane) to thereby give 150 mg of the title compound as a yellow powder.

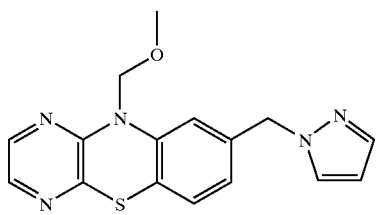

¹H-NMR(CDCl₃) δ ppm: 3.47(s, 3H), 5.20(s, 2H), 5.27(s, 2H), 6.30(t, J=2.1 Hz, 1H), 6.79(dd, J=1.6, 7.8 Hz, 1H), 6.82(d, J=1.6 Hz, 1H), 6.97(d, J=7.8 Hz, 1H), 7.42(d, J=2.1 Hz, 1H), 7.56(d, J=2.1 Hz, 1H), 7.83(d, J=2.9 Hz, 1H), 7.84(d, J=2.9 Hz, 1H)

Example 1095

10-Methoxymethyl-8-(1H-tetrazol-1-ylmethyl)-10H-pyrazino[2,3-b][1,4]benzothiazine. and 10-methoxymethyl-8-(2H-tetrazol-2-ylmethyl)-10H-pyrazino[2,3-b][1,4]benzothiazine The title compounds were obtained by treating 1H-tetrazole and 10-methoxymethyl-8-chloromethyl-10H-pyrazino[2,3-b][1,4]benzothiazine by the same method as the one of Example 1094.

10-methoxymethyl-8-(1H-tetrazol-1-ylmethyl)-10H-pyrazino[2,3-b][1,4]benzothiazine

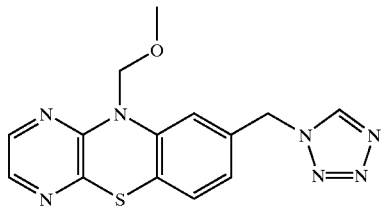

¹H-NMR(CDCl₃) δ ppm: 3.51(s, 3H), 5.33(s, 2H), 5.53(s, 2H), 6.88(dd, J=1.5, 8.1 Hz, 1H), 7.04(d, J=8.1 Hz, 1H), 7.07(d, J=1.5 Hz, 1H), 7.85(d, J=2.7 Hz, 1H), 7.88(d, J=2.7 Hz, 1H), 8.56(s, 1H)

847

10-methoxymethyl-8-(2H-tetrazol-2-ylmethyl)-10H-pyrazino[2,3-b][1,4]benzothiazine

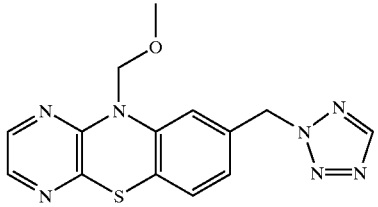

¹H-NMR(CDCl₃) δ ppm: 3.52(s, 3H), 5.23(s, 2H), 5.73(s, 2H), 6.97(dd, J=1.6, 7.8 Hz, 1H), 7.01(d, J=7.8 Hz, 1H), 7.15(d, J=1.6 Hz, 1H), 7.84(d, J=3.0 Hz, 1H), 7.86(d, J=3.0 Hz, 1H), 8.53(s, 1H)

Example 1096

10-Methoxymethyl-8-[1H-pyrrolo[2,3-b]pyridin-1-ylmethyl)-10H-pyrazino[2,3-b][1,4]benzothiazine and 10-methoxymethyl-8-[1H-pyrrolo[2,3-b]pyridin-³-ylmethyl]-10H-pyrazino[2,3-b][1,4]benzothiazine The title compounds were obtained by reacting 1H-pyrrolo[2,3-b]pyridine with 10-methoxymethyl-8-chloromethyl-10H-pyrazino[2,3-b][1,4]benzothiazine by the same method as the one of Example 1094.

848

10-methoxymethyl-8-[1H-pyrrolo[2,3-b]pyridin-1-ylmethyl]-10H-pyrazino[2,3-b][1,4]benzothiazine

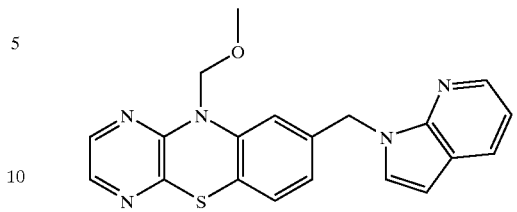

¹H-NMR(CDCl₃) δ ppm: 3.31(s, 3H), 5.09(s, 2H), 5.44(s, 2H), 6.50(d, J=4 Hz, 1H), 6.78(dd, J=2, 8 Hz, 1H), 6.91(d, J=2 Hz, 1H), 6.93(d, J=8 Hz, 1H), 7.09(dd, J=5, 8 Hz, 1H), 7.20(d, J=4 Hz, 1H), 7.81(d, J=3 Hz, 1H), 7.82(d, J=3 Hz, 1H), 7.93(dd, J=1, 8 Hz, 1H), 8.34(dd, J=1, 5 Hz, 1H)

10-methoxymethyl-8-[1H-pyrrolo[2,3-b]pyridin-3-ylmethyl]-10H-pyrazino[2,3-b][1,4]benzothiazine

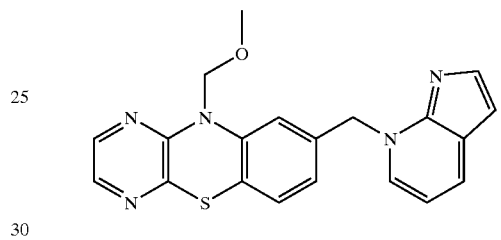

¹H-NMR(CDCl₃) δ ppm: 3.37(s, 3H), 5.13(s, 2H), 5, 84(s, 2H), 6.72(d, J=3 Hz, 1H), 6.91(dd, J=6, 8 Hz, 1H), 6.94(dd, J=2, 8 Hz, 1H), 6.98(d, J=8 Hz, 1H), 7.15(d, J=2 Hz, 1H), 7.60(d, J=6 Hz, 1H), 7.83(d, J=3 Hz, 1H), 7.84(d, J=3 Hz, 1H), 7.92(d, J=3 Hz, 1H), 8.13(d, J=8 Hz, 1H)

Examples

Starting with 10-methoxymethyl-8-chloromethyl-10H-pyrazino[2,3-b][1,4]benzothiazine, the following compounds were obtained by the same method as the one of Example 1094.

| Ex. | Structural formula | NMR |
|---|---|---|
| 1097 | 10-methoxymethyl-8-[2,4(1H,3H)-pyrimidinedion-1-ylmethyl]-10H-pyrazino[2,3-b][1,4]benzothiazine | ¹H-NMR(DMSO-d₆) δ ppm: 3.33(s, 3H), 4.80(s, 2H), 5.19(s, 2H), 5.60(d, J=8.2Hz, 1H), 6.91(d, J=7.9Hz, 1H), 7.02(s, 1H), 7.11(d, J=7.9Hz, 1H), 7.73(d, J=8.2Hz, 1H), 7.93(d, J=3.0Hz, 1H), 7.96(d, J=3.0Hz, 1H), 11.34(br.s, 1H) |

| Ex. | Structural formula | NMR |
|---|---|---|
| 1098 | 10-methoxymethyl-8-(benzimidazol-1-ylmethyl)-10H-pyrazino[2,3-b][1,4]benzothiazine | $^1$H-NMR(DMSO-d$_6$) δ ppm: 3.30(s, 3H), 5.09(s, 2H), 5.31(s, 2H), 6.77(dd, J=1.7, 8.1Hz, 1H), 6.88(d, J=1.7Hz, 1H), 6.97(d, J=8.1Hz, 1H), 7.25–7.33(m, 4H), 7.83(d, J=2.7Hz, 1H), 7.85(d, J=2.7Hz, 1H), 7.96(s, 1H) |
| 1099 | 10-methoxymethyl-8-(1H-imidazo[4,5-b]pyridin-1-ylmethyl)-10H-pyrazino[2,3-b][1,4]benzothiazine | $^1$H-NMR(DMSO-d$_6$) δ ppm: 3.23(s, 3H), 5.14(s, 2H), 5.49(s, 2H), 6.93(d, J=7.8Hz, 1H), 7.02(s, 1H), 7.09(d, J=7.8Hz, 1H), 7.24(dd, J=5.1, 8.1Hz, 1H), 7.91(d, J=2.9Hz, 1H), 7.94(d, J=2.9Hz, 1H), 7.99(d, J=8.1Hz, 1H), 8.40(d, J=5.1Hz, 1H), 8.64(s, 1H) |
| 1100 | 10-methoxymethyl-8-(3H-imidazo[4,5-b]pyridin-3-ylmethyl)-10H-pyrazino[2,3-b][1,4]benzothiazine | $^1$H-NMR(DMSO-d$_6$) δ ppm: 3.23(s, 3H), 5.10(s, 2H), 5.44(s, 2H), 6.94(dd, J=1.2, 8.2Hz, 1H), 7.06(d, J=1.2Hz, 1H), 7.07(d, J=8.2Hz, 1H), 7.28(dd, J=4.9, 8.6Hz, 1H), 7.91(d, J=2.9Hz, 1H), 7.93(d, J=2.9Hz, 1H), 8.09(dd, J=1.2, 8.6Hz, 1H), 8.37(dd, J=1.2, 4.9Hz, 1H), 8.58(s, 1H) |
| 1101 | 10-methoxymethyl-8-(benztriazol-1-ylmethyl)-10H-pyrazino[2,3-b][1,4]benzothiazine | $^1$H-NMR(CDCl$_3$) δ ppm: 3.38(s, 3H), 5.13(s, 2H), 5.79(s, 2H), 6.85(dd, J=2, 8Hz, 1H), 6.97(d, J=8Hz, 1H), 6.99(d, J=2Hz, 1H), 7.35–7.47(m, 3H), 7.82(d, J=3Hz, 1H), 7.84(d, J=3Hz, 1H), 8.08(dt, J=1, 8Hz, 1H) |

| Ex. | Structural formula | NMR |
|---|---|---|
| 1102 | 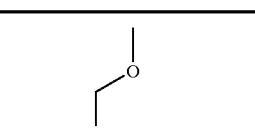<br>10-methoxymethyl-8-(3-indazolinon-2-ylmethyl)-10H-pyrazino[2,3-b][1,4]benzothiazine | $^1$H-NMR(CDCl$_3$) δ ppm: 3.33(s, 3H), 5.12(s, 2H), 5.20(s, 2H), 6.84(dd, J=2, 8Hz, 1H), 6.93(d, J=8Hz, 1H), 6.96(d, J=2Hz, 1H), 7.10(t, J=8Hz, 1H), 7.25(d, J=8Hz, 1H), 7.42(d, J=8Hz, 1H), 7.75(d, J=8Hz, 1H), 7.79(d, J=3Hz, 1H), 7.81(d, J=3Hz, 1H) |

Examples 20

The following compounds were obtained by treating the compounds obtained in Examples 1095 and 1097 by the same method as the one of Example 434.

| Ex. | Structural formula | MS | M.p. | NMR |
|---|---|---|---|---|
| 1103 | 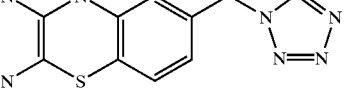<br>8-(1H-tetrazol-1-ylmethyl)-10H-pyrazino[2,3-b][1,4]benzothiazine | | 210–212° C. | $^1$H-NMR(DMSO-d$_6$) δ ppm: 5.54(s, 2H), 6.62(d, J=1.9Hz, 1H), 6.73(dd, J=1.9, 7.8Hz, 1H), 6.92(d, J=7.8Hz, 1H), 7.63(d, J=3.1Hz, 1H), 7.64(d, J=3.1Hz, 1H), 9.48(s, 1H), 9.54(s, 1H) |
| 1104 | 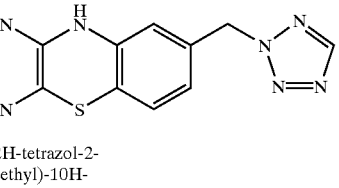<br>8-(2H-tetrazol-2-ylmethyl)-10H-pyrazino[2,3-b][1,4]benzothiazine | | 206–208° C. | $^1$H-NMR(DMSO-d$_6$) δ ppm: 5.78(s, 2H), 6.66(d, J=1.7Hz, 1H), 6.77(dd, J=1.7, 7.8Hz, 1H), 6.91(d, J=7.8Hz, 1H), 7.63(d, J=3.1Hz, 1H), 7.64(d, J=3.1Hz, 1H), 9.00(s, 1H), 9.55(s, 1H) |
| 1105 | 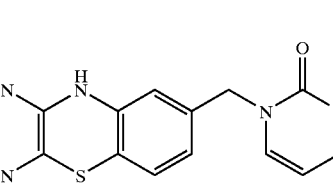<br>8-[2,4(1H,3H)-pyrimidinedion-1-ylmethyl]-10H-pyrazino[2,3-b][1,4]benzothiazine | | 269–271° C. | $^1$H-NMR(DMSO-d$_6$) δ ppm: 4.69(s, 2H), 5.60(d, J=8.4Hz, 1H), 6.62(d, J=1.8Hz, 1H), 6.68(dd, J=1.8, 8.1Hz, 1H), 6.88(d, J=8.1Hz, 1H), 7.63(s, 2H), 7.67(d, J=8.4Hz, 1H), 11.34(br.s, 1H) |

Examples

The following compounds were obtained by treating methoxymethyl compounds by the same method as the one of Example 9.

| Ex. | Structural formula | MS | M.p. | NMR |
|---|---|---|---|---|
| 1106 | 8-[1H-pyrrolo[2,3-b]pyridin-3-ylmethyl]-10H-pyrazino[2,3-b][1,4]benzothiazine | ESI (+) 332 (MH$^+$) | 202–204° C. | $^1$H-NMR(DMSO-d$_6$) δ ppm: 5.28(s, 2H), 6.50(d, J=4Hz, 1H), 6.60–6.63(m, 2H), 6.83(d, J=8Hz, 1H), 7.09(dd, J=5, 8Hz, 1H), 7.55(d, J=4Hz, 1H), 7.61(s, 2H), 7.97(dd, J=1, 8Hz, 1H), 8.23(dd, J=1, 5Hz, 1H), 9.48(s, 1H) |
| 1107 | 8-[1H-pyrrolo[2,3-b]pyridin-7-ylmethyl]-10H-pyrazino[2,3-b][1,4]benzothiazine | FAB (+) 332 (MH$^+$) | 210–214° C. | $^1$H-NMR(DMSO-d$_6$) δ ppm: 5.73(s, 2H), 6.66(s, 1H), 6.72(d, J=2Hz, 1H), 6.86(dd, J=2, 8Hz, 1H), 6.87(d, J=8Hz, 1H), 7.11(dd, J=6, 7Hz, 1H), 7.60(d, J=3Hz, 1H), 7.61(d, J=3Hz, 1H), 8.17(d, J=6Hz, 1H), 8.30(d, J=7Hz, 1H), 9.51(s, 1H) |
| 1108 | 8-(pyrazol-1-ylmethyl)-10H-pyrazino[2,3-b][1,4]benzothiazine | ESI (+) 282 (MH$^+$) | 211–212° C. | $^1$H-NMR(DMSO-d$_6$) δ ppm: 5.14(s, 2H), 6.25(t, J=2.0Hz, 1H), 6.61(d, J=1.5Hz, 1H), 6.61(d, J=8.5Hz, 1H), 6.84(dd, J=1.5, 8.5Hz, 1H), 7.44(d, J=2.0Hz, 1H), 7.62(s, 2H), 7.76(d, J=2.0Hz, 1H), 9.52(s, 1H) |
| 1109 | 8-(benzimidazol-1-ylmethyl)-10H-pyrazino[2,3-b][1,4]benzothiazine | | | $^1$H-NMR(DMSO-d$_6$) δ ppm: 5.33(s, 2H), 6.60(s, 1H), 6.70(d, J=8.1Hz, 1H), 6.87(d, J=8.1Hz, 1H), 7.14–7.23(m, 2H), 7.43(d, J=6.7Hz, 1H), 7.61(s, 1H), 7.65(d, J=6.7Hz, 1H), 8.32(s, 1H), 9.46(s, 1H) |
| 1110 | 8-(benzotriazol-1-ylmethyl)-10H-pyrazino[2,3-b][1,4]benzothiazine | FAB (+) 332 (M$^+$) | 251–258° C. | $^1$H-NMR(DMSO-d$_6$) δ ppm: 5.80(s, 2H), 6.63(d, J=2Hz, 1H), 6.67(dd, J=2, 8Hz, 1H), 6.88(d, J=8Hz, 1H), 7.40(ddd, J=1, 7, 8Hz, 1H), 7.54(ddd, J=1, 7, 8Hz, 1H), 7.61(s, 2H), 7.79(td, J=1, 8Hz, 1H), 8.25(td, J=1, 8Hz, 1H), 9.47(s, 1H) |

-continued

| Ex. | Structural formula | MS | M.p. | NMR |
|---|---|---|---|---|
| 1111 | 8-(3-indazolinon-2-ylmethyl)-10H-pyrazino[2,3-b][1,4]benzothiazine | | >275° C. | ¹H-NMR(DMSO-d₆) δ ppm: 5.15(s, 2H), 6.61(s, 1H), 6.62(d, J=8Hz, 1H), 6.81(d, J=8Hz, 1H), 6.98(t, J=8Hz, 1H), 7.31(t, J=8Hz, 1H), 7.43(d, J=8Hz, 1H), 7.60(s, 2H), 7.61(d, J=8Hz, 1H), 9.38(s, 1H) |
| 1112 | 8-(1H-imidazo[4,5-b]pyridin-2-ylmethyl)-10H-pyrazino[2,3-b][1,4]benzothiazine | | 265° C. (decompose) | ¹H-NMR(DMSO-d₆) δ ppm: 5.37(s, 2H), 6.57(t, J=1Hz, 1H), 6.76(dd, J=1, 8Hz, 1H), 6.91(dd, J=1, 8Hz, 1H), 7.24(dd, J=5, 8Hz, 1H), 7.61(m, 2H), 7.89(dd, J=2, 8Hz, 1H), 8.41(dd, J=2, 5Hz, 1H), 8.58(s, 1H), 9.44(s, 1H) |
| 1113 | 8-(3H-imidazo[4,5-b]pyridin-3-ylmethyl)-10H-pyrazino[2,3-b][1,4]benzothiazine | | 249–251° C. | ¹H-NMR(DMSO-d₆) δ ppm: 5.36(s, 2H), 6.64(t, J=1Hz, 1H), 6.73(dd, J=1, 8Hz, 1H), 6.87(dd, J=1, 8Hz, 1H), 7.29(dd, J=5, 8Hz, 1H), 7.61(m, 2H), 8.10(dd, J=2, 8Hz, 1H), 8.35(dd, J=2, 5Hz, 1H), 8.54(s, 1H), 9.47(s, 1H) |

Examples

The following compounds were obtained by treating 10-methoxymethyl-8-chloromethyl-10H-pyrazino[2,3-b][1,4]-benzothiazine successively by the same methods as those of Examples 1094 and 434.

| Ex. | Structural formula | MS | M.p. | NMR |
|---|---|---|---|---|
| 1114 | 8-(pyrrol-1-ylmethyl)-10H-pyrazino[2,3-b][1,4]benzothiazine | | 197–198° C. | ¹H-NMR(DMSO-d₆) δ ppm: 4.919s, 2H), 6.00(t, J=2.0Hz, 2H), 6.55(d, J=7.9Hz, 1H), 6.58(s, 1H), 6.73(t, J=2.0Hz, 2H), 6.86(d, J=7.9Hz, 1H), 7.62(s, 2H), 9.52(s, 1H) |
| 1115 | 8-(1H-1,2,4-triazol-1-ylmethyl)-10H-pyrazino[2,3-b][1,4]benzothiazine | | 223–226° C. | ¹H-NMR(DMSO-d₆) δ ppm: 5.23(s, 2H), 6.60(d, J=1.6Hz, 1H), 6.67(dd, J=1.6, 7.8Hz, 1H), 6.88(d, J=7.8Hz, 1H), 7.62(s, 2H), 7.98(s, 1H), 8.61(s, 1H), 9.53(s, 1H) |

Example 1116

10-Methoxymethyl-8-(thiazol-2-ylmethyl)-10H-pyrazino[2,3-b][1,4]benzothiazine

150 mg of the title compound was obtained as a yellow oily substance by treating 380 mg of (10-methoxymethyl-10H-pyrazino[2,3-b][1,4]benzothiazin-8-yl)thioacetamide with chloroacetaldehyde by the same method as the one of Example 1125.

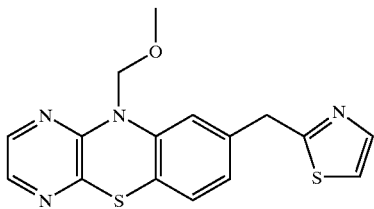

$^1$H-NMR(CDCl$_3$) δ ppm: 3.49(s, 3H), 4.29(s, 2H), 5.25(s, 2H), 6.91(dd, J=1.6, 7.9 Hz, 1H), 6.98(d, J=7.9 Hz, 1H), 7.09(dd, J=1.6 Hz, 1H), 7.24(d, J=3.3 Hz, 1H), 7.72(d, J=3.3 Hz, 1H), 7.84(s, 2H)

Example 1117

O-[[10-(Methoxymethyl)-10H-pyrazino[2,3-b][1,4]benzothiazin-8-yl]-[1-(N,N-dimethylsulfamoyl)imidazol-2-yl]methyl]O-phenyl thiocarbonate

Into a solution of 0.317 g of N,N-dimethyl-2-[[10-(methoxymethyl)-10H-pyrazino[2,3-b][1,4]benzothiazin-8-yl)-hydroxymethyl]]imidazole-1-sulfonamide and 0.117 g of 4-dimethylaminopyridine in acetonitrile (15 ml) was dropped in a nitrogen atmosphere at 0° C. a solution of 0.146 g of phenyl chlorothioformate in acetonitrile (1 ml) and the resulting mixture was stirred at room temperature for 16 hours. Then the reaction mixture was distilled off under reduced pressure and the residue was purified by silica gel column chromatography (eluted with dichloromethane/methanol) to thereby give 0.202 g of the title compound as a yellow oily substance.

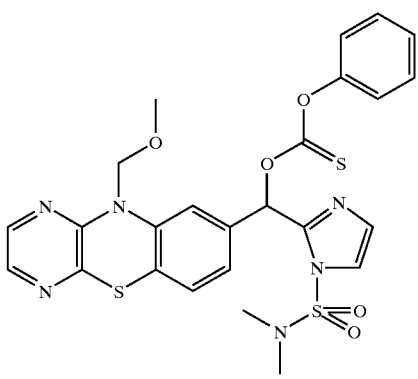

$^1$H-NMR(CDCl$_3$) δ ppm: 2.78(s, 6H), 3.48(s, 3H), 5.17(d, J=10Hz, 1H), 5.22(d, J=10 Hz, 1H), 6.96(d, J=8 Hz, 1H), 7.10–7.41(m, 10H), 7.82(s, 2H)

Example 1118

N,N-Dimethyl-[2-[10-(methoxymethyl)-10H-pyrazino[2,3-b][1,4]benzothiazin-8-yl]methyl]imidazol-1-yl sulfonamide

To a solution of 0.202 g of O-[[10-(methoxymethyl)-10H-pyrazino[2,3-b][1,4]benzothiazin-8-yl]-[1-(N,N-dimethylsulfamoyl)imidazol-2-yl]methyl]O-phenyl thiocarbonate in toluene (15 ml) were added 0.20 ml of tri-n-butyltin hydride and 0.02 g of a,a'-azobis(isobutyronitrile). After degassing, the reaction mixture was heated to 75° C. in a nitrogen atmosphere for 3 hours. After further adding 0.10 ml of tri-n-butyltin hydride, the reaction mixture was heated for 2 hours. After distilling off the solvent under-reduced pressure completely, the residue was purified by silica gel column chromatography (eluted with dichloromethane/methanol) to thereby give 0.064 g of the title compound as a yellow solid.

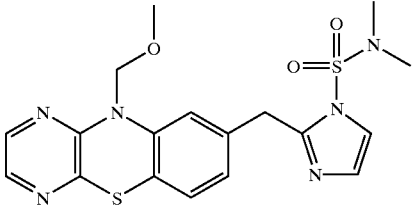

$^1$H-NMR(CDCl$_3$) δ ppm: 2.75(s, 6H), 3.47(s, 3H), 4.38(s, 2H), 5.21(s, 2H), 6.89(dd, J=2, 8 Hz, 1H), 6.94(d, J=8 Hz, 1H), 7.02(d, J=2 Hz, 1H), 7.03(d, J=2 Hz, 1H), 7.24(d, J=2 Hz, 1H), 7.82(d, J=2 Hz, 1H), 7.83(d, J=2 Hz, 1H)

Example 1119

10-(Methoxymethyl)-8-(imidazol-2-ylmethyl)-10H-pyrazino[2,3-b][1,4]benzothiazine

To 0.064 g of N,N-dimethyl-[2–110-(methoxymethyl)-10H-pyrazino[2,3-b][1,4]benzothiazin-8-yl]methyl]imidazol-1-yl]sulfonamide was added 5 ml of a 10% aqueous solution of sodium hydroxide. After degassing, the resulting mixture was heated under reflux in a nitrogen atmosphere for 14 hours. After distilling off the solvent under reduced pressure completely, the residue was purified by silica gel column chromatography (eluted with dichloromethane/methanol) to thereby give 0.020 g of the title compound as a yellow solid.

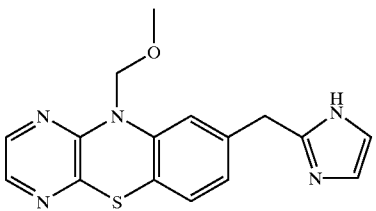

$^1$H-NMR(CDCl$_3$) δ ppm: 3.47(s, 3H), 4.03(s, 2H), 5.20(s, 2H), 6.81(d, J=8 Hz, 1H), 6.92–6.97(m, 4H), 7.82(d, J=3 Hz, 1H), 7.83(d, J=3 Hz, 1H)

Example 1120

8-[2-(Pyridin-4-yl)ethyl]-10-methoxymethyl-10H-pyrazino[2,3-b][1,4]benzothiazine

Similar to Production Example 14, 0.82 g of (10-methoxymethyl-10H-pyrazino[2,3-b][1,4]benzothiazin-8-yl)carbaldehyde was treated with (pyridin-4-ylmethyl)triphenylphosphonium bromide in the presence of tert-butoxypotassium to thereby give 1.10 g of 8-[2-(pyridin-4-yl)vinyl]-10-methoxymethyl-10H-pyrazino[2,3-b][1,4]benzothiazine as yellow crystals. Subsequently, the obtained product was hydrogenated in a solvent mixture of ethanol (20 ml) with tetrahydrofuran (20 ml) in the presence of 0.2 g of 10% palladium-carbon (moisture content: 50%) at room temperature under atmospheric pressure for 5 hours to thereby give 1.00 g of the title compound as yellow crystals.

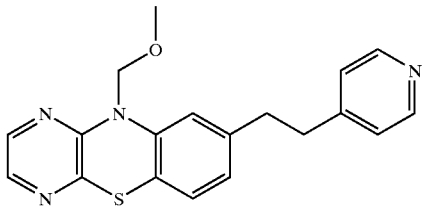

$^1$H-NMR(CDCl$_3$) δ ppm: 2.98(s, 4H), 3.47(s, 3H), 5.19(s, 2H), 6.75(d, J=8 Hz, 1H), 6.87(s, 1H), 6.92(d, J=8 Hz, 1H), 7.54(d, J=8 Hz, 2H), 7.81(d, J=3 Hz, 1H), 7.83(d, J=3 Hz, 1H), 8.48(d, J=8 Hz, 2H)

Example 1121

8-(Thiazol-2-ylmethyl)-10H-pyrazino[2,3-b][1,4]benzothiazine

The title compound was obtained by treating 10-methoxymethyl-8-(thiazol-2-ylmethyl)-10H-pyrazino[2,3-b][1,4]benzothiazine by the same method as the one of Example 434.

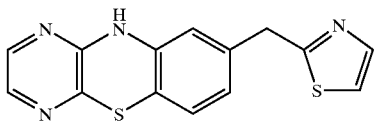

$^1$H-NMR(CDCl$_3$) δ ppm: 4.18(s, 2H), 6.45(d, J=1.7 Hz, 1H), 6.52(br.s, 1H), 6.79(dd, J=1.7, 8.0 Hz, 1H), 6.86(d, J=8.0 Hz, 1H), 7.24(d, J=3.3 Hz, 1H), 7.56(d, J=2.9 Hz, 1H), 7.69(d, J=2.9 Hz, 1H), 7.72(d, J=3.3 Hz, 1H)

MS: ESI(+)298(M$^+$)

m.p.: 160–161° C.

Example 1122

8-(Imidazol-2-ylmethyl)-10H-pyrazino(2,3-b][1,4]benzothiazine

The title compound was obtained as a yellow amorphous product by treating 10-(methoxymethyl)-8-(imidazol-2-ylmethyl)-10H-pyrazino[2,3-b][1,4]benzothiazine by the same method as the one of Example 9.

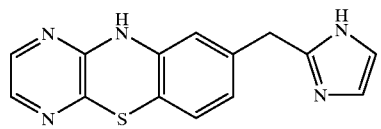

$^1$H-NMR(CD$_3$OD) δ ppm: 3.96(s, 2H), 6.54(s, 1H), 6.68 (d, J=8 Hz, 1H), 6.81(d, J=8 Hz, 1H), 7.01–7.18(br.s, 2H), 7.55(d, J=3 Hz, 1H), 7.56(d, J=3 Hz, 1H)

MS: FAB(+)262(MH$^+$)

Examples

The following compounds were obtained by treating 8-[2-(pyridin-4-yl)vinyl]-10-methoxymethyl-10H-pyrazino[2,3-b][1,4]benzothiazine and 8-[2-(pyridin-4-yl)ethyl]-10-methoxymethyl-1H-pyrazino[2,3-b][1,4]benzothiazine by the same method as the one of Example 8.

| Ex. | Structural formula | MS | M.p. | NMR |
|---|---|---|---|---|
| 1123 | (E)-8-[2-(pyridin-4-yl)vinyl]-10H-pyrazino[2,3-b][1,4]benzothiazine | ESI(+) 305 (MH$^+$) | >275° C. | $^1$H-NMR(DMSO-d$_6$) δ pm: 6.99(d, J=1Hz, 1H), 7.02(d, J=8Hz, 1H), 7.19(dd, J=1, 8Hz, 1H), 7.28(d, J=16Hz, 1H), 7.64(d, J=3Hz, 1H), 7.66(d, J=3Hz, 1H), 7.77(d, J=16Hz, 1H), 8.14(d, J=7Hz, 2H), 8.79(d, J=7Hz, 2H), 9.65(s, 1H) |
| 1124 | 8-[2-(pyridin-4-yl)ethyl]-10H-pyrazino[2,3-b][1,4]benzothiazine | ESI(+) 307 (MH$^+$) | 179–183° C. | $^1$H-NMR(DMSO-d$_6$) δ ppm: 2.62(t, J=8Hz, 2H), 2.82(t, J=8Hz, 2H), 6.59(d, J=2Hz, 1H), 6.75(dd, J=2, 8Hz, 1H), 6.80(d, J=8Hz, 1H), 7.22(d, J=5Hz, 2H), 7.62(d, J=3Hz, 1H), 7.63(d, J=3Hz, 1H), 8.43(d, J=5Hz, 2H), 9.43(s, 1H) |

Example 1125

8-[4-(2-Pyridyl)thiazol-2-ylmethyl]-10H-pyrazino[2,3-b][1,4]benzothiazine

To a solution of 550 mg of (10H-pyrazino[2,3-b][1,4]benzothiazin-8-yl)thioacetamide in a solvent mixture of ethanol (10 ml) with N,N-dimethylformamide (10 ml) was added 560 mg of (2-bromoacetyl)pyridine hydrobromide and the resulting mixture was heated to 60 to 70° C. for 2 hours. Then the reaction mixture was brought back to room temperature and distributed into dichloromethane and an aqueous solution of sodium bicarbonate. After extracting the organic layer, the extract was washed with water and dried over anhydrous sodium sulfate. After distilling off the solvent under reduced pressure, the crystals thus precipitated were washed successively with ethyl acetate and diethyl ether to thereby give 420 mg of the title compound as yellow crystals.

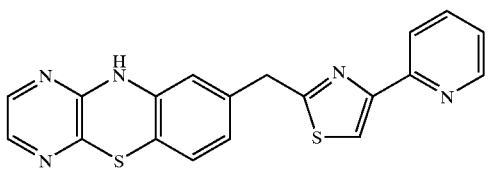

$^1$H-NMR(DMSO-d$_6$) δ ppm: 4.21(s, 2H), 6.77(s, 1H), 6.81(d, J=8.6 Hz, 1H), 6.89(d, J=8.6 Hz, 1H), 7.33(dd, J=5.4, 7.4 Hz, 1H), 7.62(s, 2H), 7.88(t, J=7.4 Hz, 1H), 8.05(d, J=7.4 Hz, 1H), 8.14(s, 1H), 8.59(d, J=5.4 Hz, 1H), 9.52(s, 1H)
m.p.: 194–195° C.

Example 1126

8-(1,2,4-Triazol-3-ylmethyl)-10H-pyrazino[2,3-b][1,4]benzothiazine 330 mg of N-formyl-(10H-pyrazino[2,3-b][1,4]benzothiazin-8-yl)acetamidrazone was dissolved in N,N-dimethylformamide (5 ml) and heated to 120° C. for 2 hours. Then the reaction mixture was brought back to room temperature. After distilling off the solvent under reduced pressure, the obtained residue was crystallized from ethyl acetate/diethyl ether to thereby give 287 mg of the title compound as yellow crystals.

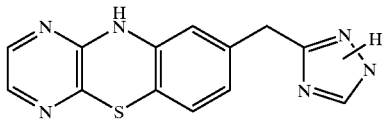

$^1$H-NMR(DMSO-d$_6$) δ ppm: 3.79 and 3.78(br.s, 2H), 6.59–6.69(m, 2H), 6.87–6.88(m, 1H), 7.62(s, 2H), 7.83 and 8.42(br.s, 1H), 9.42–9.51(br.s, 1H), 13.37(br.s, 1H)
MS: FAB(+)282(M$^+$)

Example 1127

8-(6-Methyl-1,4-dihydro-1,2,4,5-tetrazin-3-yl)-10H-pyrazino-[2,3-b][1,4]benzothiazine To a solution of 0.274 g of (10H-pyrazino[2,3-b][1,4]benzothiazin-8-yl)thioacetamide in tetrahydrofuran (40 ml) was added 0.1 ml of hydrazine monohydrate and the resulting mixture was stirred for 30 minutes. After further adding 1.0 ml of hydrazine monohydrate, the mixture was stirred for additional 1 hour. After distilling off the solvent under reduced pressure, the residue was dissolved in ethanol (40 ml) and tetrahydrofuran (20 ml). After adding 5 ml of triethyl orthoacetate, the resulting mixture was heated under reflux for 4 hours. Then the reaction mixture was distilled off under reduced pressure and the residue was purified by silica gel column chromatography (eluted with dichloromethane/methanol) to thereby give 50 mg of the title compound as a pale yellow solid.

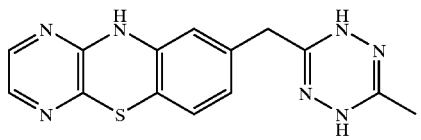

$^1$H-NMR(DMSO-d$_6$) δ ppm: 1.65(s, 3H), 3.12(s, 2H), 6.65(d, J=1 Hz, 1H), 6.70(dd, J=1, 8 Hz, lH), 6.83(d, J=8 Hz, 1H), 7.63(d, J=3 Hz, 1H), 7.64(d, J=3 Hz, 1H), 7.76(s, 1H), 7.83(s, 1H), 9.50(s, 1H)
MS: FAB(+)311(MH$^+$)
m.p.: 233–235° C.

Example 1128

(10-Methoxymethyl-10H-pyrazino[2,3-b][1,4]benzothiazin-8-yl)-(pyridin-3-yl)methanol Into a solution of 0.45 ml of 3-bromopyridine in dry ether (20 ml) was dropped in a nitrogen atmosphere at −78° C. 3.2 ml of a 1.6 M solution of n-butyllithium in hexane and the resulting mixture was stirred for 30 minutes. Then 5 ml of a solution of 450 mg of (10-methoxymethyl-10H-pyrazino[2,3-b][1,4]benzothiazin-8-yl)carbaldehyde in dry tetrahydrofuran was dropped into the reaction mixture and the resulting mixture was stirred at −45 to −20° C. for 1 hour. After adding water carefully, the reaction mixture was extracted with ethyl acetate. The extract was washed with water, dried over anhydrous sodium sulfate and filtered. After distilling off the solvent under reduced pressure, the reside was purified by silica gel column chromatography (eluted with dichloromethane/methanol) to thereby give 500 mg of the title compound as a yellow oily substance.

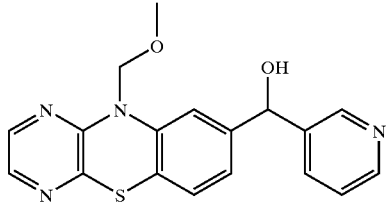

$^1$H-NMR(CDCl$_3$) δ ppm: 2.80–2.93(br.s, 1H), 3.48(s, 3H), 5.22(s, 2H), 5.80(s, 1H), 6.94(br.d, J=8.2 Hz, 1H), 6.99(br.d, J=8.2 Hz, 1H), 7.15(s, 1H), 7.27(dd, J=4.9, 8.2 Hz, 1H), 7.68(br.d, J=8.2 Hz, 1H), 7.83(d, J=3.1 Hz, 1H), 7.84(d, J=3.1 Hz, 1H), 8.50(d, J=4.9 Hz, 1H), 8.61(br.s, 1H)

Examples

Similar to Example 1128, aromatic halides were reacted with (10-methoxymethyl-10H-pyrazino[2,3-b][1,4]benzothiazin-8-yl)carbaldehyde to thereby give the following compounds. Two compounds were obtained by treating 1-bromo-2,4-difluorobenzene with n-butyllithium and then reacting with (10-methoxymethyl-10H-pyrazino[2,3-b][1,4]benzothiazin-8-yl)carbaldehyde.

| Ex. | Structural formula | NMR |
|---|---|---|
| 1129 | (10-methoxymethyl-10H-pyrazino[2,3-b][1,4]benzothiazin-8-yl)-(pyridin-2-yl)methanol | ¹H-NMR(CDCl₃) δ ppm: 3.46(s, 3H), 5.20–5.40(br.s, 1H), 5.22(s, 2H), 5.41(s, 1H), 6.96(s, 2H), 7.15(s, 1H), 7.18(d, J=7.8Hz, 1H), 7.20(dd, J=4.8, 7.8Hz, 1H), 7.63(dt, J=1.5, 7.8Hz, 1H), 7.81(s, 2H), 8.54(d, J=1.5, 4.8Hz, 1H) |
| 1130 | (10-methoxymethyl-10H-pyrazino[2,3-b][1,4]benzothiazin-8-yl)-(pyrazin-2-yl)methanol | ¹H-NMR(CDCl₃) δ ppm: 3.49(s, 3H), 4.40(d, J=6Hz, 1H), 5.25(s, 2H), 5.80(d, J=6Hz, 1H), 6.97(dd, J=2, 8Hz, 1H), 6.99(d, J=8Hz, 1H), 7.20(d, J=2Hz, 1H), 7.82(d, J=3Hz, 1H), 7.83(d, J=3Hz, 1H), 8.51(d, J=3Hz, 1H), 8.52(dd, J=2, 3Hz, 1H), 8.61(d, J=2Hz, 1H) |
| 1131 | (10-methoxymethyl-10H-pyrazino[2,3-b][1,4]benzothiazin-8-yl)-(pyrimidin-5-yl)methanol | ¹H-NMR(CDCl₃) δ ppm: 3.35(s, 3H), 5.24(s, 2H), 5.78(d, J=4Hz, 1H), 6.34(d, J=4Hz, 1H), 7.03(dd, J=2, 8Hz, 1H), 7.08(d, J=8Hz, 1H), 7.20(d, J=2Hz, 1H), 7.93(d, J=3Hz, 1H), 7.96(d, J=3Hz, 1H), 8.77(s, 2H), 9.07(s, 1H) |
| 1132 | (10-methoxymethyl-10H-pyrazino[2,3-b][1,4]benzothiazin-8-yl)-(2-bromopyridin-5-yl)methanol | ¹H-NMR(CDCl₃) δ ppm: 2.52(s, 1H), 3.48(s, 3H), 5.23(s, 2H), 5.77(s, 1H), 6.91(dd, J=2, 8Hz, 1H), 6.99(d, J=8Hz, 1H), 7.13(d, J=2Hz, 1H), 7.42(d, J=8Hz, 1H), 7.53(dd, J=2, 8Hz, 1H), 7.83(d, J=3Hz, 1H), 7.84(d, J=3Hz, 1H), 8.40(d, J=2Hz, 1H) |

| Ex. | Structural formula | NMR |
|---|---|---|
| 1133 | α-(10-methoxymethyl-10H-pyrazino[2,3-b][1,4]benzothiazin-8-yl)benzyl alcohol | ¹H-NMR(CDCl₃) δ ppm: 2.76(br.s, 1H), 3.43(s, 3H), 5.18(d, J=9.0Hz, 1H), 5.22(d, J=9.0Hz, 1H), 5.72(br.s, 1H), 6.92(d, J=7.8Hz, 1H), 6.94(d, J=7.8Hz, 1H), 7.13(s, 1H), 7.23–7.29(m, 1H), 7.30–7.37(m, 4H), 7.79(d, J=2.9Hz, 1H), 7.81(d, J=2.9Hz, 1H) |
| 1134 | α-(10-methoxymethyl-10H-pyrazino[2,3-b][1,4]benzothiazin-8-yl)-3-bromo-2,6-difluorobenzyl alcohol | ¹H-NMR(CDCl₃) δ ppm: 2.73(d, J=8Hz, 1H), 3.47(s, 3H), 5.21(d, J=9Hz, 1H), 5.24(d, J=9Hz, 1H), 6.17(d, J=8Hz, 1H), 6.86(dt, J=3, 9Hz, 1H), 6.86(br.d, J=8Hz, 1H), 6.99(d, J=8Hz, 1H), 7.20(br.s, 1H), 7.49(ddd, J=6, 8, 9Hz, 1H), 7.84(m, 2H) |
| 1135 | α-(10-methoxymethyl-10H-pyrazino[2,3-b][1,4]benzothiazin-8-yl)-2,4-difluorobenzyl alcohol | ¹H-NMR(CDCl₃) δ ppm: 2.78(d, J=9Hz, 1H), 3.44(s, 3H), 5.21(s, 2H), 6.16(d, J=9Hz, 1H), 6.90–6.94(m, 2H), 6.95–7.00(m, 2H), 7.20(s, 1H), 7.24–7.31(m, 1H), 7.84(s, 2H) |
| 1136 | α-(10-methoxymethyl-10H-pyrazino[2,3-b]1,4]benzothiazin-8-yl)-5-bromo-2-fluorobenzyl alcohol | ¹H-NMR(CDCl₃) δ ppm: 2.57(d, J=6Hz, 1H), 3.48(s, 3H), 5.19(d, J=9Hz, 1H), 5.22(d, J=9Hz, 1H), 6.019d, J=6Hz, 1H), 6.90(t, J=9Hz, 1H), 6.96(m, 2H), 7.14(s, 1H), 7.36(ddd, J=3, 5, 9Hz, 1H), 7.69(dd, J=3, 6Hz, 1H), 7.83(s, 2H) |

Example 1137

(10-Methoxymethyl-10H-pyrazino[2,3-b][1,4]benzothiazin-8-yl)-[1-(triphenylmethyl)imidazol-2-yl]methanol 50 ml of a solution of 1.32 g of 1-(triphenylmethyl)imidazole in dry tetrahydrofuran was ice-cooled in a nitrogen atmosphere. After adding 2.8 ml of a 1.6 M solution of n-butyllithium in hexane, the resulting mixture was stirred for 2 hours. Then the reaction mixture was cooled to −78° C. After adding 1.23 g of cerium (III) chloride, the reaction mixture was stirred for 30 minutes. Further, 40 ml of a solution of 0.546 g of (10-methoxymethyl-10H-pyrazino[2,3-b][1,4]benzothiazin-8-yl)carbaldehyde in dry tetrahydrofuran was dropped thereinto. Then the reaction mixture was brought back to room temperature and distributed into an aqueous solution of sodium dihydrogenphosphate and ethyl acetate. After filtering off the inorganic matters, the aqueous layer was extracted with ethyl acetate, washed successively with water and a saturated aqueous solution of sodium chloride and dried over anhydrous sodium sulfate followed by filtration. After distilling off the solvent under reduced pressure, the residue was purified by silica gel column chromatography (eluted with dichloromethane/methanol) to thereby give 716 mg of the title compound as a yellow solid.

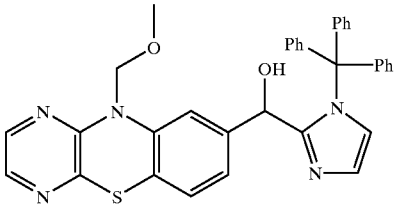

$^1$H-NMR(CDCl$_3$) δ ppm: 2.84(d, J=8 Hz, 1H), 3.44(s, 3H), 4.98(d, J=8 Hz, 1H), 5.07(d, J=9 Hz, 1H), 5.19(d, J=9 Hz, 1H), 6.40(dd, J=2, 8 Hz, 1H), 6.68(d, J=8 Hz, 1H), 6.77(d, J=2 Hz, 1H), 6.78(d, J=2 Hz, 1H), 7.09–7.12(m, 7H), 7.23–7.26(m, 9H), 7.82(s, 2H)

Examples

The following compounds were obtained by starting with (10-methoxymethyl-10H-pyrazino[2,3-b][1,4]benzothiazin-8-yl)carbaldehyde and each of 1-bromo-4-fluorobenzene, 4-bromoanisole and 2-bromothiazole.

| Ex. | Structural formula | NMR |
|---|---|---|
| 1138 | α-(10-methoxymethyl-10H-pyrazino[2,3-b][1,4]benzothiazin-8-yl)-4-fluorobenzyl alcohol | $^1$H-NMR(CDCl$_3$) δ ppm: 2.23(s, 1H), 3.46(s, 3H), 5.21(d, J=9Hz, 1H), 5.24(d, J=9Hz, 1H), 5.76(s, 1H), 6.95(dd, J=2, 8Hz, 1H), 6.98(d, J=8Hz, 1H), 7.039t, J=9Hz, 2H), 7.12(d, J=2Hz, 1H), 7.34(dd, J=5, 9Hz, 2H), 7.83(d, J=3Hz, 1H), 7.84(d, J=3Hz, 1H) |
| 1139 | α-(10-methoxymethyl-10H-pyrazino[2,3-b][1,4]benzothiazin-8-yl)-4-methoxybenzyl alcohol | $^1$H-NMR(CDCl$_3$) δ ppm: 3.53(s, 3H), 3.78(s, 3H), 4.63(s, 1H), 5.29(s, 1H), 5.32(s, 2H), 6.78(d, J=8Hz, 2H), 7.08(d, J=8Hz, 1H), 7.15(d, J=8Hz, 1H), 7.16(s, 1H), 7.36(d, J=8Hz, 2H), 7.87(s, 2H) |

| Ex. | Structural formula | NMR |
|---|---|---|
| 1140 | α-(10-methoxymethyl-10H-pyrazino[2,3-b][1,4]benzothiazin-8-yl)-(thiazol-2-yl)methanol | ¹H-NMR(CDCl₃) δ ppm: 3.44(s, 1H), 3.509s, 3H), 5.26(s, 2H), 6.01(s, 1H), 7.02(d, J=8Hz, 1H), 7.18(dd, J=2, 8Hz, 1H), 7.26(d, J=2Hz, 1H), 7.33(d, J=3Hz, 1H), 7.75(d, J=3Hz, 1H), 7.83(d, J=3Hz, 1H), 7.84(d, J=3Hz, 1H) |

Example 1141

(10-Methoxymethyl-10H-pyrazino[2,3-b][1,4]benzothiazin-8-yl)-(pyrimidin-2-yl)methanol 10 ml of a solution of 1.85 g of 2-(tributylstannyl)pyrimidine in tetrahydrofuran was cooled to −75° C. in a nitrogen atmosphere. Then 3.1 ml of a 1.6 M solution of n-butyllithium in hexane was dropped thereinto. After stirring for 10 minutes, 1.23 g of cerium (III) chloride was added thereto and the reaction mixture was stirred for 30 minutes. Further, 40 ml of a solution of 0.54 g of (10-methoxymethyl-10H-pyrazino[2,3-b][1,4]benzothiazin-8-yl)carbaldehyde in tetrahydrofuran was dropped thereinto. After stirring at −75° C. for 30 minutes, the reaction mixture was brought back to room temperature and distributed into water and ethyl acetate. After filtering off the inorganic matters, the aqueous layer was extracted with ethyl acetate, washed successively with water and a saturated aqueous solution of sodium chloride and dried over anhydrous sodium sulfate followed by filtration. After distilling off the solvent under reduced pressure, the residue was purified by silica gel column chromatography (eluted with dichloromethane/methanol) to thereby give 532 mg of the title compound as a yellow solid.

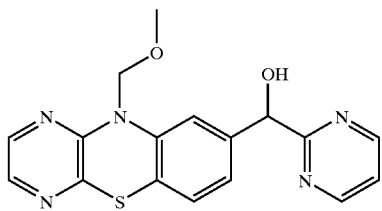

¹H-NMR(CDCl₃) δ ppm: 3.52(s, 3H), 4.98(d, J=6 Hz, 1H), 5.25(d, J=10 Hz, 1H), 5.29(d, J=10 Hz, 1H), 5.80(d, J=6 Hz, 1H), 6.97(d, J=8 Hz, 1H), 7.11(d, J=8 Hz, 1H), 7.23(t, J=5 Hz, 1H), 7.30(s, 1H), 7.81(s, 2H), 8.73(d, J=5 Hz, 2H)

Example 1142

(10-Methoxymethyl-10H-pyrazino[2,3-b][1,4]benzothiazin-8-yl)-(pyridin-4-yl)methanol A solution of 609 mg of phenyl (pyridin-4-yl) sulfoxide in tetrahydrofuran was cooled to −150° C. in a nitrogen atmosphere. Then 1.5 ml of a 2 M solution of phenylmagnesium bromide in tetrahydrofuran was dropped thereinto. After stirring at room temperature for 10 minutes, 3 ml of a solution of 819 mg of (10-methoxymethyl-10H-pyrazino[2,3-b][1,4]benzothiazin-8-yl)carbaldehyde in tetrahydrofuran was dropped into the reaction mixture. After stirring for 10 minutes, the reaction mixture was distributed into water and ethyl acetate. Then the organic layer was extracted, washed with water and dried over anhydrous sodium sulfate followed by filtration. After distilling off the solvent under reduced pressure, the residue was purified by silica gel column chromatography (eluted with dichloromethane/methanol) and recrystallized from ethyl acetate/n-hexane to thereby give 260 mg of the title compound as yellow crystals.

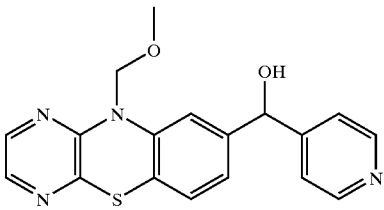

¹H-NMR(CDCl₃) δ ppm: 3.45(s, 3H), 3.58–3.78(br.s, 1H), 5.20(s, 2H), 5.70(s, 1H), 6.91(dd, J=1.5, 8.6 Hz, 1H), 6.96(d, J=8.6 Hz, 1H), 7.15(d, J=1.5 Hz, 1H), 7.31(d, J=6.4 Hz, 2H), 7.83(s, 2H), 8.49(d, J=6.4 Hz, 2H)

Example 1143

(10-Methoxymethyl-10H-pyrazino[2,3-b][1,4]benzothiazin-8-yl)-(imidazo[1,2-a]pyridin-5-yl)methanol To 40 ml of a tetrahydrofuran solution were added 1.20 g of magnesium and 0.1 ml of 1,2-dibromoethane in a nitrogen atmosphere. Subsequently, 10 ml of a solution of 2.96 g of 5-bromoimidazo[1,2-a]pyridine and 2.8 ml of 1,2-dibromoethane in tetrahydrofuran were dropped into the reaction mixture while heating under reflux. Further, 10 ml of a solution of 2.73 g of (10-methoxymethyl-10H-pyrazino[2,3-b][1,4]benzothiazin-8-yl)carbaldehyde in tetrahydrofuran was dropped thereinto. After heating to 50° C. for 1 hour, the reaction mixture was brought back to room temperature and distributed into an aqueous solution of ammonium chloride and ethyl acetate. The organic layer was extracted, washed with water and dried over anhydrous sodium sulfate followed by filtration. After distilling off the solvent under reduced pressure, the residue was purified by silica gel column chromatography (eluted with dichloromethane/methanol) to thereby give 260 mg of the title compound as a yellow oily substance.

¹H-NMR(CDCl₃) δ ppm: 3.45(s, 3H), 3.60–3.85(br.s, 1H), 5.23(s, 2H), 5.74(s, 1H), 6.95(dd, J=1.4, 7.7 Hz, 1H), 6.99(d, J=7.7 Hz, 1H), 7.02(dd, J=1.7, 9.4 Hz, 1H), 7.19(d, J=1.4 Hz, 1H), 7.44(d, J=9.4 Hz, 1H), 7.52(s, 1H), 7.57(d, J=1.7 Hz, 1H), 7.83(d, J=2.6 Hz, 1H), 7.85(d, J=2.6 Hz, 1H), 8.14(s, 1H)

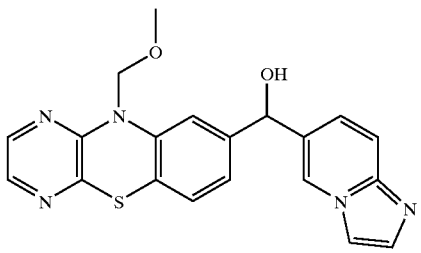

Examples

The following compounds were obtained by the same method as the one of Example 9.

| Ex. | Structural formula | MS | M.p. | NMR |
|---|---|---|---|---|
| 1144 | (10H-pyrazino[2, 3-b][1, 4]benzothiazin-8-yl)-(pyridin-2-yl)methanol | | | ¹H-NMR(CDCl₃) δ ppm: 5.20–5.40(br.s, 1H), 6.50(s, 1H), 6.78–6.83(br.s, 1H), 6.85(s, 2H), 7.18(d, J=7.8Hz, 1H), 7.23(dd, J=5.2, 7.8Hz, 1H), 7.52(d, J=2.6Hz, 1H), 7.66(d, J=2.6Hz, 1H), 7.66(dt, J=1.6, 7.8Hz, 1H), 8.55(dd, J=1.6, 5.2Hz, 1H) |
| 1145 | (10H-pyrazino[2, 3-b][1, 4]benzothiazin-8-yl)-(pyridin-2-yl)methanol | | | ¹H-NMR(DMSO-d₆) δ ppm: 5.79(s, 1H), 6.80(d, J=7.7Hz, 1H), 6.82(s, 1H), 6.89(d, J=7.7Hz, 1H), 7.62(s, 2H), 7.94(dd, J=5.2, 8.6Hz, 1H), 8.35(d, J=8.6Hz, 1H), 8.77(d, J=5.2Hz, 1H), 8.82(s, 1H), 9.49(s, 1H) |
| 1146 | (10H-pyrazino[2, 3-b][1, 4]benzothiazin-8-yl)-(pyridin-2-yl)methanol | | | ¹H-NMR(DMSO-d₆) δ ppm: 5.51(d, J=4.0Hz, 1H), 6.11(d, J=4.0Hz, 1H), 6.78(d, J=7.6Hz, 1H), 6.79(s, 1H), 6.84(d, J=7.6Hz, 1H), 7.31(d, J=5.8Hz, 2H), 7.61(s, 2H), 8.48(d, J=5.8Hz, 2H), 9.43(s, 1H) |

-continued

| Ex. | Structural formula | MS | M.p. | NMR |
|---|---|---|---|---|
| 1147 | (10H-pyrazino[2, 3-b][1, 4]benzothiazin-8-yl)-(pyrimidin-4-yl)methanol | ESI(+) 310 (MH+) | 218–221° C. | $^1$H-NMR(DMSO-d$_6$) δ ppm: 5.65(d, J=4Hz, 1H), 6.26(d, J=4Hz, 1H), 6.80(d, J=8Hz, 1H), 6.83(s, 1H), 6.87(d, J=8Hz, 1H), 7.63(s, 2H), 8.73(s, 2H), 9.07(s, 1H), 9.45(s, 1H) |
| 1148 | (10H-pyrazino[2, 3-b][1, 4]benzothiazin-8-yl)-(pyridin-2-yl)methanol | FAB(+) 310 (MH+) | 105–107° C. | $^1$H-NMR(DMSO-d$_6$) δ ppm: 5.65(d, J=5Hz, 1H), 6.25(d, J=5Hz, 1H), 6.80(d, J=8Hz, 1H), 6.82(s, 1H), 6.86(d, J=8Hz, 1H), 7.64(s, 2H), 8.72(s, 2H), 9.06(s, 1H), 9.45(s, 1H) |
| 1149 | (10H-pyrazino[2, 3-b][1, 4]benzothiazin-8-yl)-(pyridin-2-yl)methanol | | | $^1$H-NMR(CDCl$_3$) δ ppm: 4.64(d, J=4Hz, 1H), 5.78(br.s, 1H), 6.55(br.s, 2H), 6.85(dd, J=1, 8Hz, 1H), 6.88(d, J=8Hz, 1H), 7.55(d, J=3Hz, 1H), 7.68(d, J=3Hz, 1H), 8.52(s, 2H), 8.60(s, 1H) |
| 1150 | (10H-pyrazino[2, 3-b][1, 4]benzothiazin-8-yl)-(thiazol-2-yl)methanol | FAB(+) 314(M+) | 110–114° C. | $^1$H-NMR(CDCl$_3$) δ ppm: 3.48(s, 1H), 5.95(s, 1H), 6.59(d, J=1Hz, 1H), 6.82(d, J=8Hz, 1H), 6.91(dd, J=1, 8Hz, 1H), 7.13(s, 1H), 7.31(d, J=4Hz, 1H), 7.50(d, J=3Hz, 1H), 7.64(d, J=3Hz, 1H), 7.70(d, J=4Hz, 1H) |
| 1151 | (10H-pyrazino[2, 3-b][1, 4]benzothiazin-8-yl)-(imidazol-2-yl)methanol | ESI(+) 298(MH+) | | $^1$H-NMR(DMSO-d$_6$) δ ppm: 5.52(d, J=6Hz, 1H), 6.14(d, J=6Hz, 1H), 6.77(d, J=8Hz, 1H), 6.82(s, 1H), 6.83(d, J=8Hz, 1H), 6.87(br.s, 2H), 7.62(d, J=3Hz, 1H), 7.3(d, J=3Hz, 1H), 9.51(s, 1H) |

| Ex. | Structural formula | MS | M.p. | NMR |
|---|---|---|---|---|
| 1152 | (10H-pyrazino[2, 3-b][1, 4]benzothiazin-8-yl)-(imidazol[1, 2-a]pyridin-5-yl)methanol | | | ¹H-NMR(DMSO-d₆) δ ppm: 5.53(d, J=4.3Hz, 1H), 6.08(d, J=4.3Hz, 1H), 6.71(d, J=7.7Hz, 1H), 6.72(s, 1H), 6.86(d, J=7.7Hz, 1H), 7.01(dd, J=1.3, 9.0Hz, 1H), 7.46(d, J=9.0Hz, 1H), 7.52(s, 1H), 7.61(s, 2H), 7.95(s, 1H), 8.50(d, J=1.3Hz, 1H), 9.44(s, 1H) |
| 1153 | (10H-pyrazino[2, 3-b][1, 4]benzothiazin-8-yl)-(phenyl)methanol | | | ¹H-NMR(CDCl₃) δ ppm: 2.38–2.50(br.s, 1H), 5.68(br.s, 1H), 6.54(s, 1H), 6.66–6.72(br.s, 1H), 6.82(d, J=8.6Hz, 1H), 6.83(d, J=8.6Hz, 1H), 7.27–7.32(m, 2H), 7.32–7.38(m, 2H), 7.49(d, J=2.9Hz, 1H), 7.65(d, J=2.9Hz, 1H) |
| 1154 | (10H-pyrazino[2, 3-b][1, 4]benzothiazin-8-yl)-(4-fluorophenyl)methanol | FAB(+) 325 (MH⁺) | 150–152° C. | ¹H-NMR(DMSO-d₆) δ ppm: 5.51(d, J=4Hz, 1H), 5.93(d, J=4Hz, 1H), 6.74(dd, J=1, 8Hz, 1H), 6.80(d, J=1Hz, 1H), 6.82(d, J=8Hz, 1H), 7.12(t, J=9Hz, 2H), 7.33(dd, J=6, 9Hz, 2H), 7.61(d, J=3Hz, 1H), 7.62(d, J=3Hz, 1H), 9.44(s, 1H) |
| 1155 | (10H-pyrazino[2, 3-b][1, 4]benzothiazin-8-yl)-(5-bromo-2-fluorophenyl)methanol | FAB(+) 405(M⁺) | 202–203° C. | ¹H-NMR(CDCl₃) δ ppm: 5.94(s, 1H), 6.50(br.s, 1H), 6.55(d, J=1Hz,1H), 6.84(dd, J=1, 8Hz, 1H), 6.87(d, J=8Hz, 1H), 6.92(t, J=9Hz, 1H), 7.38(ddd, J=3, 5, 9Hz, 1H), 7.40(dd, J=3, 6Hz, 1H), 7.55(d, J=3Hz, 1H), 7.69(d, J=3Hz, 1H) |
| 1156 | (10H-pyrazino[2, 3-b][1, 4]benzothiazin-8-yl)-(2, 4-difluorophenyl)methanol | FAB(+) 387(M⁺) | 175–176° C. | ¹H-NMR(DMSO-d₆) δ ppm: 5.90(s, 1H), 6.15(br.s, 1H), 6.71(d, J=8Hz, 1H), 6.83(d, J=8Hz, 1H), 6.88(s, 1H), 7.04(br.t, J=9Hz, 2H), 7.36(tt, J=7, 9Hz, 1H), 7.62(s, 2H), 9.45(s, 1H) |

| Ex. | Structural formula | MS | M.p. | NMR |
|---|---|---|---|---|
| 1157 | (10H-pyrazino[2, 3-b][1, 4]benzothiazin-8-yl)-(3-bromo-2, 6-difluorophenyl)methanol | FAB(+) 467(M⁺) | 198–200° C. | ¹H-NMR(CDCl₃) δ ppm: 6.09(s, 1H), 6.60(br.s, 1H), 6.61(s, 1H), 6.79(d, J=8Hz, 1H), 6.85(d, J=8Hz, 1H), 6.88(td, J=8, 11Hz, 1H), 7.51(ddd, J=5, 7, 8Hz, 1H), 7.65(d, J=3Hz, 1H), 7.69(d, J=3Hz, 1H) |
| 1158 | (10H-pyrazino[2, 3-b][1, 4]benzothiazin-8-yl)-(4-methoxyphenyl)methanol | FAB(+) 337(M⁺) | 84–86° C. | ¹H-NMR(CDCl₃) δ ppm: 3.79(s, 3H), 5.43(s, 1H), 6.54(d, J=1Hz, 1H), 6.66(br.s, 1H), 6.81(dd, J=1, 8Hz, 1H), 6.84(d, J=8Hz, 1H), 6.88(d, J=9Hz, 2H), 7.25(d, J=9Hz, 2H), 7.50(d, J=3Hz, 1H), 7.66(d, J=3Hz, 1H) |

Example 1159

(10H-Pyrazino[2,3-b][1,4]benzothiazin-8-yl)-(2-bromopyridin-5-yl)methanol

The title compound was obtained by treating (10-methoxymethyl-10H-pyrazino [2,3-b][1,4]benzothiazin-8-yl)-(2-bromopyridin-5-yl)methanol by the same method as the one of Example 434.

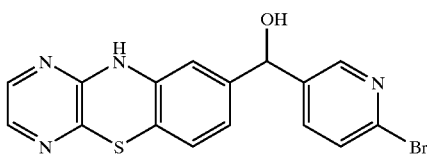

¹H-NMR(DMSO-d₆) δ ppm: 5.50(s, 1H), 6.20(br.s, 1H), 6.77(d, J=8 Hz, 1H), 6.78(s, 1H), 6.85(d, J=8 Hz, 1H), 7.60(d, J=8 Hz, 1H), 7.61(d, J=8 Hz, 1H), 7.62(d, J=3 Hz, 1H), 7.63(d, J=3 Hz, 1H), 8.36(s, 1H), 9.45(s, 1H)

MS: FAB(+)388(M⁺)

m.p.: 221–223° C.

Example 1160

(10-Methoxymethyl-10H-pyrazino[2,3-b][1,4]benzothiazin-8-yl)(pyridin-3-yl)ketone 1.25 g of the title compound was obtained by oxidizing 1.48 g of (10-methoxymethyl-10H-pyrazino[2,3-b][1,4]benzothiazin-8-yl)-(pyridin-3-yl)methanol with manganese dioxide by the same method as the one of Example 625.

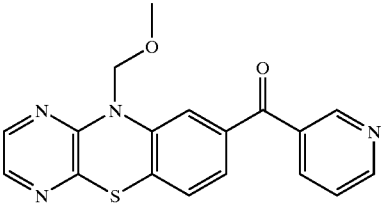

¹H-NMR(CDCl₃) δ ppm: 3.48(s, 3H), 5.29(s, 2H), 7.13(d, J=8 Hz, 1H), 7.36(dd, J=2, 8 Hz, 1H), 7.45(ddd, J=1, 5, 8 Hz, 1H), 7.58(d, J=2 Hz, 1H), 7.88(d, J=3 Hz, 1H), 7.89(d, J=3 Hz, 1H), 8.10(td, J=2, 8 Hz, 1H), 8.82(dd, J=2, 5 Hz, 1H), 8.99(dd, J=1, 2 Hz, 1H)

Example 1161

8-[(Pyridin-3-yl)difluoromethyl]-10-methoxymethyl-10H-pyrazino[2,3-b][1,4]benzothiazine 350 mg of (10-methoxymethyl-1H-pyrazino[2,3-b][1,4]benzothiazin-8-yl)(pyridin-3-yl)ketone was added in a nitrogen atmosphere to 3 ml of dimethylaminosulfur trifluoride and the resulting mixture was stirred at room temperature for 16 hours and then at 50° C. for additional 5 hours. The reaction mixture was ice-cooled and diluted with ethyl acetate. After adding water under ice-cooling, the extract was dried over anhydrous magnesium sulfate and filtered. After distilling off the solvent under reduced pressure, the residue was purified by silica gel column chromatography (eluted with dichloromethane/ethyl acetate) to thereby give 287 mg of the title compound as a yellow solid.

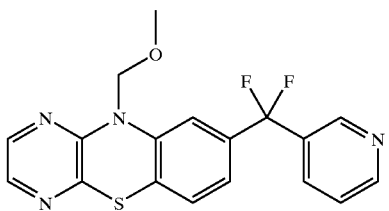

¹H-NMR(CDCl₃) δ ppm: 3.48(s, 3H), 5.24(s, 2H), 7.06(s, 2H), 7.25(s, 1H), 7.37(dd, J=5, 8 Hz, 1H), 7.80(d, J=8 Hz, 1H), 7.86(d, J=3 Hz, 1H), 7.87(d, J=3 Hz, 1H), 8.70(d, J=5 Hz, 1H), 8.77(s, 1H)

Example 1162

8-[(Pyridin-3-yl)fluoromethyl]-10-methoxymethyl-10H-pyrazino[2,3-b][1,4]benzothiazine 177 mg of the title compound was obtained by treating 352 mg of (10-methoxymethyl10H-pyrazino[2,3-b][1,4] benzothiazin-8-yl)-(pyridin-3-yl)methanol by the same method as the one of Example 1161.

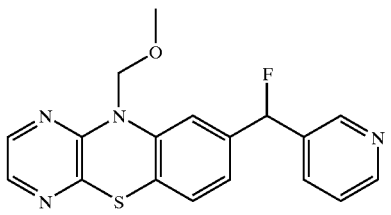

¹H-NMR(CDCl₃) δ ppm: 3.46(s, 3H), 5.21(d, J=9 Hz, 1H), 5.24(d, J=9 Hz, 1H), 6.44(d, J=45 Hz, 1H), 6.91(d, J=8 Hz, 1H), 7.04(d, J=8 Hz, 1H), 7.11(s, 1H), 7.32(dd, J=5, 8 Hz, 1H), 7.64(d, J=8 Hz, 1H), 7.83–7.85(m, 2H), 8.60–8.63 (m, 2H)

Example 1163

8-[1-(Pyridin-3-yl)-1-methoxymethyl]-10-methoxymethyl-10H-pyrazino[2,3-b][1,4]benzothiazine 504 mg of the title compound was obtained as yellow crystals by treating 704 mg of (10-methoxymethyl-10H-pyrazino[2,3-b][1,4]-benzothiazin-8-yl)-(pyridin-3-yl) methanol with methyl iodide in the. presence of sodium hydride by the same method as the one of Example 788.

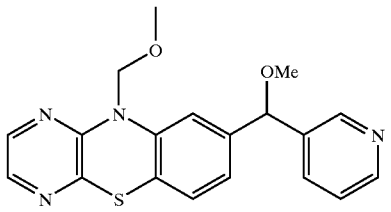

¹H-NMR(CDCl₃) δ ppm: 3.48(s, 3H), 3.48(s, 3H), 5.20(s, 1H), 5.22(d, J=10 Hz, 1H), 5.25(d, J=10 Hz, 1H), 6.94(dd, J=2, 8 Hz, 1H), 7.00(d, J=8 Hz, 1H), 7.11(d, J=2 Hz, 1H), 7.26(dd, J=5, 8 Hz, 1H), 7.63(td, J=2, 8 Hz, 1H), 7.83(d, J=3 Hz, 1H), 7.84(d, J=3 Hz, 1H), 8.52(dd, J=2, 5 Hz, 1H), 8.60(d, J=2 Hz, 1H)

Example 1164

1-(10-Methoxymethyl-10H-pyrazino[2,3-b][1,4] benzothiazin-8-yl)-1-(pyridin-3-yl)ethanol 303 mg of the title compound was obtained as yellow crystals by treating 350 mg of (10-methoxymethyl-10H-pyrazino[2,3-b][1,4]-benzothiazin-8-yl)(pyridin-3-yl) ketone with methyllithium by the same method as the one of Production Example 86.

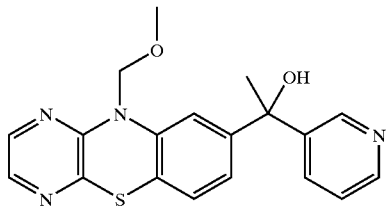

¹H-NMR(CDCl₃) δ ppm: 1.95(s, 3H), 2.38(br.s, 1H), 3.43(s, 3H), 5.18(d, J=10 Hz, 1H), 5.21(d, J=10 Hz, 1H), 6.97(d, J=8 Hz, 1H), 6.99(dd, J=2, 8 Hz, 1H), 7.21(d, J=2 Hz, 1H), 7.25(dd, J=5, 8 Hz, 1H), 7.63(td, J=2, 8 Hz, 1H), 7.83(d, J=3 Hz, 1H), 7.84(d, J=3 Hz, 1H), 8.50(dd, J=2, 5 Hz, 1H), 8.70(d, J=2 Hz, 1H)

Example 1165

8-[1-(Pyridin-3-yl)vinyl]-10-methoxymethyl-10H-pyrazino[2,3-b][1,4]benzothiazine To a solution of 303 mg of 1-(10-methoxymethyl-10H-pyrazino[2,3-b][1,4]benzothiazin-8-yl)1-(pyridin-3-yl) ethanol in dichloromethane was added in a nitrogen atmosphere 0.32 ml of methyl chlorosulfonate and the resulting mixture was heated under reflux for 2 hours. Then the reaction mixture was brought back to room temperature and distributed into water and ethyl acetate. The extract was dried over anhydrous magnesium sulfate and filtered. After distilling off the solvent under reduced pressure, the residue was purified by silica gel column chromatography (eluted with dichloromethane/methanol) to thereby give 230 mg of the title compound as a yellow solid.

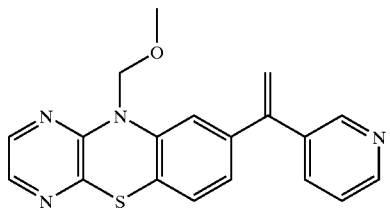

¹H-NMR(CDCl₃) δ ppm: 3.39(s, 3H), 5.21(s, 2H), 5.50(s, 1H), 5.59(s, 1H), 6.91(dd, J=2, 8 Hz, 1H), 7.00(d, J=8 Hz, 1H), 7.07(d, J=2 Hz, 1H), 7.29(br.s, 1H), 7.62(br.d, J=8 Hz, 1H), 7.85(d, J=3 Hz, 1H), 7.86(d, J=3 Hz, 1H), 8.59(br.m, 1H), 8.65(br.m, 1H)

Example 1166

8-[1-(Pyridin-3-yl)ethyl]-10-methoxymethyl-10H-pyrazino[2,3-b][1,4]benzothiazine 0.23 g of 8-[1-(pyridin-3-yl)vinyl]-10-methoxymethyl-10H-pyrazino[2,3-b][1,4]benzothiazine was dissolved in 10 ml of ethanol and then hydrogenated in the presence of 0.056 g of 10% palladium-carbon (moisture content: 50%) in a hydrogen gas stream at room temperature for 26 hours. Thus 0.106 g of the title compound was obtained as yellow crystals.

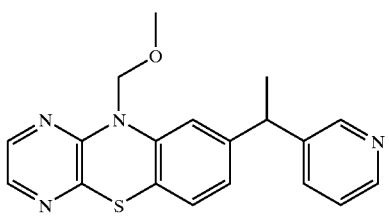

¹H-NMR(CDCl₃) δ ppm: 1.63(d, J=7 Hz, 3H), 3.45(s, 3H), 4.11(q, J=7 Hz, 1H), 5.20(s, 2H), 6.82(dd, J=2, 8 Hz, 1H), 6.96(d, J=8 Hz, 1H), 6.98(d, J=2 Hz, 1H), 7.23(dd, J=5, 8 Hz, 1H), 7.50(td, J=2, 8 Hz, 1H), 7.85(m, 2H), 8.46(br.m, 1H), 8.53(br.m, 1H)

Examples

The following compounds were obtained by the same method as the one of Example 9.

| Ex. | Structural formula | MS | M.p. | NMR |
|---|---|---|---|---|
| 1167 | 8-[(pyridin-3-yl)difluoromethyl]-10H-pyrazino[2,3-b][1,4]benzothiazine | FAB(+) 329 (MH⁺) | 183–184° C. | ¹H-NMR(CDCl₃) δ ppm: 6.54(br.s, 1H), 6.61(d, J=1Hz, 1H), 6.91(dd, J=1, 8Hz, 1H), 6.95(d, J=8Hz, 1H), 7.38(dd, J=5, 8Hz, 1H), 7.59(d, J=3Hz, 1H), 7.73(d, J=3Hz, 1H), 7.80(d, J=8Hz, 1H), 8.71(d, J=5Hz, 1H), 8.75(s, 1H) |
| 1168 | 8-[(pyridin-3-yl)fluoromethyl]-10H-pyrazino[2,3-b][1,4]benzothiazine | FAB(+) 311 (MH⁺) | 157–159° C. | ¹H-NMR(DMSO-d₆) δ ppm: 6.63(d, J=46Hz, 1H), 6.77(s, 1H), 6.78(d, J=8Hz, 1H), 6.95(d, J=8Hz, 1H), 7.46(dd, J=5, 8Hz, 1H), 7.63(s, 2H), 7.74(d, J=8Hz, 1H), 8.60(br.s, 2H), 9.53(s, 1H) |
| 1169 | 8-[1-(pyridin-3-yl)-1-methoxymethyl]-10H-pyrazino[2,3-b]-[1,4]benzothiazine | FAB(+) 323 (MH⁺) | 156–188° C. | ¹H-NMR(CDCl₃) δ ppm: 3.37(s, 3H), 5.11(br.s, 1H), 6.40(br.s, 1H), 6.50(d, J=1Hz, 1H), 6.78(dd, J=1, 8Hz, 1H), 6.85(d, J=8Hz, 1H), 7.27(dd, J=5, 8Hz, 1H), 7.57(d, J=3Hz, 1H), 7.61(td, J=2, 8Hz, 1H), 7.70(d, J=3Hz, 1H), 8.53(dd, J=2, 5Hz, 1H), 8.57(d, J=2Hz, 1H) |
| 1170 | 8-[1-(pyridin-3-yl)ethyl]-10H-pyrazino[2,3-b][1,4]benzothiazine | FAB(+) 307 (MH⁺) | 180–181° C. | ¹H-NMR(DMSO-d₆) δ ppm: 1.50(d, J=7Hz, 3H), 4.03(q, J=7Hz, 1H), 6.66(d, J=1Hz, 1H), 6.71(dd, J=1, 8Hz, 1H), 6.84(d, J=8Hz, 1H), 7.31(dd, J=5, 8Hz, 1H), 7.59(td, J=2, 8Hz, 1H), 7.62(s, 2H), 8.39(dd, J=2, 5Hz, 1H), 8.46(d, J=2Hz, 1H), 9.39(s, 1H) |

Example 1171

(10-Methoxymethyl-10H-pyrazino[2,3-b][1,4]
benzothiazin-8-yl)-[2-[(trimethylsilyl)ethynyl]
pyridin-5-yl]methanol 0.198 g of the title compound was obtained by treating 0.215 g of (10-methoxymethyl-10H-pyrazino[2,3-][1,4] benzothiazin-8-yl)-(2-bromopyridin-5-yl)methanol by the same method as the one of Example 1417.

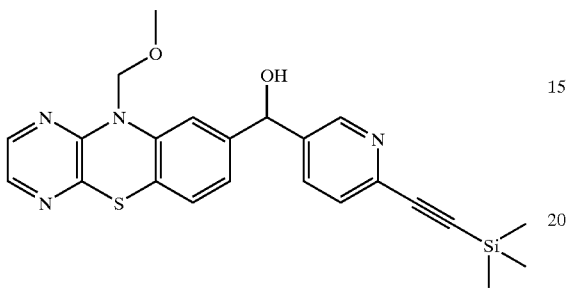

$^1$H-NMR(CDCl$_3$) δ ppm: 0.27(s, 9H), 2.41(s, 1H), 3.40(s, 3H), 5.24(s, 2H), 5.82(s, 1H), 6.92(dd, J=2, 8 Hz, 1H), 7.00(d, J=8 Hz, 1H), 7.15(d, J=2 Hz, 1H), 7.40(d, J=8 Hz, 1H), 7.65(dd, J=2, 8 Hz, 1H), 7.85(d, J=3 Hz, 1H), 7.86(d, J=3 Hz, 1H), 8.51(d, J=2 Hz, 1H)

Example 1172

(10-Methoxymethyl-10H-pyrazino[2,3-b][1,4]
benzothiazin-8-yl)-(2-ethynylpyridin-5-yl)methanol 0.316 g of the title compound was obtained by treating 0.392 g of (10-methoxymethyl-10H-pyrazin[2,3-b][1,4] benzothiazin-8-yl)-[2-[(trimethylsilyl)ethynyl]pyridin-5-yl] methanol with tetra-n-butylammonium fluoride by the same method as the one of Example 1418.

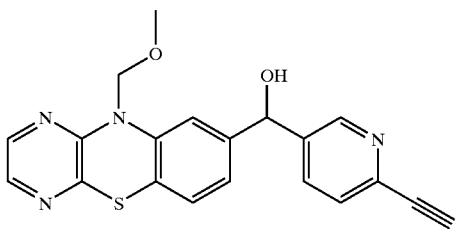

$^1$H-NMR(CDCl$_3$) δ ppm: 2.36(d, J=4 Hz, 1H), 3.15(s, 1H), 3.49(s, 3H), 5.23(s, 2H), 5.82(d, J=4 Hz, 1H), 6.93(dd, J=2, 8 Hz, 1H), 7.00(d, J=8 Hz, 1H), 7.14(d, J=2 Hz, 1H), 7.45(d, J=8 Hz, 1H), 7.66(dd, J=2, 8 Hz, 1H), 7.84(d, J=3 Hz, 1H), 7.85(d, J=3 Hz, 1H), 8.62(d, J=2 Hz, 1H)

Example 1173

(10-Methoxymethyl-10H-pyrazino[2,3-b][1,4]
benzothiazin-8-yl)-(2-ethylpyridin-5-yl)methanol 0.262 g of the title compound was obtained by treating 0.316 g of (10-methoxymethyl-10H-pyrazino[2,3-b][1,4] benzothiazin-8-yl)-(2-ethynylpyridin-5-yl)methanol by the same method as the one of Example 20.

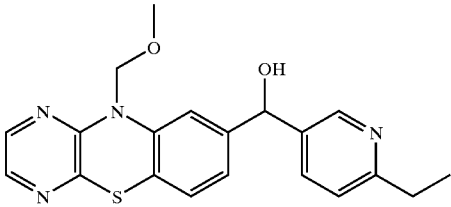

$^1$H-NMR(CDCl$_3$) δ ppm: 1.28(t, J=7 Hz, 3H), 2.39(s, 1H), 2.81(q, J=7 Hz, 2H), 3.47(s, 3H), 5.22(d, J=9 Hz, 1H), 5.26(d, J=9 Hz, 1H), 5.80(s, 1H), 6.96(dd, J=2, 8 Hz, 1H), 7.00(d, J=8 Hz, 1H), 7.14(d, J=8 Hz, 1H), 7.17(d, J=2 Hz, 1H), 7.58(dd, J=2, 8 Hz, 1H), 7.84(d, J=3 Hz, 1H), 7.85(d, J=3 Hz, 1H), 8.55(d, J=2 Hz, 1H)

Example 1174

Methyl[5-[(10-methoxymethyl-10H-pyrazino[2,3-b]
[1,4]-benzothiazin-8-yl)hydroxymethyl]pyridin-2-
ylthiol]acetate To a solution of 0.106 g of methyl thioacetate in N,N-dimethylformamide (8 ml) was added in a nitrogen atmosphere 0.040 g of sodium hydride (60% oily) and the resulting mixture was stirred for 15 minutes. After adding 0.215 g of (10-methoxymethyl-10H-pyrazino[2,3-b][1,4] benzothiazin-8-yl)-(2-bromopyridin-5-yl)methanol, the resulting mixture was stirred at room temperature for 14 hours and heated to 60° C. for 2 hours. Then the reaction mixture was distributed into water and ethyl acetate and the aqueous layer was extracted with ethyl acetate. The organic layer was washed with water and dried over anhydrous sodium sulfate. After distilling off the solvent under reduced pressure, the residue was purified by silica gel column chromatography (eluted with n-hexane/ethyl acetate) to thereby give 0.128 g of the title compound as a yellow solid.

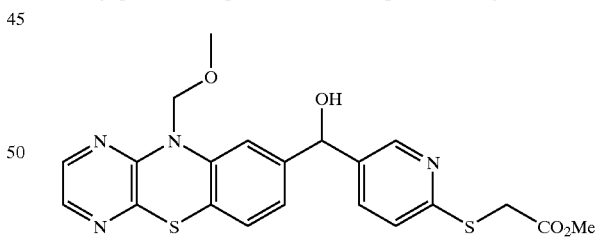

$^1$H-NMR(CDCl$_3$) δ ppm: 3.48(s, 3H), 3.74(s, 3H), 3.97(s, 2H), 5.23(s, 2H), 5.74(s, 1H), 6.92(dd, J=2, 8 Hz, 1H), 7.00(d, J=8 Hz, 1H), 7.05(d, J=2 Hz, 1H), 7.44(d, J=8 Hz, 1H), 7.54(d, J=8 Hz, 1H), 7.83(m, 2H), 8.40(br.s, 1H)

Examples

The following compounds were obtained by treating the compounds obtained in Examples 1173 and 1174 by the same method as the one of Example 9.

| Ex. | Structural formula | MS | M.p. | NMR |
|---|---|---|---|---|
| 1175 | 8-[1-(pyrazino-[2, 3-b][1, 4]benzothiazin-8-yl)-(2-(ethylpyridin-5-yl)methanol | FAB(+) 337 (MH⁺) | 161–163° C. | ¹H-NMR(CDCl₃) δ ppm: 1.30(t, J=7Hz, 3H), 2.82(q, J=7Hz, 2H), 5.70(s, 1H), 6.55(s, 1H), 6.60(s, 1H), 6.81(d, J=8Hz, 1H), 6.86(d, J=8Hz, 1H), 7.17(d, J=9Hz, 1H), 7.55(d, J=3Hz, 1H), 7.58(dd, J=1, 9Hz, 1H), 7.68(d, J=3Hz, 1H), 8.51(d, J=1Hz, 1H) |
| 1176 | methyl [5-[(10H-pyrazino[2, 3-b][1, 4]benzothiazin-8-yl)hydroxymethyl]pyridin-2-ylthio]acetate | FAB(+) 399 (MH⁺) | 65–70° C. | solvent unknown 3.91(s, 2H), 5.53(d, J=4Hz, 1H), 6.02(d, J=4Hz, 1H), 6.75(dd, J=1, 8Hz, 1H), 6.81(d, J=1Hz, 1H), 6.84(d, J=8Hz, 1H), 7.26(d, J=8Hz, 1H), 7.50(dd, J=2, 8Hz, 1H), 7.62(d, J=3Hz, 1H), 7.63(d, J=3Hz, 1H), 8.35(d, J=2Hz, 1H), 9.44(s, 1H) |

Example 1177

(10-Methoxymethyl-10H-pyrazino[2,3-b][1,4]benzothiazin-8-yl)-(6-bromopyridin-2-yl)methanol 30 ml of a solution of 2.84 g of 2,6-dibromopyridine in diethyl ether was cooled in a nitrogen atmosphere in a methanol/liquefied nitrogen bath to –85° C. and 7.5 ml of a 1.6 M solution of n-butyllithium in hexane was dropped thereinto. After stirring for 30 minutes, the reaction mixture was heated to –78° C. and 40 ml of a solution of 1.05 g of (10-methoxymethyl-10H-pyrazino[2,3-b][1,4]benzothiazin-8-yl)carbaldehyde in dry tetrahydrofuran was dropped thereinto. Then the reaction mixture was brought back to room temperature and distributed into an aqueous solution of sodium dihydrogenphosphate and ethyl acetate. The aqueous layer was extracted with ethyl acetate, washed successively with water and a saturated aqueous solution of sodium chloride and dried over anhydrous sodium sulfate followed by filtration. After distilling off the solvent under reduced pressure, the residue was purified by silica gel column chromatography (eluted with dichloromethane/methanol) to thereby give 1.05 g of the title compound as a yellow solid.

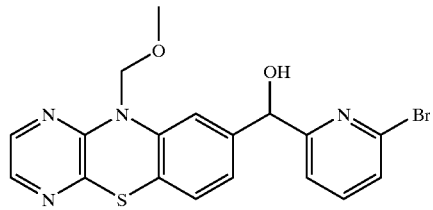

¹H-NMR(CDCl₃) δ ppm: 3.51(s, 3H), 4.40(d, J=5 Hz, 1H), 5.25(s, 2H), 5.66(d, J=5 Hz, 1H), 6.98(m, 2H), 7.16(d, J=8 Hz, 1H), 7.17(s, 1H), 7.40(d, J=8 Hz, 1H), 7.50(t, J=8 Hz, 1H), 7.83(d, J=3 Hz, 1H), 7.84(d, J=3 Hz, 1H)

Example 1178

8-[(6-Bromopyridin-2-yl)-(tert-butyldimethylsiloxy)methyl]-10-methoxymethyl-10H-pyrazino[2,3-b][1,4]benzothiazine To a solution of 1.05 g of (10-methoxymethyl-10H-pyrazino[2,3-b][1,4]benzothiazin-8-yl)-(6-bromopyridin-2-yl)methanol in 15 ml of acetonitrile was added in a nitrogen atmosphere 3.2 ml of N-(tert-butyldimethylsilyl)-N-methyltrifluoroacetamide and the resulting mixture was stirred at room temperature for 22 hours. After distilling off the solvent under reduced pressure, the residue was purified by silica gel column chromatography (eluted with n-hexane/ethyl acetate) to thereby give 0.72 g of the title compound as a yellow solid.

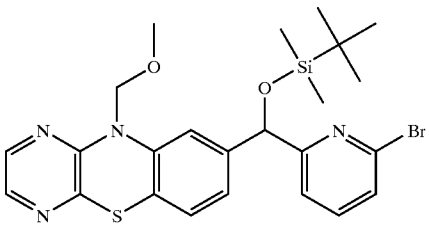

¹H-NMR(CDCl₃) δ ppm: 0.01(s, 3H), 0.04(s, 3H), 0.93(s, 9H), 3.53(s, 3H), 5.23(s, 2H), 5.77(s, 1H), 6.93(d, J=8 Hz, 1H), 7.09(dd, J=2, 8 Hz, 1H), 7.31(dd, J=2, 7 Hz, 1H), 7.36(d, J=2 Hz, 1H), 7.48(dd, J=2, 7 Hz, 1H), 7.51(t, J=7 Hz, 1H), 7.82(m, 2H)

Example 1179

Ethyl(E)-3-[6-[(10-methoxymethyl-10H-pyrazino[2,3-b][1,4]-benzothiazin-8-yl)-(tert-butyldimethylsilyloxy)methyl]pyridin-2-yl]-2-propenoate To a solution of 0.72 g of 8-[(6-bromopyridin-2-yl)-(tert-butyldimethylsiloxy)methyl]-10-methoxymethyl-10H- pyrazino[2,3-b][1,4]benzothiazine in N,N-dimethylformamide (8 ml) were added 0.17 ml of ethyl acrylate, 0.22 ml of triethylamine, 12 mg of palladium (II) acetate and 33 mg of triphenylphosphine and the resulting mixture was heated to 90° C. for 30 hours. Then the reaction mixture was brought back to room temperature and distributed into water and ethyl acetate. The organic layer was extracted, washed successively with water and a saturated aqueous solution of sodium chloride, dried over anhydrous magnesium sulfate and filtered. After distilling off the solvent under reduced pressure, the residue was purified by silica gel column chromatography (diluted with dichloromethane/ethyl acetate) to thereby give 540 mg of the title compound as a yellow oily substance.

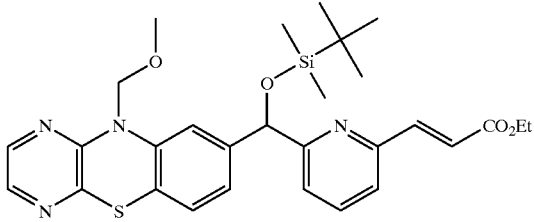

$^1$H-NMR(CDCl$_3$) δ ppm: 0.01(s, 3H), 0.07(s, 3H), 0.96(s, 9H), 1.35(t, J=7 Hz, 3H), 3.53(s, 3H), 4.28(q, J=7 Hz, 2H), 5.23(s, 2H), 5.82(s, 1H), 6.84(d, J=8 Hz, 1H), 6.94(d, J=16 Hz, 1H), 7.12(dd, J=2, 8 Hz, 1H), 7.25(d, J=8 Hz, 1H), 7.42(d, J=2 Hz, 1H), 7.50(d, J=8 Hz, 1H), 7.65(d, J=16 Hz, 1H), 7.67(t, J=8 Hz, 1H), 7.82(s, 2H)

Example 1180
Ethyl3-[6-[(10-methoxymethyl-10H-pyrazino[2,3-b][1,4]-benzothiazin-8-yl)-(tert-butyldimethylsiloxy)methyl]pyridin-2-yl]propanoate 201 mg of the title compound was obtained by treating 249 mg of ethyl 3-[6-[(10-methoxymethyl-10H-pyrazino[2,3-b][1,4]-benzothiazin-8-yl)-(tert-butyldimethylsiloxy)methyl]pyridin-2-yl]-2-propenoate by the same method as the one of Example 20.

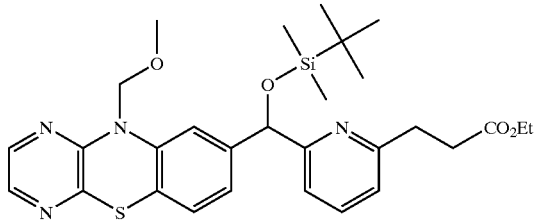

$^1$H-NMR(CDCl$_3$) δ ppm: 0.05(s, 3H), 0.03(s, 3H), 0.93(s, 9H), 1.20(t, J=7 Hz, 3H), 2.77(m, 2H), 3.06(m, 2H), 3.51(s, 3H), 4.11(q, J=7 Hz, 2H), 5.22(s, 2H), 5.74(s, 1H), 6.91(d, J=8 Hz, 1H), 7.00(d, J=8 Hz, 1H), 7.06(dd, J=2, 8 Hz, 1H), 7.30(d, J=8 Hz, 1H), 7.36(d, J=2 Hz, 1H), 7.53(t, J=8 Hz, 1H), 7.81(s, 2H)

Examples

The following compounds were obtained by treating the compounds obtained in Examples 1179 and 1180 with tetrabutylammonium fluoride by the same method as the one of Example 1418 and followed by the same treatment as the one of Example 9.

| Ex. | Structural formula | MS | M.p. | NMR |
|---|---|---|---|---|
| 1181 | ethyl (E)-3-[6-[(10H-pyrazino[2, 3-b][1, 4]-benzothiazin-8-yl) hydroxymethyl]pyridin-2-yl]-2-propenoate | ESI (+) 429 (MNa$^+$) | 160–170° C. (decompose) | $^1$H-NMR(CDCl$_3$) δ ppm: 1.37(t, J=7Hz, 3H), 4.30(q, J=7Hz, 2H), 5.59(s, 1H), 6.86(s, 2H), 6.99(d, J=16Hz, 1H), 7.12(d, J=8Hz, 1H), 7.12(d, J=8Hz, 1H), 7.35(d, J=8Hz, 1H), 7.55(d, J=3Hz, 1H), 7.67(d, J=3Hz, 1H), 7.69(t, J=8Hz, 1H), 7.69(d, J=16Hz, 1H) |
| 1182 | ethyl 3-[6-[(10H-pyrazino[2, 3-b][1, 4]-benzothiazin-8-yl)hydroxymethyl]pyridin-2-yl]propenoate | ESI (+) 431 (MNa$^+$) | | $^1$H-NMR(CDCl$_3$) δ ppm: 1.24(t, J=7Hz, 3H), 2.83(t, J=6Hz, 2H), 3.18(t, J=6Hz, 2H), 4.14(q, J=7Hz, 2H), 5.52(s, 1H), 6.51(s, 1H), 6.66(s, 1H), 6.84(s, 2H), 6.94(d, J=8Hz, 1H), 7.12(d, J=8Hz, 1H), 7.53(d, J=3Hz, 1H), 7.55(t, J=8Hz, 1H), 7.60(d, J=3Hz, 1H) |

Example 1183

(10-Methoxymethyl-10H-pyrazino[2,3-b][1,4]benzothiazin-8-yl)(pyridin-2-yl)ketone The title compound was synthesized by oxidizing (10-methoxymethyl-10H-pyrazino[2,3-b][1,4]benzothiazin-8-yl)-(pyridin-3-yl)methanol with manganese dioxide by the same method as the one of Example 625.

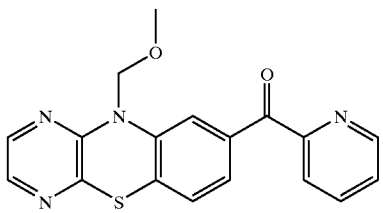

$^1$H-NMR(CDCl$_3$) δ ppm: 3.47(s, 3H), 5.30(s, 2H), 7.10(d, J=8.2 Hz, 1H), 7.50(ddd, J=1.3, 4.3, 7.6 Hz, 1H), 7.70(dd, J=1.5, 8.2 Hz, 1H), 7.85(s, 2H), 7.87(d, J=1.5 Hz, 1H), 7.91(dt, J=1.9, 7.6 Hz, 1H), 8.05(d, J=1.3, 7.6 Hz, 1H), 8.72(d, J=1.9, 4.3 Hz, 1H)

Example 1184

1-(10-Methoxymethyl-10H-pyrazino[2,3-b][1,4]benzothiazin-8-yl)-2-(pyridin-2-yl)ethanol 90 mg of the title compound was obtained as a yellow oily substance by treating 260 mg of 2-methylpyridine and (10-methoxymethyl-10H-pyrazino[2,3-b][1,4]benzothiazin-8-yl)carbaldehyde by the same method as the one of Example 1128.

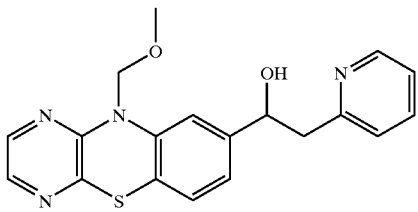

$^1$H-NMR(CDCl$_3$) δ ppm: 3.10(d, J=5.9 Hz, 2H), 3.52(s, 3H), 5.10(d, J=5.9 Hz, 1H), 5.25(s, 2H), 5.8–6.0(br.s, 1H), 6.97(d, J=7.9 Hz, 1H), 7.02(dd, J=1.6, 7.9 Hz, 1H), 7.11(br.d, J=7.5 Hz, 1H), 7.19(br.dd, J=5.0, 7.5 Hz, 1H), 7.21(br.d, J=1.6 Hz, 1H), 7.62(dt, J=1.8, 7.5 Hz, 1H), 7.82(s, 2H), 8.52(br.d, J=5.0 Hz, 1H)

Example 1185

(10H-Pyrazino[2,3-b][1,4]benzothiazin-8-yl)(pyridin-2-yl)ketone

The title compound was obtained by treating (10-methoxymethyl-10H-pyrazino[2,3-b][1,4]benzothiazin-8-yl)(pyridin-2-yl)ketone by the same method as the one of Example 9.

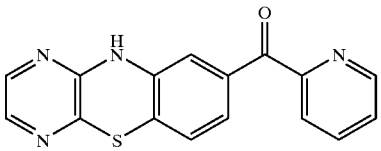

$^1$H-NMR(DMSO-d$_6$) δ ppm: 7.05(d, J=8.6 Hz, 1H), 7.35 (d, J=1.6 Hz, 1H), 7.37(dd, J=1.6, 8.6 Hz, 1H), 7.65(d, J=3.2 Hz, 1H), 7.66(dd, J=4.3, 7.6 Hz, 1H), 7.67(d, J=3.2 Hz, 1H), 7.92(d, J=7.6 Hz, 1H), 8.04(dt, J=1.6, 7.6 Hz, 1H), 8.70(dd, J=1.6, 4.3 Hz, 1H), 9.64(s, 1H)

Example 1186

1-(10H-Pyrazino-[2,3-b][1,4]benzothiazin-8-yl)-2-(pyridin-2-yl)ethanol

The following compound was obtained by treating 1-(10-methoxymethyl-10H-pyrazino[2,3-b][1,4]benzothiazin-8-yl)-2-(pyridin-2-yl)ethanol by the same method as the one of Example 434.

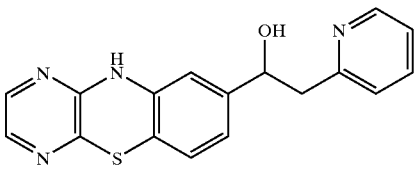

$^1$H-NMR(DMSO-d$_6$) δ ppm: 2.89(dd, J=5.5, 13.5 Hz, 1H), 2.95(dd, J=8.3, 13.5 Hz, 1H), 4.79(ddd, J=4.3, 5.5, 13.5 Hz, 1H), 5.37(d, J=4.3 Hz, 1H), 6.69(dd, J=1.3, 8.3 Hz, 1H), 6.80(d, J=8.3 Hz, 1H), 6.81(d, J=1.3 Hz, 1H), 7.17(d, J=7.6 Hz, 1H), 7.18(t, J=4.3 Hz, 1H), 7.62(d, J=3.2 Hz, 1H), 7.63(d, J=3.2 Hz, 1H), 7.64(dt, J=1.7, 7.6 Hz, 1H), 8.47(d, J=4.3 Hz, 1H), 9.46(s, 1H)

MS: FAB(+)325(MH$^+$)

Example 1187

(10H-Pyrazino[2,3-b][1,4]benzothiazin-8-yl)(pyridin-2-ylmethyl)ketone 0.15 ml of diisopropylamine in tetrahydrofuran (10 ml) was ice-cooled and 1.0 ml of a 1.6 M solution of n-butyllithium in hexane was added thereto. After stirring for 10 minutes, the reaction mixture was cooled to −78° C. After adding 0.15 ml of 2-methylpyridine, the mixture was stirred for 30 minutes and then a solution of 303 mg of methyl(10-methoxymethyl-10H-pyrazino[2,3-b][1,4]benzothiazin-8-yl)carboxylate in tetrahydrofuran (5 ml) was dropped thereinto. The reaction mixture was brought back to room temperature and distributed into an aqueous solution of ammonium chloride and ethyl acetate. The organic layer was extracted, dried over anhydrous sodium sulfate and filtered. After distilling off the solvent under reduced pressure, the residue was purified by silica gel column chromatography (eluted with n-hexane/ethyl acetate) to thereby give 30 mg of (10-methoxymethyl-10H-pyrazino[2,3-b][1,4]benzothiazin-8-yl)(pyridin-2-ylmethyl)ketone as yellow crystals. This ketone was further treated by the same method as the one of Example 119 to thereby give 13 mg of the title compound as yellow crystals.

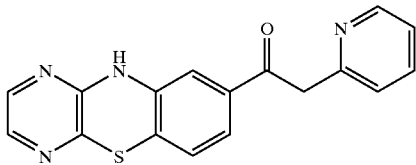

¹H-NMR(DMSO-d₆) δ ppm: 4.36(s, initial, 2H, keto), 6.68(s, initial 1H, enol), 6.94 and 7.04(d, J=8.8 Hz, total 1H, enol:keto=8:1), 7.12 and 7.25(t, J=6.4 Hz, total 1H, 8:1), 7.25 and 7.33(d, J=8.8 Hz, total 1H, 8:1), 7.25 and 7.44(d, J=8.0 Hz, total 1H, 8:1), 7.26 and 7.28(s, total 1H, 8:1), 7.53(d, J=2.4 Hz, total 1H), 7.54(d, J=2.4 Hz, total 1H), 8.37 and 8.44(t, J=6.4 Hz, total 1H, 8:1), 8.73 and 8.78(t, J=8.0 Hz, total 1H, 1:8), 9.57 and 9.64(s, total 1H, 8:1)

MS: FAB(+)321(M⁺)

Example 1188

(10H-Pyrazino[2,3-b][1,4]benzothiazin-8-yl)hydroxyacetic acid 5 ml of an aqueous solution of 780 mg of potassium hydroxide and 300 mg of lithium chloride was ice-cooled. Into the mixture was dropped 5 ml of a solution of 900 mg of bromoform and 960 mg of (10-methoxymethyl-10H-pyrazino[2,3-b][1,4]benzothiazin-8-yl)carbaldehyde in dioxane. After stirring at 0° C. to room temperature over day and night, the reaction mixture was distributed into dilute hydrochloric acid and ethyl acetate. The organic layer was extracted with ethyl acetate, washed with water and dried over anhydrous sodium sulfate and then the extract was filtered. After distilling off the solvent under reduced pressure, the residue was purified by silica gel column chromatography (eluted with dichloromethane/methanol). After recrystallizing from ethyl acetate, 260 mg of the title compound was obtained as yellow crystals.

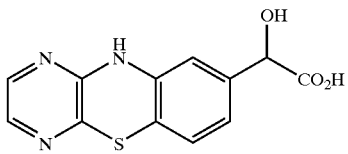

¹H-NMR(DMSO-d₆) δ ppm: 4.81(s, 1H), 6.81(dd, J=1.5, 8.2 Hz, 1H), 6.84(d, J=1.5 Hz, 1H), 6.86(d, J=8.2 Hz, 1H), 7.62(d, J=2.8 Hz, 1H), 7.63(d, J=2.8 Hz, 1H)

MS: FAB(+)275(M⁺), 276(MH⁺)

Example 1189

Methyl(10H-pyrazino[2,3-b][1,4]benzothiazin-8-yl)hydroxyacetate 150 mg of methyl iodide was added to a solution of 100 mg of (10H-pyrazino[2,3-b][1,4]benzothiazin-8-yl)hydroxyacetic acid in N,N-dimethylformamide (8 ml) in the presence of 260 mg of potassium carbonate. After purifying by silica gel column chromatography (eluted with dichloromethane/methanol) and recrystallizing from ethyl acetate/diisopropyl ether, 68 mg of the title compound was obtained as yellow crystals.

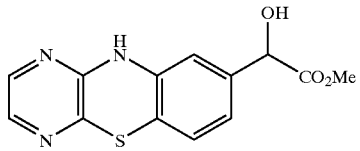

¹H-NMR(CDCl₃) δ ppm: 3.48–3.68(br.s, 1H), 3.77(s, 3H), 5.01(s, 1H), 6.58(s, 1H), 6.65–6.71(br.s, 1H), 6.88(s, 2H), 7.57(d, J=2.7 Hz, 1H), 7.69(d, J=2.7 Hz, 1H)

Example 1190

Methyl3-(10H-pyrazino[2,3-b][1,4]benzothiazin-8-yl)-3-hydroxypropanoate 820 mg of (10-methoxymethyl-10H-pyrazino[2,3-b][1,4]-benzothiazin-8-yl)carbaldehyde was dissolved in tetrahydrofuran (5 ml)/trimethyl borate (5 ml) in a nitrogen atmosphere and 195 mg of zinc dust (400-mesh) was added thereto. After stirring, 460 mg of methyl bromoacetate was further added to the reaction mixture. After heating under reflux for 8 hours, the reaction mixture was brought back to room temperature and distributed into an aqueous solution of ammonium chloride and ethyl acetate. The organic layer was extracted, washed with water and dried over anhydrous sodium sulfate and the extract was filtered. After distilling off the solvent under reduced pressure, the residue was purified by silica gel column chromatography (eluted with dichloromethane/methanol) to thereby give 300 mg of methyl 3-(10-methoxymethyl-10H-pyrazino[2,3-b][1,4]benzothiazin-8-yl)-3-hydroxypropanoate as a yellow oily substance. A 100 mg portion of this product was treated by the same method as the one of Example 9 to thereby give 30 mg of the title compound as yellow crystals.

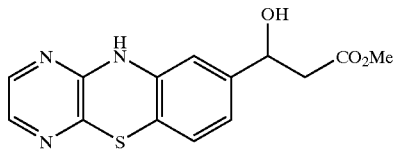

¹H-NMR(CDCl₃) δ ppm: 2.68(d, J=9.2 Hz, 2H), 3.35 (br.d, J=3.3 Hz, 1H), 3.73(s, 3H), 4.99(dt, J=3.3, 9.2 Hz, 1H), 6.50(br.s, 1H), 6.59(dd, J=1.3, 8.2 Hz, 1H), 6.87(d, J=8.2 Hz, 1H), 6.95(d, J=1.3 Hz, 1H)7.58(d, J=2.6 Hz, 1H), 7.70(d, J=2.6 Hz, 1H)

Example 1191

3-(10-Methoxymethyl-10H-pyrazino[2,3-b][1,4]benzothiazin-8-yl)-3-hydroxypropanoic acid 80 mg of the title compound was obtained as yellow crystals by treating 100 mg of methyl 3-(10-methoxymethyl-10H-pyrazino[2,3-b][1,4]benzothiazin-8-yl)-3-hydroxypropanoate by the same method as the one of Example 18.

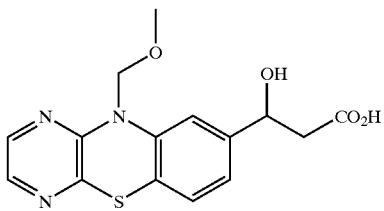

¹H-NMR(CDCl₃) δ ppm: 2.68(dd, J=3, 14 Hz, 1H), 2.74(dd, J=9, 14 Hz, 1H), 3.49(s, 3H), 5.03(dd, J=3, 9 Hz, 1H), 5.24(s, 2H), 6.90(d, J=8.5 Hz, 1H), 6.92(d, J=8.5 Hz, 1H), 7.10(s, 1H), 7.80(s, 2H)

Example 1192

3-(10H-Pyrazino[2,3-b][1,4]benzothiazin-8-yl)-3-hydroxypropanoic acid 40 mg of the title compound was obtained as yellow crystals by treating 3-(10-methoxymethyl-10H-pyrazino[2,3-b][1,4]benzothiazin-8-yl)-3-hydroxypropanoic acid by the same method as the one of Example 434.

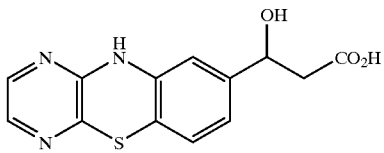

¹H-NMR(DMSO-d₆) δ ppm: 2.43(d, J=6.9 Hz, 2H), 4.72 (t, J=6.9 Hz, 1H), 5.39–5.46(br.s, 1H), 6.73(d, J=7.8 Hz, 1H), 6.79(d, J=1.4 Hz, 1H), 6.83(dd, J=1.4, 7.8 Hz, 1H), 7.61(d, J=3.2 Hz, 1H), 7.62(d, J=3.2 Hz, 1H), 9.48(s, 1H), 12.06–12.17(br.s, 1H)
MS: FAB(+)289(M⁺)

Example 1193

1-(10H-Pyrazino[2,3-b][1,4]benzothiazin-8-yl)-1,3-propanediol 50 mg of the title compound was obtained as yellow crystals by treating 100 mg of methyl 3-(10-methoxymethyl-10H-pyrazino[2,3-b][1,4]benzothiazin-8-yl)-3-hydroxypropanoate by the same methods as those of Examples 2 and 434.

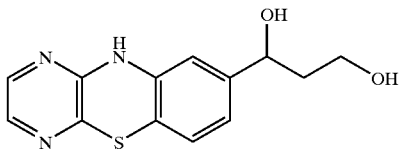

¹H-NMR(DMSO-d₆) δ ppm: 1.52–1.71(m, 2H), 3.30–3.41(m, 1H), 3.41–3.52(m, 1H), 4.41(t, J=5.2 Hz, 1H), 4.40–4.48(m, 1H), 5.12(d, J=4.3 Hz, 1H), 6.71(d, J=7.6 Hz, 1H), 6.77(s, 1H), 6.82(d, J=7.6 Hz, 1H), 7.61(d, J=2.4 Hz, 1H), 7.63(d, J=2.4 Hz, 1H), 9.47(s, 1H)
MS: FAB(+)275(M⁺)

Example 1194

8-Vinyl-10-methoxymethyl-10H-pyrazino[2,3-b][1,4]benzothiazine

To 2.94 g of methyltriphenylphosphonium bromide in N,N-dimethylformamide (20 ml) was added at room temperature 360 mg of sodium hydride (60% oily) and the resulting mixture was stirred for 1 hour. Next, 1.50 g of (10-methoxymethyl-10H-pyrazino[2,3-b][1,4]benzothiazin-8-yl)carbaldehyde was added thereto and the resulting mixture was heated to 65° C. for 1.5 hours. Then the reaction mixture was brought back to room temperature and distributed into water and ethyl acetate. The organic layer was extracted, washed with water and dried over anhydrous sodium sulfate and the extract was filtered. After distilling off the solvent under reduced pressure, the residue was purified by silica gel column chromatography (eluted with n-hexane/ethyl acetate) to thereby give 1.42 g of the title compound as a yellow oily substance.

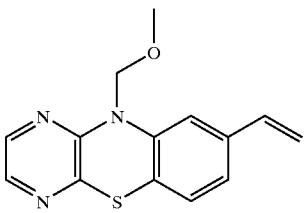

¹H-NMR(CDCl₃) δ ppm: 3.53(s, 3H), 5.26(d, J=10.9 Hz, 1H), 5.30(s, 2H), 5.72(d, J=17.5 Hz, 1H), 6.63(dd, J=10.9, 17.5 Hz, 1H), 6.96(d, J=7.9 Hz, 1H), 7.03(dd, J=1.7, 7.9 Hz, 1H), 7.18(d, J=1.7 Hz, 1H), 7.83(s, 2H)

Example 1195

1-(10-Methoxymethyl-10H-pyrazino[2,3-b][1,4]benzothiazin-8-yl)-1,2-ethanediol

To 30 ml of a solution of 2.6 g of 8-vinyl-10-methoxymethyl-10H-pyrazino[2,3-b][1,4]benzothiazine and 1.06 g of N-methylmorpholine oxide in acetone was added 4.2 ml of a 1% solution of osmium tetraoxide in tert-butanol and the resulting mixture was stirred at room temperature for 12 hours. Then it was distributed into an aqueous solution of sodium hydrogenthiosulfate and ethyl acetate. After filtering off the inorganic matters through celite, the organic layer was extracted, washed with water and dried over anhydrous sodium sulfate and the extract was filtered. After distilling off the solvent under reduced pressure, the residue was purified by silica gel column chromatography (eluted with dichloromethane/methanol) to thereby give 0.35 g of the title compound as yellow crystals.

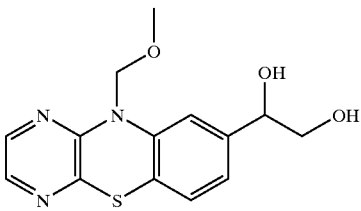

¹H-NMR(CDCl₃) δ ppm: 3.50(s, 3H), 3.59(dd, J=8.1, 11.4 Hz, 1H), 3.71(dd, J=3.0, 11.4 Hz, 1H), 4.71(dd, J=3.0, 8.1 Hz, 1H), 5.24(s, 2H), 6.90(dd, J=1.4, 7.9 Hz, 1H), 6.94(d, J=7.9 Hz, 1H), 7.10(d, J=1.4 Hz, 1H), 7.81(s, 2H)

Example 1196

1-(10H-Pyrazino[2,3-b][1,4]benzothiazin-8-yl)-1,2-ethanediol 100 mg of the title compound was obtained as yellow crystals by treating 350 mg of 1-(10-methoxymethyl-10H- pyrazino[2,3-b][1,4]benzothiazin-8-yl)-1,2-ethanediol by the same method as the one of Example 9.

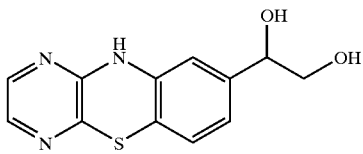

¹H-NMR(DMSO-d₆) δ ppm: 3.24–3.43(m, 2H), 4.32(t, J=5.5 Hz, 1H), 6.73(d, J=8.4 Hz, 1H), 6.78(d, J=1.4 Hz, 1H), 6.82(dd, J=1.4, 8.4 Hz, 1H), 7.61(d, J=3.4 Hz, 1H), 7.62(d, J=3.4 Hz, 1H), 9.46(s, 1H)
MS: FAB(+)261(M⁺), 262(MH⁺)

Examples

The following compounds were obtained by treating (10H-pyrazino[2,3-b][1,4]benzothiazin-8-yl)carbaldehyde successively by the same methods as those of Examples 1128 and 9.

1H), 6.78(d, J=8 Hz, 1H), 6.85(d, J=8 Hz, 1H), 7.15–7.23(m, 2H), 7.25–7.30(m, 4H), 7.58(d, J=3 Hz, 1H), 7.72(d, J=3 Hz, 1H)

MS: ESI(+)336(MH⁺)

m.p.: 156–158° C.

Example 1200

(E)-3-(10H-Pyrazino[2,3-b][1,4]benzothiazin-8-yl)-2-propen-1-ol

The title compound was obtained as yellow crystals by treating (E)-3-[10-(methoxymethyl)-10H-pyrazino[2,3-b][1,4]benzothiazin-8-yl)-2-propen-1-ol by the same method as the one of Example 434.

| Ex. | Structural formula | MS | M.p. | NMR |
|---|---|---|---|---|
| 1197 | 1-(10H-pyrazino[2,3-b][1,4]benzothiazin-8-yl)-3-phenyl-2-propyn-1-ol | | 192–194° C. | ¹H-NMR(CDCl₃) δ ppm: 5.54(br.s, 1H), 6.50(br.s, 1H), 6.77(s, 1H), 6.92(d, J=8Hz, 1H), 7.05(d, J=8Hz, 1H), 7.28–7.40(m, 4H), 7.43–7.48(m, 2H), 7.58(d, J=3Hz, 1H), 7.67(d, J=3Hz, 1H) |
| 1198 | 1-(10H-pyrazino[2,3-b][1,4]benzothiazin-8-yl)hept-2-yn-1-ol | ESI312 (MH⁺) | 116–118° C. | ¹H-NMR(CDCl₃) δ ppm: 1.20(t, J=6Hz, 3H), 1.34–1.48(m, 2H), 1.50–1.60(m, 2H), 2.15–2.20(br.s, 1H), 2.25(dt, J=2, 6Hz, 2H), 5.28–5.35(br.s, 1H), 6.43–6.50(br.s, 1H), 6.72(s, 1H), 6.88(d, J=8Hz, 1H), 6.97(d, J=8Hz, 1H), 7.57(d, J=3Hz, 1H), 7.69(d, J=3Hz, 1H) |

Example 1199

1-(10H-Pyrazino[2,3-b][1,4]benzothiazin-8-yl)-3-phenylpropan-1-ol

The title compound was obtained by treating 1-(10H-pyrazino[2,3-b][1,4]benzothiazin-8-yl)-3-phenyl-2-propyn-1-ol by the same method as the one of Example 20.

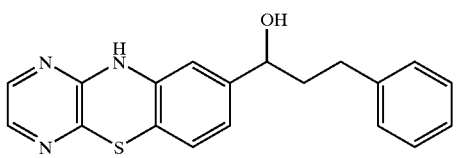

¹H-NMR(CDCl₃) δ ppm: 1.90–2.10(m, 2H), 2.60–2.80 (m, 2H), 4.50–4.60(br.s, 1H), 6.40–6.46(br.s, 1H), 6.52(s,

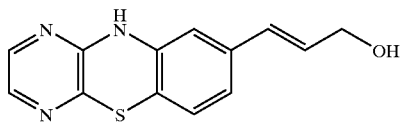

¹H-NMR(D, O-d₆) δ ppm: 4.07(dd, J=4.9, 5.5 Hz, 2H), 4.87(t, J=5.5 Hz, 1H), 6.21(dt, J=4.9, 16.2 Hz, 1H), 6.33(d, J=16.2 Hz, 1H), 6.79(s, 1H), 6.84(s, 2H), 7.61–7.65(m, 2H), 9.47(s, 1H)

Example 1201

3-(10-Methoxymethyl-10H-pyrazino[2,3-b][1,4]benzothiazin-8-yl)-1-propanol 6.0 g of the title compound was obtained as yellow crystals by treating 7.5 g of ethyl 3-(10-methoxymethyl- 10H-pyrazino[2,3-b][1,4]benzothiazin-8-yl)propanoate by the same method as the one of Example 2 followed by purification by silica gel column chromatography (eluted with dichloromethane/methanol).

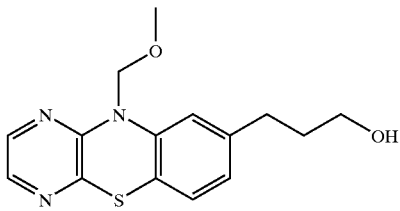

¹H-NMR(CDCl₃) δ ppm: 1.33–1.38(m, 1H), 1.87(dt, J=7.0, 14.9 Hz, 2H), 2.66(dd, J=7.0, 9.3 Hz, 2H), 3.53(s, 3H), 3.65–3.72(m, 2H), 5.28(s, 2H), 6.83(dd, J=1.6, 7.7 Hz, 1H), 6.94(d, J=7.7 Hz, 1H), 7.00(d, J=1.6 Hz, 1H), 7.82(d, J=2.8 Hz, 1H), 7.84(d, J=2.8 Hz, 1H)

Example 1202

3-(10H-Pyrazino[2,3-b][1,4]benzothiazin-8-yl)-1-propanol 120 mg of the title compound was obtained as yellow crystals by treating 250 mg of 3-(10-methoxymethyl-10H-pyrazino[2,3-b][1,4]benzothiazin-8-yl)-1-propanol by the same method as the one of Example 434.

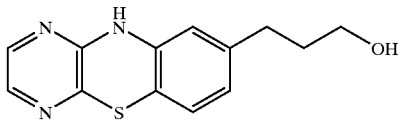

¹H-NMR(CDCl₃) δ ppm: 1.33–1.45(br.s, 1H), 1.83(quint, J=7.1 Hz, 2H), 2.58(t, J=7.1 Hz, 2H), 3.68(t, J=7.1 Hz, 2H), 6.36(d, J=1.9 Hz, 1H), 6.46–6.53(br.s, 1H), 6.69(dd, J=1.9, 7.9 Hz, 1H), 6.81(d, J=7.9 Hz, 1H), 7.57(d, J=2.8 Hz, 1H), 7.69(d, J=2.8 Hz, 1H)

Example 1203

(E)-5-(10-Methoxymethyl-10H-pyrazino[2,3-b][1,4]benzothiazin-8-yl)-2-hydroxy-2-methyl-4-penten-3-one 550 mg of (10-methoxymethyl-10H-pyrazino[2,3-b][1,4]benzothiazin-8-yl)carbaldehyde and 3-hydroxy-3-methyl-2-butanone was dissolved in methanol (10 ml)/tetrahydrofuran (2 ml). After adding 250 mg of lithium hydroxide, the reaction mixture was stirred at room temperature over day and night. Then the reaction mixture was distributed into an aqueous solution of ammonium chloride and ethyl acetate. The organic layer was extracted, washed with water and dried over anhydrous sodium sulfate. After filtering, the filtrate was distilled off under reduced pressure and the residue was purified by silica gel column chromatography (eluted with dichloromethane/methanol) to thereby give 420 mg of the title compound as a yellow oily substance.

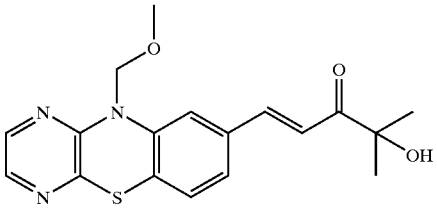

¹H-NMR(CDCl₃) δ ppm: 1.45(s, 6H), 3.55(s, 3H), 3.92(s, 1H), 5.29(s, 2H), 6.96(d, J=15.7 Hz, 1H), 7.03(d, J=8.0 Hz, 1H), 7.23(dd, J=1.7, 8.0 Hz, 1H), 7.30(d, J=1.7 Hz, 1H), 7.75(d, J=15.7 Hz, 1H), 7.85(d, J=2.8 Hz, 1H), 7.86(d, J=2.8 Hz, 1H)

Example 1204

(E)-5-(10H-Pyrazino[2,3-b][1,4]benzothiazin-8-yl)-2-hydroxy-2-methyl-4-penten-3-one 320 mg of the title compound was obtained as yellow crystals by treating 420 mg of (E)-5-(10-methoxymethyl-10H-pyrazino[2,3-b][1,4]benzothiazin-8-yl)-2-hydroxy-2-methyl-1-penten-3-one by the same method as the one of Example 9.

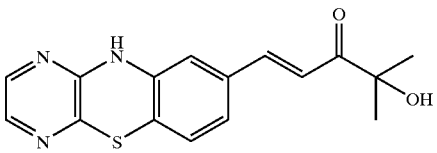

¹H-NMR(DMSO-d₆) δ ppm: 1.23(s, 6H), 5.43(s, 1H), 6.97(d, J=8.2 Hz, 1H), 7.06(s, 1H), 7.12(d, J=8.2 Hz, 1H), 7.33(d, J=16.9 Hz, 1H), 7.37(d, J=16.9 Hz, 1H), 7.64(d, J=3.0 Hz, 1H), 7.65(d, J=3.0 Hz, 1H), 9.51(s, 1H)

Example 1205

5-(10-Methoxymethyl-10H-pyrazino[2,3-b][1,4]benzothiazin-8-yl)-2-hydroxy-2-methylpentan-3-one 320 mg of the title compound was obtained as yellow crystals by treating 450 mg of (E)-5-(10-methoxymethyl-10H-pyrazino[2,3-b][1,4]benzothiazin-8-yl)-2-hydroxy-2-methyl-4-penten-3-one successively by the same methods as those of Examples 20 and 9.

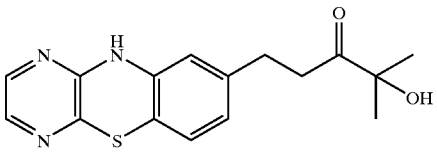

¹H-NMR(DMSO-d₆) δ ppm: 1.14(s, 6H), 2.55(t, J=7 Hz, 2H), 2.88(t, J=7 Hz, 2H), 5.24(br.s, 1H), 6.61(t, J=1 Hz, 1H), 6.63(dd, J=1, 8 Hz, 1H), 6.79(dd, J=1, 8 Hz, 1H), 7.62(m, 2H), 9.43(s, 1H)
MS: FAB(+)315(M⁺)

Example 1206

1-(10H-Pyrazino[2,3-b][1,4]benzothiazin-8-yl)ethanol 5.0 g of (10-methoxymethyl-10H-pyrazino[2,3-b][1,4]benzothiazin-8-yl)carbaldehyde was treated by the same method as the one of Production Example 86 to thereby give 5.0 g of 1-(10-methoxymethyl-10H-pyrazino[2,3-b][1,4]benzothiazin-8-yl)ethanol as a yellow oily substance. Next, a 0.5 g portion of this product was treated by the same method as the one of Example 9 to thereby give 0.1 g of the title compound as yellow crystals.

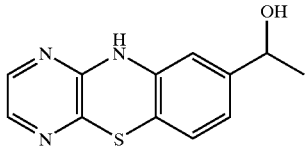

¹H-NMR(CDCl₃) δ ppm: 1.43(d, J=4.0 Hz, 3H), 1.91 (br.s, 1H), 4.78(q, J=4.0 Hz, 1H), 6.50–6.60(br.s, 1H), 6.57(d, J=1.6 Hz, 1H), 6.81(dd, J=1.6, 8.3 Hz, 1H), 6.86(d, J=8.3 Hz, 1H), 7.57(d, J=3.1 Hz, 1H), 7.69(d, J=3.1 Hz, 1H)

Example 1207

Diethyl(10H-pyrazino[2,3-b][1,4]benzothiazin-8-yl)phosphonate

To 2 ml of triethyl phosphite was added 0.374 g of 8-chloromethyl-10H-pyrazino[2,3-b][1,4]benzothiazine and the resulting mixture was heated to 160° C. for 3 hours. Then the reaction mixture was brought back to room temperature and diethyl ether (10 ml) and n-hexane (20 ml) were added thereto. The precipitate was taken up by filtration and washed several times with n-hexane to thereby give 0.413 g of the title compound as a yellow powder.

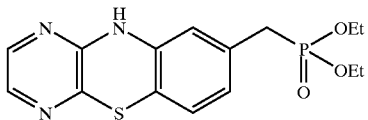

¹H-NMR(CDCl₃) δ ppm: 1.28(t, J=6 Hz, 6H), 2.94(d, J=23 Hz, 2H), 4.05(m, 4H), 6.50(s, 1H), 6.51(d, J=2 Hz, 1H), 6.73(dd, J=2, 8 Hz, 1H), 6.82(d, J=8 Hz, 1H), 7.57(d, J=3 Hz, 1H), 7.69(d, J=3 Hz, 1H)

MS: FAB(+)352(MH⁺)

m.p.: 164–165° C.

Example 1208

5-(10-Methoxymethyl-10H-pyrazino[2,3-b][1,4]benzothiazin-8-yl)-1,3-oxazole

To 10 ml of a solution of 560 mg of (10-methoxymethyl-10H-pyrazino[2,3-b][1,4]benzothiazin-8-yl)carbaldehyde in methanol were added 280 mg of potassium carbonate and 392 mg of (p-toluenesulfonyl)methyl isocyanide and the resulting mixture was heated under reflux for 1.5 hours. Then the reaction mixture was brought back to room temperature and diluted with water. The crystals thus precipitated were taken up by filtration and washed successively with water and diethyl ether to thereby give 400 mg of the title compound as yellow crystals.

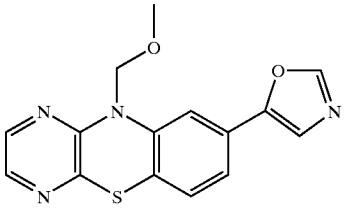

¹H-NMR(DMSO-d₆) δ ppm: 3.41(s, 3H), 5.33(s, 2H), 7.22(d, J=8.2 Hz, 1H), 7.37(dd, J=1.7, 8.2 Hz, 1H), 7.39(d, J=1.7 Hz, 1H), 7.68(s, 1H), 7.94(d, J=2.8 Hz, 1H), 7.98(d, J=2.8 Hz, 1H), 8.45(s, 1H)

Example 1209

1-(10-Methoxymethyl-10H-pyrazino[2,3-b][1,4]benzothiazin-8-yl)-1,3-butanedione

Into 20 ml of ice-cooled solution of 1.27 ml of diisopropylamine in dry tetrahydrofuran was dropped in a nitrogen atmosphere 5.5 ml of a 1.6 M solution of n-butyllithium in hexane. After stirring for 10 minutes, the reaction mixture was cooled to −78° C. Next, 5 ml of a solution of 2.0 g of (10-methoxymethyl-10H-pyrazino[2,3-b][1,4]benzothiazin-8-yl)methyl ketone in dry tetrahydrofuran was added thereto and the mixture was stirred for 30 minutes. After further dropping 700 mg of acetyl chloride thereinto, the reaction mixture was brought back to room temperature. Then the reaction mixture was distributed into water and ethyl acetate and the organic layer was extracted, washed with water, dried over anhydrous sodium sulfate and filtered. The filtrate was distilled off under reduced pressure and the residue was purified by silica gel column chromatography (eluted with toluene/acetone) to thereby give 420 mg of the title compound as a yellow oily substance.

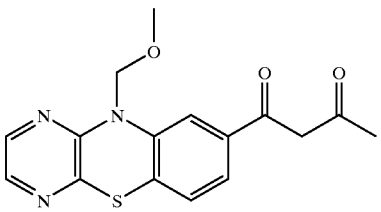

¹H-NMR(CDCl₃) δ ppm: 2.20(s, 3H), 3.56(s, 3H), 5.33(s, 2H), 6.10(s, 1H), 7.06(d, J=7.8 Hz, 1H), 7.43(dd, J=1.6, 7.8 Hz, 1H), 7.64(d, J=1.6 Hz, 1H), 7.86(s, 2H)

Example 1210

8-(5-Methylpyrazol-3-yl)10H-pyrazino[2,3-b][1,4benzothiazine

To 10 ml of a solution of 180 mg of 1-(10-methoxymethyl)-10H-pyrazino[2,3-b][1,4]benzothiazin-8-yl)-1,3-butanedione in methanol was added 50 mg of hydrazine monohydrate and the resulting mixture was heated under reflux for 30 minutes. Then the reaction mixture was brought back to room temperature. After distilling off the solvent under reduced pressure, the crystals thus precipitated were taken up by filtration and washed with diethyl ether to thereby give 150 mg of 8-(5-methylpyrazol-3-yl)-10-methoxymethyl-10H-pyrazino[2,3-b][1,4]benzothiazine as yellow crystals. Further, this product was treated by the same method as the one of Example 9 to thereby give 110 mg of the title compound as yellow crystals.

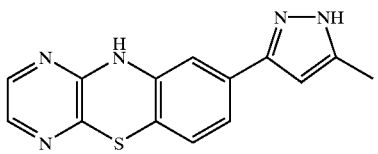

¹H-NMR(DMSO-d₆) δ ppm: 2.22(br.s, 3H), 6.27(s, 1H), 6.89(br.d, J=8.0 Hz, 1H), 7.12(d, J=8.0 Hz, 1H), 7.23(br.s, 1H), 7.63(d, J=2.9 Hz, 1H), 7.64(d, J=2.9 Hz, 1H), 9.52(br.s, 1H), 12.50–12.60(br.s, 1H)
MS: FAB(+)285(M⁺)

Example 1211

(10H-Pyrazino[2,3-b][1,4]benzothiazin-8-yl)-3-methylisoxazole

Similar to Example 1223, 1-(10-methoxymethyl-10H-pyrazino[2,3-b][1,4]benzothiazin-8-yl)-1,3-butanedione was treated with hydroxylamine to thereby give (10-methoxymethyl-10H-pyrazino[2,3-b][1,4]benzothiazin-8-yl)-3-methylisoxazole. Further, this product was treated by the same method as the one of Example 9 to thereby give the title compound.

¹H-NMR(DMSO-d₆) δ ppm: 2.26(s, 3H), 6.72(s, 1H), 7.04(d, J=8.0 Hz, 1H), 7.15(d, J=1.4 Hz, 1H), 7.21(dd, J=1.4, 8.0 Hz, 1H), 7.66(d, J=3.0 Hz, 1H), 7.67(d, J=3.0 Hz, 1H), 9.65(s, 1H)

Example 1212

2-Amino-1-[N-[(10-methoxymethyl-10H-pyrazino[2,3-b][1,4]benzothiazin-8-yl)methylene]]aminobenzene 820 mg of (10-methoxymethyl-10H-pyrazino[2,3-b][1,4]benzothiazin-8-yl)carbaldehyde and 360 mg of o-phenylenediamine were suspended in 2 ml of pyridine in a nitrogen atmosphere and heated under reflux for 10 minutes. Then the reaction mixture was brought back to room temperature and a small amount of ethyl acetate was added thereto. The crystals thus precipitated were ground by ultrasonication and filtered. Thus 610 mg of the title compound was obtained as yellow crystals.

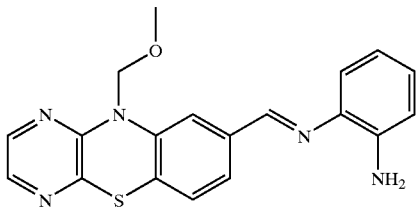

¹H-NMR(CDCl₃) δ ppm: 3.57(s, 3H), 4.26(br.s, 2H), 5.35(s, 2H), 6.75(dt, J=1.2, 7.4 Hz, 1H), 6.78(dd, J=1.2, 7.4 Hz, 1H), 7.07(d, J=7.4 Hz, 1H), 7.08(t, J=7.4 Hz, 1H), 7.09(d, J=8.3 Hz, 1H), 7.50(dd, J=1.5, 8.3 Hz, 1H), 7.66(d, J=1.5 Hz, 1H), 7.86(s, 2H), 8.46(s, 1H)

Example 1213

8-(Benzimidazol-2-yl)-10-methoxymethyl-10H-pyrazino[2,3-b][1,4]benzothiazine 610 mg of 2-amino-1-[N-[(10-methoxymethyl-10H-pyrazino[2,3-b][1,4]benzothiazin-8-yl)methylene]]aminobenzene was heated under reflux in 3 ml of pyridine for 8 hours. Then the reaction mixture was brought back to room temperature and eluted with ethyl acetate. The crystals thus precipitated were ground and filtered to thereby give 310 mg of the title compound as yellow crystals.

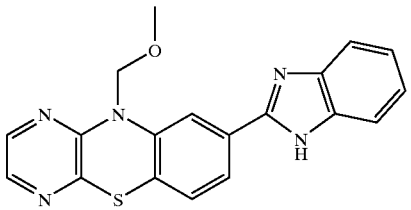

¹H-NMR(DMSO-d₆) δ ppm: 3.45(s, 3H), 5.39(s, 2H), 7.15–7.25(m, 2H), 7.31(d, J=8.3 Hz, 1H), 7.48–7.56(br.d, J=7.2 Hz, 1H), 7.63–7.70(br.d, J=7.2 Hz, 1H), 7.75(dd, J=1.7, 8.3 Hz, 1H), 7.94(d, J=1.7 Hz, 1H), 7.96(d, J=2.6 Hz, 1H), 8.00(d, J=2.6 Hz, 1H), 12.93(br.s, 1H)

Example 1214

8-(Benzothiazol-2-yl)-10-methoxymethyl-10H-pyrazino[2,3-b][1,4]benzothiazine

Similar to Example 1212, 2-aminobenzenethiol employed as a substitute for o-phenylenediamine was heated under reflux in pyridine for 30 minutes to thereby give 820 mg of (10-methoxymethyl-10H-pyrazino[2,3-b][1,4]benzothiazin-8-yl)carbaldehyde, from which 250 mg of the title compound was obtained as yellow crystals.

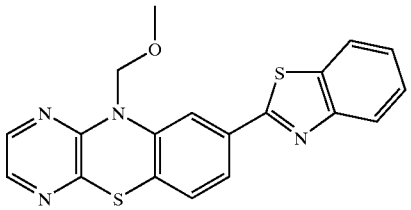

¹H-NMR(CDCl₃) δ ppm: 3.61(s, 3H), 5.40(s, 2H), 7.13(t, J=8.1 Hz, 1H), 7.40(t, J=8.3 Hz, 1H), 7.50(t, J=8.3 Hz, 1H), 7.68(dd, J=1.8, 8.1 Hz, 1H), 7.85(d, J=1.8 Hz, 1H), 7.88(s, 2H), 7.90(d, J=8.3 Hz, 1H), 8.07(d, J=8.3 Hz, 1H)

Examples

The following compounds were obtained each as yellow crystals by treating the compounds obtained in Examples 1213 and 1214 by the same method as the one of Example 434.

| Ex. | Structural formula | NMR |
|---|---|---|
| 1215 | 8-benzimidazol-2-yl)-10H-pyrazino[2, 3-b][1, 4]benzothiazine | ¹H-NMR(DMSO-d₆) δ ppm: 7.09(d, J=7.7Hz, 1H), 7.13–7.23(m, 2H), 7.45–7.52(m, 1H), 7.48(dd, J=1.7, 7.7Hz, 1H), 7.59–7.65(m, 1H), 7.63(d, J=1.7Hz, 1H), 7.66(d, J=2.7Hz, 1H), 7.68(d, J=2.7Hz, 1H), 9.70(s, 1H), 12.83(br.s, 1H) |
| 1216 | 8-benzothiazol-2-yl)-10H-pyrazino[2, 3-b][1, 4]benzothiazine | ¹H-NMR(DMSO-d₆) δ ppm: 7.08(d, J=8.1Hz, 1H), 7.44(dd, J=1.8, 8.1Hz, 1H), 7.45(t, J=8.0Hz, 1H), 7.52(d, J=1.8Hz, 1H), 7.53(t, J=8.0Hz, 1H), 7.67(d, J=2.8Hz, 1H), 7.68(d, J=2.8Hz, 1H), 8.01(d, J=8.0Hz, 1H), 8.13(d, J=8.0Hz, 1H), 9.69(s, 1H) |

Example 1217
(E)-8-(Benzenesulfonylvinyl)-10-methoxymethyl-10H-pyrazino-[2,3-b][1,4]benzothiazine A solution of 1.40 g of diethyl(benzenesulfonyl)-methylphosphonate in N,N-dimethylformamide (15 ml) was cooled to 0° C. in a nitrogen atmosphere. After adding 210 mg of sodium hydride, the resulting mixture was stirred for 5 minutes. Into the reaction mixture was dropped a solution of 1.00 g of (10-methoxymethyl-10H-pyrazino[2,3-b][1,4]benzothiazin-8-yl)carbaldehyde in N,N-dimethylformamide (5 ml). After stirring for additional 10 minutes, the reaction mixture was distributed into water and ethyl acetate. The organic layer was extracted, washed with water and dried over magnesium sulfate. After distilling off the solvent under reduced pressure, the residue was diluted with diisopropyl ether and the crystals thus precipitated were filtered to thereby give 1.38 g of the title compound as yellow crystals.

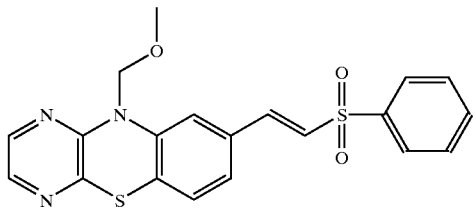

¹H-NMR(DMSO-d₆) δ ppm: 3.36(s, 3H), 5.33(s, 2H), 7.18(d, J=8.0 Hz, 1H), 7.35(d, J=1.7 Hz, 1H), 7.40(dd, J=1.7, 8.0 Hz, 1H), 7.58(s, 2H), 7.62–7.69(m, 2H), 7.70–7.75(m, 1H), 7.89–7.93(m, 2H), 7.95(d, J=2.9 Hz, 1H), 7.97(d, J=2.9 Hz, 1H)

Example 1218
8-(1,2,3-Triazol-4(5)-yl)-10-methoxymethyl-10H-pyrazino[2,3-b][1,4]benzothiazine To a solution of 410 mg of 8-(2-benzenesulfonylvinyl)-10-methoxymethyl-10H-pyrazino[2,3-b][1,4]benzothiazine in a mixture of N,N-dimethylformamide (3 ml) and dimethyl sulfoxide (7 ml) was added sodium azide (450 mg in total) and the resulting mixture was heated to 120° C. for 3 hours. Then the reaction mixture was brought back to room temperature and distributed into 1 N hydrochloric acid and ethyl acetate. The organic layer was extracted, washed with water and dried over anhydrous magnesium sulfate. After distilling off the solvent under reduced pressure, the crystals thus precipitated were filtered and washed with diisopropyl ether. Thus 220 mg of the title compound was obtained.

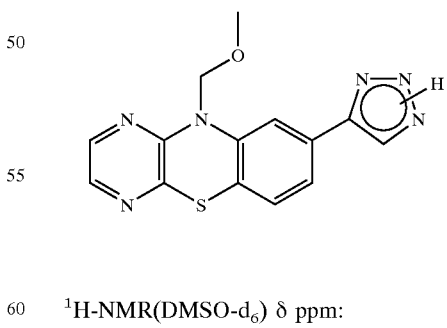

¹H-NMR(DMSO-d₆) δ ppm:

3.41(s, 3H), 5.33(s, 2H), 7.19 and 7.21(d, J=7.7 Hz, total 1H, 1:2), 7.47 and 7.49(dd, J=1.4, 7.7 Hz, total 1H, 1:2), 7.62 and 7.69(d, J=1.4 Hz, total 1H, 2:1), 7.94(d, J=2.8 Hz, 1H), 7.98(d, J=2.8 Hz, 1H), 8.23 and 8.57(d, J=1.2 Hz, initial 1H, and, br.s, initial 1H, 2:1)

Example 1219

8-(3-Trimethylsilylpyrazol-4-yl)-10-methoxymethyl-10H-pyrazino[2,3-b][1,4]benzothiazine 1.5 ml of a 2.0 M solution of (trimethylsilyl)-diazomethane in hexane was added to dry tetrahydrofuran (7 ml) in a nitrogen atmosphere and cooled to −78° C. After dropping 1.0 ml of a 1.6 M n-butyllithium solution in n-hexane thereinto, the resulting mixture was stirred for 30 minutes. Into the reaction mixture was dropped a solution of 410 mg of 8-(2-benzenesulfonylvinyl)-10-methoxymethyl-10H-pyrazino[2,3-b][1,4]benzothiazine obtained in Example 1080-1 in dry tetrahydrofuran (5 ml). Then the reaction mixture was gradually heated to room temperature and an aqueous solution of ammonium chloride was added thereto followed by extraction with ethyl acetate. Then the mixture was dried over anhydrous sodium sulfate. After distilling off the solvent under reduced pressure, the obtained residue was purified by silica gel column chromatography (eluted with ethyl acetate/n-hexane) to thereby give 130 mg of the title compound as yellow crystals.

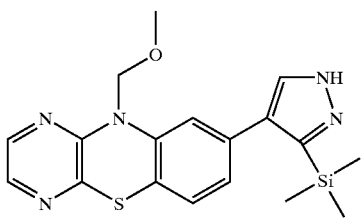

$^1$H-NMR(CDCl$_3$) δ ppm: 0.00(s, 9H), 3.20(s, 3H), 4.96(s, 2H), 6.68(dd, J=1.5, 7.6 Hz, 1H), 6.72(d, J=7.6 Hz, 1H), 6.68(d, J=1.5 Hz, 1H), 7.38(s, 1H), 7.54(d, J=2.8 Hz, 1H), 7.55(d, J=2.8 Hz, 1H)

Example 1220

8-(Pyrazol-4-yl)-10-methoxymethyl-10H-pyrazino[2,3-b][1,4]benzothiazine 5 ml of a solution of 130 mg of 8-(3-trimethylsilyl-pyrazol-4-yl)-10-methoxymethyl-10H-pyrazino(2,3-b][1,4]-benzothiazine in tetrahydrofuran was stirred at room temperature and 1.1 ml of a 1M solution of tetrabutylammonium fluoride in tetrahydrofuran was added thereto. After stirring for 5 minutes, the reaction mixture was distributed into ethyl acetate and 1 N hydrochloric acid. The organic layer was extracted, washed with water and dried over anhydrous sodium sulfate. After distilling off the solvent under reduced pressure, the obtained residue was purified by silica gel column chromatography (eluted with dichloromethane/methanol) to thereby give 42 mg of the title compound as yellow crystals.

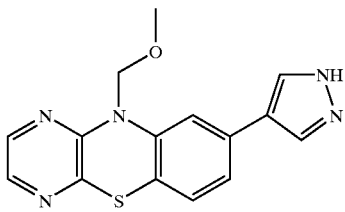

$^1$H-NMR(CDCl$_3$) δ ppm: 3.56(s, 3H), 5.33(s, 2H), 7.03(d, J=7.8 Hz, 1H), 7.12(dd, J=1.6, 7.8 Hz, 1H), 7.32(d, J=1.6 Hz, 1H), 7.85(s, 2H), 7.85(d, J=2.8 Hz, 1H), 7.86(d, J=2.8 Hz, 1H)

Example 1221

8-(1,2,3-Triazol-4(5)-yl)-10H-pyrazino[2,3-b][1,4-benzothiazine

The title compound was obtained by treating 8-(1,2,3-triazol-4(5)-yl)-10-methoxymethyl-10H-pyrazino[2,3-b][1,4]-benzothiazine by the same method as the one of Example 434.

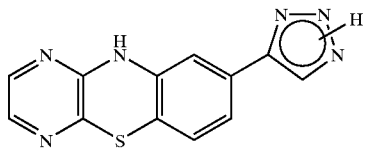

$^1$H-NMR(DMSO-d$_6$) δ ppm: 6.69(d, J=8.6 Hz, 1H), 7.23(d, J=8.6 Hz, 1H), 7.27–7.35(br.s, 1H), 7.64(d, J=3.0 Hz, 1H), 7.65(d, J=3.0 Hz, 1H), 8.12–8.27(br.s, 1H), 9.61(s, 1H)

MS: FAB(+)269(MH$^+$)

Example 1222

8-(Pyrazol-4-yl)10H-pyrazino[2,3-b][1,4]benzothiazine

The title compound was obtained by treating 8-(pyrazol-4-yl)-10-methoxymethyl-10H-pyrazino[2,3-b][1,4]benzothiazine by the same method as the one of Example 9.

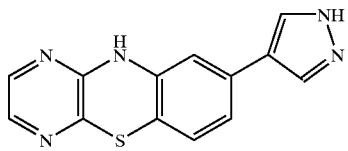

$^1$H-NMR(DMSO-d$_6$) δ ppm: 6.88(d, J=7.6 Hz, 1H), 6.96 (d, J=1.8 Hz, 1H), 7.02(dd, J=1.8, 7.6 Hz, 1H), 7.63(d, J=2.9 Hz, 1H), 7.64(d, J=2.9 Hz, 1H), 7.87(br.s, 2H), 9.44(s, 1H)

MS: FAB(+)268(MH$^+$)

Example 1223

(10-Methoxymethyl-10H-pyrazino[2,3-b][1,4]benzothiazin-8-yl)carbaldehyde oxime To 10 ml of a solution of 820 mg of (10-methoxymethyl-10H-pyrazino[2,3-b][1,4]benzothiazin-8-yl)carbaldehyde and 430 mg of ammonium acetate in ethanol was added 1 ml of an aqueous solution of 230 mg of hydroxylamine hydrochloride. Then the resulting mixture was heated under reflux for 1 hour while adding tetrahydrofuran if necessary. The reaction mixture was brought back to room temperature and the solvent was distilled off under reduced pressure. The crystals thus precipitated were taken up by filtration and washed successively with water and diethyl ether to thereby give 760 mg of the title compound as yellow crystals.

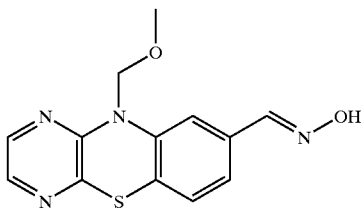

¹H-NMR(CDCl₃) δ ppm: 3.54(s, 3H), 5.30(s, 2H), 7.02(d, J=8.0 Hz, 1H), 7.14(dd, J=1.6, 8.0 Hz, 1H), 8.38(d, J=1.6 Hz, 1H), 7.58(s, 1H), 7.85(d, J=3.1 Hz, 1H), 7.86(d, J=3.1 Hz, 1H), 8.06(s, 1H)

Example 1224

(10-Methoxymethyl-10H-pyrazino[2,3-b][1,4]benzothiazin-8-yl)carbonitrile 100 mg of (10-methoxymethyl-10H-pyrazino[2,3-b][1,4]benzothiazin-8-yl)carbaldehyde oxime was suspended in 2 ml of trichloroacetonitrile in a nitrogen atmosphere and heated under reflux for 30 minutes. After distilling off the low-boiling fraction, the crystals thus precipitated were ground after adding diethyl ether thereto and taken up by filtration to thereby give 90 mg of the title compound as colorless crystals.

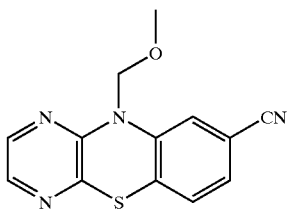

¹H-NMR(CDCl₃) δ ppm: 3.54(s, 3H), 5.26(s, 2H), 7.08(d, J=7.8 Hz, 1H), 7.22(dd, J=1.6, 7.8 Hz, 1H), 7.38(d, J=1.6 Hz, 1H), 7.88(d, J=2.7 Hz, 1H), 7.90(d, J=2.7 Hz, 1H)

Example 1225

8-(Tetrazol-5-yl)-10-methoxymethyl-10H-pyrazino[2,3-b][1,4]benzothiazine

To a solution of 150 mg of (10-methoxymethyl-10H-pyrazino[2,3-b][1,4]benzothiazin-8-yl)carbonitrile in dimethyl sulfoxide were added 360 mg of sodium azide and 300 mg of ammonium chloride and the resulting mixture was heated to 100° C. for 4 hours. Then the reaction mixture was brought back to room temperature and distributed into ethyl acetate and 1 N hydrochloric acid. The organic layer was extracted, washed with water and dried over anhydrous sodium sulfate. After distilling off the solvent under reduced pressure, the obtained residue was purified by silica gel column chromatography (eluted with dichloromethane/methanol/acetic acid) to thereby give 130 mg of the title compound as yellow crystals.

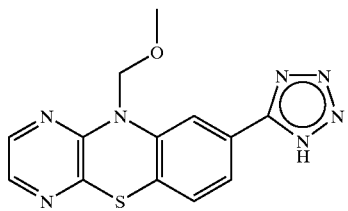

¹H-NMR(DMSO-d₆) δ ppm: 3.43(s, 3H), 5.32(s, 2H), 7.35(d, J=7.9 Hz, 1H), 7.61(dd, J=1.7, 7.9 Hz, 1H), 7.76(d, J=1.7 Hz, 1H), 7.96(d, J=2.6 Hz, 1H), 8.00(d, J=2.6 Hz, 1H)

Example 1226

8-(Tetrazol-5-yl)10H-pyrazino[2,3-b][1,4]benzothiazine 40 mg of 8-(tetrazol-5-yl)-10-methoxymethyl-10H-pyrazino[2,3-b][1,4]benzothiazine was heated 5 ml of glacial acetic acid to 60° C. for 30 minutes. After the completion of the reaction, silica gel was added thereto. After distilling off the solvent under reduced pressure, the residue was purified by silica gel column chromatography (eluted with dichloromethane/methanol/acetic acid) to thereby give 18 mg of the title compound as yellow crystals.

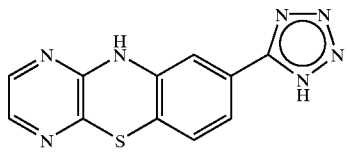

¹H-NMR(DMSO-d₆) δ ppm: 7.13(d, J=8.2 Hz, 1H), 7.34(dd, J=1.7, 8.2 Hz, 1H), 7.45(d, J=1.7 Hz, 1H), 7.67(d, J=3.0 Hz, 1H), 7.68(d, J=3.0 Hz, 1H), 9.77(s, 1H)

MS: FAB(+)270(MH⁺)

Example 1227

[N-(2-Pyridyl)aminometyl](10-methoxymethyl-10H-pyrazino[2,3-b][1,4]benzothiazin-8-yl)ketone To 3 ml of a solution of 140 mg of 2-aminopyridine in ethanol was added 130 mg of sodium hydrogencarbonate and the resulting mixture was stirred at room temperature. Next, 2 ml of a solution of 360 mg of bromomethyl(10-methoxymethyl-10H-pyrazino[2,3-b][1,4]benzothiazin-8-yl)ketone in tetrahydrofuran was dropped thereinto and the resulting mixture was heated under reflux for 2 hours. Then the reaction mixture was brought back to room temperature and silica gel was added thereto. After distilling off the solvent under reduced pressure, the residue was purified by silica gel column chromatography (eluted with dichloromethane/methanol) to thereby give 200 mg of the title compound as yellow crystals.

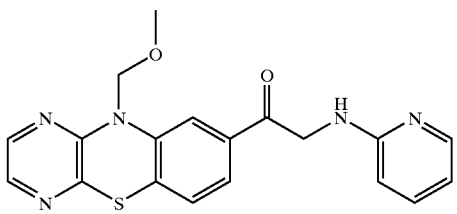

$^1$H-NMR(CDCl$_3$) δ ppm: 3.47(s, 2H), 3.58(s, 3H), 5.41(s, 2H), 6.78(dt, J=0.9, 6.7 Hz, 1H), 7.06(d, J=8.3 Hz, 1H), 7.18(ddd, J=1.3, 6.7, 9.1 Hz, 1H), 7.55(dd, J=1.7, 8.3 Hz, 1H), 7.62(br.d, J=9.1 Hz, 1H), 7.72(d, J=1.7 Hz, 1H), 7.83(s, 1H), 7.84(s, 2H), 8.11(br.d, J=6.7 Hz, 1H)

Example 1228

8-(Imidazo[1,2-a]pyridin-3-yl)-10H-pyrazino[2,3-b] [1,4]-benzothiazine 10 ml of a solution of 200 mg of [N-(2-pyridyl) aminometyl](10-methoxymethyl-10H-pyrazino[2,3-b][1,4] benzothiazin-8-yl)ketone in carbon tetrachloride was stirred at room temperature and 240 mg of thionyl chloride was dropped thereinto. The reaction mixture was distributed into dichloromethane and an aqueous solution of sodium bicarbonate and the organic layer was separated. To the organic layer were added methanol and tetrahydrofuran to give a homogeneous solution. After adding silica gel and distilling off the solvent under reduced pressure, the residue was purified by silica gel column chromatography (eluted with dichloromethane/methanol) to thereby give 103 mg of the title compound as yellow crystals.

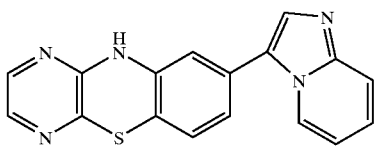

$^1$H-NMR(DMSO-d$_6$) δ ppm: 6.88(dt, J=1.1, 7.7 Hz, 1H), 6.95(d, J=7.7 Hz, 1H), 7.23(ddd, J=1.1, 7.0, 9.5 Hz, 1H), 7.37(dd, J=1.8, 7.7 Hz, 1H), 7.44(d, J=1.8 Hz, 1H), 7.53(d, J=9.5 Hz, 1H), 7.63(d, J=2.6 Hz, 1H), 7.65(d, J=2.6 Hz, 1H), 8.26(s, 1H), 8.52(dd, J=1.1, 7.0 Hz, 1H), 9.59(s, 1H)
MS: FAB(+)218(MH$^+$)

Example 1229

8-(1,3-Thiazol-5-yl)-10-methoxymethyl-10H-pyrazino2,3-b][1,4]benzothiazine

To 3 ml of a solution of 180 mg of crude thioformamide in ethanol was added 130 mg of sodium hydrogencarbonate and the resulting mixture was stirred at room temperature. After dropping 2 ml of a solution of 360 mg of bromomethyl (10-methoxymethyl-10H-pyrazino[2,3-b][1,4]benzothiazin-8-yl)ketone in tetrahydrofuran, the resulting mixture was stirred for 1 hour. Then the reaction mixture was distributed into water and ethyl acetate. The organic layer was extracted and dried over anhydrous sodium sulfate. After distilling off the solvent under reduced pressure, the residue was purified by silica gel column chromatography (eluted with ethyl acetate/n-hexane) to thereby give 100 mg of the title compound as yellow crystals.

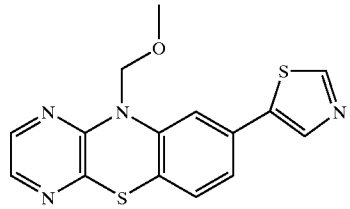

$^1$H-NMR(DMSO-d$_6$) δ ppm: 3.42(s, 3H), 5.33(s, 2H), 7.20(d, J=8.3 Hz, 1H), 7.61(dd, J=1.5, 8.3 Hz, 1H), 7.78(d, J=1.5 Hz, 1H), 7.94(d, J=2.4 Hz, 1H), 7.98(d, J=2.4 Hz, 1H), 8.17(d, J=2.0 Hz, 1H), 9.19(d, J=2.0 Hz, 1H)

Example 1230

8-(Imidazo[2,1-b]benzothiazol-1-yl)-10-methoxymethyl-10H-pyrazino[2,3-b][1,4] benzothiazine 180 mg of the title compound was obtained as yellow crystals by the same method as the one of Example 1229 by starting with 550 mg of bromomethyl(10-methoxymethyl-10H-pyrazino[2,3-b][1,4]-benzothiazin-8-yl)ketone and 300 mg of 2-aminobenzothiazole.

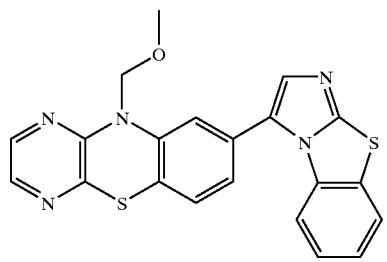

$^1$H-NMR(DMSO-d$_6$) δ ppm: 3.46(s, 3H), 5.35(s, 2H), 7.18(d, J=8.3 Hz, 1H), 7.42(t, J=7.6 Hz, 1H), 7.48(dd, J=1.6, 8.3 Hz, 1H), 7.56(t, J=7.6 Hz, 1H), 7.68(d, J=1.6 Hz, 1H), 7.94(d, J=2.6 Hz, 1H), 7.98(d, J=2.6 Hz, 1H), 8.00(d, J=7.6 Hz, 1H), 8.03(d, J=7.6 Hz, 1H), 8.77(s, 1H)

Examples

The following compounds were obtained each as yellow crystals by treating the compounds obtained in Examples 1229 and 1230.

| Ex. | Structural formula | MS | NMR |
|---|---|---|---|
| 1231 | 8-(thiazol-5-yl)-10H-pyrazino[2, 3-b][1, 4]enzothiazine | FAB(+) 284(M⁺) | ¹H-NMR(DMSO-d₆) δ ppm: 6.98(d, J=8.4Hz, 1H), 7.16(dd, J=1.5, 8.4Hz, 1H), 7.45(d, J=1.5Hz, 1H), 7.62–7.65(m, 2H), 8.02(d, J=1.8Hz, 1H), 9.16(d, J=1.8Hz, 1H), 9.59(s, 1H) |
| 1232 | 8-(imidazo[2, 1-b]enzothiazol-1-yl)-10H-pyrazino[2, 3-b][1, 4]enzothiazine | | ¹H-NMR(DMSO-d₆) δ ppm: 6.95(d, J=8.1Hz, 1H), 7.23(dd, J=1.6, 8.1Hz, 1H), 7.33(d, J=1.6Hz, 1H), 7.42(t, J=7.7Hz, 1H), 7.55(t, J=7.7Hz, 1H), 7.64(d, J=3.1Hz, 1H), 7.66(d, J=3.1Hz, 1H), 8.00(d, J=7.7Hz, 1H), 8.02(d, J=7.7Hz, 1H), 8.65(s, 1H), 9.63(s, 1H) |

Example 1233

2-(10-Methoxymethyl-10H-pyrazino[2,3-b][1,4]benzothiazin-8-yl)-4,5-dihydro-1,3-thiazol-4-ol 450 mg of (10-methoxymethyl-10H-pyrazino[2,3-b][1,4]benzothiazin-8-yl)carbothioamide was dissolved in a solvent mixture of tetrahydrofuran (5 ml) with 1,2-dimethoxyethane (5 ml). Under stirring, 610 mg of potassium hydrogencarbonate and 2 ml of a 40% chloroacetaldehyde solution were added thereto at room temperature and the resulting mixture was stirred for half a day. Then the reaction mixture was distributed into an aqueous solution of ammonium chloride and ethyl acetate. The organic layer was extracted and dried over anhydrous sodium sulfate. After distilling off the solvent, the crystals thus precipitated were taken up by filtration to thereby give 475 mg of the title compound as yellow crystals.

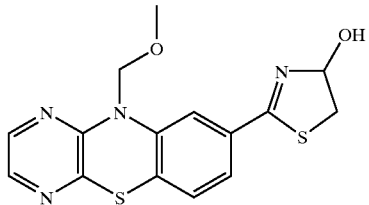

¹H-NMR(CDCl₃) δ ppm: 3.41(dd, J=4.5, 11.8 Hz, 1H), 3.56(s, 3H), 3.63(dd, J=6.9, 11.8 Hz, 1H), 5.33(s, 2H), 6.28(dd, J=4.5, 6.9 Hz, 1H), 7.05(d, J=8.2 Hz, 1H), 7.43(dd, J=1.5, 8.2 Hz, 1H), 7.64(d, J=1.5 Hz, 1H), 7.86(s, 2H)

Example 1234

8-(Thiazol-2-yl)-10H-pyrazino[2,3-b][1,4]benzothiazine 450 mg of 2-(10-methoxymethyl-10H-pyrazino[2,3-b][1,4]benzothiazin-8-yl)-4,5-dihydro-1,3-thiazol-4-ol and 0.83 ml of pyridine were dissolved in 15 ml of 1,2-dimethoxyethane. While stirring the reaction mixture under ice-cooling, 300 mg of trifluoroacetic anhydride was dropped thereinto and the resulting mixture was stirred for 1 hour. Then the reaction mixture was distributed into an aqueous solution of sodium bicarbonate and ethyl acetate. The organic layer was extracted, washed with water and dried over anhydrous magnesium sulfate. After distilling off the solvent under reduced pressure, the oily residue thus obtained was treated in the same manner as the one of Example 434 and purified by silica gel column chromatography (eluted with dichloromethane/methanol). Thus 230 mg of the title compound was obtained as yellow crystals.

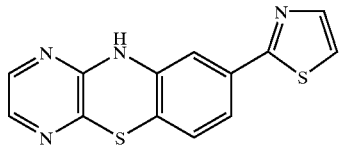

¹H-NMR(DMSO-d₆) δ ppm: 7.01(d, J=7.7 Hz, 1H), 7.31 (dd, J=1.9, 7.7 Hz, 1H), 7.39(d, J=1.9 Hz, 1H), 7.66(d, J=2.4 Hz, 1H), 7.67(d, J=2.4 Hz, 1H), 7.76(d, J=3.2 Hz, 1H), 7.89(d, J=3.2 Hz, 1H), 9.66(s, 1H)

Example 1235

8-(3H,4H-Dihydrothiazol-2-ylmethyl)-10-methoxymethyl-10H-pyrazino[2,3-b][1,4]benzothiazine 670 mg of 2-aminoethanethiol hydrochloride was suspended in 20 ml of methanol. Then 1.2 g of a 28% solution of sodium methoxide in methanol was added thereto and the resulting mixture was subjected to ultrasonication at room temperature for about 5 minutes. Next, 570 mg of (10-methoxymethyl-10H-pyrazino[2,3-b][1,4]benzothiazin-8-yl)carbaldehyde was added thereto and the resulting mixture was heated under reflux for 3 hours. The reaction mixture was then distributed into water and ethyl acetate. The organic layer was extracted, washed with water and dried over anhydrous sodium sulfate. After distilling off the solvent under reduced pressure, the residue was purified by silica gel column chromatography (eluted with dichloromethane/methanol) to thereby give 510 mg of the title compound as a yellow oily substance.

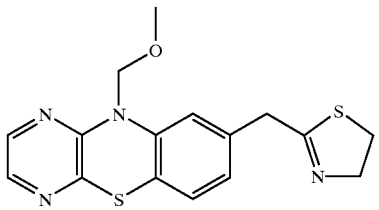

$^1$H-NMR(DMSO-d$_6$) δ ppm: 3.29(t, J=8.5 Hz, 2H), 3.53 (s, 3H), 3.76(s, 2H), 4.25(t, J=8.5 Hz, 2H), 5.27(s, 2H), 6.90(dd, J=1.4, 8.0 Hz, 1H), 6.97(d, J=8.0 Hz, 1H), 7.08(d, J=1.4 Hz, 1H), 7.83(d, J=2.7 Hz, 1H), 7.84(d, J=2.7 Hz, 1H)

Example 1236

8-(3H,4H-Dihydrothiazol-2-ylmethyl)-10H-pyrazino [2,3-b][1,4]benzothiazine 15 mg of the title compound was obtained as yellow crystals by treating 400 mg of 8-(3H,4H-dihydrothiazol-2-ylmethyl)-10-methoxymethyl-10H-pyrazino[2,3-b][1,4] benzothiazine by the same method as the one of Example 434.

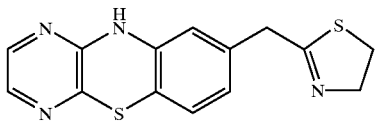

$^1$H-NMR(DMSO-d$_6$) δ ppm: 3.25(t, J=8.6 Hz, 2H), 3.60 (s, 2H), 4.12(t, J=8.6 Hz, 2H), 6.65(s, 1H), 6.67(d, J=7.8 Hz, 1H), 6.84(d, J=7.8 Hz, 1H), 7.63(s, 2H), 9.48(s, 1H).

Example 1237

N-(10-Methoxymethyl-10H-pyrazino[2,3-b][1,4] benzothiazin-8-ylmethyl)phthalimide A solution of 3.32 g of (10-methoxymethyl-10H-pyrazino [2,3-b][1,4]benzothiazin-8-yl)methanol, 2.12 g of phthalimide and 3.77 g of triphenylphosphine in tetrahydrofuran (50 ml) was ice-cooled and 2.24 ml of diethyl azodicarboxylate was dropped thereinto. After stirring at room temperature for 1 hour, the solvent was distilled off under reduced pressure and diethyl ether was added to the residue. Then it was subjected to ultrasonication and the crystals thus precipitated were taken up by filtration to thereby give 2.6 g of the title compound as pale yellow crystals.

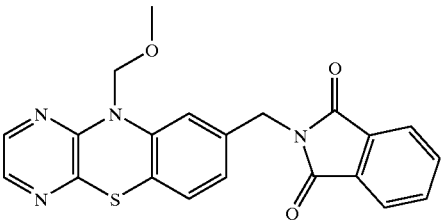

$^1$H-NMR(CDCl$_3$) δ ppm: 3.51(s, 3H), 4.76(s, 2H), 5.22(s, 2H), 6.95(d, J=7.9 Hz, 1H), 7.03(dd, J=1.7, 7.9 Hz, 1H), 7.21(d, J=1.7 Hz, 1H), 7.71(dd, J=3.0, 5.4 Hz, 2H), 7.82(s, 2H), 7.84(dd, J=3.0, 5.4 Hz, 2H)

Example 1238

N-(-10H-Pyrazino[2,3-b][1,4]benzothiazin-8-ylmethyl)phthalimide 7.9 g of the title compound was obtained as yellow crystals by treating 10.0 g of N-(10-methoxymethyl-10H-pyrazino[2,3-b][1,4]benzothiazin-8-ylmethyl)phthalimide by the same method as the one of Example 434.

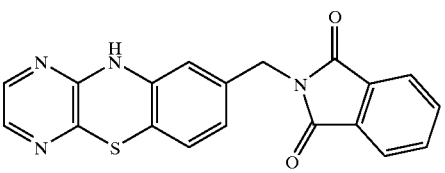

$^1$H-NMR(DMSO-d$_6$) δ ppm: 4.58(s, 2H), 6.68(s, 1H), 6.74(d, J=7.6 Hz, 1H), 6.86(d, J=7.6 Hz, 1H), 7.61(s, 2H), 7.85(dd, J=2.9, 5.7 Hz, 2H), 7.90(dd, J=2.9, 5.7 Hz, 2H), 9.42(s, 1H)

Example 1239

8-(Aminomethyl)10H-pyrazino[2,3-b][1,4] benzothiazine 7.9 g of N-(10H-pyrazino[2,3-b][1,4]benzothiazin-8-ylmethyl)phthalimide was suspended in hydrazine monohydrate (10 ml)/ethanol (50 ml) and the reaction mixture was heated to 80° C. for 20 minutes. Then the reaction mixture was brought back to room temperature. After distilling off the solvent under reduced pressure, the residue was distributed into an aqueous solution of potassium carbonate and ethyl acetate. The organic layer was extracted and dried over anhydrous sodium sulfate. After distilling off the solvent under reduced pressure, the residue thus obtained was purified by silica gel column chromatography (eluted with dichloromethane/methanol/aqueous ammonia) to thereby give 5.0 g of the title compound as yellow orthorhombic crystals.

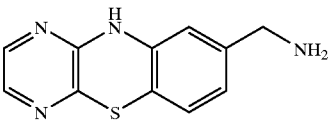

$^1$H-NMR(CDCl$_3$) δ ppm: 3.72(s, 2H), 6.50(d, J=1.4 Hz, 1H), 6.74(dd, J=1.4, 7.9 Hz, 1H), 6.81(d, J=7.9 Hz, 1H), 7.09–7.20(br.s, 1H), 7.54(d, J=2.7 Hz, 1H), 7.66(d, J=2.7 Hz, 1H)

Example 1240

N-[3-(10H-Pyrazino[2,3-b][1,4]benzothiazin-8-yl)propyl]phthalimide

The title compound was obtained as yellow crystals by treating 3-(10H-pyrazino[2,3-b][1,4]-benzothiazin-8-yl)propanol with phthalimide by the same method as the one of Example 1237 followed by the same treatment as the one of Example 434.

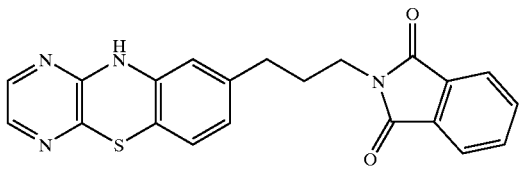

$^1$H-NMR(DMSO-d$_6$) δ ppm: 1.83(quint, J=7.2 Hz, 2H), 2.43(t, J=7.2 Hz, 2H), 3.58(t, J=7.2 Hz, 2H), 6.56(s, 1H), 6.61(d, J=7.8 Hz, 1H), 6.72(d, J=7.8 Hz, 1H), 7.51(d, J=3.3 Hz, 1H), 7.53(d, J=3.3 Hz, 1H), 7.72–7.77(m, 2H), 7.77–7.82(m, 2H), 9.38(s, 1H)

Example 1241

8-(Aminomethyl)10H-pyrazino[2,3-b][1,4]benzothiazine hydrochloride

To a solution of 5.0 g of 8-(aminomethyl)-10H-pyrazino[2,3-b][1,4]benzothiazine in a mixture of dry methanol (5 ml)/ethyl acetate (30 ml) was added 10 ml of a solution of 22 g of hydrogen chloride in 500 ml of ethyl acetate and the resulting mixture was subjected to ultrasonication. To the crystals thus precipitated was added diethyl ether followed by filtration. Thus, the title compound was obtained as orange crystals almost quantitatively.

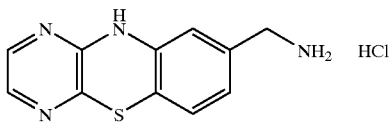

$^1$H-NMR(DMSO-d$_6$) δ ppm: 3.79(br.q, J=5.7 Hz, 2H), 6.73(d, J=1.7 Hz, 1H), 6.90(dd, J=1.7, 7.8 Hz, 1H), 6.95(d, J=7.8 Hz, 1H), 7.64(d, J=3.1 Hz, 1H), 7.66(d, J=3.1 Hz, 1H), 8.25–8.45(br.s, 3H), 9.70(s, 1H)

Example 1242

8-(3-Aminopropyl)-10H-pyrazino[2,3-b][1,4]benzothiazine hydrochloride

The title compound was obtained by treating N-[3-(10H-pyrazino[2,3-b][1,4]benzothiazin-8-yl)-propyl]phthalimide successively by the same methods as those of Examples 1239 and 1241.

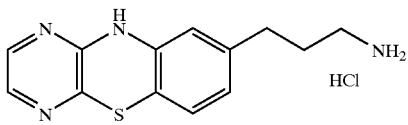

$^1$H-NMR(CDCl$_3$) δ ppm: 1.73(quint, J=7.2 Hz, 2H), 2.45(t, J=7.2 Hz, 2H), 2.68–2.80(m, 2H), 6.60(d, J=1.5 Hz, 1H), 6.64(dd, J=1.5, 8.0 Hz, 1H), 6.83(d, J=8.0 Hz, 1H), 7.62(d, J=3.1 Hz, 1H), 7.63(d, J=3.1 Hz, 1H), 7.82–8.02(br.s, 3H), 9.50(s, 1H)

Example 1243

α-(10H-Pyrazino[2,3-b][1,4]benzothiazin-8-yl)benzylamine

The title compound was obtained by treating α-(10H-pyrazino[2,3-b][1,4]benzothiazin-8-yl)benzyl alcohol successively by the same methods as those of Examples 1237 and 1239.

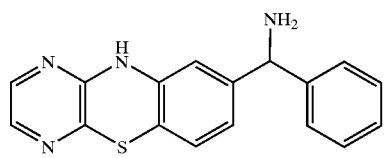

$^1$H-NMR(CDCl$_3$) δ ppm: 5.03(s, 1H), 6.54(d, J=1.2 Hz, 1H), 6.78(d, J=7.8 Hz, 1H), 6.82(dd, J=1.2, 7.8 Hz, 1H), 7.09–7.18(br.s, 1H), 7.20–7.26(m, 2H), 7.28–7.33(m, 3H), 7.40(d, J=3.0 Hz, 1H), 7.41–7.47(br.s, 2H), 7.60(d, J=3.0 Hz, 1H)

Example 1244

8-(N-Methyl)aminomethyl-10-methoxymethyl-10H-pyrazino[2,3-b][1,4]benzothiazine 8-Chloromethyl-10-methoxymethyl-10H-pyrazino[2,3-b][1,4]benzothiazine was stirred in a solution of methylamine in methanol at room temperature over day and night. Then the reaction mixture was distilled under reduced pressure and the residue was distributed into sodium hydroxide and ethyl acetate. The organic layer was extracted and dried over anhydrous sodium sulfate. After distilling off the solvent under reduced pressure, the obtained residue was purified by silica gel column chromatography (eluted with dichloromethane/methanol) to thereby give the title compound as a yellow oily substance.

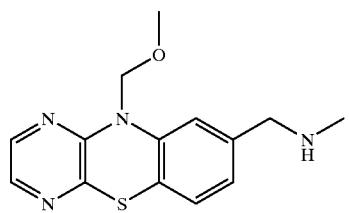

$^1$H-NMR(CDCl$_3$) δ ppm: 2.44(s, 3H), 3.53(s, 3H), 3.68(s, 2H), 5.29(s, 2H), 6.93(dd, J=1.6, 7.8 Hz, 1H), 6.97(d, J=7.8 Hz, 1H), 7.10(d, J=1.6 Hz, 1H), 7.82(d, J=2.8 Hz, 1H), 7.83(d, J=2.8 Hz, 1H)

Examples

The following compounds were obtained by treating 8-chloromethyl-10-methoxymethyl-10H-pyrazino[2,3-b][1,4]-benzothiazine by the same method as the one of Example 1244.

| Ex. | Structural formula | NMR |
|---|---|---|
| 1245 | 8-(dimethylamino)ethyl-10-methoxymethyl-10H-pyrazino[2,3-b][1,4]enzothiazine | ¹H-NMR (CDCl₃) δ ppm: 2.20(s, 6H), 3.33(s, 2H), 3.47(s, 3H), 5.25(s, 2H), 6.89(dd, J=1.5, 7.7Hz, 1H), 6.92(d, J=7.7Hz, 1H), 7.04(d, J=1.5Hz, 1H), 7.77(d, J=2.9Hz, 1H), 7.78(d, J=2.9Hz, 1H) |
| 1246 | 8-[3-(dimethylamino)ropyl]-10-methoxymethyl-10H-pyrazino[2,3-b][1,4]enzothiazine | ¹H-NMR (CDCl₃) δ ppm: 1.75(quint, J=8.1Hz, 2H), 2.21(s, 6H), 1.28(t, J=8.1Hz, 2H), 1.58(t, J=8.1Hz, 2H), 3.51(s, 3H), 5.26(s, 2H), 6.81(dd, J=1.5, 7.9Hz, 1H), 6.92(d, J=7.9Hz, 1H), 6.99(d, J=1.5Hz, 1H), 7.81(d, J=2.9Hz, 1H), 7.82(d, J=2.9Hz, 1H) |
| 1247 | 7-(dimethylamino)ethyl-10-methoxymethyl-10H-pyrazino[2,3-b][1,4]enzothiazine | ¹H-NMR (CDCl₃) δ ppm: 2.22(s, 6H), 3.30(s, 2H), 3.52(s, 3H), 5.26(s, 2H), 6.99(d, J=2.0Hz, 1H), 7.05(dd, J=2.0Hz, 8.5Hz, 1H), 7.08(d, J=8.5Hz, 1H), 7.81(d, J=2.7Hz, 1H), 7.82(d, J=2.7Hz, 1H) |

Example 1248

8-(Dimethylamino)methyl-10H-pyrazino[2,3-b][1,4]benzothiazine

The title compound was obtained by treating 8-(N-methyl)aminomethyl-10-methoxymethyl-10H-pyrazino[2,3-b][1,4]benzothiazine by the same method as the one of Example 9.

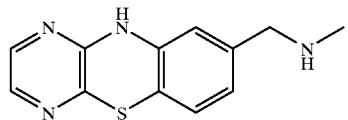

¹H-NMR(CDCl₃) δ ppm: 2.40(s, 3H), 3.57(s, 2H), 6.50(d, J=1.6 Hz, 1H), 6.73(dd, J=1.6, 7.9 Hz, 1H), 6.79(d, J=7.9 Hz, 1H), 7.10–7.38(br.s, 1H), 7.53(d, J=2.6 Hz, 1H), 7.65(d, J=2.6 Hz, 1H)

Example 1249

8-(N-Methylaminomethyl)10H-pyrazino[2,3-b][1,4]benzothiazine hydrochloride

The title compound was obtained by treating 8-(N-methylaminomethyl)10H-pyrazino[2,3-b][1,4]benzothiazine by the same method as the one of Example 1241.

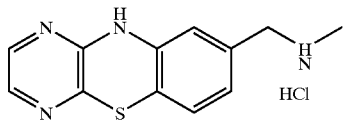

¹H-NMR(DMSO-d₆) δ ppm: 2.48(s, 3H), 3.89(t, J=5.5 Hz, 2H), 6.75(d, J=1.4 Hz, 1H), 6.93(dd, J=1.4, 7.8 Hz, 1H), 6.98(d, J=7.8 Hz, 1H), 7.64(d, J=3.2 Hz, 1H), 7.65(d, J=3.2 Hz, 1H), 8.93–9.10(m, 2H), 9.72(s, 1H)

Examples

The following compounds were obtained by treating successively by the same methods as those of Examples 9 and 1241.

| Ex. | Structural formula | NMR |
|---|---|---|
| 1250 | 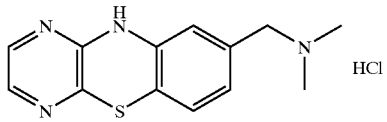<br>8-(dimethylamino)methyl-10H-pyrazino[2,3-b][1,4]benzothiazine hydrochloride | $^1$H-NMR (DMSO-$d_6$) δ ppm: 2.65(d, J=5.1Hz, 6H), 4.06(d, J=5,1Hz, 2H), 6.76(s, 1H), 6.98(d, J=8.1Hz, 1H), 6.99(d, J=8.1Hz, 1H), 7.66(s, 2H), 9.72(s, 1H), 10.38–10.50(m, 1H) |
| 1251 | 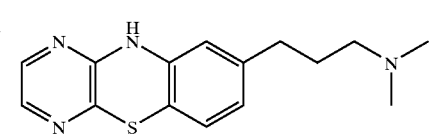<br>8-[3-(dimethylamino)propyl]-10H-pyrazino[2,3-b][1,4]benzothiazine hydrochloride | $^1$H-NMR (DMSO-$d_6$) δ ppm: 1.86(quint, J=7.8Hz, 2H), 2.44(br.t, J=7.8Hz, 2H), 2.68(d, J=5.0Hz, 6H), 2.93–3.01(m, 2H), 6.62(s, 1H), 6.67(d, J=8.3Hz, 1H), 6.84(d, J=8.3Hz, 1H), 7.63(s, 2H), 9.50(s, 1H), 10.53–10.64(br.s, 1H) |
| 1252 | 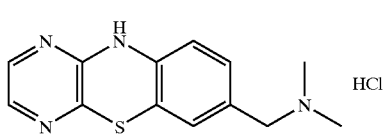<br>7-(dimethylamino)methyl-10H-pyrazino[2,3-b][1,4]benzothiazine hydrochloride | $^1$H-NMR (DMSO-$d_6$) δ ppm: 2.63(d, J=5.0Hz, 6H), 4.03(d, J=5.0Hz, 2H), 6.78(d, J=7.9Hz, 1H), 7.10(d, J=1.7Hz, 1H), 7.12(dd, J=1.7, 7.9Hz, 1H), 7.66(s, 2H), 9.69(s, 1H), 10.31–10.44(m, 1H) |
| 1253 | 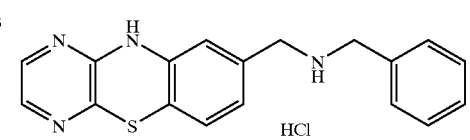<br>8-(benzylamino)methyl-10H-pyrazino[2,3-b][1,4]benzothiazine hydrochloride | $^1$H-NMR (DMSO-$d_6$) δ ppm: 3.90(t, J=5.5Hz, 2H), 4.10(t, J=5.5Hz, 2H), 6.76(d, J=1.6Hz, 1H), 6.97(d, J=8.0Hz, 1H), 7.00(dd, J=1.6, 8.0Hz, 1H), 7.38–7.45(m, 3H), 7.51(m, 2H), 7.65(d, J=2.9Hz, 1H), 7.66(d, J=2.9Hz, 1H), 9.54–9.68(m, 2H), 9.70(s, 1H) |

Examples

The following compounds were obtained by treating 8-chloromethyl-10-methoxymethyl-10H-pyrazino[2,3-b][1,4]benzothiazine by the same method as the one of Example 1244.

| Ex. | Structural formula | NMR |
|---|---|---|
| 1254 | 8-[(N-phenyl)aminomethyl]-10-(methoxymethyl)-10H-pyrazino[2,3-b][1,4]benzothiazine | $^1$H-NMR (CDCl$_3$) δ ppm: 3.44(s, 3H), 4.07(br.s, 1H), 4.29(d, J=5Hz, 2H), 5.22(s, 2H), 6.62(d, J=8Hz, 2H), 6.72(t, J=8Hz, 1H), 6.98(s, 2H), 7.13(s, 1H), 7.18(t, J=8Hz, 2H), 7.83(d, J=3Hz, 1H), 7.84(d, J=3Hz, 1H) |
| 1255 | 8-[(N-phenyl-N-methyl)aminomethyl]-10-(methoxymethyl)-10H-pyrazino[2,3-b][1,4]benzothiazine | $^1$H-NMR (CDCl$_3$) δ ppm: 3.01(s, 3H), 3.35(s, 3H), 4.47(s, 2H), 5.14(s, 2H), 6.68–6.78(m, 3H), 6.82–6.86(m, 1H), 6.96(br.s, 1H), 6.95(d, J=7Hz, 1H), 7.20–7.26(m, 2H), 7.82(d, J=3Hz, 1H), 7.83(d, J=3Hz, 1H) |

Examples

The following compounds were obtained by treating the compounds given in the above table by the same method as the one of Example 8.

| Ex. | Structural formula | MS | M. p. | NMR |
|---|---|---|---|---|
| 1256 | 8-[(N-phenyl)aminomethyl]-10H-pyrazino[2,3-b][1,4]benzothiazine | ESI (+) 307 (MH$^+$) | 183–186° C. | $^1$H-NMR (CDCl$_3$) δ ppm: 4.0–4.2(m, 1H), 4.21(s, 2H), 6.52(s, 1H), 6.59(d, J=8Hz, 1H), 6.68(br.s, 1H), 6.73(t, J=8Hz, 1H), 6.82(d, J=8Hz, 1H), 6.86(d, J=8Hz, 1H), 7.18(t, J=8Hz, 2H), 7.50(d, J=3Hz, 1H), 7.66(d, J=3Hz, 1H) |
| 1257 | 8-[(N-phenyl-N-methyl)aminomethyl]-10H-pyrazino[2,3-b][1,4]benzothiazine | ESI (+) 321 (MH$^+$) | 172–174° C. | $^1$H-NMR (CDCl$_3$) δ ppm: 2.99(s, 3H), 4, 37(s, 2H), 6.37(s, 1H), 6.66–6.78(m, 4H), 6.84(d, J=8Hz, 1H), 7.20–7.28(m, 2H), 7.46(d, J=3Hz, 1H), 7.63(d, J=3Hz, 1H) |

Example 1258

4-[N-[10-(Methoxymethyl)10H-pyrazino[2,3-b]-1,4]benzothiazin-8-ylmethyl]aminomethyl]benzenesulfonamide The title compound was obtained by treating 8-chloromethyl-10-methoxymethyl-10H-pyrazino[2,3-b][1,4]benzothiazine and 4-aminomethylbenzenesuflonamide by the same method as the one of Example 1244.

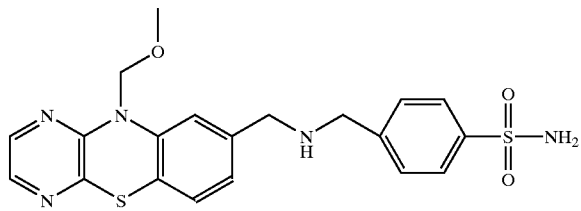

$^1$H-NMR(DMSO-d$_6$) δ ppm: 3.38(s, 3H), 3.59(s, 2H), 3.71(s, 2H), 5.25(s, 2H), 6.96–7.02(m, 1H), 7.06(d, J=8 Hz, 1H), 7.14–7.16(m, 1H), 7.29(s, 2H), 7.52(d, J=8 Hz, 2H), 7.75(d, J=8 Hz, 2H), 7.92(d, J=3 Hz, 1H), 7.96(d, J=3 Hz, 1H)

Examples

The following compounds were obtained by treating 8-chloromethyl-10-methoxymethyl-10H-pyrazino[2,3-b][1,4]benzothiazine successively by the same methods as those of Examples 1244 and 8.

Example 1261

4-[[N-[10-(Methoxymethyl)-10H-pyrazino[2,3-b][1,4]-benzothiazin-8-ylmethyl]-N-methyl]aminomethyl]benzene-sulfonamide To a solution of 0.25 g of 4-[[N-[10-(methoxymethyl)-10H-pyrazino[2,3-b][1,4]benzothiazin-8-ylmethyl]aminomethyl]-benzenesulfonamide and 0.45 ml of a 37% aqueous solution of formalin in acetonitrile (20 ml) was added 57 mg of sodium borocyanohydride. After adjusting the pH value to 4 to 5 with acetic acid, the mixture was reacted at room temperature for 2 hours. After adding a 1 N aqueous solution of sodium hydroxide, the reaction mixture was extracted with ethyl acetate, washed with a saturated aqueous solution of sodium chloride and dried over anhydrous sodium sulfate. After distilling off the solvent under reduced pressure, the residue was purified by silica gel column chromatography (eluted with dichloromethane/methanol) to thereby give 110 mg of the title compound as a yellow oily substance.

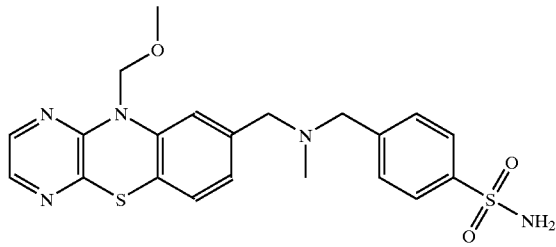

$^1$H-NMR(CDCl$_3$) δ ppm: 2.20(s, 3H), 3.48(s, 3H), 3.56(s, 4H), 4.90(s, 2H), 5.29(s, 2H), 6.96(s, 2H), 7.20(s, 1H), 7.52(d, J=8 Hz, 2H), 7.80–7.85(m, 2H), 7.86(d, J=8 Hz, 2H)

| Ex. | Structural formula | NMR |
|---|---|---|
| 1259 | ethyl 4-[N-(10H-pyrazino[2,3-b][1,4]benzothiazin-8-ylmethyl)aminomethyl]benzoate | $^1$H-NMR (DMSO-d$_6$) δ ppm: 1.30(t, J=7Hz, 3H), 3.48(s, 2H), 3.71(s, 2H), 4.28(q, J=7Hz, 2H), 6.75(dd, J=2, 8Hz, 1H), 6.78(s, 1H), 6.83(d, J=8Hz, 1H), 7.47(d, J=8Hz, 2H), 7.61(d, J=3Hz, 1H), 7.62(d, J=3Hz, 1H), 7.89(d, J=8Hz, 2H), 9.47(s, 1H) |
| 1260 | ethyl 4-[N-(10H-pyrazino[2,3-b][1,4]benzothiazin-8-ylmethyl)aminomethyl)cyclohexanecarboxylate | $^1$H-NMR (DMSO-d$_6$) δ ppm: 0.8–0.95(m, 2H), 1.14(t, J=7Hz, 3H), 1.20–1.40(m, 3H), 1.70–1.90(m, 4H), 2.10–2.23(m, 1H), 2.20–2.33(m, 2H), 3.48(s, 2H), 4.0(q, J=7Hz, 2H), 6.70–6.80(m, 1H), 6.75(s, 1H), 6.81(d, J=8Hz, 1H), 7.58–7.68(m, 2H), 9.46(s, 1H) |

Examples

The following compounds were obtained by the same method as the one of Example 1261.

| Ex. | Structural formula | NMR |
|---|---|---|
| 1262 | ethyl 4-[[N-[10-(methoxymethyl)-10H-pyrazino[2,3-b][1,4]benzothiazin-8-ylmethyl]-N-methyl]aminomethyl]benzoate | ¹H-NMR (CDCl₃) δ ppm: 1.39(t, J=7Hz, 3H), 2.20(s, 3H), 3.47(s, 2H), 3.55(s, 2H), 3.56(s, 3H), 4.37(q, J=7Hz, 2H), 5.29(s, 2H), 6.97(s, 2H), 7.22(s, 1H), 7.45(d, J=8Hz, 2H), 7.84(s, 2H), 8.00(d, J=8Hz, 2H) |
| 1263 | ethyl 4-[[N-[10-(methoxymethyl)-10H-pyrazino[2,3-b][1,4]benzothiazin-8-ylmethyl]-N-methyl]aminomethyl]cyclohexanecarboxylate | ¹H-NMR (CDCl₃) δ ppm: 0.8–1.0(m, 2H), 1.25(t, J=7Hz, 3H), 1.3–1.6(m, 2H), 1.6–1.7(m, 1H), 1.9–2.05(m, 4H), 2.1–2.2(m, 3H), 2.16(s, 3H), 3.38(s, 2H), 3.52(s, 3H), 4.11(q, J=7Hz, 2H), 5.26(s, 2H), 6.91(dd, J=1, 8Hz, 1H), 6.95(d, J=8Hz, 1H), 7.14(d, J=1Hz, 1H), 7.83(s, 2H) |

Examples

The following compounds were obtained by the same method as the one of Example 8.

| Ex. | Structural formula | MS | M. p. | NMR |
|---|---|---|---|---|
| 1264 | 4-[N-(10H-pyrazino[2,3-b][1,4]benzothiazin-8-ylmethyl)aminomethyl]benzenesulfonamide | ESI (+) 400 (MH⁺) | 210–212° C. | ¹H-NMR (DMSO-d₆) δ ppm: 3.47(s, 2H), 3.70(s, 2H), 6.76(dd, J=1, 8Hz, 1H), 6.79(s, 1H), 6.83(d, J=8Hz, 1H), 7.29(s, 2H), 7.57(d, J=8Hz, 2H), 7.62(d, J=3Hz, 1H), 7.63(d, J=3Hz, 1H), 7.75(d, J=8Hz, 2H), 9,47(s, 1H) |
| 1265 | 4-[[N-(10H-pyrazino[2,3-b][1,4]benzothiazin-8-ylmethyl)-N-methyl]aminomethyl]benzenesulfonamide | ESI (+) 414 (MH⁺) | 181–184° C. | ¹H-NMR (DMSO-d₆) δ ppm: 2.50(s, 3H), 3.31(s, 2H), 3.52(s, 2H), 6.74(d, J=8Hz, 1H), 6.80–6.88(m, 2H), 7.31(s, 2H), 7.53(d, J=8Hz, 2H), 7.62(d, J=3Hz, 1H), 7.63(d, J=3Hz, 1H), 7.77(d, J=8Hz, 2H), 9.50(s, 1H) |

| Ex. | Structural formula | MS | M. p. | NMR |
|---|---|---|---|---|
| 1266 | 4-[[N-(10H-pyrazino[2,3-b][1,4]benzothiazin-8-ylmethyl)-N-methyl]aminomethyl]benzoic acid | ESI (+) 379 (MH⁺) | 241–244° C. | ¹H-NMR (DMSO-d₆) δ ppm: 2.05(s, 3H), 3.31(s, 2H), 3.51(s, 2H), 6.74(d, J=8Hz), 6.80–6.90(m, 2H), 7.45(d, J=8Hz, H), 7.62(d, J=2Hz, 1H), 7.63(d, J=2Hz, 1H), 7.89(d, J=8Hz, 2H), 9.50(s, 1H) |
| 1267 | 4-[[N-(10H-pyrazino[2,3-b][1,4]benzothiazin-8-ylmethyl)-N-methyl]aminomethyl]cyclohexane-carboxylic acid | ESI (+) 385 (MH⁺) | 203–204° C. | ¹H-NMR (DMSO-d₆) δ ppm: 0.7–0.87(m, 2H), 1.2–1.35(m, 2H), 1.35–1.50(m, 1H), 1.75–1.90(m, 4H), 2.04(s, 3H), 2.05(d, J=8Hz, 2H), 2.0–2.15(m, 1H), 3.21(s, 2H), 6.67(dd, J=1, 8Hz, 1H), 6.75(d, J=1Hz, 1H), 6.81(d, J=8Hz, 1H), 7.61(d, J=3Hz, 1H), 7.62(d, J=3Hz, 1H), 9.48(s, 1H) |

Examples

The following compounds were obtained by treating the compounds obtained in Examples 1259 and 1260 by the same method as the one of Example 18.

| Ex. | Structural formula | MS | M. p. | NMR |
|---|---|---|---|---|
| 1268 | 4-[N-(10H-pyrazino[2,3-b][1,4]benzothiazin-8-ylmethyl]aminomethyl]benzoic acid | ESI (+) 365 (MH⁺) | 245–248° C. | ¹H-NMR (DMSO-d₆) δ ppm: 3.54(s, 2H), 3.75(s, 2H), 6.77(d, J=8Hz, 1H), 6.78(s, 1H), 6.84(d, J=8Hz, 1H), 7.46(d, J=8Hz, 2H), 7.56–7.68(m, 2H), 7.88(d, J=8Hz, 2H), 9.50(s, 1H) |
| 1269 | 4-[[N-(10H-pyrazino[2,3-b][1,4]benzothiazin-8-ylmethyl]aminomethyl]cyclohexane-carboxylic acid | ESI (+) 371 (M⁺) | 217–220° C. | ¹H-NMR (DMSO-d₆) δ ppm: 0.8–0.96(m, 2H), 1.14–1.32(m, 2H), 1.32–1.48(m, 1H), 1.70–1.86(m, 2H), 1.74–1.92(m, 2H), 2.02–2.16(m, 1H), 2.40(d, J=7Hz, 2H), 3.61(s, 2H), 6.75(s, 1H), 6.78(d, J=8Hz, 1H), 6.85(d, J=8Hz, 1H), 7.56–7.68(m, 2H), 9.53(s, 1H) |

Examples

Similar to Example 1244, 8-(N-methyl)aminomethyl-10H-pyrazino[2,3-b][1,4]benzothiazine was treated with various alkyl halides to thereby give the following compounds.

| Ex. | Structural formula | NMR |
|---|---|---|
| 1270 | 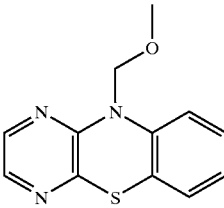<br>ethyl 6-[[N-[10-(methoxymethyl)-10H-pyrazino[2,3-b][1,4]benzothiazin-8-ylmethyl]-N-methyl]amino]hexanoate | $^1$H-NMR (CDCl$_3$) δ ppm: 1.25(t, J=7Hz, 3H), 1.30–1.40(m, 2H), 1.45–1.60(m, 2H), 1.60–1.75(m, 2H), 2.18(s, 3H), 2.30(t, J=7Hz, 2H), 2.60–2.80(m, 2H), 3.41(s, 2H), 3.53(s, 3H), 4.12(q, J=7Hz, 2H), 5.29(s, 2H), 6.90–6.96(m, 1H), 6.96(d, J=8Hz, 1H), 7.10(s, 1H), 7.83(d, J=3Hz, 1H), 7.84(d, J=3Hz, 1H) |
| 1271 | 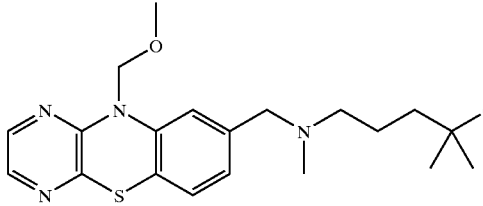<br>methyl 5-[N-[10-(methoxymethyl)-10H-pyrazino[2,3-b][1,4]benzothiazin-8-ylmethyl]-N-methyl]amino-2,2-dimethylpentanoate | $^1$H-NMR (CDCl$_3$) δ ppm: 1.17(s, 6H), 1.36–1.48(m, 2H), 1.64–1.70(m, 2H), 2.15(s, 3H), 2.32(t, J=7Hz, 2H), 3.39(s, 2H), 3.53(s, 3H), 3.64(s, 3H), 5.28(s, 2H), 6.92(dd, J=1, 8Hz, 1H), 6.96(d, J=8Hz, 1H), 7.09(d, J=1Hz, 1H), 7.82(d, J=3Hz, 1H), 7.83(d, J=3Hz, 1H) |
| 1272 | 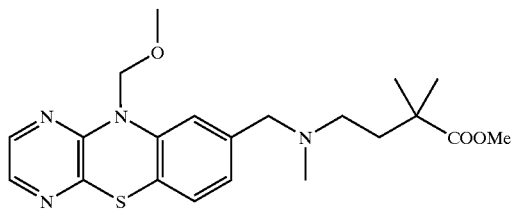<br>methyl 4-[N-[10-(methoxymethyl)-10H-pyrazino[2,3-b][1,4]benzothiazin-8-ylmethyl]-N-methyl]amino-2,2-dimethylbutanoate | $^1$H-NMR (CDCl$_3$) δ ppm: 1.18(s, 6H), 1.77(t, J=7Hz, 2H), 2.16(s, 3H), 2.34(t, J=7Hz, 2H), 3.40(s, 2H), 3.53(s, 3H), 3.62(s, 3H), 5.31(s, 2H), 6.90–6.96(m, 1H), 6.96(d, J=8Hz, 1H), 7.07(s, 1H), 7.80–7.86(m, 2H) |

Examples

The following compounds were obtained by treating the compounds obtained in the above table successively by the same methods as those of Examples 18 and 8.

| Ex. | Structural formula | MS | M. p. | NMR |
|---|---|---|---|---|
| 1273 | 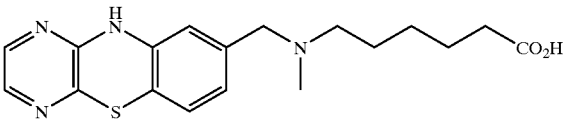<br>6-[[N-(10H-pyrazino[2,3-b][1,4]benzothiazin-8-ylmethyl)-N-methyl]amino]hexanoic acid | ESI (+)<br>359 (MH$^+$) | 191–193° C. | $^1$H-NMR (DMSO-d$_6$) δ ppm: 1.20–1.30(m, 2H), 1.36–1.54(m, 4H), 2.06(s, 3H), 2.18(t, J=7Hz, 2H), 2.26(t, J=7Hz, 2H), 3.25(s, 2H), 6.68(dd, J=2, 8Hz, 1H), 6.74(d, J=2Hz, 1H), 6.81(d, J=8Hz, 1H), 7.61(d, J=3Hz, 1H), 7.62(d, J=3Hz, 1H), 9.44(s, 1H) |
| 1274 | 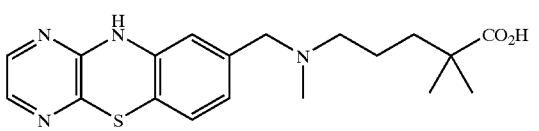<br>5-[N-(10H-pyrazino[2,3-b][1,4]benzothiazin-8-ylmethyl)-N-methyl]amino-2,2-dimethylpentanoic acid | ESI (+)<br>373 (MH$^+$) | 200–202° C. | $^1$H-NMR (DMSO-d$_6$) δ ppm: 1.06(s, 6H), 1.3–1.46(m, 4H), 2.05(s, 3H), 2.24–2.32(m, 2H), 3.26(s, 2H), 6.69(d, J=8Hz, 1H), 6.73(s, 1H), 6.83(d, J=8Hz, 1H), 7.61(d, J=3Hz, 1H), 7.62(d, J=3Hz, 1H), 9.46(s, 1H) |
| 1275 | 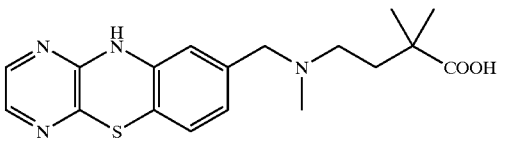<br>4-[N-(10H-pyrazino[2,3-b][1,4]benzothiazin-8-ylmethyl)-N-methyl]amino-2,2-dimethylbutanoic acid | FAB (+)<br>359 (MH$^+$) |  | $^1$H-NMR (CDCl$_3$) δ ppm: 1.21(s, 6H), 1.72–1.84(m, 2H), 2.36(s, 3H), 2.68–2.84(m, 2H), 3.56(br.s, 2H), 6.65–6.82(m, 3H), 7.56(d, J=2.8Hz, 1H), 7.65(d, J=2.8Hz, 1H) |

Example 1276

N-Methyl-2-[[N-(10H-pyrazino[2,3-b][1,4]benzothiazin-8-ylmethyl)-N-methyl]amino]ethanesulfonamide The title compound was obtained as yellow crystals by treating 8-chloromethyl-10H-pyrazino[2,3-b][1,4]benzothiazine with N-methyl-2-aminoethanesulfonamide in the presence of sodium bicarbonate by the same method as the one of Example 1244.

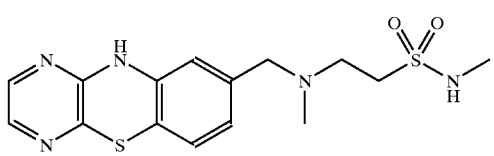

$^1$H-NMR(DMSO-d6) δ ppm: 2.13(s, 3H), 2.54(d, J=5 Hz, 3H), 2.64–2.70(m, 2H), 3.14–3.20(m, 2H), 3.32(s, 2H), 6.71(d, J=8 Hz, 1H), 6.73(s, 1H), 6.84(d, J=8 Hz, 1H), 6.80–6.90(m, 1H), 7.56–7.66(m, 2H), 9.45(s, 1H)

MS: ESI(+)366(MH$^+$)

m.p.: 143–146° C.

Examples

The following compounds were obtained by treating (10-methoxymethyl-10H-pyrazino[2,3-b][1,4]benzothiazin-8-yl)carbaldehyde successively by the same methods as those of Examples 900 and 9.

| Ex. | Structural formula | MS | M. p. | NMR |
|---|---|---|---|---|
| 1277 | 2-[N-(10H-pyrazino[2,3-b][1,4]benzothiazin-8-ylmethyl)amino]ethanol | | | ¹H-NMR (DMSO-d₆) δ ppm: 1.90(br.s, 1H), 2.66(t, J=7Hz, 2H), 3.30(s, 2H), 3.50(t, J=7Hz, 2H), 3.65(br.s, 1H), 6.75(s, 1H), 6.79(d, J=8Hz, 1H), 6.87(d, J=8Hz, 1H), 7.62(s, 2H), 9.56(br.s, 1H) |
| 1278 | 4-[N-(10H-pyrazino[2,3-b][1,4]benzothiazin-8-ylmethyl)amino]butanol | | | ¹H-NMR (DMSO-d₆) δ ppm: 1.42(m, 2H), 1.53(m, 2H), 2.73(t, J=6Hz, 2H), 3.35(t, J=6Hz, 2H), 3.35(br.s, 2H), 3.76(s, 2H), 6.75(s, 1H), 6.84(d, J=8Hz, 1H), 6.92(d, J=8Hz, 1H), 7.63(d, J=3Hz, 1H), 7.66(d, J=3Hz, 1H), 9.63(s, 1H) |
| 1279 | 8-[N-[2-N′,N′-dimethyl)ethyl]aminomethyl]-10H-pyrazino[2,3-b][1,4]benzothiazine dihydrochloride | FAB (+) 302 (MH⁺) | Hygroscopic | ¹H-NMR (DMSO-d₆) δ ppm: 2.78(s, 6H), 3.37(br.s, 2H), 3.50(br.s, 2H), 4.02(s, 2H), 6.81(s, 1H), 6.95(d, J=8Hz, 1H), 7.08(d, J=8Hz, 1H), 7.65(d, J=3Hz, 1H), 7.66(d, J=3Hz, 1H), 9.78(s, 1H), 9.91(br.s, 2H), 11.14(br.s, 1H) |

Examples

The following compounds were obtained from (10-methoxymethyl-10H-pyrazino[2,3-b][1,4]benzothiazin-8-yl)carbaldehyde by the same method as the one of Example 900.

| Ex. | Structural formula | NMR |
|---|---|---|
| 1280 | ethyl 4-[N-(10-methoxymethyl-10H-pyrazino[2,3-b][1,4]benzothiazin-8-ylmethyl)amino]phenylacetate | ¹H-NMR (CDCl₃) δ ppm: 1.24(t, J=7Hz, 3H), 3.44(s, 3H), 3.49(s, 2H), 4.0–4.1(m, 1H), 4.12(q, J=7Hz, 2H), 4.27(s, 2H), 5.22(s, 2H), 6.55–6.60(m, 2H), 6.97(s, 2H), 7.04–7.12(m, 2H), 7.12(s, 1H), 7.83(d, J=3Hz, 1H), 7.84(d, J=3Hz, 1H) |

-continued

| Ex. | Structural formula | NMR |
|---|---|---|
| 1281 | methyl 2-[4-[N-(10-methoxymethyl-10H-pyrazino[2,3-b][1,4]benzothiazin-8-ylmethyl)amino]phenyl]propanoate | ¹H-NMR (CDCl₃) δ ppm: 1.44(d, J=7Hz, 3H), 3.43(s, 3H), 3.55–3.70(m, 1H), 3.64(s, 3H), 4.00–4.10(m, 1H), 4.26(s, 2H), 5.22(s, 2H), 6.54–6.60(m, 2H), 6.97(s, 2H), 7.06–7.14(m, 2H), 7.12(s, 1H), 7.82(d, J=3Hz, 1H), 7.84(d, J=3Hz, 1H) |

Examples

The following compounds were obtained by treating the compounds obtained in the above table successively by the same methods as those of Examples 18 and 8.

| Ex. | Structural formula | MS | M. p. | NMR |
|---|---|---|---|---|
| 1282 | 4-[N-(10-pyrazino[2,3-b][1,4]benzothiazin-8-ylmethyl)amino]phenylacetic acid hydrochloride | FAB (+) 365 (MH⁺) | 252–256° C. | ¹H-NMR (DMSO-d₆) δ ppm: 3.21(s, 2H), 4.05(s, 2H), 6.44(d, J=8.4Hz, 2H), 6.75(d, J=8.0Hz, 1H), 6.76(s, 1H), 6.83(d, J=8.0Hz, 1H), 6.91(d, J=8.4Hz, 2H), 7.61(m, 2H), 9.49(s, 1H) |
| 1283 | 2-[4-[N-(10H-pyrazino[2,3-b][1,4]benzothiazin-8-ylmethyl)amino]phenyl]propanoic acid hydrochloride | | 228–233° C. | ¹H-NMR (DMSO-d₆) δ ppm: 1.26(d, J=8.0Hz, 3H), 3.40–3.60(m, 1H), 4.10(s, 2H), 6.58–6.70(m, 2H), 6.76(s, 1H), 6.77(d, J=8.0Hz, 1H), 6.85(d, J=8.0Hz, 1H), 7.02(d, J=8.0Hz, 2H), 7.61(d, J=2.8Hz, 1H), 7.62(d, J=2.8Hz, 1H), 9.52(s, 1H) |

Example 1284

8-Aminomethyl-10-methoxymethyl-10H-pyrazino[2,3-b][1,4]benzothiazine

To a solution of 1.3 g of N-(10-methoxymethyl-10H-pyrazino[2,3-b][1,4]benzothiazin-8-ylmethyl)phthalimide in 20 ml of ethanol was added 5 ml of hydrazine monohydrate and the resulting mixture was heated to 60° C. for 10 minutes. After distilling off the solvent under reduced pressure, the residue was distributed into a 5% aqueous solution of sodium hydroxide and ethyl acetate. The organic layer was extracted and the extract was dried over potassium carbonate. After distilling off the solvent under reduced pressure, the obtained residue was purified by silica gel column chromatography (eluted with dichloromethane/methanol/aqueous ammonia) to thereby give 890 mg of the title compound as a yellow oily substance.

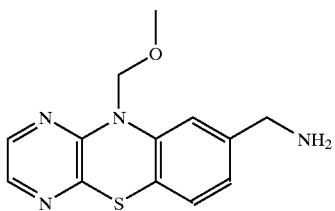

¹H-NMR(CDCl₃) δ ppm: 3.53(s, 3H), 3.80(s, 2H), 5.28(s, 2H), 6.92(dd, J=1.5, 8.0 Hz, 1H), 6.96(d, J=8.0 Hz, 1H), 7.10(d, J=1.5 Hz, 1H), 7.81(d, J=2.8 Hz, 1H), 7.83(d, J=2.8 Hz, 1H)

Example 1285

N-(10-Methoxymethyl-10H-pyrazino[2,3-b][1,4]benzothiazin-8-ylmethyl)formamide 250 mg of 8-aminomethyl-10-methoxymethyl-10H-pyrazino-[2,3-b][1,4]benzothiazine was heated under reflux in 10 ml of ethyl formate for 3 hours. Then the reaction mixture was brought back to room temperature and distributed into an aqueous solution of ammonium chloride and ethyl acetate. The organic layer was extracted, washed with water and then dried over anhydrous sodium sulfate. After distilling off the solvent under reduced pressure, the crystals thus precipitated were filtered after adding diisopropyl ether. Thus 230 mg of the title compound was obtained as yellow crystals.

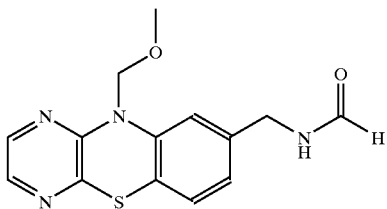

¹H-NMR(DMSO-d₆) δ ppm: 3.37(s, 3H), 4.22(d, J=6.0 Hz, 2H), 5.22(s, 2H), 6.91(dd, J=1.4, 8.0 Hz, 1H), 7.03(d, J=1.4 Hz, 1H), 7.07(d, J=8.0 Hz, 1H), 7.92(d, J=2.8 Hz, 1H), 7.96(d, J=2.8 Hz, 1H), 8.12(s, 1H), 8.51(br.t, J=6.0 Hz, 1H)

Example 1286

N-(10H-Pyrazino[2,3-b][1,4]benzothiazin-8-ylmethyl)formamide 75 mg of the title compound was obtained as yellow crystals by treating 150 mg of N-(10-methoxymethyl-10H-pyrazino[2,3-b][1,4]benzothiazin-8-ylmethyl)formamide by the same method as the one of Example 9.

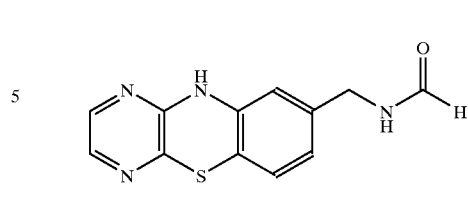

¹H-NMR(DMSO-d₆) δ ppm: 4.10(d, J=6.0 Hz, 2H), 6.67 (s, 1H), 6.68(d, J=7.7 Hz, 1H), 6.86(d, J=7.7 Hz, 1H), 7.63(br.s, 2H), 8.10(br.s, 1H), 8.73–8.53(br.t, J=6.0 Hz, 1H), 9.50(s, 1H)

Example 1287

N-(10-Methoxymethyl-10H-pyrazino[2,3-b][1,4]benzothiazin-8-ylmethyl)acetamide 1 ml of acetic anhydride was added to 5 ml of a solution of 350 mg of 8-aminomethyl-10-methoxymethyl-10H-pyrazino[2,3-b][1,4]benzothiazine in dichloromethane and the resulting mixture was stirred at room temperature for 2 hours. After adding diethyl ether, the precipitate thus formed was taken up by filtration to thereby give 350 mg of the title compound as yellow crystals.

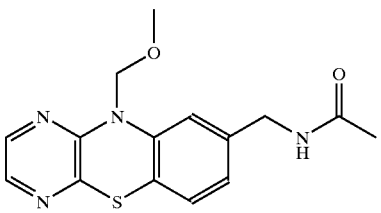

¹H-NMR(DMSO-d₆) δ ppm: 1.86(s, 3H), 3.36(s, 3H), 4.16(d, J=5.9 Hz, 2H), 5.21(s, 2H), 6.89(dd, J=1.6, 7.9 Hz, 1H), 7.00(d, J=1.6 Hz, 1H), 7.06(d, J=7.9 Hz, 1H), 7.92(d, J=2.6 Hz, 1H), 7.96(d, J=2.6 Hz, 1H), 8.36(t, J=5.9 Hz, 1H)

Example 1288

N-(10H-Pyrazino[2,3-b][1,4]benzothiazin-8-ylmethyl)acetamide 150 mg of the title compound was obtained by treating 250 mg of N-(10-methoxymethyl-10H-pyrazino[2,3-b][1,4]benzothiazin-8-ylmethyl)acetamide by the same method as the one of Example 9.

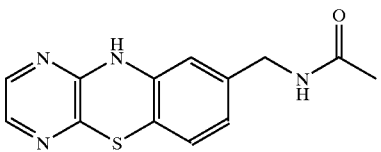

¹H-NMR(DMSO-d₆) δ ppm: 1.84(s, 3H), 4.04(d, J=6.2 Hz, 2H), 6.65(s, 1H), 6.66(d, J=8.4 Hz, 1H), 6.84(d, J=8.4 Hz, 1H), 7.52(d, J=3.2 Hz, 1H), 7.53(d, J=3.2 Hz, 1H), 8.29(t, J=6.2 Hz, 1H), 9.49(s, 1H)

Examples

The following compounds were obtained by treating 8-aminomethyl-10-methoxymethyl-10H-pyrazino[2,3-b][1,4]benzothiazine successively by the same methods as those of Examples 1287 and 434.

| Ex. | Structural formula | MS | M.p. | NMR |
|---|---|---|---|---|
| 1289 | | ooi | ooi | ¹H-NMR(DMSO-d₆) δ ppm: 1.25(t, J=7.3Hz, 3H), 4.12(d, J=6.3Hz, 2H), 4.22(q, J=7.3Hz, 2H), 6.67(s, 1H), 6.68(d, J=7.4Hz, 1H), 6.85(d, J=7.4Hz, 1H), 7.62(d, J=3.1Hz, 1H), 7.63(d, J=3.1Hz, 1H), 9.40(t, J=6.3Hz, 1H), 9.51(s, 1H) |
| 1290 | N-(10H-pyrazino[2,3-b][1,4]benzothiazin-8-ylmethyl)-benzamide | | | ¹H-NMR(DMSO-d₆) δ ppm: 4.28(d, J=6.0Hz, 2H), 6.73(d, J=7.8Hz, 1H), 6.74(s, 1H), 6.85(d, J=7.8Hz, 1H), 7.45(t, J=7.7Hz, 2H), 7.52(t, J=7.7Hz, 1H), 7.61(s, 2H), 7.87(t, J=7.7Hz, 2H), 8.97(t, J=6.0Hz, 1H), 9.50(s, 1H) |

Examples

The following compounds were obtained by treating 8-aminomethyl-10-methoxymethyl-10H-pyrazino[2,3-b][1,4]benzothiazine successively by the same methods as those of Examples 1287 and 8.

| Ex. | Structural formula | MS | M.p. | NMR |
|---|---|---|---|---|
| 1291 | N-(10H-pyrazino[2,3-b][1,4]benzothiazin-8-ylmethyl)isonicotinamide | FAB (+) 336 (MH⁺) | 249–253° C. (decompose) | ¹H-NMR(DMSO-d₆) δ ppm: 4.33(d, J=5.9Hz, 2H), 6.72–6.79(m, 2H), 6.88(d, J=8.8Hz, 1H), 7.64(d, J=2.9Hz, 1H), 7.65(d, J=2.9Hz, 1H), 7.80(m, 2H), 8.76(m, 2H), 9.31(t, J=5.9Hz, 1H), 9.53(s, 1H) |
| 1292 | N-(10H-pyrazino[2,3-b][1,4]benzothiazin-8-ylmethyl)nicotinamide | FAB (+) 336 (MH⁺) | 243–245° C. (decompose) | ¹H-NMR(DMSO-d₆) δ ppm: 4.33(d, J=5.9Hz, 2H), 6.75–6.80(m, 2H), 6.88(d, J=8.4Hz, 1H), 7.54(m, 1H), 7.64(d, J=2.9Hz, 1H), 7.64(d, J=2.9Hz, 1H), 8.23(m, 1H), 8.73(m, 1H), 9.06(m, 1H), 9.21(t, J=5.9Hz, 1H,) 9.53(s, 1H) |

Example 1293

N-(10H-Pyrazino[2,3-b][1,4]benzothiazin-8-ylmethyl)-1-methylpiperidine-4-carboxamide

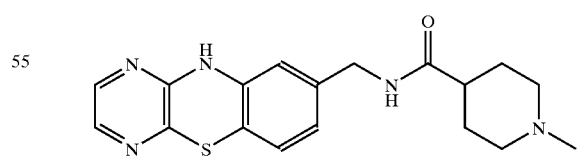

The title compound was obtained as yellow crystals by treating 8-aminomethyl-10-methoxymethyl-10H-pyrazino[2,3-b][1,4]-benzothiazine and 1-methylpiperidine-4-carboxylic acid successively by the same methods as those of Examples 1303 and 8.

¹H-NMR(CDCl₃) δ ppm: 1.71–1.98(m, 5H), 2.04–2.18 (m, 2H), 2.26(s, 3H), 2.86–2.94(m, 2H), 4.26(d, J=5.9 Hz, 2H), 5.99(d, J=5.9 Hz, 1H), 6.43(d, J=1.6 Hz, 1H), 6.67(dd, J=1.6, 7.9 Hz, 1H), 6.79(d, J=7.9 Hz, 1H), 7.01(s, 1H), 7.56(d, J=2.9 Hz, 1H), 7.67(d, J=2.9 Hz, 1H)
MS: FAB(+)336(MH⁺)
m.p.: 230–232° C. (decompose)

Example 1294

N-(10H-Pyrazino[2,3-b][1,4]benzothiazin-8-ylmethyl)-5-methyl-1,2-oxazole-4-carboxamide A solution of 520 mg of 5-methyl-1,2-oxazole-4-carboxylic acid and 0.75 ml of triethylamine in tetrahydrofuran (10 ml) was ice-cooled. After adding 0.8 ml of diethyl chlorophosphate, the resulting mixture was stirred at room temperature for 30 minutes. To the reaction mixture was added 5 ml of a solution of 750 mg of 8-aminomethyl-10-methoxymethyl-10H-pyrazino[2,3-b][1,4]-benzothiazine in tetrahydrofuran and the resulting mixture was stirred at room temperature for 1.5 hours. Next, the reaction mixture was distributed into ethyl acetate and an aqueous solution of ammonium chloride. The organic layer was extracted, washed with water and dried over anhydrous sodium sulfate. After distilling off the solvent under reduced pressure, the residue was purified by silica gel column chromatography (eluted with dichloromethane/methanol) to thereby give 520 mg of N-(10-methoxymethyl-10H-pyrazino[2,3-b][1,4]benzothiazin-8-ylmethyl)-5-methyl-1,2-oxazole-4-carboxamide. Further, the product was treated by the same method as the one of Example 434 to thereby give 310 mg of the title compound as yellow crystals.

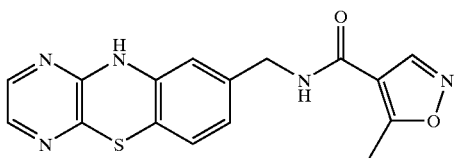

$^1$H-NMR(DMSO-d$_6$) δ ppm: 2.63(s, 3H), 4.23(d, J=6.3 Hz, 2H), 6.71(s, 1H), 6.72(d, J=7.5 Hz, 1H), 6.86(d, J=7.5 Hz, 1H), 7.62(s, 2H), 8.79(t, J=6.3 Hz, 1H), 8.89(s, 1H), 9.50(s, 1H)

Example 1295

N-(1H-Pyrazino[2,3-b][1,4]benzothiazin-8-ylmethyl)-2-cyano-3-oxobutanamide 120 mg of the title compound was obtained as yellow crystals by treating 170 mg of N-(10H-pyrazino[2,3-b][1,4]-benzothiazin-8-ylmethyl)-5-methyl-1,2-oxazole-4-carboxamide with 0.17 ml of dimethylformamide dimethyl acetal by the same method as the one of Example 505.

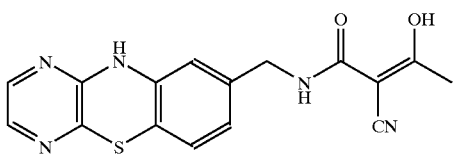

$^1$H-NMR(DMSO-d$_6$) δ ppm: 2.05(s, 3H), 4.13(s, 2H), 6.64–6.68(m, 2H), 6.83(dd, J=2, 8 Hz, 1H), 7.61–7.63(m, 2H), 9.51(s, 1H)
MS: FAB(+)339(M$^+$)

Example 1296

(10-Methoxymethyl-10H-pyrazino[2,3-b][1,4]benzothiazin-8-ylmethyl)acetamide 200 mg of (10-methoxymethyl-10H-pyrazino[2,3-b][1,4]-benzothiazin-8-ylmethyl)acetonitrile was dissolved in 5 ml of dimethyl sulfoxide. After adding 200 mg of powdered potassium hydroxide, the resulting mixture was heated to 40 to 60° C. for 10 minutes. Then the reaction mixture was distributed into 1 N hydrochloric acid and ethyl acetate. The organic layer was extracted, washed successively with a saturated aqueous solution of sodium bicarbonate and water and dried over anhydrous magnesium sulfate. After distilling off the solvent under reduced pressure, the residue was purified by silica gel column chromatography (eluted with dichloromethane/methanol) to thereby give 35 mg of the title compound as yellow crystals.

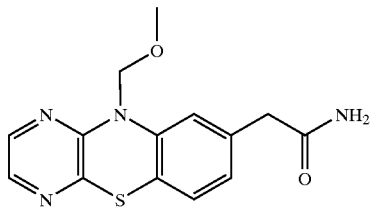

$^1$H-NMR(DMSO-d$_6$) δ ppm: 3.31(s, 2H), 3.38(s, 3H), 5.22(s, 2H), 6.87–6.95(br.s, 1H), 6.91(dd, J=1.7, 8.0 Hz, 1H), 7.03(d, J=1.7 Hz, 1H), 7.04(d, J=8.0 Hz, 1H), 7.42–7.50(br.s, 1H), 7.92(d, J=2.8 Hz, 1H), 7.96(d, J=2.8 Hz, 1H)

Example 1297

(10H-Pyrazino[2,3-b][1,4]benzothiazin-8-yl)acetamide

The title compound was obtained by treating (10-methoxymethyl-10H-pyrazino[2,3-b][1,4]benzothiazin-8-yl)acetamide by the same method as the one of Example 9.

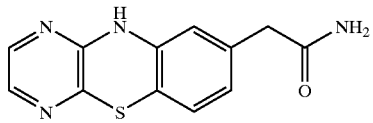

$^1$H-NMR(DMSO-d$_6$) δ ppm: 3.18(s, 2H), 6.66(s, 1H), 6.67(d, J=7.6 Hz, 1H), 6.82(d, J=7.6 Hz, 1H), 6.83–6.95 (br.s, 1H), 7.37–7.48(br.s, 1H), 7.61(d, J=2.6 Hz, 1H), 7.63(d, J=2.6 Hz, 1H), 9.50(s, 1H)

Example 1298

3-[(10H-Pyrazino[2,3-b][1,4]benzothiazin-8-yl)acetamido]propanoic acid

The title compound was obtained by treating (10-methoxymethyl-10H-pyrazino[2,3-b][1,4]benzothiazin-8-yl)acetic acid successively by the same methods as those of Examples 1294, 18 and 8.

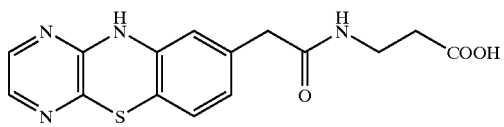

$^1$H-NMR(DMSO-d$_6$) δ ppm:
2.36(t, 2H, J=6.8 Hz)3.20(s, 2H)3.21(t, 2H, J=6.8 Hz)6.64 (s, 1H)6.65(d, 1H, J=8.0 Hz)6.80(d, 1H, J=8.0 Hz)7.61(d, 1H, J=2.8 Hz)7.63(d, 1H, J=2.8 Hz)9.48(s, 1H)
MS: FAB(+)331(MH$^+$)
m.p.: 220–225° C.

Example 1299

8-Amino-10-methoxymethyl-10H-pyrazino[2,3-b][1,4]benzothiazine 10 ml of an aqueous solution of 720 mg of sodium hydroxide was ice-cooled and 0.24 ml of bromine was dropped thereinto. After stirring for 5 minutes, 900 mg of (10-methoxymethyl-10H-pyrazino[2,3-b][1,4]benzothiazin-8-yl)carboxamide was added thereto at once and the resulting mixture was heated to 40 to 60° C. for 15 minutes. Next, the reaction mixture was distributed into water and ethyl acetate. After filtering off the insoluble matters through celite, the organic layer was extracted, washed with water and dried over anhydrous sodium sulfate. After distilling off the solvent under reduced pressure, the residue was purified by silica gel column chromatography (eluted with dichloromethane/methanol) to thereby give 400 mg of the title compound as yellow crystals.

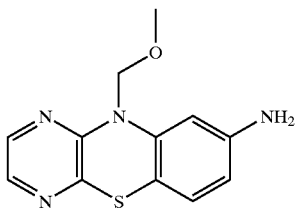

H-NMR(DMSO-$d_6$) δ ppm: 3.37(s, 3H), 5.14(s, 2H), 5.31(br.s, 2H), 6.25(dd, J=1.9, 8.1 Hz, 1H), 6.46(d, J=1.9 Hz, 1H), 6.72(d, J=8.1 Hz, 1H), 7.88(d, J=2.5 Hz, 1H), 7.91(d, J=2.5 Hz, 1H)

Example 1300

N-(10-Methoxymethyl-10H-pyrazino[2,3-b][1,4]benzothiazin-8-yl)acetamide 200 mg of 8-amino-10-methoxymethyl-10H-pyrazino[2,3-b][1,4]benzothiazine was suspended in 10 ml of ethyl acetate. After adding 1 ml of acetic anhydride, the reaction mixture was subjected to ultrasonication. The crystals thus precipitated were filtered and washed with diethyl ether to thereby give 206 mg of the title compound as yellow crystals.

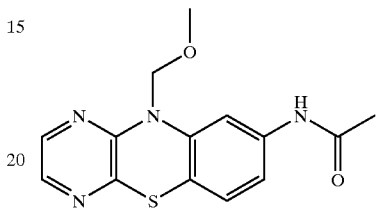

$^1$H-NMR(DMSO-$d_6$) δ ppm: 2.01(s, 3H), 3.38(s, 3H), 5.17(s, 2H), 7.01(d, J=8.6 Hz, 1H), 7.31(d, J=1.8, 8.6 Hz, 1H), 7.44(d, J=1.8 Hz, 1H), 7.91(d, J=2.6 Hz, 1H), 7.95(d, J=2.6 Hz, 1H), 10.02(s, 1H)

Examples

The following compounds were obtained by treating the compounds obtained in Examples 1299 and 1300 by the same method as the one of Example 8.

| Ex. | Structural formula | MS | NMR |
|---|---|---|---|
| 1301 | 8-amino-10H-pyrazino[2,3-b][1,4]benzothiazin | FAB (+) 216 (M+) | $^1$H-NMR(DMSO-$d_6$) δ ppm: 5.14(br.s, 2H), 6.04(dd, J=1.9, 8.2Hz, 1H), 6.07(d, J=1.9Hz, 1H), 6.52(d, J=8.2Hz, 1H), 7.58(d, J=2.8Hz, 1H), 7.60(d, J=2.8Hz, 1H), 9.31(s, 1H) |
| 1302 | N-(10H-pyrazino[2,3-b][1,4]benzothiazin-8-ylmethyl)acetamide | | $^1$H-NMR(DMSO-$d_6$) δ ppm: 1.97(s, 3H), 6.80(d, J=8.5Hz, 1H,) 6.96(d, J=1.6, 8.5Hz, 1H), 7.16(d, J=1.6Hz, 1H), 7.62(d, J=2.9Hz, 1H), 7.63(d, J=2.9Hz, 1H), 9.57(s, 1H), 9.88(s, 1H) |

Example 1303

(10-Methoxymethyl-10H-pyrazino[2,3-b][1,4]benzothiazin-8-yl)carboxamide 1.04 g of (10-methoxymethyl-10H-pyrazino[2,3-b][1,4]benzothiazin-8-yl)carboxylic acid was dissolved in a mixture of dichloromethane (20 ml) with tetrahydrofuran (20 ml) in a nitrogen atmosphere. Under ice-cooling, 1.04 g of 1-ethyl-3-(3-dimethylaminopropyl)carbodiimide hydrochloride and 200 mg of 1-hydroxybenzotriazole were added thereto and the resulting mixture was stirred at room temperature for 30 minutes. After blowing ammonia gasthereinto, the reaction mixture was distributed into an aqueous solution of sodium bicarbonate and ethyl acetate. The organic layer was extracted, washed with water and dried over anhydrous sodium sulfate. After distilling off the solvent under reduced pressure, the crystals thus precipitated were filtered. Further, the aqueous layer was acidified and the starting materials were recovered. After repeating the above-mentioned procedures, the title compound (620 mg in total) was obtained as yellow crystals.

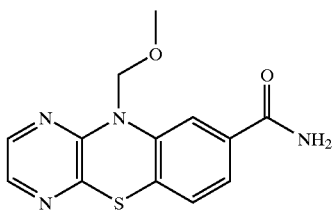

$^1$H-NMR(DMSO-d$_6$) δ ppm: 3.38(s, 3H), 5.28(s, 2H), 7.19(d, J=8.4 Hz, 1H), 7.40–7.46(br.s, 1H), 7.47(dd, J=1.8, 8.4 Hz, 1H), 7.56(d, J=1.8 Hz, 1H), 7.93(d, J=2.8 Hz, 1H), 7.95–8.02(br.s, 1H), 7.97(d, J=2.8 Hz, 1H)

Example 1304

(10H-Pyrazino[2,3-b][1,4]benzothiazin-8-yl)carboxamide

The title compound was obtained by treating (10-methoxymethyl-10H-pyrazino[2,3-b][1,4]benzothiazin-8-yl)carboxamide by the same method as the one of Example 9.

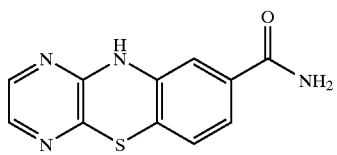

$^1$H-NMR(DMSO-d$_6$) δ ppm: 6.96(d, J=7.8 Hz, 1H), 7.21 (s, 1H), 7.23(d, J=7.8 Hz, 1H), 7.27–7.34(br.s, 1H), 7.64(d, J=2.7 Hz, 1H), 7.65(d, J=2.7 Hz, 1H), 7.80–7.87(br.s, 1H), 9.59(s, 1H)

Examples

The following compounds were obtained by the same method as the one of Example 1303.

| Ex. | Structural formula | NMR |
|---|---|---|
| 1305 | N-phenyl-(10-methoxymethyl-10H-pyrazino[2,3-b][1,4]benzothiazin-8-yl)carboxamide | $^1$H-NMR(DMSO-d$_6$) δ ppm: 3.40(s, 3H), 5.33(s, 2H), 7.09(t, J=8.4Hz, 1H), 7.28(d, J=8.2Hz, 1H), 7.34(t, J=8.4Hz, 2H), 7.60(d, J=1.6Hz, 1H), 7.60(dd, J=1.6, 8.2Hz, 1H), 7.73(d, J=8.4Hz, 2H), 7.95(d, J=2.5Hz, 1H), 7.99(d, J=2.5Hz, 1H), 10.24(s, 1H) |
| 1306 | N-(thiazol-2-yl)-(10-methoxymethyl-10H-pyrazino[2,3-b][1,4]benzothiazin-8-yl)carboxamide | $^1$H-NMR(DMSO-d$_6$) δ ppm: 3.41(s, 3H), 5.36(s, 2H), 7.28(d, J=8.8Hz, 1H), 7.29(d, J=3.7Hz, 1H), 7.55(d, J=3.7Hz, 1H), 7.70(dd, J=1.7, 8.8Hz, 1H), 7.71(d, J=1.7Hz, 1H), 7.94(d, J=2.8Hz, 1H), 7.99(d, J=2.8Hz, 1H), 12.65–12.75(br.s, 1H) |
| 1307 | N-ethyl-(10-methoxymethyl-10H-pyrazinobenzothiazin-8-yl)carboxamide | $^1$H-NMR(DMSO-d$_6$) δ ppm: 1.09(t, J=6.5Hz, 3H), 3.25(dt, J=5.5, 6.5Hz, 2H), 3.38(s, 3H), 5.28(s, 2H), 7.19(d, J=8.3Hz, 1H), 7.44(dd, J=1.5, 8.3Hz, 1H), 7.53(d, J=1.5Hz, 1H), 7.93(d, J=2.7Hz, 1H), 7.97(d, J=2.7Hz, 1H), 8.48(t, J=5.5Hz, 1H) |

Examples

The following compounds were obtained by treating the compounds obtained in the above table by the same method as the one of Example 434.

| Ex. | Structural formula | MS | M.p. | NMR |
|---|---|---|---|---|
| 1308 | N-phenyl-(10H-pyrazino[2,3-b][1,4]benzothiazin-8-yl)carboxamide | | 281–282° C. | $^1$H-NMR(DMSO-$d_6$) δ ppm: 7.05(d, J=8.5Hz, 1H), 7.07(t, J=8.1Hz, 1H), 7.26(s, 1H), 7.31(d, J=8.5Hz, 1H), 7.33(t, J=8.1Hz, 2H), 7.65(d, J=2.9Hz, 1H), 7.66(d, J=2.9Hz, 1H), 7.70(d, J=8.1Hz, 2H), 9.66(s, 1H), 10.16(s, 1H) |
| 1309 | N-(thiazol-2-yl)-(10H-pyrazino[2,3-b][1,4]benzothiazin-8-yl)carboxamide | | 320–322° C. | $^1$H-NMR(DMSO-$d_6$) δ ppm: 7.04(d, J=8.4Hz, 1H), 7.25(d, J=3.9Hz, 1H), 7.32(d, J=1.6Hz, 1H), 7.50(dd, J=1.6, 8.4Hz, 1H), 7.53(d, J=3.9Hz, 1H), 7.64(d, J=2.9Hz, 1H), 7.67(d, J=2.9Hz, 1H), 9.71(s, 1H), 12.47–12.60(br.s, 1H) |
| 1310 | N-ethyl-(10H-pyrazino[2,3-b][1,4]benzothiazin-8-yl)carboxamide | | 274–275° C. | $^1$H-NMR(DMSO-$d_6$) δ ppm: 1.06(t, J=7.0Hz, 3H), 3.21(dq, J=5.7, 7.0Hz, 2H), 6.96(d, J=8.3Hz, 1H), 7.18(dd, J=1.6, 8.3Hz, 1H), 7.19(d, J=1.6Hz, 1H), 7.63(d, J=2.9Hz, 1H), 7.64(d, J=2.9Hz, 1H), 8.35(t, J=5.7Hz, 1H), 9.59(s, 1H) |

Examples

The following compounds were obtained by effecting dehydration/condensation with various amines by the same method as the one of Example 1303 and treating the compounds thus obtained by the same method as the one of Example 9.

| Ex. | Structural formula | MS | NMR |
|---|---|---|---|
| 1311 | N,N-(3-methyl-3-azapentamethylene)-(10H-pyrazino[2,3-b][1,4]benzothiazin-8-yl)carboxamide | ESI (+) 328.0 (MH$^+$) | $^1$H-NMR(DMSO-$d_6$) δ ppm: 2.80(s, 3H), 2.95–3.10(br.s, 4H), 3.22–3.33(br.s, 4H), 6.78(d, J=2Hz, 1H), 6.84(dd, J=2, 8Hz, 1H), 7.00(d, J=8Hz, 1H), 7.67(s, 2H), 9.66(s, 1H) |

-continued

| Ex. | Structural formula | MS | NMR |
|---|---|---|---|
| 1312 | N,N-(3-oxapenta methylene)-(10H-pyrazino[2,3-b][1,4]benzothiazin-8-yl) carboxamide | FAB (+) 314 (MH+) | ¹H-NMR(DMSO-d₆) δ ppm: 3.40–3.65(m, 8H), 6.75(d, J=1.7Hz, 1H), 6.78(dd, J=1.7, 7.7Hz, 1H), 6.96(d, J=7.7Hz, 1H), 7.65(s, 2H, 9.60(s, 1H) |
| 1313 | ethyl 4-[(10H-pyrazino[2,3-b][1,4]benzothiazin-8-yl) carboxamido]benzoate | | ¹H-NMR(DMSO-d₆) δ ppm: 1.17(t, J=7.4Hz, 3H), 4.28(q, J=7.4Hz, 2H), 7.07(d, J=8.1Hz, 1H), 7.26(d, J=1.7Hz, 1H), 7.37(dd, J=1.7, 8.1Hz, 1H), 7.65(d, J=2.8Hz, 1H), 7.88(d, J=8.7Hz, 2H), 7.93(d, J=8.7Hz, 2H), 9.68(s, 1H), 10.47(s, 1H) |

Example 1314

4-[(10H-Pyrazino[2,3-b][1,4]benzothiazin-8-yl) carboxamido]-benzoic acid

The title compound was obtained by treating ethyl 4-[(10H-pyrazino[2,3-b][1,4]benzothiazin-8-yl) carboxamido]benzoate by the same method as the one of Example 18.

¹H-NMR(DMSO-d₆) δ ppm: 7.07(d, J=7.8 Hz, 1H), 7.26 (d, J=1.8 Hz, 1H), 7.37(dd, J=1.8, 7.8 Hz, 1H), 7.65(d, J=3.1 Hz, 1H), 7.67(d, J=3.1 Hz, 1H), 7.85(d, J=9.1 Hz, 2H), 7.91(d, J=9.1 Hz, 2H), 9.68(s, 1H), 10.45(s, 1H)

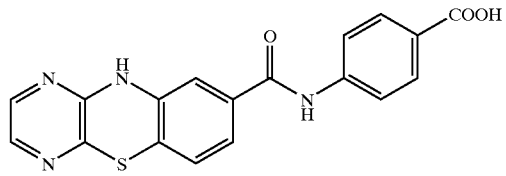

Examples

The following compounds were obtained by dehydrating/condensing (10H-pyrazino[2,3-b][1,4]benzothiazin-8-yl) acetic acid with various amines by the same method as the one of Example 1303.

| Ex. | Structural formula | MS | M.p. | NMR |
|---|---|---|---|---|
| 1315 | N-[3-(dimethylamino)propyl]-(10H-pyrazino[2,3-b][1,4]benzothiazin-8-yl) acetamide | FAB (+) 344 (MH+) | 145–148° C. | ¹H-NMR(CDCl₃) δ ppm: 1.61(quint, J=6.0Hz, 2H), 2.13(s, 6H), 2.34(t, J=6.0Hz, 2H), 3.33(m, 2H), 3.38(s, 2H), 6.48(d, J=1.5Hz, 1H), 6.69(dd, J=1.5, 7.9Hz, 1H), 6.84(d, J=7.9Hz, 1H), 7.01(br.s, 1H), 7.38(br.s, 1H), 7.58(d, J=2.9Hz, 1H), 7.69(d, J=2.9Hz, 1H) |

-continued

| Ex. | Structural formula | MS | M.p. | NMR |
|---|---|---|---|---|
| 1316 | N-[3-(dimethylamino)propyl]-N-methyl-(10H-pyrazino[2,3-b][1,4]benzothiazin-8-yl)acetamide | FAB (+) 358 (MH⁺) | | ¹H-NMR(CDCl₃) δ ppm: 1.63–1.75(m, 2H), 2.20(s, 6H),2.22, 2.26(t, J=7.1Hz, total2H), 2.94, 2.99(s, total3H), 3.34, 3.41(t, J=7.1Hz, total2H), 3.54, 3.62(s, total2H), 6.51(d, J=1.8Hz, 1H), 6.64(dd, J=1.8, 7.9Hz, 1H), 6.76, 6.77(d, J=7.9Hz, total1H), 7.55(d, J=2.9Hz, 1H), 7.58, 7.64(br.s, total1H), 7.63(d, J=2.9Hz, 1H), 7.65(m, 1H) |
| 1317 | N-propyl-(10H-pyrazino[2,3-b][1,4]benzothiazin-8-yl)acetamide | FAB (+) 300 (M⁺) | 212° C. (decompose) | ¹H-NMR(CDCl₃) δ ppm: 0.88(t, J=7.5Hz, 3H), 1.49(m, 2H), 3.20(q, J=6.6Hz, 2H), 3.39(s, 2H), 5.54(m, 1H), 6.45(d, J=1.5Hz, 1H), 6.69(dd, J=1.5, 7.7Hz, 1H), 6.84(d, J=7.7Hz, 1H), 6.93(s, 1H), 7.57(d, J=2.9Hz, 1H), 7.69(d, J=2.9Hz, 1H) |

Example 1318

(E)-N,N-Pentamethylene-3-(10-methoxymethyl-10H-pyrazino[2,3-b][1,4]benzothiazin-8-yl)propenamide 140 mg of the title compound was obtained as yellow crystals from 273 mg of (10-methoxymethyl-10H-pyrazino[2,3-b][1,4]benzothiazin-8-yl)carboxamide by the same method as the one of Production Example 25.

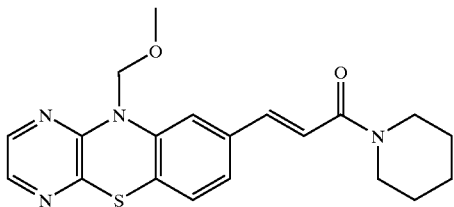

¹H-NMR(CDCl₃) δ ppm: 1.56–1.66(m, 4H), 1.66–1.74 (m, 2H), 3.52–3.63(m, 2H), 3.54(s, 3H), 3.63–3.72(m, 2H), 5.28(s, 2H), 6.85(d, J=15.3 Hz, 1H), 7.00(d, J=7.8 Hz, 1H), 7.16(dd, J=1.6, 7.8 Hz, 1H), 7.24(d, J=1.6 Hz, 1H), 7.55(d, J=15.3 Hz, 1H), 7.85(s, 2H)

Example 1319

(E)-3-(10-Methoxymethyl-10H-pyrazino[2,3-b][1,4]benzothiazin-8-yl)propenoic acid The title compound was obtained as yellow crystals by treating ethyl (E)-3-(10-methoxymethyl-10H-pyrazino[2,3-b][1,4]benzothiazin-8-yl)propenoate by the same method as the one of Example 18.

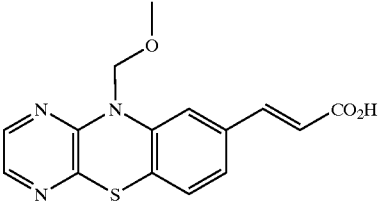

¹H-NMR(DMSO-d₆) δ ppm: 3.38(s, 3H), 5.33(s, 2H), 6.48(d, J=15.8 Hz, 1H), 7.16(d, J=7.9 Hz, 1H), 7.32(s, 1H), 7.34(d, J=7.9 Hz, 1H), 7.50(d, J=15.8 Hz, 1H), 7.93(d, J=2.4 Hz, 1H), 7.97(d, J=2.4 Hz, 1H), 12.4–12.5(br.s, 1H)

Example 1320

3-(10-Methoxymethyl-10H-pyrazino[2,3-b][1,4]benzothiazin-8-yl)propenamide 950 mg of (E)-3-(10-methoxymethyl-10H-pyrazino[2,3-b][1,4]benzothiazin-8-yl)propenoic acid was dissolved in a solvent mixture of tetrahydrofuran (10 ml) with N,N-dimethylformamide (10 ml) in a nitrogen atmosphere. Under ice-cooling, 0.48 ml of diethyl chlorophosphonate was dropped into the reaction mixture. After stirring at room temperature for 30 minutes, ammonia gas was blown into the system. Then the reaction mixture was distributed into an aqueous solution of sodium carbonate and ethyl acetate and extracted with ethyl acetate. The extract was washed with water and dried over anhydrous sodium sulfate. After distilling off the solvent under reduced pressure, the crystals thus precipitated were recrystallized from diisopropyl ether/ethyl acetate to thereby give 400 mg of the title compound as yellow crystals.

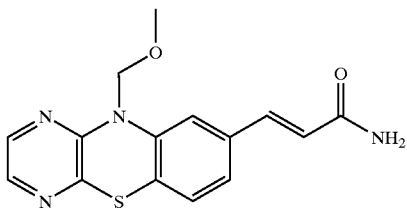

¹H-NMR(DMSO-d₆) δ ppm: 3.41(s, 3H), 5.30(s, 2H), 6.54(d, J=16.0 Hz, 1H), 7.12(br.s, 1H), 7.15(d, J=7.9 Hz, 1H), 7.20(dd, J=1.3, 7.9 Hz, 1H), 7.26(d, J=1.3 Hz, 1H), 7.33(d, J=16.0 Hz, 1H), 7.59(br.s, 1H), 7.93(d, J=2.4 Hz, 1H), 7.97(d, J=2.4 Hz, 1H)

Examples

The following compounds were obtained by treating the compounds obtained in Examples 1318 and 1320 by the same method as the one of Example 9.

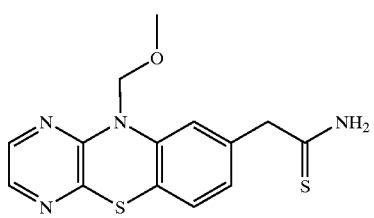

¹H-NMR(CDCl₃) δ ppm: 3.53(s, 3H), 4.01(s, 2H), 5.25(s, 2H), 6.86(br.s, 1H), 6.88(dd, J=1.7, 7.7 Hz, 1H), 7.00(d,

| Ex. | Structural formula | NMR |
|---|---|---|
| 1321 | (E)-N,N-pentamethylene-3-(10H-pyrazino[2,3-b][1,4]benzothiazin-8-yl)propenamide | ¹H-NMR(DMSO-d₆) δ ppm: 1.40–1.55(m, 4H), 1.55–1.64(m, 2H), 3.46–3.54(m, 2H), 3.54–3.63(m, 2H), 6.91(s, 1H), 6.93(d, J=8.3Hz, 1H), 7.05(d, J=15.1Hz, 1H), 7.19(d, J=8.3Hz, 1H), 7.21(d, J=15.1Hz, 1H), 7.63(d, J=3.0Hz, 1H), 7.65(d, J=3.0Hz, 1H), 9.46(s, 1H) |
| 1322 | (E)-3-(10H-pyrazino[2,3-b][1,4]benzothiazin-8-yl)propenamide | ¹H-NMR(DMSO-d₆) δ ppm: 6.41(d, J=15.3Hz, 1H), 6.89(s, 1H), 6.93(d, J=8.4Hz, 1H), 6.96(d, J=8.4Hz, 1H), 7.12(br.s, 1H), 7.18(d, J=15.3Hz, 1H), 7.60(br.s, 1H), 7.63–7.67(m, 2H), 9.61(s, 1H) |

Example 1323

(10-Methoxymethyl-10H-pyrazino[2,3-b][1,4]benzothiazin-8-yl)thioacetamide

The title compound was obtained by treating (10-methoxymethyl-10H-pyrazino[2,3-b][1,4]benzothiazin-8-yl)acetonitrile by the same method as the one of Example 1533.

J=7.7 Hz, 1H), 7.05(d, J=1.7 Hz, 1H), 7.73–7.85(br.s, 1H), 7.85(d, J=2.9 Hz, 1H), 7.86(d, J=2.9 Hz, 1H)

Examples

The following compounds were obtained by treating (10-methoxymethyl-10H-pyrazino[2,3-b][1,4]benzothiazin-8-yl)carbonitrile successively by the same methods as those of Examples 1339-1 and 9.

| Ex. | Structural formula | MS | NMR |
|---|---|---|---|
| 1324 | (10H-pyrazino[2,3-b][1,4]benzothiazin-8-yl)thioacetamide | FAB (+) 274 (M⁺) | ¹H-NMR(DMSO-d₆) δ ppm: 3.61(s, 2H), 6.73(d, J=1.7Hz, 1H), 6.74(dd, J=1.7, 7.7Hz, 1H), 6.83(d, J=7.7Hz, 1H), 7.62(d, J=2.8Hz, 1H), 7.63(d, J=2.8Hz, 1H), 9.29–9.35(br.s, 1H), 9.47–9.54(br.s, 1H), 9.53(s, 1H) |
| 1325 | (10H-pyrazino[2,3-b][1,4]benzothiazin-8-yl)carboxamide | FAB (+) 260 (M⁺) | ¹H-NMR(DMSO-d₆) δ ppm: 6.93(d, J=7.8Hz, 1H), 7.13(d, J=7.8Hz, 1H), 7.32(s, 1H), 7.64(br.s, 2H), 9.40(br.s, 1H), 9.61(s, 1H), 9.80(br.s, 1H) |

Examples

The following compounds were obtained by treating 8-aminomethyl-10-methoxymethyl-10H-pyrazino[2,3-b][1,4]benzothiazine by the same method as the one of Example 316.

| Ex. | Structural formula | NMR |
|---|---|---|
| 1326 | N-(10-methoxymethyl-10H-pyrazino[2,3-b][1,4]benzothiazin-8-ylmethyl)methanesulfonamide | ¹H-NMR(CDCl₃) δ ppm: 2.93(s, 3H), 3.54(s, 3H), 4.23(d, J=6.0Hz, 2H), 4.76(br.t, J=6.0Hz, 1H), 5.26(s, 2H), 6.95(dd, J=1.7, 7.6Hz, 1H), 7.00(d, J=7.6Hz, 1H), 7.13(d, J=1.7Hz, 1H), 7.84(d, J=2.7Hz, 1H), 7.86(d, J=2.7Hz, 1H) |
| 1327 | N-(10-methoxymethyl-(10H-pyrazino[2,3-b][1,4]benzothiazin-8-ylmethyl)trifluoromethane-sulfonamide | ¹H-NMR(CDCl₃) δ ppm: 3.53(s, 3H), 4.33(d, J=6.0Hz, 2H), 5.22(s, 2H), 5.64–5.74(br.d, J=6.0Hz, 1H), 6.78(dd, J=1.7, 8.0Hz, 1H), 6.96(d, J=8.0Hz, 1H), 7.03(d, J=1.7Hz, 1H), 7.87(d, J=3.0Hz, 1H), 7.88(d, J=3.0Hz, 1H) |

Examples

The following compounds were obtained by treating 8-aminomethyl-10-methoxymethyl-10H-pyrazino[2,3-b][1,4]-benzothiazine successively by the same methods as those of Examples 316 and 434.

| Ex. | Structural formula | MS | NMR |
|---|---|---|---|
| 1328 | N-(10H-pyrazino[2,3-b][1,4]benzothiazin-8-ylmethyl)benzenesulfonamide | FAB (+) 370 (M+), 371 (MH+) | $^1$H-NMR(DMSO-d$_6$) δ ppm: 3.76(d, J=6.4Hz, 2H), 6.62(d, J=7.3Hz, 1H), 6.69(s, 1H), 6.80(d, J=7.3Hz, 1H), 7.57(t, J=8.0Hz, 2H), 7.61(t, J=8.0Hz, 1H), 7.53(s, 2H), 7.77(d, J=8.0Hz, 2H), 8.11(d, J=6.4Hz, 1H), 9.52(s, 1H) |
| 1329 | N-(10H-pyrazino[2,3-b][1,4]benzothiazin-8-ylmethyl)methanesulfonamide | | $^1$H-NMR(DMSO-d$_6$) δ ppm: 2.86(s, 3H), 3.95(d, J=6.2Hz, 2H), 6.74(d, J=8.3Hz, 1H), 6.75(s, 1H), 6.87(d, J=8.3Hz, 1H), 7.50(t, J=6.2Hz, 1H), 7.62(d, J=2.8Hz, 1H), 7.63(d, J=2.8Hz, 1H), 9.54(s, 1H) |
| 1330 | N-(10H-pyrazino[2,3-b][1,4]benzothiazin-8-ylmethyl)trifluoromethane-sulfonamide | | $^1$H-NMR(DMSO-d$_6$) δ ppm: 4.15(s, 2H), 6.73(d, J=8.6Hz, 1H), 6.74(s, 1H), 6.91(d, J=8.6Hz, 1H), 7.63(d, J=2.8Hz, 1H), 7.65(d, J=2.8Hz, 1H), 9.62(s, 1H), 9.87–9.96(br.s, 1H) |

Example 1331

N-(10H-Pyrazino[2,3-b][1,4]benzothiazin-8-ylmethyl)sulfamide 5 ml of a solution of 283 mg of chlorosulfonyl isocyanate in tetrahydrofuran was ice-cooled and 92 mg of formic acid was added thereto. After stirring at room temperature for 30 minutes, the mixture was added to a solution of 276 mg of 8-aminomethyl-10H-pyrazino[2,3-b][1,4]benzothiazine in tetrahydrofuran (5 ml) and the resulting mixture was stirred at room temperature for 20 minutes. Next, it was distributed into an aqueous solution of potassium carbonate and ethyl acetate and the aqueous layer was extracted. The aqueous layer was well washed with ethyl acetate and the organic solvent contained therein was distilled off under reduced pressure. The residual aqueous solution was purified by High-porous gel chromatography (CHP20P mfd. by Mitsubishi Chemical Industries, Ltd., 75–150 µ) (eluted with water/methanol) to thereby give 45 mg of the title compound as yellow crystals.

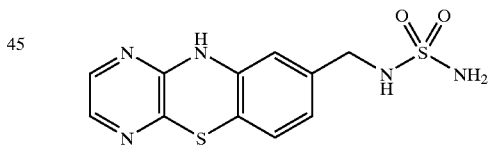

$^1$H-NMR(DMSO-d$_6$) δ ppm: 3.70(d, J=7.0 Hz, 2H), 4.57 (t, J=7.0 Hz, 1H), 6.73(d, J=8.0 Hz, 1H), 6.74(s, 1H), 6.78(d, J=8.0 Hz, 1H), 7.57–7.64(m, 2H), 9.46(s, 1H)
MS: FAB(−)309(M−)

Example 1332

N-(10H-Pyrazino[2,3-b][1,4]benzothiazin-8-ylmethyl)phenylcarbamate

Into a solution of 350 mg of 8-aminomethyl-10H-pyrazino[2,3-b][1,4]benzothiazine and 100 mg of pyridine in tetrahydrofuran (8 ml) was dropped 270 mg of phenyl chlorocarbonate and the resulting mixture was stirred for 5 minutes. Then the reaction mixture was distributed into water and ethyl acetate. The organic layer was extracted, washed with water and dried over anhydrous sodium sulfate. After distilling off the solvent under reduced pressure, diisopropyl ether was added to the crystals thus precipitated followed by filtration. Thus, 230 mg of the title compound was obtained as yellow crystals.

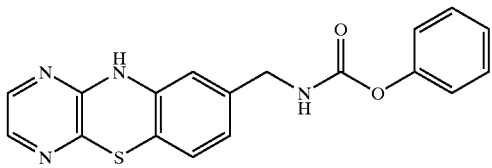

¹H-NMR(DMSO-d₆) δ ppm: 4.08(d, J=5.9 Hz, 2H), 6.72 (d, J=8.6 Hz, 1H), 6.73(s, 1H), 6.88(d, J=8.6 Hz, 1H), 7.11(d, J=7.8 Hz, 2H), 7.19(t, J=7.8 Hz, 1H), 7.37(t, J=7.8 Hz, 2H), 7.62–7.65(m, 2H), 8.25(t, J=5.9 Hz, 1 H), 9.57(s, 1H)

Examples

The following compounds were obtained by treating (10-methoxymethyl-10H-pyrazino[2,3-b][1,4]benzothiazin-8-yl)methanol successively by the same methods as those of Examples 1336 and 9.

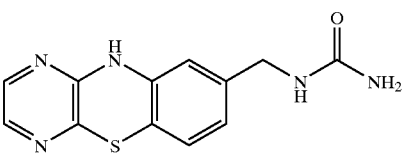

¹H-NMR(DMSO-d₆) δ ppm: 3.97(d, J=6.4 Hz, 2H), 5.52 (s, 2H), 6.33(t, J=6.4 Hz, 1H), 6.66(d, J=8.7 Hz, 1H), 6.67(s, 1H), 6.83(d, J=8.7 Hz, 1H), 7.62(d, J=2.5 Hz, 1H), 7.63(d, J=2.5 Hz, 1H), 9.52(s, 1H)

MS: FAB(+)273(M⁺)

Example 1336

N-(10H-Pyrazino[2,3-b][1,4]benzothiazin-8-ylmethyl)-N'-phenylurea

To 5 ml of a solution of 200 mg of 8-aminomethyl-10H-pyrazino[2,3-b][1,4]benzothiazine in tetrahydrofuran was added 120 mg of phenyl isocyanate and the resulting mixture was stirred at room temperature for 1 hour. The crystals

| Ex. | Structural formula | MS | M.p. | NMR |
|---|---|---|---|---|
| 1333 | N-butyl-(10H-pyrazino[2,3-b][1,4]benzothiazin-8-ylmethyl)carbamate | FAB (+) 330 (M⁺) | 169– 171° C. | ¹H-NMR(CDCl₃) δ ppm: 0.93(t, J=6Hz, 3H), 1.30–1.40(m, 2H), 1.40–1.50(m, 2H), 3.10–3.22(m, 2H), 4.70–4.80(br.s, 1H), 4.92(s, 2H), 6.40–6.50(br.s, 1H), 6.53(s, 1H), 6.82(d, J=8Hz, 1H), 6.88(d, J=8Hz, 1H), 7.58(d, J=2Hz, 1H) 7.80(d, J=2Hz, 1H) |
| 1334 | N-phenyl-(10H-pyrazino[2,3-b][1,4]benzothiazin-8-ylmethyl)carbamate | FAB (+) 350 (M⁺) | 237– 240° C. | ¹H-NMR(DMSO-d₆) δ ppm: 4.93(s, 2H), 6.80(d, J=8Hz, 1H), 6.86(s, 1H), 6.92(d, J=8Hz, 1H), 6.93–6.99(m, 1H), 7.22–7.28(m, 2H), 7.41–7.48(m, 2H), 7.62(d, J=2Hz, 2H), 9.58(s, 1H), 9.77(br.s, 1H) |

Example 1335

N-(10H-Pyrazino[2,3-b][1,4]benzothiazin-8-ylmethyl)urea

A solution of 420 mg of 8-aminomethyl-10H-pyrazino[2,3-b][1,4]benzothiazine in acetic acid (2 ml)/water (4 ml) was heated to 70° C. and potassium cyanate (1 g in total) was added thereto over 2 hours. Then the reaction mixture was brought back to room temperature and diluted with water. The solid thus precipitated was filtered, washed well with water and recrystallized from dimethyl sulfoxide/ethyl acetate to thereby give 70 mg of the title compound as yellow crystals.

thus precipitated were filtered after adding diethyl ether thereto and thus the title compound was obtained as yellow crystals almost quantitatively.

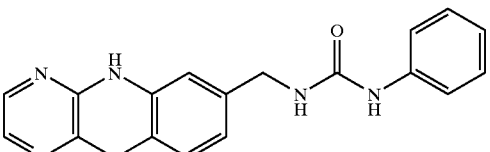

¹H-NMR(DMSO-d₆) δ ppm: 4.10(d, J=5.8 Hz, 2H), 6.53 (t, J=5.8 Hz, 1H), 6.70(d, J=7.9 Hz, 1H), 6.71(s, 1H), 6.85(d, J=7.9 Hz, 1H), 6.88(d, J=8.1 Hz, 1H), 7.20(t, J=8.1 Hz, 2H), 7.38(d, J=8.1 Hz, 2H), 7.62(s, 2H), 8.54(s, 1H), 9.53(s, 1H)

Example 1337

N-(10-Methoxymethyl-10H-pyrazino[2,3-b][1,4]benzothiazin-8-ylmethyl)-N'-benzoylthiourea To 5 ml of a solution of 350 mg of ammonium thiocyanate in acetone was added in a nitrogen atmosphere 0.50 ml of benzoyl chloride and the resulting mixture was heated under reflux for 5 minutes. Then 5 ml of a solution of 890 mg of 8-aminomethyl-10-methoxymethyl-10H-pyrazino[2,3-b][1,4]benzothiazine in acetone was added thereto and the resulting mixture was heated under reflux for additional 1.5 hours. Next, the reaction mixture was distributed into water and ethyl acetate, washed with water and dried over anhydrous sodium sulfate. After distilling off the solvent under reduced pressure, the residue was purified by silica gel column chromatography (eluted with n-hexane/ethyl acetate) and recrystallized from diisopropyl ether to thereby give 710 mg of the title compound as yellow crystals.

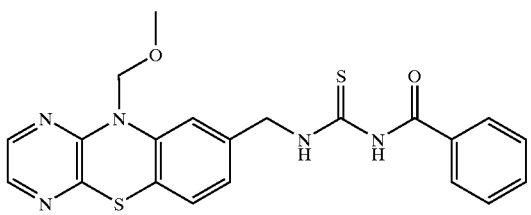

$^1$H-NMR(CDCl$_3$) δ ppm: 3.53(s, 3H), 4.85(d, J=6 Hz, 2H), 5.28(s, 2H), 7.01(s, 2H), 7.20(s, 1H), 7.52(t, J=8.0 Hz, 2H), 7.64(tt, J=1.3, 8.0 Hz, 1H), 7.83(dd, J=1.3, 8.0 Hz, 2H), 7.84(d, J=2.9 Hz, 1H), 7.85(d, J=2.9 Hz, 1H), 9.05(br.s, 1H), 10.98–11.07(br.s, 1H)

Example 1338

N-(10H-Pyrazino[2,3-b][1,4]benzothiazin-8-ylmethyl)-N'-benzoylthiourea 250 mg of the title compound was obtained as yellow crystals by treating 300 mg of N-(10-methoxymethyl-10H-pyrazino[2,3-b][1,4]benzothiazin-8-ylmethyl)-N'-benzoylthiourea by the same method as the one of Example 434.

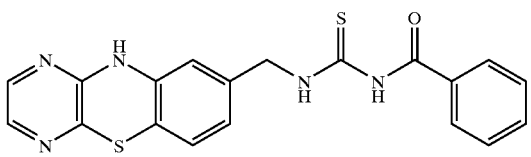

$^1$H-NMR(CDCl$_3$) δ ppm: 5.77(d, J=6 Hz, 2H), 6.58(d, J=1.5 Hz, 1H), 6.84(dd, J=1.5, 8.1 Hz, 1H), 6.87(d, J=8.1 Hz, 1H), 7.30–7.39(br.s, 1H), 7.49(d, J=3.1 Hz, 1H), 7.53(t, J=7.7 Hz, 2H), 7.64(tt, J=1.0, 7.7 Hz, 1H), 7.67(d, J=3.1 Hz, 1H), 7.84(dd, J=1.0, 7.7 Hz, 2H), 9.10(br.s, 1H), 10.96–11.16(br.s, 1H)

Example 1339

N-(10H-Pyrazino[2,3-b][1,4]benzothiazin-8-ylmethyl)thiourea 250 mg of N-(10H-pyrazino[2,3-b][1,4]benzothiazin-8-ylmethyl)-N'-benzoylthiourea was added to a mixture of a 20% aqueous solution of potassium hydroxide (5 ml) with methanol (5 ml). After further adding a small portion of tetrahydrofuran, the resulting mixture was heated to 50° C. for 5 minutes. Then the reaction mixture was brought back to room temperature and distributed into water and ethyl acetate. The organic layer was extracted, washed with water and dried over anhydrous sodium sulfate. After distilling off the solvent under reduced pressure, the crystals thus precipitated were suspended in ethyl acetate and filtered. Thus, 140 mg of the title compound was obtained as yellow crystals.

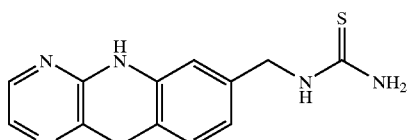

$^1$H-NMR(DMSO-d$_6$) δ ppm: 4.36–4.48(br.s, 2H), 6.68 (br.s, 1H), 6.69(br.d, J=7.8 Hz, 1H), 6.85(d, J=7.8 Hz, 1H), 6.97–7.22(br.s, 2H), 7.62(d, J=3.2 Hz, 1H), 7.64(d, J=3.2HZ, 1H), 7.85–7.95(br.s, 1H), 9.50–9.60(br.s, 1H)

MS: FAB(+)289(M$^+$)

Examples

The following compounds were obtained by treating (10-methoxymethyl-10H-pyrazino[2,3-b][1,4]benzothiazin-8-ylmethyl)methanol successively by the same methods as those of Examples 788 and 9.

| Ex. | Structural formula | MS | M.p. | NMR |
|---|---|---|---|---|
| 1340 | 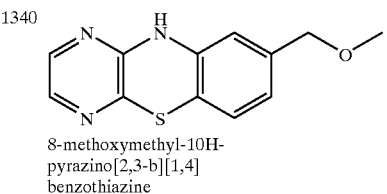<br>8-methoxymethyl-10H-pyrazino[2,3-b][1,4]benzothiazine | ESI(+) 246 (MH$^+$) | 189–192° C. | $^1$H-NMR(CDCl$_3$)δppm: 3.37(s, 3H), 4.30(s, 2H), 6.51(s, 1H), 6.52(s, 1H), 6.78(d, J=8Hz, 1H), 6.85(d, J=8Hz, 1H), 7.57(d, J=3Hz, 1H), 7.68(d, J=3Hz, 1H) |

| Ex. | Structural formula | MS | M.p. | NMR |
|---|---|---|---|---|
| 1341 | 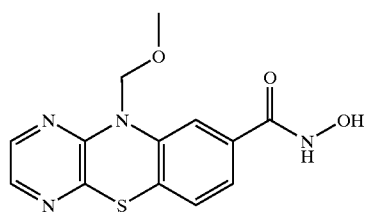<br>8-benzyloxymethyl-10H-pyrazino[2,3-b][1,4]benzothiazine | ESI(+)<br>322<br>(MH⁺) | 118–120° C. | ¹H-NMR(CDCl₃)δppm:<br>4.40(s, 2H), 4.54(s, 2H),<br>6.54(s, 1H), 6.60–<br>6.70(br.s, 1H), 6.59(d,<br>J=8Hz, 1H), 6.85(d, J=8Hz,<br>1H), 7.22–7.45(m, 5H),<br>7.57(s, 1H), 7.67(s, 1H) |

Example 1342

(10-Methoxymethyl-10H-pyrazino[2,3-b][1,4]benzothiazin-8-yl)carbohydroxamic acid To 2 ml of an aqueous solution of 280 mg of sodium hydroxide and 210 mg of hydroxylamine hydrochloride was added 5 ml of a solution of 303 mg of methyl (10-methoxymethyl-10H-pyrazino[2,3-b][1,4]benzothiazin-8-yl)carboxylate in tetrahydrofuran and the resulting mixture was stirred at room temperature for 1 hour. Then the reaction mixture was distributed into dilute hydrochloric acid and ethyl acetate. The organic layer was extracted, washed with water and dried over anhydrous sodium sulfate. After distilling off the solvent under reduced pressure, the residue was purified by silica gel column chromatography (eluted with n-hexane/ethyl acetate) to thereby give 240 mg of the title compound as yellow crystals.

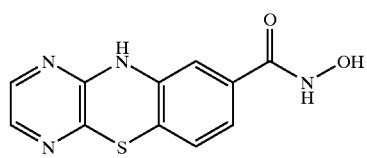

¹H-NMR(CDCl₃) δ ppm: 3.38(s, 3H), 5.28(s, 2H), 7.18(d, J=8.0 Hz, 1H), 7.32(dd, J=1.4, 8.0 Hz, 1H), 7.45(d, J=1.4 Hz, 1H), 7.93(d, J=3.1 Hz, 1H), 7.97(d, J=3.1 Hz, 1H), 9.06(s, 1H), 11.23(br.s, 1H)

Example 1343

(10H-Pyrazino[2,3-b][1,4]benzothiazin-8-yl)carbohydroxamic acid 40 mg of the title compound was obtained as yellow crystals by treating 240 mg of (10-methoxymethyl-10H-pyrazino[2,3-b][1,4]benzothiazin-8-yl)carbohydroxamic acid by the same method as the one of Example 434.

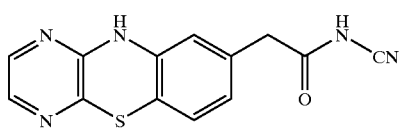

¹H-NMR(DMSO-d₆) δ ppm: 6.95(d, J=8.2 Hz, 1H), 7.06 (dd, J=1.6, 8.2 Hz, 1H), 7.14(d, J=1.6 Hz, 1H), 7.63(d, J=3.2 Hz, 1H), 7.65(d, J=3.2 Hz, 1H), 9.00(br.s, 1H), 9.60(s, 1H), 11.05–11.17(br.s, 1H)

Example 1344

N-(Methanesulfonyl)-(10H-pyrazino[2,3-b][1,4]benzothiazin-8-yl)acetamide

To a solution of 0.259 g of (10H-pyrazino[2,3-b][1,4]benzothiazin-8-yl)acetic acid in tetrahydrofuran (10 ml) was added in a nitrogen atmosphere 0.18 g of carbonyldiimidazole and the resulting mixture was heated under reflux for 30 minutes. Then the reaction mixture was brought back to room temperature and 0.285 g of methanesulfonamide was added thereto. After stirring at room temperature for 16 hours, the solvent was distilled off under reduced pressure and the residue was purified by silica gel column chromatography (eluted with dichloromethane/methanol) to thereby give 0.163 g of the title compound as a yellow solid.

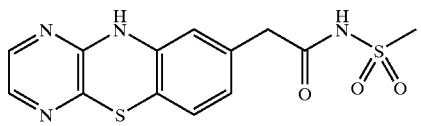

¹H-NMR(DMSO-d₆) δ ppm: 3.10(s, 3H), 3.33(s, 2H), 6.65(s, 1H), 6.66(d, J=8 Hz, 1H), 6.83(d, J=8 Hz, 1H), 7.62(d, J=4 Hz, 1H), 7.63(d, J=4 Hz, 1H), 9.52(s, 1H)
m.p.: 236–238° C.
MS: FAB(+)336(MH⁺)

Example 1345

N-Cyano-(10H-pyrazino[2,3-b][1,4]benzothiazin-8-yl)acetamide 0.100 g of the title compound was obtained as a yellow solid by treating 0.259 g of (10H-pyrazino[2,3-b][1,4]benzothiazin-8-yl)acetic acid by the same method as the one of Example 1344 by using 0.126 g of cyanamide as a substitute for the methanesulfonamide.

¹H-NMR(DMSO-d₆) δ ppm: 3.37(s, 2H), 6.65(s, 1H), 6.67(d, J=8 Hz, 1H), 6.93(d, J=8 Hz, 1H), 7.62(d, J=3 Hz, 1mH), 7.63(d, J=3 Hz, 1H), 9.51(s, 1H)
MS: FAB(+)263(M⁺)
m.p.: 197–198° C.

Example 1346

Sodium(10-methoxymethyl-10H-pyrazino[2,3-b][1,4]benzothiazin-8-yl)methanesulfonate To a solution of 900 mg of 8-chloromethyl-10-methoxymethyl-10H-pyrazino[2,3-b][1,4]benzothiazine in a mixture of water (8 ml)/methanol (4 ml) was added 0.8 g of sodium sulfite and the resulting mixture was heated to 90° C. for 2 hours. Then the reaction mixture was brought back to room temperature and diluted with ethanol. After filtering off the inorganic salt, silica gel was added to the filtrate. After distilling off the solvent under reduced pressure, the residue was purified by silica gel column chromatography (eluted with dichloromethane/methanol/acetic acid) to thereby give 650 mg of the title compound as yellow crystals.

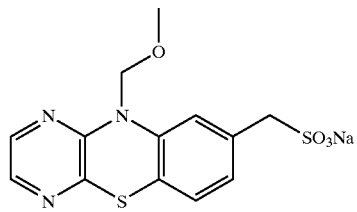

$^1$H-NMR(DMSO-d$_6$) δ ppm: 3.37(s, 3H), 3.62(s, 2H), 5.20(s, 2H), 6.95(dd, J=1.2, 7.8 Hz, 1H)6.99(d, J=7.8 Hz, 1H), 7.09(d, J=1.2 Hz, 1H), 7.90(d, J=2.5 Hz, 1H), 7.95(d, J=2.5 Hz, 1H)

Example 1347

Sodium(10H-pyrazino[2,3-b][1,4]benzothiazin-8-yl)methane-sulfonate 200 mg of the title compound was obtained as yellow crystals by treating 320 mg of sodium(10-methoxymethyl-10H-pyrazino[2,3-b][1,4]benzothiazin-8-yl)methanesulfonate by the same method as the one of Example 434.

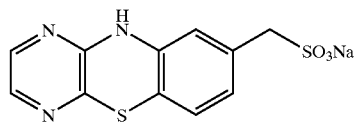

$^1$H-NMR(DMSO-d$_6$) δ ppm: 3.49(s, 2H), 6.69(dd, J=1.6, 7.7 Hz, 1H), 6.74(d, J=1.6 Hz, 1H), 6.77(d, J=7.7 Hz, 1H), 7.60(d, J=2.9 Hz, 1H), 7.62(d, J=2.9 Hz, 1H), 9.47(s, 1H) MS: FAB(+)317(M$^+$)

Example 1348

8-(Purin-9-ylmethyl)-10-methoxymethyl-10H-pyrazino[2,3-b][1,4]benzothiazine and 8-(purin-7-ylmethyl)-10-methoxymethyl-10H-pyrazino[2,3-b][1,4]benzothiazine In accordance with the procedure of Example 1094, 740 mg of 8-chloromethyl-10-methoxymethyl-10H-pyrazino[2,3-b][1,4]benzothiazine was reacted with 460 mg of purine in the presence of sodium hydride (60% oily) in N,N-dimethylformamide (10 ml). The two isomers thus obtained were purified by silica gel column chromatography (eluted with dichloromethane/methanol) to thereby give 320 mg of 8-(purin-9-ylmethyl)-10-methoxymethyl-10H-pyrazino[2,3-b][1,4]benzothiazine and 125 mg of 8-(purin-7-ylmethyl)-10-methoxymethyl-10H-pyrazino[2,3-b][1,4]benzothiazine each as yellow crystals.

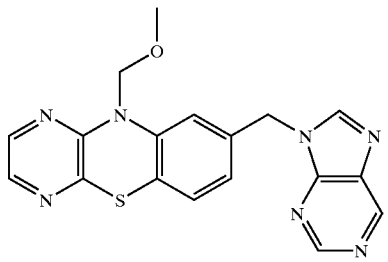

$^1$H-NMR(DMSO-d$_6$) δ ppm: 3.24(s, 3H), 5.12(s, 2H), 5.46(s, 2H), 6.96(d, J=7.8 Hz, 1H), 7.07(s, 1H), 7.09(d, J=7.8 Hz, 1H), 7.91(d, J=2.8 Hz, 1H), 7.94(d, J=2.8 Hz, 1H), 8.72(s, 1H), 8.94(s, 1H), 9.17(s, 1H)

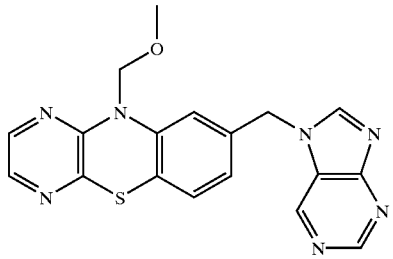

$^1$H-NMR(DMSO-d$_6$) δ ppm: 3.26(s, 3H), 5.19(s, 2H), 5.56(s, 2H), 7.01(d, J=7.8 Hz, 1H), 7.09(s, 1H), 7.11(d, J=7.8 Hz, 1H), 7.91(d, J=2.8 Hz, 1H), 7.94(d, J=2.8 Hz, 1H), 8.87(s, 1H), 8.96(s, 1H), 9.14(s, 1H)

Examples

The following compounds having substituents at different sites were obtained by reacting 8-chloromethyl-10-methoxymethyl-10H-pyrazino(2,3-b][1,4]benzothiazine with various purines by the same method as the one of Example 1348.

| Ex. | Purine | Structural formula | NMR |
|---|---|---|---|
| 1349 | | 8-(6-methylpurin-9-ylmethyl)-10-methoxymethyl-10H-pyrazino[2,3-b][1,4]benzothiazine | ¹H-NMR(DMSO-d₆)δppm: 2.58(s, 3H), 3.12(s, 3H), 5.05(s, 2H), 5.68(s, 2H), 6.70–6.75(m, 2H), 7.11(d, J=8Hz, 1H), 7.91(d, J=3Hz, 1H), 7.94(d, J=3Hz, 1H), 8.75(s, 1H), 8.78(s, 1H) |
| 1350 | | 8-(6-methylpurin-7-ylmethyl)-10-methoxymethyl-10H-pyrazino[2,3-b][1,4]benzothiazine | ¹H-NMR(DMSO-d₆)δppm: 2.70(s, 3H), 3.25(s, 3H), 5.11(s, 2H), 5.42(s, 2H), 6.93(dd, J=2, 8Hz, 1H), 7.06(d, J=2Hz, 1H), 7.07(d, J=8Hz, 1H), 7.90(d, J=3Hz, 1H), 7.94(d, J=3Hz, 1H), 8.62(s, 1H), 8.77(s, 1H) |
| 1351 | | 8-(6-dimethylaminopurin-9-ylmethyl)-10-methoxymethyl-10H-pyrazino[2,3-b][1,4]benzothiazine | ¹H-NMR(CDCl₃)δppm: 3.43(s, 3H), 3.42–3.65(br.s, 6H), 5.17(s, 2H), 5.28(s, 2H), 6.82(dd, J=2, 8Hz, 1H), 6.96(d, J=8Hz, 1H), 7.08(d, J=2Hz, 1H), 7.72(s, 1H), 7.83(d, J=3Hz, 1H), 7.84(d, J=3Hz, 1H), 8.38(s, 1H) |
| 1352 | | 8-(6-dimethylaminopurin-7-ylmethyl)-10-methoxymethyl-10H-pyrazino[2,3-b][1,4]benzothiazine | ¹H-NMR(CDCl₃)δppm: 3.33(br.s, 3H), 3.43(s, 3H), 3.92(br.s, 3H), 5.17(s, 2H), 5.44(s, 2H), 6.93(dd, J=2, 8Hz, 1H), 6.97(d, J=8Hz, 1H), 7.21(d, J=2Hz, 1H), 7.83(d, J=3Hz, 1H), 7.84(d, J=3Hz, 1H), 7.95(s, 1H), 8.02(s, 1H) |

-continued

| Ex. | Purine | Structural formula | NMR |
|---|---|---|---|
| 1353 | | 8-(6-chloropurin-9-ylmethyl)-10-methoxymethyl-10H-pyrazino[2,3-b][1,4]benzothiazine | ¹H-NMR(CDCl₃)δppm: 3.45(s, 3H), 5.20(s, 2H), 5.39(s, 2H), 6.88(dd, J=2, 8Hz, 1H), 7.00(d, J=8Hz, 1H), 7.12(d, J=2Hz, 1H), 7.83(d, J=3Hz, 1H), 7.85(d, J=3Hz, 1H), 8.13(s, 1H), 8.79(s, 1H) |
| 1354 | | 8-(6-chloropurin-7-ylmethyl)-10-methoxymethyl-10H-pyrazino[2,3-b][1,4]benzothiazine | ¹H-NMR(CDCl₃)δppm: 3.40(s, 3H), 5.15(s, 2H), 5.61(s, 2H), 6.75(dd, J=2, 8Hz, 1H), 6.96(d, J=2Hz, 1H), 7.01(d, J=8Hz, 1H), 7.83(d, J=3Hz, 1H), 7.86(d, J=3Hz, 1H), 8.26(s, 1H), 8.91(s, 1H) |
| 1355 | | 9-(10-methoxymethyl-10H-pyrazino[2,3-b][1,4]benzothiazin-8-ylmethyl)purine-6-carbonitrile | ¹H-NMR(CDCl₃)δppm: 3.46(s, 3H), 5.21(s, 2H), 5.42(s, 2H), 6.90(dd, J=2, 8Hz, 1H), 7.00(d, J=8Hz, 1H), 7.15(d, J=2Hz, 1H), 7.83(d, J=3Hz, 1H), 7.86(d, J=3Hz, 1H), 8.29(s, 1H), 9.01(s, 1H) |
| 1356 | | 8-(6-aminopurin-9-yl)-10-methoxymethyl-10H-pyrazino[2,3-b][1,4]benzothiazine | ¹H-NMR(DMSO-d₆)δppm: 3.28(s, 3H), 5.13(s, 2H), 5.32(s, 2H), 6.93(dd, J=2, 8Hz, 1H), 7.06(d, J=2Hz, 1H), 7.10(d, J=8Hz, 1H), 7.27(s, 2H), 7.90–7.94(m, 1H), 7.95–7.98(m, 1H), 8.16(s, 1H), 8.24(s, 1H) |

-continued

| Ex. | Purine | Structural formula | NMR |
|---|---|---|---|
| 1357 | 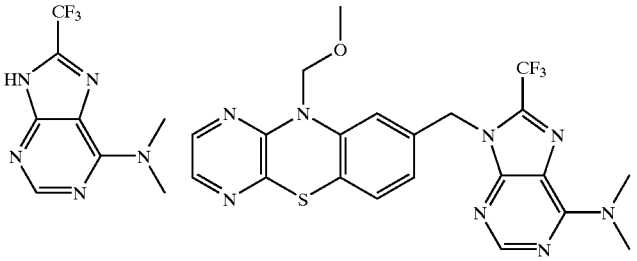 | 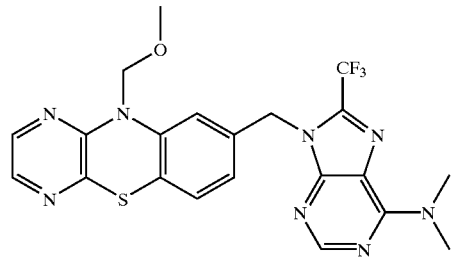  8-(8-trifluoromethyl-6-dimethylaminopurin-9-yl)-10-methoxymethyl-10H-pyrazino[2,3-b][1,4]benzothiazine | $^1$H-NMR(CDCl$_3$)δppm: 3.34(s, 3H), 3.45(s, 3H), 3.92(s, 3H), 5.17(s, 2H), 5.43(s, 2H), 6.91–6.99(m, 3H), 7.82(m, 2H), 8.00(s, 1H) |
| 1358 | 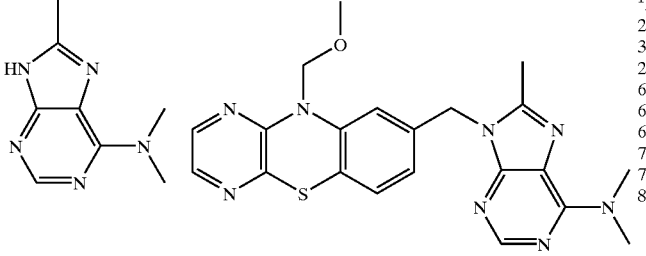 | 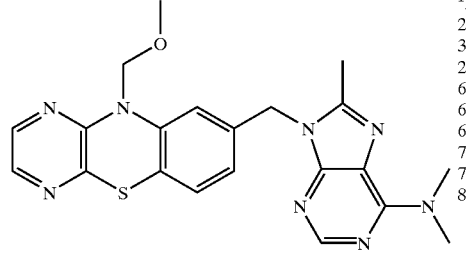  8-(8-methyl-6-dimethyl aminopurin-9-ylmethyl)-10-methoxymethyl-10H-pyrazino[2,3-b][1,4]benzothiazine | $^1$H-NMR(CDCl$_3$)δppm: 2.47(s, 3H), 3.38(s, 3H), 3.52(br.s, 6H), 5.12(s, 2H), 5.26(s, 2H), 6.72(dd, J=2, 8Hz, 1H), 6.93(d, J=8Hz, 1H), 6.96(d, J=2Hz, 1H), 7.82(d, J=3Hz, 1H), 7.84(d, J=3Hz, 1H), 8.32(s, 1H) |
| 1359 | 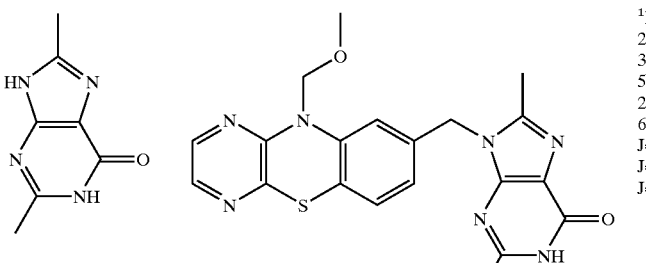 | 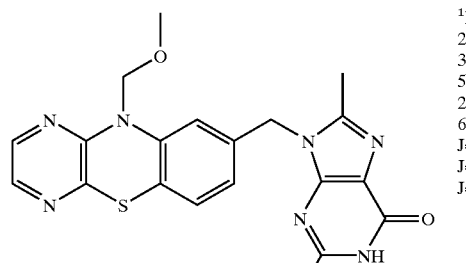  8-(2,8-dimethylhypoxanthin-9-ylmethyl)-10-methoxymethyl-10H-pyrazino[2,3-b][1,4]benzothiazine | $^1$H-NMR(DMSO-d$_6$)δppm: 2.35(s, 3H), 2.48(s, 3H), 3.24(s, 3H), 5.09(s, 2H), 5.24(s, 2H), 6.79(d, J=8Hz, 1H), 6.90(s, 1H), 7.09(d, J=8Hz, 1H), 7.92(d, J=3Hz, 1H), 7.95(d, J=3Hz, 1H), 12.14(s, 1H) |

-continued

| Ex. | Purine | Structural formula | NMR |
|---|---|---|---|
| 1360 | | 9-(10-methoxymethyl-10H-pyrazino[2,3-b][1,4]benzothiazine-8-ylmethyl)-6-dimethylamino-8-oxo-7(H),8(H)-purine | ¹H-NMR(CDCl₃)δppm: 3.24(s, 6H), 3.47(s, 3H), 4.99(s, 2H), 5.20(s, 2H), 6.93(d, J=8Hz, 1H), 7.00(dd, J=2, 8Hz, 1H), 7.27(d, J=2Hz, 1H), 7.82(m, 2H), 8.24(s, 1H), 10.36(s, 1H) |
| 1361 | | 9-(10-methoxymethyl-10H-pyrazino[2,3-b][1,4]benzothiazine-8-ylmethyl)-3,7-dihydro-1,3-dimethyl-1H-purine-2,6-dione | ¹H-NMR(DMSO-d₆)δppm: 3.20(s, 3H), 3.31(s, 3H)m 3.39(s, 3H), 5.14(s, 2H), 5.40(s, 2H), 6.95(dd, J=1.4, 8.2Hz, 1H), 7.08(d, J=1.4Hz, 1H), 7.09(d, J=8.2Hz, 1H), 7.91(d, J=2.8Hz, 1H), 7.95(d, J=2.8Hz, 1H), 8.26(s, 1H) |
| 1362 | | 8-(6-bromopurin-9-ylmethyl)-10-methoxymethyl-10H-pyrazino[2,3-b][1,4]benzothiazine | ¹H-NMR(CDCl₃)δppm: 3.39(s, 3H), 5.13(s, 2H), 5.32(s, 2H), 6.82(dd, J=2, 8Hz, 1H), 6.93(d, J=8Hz, 1H), 7.06(d, J=2Hz, 1H), 7.73(d, J=3Hz, 1H), 7.79(d, J=3Hz, 1H), 8.08(s, 1H), 8.68(s, 1H) |

-continued

| Ex. | Purine | Structural formula | NMR |
|---|---|---|---|
| 1363 | 8-(6-bromopurin-7-ylmethyl)-10-methoxymethyl-10H-pyrazino[2,3-b][1,4]benzothiazine | | $^1$H-NMR(CDCl$_3$)δppm: 3.32(s, 3H), 5.08(s, 2H), 5.59(s, 2H), 6.67(dd, J=2, 8Hz, 1H), 6.87(d, J=2Hz, 1H), 6.95(d, J=8Hz, 1H), 7.77(d, J=3Hz, 1H), 7.80(d, J=3Hz, 1H), 8.21(s, 1H), 8.80(s, 1H) |

Examples

The following compounds were obtained each as yellow crystals by treating the methoxymethyl compounds in the above table by the same method as the one of Example 434.

| Ex. | Structural formula | MS | M.p. | NMR |
|---|---|---|---|---|
| 1364 | 8-(purin-9-ylmethyl)-10H-pyrazino[2,3-b][1,4]benzothiazine | ESI(+) 334.1 (MH$^+$) | 264–265° C. | $^1$H-NMR(DMSO-d$_6$)δppm: 5.34(s, 2H), 6.59(s, 1H), 6.74(d, J=8.6Hz, 1H), 6.88(d, J=8.6Hz, 1H), 7.61(s, 2H), 8.69(s, 1H), 8.93(s, 1H), 9.18(s, 1H), 9.44(br.s, 1H) |
| 1365 | 8-(purin-7-ylmethyl)-10H-pyrazino[2,3-b][1,4]benzothiazine | ESI(+) 334.2 (MH$^+$) | 277–280° C. | $^1$H-NMR(DMSO-d$_6$)δppm: 5.46(s, 2H), 6.60(s, 1H), 6.80(d, J=8.0Hz, 1H), 6.91(d, J=8.0Hz, 1H), 7.61(s, 2H), 8.81(s, 1H), 8.97(s, 1H), 9.07(s, 1H), 9.43(br.s, 1H) |
| 1366 | 8-(6-aminopurin-9-ylmethyl)-10H-pyrazino[2,3-b][1,4]benzothiazine | ESI(+) 349 (MH$^+$) | 290° C.< | $^1$H-NMR(DMSO-d$_6$)δppm: 5.20(s, 2H), 6.60(d, J=2Hz, 1H), 6.72(dd, J=2, 8Hz, 1H), 6.89(d, J=8Hz, 1H), 7.27(s, 2H), 7.63(s, 2H), 8.14(s, 1H), 8.20(s, 1H), 9.50(s, 1H) |

Examples

The following compounds were obtained each as yellow crystals by treating the methoxymethyl compounds in the above table by the same method as the one of Example 9.

| Ex. | Structural formula | MS | M.p. | NMR |
|---|---|---|---|---|
| 1367 | 8-(6-methylpurin-9-ylmethyl)-10H-pyrazino[2,3-b][1,4]benzothiazine | ESI (+) 348 (MH$^+$) | 276–278° C. | $^1$H-NMR(DMSO-d$_6$) δ ppm: 2,57(s, 3H), 5.57(s, 2H), 6.32(s, 1H), 6.57(d, J=8Hz, 1H), 6.90(d, J=8Hz, 1H), 7.60(s, 2H), 8.71(s, 1H), 8.79(s, 1H), 9.38(s, 1H) |
| 1368 | 8-(6-methylpurin-7-ylmethyl)-10H-pyrazino[2,3-b][1,4]benzothiazine | | | $^1$H-NMR(DMSO-d$_6$) δ ppm: 2.71(s, 3H), 5.31(s, 2H), 6.57(s, 1H), 6.72(d, J=8Hz, 1H), 7.61(s, 2H), 8.59(s, 1H), 8.76(s, 1H), 9.43(s, 1H) |
| 1369 | 8-(6-dimethylaminopurin-9-ylmethyl)-10H-pyrazino[2,3-b][1,4]benzothiazine | FAB (+) 377 (MH$^+$) | 229–233° C. | $^1$H-NMR(DMSO-d$_6$) δ ppm: 3.43(s, 6H), 5.20(s, 2H), 6.56(d, J=1Hz, 1H), 6.67(dd, J=1, 8Hz, 1H), 6.86(d, J=8Hz, 1H), 7.62(s, 2H), 8.19(s, 1H), 8.21(s, 1H), 9.46(s, 1H) |
| 1370 | 8-(6-dimethylaminopurin-7-ylmethyl)-10H-pyrazino[2,3-b][1,4]benzothiazine | FAB (+) 377 (MH$^+$) | 265–268° C. | $^1$H-NMR(DMSO-d$_6$) δ ppm: 3.39(s, 3H), 3.83(s, 3H), 5.34(s, 2H), 6.69(d, J=1Hz, 1H), 6.78(dd, J=1, 8Hz, 1H), 6.87(d, J=8Hz, 1H), 7.61(s, 2H), 7.71(s, 1H), 8.52(s, 1H), 9.40(s, 1H) |
| 1371 | 8-(6-chloropurin-9-ylmethyl)-10H-pyrazino[2,3-b][1,4]benzothiazine | FAB (+) 367 (M$^+$) | | $^1$H-NMR(DMSO-d$_6$) δ ppm: 5.36(s, 2H), 6.54(s, 1H), 6.75(d, J=8Hz, 1H), 6.87(d, J=8Hz, 1H), 7.61(s, 2H), 8.78(s, 2H), 9.40(s, 1H) |

| Ex. | Structural formula | MS | M.p. | NMR |
|---|---|---|---|---|
| 1372 | 8-(6-chloropurin-7-ylmethyl)-10H-pyrazino[2,3-b][1,4]benzothiazine | FAB (+) 367 (M⁺) | | ¹H-NMR(DMSO-d₆) δ ppm: 5.57(s, 2H), 6.39(d, J=1Hz, 1H), 6.65(dd, J=1, 8Hz, 1H), 6.89(d, J=8Hz, 1H), 7.60(d, J=3Hz, 1H), 7.61(d, J=3Hz, 1H), 8,83(s, 1H), 8.94(s, 1H), 9.35(s, 1H) |
| 1373 | 9-(10H-pyrazino[2,3-b][1,4]benzothiazin-8-ylmethyl)purine-6-carbonitrile | | 272–274° C. | ¹H-NMR(DMSO-d₆) δ ppm: 5.42(s, 2H), 6.56(d, J=2Hz, 1H), 6.78(dd, J=2, 8Hz, 1H), 6.88(d, J=8Hz, 1H), 7,62(s, 2H), 9.02(s, 1H), 9.39(s, 1H), 9.40(s, 1H) |
| 1374 | 8-(8-trifluoromethyl-6-dimethylaminopurin-9-ylmethyl)-10H-pyrazino[2,3-b][1,4]benzothiazine | FAB (+) 444 (M⁺) | 231–233° C. | ¹H-NMR(CDCl₃) δ ppm: 3.37(s, 3H), 3.95(s, 3H), 5.35(s, 2H), 6.44(d, J=1Hz, 1H), 6.75(dd, J=1, 8Hz, 1H), 6.78(br.s, 1H), 6.83(d, J=8Hz, 1H), 7.55(d, J=3Hz, 1H), 7.67(d, J=3Hz, 1H), 7.90(s, 1H) |
| 1375 | 8-(8-methyl-6-dimethylaminopurin-9-ylmethyl)-10H-pyrazino[2,3-b][1,4]benzothiazine | | | ¹H-NMR(CDCl₃) δ ppm: 2.45(s, 3H), 3.54(s, 6H), 5.19(s, 2H), 6.22(d, J=1Hz, 1H), 6.42(br.s, 1H), 6.63(dd, J=1, 8Hz, 1H), 6.83(d, J=8Hz, 1H), 7.54(d, J=3Hz, 1H), 7.68(d, J=3Hz, 1H), 8.33(s, 1H) |
| 1376 | 8-(2,8-dimethylhypoxanthin-9-ylmethyl)-10H-pyrazino[2,3-b][1,4]benzothiazine | | 206–211° C. | ¹H-NMR(DMSO-d₆) δ ppm: 2.30 and 2.31(s, total 3H), 2.34 and 2.35(s, total 3H), 5.13 and 5.49(s, total 2H), 6.43 and 6.46(s, total 1H), 6.59(d, J=8Hz, 1H), 6.87(d, J=8Hz, 1H), 7.61(s, 2H), 9.44 and 9.46(s, total 1H), 12.13(br.s, 1H) |

-continued

| Ex. | Structural formula | MS | M.p. | NMR |
|---|---|---|---|---|
| 1377 | 9-(10H-pyrazino[2,3-b][1,4]benzothiazin-8-ylmethyl)-6-dimethylamino-1,7-dihydro-8H-purin-8-one | FAB (+) 392 (M+) | >280° C. | $^1$H-NMR(DMSO-$d_6$) δ ppm: 3.20(s, 3H), 3.35(s, 3H), 4.75(s, 2H), 6.65(s, 1H), 6.72(d, J=8Hz, 1H), 6.85(d, J=8Hz, 1H), 7.60(s, 2H), 8.09(s, 1H), 9.46(s, 1H), 10.95(s, 1H) |

Examples

The following compounds were obtained by treating 8-(6-bromopurin-9-ylmethyl)-10-methoxymethyl-10H-pyrazino[2,3-b][1,4]benzothiazine by the same method as the one of Example 9 and separating and purifying each of the two compounds thus formed.

| Ex. | Structural formula | MS | M.p. | NMR |
|---|---|---|---|---|
| 1378 | 7-(10H-pyrazino[2,3-b][1,4]benzothiazin-8-ylmethyl)-6-oxo-1(H),6(H)-purine | FAB (+) 350 (MH+) | >275° C. | $^1$H-NMR(DMSO-$d_6$)δppm: 5.38(s, 2H), 6.57(d, J=1Hz, 1H), 6.68(dd, J=1, 8Hz, 1H), 6.87(d, J=8Hz, 1H), 7.61(s, 2H), 7.97(d, J=4Hz, 1H), 8.30(s, 1H), 9.48(s, 1H), 12.30(s, 1H) |
| 1379 | 5-(6-bromopurin-7-ylmethyl)-10H-pyrazino[2,3-b][1,4]benzothiazine | | | $^1$H-NMR(CDCl$_3$)δppm: 5.21(s, 2H), 6.39(d, J=1Hz, 1H), 6.60(br.s, 1H), 6.74(dd, J=1, 8Hz, 1H), 6.86(d, J=8Hz, 1H), 7.55(d, J=3Hz, 1H), 7.69(d, J=3Hz, 1H), 7.90(s, 1H), 8.56(s, 1H) |

Examples

The following compounds were obtained by treating 8-(6-bromopurin-9-ylmethyl)-10-methoxymethyl-10H-pyrazino[2,3-b][1,4]benzothiazine by the same method as the one of Example 9 and separating and purifying each of the two compounds thus formed.

| Ex. | Structural formula | MS | M.p. | NMR |
|---|---|---|---|---|
| 1380 | 8-(hypoxanthin-9-ylmethyl)-10H-pyrazino[2,3-b][1,4]benzothiazine | FAB (+) 349 (M⁺) | >275° C. | ¹H-NMR(DMSO-d₆)δppm: 5.20(s, 2H), 6.53(d, J=1Hz, 1H), 6.69(dd, J=1, 8Hz, 1H), 6.87(d, J=8Hz, 1H), 7.62(s, 2H), 8.02(d, J=4Hz, 1H), 8.14(s, 1H), 9.45(s, 1H), 12.31(s, 1H) |
| 1381 | 8-(6-bromopurin-9-ylmethyl)-10H-pyrazino[2,3-b][1,4]benzothiazine | | | ¹H-NMR(CDCl₃)δppm: 5.22(s, 2H), 6.36(d, J=1Hz, 1H), 6.43(br.s, 1H), 6.70(dd, J=1, 8Hz, 1H), 6.82(d, J=8Hz, 1H), 7.50(d, J=3Hz, 1H), 7.64(d, J=3Hz, 1H), 8.06(s, 1H), 8.67(s, 1H) |

Example 1382

9-(10H-Pyrazino[2,3-b][1,4]benzothiazin-8-ylmethyl)-3,7-dihydro-1,3-dimethyl-1H-purine-2,6-dione The title compound was obtained by treating 9-(10-methoxymethyl-10H-pyrazino[2,3-b][1,4]benzothiazin-8-ylmethyl)-3,7-dihydro-1,3-dimethyl-1H-purine-2,6-dione by the same method as the one of Example 9.

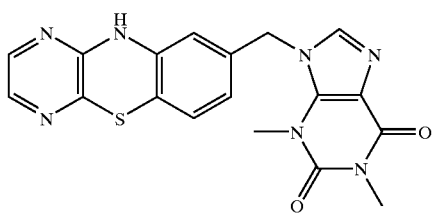

¹H-NMR(DMSO-d₆) δ ppm: 3.19(s, 3H), 3.43(s, 3H), 5.32(s, 2H), 6.59(d, J=2 Hz, 1H), 6.68(d, J=8 Hz, 1H), 6.87(dd, J=2, 8 Hz, 1H), 7.62(m, 2H), 8.20(s, 1H), 9.47(s, 1H)

m.p.: 264–266° C.

Example 1383

8-(2,6-Dichloropurin-9-ylmethyl)-10H-pyrazino[2,3-b][1,4]benzothiazine

The title compound was obtained by reacting 8-chloromethyl-10-methoxymethyl-10H-pyrazino[2,3-b][1,4]benzothiazine with 2,6-dichloropurine by the same method as the one of Example 1348 followed by the same treatment as the one of Example 434.

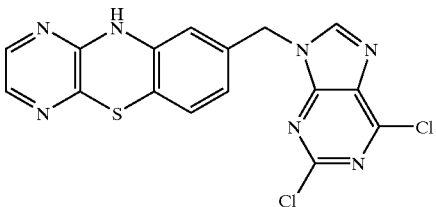

¹H-NMR(CDCl₃) δ ppm: 5.44(s, 2H), 6.20(d, J=1 Hz, 1H), 6.55(dd, J=1, 8 Hz, 1H), 6.59(br.s, 1H), 6.83(d. J=8 Hz, 1H), 7.49(d, =3 Hz, 1H), 7.65(d, J=3 Hz, 1H), 8.19(s, 1H)

MS: FAB(+)401(M⁺)

Examples

The following compounds were obtained by reacting 8-chloromethyl-10-methoxymethyl-10H-pyrazino[2,3-b][1,4]benzothiazine with 8-methylpurine by the same method as the one of Example 1348 to thereby give 8-(8-methylpurin-9(7)-ylmethyl)-10-methoxymethyl-10H-pyrazino[2,3-b][1,4]benzothiazine and then treating this product by the same method as the one of Example 9.

| Ex. | Structural formula | MS | M.p. | NMR |
|---|---|---|---|---|
| 1384 | 8-(8-methylpurin-9-ylmethyl)-10H-pyrazino[2,3-b][1,4]benzothiazine | ESI(+) 348 (MH+) | 191–193° C. | $^{1}$H-NMR(DMSO-d$_{6}$)δppm: 248(s, 3H), 5.31(s, 2H), 6.48(s, 1H), 6.68(d, J=8Hz, 1H), 6.88(d, J=8Hz, 1H), 7.60(s, 2H), 8.86(d, J=1Hz, 1H), 9.01(d, J=1Hz, 1H), 9.39(br.s, 1H) |
| 1385 | 8-(8-methylpurin-7-ylmethyl)-10H-pyrazino[2,3-b][1,4]benzothiazine | ESI(+) 348 (MH+) | >275° C. | $^{1}$H-NMR(DMSO-d$_{6}$)δppm: 2.59(s, 3H), 5.42(s, 2H), 6.47(d, J=2Hz, 1H), 6.70(dd, J=2, 8Hz, 1H), 6.89(d, J=8Hz, 1H), 7.59(s, 2H), 8.89(s, 1H), 9.00(s, 1H), 9.37(s, 1H |

Example 1386

8-[6-(Morpholin-4-yl)purin-9-ylmethyl]-10-methoxymethyl-10H-pyrazino[2,3-b][1,4]benzothiazine 0.222 g of the title compound was obtained as a yellow solid by treating 0.21 g of 8-(6-chloropurin-9-ylmethyl)-10-methoxymethyl-10H-pyrazino[2,3-b][1,4]benzothiazine with 0.5 ml of morpholine in dichloromethane by the same method as the one of Example 1244.

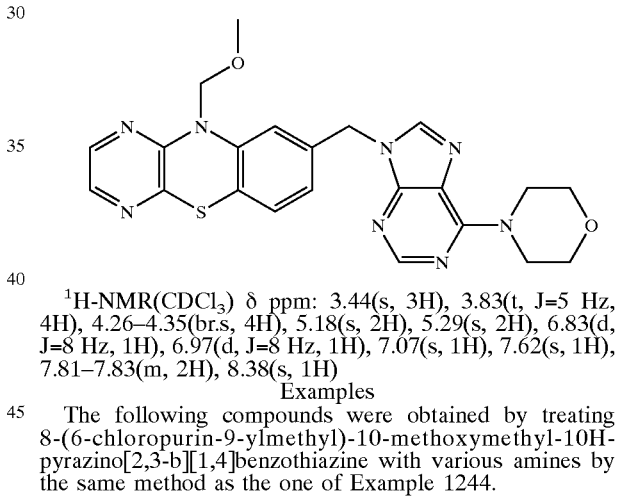

$^{1}$H-NMR(CDCl$_{3}$) δ ppm: 3.44(s, 3H), 3.83(t, J=5 Hz, 4H), 4.26–4.35(br.s, 4H), 5.18(s, 2H), 5.29(s, 2H), 6.83(d, J=8 Hz, 1H), 6.97(d, J=8 Hz, 1H), 7.07(s, 1H), 7.62(s, 1H), 7.81–7.83(m, 2H), 8.38(s, 1H)

Examples

The following compounds were obtained by treating 8-(6-chloropurin-9-ylmethyl)-10-methoxymethyl-10H-pyrazino[2,3-b][1,4]benzothiazine with various amines by the same method as the one of Example 1244.

| Ex. | Structural formula | NMR |
|---|---|---|
| 1387 | 8-[6-(piperidin-1-yl)purin-9-ylmethyl]-10-methoxymethyl-10H-pyrazino[2,3-b][1,4]benzothiazine | $^{1}$H-NMR (CDCl$_{3}$) δ ppm: 1.65–1.77(m, 6H), 3.43(s, 3H), 4.24(br.s, 4H), 5.17(s, 2H), 5.28(s, 2H), 6.84(dd, J=2, 8Hz, 1H), 6.94(d, J=8Hz, 1H), 7.08(d, J=2Hz, 1H), 7.71(s, 1H), 7.83(d, J=3Hz, 1H), 7.84(d, J=3Hz, 1H), 8.36(s, 1H) |

| Ex. | Structural formula | NMR |
|---|---|---|
| 1388 | 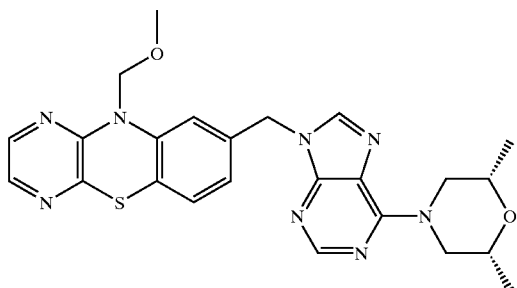<br>8-[6-(2,6-dimethylmorpholin-4-yl)purin-9-ylmethyl]-10-methoxymethyl-10H-pyrazino[2,3-b][1,4]benzothiazine | ¹H-NMR (CDCl₃) δ ppm: 1.28(d, J=7Hz, 6H), 2.75–2.87(br.s, 2H), 3.44(s, 3H), 3.72(br.s, 2H), 5,18(s, 2H), 5.29(s, 2H), 5.30(br.s, 2H), 6.83(dd, J=2, 8Hz, 1H), 6.96(d, J=8Hz, 1H), 7.09(d, J=2Hz, 1H), 7.73(s, 1H), 7.83(d, J=3Hz, 1H), 7.84(d, J=3Hz, 1H), 8.37(s, 1H) |
| 1389 | 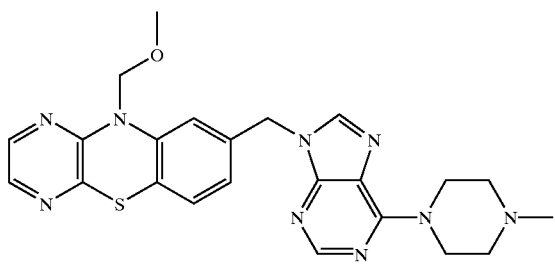<br>8-[6-(4-methylpiperazin-1-yl) purin-9-ylmethyl]-10-methoxymethyl-10H-pyrazino[2,3-b][1,4]benzothiazine | ¹H-NMR (CDCl₃) δ ppm: 2.35(s,3H), 2.55(m, 4H), 3.43(s, 3H), 4.33(br.s, 4H), 5.18(s, 2H), 5.29(s, 2H), 6.83(dd, J=2, 8Hz, 1H), 6.94(d, J=8Hz, 1H), 7.08(d, J=2Hz, 1H), 7.63(s, 1H), 7.83(d, J=3Hz, 1H), 7.84(d, J=3Hz, 1H), 8.37(s, 1H) |
| 1390 | 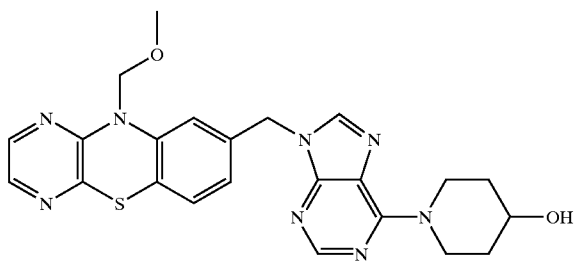<br>1-[9-(10-methoxymethyl-10H-pyrazino[2,3-b][1,4]benzothiazin-8-ylmethyl)purin-6-yl]piperidin-4-ol | ¹H-NMR (CDCl₃) δ ppm: 1.62(m, 2H), 2.03(m, 2H), 3.43(s, 3H), 3.72(br.s, 2H), 4.02(br.s, 2H), 4.91(br.m, 1H), 5.17(s, 2H), 5.28(s, 2H), 6.84(dd, J=2, 8Hz, 1H), 6.96(d, J=8Hz, 1H), 7.09(d, J=2Hz, 1H), 7.73(s, 1H), 7.83(d, J=3Hz, 1H), 7.84(d, J=3Hz, 1H), 8.37(s, 1H) |

| Ex. | Structural formula | NMR |
|---|---|---|
| 1391 | 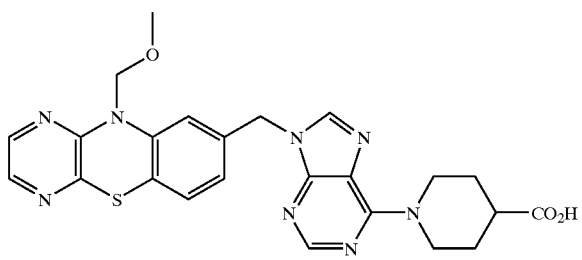<br>1-[9-(10-methoxymethyl-10H-pyrazino[2,3-b][1,4]benzothiazin-8-ylmethyl)purin-6-yl]piperidine-4-carboxylic acid | $^1$H-NMR (CDCl$_3$) δ ppm: 1.52(m, 2H), 1.91(m, 2H), 2.59(m, 1H), 3.2(m, 4H), 3.24(s, 3H), 5.11(s, 2H), 5.22(s, 2H), 6.91(dd, J=2, 8Hz, 1H), 7.02(d, J=2Hz, 1H), 7.07(d, J=8Hz, 1H), 7.91(d, J=3Hz, 1H), 7.94(d, J=3Hz, 1H), 8.23(s, 1H), 8.28(s, 1H) |
| 1392 | 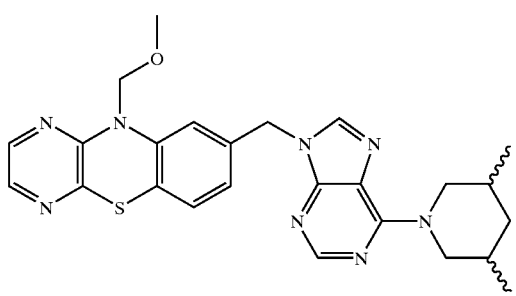<br>8-[6-(3,5-dimethypiperidin-1-yl)purin-9-ylmethyl]-10-methoxymethyl-10H-pyrazino[2,3-b][1,4]benzothiazine | $^1$H-NMR (CDCl$_3$) δ ppm: 0.97 and 0.99(d, J=7Hz, total 6H), 1.50–1.92(m, 4H), 2.48(br.s, 2H), 3.43(s, 3H), 5.17(s, 2H), 5.28(s, 2H), 5.32(br.s, 2H), 6.83(dd, J=2, 8Hz, 1H), 6.94(d, J=8Hz, 1H), 7.08(d, J=2Hz, 1H), 7.71(s, 1H), 7.83(d, J=3Hz, 1H), 7.84(d, J=3Hz, 1H), 8.36(s, 1H) |
| 1393 | 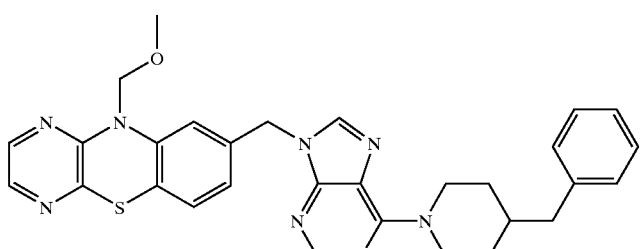<br>8-[6-(4-benzylpiperidin-1-yl)purin-9-ylmethyl]-10-methoxymethyl-10H-pyrazino[2,3-b][1,4]benzothiazine | $^1$H-NMR (CDCl$_3$) δ ppm: 1.32(dq, J=4, 11Hz, 2H), 1.81(br.d, J=11Hz, 2H), 1.85–1.94(m, 1H), 2.56(d, J=8Hz, 2H), 3.02(m, 2H), 3.44(s, 3H), 5.18(s, 2H), 5.28(s, 2H), 5.43(m, 2H), 6.83(dd, J=2, 8Hz, 1H), 6.96(d, J=8Hz, 1H), 7.08(d, J=2Hz, 1H), 7.13—7.31(m, 5H), 7.71(s, 1H), 7.83(d, J=3Hz, 1H), 7.84(d, J=3Hz, 1H), 8.35(s, 1H) |

-continued

| Ex. | Structural formula | NMR |
|---|---|---|
| 1394 | 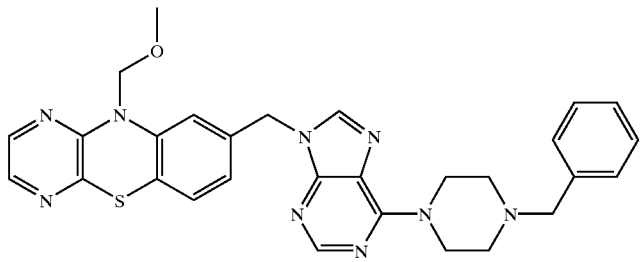<br>8-[6-(4-benzylpiperazin-1-yl)purin-9-ylmethyl]-10-methoxymethyl-10H-pyrazino[2,3-b][1,4]benzothiazine | $^1$H-NMR (CDCl$_3$) δ ppm: 2.58(t, J=5Hz, 4H), 3.43(s, 3H), 3.57(s, 2H), 4.32(br.s, 4H), 5.17(s, 2H), 5.28(s, 2H), 6.83(dd, J=2, 8Hz, 1H), 6.94(d, J=8Hz, 1H), 7.07(d, J=2Hz, 1H), 7.26–7.35(m, 5H), 7.71(s, 1H), 7.83(d, J=3Hz, 1H), 7.84(d, J=3Hz, 1H), 8.36(s, 1H) |
| 1395 | 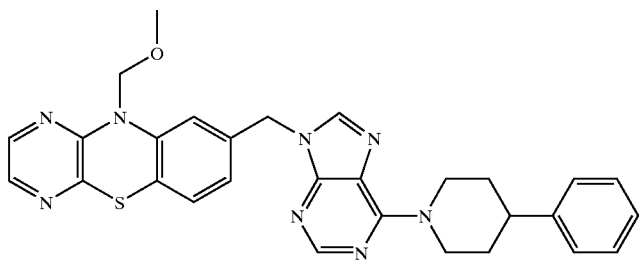<br>8-[6-(4-phenylpiperidin-1-yl)purin-9-ylmethyl]-10-methoxymethyl-10H-pyrazino[2,3-b][1,4]benzothiazine | $^1$H-NMR (CDCl$_3$) δ ppm: 1.79(dq, J=4, 11Hz, 2H), 2.03(br.d, J=11Hz, 2H), 2.88(tt, J=1, 11Hz, 1H), 3.16(br.t, J=11Hz, 2H),3.45(s, 3H), 5.19(s, 2H), 5.30(s, 2H), 5.65(br.s, 2H), 6.85(dd, J=2, 8Hz, 1H), 6.97(d, J=8Hz, 1H), 7.10(d, J=2Hz, 1H), 7.21–7.32(m, 5H), 7.74(s, 1H), 7.83(d, J=3Hz, 1H), 7.84(d, J=3Hz, 1H), 8.39(s, 1H) |
| 1396 | 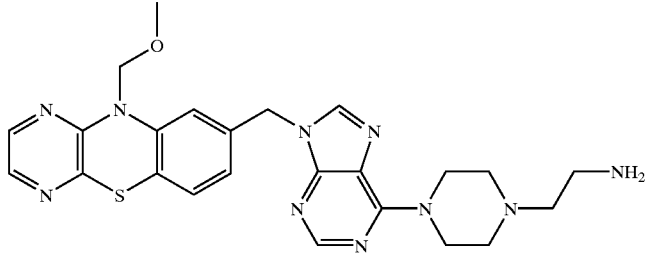<br>8-[[4-(2-aminoethyl)piperazin-1-yl]purin-9-ylmethyl]-10-methoxymethyl-10H-pyrazino[2,3-b][1,4]benzothiazine | $^1$H-NMR (CDCl$_3$) δ ppm: 2.32(t, J=6Hz, 2H), 2.45(m, 4H), 2.66(t, J=6Hz, 2H), 3.26(s, 3H), 4.39(m, 4H), 5.11(s, 2H), 5.30(s, 2H), 6.90(dd, J=2, 8Hz, 1H), 7.03(d, J=2Hz, 1H), 7.07(d, J=8Hz, 1H), 7.91(d, J=3Hz, 1H), 7.94(d, J=3Hz, 1H), 8.23(s, 1H), 8.28(s, 1H) |
| 1397 | 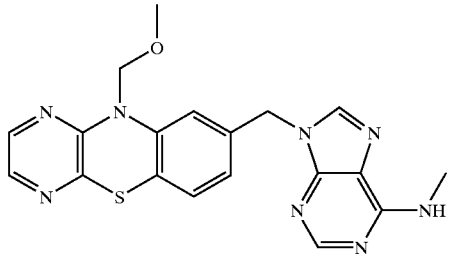<br>8-[6-(N-methylamino)purin-9-ylmethyl]-10-methoxymethyl-10H-pyrazino[2,3-b][1,4]benzothiazine | $^1$H-NMR (CDCl$_3$) δ ppm: 3.21(br.s, 3H), 3.43(s, 3H), 5.18(s, 2H), 5.29(s, 2H), 6.84(d, J=2, 8Hz, 1H), 6.97(d, J=8Hz, 1H), 7.08(s, 1H), 7.62(s, 1H), 7.82–7.84(m, 2H), 8.44(s, 1H) |

Examples

The following compounds were obtained by treating the compounds obtained in the above table by the same method as the one of Example 9.

| Ex. | Structural formula | MS | M.p. | NMR |
|---|---|---|---|---|
| 1398 | 8-[6-(morpholin-4-yl)purin-9-ylmethyl]-10H-pyrazino[2,3-b][1,4]benzothiazine | FAB (+) 419 (MH+) | | $^1$H-NMR (CDCl$_3$) δ ppm: 3.84(t, J=5Hz, 4H), 4.30(br.s, 4H), 5.20(s, 2H), 6.37(d, J=1, 1H), 6.40(br.s, 1H), 6.73(dd, J=1, 8Hz, 1H), 6.85(d, J=8Hz, 1H), 7.55(d, J=3Hz, 1H), 7.69(d, J=3Hz, 1H), 7.72(s, 1H), 8.38(s, 1H) |
| 1399 | 8-[6-(piperidin-1-yl)purin-9-ylmethyl]-10H-pyrazino[2,3-b][1,4]benzothiazine | FAB (+) 417 (MH+) | 228–229° C. | $^1$H-NMR (DMSO-d$_6$) δ ppm: 1.56(br.s, 4H), 1.65(br.s, 2H), 4.17(br.s, 4H), 5.20(s, 2H), 6.58(d, J=1Hz, 1H), 6.70(dd, J=1, 8Hz, 1H), 6.87(d, J=8Hz, 1H), 7.61(s, 2H), 8.19(s, 1H), 8.21(s, 1H), 9.45(s, 1H) |
| 1400 | 8-[6-(2,6-dimethylmorpholine-4-yl)purin-9-ylmethyl]-10H-pyrazino[2,3-b][1,4]benzothiazine | FAB (+) 447 (MH+) | 227–229° C. | $^1$H-NMR (CDCl$_3$) δ ppm: 1.29(d, J=7Hz, 6H), 2.80(m, 2H), 3.74(m, 2H), 5.20(s, 2H), 5.30(br.s, 2H), 6.36(d, J=8Hz, 1H), 6.39(s, 1H), 6.73(dd, J=1, 8Hz, 1H), 6.85(d, J=8Hz, 1H), 7.55(d, J=3Hz, 1H), 7.69(d, J=3Hz, 1H), 7.72(s, 1H), 8.36(s, 1H) |
| 1401 | 8-[6-(4-methylpiperazin-1-yl)purin-9-ylmethyl]-10H-pyrazino[2,3-b][1,4]benzothiazine | FAB (+) 432 (MH$^+$) | 197–202° C. | $^1$H-NMR (DNSO-d$_6$) δ ppm: 2.52(s, 3H), 2.80(br.s, 4H), 4.35(br.s, 4H), 5.23(s, 2H), 6.64(d, J=1Hz, 1H), 6.67(d, J=1, 8Hz, 1H), 6.87(d, J=8Hz, 1H), 7.62(s, 2H), 8.33(s, 1H), 8.37(s, 1H), 9.49(s, 1H) |
| 1402 | 1-[9-(10H-pyrazino[2,3-b][1,4]benzothiazin-8-ylmethyl)purin-6-yl]piperidin-4-ol | | | $^1$H-NMR (CDCl$_3$) δ ppm: 1.65(m, 2H), 2.05(m, 2H), 3.75(m,2H), 4.05(m, 2H), 4.85(m, 1H), 5.20(s, 2H), 6.38(d, J=1Hz, 1H), 6.47(s, 1H), 6.73(dd, J=1, 8Hz, 1H), 6.85(d, J=8Hz, 1H), 7.55(d, J=3Hz, 1H), 7.67(d, J=3Hz, 1H), 7.71(s, 1H), 8.36(s, 1H) |

-continued

| Ex. | Structural formula | MS | M.p. | NMR |
|---|---|---|---|---|
| 1403 | 1-[9-(10H-pyrazino[2,3-b][1,4]benzothiazin-8-ylmethyl)purin-6-yl]piperidine-4-carboxylic acid | FAB (+) 461 (MH$^+$) | 238–240° C. | $^1$H-NMR (DMSO-d$_6$) δ ppm: 1.53(t, J=10Hz, 2H), 1.93(d, J=10Hz, 2H), 2.60(m, 1H), 3.2(br.s, 4H), 5.20(s, 2H), 6.57(d, J=1Hz, 1H), 6.70(dd, J=1, 8Hz, 1H), 6.86(d, J=8Hz, 1H), 7.62(s, 2H), 8.22(s, 1H), 8.25(s, 1H), 9.45(s, 1H) |
| 1404 | 8-[6-(3,5-dimethylpiperidin-1-yl)purin-9-ylmethyl]-10H-pyrazino[2,3-b][1,4]benzothiazine | FAB (+) 445 (MH$^+$) | 237–238° C. | $^1$H-NMR (CDCl$_3$) δ ppm: 0.87 and 0.91(d, J=7Hz, total 6H), 1.5 and 1.6(m, total 2H), 1.8 and 1.9(m, total 2H), 3.2(m, 4H), 5.20(s, 2H), 6.58 and 6.61(d, J=1Hz, total 1H), 6.70(dd, J=1, 8Hz, 1H), 6.85(d, J=8Hz, 1H), 7.62(s, 2H), 8.17 and 8.20(s, total 1H), 8.20 and 8.22(s, total 1H), 9.47 and 9.48(s, total 1H) |
| 1405 | 8-[6-(4-benzylpiperidin-1-yl)purin-9-ylmethyl]-10H-pyrazino[2,3-b][1,4]benzothiazine | FAB (+) 507 (MH$^+$) | 186–188° C. | $^1$H-NMR (DMSO-d$_6$) δ ppm: 1.2(m, 4H), 1.65(m, 1H), 2.50(d, J=7Hz, 2H), 3.2(br.s, 4H), 5.20(s, 2H), 6.59(d, J=1Hz, 1H), 6.70(dd, J=1, 8Hz, 1H), 6.87(d, J=8Hz, 1H), 7.15–7.18(m, 3H), 7.27(dd, J=7, 8Hz, 2H), 7.62(s, 2H), 8.19(s, 1H), 8.21(s, 1H), 9.47(s, 1H) |
| 1406 | 8-[6-(4-benzylpiperazin-1-yl)purin-9-ylmethyl]-10H-pyrazino[2,3-b][1,4]benzothiazine | FAB (+) 508 (MH$^+$) | 213–214° C. | $^1$H-NMR (DMSO-d$_6$) δ ppm: 2.45(br.t, J=7Hz, 4H), 3.50(s, 2H), 4.20(br.s, 4H), 5.21(s, 2H), 6.56(d, J=1Hz, 1H), 6.69(dd, J=1, 7Hz, 1H), 6.86(d, J=7Hz, 1H), 7.25(m, 1H), 7.30–7.36(m, 4H), 7.61(s, 2H), 8.21(s, 1H), 8.23(s, 1H), 9.45(s, 1H) |
| 1407 | 8-[6-(4-phenylpiperidin-1-yl)purin-9-ylmethyl]-10H-pyrazino[2,3-b][1,4]benzothiazine | FAB (+) 493 (MH$^+$) | 239–241° C. | $^1$H-NMR (DMSO-d$_6$) δ ppm: 1.63(dq, J=4, 12Hz, 2H), 1.99(br.d, J=12Hz, 2H), 2.89(tt, J=2, 12Hz, 1H), 3.1(br.s, 2H), 3.3(br.s, 2H), 5.22(s, 2H), 6.60(d, J=1Hz, 1H), 6.72(dd, J=1, 8Hz, 1H), 6.87(d, J=8Hz, 1H), 7.16(tt, J=1, 7Hz, 1H), 7.22–7.29(m, 4H), 7.62(s, 2H), 8.23(s, 1H), 8.25(s, 1H), 9.47(s, 1H) |

| Ex. | Structural formula | MS | M.p. | NMR |
|---|---|---|---|---|
| 1408 | 8-[[4-(2-aminoethyl)piperazin-1-yl]purin-9-ylmethyl]-10H-pyrazino[2,3-b][1,4]benzothiazine | FAB (+) 461 (MH⁺) | 226–229° C. | ¹H-NMR (DMSO-d₆) δ ppm: 2.37(t, J=7Hz, 2H), 2.49(br.s, 4H), 2.72(t, J=7Hz, 2H), 4.2(br.s, 4H), 5.21(s, 2H), 6.60(d, J=1Hz, 1H), 6.69(dd, J=1, 8Hz, 1H), 6.87(d, J=8Hz, 1H), 7.62(s, 2H), 7.63(br.s, 2H), 8.23(s, 1H), 8.26(s, 1H), 9.47(s, 1H) |
| 1409 | 8-[6-(N-methylamino)purin-9-ylmethyl]-10H-pyrazino[2,3-b][1,4]benzothiazine | FAB (+) 363 (MH⁺) | 279–281° C. | ¹H-NMR (DMSO-d₆) δ ppm: 2.95(br.s, 3H), 5.20(s, 2H), 6.57(d, J=1Hz, 1H), 6.79(dd, J=1, 8Hz, 1H), 6.86(d, J=8Hz, 1H), 7.61(s, 2H), 7.63(br.s, 1H), 8.17(s, 1H), 8.21(br.s, 1H), 9.47(s, 1H) |

Examples

The following compounds were obtained by reacting 8-(6-chloropurin-7-ylmethyl)-10-methoxymethyl-10H-pyrazino[2,3-b][1,4]benzothiazine with various amines by the same method as the one of Example 1244.

| Ex. | Structural formula | NMR |
|---|---|---|
| 1410 | 8-[6-(morpholine-4-yl)purin-7-ylmethyl)-10-methoxymethyl-10H-pyrazino[2,3-b][1,4]benzothiazine | ¹H-NMR (CDCl₃) δ ppm: 3.39(s, 3H), 3.40(t, J=5Hz, 4H), 3.85(t, J=5Hz, 4H), 5.13(s, 2H), 5.41(s, 2H), 6.69(dd, J=2, 8Hz, 1H), 6.82(d, J=2Hz, 1H), 6.97(d, J=8Hz, 1H), 7.82(d, J=3Hz, 1H), 7.85(d, J=3Hz, 1H), 8.09(s, 1H), 8.75(s, 1H) |
| 1411 | 8-[6-(N-methylamino)purin-7-ylmethyl)-10-methoxymethyl-10H-pyrazino[2,3-b][1,4]benzothiazine | ¹H-NMR (CDCl₃) δ ppm: 2.98(d, J=5Hz, 3H), 3.34(s, 3H), 4.61(q, J=5Hz, 1H), 5.12(s, 2H), 5.40(s, 2H), 6.72(dd, J=2, 8Hz, 1H), 6.83(d, J=2Hz, 1H), 7.05(d, J=8Hz, 1H), 7.85(d, J=3Hz, 1H), 7.88(d, J=3Hz, 1H), 7.97(s, 1H), 8.56(s, 1H) |

Examples

The following compounds were obtained by treating the compounds obtained in the above table by the same method as the one of Example 9.

| Ex. | Structural formula | MS | M.p. | NMR |
|---|---|---|---|---|
| 1412 | 8-[6-(morpholin-4-yl)purin-7-ylmethyl]-10H-pyrazino[2,3-b][1,4]benzothiazine | FAB (+) 419 (MH$^+$) | 269–273° C. | $^1$H-NMR (CDCl$_3$) δ ppm: 3.40(t, J=4Hz, 4H), 3.82(t, J=4Hz, 4H), 5.35(s, 2H), 6.27(d, J=1Hz, 1H), 6.62(dd, J=1, 8Hz, 1H), 6.86(d, J=8Hz, 1H), 7.23(s, 1H), 7.56(d, J=3Hz, 1H), 7.68(d, J=3Hz, 1H), 8.01(s, 1H), 8.71(s, 1H) |
| 1413 | 8-[6-(N-methylamino)purin-7-ylmethyl]-10H-pyrazino[2,3-b][1,4]benzothiazine | FAB (+) 363 (MH$^+$) | | $^1$H-NMR (DMSO-d$_6$) δ ppm: 2.89(d, J=4Hz, 3H), 5.54(s, 2H), 6.38(s, 1H), 6.55(d, J=8Hz, 1H), 6.72(q, J=4Hz, 1H), 6.86(d, J=8Hz, 1H), 7.60(s, 2H), 8.28(s, 1H), 8.29(s, 1H), 9.50(s, 1H) |

Example 1414

8-(6-Dimethylamino-2-chloropurin-9-yl)-10-methoxymethyl-10H-pyrazino[2,3-b][1,4]benzothiazine 1.1 g of the title compound was obtained as a yellow solid by reacting 0.81 g of 8-chloromethyl-10-methoxymethyl-10H-pyrazino2,3-b][1,4]benzothiazine with 6-dimethylamino-2-chloropurine by the same method as the one of Example 1348.

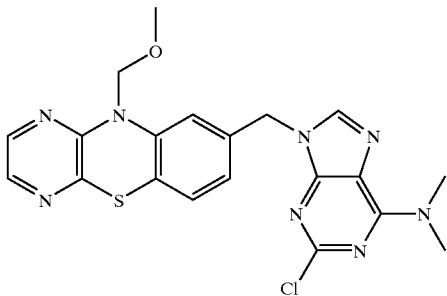

$^1$H-NMR(CDCl$_3$) δ ppm: 3.22–3.35(br.s, 3H), 3.48(s, 3H), 3.71(br.s, 3H), 5.20(s, 2H), 5.23(s, 2H), 6.83(dd, J=2, 8 Hz, 1H), 6.97(d, J=8 Hz, 1H), 7.11(d, J=2 Hz, 1H), 7.65(s, 1H), 7.83(d, J=3 Hz, 1H), 7.84(d, J=3 Hz, 1H)

Example 1415

8-[2,6-Bis(dimethylamino)purin-9-ylmethyl]-10-methoxymethyl-10H-pyrazino[2,3-b][1,4]benzothiazine To a solution of 0.27 g of 8-(6-dimethylamino-2-chloropurin-9-yl)-10-methoxymethyl-10H-pyrazino[2,3-b][1,4]benzothiazine in tetrahydrofuran (10 ml) was added a 50% solution of dimethylamine in methanol. Then the resulting mixture was heated to 110° C. for 50 hours in a sealed tube. After distilling off the solvent under reduced pressure, the residue was purified by silica gel column chromatography (eluted with dichloromethane/methanol) to thereby give 0.23 g of the title compound as a yellow solid.

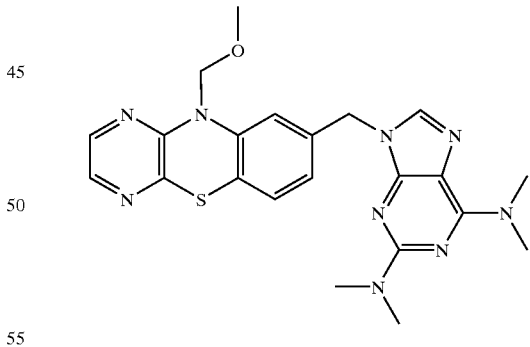

$^1$H-NMR(CDCl$_3$) δ ppm: 3.16(s, 6H), 3.42(s, 3H), 3.46 (br.s, 6H), 5.14(s, 2H), 5.17(s, 2H), 6.87(dd, J=2, 8 Hz, 1H), 6.94(d, J=8 Hz, 1H), 7.06(d, J=2 Hz, 1H), 7.42(s, 1H), 7.82(d, J=3 Hz, 1H), 7.83(d, J=3 Hz, 1H)

Example 1416

8-[2,6-Bis(dimethylamino)purin-9-ylmethyl]-10H-pyrazino[2,3-b[]1,4]benzothiazine The title compound was obtained by treating 8-[2,6-bis(dimethylamino)purin-9-ylmethyl]-10-methoxymethyl- 10H-pyrazino[2,3-b][1,4]benzothiazine by the same method as the one of Example 9.

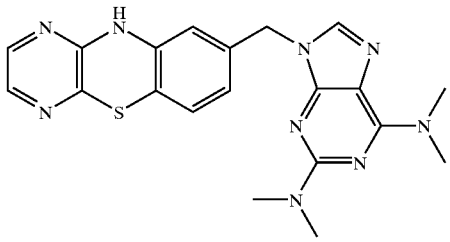

¹H-NMR(DMSO-d₆) δ ppm: 3.07(s, 6H), 3.60(br.s, 6H), 5.03(s, 2H), 6.62(d, J=1 Hz, 1H), 6.71(dd, J=1, 8 Hz, 1H), 6.85(d, J=8 Hz, 1H), 7.61(s, 2H), 7.77(s, 1H), 9.50(s, 1H)
MS: FAB(+)419(M⁺)
m.p.: 239–240° C.

Example 1417

8-[6-(Trimethylsilyl)ethynylpurin-9-ylmethyl]-10-methoxymethyl-10H-pyrazino[2,3-b][1,4]benzothiazine To a solution of 2.05 g of 8-(6-bromopurin-9-ylmethyl)-10-methoxymethyl-10H-pyrazino[2,3-b][1,4]benzothiazine in N,N-dimethylformamide (20 ml) were added in a nitrogen atmosphere 0.32 g of bis(triphenylphosphine) palladium (II) chloride, 0.10 g of cuprous iodide, 1.23 ml of (tirmethylsilyl)acetylene and 0.97 ml of triethylamine and the resulting mixture was stirred for 16 hours. After further adding bis(triphenylphosphine) palladium (II) chloride, cuprous iodide, (tirmethylsilyl)acetylene and triethylamine each in the same amount as the one defined above, the resulting mixture was stirred at room temperature for 24 hours and heated to 55° C. for 6 hours. Then the reaction mixture was distributed into ethyl acetate and water and filtered through celite. The organic layer was washed with aqueous ammonia several times, dried over anhydrous magnesium sulfate and concentrated under reduced pressure. Then the residue was purified by silica gel column chromatography (eluted with n-hexane/ethyl acetate) to thereby give 1.22 g of the title compound as a yellow solid.

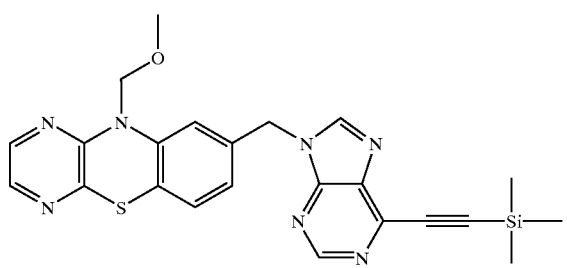

¹H-NMR(CDCl₃) δ ppm: 0.33(s, 9H), 3.44(s, 3H), 5.17(s, 2H), 5.45(s, 2H), 6.84(dd, J=2, 8 Hz, 1H), 6.98(d, J=8 Hz, 1H), 7.10(d, J=2 Hz, 1H), 7.83(d, J=3 Hz, 1H), 7.85(d, J=3 Hz, 1H), 8.12(s, 1H), 8.95(s, 1H)

Example 1418

8-(6-Ethynylpurin-9-ylmethyl)-10-methoxymethyl-10H-pyrazino[2,3-b][1,4]benzothiazine To a solution of 0.194 g of 8-[6-(tirmehtylsilyl)-ethynylpurin-9-ylmethyl]-10-methoxymethyl-10H-pyrazino[2,3-b][1,4]benzothiazine in tetrahydrofuran (15 ml) was added in a nitrogen atmosphere 0.8 ml of a 1 M solution of tetra-n-butylammonium fluoride in tetrahydrofuran and the resulting mixture was stirred for 16 hours. After adding ethyl acetate and water, the organic layer was dried over anhydrous magnesium sulfate and concentrated under reduced pressure. The residue was then purified by silica gel column chromatography (eluted with n-hexane/ethyl acetate) to thereby give 0.076 g of the title compound as a yellow solid.

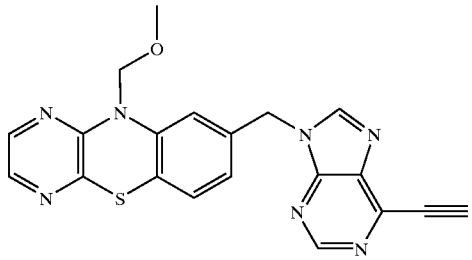

¹H-NMR(CDCl₃) δ ppm: 3.44(s, 3H), 3.72(s, 1H), 5.19(s, 2H), 5.38(s, 2H), 6.88(dd, J=2, 8 Hz, 1H), 6.99(d, J=8 Hz, 1H), 7.12(d, J=2 Hz, 1H), 7.83(d, J=3 Hz, 1H), 7.85(d, J=3 Hz, 1H), 8.14(s, 1H), 8.99(s, 1H)

Example 1419

8-(6-Ethylpurin-9-ylmethyl)-10-methoxymethyl-10H-pyrazino[2,3-b][1,4]benzothiazine 0.070 g of the title compound was obtained as a yellow solid by treating 0.076 g of 8-(6-ethynylpurin-9-ylmethyl)-10-methoxymethyl-10H-pyrazino[2,3-b][1,4]benzothiazine by the same method as the one of Example 20.

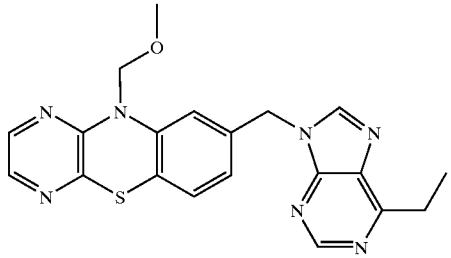

¹H-NMR(CDCl₃) δ ppm: 1.44(t, J=7 Hz, 3H), 3.23(q, J=7 Hz, 2H), 3.43(s, 3H), 5.19(s, 2H), 5.37(s, 2H), 6.88(d, J=8 Hz, 1H), 6.97(d, J=8 Hz, 1H), 7.12(s, 1H), 7.83(m, 2H), 8.09(s, 1H), 8.94(s, 1H)

Example 1420

3-[9-(10-Methoxymethyl-10H-pyrazino[2,3-b][1,4]benzothiazin-8-ylmethyl)purin-6-yl]-2-propyn-1-ol The title compound was obtained by reacting 8-(6-bromopurin-9-ylmethyl)-10-methoxymethyl-10H-pyrazino[2,3-b][1,4]benzothiazine with propargyl alcohol by the same method as the one of Example 1417.

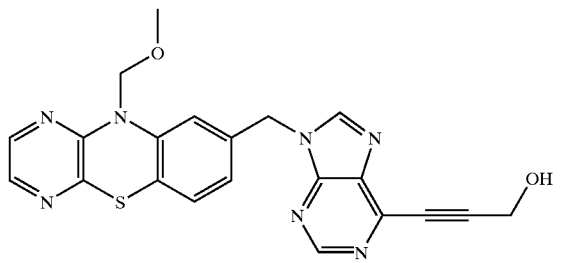

¹H-NMR(CDCl₃) δ ppm: 3.44(s, 3H), 4.63(s, 2H), 5.19(s, 2H), 5.38(s, 2H), 6.86(dd, J=2, 8 Hz, 1H), 6.98(d, J=8 Hz, 1H), 7.12(d, J=2 Hz, 1H), 7.84(m, 2H), 8.14(s, 1H), 8.97(s, 1H)

Example 1421

3-[9-(10-Methoxymethyl-10H-pyrazino[2,3-b][1,4]benzothiazin-8-ylmethyl)purin-6-yl]-1-propanol 0.028 g of the title compound was obtained as yellow crystals by treating 0.088 g of 3-[9-(10-methoxymethyl-10H-pyrazino[2,3-b][1,4]benzothiazin-8-ylmethyl)purin-6-yl]-2-propyn-1-ol by the same method as the one of Example 20.

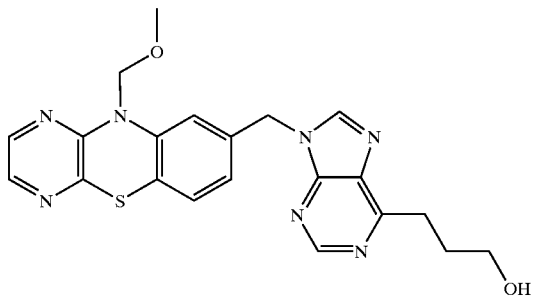

¹H-NMR(CDCl₃) δ ppm: 2.11(quint, J=7 Hz, 2H), 3.38(d, J=7 Hz, 2H), 3.44(s, 3H), 3.65(t, J=7 Hz, 2H), 5.19(s, 2H), 5.37(s, 2H), 6.89(dd, J=2, 8 Hz, 1H), 6.98(d, J=8 Hz, 1H), 7.03(d, J=2 Hz, 1H), 7.83(d, J=3 Hz, 1H), 7.84(d, J=3 Hz, 1H), 8.05(s, 1H), 8.91(s, 1H)

Examples

The following compounds were obtained by treating 8-(6-ethylpurin-9-ylmethyl)-10-methoxymethyl-10H-pyrazino[2,3-b][1,4]benzothiazine, 3-[9-(10-methoxymethyl-10H-pyrazino[2,3-b][1,4]benzothiazin-8-ylmethyl)purin-6-yl]-1-propanol and 3-[9-(10-methoxymethyl-10H-pyrazino[2,3-b][1,4]benzothiazin-8-ylmethyl)purin-6-yl]-2-propyn-1-ol by the same method as the one of Example 9.

| Ex. | Structural formula | MS | M.p. | NMR |
|---|---|---|---|---|
| 1422 | 8-(6-ethylpurin-9-ylmethyl)-10H-pyrazino[2,3-b][1,4]benzothiazine | FAB (+) 361 (M⁺) | 215–217° C. | ¹H-NMR (CDCl₃) δ ppm: 1.45(t, J=7Hz, 3H), 3.22(q, J=7Hz, 2H), 5.26(s, 2H), 6.43(d, J=1Hz, 1H), 6.68(br.s, 1H), 6.77(dd, J=1, 8Hz, 1H), 6.87(d, J=8Hz, 1H), 7.54(d, J=3Hz, 1H), 7.69(d, J=3Hz, 1H), 8.01(s, 1H), 8.90(s, 1H) |
| 1423 | 3-[9-(10H-pyrazino[2,3-b][1,4]benzothiazin-8-ylmethyl)purin-6-yl]-1-propanol | FAB (+) 392 (MH⁺) | 174–177° C. | ¹H-NMR (DMSO-d₆) δ ppm: 1.95(quint, J=7Hz, 2H), 3.10(t, J=7Hz, 2H), 3.47(q, J=7Hz, 2H), 4.55(t, J=7Hz, 1H), 5.21(s, 2H), 6.60(d, J=1Hz, 1H), 6.75(dd, J=1, 9Hz, 1H), 6.87(d, J=9Hz, 1H), 7.61(s, 2H), 8.57(s, 1H), 8.78(s, 1H), 9.45(s, 1H) |
| 1424 | 3-[9-(10H-pyrazino[2,3-b][1,4]benzothiazin-8-ylmethyl)purin-6-yl]-2-propyn-1-ol | | 152–154° C. (decompose) | ¹H-NMR (DMSO-d₆) δ ppm: 4.46(d, J=6Hz, 2H), 5.34(s, 2H), 5.61(t, J=6Hz, 1H), 6.54(s, 1H), 6.76(d, J=8Hz, 1H), 6.88(d, J=8Hz, 1H), 7.61(s, 2H), 8.72(s, 1H), 8.87(s, 1H), 9.42(s, 1H) |

Example 1425

8-(6-Iodopurin-9-ylmethyl)-10-methoxymethyl-10H-pyrazino[2,3-b][1,4]benzothiazine The title compound was obtained by treating 8-chloromethyl-10-methoxymethyl-10H-pyrazino[2,3-b][1,4]benzothiazine with 6-iodopurine by the same method as the one of Example 1094.

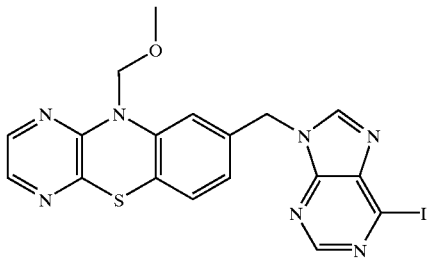

$^1$H-NMR(CDCl$_3$) δ ppm: 3.46(s, 3H), 5.20(s, 2H), 5.36(s, 2H), 6.88(dd, J=2, 8 Hz, 1H), 6.99(d, J=8 Hz, 1H), 7.12(d, J=2 Hz, 1H), 7.84(d, J=3 Hz, 1H), 7.86(d, J=3 Hz, 1H), 8.14(s, 1H), 8.68(s, 1H)

Example 1426

4-[9-(10H-Pyrazino[2,3-b][1,4]benzothiazin-8-ylmethyl)purin-6-yl]-2-methyl-3-butyn-2-ol 8-(6-Iodopurin-9-ylmethyl)-10-methoxymethyl-10H-pyrazino[2,3-b][1,4]benzothiazine was treated by the same method as the one of Example 9 to thereby give 8-(6-iodopurin-9-ylmethyl)-10H-pyrazino[2,3-b][1,4]benzothiazine. Next, this product was treated with 2-methyl-3-butyn-2-ol by the same method as the one of Example 1417 to thereby give the title compound.

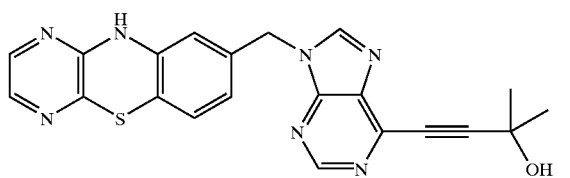

$^1$H-NMR(DMSO-d$_6$) δ ppm: 1.52(s, 6H), 5.32(s, 2H), 5.78(s, 1H), 6.51(d, J=1Hz, 1H), 6.73(dd, J=1, 8 Hz, 1H), 6.87(d, J=8 Hz, 1H), 7.60(s, 2H), 8.71(s, 1H), 8.85(s, 1H), 9.40(s, 1H)

Example 1427

4-[[9-(10H-Pyrazino[2,3-b][1,4]benzothiazin-8-ylmethyl)purin-6-yl]-2-hydroxymethyl-3-butyne-1,2-diol 8-(6-Iodopurin-9-ylmethyl)-10-methoxymethyl-10H-pyrazino[2,3-b][1,4]benzothiazine was treated by the same method as the one of Example 9 to thereby give 8-(6-iodopurin-9-ylmethyl)-10H-pyrazino[2,3-b][1,4]benzothiazine. Next, this product was treated with bis(tert-butyldimethylsiloxymethyl)-2-propyn-1-ol by the same method as the one of Example 1417. The compound thus obtained was further treated with tetrabutylammonium fluoride in accordance with the method of Example 1386-3 to thereby give the title compound.

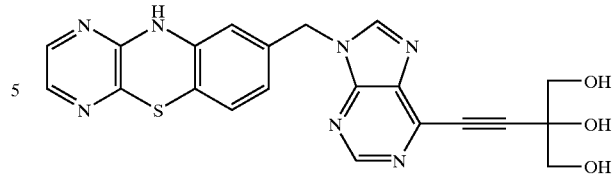

$^1$H-NMR(DMSO-d$_6$) δ ppm: 3.53–3.61(m, 4H), 4.94(t, J=6 Hz, 2H), 5.34(s, 2H), 5.62(s, 1H), 6.51(s, 1H), 6.73(d, J=8 Hz, 1H), 6.87(d, J=8 Hz, 1H), 7.61(s, 2H), 8.70(s, 1H), 8.85(s, 1H), 9.40(s, 1H)

m.p.: 79–84° C.

Example 1428

10-Methoxymethyl-8-(6-ethylpurin-7-ylmethyl)-10H-pyrazino[2,3-b][1,4]benzothiazine To a solution of 0.30 g of 8-(6-chloropurin-7-ylmethyl)-10-methoxymethyl-10H-pyrazino[2,3-b][1,4]benzothiazine in N,N-dimethylformamide (10 ml) were added in a nitrogen atmosphere 0.312 g of vinyl-tri-n-butyltin (IV) and 0.050 g of bis(triphenylphosphine) palladium (II) chloride. After degassing, the mixture was heated to 80° C. for 20 hours. Then the insoluble matters were removed by filtering through celite. After distilling off the solvent under reduced pressure, the residue was purified by silica gel column chromatography (eluted with dichloromethane/methanol) to thereby give 0.19 g of 10-methoxymethyl-8-(6-vinylpurin-7-ylmethyl)-10H-pyrazino[2,3-b][1,4]benzothiazine as a yellow solid. To a solution of 190 mg of the obtained compound in methanol (20 ml) was added 0.018 g of palladium/carbon and hydrogenation was effected in a hydrogengas stream for 2 hours. Thus, 0.10 g of the title compound was obtained as a yellow solid.

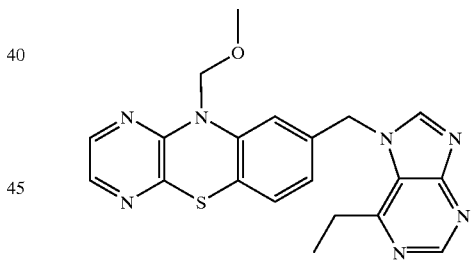

$^1$H-NMR(CDCl$_3$) δ ppm: 1.28(t, J=7 Hz, 3H), 2.97(q, J=7 Hz, 2H), 3.31(s, 3H), 5.08(s, 2H), 5.50(s, 2H), 6.62(dd, J=2, 8 Hz, 1H), 6.74(d, J=2 Hz, 1H), 6.99(d, J=8 Hz, 1H), 7.83(d, J=3 Hz, 1H), 7.86(d, J=3 Hz, 1H), 8.20(s, 1H), 9.05(s, 1H)

Example 1429

8-[6-(1-Ethoxyvinyl)purin-7-ylmethyl]-10-methoxymethyl-10H-pyrazino[2,3-b][1,4]benzothiazine To a solution of 0.9 g of 8-(6-chloropurin-7-ylmethyl)-10-methoxymethyl-10H-pyrazino[2,3-b][1,4]benzothiazine in N,N-dimethylformamide (15 ml) were added in a nitrogen atmosphere 1.03 g of 1-ethoxyvinyl-tri-n-butyltin (IV) and 0.015 g of bis(triphenylphosphine) palladium (II) chloride. After degassing, the mixture was heated to 80° C. for 20 hours. Then the insoluble matters were removed by filtering through celite. After distilling off the solvent under reduced pressure, the residue was purified by silica gel column chromatography (eluted with dichloromethane/methanol) to thereby give 0.77 g of the title compound as yellow crystals.

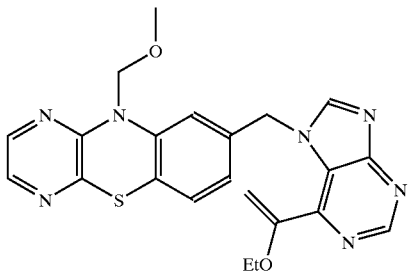

$^1$H-NMR(CDCl$_3$) δ ppm: 1.34(t, J=7 Hz, 3H), 3.32(s, 3H), 3.93(q, J=7 Hz, 2H), 4.54(d, J=3 Hz, 1H), 4.94(d, J=3 Hz, 1H), 5.09(s, 2H), 5.54(s, 2H), 6.60(dd, J=2, 8 Hz, 1H), 6.77(d, J=2 Hz, 1H), 6.94(d, J=8 Hz, 1H), 7.82(d, J=3 Hz, 1H), 7.85(d, J=3 Hz, 1H), 8.23(s, 1H), 9.09(s, 1H)

Example 1430

8-(6-(Ethylpurin-7-ylmethyl)-10H-pyrazino[2,3-b][1,4]benzothiazine

The title compound was obtained by treating 10-methoxymethyl-8-(6-ethylpurin-7-ylmethyl)-10H-pyrazino[2,3-b][1,4]benzothiazine by the same method as the one of Example 9.

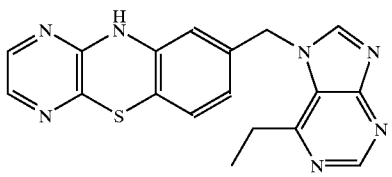

$^1$H-NMR(CDCl$_3$) δ ppm: 1.45(t, J=7 Hz, 3H), 3.24(q, J=7 Hz, 2H), 5.26(s, 2H), 6.44(s, 1H), 6.62(br.s, 1H), 6.75(d, J=8 Hz, 1H), 6.87(d, J=8 Hz, 1H), 7.55(s, 1H), 7.69(s, 1H), 8.02(s, 1H), 8.90(s, 1H)
MS: FAB(+)362(MH$^+$)
M.P.: >275° C.

Example 1431

8-(6-Acetylpurin-7-ylmethyl)-10H-pyrazino[2,3-b][1,4]benzothiazine

The title compound was obtained by treating 8-[6-(1-ethoxyvinyl)purin-7-ylmethyl]-10H-pyrazino[2,3-b][1,4]benzothiazine by the same method as the one of Example 8.

$^1$H-NMR(DMSO-d$_6$) δ ppm: 2.59(s, 3H), 5.58(s, 2H), 6.25(s, 1H), 6.47(d, J=8 Hz, 1H), 6.84(d, J=8 Hz, 1H), 7.59(d, J=3 Hz, 1H), 7.60(d, J=3 Hz, 1H), 8.98(s, 1H), 9.15(s, 1H), 9.34(s, 1H)
MS: FAB(+)375(M$^+$)
m.p.: 266–268° C.

Example 1432

8-(6-Acetylpurin-7-ylmethyl)-10-methoxymethyl-10H-pyrazino[2,3-b][1,4]benzothiazine 0.21 g of the title compound was obtained as yellow crystals by treating 0.316 g of 8-(6-acetylpurin-7-ylmethyl)-10H-pyrazino[2,3-b][1,4]benzothiazine by the same method as the one of Example 5.

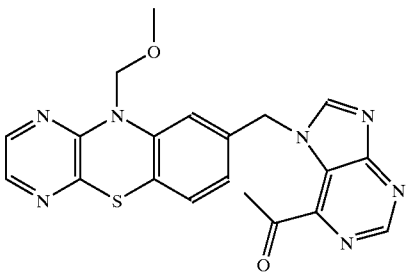

$^1$H-NMR(CDCl$_3$) δ ppm: 2.71(s, 3H), 3.36(s, 3H), 5.09(s, 2H), 5.72(s., 2H), 6.62(dd, J=2, 8 Hz, 1H), 6.92(d, J=2 Hz, 1H), 6.94(d, J=8 Hz, 1H), 7.81(d, J=3 Hz, 1H), 7.84(d, J=3 Hz, 1H), 8.40(s, 1H), 9.21(s, 1H)

Example 1433

1-[7-(10-Methoxymethyl-10H-pyrazino[2,3-b][1,4]benzothiazin-8-ylmethyl)purin-6-yl]ethanol 0.08 g of the title compound was obtained as yellow crystals by treating 0.13 g of 8-(6-acetylpurin-7-ylmethyl)-10-methoxymethyl-10H-pyrazino[2,3-b][1,4]benzothiazine with diisobutylaluminum hydride by the same method as the one of Example 6.

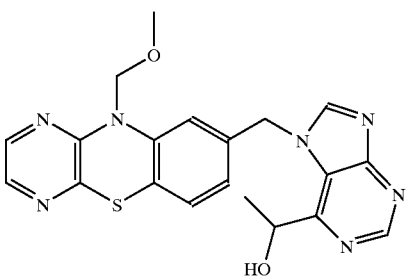

$^1$H-NMR(CDCl$_3$) δ ppm: 1.46(d, J=7 Hz, 3H), 1.93(br.s, 1H), 3.32(s, 3H), 5.07–5.14(m, 3H), 5.50(d, J=15 Hz, 1H), 5.64(d, J=15 Hz, 1H), 6.62(dd, J=2, 8 Hz, 1H), 6.77(d, J=2 Hz, 1H), 6.97(d, J=8 Hz, 1H), 7.81(d, J=3 Hz, 1H), 7.84(d, J=3 Hz, 1H), 8.21(s, 1H), 9.03(s, 1H)

Example 1434

2-[7-(10-Methoxymethyl-10H-pyrazino[2,3-b][1,4]benzothiazin-8-ylmethyl)purin-6-yl]-2-propanol 0.148 g of the title compound was obtained as yellow crystals by treating 0.21 g of 8-(6-acetylpurin-7-ylmethyl)-10-methoxymethyl-10H-pyrazino[2,3-b][1,4]benzothiazine with methylmagnesium bromide by the same method as the one of Production Example 86.

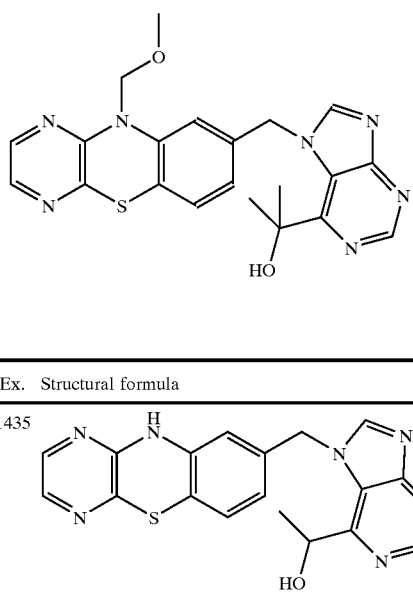

¹H-NMR(CDCl₃) δ ppm: 1.66(s, 6H), 2.64(br.s, 1H), 3.30(s, 3H), 5.07(s, 2H), 5.90(s, 2H), 6.60(d, J=8 Hz, 1H), 6.65(s, 1H), 6.96(d, J=8 Hz, 1H), 7.81–7.84(m, 2H), 8.18(s, 1H), 9.01(s, 1H)

Examples

The following compounds were obtained by treating 1-[7-(10-methoxymethyl-10H-pyrazino[2,3-b][1,4]benzothiazin-8-ylmethyl)purin-6-yl]ethanol and 2-[7-(10-methoxymethyl-10H-pyrazino[2,3-b](1,4]benzothiazin-8-ylmethyl)purin-6-yl]-2-propanol by the same method as the one of Example 9.

| Ex. | Structural formula | MS | M.p. | NMR |
|---|---|---|---|---|
| 1435 | 1-[7-(10H-pyrazino[2,3-b][1,4]benzothiazin-8-ylmethyl)purin-6-yl]ethanol | FAB (+) 377 (M⁺) | 205–208° C. | ¹H-NMR (DMSO-d₆) δ ppm: 1.37(d, J=6Hz, 3H), 4.89(quint, J=6Hz, 1H), 5.70(s, 2H), 5.78(d, J=6Hz, 1H), 6.30(d, J=1Hz, 1H), 6.52(dd, J=1, 9Hz, 1H), 6.68(d, J=9Hz, 1H), 7.60(s, 2H), 8.73(s, 1H), 8.90(s, 1H), 9.35(s, 1H) |
| 1436 | 2-[7-(10H-pyrazino[2,3-b][1,4]benzothiazin-8-ylmethyl)purin-6-yl]-2-propanol | FAB (+) 391 (M⁺) | 268–271° C. | ¹H-NMR (DMSO-d₆) δ ppm: 1.42(s, 6H), 5.90(s, 1H), 5.96(s, 2H), 6.25(d, J=1Hz, 1H), 6.39(dd, J=1, 8Hz, 1H), 6.85(d, J=8Hz, 1H), 7.61(s, 2H), 8.67(s, 1H), 8.85(s, 1H), 9.38(s, 1H) |

Examples

The following compounds were obtained by reacting 8-chloromethyl-10-methoxymethyl-10H-pyrazino[2,3-b][1,4]benzoxazine and 8-chloromethyl-10-methoxymethyl-10H-pyrazino[2,3-b][1,4]benzothiazine with 2-(purin-6-yl)-2-propanol by the same method as the one of Example 1094.

| Ex. | Structural formula | NMR |
|---|---|---|
| 1437 | 2-[9-(10-methoxymethyl-10H-pyrazino[2,3-b][1,4]benzothiazin-8-ylmethyl)purin-6-yl]-2-propanol | ¹H-NMR (CDCl₃) δ ppm: 1.75(s, 6H), 3.40(s, 3H), 5.16(s, 2H), 5.36(s, 2H), 6.88(dd, J=2, 8Hz, 1H), 6.96(d, J=8Hz, 1H), 7.10(d, J=2Hz, 1H), 7.80(d, J=3Hz, 1H), 7.81(d, J=3Hz, 1H), 8.07(s, 1H), 8.91(s, 1H) |

| Ex. | Structural formula | NMR |
|---|---|---|
| 1438 | 2-[9-(10-methoxymethyl-10H-pyrazino[2,3-b][1,4]benzoxazin-8-ylmethyl)purin-6-yl]-2-propanol | $^1$H-NMR (CDCl$_3$) δ ppm: 1.78(s, 6H), 3.42(s, 3H), 5.26(s, 2H), 5.34(s, 2H), 5.42(br.s, 1H), 6.79(d, J=8Hz, 1H), 6.81(d, J=8Hz, 1H), 6.97(s, 1H), 7.44(d, J=3Hz, 1H), 7.59(d, J=3Hz, 1H), 8.08(s, 1H), 8.94(s, 1H) |

Examples

The following compounds were obtained by treating the compounds in the above table by the same method as the one of Example 9.

| Ex. | Structural formula | MS | M.p. | NMR |
|---|---|---|---|---|
| 1439 | 2-[9-(10H-pyrazino[2,3-b][1,4]benzothiazin-8-ylmethyl)purin-6-yl]-2-propanol | ESI (+) 392 (MH$^+$) | 178–179° C. | $^1$H-NMR (CDCl$_3$) δ ppm: 1.79(s, 6H), 5.31(s, 2H), 6.47(d, J=2Hz, 1H), 6.59(br.s, 1H), 6.79(dd, J=2, 8Hz, 1H), 6.88(d, J=8Hz, 1H), 7.56(d, J=3Hz, 1H), 7.70(d, J=3Hz, 1H), 8.07(s, 1H), 8.95(s, 1H) |
| 1440 | 2-[9-(10H-pyrazino[2,3-b][1,4]benzoxazin-8-ylmethyl)purin-6-yl]-2-propanol | ESI (+) 376 (MH$^+$) | 143–145° C. | $^1$H-NMR (CDCl$_3$) δ ppm: 1.79(s, 6H), 5.29(s, 2H), 6.52(s, 1H), 6.76(d, J=8Hz, 1H), 6.80(d, J=8Hz, 1H), 7.38(d, J=3Hz, 1H), 7.44(d, J=3Hz, 1H), 8.10(s, 1H), 8.96(s, 1H) |

Examples

The following compounds were obtained by reacting 8-chloromethyl-10-methoxymethyl-10H-pyrazino[2,3-b][1,4]benzothiazine with 2-(benzimidazol-5-yl)-2-propanol by the same method as the one of Example 1094 followed by the same treatment as the one of Example 9.

| Ex. | Structural formula | MS | M.p. | NMR |
|---|---|---|---|---|
| 1441 | 2-[1-(10H-pyrazino[2,3-b][1,4]benzothiazin-8-ylmethyl)benzimidazol-5-yl]-2-propanol | | | $^1$H-NMR (DMSO-d$_6$) δ ppm: 1.43(s, 6H), 5.00(s, 1H), 5.32(s, 2H), 6.59(d, J=1Hz, 1H), 6.67(dd, J=1, 8Hz, 1H), 6.88(d, J=8Hz, 1H), 7.29(d, J=8Hz, 1H), 7.53(s, 1H), 7.55(d, J=8Hz, 1H), 7.61(s, 2H), 8.27(s, 1H), 9.50(s, 1H) |
| 1442 | 2-[1-(10H-pyrazino[2,3-b][1,4]benzothiazin-8-ylmethyl)benzimidazol-6-yl]-2-propanol | | | $^1$H-NMR (DMSO-d$_6$) δ ppm: 1.44(s, 6H), 4.97(s, 1H), 5.29(s, 2H), 6.60(s, 1H), 6.69(d, J=8Hz, 1H), 6.87(d, J=8Hz, 1H), 7.30–7.33(m, 2H), 7.60(s, 2H), 7.71(s, 1H), 8.27(s, 1H), 9.46(s, 1H) |

Example 1443

8-[6-(1-Ethoxyvinyl)purin-9-ylmethyl]-10-methoxymethyl-10H-pyrazino[2,3-b][1,4]benzothiazine 1.0 g of the title compound was obtained as a yellow solid by treating 1.33 g of 8-(6-chloropurin-7-ylmethyl)-10-methoxymethyl-10H-pyrazino[2,3-b][1,4]benzothiazine by the same method as the one of Example 1429.

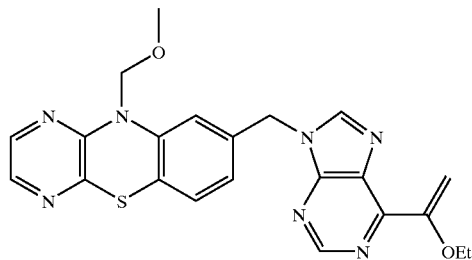

$^1$H-NMR(CDCl$_3$) δ ppm: 1.52(t, J=7 Hz, 3H), 3.43(s, 3H), 4.12(q, J=7 Hz, 2H), 4.98(d, J=4 Hz, 1H), 5.18(s, 2H), 5.39(s, 2H), 6.15(d, J=4 Hz, 1H), 6.87(d, J=8 Hz, 1H), 6.98(d, J=8 Hz, 1H), 7.12(s, 1H), 7.83(d, J=3 Hz, 1H), 7.84(d, J=3 Hz, 1H), 8.09(s, 1H), 9.10(s, 1H)

Example 1444

8-(6-Acetylpurin-9-ylmethyl)-10-methoxymethyl-10H-pyrazino-[2,3-b][1,4]benzothiazine 0.2 g of the title compound was obtained as a yellow solid by treating 0.66 g of 8-[6-(1-ethoxyvinyl)purin-9-ylmethyl]-10-methoxymethyl-10H-pyrazino[2,3-b][1,4]benzothiazine by the same method as the one of Example 8.

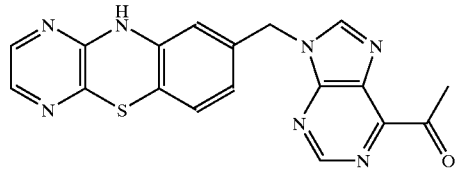

H-NMR(DMSO-d$_6$) δ ppm: 2.79(s, 3H), 5.39(s, 2H), 6.57(d, J=1 Hz, 1H), 6.75(dd, J=1, 8 Hz, 1H), 6.88(d, J=8 Hz, 1H), 7.61(s, 2H), 8.86(s, 1H), 9.07(s, 1H), 9.43(s, 1H)

MS: FAB(+)376(MH$^+$)

Example 1445

8-[6-[1-(tert-Butyldimethylsiloxy)ethyl]purin-9-ylmethyl]-10-methoxymethyl-10H-pyrazino[2,3-b](1,4]benzothiazine 1.63 g of the title compound was obtained as a yellow solid by reacting 1.78 g of 8-chloromethyl-10-methoxymethyl-10H-pyrazino 2,3-b][]1,4]benzothiazine with 1.26 g of 6-[1-(tert-butyldimethylsiloxy)ethyl]purine by the same method as the one of Example 1094.

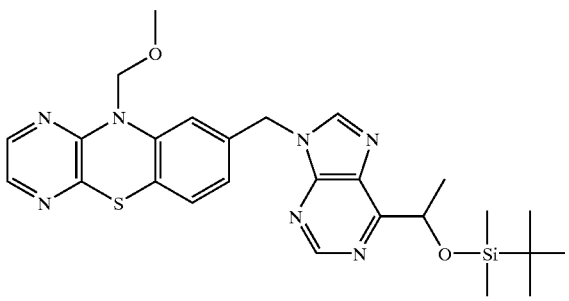

¹H-NMR(CDCl₃) δ ppm: 0.01(s, 3H), 0.04(s, 3H), 0.86(s, 9H), 1.64(d, J=7 Hz, 3H), 3.41(s, 3H), 5.17(s, 2H), 5.34(d, J=15 Hz, 1H), 5.38(d, J=15 Hz, 1H), 5.60(q, J=7 Hz, 1H), 6.89(dd, J=2, 8 Hz, 1H), 6.99(d, J=8 Hz, 1H), 7.12(d, J=2 Hz, 1H), 7.82(d, J=3 Hz, 1H), 7.84(d, J=3 Hz, 1H), 8.03(s, 1H), 8.98(s, 1H)

Example 1446

8-[6-[1-(tert-Butyldimethylsiloxy)ethyl]purin-7-ylmethyl]-10H-pyrazino[2,3-b][1,4]benzothiazine 1.35 g of the title compound was obtained by treating 1.55 g of 8-[6-[1-(tert-butyldimethylsiloxy)ethyl]purin-9-ylmethyl]-10-methoxymethyl-10H-pyrazino[2,3-b][1,4]benzothiazine by the same method as the one of Example 9.

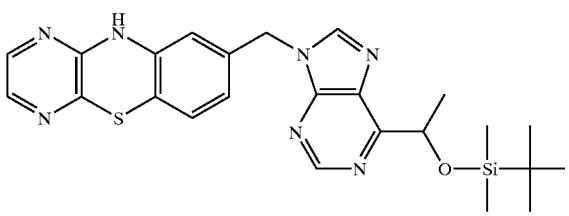

¹H-NMR(CDCl₃) δ ppm: 0.1(s, 3H), 0.04(s, 3H), 0.87(s, 9H), 1.63(d, J=7 Hz, 3H), 5.26(m, 2H), 5.59(q, J=7 Hz, 1H), 6.43(br.s, 1H), 6.45(d, J=2 Hz, 1H), 6.77(dd, J=2, 8 Hz, 1H), 6.86(d, J=8 Hz, 1H), 7.53(d, J=3 Hz, 1H), 7.68(d, J=3 Hz, 1H), 8.01(s, 1H), 8.97(s, 1H)

Example 1447

1-[9-(10H-Pyrazino[2,3-b][1,4]benzothiazin-8-ylmethyl)purin-6-yl]ethanol 0.52 g of the title compound was obtained by treating 8-[6-[1-(tert-butyldimethylsiloxy)ethyl]purin-9-ylmethyl]-10H-pyrazino[2,3-b][1,4]benzothiazine with tetrabutylammonium fluoride by the same method as the one of Example 1418.

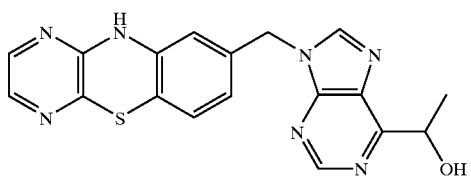

¹H-NMR(DMSO-d₆) δ ppm: 1.50(d, J=6 Hz, 3H), 5.29 (quint, J=6 Hz, 1H), 5.34(s, 2H), 5.35(d, J=6 Hz, 1H), 6.63(d, J=1 Hz, 1H), 6.75(dd, J=1, 8 Hz, 1H), 6.87(d, J=8 Hz, 1H), 7.61(s, 2H), 8.64(s, 1H), 8.86(s, 1H).9.46(s, 1H)
m.p.: 210–212° C.
MS: FAB(+)378(MH⁺)

Examples

The following compounds were obtained by treating 8-chloromethyl-10-methoxymethyl-10H-pyrazino[2,3-b][1,4]-benzothiazine with ethyl 4-(purin-6-ylthio)butanoate by the same method as the one of Example 1094.

| Ex. | Structural formula | NMR |
|---|---|---|
| 1448 | ethyl 4-[9-(10-methoxymethyl-10H-pyrazino[2,3-b][1,4]benzothiazin-8-ylmethyl)purin-6-ylthio]butanoate | ¹H-NMR(CDCl₃) δ ppm: 1.25(t, J=7Hz, 3H), 2.13(quint, J=7Hz, 2H), 2.51(t, J=7Hz, 2H), 3.43(s, 3H), 3.44(t, J=7Hz, 2H), 4.13(q, J=7Hz, 2H), 5.18(s, 2H), 5.33(s, 2H), 6.85(dd, J=2, 8Hz, 1H), 6.98(d, J=8Hz, 1H), 7.11(d, J=2Hz, 1H), 7.83(d, J=3Hz, 1H), 7.85(d, J=3Hz, 1H), 7.95(s, 1H), 8.62(s, 1H) |

| Ex. | Structural formula | NMR |
|---|---|---|
| 1449 | ethyl 4-[7-(10-methoxymethyl-10H-pyrazino[2,3-b][1,4]benzothiazin-8-ylmethyl)purin-6-ylthio]butanoate | $^1$H-NMR(CDCl$_3$) δ ppm: 1.24(t, J=7Hz, 3H), 2.08(quint, J=7Hz, 2H), 2.44(t, J=7Hz, 2H), 3.37(s, 3H), 3.44(t, J=7Hz, 2H), 4.13(q, J=7Hz, 2H), 5.12(s, 2H), 5.57(s, 2H), 6.73(dd, J=2, 8Hz, 1H), 6.87(d, J=2Hz, 1H), 7.00(d, J=8Hz, 1H), 7.83(d, J=3Hz, 1H), 7.85(d, J=3Hz, 1H), 8.07(s, 1H), 8.84(s, 1H) |

Example 1450

4-[7-(10H-Pyrazino[2,3-b][1,4]benzothiazin-8-ylmethyl)purin-6-ylthio]butanoic acid To 15 ml of a solution of 0.109 g of ethyl 4-[7-(10-methoxymethyl-10H-pyrazino[2,3-b][1,4]benzothiazin-8-ylmethyl)purin-6-ylthio]butanoate in dichloromethane was added in a nitrogen atmosphere 0.84 ml of a 1 M solution of boron tribromide in dichloromethane and the resulting mixture was heated under reflux for 2 hours. Then the reaction mixture was distributed into dichloromethane and water. The organic layer was extracted and dried over anhydrous sodium sulfate. After distilling off the solvent under reduced pressure, the obtained residue was purified by silica gel column chromatography (eluted with dichloromethane/methanol) and recrystallized from diethyl ether to thereby give 40 mg of the title compound as yellow crystals.

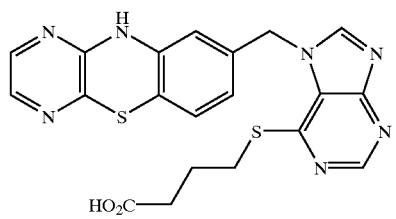

$^1$H-NMR(DMSO-d$_6$) δ ppm: 1.95(quint, J=7 Hz, 2H), 2.17(t, J=7 Hz, 2H), 3.35(t, J=7 Hz, 2H), 5.55(s, 2H), 6.35(d, J=1 Hz, 1H), 6.58(dd, J=1, 8 Hz, 1H), 6.87(d, J=8 Hz, 1H), 7.60(d, J=3 Hz, 1H), 7.61(d, J=3 Hz, 1H), 8.67(s, 1H), 8.75(s, 1H), 9.41(s, 1H)

m.p.: 120–130° C.(decompose)

Example 1451

4-[9-(10H-Pyrazino[2,3-b][1,4]benzothiazin-8-ylmethyl)purin-6-ylthio]butanoic acid The title compound was obtained by treating ethyl 4-[9-(10-methoxymethyl-10H-pyrazino[2,3-b][1,4]benzothiazin-8-ylmethyl)purin-6-ylthio]butanoate by the same method as the one of Example 1450.

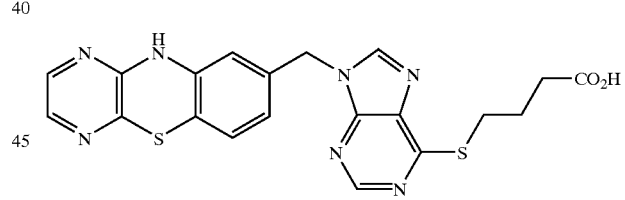

$^1$H-NMR(DMSO-d$_6$) δ ppm: 1.91(quint, J=8 Hz, 2H), 2.30(t, J=8 Hz, 2H), 3.36(t, J=8 Hz, 2H), 5.30(s, 2H), 6.55(d, J=1 Hz, 1H), 6.72(dd, J=1, 8 Hz, 1H), 6.88(d, J=8 Hz, 1H), 7.60(s, 2H), 8.53(s, 1H), 8.70(s, 1H), 9.42(s, 1H)

m.p.: >180° C.(decompose)

Examples

The following compounds were obtained by reacting ethyl 5-(purin-6-ylthio)pentanoate with 8-chloromethyl-10-methoxymethyl-10H-pyrazino[2,3-b][1,4]benzothiazine by the same method as the one of Example 1094.

| Ex. | Structural formula | NMR |
|---|---|---|
| 1452 | ethyl 5-[9-(10-methoxymethyl-10H-pyrazino[2,3-b][1,4]benzothiazin-8-ylmethyl)purin-6-ylthio]pentanoate | $^1$H-NMR(CDCl$_3$) δ ppm: 1.24(t, J=7Hz, 3H), 1.82(m, 4H), 2.37(t, J=7Hz, 2H), 3.40(t, J=7Hz, 2H), 3.44(s, 3H), 4.12(q, J=7Hz, 2H), 5.18(s, 2H), 5.33(s, 2H), 6.84(d, J=8Hz, 1H), 6.97(d, J=8Hz, 1H), 7.09(s, 1H), 7.82(d, J=3Hz, 1H), 7.84(d, J=3Hz, 1H), 7.94(s, 1H), 8.73(s, 1H) |
| 1453 | ethyl 5-[7-(10-methoxymethyl-10H-pyrazino[2,3-b][1,4]benzothiazin-8-ylmethyl)purin-6-ylthio]pentanoate | $^1$H-NMR(CDCl$_3$) δ ppm: 1.23(t, J=7Hz, 3H), 1.79(m, 4H), 2.33(m, 2H), 3.35(s, 3H), 3.39(t, J=7Hz, 2H), 4.11(q, J=7Hz, 2H), 5.11(s, 2H), 5.57(s, 2H), 6.72(d, J=8Hz, 1H), 6.86(s, 1H), 6.98(d, J=8Hz, 1H), 7.82(m, 2H), 8.07(s, 1H), 8.83(s, 1H) |

Examples

The following compounds were obtained by treating ethyl 5-[9-(10-methoxymethyl-10H-pyrazino[2,3-b][1,4]benzothiazin-8-ylmethyl)purin-6-ylthio]pentanoate and ethyl 5-[7-(10-methoxymethyl-10H-pyrazino[2,3-b][1,4]benzothiazin-8-ylmethyl)purin-6-ylthio]pentanoate by the same method as the one of Example 1450.

| Ex. | Structural formula | MS | M.p. | NMR |
|---|---|---|---|---|
| 1454 | 5-[9-(10H-pyrazino[2,3-b][1,4]benzothiazin-8-ylmethyl)purin-6-ylthio]pentanoic acid | FAB (+) 466 (MH$^+$) | 243–244° C. | $^1$H-NMR(DMSO-d$_6$) δ ppm: 1.40–1.55(m, 4H), 2.14(t, J=8Hz, 2H), 3.35(t, J=8Hz, 2H), 5.30(s, 2H), 6.55(s, 1H), 6.74(d, J=8Hz, 1H), 6.87(d, J=8Hz, 1H), 7.61(s, 2H), 8.53(s, 1H), 8.70(s, 1H), 9.43(s, 1H), 12.15(s, 1H) |

-continued

| Ex. | Structural formula | MS | M.p. | NMR |
|---|---|---|---|---|
| 1455 | 5-[7-(10H-pyrazino[2,3-b][1,4]benzothiazin-8-ylmethyl)purin-6-ylthio]pentanoic acid | FAB (+) 488 (MNa+) | | $^1$H-NMR(DMSO-d$_6$) δ ppm: 1.56(m, 2H), 1.63(m, 2H), 2.17(t, J=7Hz, 2H), 3.40(t, J=7Hz, 2H), 5.55(s, 2H), 6.35(d, J=1Hz, 1H), 6.58(dd, J=1, 8Hz, 1H), 6.87(d, J=8Hz, 1H), 7.60(d, J=2Hz, 1H), 7.61(d, J=2Hz, 1H), 8.67(s, 1H), 8.75(s, 1H), 9.42(s, 1H) |
| 1456 | ethyl 5-[7-(10H-pyrazino[2,3-b][1,4]benzothiazin-8-ylmethyl)purin-6-ylthio]pentanoate | FAB (+) 494 (MH+) | 175–178° C. | $^1$H-NMR(CDCl$_3$) δ ppm: 1.25(t, J=7Hz, 3H), 1.78(m, 2H), 1.85(m, 2H), 2.38(m, 2H), 3.12(t, J=8Hz, 2H), 4.14(q, J=7Hz, 2H), 5.48(s, 2H), 6.35(s, 1H), 6.65(d, J=8Hz, 1H), 6.86(d, J=8Hz, 1H), 7.12(s, 1H), 7.53(s, 1H), 7.67(s, 1H), 8.06(s, 1H), 8.85(s, 1H) |

Examples

The following compounds were obtained by treating ethyl 2-(purin-6-ylthio)hexanoate with 8-chloromethyl-10-methoxymethyl-10H-pyrazino[2,3-b][1,4]benzothiazine by the same method as the one of Example 1094.

| Ex. | Structural formula | NMR |
|---|---|---|
| 1457 | ethyl 2-[9-(10-methoxymethyl-10H-pyrazino[2,3-b][1,4]benzothiazin-8-ylmethyl)purin-6-ylthio]hexanoate | $^1$H-NMR(CDCl$_3$) δ ppm: 0.90(t, J=7Hz, 3H), 1.26(t, J=7Hz, 3H), 1.37(m, 2H), 1.48(m, 2H), 1.97(m, 1H), 2.06(m, 1H), 3.43(s, 3H), 4.20(q, J=7Hz, 2H), 4.88(t, J=7Hz, 1H), 5.17(s, 2H), 5.33(s, 2H), 6.83(d, J=8Hz, 1H), 6.94(s, 1H), 6.97(d, J=8Hz, 1H), 7.83(m, 2H), 7.95(s, 1H), 8.75(s, 1H) |

-continued

| Ex. | Structural formula | NMR |
|---|---|---|
| 1458 | ethyl 2-[7-(10-methoxymethyl-10H-pyrazino[2,3-b][1,4]benzothiazin-8-ylmethyl)purin-6-ylthio]hexanoate | $^1$H-NMR(CDCl$_3$) δ ppm: 0.89(m, 3H), 1.25(t, J=7Hz, 3H), 1.35–1.46(m, 4H), 1.97–2.06(m, 2H), 3.38(s, 3H), 4.15–4.27(m, 1H), 4.86(t, J=7Hz, 2H), 5.17(m, 2H), 5.45(d, J=10Hz, 1H), 5.59(d, J=10Hz, 1H), 6.75(d, J=8Hz, 1H), 6.99(m, 2H), 7.84(m, 2H), 8.07(s, 1H), 8.82(s, 1H) |

Examples

The following compounds were obtained by treating the compounds in the above table by the same method as the one of Example 1450.

| Ex. | Structural formula | MS | M.p. | NMR |
|---|---|---|---|---|
| 1459 | 2-[9-(10H-pyrazino[2,3-b][1,4]benzothiazin-8-ylmethyl)purin-6-ylthio]hexanoic acid | FAB (+) 480 (MH$^+$) | 110–120° C. (dec) | $^1$H-NMR(DMSO-d$_6$) δ ppm: 0.84(t, J=7Hz, 3H), 1.19–1.41(m, 4H), 1.80–2.00(m, 2H), 4.80(t, J=7Hz, 1H), 5.30(s, 2H), 6.55(s, 1H), 6.74(d, J=8Hz, 1H), 6.87(d, J=8Hz, 1H), 7.60(s, 2H), 8.56(s, 1H), 8.70(s, 1H), 9.42(s, 1H) |
| 1460 | ethyl 2-[7-(10H-pyrazino[2,3-b][1,4]benzothiazin-8-ylmethyl)purin-6-ylthio]hexanoate | FAB (+) 506 (MH$^+$) | 152–156° C. | $^1$H-NMR(CDCl$_3$) δ ppm: 0.91(t, J=7Hz, 3H), 1.10(t, J=7Hz, 3H), 1.13–1.32(m, 4H), 1.72–1.95(m, 2H), 4.10(q, J=7Hz, 2H), 4.79(t, J=8Hz, 1H), 5.25(d, J=16Hz, 1H), 5.37(d, J=16Hz, 1H), 6.42(s, 1H), 6.53(d, J=8Hz, 1H), 6.69(d, J=8Hz, 1H), 7.37(s, 1H), 7.48(s, 1H), 7.95(s, 1H), 8.67(s, 1H) |

Examples

The following compounds were obtained by treating methyl 11-(purin-6-ylthio)undecanoate with 8-chloromethyl-10-methoxymethyl-10H-pyrazino[2,3-b][1,4]benzothiazine by the same method as the one of Example 1094.

| Ex. | Structural formula | NMR |
|---|---|---|
| 1461 | 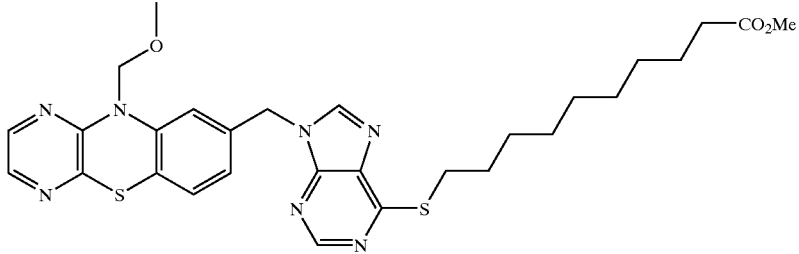<br>methyl 11-[9-(10-methoxymethyl-10H-pyrazino[2,3-b][1,4]benzothiazin-8-ylmethyl)purin-6-ylthio]undecanoate | $^1$H-NMR(CDCl$_3$) δ ppm: 1.23–1.35(m, 12H), 1.47(quint, J=7Hz, 2H), 1.78(quint, J=7Hz, 2H), 2.30(t, J=7Hz, 2H), 3.38(t, J=7Hz, 2H), 3.43(s, 3H), 3.66(s, 3H), 5.17(s, 2H), 5.34(s, 2H), 6.84(d, J=8Hz, 1H), 6.97(d, J=8Hz, 1H), 7.08(s, 1H), 7.82(d, J=3Hz, 1H), 7.83(d, J=3Hz, 1H), 7.94(s, 1H), 8.73(s, 1H) |
| 1462 | 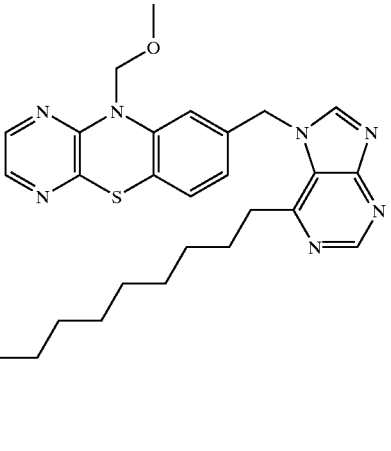<br>methyl 11-[7-(10-methoxymethyl-10H-pyrazino[2,3-b][1,4]benzothiazin-8-ylmethyl)purin-6-ylthio]undecanoate | $^1$H-NMR(CDCl$_3$) δ ppm: 1.24–1.36(m, 12H), 1.41(m, 2H), 1.71(quint, J=7Hz, 2H), 2.39(t, J=7Hz, 2H), 3.35(s, 3H), 3.37(t, J=7Hz, 2H), 3.66(s, 3H), 5.12(s, 2H), 5.58(s, 2H), 6.73(d, J=8Hz, 1H), 6.87(s, 1H), 6.99(d, J=8Hz, 1H), 7.82–7.84(m, 2H), 8.06(s, 1H), 8.85(s, 1H) |

Examples

The following compounds were obtained by treating the compounds in the above table by the same method as the one of Example 1450.

| Ex. | Structural formula | MS | M.p. | NMR |
|---|---|---|---|---|
| 1463 | 11-[9-(10H-pyrazino[2,3-b][1,4]benzothiazin-8-ylmethyl)purin-6-ylthio]undecanoic acid | FAB (+) 550 (MH⁺) | 154–156° C. | ¹H-NMR(DMSO-d₆) δ ppm: 1.20–1.30(m, 10H), 1.35–1.50 (m, 4H), 1.70(m, 2H), 2.16(t, J=7Hz, 2H), 3.37(t, J=7Hz, 2H), 5.30(s, 2H), 6.55(d, J=1Hz, 1H), 6.73(dd, J=1, 8Hz, 1H), 6.87(d, J=8Hz, 1H), 7.61(s, 2H), 8.52(s, 1H), 8.69 (s, 1H), 9.43(s, 1H) |
| 1464 | 11-[7-(10H-pyrazino[2,3-b][1,4]benzothiazin-8-ylmethyl)purin-6-ylthio]undecanoic acid | FAB (+) 549 (M⁺) | 166–170° C. | ¹H-NMR(DMSO-d₆) δ ppm: 1.02–1.30(m, 12H), 1.42(quint, J=7Hz, 2H), 1.57(quint, J=7Hz, 2H), 2.13(t, J=7Hz, 2H), 3.35(t, J=7Hz, 2H), 5.55(s, 2H), 6.30(s, 1H), 6.55 (d, J=8Hz, 1H), 6.76(d, J=8Hz, 1H), 7.58(d, J=3Hz, 1H), 7.59(d, J=3Hz, 1H), 8.67(s, 1H), 8.75 (s, 1H), 9.36(s, 1H) |

Examples

The following compounds were obtained by treating 8-chloromethyl-10-methoxymethyl-10H-pyrazino[2,3-b][1,4]-benzothiazine with various purine compounds by the same method as the one of Example 1094.

| Ex. | Purine derivative | Structural formula |
|---|---|---|
| 1465 | | ethyl 3-[9-(10-methoxymethyl-10H-pyrazino[2,3-b][1,4]benzothiazin-8-ylmethyl)purin-6-ylthio]propanoate |

-continued

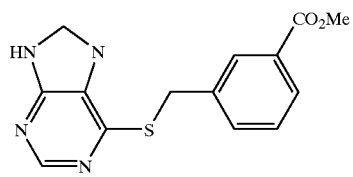

1466

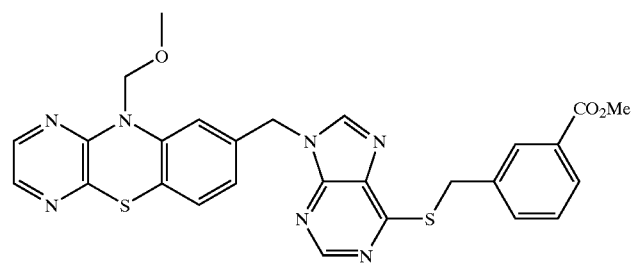

methyl 3-[[9-(10-methoxymethyl-10H-pyrazino[2,3-b][1,4]benzothiazin-8-ylmethyl)purin-6-ylthiomethyl]benzoate

1467

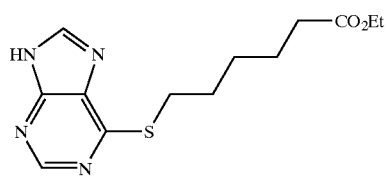

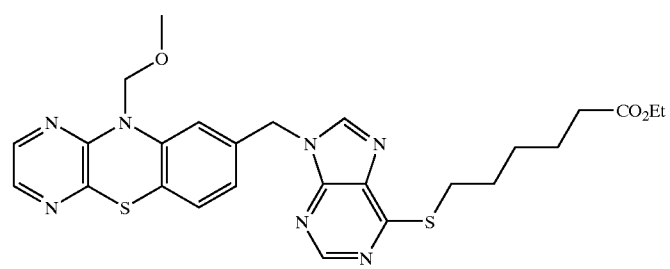

ethyl 6-[9-(10-methoxymethyl-10H-pyrazino[2,3-b][1,4]benzothiazin-8-ylmethyl)purin-6-ylthio]hexanoate

| Ex. | NMR |
|---|---|
| 1465 | $^1$H-NMR(CDCl$_3$) δ ppm: 1.26(t, J=7Hz, 3H), 2.87(t, J=7Hz, 2H), 3.43(s, 3H), 3.64(t, J=7Hz, 2H), 4.17(t, J=7Hz, 2H), 5.23(s, 2H), 5.32(s, 2H), 6.82(d, J=8Hz, 1H), 6.96(d, J=8Hz, 1H), 7.27(s, 1H), 7.82(m, 2H), 7.95(s, 1H), 8.76(s, 1H) |
| 1466 | $^1$H-NMR(CDCl$_3$) δ ppm: 3.41(s, 3H), 3.89(s, 3H), 4.68(s, 2H), 5.17(s, 2H), 5.34(s, 2H), 6.85(dd, J=2, 8Hz, 1H), 6.97(d, J=8Hz, 1H), 7.08(d, J=2Hz, 1H), 7.37(t, J=8Hz, 1H), 7.68(td, J=1, 8Hz, 1H), 7.83(d, J=3Hz, 1H), 7.85(d, J=3Hz, 1H), 7.91(td, J=1, 8Hz, 1H), 7.96(s, 1H), 8.16(t, J=1Hz, 1H), 8.78(s, 1H) |
| 1467 | $^1$H-NMR(CDCl$_3$) δ ppm: 1.24(t, J=7Hz, 3H), 1.53(m, 2H), 1.68(quint, J=7Hz, 2H), 1.81(quint, J=7Hz, 2H), 2.32(t, J=7Hz, 2H), 3.39(t, J=7Hz, 2H), 3.43(s, 3H), 4.12(q, J=7Hz, 2H), 5.23(s, 2H), 5.34(s, 2H), 6.86(dd, J=2, 8Hz, 1H), 6.96(d, J=8Hz, 1H), 7.10(d, J=2Hz, 1H), 7.80(d, J=3Hz, 1H), 7.82(d, J=3Hz, 1H), 7.94(s, 1H), 8.72(s, 1H) |

Examples

The following compounds were obtained by treating the compounds in the above table by the same method as the one of Example 1450.

| Ex. | Structural formula | MS | M.p. | NMR |
|---|---|---|---|---|
| 1468 | 3-[9-(10H-pyrazino[2,3-b][1,4]benzothiazin-8-ylmethyl)purin-6-ylthio]propanoic acid | | | $^1$H-NMR(DMSO-$d_6$) δ ppm: 2.55(t, J=7Hz, 2H), 3.35(t, J=7Hz, 2H), 5.74(s, 2H), 6.55(d, J=1Hz, 1H), 6.73(dd, J=1, 8Hz, 1H), 6.87(d, J=8Hz, 1H), 7.61(s, 2H), 8.54(s, 1H), 8.72(s, 1H), 9.43(s, 1H) |
| 1469 | methyl 3-[[9-(10-H-pyrazino[2,3-b][1,4]benzothiazin-8-ylmethyl)purin-6-ylthiomethyl]benzoate | FAB (+) 514 (MH$^+$) | | $^1$H-NMR(CDCl$_3$) δ ppm: 3.90(s, 3H), 4.70(s, 2H), 5.25(s, 2H), 6.38(d, J=1Hz, 1H), 6.40(br.s, 1H), 6.76(dd, J=1, 8Hz, 1H), 6.86(d, J=8Hz, 1H), 7.37(t, J=8Hz, 1H), 7.57(d, J=3Hz, 1H), 7.68(td, J=1, 8Hz, 1H), 7.70(d, J=3Hz, 1H), 7.91(td, J=1, 8Hz, 1H), 7.94(s, 1H), 8.15(t, J=1Hz, 1H), 8.77(s, 1H) |
| 1470 | 6-[9-(10H-pyrazino[2,3-b][1,4]benzothiazin-8-ylmethyl)purin-6-ylthio]hexanoic acid | FAB (+) 480 (MH$^+$) | | $^1$H-NMR(DMSO-$d_6$) δ ppm: 1.41(quint, J=7Hz, 2H), 1.52(quint, J=7Hz, 2H), 1.69(quint, J=7Hz, 2H), 2.20(t, J=7Hz, 2H), 3.35(t, J=7Hz, 2H), 5.30(s, 2H), 6.55(d, J=1Hz, 1H), 6.74(dd, J=1, 8Hz, 1H), 6.87(d, J=8Hz, 1H), 7.61(s, 2H), 8.53(s, 1H), 8.69(s, 1H), 9.43(s, 1H), 11.9(s, 1H) |
| 1471 | ethyl 6-[9-(10H-pyrazino[2,3-b][1,4]benzothiazin-8-ylmethyl)purin-6-ylthio]hexanoate | FAB (+) 508 (MH$^+$) | 78–79° C. | $^1$H-NMR(CDCl$_3$) δ ppm: 1.16(t, J=7Hz, 3H), 1.35(quint, J=7Hz, 2H), 1.65(quint, J=7Hz, 2H), 1.81(quint, J=7Hz, 2H), 2.31(t, J=7Hz, 2H), 3.40(t, J=7Hz, 2H), 4.12(q, J=7Hz, 2H), 5.25(s, 2H), 6.39(s, 2H), 6.74(d, J=8Hz, 1H), 6.85(d, J=8Hz, 1H), 7.55(s, 1H), 7.70(s, 1H), 7.94(s, 1H), 8.73(s, 1H) |

Example 1472

[9-(10H-Pyrazino[2,3-b][1,4]benzothiazin-8-ylmethyl)purin-6-yl]carbothioamide

In a steel container, 2.75 g of 9-(10H-pyrazino[2,3-b][1,4]benzothiazin-8-ylmethyl)purine-6-carbonitrile and 6.5 g of powdery sodium hydrogensulfide were suspended in 150 ml of methanol. Next, hydrogen sulfide was blown into the system at −30° C. to ensure saturation thereof and then the container was hermetically sealed. After heating the reactor to 80 to 90° C. for 4 hours, the reaction mixture was poured into an aqueous solution of potassium hydrogensulfate. The crystals thus precipitated were taken up by filtration and washed with water. Thus, 3.1 g of the title compound was obtained as yellow crystals.

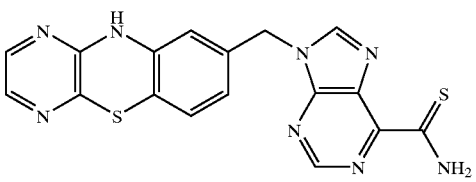

$^1$H-NMR(DMSO-$d_6$) δ ppm: 5.48(s, 2H), 6.66(s, 1H), 6.75(d, J=8.3 Hz, 1H), 6.88(d, J=8.3 Hz, 1H), 7.61(s, 2H), 8.75(s, 1H), 8.92(s, 1H), 9.47(s, 1H), 9.90–10.03(br.s, 1H), 10.38–10.51(br.s, 1H)

Example 1473

[9-(10H-Pyrazino[2,3-b][1,4]benzothiazin-8-ylmethyl)purin-6-yl]-N²-cyanocarboxamidine 500 mg of [9-(10H-pyrazino[2,3-b][1,4]benzothiazin-8-ylmethyl)purin-6-yl]carbothioamide was dissolved in a solvent mixture of acetone (200 ml) with N,N-dimethylformamide (10 ml). Under ice-cooling, 300 mg of methyl iodide was added thereto and the resulting mixture was stirred at 0° C. to room temperature for 3 hours. Then the reaction mixture was distributed into an aqueous solution of potassium carbonate and ethyl acetate and the organic layer was extracted. After distilling off the solvent under reduced pressure, the residue was dissolved in dry methanol (5 ml) and tetrahydrofuran (10 ml). After adding 1.0 g of cyanamide, the reaction mixture was stirred at 30 to 40° C. for 3 hours. Then the reaction mixture was distributed into water and ethyl acetate. The organic layer was extracted, washed with water and dried over anhydrous sodium sulfate. After distilling off the solvent under reduced pressure, the residue was purified by silica gel column chromatography (eluted with dichloromethane/methanol) to thereby give 78 mg of the title compound as yellow crystals.

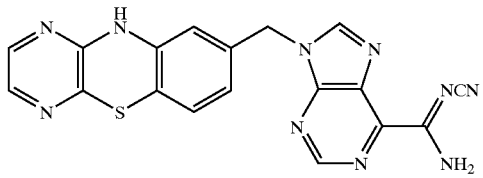

¹H-NMR(DMSO-d₆) δ ppm: 5.40(s, 2H), 6.53–6.70(br.s, 1H), 6.76(d, J=7.9 Hz, 1H), 6.88(d, J=7.9 Hz, 1H), 7.61(s, 2H), 8.89(s, 1H), 9.03–9.10(br.s, 1H), 9.30–9.50(m, 3H)
MS: FAB(+)400(M⁺)
m.p.: >290° C.

Example 1474

N²-[9-(10H-Pyrazino[2,3-b][1,4]benzothiazin-8-ylmethyl)purin-6-yl]-N¹,N¹-dimethylformamidine The title compound was obtained by treating 8-(6-aminopurin-9-yl)-10H-pyrazino[2,3-b][1,4]benzothiazine with N,N-dimethylformamide dimethyl acetal by the same method as the one of Example 1540.

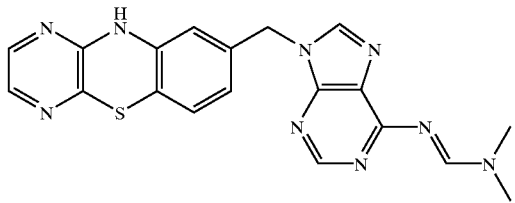

¹H-NMR(DMSO-d₆) δ ppm: 3.11(s, 3H), 3.17(s, 3H), 3.24(s, 2H), 6.58(s, 1H), 6.70(d, J=8 Hz, 1H), 6.86(d, J=8 Hz, 1H), 7.61(s, 2H), 8.31(s, 1H), 8.39(s, 1H), 8.90(s, 1H), 9.47(s, 1H)

Example 1475

8-(6-Aminopurin-9-yl)-10H-pyrazino[2,3-b][1,4]benzothiazine hemioxalate

The title compound was obtained by hydrogenating 9-(10H-pyrazino[2,3-b][1,4]benzothiazin-8-ylmethyl)purine-6-carbonitrile by the same method as the one of Example 16.

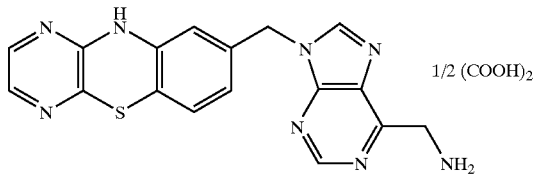

¹H-NMR(DMSO-d₆) δ ppm: 4.58(br.s, 2H), 5.37(s, 2H), 6.68(s, 1H), 6.71(d, J=8 Hz, 1H), 6.88(d, J=8 Hz, 1H), 7.62(s, 2H), 8.61(br.s, 3H), 8.79(s, 1H), 8.99(s, 1H), 9.50(s, 1H)
MS: ESI(+)363(MH⁺)
m.p.: 97–104° C.(dec)

Example 1476

N¹-[9-(10H-Pyrazino[2,3-b][1,4]benzothiazin-8-ylmethyl)purin-6-ylmethy]-N²-cyanoformamidine The title compound was obtained by treating 8-(6-aminomethylpurin-9-yl)-10H-pyrazino[2,3-b][1,4]benzothiazine with ethyl N-cyanoformimidate by the same method as the one of Example 1534.

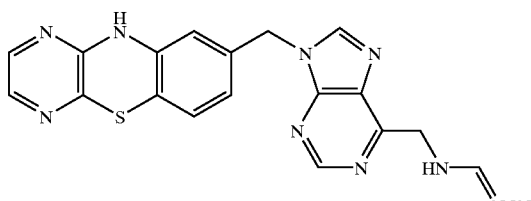

¹H-NMR(DMSO-d₆) δ ppm: 5.24(s, 2H), 6.30(s, 2H), 6.60(s, 1H), 6.74(d, J=8 Hz, 2H), 6.87(d, J=8 Hz, 1H), 7.62(s, 2H), 8.48(s, 1H), 8.69(s, 1H), 8.88(s, 1H), 9.46(s, 1H)

Example 1477

(10H-Pyrazino[2,3-b][1,4]benzothiazin-8-yl)carbonitrile 150 mg of the title compound was obtained by treating 300 mg of (10-methoxymethyl-10H-pyrazino[2,3-b][1,4]benzothiazin-8-yl)carbonitrile by the same method as the one of Example 434.

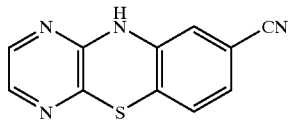

¹H-NMR(DMSO-d₆) δ ppm: 6.96(d, J=1.8 Hz, 1H), 7.10 (dd, J=1.8, 8.2 Hz, 1H), 7.18(d, J=8.2 Hz, 1H), 7.67(d, J=3.3 Hz, 1H), 7.68(d, J=3.3 Hz, 1H), 9.74(s, 1H)
MS: FAB(+)227(MH⁺)
m.p.: 263–264° C.

Example 1478

(10H-Pyrazino[2,3-b][1,4]benzothiazin-8-yl)carboxamidine hydrochloride

Into a metallic pressure container (50 ml) were fed 300 mg of (10H-pyrazino[2,3-b][1,4]benzothiazin-8-yl)

carbonitrile and 450 mg of ammonium chloride. After adding about 20 ml of liquefied ammonia at −78° C., the container was sealed and heated to 120° C. for 15 hours. Then it was opened under ice-cooling and the ammonia was released. The obtained residue was distributed into dilute hydrochloric acid and ethyl acetate. The aqueous layer was washed with ethyl acetate several times. Then the pH value of the aqueous layer was adjusted to about 10 with potassium hydroxide. Next, it was extracted with ethyl acetate and dried over anhydrous potassium carbonate. After distilling off the solvent under reduced pressure, the obtained residue was dissolved in a small amount of methanol. After adding hydrogen chloride and ethyl acetate, crystallization was effected to thereby give 45 mg of the title compound as orange crystals.

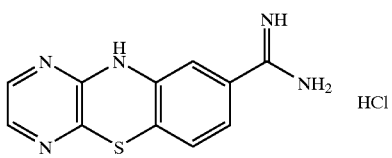

$^1$H-NMR(DMSO-d$_6$) δ ppm: 6.99(s, 1H), 7.09(d, J=8.0 Hz, 1H), 7.14(d, J=8.0 Hz, 1H), 7.70(d, J=2.8 Hz, 1H), 7.71(d, J=2.8 Hz, 1H), 9.10(br.s, 2H), 9.31(br.s, 2H), 9.82 (br.s, 1H)
MS: FAB(+)244(MH$^+$)
m.p.: >280° C.

Example 1479

(10H-Pyrazino[2,3-b][1,4]benzothiazin-8-yl) acetamidine 2.68 g of ammonium chloride was added to 20 ml of dry toluene in a nitrogen atmosphere. Then 36.5 ml of a 15% solution of trimethylaluminum in n-hexane was added thereto under stirring and ice-cooling. The reaction mixture was brought back to room temperature and 70 ml of dry toluene was further added. The resulting mixture was subjected to ultrasonication until the ammonium chloride disappeared completely. A 60 ml portion of the solution thus obtained was taken and 1.5 g of (10H-pyrazino[2,3-b][1,4] benzothiazin-8-yl)acetonitrile was added thereto. The obtained mixture was heated under reflux for 18 hours. After bringing back to room temperature, the reaction mixture was distributed into ethyl acetate and dilute hydrochloric acid and repeatedly extracted with water. The aqueous layer was washed with methylene chloride and the solvent contained in the solution was eliminated under reduced pressure. The obtained residue was purified by High-porous gel column chromatography (CHP20, mfd. by Mitsubishi Chemical Industries, Ltd., 75–15μ) (eluted with water/methanol) to thereby give 620 mg of the title compound as yellow crystals.

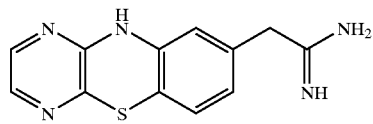

$^1$H-NMR(DMSO-d$_6$) δ ppm: 3.52(br.s, 2H), 6.70(br.s, 1H), 6.75(br.d, J=8.0 Hz, 1H), 6.91(br.d, J=8.0 Hz, 1H), 7.64(br.s, 2H)

Example 1480

(10H-Pyrazino[2,3-b][1,4]benzothiazin-8-yl) acetamidine hydrochloride (10H-Pyrazino[2,3-b][1,4]benzothiazin-8-yl) acetamidine was dissolved in a small amount of methanol and a solution of hydrogen chloride in ethyl acetate was added thereto under ultrasonication. Thus, the title compound was obtained almost quantitatively as the precipitated orange crystals.

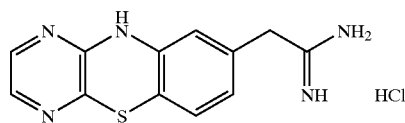

$^1$H-NMR(DMSO-d$_6$) δ ppm: 3.56(s, 2H), 6.71(s, 1H), 6.79(d, J=8.2 Hz, 1H), 6.91(d, J=8.2 Hz, 1H), 7.64(s, 2H), 8.76(br.s, 2H), 9.18(br.s, 2H), 9.65(s, 1H)
MS: FAB(+)258(MH$^+$)
m.p.: >280° C.

Examples

The following compounds were obtained by the same method as the one of Example 1479 by using methylamine hydrochloride and dimethylamine hydrochloride each as a substitute for the ammonium chloride followed by the same treatment as the one of Example 1399.

| Ex. | Structural formula | MS | M.p. | NMR |
|---|---|---|---|---|
| 1481 | N$^1$-methyl -(10-pyrazino[2,3-b][1,4]benzothiazin-8-yl) acetamidine hydrochloride | FAB (+) 272 (MH$^+$) | 244– 247° C. | $^1$H-NMR(DMSO-d$_6$) δ ppm: 2.81(s, 3H), 3.59(s, 2H), 6.69(s, 1H), 6.78(d, J=8.1Hz, 1H), 6.91(d, J=8.1Hz, 1H), 7.64(s, 2H), 8.72–8.83(br.s, 1H), 9.26–9.37(br.s, 1H), 9.62(s, 1H), 9.76–9.86(br.s, 1H) |

-continued

| Ex. | Structural formula | MS | M.p. | NMR |
|---|---|---|---|---|
| 1482 | 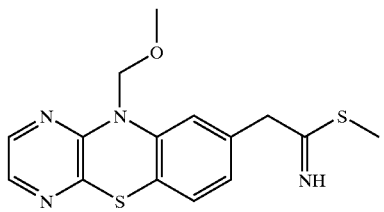<br>N¹,N¹-dimethyl-(10H-pyrazino[2,3-b][1,4]benzothiazin-8-yl)acetamidine hydrochloride | FAB (+) 286 (MH⁺) | >280° C. | ¹H-NMR(DMSO-$d_6$) δ ppm: 3.05(s, 3H), 3.07(s, 3H), 3.84(s, 2H), 6.66(s, 1H), 6.71(d, J=8.2Hz, 1H), 6.92(d, J=8.2Hz, 1H), 7.64(s, 2H), 8.79–8.87(br.s, 1H), 9.43–9.50(br.s, 1H), 9.60(s, 1H) |

Example 1483

Methyl(10-methoxymethyl-10H-pyrazino[2,3-b][1,4]benzothiazin-8-yl)acetothioimidate Into 15 ml of a solution of 318 mg of (10-methoxymethyl-10H-pyrazino[2,3-b][1,4]benzothiazin-8-yl)thioacetamide in acetone was dropped 1.5 m of methyl iodide. After stirring at room temperature for 2 hours, the reaction mixture was distributed into ethyl acetate and an aqueous solution of potassium carbonate. The organic layer was extracted and the extract was washed with water and dried over anhydrous sodium sulfate. After distilling off the solvent under reduced pressure, 350 mg of the title compound was obtained as a yellow oily substance.

¹H-NMR(CDCl₃) δ ppm: 2.29(br.s, 3H), 3.53(s, 3H), 3.68(s, 2H), 5.27(s, 2H), 6.88(br.d, J=7.7 Hz, 1H), 6.98(d, J=7.7 Hz, 1H), 7.04(br.s, 1H), 7.83(d, J=2.8 Hz, 1H), 7.84(d, J=2.8 Hz, 1H)

Example 1484

N-Phenyl-(10-methoxymethyl-10H-pyrazino[2,3-b][1,4]-benzothiazin-8-yl)acetamidine 350 mg of methyl(10-methoxymethyl-10H-pyrazino[2,3-b][1,4]benzothiazin-8-yl)acetothioimidate was dissolved in a solvent mixture of tetrahydrofuran (7 ml) with methanol (15 ml). After adding 0.5 ml of aniline, the resulting mixture was heated under reflux for 5 hours. Then the reaction mixture was brought back to room temperature. After distilling off the solvent under reduced pressure, the residue was purified by silica gel column chromatography (eluted with dichloromethane/methanol/aqueous ammonia) to thereby give 250 mg of the title compound as yellow crystals.

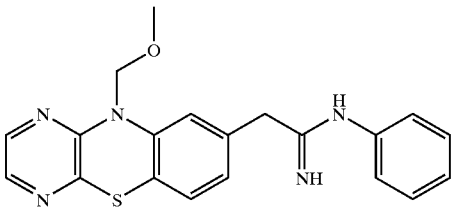

¹H-NMR(CDCl₃) δ ppm: 3.53(s, 3H), 3.60(s, 2H), 3.6–4.1(br.s, 2H), 5.24(s, 2H), 6.92(d, =7.3 Hz, 2H), 6.94 (br.d, J=7.7 Hz, 1H), 6.98(d, J=7.7 Hz, 1H), 7.04(t, J=7.3 Hz, 1H), 7.17(br.s, 1H), 7.31(t, J=7.3 Hz, 2H), 7.83(d, J=2.7 Hz, 1H), 7.84(d, J=2.7 Hz, 1H)

Example 1485

N-Phenyl-(10H-pyrazino[2,3-b][1,4]benzothiazin-8-yl)acetamidine hydrochloride 250 mg of N-phenyl-(10-methoxymethyl-10H-pyrazino[2,3-b][1,4]benzothiazin-8-yl)acetamidine was treated by the same method as the one of Example 434 and then crystallized from ethyl acetate containing hydrogen chloride. Thus, 130 mg of the title compound was obtained as orange crystals.

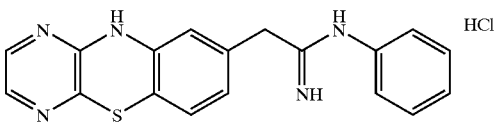

¹H-NMR(DMSO-$d_6$) δ ppm: 3.78(s, 2H), 6.81(s, 1H), 6.86(d, J=8.2 Hz, 1H), 6.95(d, J=8.2 Hz, 1H), 7.32(d, J=7.4 Hz, 2H), 7.44(t, J=7.4 Hz, 1H), 7.53(t, J=7.4 Hz, 2H), 7.64(d, J=2.2 Hz, 1H), 7.65(d, J=2.2 Hz, 1H), 8.76(s, 1H), 9.67–9.75(br.s, 1H), 9.70(s, 1H), 11.66(s, 1H)

MS: FAB(+)334(MH⁺)

m.p.: 245–249° C.(decompose)

Example 1486

Methyl(10H-pyrazino[2,3-b][1,4]benzothiazin-8-yl)acetothioimidate

The title compound was obtained as a yellow oily substance quantitatively by treating (10H-pyrazino[2,3-b][1,4]benzothiazin-8-yl)thioacetamide with methyl iodide by the same method as the one of Example 1483.

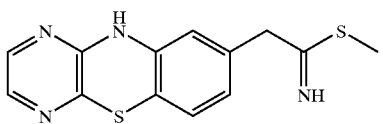

¹H-NMR(DMSO-d₆) δ ppm: 2.61(s, 3H), 4.00(s, 2H), 6.68(s, 1H), 6.77(d, J=8.1 Hz, 1H), 6.94(d, J=8.1 Hz, 1H), 7.65(s, 2H), 9.62(s, 1H)

Example 1487

N²-Cyano-(10H-pyrazino[2,3-b][1,4]benzothiazin-8-yl)acetamidine

To 15 ml of a solution of 410 mg of methyl (10H-pyrazino[2,3-b][1,4]benzothiazin-8-yl)acetothioimidate in methanol was added 250 mg of cyanamide and the resulting mixture was heated to 60° C. or below for 1 hour. Then the reaction mixture was brought back to room temperature and the solvent was distilled off under reduced pressure to reduce its amount. The crystals thus precipitated were taken up by filtration and washed successively with methanol and ethyl acetate. Thus, 295 mg of the title compound was obtained as yellow crystals.

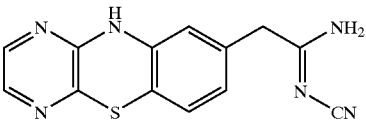

¹H-NMR(CD₃OD) δ ppm: 3.62(br.s, 2H), 6.67(br.s, 1H), 6.78(d, J=8 Hz, 1H), 6.84(d, J=8 Hz, 1H), 7.57(d, J=3 Hz, 1H), 7.58(d, J=3 Hz, 1H)
MS: FAB(+)286(MH⁺)
m.p.: 230–232° C.

Examples

The following compounds were synthesized by treating methyl(10H-pyrazino[2,3-b][1,4]benzothiazin-8-yl)acetothioimidate with various amines by the same method as the one of Example 1487.

| Ex. | Structural formula | MS | M.p. | NMR |
|---|---|---|---|---|
| 1488 | N²-(methanesulfonyl)-(10H-pyrazino[2,3-b][1,4]benzothiazin-8-yl)acetamidine | FAB (+) 336 (MH⁺) | | ¹H-NMR(DMSO-d₆) δ ppm: 2.83(s, 3H), 3.33(s, 2H), 6.70(s, 1H), 6.71(d, J=7.8Hz, 1H), 6.85(d, J=7.8Hz, 1H), 7.60–7.65(m, 2H), 7.79(s, 1H), 8.58(s, 1H), 9.57(s, 1H) |
| 1489 | N²-(trifluoromethanesulfonyl)-(10H-pyrazino[2,3-b][1,4]benzothiazin-8-yl)acetamidine | FAB (+) 390 (MH⁺), 389 (M⁺) | 200–202° C. | ¹H-NMR(DMSO-d₆) δ ppm: 3.57(s, 2H), 6.67(s, 1H), 6.70(d, J=7.5Hz, 1H), 6.89(d, J=7.5Hz, 1H), 7.61–7.66(m, 2H), 9.00–9.10(br.s, 1H), 9.58(s, 1H), 9.63–9.72(br.s, 1H) |
| 1490 | N²-(benzenesulfonyl)-(10H-pyrazino[2,3-b][1,4]benzothiazin-8-yl)acetamidine | FAB (+) 398 (MH⁺), 397 (M⁺) | 206–207° C. | ¹H-NMR(DMSO-d₆) δ ppm: 3.34(s, 2H), 6.62(d, J=7.8Hz, 1H), 6.66(s, 1H), 6.79(d, J=7.8Hz, 1H), 7.43–7.57(m, 3H), 7.61–7.69(m, 2H), 7.70–7.78(m, 2H), 8.00–8.10(br.s, 1H), 8.73–8.84(br.s, 1H), 9.53(s, 1H) |

| Ex. | Structural formula | MS | M.p. | NMR |
|---|---|---|---|---|
| 1491 | N²-(2-propynyl)-(10H-pyrazino[2,3-b][1,4]benzothiazin-8-yl)acetamidine hydrochloride | FAB (+) 296 (MH⁺) | 222–223° C. | ¹H-NMR(DMSO-d₆) δ ppm: 3.48(t, J=2.5Hz, 1H), 3.62(s, 2H), 4.15(dd, J=2.5, 5.4Hz, 2H), 6.71(s, 1H), 6.78(d, J=8.2Hz, 1H), 6.91(d, J=8.2Hz, 1H), 7.64(s, 2H), 9.11(s, 1H), 9.66(d, J=2.4Hz, 2H), 10.25(t, J=5.4Hz, 1H) |
| 1492 | N²-sulfamoyl-(10H-pyrazino[2,3-b][1,4]benzothiazin-8-yl)acetamidine | FAB (+) 336 (M⁺) | >260° C. (decompose) | ¹H-NMR(DMSO-d₆) δ ppm: 3.51(s, 2H), 4.3–4.5(br.s, 1H), 5.1–5.3(br.s, 1H), 6.70(br.s, 1H), 6.76(br.d, J=7.9Hz, 1H), 6.91(br.d, J=7.9Hz, 1H), 7.65(br.s, 2H) |
| 1493 | N-(benzenesulfonyl)-(10H-pyrazino[2,3-b][1,4]benzothiazin-8-yl)acetamidrazone | FAB (+) 413 (MH⁺) | 226–227° C. | ¹H-NMR(DMSO-d₆) δ ppm: 3.03–3.10(br.s, 2H), 6.09–6.12(br.s, 1H), 6.50–6.62(br.d, J=7.6Hz, 1H), 6.58(s, 1H), 6.74(d, J=7.6Hz, 1H), 7.27–7.42(br.s, 1H), 7.47–7.59(m, 3H), 7.60–7.66(m, 2H), 7.70–7.80(m, 2H), 8.82–8.92(br.s, 1H), 9.43–9.55(br.s, 1H) |
| 1494 | N-formyl-(10H-pyrazino[2,3-b][1,4]benzothiazin-8-yl)acetamidrazone | FAB (+) 301 (MH⁺) |  | ¹H-NMR(DMSO-d₆) δ ppm: 3.13 and 3.17(s, total 2H), 6.03 and 6.10(s, total 1H), 6.67–6.77(m, 2H), 7.60–7.63(m, 1H), 7.80(s, initial 1H), 8.33(d, J=9.8Hz, initial 1H), 9.47(s, 2H), 9.51(s, initial 1H), 9.34(d, J=9.8Hz, initial 1H) |
| 1495 | N²-(dimethylaminocarbonyl)-(10H-pyrazino[2,3-b][1,4]benzothiazin-8-yl)acetamidine | FAB (+) 329 (MH⁺) | 158–161° C. | ¹H-NMR(DMSO-d₆) δ ppm: 2.76(s, 3H), 2.96(s, 3H), 3.23(s, 2H), 6.73(s, 1H), 6.74(d, J=7.9Hz, 1H), 6.82(d, J=7.9Hz, 1H), 7.61(d, J=2.3Hz, 1H), 7.62(d, J=2.3Hz, 1H), 7.82–8.00(br.s, 1H), 8.82–9.04(br.s, 1H), 9.53(s, 1H) |
| 1496 | (10H-pyrazino[2,3-b][1,4]benzothiazin-8-yl)acetamidine O-methyl oxime | FAB (+) 287 (M⁺) | 217–218° C. | ¹H-NMR(DMSO-d₆) δ ppm: 3.04(s, 2H), 3.57(s, 3H), 5.57–5.63(br.s, 2H), 6.68(d, J=1.5Hz, 1H), 6.72(d, J=7.7Hz, 1H), 6.82(dd, J=1.5, 7.7Hz, 1H), 7.61–7.64(m, 2H), 9.50(s, 1H) |

| Ex. | Structural formula | MS | M.p. | NMR |
|---|---|---|---|---|
| 1497 | (10H-pyrazino[2,3-b][1,4]benzothiazin-8-yl)acetamidine oxime | FAB (+) 273 (M⁺) | 252–254° C. | ¹H-NMR(DMSO-d₆) δ ppm: 3.06(s, 2H), 5.30–5.36(br.s, 2H), 6.66(d, J=1.0Hz, 1H), 6.70(dd, J=1.0, 7.5Hz, 1H), 6.81(d, J=7.5Hz, 1H), 7.61(d, J=2.3Hz, 1H), 7.62(d, J=2.3Hz, 1H), 8.89(s, 1H), 9.49(s, 1H) |

Example 1498

N²-Cyano-(10H-pyrazino[2,3-b][1,4]benzothiazin-8-yl)acetamidine 500 mg of 7-chloromethyl-10-methoxymethyhl-10H-pyrazino[2,3-b][1,4]benzothiazine was treated by the same method as the one of Example 1513 to thereby give (10-methoxymethyhl-10H-pyrazino[2,3-b][1,4]benzothiazin-7-yl)acetonitrile. Next, this product was converted into methyl (10-methoxymethyl-10H-pyrazino[2,3-b][1,4]benzothiazin-7-yl)acetimidate by the same method as the one of Example 1518. After treating with cyanamide by the same method as the one of Example 1487, 110 mg of the title compound was obtained as yellow crystals.

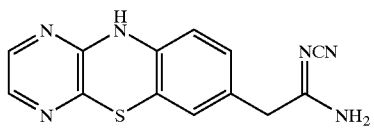

¹H-NMR(CD₃OD) δ ppm: 3.63(br.s, 2H), 6.62 and 6.64 (d, J=8 Hz, 1H), 6.81(d, J=2 Hz) and 6.86(br.s)(total 1H), 6.91(dd, J=2, 8 Hz) and 6.97(d, J=8 Hz)(total 1H), 7.55 and 7.57(d, J=3 Hz, 1H), 7.56 and 7.58(d, J=3 Hz, 1H)

MS: FAB(+)283(MH⁺)

m.p.: 218–219° C.

Example 1499

N²-Cyano-(10H-pyrazino[2,3-b][1,4]benzothiazin-8-yl)acetamidine S-oxide

To a solution of 150 mg of N²-cyano-(10H-pyrazino[2,3-b][1,4]benzothiazin-8-yl)acetamidine in acetic acid (10 ml) was added 1.0 ml of 30% hydrogen peroxide and the resulting mixture was heated to 40 to 45° C. for 30 minutes. Then 5 ml of an aqueous solution of 3 g of sodium thiosulfate was added to the reaction mixture. After distilling off the solvent under reduced pressure, the obtained residue was extracted by decantation with dichloromethane/methanol (20%). The extract was distilled under reduced pressure. The residue thus obtained was purified by silica gel column chromatography (eluted with dichloromethane/methanol) to thereby give 110 mg of the title compound as colorless crystals.

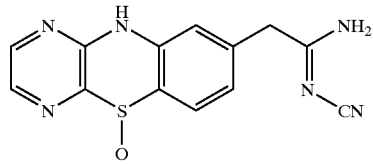

¹H-NMR(DMSO-d₆) δ ppm: 3.90(br.s, 2H), 7.22–7.30(m, 1H), 7.47–7.56(m, 1H), 7.97–8.06(m, 1H), 8.50(d, J=2.1 Hz, 1H), 8.69(d, J=2.1 Hz, 1H)

MS: FAB(+)299(MH⁺)

m.p.: >280° C.

Examples

The following compounds were obtained by treating methyl(10H-pyrazino[2,3-b][1,4]benzothiazin-8-yl)acetimidate hydrochloride with various amines.

| Ex. | Amine | Structural formula | MS | M.p. | NMR |
|---|---|---|---|---|---|
| 1500 | H₂N-(CH₂)₃-NH₂ | 8-(1,4,5,6-tetrahydropyrimidin-2-ylmethyl)-10H-pyrazino[2,3-b][1,4]benzothiazine hydrochloride · HCl | FAB (+) 298 (MH⁺) | >280° C. | ¹H-NMR(DMSO-d₆) δ ppm: 1.76–1.90(m, 2H), 3.23–3.40(m, 4H), 3.58(s, 2H), 6.69(d, J=1.5Hz, 1H), 6.78(dd, J=1.5, 8.4Hz, 1H), 6.91(d, J=8.4Hz, 1H), 7.63(d, J=2.4Hz, 1H), 7.65(d, J=2.4Hz, 1H), 9.61(s, 1H), 9.82–9.90(br.s, 2H) |

| Ex. | Amine | Structural formula | MS | M.p. | NMR |
|---|---|---|---|---|---|
| 1501 | 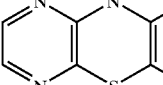 | 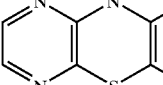 N¹-(2-hydroxyethyl)-(10H-pyrazino[2,3-b][1,4]-benzothiazin-8-yl)acetamidine hydrochloride | FAB (+) 302 (MH⁺) | 174–175° C. | ¹H-NMR(DMSO-d₆) δ ppm: 3.26–3.33(m, 2H), 3.53–3.59(m, 2H), 3.60(s, 2H), 5.07(t, J=5.0Hz, 1H), 6.69(d, J=1.5Hz, 1H), 6.77(dd, J=1.5, 8.0Hz, 1H), 6.80(d, J=8.0Hz, 1H), 7.63(d, J=2.4Hz, 1H), 7.64(d, J=2.4Hz, 1H), 8.74–8.81(br.s, 1H), 9.16–9.23(br.s, 1H), 9.62(s, 1H), 9.74–9.82(br.s, 1H) |
| 1502 | 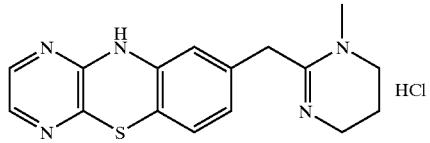 | 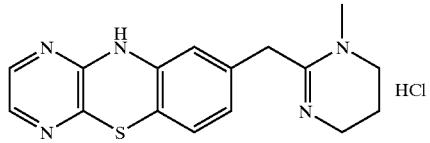 8-(1-methyl-1,4,5,6-tetrahydropyrimidin-2-ylmethyl)-10H-pyrazino[2,3-b][1,4]benzothiazine hydrochloride | FAB (+) 312 (MH⁺) | >280° C. | ¹H-NMR(DMSO-d₆) δ ppm: 1.91–2.00(m, 2H), 2.99(s, 3H), 3.29–3.36(m, 2H), 3.39–3.46(m, 2H), 3.84(s, 2H), 6.68(d, J=1.2Hz, 1H), 6.73(dd, J=1.2, 8.1Hz, 1H), 6.92(d, J=8.1Hz, 1H), 7.65(s, 2H), 9.59(s, 1H), 10.07–10.12(br.s, 1H) |
| 1503 | 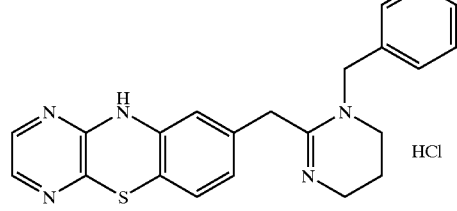 | 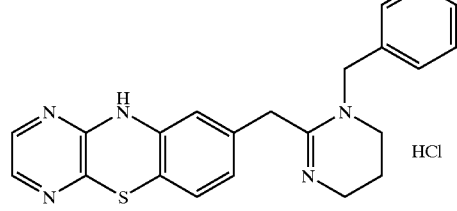 8-(1-benzyl-1,4,5,6-tetrahydropyrimidin-2-ylmethyl)-10H-pyrazino[2,3-b][1,4]benzothiazine hydrochloride | FAB (+) 388 (MH⁺) | 153–155° C. (decompose) | ¹H-NMR(DMSO-d₆) δ ppm: 1.90–2.00(m, 2H), 3.26–3.32(m, 2H), 3.36–3.43(m, 2H), 3.96(s, 2H), 4.57(s, 2H), 6.72(s, 1H), 6.77(d, J=7.8Hz, 1H), 6.89(d, J=7.8Hz, 1H), 7.12–7.18(m, 2H), 7.25–7.37(m, 3H), 7.65(s, 2H), 9.56(s, 1H), 10.38–10.43(br.s, 1H) |
| 1504 | 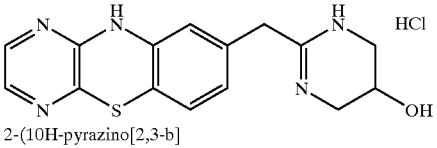 | 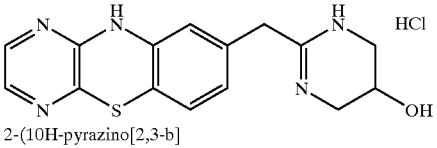 2-(10H-pyrazino[2,3-b][1,4]benzothiazin-8-ylmethyl)-1,4,5,6-tetrahydropyrimidin-4-ol hydrochloride | FAB (+) 314 (MH⁺) | 156–163° C. | ¹H-NMR(DMSO-d₆) δ ppm: 3.15–3.22(m, 2H), 3.31–3.38(m, 2H), 3.60(s, 2H), 4.08–4.13(m, 1H), 5.51(d, J=3.7Hz, 1H), 6.71(d, J=1.4Hz, 1H), 6.78(dd, J=1.4, 8.4Hz, 1H), 6.90(d, J=8.4Hz, 1H), 7.63(d, J=2.0Hz, 1H), 7.65(d, J=2.0Hz, 1H), 9.62(s, 1H), 9.78–9.88(br.s, 2H) |

-continued

| Ex. | Amine | Structural formula | MS | M.p. | NMR |
|---|---|---|---|---|---|
| 1505 | (structure) | N-[2-(10H-pyrazino[2,3-b][1,4]benzothiazin-8-ylmethyl)-1,4,5,6-tetrahydropyrimidin-4-yl]methanesulfonamide hydrochloride | FAB (+) 391 (MH+) | 275–277° C. | ¹H-NMR(DMSO-d₆) δ ppm: 3.20(s, 3H), 3.24–3.31(m, 2H), 3.45–3.52(m, 2H), 3.60(s, 2H), 3.85–3.91(m, 1H), 6.72(s, 1H), 6.80(d, J=7.5Hz, 1H), 6.91(d, J=7.5Hz, 1H), 7.58–7.69(m, 1H), 7.64(d, J=2.5Hz, 1H), 7.65(d, J=2.5Hz, 1H), 9.59(s, 1H) |
| 1506 | (structure) | N-[2-(10H-pyrazino[2,3-b][1,4]benzothiazin-8-ylmethyl)-1,4,5,6-tetrahydropyrimidin-4-yl]-N',N'-dimethylsulfamide | FAB (+) 420 (MH+) | 251–254° C. | ¹H-NMR(DMSO-d₆) δ ppm: 2.66(s, 6H), 3.25–3.33(m, 3H), 3.42–3.49(m, 2H), 3.56–3.60(br.s, 2H), 3.70–3.76(m, 1H), 6.71(d, J=1.4Hz, 1H), 6.80(dd, J=1.4, 7.8Hz, 1H), 6.91(d, J=7.8Hz, 1H), 7.65(s, 2H), 9.59(s, 1H) |
| 1507 | (structure) | N¹,N¹-(3-hydroxypenta-methylene)-(10H-pyrazino[2,3-b][1,4]benzothiazin-8-yl)acetamidine | FAB (+) 342 (MH+) | 265–267° C. | ¹H-NMR(DMSO-d₆) δ ppm: 1.18–1.43(m, 2H), 1.55–1.85(m, 2H), 3.24–3.47(m, 2H), 3.57–3.82(m, 3H), 3.88(s, 2H), 3.93(d, J=4.1Hz, 1H), 6.64(s, 1H), 6.71(d, J=7.8Hz, 1H), 6.91(d, J=7.8Hz, 1H), 7.64(s, 2H), 9.61(s, 1H) |
| 1508 | (structure) | ethyl 4-[1-[1-imino-2-(10H-pyrazino[2,3-b][1,4]benzothiazin-8-yl)ethyl]piperidin-4-yl]-2-methylbutanoate hydrochloride | FAB (+) 454 (MH+) | 219–220° C. | ¹H-NMR(DMSO-d₆) δ ppm: 0.76–0.90(m, 1H), 1.01(d, J=7.0Hz, 3H), 1.06–1.20(m, 2H), 1.13(t, J=6.8Hz, 3H), 1.26–1.39(m, 1H), 1.43–1.55(m, 2H), 1.55–1.66(m, 1H), 1.69–1.81(m, 1H), 2.27–2.38(m, 1H), 3.00–3.12(m, 2H), 3.24–3.36(m, 1H), 3.71–3.82(m, 1H), 3.83–3.88(br.s, 2H), 4.01(q, J=6.8Hz, 2H), 4.08–4.19(m, 1H), 6.63(d, J=1.3Hz, 1H), 6.71(dd, J=1.3, 8.3Hz, 1H), 6.92(d, J=8.3Hz, 1H), 7.64(s, 2H), 8.93–9.03(br.s, 1H), 9.43–9.52(br.s, 1H), 9.61(s, 1H) |

| Ex. | Amine | Structural formula | MS | M.p. | NMR |
|---|---|---|---|---|---|
| 1509 | N-[1-[1-imino-2-(10H-pyrazino[2,3-b][1,4]benzothiazin-8-yl)ethyl]piperidin-4-yl-N',N'-dimethylsulfamide hydrochloride | | FAB (+) 448 (MH+) | 215–218° C. | $^1$H-NMR(DMSO-d$_6$) δ ppm: 1.20(m, 1H), 1.38(m, 1H), 1.53–1.72(m, 1H), 1.72–1.83(m, 1H), 1.86–2.00(m, 1H), 2.50–2.70(m, 1H), 2.62(s, 6H), 3.17–3.43(m, 2H), 3.67–3.80(m, 1H), 3.87(br.s, 2H), 6.66(d, J=2.0Hz, 1H), 6.71(dd, J=2.0, 7.8Hz, 1H), 6.92(d, J=7.8Hz, 1H), 7.34(d, J=7.4Hz, 1H), 7.65(s, 2H), 9.00–9.13(br.s, 1H), 9.50–9.58(br.s, 1H), 9.60(s, 1H) |
| 1510 | N,N-[3-[1-imino-2-(10H-pyrazino[2,3-b][1,4]benzothiazin-8-yl)ethyl]-3-azapentamethylene]acetamide hydrochloride | | FAB (+) 369 (MH+) | 268–269° C. | $^1$H-NMR(DMSO-d$_6$) δ ppm: 1.93–2.03(br.s, 3H), 3.35–3.74(m, 8H), 3.87–3.96(br.s, 2H), 6.64(d, J=1.1Hz, 1H), 6.73(dd, J=1.1, 8.4Hz, 1H), 6.93(d, J=8.4Hz, 1H), 7.65(s, 2H), 9.11–9.26(br.s, 1H), 9.59(s, 1H), 9.60–9.74(br.s, 1H) |
| 1511 | N$^1$, N$^1$-[3-[1-imino-2-(10H-pyrazino[2,3-b][1,4]benzothiazin-8-yl)ethyl]piperidin-4-yl]-3-azapentamethylene]-N$^2$-(methanesulfonyl)formamidine hydrochloride | | FAB (+) 432 (MH+) | 215–218° C. | $^1$H-NMR(DMSO-d$_6$) δ ppm: 2.85 and 2.86(s, total 3H), 3.28–3.31 and 3.46–3.52(m, total 2H), 3.54–3.65(m, 4H), 3.65–3.71 and 3.72–3.79(m, total 2H), 6.66(s, 1H), 6.73(d, J=7.5Hz, 1H), 6.93(d, J=7.5Hz, 1H), 7.64(s, 2H), 8.13 and 8.17(br.s, total 1H), 9.22–9.28 and 9.28–9.36(br.s, total 1H), 9.59(s, 1H), 9.73–9.83(br.s, 1H) |

Example 1512

4-[1-[1-Imino-2-(10H-pyrazino[2,3-b][1,4]benzothiazin-8-yl)-ethyl]piperidin-4-yl]-2-methylbutanoic acid hydrochloride

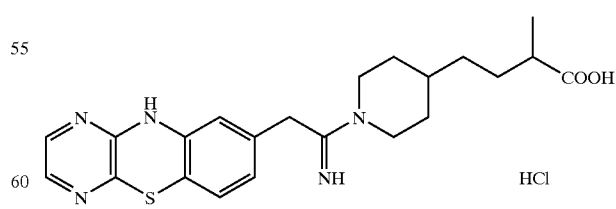

The title compound was obtained by hydrolyzing ethyl 4-[1-[1-imino-2-(10H-pyrazino[2,3-b][1,4]benzothiazin-8-yl)ethyl]piperidin-4-yl]-2-methylbutanoate hydrochloride by the same method as the one of Example 18.

$^1$H-NMR(DMSO-d$_6$) δ ppm: 0.83–1.01(m, 2H), 0.90(d, J=6.9 Hz, 3H), 1.03–1.22(m, 3H), 1.33–1.51(m, 2H), 1.54–1.65(m, 2H), 1.94–2.05(m, 1H), 2.80–2.94(m, 2H), 3.70–3.77(br.s, 2H), 3.94–4.09(m, 2H), 6.65(d, J=8.0 Hz, 1H), 6.66(s, 1H), 6.86(d, J=8.0 Hz, 1H), 7.62(s, 2H), 9.60–9.76(br.s, 1H)

MS: FAB(+)426(MH+)

| Ex. | Amine | Structural formula | NMR |
|---|---|---|---|
| 1514 | H₂N—CN | N²-cyano-(5H-pyrido[3,4-b][1,4]benzothiazin-7-yl)acetamidine dihydrochloride | ¹H-NMR(D₂O) δ ppm: 3.51(s, 2H), 6.40(d, J=6Hz, 1H), 6.44(d, J=2Hz, 1H), 6.63(d, J=8Hz, 1H), 6.70(dd, J=2, 8Hz, 1H), 7.52(d, J=1Hz, 1H), 7.63(dd, J=1, 6Hz, 1H) |
| 1515 | morpholine | N¹,N¹-(3-oxopentamethylene)-(5H-pyrido[3,4-b][1,4]benzothiazin-7-yl)acetamidine | ¹H-NMR(D₂O) δ ppm: 3.44–3.53(m, 6H), 3.68(t, J=5Hz, 2H), 3.75(s, 2H), 6.44–6.48(m, 2H), 6.70(d, J=9Hz, 1H), 6.75(d, J=9Hz, 1H), 7.56(s, 2H), 7.70(d, J=6Hz, 1H) |
| 1516 | prolinamide | [1-[1-imino-2-(5H-pyrido[3,4-b][1,4]benzothiazin-7-yl)ethyl]pyrrolidin-2-yl]carboxamide | ¹H-NMR(D₂O) δ ppm: 1.72–2.34(m, 3H), 3.40–3.78(m, 6H), 6.38–6.48(m, 2H), 6.63–6.77(m, 2H), 7.52–7.57(m, 1H), 7.63–7.70(m, 1H) | m.p.: 166–171° C.

Example 1513

(5H-Pyrido[3,4-b][1,4]benzothiazin-7-yl)acetonitrile

The title compound was obtained by treating 5-methoxymethyl-7-(chloromethyl)-5H-pyrido[3,4-b][1,4]benzothiazine by the same method as the one of Example 53 and then deblocking by the same method as the one of Example 8.

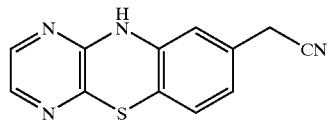

¹H-NMR(CDCl₃) δ ppm: 3.61(s, 2H), 6.18(br.s, 1H), 6.39(d, J=6 Hz, 1H), 6.56(br.s, 1H), 6.78(d, J=8 Hz, 1H), 6.95(d, J=8 Hz, 1H), 7.98(s, 1H), 8.08(d, J=6 Hz, 1H)

Examples

The following compounds were obtained by treating (5H-pyrido[3,4-b][1,4]benzothiazin-7-yl)acetonitrile by the same method as the one of Example 1518 and treating the corresponding imidates thus obtained with various amines by the same method as the one of Example 1520.

Example 1517

(10H-Pyrazino[2,3-b][1,4]benzothiazin-8-yl)acetonitrile

The title compound was obtained from 8-chloromethyl-10H-pyrazino[2,3-b][1,4]benzothiazine by the same method as the one of Example 53.

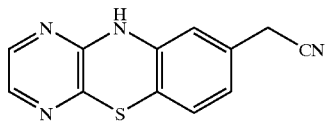

¹H-NMR(DMSO-d₆) δ ppm: 3.88(s, 2H), 6.73(d, J=7.6 Hz, 1H), 6.74(s, 1H), 6.91(d, J=7.6 Hz, 1H), 7.65(s, 2H), 9.60(s, 1H)

Example 1518

Methyl(10H-pyrazino[2,3-b][1,4]benzothiazin-8-yl)acetimidate hydrochloride 480 mg of (10H-pyrazino[2,3-b][1,4]benzothiazin-8-yl)acetonitrile was suspended in a solution of dry methanol (20 ml)/dry dichloromethane and cooled to −20° C. Then dry hydrogen chloride gas was blown thereinto until saturation was attained while paying attention lest the bulk temperature exceed 0° C. Then the reaction mixture was hermetically sealed and allowed to stand under ice-cooling over day and night. Next, the solvent was distilled off under reduced pressure while maintaining the bulk temperature at room temperature or below. Then a small amount of dry methanol was added to the residue and ethyl acetate was gradually added thereto under ultrasonication. The orange crystals thus precipitated were taken up by filtration, washed with diethyl ether and dried under reduced pressure. Thus, 570 mg of the title compound was obtained.

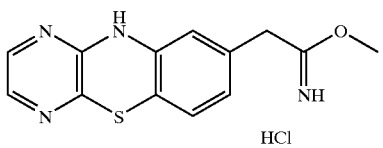

HCl $^1$H-NMR(DMSO-d$_6$) δ ppm: 3.85(s, 2H), 4.05(s, 3H), 6.69(s, 1H), 6.77(d, J=7.9 Hz, 1H), 6.90(d, J=7.9 Hz, 1H), 7.00–7.25(br.s, 2H), 7.53(s, 2H), 9.61(s, 1H)

Example 1519

Methyl N$^2$-cyano(10H-pyrazino[2,3-b][1,4]benzothiazin-8-yl)acetimidate

To 40 ml of an aqueous solution of 1.4 g of monosodium dihydrogenphosphate, 3.2 g of disodium monohydrogenphosphate and 5 g of cyanamide was added 20 ml of acetonitrile. To the obtained solution was gradually added 30 ml of a suspension of 1.2 g of methyl(10H-pyrazino[2,3-b][1,4]benzothiazin-8-yl)acetimidate hydrochloride in acetonitrile. The pH value of the reaction mixture was strictly adjusted to 6.0 to 6.5 by adding aqueous solutions of monosodium dihydrogenphosphate and disodium monohydrogenphosphate respectively. After further adding about 100 ml of acetonitrile, the reaction mixture was stirred at room temperature for 30 minutes and then distributed into an aqueous solution of ammonium chloride and ethyl acetate. The organic layer was extracted, washed with water and dried over anhydrous sodium sulfate. After distilling off the solvent under reduced pressure, 1.2 g of the title compound was obtained as a yellow oily substance almost quantitatively.

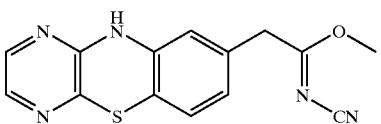

$^1$H-NMR(CDCl$_3$) δ ppm: 3.77(s, 2H), 3.87(s, 3H), 6.50(d, J=1.8 Hz, 1H), 6.75(dd, J=1.8, 8.2 Hz, 1H), 6.81(d, J=8.2 Hz, 1H), 7.09(br.s, 1H), 7.57(d, J=3.2 Hz, 1H), 7.68(d, J=3.2 Hz, 1H)

Example 1520

N$^1$-Methyl-N$^2$-cyano(10H-pyrazino[2,3-b][1,4]benzothiazin-8-yl)acetamidine

To 10 ml of a solution of 420 mg of methyl N$^2$-cyano(10H-pyrazino[2,3-b][1,4]benzothiazin-8-yl)acetimidate in tetrahydrofuran was added 1 ml of a 40% aqueous solution of methylamine and the resulting mixture was stirred at room temperature for 5 minutes. Then the reaction mixture was distributed into water and ethyl acetate. The organic layer was extracted, washed with water and dried over anhydrous sodium sulfate. After adding 3 g of silica gel, the solvent was distilled off under reduced pressure. The residue thus obtained was purified by silica gel column chromatography (eluted with dichloromethane/methanol/aqueous ammonia) to thereby give 340 mg of the title compound as yellow crystals.

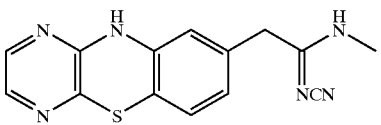

$^1$H-NMR(DMSO-d$_6$) δ ppm: 2.72(s, 3H), 3.64(s, 2H), 6.68(s, 1H), 6.71(d, J=7.3 Hz, 1H), 6.88(d, J=7.3 Hz, 1H), 7.64(s, 2H), 8.86–8.93(br.s, 1H), 9.58(s, 1H)
MS: FAB(+)297(MH$^+$)
m.p.: 233–234° C.(decompose)

Examples

The following compounds were obtained by reacting methyl N$^2$-cyano (10H-pyrazino [2,3-b][1,4]benzothiazin-8-yl)acetimidate with various amines by the same method as the one of Example 1520.

| Ex. | Amine | Structural formula | MS | M.p. | NMR |
|---|---|---|---|---|---|
| 1521 | (dimethylamine structure) | N$^1$,N$^1$-dimethyl-N$^2$-cyano(10H-pyrazino[2,3-b][1,4]benzothiazin-8-yl)acetamidine | FAB (+) 311 (MH$^+$) | 247–249° C. (decompose) | $^1$H-NMR(DMSO-d$_6$) δ ppm: 3.02(s, 3H), 3.04(s, 3H), 3.95(s, 2H), 6.62(d, J=1.7Hz, 1H), 6.65(d, J=7.9Hz, 1H), 6.91(dd, J=1.7, 7.9Hz, 1H), 7.64(s, 2H), 9.54(s, 1H) |

| Ex. | Amine | Structural formula | MS | M.p. | NMR |
|---|---|---|---|---|---|
| 1522 | isopropylamine | $N^1$-(2-propyl)-$N^2$-cyano(10H-pyrazino[2,3-b][1,4]benzothiazin-8-yl)acetamidine | FAB (+) 325 (MH+) | 266–268° C. | $^1$H-NMR(DMSO-$d_6$) δ ppm: 1.12(d, J=6.8Hz, 6H), 3.60(s, 2H), 3.87–3.99(m, 1H), 6.67(d, J=1.7Hz, 1H), 6.69(dd, J=1.7, 7.5Hz, 1H), 6.88(d, J=7.5Hz, 1H), 7.63(d, J=2.4Hz, 1H), 7.64(d, J=2.4Hz, 1H), 8.93(d, J=7.9Hz, 1H), 9.66(s, 1H) |
| 1523 | 2-(aminomethyl)pyridine | $N^1$-(pyridine-2-ylmethyl)-$N^2$-cyano(10H-pyrazino[2,3-b][1,4]benzothiazin-8-yl)acetamidine | FAB (+) 374 (MH+) | 195–196° C. | $^1$H-NMR(DMSO-$d_6$) δ ppm: 3.75(s, 2H), 4.50(s, 2H), 6.75(s, 1H), 6.78(d, J=7.9Hz, 1H), 6.90(d, J=7.9Hz, 1H), 7.27–7.32(m, 1H), 7.29(d, J=7.8Hz, 1H), 7.63–7.66(m, 2H), 7.77(d, J=7.8Hz, 1H), 8.52(d, J=6.0Hz, 1H), 9.45–9.55(m, 1H), 9.62(s, 1H) |
| 1524 | $H_2N$-CH$_2$CH$_2$-OH | $N^1$-(2-hydroxyethyl)-$N^2$-cyano(10H-pyrazino[2,3-b][1,4]benzothiazin-8-yl)acetamidine | FAB (+) 327 (MH+) | 268–270° C. | $^1$H-NMR(DMSO-$d_6$) δ ppm: 3.23–3.29(m, 2H), 3.46–3.52(m, 2H), 3.66(s, 2H), 4.83(t, J=5.4Hz, 1H), 6.69(d, J=1.0Hz, 1H), 6.72(dd, J=1.0, 8.4Hz, 1H), 6.88(d, J=8.4Hz, 1H), 7.63(d, J=2.6Hz, 1H), 7.64(d, J=2.6Hz, 1H), 9.05(t, J=5.1Hz, 1H), 9.59(s, 1H) |
| 1525 | $H_2N$-CH$_2$CH$_2$-SO$_3$H | sodium 2-[$N^1$-[1-($N^2$-cyanoimino)-2-(10H-pyrazino[2,3-b][1,4]benzothiazin-8-yl)ethyl]amino]ethanesulfonate | FAB (+) 413 (MH+), 435 (MNa+) | 213–215° C. | $^1$H-NMR(DMSO-$d_6$) δ ppm: 2.65(t, J=7.4Hz, 2H), 3.39–3.46(m, 2H), 3.62(s, 2H), 6.69(s, 1H), 6.71(d, J=7.7Hz, 1H), 6.86(d, J=7.7Hz, 1H), 7.60–7.65(m, 2H), 8.96(t, J=5.6Hz, 1H), 9.54(s, 1H) |
| 1526 | $H_2N$-(CH$_2$)$_3$-CO$_2$Et | ethyl 4-[$N^1$-[1-($N^2$-cyanoimino)-2-(10H-pyrazino[2,3-b][1,4]benzothiazin-8-yl)ethyl]amino]butanoate | FAB (+) 396 (M+) | 154–155° C. | $^1$H-NMR(DMSO-$d_6$) δ ppm: 1.16(t, J=6.9Hz, 3H), 1.68–1.78(m, 2H), 2.31(t, J=7.6Hz, 2H), 3.16–3.24(m, 2H), 3.63(s, 2H), 4.03(q, J=6.9Hz, 2H), 6.69(d, J=1.6Hz, 1H), 6.71(dd, J=1.6, 7.8Hz, 1H), 6.89(d, J=7.8Hz, 1H), 7.63(d, J=2.4Hz, 1H), 7.64(d, J=2.4Hz, 1H), 8.97(t, J=5.0Hz, 1H), 9.62(s, 1H) |

| Ex. | Amine | Structural formula | MS | M.p. | NMR |
|---|---|---|---|---|---|
| 1527 | 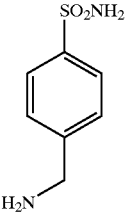 4-[N¹-[1-(N²-cyanoimino)-2-(10H-pyrazino[2,3-b][1,4]benzothiazin-8-yl)ethyl]aminomethyl]benzenesulfonamide | 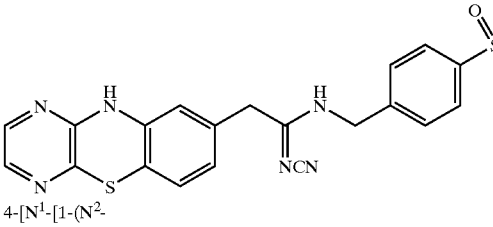 | FAB (+) 452 (MH⁺) | 241–245° C. | ¹H-NMR(DMSO-d₆) δ ppm: 3.72(s, 2H), 4.47(d, J=5.6Hz, 2H), 6.74(d, J=8.1Hz, 1H), 6.75(s, 1H), 6.91(d, J=8.1Hz, 1H), 7.28–7.36(br.s, 2H), 7.43(d, J=7.8Hz, 2H, 7.64(d, J=2.4Hz, 1H), 7.66(d, J=2.4Hz, 1H), 7.78(d, J=7.8Hz, 2H), 9.46(t, J=5.6Hz, 1H), 9.66(s, 1H) |
| 1528 | H₂N—OH | 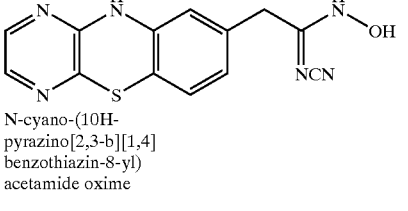 N-cyano-(10H-pyrazino[2,3-b][1,4]benzothiazin-8-yl)acetamide oxime | FAB (+) 298 (M⁺) | 253–256° C. | ¹H-NMR(DMSO-d₆) δ ppm: 3.58(s, 2H), 6.64(d, J=1.1Hz, 1H), 6.68(dd, J=1.1, 8.4Hz, 1H), 6.82(d, J=8.4Hz, 1H), 7.61(d, J=2.2Hz, 1H), 7.63(d, J=2.2Hz, 1H), 7.66–7.71(br.m, 2H), 9.47(s, 1H) |
| 1529 | H₂N—OMe | 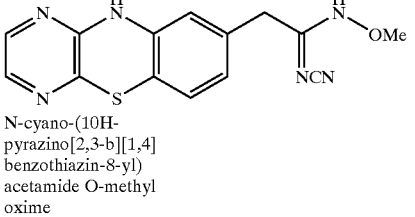 N-cyano-(10H-pyrazino[2,3-b][1,4]benzothiazin-8-yl)acetamide O-methyl oxime | FAB (+) 312 (M⁺) | 172–174° C. | ¹H-NMR(DMSO-d₆) δ ppm: 3.43–3.46(br.s, 2H), 3.73(s, 3H), 6.13–6.25(br.s, 1H), 6.67(d, J=8.0Hz, 1H), 6.68(s, 1H), 6.87(d, J=8.0Hz, 1H), 7.63(d, J=2.0Hz, 1H), 7.64(d, J=2.0Hz, 1H), 9.57(s, 1H) |
| 1530 | H₂N—NH₂ | 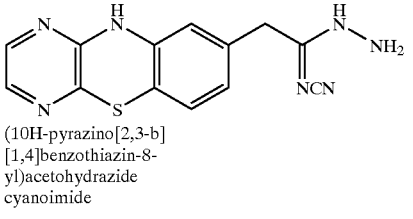 (10H-pyrazino[2,3-b][1,4]benzothiazin-8-yl)acetohydrazide cyanoimide | FAB (+) 297 (M⁺) | | ¹H-NMR(DMSO-d₆) δ ppm: 3.53(s, 2H), 5.50–5.80(br.s, 2H), 6.63(s, 1H), 6.65(d, J=8.5Hz, 1H), 6.78(d, J=8.5Hz, 1H), 7.60(d, J=2.2Hz, 1H), 7.61(d, J=2.2Hz, 1H), 9.36–9.55(br.s, 1H) |
| 1531 | 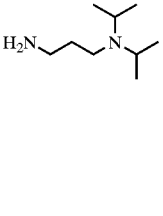 | 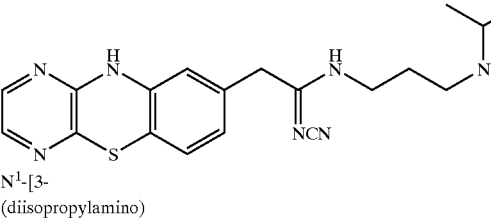 N¹-[3-(diisopropylamino)propyl]-N²-cyano-(10H-pyrazino[2,3-b][1,4]benzothiazin-8-yl)acetamidine | FAB (+) 410 (MH⁺) | >280° C. | ¹H-NMR(DMSO-d₆) δ ppm: 0.91(d, J=6.7Hz, 12H), 2.43–2.49(m, 2H), 2.90(sept, J=6.7Hz, 2H), 3.09–3.17(m, 2H), 3.65(s, 2H), 6.69(d, J=1.1Hz, 1H), 6.72(dd, J=1.1, 8.2Hz, 1H), 6.89(d, J=8.2Hz, 1H), 7.63(d, J=2.4Hz, 1H), 7.65(d, J=2.4Hz, 1H), 8.63(br.t, J=5.7Hz, 1H), 9.57–9.64(br.s, 1H) |

| Ex. | Amine | Structural formula | MS | M.p. | NMR |
|---|---|---|---|---|---|
| 1532 | 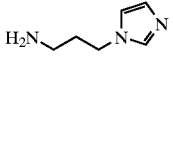 | 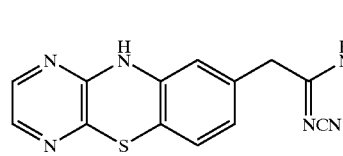<br>$N^1$-[3-(imidazol-1-yl)propyl]-$N^2$-cyano-(10H-pyrazino[2,3-b][1,4]benzothiazin-8-yl)acetamidine | FAB (+) 391 (MH$^+$) | 205–208° C. | $^1$H-NMR(DMSO-d$_6$) δ ppm: 1.86–1.98(m, 2H), 3.10–3.16(m, 2H), 3.64(s, 2H), 3.97(t, J=7.1Hz, 2H), 6.69(s, 1H), 6.72(d, J=8.6Hz, 1H), 6.87(s, 1H), 6.89(d, J=8.6Hz, 1H), 7.14(s, 1H), 7.56(s, 1H), 7.62–7.65(m, 2H), 9.00(t, J=5.4Hz, 1H), 9.63(s, 1H) |

Example 1533

4-[[1-(N-Cyanoimino)-2-(10H-pyrazino[2,3-b][1,4]benzothiazin-8-yl)ethy]amino]butanoic acid The title compound was obtained by hydrolyzing ethyl 4-[$N^1$-[1-($N^2$-cyanoimino)-2-(10H-pyrazino[2,3-b][1,4]benzothiazin-8-yl)ethy]amino]butanoate by the same method as the one of Example 18.

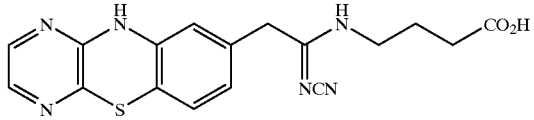

$^1$H-NMR(DMSO-d$_6$) δ ppm: 1.65–1.76(m, 2H), 2.24(t, J=7.5 Hz, 2H), 3.16–3.23(m, 2H), 3.63(s, 2H), 6.69(d, J=7.8 Hz, 1H), 6.71(dd, J=1.7, 7.8 Hz, 1H), 6.89(d, J=1.7 Hz, 1H), 7.62(d, J=2.5 Hz, 1H), 7.64(d, J=2.5 Hz, 1H), 8.99(t, J=5.4 Hz, 1H), 9.62(s, 1H), 12.11(s, 1H)
MS: FAB(+)369(MH$^+$)
m.p.: 217–218° C.(decompose)

Example 1534

$N^2$-Cyano-$N^1$-(10H-pyrazino[2,3-b][1,4]benzothiazin-8-ylmethyl)formamidine 500 mg of 8-aminomethyl-10H-pyrazino[2,3-b][1,4]benzothiazine and 400 mg of ethyl $N^2$-cyanocarboxyimidate were dissolved in a solvent mixture of tetrahydrofuran (5 ml) with methanol (5 ml) and stirred at 40° C. for 1.5 hours. Then the reaction mixture was distributed into an aqueous solution of potassium carbonate and ethyl acetate. The organic layer was extracted, washed with water and dried over anhydrous sodium sulfate. After distilling off the solvent under reduced pressure, the obtained residue was purified by silica gel column chromatography (eluted with dichloromethane/methanol) and recrystallized from methanol/ethyl acetate. Thus, 170 mg of the title compound was obtained as yellow crystals.

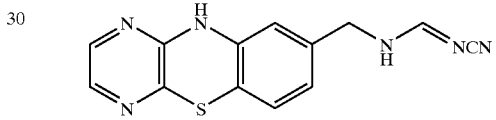

$^1$H-NMR(DMSO-d$_6$) δ ppm: 4.20(d, J=5 Hz, 2H), 6.66(s, 1H), 6.68(d, J=8.0 Hz, 1H), 6.87(d, J=8.0 Hz, 1H), 7.63(s, 2H), 8.41(d, J=4.4 Hz, 1H), 9.30–9.38(m, 1H), 9.54(s, 1H)
MS: FAB(+)282(M$^+$)
m.p.: 224–226° C.

Examples

The following compounds were obtained by treating 8-(aminomethyl)-10-methoxymethyl-10H- pyrazino[2,3-b][1,4]benzothiazine with various imidates by the same method as the one of Example 1534 followed by deblocking in accordance with Example 9.

| Ex. | Imidate | Structural formula | MS | M.p. | NMR |
|---|---|---|---|---|---|
| 1535 | EtO-C(CH3)=NCN | N²-cyano-N¹-(10H-pyrazino[2,3-b][1,4]benzothiazin-8-ylmethyl)acetamidine | FAB(+) 296 (M⁺) | 275–277° C. | ¹H-NMR(DMSO-d₆) δ ppm: 2.22(s, 3H), 4.18(d, J=5.8Hz, 2H), 6.66(s, 1H), 6.68(d, J=7.7Hz, 1H), 6.87(d, J=7.7Hz, 1H), 7.59–7.66(m, 2H), 9.19(t, J=5.8Hz, 1H), 9.52(s, 1H) |
| 1536 | EtO-CH=N-SO2CH3 | N²-(methanesulfonyl)-N¹-(10H-pyrazino[2,3-b][1,4]benzothiazin-8-ylmethyl)formamidine | FAB(+) 335 (M⁺) | 175–176° C. | ¹H-NMR(DMSO-d₆) δ ppm: 2.86(s, 3H), 4.24(s, 2H), 6.68(s, 1H), 6.71(d, J=7.6Hz, 1H), 6.88(d, J=7.6Hz, 1H), 7.63(s, 2H), 8.06(d, J=4.0Hz, 1H), 9.02(br.d, J=4.0Hz, 1H), 9.56(s, 1H) |
| 1537 | EtO-CH=N-(pyridin-2-yl) | N²-(pyridine-2-yl)-N¹-(10H-pyrazino[2,3-b][1,4]benzothiazin-8-ylmethyl)formamidine | FAB(+) 335 (MH⁺) | 137–142° C. | ¹H-NMR(DMSO-d₆) δ ppm: 4.61 and 4.74(s, total 2H), 6.75(d, J=8Hz, 1H), 6.84(m, 1H), 6.94(d, J=8Hz, 1H), 7.28–7.41 and 7.55–7.59(m, total 2H), 7.91–8.02(m, 1H), 8.37–8.45(m, 1H), 9.58–9.63(m, 1H) |

-continued

| Ex. | Imidate | Structural formula | MS | M.p. | NMR |
|---|---|---|---|---|---|
| 1538 | (structure) | (structure) N²-cyano-N¹-methyl-N¹-(10H-pyrazino[2,3-b][1,4]benzothiazin-8-ylmethyl)formamidine | FAB(+) 296 (M⁺) | 197–198° C. | ¹H-NMR(DMSO-d₆) δ ppm: 2.73 and 2.98(s, 3H), 4.37 and 4.41(s, total 2H), 6.63 and 6.68(s, total 1H), 6.69 and 6.71(d, J=7.8Hz, total 1H), 6.89 and 6.92(d, J=7.8Hz, total 1H), 7.63(s, total 2H), 8.53 and 8.67(s, total 1H), 9.51 and 9.53(s, total 1H) |
| 1539 | (structure) | (structure) N²-cyano-N¹-(pyridin-2-yl)-N¹-(10H-pyrazino[2,3-b][1,4]benzothiazin-8-ylmethyl)formamidine | FAB(+) 373 (M⁺) | 208–210° C. | ¹H-NMR(DMSO-d₆) δ ppm: 4.28 and 4.58(s, total 2H), 4.48(s, 2H), 6.61 and 6.72(d, J=7.8Hz, total 1H), 6.64 and 6.67(s, total 1H), 6.83 and 6.90(d, J=7.8Hz, total 1H), 7.26 and 7.36(d, J=8.8Hz, total 1H), 7.28–7.32 and 7.32–7.35(m, total 1H), 7.62–7.66(m, 2H), 7.55–7.80(d, =8.8Hz, 1H), 8.51 and 8.56(d, J=5.3Hz, total 1H), 8.83 and 8.85(s, total 1H), 9.50(s, 1H) |

Example 1540

N¹,N¹-Dimethyl-N²-(10H-pyrazino[2,3-b][1,4]benzothiazin-8-ylmethyl)formamidine 400 mg of 8-(aminomethyl)-10H-pyrazino[2,3-b][1,4]benzothiazine was dissolved in tetrahydrofuran (5 ml)/methanol (5 ml). After adding 250 mg of N,N-dimethylformamide dimethyl acetal, the resulting mixture was heated to 40° C. for 1.5 hours. After distilling off the solvent under reduced pressure, the crystals thus precipitated were taken up by filtration and washed successively with diethyl ether and diisopropyl ether. Thus 400 mg of the title compound was obtained as yellow crystals.

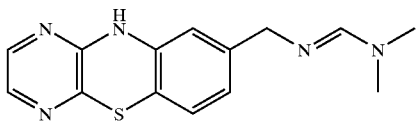

¹H-NMR(DMSO-d$_6$) δ ppm: 2.77(s, 6H), 4.15(s, 2H), 6.64(dd, J=1.4, 7.9 Hz, 1H), 6.68(d, J=1.4 Hz, 1H), 6.79(d, J=7.9 Hz, 1H), 7.42(s, 1H), 7.61(d, J=2.4 Hz, 1H), 7.62(d, J=2.4 Hz, 1H), 9.44(s, 1H)

MS: ESI(+)286(MH⁺)

m.p.: 218–219° C.

Example 1541

N-(10H-Pyrazino[2,3-b][1,4]benzothiazin-8-ylmethyl)-S-methylisothiourea

To a solution of 1.0 g of N-(10H-pyrazino[2,3-b][1,4]benzothiazin-8-ylmethyl)thiourea in acetone (10 ml)/N,N-dimethylformamide (10 ml) was added 1.0 ml of methyl iodide and the resulting mixture was stirred at room temperature for 0.5 hour. Next, the reaction mixture was distributed into an aqueous solution of potassium carbonate and ethyl acetate. The organic layer was extracted and washed with water. After distilling off the solvent under reduced pressure, the crystals thus precipitated were taken up by filtration and washed with ethyl acetate to thereby give 0.900 g of the title compound as yellow crystals.

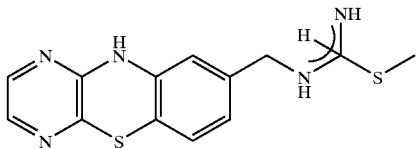

¹H-NMR(DMSO-d$_6$) δ ppm: 2.25(s, 3H), 4.02 and 4.14(s, total 2H), 6.21 and 6.67(br.s, total 2H), 6.68 and 6.69(s, total 1H), 6.75 and 6.80(d, J=8.2 Hz, total 1H), 6.79 and 6.85(s, total 1H), 7.58–7.63(m, 2H), 9.51(s, 1H)

Example 1542

1-(10H-Pyrazino[2,3-b][1,4]benzothiazin-8-ylmethyl)-2-cyanoguanidine 450 mg of N-(10H-pyrazino[2,3-b][1,4]benzothiazin-8-ylmethyl)-S-methylisothiourea and 500 mg of cyanamide were heated in 30 ml of N,N-dimethylformamide to 70° C. for 12 hours. Then the reaction mixture was brought back to room temperature and distributed into water and ethyl acetate. The organic layer was extracted and washed with water. After adding 5 g of silica gel, the solvent was distilled off under reduced pressure. The residue was purified by silica gel column chromatography (eluted with dichloromethane/methanol/aqueous ammonia) to thereby give 340 mg of the title compound as yellow crystals.

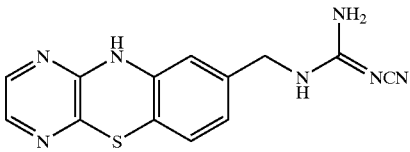

¹H-NMR(DMSO-d$_6$) δ ppm: 4.08(d, J=5.0 Hz, 2H), 6.65 (d, J=8.4 Hz, 1H), 6.66(d, J=1.7 Hz, 1H), 6.68–6.82(br.s, 2H), 6.86(dd, J=1.7, 8.4 Hz, 1H), 7.06–7.25(br.s, 1H), 7.62(d, J=2.8 Hz, 1H), 7.63(d, J=2.8 Hz, 1H), 9.55(s, 1H)

MS: FAB(+)298(MH⁺), 297(M⁺)

m.p.: 246–248° C.

Example 1543

N-(10H-Pyrazino[2,3-b][1,4]benzothiazin-8-ylmethyl)guanidine hydrochloride 330 mg of 8-aminomethyl-10H-pyrazino[2,3-b][1,4]benzothiazine and 400 mg of methylisothiourea hemisulfate were heated under reflux in 10 ml of ethanol for 3 hours. The crystals thus precipitated were taken up by filtration and washed with ethyl acetate. Then these crystals were dissolved in ethyl acetate containing hydrochloric acid and recrystallized from methanol/ethyl acetate to thereby give 30 mg of the title compound as yellow crystals.

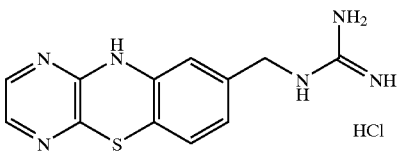

¹H-NMR(DMSO-d$_6$) δ ppm: 4.20(d, J=6.0 Hz, 2H), 6.67 (s, 1H), 6.69(d, J=8.2 Hz, 1H), 6.92(d, J=8.2 Hz, 1H), 7.65(s, 2H), (t, J=6.0 Hz, 1H), 9.63(s, 1H)

MS: FAB(+)273(MH⁺)

m.p.: 279–282° C.

Examples

The following compounds were obtained by treating 8-aminomethyl-10H-pyrazino[2,3-b][1,4]benzothiazine with various isothiourea compounds by the same method as the one of Example 1543.

| Ex. | Isothiourea | Structural formula | MS | M.p. | NMR |
|---|---|---|---|---|---|
| 1544 | ![structure] | 1-(10H-pyrazino[2,3-b][1,4]benzothiazin-8-ylmethyl)-2-nitroguanidine | FAB(+) 318(MH⁺) 317(M⁺) | 226–228° C. | ¹H-NMR(DMSO-d₆) δ ppm: 4.11–4.33(br.s, 2H), 6.67(s, 1H), 6.68(d, J=7.5Hz, 1H), 6.88(d, J=7.5Hz, 1H), 7.62(d, J=2.5Hz, 1H), 7.64(d, J=2.5Hz, 1H), 7.70–8.10(br.s, 2H), 8.85–9.00(br.s, 1H), 9.57(s, 1H) |
| 1545 | ![structure] | 1-(10H-pyrazino[2,3-b][1,4]benzothiazin-8-ylmethyl)-2-(methanesulfonyl)guanidine | FAB(+) 350(M⁺) | 244–245° C. | ¹H-NMR(DMSO-d₆) δ ppm: 2.78(s, 3H), 4.11(d, J=6.0Hz, 2H), 6.54–6.78(br.s, 2H), 6.65(s, 1H), 6.68(d, J=7.9Hz, 1H), 6.85(d, J=7.9Hz, 1H), 7.02–7.15(br.s, 1H), 7.61–7.64(m, 2H), 9.38(s, 1H) |

(Note: MS values in table — for 1544: FAB(+) 318(MH⁺), 317(M⁺); M.p. 226–228° C.)

Example 1546

8-(1,4,5,6-Tetrahydropyrimidin-1-ylmethyl)-10H-pyrazino[2,3-b][1,4]benzothiazine hydrochloride The title compound was obtained by reacting 8-(chloromethyl)-10H-pyrazino[2,3-b][1,4]benzothiazine by the same method as the one of Example 14 by using potassium carbonate as a base.

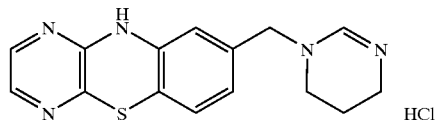

¹H-NMR(DMSO-d₆) δ ppm: 1.84–1.92(m, 2H), 2.18–2.24(m, 2H), 2.24–2.29(m, 2H), 4.48(s, 2H), 6.68(d, J=1.3 Hz, 1H), 6.76(dd, J=1.3, 8.6 Hz, 1H), 6.95(d, J=8.6 Hz, 1H), 7.64(s, 2H), 8.43(d, J=6.5 Hz, 1H), 9.58(s, 1H), 10.08–10.14(br.s, 1H)

MS: FAB(+)298(MH⁺)

m.p.: 238~° C.(decompose)

Example 1547

N-(10H-Pyrazino[2,3-b][1,4]benzothiazin-8-ylmethyl)-N'-methyl-2-nitro-1,1-ethenediamine 0.7 g of 8-aminomethyl-10H-pyrazino[2,3-b][1,4]-benzothiazine and 1.35 g of N-methyl-1-methylthio-2-nitro-1-ethenamine were dissolved in a solvent mixture of tetrahydrofuran (50 ml) with water (3 ml) and stirred at 60° C. for 8 hours. After filtering off the insoluble matters, the filtrate was concentrated under reduced pressure. The residue was purified by silica gel column chromatography (eluted with methanol/dichloromethane) to thereby give 0.14 g of the title compound as yellow crystals.

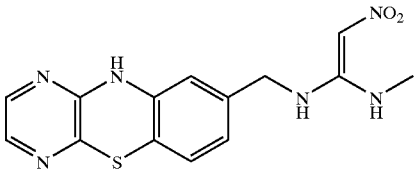

¹H-NMR(CD₃OD) δ ppm: 2.95(br.s, 3H), 4.31(s, 2H), 6.63(s, 2H), 6.74(d, J=8 Hz, 1H), 6.86(d, J=8 Hz, 1H), 7.58(s, 2H)

MS: ESI(+)331(MH⁺)

m.p.: >265° C.(decompose)

Example 1548

4-(10H-Pyrazino[2,3-b][1,4]benzothiazin-8-yl)-3-imino-1,2,5-thiazolidine 1,1-dioxide To 50 ml of a 70% solution of 0.573 g of 10H-pyrazino[2,3-b][1,4]benzothiazine-8-carbaldehyde in ethanol were added 0.48 g of sulfamide and 0.135 g of sodium cyanide and the resulting mixture was heated under reflux for 6 hours. After distilling off the solvent under reduced pressure, the residue was dissolved in 50 ml of a 10% aqueous solution of sodium hydroxide. After filtering off the insoluble matters, the filtrate was ice-cooled and the pH value thereof was adjusted to 2 with 1 N hydrochloric acid. The precipitate thus formed was taken up by filtration and washed with water to thereby give 0.90 g of the title compound as a yellow solid.

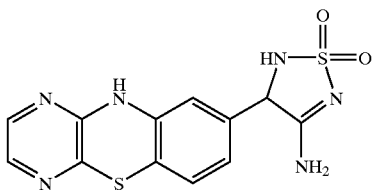

$^1$H-NMR(DMSO-d$_6$) δ ppm: 5.12(d, J=6 Hz, 1H), 6.76(s, 1H), 6.77(d, J=8 Hz, 1H), 6.93(d, J=8 Hz, 1H), 7.54(s, 1H), 7.60(d, J=6 Hz, 1H), 7.65(s, 2H), 8.38(s, 1H), 9.65(s, 1H)
MS: FAB(+)357(M$^+$)

Example 1549

(5H-Pyrido[3,4-b][1,4]benzothiazin-2-yl)carboxamidine hydrochloride

The title compound was obtained by treating (5H-pyrido[3,4-b][1,4]benzothiazin-2-yl)carboxamide successively by the same methods as those of Examples 1518 and 1520.

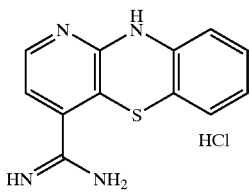

$^1$H-NMR(DMSO-d$_6$) δ ppm: 6.84(t, J=7.5 Hz, 1H), 6.89 (d, J=7.5 Hz, 1H), 6.92(d, J=4.8 Hz, 1H), 7.01(d, J=7.5 Hz, 1H), 7.06(t, J=7.5 Hz, 1H), 7.97(d, J=4.8 Hz, 1H), 9.4–9.5 (br.s, 2H), 9.5–9.6(br.s, 2H), 9.63(s, 1H)
MS: FAB(+)243(MH$^+$)
m.p.: >280° C.

Example 1550

Ethyl(E)-3-[10-(tert-butoxycarbonyl)-10H-pyrazino[2,3-b][1,4]benzothiazin-8-yl]propenoate The title compound was obtained by treating 3-[10-(tert-butoxycarbonyl)-10H-pyrazino[2,3-b][1,4]benzothiazin-8-yl]carbaldehyde by the same method as the one of Production Example 25.

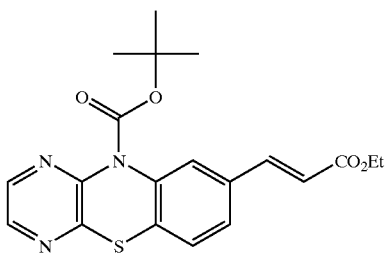

$^1$H-NMR(CDCl$_3$) δ ppm: 1.31(t, J=7.1 Hz, 3H), 1.47(s, 9H), 4.25(q, J=7.1 Hz, 2H), 6.44(d, J=15.8 Hz, 1H), 7.36(s, 2H), 7.64(d, J=15.8 Hz, 1H), 7.82(s, 1H), 8.29(d, J=2.8 Hz, 1H), 8.35(d, J=2.8 Hz, 1H)

Example 1551

Ethyl 3-(10H-pyrazino[2,3-b][1,4]benzothiazin-8-yl)propanoate

The title compound was obtained by treating ethyl(E)-3-(10H-pyrazino[2,3-b][1,4]benzothiazin-8-yl)propenoate by the same method as the one of Example 20.

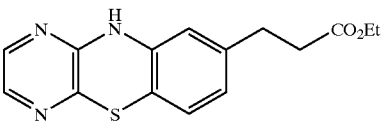

$^1$H-NMR(CDCl$_3$) δ ppm: 1.23(t, J=7.1 Hz, 3H), 2.56(t, J=8.0 Hz, 2H), 2.80(t, J=8.0 Hz, 2H), 4.12(q, J=7.1 Hz, 2H), 6.36(d, J=1.4 Hz, 1H), 6.40–6.48(br.s, 1H), 6.36(d, J=1.4 Hz, 1H), 6.68(dd, J=1.4, 8.1 Hz, 1H), 6.81(d, J=8.1 Hz, 1H), 7.57(d, J=3.0 Hz, 1H), 7.69(d, J=3.0 Hz, 1H)
m.p.: 95–97° C.

Example 1552

Ethyl(E)-3-[10H-pyrazino[2,3-b][1,4]benzothiazin-8-yl]propenoate

The title compound was obtained by treating ethyl(E)-3-[10-(tert-butoxycarbonyl)-10H-pyrazino[2,3-b][1,4]benzothiazin-8-yl]propenoate by the same method as the one of Example 9.

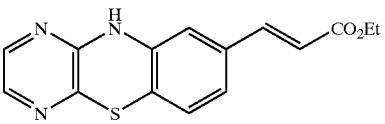

$^1$H-NMR(DMSO-d$_6$) δ ppm: 1.23(t, J=6.8 Hz, 3H), 4.16 (q, J=6.8 Hz, 2H), 6.37(d, J=15.8 Hz, 1H), 6.93(d, J=1.7 Hz, 1H), 6.95(d, J=7.5 Hz, 1H), 7.14(dd, J=1.7, 7.5 Hz, 1H), 7.40(d, J=15.8 Hz, 1H), 7.64(d, J=2.8 Hz, 1H), 7.65(d, J=2.8 Hz, 1H), 9.54(s, 1H)
m.p.: 177–178° C.

Example 1553

(E)-3-[10H-Pyrazino[2,3-b][1,4]benzothiazin-8-yl]propenoic acid

The title compound was obtained as yellow crystals by hydrolyzing ethyl(E)-3-(10H-pyrazino[2,3-b][1,4]benzothiazin-8-yl)propenoate by the same method as the one of Example 18.

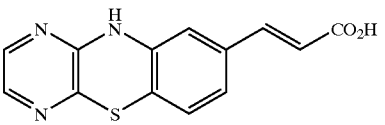

$^1$H-NMR(DMSO-d$_6$) δ ppm: 6.28(d, J=16.3 Hz, 1H), 6.93(d, J=1.5 Hz, 1H), 6.95(d, J=8.1 Hz, 1H), 7.09(dd, J=1.5, 8.1 Hz, 1H), 7.35(d, J=16.3 Hz, 1H), 7.64(d, J=2.9 Hz, 1H), 7.65(d, J=2.9 Hz, 1H), 9.54(s, 1H), 12.34–12.52 (br.s, 1H)
m.p.: 280–281° C.

Example 1554

(10H-Pyrazino[2,3-b][1,4]benzothiazin-8-yl)carbaldehyde

The title compound was obtained as yellow crystals by treating (10-methoxymethyl-10H-pyrazino[2,3-b][1,4]benzothiazin-8-yl)carbaldehyde by the same method as the one of Example 9.

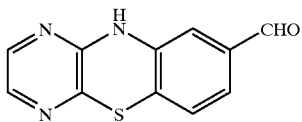

¹H-NMR(DMSO-d₆) δ ppm: 7.13(d, J=8.1 Hz, 1H), 7.14 (d, J=1.5 Hz, 1H), 7.19(dd, J=1.5, 8.1 Hz, 1H), 7.65(d, J=2.7 Hz, 1H), 7.67(d, J=2.7 Hz, 1H), 9.73(s, 1H), 9.74(s, 1H) m.p.: 248–252° C.

Example 1555

(E)-3-(10-Methoxymethyl-10H-pyrazino[2,3-b][1,4]benzothiazin-8-yl)propenenitrile The title compound was obtained as yellow crystals by treating (10-methoxymethyl-10H-pyrazino[2,3-b][1,4]benzothiazin-8-yl)carbaldehyde by the same method as the one of Production Example 25.

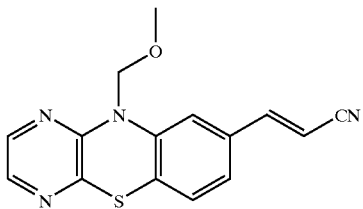

¹H-NMR(CDCl₃) δ ppm: 3.55(s, 3H), 5.28(s, 2H), 5.84(d, J=17.3 Hz, 1H), 7.02(d, J=7.9 Hz, 1H), 7.04(dd, J=1.5, 7.9 Hz, 1H), 7.19(d, J=1.5 Hz, 1H), 7.30(d, J=17.3 Hz, 1H), 7.85(d, J=2.9 Hz, 1H), 7.86(d, J=2.9 Hz, 1H)

Example 1556

(E)-4-(10-Methoxymethyl-10H-pyrazino[2,3-b][1,4]benzothiazin-8-yl)-3-propen-2-one The title compound was obtained as yellow crystals by treating (10-methoxymethyl-10H-pyrazino[2,3-b][1,4]benzothiazin-8-yl)carbaldehyde by the same method as the one of Production Example 25.

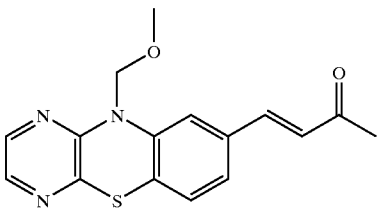

¹H-NMR(CDCl₃) δ ppm: 2.39(s, 3H), 3.56(s, 3H), 5.30(s, 2H), 6.66(d, J=16.2 Hz, 1H), 7.03(d, J=8.3 Hz, 1H), 7.15(dd, J=1.6, 8.3 Hz, 1H), 7.30(d, J=1.6 Hz, 1H), 7.42(d, J=16.2 Hz, 1H), 7.85(d, J=2.9 Hz, 1H), 7.86(d, J=2.9 Hz, 1H)

Example 1557

Ethyl(E)-4-[2-(10-methoxymethyl-10H-pyrazino[2,3-b][1,4]-benzothiazin-8-yl)vinyl]benzoate The title compound was obtained as yellow crystals by treating (10-methoxymethyl-10H-pyrazino[2,3-b][1,4]benzothiazin-8-yl)carbaldehyde by the same method as the one of Production Example 25.

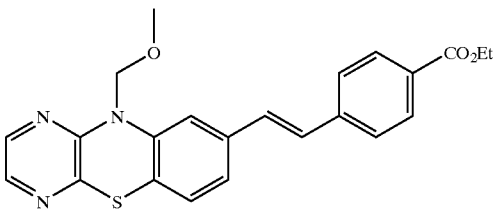

¹H-NMR(DMSO-d₆) δ ppm: 1.41(t, J=6.7 Hz, 3H), 3.59 (s, 3H), 4.38(q, J=6.7 Hz, 2H), 5.34(s, 2H), 7.01(d, J=7.9 Hz, 1H), 7.08(d, J=7.9 Hz, 1H), 7.08(d, J=15.3 Hz, 1H), 7.13(d, J=15.3 Hz, 1H), 7.17(dd, J=1.6, 7.9 Hz, 1H), 7.29(d, J=1.6 Hz, 1H), 7.56(d, J=8.4 Hz, 2H), 7.84(d, J=2.9 Hz, 1H), 7.85(d, J=7.9 Hz, 2H), 8.03(d, J=8.4 Hz, 2H)

Examples

The following compounds were obtained by treating (E)-3-(10-methoxymethyl-10H-pyrazino[2,3-b][1,4]benzothiazin-8-yl)propenenitrile, (E)-4-(10-methoxymethyl-10H-pyrazino[2,3-b][1,4]benzothiazin-8-yl)-3-propen-2-one and ethyl(E)-4-[2-(10-methoxymethyl-10H-pyrazino[2,3-b][1,4]benzothiazin-8-yl)vinyl]benzoate by the same method as the one of Example 9.

| Ex. | Structural formula | MS | NMR |
|---|---|---|---|
| 1558 | (E)-3-(10H-pyrazino[2,3-b][1,4]benzothiazin-8-yl)propenenitrile | 296–299° C. | ¹H-NMR(DMSO-d₆) δ ppm: 6.21(d, J=16.8Hz, 1H), 6.84(d, J=1.6Hz, 1H), 6.98(d, J=8.0Hz, 1H), 7.08(d, J=1.6, 8.0Hz, 1H), 7.46(d, J=16.8Hz, 1H), 7.64(d, J=2.8Hz, 1H), 7.65(d, J=2.8Hz, 1H), 9.63(s, 1H) |

-continued

| Ex. | Structural formula | MS | NMR |
|---|---|---|---|
| 1559 | (E)-4-(10H-pyrazino[2,3-b][1,4]benzothiazin-8-yl)-3-propen-2-one | 214–215° C. | ¹H-NMR(DMSO-d$_6$) δ ppm: 2.31(s, 3H), 6.54(d, J=16.3Hz, 1H), 6.96(d, J=1.4Hz, 1H), 6.97(d, J=8.4Hz, 1H), 7.11(dd, J=1.4, 8.4Hz, 1H), 7.40(d, J=16.3Hz, 1H), 7.64(d, J=2.7Hz, 1H), 7.66(d, J=2.7Hz, 1H), 9.58(s, 1H) |
| 1560 | ethyl (E)-4-[2-(10H-pyrazino[2,3-b][1,4]benzothiazin-8-yl)vinyl]benzoate | 235–236° C. | ¹H-NMR(DMSO-d$_6$) δ ppm: 1.31(t, J=6.5Hz, 3H), 4.29(q, J=6.5Hz, 2H), 6.94(d, J=8.3Hz, 1H), 6.95(d, J=1.4Hz, 1H), 7.09(dd, J=1.4, 8.3Hz, 1H), 7.12(d, J=16.7Hz, 1H), 7.23(d, J=16.7Hz, 1H), 7.64(d, J=2.2Hz, 1H), 7.65(d, J=2.2Hz, 1H), 7.71(d, J=8.5Hz, 2H), 7.92(d, J=8.5Hz, 2H), 9.57(s, 1H) |

Example 1561

(E)-4-[2-(10H-Pyrazino [2,3-b][1,4]benzothiazin-8-yl)vinyl]-benzoic acid

The title compound was obtained as yellow crystals by hydrolyzing ethyl(E)-4-[2-(10H-pyrazino[2,3-b][1,4]benzothiazin-8-yl)vinyl]benzoate by the same method as the one of Example 18.

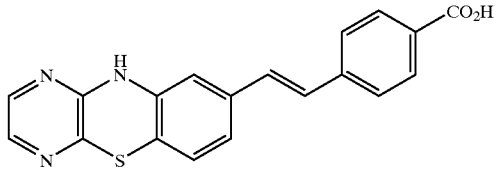

¹H-NMR(DMSO-d$_6$) δ ppm: 6.93(dd, J=1.6, 8.1 Hz, 1H), 6.95(d, J=1.6 Hz, 1H), 7.08(d, J=8.1 Hz, 1H), 7.12(d, J=16.6 Hz, 1H), 7.21(d, J=16.6 Hz, 1H), 7.62–7.67(m, 2H), 7.62–7.67(m, 2H), 7.69(d, J=8.1 Hz, 2H), 7.90(d, J=8.1 Hz, 2H), 9.58(s, 1H)

m.p.: 322–325° C.

Example 1562

(10H-Pyrazino[2,3-b][1,4]benzothiazin-8-yl) carboxylic acid

The title compound was obtained as yellow crystals by hydrolyzing methyl(10H-pyrazino[2,3-b][1,4]benzothiazin-8-yl)carboxylate by the same method as the one of Example 18.

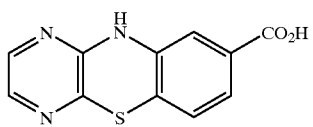

¹H-NMR(DMSO-d$_6$) δ ppm: 6.99(d, J=8.5 Hz, 1H), 7.28 (dd, J=1.6, 8.5 Hz, 1H), 7.30(d, J=1.6 Hz, 1H), 7.63(d, J=2.5 Hz, 1H), 7.65(d, J=2.5 Hz, 1H), 9.63(s, 1H)

m.p.: 321–323° C.(decmpose)

Example 1563

(E)-8-(2-Benzenesulfonylvinyl)-10H-pyrazino[2,3-b][1,4]benzothiazine

The title compound was obtained as yellow crystals by treating (E)-8-(2-benzenesulfonylvinyl)-10-methoxymethyl-10H-pyrazino[2,3-b][1,4]benzothiazine by the same method as the one of Example 9.

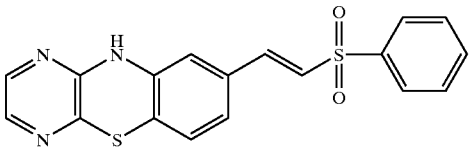

¹H-NMR(DMSO-d$_6$) δ ppm: 6.87(d, J=1.7 Hz, 1H), 6.97 (d, J=8.1 Hz, 1H), 7.17(dd, J=1.7, 8.1 Hz, 1H), 7.35(d, J=15.4 Hz, 1H), 7.40(d, J=15.4 Hz, 1H), 7.61–7.67(m, 2H), 7.63(d, J=2.9 Hz, 1H), 7.65(d, J=2.9 Hz, 1H), 7.69–7.74(m, 1H), 7.88–7.92(m, 2H), 9.57(s, 1H)

m.p. 201–202° C.

Example 1564

8-Vinyl-10H-pyrazino[2,3-b][1,4]benzothiazine

The title compound was obtained as yellow crystals by treating 8-vinyl-10-methoxymethyl-10H-pyrazino[2,3-b][1,4]benzothiazine by the same method as the one of Example 9.

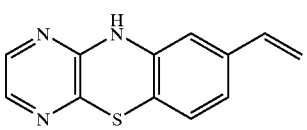

¹H-NMR(CDCl$_3$) δ ppm: 5.30(d, J=10.7 Hz, 1H), 5.37(d, J=17.6 Hz, 1H), 6.55(dd, J=10.7, 17.6 Hz, 1H), 6.79(d, J=1.6

Hz, 1H), 6.82(d, J=8.5 Hz, 1H), 6.99(dd, J=1.6, 8.5 Hz, 1H), 7.16(d, J=3.5 Hz, 1H), 7.59(d, J=3.5 Hz, 1H), 11.05–11.15 (br.s, 1H)

m.p.: 140–142° C.

Example 1565

1-(10H-Pyrazino[2,3-b][1,4]benzothiazin-8-yl)-1,3-butadione

The title compound was obtained as yellow crystals by treating 1-(10-methoxymethyl-10H-pyrazino[2,3-b][1,4]benzothiazin-8-yl)-1,3-butadione by the same method as the one of Example 9.

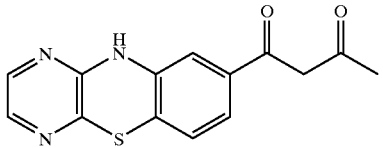

¹H-NMR(DMSO-d₆) δ ppm: 2.14 and 2.19(s, total 3H, enol:keto=4:1), 4.11(s, initial 2H, keto), 6.34(s, initial 1H, enol), 7.03 and 7.05(d, J=8.1 Hz, total 1H, 4:1), 7.19 and 7.27(d, J=1.8 Hz, total 1H, 1:4), 7.32 and 7.33(dd, J=1.8, 8.1 Hz, total 1H, 1:4), 7.64(d, J=3.2 Hz, total 1H), 7.66(d, J=3.2 Hz, total 1H), 9.52 and 9.54(br.s, total 1H, 4:1)

m.p.: 218–220° C.

Example 1566

Methyl (anti)-(3-azabicyclo[3.3.1]non-9-yl)acetate hydrochloride 25.6 g of ethyl (anti)-(3-methyl-3-azabicyclo[3.3.1]non-9-yl)acetate was cooled to 0° C. and 25 ml of 1-chloroethyl chloroformate was dropped thereinto. After stirring at the same temperature for 15 minutes, the mixture was reacted for an additional 1 hour. Then it was brought back to room temperature and the 1-chloroethyl chloroformate was distilled off under reduced pressure. 400 ml of methanol was added to the residue and the resulting mixture was heated under reflux for 2 hours. After distilling off the solvent under reduced pressure, 20 ml of methanol and 200 ml of ethyl acetate were added to the residue. The crystals thus precipitated were collected by filtration to thereby give 20 g of methyl (anti)-(3-azabicyclo[3.3.1]non-9-yl)acetate hydrochloride.

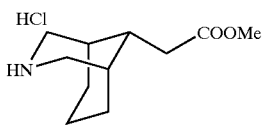

¹H-NMR(CDCl₃) δ ppm: 1.62–1.90(m, 5H), 1.91(br.s, 2H), 2.16–2.34(m, 2H), 2.51(d, J=8 Hz, 2H), 3.20–3.32(m, 2H), 3.47(dd, J=4, 13 Hz, 2H), 3.66(d, J=1 Hz, 3H), 8.51 (br.s, 1H), 10.08(br.s, 1H)

Example 1567

Methyl (anti)-[3-(10H-pyrazino[2,3-b][1,4]benzothiazin-8-ylmethyl)-3-azabicyclo[3.3.1]non-9-yl]acetate To 12 ml of a solution of 1.00 g of 8-chloromethyl-10H-pyrazino[2,3-b][1,4]benzothiazine in 1,2-dichloroethane were added 1.59 g of methyl (anti)-(3-azabicyclo[3.3.1]non-9-yl)acetate hydrochloride and 2.1 ml of diisopropylamine and the resulting mixture was heated under reflux for 1 hour. Then the reaction mixture was brought back to room temperature and purified as it was by silica gel column chromatography (eluting with hexane/ethyl acetate) to thereby give 1.24 g of the title compound as a yellow powder.

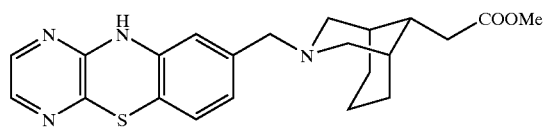

¹H-NMR(DMSO-d₆) δ ppm: 1.34–1.48(m, 3H), 1.57(br.s, 2H), 1.60–1.76(m, 2H), 1.82–1.92(m, 1H), 2.15(br.d, J=10 Hz, 2H), 2.46(d, J=8 Hz, 2H), 2.44–2.6(m, 1H), 2.86(br.d, J=10 Hz, 2H), 3.15(s, 2H), 3.56(s, 3H), 6.68(dd, J=1, 8 Hz, 1H), 6.71(d, J=1 Hz, 1H), 6.83(d, J=8 Hz, 1H), 7.61(d, J=3 Hz, 1H), 7.62(d, J=3 Hz, 1H), 9.55(s, 1H)

m.p.: 127–129° C.

MS: ESI(+)411(MH⁺)

Example 1568

(endo,anti)-[3-(10H-Pyrazino[2,3-b][1,4]benzothiazin-8-ylmethyl)-3-azabicyclo[3.3.1]non-9-yl]acetic acid 0.45 g of the title compound was obtained as a yellow powder by treating 0.5 g of methyl (anti)-[3-(10H-pyrazino[2,3-b][1,4]benzothiazin-8-methyl)-3-azabicyclo[3.3.1]non-9-yl]acetate by the same method as described in Example 18.

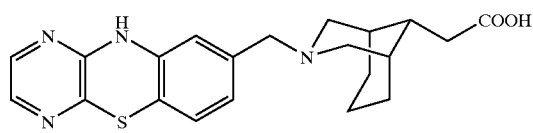

¹H-NMR(DMSO-d₆) δ ppm: 1.34–1.48(m, 3H), 1.58(br.s, 2H), 1.60–1.76(m, 2H), 1.80–1.90(m, 1H), 2.14(br.d, J=10 Hz, 2H), 2.33(d, J=8 Hz, 2H), 2.44–2.60(m, 1H), 2.85(br.d, J=10 Hz, 2H), 3.15(s, 2H), 6.67(d, J=8 Hz, 1H), 6.72(s, 1H), 6.82(d, J=8 Hz, 1H), 7.60(d, J=3 Hz, 1H), 7.62(d, J=3 Hz, 1H), 9.54(s, 1H)

m.p.: 215–217° C.

MS: FAB(+)397(MH⁺)

Example 1569

8-(tert-Butyldimethylsiloxymethyl)-10H-pyrazino[2,3-b][1,4]benzothiazine 10 g of (10H-pyrazino[2,3-b][1,4]benzothiazin-8-yl)methanol was subjected to the procedure described in Example 179 to thereby give 13 g of the title compound as a yellow solid.

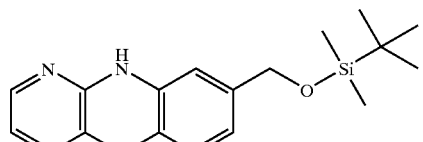

¹H-NMR(CDCl₃) δ ppm: 0.63(s, 6H), 0.88(s, 9H), 4.54(s, 2H), 6.48(s, 1H), 6.71(d, J=8 Hz, 1H), 6.80(d, J=8 Hz, 1H), 7.53(s, 1H), 7.64(s, 1H)

Example 1570

10-Acetyl-8-(tert-butyldimethylsiloxymethyl)-10H-pyrazino[2,3-b][1,4]benzothiazine

To a solution of 4.0 g of 8-(tert-butyldimethylsiloxymethyl)-10H-pyrazino[2,3-b][1,4]benzothiazine in 50 ml of N,N-dimethylformamide was added 0.73 g of sodium hydride (60%) and the resulting mixture was stirred for 10 minutes. After adding 1.4 ml of acetyl chloride thereto, the resulting mixture was reacted at room temperature for 10 minutes. After adding water followed by extraction with ethyl acetate, the extract was washed with a saturated aqueous solution of sodium chloride and dried over anhydrous magnesium sulfate. After distilling off the solvent under reduced pressure, the residue was purified by silica gel column chromatography (eluting with ethyl acetate/hexane) to thereby give 2.5 g of the title compound as a yellow oily substance.

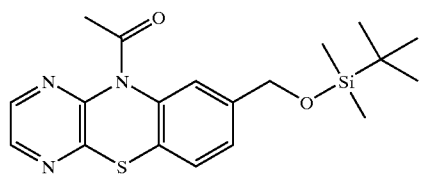

$^1$H-NMR(CDCl$_3$) δ ppm: 0.1(s, 6H), 0.93(s, 9H), 2.28(s, 3H), 4.76(s, 2H), 7.24–7.28(m, 1H), 7.38(d, J=8 Hz, 1H), 7.66(d, J=2 Hz, 1H), 8.32(d, J=3 Hz, 1H), 8.35(d, J=3 Hz, 1H)

Example 1571

(10-Acetyl-10H-pyrazino[2,3-b][1,4]benzothiazin-8-yl)methanol

2.5 g of 10-acetyl-8-(tert-butyldimethylsiloxymethyl)-10H-pyrazino[2,3-b][1,4]benzothiazine was subjected to the procedure described in Example 181 to thereby give 1.0 g of the title compound as an oily substance.

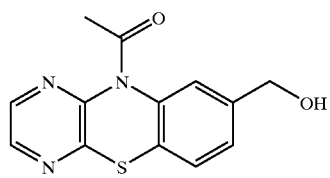

$^1$H-NMR(CDCl$_3$) δ ppm: 2.29(s, 3H), 4.73(s, 2H), 7.29 (dd, J=2, 8 Hz, 1H), 7.33(d, J=8 Hz, 1H), 7.74(m, 1H), 8.25(d, J=3 Hz, 1H), 8.28(d, J=3 Hz, 1H)

Example 1572

(10-Acetyl-10H-pyrazino[2,3-b][1,4]benzothiazin-8-yl)carboxaldehyde

1.0 g of (10-acetyl-10H-pyrazino[2,3-b][1,4]benzothiazin-8-yl)methanol was subjected to the procedure described in Example 174 to thereby give 0.6 g of the title compound as a pale brown solid.

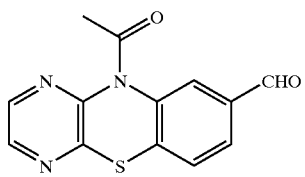

$^1$H-NMR(CDCl$_3$) δ ppm: 2.34(s, 3H), 7.57(d, J=8 Hz, 1H), 7.80(dd, J=2, 8 Hz, 1H), 8.22(d, J=2 Hz, 1H), 8.38(d, J=3 Hz, 1H), 8.41(d, J=3 Hz, 1H), 10.2(s, 1H)

Example 1573

4-[1-(10-Acetyl-10H-pyrazino[2,3-b][1,4]benzothiazin-8-ylmethyl)piperidin-4-yl]-2-methylbutanoic acid

To a solution of 0.13 g of (10-acetyl-10H-pyrazino[2,3-b][1,4]benzothiazin-8-yl)carboxaldehyde and 0.13 g of 4-(piperidin-4-yl)-2-methylbutanoic acid in 20 ml of acetonitrile were added 51 mg of sodium cyanoborohydride and 0.1 ml of acetic acid and the resulting mixture was reacted at room temperature for 12 hours. The reaction mixture was concentrated under reduced pressure and the residue was purified by silica gel column chromatography (eluted with methanol/dichloromethane) to thereby give 70 mg of the title compound as a colorless oily substance.

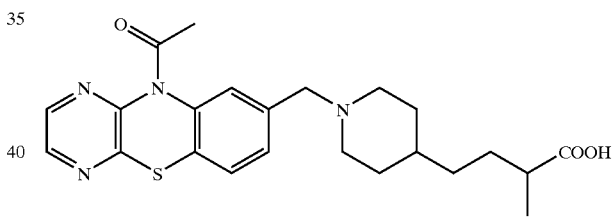

$^1$H-NMR(CD$_3$OD) δ ppm: 1.14(d, J=7 Hz, 3H), 1.25–1.40(m, 2H), 1.35–1.50(m, 3H), 1.50–1.73(m, 2H), 1.93–2.05(m, 2H), 2.30(s, 3H), 2.33–2.45(m, 1H), 2.97–3.10(m, 2H), 3.45–3.55(m, 2H), 4.35(s, 2H), 7.46(dd, J=2, 8 Hz, 1H), 7.64(d, J=8 Hz, 1H), 7.84(d, J=2 Hz, 1H), 8.45(s, 2H)

MS: FAB(+)441(MH$^+$)

Example 1574

10-(Methoxycarbonyl)-8-(tert-butyldimethylsiloxymethyl)-10H-pyrazino[2,3-b][1,4]benzothiazine

4.0 g of 8-(tert-butyldimethylsiloxymethyl)-10H-pyrazino[2,3-b][1,4]benzothiazine was subjected to the procedure described in Example 1570 but using methyl chlorocarbonate instead of acetyl chloride to thereby give 2.5 g of the title compound as a yellow oily substance.

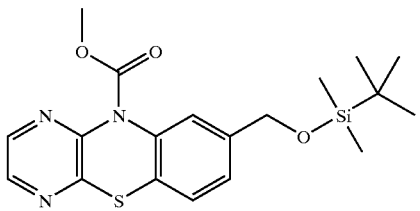

¹H-NMR(CDCl₃) δ ppm: 0.1(s, 6H), 0.94(s, 9H), 3.83(s, 3H), 4.75(s, 2H), 7.18–7.24(m, 1H), 7.34(d, J=8 Hz, 1H), 7.63(d, J=2 Hz, 1H), 8.3–8.34(m, 1H), 8.34–8.38(m, 1H)

Example 1575

[10-(Methoxycarbonyl)-10H-pyrazino[2,3-b][1,4]benzothiazin-8-yl]methanol 2.5 g of 10-(methoxycarbonyl)-8-(tert-butyldimethylsilyloxymethyl)-10H-pyrazino[2,3-b][1,4]benzothiazine was subjected to the procedure described in Example 181 to thereby give 1.0 g of the title compound as a yellow oily substance.

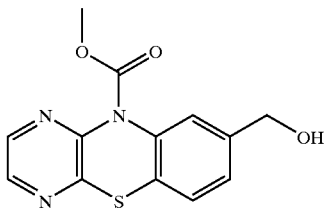

¹H-NMR(CDCl₃) δ ppm: 3.84(s, 3H), 4.72–4.76(m, 2H), 7.28(dd, J=2, 8 Hz, 1H), 7.39(d, J=8 Hz, 1H), 7.67–7.70(m, 1H), 8.33(d, J=3 Hz, 1H), 8.37(d, J=3 Hz, 1H)

Example 1576

[10-(Methoxycarbonyl)-10H-pyrazino[2,3-b][1,4]benzothiazin-8-yl]carboxaldehyde 1.8 g of [10-(methoxycarbonyl)-10H-pyrazino[2,3-b][1,4]benzothiazin-8-yl]methanol was subjected to the procedure described in Example 174 to thereby give 0.8 g of the title compound as pale brown crystals.

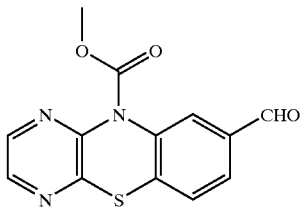

¹H-NMR(CDCl₃) δ ppm: 3.87(s, 3H), 7.54(d, J=8 Hz, 1H), 7.78(dd, J=2, 8 Hz, 1H), 8.16(d, J=2 Hz, 1H), 8.36(d, J=3 Hz, 1H), 8.41(d, J=3 Hz, 1H), 10.01(s, 1H)

Example 1577

4-[1-(10-(Methoxycarbonyl)-10H-pyrazino[2,3-b][1,4]benzothiazin-8-ylmethyl)piperidin-4-yl]-2-methylbutanoic acid 0.8 g of [10-(methoxycarbonyl)-10H-pyrazino[2,3-b][1,4]benzothiazin-8-yl]carboxaldehyde was subjected to the procedure described in Example 1573 to thereby give 0.29 g of the title compound as a yellow amorphous substance.

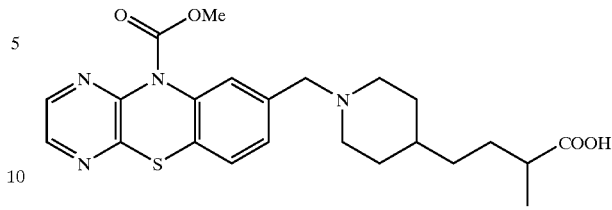

¹H-NMR(CD₃OD) δ ppm: 1.09(d, J=7 Hz, 3H), 1.20–1.45(m, 5H), 1.45–1.70(m, 2H), 1.85–2.0(m, 2H), 2.28–2.40(m, 1H), 2.90–3.0(m, 2H), 3.35–3.50(m, 2H), 3.77(s, 3H), 4.29(s, 2H), 7.40(dd, J=2, 8 Hz, 1H), 7.56(d, J=8 Hz, 1H), 7.81(d, J=2 Hz, 1H), 8.37(d, J=3 Hz, 1H), 8.38(d, J=3 Hz, 1H)

Example 1578

Methyl (anti)-[3-[10-(methoxycarbonyl)-10 H-pyrazino[2,3-b][1,4]benzothiazin-8-ylmethyl]-3-azabicyclo[3.3.1]non-9-yl]acetate 1.0 g of methyl (anti)-[3-(10H-pyrazino[2,3-b][1,4]benzothiazin-8-ylmethyl)-3-azabicyclo[3.3.1]non-9-yl]acetate was treated in the same manner as the one of Example 1574 to thereby give 0.14 g of the title compound as a pale yellow solid.

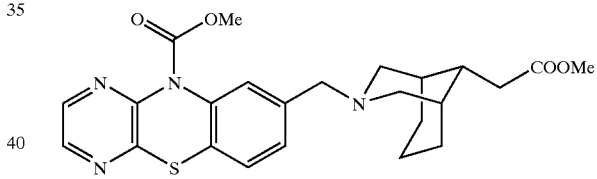

¹H-NMR(CDCl₃) δ ppm: 1.4–1.6(m, 3H), 1.62–1.68(m, 2H), 1.68–1.84(m, 2H), 2.00–2.08(m, 1H), 2.31(br.d, J=11 Hz, 2H), 2.50(d, J=8 Hz, 2H), 2.52–2.68(m, 1H), 2.9–2.98(m, 2H), 3.41(s, 2H), 3.66(s, 3H), 3.83(s, 3H), 7.21(dd, J=2, 8 Hz, 1H), 7.32(d, J=8 Hz, 1H), 7.63(d, J=2 Hz, 1H), 8.32(d, J=3 Hz, 1H), 8.36(d, J=3 Hz, 1H)

m.p.: 106–108° C.

MS: ESI(+)469(MH⁺)

Example 1579

Methyl (anti)-[3-(10-acetyl-10H-pyrazino[2,3-b][1,4]benzothiazin-8-ylmethyl)-3-azabicyclo[3.3.1]non-9-yl]acetate 1.0 g of methyl (anti)-[3-(10H-pyrazino[2,3-b][1,4]benzothiazin-8-ylmethyl)-3-azabicyclo[3.3.1]non-9-yl]acetate was subjected to the procedure described in Example 1570 to thereby give 0.4 g of the title compound as a pale yellow solid.

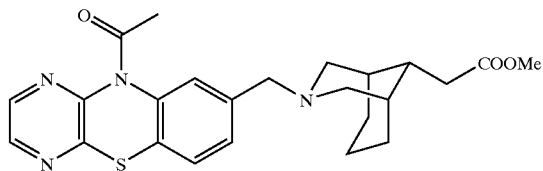

¹H-NMR(CDCl₃) δ ppm: 1.44–1.60(m, 3H), 1.60–1.68 (m, 2H), 1.68–1.82(m, 2H), 1.96–2.08(m, 1H), 2.28(s, 3H), 2.31(br.d, J=11 Hz, 2H), 2.49(d, J=8 Hz, 2H), 2.50–2.70(m, 1H), 2.90–2.98(m, 2H), 3.41(s, 2H), 3.66(s, 3H), 7.23(dd, J=1, 8 Hz, 1H), 7.36(d, J=8 Hz, 1H), 7.66(s, 1H), 8.3–8.38 (m, 2H)

m.p.: 160–162° C.

MS: ESI(+)453(MH⁺)

Example 1580

Methyl (anti)-[3-[10-(benzyloxycarbonyl)-10H-pyrazino[2,3-b][1,4]benzothiazin-8-ylmethyl]-3-azabicyclo[3.3.1]non-9-yl]acetate 1.0 g of methyl (anti)-[3-(10H-pyrazino[2,3-b][1,4]benzotiazin-8-ylmethyl)-3-azabicyclo[3.3.1]non-9-yl]acetate was subjected to the procedure described in Example 1570 but using benzyl chlorocarbonate instead of acetyl chloride to thereby give 0.4 g of the title compound as a pale brown oily substance.

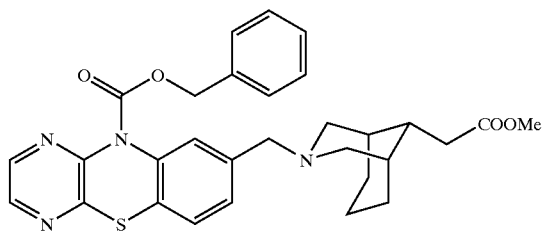

¹H-NMR(CDCl₃) δ ppm: 1.4–1.6(m, 3H), 1.56–1.66(m, 2H), 1.66–1.80(m, 2H), 1.96–2.24(m, 1H), 2.27(br.d, J=11 Hz, 2H), 2.49(d, J=8 Hz, 2H), 2.46–2.68(m, 1H), 2.86–2.94 (m, 2H), 3.37(s, 2H), 3.67(s, 3H), 5.28(s, 2H), 7.10–7.40(m, 7H), 7.61(d, J=1 Hz, 1H), 8.31(d, J=2 Hz, 1H), 8.36(d, J=2 Hz, 1H)

MS: ESI(+)545(MH⁺)

What is claimed is:

1. A benzopiperidine derivative represented by the formula:

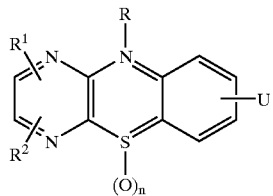

and salts and hydrates thereof, wherein

R¹ and R² may be the same or different and each represents hydrogen or $C_{1-6}$ lower alkyl; and U represents:
1) a group represented by the formula:

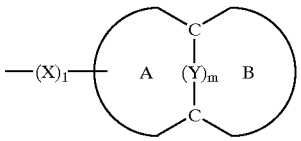

wherein l and m may be the same or different and each represents 0 or 1; and wherein X and Y each represents $C_{1-6}$ lower alkylene optionally substituted with one to three substituents selected from H, =O, —OH, —COOH, $C_{1-6}$ lower alkyl, —C(O)—$C_{1-6}$ lower alkyl, —C(O)O—$C_{1-6}$ lower alkyl, $C_{1-6}$ lower alkoxy, optionally having one to three heteroatoms selected from O, N, or S, $C_{1-6}$ lower alkenylene optionally substituted with one to three substituents selected from H, =O, —OH, —COOH, $C_{1-6}$ lower alkyl, —C(O)—$C_{1-6}$ lower alky, —C(O)O—$C_{1-6}$ lower alkyl, $C_{1-6}$ lower alkoxy, optionally having one to three heteroatoms selected from O, N, or S, $C_{1-6}$ lower alkynylene optionally substituted with one to three substituents selected from H, =O, —OH, —COOH, $C_{1-6}$ lower alkyl, —C(O)—$C_{1-6}$ lower alkyl, —C(O)O—$C_{1-6}$ lower alkyl, $C_{1-6}$ lower alkoxy, optionally having one to three heteroatoms selected from O, N, or S; and wherein the ring A represents a cycloalkyl ring optionally substituted with one to three substituents selected from H, =O, —OH, —COOH, $C_{1-6}$ lower alkyl, —C(O)—$C_{1-6}$ lower alkyl, —C(O)O—$C_{1-6}$ lower alkyl, $C_{1-6}$ lower alkoxy, optionally having one to three heteroatoms selected from O or N; and wherein the ring B represents a ring optionally having one to three double bonds in the ring selected from the following ones:

a) a cycloalkyl ring optionally substituted with one to three substituents selected from H, =O, —OH, —COOH, $C_{1-6}$ lower alkyl, —C(O)—$C_{1-6}$ lower alkyl, —C(O)O—$C_{1-6}$ lower alkyl, $C_{1-6}$ lower alkoxy, optionally having a heteroatom selected from O or N; or b) a bicycloalkyl ring optionally substituted with one to three substituents selected from H, =O, —OH, —COOH, $C_{1-6}$ lower alkyl, —C(O)—$C_{1-6}$ lower alkyl, —C(O)O—$C_{1-6}$ lower alkyl, $C_{1-6}$ lower alkoxy, optionally having a heteroatom of O or N, wherein bridgehead carbon atoms in the ring B are bonded to each other via a $C_1$ or higher alkylene group optionally having a heteroatom selected from O or N; or c) a spiro-cycloalkyl ring optionally substituted with one to three substituents selected from H, =O, —OH, —COOH, $C_{1-6}$ lower alkyl, —C(O)—$C_{1-6}$ lower alkyl, —C(O)O—$C_{1-6}$ lower alkyl, $C_{1-6}$ lower alkoxy, optionally having a heteroatom of O or N, wherein both ends of a $C_1$ or higher alkylene group optionally having a heteroatom selected from O or N are bonded to a carbon atom (bridgehead carbon atom) in the ring B; or U represents:
2) a group represented by the following formula:

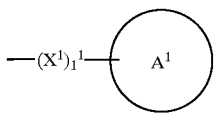

wherein $l^1$ is 0 or 1; and wherein $X^1$ represents $C_{1-6}$ lower alkylene, $C_{1-6}$ lower alkenylene, or $C_{1-6}$ lower alkynylene, which are optionally substituted with a substituent selected from H, =O, —OH, —COOH, $C_{1-6}$ lower alkyl, —C(O)—$C_{1-6}$ lower alkyl, —C(O)O—$C_{1-6}$ lower alkyl, $C_{1-6}$ lower alkoxy, optionally having one to three heteroatoms selected from O, N, or S; and wherein the ring $A^1$ represents:
- a) a cycloalkyl ring optionally substituted with a substituent selected from H, =O, —OH, —COOH, $C_{1-6}$ lower alkyl, —C(O)—$C_{1-6}$ lower alkyl, —C(O)O—$C_{1-6}$ lower alkyl, $C_{1-6}$ lower alkoxy, optionally having a heteroatom selected from O, N, and S; or
- b) a bicycloalkyl ring optionally substituted with one to three substituents selected from H, =O, —OH, —COOH, $C_{1-6}$ lower alky, —C(O)—$C_{1-6}$ lower alkyl, —C(O)O—$C_{1-6}$ lower alkyl, $C_{1-6}$ lower alkoxy, optionally having a heteroatom selected from O, N, and S; or
- c) a spiro-cycloalkyl ring optionally having a heteroatom selected from O, N, and S, wherein both ends of an optionally substituted $C_1$ or higher alkylene group optionally having a heteroatom selected from O, N, and S are bonded to a carbon atom (bridgehead carbon atom) in the ring $A^1$; or U represents
3) nitroso; or U represents
4) a group represented by the formula:

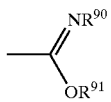

wherein $R^{90}$ and $R^{91}$ represent each hydrogen or $C_{1-6}$ lower alkyl;

R represents:
1) hydrogen;
2) $C_{1-6}$ lower alkyl;
3) aryl $C_{1-6}$ lower alkyl;
4) heteroaryl $C_{1-6}$ lower alkyl, wherein a heteroatom is selected form O, N, and S;
5) a group represented by the following formula:

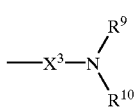

wherein $X^3$ represents $C_{1-6}$ lower alkylene optionally having a heteroatom selected from O, N, and S, $C_{1-6}$ lower alkenylene optionally having a heteroatom selected from O, N, and S, or $C_{1-6}$ lower alkynylene optionally having a heteroatom selected from O, N, and S; and $R^9$ and $R^{10}$ may be the same or different and each represents hydrogen, $C_{1-6}$ lower alkyl, or an amino protective group; or 6) a group represented by the formula:

wherein
$X^4$ represents $C_{1-6}$ lower alkylene optionally having a heteroatom selected from O, N, and S, $C_{1-6}$ lower alkenylene optionally having a heteroatom selected from O, N, and S, or $C_{1-6}$ lower alkynylene optionally having a heteroatom selected from O, N, and S; and $R^{11}$ represents hydrogen, $C_{1-6}$ lower alkyl, or a carboxy protective group; and n represents 0, 1, or 2.

2. The benzopiperidine derivative as set forth in claim 1, its salt or hydrates thereof, wherein U represents:
1) a group represented by the formula:

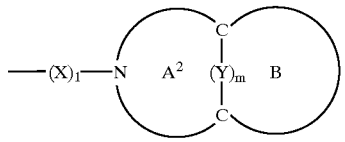

wherein
X, Y, l, m, and the ring B are each as defined in claim 1; and
the ring $A^2$ represents an optionally substituted cycloalkyl ring having one or more heteroatoms; or 2) a group represented by the formula:

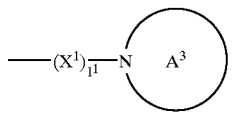

wherein
$X^1$ and $l^1$ are each as defined in claim 1; and
the ring $A^3$ represents:
- a) an optionally substituted cycloalkyl ring having one or more heteroatoms;
- b) an optionally substituted cycloalkenyl ring having one or more heteroatoms; or
- c) an optionally substituted spiro-hydrocarbon ring having one or more heteroatoms, wherein the both ends of an optionally substituted $C_1$ or higher alkylene group optionally having a heteroatom are bonded to a carbon atom (bridgehead carbon atom) in the ring $A^3$.

3. A benzopiperidine derivative represented by the formula (III), its salt or hydrates thereof:

(III)

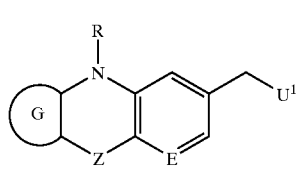

wherein
R is as defined in claim 1 and the ring G represents an optionally substituted heteroaryl ring having one or more nitrogen atoms;
$U^1$ represents:

1) a group represented by the formula:

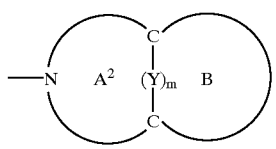

wherein Y, m and the rings $A^2$ and B are each as defined in claim 2; or 2) a group represented by the following formula:

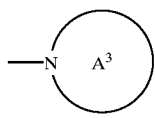

wherein the ring $A^3$ is as defined in claim 2.

4. The benzopiperidine derivative as set forth in any of claim 2, 3, or 1, its salt or hydrates thereof, wherein the ring G is an optionally substituted pyrazine ring.

5. The benzopiperidine derivative as set forth in claim 1 selected from among those represented by the formulae 1) to 3):

1)

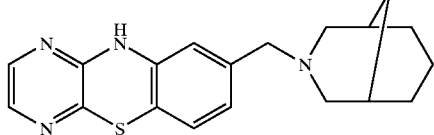

2)

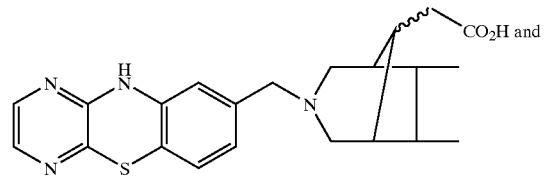

3)

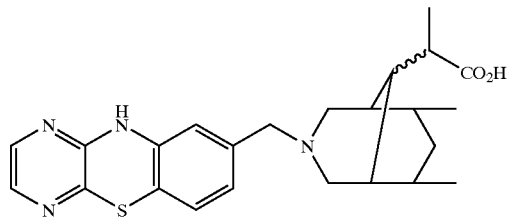

or a salt thereof or a hydrate thereof.

6. The benzopiperidine derivative as set forth in claim 5, which is represented by the formula

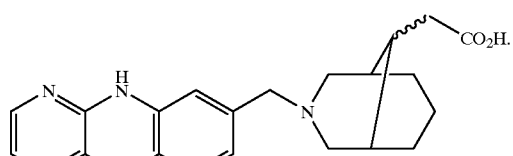

* * * * *

UNITED STATES PATENT AND TRADEMARK OFFICE
CERTIFICATE OF CORRECTION

PATENT NO. : 6,518,423 B1
DATED : February 11, 2003
INVENTOR(S) : Toshihiko Kaneko et al.

It is certified that error appears in the above-identified patent and that said Letters Patent is hereby corrected as shown below:

Column 1081,
Line 54, delete the first structural formula, and replace it with
--

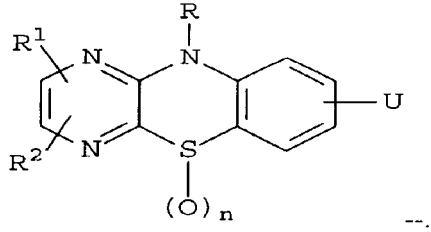

--.

Column 1084,
Line 64, delete the second line after the first structural formula, and replace it with
-- R is as defined in claim 1, Z represents -S-, -SO-, or –SO$_2$-, E represents –CH=, and the ring G represents an --.

Signed and Sealed this

Twentieth Day of July, 2004

JON W. DUDAS
*Acting Director of the United States Patent and Trademark Office*